(12) United States Patent
Blaquiere et al.

(10) Patent No.: US 9,605,005 B2
(45) Date of Patent: Mar. 28, 2017

(54) ALKYNYL ALCOHOLS AND METHODS OF USE

(71) Applicant: Genentech, Inc., South San Francisco, CA (US)

(72) Inventors: Nicole Blaquiere, San Francisco, CA (US); Georgette Castanedo, Redwood City, CA (US); Jianwen A. Feng, Millbrae, CA (US); Baihua Hu, Plainsboro, NJ (US); Steven Staben, San Francisco, CA (US); Po-wai Yuen, Ann Arbor, MI (US); Guosheng Wu, Beijing (CN); Jason Burch, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/074,100

(22) Filed: Mar. 18, 2016

(65) Prior Publication Data

US 2016/0200739 A1     Jul. 14, 2016

Related U.S. Application Data

(63) Continuation of application No. 14/466,153, filed on Aug. 22, 2014, now abandoned.

(30) Foreign Application Priority Data

| Aug. 22, 2013 | (WO) | PCT/CN2013/000993 |
| May 28, 2014 | (WO) | PCT/CN2014/078680 |
| Jul. 22, 2014 | (WO) | PCT/CN2014/082687 |

(51) Int. Cl.

| C07D 401/00 | (2006.01) |
| C07D 513/04 | (2006.01) |
| C07D 401/14 | (2006.01) |
| C07D 413/14 | (2006.01) |
| C07D 401/10 | (2006.01) |
| C07D 403/10 | (2006.01) |
| C07D 403/14 | (2006.01) |
| C07D 413/10 | (2006.01) |
| C07D 417/10 | (2006.01) |
| C07D 471/04 | (2006.01) |
| C07D 487/04 | (2006.01) |
| C07D 491/048 | (2006.01) |
| C07D 491/052 | (2006.01) |
| C07D 495/04 | (2006.01) |

(52) U.S. Cl.
CPC ......... *C07D 513/04* (2013.01); *C07D 401/10* (2013.01); *C07D 401/14* (2013.01); *C07D 403/10* (2013.01); *C07D 403/14* (2013.01); *C07D 413/10* (2013.01); *C07D 413/14* (2013.01); *C07D 417/10* (2013.01); *C07D 471/04* (2013.01); *C07D 487/04* (2013.01); *C07D 491/048* (2013.01); *C07D 491/052* (2013.01); *C07D 495/04* (2013.01)

(58) Field of Classification Search
None
See application file for complete search history.

(56) References Cited

FOREIGN PATENT DOCUMENTS

| WO | 2009/158011 A1 | 12/2009 |
| WO | 2012/123522 A1 | 9/2012 |
| WO | 2014/174021 A1 | 10/2014 |

OTHER PUBLICATIONS

PCT ISR and Written Opinion for PCT/CN2013/000993 mailed on Jun. 9, 2014.
PCT ISR for PCT/EP2014/067872 mailed on Dec. 9, 2014.
U.S. Appl. No. 14/466,176, filed Aug. 22, 2014, Wu et al.

*Primary Examiner* — Heidi Reese
(74) *Attorney, Agent, or Firm* — Tamara A. Kale

(57) ABSTRACT

The invention relates to compounds of Formula (0):

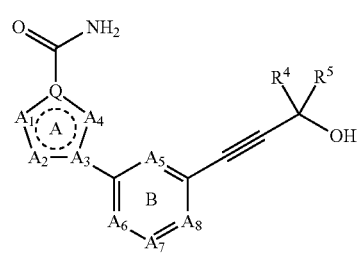

wherein Q, $A^1$-$A^8$, $R^4$ and $R^5$ and each has the meaning as described herein. Compounds of Formula (0) and pharmaceutical compositions thereof are useful in the treatment of diseases and disorders in which undesired or over-activation of NF-kB signaling is observed.

4 Claims, No Drawings

ALKYNYL ALCOHOLS AND METHODS OF USE

CROSS-REFERENCE TO RELATED APPLICATIONS

This application is a continuation of U.S. application Ser. No. 14/466,153, filed Aug. 22, 2014, which claims the benefit of priority under 35 U.S.C. §119(a) to: International Application No. PCT/CN2014/082687, filed Jul. 22, 2014; International Application No. PCT/CN2014/078680, filed May 28, 2014; and International Application No. PCT/CN2013/000993, filed Aug. 22, 2013, each of which is incorporated herein by reference in its entirety.

FIELD OF THE INVENTION

The present invention relates to organic compounds useful for therapy or prophylaxis in a mammal, and in particular to inhibitors of NF-kB-inducing kinase (NIK) useful for treating cancer and inflammatory conditions, among others.

NF-kB inducing kinase (NIK) is also known as MAPK kinase kinase 14 (MAP3K14) and is a serine/threonine kinase and a member of the MAPK family. It was originally identified in a two-hybrid screen as a binding partner of TNF receptor (TNFR) associated factor 2 (TRAF2) [See, Malinin, N L, et al., Nature, 1997, 385:540-4]. Overexpression of NIK leads to the activation of NF-kB and dominant negative forms of NIK lacking kinase activity were able to inhibit NF-kB activation in response to TNF and IL-1 treatment. Thus, NIK has been identified as an important component of the NF-kB signaling pathway. Scientific research has shown that in blocking the NF-kB signaling pathway in cancer cells can cause such cells to stop proliferating, to die, or to become more sensitive to the action of other anti-cancer therapies. Additionally, research has shown that NF-kB controls the expression of many genes involved in inflammation and that NF-kB signaling is found to be chronically active in many inflammatory conditions, such as lupus (including systemic lupus erythematosus), rheumatoid arthritis, inflammatory bowel disease, arthritis, sepsis, gastritis and asthma, among others. Accordingly, organic compounds capable of inhibiting NIK and thereby inhibiting, weakening or lessening the undesired or over-activation of the NF-kB signaling pathway can have a therapeutic benefit for the treatment diseases and disorders for which such undesired or over-activation of NF-kB signaling is observed.

SUMMARY OF THE INVENTION

Provided herein are compounds of Formula (0):

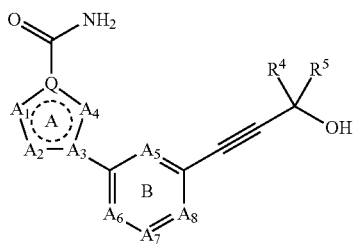

(0)

or a stereoisomer or salt thereof, wherein:
ring A is a monocycle or a fused bicycle;
Q is N or C, wherein when Q is N, then the bond between $A_1$ and Q is not a double bond and the bond between Q and $A_4$ is not a double bond;
$A_1$ is $NR^1$, S or $CR^1$;
$A_2$ is $NR^2$, S or $CR^2$;
$A_3$ is N or C;
$A_4$ is N; and
one, two or three of $A_1$-$A_4$ are N, wherein:
$R^1$ is selected from the group consisting of H, halogen, $NR^aR^b$, $C_1$-$C_3$ alkyl, $C_3$-$C_7$ cycloalkyl, $C_1$-$C_3$ alkoxy and 3-11 membered heterocyclyl, wherein $R^1$ is optionally substituted by F, OH, CN, SH, $CH_3$ or $CF_3$;
$R^2$ is selected from the group consisting of H, $NR^aR^b$, $C_1$-$C_6$ alkyl, $C_3$-$C_7$ cycloalkyl, $C_1$-$C_6$ alkoxy, phenyl and 3-11 membered heterocyclyl, wherein $R^2$ is optionally substituted by $R^c$; or
$R^1$ and $R^2$ taken together form a cyclic group selected from the group consisting of $C_3$-$C_7$ cycloalkyl, phenyl and 3-11 membered heterocyclyl, wherein the cyclic group is optionally substituted by $R^d$;
$R^4$ is selected from the group consisting of H, $C_1$-$C_6$ alkyl, $CH_2F$ and $CH_2OH$;
$R^5$ is 3-11 membered heterocyclyl optionally substituted by $R^e$ or $-C(=O)N(C_1$-$C_6$ alkyl$)_2$; or
$R^4$ and $R^5$ together form a $C_3$-$C_{11}$ cycloalkyl optionally substituted by $R^e$ or a 3-11 membered heterocyclyl optionally substituted by $R^e$;
one of $A_5$-$A_8$ is N and the remaining are $CR^6$ or all are $CR^6$;
$R^6$, independently at each occurrence, is selected from the group consisting of H, F, Cl, $NH_2$, $NHCH_3$, $N(CH_3)_2$, OH, $OCH_3$, $OCHF_2$, $OCH_2F$, $OCF_3$, SH, $SCH_3$, $SCHF_2$, $SCH_2F$, CN, $CH_3$, $CHF_2$, $CH_2F$, $CH_2OH$, $CF_3$, $NO_2$ and $N_3$;
$R^a$ is selected from the group consisting of H and $C_1$-$C_6$ alkyl optionally substituted by $C_1$-$C_3$ alkoxy, F, OH, CN, SH, $CH_3$ or $CF_3$;
$R^b$ is selected from the group consisting of H, $C_1$-$C_6$ alkyl, $C_1$-$C_6$ alkoxy, $C_3$-$C_6$ cycloalkyl, $C(O)R^g$, phenyl and 3-11 membered heterocyclyl wherein $R^b$ may be optionally substituted by $C_1$-$C_3$ alkoxy, F, OH, CN, SH, $CH_3$ or $CF_3$;
$R^c$ and $R^d$ are each independently selected from the group consisting of halogen, $-(X^1)_{0-1}$—CN, $-(X^1)_{0-1}$—$NO_2$, $-(X^1)_{0-1}$—$SF_5$, $-(X^1)_{0-1}$—OH, $-(X^1)_{0-1}$—$NH_2$, $-(X^1)_{0-1}$—N(H)($R^{1a}$), $-(X^1)_{0-1}$—N($R^{1b}$)($R^{1a}$), $-(X^1)_{0-1}$—$CF_3$, $C_1$-$C_6$ alkyl, $C_1$-$C_6$ haloalkyl, $C_1$-$C_6$ heteroalkyl, $C_1$-$C_6$ alkoxy, $C_1$-$C_6$ alkylthio, oxo, $-(X^1)_{0-1}$—$C_1$-$C_6$ alkyl, $-(X^1)_{0-1}$—$C_3$-$C_{10}$ cycloalkyl, $-O$—$C_3$-$C_{10}$ cycloalkyl, $-(X^1)_{0-1}$-3-11 membered heterocyclyl, $-(X^1)_{0-1}$—$C_6$-$C_{10}$ aryl, $-C(=O)(X^1)_1$—$C_3$-$C_{10}$ cycloalkyl, $-C(=O)(X^1)_1$-3-11 membered heterocyclyl, $-(X^1)_{0-1}$—$C(=Y^1)$N(H)($R^{1a}$), $-(X^1)_{0-1}$—$C(=Y^1)NH_2$, $-(X^1)_{0-1}$—$C(=Y^1)$N($R^{1a}$)($R^{1b}$), $-(X^1)_{0-1}$—$C(=Y^1)OR^{1a}$, $-(X^1)_{0-1}$—$C(=Y^1)$OH, $-(X^1)_{0-1}$—N(H)C($=Y^1$)($R^{1a}$), $-(X^1)_{0-1}$—N($R^{1b}$)C($=Y^1$)($R^{1a}$), $-(X^1)_{0-1}$N($R^{1b}$)C($=Y^1$)(H), $-(X^1)_{0-1}$—N(H)C($=Y^1$)$OR^{1a}$, $-(X^1)_{0-1}$—N($R^{1b}$)C($=Y^1$)$OR^{1a}$, $-(X^1)_{0-1}$—S(O)$_{1-2}R^{1a}$, $-(X^1)_{0-1}$—N(H)S(O)$_{1-2}R^{1a}$, $-(X^1)_{0-1}$—N($R^{1b}$)S(O)$_{1-2}R^{1a}$, $-(X^1)_{0-1}$—S(O)$_{0-1}$N(H)($R^{1a}$), $-(X^1)_{0-1}$—S(O)$_{0-1}$—N($R^{1b}$)($R^{1a}$), $-(X^1)_{0-1}$—S(O)$_{0-1}NH_2$, $-(X^1)_{0-1}$—S($=O$)($=NR^{1b}$)$R^{1a}$, $-(X^1)_{0-1}$—C($=Y^1$)$R^{1a}$, $-(X^1)_{0-1}$—C($=Y^1$)H, $-(X^1)_{0-1}$—C($=$NOH)$R^{1a}$, $-(X^1)_{0-1}$—C($=NOR^{1b}$)$R^{1a}$, $-(X^1)_{0-1}$—NHC($=Y^1$)N(H)($R^{1a}$), $-(X^1)_{0-1}$—NHC($=Y^1$)$NH_2$, $-(X^1)_{0-1}$—NHC($=Y^1$)N(R($R^{1b}$)($R^{1a}$), $-(X^1)_{0-1}$—N($R^{1a}$)C($=Y^1$)N(H)($R^{1a}$), $-(X^1)_{0-1}$—N($R^{1a}$)C($=Y^1$)N($R^{1a}$)($R^{1b}$), $-(X^1)_{0-1}$—N($R^{1a}$)C($=Y^1$)$NH_2$, $-(X^1)_{0-1}$—OC($=Y^1$)$R^{1a}$, $-(X^1)_{0-1}$—OC($=Y^1$)H, $-(X^1)_{0-1}$—OC($=Y^1$)$OR^{1a}$, $-(X^1)_{0-1}$—OP($=^1$)($OR^{1a}$)($OR^{1b}$), $-(X^1)$—SC($=Y^1$)$OR^{1a}$ and —($X^1$)—SC(=¹)N($R^{1a}$)($R^{1b}$) wherein $X^1$ is selected from the group consisting of $C_1$-$C_6$ alkylene, $C_1$-$C_6$ heteroalkylene, $C_2$-$C_6$ alkenylene, $C_2$-$C_6$ alkynylene, $C_1$-$C_6$ alkyleneoxy, $C_3$-$C_7$ cycloalkylene, 3-11 membered heterocyclylene and phenylene; $R^{1a}$ and $R^{1b}$ are each independently selected from the group consisting of $C_1$-$C_6$ alkyl, $C_1$-$C_6$ haloalkyl, $C_1$-$C_6$ heteroalkyl, $C_3$-$C_7$ cycloalkyl, ($C_3$-$C_7$ cycloalkylene)$C_1$-$C_6$ alkyl, 3-11 membered heterocyclyl, (3-11 membered heterocyclylene)$C_1$-$C_6$ alkyl, $C_6$ aryl, and ($C_6$-$C_{10}$ arylene)$C_1$-$C_6$ alkyl, or $R^{1a}$ and $R^{1b}$ when attached to the same nitrogen atom are optionally combined to form a 3-11 membered heterocyclyl comprising 0-3 additional heteroatoms selected from N, O and S; $Y^1$ is O, $NR^{1c}$ or S wherein $R^{1c}$ is H or $C_1$-$C_6$ alkyl; wherein any portion of an $R^c$ or $R^d$ substituent, including $R^{1a}$, $R^{1b}$ and $R^{1c}$, at each occurrence is each independently further substituted by from 0 to 4 $R^f$ substituents selected from the group consisting of halogen, CN, $NO_2$, $SF_5$, OH, $NH_2$, —N($C_1$-$C_6$ alkyl)$_2$, —NH($C_1$-$C_6$ alkyl), oxo, $C_1$-$C_6$ alkyl, —($C_2$-$C_6$ alkynylene)-(3-11 membered heterocyclyl, wherein the heterocyclyl is optionally substituted by $R^e$), $C_1$-$C_6$ hydroxyalkyl, $C_1$-$C_6$ heteroalkyl, $C_1$-$C_6$ alkoxy, $C_1$-$C_6$ alkylthio, $C_3$-$C_7$ cycloalkyl, 3-11 membered heterocyclyl, —C(=O)N(H)($C_1$-$C_6$ alkyl), —C(=O)N($C_1$-$C_6$ alkyl)$_2$, —C(=O)$NH_2$, —C(=O)O$C_1$-$C_6$ alkyl, —C(=O)OH, —N(H)C(=O)$C_1$-$C_6$ alkyl), —N($C_1$-$C_6$ alkyl)C(=O)($C_1$-$C_6$ alkyl), —N(H)C(=O)O$C_1$-$C_6$ alkyl, —N($C_1$-$C_6$ alkyl)C(=O)O$C_1$-$C_6$ (halo)alkyl, —S(O)$_{1-2}$$C_1$-$C_6$ alkyl, —N(H)S(O)$_{1-2}$$C_1$-$C_6$ alkyl, —N($C_1$-$C_6$ alkyl)S(O)$_{1-2}$$C_1$-$C_6$ alkyl, —S(O)$_{0-1}$N(H)($C_1$-$C_6$ alkyl), —S(O)$_{0-1}$N($C_1$-$C_6$ alkyl)$_2$, —S(O)$_{0-1}$$NH_2$, —C(=O)$C_1$-$C_6$ alkyl, —C(=O)$C_3$-$C_7$ cycloalkyl, —C(=NOH)$C_1$-$C_6$ alkyl, —C(=NO$C_1$-$C_6$ alkyl)$C_1$-$C_6$ alkyl, —NHC(=O)N(H)($C_1$-$C_6$ alkyl), —NHC(=O)N($C_1$-$C_6$ alkyl)$_2$, —NHC(=O)$NH_2$, —N($C_1$-$C_6$ alkyl)C(=O)N(H)($C_1$-$C_6$ alkyl), —N($C_1$-$C_6$ alkyl)C(=O)$NH_2$, —OC(=O)$C_1$-$C_6$ alkyl, —OC(=O)O$C_1$-$C_6$ alkyl, —OP(=O)(O$C_1$-$C_6$ alkyl)$_2$, —SC(=O)O$C_1$-$C_6$ alkyl and —SC(=O)N($C_1$-$C_6$ alkyl)$_2$, wherein any alkyl portion of $R^f$ is optionally substituted with halogen;

$R^e$ is selected from the group consisting of halogen, OH, $C_1$-$C_6$ alkyl and oxo; and $R^g$ is selected from the group consisting of $C_1$-$C_6$ alkyl and $C_3$-$C_6$ cycloalkyl.

In another aspect, the invention provides for pharmaceutical compositions comprising a compound of Formula (0) and a pharmaceutically acceptable carrier, diluent or excipient.

In another aspect, the invention provides for a compounds of Formula (0) or pharmaceutical compositions thereof for use in therapy. In another embodiment, the invention provides the use of a compound or pharmaceutical composition for the preparation of a medicament for the treatment of an inflammatory condition.

In another aspect, the inventions provides for compounds of Formula (0) and pharmaceutical compositions thereof for the treatment of diseases and disorders, including, cancer, inflammatory conditions, and autoimmune diseases, among others.

In another aspect, the invention provides for a method (or use) of compounds of Formula (0) or pharmaceutical compositions thereof in the treatment of diseases and disorders, such as, for example, cancer, inflammatory conditions, or autoimmune diseases, among others.

In another aspect, the invention provides for compounds of Formula (0) for the preparation of a medicament for the treatment of cancer, inflammatory conditions, or autoimmune diseases, among others.

In another aspect, the invention provides for compound intermediates useful in synthesis of compounds of Formula (0).

DETAILED DESCRIPTION OF THE INVENTION

The invention provides for compounds of Formula (0), pharmaceutical compositions comprising compounds of Formula (0) and methods of using such compounds and compositions in treating diseases and disorders related to undesired or overactivation of the NF-kB signaling pathway, such as, for example, certain cancers and inflammatory conditions.

Definitions

The term "alkyl" refers to a saturated linear or branched-chain monovalent hydrocarbon radical, wherein the alkyl radical may be optionally substituted independently with one or more substituents described herein. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. $C_0$ alkyl refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2$$CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2$$CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$, 1-heptyl and 1-octyl. In some embodiments, substituents for "optionally substituted alkyls" include one to six instances of F, Cl, Br, I, OH, SH, CN, $NH_2$, $NO_2$, $N_3$, COOH, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, or pyrimidinyl, wherein the alkyl, aryl and heterocyclic portions thereof may be optionally substituted.

The term "alkylene" by itself or as part of another substituent means a divalent radical derived from an alkane, as exemplified by —$CH_2CH_2CH_2CH_2$—. Typically, an alkyl (or alkylene) group will have from 1 to 12 carbon atoms, such as 1-8, 1-6 or 1-3 carbon atoms. "Alkenylene" and "alkynylene" refer to the unsaturated forms of "alkylene" having double or triple bonds, respectively, and typically have from 2 to 12 carbon atoms, such as 2-8, 2-6 or 2-3 carbon atoms. "Alkylene", "alkenylene" and "alkynylene" groups may be optionally substituted.

The term "heteroalkyl" refers to a straight or branched chain monovalent hydrocarbon radical, consisting of the stated number of carbon atoms, or, if none are stated, up to 18 carbon atoms, and from one to five heteroatoms selected from the group consisting of O, N, Si and S, and wherein the nitrogen and sulfur atoms can optionally be oxidized and the nitrogen heteroatom can optionally be quaternized. In some embodiments, the heteroatom is selected from O, N and S, wherein the nitrogen and sulfur atoms can optionally be oxidized and the nitrogen heteroatom can optionally be quaternized. The heteroatom(s) can be placed at any interior position of the heteroalkyl group, including the position at which the alkyl group is attached to the remainder of the molecule (e.g., —O—CH$_2$—CH$_3$). Examples include —CH$_2$—CH$_2$—O—CH$_3$, —CH$_2$—CH$_2$—O—CF$_3$, —CH$_2$—CH$_2$—NH—CH$_3$, —CH$_2$—CH$_2$—N(CH$_3$)—CH$_3$, —CH$_2$—S—CH$_2$—CH$_3$, —S(O)—CH$_3$, —CH$_2$—CH$_2$—S(O)$_2$—CH$_3$, —Si(CH$_3$)$_3$, —CH$_2$—CH=N—OCH$_3$, and —OCF$_3$. Up to two heteroatoms can be consecutive, such as, for example, —CH$_2$—NH—OCH$_3$ and —CH$_2$—O—Si(CH$_3$)$_3$. Heteroalkyl groups can be optionally substituted. In some embodiments, substituents for "optionally substituted heteroalkyls" include one to four instances of F, Cl, Br, I, OH, SH, CN, NH$_2$, NO$_2$, N$_3$, COOH, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonyl amino, SO, SO$_2$, phenyl, piperidinyl, piperizinyl, and pyrimidinyl, wherein the alkyl, aryl and heterocyclic portions thereof may be optionally substituted.

The term "heteroalkylene" means a divalent radical derived from heteroalkyl, as exemplified by —CH$_2$CH$_2$SCH$_2$CH$_2$—, —CH$_2$SCH$_2$CH$_2$NHCH$_3$ and —OCH$_2$CH$_3$. For heteroalkylene groups, heteroatoms can also occupy either or both of the chain termini (e.g., alkyleneoxy, alkylenedioxy, alkyleneamino, alkylenediamino, and the like). A heteroalkylene group may be optionally substituted.

"Cycloalkyl" refers to a non-aromatic, saturated or partially unsaturated hydrocarbon ring group wherein the cycloalkyl group may be optionally substituted with one or more substituents described herein. In one example, the cycloalkyl group is 3 to 12 carbon atoms (C$_3$-C$_{12}$). In other examples, cycloalkyl is C$_3$-C$_6$, C$_3$-C$_8$, C$_3$-C$_{10}$ or C$_5$-C$_{10}$. In other examples, the cycloalkyl group, as a monocycle, is C$_3$-C$_8$, C$_3$-C$_6$ or C$_5$-C$_6$. In another example, the cycloalkyl group, as a bicycle, is C$_7$-C$_{12}$. In another example, the cycloalkyl group, as a spiro system, is C$_5$-C$_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[4.1.0]heptane, bicycle[3.1.1]heptane, bicyclo[2.2.1]heptane, bicyclo[2.2.2]octane, bicyclo[4.1.0]heptane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane. In some embodiments, substituents for "optionally substituted cycloalkyls" include one to four instances of F, Cl, Br, I, OH, SH, CN, NH$_2$, NO$_2$, N$_3$, COOH, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, aryl and heterocyclic portions thereof may be optionally substituted.

The term "cycloalkylene" means a divalent radical derived from a cycloalkyl group. A cycloalkylene group may be optionally substituted.

"Heterocyclic group", "heterocyclic", "heterocycle", "heterocyclyl", or "heterocyclo" are used interchangeably and refer to any monocyclic, bicyclic, or spiro, saturated or unsaturated, aromatic (heteroaryl) or non-aromatic (e.g., heterocycloalkyl), ring system, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-11 ring atoms ("members", that is, a 3-11 membered heterocycle) and includes monocycles, bicycles, and spiro ring systems, wherein the ring atoms are carbon, and at least one atom in the ring or ring system is a heteroatom selected from nitrogen, sulfur or oxygen. In one example, heterocyclyl includes 1 to 4 heteroatoms. In another example, heterocyclyl includes 3- to 7-membered monocycles having one or more heteroatoms selected from nitrogen, sulfur or oxygen. In another example, heterocyclyl includes 4- to 6-membered monocycles having one or more heteroatoms selected from nitrogen, sulfur or oxygen. In another example, heterocyclyl includes 3-membered monocycles. In another example, heterocyclyl includes 4-membered monocycles. In another example, heterocyclyl includes 5-6-membered monocycles. In one example, the heterocyclyl group includes 0 to 3 double bonds. Any nitrogen or sulfur heteroatom may optionally be oxidized (e.g., NO, SO, SO$_2$), and any nitrogen heteroatom may optionally be quaternized (e.g., [NR$_4$]$^+$Cl$^-$, [NR$_4$]$^+$OH$^-$). In another example, heterocyclyl includes 3- to 9-membered spiro cycles having one or more heteroatoms selected from nitrogen, sulfur or oxygen. Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocycles containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocycles are benzoxazol-2-yl, benzthiazol-2-yl and benzimidazol-2-yl. Example 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocycle groups. Heterocycles may be optionally substituted. For example, substituents for "optionally substituted heterocycles" include one to six instances of F, Cl, Br, I, OH, SH, CN, $NH_2$, $NO_2$, $N_3$, COOH, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted.

The term "heterocyclylene" means a divalent radical derived from a heterocyclyl group. A heterocyclylene group may be optionally substituted.

"Heteroaryl" refers to any mono-, bi-, or tricyclic ring system where at least one ring is a 5- or 6-membered aromatic ring containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.) $13^{th}$ ed. Table 7-2 [1985]. Included in the definition are any bicyclic groups where any of the above heteroaryl rings are fused to an aryl ring, wherein the aryl ring or the heteroaryl ring is joined to the remainder of the molecule. In one embodiment, heteroaryl includes 4-6 membered monocyclic aromatic groups where one or more ring atoms is nitrogen, sulfur or oxygen. In another embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl and indolyl. Heteroaryl groups can be optionally substituted. In some embodiments, substituents for "optionally substituted heteroaryls" include one to six instances of F, Cl, Br, I, OH, SH, CN, $NH_2$, $NO_2$, $N_3$, COOH, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted.

In particular embodiments, a heterocyclyl group is attached at a carbon atom of the heterocyclyl group. By way of example, carbon bonded heterocyclyl groups include bonding arrangements at position 2, 3, 4, 5, or 6 of a pyridine ring, position 3, 4, 5, or 6 of a pyridazine, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group is N-attached. By way of example, the nitrogen bonded heterocyclyl or heteroaryl group include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of an isoindole, or isoindoline, position 4 of a morpholine, and position 9 of a carbazole, or β-carboline.

The term "alkoxy" refers to those alkyl groups attached to the remainder of the molecule via an oxygen atom. Non-limiting examples include methoxy, ethoxy and propoxy. Alkoxy groups may be optionally substituted, such as by halogen.

The term "alkylthio" refers to those alkyl groups attached to the remainder of the molecule via an sulfur atom. Non-limiting examples include $—SCH_3$, $—SCH_2CH_3$ and $—SCH_2CH_2CH_3$. Alkylthio groups may be optionally substituted, such as by halogen.

The terms "halo" or "halogen," by themselves or as part of another substituent, mean, unless otherwise stated, a fluorine, chlorine, bromine, or iodine atom. The term "haloalkyl" is meant to include both an "alkyl" and a "haloalkyl" substituent. Additionally, the term "haloalkyl," is meant to include monohaloalkyl and polyhaloalkyl.

The term "oxo" refers to $=O$ or $(=O)_2$.

The term "aryl" means, unless otherwise stated, a polyunsaturated, typically aromatic, hydrocarbon ring radical, which can be a single ring or multiple rings (up to three rings) which are fused together and having the stated number of aryl ring atoms. An aryl group can be optionally substituted.

A "phenylene" group refers to a divalent radical derived from a phenyl group. A phenylene group may be optionally substituted.

"Optionally substituted" unless otherwise specified means that a group may be unsubstituted or substituted by one or more (e.g., 0, 1, 2, 3, 4, or 5 or more) of the substituents listed for that group in which said substituents may be the same or different. That is, an optionally substituted substituent is independent at each occurrence. In an embodiment an optionally substituted group has 1 substituent. In another embodiment an optionally substituted group has 2 substituents. In another embodiment an optionally substituted group has 3 substituents. In another embodiment an optionally substituted group has 4 substituents.

Optional substituents for alkyl and cycloalkyl can be a variety of groups including, but not limited to, halogen, oxo, CN, $NO_2$, $N_3$, OR', perfluoro-$C_{1-4}$ alkoxy, unsubstituted cycloalkyl, unsubstituted aryl (e.g., phenyl), unsubstituted heterocyclyl, NR'R", SR', SiR'R"R'", OC(O)R', C(O)R', CO$_2$R', CONR'R", OC(O)NR'R", NR"C(O)R', NR'"C(O)NR'R", NR"C(O)$_2$R', S(O)$_2$R', S(O)$_2$NR'R", NR'S(O)$_2$R", NR'"S(O)$_2$NR'R", amidino, guanidine, (CH$_2$)$_{1-4}$OR', (CH$_2$)$_{1-4}$NR'R", (CH$_2$)$_{1-4}$SR', (CH$_2$)$_{1-4}$SiR'R"R'", (CH$_2$)$_{1-4}$OC(O)R', (CH$_2$)$_{1-4}$C(O)R', (CH$_2$)$_{1-4}$CO$_2$R', and (CH$_2$)$_{1-4}$CONR'R", or combinations thereof, in a number ranging from zero to (2m'+1), where m' is the total number of carbon atoms in such radical. R', R" and R'" each independently refer to groups including, for example, hydrogen; unsubstituted C$_{1-6}$ alkyl; unsubstituted heteroalkyl; unsubstituted aryl; aryl substituted with 1-3 halogens, unsubstituted C$_1$-C$_6$ alkyl, C$_1$-C$_6$ alkoxy or C$_1$-C$_6$ thioalkoxy groups, unsubstituted aryl-C$_1$-C$_4$ alkyl groups, and unsubstituted heteroaryl. When R' and R" are attached to the same nitrogen atom, they can be combined with the nitrogen atom to form a 3-, 4-, 5-, 6-, or 7-membered ring wherein a ring atom is optionally substituted with N, O or S. For example, NR'R" is meant to include 1-pyrrolidinyl and 4-morpholinyl.

Similarly, optional substituents for the aryl and heterocyclyl groups are varied. In some embodiments, substituents for aryl and heterocyclyl groups are selected from the group including, but not limited to, halogen, OR', OC(O)R', NR'R", SR', R', CN, NO$_2$, CO$_2$R', CONR'R", C(O)R', OC(O)NR'R", NR"C(O)R', NR"C(O)$_2$R', NR'C(O)NR"R'", S(O)R', S(O)$_2$R', S(O)$_2$NR'R", NR'S(O)$_2$R", N$_3$, perfluoro-C$_1$-C$_4$ alkoxy, perfluoro-C$_1$-C$_4$ alkoxy, (CH$_2$)$_{1-4}$OR', (CH$_2$)$_{1-4}$NR'R", (CH$_2$)$_{1-4}$SR', (CH$_2$)$_{1-4}$SiR'R"R'", (CH$_2$)$_{1-4}$OC(O)R', (CH$_2$)$_{1-4}$C(O)R', (CH$_2$)$_{1-4}$CO$_2$R', (CH$_2$)$_{1-4}$CONR'R", or combinations thereof, in a number ranging from zero to the total number of open valences on the aromatic ring system; and where R', R" and R'" are independently selected from hydrogen, C$_1$-C$_6$ alkyl, C$_3$-C$_6$ cycloalkyl, C$_2$-C$_6$ alkenyl, C$_2$-C$_6$ alkynyl, unsubstituted aryl, and unsubstituted heteroaryl. Other suitable substituents include each of the above aryl substituents attached to a ring atom by an alkylene tether of from 1-4 carbon atoms.

As used herein, the term "heteroatom" is meant to include oxygen (O), nitrogen (N), sulfur (S) and silicon (Si). In some embodiments, heteroatom refers to O, N or S. In some embodiments, heteroatom refers to O or N.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended. If a discrepancy exists between a structure and its name, the structure governs.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethyleneoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenyl sulfonylethyl, cyanoethyl, $_2$-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep.

A "subject," "individual," or "patient" is a vertebrate. In certain embodiments, the vertebrate is a mammal. A subject, individual or patient may be in need of a compound of the present invention.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", J. Pharm. Sci., 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O C_{1-6}$ alkyl$)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191

(1991); c) H. Bundgaard, Advanced Drug Delivery Reviews, 8:1-38 (1992); d) H. Bundgaard, et al., Journal of Pharmaceutical Sciences, 77: 285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. Compounds of the present invention may exist in multiple crystalline or amorphous forms. In general, all physical forms are intended to be within the scope of the present invention.

The compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms are replace by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically labeled compounds of the present invention (e.g., those labeled with $^{3}H$ or $^{14}C$) are useful in compound or substrate tissue distribution assays. Tritiated ($^{3}H$) and carbon-14 ($^{14}C$) isotopes are useful for their ease of preparation and detectability. Further substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present inventions can generally be prepared by following procedures analogous to those disclosed in the Schemes and Examples herein, by substituting an isotopically labeled reagent for a non-isotopically labeled reagent. One non-limiting example of an isotopically substituted moiety is the following:

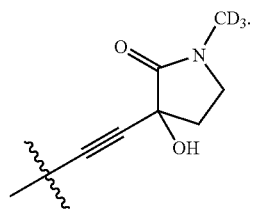

The terms "compound(s) of this invention," and "compound(s) of the present invention" and the like, unless otherwise indicated, include compounds of Formula (0) and stereoisomers (including atropisomers), geometric isomers, tautomers, solvates, metabolites, isotopes, salts (e.g., pharmaceutically acceptable salts), and prodrugs thereof. In some embodiments, solvates, metabolites, isotopes or prodrugs are excluded, or any combination thereof.

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, compounds of the invention are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented. In some embodiments, prophylaxis is excluded from the definition of "treatment."

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) or determining the response rate (RR). In the case of immunological disease, the therapeutically effective amount is an amount sufficient to decrease or alleviate an allergic disorder, the symptoms of an autoimmune or inflammatory condition (e.g., psoriasis or inflammatory bowel disease), or the symptoms of an acute inflammatory reaction (e.g. asthma). In some embodiments, a therapeutically effective amount is an amount of a chemical entity described herein sufficient to significantly decrease the activity or number of B-cells.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., NIK activity) compared to normal.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

"Inflammatory condition" as used herein refers to any disease, disorder, or syndrome in which an excessive or unregulated inflammatory response leads to excessive inflammatory symptoms, host tissue damage, or loss of tissue function.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes or neutrophil chemotaxis. Inflammation can result from infection with pathogenic organisms and viruses and from noninfectious means such as trauma or reperfusion following myocardial infarction or stroke, immune response to foreign antigen, and autoimmune responses.

The terms "cancer" and "cancerous" refer to or describe the physiological condition in mammals that is typically characterized by unregulated cell growth or proliferation. A "tumor" comprises one or more cancerous cells. Examples of cancer include, but are not limited to, carcinoma, lymphoma, blastoma, sarcoma, and leukemia or lymphoid malignancies.

"Autoimmune disease" as used herein refers to any group of disorders in which tissue injury is associated with humoral or cell-mediated responses to the body's own constituents.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

The use of the term "or" is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used herein, "a" or "an" means one or more, unless clearly indicated otherwise. As used herein, "another" means at least a second or more.

Headings used herein are intended only for organizational purposes.

Inhibitors of NIK

One aspect of the invention provides compounds of Formula (0):

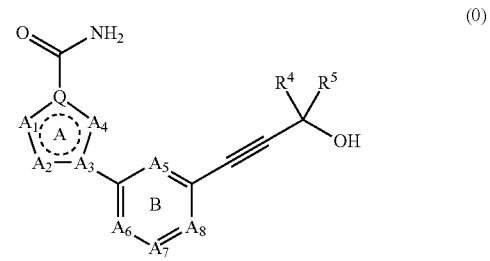

or a stereoisomer or salt thereof, wherein:
ring A is a monocycle or a fused bicycle;
Q is N or C, wherein when Q is N, then the bond between $A_1$ and Q is not a double bond and the bond between Q and $A_4$ is not a double bond;
$A_1$ is $NR^1$, S or $CR^1$;
$A_2$ is $NR^2$, S or $CR^2$;
$A_3$ is N or C;
$A_4$ is N; and
one, two or three of $A_1$-$A_4$ are N, wherein:
$R^1$ is selected from the group consisting of H, halogen, $NR^aR^b$, $C_1$-$C_3$ alkyl, $C_3$-$C_7$ cycloalkyl, $C_1$-$C_3$ alkoxy and 3-11 membered heterocyclyl (e.g., a 4-7 membered heterocycloalkyl or a 5-6 membered heteroaryl), wherein $R^1$ is optionally substituted by F, OH, CN, SH, $CH_3$ or $CF_3$;
$R^2$ is selected from the group consisting of H, $NR^aR^b$, $C_1$-$C_6$ alkyl, $C_3$-$C_7$ cycloalkyl, $C_1$-$C_6$ alkoxy, phenyl and 3-11 membered heterocyclyl (e.g., a 4-7 membered heterocycloalkyl or a 5-6 membered heteroaryl), wherein $R^2$ is optionally substituted by $R^c$; or
$R^1$ and $R^2$ taken together form a cyclic group selected from the group consisting of $C_3$-$C_7$ cycloalkyl, phenyl and 3-11 membered heterocyclyl (e.g., a 4-7 membered heterocycloalkyl or a 5-6 membered heteroaryl), wherein the cyclic group is optionally substituted by $R^d$;
$R^4$ is selected from the group consisting of H, $C_1$-$C_6$ alkyl, $CH_2F$ and $CH_2OH$;
$R^5$ is 3-11 membered heterocyclyl (e.g., a 4-7 membered heterocycloalkyl or a 5-6 membered heteroaryl) optionally substituted by $R^e$ or —C(=O)N($C_1$-$C_6$ alkyl)$_2$; or
$R^4$ and $R^5$ together form a $C_3$-$C_{11}$ cycloalkyl optionally substituted by $R^e$ or a 3-11 membered heterocyclyl (e.g., a 4-7 membered heterocycloalkyl or a 5-6 membered heteroaryl) optionally substituted by $R^e$;
one of $A_5$-$A_8$ is N and the remaining are $CR^6$ or all are $CR^6$;
$R^6$, independently at each occurrence, is selected from the group consisting of H, F, Cl, $NH_2$, $NHCH_3$, $N(CH_3)_2$, OH, $OCH_3$, $OCHF_2$, $OCH_2F$, $OCF_3$, SH, $SCH_3$, $SCHF_2$, $SCH_2F$, CN, $CH_3$, $CHF_2$, $CH_2F$, $CH_2OH$, $CF_3$, $NO_2$ and $N_3$;
$R^a$ is selected from the group consisting of H and $C_1$-$C_6$ alkyl optionally substituted by $C_1$-$C_3$ alkoxy, F, OH, CN, SH, $CH_3$ or $CF_3$;
$R^b$ is selected from the group consisting of H, $C_1$-$C_6$ alkyl, $C_1$-$C_6$ alkoxy, $C_3$-$C_6$ cycloalkyl, $C(O)R^g$, phenyl and 3-11 membered heterocyclyl (e.g., a 4-7 membered heterocycloalkyl or a 5-6 membered heteroaryl) wherein $R^b$ may be optionally substituted by $C_1$-$C_3$ alkoxy, F, OH, CN, SH, $CH_3$ or $CF_3$;
$R^c$ and $R^d$ are each independently selected from the group consisting of halogen, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)$ $_{0-1}$—N(H)(R$^{1a}$), —(X$^1$)$_{0-1}$—N(R$^{1b}$)(R$^{1a}$), —(X$^1$)$_{0-1}$—CF$_3$, C$_1$-C$_6$ alkyl, C$_1$-C$_6$ haloalkyl, C$_1$-C$_6$ heteroalkyl, C$_1$-C$_6$ alkoxy, C$_1$-C$_6$ alkylthio, oxo, —(X$^1$)$_{0-1}$—C$_1$-C$_6$ alkyl, —(X$^1$)$_{0-1}$—C$_3$-C$_{10}$ cycloalkyl, —O—C$_3$-C$_{10}$ cycloalkyl, —(X$^1$)$_{0-1}$-3-11 membered heterocyclyl (e.g., a 4-7 membered heterocycloalkyl or a 5-6 membered heteroaryl), —(X$^1$)$_{0-1}$—C$_6$-C$_{10}$ aryl, —C(=O)(X$^1$)$_1$—C$_3$-C$_{10}$ cycloalkyl, —C(=O)(X$^1$)$_1$-3-11 membered heterocyclyl (e.g., a 4-7 membered heterocycloalkyl or a 5-6 membered heteroaryl), —(X$^1$)$_{0-1}$—C(=Y$^1$)N(H)(R$^{1a}$), —(X$^1$)$_{0-1}$—C(=Y$^1$)NH$_2$, —(X$^1$)$_{0-1}$—C(=Y$^1$)N(R$^{1a}$)(R$^{1b}$), —(X$^1$)$_{0-1}$—C(=Y$^1$)OR$^{1a}$, —(X$^1$)$_{0-1}$—C(=Y$^1$)OH, —(X$^1$)$_{0-1}$—N(H)C(=Y$^1$)(R$^{1a}$), —(X$^1$)$_{0-1}$—N(R$^{1b}$)C(=Y$^1$)(R$^{1a}$), —(X$^1$)$_{0-1}$—N(R$^{1b}$)(=Y$^1$)(H), —(X$^1$)$_{0-1}$—N(H)C(=Y$^1$)OR$^{1a}$, —(X$^1$)$_{0-1}$—N(R$^{1b}$)C(=Y$^1$)OR$^{1a}$, —(X$^1$)$_{0-1}$—S(O)$_{1-2}$R$^{1a}$, —(X$^1$)$_{0-1}$—N(H)S(O)$_{1-2}$R$^{1a}$, —(X$^1$)$_{0-1}$—N(R$^{1b}$)S(O)$_{1-2}$R$^{1a}$, —(X$^1$)$_{0-1}$—S(O)$_{0-1}$N(H)(R$^{1a}$), —(X$^1$)$_{0-1}$—S(O)$_{0-1}$N(R$^{1b}$)(R$^{1a}$), —(X$^1$)$_{0-1}$—S(O)$_{0-1}$NH$_2$, —(X$^1$)$_{0-1}$—S(=O)(=NR$^{1b}$)R$^{1a}$, —(X$^1$)$_{0-1}$—C(=Y$^1$)R$^{1a}$, —(X$^1$)$_{0-1}$—C(=Y$^1$)H, —(X$^1$)$_{0-1}$—C(=NOH)R$^{1a}$, —(X$^1$)$_{0-1}$—C(=NOR$^{1b}$)R$^{1a}$, —(X$^1$)$_{0-1}$—NHC(=Y$^1$)N(H)(R$^{1a}$), —(X$^1$)$_{0-1}$—NHC(=Y$^1$)NH$_2$, —(X$^1$)$_{0-1}$—NHC(=Y$^1$)N(R$^{1b}$)(R$^{1a}$), —(X$^1$)$_{0-1}$—N(R$^{1a}$)C(=Y$^1$)N(H)(R$^{1a}$), —(X$^1$)$_{0-1}$—N(R$^{1a}$)C(=Y$^1$)N(R$^{1a}$)(R$^{1b}$), —(X$^1$)$_{0-1}$—N(R$^{1a}$)C(=Y$^1$)NH$_2$, —(X$^1$)$_{0-1}$—OC(=Y$^1$)R$^{1a}$, —(X$^1$)$_{0-1}$OC(=Y$^1$)H, —(X$^1$)$_{0-1}$—OC(=Y$^1$)OR$^{1a}$, —(X$^1$)$_{0-1}$—OP(=Y$^1$)(OR$^{1a}$)(OR$^{1b}$), —(X$^1$)—SC(=Y$^1$)OR$^{1a}$ and —(X$^1$)—SC(=Y$^1$)N(R$^a$)(R$^{1b}$) wherein X$^1$ is selected from the group consisting of C$_1$-C$_6$ alkylene, C$_1$-C$_6$ heteroalkylene, C$_2$-C$_6$ alkenylene, C$_2$-C$_6$ alkynylene, C$_1$-C$_6$ alkyleneoxy, C$_3$-C$_7$ cycloalkylene, 3-11 membered heterocyclylene (e.g., a 4-7 membered heterocycloalkylene or a 5-6 membered heteroarylene) and phenylene; R$^{1a}$ and R$^{1b}$ are each independently selected from the group consisting of C$_1$-C$_6$ alkyl, C$_1$-C$_6$ haloalkyl, C$_1$-C$_6$ heteroalkyl, C$_3$-C$_7$ cycloalkyl, (C$_3$-C$_7$ cycloalkylene) C$_1$-C$_6$ alkyl, 3-11 membered heterocyclyl (e.g., a 4-7 membered heterocycloalkyl or a 5-6 membered heteroaryl), (3-11 membered heterocyclylene (e.g., a 4-7 membered heterocycloalkylene or a 5-6 membered heteroarylene))C$_1$-C$_6$ alkyl, C$_6$ aryl, and (C$_6$-C$_{10}$ arylene)C$_1$-C$_6$ alkyl, or R$^{1a}$ and R$^{1b}$ when attached to the same nitrogen atom are optionally combined to form a 3-11 membered heterocyclyl (e.g., a 4-7 membered heterocycloalkyl or a 5-6 membered heteroaryl) comprising 0-3 additional heteroatoms selected from N, O and S; Y$^1$ is O, NR$^{1c}$ or S wherein R$^{1c}$ is H or C$_1$-C$_6$ alkyl; wherein any portion of an R$^c$ or R$^d$ substituent, including R$^{1a}$, R$^{1b}$ and R$^{1c}$, at each occurrence is each independently further substituted by from 0 to 4 R$^f$ substituents selected from the group consisting of halogen, CN, NO$_2$, SF$_5$, OH, NH$_2$, —N(C$_1$-C$_6$ alkyl)$_2$, —NH(C$_1$-C$_6$ alkyl), oxo, C$_1$-C$_6$ alkyl, —(C$_2$-C$_6$ alkynylene)-(3-11 membered heterocyclyl (e.g., a 4-7 membered heterocycloalkyl or a 5-6 membered heteroaryl), wherein the heterocyclyl is optionally substituted by R$^e$), C$_1$-C$_6$ hydroxyalkyl, C$_1$-C$_6$ heteroalkyl, C$_1$-C$_6$ alkoxy, C$_1$-C$_6$ alkylthio, C$_3$-C$_7$ cycloalkyl, 3-11 membered heterocyclyl (e.g., a 4-7 membered heterocycloalkyl or a 5-6 membered heteroaryl), —C(=O)N(H)(C$_1$-C$_6$ alkyl), —C(=O)N(C$_1$-C$_6$ alkyl)$_2$, —C(=O)NH$_2$, —C(=O)OC$_1$-C$_6$ alkyl, —C(=O)OH, —N(H)C(=O)(C$_1$-C$_6$ alkyl), —N(C$_1$-C$_6$ alkyl)C(=O)(C$_1$-C$_6$ alkyl), —N(H)C(=O) OC$_1$-C$_6$ alkyl, —N(C$_1$-C$_6$ alkyl)C(=O)OC$_1$-C$_6$ (halo)alkyl, —S(O)$_{1-2}$C$_1$-C$_6$ alkyl, —N(H)S(O)$_{1-2}$C$_1$-C$_6$ alkyl, —N(C$_1$-C$_6$ alkyl)S(O)$_{1-2}$C$_1$-C$_6$ alkyl, —S(O)$_{0-1}$N(H)(C$_1$-C$_6$ alkyl), —S(O)$_{0-1}$N(C$_1$-C$_6$ alkyl)$_2$, —S(O)$_{0-1}$NH$_2$, —C(=O)C$_1$-C$_6$ alkyl, —C(=O)C$_3$-C$_7$ cycloalkyl, —C(=NOH)C$_1$-C$_6$ alkyl, —C(=NOC$_1$-C$_6$ alkyl)C$_1$-C$_6$ alkyl, —NHC(=O)N(H)(C$_1$-C$_6$ alkyl), —NHC(=O)N(C$_1$-C$_6$ alkyl)$_2$, —NHC(=O)NH$_2$, —N(C$_1$-C$_6$ alkyl)C(=O)N(H)(C$_1$-C$_6$ alkyl), —N(C$_1$-C$_6$ alkyl)C(=O)NH$_2$, —OC(=O)C$_1$-C$_6$ alkyl, —OC(=O)OC$_1$-C$_6$ alkyl, —OP(=O)(OC$_1$-C$_6$ alkyl)$_2$, —SC(=O)OC$_1$-C$_6$ alkyl and —SC(=O)N(C$_1$-C$_6$ alkyl)$_2$, wherein any alkyl portion of R$^f$ is optionally substituted with halogen;

R$^e$ is selected from the group consisting of halogen, OH, C$_1$-C$_6$ alkyl and oxo; and R$^g$ is selected from the group consisting of C$_1$-C$_6$ alkyl and C$_3$-C$_6$ cycloalkyl.

In some embodiments, a compound of Formula (0) is further defined as a compound of Formula (0a):

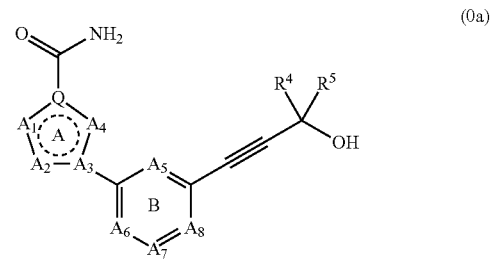

(0a)

or a stereoisomer or salt thereof, wherein:
ring A is a monocycle or a fused bicycle;
Q is N or C, wherein when Q is N, then the bond between A$_1$ and Q is not a double bond and the bond between Q and A$_4$ is not a double bond;
A$_1$ is NR$^1$, S or CR$^1$;
A$_2$ is NR$^2$ or CR$^2$;
A$_3$ is N or C;
A$_4$ is N; and
one, two or three of A$_1$-A$_4$ are N, wherein:
R$^1$ is selected from the group consisting of H, halogen, NR$^a$R$^b$, C$_1$-C$_3$ alkyl, C$_3$-C$_7$ cycloalkyl, C$_1$-C$_3$ alkoxy and 3-11 membered heterocyclyl (e.g., a 4-7 membered heterocycloalkyl or a 5-6 membered heteroaryl), wherein R$^1$ is optionally substituted by F, OH, CN, SH, CH$_3$ or CF$_3$;
R$^2$ is selected from the group consisting of H, NR$^a$R$^b$, C$_1$-C$_6$ alkyl, C$_3$-C$_7$ cycloalkyl, C$_1$-C$_6$ alkoxy, phenyl and 3-11 membered heterocyclyl (e.g., a 4-7 membered heterocycloalkyl or a 5-6 membered heteroaryl), wherein R$^2$ is optionally substituted by R$^c$; or
R$^1$ and R$^2$ taken together form a cyclic group selected from the group consisting of C$_3$-C$_7$ cycloalkyl, phenyl and 3-11 membered heterocyclyl (e.g., a 4-7 membered heterocycloalkyl or a 5-6 membered heteroaryl), wherein the cyclic group is optionally substituted by R$^d$;
R$^4$ is selected from the group consisting of H, C$_1$-C$_6$ alkyl, CH$_2$F and CH$_2$OH;
R$^5$ is 3-11 membered heterocyclyl (e.g., a 4-7 membered heterocycloalkyl or a 5-6 membered heteroaryl) optionally substituted by R$^e$ or —C(=O)N(C$_1$-C$_6$ alkyl)$_2$; or
R$^4$ and R$^5$ together form a C$_3$-C$_{11}$ cycloalkyl optionally substituted by R$^e$ or a 3-11 membered heterocyclyl (e.g., a 4-7 membered heterocycloalkyl or a 5-6 membered heteroaryl) optionally substituted by R$^e$;
one of A$_5$-A$_8$ is N and the remaining are CR$^6$ or all are CR$^6$;
R$^6$, independently at each occurrence, is selected from the group consisting of H, F, Cl, NH$_2$, NHCH$_3$, N(CH$_3$)$_2$, OH, OCH$_3$, OCHF$_2$, OCH$_2$F, OCF$_3$, SH, SCH$_3$, SCHF$_2$, SCH$_2$F, CN, CH$_3$, CHF$_2$, CH$_2$F, CH$_2$OH, CF$_3$, NO$_2$ and N$_3$;

R$^a$ is selected from the group consisting of H and C$_1$-C$_6$ alkyl optionally substituted by C$_1$-C$_3$ alkoxy, F, OH, CN, SH, CH$_3$ or CF$_3$;

R$^b$ is selected from the group consisting of H, C$_1$-C$_6$ alkyl, C$_1$-C$_6$ alkoxy, C$_3$-C$_6$ cycloalkyl, C(O)R$^g$, phenyl and 3-11 membered heterocyclyl (e.g., a 4-7 membered heterocycloalkyl or a 5-6 membered heteroaryl) wherein R$^b$ may be optionally substituted by C$_1$-C$_3$ alkoxy, F, OH, CN, SH, CH$_3$ or CF$_3$;

R$^c$ and R$^d$ are each independently selected from the group consisting of halogen, —(X$^1$)$_{0-1}$—CN, —(X$^1$)$_{0-1}$—NO$_2$, —(X$^1$)$_{0-1}$—SF$_5$, —(X$^1$)$_{0-1}$—OH, —(X$^1$)$_{0-1}$—NH$_2$, —(X$^1$)$_{0-1}$—N(H)(R$^{1a}$), —(X$^1$)$_{0-1}$—N(R$^{1b}$)(R$^{1a}$), —(X$^1$)$_{0-1}$—CF$_3$, C$_1$-C$_6$ alkyl, C$_1$-C$_6$ haloalkyl, C$_1$-C$_6$ heteroalkyl, C$_1$-C$_6$ alkoxy, C$_1$-C$_6$ alkylthio, oxo, —(X$^1$)$_{0-1}$—C$_1$-C$_6$ alkyl, —(X$^1$)$_{0-1}$—C$_3$-C$_{10}$ cycloalkyl, —O—C$_3$-C$_{10}$ cycloalkyl, —(X$^1$)$_{0-1}$-3-11 membered heterocyclyl (e.g., a 4-7 membered heterocycloalkyl or a 5-6 membered heteroaryl), —(X$^1$)$_{0-1}$—C$_6$-C$_{10}$ aryl, —C(=O)(X$^1$)$_1$—C$_3$-C$_{10}$ cycloalkyl, —C(=O)(X$^1$)$_1$-3-11 membered heterocyclyl (e.g., a 4-7 membered heterocycloalkyl or a 5-6 membered heteroaryl), —(X$^1$)$_{0-1}$—C(=Y$^1$)N(H)(R$^{1a}$), —(X$^1$)$_{0-1}$—C(=Y$^1$)NH$_2$, —(X$^1$)$_{0-1}$—C(=Y$^1$)N(R$^{1a}$)(R$^{1b}$), —(X$^1$)$_{0-1}$—C(=Y$^1$)OR$^{1a}$, —(X$^1$)$_{0-1}$—C(=Y$^1$)OH, —(X$^1$)$_{0-1}$—N(H)C(=Y$^1$)(R$^{1a}$), —(X$^1$)$_{0-1}$—N(R$^{1b}$)C(=Y$^1$)(R$^{1a}$), —(X$^1$)$_{0-1}$—N(R$^{1b}$)C(=Y$^1$)(H), —(X$^1$)$_{0-1}$—N(H)C(=Y$^1$)OR$^{1a}$, —(X$^1$)$_{0-1}$—N(R$^{1b}$)C(=Y$^1$)OR$^{1a}$, —(X$^1$)$_{0-1}$—S(O)$_{1-2}$R$^{1a}$, —(X$^1$)$_{0-1}$—N(H)S(O)$_{1-2}$R$^{1a}$, —(X$^1$)$_{0-1}$—N(R$^{1b}$)S(O)$_{1-2}$R$^{1a}$, —(X$^1$)$_{0-1}$—S(O)$_{0-1}$N(H)(R$^{1a}$), —(X$^1$)$_{0-1}$—S(O)$_{0-1}$N(R$^{1b}$)(R$^{1a}$), —(X$^1$)$_{0-1}$—S(O)$_{0-1}$NH$_2$, —(X$^1$)$_{0-1}$—S(=O)(=NR$^{1b}$)R$^{1a}$, —(X$^1$)$_{0-1}$—C(=Y$^1$)R$^{1a}$, —(X$^1$)$_{0-1}$—C(=Y$^1$)H, —(X$^1$)$_{0-1}$—C(=NOH)R$^{1a}$, —(X$^1$)$_{0-1}$—C(=NOR$^{1b}$)R$^{1a}$, —(X$^1$)$_{0-1}$—NHC(=Y$^1$)N(H)(R$^{1a}$), —(X$^1$)$_{0-1}$—NHC(=Y$^1$)NH$_2$, —(X$^1$)$_{0-1}$—NHC(=Y$^1$)N(R$^{1b}$)(R$^{1a}$), —(X$^1$)$_{0-1}$—N(R$^{1a}$)C(=Y$^1$)N(H)(R$^{1a}$), —(X$^1$)$_{0-1}$—N(R$^{1a}$)C(=Y$^1$)N(R$^{1a}$)(R$^{1b}$), —(X$^1$)$_{0-1}$—N(R$^{1a}$)C(=Y$^1$)NH$_2$, —(X$^1$)$_{0-1}$—OC(=Y$^1$)R$^{1a}$, —(X$^1$)$_{0-1}$—OC(=Y$^1$)H, —(X$^1$)$_{0-1}$—OC(=Y$^1$)OR$^{1a}$, —(X$^1$)$_{0-1}$—OP(=Y$^1$)(OR$^{1a}$)(OR$^{1b}$), —(X$^1$)—SC(=Y$^1$)OR$^{1a}$ and —(X$^1$)—SC(=Y$^1$)N(R$^{1a}$)(R$^{1b}$) wherein X$^1$ is selected from the group consisting of C$_1$-C$_6$ alkylene, C$_1$-C$_6$ heteroalkylene, C$_2$-C$_6$ alkenylene, C$_2$-C$_6$ alkynylene, C$_1$-C$_6$ alkyleneoxy, C$_3$-C$_7$ cycloalkylene, 3-11 membered heterocyclylene (e.g., a 4-7 membered heterocycloalkylene or a 5-6 membered heteroarylene) and phenylene; R$^{1a}$ and R$^{1b}$ are each independently selected from the group consisting of C$_1$-C$_6$ alkyl, C$_1$-C$_6$ haloalkyl, C$_1$-C$_6$ heteroalkyl, C$_3$-C$_7$ cycloalkyl, (C$_3$-C$_7$ cycloalkylene)C$_1$-C$_6$ alkyl, 3-11 membered heterocyclyl (e.g., a 4-7 membered heterocycloalkyl or a 5-6 membered heteroaryl), (3-11 membered heterocyclylene (e.g., a 4-7 membered heterocycloalkylene or a 5-6 membered heteroarylene))C$_1$-C$_6$ alkyl, C$_6$ aryl, and (C$_6$-C$_{10}$ arylene)C$_1$-C$_6$ alkyl, or R$^{1a}$ and R$^{1b}$ when attached to the same nitrogen atom are optionally combined to form a 3-11 membered heterocyclyl (e.g., a 4-7 membered heterocycloalkyl or a 5-6 membered heteroaryl) comprising 0-3 additional heteroatoms selected from N, O and S; Y$^1$ is O, NR$^{1c}$ or S wherein R$^{1c}$ is H or C$_1$-C$_6$ alkyl; wherein any portion of an R$^c$ or R$^d$ substituent, including R$^{1a}$, R$^{1b}$ and R$^{1c}$, at each occurrence is each independently further substituted by from 0 to 4 R$^f$ substituents selected from the group consisting of halogen, CN, NO$_2$, SF$_5$, OH, NH$_2$, —N(C$_1$-C$_6$ alkyl)$_2$, —NH(C$_1$-C$_6$ alkyl), oxo, C$_1$-C$_6$ alkyl, —(C$_2$-C$_6$ alkynylene)-(3-11 membered heterocyclyl (e.g., a 4-7 membered heterocycloalkyl or a 5-6 membered heteroaryl), wherein the heterocyclyl is optionally substituted by R$^e$), C$_1$-C$_6$ hydroxyalkyl, C$_1$-C$_6$ heteroalkyl, C$_1$-C$_6$ alkoxy, C$_1$-C$_6$ alkylthio, C$_3$-C$_7$ cycloalkyl, 3-11 membered heterocyclyl (e.g., a 4-7 membered heterocycloalkyl or a 5-6 membered heteroaryl), —C(=O)N(H)(C$_1$-C$_6$ alkyl), —C(=O)N(C$_1$-C$_6$ alkyl)$_2$, —C(=O)NH$_2$, —C(=O)OC$_1$-C$_6$ alkyl, —C(=O)OH, —N(H)C(=O)(C$_1$-C$_6$ alkyl), —N(C$_1$-C$_6$ alkyl)C(=O)(C$_1$-C$_6$ alkyl), —N(H)C(=O)OC$_1$-C$_6$ alkyl, —N(C$_1$-C$_6$ alkyl)C(=O)OC$_1$-C$_6$ (halo)alkyl, —S(O)$_{1-2}$C$_1$-C$_6$ alkyl, —N(H)S(O)$_{1-2}$C$_1$-C$_6$ alkyl, —N(C$_1$-C$_6$ alkyl)S(O)$_{1-2}$C$_1$-C$_6$ alkyl, —S(O)$_{0-1}$N(H)(C$_1$-C$_6$ alkyl), —S(O)$_{0-1}$N(C$_1$-C$_6$ alkyl)$_2$, —S(O)$_{0-1}$NH$_2$, —C(=O)C$_1$-C$_6$ alkyl, —C(=O)C$_3$-C$_7$ cycloalkyl, —C(=NOH)C$_1$-C$_6$ alkyl, —C(=NOC$_1$-C$_6$ alkyl)C$_1$-C$_6$ alkyl, —NHC(=O)N(H)(C$_1$-C$_6$ alkyl), —NHC(=O)N(C$_1$-C$_6$ alkyl)$_2$, —NHC(=O)NH$_2$, —N(C$_1$-C$_6$ alkyl)C(=O)N(H)(C$_1$-C$_6$ alkyl), —N(C$_1$-C$_6$ alkyl)C(=O)NH$_2$, —OC(=O)C$_1$-C$_6$ alkyl, —OC(=O)OC$_1$-C$_6$ alkyl, —OP(=O)(OC$_1$-C$_6$ alkyl)$_2$, —SC(=O)OC$_1$-C$_6$ alkyl and —SC(=O)N(C$_1$-C$_6$ alkyl)$_2$, wherein any alkyl portion of R$^f$ is optionally substituted with halogen;

R$^e$ is selected from the group consisting of halogen, OH, C$_1$-C$_6$ alkyl and oxo; and R$^g$ is selected from the group consisting of C$_1$-C$_6$ alkyl and C$_3$-C$_6$ cycloalkyl.

In some embodiments, a compound of Formula (0) is further defined as a compound of Formula (0-0):

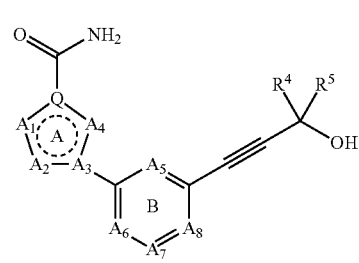

(0-0)

or a stereoisomer or salt thereof, wherein:
ring A is a monocycle or a fused bicycle;
Q is C;
A$_1$ is NR$^1$, S or CR$^1$;
A$_2$ is NR$^2$ or CR$^2$;
A$_3$ is N or C;
A$_4$ is N; and
one, two or three of A$_1$-A$_4$ are N, wherein:
R$^1$ is selected from the group consisting of H, halogen, NR$^a$R$^b$, C$_1$-C$_3$ alkyl, C$_3$-C$_7$ cycloalkyl, C$_1$-C$_3$ alkoxy and 3-11 membered heterocyclyl (e.g., a 4-7 membered heterocycloalkyl or a 5-6 membered heteroaryl), wherein R$^1$ is optionally substituted by F, OH, CN, SH, CH$_3$ or CF$_3$;
R$^2$ is selected from the group consisting of H, NR$^a$R$^b$, C$_1$-C$_6$ alkyl, C$_3$-C$_7$ cycloalkyl, C$_1$-C$_6$ alkoxy, phenyl and 3-11 membered heterocyclyl (e.g., a 4-7 membered heterocycloalkyl or a 5-6 membered heteroaryl), wherein R$^2$ is optionally substituted by R$^c$; or
R$^1$ and R$^2$ taken together form a cyclic group selected from the group consisting of C$_3$-C$_7$ cycloalkyl, phenyl and 3-11 membered heterocyclyl (e.g., a 4-7 membered heterocycloalkyl or a 5-6 membered heteroaryl), wherein the cyclic group is optionally substituted by R$^d$;
R$^4$ is selected from the group consisting of H, C$_1$-C$_6$ alkyl, CH$_2$F and CH$_2$OH;

R[5] is 3-11 membered heterocyclyl (e.g., a 4-7 membered heterocycloalkyl or a 5-6 membered heteroaryl) optionally substituted by R[e]; or R[4] and R[5] together form a $C_3$-$C_{11}$ cycloalkyl optionally substituted by R[e] or a 3-11 membered heterocyclyl (e.g., a 4-7 membered heterocycloalkyl or a 5-6 membered heteroaryl) optionally substituted by R[e];

one of $A_5$-$A_8$ is N and the remaining are CR[6] or all are CR[6];

R[6], independently at each occurrence, is selected from the group consisting of H, F, Cl, $NH_2$, $NHCH_3$, $N(CH_3)_2$, OH, $OCH_3$, $OCHF_2$, $OCH_2F$, $OCF_3$, SH, $SCH_3$, $SCHF_2$, $SCH_2F$, CN, $CH_3$, $CHF_2$, $CH_2F$, $CH_2OH$, $CF_3$, $NO_2$ and $N_3$;

R[a] is selected from the group consisting of H and $C_1$-$C_6$ alkyl optionally substituted by $C_1$-$C_3$ alkoxy, F, OH, CN, SH, $CH_3$ or $CF_3$;

R[b] is selected from the group consisting of H, $C_1$-$C_6$ alkyl, $C_1$-$C_6$ alkoxy, $C_3$-$C_6$ cycloalkyl, C(O)R[g], phenyl and 3-11 membered heterocyclyl (e.g., a 4-7 membered heterocycloalkyl or a 5-6 membered heteroaryl) wherein R[b] may be optionally substituted by $C_1$-$C_3$ alkoxy, F, OH, CN, SH, $CH_3$ or $CF_3$;

R[c] and R[d] are each independently selected from the group consisting of halogen, $-(X^1)_{0-1}$—CN, $-(X^1)_{0-1}$—$NO_2$, $-(X^1)_{0-1}$—$SF_5$, $-(X^1)_{0-1}$—OH, $-(X^1)_{0-1}$—$NH_2$, $-(X^1)_{0-1}$—N(H)(R[1a]), $-(X^1)_{0-1}$—N(R[1b])(R[1a]), $-(X^1)_{0-1}$—$CF_3$, $C_1$-$C_6$ alkyl, $C_1$-$C_6$ haloalkyl, $C_1$-$C_6$ heteroalkyl, $C_1$-$C_6$ alkoxy, $C_1$-$C_6$ alkylthio, oxo, $-(X^1)_{0-1}$—$C_1$-$C_6$ alkyl, $-(X^1)_{0-1}$—$C_3$-$C_{10}$ cycloalkyl, $-(X^1)_{0-1}$-3-11 membered heterocyclyl (e.g., a 4-7 membered heterocycloalkyl or a 5-6 membered heteroaryl), $-(X^1)_{0-1}$—$C_6$-$C_{10}$ aryl, —C(=O)$(X^1)_1$—$C_3$-$C_{10}$ cycloalkyl, —C(=O)$(X^1)_1$-3-11 membered heterocyclyl, $-(X^1)_{0-1}$—C(=Y[1])N(H)(R[1a]), $-(X^1)_{0-1}$—C(=Y[1])$NH_2$, $-(X^1)_{0-1}$—C(=Y[1])N(R[1a])(R[1b]), $-(X^1)_{0-1}$—C(=Y[1])OR[1a], $-(X^1)_{0-1}$—C(=Y[1])OH, $-(X^1)_{0-1}$—N(H)C(=Y[1])(R[1a]), $-(X^1)_{0-1}$—N(R[1b])C(=Y[1])(R[1a]), $-(X^1)_{0-1}$—N(R[1b])(=Y[1])(H), $-(X^1)_{0-1}$—N(H)C(=Y[1])OR[1a], $-(X^1)_{0-1}$—N(R[1b])(=Y[1])OR[1a], $-(X^1)_{0-1}$—S(O)$_{1-2}$R[1a], $-(X^1)_{0-1}$—N(H)S(O)$_{1-2}$R[1a], $-(X^1)_{0-1}$—N(R[1b])S(O)$_{1-2}$R[1a], $-(X^1)_{0-1}$—S(O)$_{0-1}$N(H)(R[1a]), $-(X^1)_{0-1}$—S(O)$_{0-1}$N(R[1b])(R[1a]), $-(X^1)_{0-1}$—S(O)$_{0-1}$$NH_2$, $-(X^1)_{0-1}$—S(=O)(=NR[1b])R[1a], $-(X^1)_{0-1}$—C(=Y[1])R[1a], $-(X^1)_{0-1}$—C(=Y[1])H, $-(X^1)_{0-1}$—C(=NOH)R[1a], $-(X^1)_{0-1}$—C(=NOR[1b])R[1a], $-(X^1)_{0-1}$NHC(=Y[1])N(H)(R[1a]), $-(X^1)_{0-1}$—NHC(=Y[1])$NH_2$, $-(X^1)_{0-1}$—NHC(=Y[1])N(R[1b])(R[1a]), $-(X^1)_{0-1}$—N(R[1a])C(=Y[1])N(H)(R[1a]), $-(X^1)_{0-1}$—N(R[1a])C(=Y[1])N(R[1a])(R[1b]), $-(X^1)_{0-1}$—N(R[1a])C(=Y[1])$NH_2$, $-(X^1)_{0-1}$—OC(=Y[1])R[1a], $-(X^1)_{0-1}$—OC(=Y[1])H, $-(X^1)_{0-1}$—OC(=Y[1])OR[1a], $-(X^1)_{0-1}$—OP(=Y[1])(OR[1a])(OR[1b]), $-(X^1)$—SC(=Y[1])OR[1a] and $-(X^1)$—SC(=Y[1])N(R[1a])(R[1b]) wherein $X^1$ is selected from the group consisting of $C_1$-$C_6$ alkylene, $C_1$-$C_6$ heteroalkylene, $C_2$-$C_6$ alkenylene, $C_2$-$C_6$ alkynylene, $C_1$-$C_6$ alkyleneoxy, $C_3$-$C_7$ cycloalkylene, 3-11 membered heterocyclylene (e.g., a 4-7 membered heterocycloalkylene or a 5-6 membered heteroarylene) and phenylene; R[1a] and R[1b] are each independently selected from the group consisting of $C_1$-$C_6$ alkyl, $C_1$-$C_6$ haloalkyl, $C_1$-$C_6$ heteroalkyl, $C_3$-$C_7$ cycloalkyl, ($C_3$-$C_7$ cycloalkylene)$C_1$-$C_6$ alkyl, 3-11 membered heterocyclyl (e.g., a 4-7 membered heterocycloalkyl or a 5-6 membered heteroaryl), (3-11 membered heterocyclylene (e.g., a 4-7 membered heterocycloalkylene or a 5-6 membered heteroarylene))$C_1$-$C_6$ alkyl, $C_6$ aryl, and ($C_6$-$C_{10}$ arylene)$C_1$-$C_6$ alkyl, or R[1a] and R[1b] when attached to the same nitrogen atom are optionally combined to form a 3-11 membered heterocyclyl (e.g., a 4-7 membered heterocycloalkyl or a 5-6 membered heteroaryl) comprising 0-3 additional heteroatoms selected from N, O and S; $Y^1$ is O, NR[1c] or S wherein R[1c] is H or $C_1$-$C_6$ alkyl; wherein any portion of an R[c] or R[d] substituent, including R[1a], R[1b] and R[1c], at each occurrence is each independently further substituted by from 0 to 4 R[f] substituents selected from the group consisting of halogen, CN, $NO_2$, $SF_5$, OH, $NH_2$, —N($C_1$-$C_6$ alkyl)$_2$, —NH($C_1$-$C_6$ alkyl), oxo, $C_1$-$C_6$ alkyl, —($C_2$-$C_6$ alkynylene)-(3-11 membered heterocyclyl (e.g., a 4-7 membered heterocycloalkyl or a 5-6 membered heteroaryl), wherein the heterocyclyl is optionally substituted by R[e]), $C_1$-$C_6$ hydroxyalkyl, $C_1$-$C_6$ heteroalkyl, $C_1$-$C_6$ alkoxy, $C_1$-$C_6$ alkylthio, $C_3$-$C_7$ cycloalkyl, 3-11 membered heterocyclyl (e.g., a 4-7 membered heterocycloalkyl or a 5-6 membered heteroaryl), —C(=O)N(H)($C_1$-$C_6$ alkyl), —C(=O)N($C_1$-$C_6$ alkyl)$_2$, —C(=O)$NH_2$, —C(=O)O$C_1$-$C_6$ alkyl, —C(=O)OH, —N(H)C(=O)($C_1$-$C_6$ alkyl), —N($C_1$-$C_6$ alkyl)C(=O)($C_1$-$C_6$ alkyl), —N(H)C(=O)O$C_1$-$C_6$ alkyl, —N($C_1$-$C_6$ alkyl)C(=O)O$C_1$-$C_6$ (halo)alkyl, —S(O)$_{1-2}$$C_1$-$C_6$ alkyl, —N(H)S(O)$_{1-2}$$C_1$-$C_6$ alkyl, —N($C_1$-$C_6$ alkyl)S(O)$_{1-2}$$C_1$-$C_6$ alkyl, —S(O)$_{0-1}$N(H)($C_1$-$C_6$ alkyl), —S(O)$_{0-1}$N($C_1$-$C_6$ alkyl)$_2$, —S(O)$_{0-1}$$NH_2$, —C(=O)$C_1$-$C_6$ alkyl, —C(=O)$C_3$-$C_7$ cycloalkyl, —C(=NOH)$C_1$-$C_6$ alkyl, —C(=NO$C_1$-$C_6$ alkyl)$C_1$-$C_6$ alkyl, —NHC(=O)N(H)($C_1$-$C_6$ alkyl), —NHC(=O)N($C_1$-$C_6$ alkyl)$_2$, —NHC(=O)$NH_2$, —N($C_1$-$C_6$ alkyl)C(=O)N(H)($C_1$-$C_6$ alkyl), —N($C_1$-$C_6$ alkyl)C(=O)$NH_2$, —OC(=O)$C_1$-$C_6$ alkyl, —OC(=O)O$C_1$-$C_6$ alkyl, —OP(=O)(O$C_1$-$C_6$ alkyl)$_2$, —SC(=O)O$C_1$-$C_6$ alkyl and —SC(=O)N($C_1$-$C_6$ alkyl)$_2$, wherein any alkyl portion of R[f] is optionally substituted with halogen;

R[e] is selected from the group consisting of halogen, OH, $C_1$-$C_6$ alkyl and oxo; and R[g] is selected from the group consisting of $C_1$-$C_6$ alkyl and $C_3$-$C_6$ cycloalkyl.

In some embodiments, a compound of Formula (0) is further defined as a compound of Formula (I):

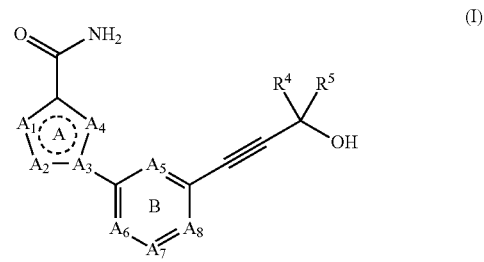

(I)

or a stereoisomer or salt thereof, wherein:
ring A is a monocycle or a fused bicycle;
$A_1$ is N, S or CR[1];
$A_2$ is N or CR[2];
$A_3$ is N or C;
$A_4$ is N; and
one, two or three of $A_1$-$A_4$ are N, wherein:
R[1] is selected from the group consisting of H, halogen, NR[a]R[b], $C_1$-$C_3$ alkyl, $C_3$-$C_7$ cycloalkyl, $C_1$-$C_3$ alkoxy and 3-11 membered heterocyclyl (e.g., a 4-7 membered heterocycloalkyl or a 5-6 membered heteroaryl), wherein R[1] is optionally substituted by F, OH, CN, SH, $CH_3$ or $CF_3$;
R[2] is selected from the group consisting of H, NR[a]R[b], $C_1$-$C_6$ alkyl, $C_3$-$C_7$ cycloalkyl, $C_1$-$C_6$ alkoxy, phenyl and 3-11 membered heterocyclyl (e.g., a 4-7 membered heterocycloalkyl or a 5-6 membered heteroaryl), wherein R[2] is optionally substituted by R[c]; or R¹ and R² taken together form a cyclic group selected from the group consisting of $C_3$-$C_7$ cycloalkyl, phenyl and 3-11 membered heterocyclyl (e.g., a 4-7 membered heterocycloalkyl or a 5-6 membered heteroaryl), wherein the cyclic group is optionally substituted by $R^d$;

$R^4$ is selected from the group consisting of $C_1$-$C_6$ alkyl, $CH_2F$ and $CH_2OH$;

$R^5$ is 3-11 membered heterocyclyl (e.g., a 4-7 membered heterocycloalkyl or a 5-6 membered heteroaryl) optionally substituted by $R^e$; or $R^4$ and $R^5$ together form a $C_3$-$C_{11}$ cycloalkyl optionally substituted by $R^e$ or a 3-11 membered heterocyclyl (e.g., a 4-7 membered heterocycloalkyl or a 5-6 membered heteroaryl) optionally substituted by $R^e$;

one of $A_5$-$A_8$ is N and the remaining are $CR^6$ or all are $CR^6$;

$R^6$, independently at each occurrence, is selected from the group consisting of H, F, Cl, $NH_2$, $NHCH_3$, $N(CH_3)_2$, OH, $OCH_3$, $OCHF_2$, $OCH_2F$, $OCF_3$, SH, $SCH_3$, $SCHF_2$, $SCH_2F$, CN, $CH_3$, $CHF_2$, $CH_2F$, $CH_2OH$, $CF_3$, $NO_2$ and $N_3$;

$R^a$ is selected from the group consisting of H and $C_1$-$C_6$ alkyl optionally substituted by $C_1$-$C_3$ alkoxy, F, OH, CN, SH, $CH_3$ or $CF_3$;

$R^b$ is selected from the group consisting of H, $C_1$-$C_6$ alkyl, $C_1$-$C_6$ alkoxy, $C_3$-$C_6$ cycloalkyl, $C(O)R^g$, phenyl and 3-11 membered heterocyclyl (e.g., a 4-7 membered heterocycloalkyl or a 5-6 membered heteroaryl) wherein $R^b$ may be optionally substituted by $C_1$-$C_3$ alkoxy, F, OH, CN, SH, $CH_3$ or $CF_3$;

$R^c$ and $R^d$ are each independently selected from the group consisting of halogen, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—N(H)($R^{1a}$), —$(X^1)_{0-1}$—N($R^{1b}$)($R^{1a}$), —$(X^1)_{0-1}$—$CF_3$, $C_1$-$C_6$ alkyl, $C_1$-$C_6$ haloalkyl, $C_1$-$C_6$ heteroalkyl, $C_1$-$C_6$ alkoxy, $C_1$-$C_6$ alkylthio, oxo, —$(X^1)_{0-1}$—$C_1$-$C_6$ alkyl, —$(X^1)_{0-1}$—$C_3$-$C_{10}$ cycloalkyl, —$(X^1)_{0-1}$-3-11 membered heterocyclyl (e.g., a 4-7 membered heterocycloalkyl or a 5-6 membered heteroaryl), —$(X^1)_{0-1}$—$C_6$-$C_{10}$ aryl, —C(=O)($X^1$)$_1$—$C_3$-$C_{10}$ cycloalkyl, —C(=O)($X^1$)$_1$-3-11 membered heterocyclyl, —$(X^1)_{0-1}$—C(=$Y^1$)N(H)($R^{1a}$), —$(X^1)_{0-1}$—C(=$Y^1$)$NH_2$, —$(X^1)_{0-1}$—C(=$Y^1$)N($R^{1a}$)($R^{1b}$), —$(X^1)_{0-1}$—C(=$Y^1$)$OR^{1a}$, —$(X^1)_{0-1}$—C(=$Y^1$)OH, —$(X^1)_{0-1}$—N(H)C(=$Y^1$)($R^{1a}$), —$(X^1)_{0-1}$—N($R^{1b}$)C(=$Y^1$)($R^{1a}$), —$(X^1)_{0-1}$—N($R^{1b}$)(=$Y^1$)(H), —$(X^1)_{0-1}$—N(H)C(=$Y^1$)$OR^{1a}$, —$(X^1)_{0-1}$—N($R^{1b}$)(=$Y^1$)$OR^{1a}$, —$(X^1)_{0-1}$—S(O)$_{1-2}R^{1a}$, —$(X^1)_{0-1}$—N(H)S(O)$_{1-2}R^{1a}$, —$(X^1)_{0-1}$—N($R^{1b}$)S(O)$_{1-2}R^{1a}$, —$(X^1)_{0-1}$—S(O)$_{0-1}$N(H)($R^{1a}$), —$(X^1)_{0-1}$—S(O)$_{0-1}$N($R^{1b}$)($R^{1a}$), —$(X^1)_{0-1}$—S(O)$_{0-1}NH_2$, —$(X^1)_{0-1}$—S(=O)(=$NR^{1b}$)$R^{1a}$, —$(X^1)_{0-1}$—C(=$Y^1$)$R^{1a}$, —$(X^1)_{0-1}$—C(=$Y^1$)H, —$(X^1)_{0-1}$—C(=NOH)$R^{1a}$, —$(X^1)_{0-1}$—C(=$NOR^{1b}$)$R^{1a}$, —$(X^1)_{0-1}$—NHC(=$Y^1$)N(H)($R^{1a}$), —$(X^1)_{0-1}$—NHC(=$Y^1$)$NH_2$, —$(X^1)_{0-1}$—NHC(=$Y^1$)N($R^{1b}$)($R^{1a}$), —$(X^1)_{0-1}$—N($R^{1a}$)C(=$Y^1$)N(H)($R^{1a}$), —$(X^1)_{0-1}$—N($R^{1a}$)C(=$Y^1$)N($R^{1a}$)($R^{1b}$), —$(X^1)_{0-1}$—N($R^{1a}$)C(=$Y^1$)$NH_2$, —$(X^1)_{0-1}$—OC(=$Y^1$)$R^{1a}$, —$(X^1)_{0-1}$—OC(=$Y^1$)H, —$(X^1)_{0-1}$—OC(=$Y^1$)$OR^{1a}$, —$(X^1)_{0-1}$—OP(=$Y^1$)($OR^{1a}$)($OR^{1b}$), —$(X^1)$—SC(=$Y^1$)$OR^{1a}$ and —$(X^1)$—SC(=$Y^1$)N($R^{1a}$)($R^{1b}$) wherein $X^1$ is selected from the group consisting of $C_1$-$C_6$ alkylene, $C_1$-$C_6$ heteroalkylene, $C_2$-$C_6$ alkenylene, $C_2$-$C_6$ alkynylene, $C_1$-$C_6$ alkyleneoxy, $C_3$-$C_7$ cycloalkylene, 3-11 membered heterocyclylene and phenylene; $R^{1a}$ and $R^{1b}$ are each independently selected from the group consisting of $C_1$-$C_6$ alkyl, $C_1$-$C_6$ haloalkyl, $C_1$-$C_6$ heteroalkyl, $C_3$-$C_7$ cycloalkyl, ($C_3$-$C_7$ cycloalkylene)$C_1$-$C_6$ alkyl, 3-11 membered heterocyclyl, (3-11 membered heterocyclylene)$C_1$-$C_6$ alkyl, $C_6$ aryl, and ($C_6$-$C_{10}$ arylene)$C_1$-$C_6$ alkyl, or $R^{1a}$ and $R^{1b}$ when attached to the same nitrogen atom are optionally combined to form a 3-11 membered heterocyclyl comprising 0-3 additional heteroatoms selected from N, O and S; $Y^1$ is O, $NR^{1c}$ or S wherein $R^{1c}$ is H or $C_1$-$C_6$ alkyl; wherein any portion of an $R^c$ or $R^d$ substituent, including $R^{1a}$, $R^{1b}$ and $R^{1c}$, at each occurrence is each independently further substituted by from 0 to 4 $R^f$ substituents selected from the group consisting of halogen, CN, $NO_2$, $SF_5$, OH, $NH_2$, —N($C_1$-$C_6$ alkyl)$_2$, —NH($C_1$-$C_6$ alkyl), oxo, $C_1$-$C_6$ alkyl, $C_1$-$C_6$ haloalkyl, $C_1$-$C_6$ hydroxyalkyl, $C_1$-$C_6$ heteroalkyl, $C_1$-$C_6$ alkoxy, $C_1$-$C_6$ alkylthio, $C_3$-$C_7$ cycloalkyl, 3-11 membered heterocyclyl, —C(=O)N(H)($C_1$-$C_6$ (halo)alkyl), —C(=O)N($C_1$-$C_6$ (halo)alkyl)$_2$, —C(=O)$NH_2$, —C(=O)$OC_1$-$C_6$ (halo)alkyl, —C(=O)OH, —N(H)C(=O)($C_1$-$C_6$ (halo)alkyl), —N($C_1$-$C_6$ (halo)alkyl)C(=O)($C_1$-$C_6$ (halo)alkyl), —N(H)C(=O)$OC_1$-$C_6$ (halo)alkyl, —N($C_1$-$C_6$ (halo)alkyl)C(=O)$OC_1$-$C_6$ (halo)alkyl, —S(O)$_{1-2}C_1$-$C_6$ (halo)alkyl, —N(H)S(O)$_{1-2}C_1$-$C_6$ (halo)alkyl, —N($C_1$-$C_6$ (halo)alkyl)S(O)$_{1-2}C_1$-$C_6$ (halo)alkyl, —S(O)$_{0-1}$N(H)($C_1$-$C_6$ (halo)alkyl), —S(O)$_{0-1}$N($C_1$-$C_6$ (halo)alkyl)$_2$, —S(O)$_{0-1}NH_2$, —C(=O)$C_1$-$C_6$ (halo)alkyl, —C(=O)$C_3$-$C_7$ cycloalkyl, —C(=NOH)$C_1$-$C_6$ (halo)alkyl, —C(=$NOC_1$-$C_6$ alkyl)$C_1$-$C_6$ (halo)alkyl, —NHC(=O)N(H)($C_1$-$C_6$ (halo)alkyl), —NHC(=O)N($C_1$-$C_6$ (halo)alkyl)$_2$, —NHC(=O)$NH_2$, —N($C_1$-$C_6$ (halo)alkyl)C(=O)N(H)($C_1$-$C_6$ (halo)alkyl), —N($C_1$-$C_6$ (halo)alkyl)C(=O)$NH_2$, —OC(=O)$C_1$-$C_6$ (halo)alkyl, —OC(=O)$OC_1$-$C_6$ (halo)alkyl, —OP(=O)($OC_1$-$C_6$ (halo)alkyl)$_2$, —SC(=O)$OC_1$-$C_6$ (halo)alkyl and —SC(=O)N($C_1$-$C_6$ (halo)alkyl)$_2$;

$R^e$ is selected from the group consisting of halogen, OH, $C_1$-$C_6$ alkyl and oxo; and $R^g$ is selected from the group consisting of $C_1$-$C_6$ alkyl and $C_3$-$C_6$ cycloalkyl, wherein $R^g$ may be optionally substituted, such as by halogen or oxo.

In some embodiments, a compound of Formula (0) is further defined as a compound of Formula (II):

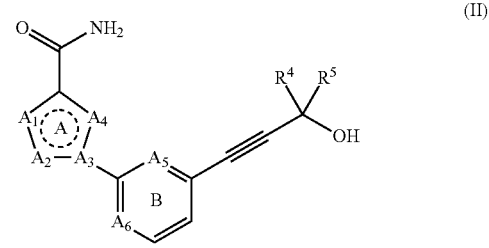

or a stereoisomer or salt thereof, wherein:
ring A is a monocycle or a fused bicycle;
$A_1$ is N or $CR^1$;
$A_2$ is N or $CR^2$;
$A_3$ is N or C;
$A_4$ is N; and
one or two of $A_1$-$A_4$ are N, wherein:
$R^1$ is selected from the group consisting of H, halogen and $C_1$-$C_3$ alkyl or 3-6 membered heterocyclyl, wherein $R^1$ is optionally substituted by F or OH;
$R^2$ is selected from the group consisting of H, $NH_2$, $C_1$-$C_3$ alkyl, $C_3$-$C_6$ cycloalkyl and 3-6 membered heterocyclyl, wherein $R^2$ is optionally substituted by $R^c$; or
$R^1$ and $R^2$ taken together form a cyclic group selected from the group consisting of $C_3$-$C_7$ cycloalkyl, phenyl and 3-6 membered heterocyclyl, wherein the cyclic group is optionally substituted by $R^d$;
$A_5$ is $CR^6$ or N;

$A_6$ is $CR^6$ or N;
wherein only one of $A_5$ and $A_6$ is N;
$R^4$ is $C_1$-$C_3$ alkyl;
$R^5$ is 5-6 membered heterocyclyl optionally substituted by $R^e$; or
$R^4$ and $R^5$ together form a 5-11 membered heterocyclyl (e.g., a 4-7 membered heterocycloalkyl or a 5-6 membered heteroaryl) optionally substituted by $R^e$;
$R^6$, independently at each occurrence, is selected from the group consisting of H, F, Cl, $CF_3$ and $OCH_3$;
$R^a$ is selected from the group consisting of H and $C_1$-$C_6$ alkyl;
$R^b$ is selected from the group consisting of H, $C_1$-$C_6$ alkyl and $C(O)R^g$;
$R^c$ and $R^d$ are each independently selected from the group consisting of halogen, OH, $C_1$-$C_6$ alkyl, $C_3$-$C_6$ cycloalkyl, $C_1$-$C_6$ alkoxy, $C_1$-$C_6$ alkylamino, $C_1$-$C_6$ dialkylamino, $C(O)(C_1$-$C_6$ alkyl), $C(O)_2(C_1$-$C_6$ alkyl), phenyl, and 3-6 membered heterocyclyl, wherein each of $R^c$ and $R^d$ are each independently optionally substituted by halogen, OH, $C_1$-$C_3$ haloalkyl, $C_1$-$C_3$ alkoxy, 5-6 membered heterocyclyl, or oxo;
$R^e$ is selected from the group consisting of OH, $C_1$-$C_6$ alkyl and oxo; and
$R^g$, independently at each occurrence, is selected from the group consisting of $C_1$-$C_6$ alkyl and $C_3$-$C_6$ cycloalkyl.

In some embodiments, a compound of Formula (0) is further defined as a compound of Formula (III):

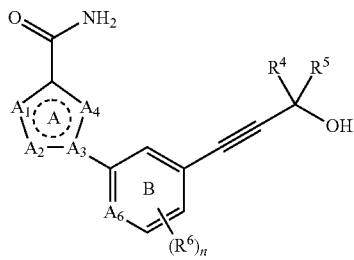

(III)

or a stereoisomer or salt thereof, wherein:
ring A is a monocycle or a fused bicycle;
$A_1$ is N or $CR^1$;
$A_2$ is N or $CR^2$;
$A_3$ is N or C;
$A_4$ is N; and
one or two of $A_1$-$A_4$ are N, wherein:
$R^1$ is selected from the group consisting of H and halogen;
$R^2$ is selected from the group consisting of H, $NH_2$, $C_1$-$C_3$ alkyl and $C_3$-$C_6$ cycloalkyl; or
$R^1$ and $R^2$ taken together form a cyclic group selected from the group consisting of $C_3$-$C_7$ cycloalkyl, phenyl and 3-6 membered heterocyclyl, wherein the cyclic group is optionally substituted by $R^d$;
$R^4$ is $C_1$-$C_6$ alkyl, such as methyl;
$R^5$ is 5-6 membered heterocyclyl optionally substituted by $R^e$; or
$R^4$ and $R^5$ together form a 5-11 membered heterocyclyl (e.g., a 4-7 membered heterocycloalkyl or a 5-6 membered heteroaryl) optionally substituted by $R^e$;
$A_6$ is CH, $CR^6$ or N;
$R^6$, independently at each occurrence, is selected from the group consisting of H, F, Cl, $NH_2$, $NHCH_3$, $N(CH_3)_2$, OH, $OCH_3$, $OCHF_2$, $OCH_2F$, $OCF_3$, SH, $SCH_3$, $SCHF_2$, $SCH_2F$, CN, $CH_3$, $CHF_2$, $CH_2F$, $CH_2OH$, $CF_3$, $NO_2$ and $N_3$, such as a group consisting of F, Cl, $CF_3$ and $OCH_3$;
n is 0, 1, or 2, such as 0 or 1;
$R^a$ is selected from the group consisting of H and $C_1$-$C_6$ alkyl;
$R^b$ is selected from the group consisting of H, $C_1$-$C_6$ alkyl and $C(O)R^g$;
$R^d$ is selected from the group consisting of OH, CN, halogen, $C_1$-$C_6$ alkoxy, —O—$C_1$-$C_6$ alkyl-phenyl, $NR^aR^b$, 4-6 membered heterocyclyl, $C(O)R^g$, $C(O)_2R^g$ and $C_1$-$C_6$ alkyl optionally substituted by OH, CN, or 4-6 membered heterocyclyl;
$R^e$ is selected from the group consisting of methyl and oxo; and
$R^g$, independently at each occurrence, is selected from the group consisting of $C_1$-$C_4$ alkyl and $C_3$-$C_6$ cycloalkyl.

In some embodiments, $R^4$ is $CH_3$. In some embodiments, $R^5$ is a 5-6 membered heterocyclyl optionally substituted by $R^e$.

In some embodiments, such as in a compound of Formula (0), (0a), (0-0), (I), (II), or (III), the following moiety

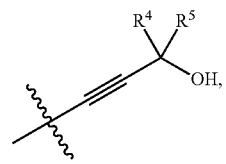

is defined as

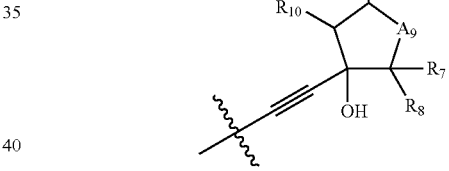

wherein:
$A_9$ is O, $NR^{11}$ or $CR^{11}R^{12}$, wherein $R^{11}$ and $R^{12}$ are each independently selected from the group consisting of H, halogen, OH and $C_1$-$C_3$ alkyl;
$R^7$ and $R^8$ are each independently selected from halogen, OH, $C_1$-$C_6$ alkyl, or $R^7$ and $R^8$ together form =O, and
$R^9$ and $R^{10}$ are each independently selected from $R^e$, or $R^9$ and $R^{10}$ together form a $C_5$-$C_6$ cycloalkyl or a 5-6 membered heterocyclyl, wherein said cycloalkyl and said heterocyclyl are each optionally substituted by $R^e$.

In some embodiments, $R^4$ and $R^5$ together form a $C_8$-$C_{10}$ cycloalkyl optionally substituted by $R^e$. In some embodiments, $R^4$ and $R^5$ together form a 4-9 membered heterocyclyl optionally substituted by $R^e$.

In some embodiments, the following moiety

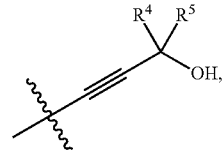

is selected from the group consisting of

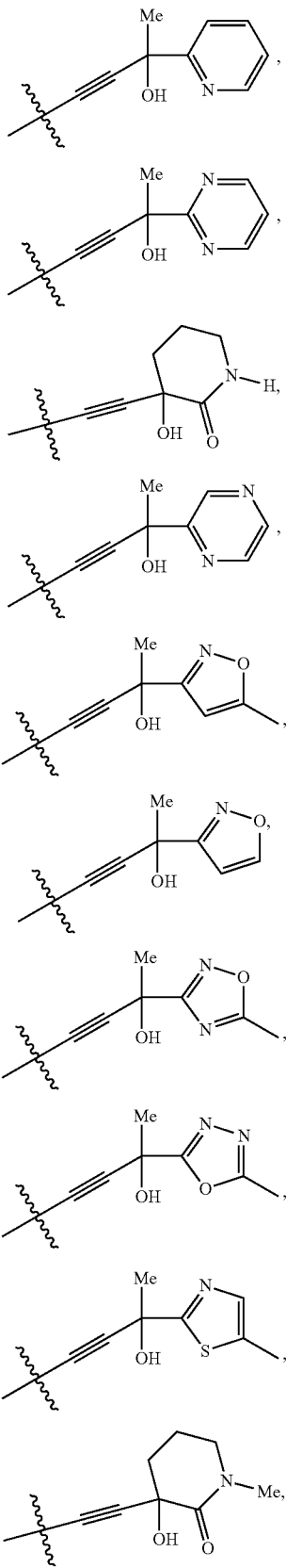

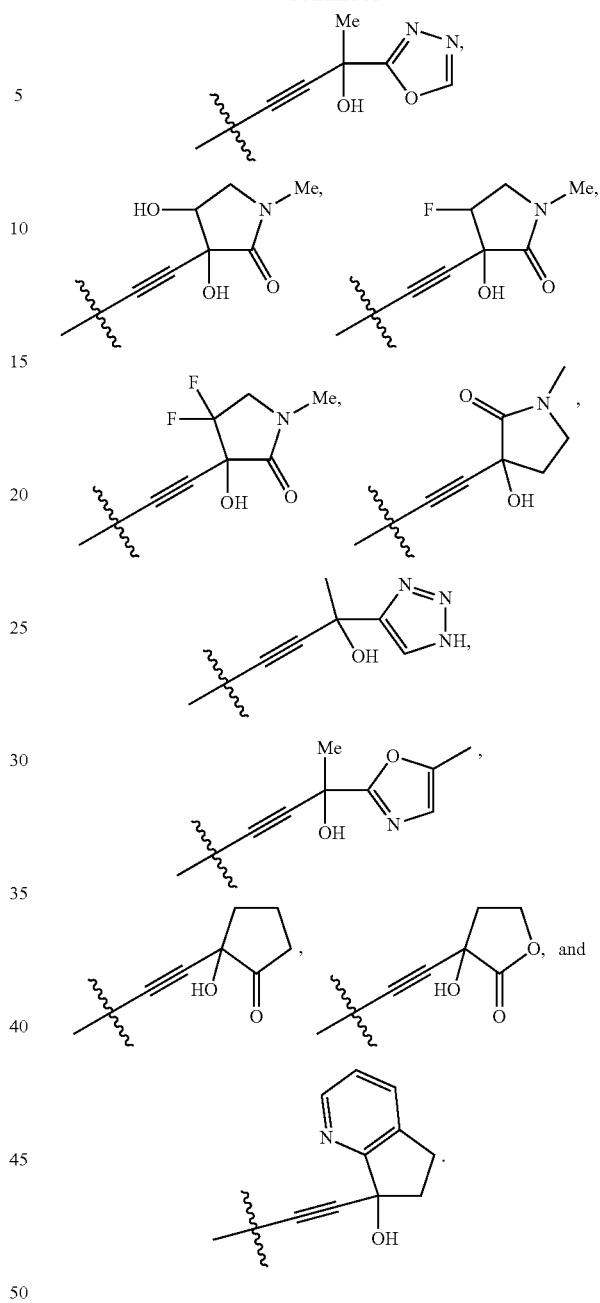

In some embodiments, one of $A_1$-$A_4$ is N. In some embodiments, $A_4$ is N. In some embodiments, two of $A_1$-$A_4$ is N. For example, in some embodiments, $A_1$ and $A_4$ are each N. In other embodiments, $A_3$ and $A_4$ are each N. In any such embodiment, ring B may be phenyl or phenyl independently substituted by one or two $R^6$.

In some embodiments, $R^1$ is selected from the group consisting of H, F and Cl. In some embodiments, $R^2$ is selected from the group consisting of H, $NH_2$, $CH_3$ and cyclopropyl. In other embodiments, $R^2$ is a $C_3$-$C_{11}$ heterocycloalkyl. In some embodiments, $R^1$ and $R^2$ together form the following cyclic group, wherein the asterisks indicate the points of ring fusion to ring A, and each cyclic group is optionally substituted by $R^d$:

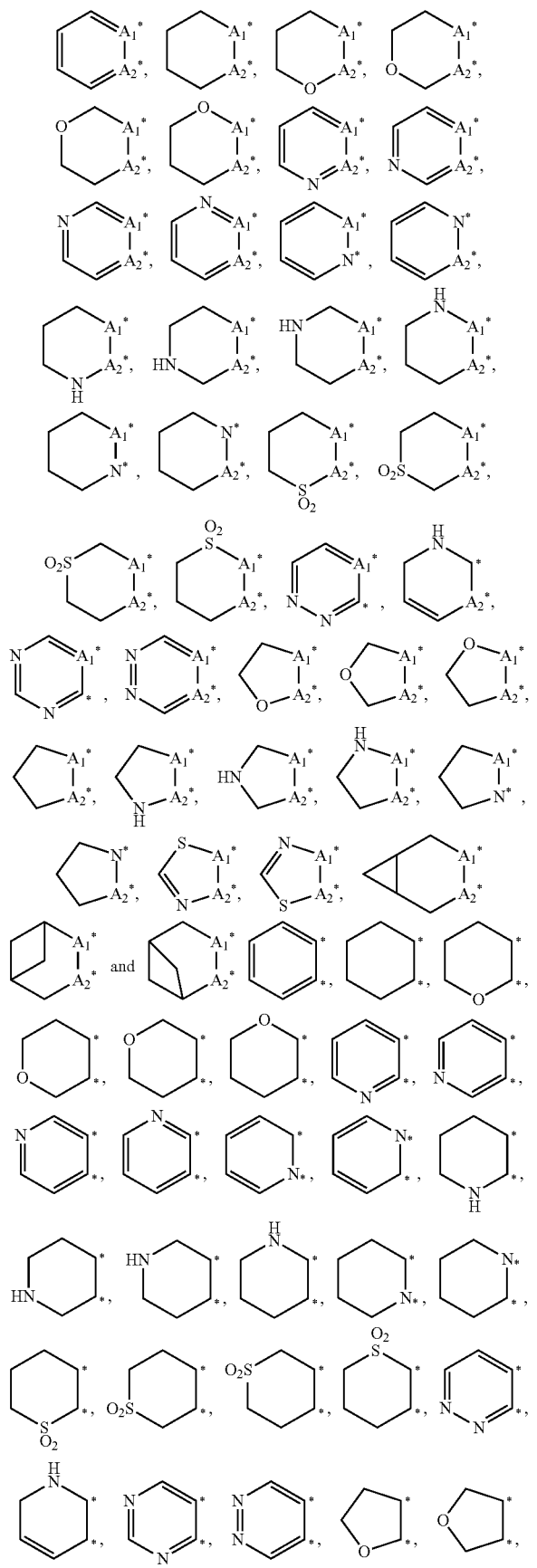

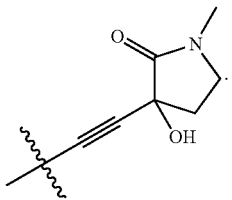 [SMILES: *C#CC1(O)CCN(C)C1=O]

In some embodiments, $R^1$ and $R^6$ together form an unsubstituted cyclic group.

In some embodiments, $R^d$ is selected from the group consisting of OH, CN, F, $C_1$-$C_3$ alkoxy, —O—$C_1$-$C_3$ alkylphenyl, $NR^aR^b$, 4-6 membered heterocyclyl, $C(O)R^g$, $C(O)_2R$ and $C_1$-$C_6$ alkyl optionally substituted by OH, CN, or 4-6 membered heterocyclyl.

In some embodiments, ring B is phenyl.

In some embodiments, $A^1$ is $CR^1$, $A^2$ is $CR^2$, $A^3$ is N and $A^4$ is N.

In some embodiments, $R^4$ and $R^5$ taken together form the following moiety:

In some embodiments, $R^c$ and $R^d$ are each independently selected from the group consisting of halogen, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—$N(H)(R^{1a})$, —$(X^1)_{0-1}$—$N(R^{1b})(R^{1a})$, —$(X^1)_{0-1}$—$CF_3$, $C_1$-$C_6$ alkyl, $C_1$-$C_6$ haloalkyl, $C_1$-$C_6$ heteroalkyl, $C_1$-$C_6$ alkoxy, $C_1$-$C_6$ alkylthio, oxo, —$(X^1)_{0-1}$—$C_1$-$C_6$ alkyl, —$(X^1)_{0-1}$—$C_3$-$C_7$ cycloalkyl, —$(X^1)_{0-1}$-3-11 membered heterocyclyl (e.g., a 4-7 membered heterocycloalkyl or a 5-6 membered heteroaryl), —$(X^1)_{0-1}$—$C_6$-$C_{10}$ aryl, —$C(=O)(X^1)_1$-$C_3$-$C_7$ cycloalkyl, —$C(=O)(X^1)_1$-3-11 membered heterocyclyl, —$(X^1)_{0-1}$—$C(=Y^1)N(H)(R^{1a})$, —$(X^1)_{0-1}$—$C(=Y^1)NH_2$, —$(X^1)_{0-1}$—$C(=Y^1)N(R^{1a})(R^{1b})$, —$(X^1)_{0-1}$—$C(=Y^1)OR^{1a}$, —$(X^1)_{0-1}$—$C(=Y^1)OH$, —$(X^1)_{0-1}$—$N(H)C(=Y^1)(R^{1a})$, —$(X^1)_{0-1}$—$N(R^{1b})C(=Y^1)(R^{1a})$, —$(X^1)_{0-1}$—$N(R^{1b})(=Y^1)(H)$, —$(X^1)_{0-1}$—$N(H)C(=Y^1)OR^{1a}$, —$(X^1)_{0-1}$—$N(R^{1b})C(=Y^1)OR^{1a}$, —$(X^1)_{0-1}$—$S(O)_{1-2}R^{1a}$, —$(X^1)_{0-1}$—$N(H)S(O)_{1-2}R^{1a}$, —$(X^1)_{0-1}$—$N(R^{1b})S(O)_{1-2}R^{1a}$, —$(X^1)_{0-1}$—$S(O)_{0-1}N(H)(R^{1a})$, —$(X^1)_{0-1}$—$S(O)_{0-1}N(R^{1b})(R^{1a})$, —$(X^1)_{0-1}$—$S(O)_{0-1}NH_2$, —$(X^1)_{0-1}$—$S(=O)(=NR^{1b})R^{1a}$, —$(X^1)_{0-1}$—$C(=Y^1)R^{1a}$, and —$(X^1)_{0-1}$—$C(=Y^1)H$, wherein $X^1$ is selected from the group consisting of $C_1$-$C_6$ alkylene, $C_1$-$C_6$ heteroalkylene, $C_2$-$C_6$ alkenylene, $C_2$-$C_6$ alkynylene, $C_1$-$C_6$ alkyleneoxy, $C_3$-$C_7$ cycloalkylene, 3-11 membered heterocyclylene and phenylene; $R^{1a}$ and $R^{1b}$ are each independently selected from the group consisting of $C_1$-$C_6$ alkyl, $C_1$-$C_6$ haloalkyl, $C_1$-$C_6$ heteroalkyl, $C_3$-$C_7$ cycloalkyl, 3-11 membered heterocyclyl, and phenyl, or $R^{1a}$ and $R^{1b}$ when attached to the same nitrogen atom are optionally combined to form a 3-11 membered heterocyclyl (e.g., a 4-7 membered heterocycloalkyl or a 5-6 membered heteroaryl) comprising 0-3 additional heteroatoms selected from N, O and S; $Y^1$ is O, $NR^{1c}$ or S wherein $R^{1c}$ is H or $C_1$-$C_6$ alkyl; wherein any portion of an $R^c$ or $R^d$ substituent, including $R^{1a}$, $R^{1b}$ and $R^{1c}$, at each occurrence is each independently further substituted by from 0 to 4 $R^f$ substituents selected from the group consisting of halogen, CN, $NO_2$, OH, $NH_2$, —$N(C_1$-$C_6$ alkyl$)_2$, —$NH(C_1$-$C_6$ alkyl), oxo, $C_1$-$C_6$ alkyl, $C_1$-$C_6$ haloalkyl, $C_1$-$C_6$ hydroxyalkyl, $C_1$-$C_6$ heteroalkyl, $C_1$-$C_6$ alkoxy, $C_1$-$C_6$ alkylthio, $C_3$-$C_7$ cycloalkyl, or 3-11 membered heterocyclyl (e.g., a 4-7 membered heterocycloalkyl or a 5-6 membered heteroaryl).

In some embodiments, a heterocyclyl group contains one to three nitrogen atoms, one oxygen atom, or one sulfur atom, or any combination thereof.

In some embodiments, Q is C.

In some embodiments, a compound of the present invention is defined as any one or more of the following:

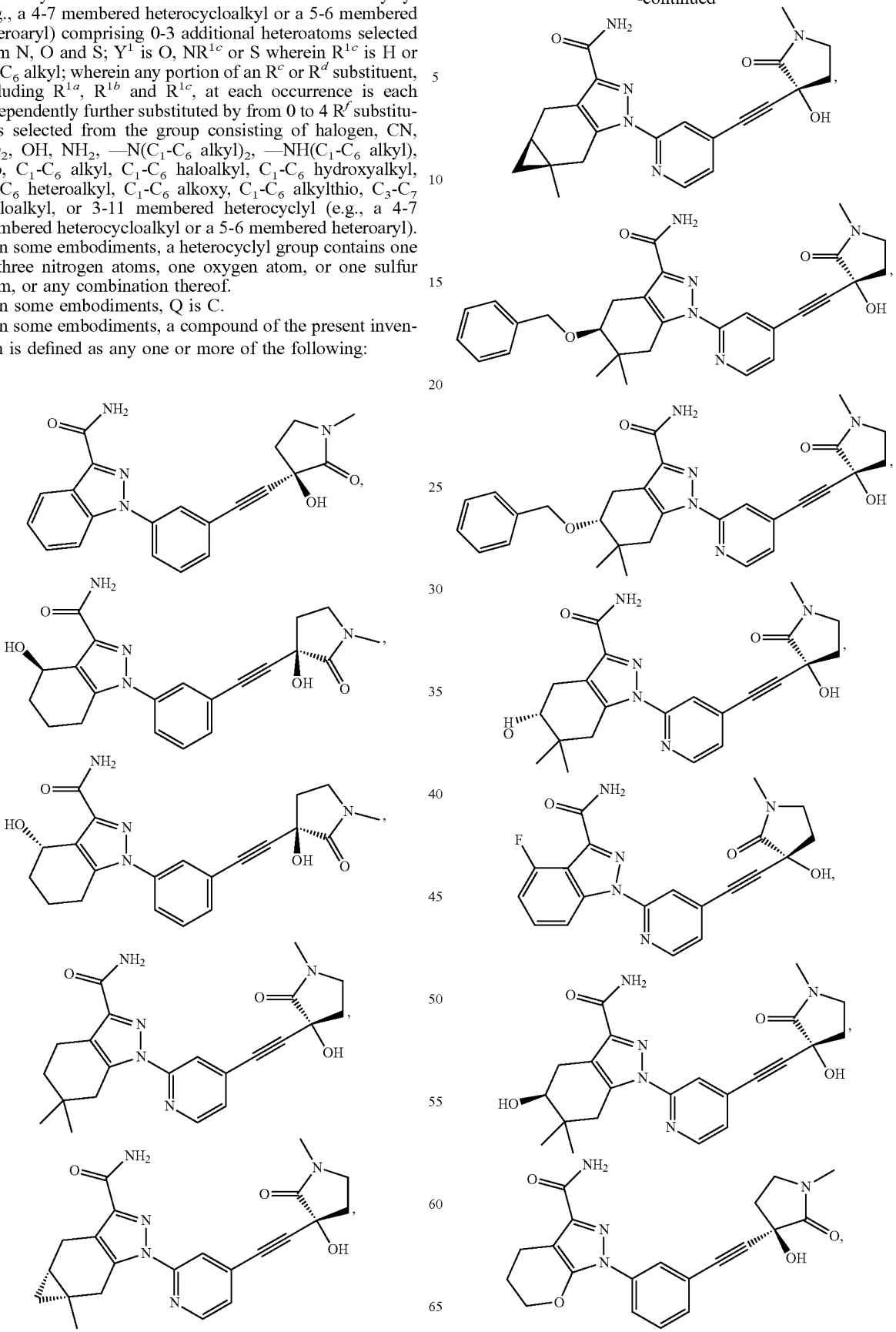

33
-continued
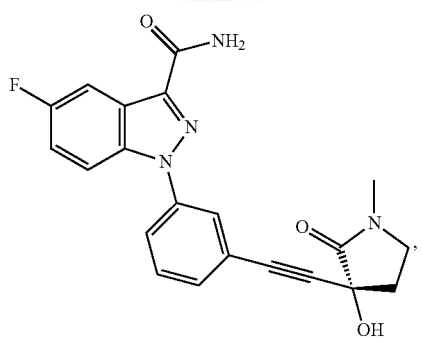
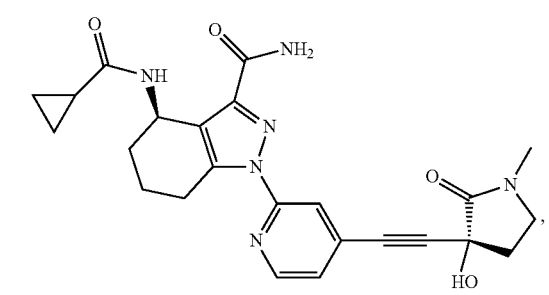
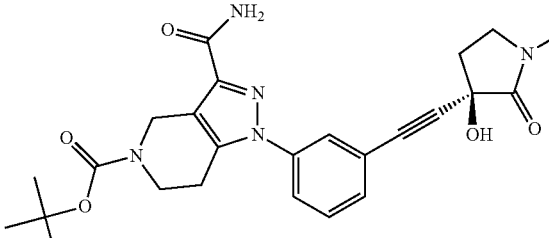
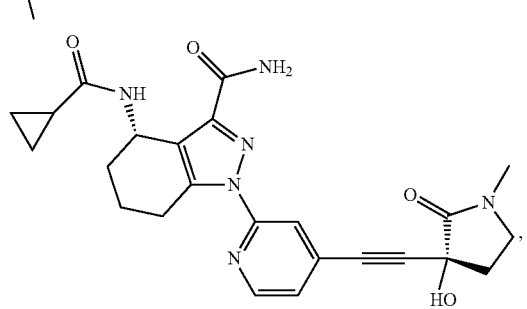
34
-continued
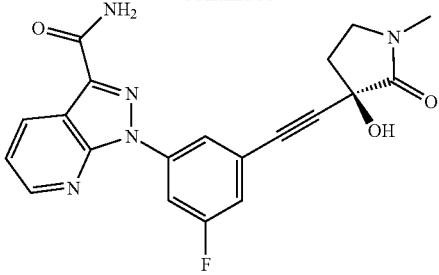
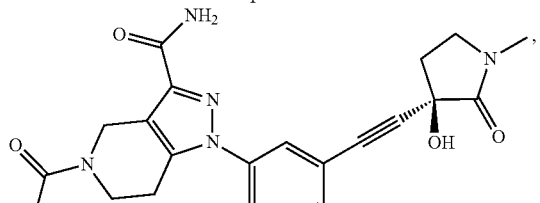
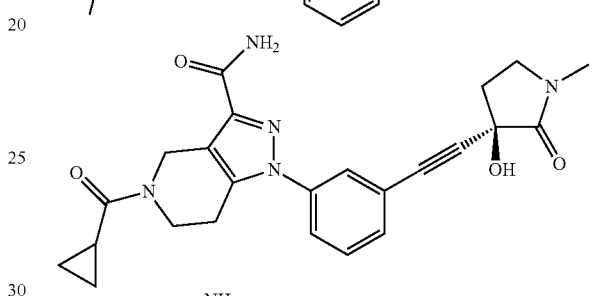
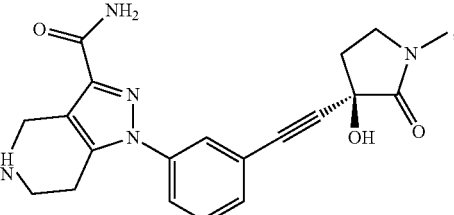
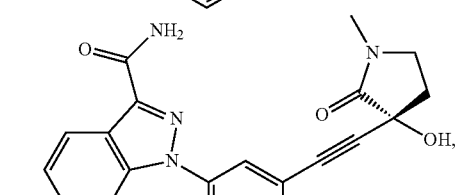
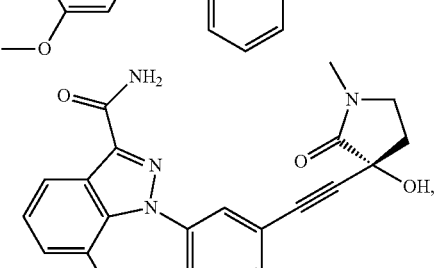
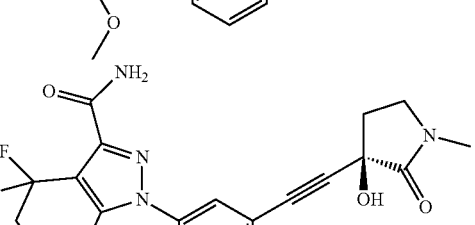

35
-continued
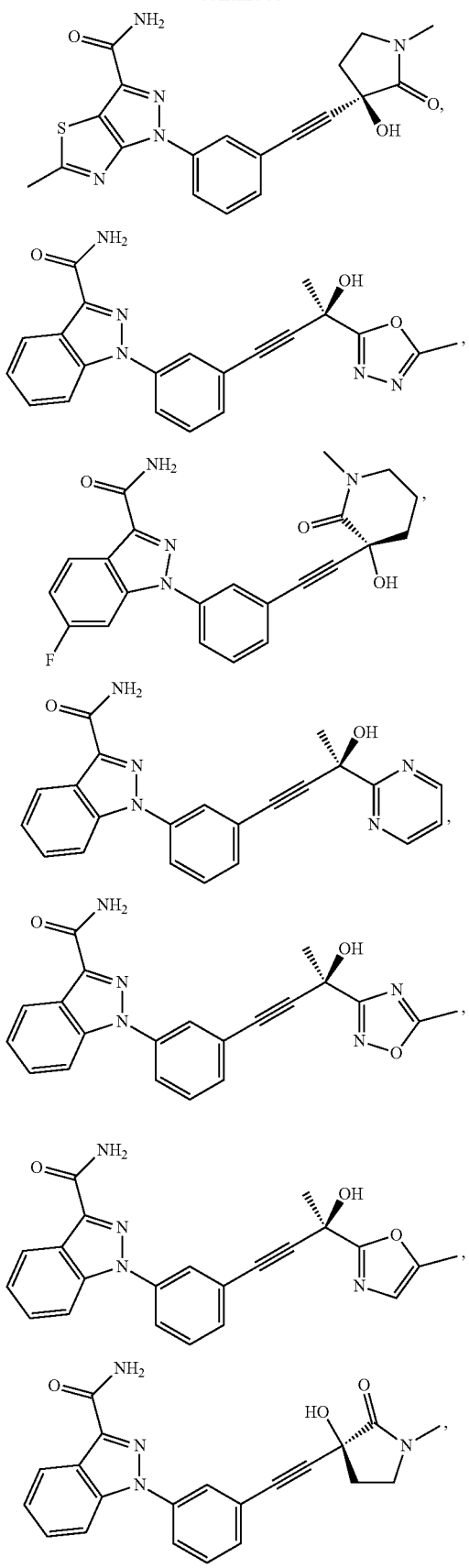
36
-continued
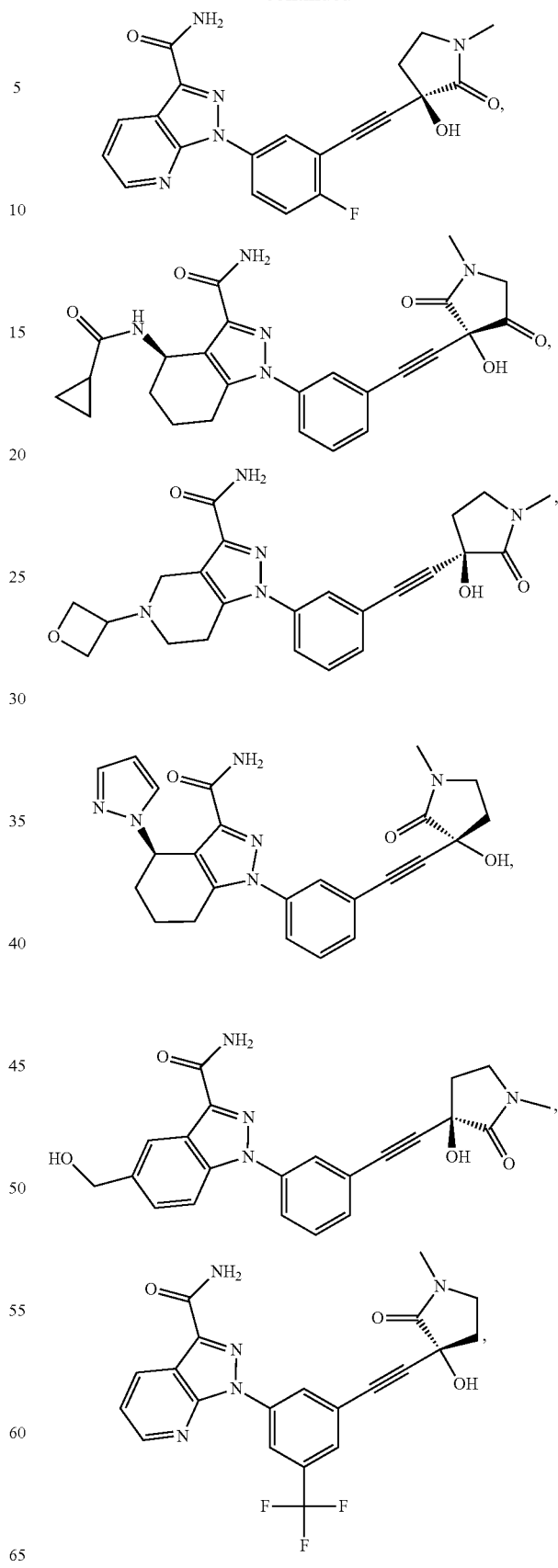

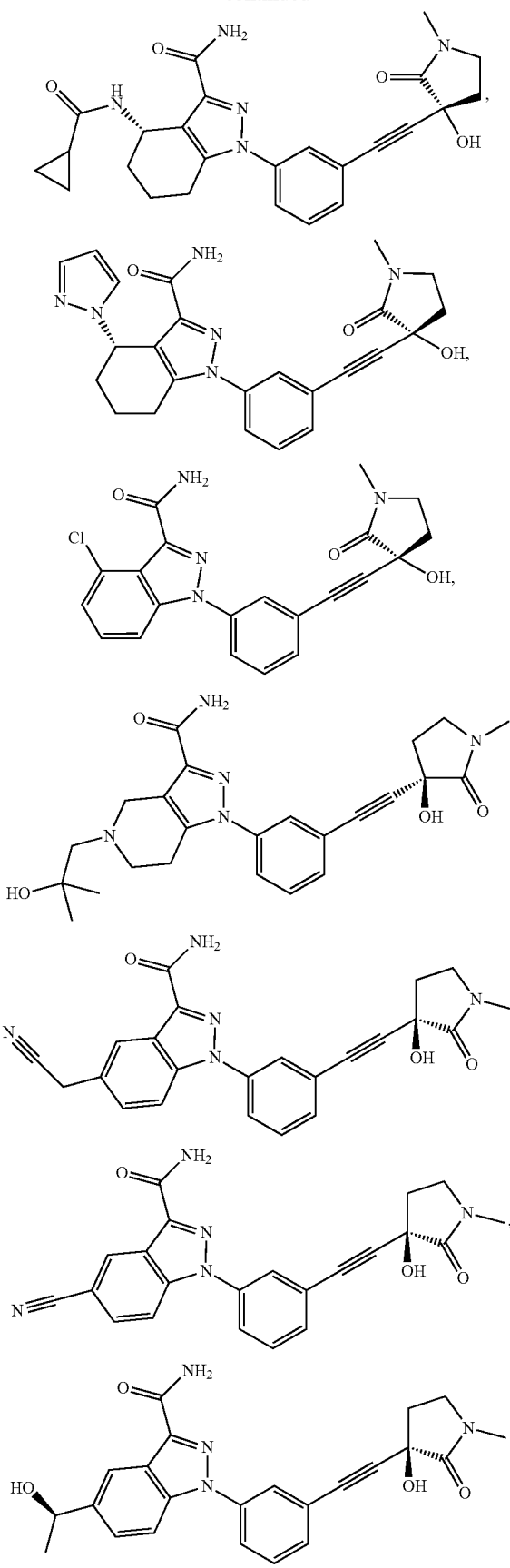
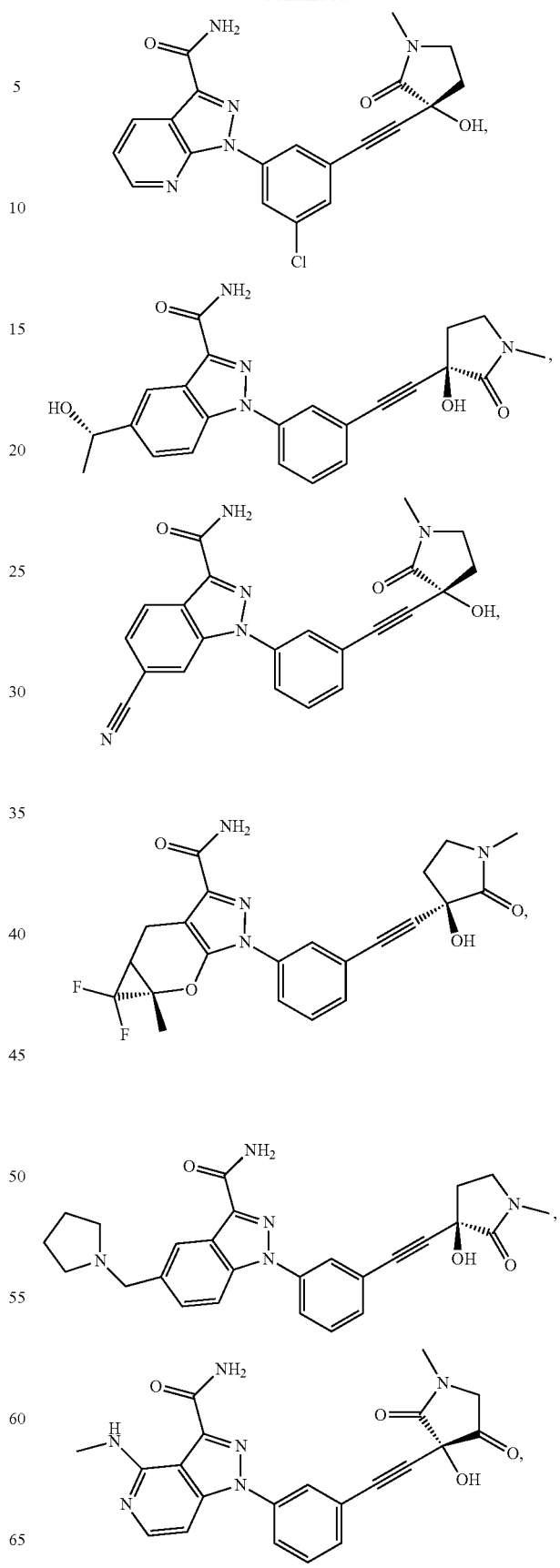

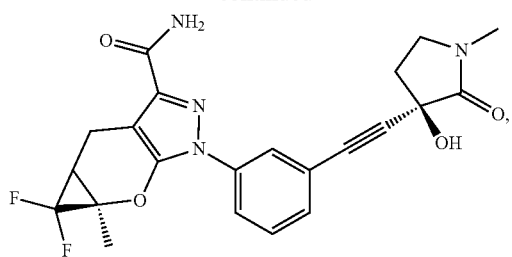
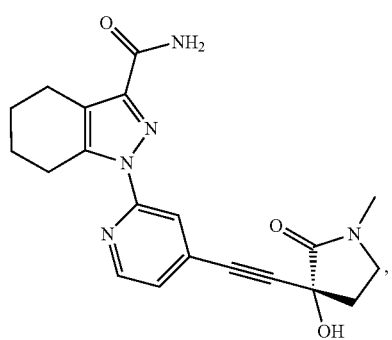
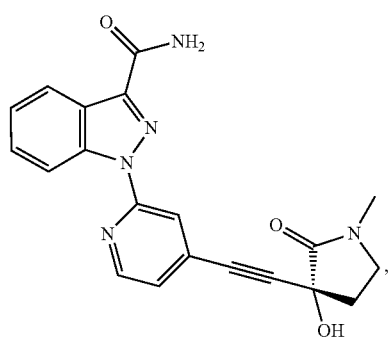
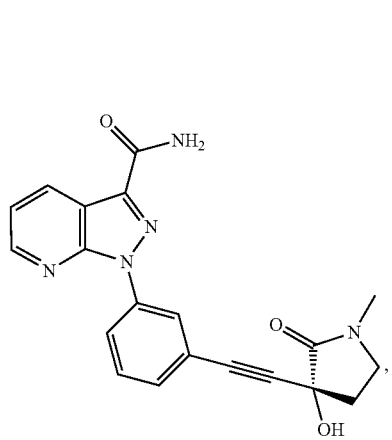
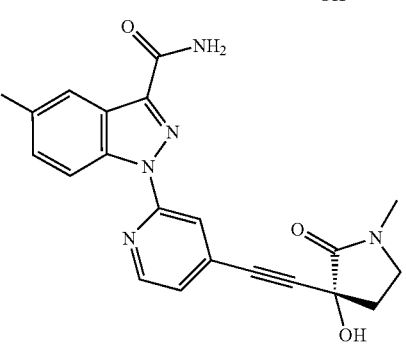
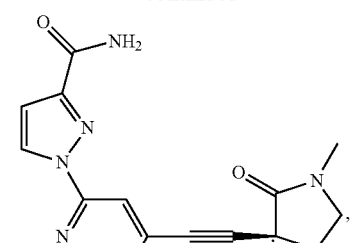
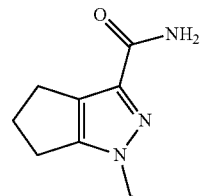
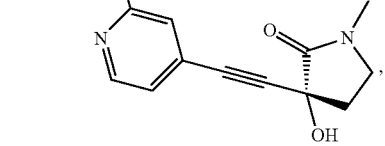
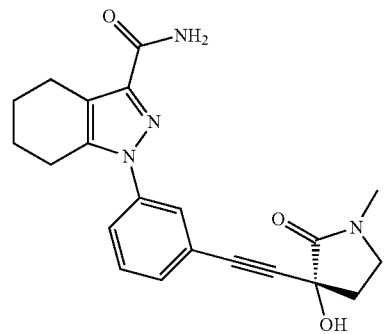
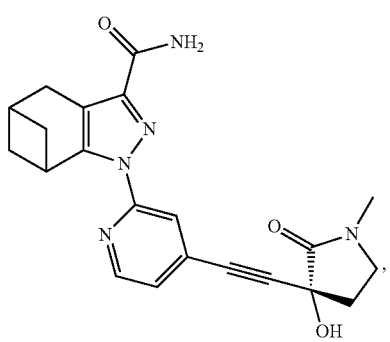
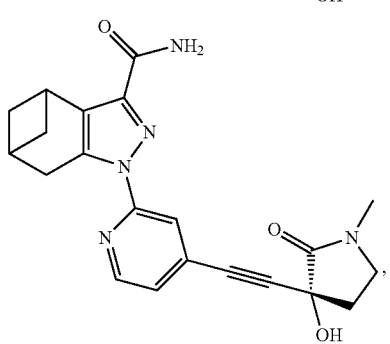

41
-continued
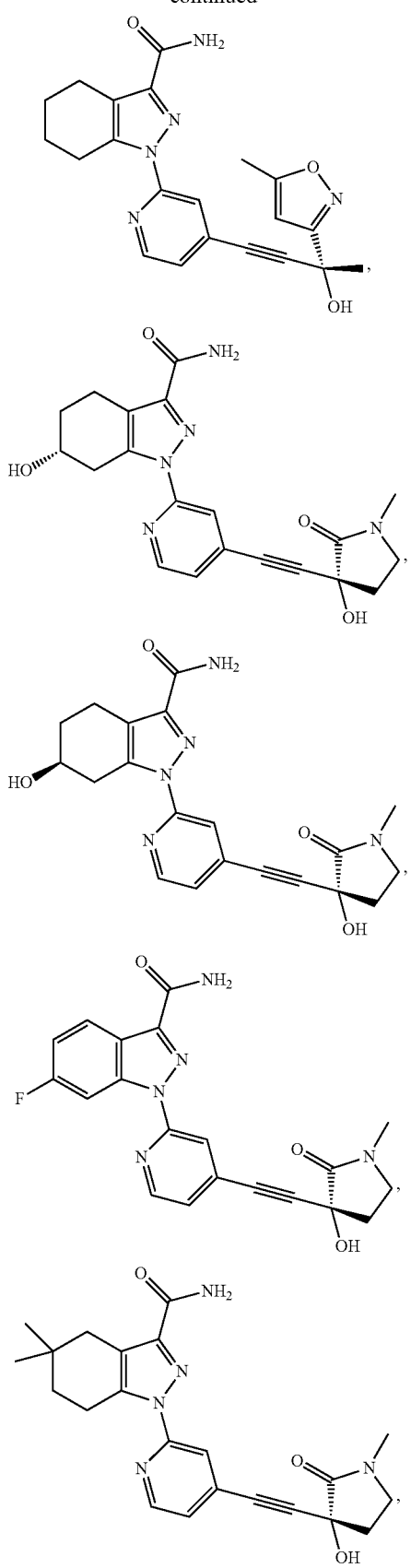
42
-continued
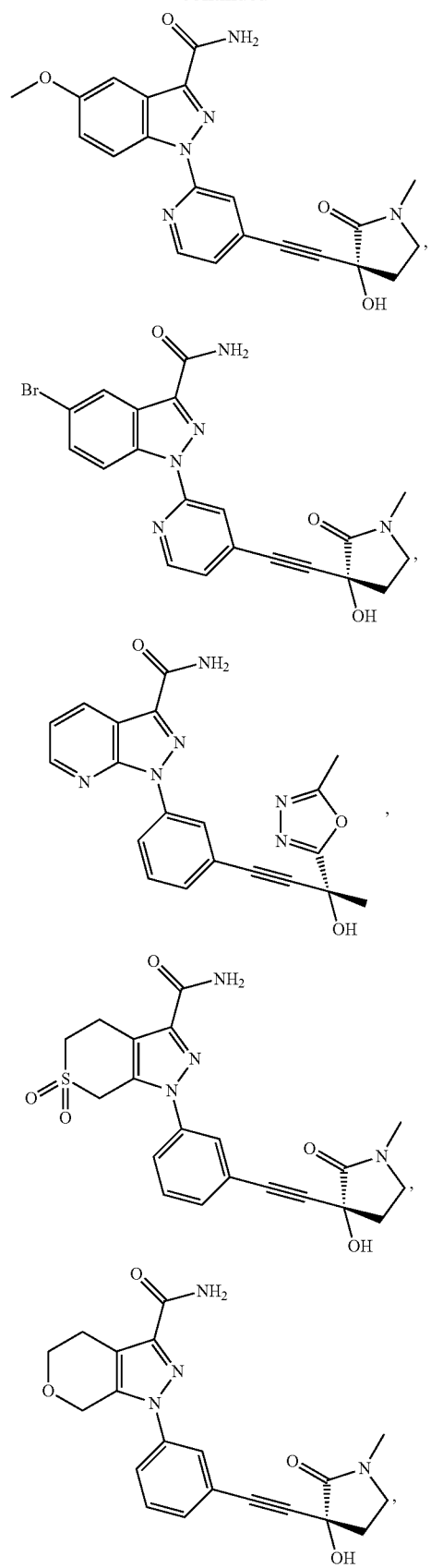

-continued
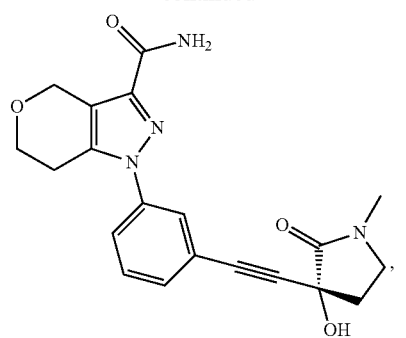
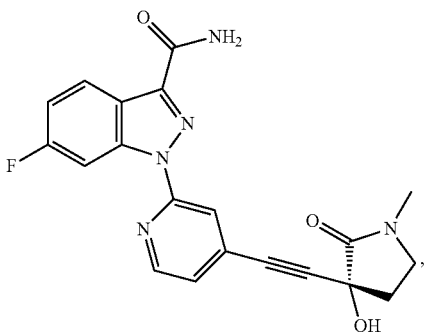
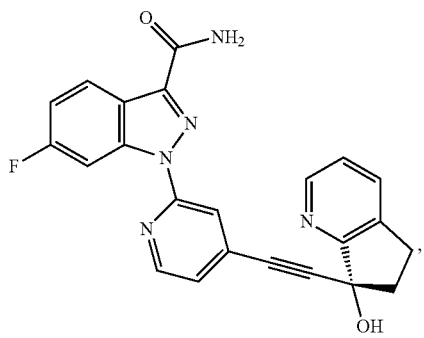
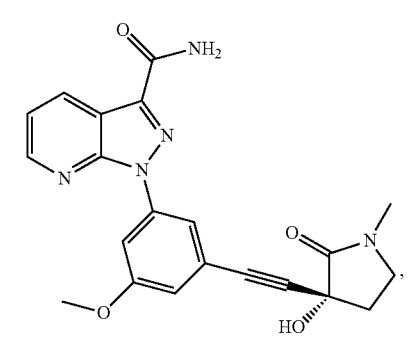
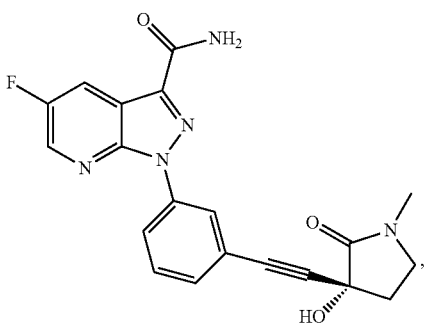
-continued
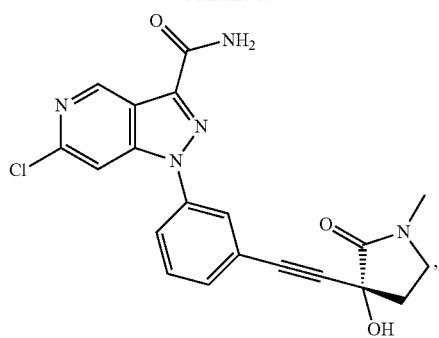
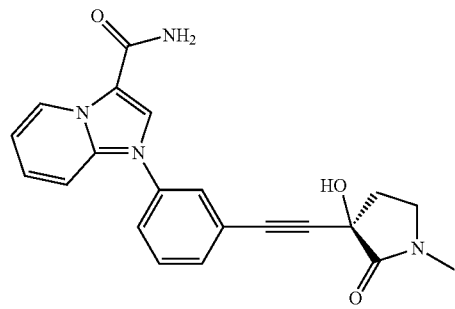
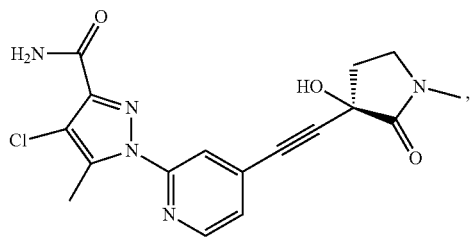
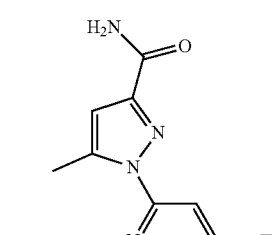
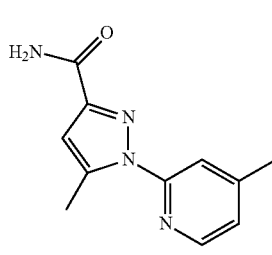

-continued
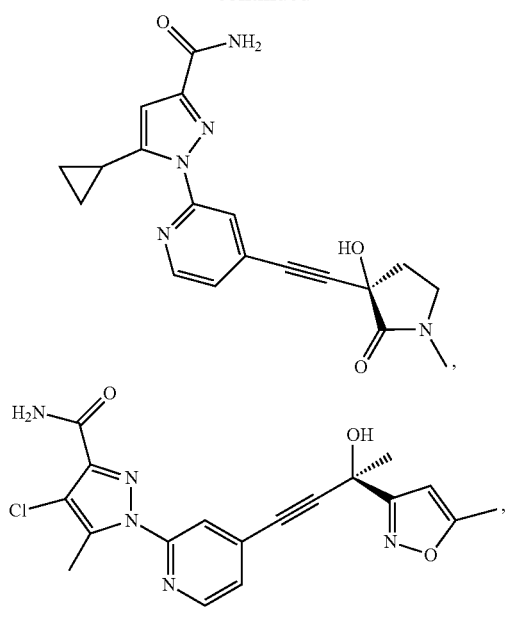
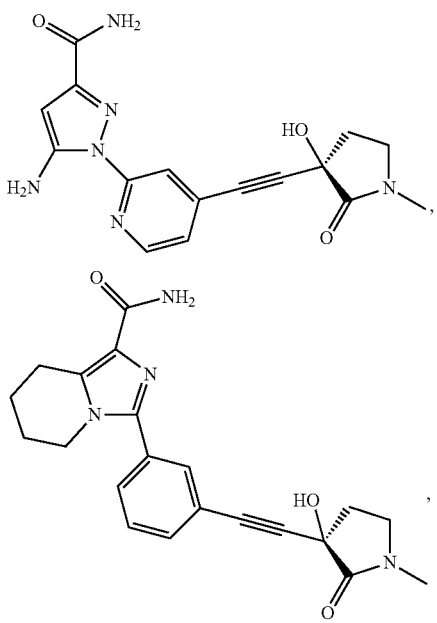
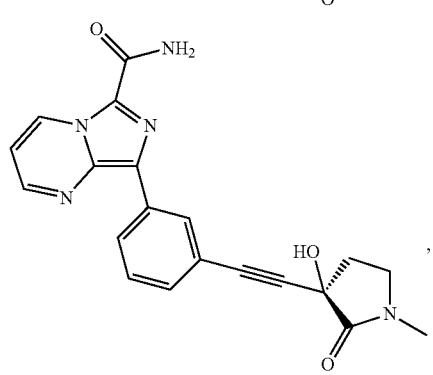
-continued
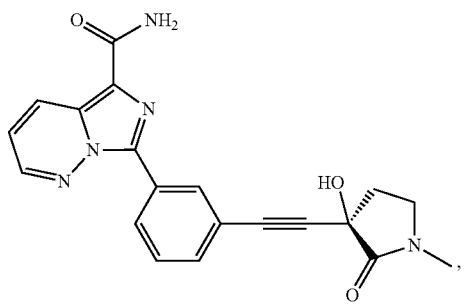
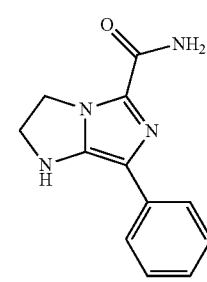
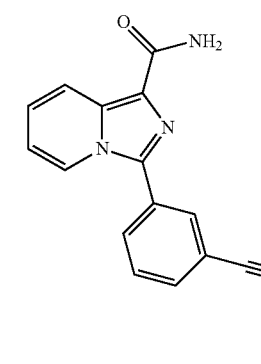
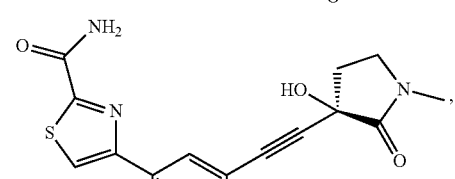
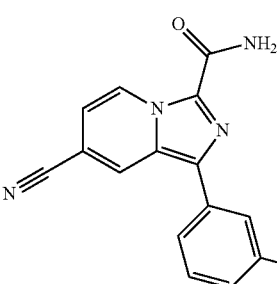

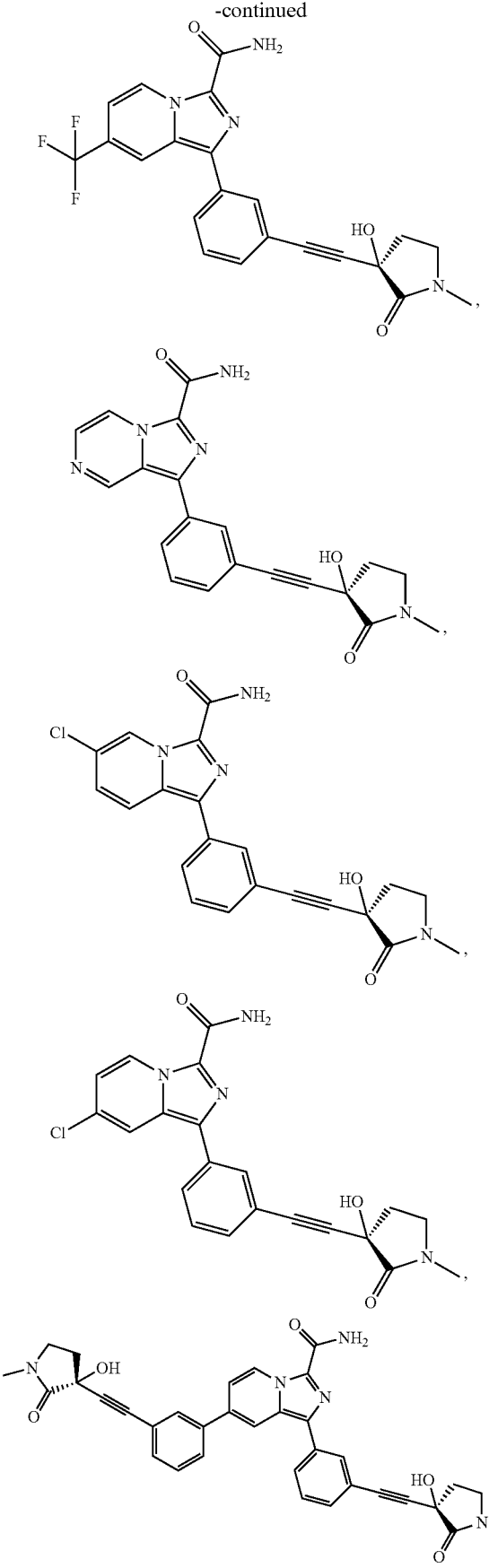
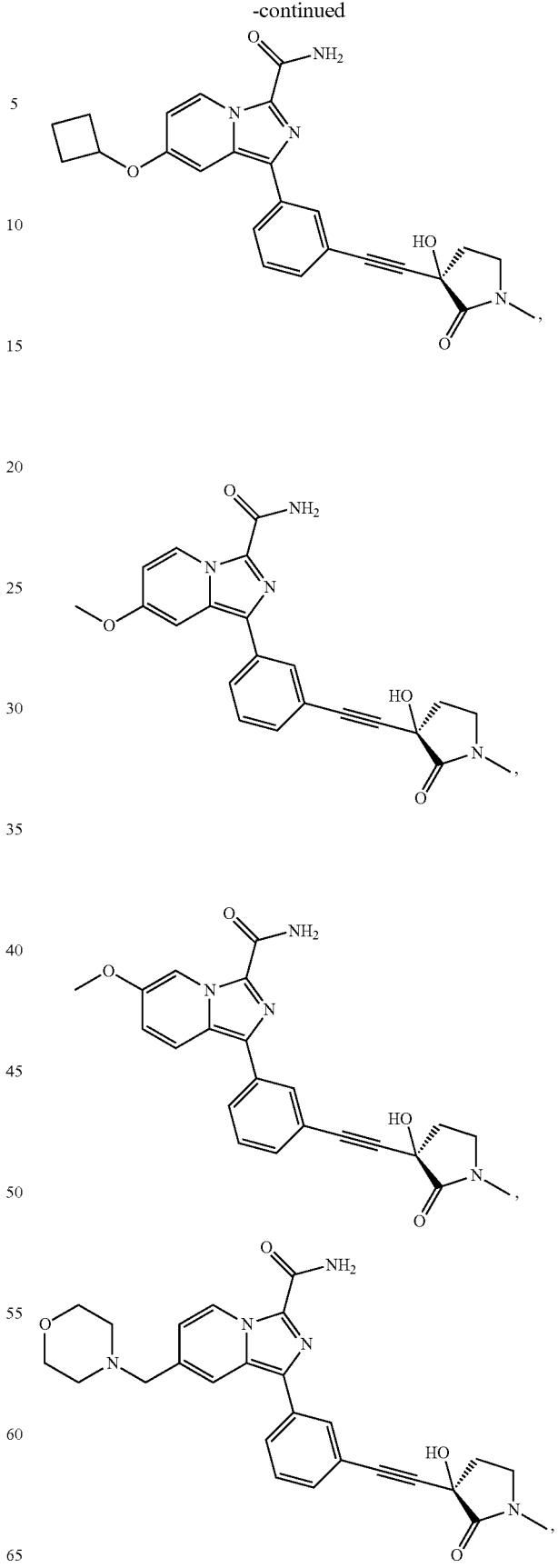

49
-continued
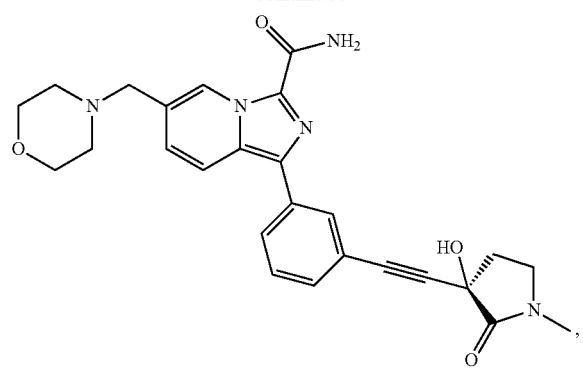
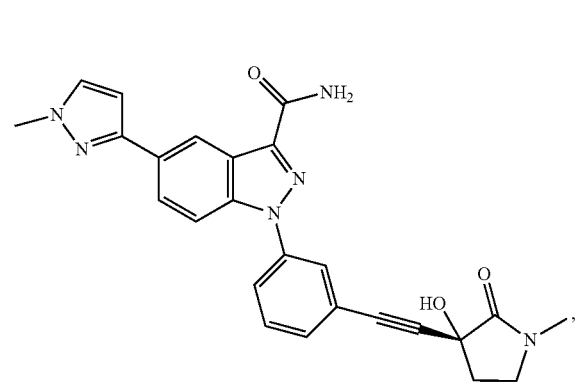
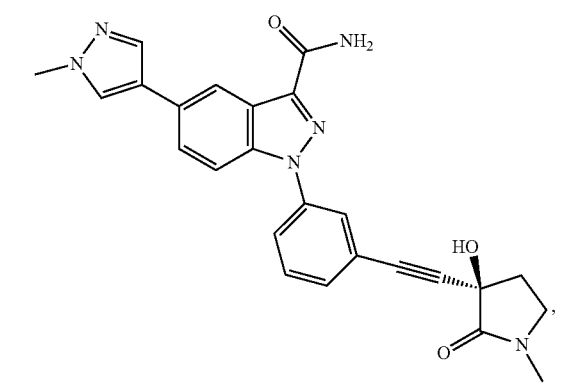
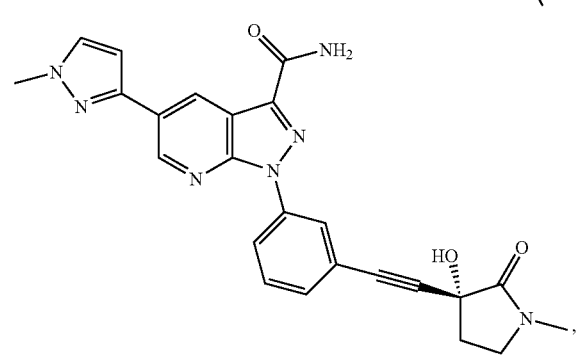
50
-continued
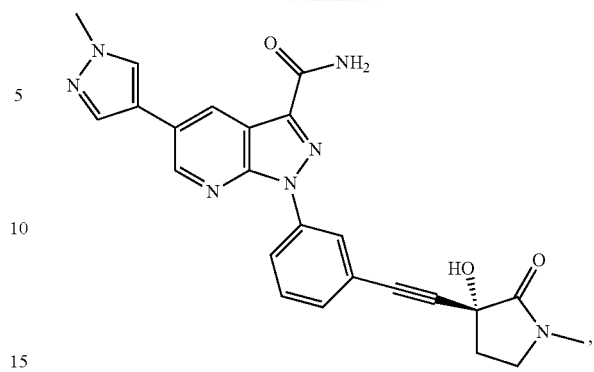
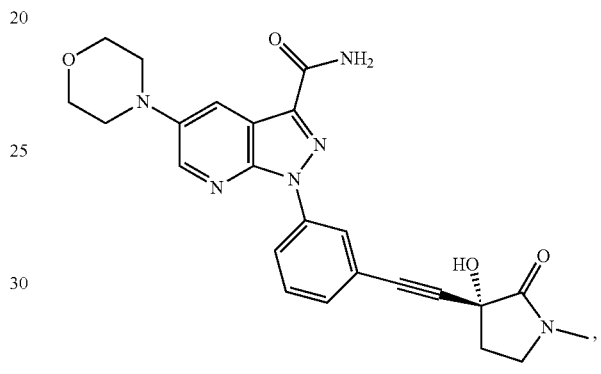
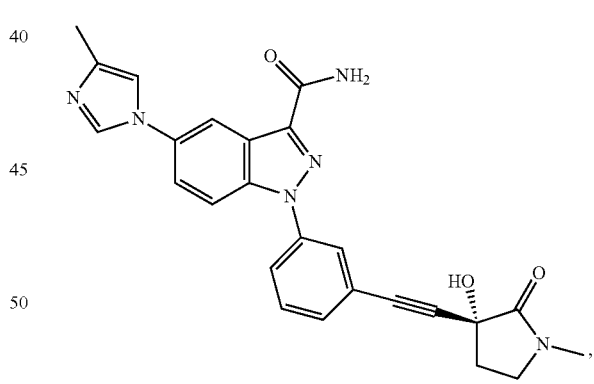
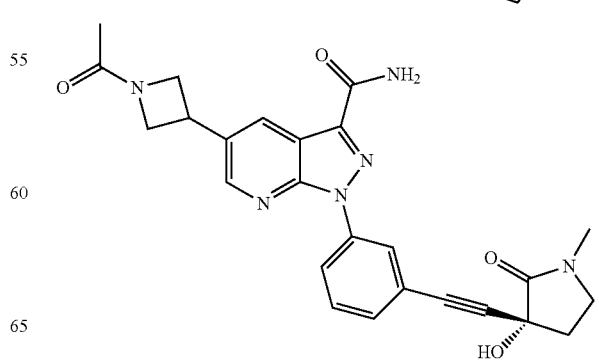

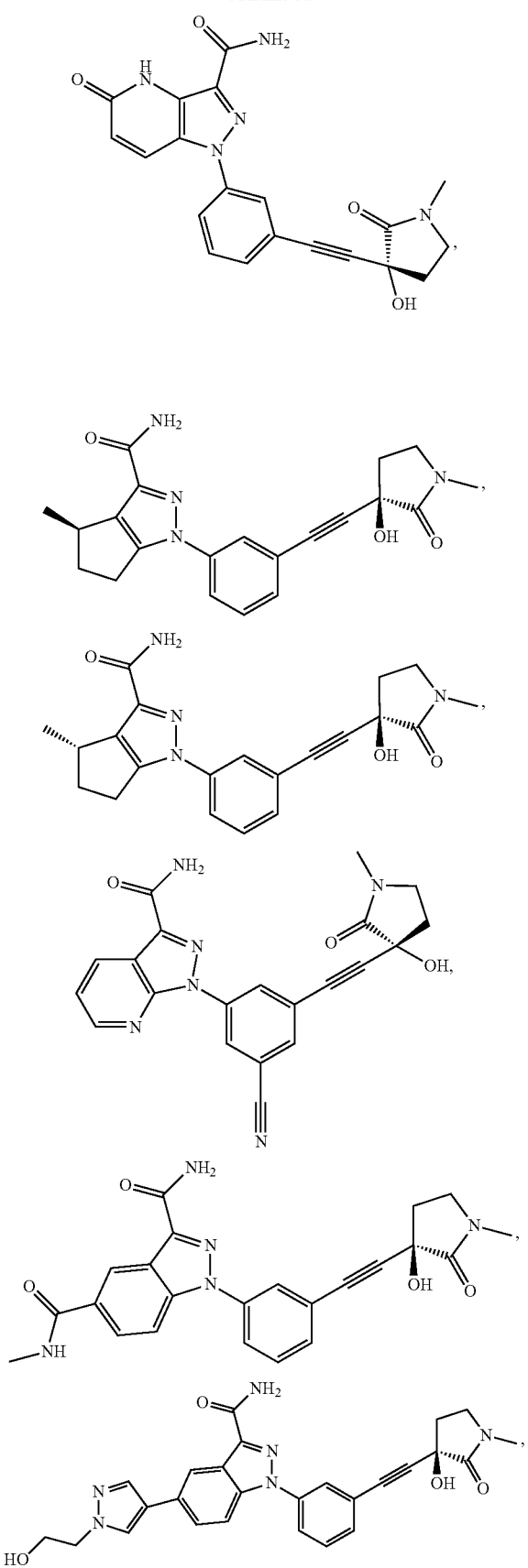
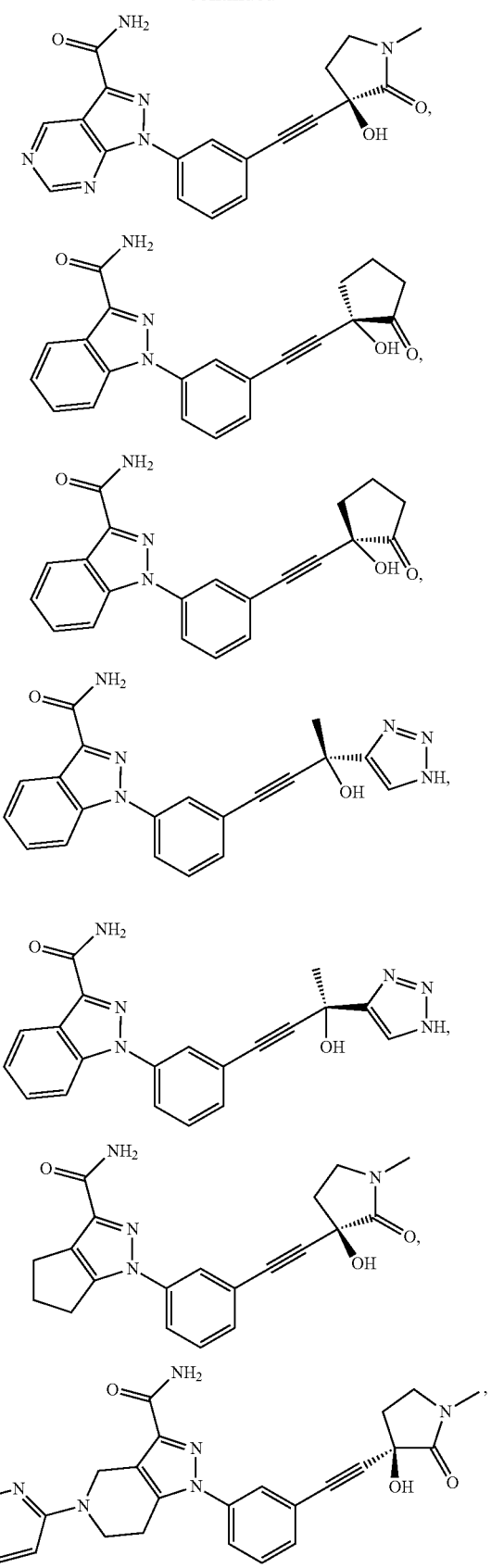

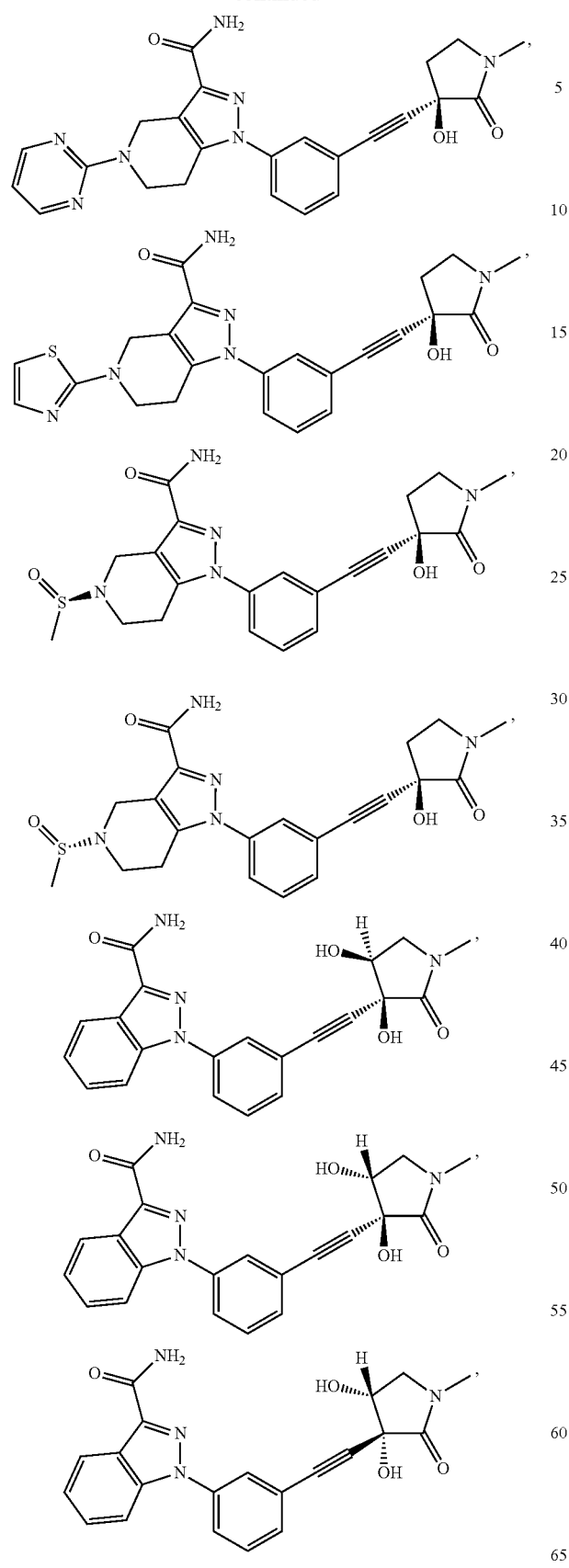
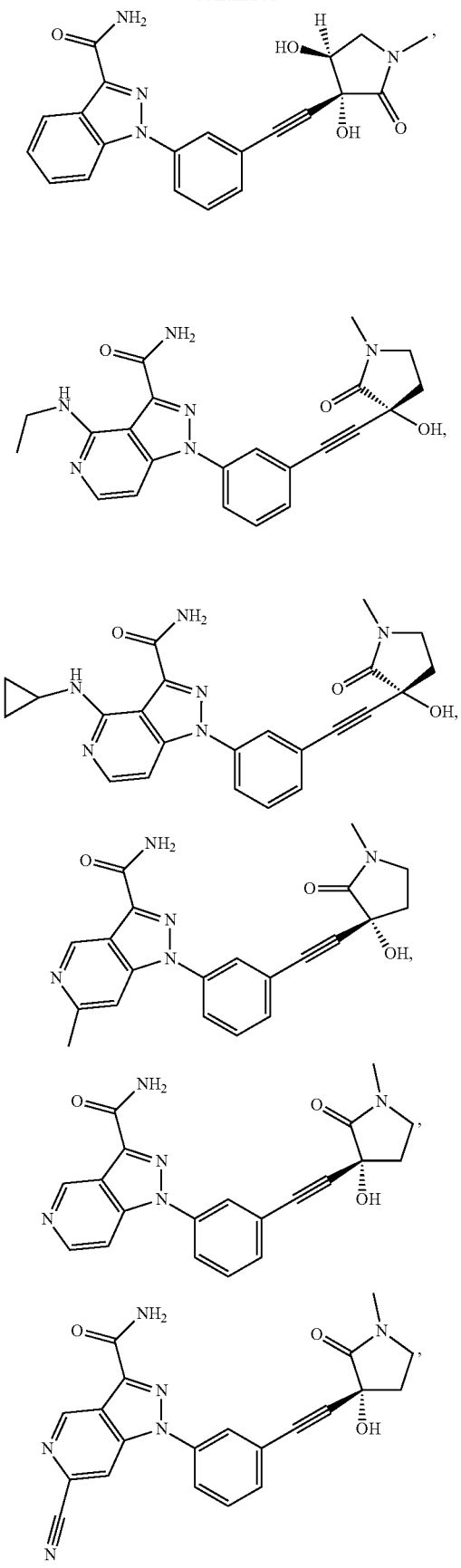

55
-continued
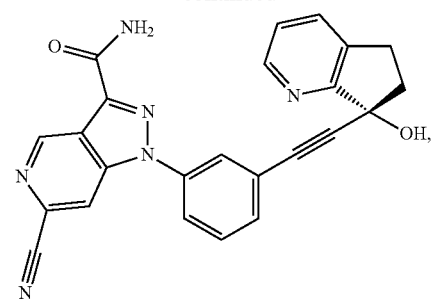
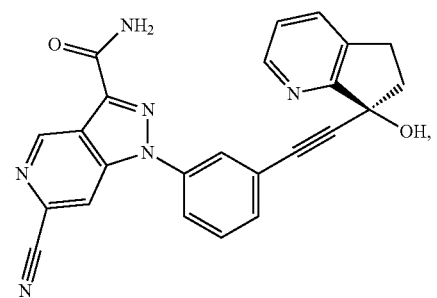
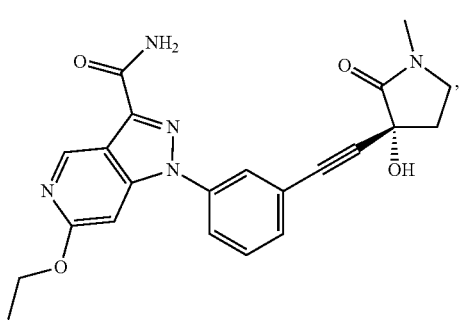
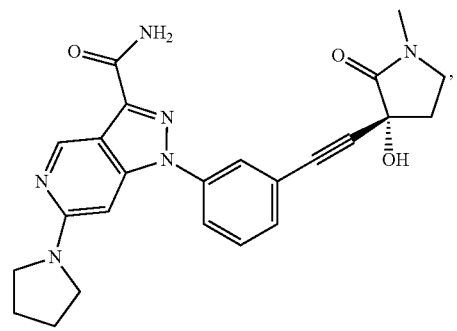
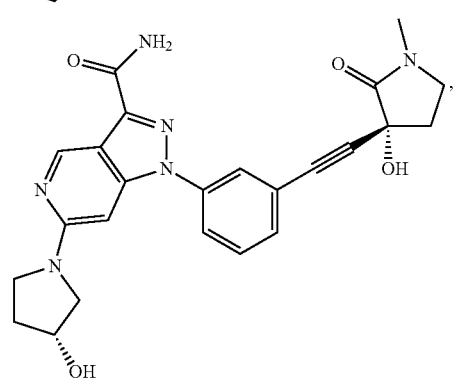
56
-continued
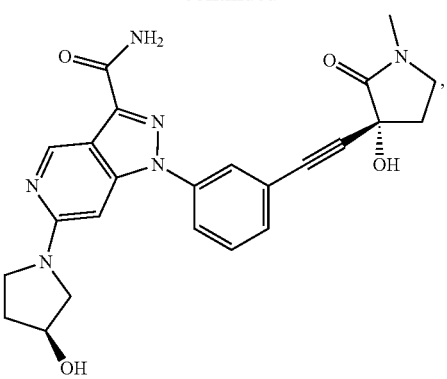
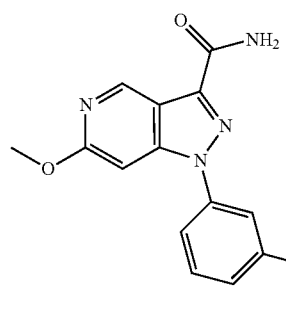
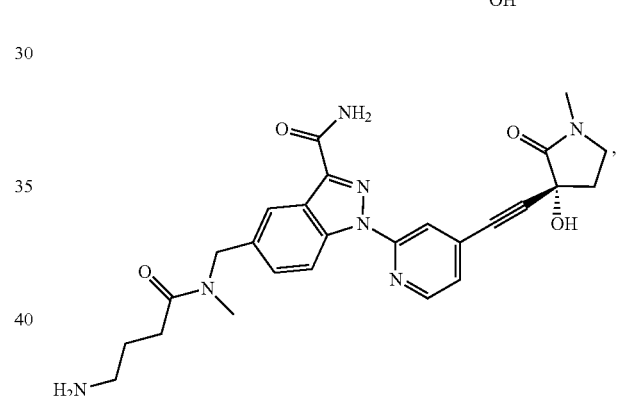
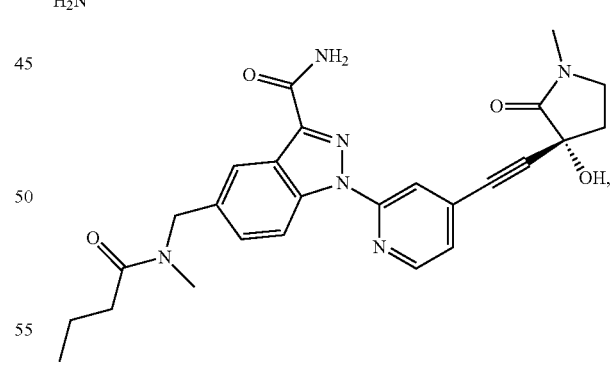
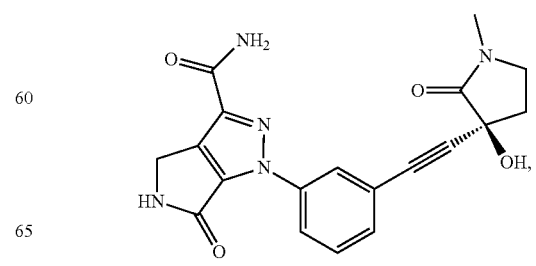

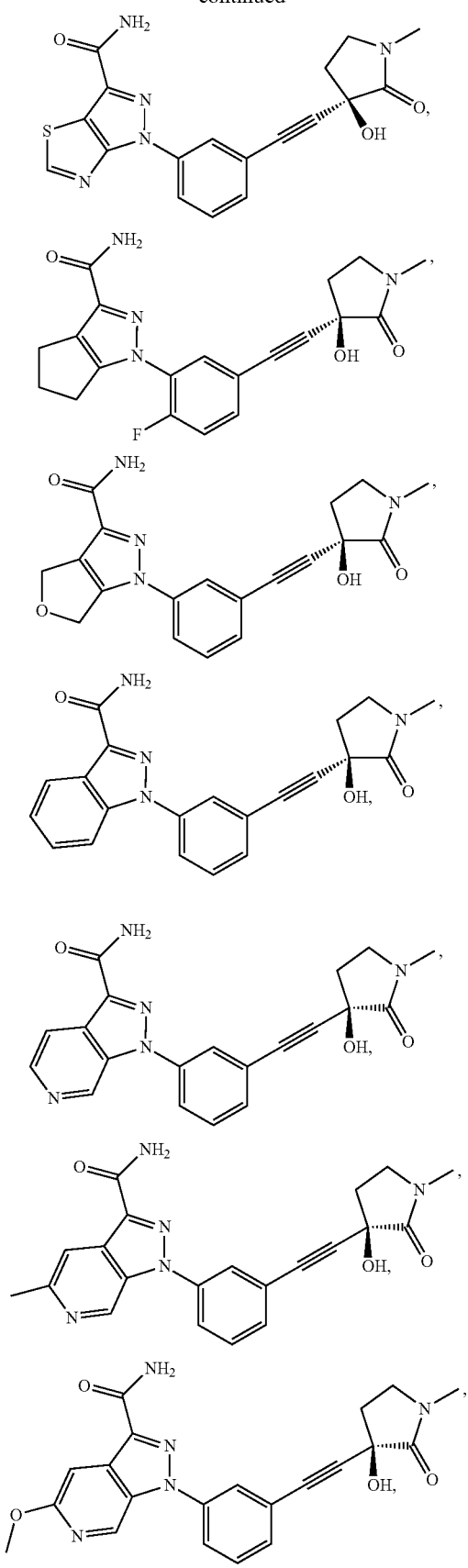
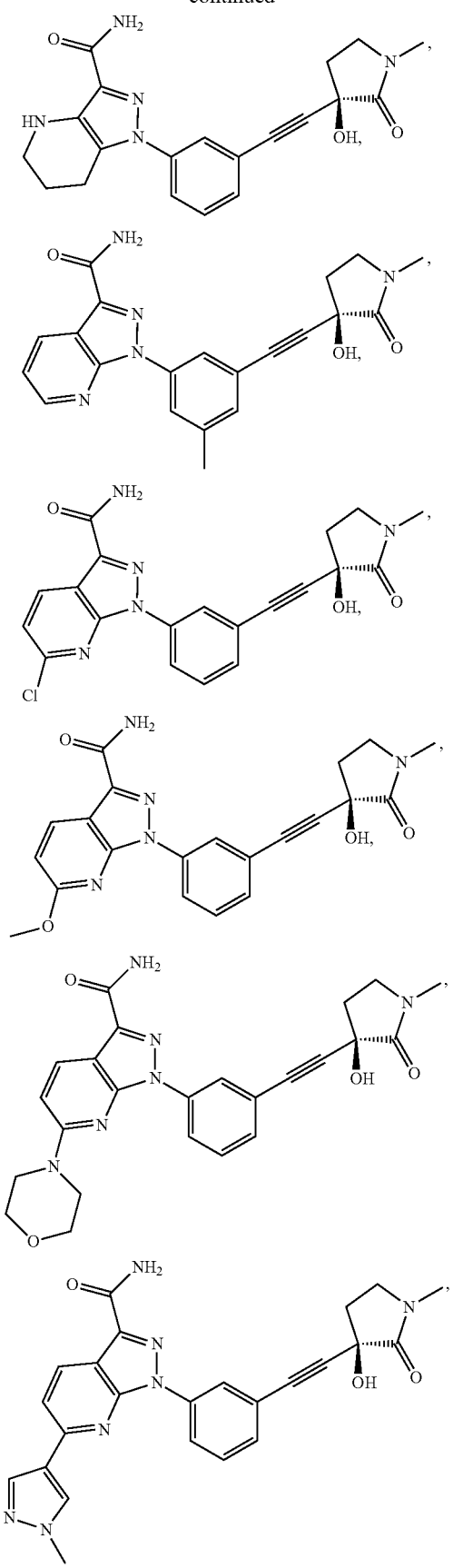

59
-continued
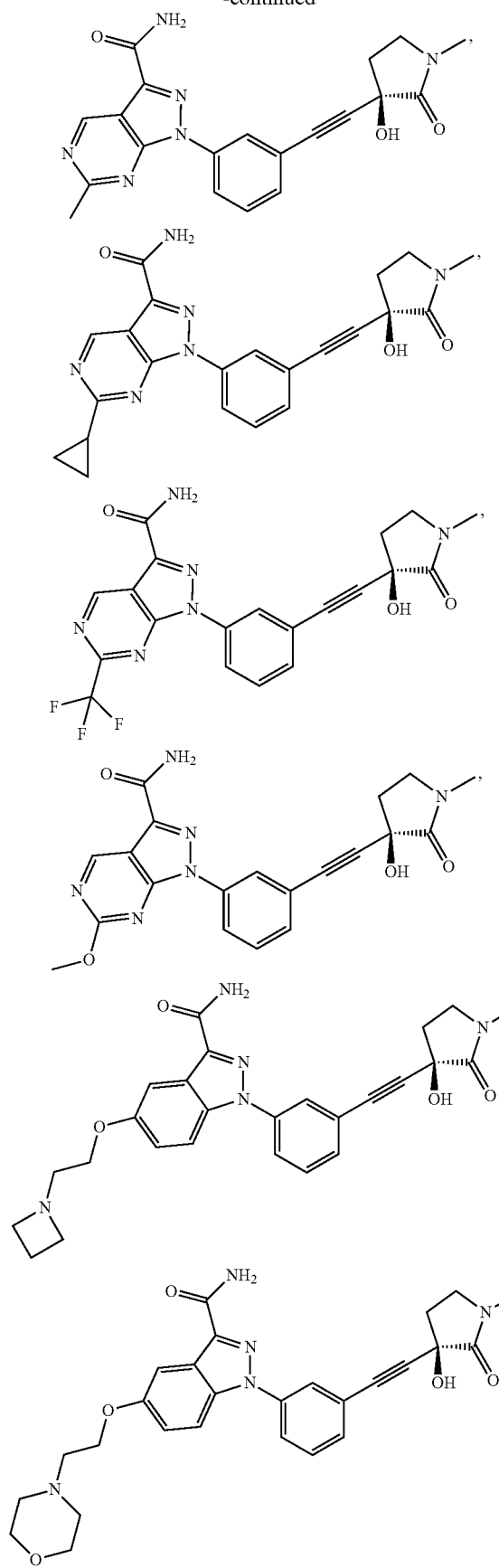
60
-continued
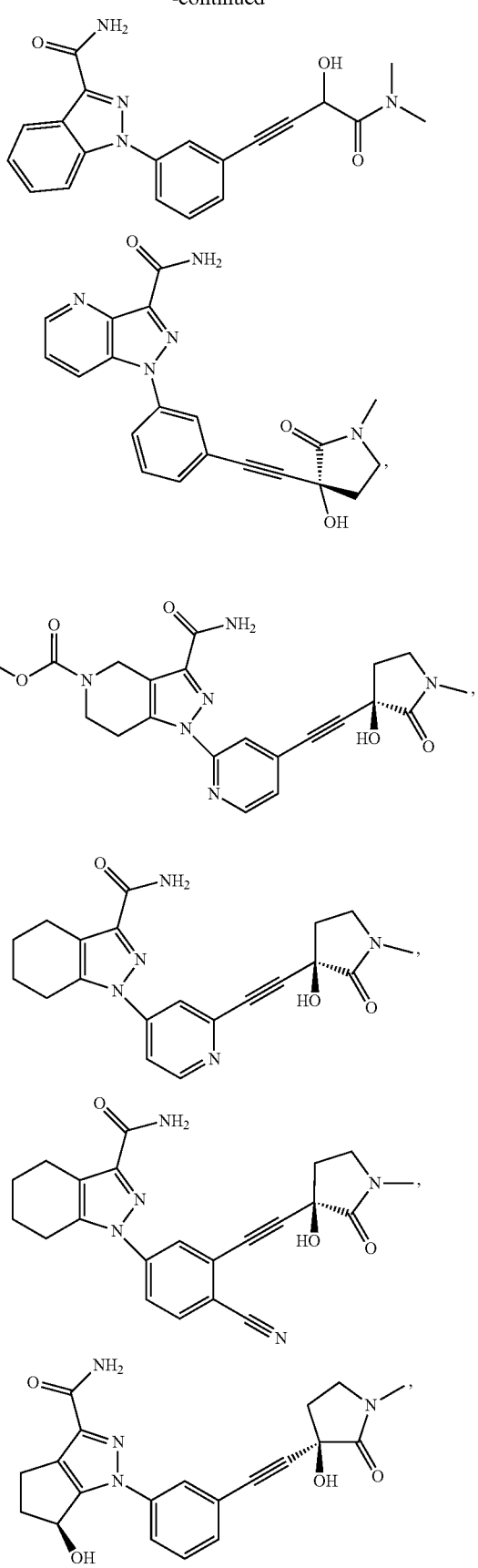

61
-continued
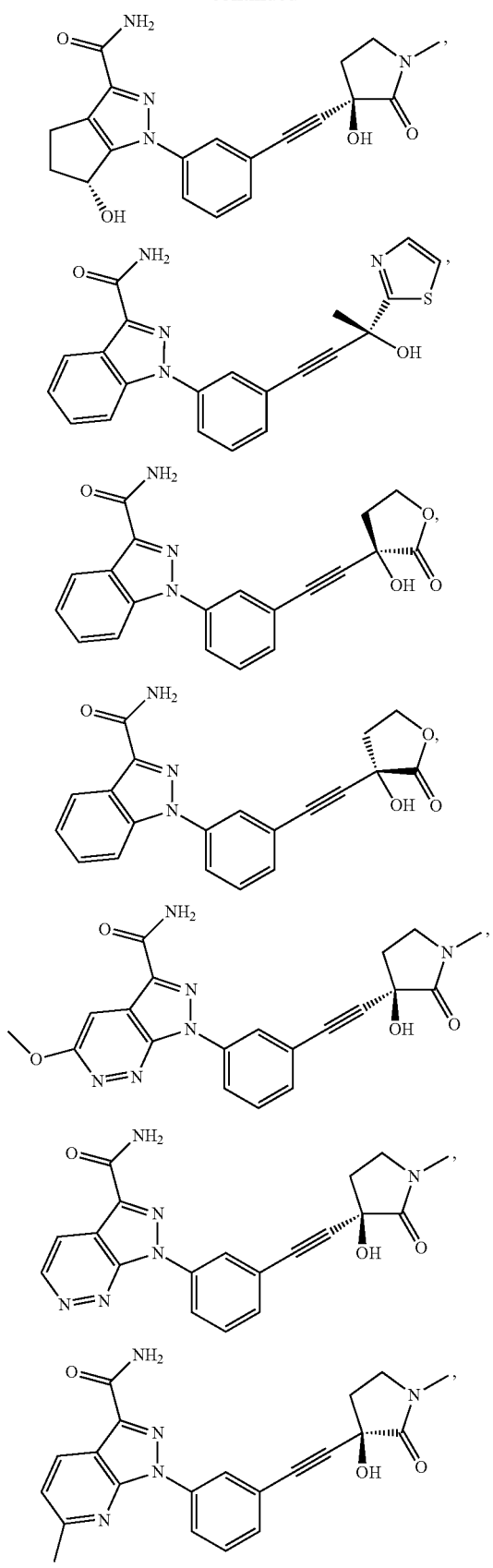
62
-continued
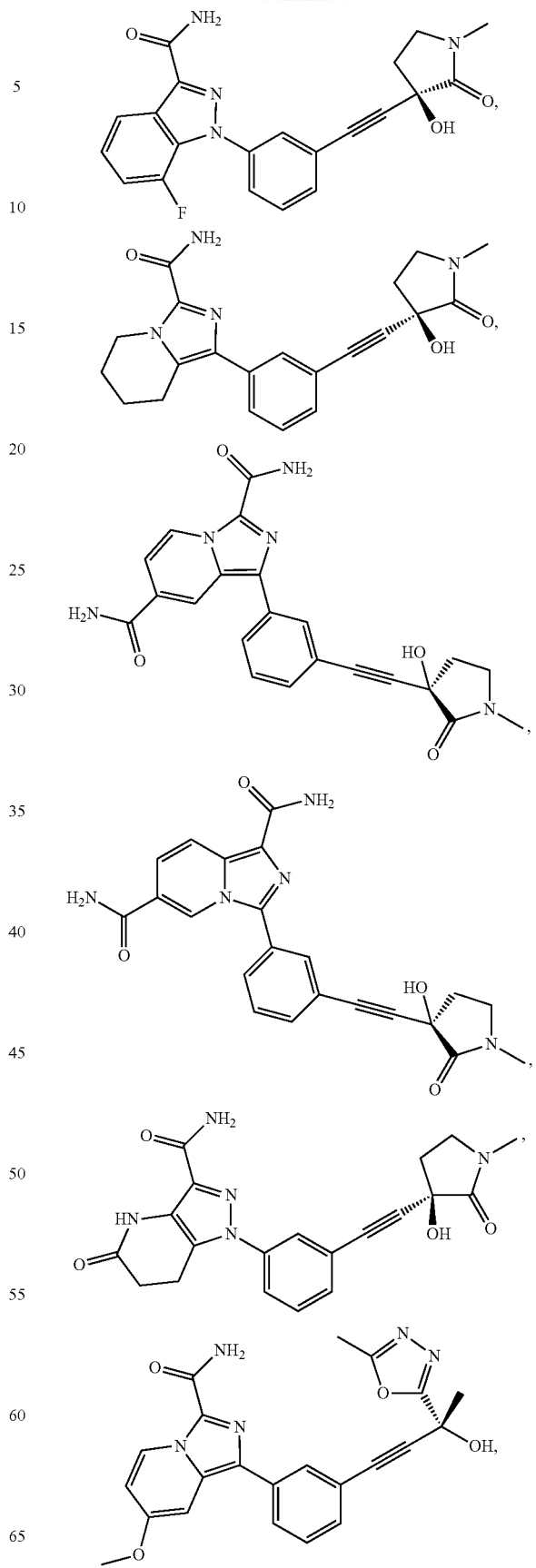

63
-continued
64
-continued
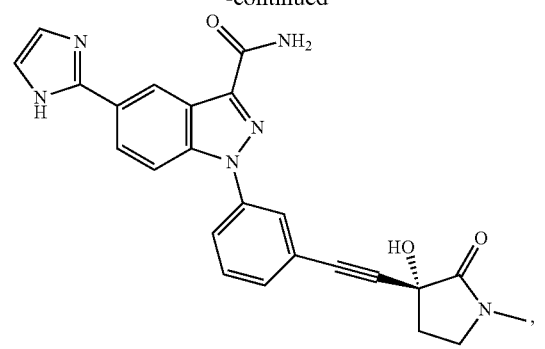
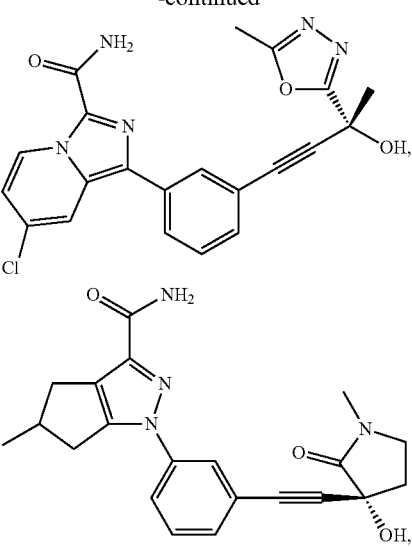
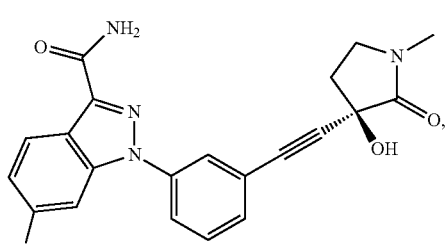
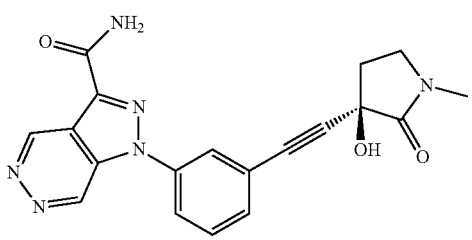
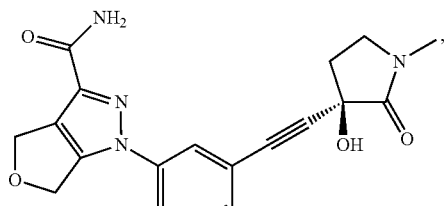
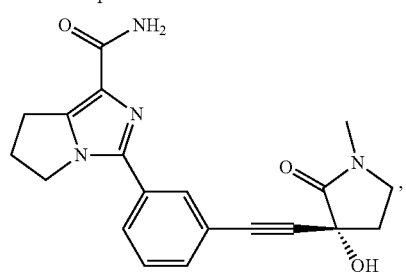

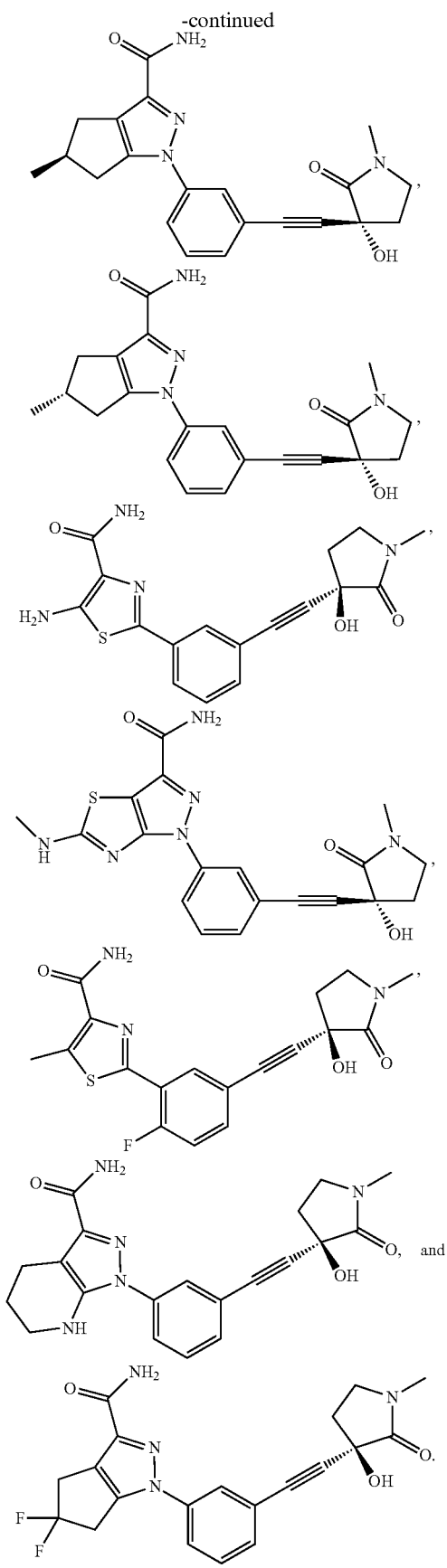

Some embodiments provide a pharmaceutical composition comprising a compound of the present invention and a pharmaceutically acceptable carrier, diluent or excipient. A compound or pharmaceutical composition described herein can be used in therapy, such as the treatment of an inflammatory condition (e.g., lupus, such as systemic lupus erythematosus, extra-renal lupus, or lupus nephritis, COPD, rhinitis, multiple sclerosis, IBD, arthritis, rheumatoid arthritis, dermatitis, endometriosis and transplant rejection). Also provided is the use of a compound or a pharmaceutical composition described herein for the preparation of a medicament for the treatment of an inflammatory condition (e.g., lupus, such as systemic lupus erythematosus, extra-renal lupus, or lupus nephritis, COPD, rhinitis, multiple sclerosis, IBD, arthritis, rheumatoid arthritis, dermatitis, endometriosis and transplant rejection).

Also provided is a method for the treatment of an inflammatory condition in a patient, comprising administering an effective amount of a compound or pharmaceutical composition as described herein to the patient. The inflammatory condition can be selected from the group consisting of lupus, such as systemic lupus erythematosus, extra-renal lupus, or lupus nephritis, COPD, rhinitis, multiple sclerosis, IBD, arthritis, rheumatoid arthritis, dermatitis, endometriosis and transplant rejection.

Further provided is a method of preparing a compound of Formula (0),

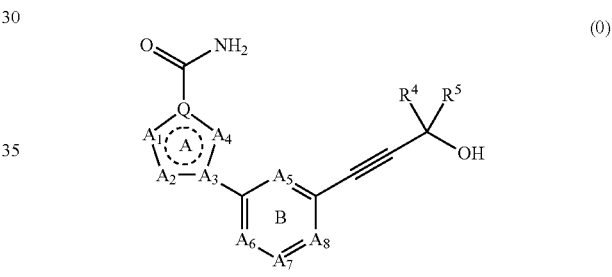

wherein Q, $A_1$-$A_8$, $R^4$ and $R^5$ are as defined above, comprising: contacting a compound of Formula (A):

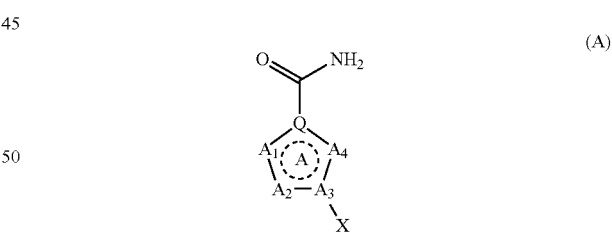

wherein X is Cl, Br or I, with a compound of Formula (B)

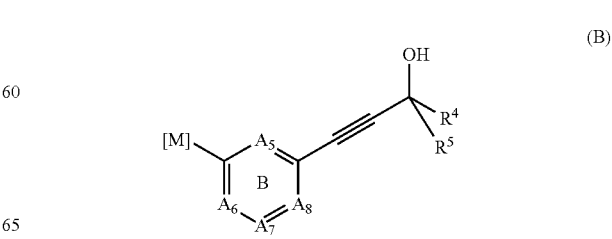

wherein [M] is a boronic acid, a boronic ester, or a trifluoroborate salt, in the presence of (a)(i) a palladium(0) catalyst or (a)(ii) a copper catalyst and (b) a base under Suzuki reaction conditions to yield a compound of Formula (0). Persons of skill in the art are familiar with Suzuki reactions and the reagents employed in such reactions. See, e.g., Suzuki, J. Organometallic Chem., 576:147-168 (1999). Non-limiting examples of palladium catalysts include $Pd(PPh_3)_4$, $Pd(OAc)_2$ and $Pd(PPh_3)_2Cl_2$. A non-limiting example of a copper catalyst is copper(II) acetate. Non-limiting examples of bases include sodium carbonate, potassium carbonate and cesium carbonate, or mixtures thereof.

In some embodiments, copper(II) acetate and pyridine as the base are employed under Chan-Lam coupling conditions, as is known in the art. For example, the carbon-nitrogen bond in an indazole or an aza-indazole can be formed using Chan-Lam coupling conditions. A variety of organic solvents may be employed, including toluene, THF, dioxane, 1,2-dichloroethane, DMF, DMSO and acetonitrile. Reaction temperatures vary depending on conditions but typically range from room temperature to 150° C.

In some embodiments, the invention provides a compound of Table 1:

TABLE 1

| Ex. | Structure | Name |
|---|---|---|
| 1 | 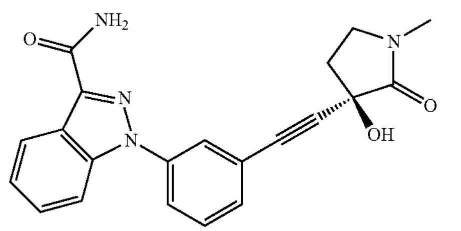 [SMILES: CN1CC[C@@](O)(C#Cc2cccc(-n3nc(C(N)=O)c4ccccc43)c2)C1=O] | 1-[3-[2-[(3R)-3-hydroxy-1-methyl-2-oxo-pyrrolidin-3-yl]ethynyl]phenyl]indazole-3-carboxamide |
| 2 | 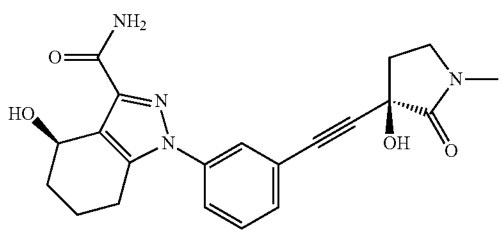 [SMILES: CN1CC[C@@](O)(C#Cc2cccc(-n3nc(C(N)=O)c4c3CCC[C@H]4O)c2)C1=O] | (4R)-4-hydroxy-1-[3-[2-[(3R)-3-hydroxy-1-methyl-2-oxo-pyrrolidin-3-yl]ethynyl]phenyl]-4,5,6,7-tetrahydroindazole-3-carboxamide |
| 3 | 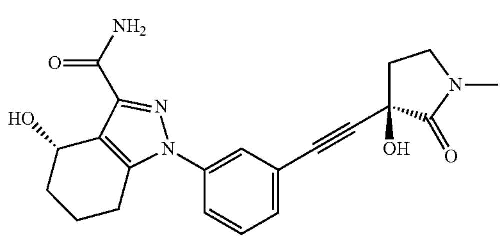 [SMILES: CN1CC[C@@](O)(C#Cc2cccc(-n3nc(C(N)=O)c4c3CCC[C@@H]4O)c2)C1=O] | (4S)-4-hydroxy-1-[3-[2-[(3R)-3-hydroxy-1-methyl-2-oxo-pyrrolidine-3-yl]ethynyl]phenyl]-4,5,6,7-tetrahydroindazole-3-carboxamide |
| 4 | 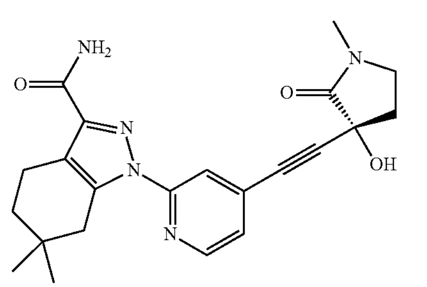 [SMILES: CN1CC[C@@](O)(C#Cc2ccnc(-n3nc(C(N)=O)c4c3CC(C)(C)CC4)c2)C1=O] | 1-[4-[2-[(3R)-3-hydroxy-1-methyl-2-oxo-pyrrolidin-3-yl]ethynyl]-2-pyridyl]-6,6-dimethyl-5,7-dihydro-4H-indazole-3-carboxamide |

TABLE 1-continued

| Ex. | Structure | Name |
|---|---|---|
| 5 | 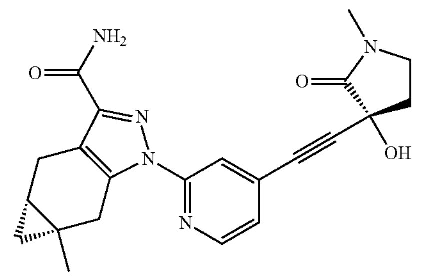 [SMILES: CN1CC[C@@](O)(C#Cc2ccnc(-n3nc(C(N)=O)c4c3C[C@]3(C)C[C@@H]3C4)c2)C1=O] | (4aR,5aS)-1-[4-[2-[(3R)-3-hydroxy-1-methyl-2-oxo-pyrrolidin-3-yl]ethynyl]-2-pyridyl]-5a-methyl-4,4a,5,6-tetrahydrocyclopropa[f]indazole-3-carboxamide |
| 6 | 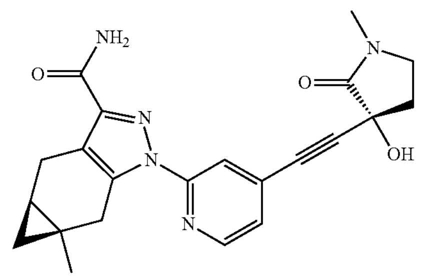 [SMILES: CN1CC[C@@](O)(C#Cc2ccnc(-n3nc(C(N)=O)c4c3C[C@@]3(C)C[C@H]3C4)c2)C1=O] | (4aS,5aR)-1-[4-[2-[(3R)-3-hydroxy-1-methyl-2-oxo-pyrrolidin-3-yl]ethynyl]-2-pyridyl]-5a-methyl-4,4a,5,6-tetrahydrocyclopropa[f]indazole-3-carboxamide |
| 7 | 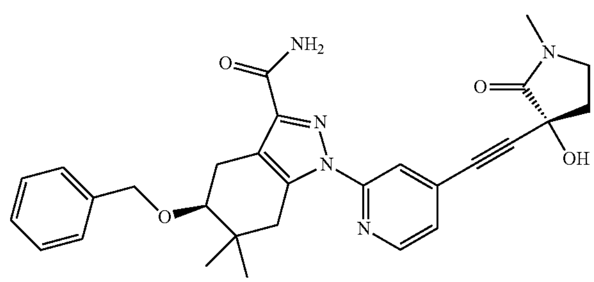 [SMILES: CN1CC[C@@](O)(C#Cc2ccnc(-n3nc(C(N)=O)c4c3CC(C)(C)[C@@H](OCc3ccccc3)C4)c2)C1=O] | (5S)-5-benzyloxy-1-[4-[2-[(3R)-3-hydroxy-1-methyl-2-oxo-pyrrolidin-3-yl]ethynyl]-2-pyridyl]-6,6-dimethyl-5,7-dihydro-4H-indazole-3-carboxamide |
| 8 | 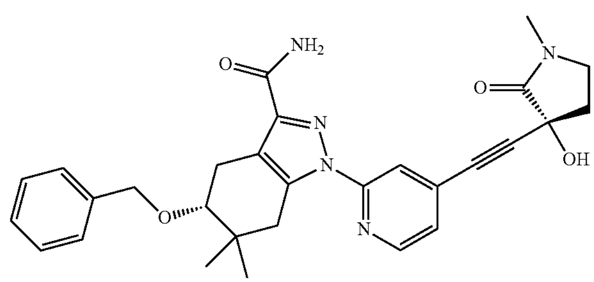 [SMILES: CN1CC[C@@](O)(C#Cc2ccnc(-n3nc(C(N)=O)c4c3CC(C)(C)[C@H](OCc3ccccc3)C4)c2)C1=O] | (5R)-5-benzyloxy-1-[4-[2-[(3R)-3-hydroxy-1-methyl-2-oxo-pyrrolidin-3-yl]ethynyl]-2-pyridyl]-6,6-dimethyl-5,7-dihydro-4H-indazole-3-carboxamide |
| 9 | 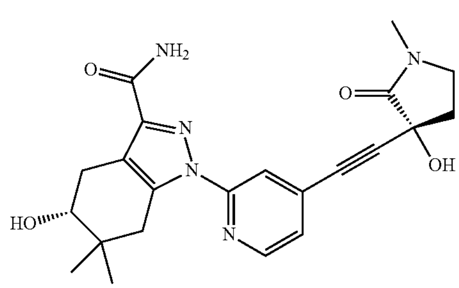 [SMILES: CN1CC[C@@](O)(C#Cc2ccnc(-n3nc(C(N)=O)c4c3CC(C)(C)[C@H](O)C4)c2)C1=O] | (5R)-5-hydroxy-1-[4-[2-[(3R)-3-hydroxy-1-methyl-2-oxo-pyrrolidin-3-yl]ethynyl]-2-pyridyl]-6,6-dimethyl-5,7-dihydro-4H-indazole-3-carboxamide |

TABLE 1-continued

| Ex. | Structure | Name |
| --- | --- | --- |
| 10 | 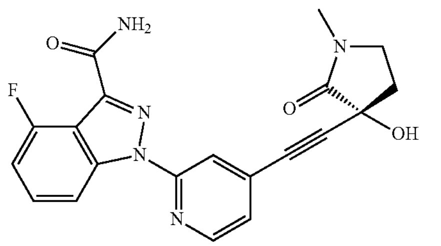 [SMILES: CN1CC[C@@](O)(C#Cc2ccnc(-n3nc(C(N)=O)c4c(F)cccc43)c2)C1=O] | 4-fluoro-1-[4-[2-[(3R)-3-hydroxy-1-methyl-2-oxo-pyrrolidin-3-yl]ethynyl]-2-pyridyl]indazole-3-carboxamide |
| 11 | 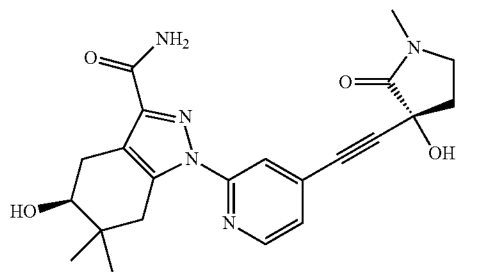 [SMILES: CN1CC[C@@](O)(C#Cc2ccnc(-n3nc(C(N)=O)c4c3CC(C)(C)[C@@H](O)C4)c2)C1=O] | (5S)-5-hydroxy-1-[4-[2-[(3R)-3-hydroxy-1-methyl-2-oxo-pyrrolidin-3-yl]ethynyl]-2-pyridyl]-6,6-dimethyl-5,7-dihydro-4H-indazole-3-carboxamide |
| 12 | 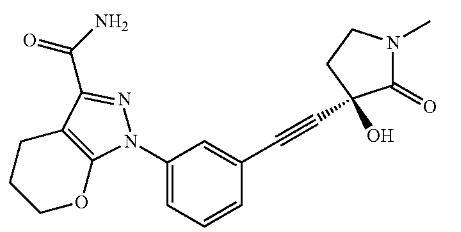 [SMILES: CN1CC[C@@](O)(C#Cc2cccc(-n3nc(C(N)=O)c4c3OCCC4)c2)C1=O] | 1-[3-[2-[(3R)-3-hydroxy-1-methyl-2-oxo-pyrrolidin-3-yl]ethynyl]phenyl]-5,6-dihydro-4H-pyrano[2,3-c]pyrazole-3-carboxamide |
| 13 | 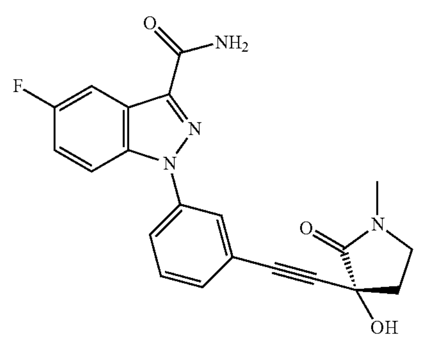 [SMILES: CN1CC[C@@](O)(C#Cc2cccc(-n3nc(C(N)=O)c4cc(F)ccc43)c2)C1=O] | 5-fluoro-1-[3-[2-[(3R)-3-hydroxy-1-methyl-2-oxo-pyrrolidin-3-yl]ethynyl]phenyl]indazole-3-carboxamide |
| 14 | 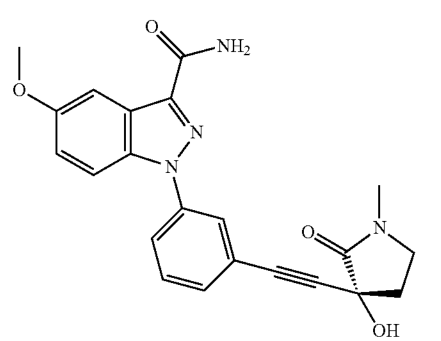 [SMILES: COc1ccc2c(c1)c(C(N)=O)nn2-c1cccc(C#C[C@]2(O)CCN(C)C2=O)c1] | 1-[3-[2-[(3R)-3-hydroxy-1-methyl-2-oxo-pyrrolidin-3-yl]ethynyl]phenyl]-5-methoxy-indazole-3-carboxamide |

TABLE 1-continued

| Ex. | Structure | Name |
|---|---|---|
| 15 | 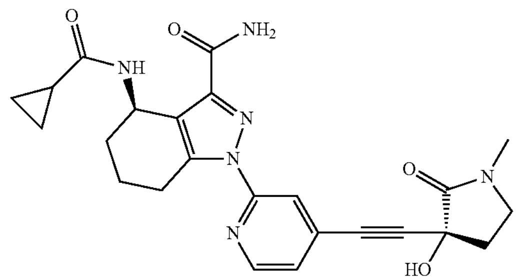 [SMILES: CN1CC[C@@](O)(C#Cc2ccnc(-n3nc(C(N)=O)c4c3CCC[C@H]4NC(=O)C3CC3)c2)C1=O] | (4R)-4-(cyclopropanecarbonylamino)-1-[4-[2-[(3R)-3-hydroxy-1-methyl-2-oxo-pyrrolidin-3-yl]ethynyl]-2-pyridyl]-4,5,6,7-tetrahydroindazole-3-carboxamide |
| 16 | 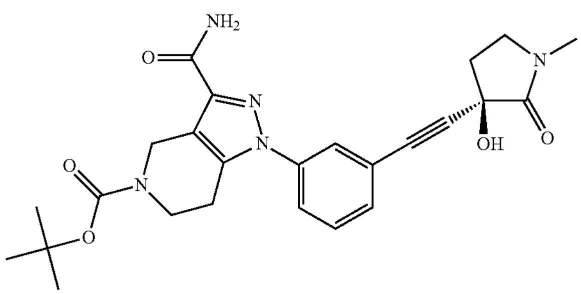 [SMILES: CN1CC[C@@](O)(C#Cc2cccc(-n3nc(C(N)=O)c4c3CCN(C(=O)OC(C)(C)C)C4)c2)C1=O] | tert-butyl 3-carbamoyl-1-[3-[2-[(3R)-3-hydroxy-1-methyl-2-oxo-pyrrolidin-3-yl]ethynyl]phenyl]-6,7-dihydro-4H-pyrazolo[4,3-c]pyridine-5-carboxylate |
| 17 | 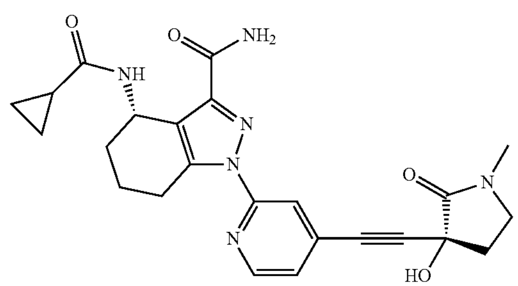 [SMILES: CN1CC[C@@](O)(C#Cc2ccnc(-n3nc(C(N)=O)c4c3CCC[C@@H]4NC(=O)C3CC3)c2)C1=O] | (4S)-4-(cyclopropanecarbonylamino)-1-[4-[2-[(3R)-3-hydroxy-1-methyl-2-oxo-pyrrolidin-3-yl]ethynyl]-2-pyridyl]-4,5,6,7-tetrahydroindazole-3-carboxamide |
| 18 | 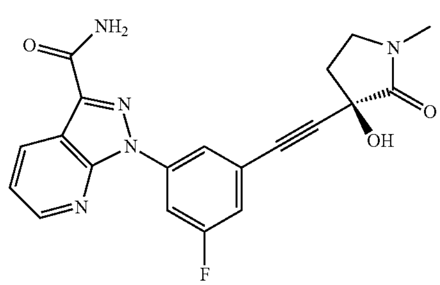 [SMILES: CN1CC[C@@](O)(C#Cc2cc(F)cc(-n3nc(C(N)=O)c4cccnc43)c2)C1=O] | 1-[3-fluoro-5-[2-[(3R)-3-hydroxy-1-methyl-2-oxo-pyrrolidin-3-yl]ethynyl]phenyl]pyrazolo[3,4-b]pyridine-3-carboxamide |
| 19 | 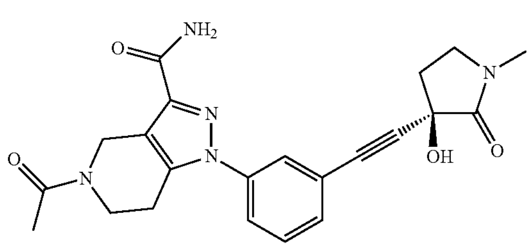 [SMILES: CC(=O)N1CCc2c(c(C(N)=O)nn2-c2cccc(C#C[C@]3(O)CCN(C)C3=O)c2)C1] | 5-acetyl-1-[3-[2-[(3R)-3-hydroxy-1-methyl-2-oxo-pyrrolidin-3-yl]ethynyl]phenyl]-6,7-dihydro-4H-pyrazolo[4,3-c]pyridine-3-carboxamide |

TABLE 1-continued

| Ex. | Structure | Name |
|---|---|---|
| 20 | 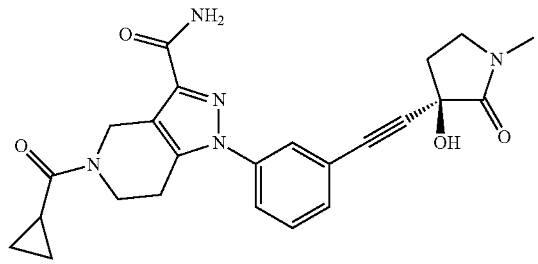 [SMILES: CN1CC[C@@](O)(C#Cc2cccc(-n3nc(C(N)=O)c4c3CCN(C(=O)C3CC3)C4)c2)C1=O] | 5-(cyclopropanecarbonyl)-1-[3-[2-[(3R)-3-hydroxy-1-methyl-2-oxo-pyrrolidin-3-yl]ethynyl]phenyl]-6,7-dihydro-4H-pyrazolo[4,3-c]pyridine-3-carboxamide |
| 21 | 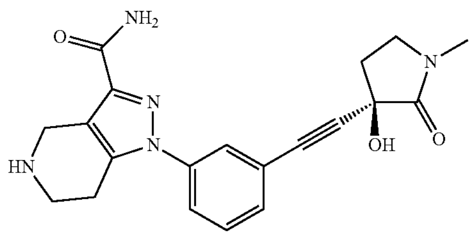 [SMILES: CN1CC[C@@](O)(C#Cc2cccc(-n3nc(C(N)=O)c4c3CCNC4)c2)C1=O] | 1-[3-[2-[(3R)-3-hydroxy-1-methyl-2-oxo-pyrrolidin-3-yl]ethynyl]phenyl]-4,5,6,7-tetrahydropyrazolo[4,3-c]pyridine-3-carboxamide |
| 22 | 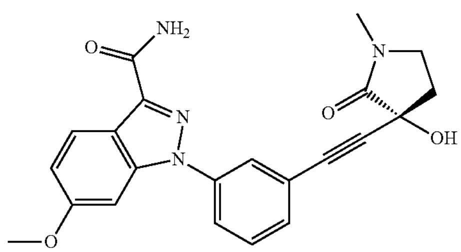 [SMILES: COc1ccc2c(C(N)=O)nn(-c3cccc(C#C[C@]4(O)CCN(C)C4=O)c3)c2c1] | 1-[3-[2-[(3R)-3-hydroxy-1-methyl-2-oxo-pyrrolidin-3-yl]ethynyl]phenyl]-6-methoxy-indazole-3-carboxamide |
| 23 | 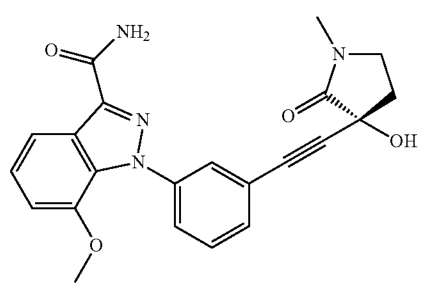 [SMILES: COc1cccc2c(C(N)=O)nn(-c3cccc(C#C[C@]4(O)CCN(C)C4=O)c3)c12] | 1-[3-[2-[(3R)-3-hydroxy-1-methyl-2-oxo-pyrrolidin-3-yl]ethynyl]phenyl]-7-methoxy-indazole-3-carboxamide |
| 24 | 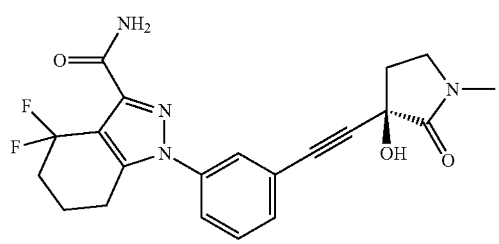 [SMILES: CN1CC[C@@](O)(C#Cc2cccc(-n3nc(C(N)=O)c4c3CCCC4(F)F)c2)C1=O] | 4,4-difluoro-1-[3-[2-[(3R)-3-hydroxy-1-methyl-2-oxo-pyrrolidin-3-yl]ethynyl]phenyl]-6,7-dihydro-5H-indazole-3-carboxamide |
| 25 | 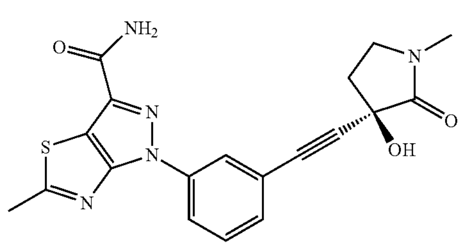 [SMILES: Cc1nc2c(s1)c(C(N)=O)nn2-c1cccc(C#C[C@]2(O)CCN(C)C2=O)c1] | 1-[3-[2-[(3R)-3-hydroxy-1-methyl-2-oxo-pyrrolidin-3-yl]ethynyl]phenyl]-5-methyl-pyrazolo[3,4-d]thiazole-3-carboxamide |

TABLE 1-continued

| Ex. | Structure | Name |
|---|---|---|
| 26 | 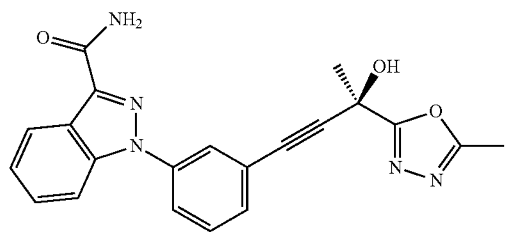 [SMILES: Cc1nnc([C@](C)(O)C#Cc2cccc(-n3nc(C(N)=O)c4ccccc43)c2)o1] | 1-[3-[(3R)-3-hydroxy-3-(5-methyl-1,3,4-oxadiazol-2-yl)but-1-ynyl]phenyl]indazole-3-carboxamide |
| 27 | 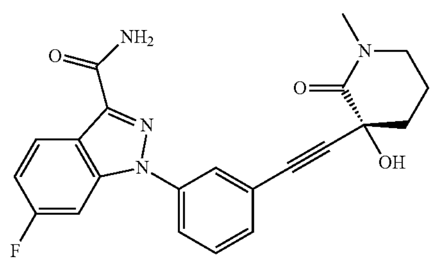 [SMILES: CN1CCC[C@@](O)(C#Cc2cccc(-n3nc(C(N)=O)c4ccc(F)cc43)c2)C1=O] | 6-fluoro-1-[3-[2-[(3R)-3-hydroxy-1-methyl-2-oxo-3-piperidyl]ethynyl]phenyl]indazole-3-carboxamide |
| 28 | 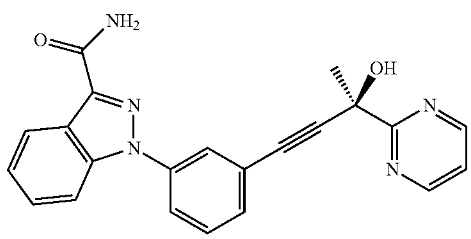 [SMILES: C[C@@](O)(C#Cc1cccc(-n2nc(C(N)=O)c3ccccc32)c1)c1ncccn1] | 1-[3-[(3R)-3-hydroxy-3-pyrimidin-2-yl-but-1-ynyl]phenyl]indazole-3-carboxamide |
| 29 | 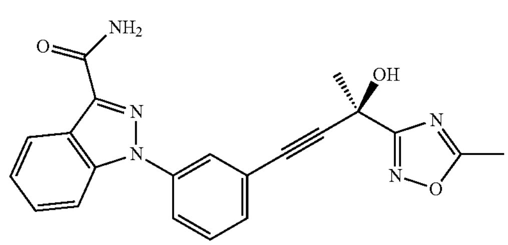 [SMILES: Cc1nc([C@](C)(O)C#Cc2cccc(-n3nc(C(N)=O)c4ccccc43)c2)no1] | 1-[3-[(3R)-3-hydroxy-3-(5-methyl-1,2,4-oxadiazol-3-yl)but-1-ynyl]phenyl]indazole-3-carboxamide |
| 30 | 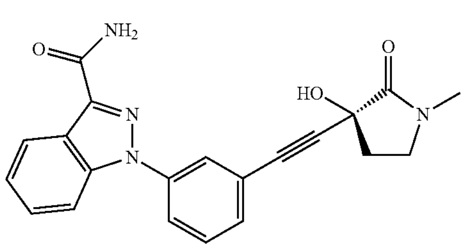 [SMILES: CN1CC[C@](O)(C#Cc2cccc(-n3nc(C(N)=O)c4ccccc43)c2)C1=O] | 1-[3-[2-[(3S)-3-hydroxy-1-methyl-2-oxo-pyrrolidin-3-yl]ethynyl]phenyl]indazole-3-carboxamide |
| 31 | 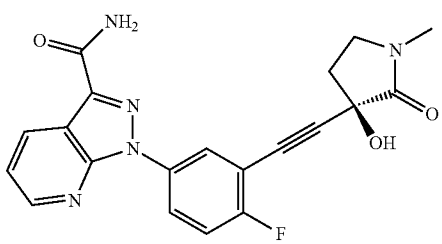 [SMILES: CN1CC[C@@](O)(C#Cc2cc(-n3nc(C(N)=O)c4cccnc43)ccc2F)C1=O] | 1-[4-fluoro-3-[2-[(3R)-3-hydroxy-1-methyl-2-oxo-pyrrolidin-3-yl]ethynyl]phenyl]pyrazolo[3,4-b]pyridine-3-carboxamide |

TABLE 1-continued

| Ex. | Structure | Name |
|---|---|---|
| 32 | 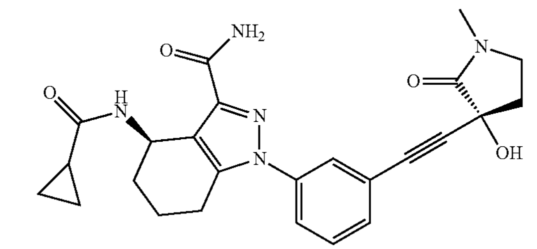 [SMILES: CN1CC[C@@](O)(C#Cc2cccc(-n3nc(C(N)=O)c4c3CCC[C@H]4NC(=O)C3CC3)c2)C1=O] | (4R)-4-(cyclopropanecarbonyl-amino)-1-[3-[2-[(3R)-3-hydroxy-1-methyl-2-oxo-pyrrolidin-3-yl]ethynyl]phenyl]-4,5,6,7-tetrahydroindazole-3-carboxamide |
| 33 | 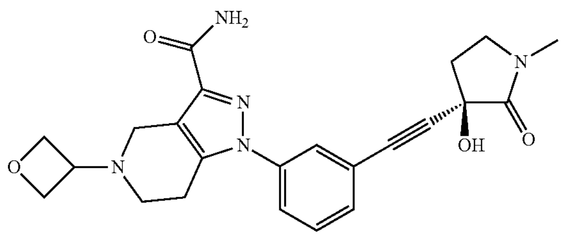 [SMILES: CN1CC[C@@](O)(C#Cc2cccc(-n3nc(C(N)=O)c4c3CCN(C3COC3)C4)c2)C1=O] | 1-[3-[2-[(3R)-3-hydroxy-1-methyl-2-oxo-pyrrolidin-3-yl]ethynyl]phenyl]-5-(oxetan-3-yl)-6,7-dihydro-4H-pyrazolo[4,3-c]pyridine-3-carboxamide |
| 34 | 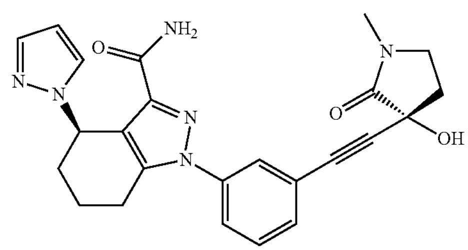 [SMILES: CN1CC[C@@](O)(C#Cc2cccc(-n3nc(C(N)=O)c4c3CCC[C@H]4n3cccn3)c2)C1=O] | (4R)-1-[3-[2-[(3R)-3-hydroxy-1-methyl-2-oxo-pyrrolidin-3-yl]ethynyl]phenyl]-4-pyrazol-1-yl-4,5,6,7-tetrahydro-indazole-3-carboxamide |
| 35 | 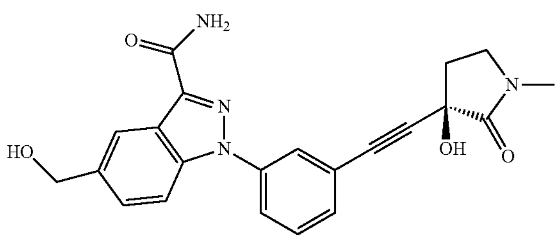 [SMILES: CN1CC[C@@](O)(C#Cc2cccc(-n3nc(C(N)=O)c4cc(CO)ccc43)c2)C1=O] | 5-(hydroxymethyl)-1-[3-[2-[(3R)-3-hydroxy-1-methyl-2-oxo-pyrrolidin-3-yl]ethynyl]phenyl]indazole-3-carboxamide |
| 36 | 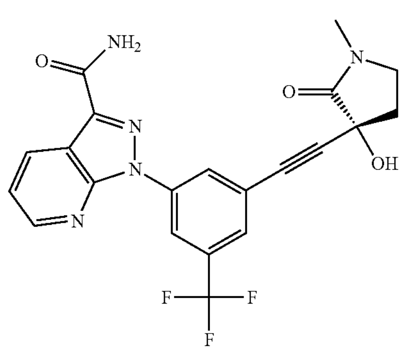 [SMILES: CN1CC[C@@](O)(C#Cc2cc(-n3nc(C(N)=O)c4cccnc43)cc(C(F)(F)F)c2)C1=O] | 1-[3-[2-[(3R)-3-hydroxy-1-methyl-2-oxo-pyrrolidin-3-yl]ethynyl]-5-(trifluoromethyl)phenyl]pyrazolo[3,4-b]pyridine-3-carboxamide |

TABLE 1-continued

| Ex. | Structure | Name |
|---|---|---|
| 37 | 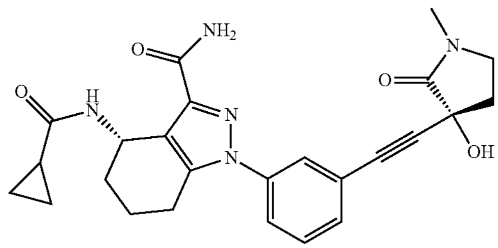 [SMILES: CN1CC[C@@](O)(C#Cc2cccc(-n3nc(C(N)=O)c4c3CCC[C@@H]4NC(=O)C3CC3)c2)C1=O] | (4S)-4-(cyclopropanecarbonylamino)-1-[3-[2-[(3R)-3-hydroxy-1-methyl-2-oxo-pyrrolidin-3-yl]ethynyl]phenyl]-4,5,6,7-tetrahydroindazole-3-carboxamide |
| 38 | 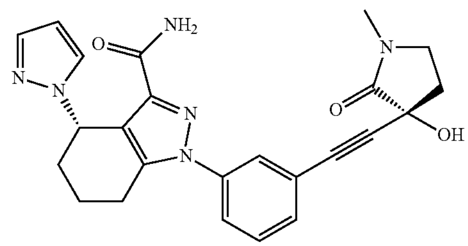 [SMILES: CN1CC[C@@](O)(C#Cc2cccc(-n3nc(C(N)=O)c4c3CCC[C@@H]4n3cccn3)c2)C1=O] | (4S)-1-[3-[2-[(3R)-3-hydroxy-1-methyl-2-oxo-pyrrolidin-3-yl]ethynyl]phenyl]-4-pyrazol-1-yl-4,5,6,7-tetrahydroindazole-3-carboxamide |
| 39 | 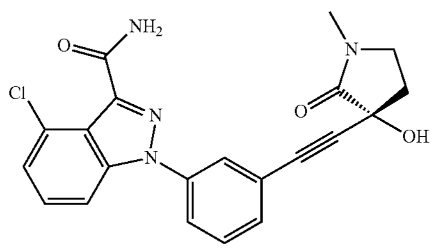 [SMILES: CN1CC[C@@](O)(C#Cc2cccc(-n3nc(C(N)=O)c4c(Cl)cccc43)c2)C1=O] | 4-chloro-1-[3-[2-[(3R)-3-hydroxy-1-methyl-2-oxo-pyrrolidin-3-yl]ethynyl]phenyl]indazole-3-carboxamide |
| 40 | 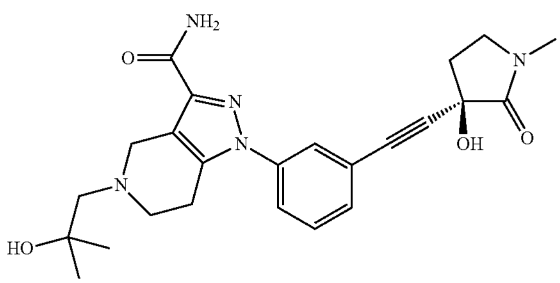 [SMILES: CN1CC[C@@](O)(C#Cc2cccc(-n3nc(C(N)=O)c4c3CCN(CC(C)(C)O)C4)c2)C1=O] | 1-[3-[2-[(3R)-3-hydroxy-1-methyl-2-oxo-pyrrolidin-3-yl]ethynyl]phenyl]-5-(2-hydroxy-2-methyl-propyl)-6,7-dihydro-4H-pyrazolo[4,3-c]pyridine-3-carboxamide |
| 41 | 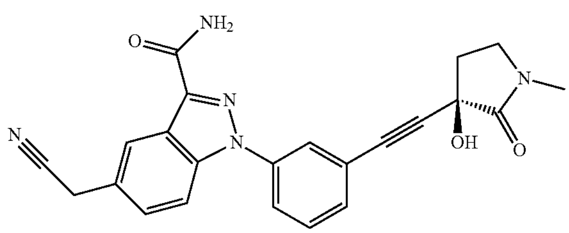 [SMILES: CN1CC[C@@](O)(C#Cc2cccc(-n3nc(C(N)=O)c4cc(CC#N)ccc43)c2)C1=O] | 5-(cyanomethyl)-1-[3-[2-[(3R)-3-hydroxy-1-methyl-2-oxo-pyrrolidin-3-yl]ethynyl]phenyl]indazole-3-carboxamide |
| 42 | 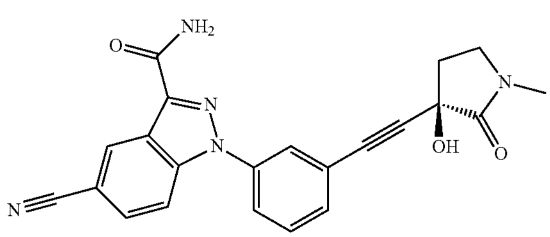 [SMILES: CN1CC[C@@](O)(C#Cc2cccc(-n3nc(C(N)=O)c4cc(C#N)ccc43)c2)C1=O] | 5-cyano-1-[3-[2-[(3R)-3-hydroxy-1-methyl-2-oxo-pyrrolidin-3-yl]ethynyl]phenyl]indazole-3-carboxamide |

TABLE 1-continued

| Ex. | Structure | Name |
|---|---|---|
| 43 | 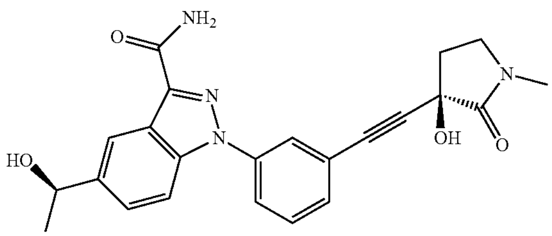 [SMILES: C[C@@H](O)c1ccc2c(c1)c(C(N)=O)nn2-c1cccc(C#C[C@]2(O)CCN(C)C2=O)c1] | 5-[(1R)-1-hydroxyethyl]-1-[3-[2-[(3R)-3-hydroxy-1-methyl-2-oxo-pyrrolidin-3-yl]ethynyl]phenyl]indazole-3-carboxamide |
| 44 | 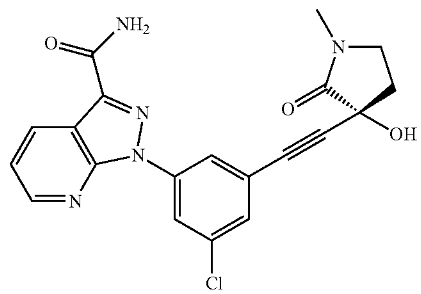 [SMILES: CN1CC[C@@](O)(C#Cc2cc(Cl)cc(-n3nc(C(N)=O)c4cccnc43)c2)C1=O] | 1-[3-chloro-5-[2-[(3R)-3-hydroxy-1-methyl-2-oxo-pyrrolidin-3-yl]ethynyl]phenyl]pyrazolo[3,4-b]pyridine-3-carboxamide |
| 45 | 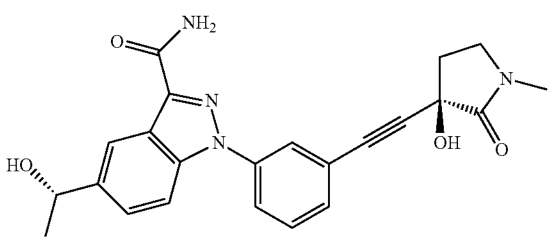 [SMILES: C[C@H](O)c1ccc2c(c1)c(C(N)=O)nn2-c1cccc(C#C[C@]2(O)CCN(C)C2=O)c1] | 5-[(1S)-1-hydroxyethyl]-1-[3-[2-[(3R)-3-hydroxy-1-methyl-2-oxo-pyrrolidin-3-yl]ethynyl]phenyl]indazole-3-carboxamide |
| 46 | 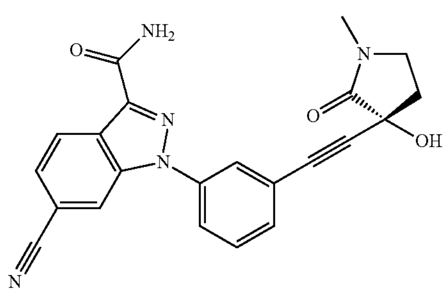 [SMILES: CN1CC[C@@](O)(C#Cc2cccc(-n3nc(C(N)=O)c4ccc(C#N)cc43)c2)C1=O] | 6-cyano-1-[3-[2-[(3R)-3-hydroxy-1-methyl-2-oxo-pyrrolidin-3-yl]ethynyl]phenyl]indazole-3-carboxamide |
| 47 | 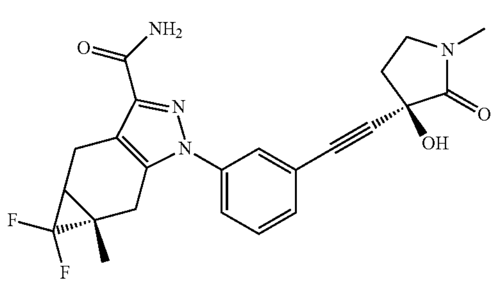 | (5aS)-5,5-difluoro-1-[3-[2-[(3R)-3-hydroxy-1-methyl-2-oxo-pyrrolidin-3-yl]ethynyl]phenyl]-5a-methyl-4a,6-dihydro-4H-cyclopropa[f]indazole-3-carboxamide |

TABLE 1-continued

| Ex. | Structure | Name |
|---|---|---|
| 48 | 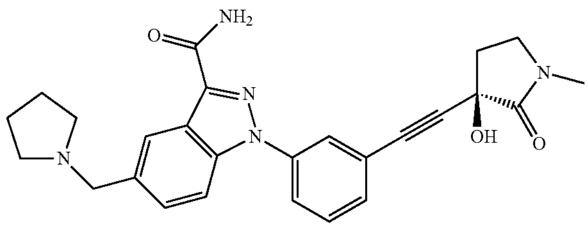 [SMILES: CN1CC[C@@](O)(C#Cc2cccc(-n3nc(C(N)=O)c4cc(CN5CCCC5)ccc43)c2)C1=O] | 1-[3-[2-[(3R)-3-hydroxy-1-methyl-2-oxo-pyrrolidin-3-yl]ethynyl]phenyl]-5-(pyrrolidine-1-ylmethyl)indazole-3-carboxamide |
| 49 | 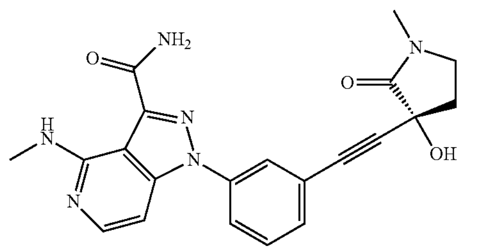 [SMILES: CNc1nccc2c1c(C(N)=O)nn2-c1cccc(C#C[C@]2(O)CCN(C)C2=O)c1] | 1-[3-[2-[(3R)-3-hydroxy-1-methyl-2-oxo-pyrrolidin-3-yl]ethynyl]phenyl]-4-(methylamino)pyrazolo[4,3-c]pyridine-3-carboxamide |
| 50 | 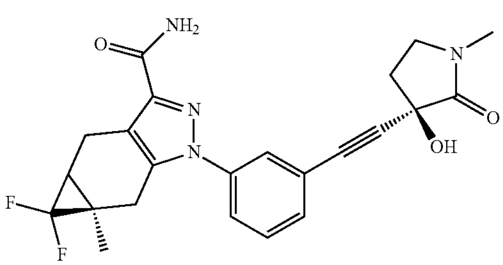 | (5aR)-5,5-difluoro-1-[3-[2-[(3R)-3-hydroxy-1-methyl-2-oxo-pyrrolidin-3-yl]ethynyl]phenyl]-5a-methyl-4a,6-dihydro-4H-cyclopropa[f]indazole-3-carboxamide |
| 51 | 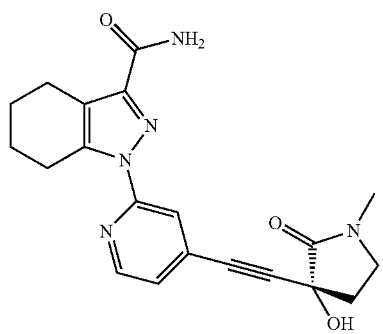 | 1-[4-[2-[(3R)-3-hydroxy-1-methyl-2-oxo-pyrrolidin-3-yl]ethynyl]-2-pyridyl]-4,5,6,7-tetrahydroindazole-3-carboxamide |
| 52 | 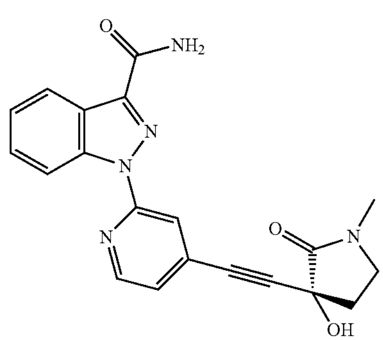 [SMILES: CN1CC[C@@](O)(C#Cc2ccnc(-n3nc(C(N)=O)c4ccccc43)c2)C1=O] | 1-[4-[2-[(3R)-3-hydroxy-1-methyl-2-oxo-pyrrolidin-3-yl]ethynyl]-2-pyridyl]indazole-3-carboxamide |

TABLE 1-continued

| Ex. | Structure | Name |
|---|---|---|
| 53 | 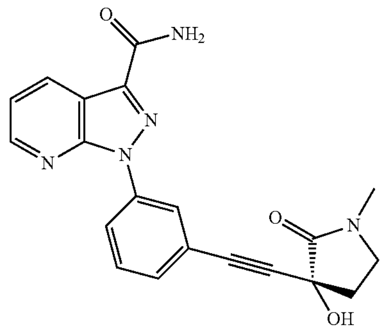 [SMILES: CN1CC[C@@](O)(C#Cc2cccc(-n3nc(C(N)=O)c4cccnc43)c2)C1=O] | 1-[3-[2-[(3R)-3-hydroxy-1-methyl-2-oxo-pyrrolidin-3-yl]ethynyl]phenyl]pyrazolo[3,4-b]pyridine-3-carboxamide |
| 54 | 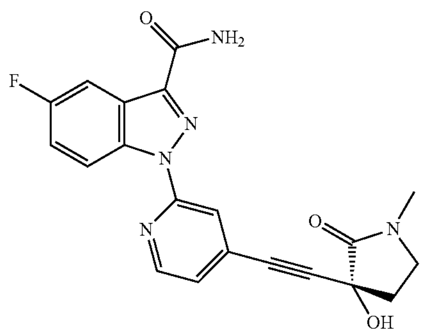 [SMILES: CN1CC[C@@](O)(C#Cc2ccnc(-n3nc(C(N)=O)c4cc(F)ccc43)c2)C1=O] | 5-fluoro-1-[4-[2-[(3R)-3-hydroxy-1-methyl-2-oxo-pyrrolidin-3-yl]ethynyl]-2-pyridiyl]indazole-3-carboxamide |
| 55 | 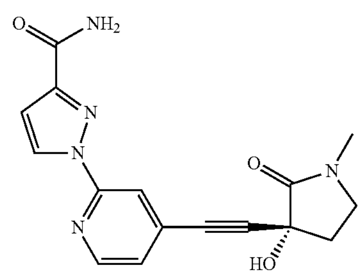 [SMILES: CN1CC[C@@](O)(C#Cc2ccnc(-n3ccc(C(N)=O)n3)c2)C1=O] | 1-[4-[2-[(3R)-3-hydroxy-1-methyl-2-oxo-pyrrolidin-3-yl]ethynyl]-2-pyridyl]pyrazole-3-carboxamide |
| 56 | 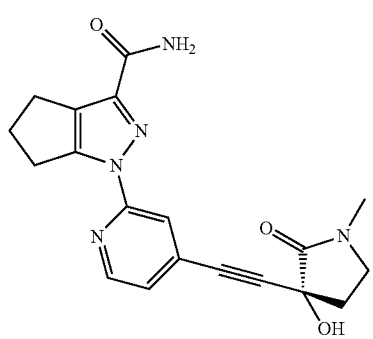 [SMILES: CN1CC[C@@](O)(C#Cc2ccnc(-n3nc(C(N)=O)c4c3CCC4)c2)C1=O] | 1-[4-[2-[(3R)-3-hydroxy-1-methyl-2-oxo-pyrrolidin-3-yl]ethynyl]-2-pyridyl]-5,6-dihydro-4H-cyclopenta[c]pyrazole-3-carboxamide |

TABLE 1-continued

| Ex. | Structure | Name |
|---|---|---|
| 57 | 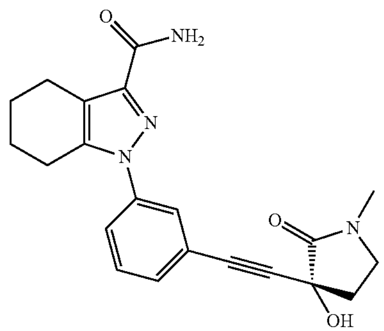 [SMILES: CN1CC[C@@](O)(C#Cc2cccc(-n3nc(C(N)=O)c4c3CCCC4)c2)C1=O] | 1-[3-[2-[(3R)-3-hydroxy-1-methyl-2-oxo-pyrrolidin-3-yl]ethynyl]phenyl]-4,5,6,7-tetrahydroindazole-3-carboxamide |
| 58 | 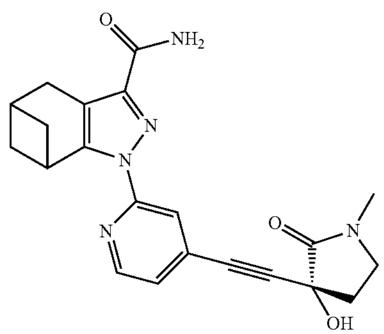 [SMILES: CN1CC[C@@](O)(C#Cc2ccnc(-n3nc(C(N)=O)c4c3C3CC(C4)C3)c2)C1=O] | (R)-1-(4-((3-hydroxy-1-methyl-2-oxopyrrolidin-3-yl)ethynyl)pyridin-2-yl)-4,5,6,7-tetrahydro-1H-5,7-methanoindazole-3-carboxamide |
| 59 | 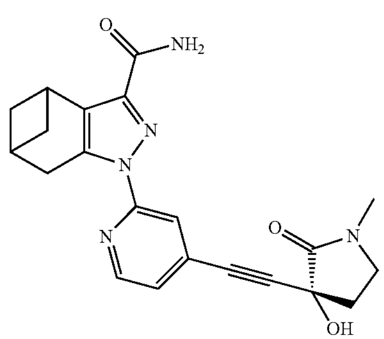 [SMILES: CN1CC[C@@](O)(C#Cc2ccnc(-n3nc(C(N)=O)c4c3CC3CC4C3)c2)C1=O] | (R)-1-(4-((3-hydroxy-1-methyl-2-oxopyrrolidin-3-yl)ethynyl)pyridin-2-yl)-4,5,6,7-tetrahydro-1H-4,6-methanoindazole-3-carboxamide |
| 60 | 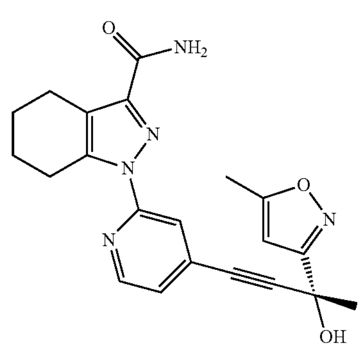 [SMILES: Cc1cc([C@](C)(O)C#Cc2ccnc(-n3nc(C(N)=O)c4c3CCCC4)c2)no1] | 1-[4-[(3R)-3-hydroxy-3-(5-methylisoxazol-3-yl)but-1-ynyl]-2-pyridyl]-4,5,6,7-tetrahydroindazole-3-carboxamide |

TABLE 1-continued

| Ex. | Structure | Name |
|---|---|---|
| 61 | 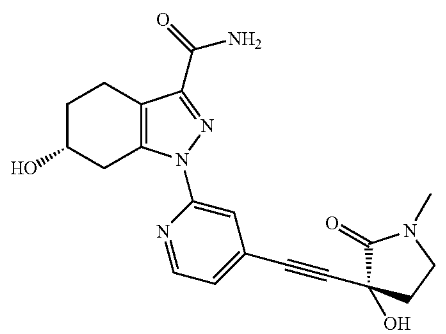 [SMILES: CN1CC[C@@](O)(C#Cc2ccnc(-n3nc(C(N)=O)c4c3C[C@H](O)CC4)c2)C1=O] | (6R)-6-hydroxy-1-[4-[2-[(3R)-3-hydroxy-1-methyl-2-oxo-pyrrolidin-3-yl]ethynyl]-2-pyridyl]-4,5,6,7-tetrahydro-indazole-3-carboxamide |
| 62 | 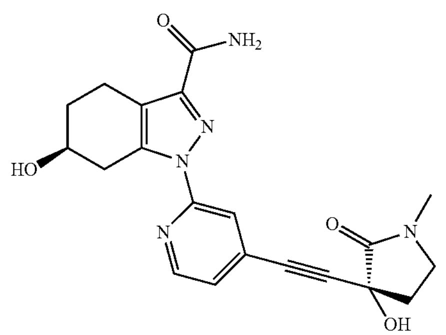 [SMILES: CN1CC[C@@](O)(C#Cc2ccnc(-n3nc(C(N)=O)c4c3C[C@@H](O)CC4)c2)C1=O] | (6S)-6-hydroxy-1-[4-[2-[(3R)-3-hydroxy-1-methyl-2-oxo-pyrrolidin-3-yl]ethynyl]-2-pyridyl]-4,5,6,7-tetrahydro-indazole-3-carboxamide |
| 63 | 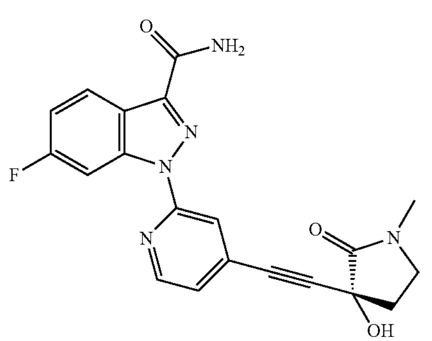 [SMILES: CN1CC[C@@](O)(C#Cc2ccnc(-n3nc(C(N)=O)c4ccc(F)cc43)c2)C1=O] | 6-fluoro-1-[4-[2-[(3R)-3-hydroxy-1-methyl-2-oxo-pyrrolidin-3-yl]ethynyl]-2-pyridyl]indazole-3-carboxamide |
| 64 | 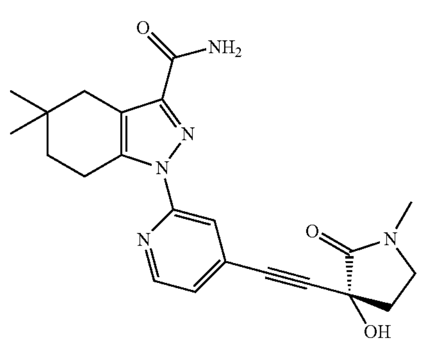 [SMILES: CN1CC[C@@](O)(C#Cc2ccnc(-n3nc(C(N)=O)c4c3CCC(C)(C)C4)c2)C1=O] | 1-[4-[2-[(3R)-3-hydroxy-1-methyl-2-oxo-pyrrolidin-3-yl]ethynyl]-2-pyridyl]-5,5-dimethyl-6,7-dihydro-4H-indazole-3-carboxamide |

TABLE 1-continued

| Ex. | Structure | Name |
|---|---|---|
| 65 | 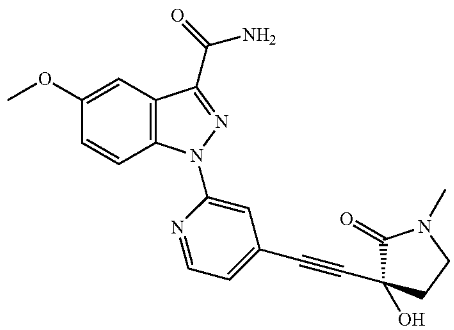 [SMILES: COc1ccc2c(c1)c(C(N)=O)nn2-c1cc(C#C[C@]2(O)CCN(C)C2=O)ccn1] | 1-[4-[2-[(3R)-3-hydroxy-1-methyl-2-oxo-pyrrolidin-3-yl]ethynyl]-2-pyridyl]-5-methoxy-indazole-3-carboxamide |
| 66 | 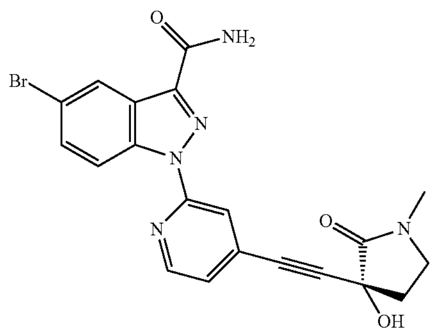 [SMILES: CN1CC[C@@](O)(C#Cc2ccnc(-n3nc(C(N)=O)c4cc(Br)ccc43)c2)C1=O] | 5-bromo-1-[4-[2-[(3R)-3-hydroxy-1-methyl-2-oxo-pyrrolidin-3-yl]ethynyl]-2-pyridyl]indazole-3-carboxamide |
| 67 | 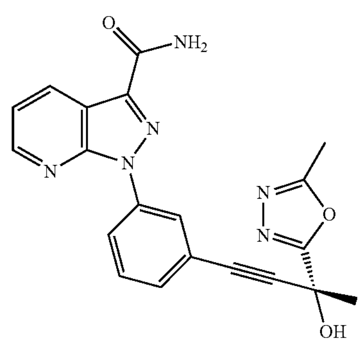 [SMILES: Cc1nnc([C@](C)(O)C#Cc2cccc(-n3nc(C(N)=O)c4cccnc43)c2)o1] | 1-[3-[(3R)-3-hydroxy-3-(5-methyl-1,3,4-oxadiazol-2-yl)but-1-ynyl]phenyl]pyrazolo[3,4-b]pyridine-3-carboxamide |
| 68 | 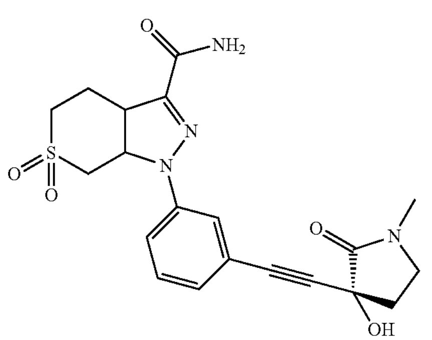 [SMILES: CN1CC[C@@](O)(C#Cc2cccc(N3N=C(C(N)=O)C4CCS(=O)(=O)CC43)c2)C1=O] | 1-[3-[2-[(3R)-3-hydroxy-1-methyl-2-oxo-pyrrolidin-3-yl]ethynyl]phenyl]-6,6-dioxo-5,7-dihydro-4H-thiopyrano[3,4-c]pyrazole-3-carboxamide |

TABLE 1-continued

| Ex. | Structure | Name |
|---|---|---|
| 69 | 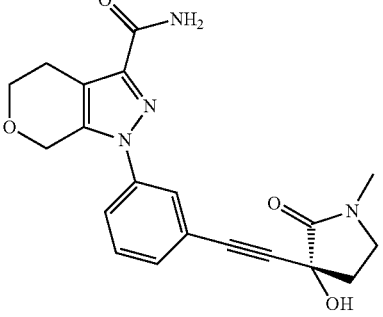 | 1-[3-[2-[(3R)-3-hydroxy-1-methyl-2-oxo-pyrrolidin-3-yl]ethynyl]phenyl]-5,7-dihydro-4H-pyrano[3,4-c]pyrazole-3-carboxamide |
| 70 | 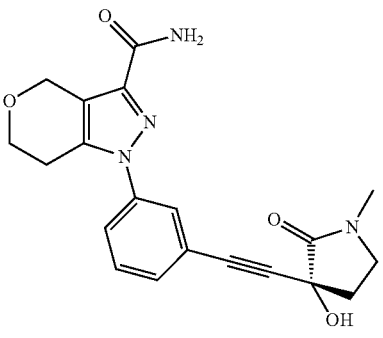 [SMILES: CN1CC[C@@](O)(C#Cc2cccc(-n3nc(C(N)=O)c4c3CCOC4)c2)C1=O] | 1-[3-[2-[(3R)-3-hydroxy-1-methyl-2-oxo-pyrrolidin-3-yl]ethynyl]phenyl]-6,7-dihydro-4H-pyrano[4,3-c]pyrazole-3-carboxamide |
| 71 | 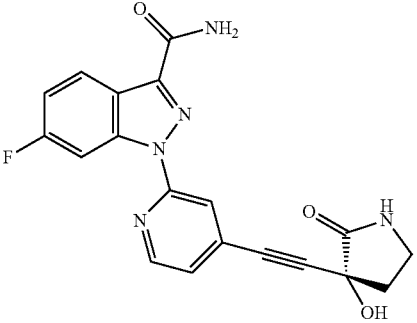 [SMILES: NC(=O)c1nn(-c2cc(C#C[C@]3(O)CCNC3=O)ccn2)c2cc(F)ccc12] | 6-fluoro-1-[4-[2-[(3R)-3-hydroxy-2-oxo-pyrrolidin-3-yl]ethynyl]-2-pyridyl]indazole-3-carboxamide |
| 72 | 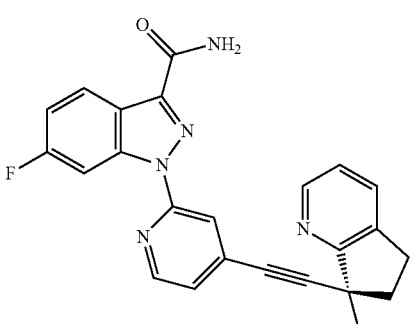 | 6-fluoro-1-[4-[2-[(7R)-7-hydroxy-5,6-dihydrocyclopenta[b]pyridin-7-yl]ethynyl]-2-pyridyl]indazole-3-carboxamide |

TABLE 1-continued

| Ex. | Structure | Name |
|---|---|---|
| 73 | 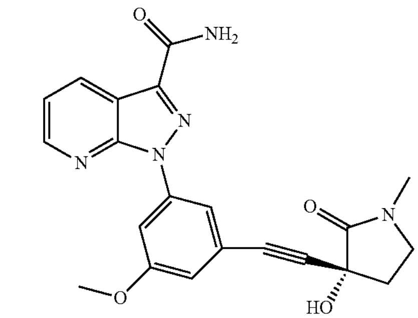 [SMILES: COc1cc(C#C[C@]2(O)CCN(C)C2=O)cc(-n2nc(C(N)=O)c3cccnc32)c1] | 1-[3-[2-[(3R)-3-hydroxy-1-methyl-2-oxo-pyrrolidin-3-yl]ethynyl]-5-methoxy-phenyl]pyrazolo[3,4-b]pyridine-3-carboxamide |
| 74 | 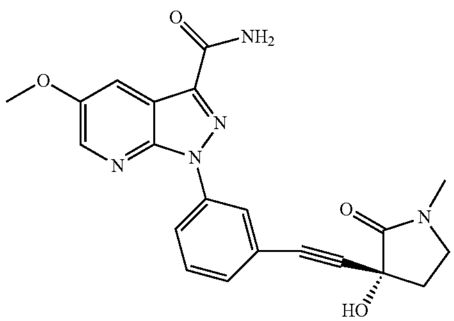 [SMILES: COc1cnc2c(c1)c(C(N)=O)nn2-c1cccc(C#C[C@]2(O)CCN(C)C2=O)c1] | 1-[3-[2-[(3R)-3-hydroxy-1-methyl-2-oxo-pyrrolidin-3-yl]ethynyl]phenyl]-5-methoxy-pyrazolo[3,4-b]pyridine-3-carboxamide |
| 75 | 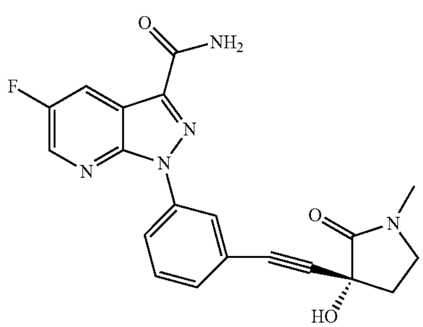 [SMILES: CN1CC[C@@](O)(C#Cc2cccc(-n3nc(C(N)=O)c4cc(F)cnc43)c2)C1=O] | 5-fluoro-1-[3-[2-[(3R)-3-hydroxy-1-methyl-2-oxo-pyrrolidin-3-yl]ethynyl]phenyl]pyrazolo[3,4-b]pyridine-3-carboxamide |
| 76 | 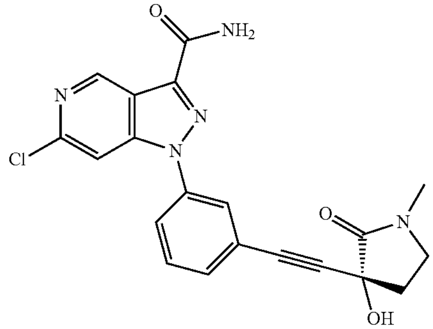 [SMILES: CN1CC[C@@](O)(C#Cc2cccc(-n3nc(C(N)=O)c4cnc(Cl)cc43)c2)C1=O] | 6-chloro-1-[3-[2-[(3R)-3-hydroxy-1-methyl-2-oxo-pyrrolidin-3-yl]ethynyl]phenyl]pyrazolo[4,3-c]pyridine-3-carboxamide |

TABLE 1-continued

| Ex. | Structure | Name |
|---|---|---|
| 77 | 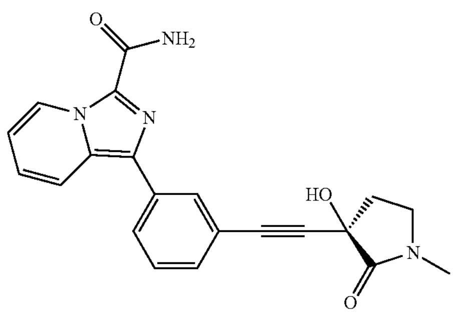 [SMILES: CN1CC[C@@](O)(C#Cc2cccc(-c3nc(C(N)=O)n4ccccc34)c2)C1=O] | 1-[3-[2-[(3R)-3-hydroxy-1-methyl-2-oxo-pyrrolidin-3-yl]ethynyl]phenyl]imidazo[1,5-a]pyridine-3-carboxamide |
| 78 | 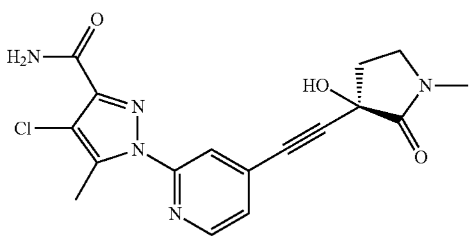 [SMILES: Cc1c(Cl)c(C(N)=O)nn1-c1cc(C#C[C@]2(O)CCN(C)C2=O)ccn1] | 4-chloro-1-[4-[2-[(3R)-3-hydroxy-1-methyl-2-oxo-pyrrolidin-3-yl]ethynyl]-2-pyridyl]-5-methyl-pyrazole-3-carboxamide |
| 79 | 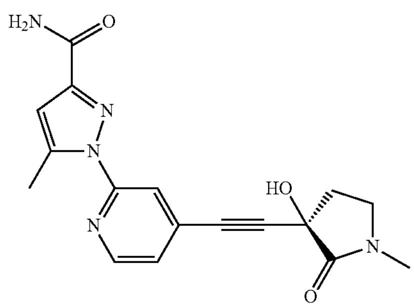 | 1-[4-[2-[(3R)-3-hydroxy-1-methyl-2-oxo-pyrrolidin-3-yl]ethynyl]-2-pyridyl]-5-methyl-pyrazole-3-carboxamide |
| 80 | 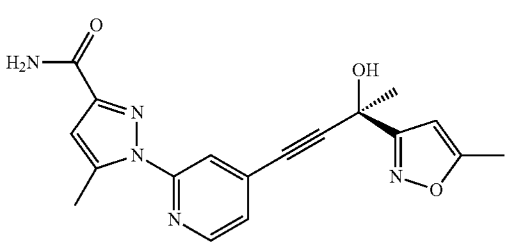 [SMILES: Cc1cc([C@](C)(O)C#Cc2ccnc(-n3nc(C(N)=O)cc3C)c2)no1] | 1-[4-[(3R)-3-hydroxy-3-(5-methylisoxazol-3-yl)but-1-ynyl]-2-pyridyl]-5-methyl-pyrazole-3-carboxamide |
| 81 | 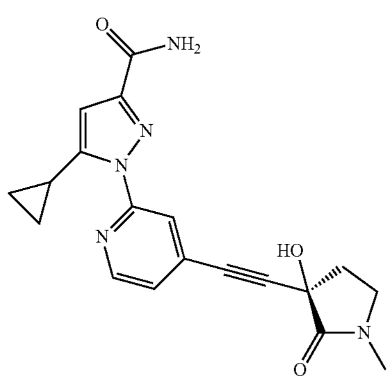 [SMILES: CN1CC[C@@](O)(C#Cc2ccnc(-n3nc(C(N)=O)cc3C3CC3)c2)C1=O] | 5-cyclopropyl-1-[4-[2-[(3R)-3-hydroxy-1-methyl-2-oxo-pyrrolidin-3-yl]ethynyl]-2-pyridyl]pyrazole-3-carboxamide |

TABLE 1-continued

| Ex. | Structure | Name |
|---|---|---|
| 82 | 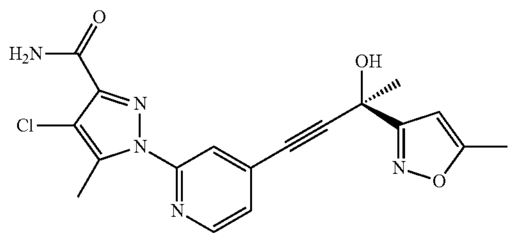 [SMILES: Cc1cc([C@](C)(O)C#Cc2ccnc(-n3nc(C(N)=O)c(Cl)c3C)c2)no1] | 4-chloro-1-[4-[(3R)-3-hydroxy-3-(5-methylisoxazol-3-yl)but-1-ynyl]-2-pyridyl]-5-methyl-pyrazole-3-carboxamide |
| 83 | 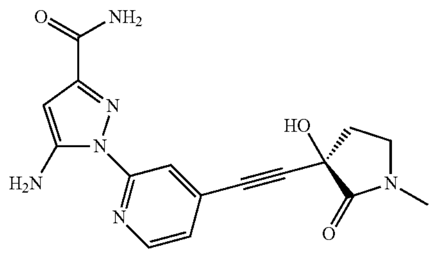 [SMILES: CN1CC[C@@](O)(C#Cc2ccnc(-n3nc(C(N)=O)cc3N)c2)C1=O] | 5-amino-1-[4-[2-[(3R)-3-hydroxy-1-methyl-2-oxo-pyrrolidin-3-yl]ethynyl]-2-pyridiyl]pyrazole-3-carboxamide |
| 84 | 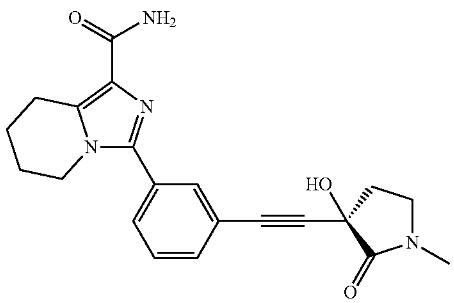 [SMILES: CN1CC[C@@](O)(C#Cc2cccc(-c3nc(C(N)=O)c4n3CCCC4)c2)C1=O] | 3-[3-[2-[(3R)-3-hydroxy-1-methyl-2-oxo-pyrrolidin-3-yl]ethynyl]phenyl]-5,6,7,8-tetrahydroimidazo[1,5-a]pyridine-1-carboxamide |
| 85 | 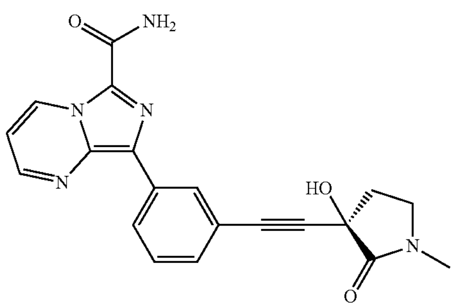 [SMILES: CN1CC[C@@](O)(C#Cc2cccc(-c3nc(C(N)=O)n4cccnc34)c2)C1=O] | 8-[3-[2-[(3R)-3-hydroxy-1-methyl-2-oxo-pyrrolidin-3-yl]ethynyl]phenyl]imidazo[1,5-a]pyrimidine-6-carboxamide |
| 86 | 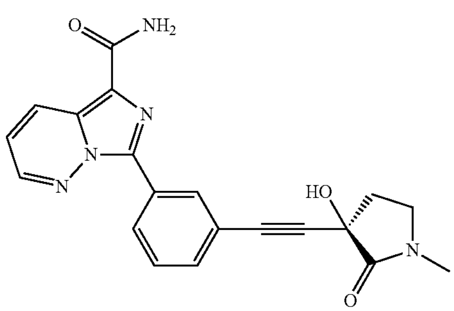 [SMILES: CN1CC[C@@](O)(C#Cc2cccc(-c3nc(C(N)=O)c4cccnn34)c2)C1=O] | 7-[3-[2-[(3R)-3-hydroxy-1-methyl-2-oxo-pyrrolidin-3-yl]ethynyl]phenyl]imidazo[1,5-b]pyridazine-5-carboxamide |

TABLE 1-continued

| Ex. | Structure | Name |
|---|---|---|
| 87 | 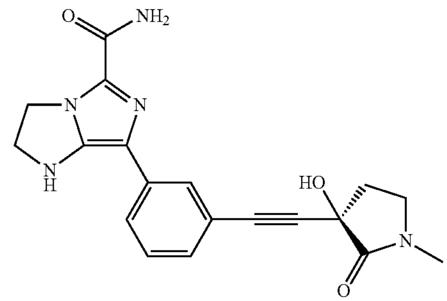 [SMILES: CN1CC[C@@](O)(C#Cc2cccc(-c3nc(C(N)=O)n4c3NCC4)c2)C1=O] | 7-[3-[2-[(3R)-3-hydroxy-1-methyl-2-oxo-pyrrolidin-3-yl]ethynyl]phenyl]-2,3-dihydro-1H-imidazo[1,5-a]imidazole-5-carboxamide |
| 88 | 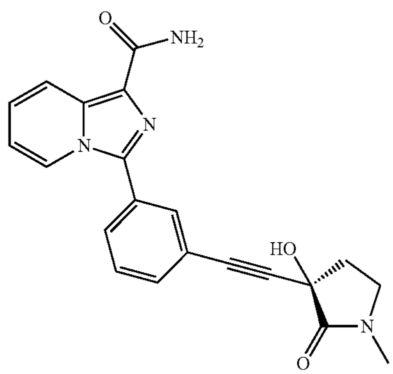 [SMILES: CN1CC[C@@](O)(C#Cc2cccc(-c3nc(C(N)=O)c4ccccn34)c2)C1=O] | 3-[3-[2-[(3R)-3-hydroxy-1-methyl-2-oxo-pyrrolidin-3-yl]ethynyl]phenyl]imidazo[1,5-a]pyridine-1-carboxamide |
| 89 | 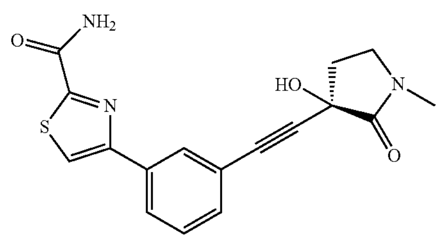 [SMILES: CN1CC[C@@](O)(C#Cc2cccc(-c3csc(C(N)=O)n3)c2)C1=O] | 4-[3-[2-[(3R)-3-hydroxy-1-methyl-2-oxo-pyrrolidin-3-yl]ethynyl]phenyl]thiazole-2-carboxamide |
| 90 | 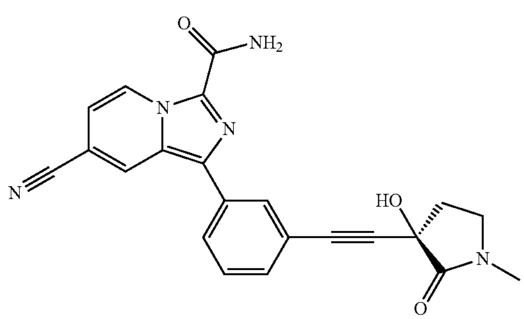 [SMILES: CN1CC[C@@](O)(C#Cc2cccc(-c3nc(C(N)=O)n4ccc(C#N)cc34)c2)C1=O] | 7-cyano-1-[3-[2-[(3R)-3-hydroxy-1-methyl-2-oxo-pyrrolidin-3-yl]ethynyl]phenyl]imidazo[1,5-a]pyridine-3-carboxamide |
| 91 | 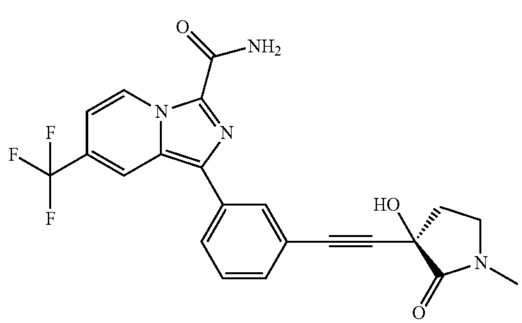 [SMILES: CN1CC[C@@](O)(C#Cc2cccc(-c3nc(C(N)=O)n4ccc(C(F)(F)F)cc34)c2)C1=O] | 1-[3-[2-[(3R)-3-hydroxy-1-methyl-2-oxo-pyrrolidin-3-yl]ethynyl]phenyl]-7-(trifluoromethyl)imidazo[1,5-a]pyridine-3-carboxamide |

TABLE 1-continued

| Ex. | Structure | Name |
|---|---|---|
| 92 | 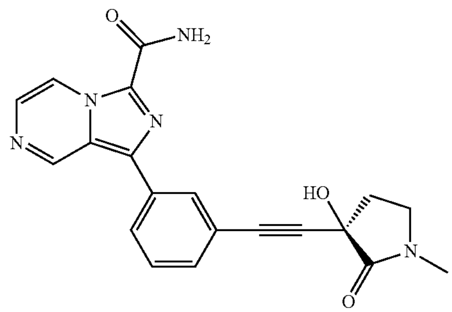 [SMILES: CN1CC[C@@](O)(C#Cc2cccc(-c3nc(C(N)=O)n4ccncc34)c2)C1=O] | 1-[3-[2-[(3R)-3-hydroxy-1-methyl-2-oxo-pyrrolidin-3-yl]ethynyl]phenyl]imidazo[1,5-a]pyrazine-3-carboxamide |
| 93 | 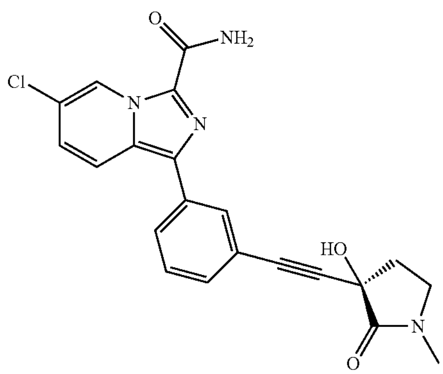 [SMILES: CN1CC[C@@](O)(C#Cc2cccc(-c3nc(C(N)=O)n4cc(Cl)ccc34)c2)C1=O] | 6-chloro-1-[3-[2-[(3R)-3-hydroxy-1-methyl-2-oxo-pyrrolidin-3-yl]ethynyl]phenyl]imidazo[1,5-a]pyridine-3-carboxamide |
| 94 | 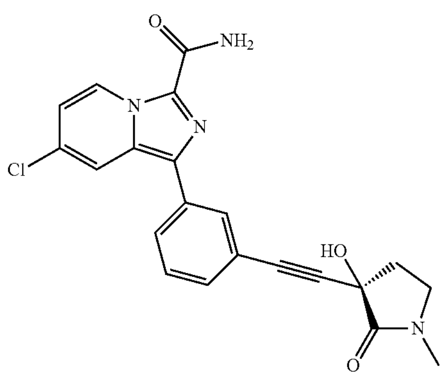 [SMILES: CN1CC[C@@](O)(C#Cc2cccc(-c3nc(C(N)=O)n4ccc(Cl)cc34)c2)C1=O] | 7-chloro-1-[3-[2-[(3R)-3-hydroxy-1-methyl-2-oxo-pyrrolidin-3-yl]ethynyl]phenyl]imidazo[1,5-a]pyridine-3-carboxamide |
| 95 | 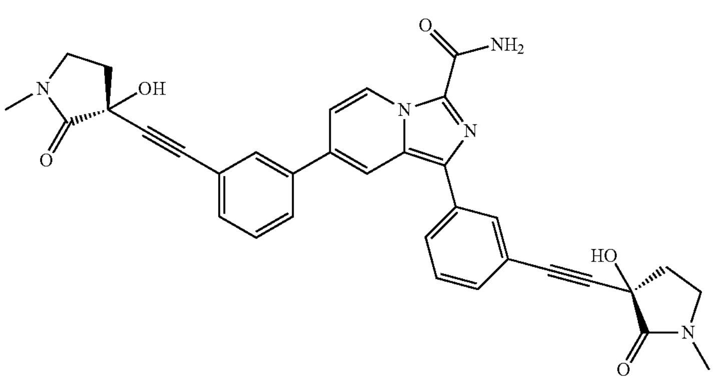 | 1,7-bis[3-[2-[(3R)-3-hydroxy-1-methyl-2-oxo-pyrrolidin-3-yl]ethynyl]phenyl]imidazo[1,5-a]pyridine-3-carboxamide |

TABLE 1-continued

| Ex. | Structure | Name |
|---|---|---|
| 96 | 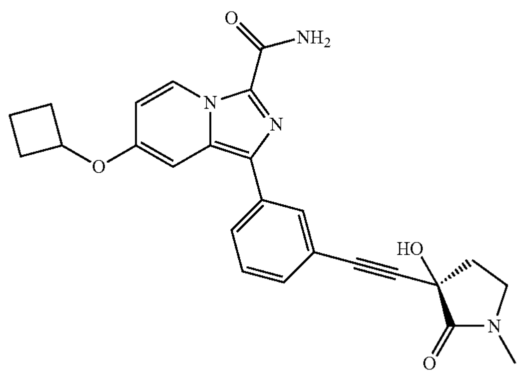 [SMILES: CN1CC[C@@](O)(C#Cc2cccc(-c3nc(C(N)=O)n4ccc(OC5CCC5)cc34)c2)C1=O] | 7-(cyclobutoxy)-1-[3-[2-[(3R)-3-hydroxy-1-methyl-2-oxo-pyrrolidin-3-yl]ethynyl]phenyl]imidazo[1,5-a]pyridine-3-carboxamide |
| 97 | 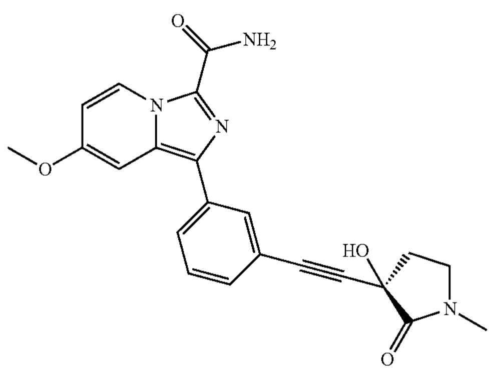 | 1-[3-[2-[(3R)-3-hydroxy-1-methyl-2-oxo-pyrrolidin-3-yl]ethynyl]phenyl]-7-methoxy-imidazo[1,5-a]pyridine-3-carboxamide |
| 98 | 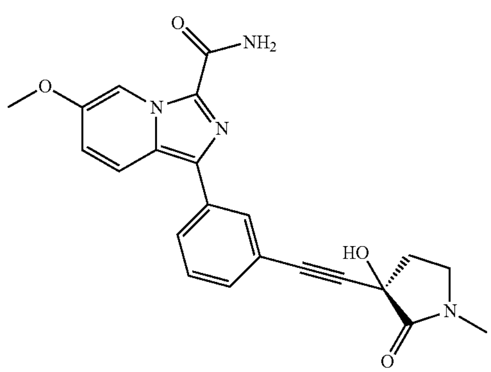 | 1-[3-[2-[(3R)-3-hydroxy-1-methyl-2-oxo-pyrrolidin-3-yl]ethynyl]phenyl]-6-methoxy-imidazo[1,5-a]pyridine-3-carboxamide |
| 99 | 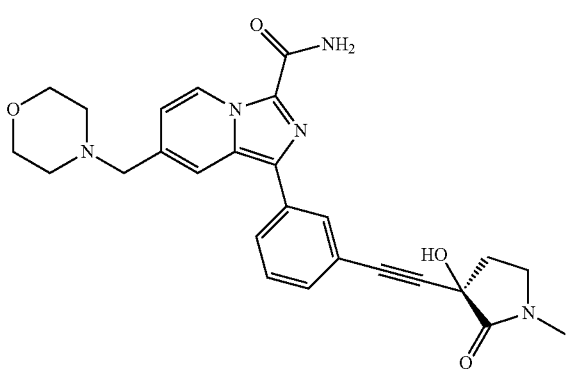 [SMILES: CN1CC[C@@](O)(C#Cc2cccc(-c3nc(C(N)=O)n4ccc(CN5CCOCC5)cc34)c2)C1=O] | 1-[3-[2-[(3R)-3-hydroxy-1-methyl-2-oxo-pyrrolidin-3-yl]ethynyl]phenyl]-7-(morpholinomethyl)imidazo[1,5-a]pyridine-3-carboxamide |

TABLE 1-continued

| Ex. | Structure | Name |
|---|---|---|
| 100 | 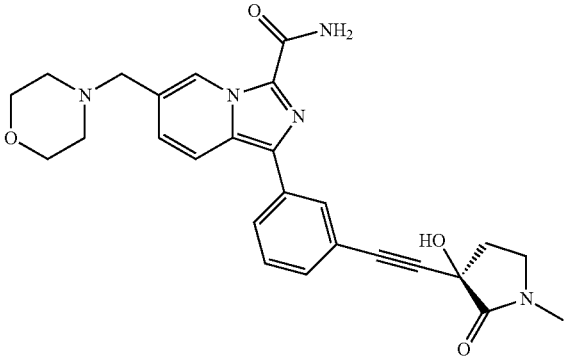 [SMILES: CN1CC[C@@](O)(C#Cc2cccc(-c3nc(C(N)=O)n4cc(CN5CCOCC5)ccc34)c2)C1=O] | 1-[3-[2-[(3R)-3-hydroxy-1-methyl-2-oxo-pyrrolidin-3-yl]ethynyl]phenyl]-6-(morpholinomethyl)imidazo[1,5-a]pyridine-3-carboxamide |
| 101 | 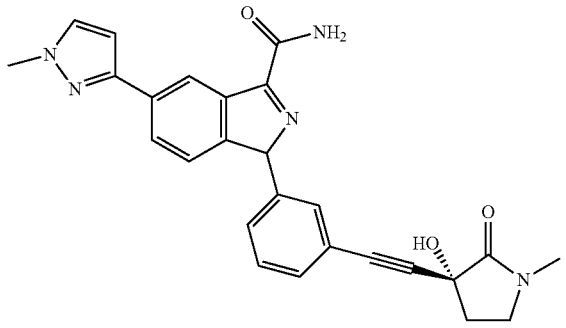 | 1-[3-[2-[(3R)-3-hydroxy-1-methyl-2-oxo-pyrrolidin-3-yl]ethynyl]phenyl]-5-(1-methylpyrazol-3-yl)indazole-3-carboxamide |
| 102 | 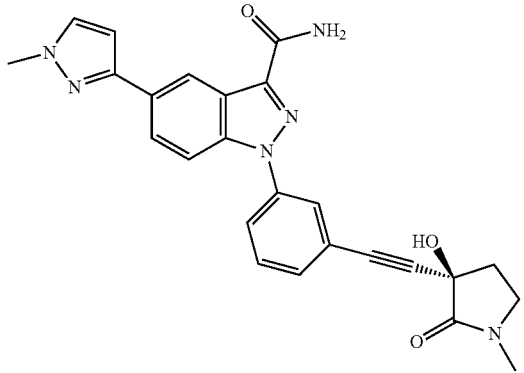 [SMILES: CN1CC[C@@](O)(C#Cc2cccc(-n3nc(C(N)=O)c4cc(-c5ccn(C)n5)ccc43)c2)C1=O] | 1-[3-[2-[(3R)-3-hydroxy-1-methyl-2-oxo-pyrrolidin-3-yl]ethynyl]phenyl]-5-(1-methylpyrazol-4-yl)indazole-3-carboxamide |
| 103 | 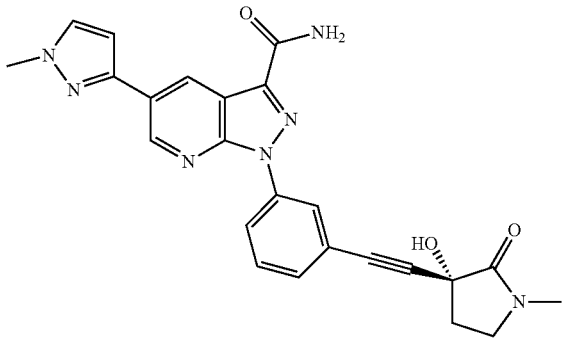 | 1-[3-[2-[(3R)-3-hydroxy-1-methyl-2-oxo-pyrrolidin-3-yl]ethynyl]phenyl]-5-(1-methylpyrazol-3-yl)pyrazolo[3,4-b]pyridine-3-carboxamide |

TABLE 1-continued

| Ex. | Structure | Name |
|---|---|---|
| 104 | 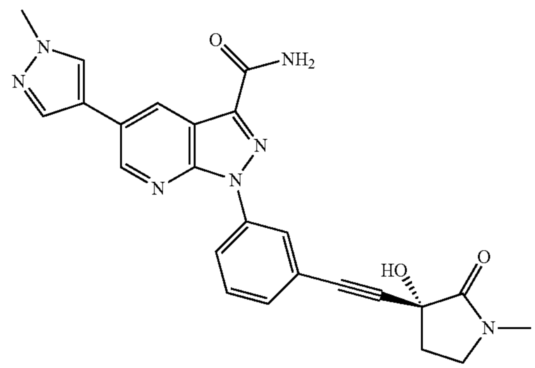 [SMILES: CN1CC[C@@](O)(C#Cc2cccc(-n3nc(C(N)=O)c4cc(-c5cnn(C)c5)cnc43)c2)C1=O] | 1-[3-[2-[(3R)-3-hydroxy-1-methyl-2-oxo-pyrrolidin-3-yl]ethynyl]phenyl]-5-(1-methylpyrazol-4-yl)pyrazolo[3,4-b]pyridine-3-carboxamide |
| 105 | 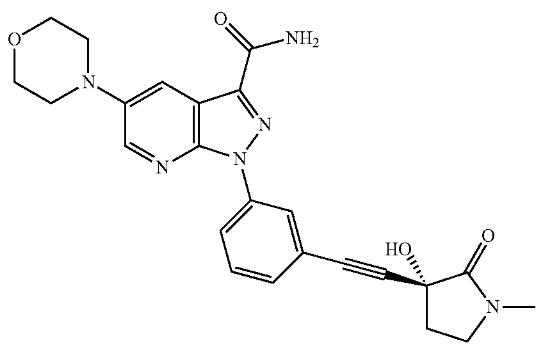 [SMILES: CN1CC[C@@](O)(C#Cc2cccc(-n3nc(C(N)=O)c4cc(N5CCOCC5)cnc43)c2)C1=O] | 1-[3-[2-[(3R)-3-hydroxy-1-methyl-2-oxo-pyrrolidin-3-yl]ethynyl]phenyl]-5-morpholino-pyrazolo[3,4-b]pyridine-3-carboxamide |
| 106 | 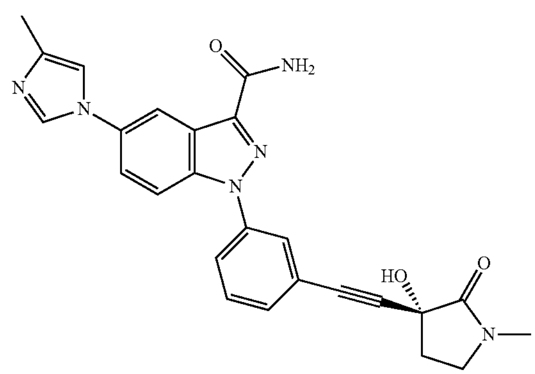 [SMILES: Cc1cn(-c2ccc3c(c2)c(C(N)=O)nn3-c2cccc(C#C[C@]3(O)CCN(C)C3=O)c2)cn1] | 1-[3-[2-[(3R)-3-hydroxy-1-methyl-2-oxo-pyrrolidin-3-yl]ethynyl]phenyl]-5-(4-methylimidazol-1-yl)indazole-3-carboxamide |
| 107 | 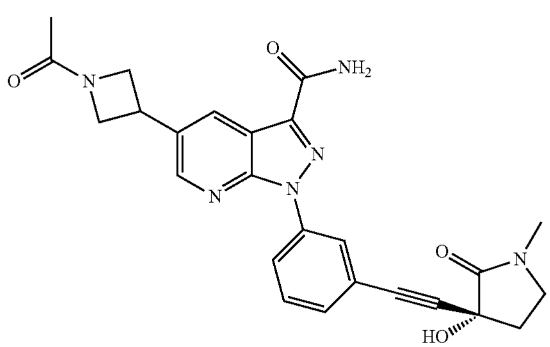 [SMILES: CC(=O)N1CC(c2cnc3c(c2)c(C(N)=O)nn3-c2cccc(C#C[C@]3(O)CCN(C)C3=O)c2)C1] | 5-(1-acetylazetidin-3-yl)-1-[3-[2-[(3R)-3-hydroxy-1-methyl-2-oxo-pyrrolidin-3-yl]ethynyl]phenyl]pyrazolo[3,4-b]pyridine-3-carboxamide |

TABLE 1-continued

| Ex. | Structure | Name |
|---|---|---|
| 108 | 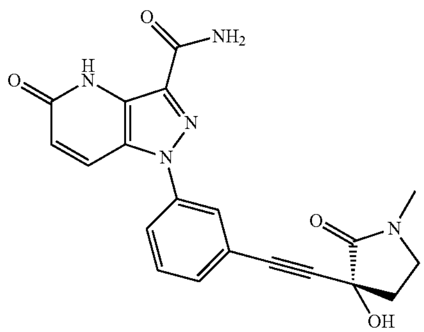 [SMILES: CN1CC[C@@](O)(C#Cc2cccc(-n3nc(C(N)=O)c4[nH]c(=O)ccc43)c2)C1=O] | 1-[3-[2-[(3R)-3-hydroxy-1-methyl-2-oxo-pyrrolidin-3-yl]ethynyl]phenyl]-5-oxo-4H-pyrazolo[4,3-b]pyridine-3-carboxamide |
| 109 | 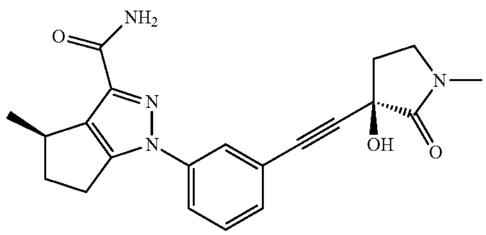 | (4R)-1-[3-[2-[(3R)-3-hydroxy-1-methyl-2-oxo-pyrrolidin-3-yl]ethynyl]phenyl]-4-methyl-5,6-dihydro-4H-cyclopenta[c]pyrazole-3-carboxamide |
| 110 | 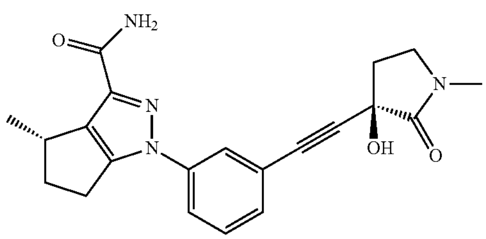 | (4S)-1-[3-[2-[(3R)-3-hydroxy-1-methyl-2-oxo-pyrrolidin-3-yl]ethynyl]phenyl]-4-methyl-5,6-dihydro-4H-cyclopenta[c]pyrazole-3-carboxamide |
| 111 | 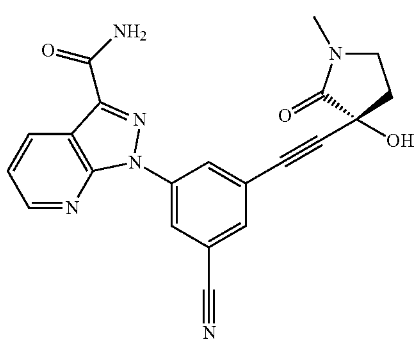 [SMILES: CN1CC[C@@](O)(C#Cc2cc(C#N)cc(-n3nc(C(N)=O)c4cccnc43)c2)C1=O] | 1-[3-cyano-5-[2-[(3R)-3-hydroxy-1-methyl-2-oxo-pyrrolidin-3-yl]ethynyl]phenyl]pyrazolo[3,4-b]pyridine-3-carboxamide |
| 112 | 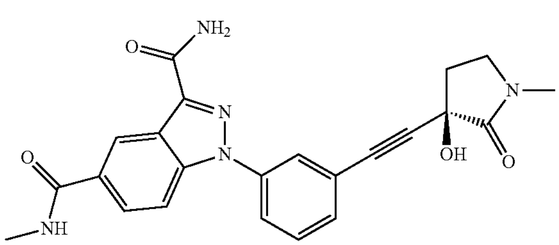 | 1-[3-[2-[(3R)-3-hydroxy-1-methyl-2-oxo-pyrrolidin-3-yl]ethynyl]phenyl]-N5-methyl-indazole-3,5-dicarboxamide |

TABLE 1-continued

| Ex. | Structure | Name |
|---|---|---|
| 113 | 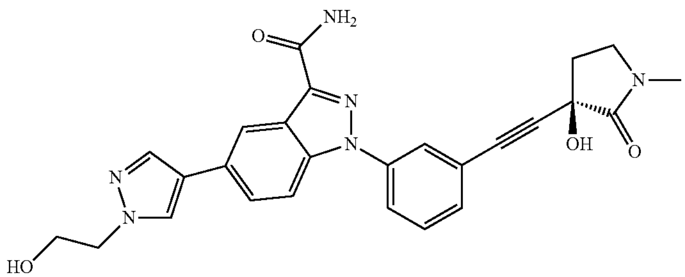 [SMILES: CN1CC[C@@](O)(C#Cc2cccc(-n3nc(C(N)=O)c4cc(-c5cnn(CCO)c5)ccc43)c2)C1=O] | 5-[1-(2-hydroxyethyl)pyrazol-4-yl]-1-[3-[2-[(3R)-3-hydroxy-1-methyl-2-oxo-pyrrolidin-3-yl]ethynyl]phenyl]indazole-3-carboxamide |
| 114 | 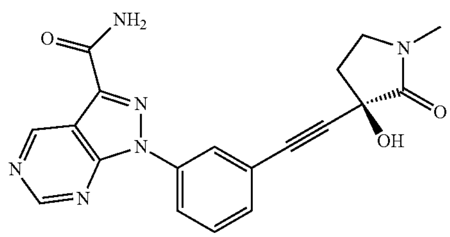 [SMILES: CN1CC[C@@](O)(C#Cc2cccc(-n3nc(C(N)=O)c4cncnc43)c2)C1=O] | 1-[3-[2-[(3R)-3-hydroxy-1-methyl-2-oxo-pyrrolidin-3-yl]ethynyl]phenyl]pyrazolo[3,4-d]pyrimidine-3-carboxamide |
| 115 | 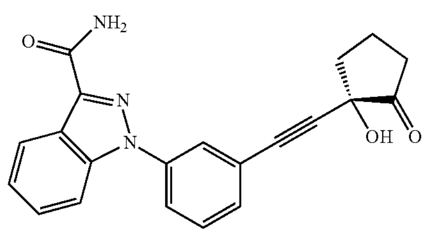 [SMILES: NC(=O)c1nn(-c2cccc(C#C[C@@]3(O)CCCC3=O)c2)c2ccccc12] | 1-[3-[2-[(1S)-1-hydroxy-2-oxo-cyclopentyl]ethynyl]phenyl]indazole-3-carboxamide |
| 116 | 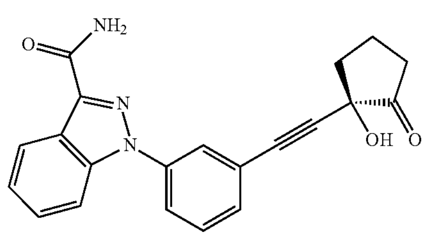 [SMILES: NC(=O)c1nn(-c2cccc(C#C[C@]3(O)CCCC3=O)c2)c2ccccc12] | 1-[3-[2-[(1R)-1-hydroxy-2-oxo-cyclopentyl]ethynyl]phenyl]indazole-3-carboxamide |
| 117 | 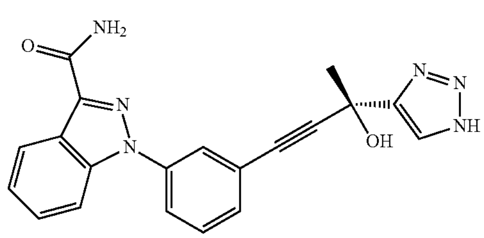 [SMILES: C[C@@](O)(C#Cc1cccc(-n2nc(C(N)=O)c3ccccc32)c1)c1c[nH]nn1] | 1-[3-[(3R)-3-hydroxy-3-(1H-triazol-4-yl)but-1-ynyl]phenyl]indazole-3-carboxamide |
| 118 | 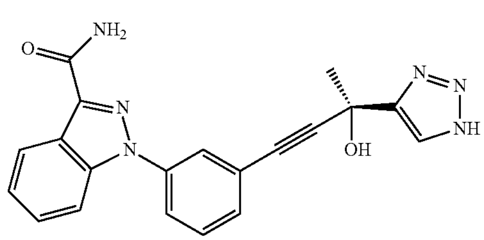 [SMILES: C[C@](O)(C#Cc1cccc(-n2nc(C(N)=O)c3ccccc32)c1)c1c[nH]nn1] | 1-[3-[(3S)-3-hydroxy-3-(1H-triazol-4-yl)but-1-ynyl]phenyl]indazole-3-carboxamide |

TABLE 1-continued

| Ex. | Structure | Name |
|---|---|---|
| 119 | 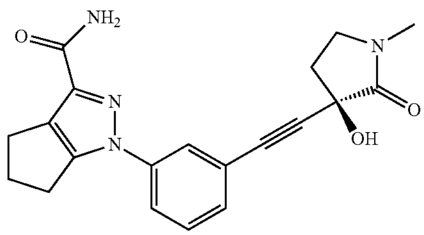 [SMILES: CN1CC[C@@](O)(C#Cc2cccc(-n3nc(C(N)=O)c4c3CCC4)c2)C1=O] | 1-[3-[2-[(3R)-3-hydroxy-1-methyl-2-oxo-pyrrolidin-3-yl]ethynyl]phenyl]-5,6-dihydro-4H-cyclopenta[c]pyrazole-3-carboxamide |
| 120 | 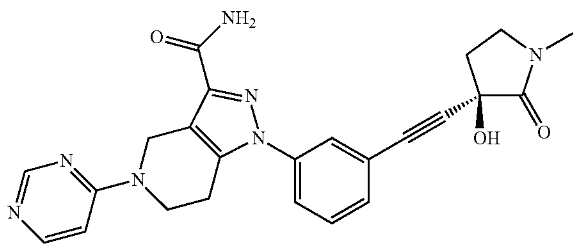 [SMILES: CN1CC[C@@](O)(C#Cc2cccc(-n3nc(C(N)=O)c4c3CCN(c3ccncn3)C4)c2)C1=O] | 1-[3-[2-[(3R)-3-hydroxy-1-methyl-2-oxo-pyrrolidin-3-yl]ethynyl]phenyl]-5-pyrimidin-4-yl-6,7-dihydro-4H-pyrazolo[4,5-c]pyridine-3-carboxamide |
| 121 | 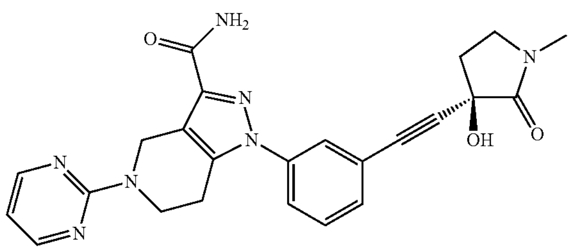 [SMILES: CN1CC[C@@](O)(C#Cc2cccc(-n3nc(C(N)=O)c4c3CCN(c3ncccn3)C4)c2)C1=O] | 1-[3-[2-[(3R)-3-hydroxy-1-methyl-2-oxo-pyrrolidin-3-yl]ethynyl]phenyl]-5-pyrimidin-2-yl-6,7-dihydro-4H-pyrazolo[4,3-c]pyridine-3-carboxamide |
| 122 | 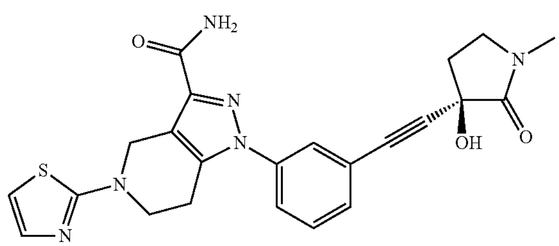 [SMILES: CN1CC[C@@](O)(C#Cc2cccc(-n3nc(C(N)=O)c4c3CCN(c3nccs3)C4)c2)C1=O] | 1-[3-[2-[(3R)-3-hydroxy-1-methyl-2-oxo-pyrrolidin-3-yl]ethynyl]phenyl]-5-thiazol-2-yl-6,7-dihydro-4H-pyrazolo[4,3-c]pyridine-3-carboxamide |
| 123 | 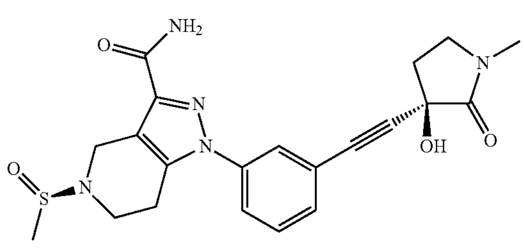 [SMILES: CN1CC[C@@](O)(C#Cc2cccc(-n3nc(C(N)=O)c4c3CCN([S@@](C)=O)C4)c2)C1=O] | 1-[3-[2-[(3R)-3-hydroxy-1-methyl-2-oxo-pyrrolidin-3-yl]ethynyl]phenyl]-5-[(R)-methylsulfinyl]-6,7-dihydro-4H-pyrazolo[4,3-c]pyridine-3-carboxamide |
| 124 | 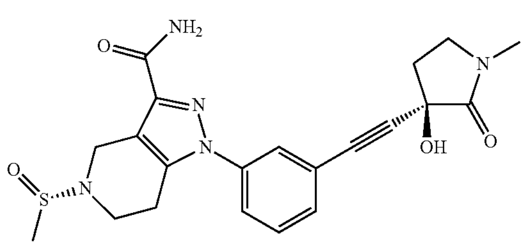 [SMILES: CN1CC[C@@](O)(C#Cc2cccc(-n3nc(C(N)=O)c4c3CCN([S@](C)=O)C4)c2)C1=O] | 1-[3-[2-[(3R)-3-hydroxy-1-methyl-2-oxo-pyrrolidin-3-yl]ethynyl]phenyl]-5-[(S)-methylsulfinyl]-6,7-dihydro-4H-pyrazolo[4,3-c]pyridine-3-carboxamide |

TABLE 1-continued

| Ex. | Structure | Name |
|---|---|---|
| 125 | 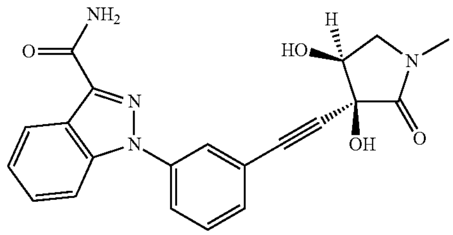 [SMILES: CN1C[C@H](O)[C@@](O)(C#Cc2cccc(-n3nc(C(N)=O)c4ccccc43)c2)C1=O] | 1-[3-[2-[(3S,4S)-3,4-dihydroxy-1-methyl-2-oxo-pyrrolidin-3-yl]ethynyl]phenyl]indazole-3-carboxamide |
| 126 | 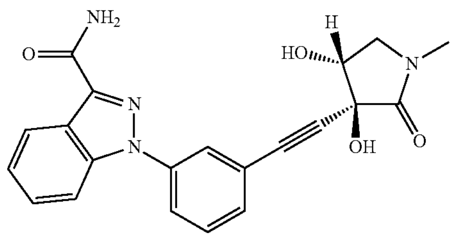 [SMILES: CN1C[C@@H](O)[C@@](O)(C#Cc2cccc(-n3nc(C(N)=O)c4ccccc43)c2)C1=O] | 1-[3-[2-[(3S,4R)-3,4-dihydroxy-1-methyl-2-oxo-pyrrolidin-3-yl]ethynyl]phenyl]indazole-3-carboxamide |
| 127 | 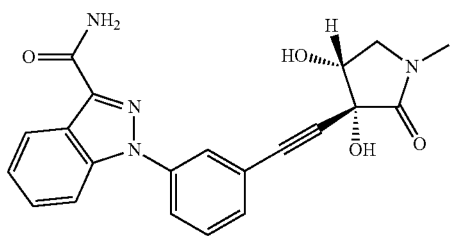 [SMILES: CN1C[C@@H](O)[C@](O)(C#Cc2cccc(-n3nc(C(N)=O)c4ccccc43)c2)C1=O] | 1-[3-[2-[(3R,4R)-3,4-dihydroxy-1-methyl-2-oxo-pyrrolidin-3-yl]ethynyl]phenyl]indazole-3-carboxamide |
| 128 | 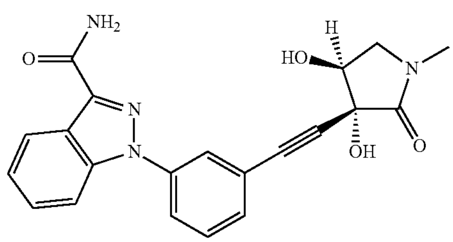 [SMILES: CN1C[C@H](O)[C@](O)(C#Cc2cccc(-n3nc(C(N)=O)c4ccccc43)c2)C1=O] | 1-[3-[2-[(3R,4S)-3,4-dihydroxy-1-methyl-2-oxo-pyrrolidin-3-yl]ethynyl]phenyl]indazole-3-carboxamide |
| 129 | 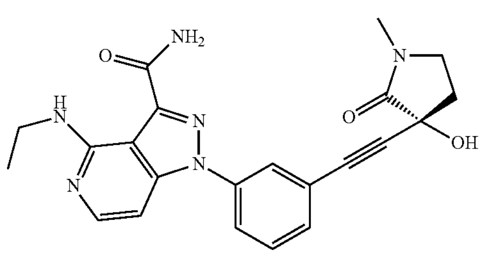 [SMILES: CCNc1nccc2c1c(C(N)=O)nn2-c1cccc(C#C[C@]2(O)CCN(C)C2=O)c1] | 4-(ethylamino)-1-[3-[2-[(3R)-3-hydroxy-1-methyl-2-oxo-pyrrolidin-3-yl]ethynyl]phenyl]pyrazolo[4,3-c]pyridine-3-carboxamide |
| 130 | 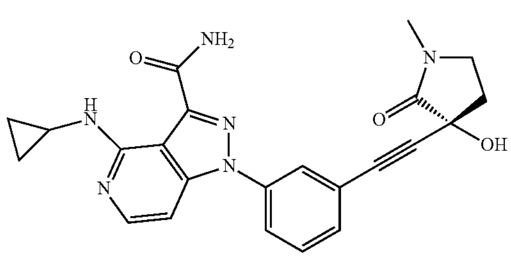 [SMILES: CN1CC[C@@](O)(C#Cc2cccc(-n3nc(C(N)=O)c4c(NC5CC5)nccc43)c2)C1=O] | 4-(cyclopropylamino)-1-[3-[2-[(3R)-3-hydroxy-1-methyl-2-oxo-pyrrolidin-3-yl]ethynyl]phenyl]pyrazolo[4,3-c]pyridine-3-carboxamide |

TABLE 1-continued

| Ex. | Structure | Name |
| --- | --- | --- |
| 131 | 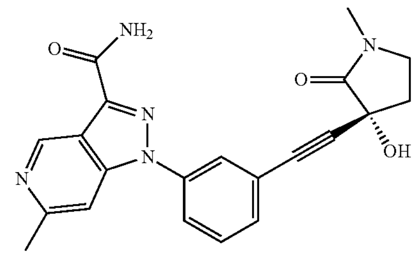 [SMILES: Cc1cc2c(cn1)c(C(N)=O)nn2-c1cccc(C#C[C@]2(O)CCN(C)C2=O)c1] | 1-[3-[2-[(3R)-3-hydroxy-1-methyl-2-oxo-pyrrolidin-3-yl]ethynyl]phenyl]-6-methyl-pyrazolo[4,3-c]pyridine-3-carboxamide |
| 132 | 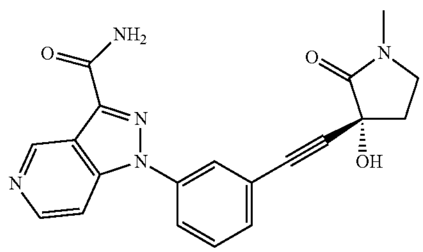 [SMILES: CN1CC[C@@](O)(C#Cc2cccc(-n3nc(C(N)=O)c4cnccc43)c2)C1=O] | 1-[3-[2-[(3R)-3-hydroxy-1-methyl-2-oxo-pyrrolidin-3-yl]ethynyl]phenyl]pyrazolo[4,3-c]pyridine-3-carboxamide |
| 133 | 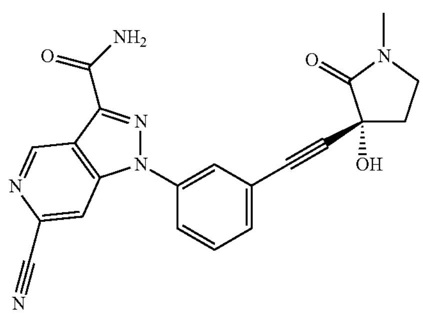 [SMILES: CN1CC[C@@](O)(C#Cc2cccc(-n3nc(C(N)=O)c4cnc(C#N)cc43)c2)C1=O] | 6-cyano-1-[3-[2-[(3R)-3-hydroxy-1-methyl-2-oxo-pyrrolidin-3-yl]ethynyl]phenyl]pyrazolo[4,3-c]pyridine-3-carboxamide |
| 134 | 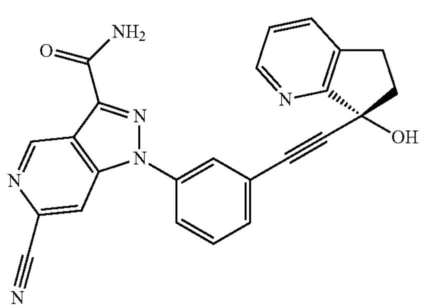 [SMILES: N#Cc1cc2c(cn1)c(C(N)=O)nn2-c1cccc(C#C[C@]2(O)CCc3cccnc32)c1] | 6-cyano-1-[3-[2-[(7R)-7-hydroxy-5,6-dihydrocyclopenta[b]pyridin-7-yl]ethynyl]phenyl]pyrazolo[4,3-c]pyridine-3-carboxamide |
| 135 | 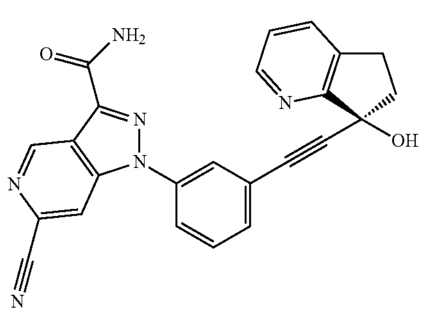 [SMILES: N#Cc1cc2c(cn1)c(C(N)=O)nn2-c1cccc(C#C[C@@]2(O)CCc3cccnc32)c1] | 6-cyano-1-[3-[2-[(7S)-7-hydroxy-5,6-dihydrocyclopenta[b]pyridin-7-yl]ethynyl]phenyl]pyrazolo[4,3-c]pyridine-3-carboxamide |

TABLE 1-continued

| Ex. | Structure | Name |
|---|---|---|
| 136 | 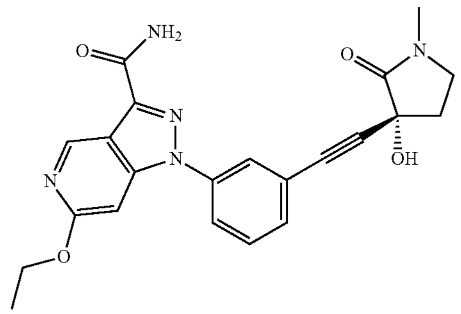 [SMILES: CCOc1cc2c(cn1)c(C(N)=O)nn2-c1cccc(C#C[C@]2(O)CCN(C)C2=O)c1] | 6-ethoxy-1-[3-[2-[(3R)-3-hydroxy-1-methyl-2-oxo-pyrrolidin-3-yl]ethynyl]phenyl]pyrazolo[4,3-c]pyridine-3-carboxamide |
| 137 | 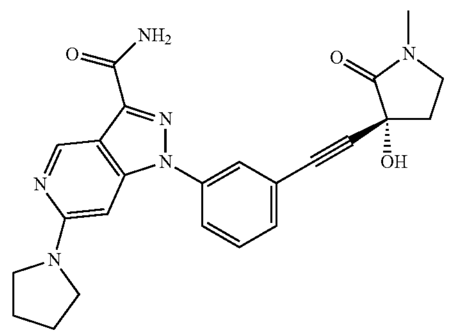 [SMILES: CN1CC[C@@](O)(C#Cc2cccc(-n3nc(C(N)=O)c4cnc(N5CCCC5)cc43)c2)C1=O] | 1-[3-[2-[(3R)-3-hydroxy-1-methyl-2-oxo-pyrrolidin-3-yl]ethynyl]phenyl]-6-pyrrolidin-1-yl-pyrazolo[4,3-c]pyridine-3-carboxamide |
| 138 | 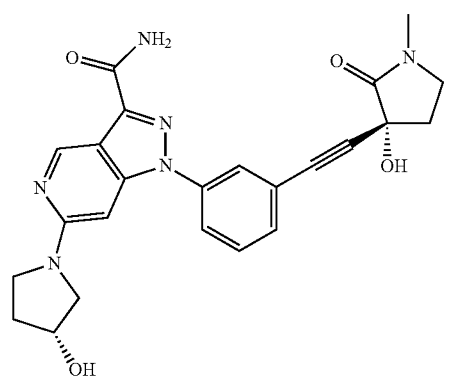 [SMILES: CN1CC[C@@](O)(C#Cc2cccc(-n3nc(C(N)=O)c4cnc(N5CC[C@@H](O)C5)cc43)c2)C1=O] | 1-[3-[2-[(3R)-3-hydroxy-1-methyl-2-oxo-pyrrolidin-3-yl]ethynyl]phenyl]-6-[(3R)-3-hydroxypyrrolidin-1-yl]pyrazolo[4,3-c]pyridine-3-carboxamide |
| 139 | 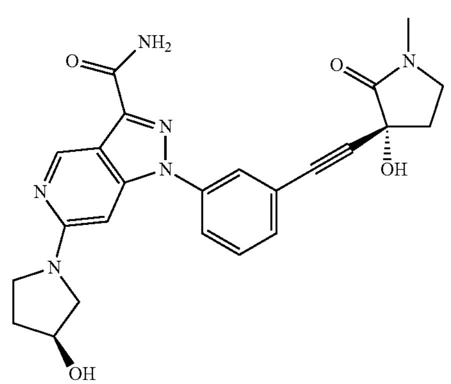 [SMILES: CN1CC[C@@](O)(C#Cc2cccc(-n3nc(C(N)=O)c4cnc(N5CC[C@H](O)C5)cc43)c2)C1=O] | 1-[3-[2-[(3R)-3-hydroxy-1-methyl-2-oxo-pyrrolidin-3-yl]ethynyl]phenyl]-6-[(3S)-3-hydroxypyrrolidin-1-yl]pyrazolo[4,3-c]pyridine-3-carboxamide |

TABLE 1-continued

| Ex. | Structure | Name |
| --- | --- | --- |
| 140 | 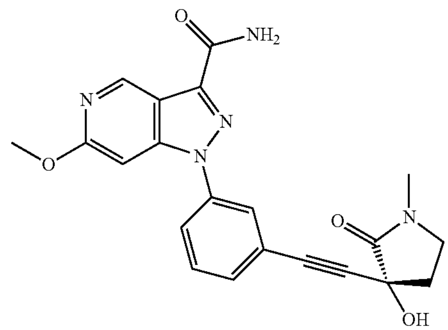 [SMILES: COc1cc2c(cn1)c(C(N)=O)nn2-c1cccc(C#C[C@]2(O)CCN(C)C2=O)c1] | 1-[3-[2-[(3R)-3-hydroxy-1-methyl-2-oxo-pyrrolidin-3-yl]ethynyl]phenyl]-6-methoxy-pyrazolo[4,3-c]pyridine-3-carboxamide |
| 141 | 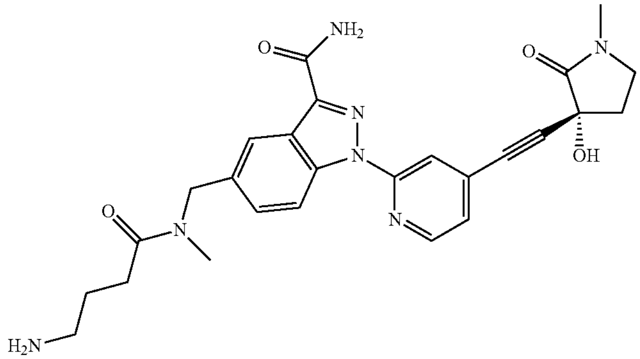 [SMILES: CN(Cc1ccc2c(c1)c(C(N)=O)nn2-c1cc(C#C[C@]2(O)CCN(C)C2=O)ccn1)C(=O)CCCN] | 5-[[4-aminobutanoyl(methyl)amino]methyl]-1-[4-[2-[(3R)-3-hydroxy-1-methyl-2-oxo-pyrrolidin-3-yl]ethynyl]-2-pyridyl]indazole-3-carboxamide |
| 142 | 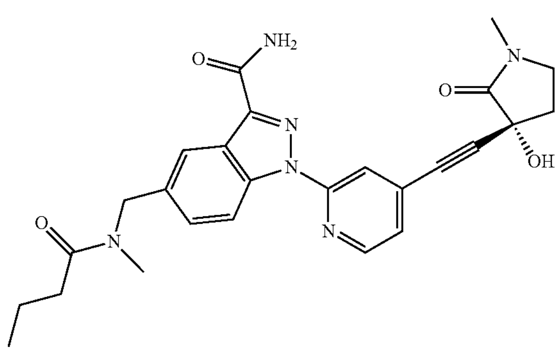 [SMILES: CCCC(=O)N(C)Cc1ccc2c(c1)c(C(N)=O)nn2-c1cc(C#C[C@]2(O)CCN(C)C2=O)ccn1] | 5-[[butanoyl(methyl)amino]methyl]-1-[4-[2-[(3R)-3-hydroxy-1-methyl-2-oxo-pyrrolidin-3-yl]ethynyl]-2-pyridyl]indazole-3-carboxamide |
| 143 | 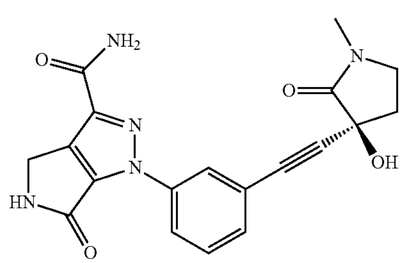 [SMILES: CN1CC[C@](O)(C#Cc2cccc(-n3nc(C(N)=O)c4c3C(=O)NC4)c2)C1=O] | 1-[3-[2-[(3S)-3-hydroxy-1-methyl-2-oxo-pyrrolidin-3-yl]ethynyl]phenyl]-6-oxo-4,5-dihydropyrrolo[3,4-c]pyrazole-3-carboxamide |
| 144 | 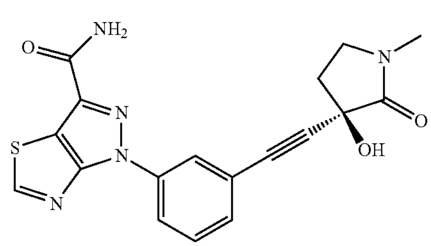 [SMILES: CN1CC[C@@](O)(C#Cc2cccc(-n3nc(C(N)=O)c4scnc43)c2)C1=O] | 1-[3-[2-[(3R)-3-hydroxy-1-methyl-2-oxo-pyrrolidin-3-yl]ethynyl]phenyl]pyrazolo[3,4-d]thiazole-3-carboxamide |

TABLE 1-continued

| Ex. | Structure | Name |
|---|---|---|
| 145 | 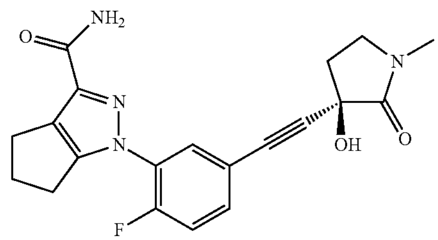 [SMILES: CN1CC[C@@](O)(C#Cc2ccc(F)c(-n3nc(C(N)=O)c4c3CCC4)c2)C1=O] | 1-[2-fluoro-5-[2-[(3R)-3-hydroxy-1-methyl-2-oxo-pyrrolidin-3-yl]ethynyl]phenyl]-5,6-dihydro-4H-cyclopenta[c]pyrazole-3-carboxamide |
| 146 | 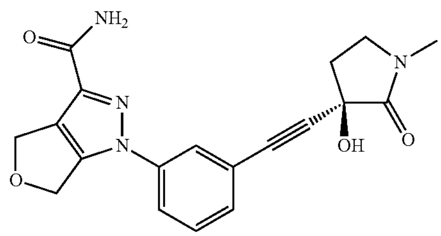 [SMILES: CN1CC[C@@](O)(C#Cc2cccc(-n3nc(C(N)=O)c4c3COC4)c2)C1=O] | 1-[3-[2-[(3R)-3-hydroxy-1-methyl-2-oxo-pyrrolidin-3-yl]ethynyl]phenyl]-4,6-dihydrofuro[3,4-c]pyrazole-3-carboxamide |
| 147 | 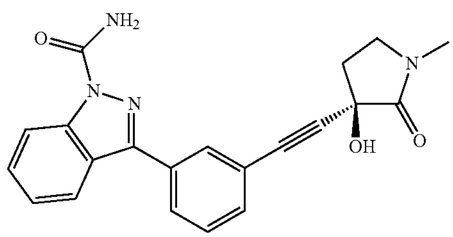 [SMILES: CN1CC[C@@](O)(C#Cc2cccc(-c3nn(C(N)=O)c4ccccc34)c2)C1=O] | 3-[3-[2-[(3R)-3-hydroxy-1-methyl-2-oxo-pyrrolidin-3-yl]ethynyl]phenyl]indazole-1-carboxamide |
| 148 | 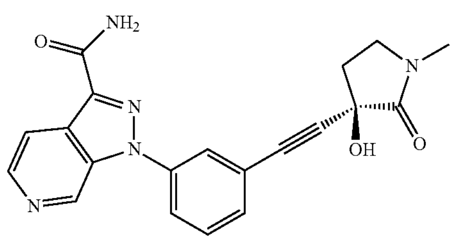 [SMILES: CN1CC[C@@](O)(C#Cc2cccc(-n3nc(C(N)=O)c4ccncc43)c2)C1=O] | 1-[3-[2-[(3R)-3-hydroxy-1-methyl-2-oxo-pyrrolidin-3-yl]ethynyl]phenyl]pyrazolo[3,4-c]pyridine-3-carboxamide |
| 149 | 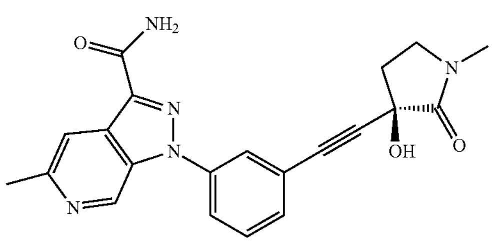 | 1-[3-[2-[(3R)-3-hydroxy-1-methyl-2-oxo-pyrrolidin-3-yl]ethynyl]phenyl]-5-methyl-pyrazolo[3,4-c]pyridine-3-carboxamide |
| 150 | 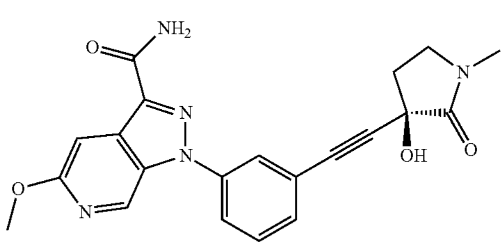 | 1-[3-[2-[(3R)-3-hydroxy-1-methyl-2-oxo-pyrrolidin-3-yl]ethynyl]phenyl]-5-methoxy-pyrazolo[3,4-c]pyridine-3-carboxamide |

TABLE 1-continued

| Ex. | Structure | Name |
|---|---|---|
| 151 | 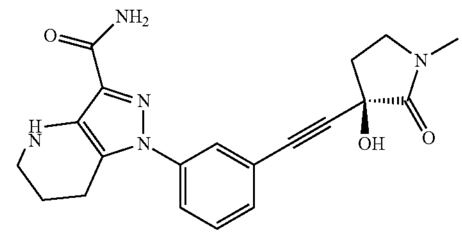 [SMILES: CN1CC[C@@](O)(C#Cc2cccc(-n3nc(C(N)=O)c4c3CCCN4)c2)C1=O] | 1-[3-[2-[(3R)-3-hydroxy-1-methyl-2-oxo-pyrrolidin-3-yl]ethynyl]phenyl]-4,5,6,7-tetrahydropyrazolo[4,3-b]pyridine-3-carboxamide |
| 152 | 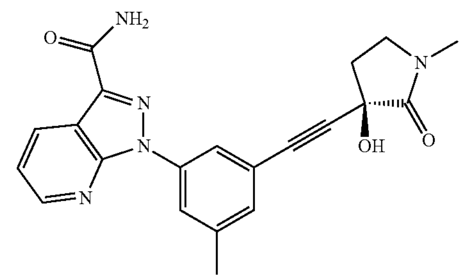 [SMILES: Cc1cc(C#C[C@]2(O)CCN(C)C2=O)cc(-n2nc(C(N)=O)c3cccnc32)c1] | 1-[3-[2-[(3R)-3-hydroxy-1-methyl-2-oxo-pyrrolidin-3-yl]ethynyl]-5-methyl-phenyl]pyrazolo[3,4-b]pyridine-3-carboxamide |
| 153 | 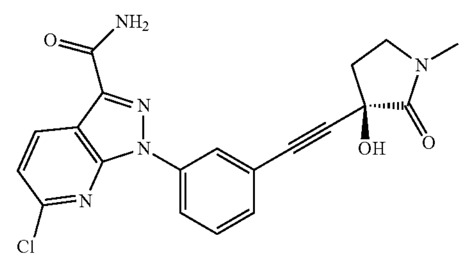 [SMILES: CN1CC[C@@](O)(C#Cc2cccc(-n3nc(C(N)=O)c4ccc(Cl)nc43)c2)C1=O] | 6-chloro-1-[3-[2-[(3R)-3-hydroxy-1-methyl-2-oxo-pyrrolidin-3-yl]ethynyl]phenyl]pyrazolo[3,4-b]pyridine-3-carboxamide |
| 154 | 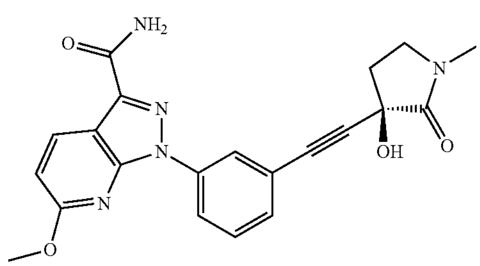 | 1-[3-[2-[(3R)-3-hydroxy-1-methyl-2-oxo-pyrrolidin-3-yl]ethynyl]phenyl]-6-methoxy-pyrazolo[3,4-b]pyridine-3-carboxamide |
| 155 | 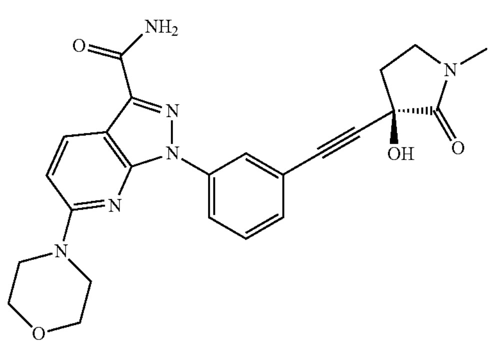 [SMILES: CN1CC[C@@](O)(C#Cc2cccc(-n3nc(C(N)=O)c4ccc(N5CCOCC5)nc43)c2)C1=O] | 1-[3-[2-[(3R)-3-hydroxy-1-methyl-2-oxo-pyrrolidin-3-yl]ethynyl]phenyl]-6-morpholino-pyrazolo[3,4-b]pyridine-3-carboxamide |

TABLE 1-continued

| Ex. | Structure | Name |
|---|---|---|
| 156 | 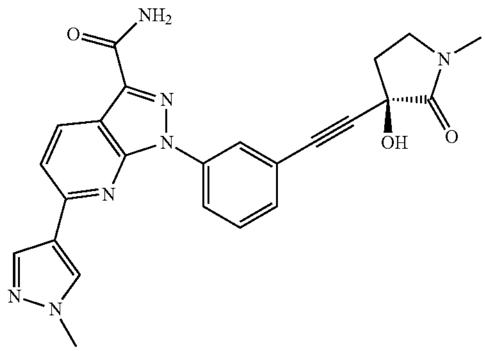 [SMILES: CN1CC[C@@](O)(C#Cc2cccc(-n3nc(C(N)=O)c4ccc(-c5cnn(C)c5)nc43)c2)C1=O] | 1-[3-[2-[(3R)-3-hydroxy-1-methyl-2-oxo-pyrrolidin-3-yl]ethynyl]phenyl]-6-(1-methylpyrazol-4-yl)pyrazolo[3,4-b]pyridine-3-carboxamide |
| 157 | 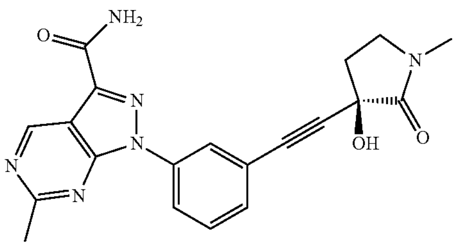 [SMILES: Cc1ncc2c(C(N)=O)nn(-c3cccc(C#C[C@]4(O)CCN(C)C4=O)c3)c2n1] | 1-[3-[2-[(3R)-3-hydroxy-1-methyl-2-oxo-pyrrolidin-3-yl]ethynyl]phenyl]-6-methyl-pyrazolo[3,4-d]pyrimidine-3-carboxamide |
| 158 | 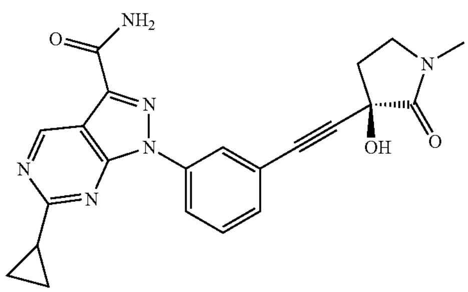 [SMILES: CN1CC[C@@](O)(C#Cc2cccc(-n3nc(C(N)=O)c4cnc(C5CC5)nc43)c2)C1=O] | 6-cyclopropyl-1-[3-[2-[(3R)-3-hydroxy-1-methyl-2-oxo-pyrrolidin-3-yl]ethynyl]phenyl]pyrazolo[3,4-d]pyrimidine-3-carboxamide |
| 159 | 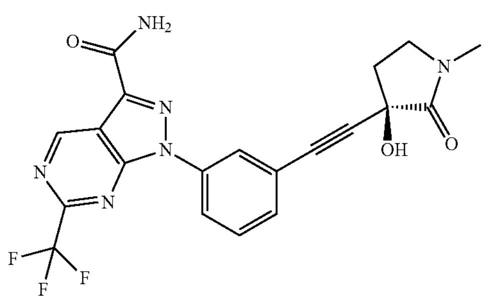 [SMILES: CN1CC[C@@](O)(C#Cc2cccc(-n3nc(C(N)=O)c4cnc(C(F)(F)F)nc43)c2)C1=O] | 1-[3-[2-[(3R)-3-hydroxy-1-methyl-2-oxo-pyrrolidin-3-yl]ethynyl]phenyl]-6-(trifluoromethyl)pyrazolo[3,4-d]pyrimidine-3-carboxamide |
| 160 | 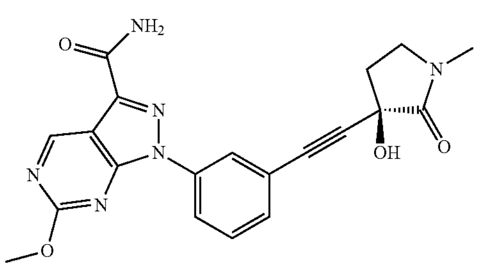 | 1-[3-[2-[(3R)-3-hydroxy-1-methyl-2-oxo-pyrrolidin-3-yl]ethynyl]phenyl]-6-methoxy-pyrazolo[3,4-d]pyrimidine-3-carboxamide |

TABLE 1-continued

| Ex. | Structure | Name |
|---|---|---|
| 161 | 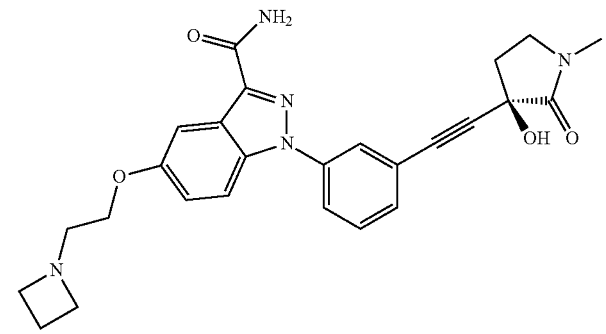 [SMILES: CN1CC[C@@](O)(C#Cc2cccc(-n3nc(C(N)=O)c4cc(OCCN5CCC5)ccc43)c2)C1=O] | 5-[2-(azetidin-1-yl)ethoxy]-1-[3-[2-[(3R)-3-hydroxy-1-methyl-2-oxo-pyrrolidin-3-yl]ethynyl]phenyl]indazole-3-carboxamide |
| 162 | 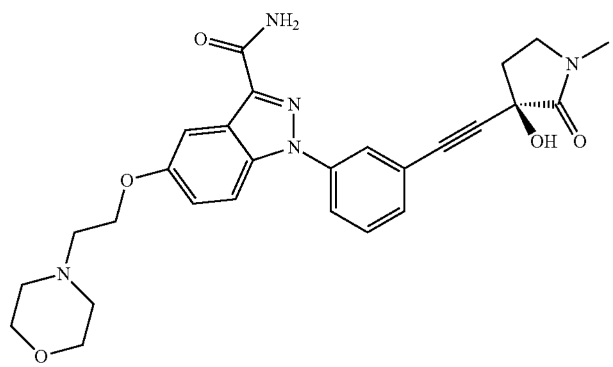 [SMILES: CN1CC[C@@](O)(C#Cc2cccc(-n3nc(C(N)=O)c4cc(OCCN5CCOCC5)ccc43)c2)C1=O] | 1-[3-[2-[(3R)-3-hydroxy-1-methyl-2-oxo-pyrrolidin-3-yl]ethynyl]phenyl]-5-(2-morpholinoethoxy)indazole-3-carboxamide |
| 163 | 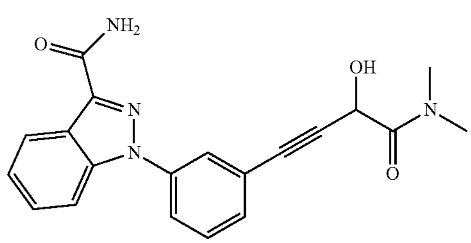 [SMILES: CN(C)C(=O)C(O)C#Cc1cccc(-n2nc(C(N)=O)c3ccccc32)c1] | 1-[3-[4-(dimethylamino)-3-hydroxy-4-oxo-but-1-ynyl]phenyl]indazole-3-carboxamide |
| 164 | 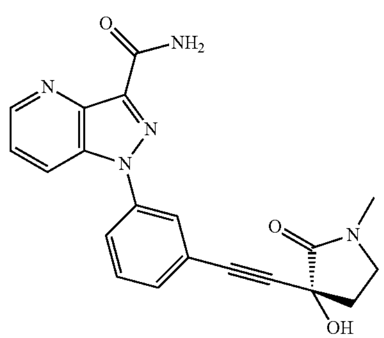 [SMILES: CN1CC[C@@](O)(C#Cc2cccc(-n3nc(C(N)=O)c4ncccc43)c2)C1=O] | 1-[3-[2-[(3R)-3-hydroxy-1-methyl-2-oxo-pyrrolidin-3-yl]ethynyl]phenyl)pyrazolo[4,3-b]pyridine-3-carboxamide |
| 165 | 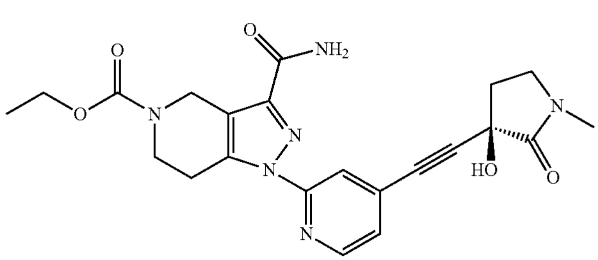 [SMILES: CCOC(=O)N1CCc2c(c(C(N)=O)nn2-c2cc(C#C[C@]3(O)CCN(C)C3=O)ccn2)C1] | ethyl 3-carbamoyl-1-[4-[2-[(3R)-3-hydroxy-1-methyl-2-oxo-pyrrolidin-3-yl]ethynyl]-2-pyridyl]-6,7-dihydro-4H-pyrazolo[4,3-c]pyridine-5-carboxylate |

TABLE 1-continued

| Ex. | Structure | Name |
|---|---|---|
| 166 | 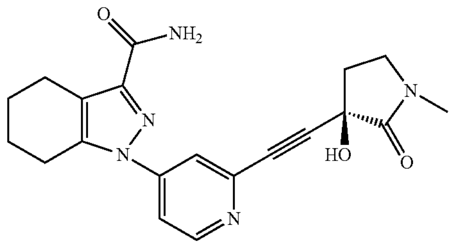 [SMILES: CN1CC[C@@](O)(C#Cc2cc(-n3nc(C(N)=O)c4c3CCCC4)ccn2)C1=O] | 1-[2-[2-[(3R)-3-hydroxy-1-methyl-2-oxo-pyrrolidin-3-yl]ethynyl]-4-pyridyl]-4,5,6,7-tetrahydroindazole-3-carboxamide |
| 167 | 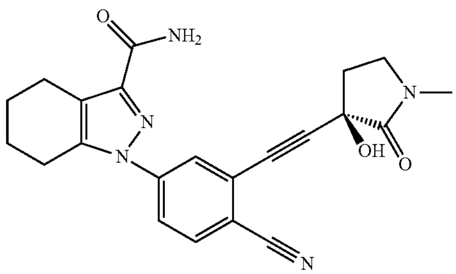 [SMILES: CN1CC[C@@](O)(C#Cc2cc(-n3nc(C(N)=O)c4c3CCCC4)ccc2C#N)C1=O] | 1-[4-cyano-3-[2-[(3R)-3-hydroxy-1-methyl-2-oxo-pyrrolidin-3-yl]ethynyl]phenyl]-4,5,6,7-tetrahydroindazole-3-carboxamide |
| 168 | 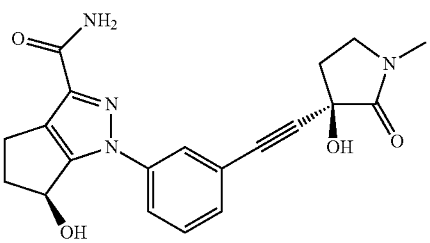 [SMILES: CN1CC[C@@](O)(C#Cc2cccc(-n3nc(C(N)=O)c4c3[C@@H](O)CC4)c2)C1=O] | (6S)-6-hydroxy-1-[3-[2-[(3R)-3-hydroxy-1-methyl-2-oxo-pyrrolidin-3-yl]ethynyl]phenyl]-5,6-dihydro-4H-cyclopenta[c]pyrazole-3-carboxamide |
| 169 | 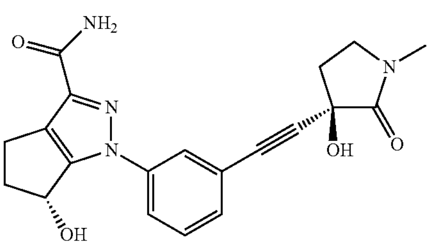 [SMILES: CN1CC[C@@](O)(C#Cc2cccc(-n3nc(C(N)=O)c4c3[C@H](O)CC4)c2)C1=O] | (6R)-6-hydroxy-1-[3-[2-[(3R)-3-hydroxy-1-methyl-2-oxo-pyrrolidin-3-yl]ethynyl]phenyl]-5,6-dihydro-4H-cyclopenta[c]pyrazole-3-carboxamide |
| 170 | 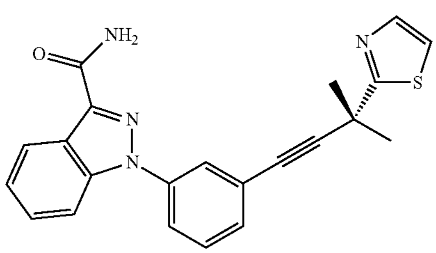 | 1-[3-[(3R)-3-hydroxy-3-thiazol-2-yl-but-1-ynyl]phenyl]indazole-3-carboxamide |
| 171 | 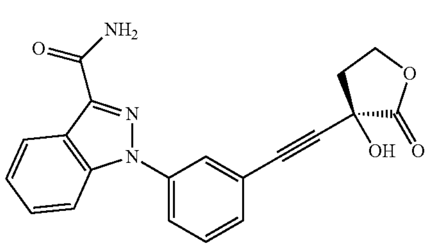 [SMILES: NC(=O)c1nn(-c2cccc(C#C[C@]3(O)CCOC3=O)c2)c2ccccc12] | 1-[3-[2-[(3R)-3-hydroxy-2-oxo-tetrahydrofuran-3-yl]ethynyl]phenyl]indazole-3-carboxamide |

TABLE 1-continued

| Ex. | Structure | Name |
|---|---|---|
| 172 | 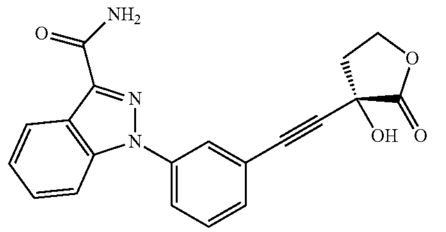 [SMILES: NC(=O)c1nn(-c2cccc(C#C[C@@]3(O)CCOC3=O)c2)c2ccccc12] | 1-[3-[2-[(3)S-3-hydroxy-2-oxo-tetrahydrofuran-3-yl]ethynyl]phenyl]indazole-3-carboxamide |
| 173 | 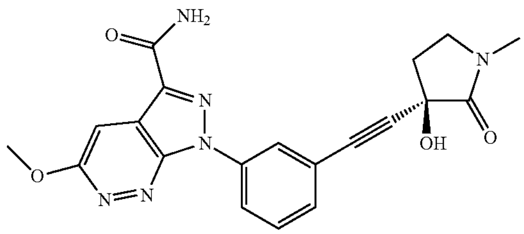 | 1-[3-[2-[(3R)-3-hydroxy-1-methyl-2-oxo-pyrrolidin-3-yl]ethynyl]phenyl]-5-methoxy-pyrazolo[3,4-c]pyridazine-3-carboxamide |
| 174 | 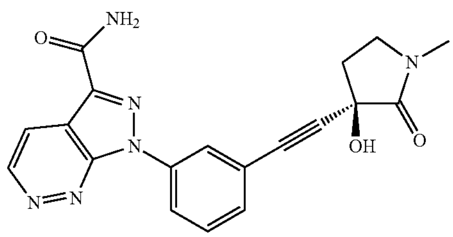 [SMILES: CN1CC[C@@](O)(C#Cc2cccc(-n3nc(C(N)=O)c4ccnnc43)c2)C1=O] | 1-[3-[2-[(3R)-3-hydroxy-1-methyl-2-oxo-pyrrolidin-3-yl]ethynyl]phenyl]pyrazolo[3,4-c]pyridazine-3-carboxamide |
| 175 | 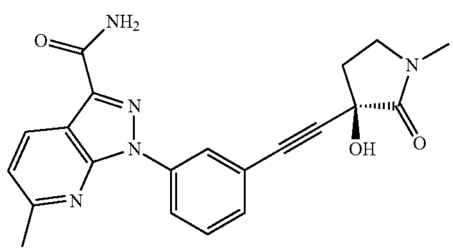 [SMILES: Cc1ccc2c(C(N)=O)nn(-c3cccc(C#C[C@]4(O)CCN(C)C4=O)c3)c2n1] | 1-[3-[2-[(3R)-3-hydroxy-1-methyl-2-oxo-pyrrolidin-3-yl]ethynyl]phenyl]-6-methyl-pyrazolo[3,4-b]pyridine-3-carboxamide |
| 176 | 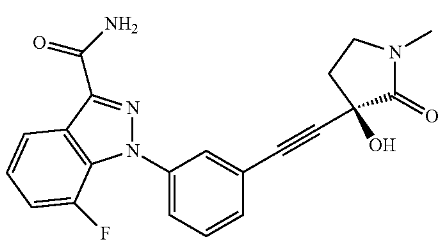 [SMILES: CN1CC[C@@](O)(C#Cc2cccc(-n3nc(C(N)=O)c4cccc(F)c43)c2)C1=O] | 7-fluoro-1-[3-[2-[(3R)-3-hydroxy-1-methyl-2-oxo-pyrrolidin-3-yl]ethynyl]phenyl]indazole-3-carboxamide |
| 177 | 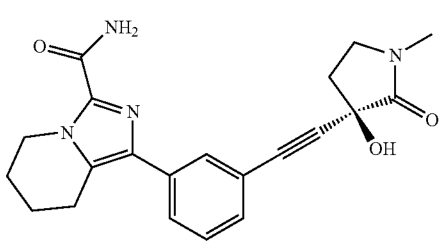 [SMILES: CN1CC[C@@](O)(C#Cc2cccc(-c3nc(C(N)=O)n4c3CCCC4)c2)C1=O] | 1-[3-[2-[(3R)-3-hydroxy-1-methyl-2-oxo-pyrrolidin-3-yl]ethynyl]phenyl]-5,6,7,8-tetrahydroimidazo[1,5-a]pyridine-3-carboxamide |

TABLE 1-continued

| Ex. | Structure | Name |
|---|---|---|
| 178 | 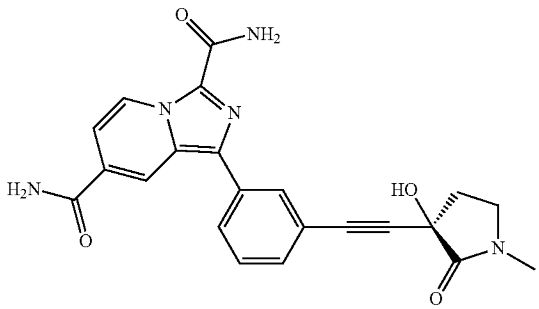 [SMILES: CN1CC[C@@](O)(C#Cc2cccc(-c3nc(C(N)=O)n4ccc(C(N)=O)cc34)c2)C1=O] | 1-[3-[2-[(3R)-3-hydroxy-1-methyl-2-oxo-pyrrolidin-3-yl]ethynyl]phenyl]imidazo[1,5-a]pyridine-3,7-dicarboxamide |
| 179 | 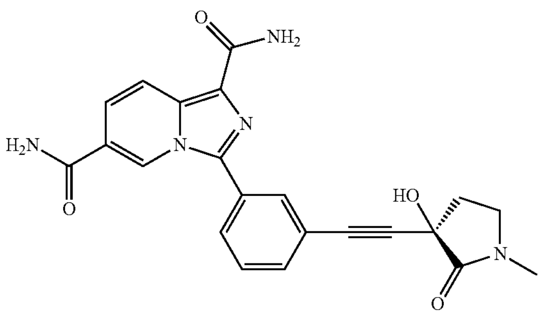 [SMILES: CN1CC[C@@](O)(C#Cc2cccc(-c3nc(C(N)=O)c4ccc(C(N)=O)cn34)c2)C1=O] | 3-[3-[2-[(3R)-3-hydroxy-1-methyl-2-oxo-pyrrolidin-3-yl]ethynyl]phenyl]imidazo[1,5-a]pyridine-1,6-dicarboxamide |
| 180 | 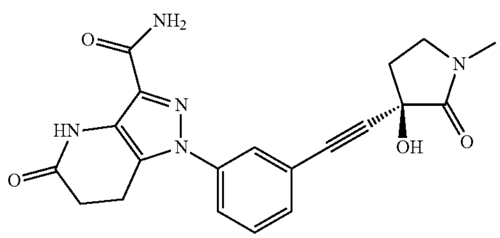 [SMILES: CN1CC[C@@](O)(C#Cc2cccc(-n3nc(C(N)=O)c4c3CCC(=O)N4)c2)C1=O] | 1-[3-[2-[(3R)-3-hydroxy-1-methyl-2-oxo-pyrrolidin-3-yl]ethynyl]phenyl]-5-oxo-6,7-dihydro-4H-pyrazolo[4,3-b]pyridine-3-carboxamide |
| 181 | 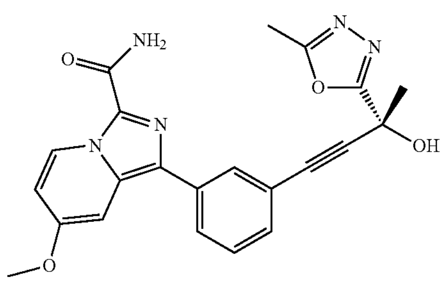 [SMILES: COc1ccn2c(C(N)=O)nc(-c3cccc(C#C[C@@](C)(O)c4nnc(C)o4)c3)c2c1] | 1-[3-[(3R)-3-hydroxy-3-(5-methyl-1,3,4-oxadiazol-2-yl)but-1-ynyl]phenyl]7-methoxy-imidazo[1,5-a]pyridine-3-carboxamide |
| 182 | 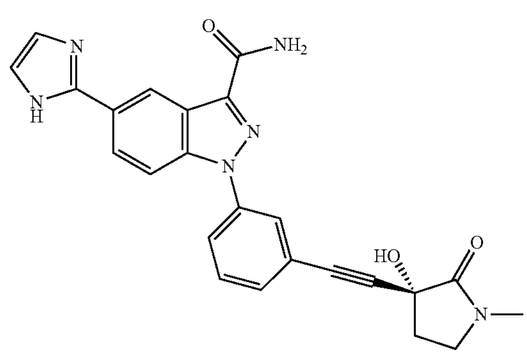 [SMILES: CN1CC[C@@](O)(C#Cc2cccc(-n3nc(C(N)=O)c4cc(-c5ncc[nH]5)ccc43)c2)C1=O] | 1-[3-[2-[(3R)-3-hydroxy-1-methyl-2-oxo-pyrrolidin-3-yl]ethynyl]phenyl]-5-(1H-imidazol-2-yl)indazole-3-carboxamide |

TABLE 1-continued

| Ex. | Structure | Name |
|---|---|---|
| 183 | 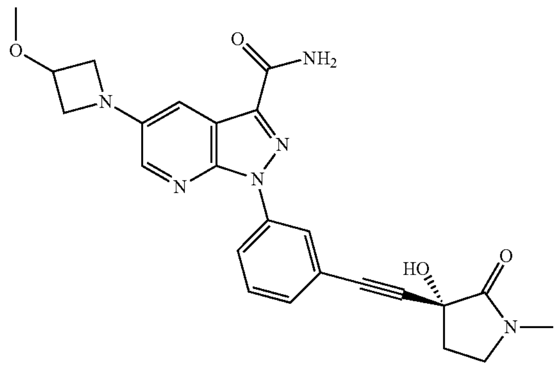 [SMILES: COC1CN(c2cnc3c(c2)c(C(N)=O)nn3-c2cccc(C#C[C@]3(O)CCN(C)C3=O)c2)C1] | 1-[3-[2-[(3R)-3-hydroxy-1-methyl-2-oxo-pyrrolidin-3-yl]ethynyl]phenyl]-5-(3-methoxyazetidin-1-yl)pyrazolo[3,4-b]pyridine-3-carboxamide |
| 184 | 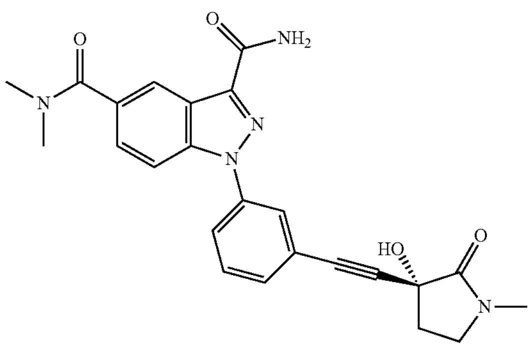 | 1-[3-[2-[(3R)-3-hydroxy-1-methyl-2-oxo-pyrrolidin-3-yl]ethynyl]phenyl]-N5,N5-dimethyl-indazole-3,5-dicarboxamide |
| 185 | 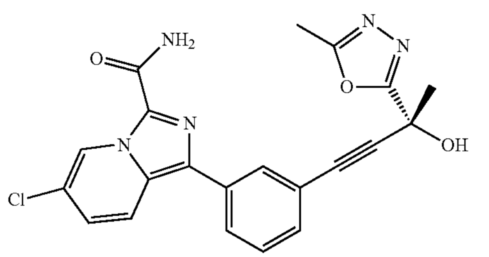 [SMILES: Cc1nnc([C@](C)(O)C#Cc2cccc(-c3nc(C(N)=O)n4cc(Cl)ccc34)c2)o1] | 6-chloro-1-[3-[(3R)-3-hydroxy-3-(5-methyl-1,3,4-oxadiazol-2-yl)but-1-ynyl]phenyl]imidazo[1,5-a]pyridine-3-carboxamide |
| 186 | 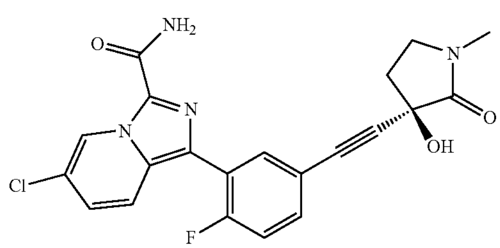 [SMILES: CN1CC[C@@](O)(C#Cc2ccc(F)c(-c3nc(C(N)=O)n4cc(Cl)ccc34)c2)C1=O] | 6-chloro-1-[2-fluoro-5-[2-[(3R)-3-hydroxy-1-methyl-2-oxo-pyrrolidin-3-yl]ethynyl]phenyl]imidazo[1,5-a]pyridine-3-carboxamide |
| 187 | 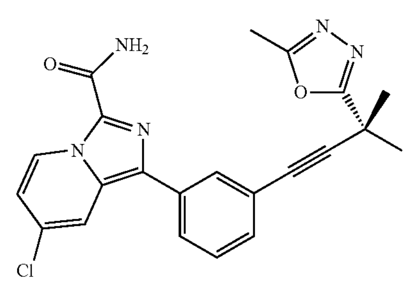 | 7-chloro-1-[3-[(3R)-3-hydroxy-3-(5-methyl-1,3,4-oxadiazol-2-yl)but-1-ynyl]phenyl]imidazo[1,5-a]pyridine-3-carboxamide |

TABLE 1-continued

| Ex. | Structure | Name |
|---|---|---|
| 188 | 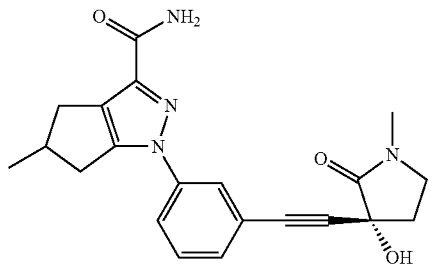 [SMILES: CC1Cc2c(C(N)=O)nn(-c3cccc(C#C[C@]4(O)CCN(C)C4=O)c3)c2C1] | 1-[3-[2-[(3R)-3-hydroxy-1-methyl-2-oxo-pyrrolidin-3-yl]ethynyl]phenyl]-5-methyl-5,6-dihydro-4H-cyclopenta[c]pyrazole-3-carboxamide |
| 189 | 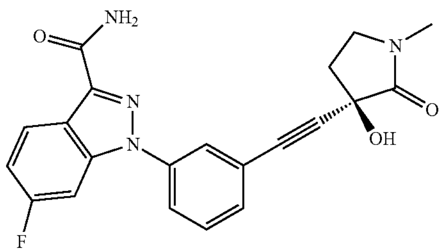 [SMILES: CN1CC[C@@](O)(C#Cc2cccc(-n3nc(C(N)=O)c4ccc(F)cc43)c2)C1=O] | 6-fluoro-1-[3-[2-[(3R)-3-hydroxy-1-methyl-2-oxo-pyrrolidine-3-yl]ethynyl]phenyl]indazole-3-carboxamide |
| 190 | 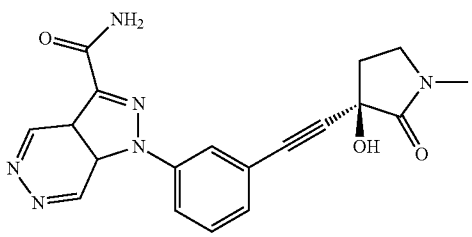 [SMILES: CN1CC[C@@](O)(C#Cc2cccc(N3N=C(C(N)=O)C4C=NN=CC43)c2)C1=O] | 1-[3-[2-[(3R)-3-hydroxy-1-methyl-2-oxo-pyrrolidin-3-yl]ethynyl]phenyl]pyrazolo[3,4-d]pyridazine-3-carboxamide |
| 191 | 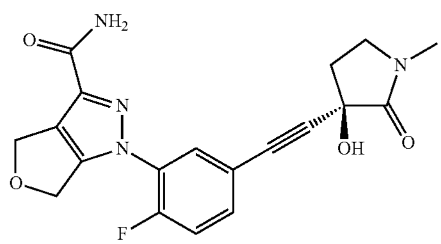 [SMILES: CN1CC[C@@](O)(C#Cc2ccc(F)c(-n3nc(C(N)=O)c4c3COC4)c2)C1=O] | 1-[2-fluoro-5-[2-[(3R)-3-hydroxy-1-methyl-2-oxo-pyrrolidin-3-yl]ethynyl]phenyl]-4,6-dihydrofuro[3,4-c]pyrazole-3-carboxamide |
| 192 | 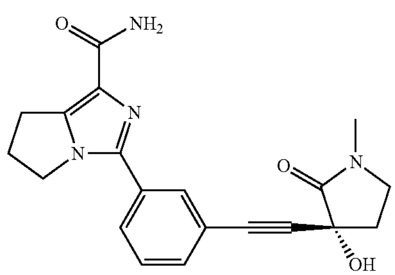 [SMILES: CN1CC[C@@](O)(C#Cc2cccc(-c3nc(C(N)=O)c4n3CCC4)c2)C1=O] | 3-[3-[2-[(3R)-3-hydroxy-1-methyl-2-oxo-pyrrolidin-3-yl]ethynyl]phenyl]-6,7-dihydro-5H-pyrrolo[1,2-c]imidazole-1-carboxamide |
| 193 | 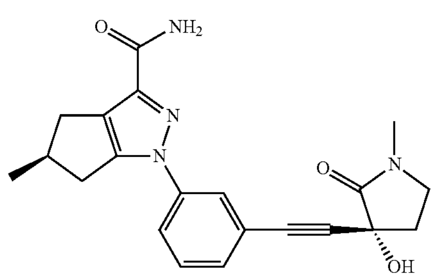 [SMILES: C[C@H]1Cc2c(C(N)=O)nn(-c3cccc(C#C[C@]4(O)CCN(C)C4=O)c3)c2C1] | (5S)-1-[3-[2-[(3R)-3-hydroxy-1-methyl-2-oxo-pyrrolidin-3-yl]ethynyl]phenyl]-5-methyl-5,6-dihydro-4H-cyclopenta[c]pyrazole-3-carboxamide |

TABLE 1-continued

| Ex. | Structure | Name |
|---|---|---|
| 194 | 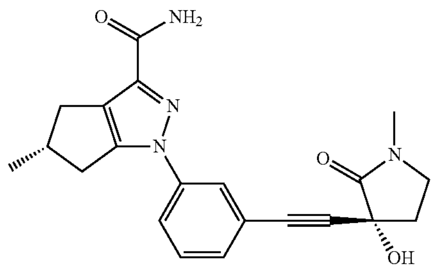 [SMILES: C[C@@H]1Cc2c(C(N)=O)nn(-c3cccc(C#C[C@]4(O)CCN(C)C4=O)c3)c2C1] | (5R)-1-[3-[2-[(3R)-3-hydroxy-1-methyl-2-oxo-pyrrolidin-3-yl]ethynyl]phenyl]-5-methyl-5,6-dihydro-4H-cyclopenta[c]pyrazole-3-carboxamide |
| 195 | 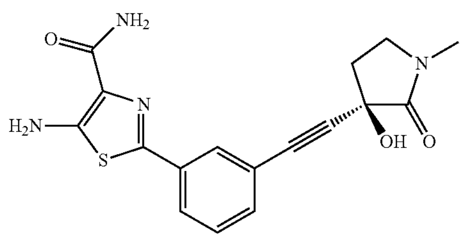 [SMILES: CN1CC[C@@](O)(C#Cc2cccc(-c3nc(C(N)=O)c(N)s3)c2)C1=O] | 5-amino-2-[3-[2-[(3R)-3-hydroxy-1-methyl-2-oxo-pyrrolidin-3-yl]ethynyl]phenyl]thiazole-4-carboxamide |
| 196 | 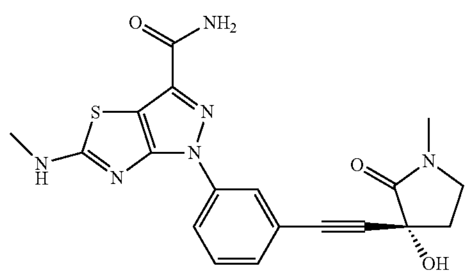 [SMILES: CNc1nc2c(s1)c(C(N)=O)nn2-c1cccc(C#C[C@]2(O)CCN(C)C2=O)c1] | 1-[3-[2-[(3R)-3-hydroxy-1-methyl-2-oxo-pyrrolidin-3-yl]ethynyl]phenyl]-5-(methylamino)pyrazolo[3,4-d]thiazole-3-carboxamide |
| 197 | 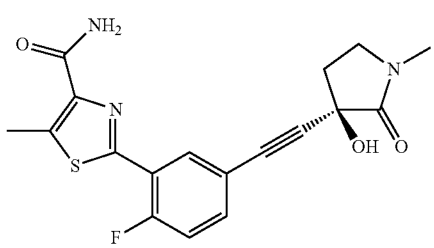 | 2-[2-fluoro-5-[2-[(3R)-3-hydroxy-1-methyl-2-oxo-pyrrolidin-3-yl]ethynyl]phenyl]-5-methyl-thiazole-4-carboxamide |
| 198 | 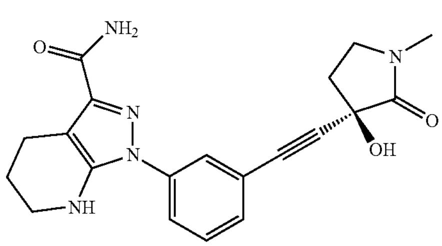 [SMILES: CN1CC[C@@](O)(C#Cc2cccc(-n3nc(C(N)=O)c4c3NCCC4)c2)C1=O] | 1-[3-[2-[(3R)-3-hydroxy-1-methyl-2-oxo-pyrrolidin-3-yl]ethynyl]phenyl]-4,5,6,7-tetrahydropyrazolo[3,4-b]pyridine-3-carboxamide |
| 199 | 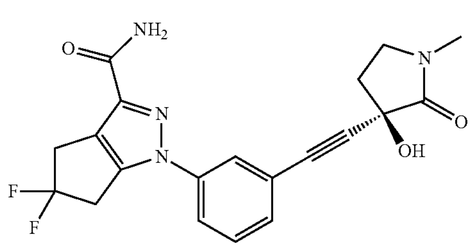 [SMILES: CN1CC[C@@](O)(C#Cc2cccc(-n3nc(C(N)=O)c4c3CC(F)(F)C4)c2)C1=O] | 5,5-difluoro-1-[3-[2-[(3R)-3-hydroxy-1-methyl-2-oxo-pyrrolidin-3-yl]ethynyl]phenyl]-4,6-dihydrocyclopenta[c]pyrazole-3-carboxamide |

In some embodiments, the invention provides a compound of Examples A-R8 below.

Synthesis of NIK Inhibitors

Methods for preparing intermediates and compounds of the present invention are presented in the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives or reaction conditions. In addition, many of the compounds prepared by the methods described below can be further modified in light of this disclosure using conventional chemistry well known to those skilled in the art.

The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y (1967-2006 ed.), or Beilstein's Handbuch der organishcen chemie, 4, Aufl. Ed. Springer-Verlag, Berlin including supplements also included via the Beilstein online database.

In preparing compounds of Formula (0), protection of remote functionality (e.g., primary or secondary amine) of intermediates may be necessary. The need for such protection will vary depending on the nature of the remote functionality and the conditions of the preparation methods. The need for such protection is readily determined by one skilled in the art. Exemplary protecting groups are provided herein. For a general description of protecting groups and their use, see T. W. Greene, Protective Groups in Organic Synthesis, John Wiley & Sons, New York, 1991.

Diastereomeric mixtures can be separated into their individual diastereoisomers on the basis of their physical chemical differences by methods well known to those skilled in the art, such as by chromatography or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column or supercritical fluid chromatography.

A single stereoisomer, e.g., an enantiomer, substantially free of its stereoisomer may be obtained by resolution of the racemic mixture using a method such as formation of diastereomers using optically active resolving agents (Eliel, E. and Wilen, S., Stereochemistry of Organic Compounds, John Wiley & Sons, Inc., New York, 1994; Lochmuller, C. H., J. Chromatogr., 113(3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Drug Stereochemistry, Analytical Methods and Pharmacology, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., Stereochemistry of Organic Compounds, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob, J. Org. Chem. 47:4165 (1982)), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (Chiral Liquid Chromatography W. J. Lough, Ed., Chapman and Hall, New York, (1989); Okamoto, J. of Chromatogr. 513:375-378 (1990)). Enriched or purified enantiomers can be distinguished by methods used to distinguish other chiral molecules with asymmetric carbon atoms, such as optical rotation and circular dichroism. The absolute stereochemistry of chiral centers and enantiomers can be determined by x-ray crystallography.

Positional isomers, for example E and Z forms, of compounds of Formula I and intermediates for their synthesis, may be observed by characterization methods such as NMR and analytical HPLC. For certain compounds where the energy barrier for interconversion is sufficiently high, the E and Z isomers may be separated, for example by preparatory HPLC.

Pharmaceutical Compositions and Administration

The compounds with which the invention is concerned are NIK kinase inhibitors, and are useful in the treatment of several diseases, for example, cancer or inflammatory conditions.

The invention also provides for compositions and medicaments comprising a compound of Formula (0) and at least one pharmaceutically acceptable carrier, diluent or excipient. The compositions of the invention can be used for inhibiting NF-kB signaling activity in mammals (e.g, human patients), by for example, inhibiting NIK activity.

By "pharmaceutically acceptable" it is meant the carrier, diluent or excipient must be compatible with the other ingredients of the formulation and not deleterious to the recipient thereof.

In one embodiment, the invention provides for pharmaceutical compositions (or medicaments) comprising a compound of Formula (0) and a pharmaceutically acceptable carrier, diluent or excipient. In another embodiment, the invention provides for preparing compositions (or medicaments) comprising compounds of the invention. In another embodiment, the invention provides for administering compounds of Formula (0) and compositions comprising compounds of Formula (0) to a mammal (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit NIK activity as required to prevent or treat the undesired disease or disorder, such as for example, neurodegeneration, amyloidosis, formation of neurofibrillary tangles, or undesired cell growth (e.g., cancer cell growth). For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, such as 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compositions comprising compounds of Formula (0) are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); or non-ionic surfactants such as TWEEN™, PLURONICS™ or polyethylene glycol (PEG). A active pharmaceutical ingredient of the invention (e.g., compound of Formula (0)) can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) 21$^{st}$ Edition, Lippincott Williams & Wilkins, Philadelphia, Pa.

Sustained-release preparations of a compound of the invention can be prepared. Suitable examples of sustained-release preparations include semipermeable matrices of solid hydrophobic polymers containing a compound of Formula (0), which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) 21$^{st}$ Edition, Lippincott Williams & Wilkins, Philadelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of Formula (0) may be formulated by mixing at ambient temperature at the appropriate pH, and at the desired degree of purity, with physiologically acceptable carriers. The pH of the formulation depends mainly on the particular use and the concentration of compound, but typically ranges anywhere from about 3 to about 8. In one example, a compound of Formula (0) is formulated in an acetate buffer, at pH 5. In another embodiment, the compounds of Formula (0) are sterile. The compound may be stored, for example, as a solid or amorphous composition, as a lyophilized formulation or as an aqueous solution.

Formulations of a compound of the invention suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention, or any range derivable therein, compounded with about 5-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of a compound of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

Formulations suitable for vaginal administration can be presented as pessaries, tampons, creams, gels, pastes, foams or spray formulations containing in addition to the active ingredient such carriers as are known in the art to be appropriate.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

Indications and Methods of Treatment

The compounds of Formula (0) inhibit the activity of NIK. Accordingly, in another aspect of the invention the compounds of the invention can be used for the treatment of diseases and disorders in a mammal, for example a human patient, in which the inhibition of NIK in the patient would be therapeutically effective. For example, the compounds of the invention are useful for the treatment of diseases or disorders in a mammal (e.g., a human patient) associated with overactive or undesired NF-kB signaling through, for example, the overactivation of NIK. In one embodiment, the compounds of the invention are used to inhibit the activity of NIK, for example in an in vitro assay setting, by contacting said compound of Formula (0) with NIK. For example, compounds of Formula (0) can be used as a control compound in an in vitro assay setting.

In another embodiment, the compounds of the invention are used to inhibit the undesired signaling of NF-kB, e.g. in an cell proliferation assay, by introducing into a cell a compound of Formula (0). In another embodiment, the present invention provides the treatment of diseases or disorders in a mammal (e.g., human patient) associated with overactive or undesired NF-kB signaling (e.g., cancer, inflammatory diseases, among others) said method comprising administering to a mammal (e.g., a human patient) in need thereof a therapeutically effective amount of a compound of the invention.

Diseases and disorders treatable according to the methods of this invention include, cancer, inflammatory conditions, autoimmune disease and proliferation induced after medical procedures (e.g., arthritis, graft rejection, inflammatory bowel disease, cell proliferation induced after surgery angioplasty, among others). In one embodiment, a mammal (e.g., a human patient) is treated with a compound of the invention and a pharmaceutically acceptable carrier, adjuvant, or vehicle, wherein said compound of the invention is present in an amount to inhibit NF-kB signaling through, for example, but not limited to, inhibition of NIK.

In one embodiment, a compound of the invention can be used in the treatment of cell proliferative disorders.

In one embodiment of the invention, cancers that may be treated by the compounds of Formula (0) are selected from the group consisting of Lung (brochogenic carcinoma (non-small cell lung); Gatrointestinal—rectal, colorectal and colon; Genitourinary tract—kidney (papillary renal cell carcinoma); and skin—head and neck squamous cell carcinoma.

In one embodiment, compounds of Formula (0) can be use for the treatment of a cancer selected from the group consisting of head and neck squamous cell carcinomas, histiocytic lymphoma, lung adenocarcinoma, small cell lung cancer, non-small cell lung cancer, pancreatic cancer, papillary renal cell carcinoma, liver cancer, gastric cancers, colon cancer, leukemias, lymphomas, multiple myeloma, glioblastomas and breast carcinoma.

In one embodiment, compounds of Formula (0) can be used for the treatment of a cancer selected from the group consisting of histiocytic lymphoma, lung adenocarcinoma, small cell lung cancer, pancreatic cancer, liver cancer, gastric cancer, colon cancer, leukemias, lymphomas, multiple myeloma, glioblastomas and breast carcinoma.

In one embodiment, compound of Formula (0) can be used for the treatment of cancer selected from the group consisting of lymphomas, leukemias and multiple myeloma.

In one embodiment, the invention provides for the preparation of a medicament comprising a compound of Formula (0) for the treatment of lymphoma, leukemia or multiple myeloma.

In one embodiment, the invention provides for the treatment of lymphoma, leukemia or multiple myeloma, which method comprises administering an effective amount of a compound of Formula (0).

In one embodiment, compounds of the invention are useful for the treatment of inflammatory diseases and conditions including, but not limited to, lupus (including systemic lupus erythematosus, extra-renal lupus and lupus nephritis), asthma, COPD, rhinitis, multiple sclerosis, IBD, arthritis, gastritis, rheumatoid arthritis, dermatitis, endometriosis, transplant rejection, cardiac infarction, Alzheimer's diseases, diabetes Type II, inflammatory bowel disease, sepsis, and artherosclerosis.

In one embodiment, the invention provides for the use of a compound of Formula (0) for the treatment of an inflammatory condition.

In one embodiment, the invention provides for the use of a compound of Formula (0) for the preparation of a medicament for the treatment of an inflammatory condition.

In one embodiment, the invention provides for a compound of Formula (0) for the treatment of an inflammatory condition.

In one embodiment, the invention provides for a method for the treatment of an inflammatory condition, which method comprises administering an effective amount of a compound of Formula (0) to a patient in need thereof.

In one embodiment, the invention provides for the treatment of an inflammatory condition selected from the group consisting of lupus (including systemic lupus erythematosus, extra-renal lupus and lupus nephritis), COPD, rhinitis, multiple sclerosis, IBD, arthritis, rheumatoid arthritis, dermatitis, endometriosis and transplant rejection, which method comprises administering an effective amount of a compound of Formula (0).

Combinations

The compounds of Formula (0) may be employed alone or in combination with other therapeutic agents for treatment. In one embodiment, compounds of this invention may be employed alone or in combination with chemotherapeutic agents. In one embodiment, compounds of this invention may be employed alone or in combination with anti-inflammatory agents. The compounds of the present invention can be used in combination with one or more additional drugs, for example an anti-inflammatory compound or anti-cancer compounds, that work by a different mechanism of action. The second compound of the pharmaceutical combination formulation or dosing regimen preferably has complementary activities to the compound of this invention such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

In certain embodiments, a compound of Formula (0) is combined in a pharmaceutical combination formulation, or dosing regimen as combination therapy, with a second therapeutic compound that has anti-inflammatory or anti-cancer properties or that is useful for treating an inflammation, immune-response disorder, or hyperproliferative disorder (e.g., cancer). The second therapeutic agent may be a NSAID (Non-Steroidal Anti-Inflammatory Drug) or other anti-inflammatory agent. The second therapeutic agent may be a chemotherapeutic agent. In one embodiment, a pharmaceutical composition of this invention comprises a compound of Formula (0) in combination with a therapeutic agent such as an NSAID.

EXAMPLES

The invention will be more fully understood by reference to the following examples. They should not, however, be construed as limiting the scope of the invention. These examples are not intended to limit the scope of the present invention, but rather to provide guidance to a skilled artisan to prepare and use the compounds, compositions, and methods of the present invention. While particular embodiments of the present invention are described, the skilled artisan will appreciate that various changes and modifications can be made without departing from the spirit and scope of the invention.

The chemical reactions in the Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

Intermediates and compounds of the invention can be synthesized according to Schemes A-AA presented below, in which, R, R', R", $R_1$ and $R_2$ at each occurrence independently represents generally a non-interfering substituent (unless otherwise a specific substituent is specified in the description of the scheme); the symbol Ar at each occurrence represents independently an aromatic group; the symbol Het at each occurrence represents independently a heteroaryl group; and the symbol X at each occurrence represents independently any halogen (unless otherwise a specific halogen is specified in the description of the scheme).

General Procedure A

SNAr

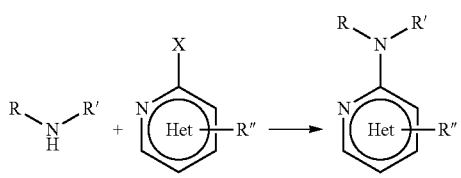

To a solution of nitrogen-containing nucleophile (1 eq.) and cesium carbonate (3.0 eq.) in N,N-dimethylformamide (2 mL/mmol) was added 2-haloheterocycle (1.1 eq.). The reaction was heated to 100° C. and stirred at this temperature for 2 hours. The reaction was then cooled to room temperature and acidified to pH=1 with 10% aqueous HCl solution if product contains a carboxylic acid, or diluted with water if neutral. The solution was extracted with twice with dichloromethane. The organic layers were combined, dried with sodium sulfate and concentrated under vacuum. The crude material was either used directly in subsequent reactions or purified by flash chromatography.

General Procedure B

Amide Synthesis from Heterocyclic Carboxylic Acids

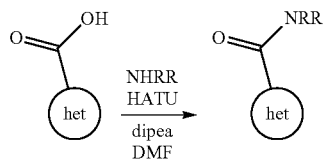

Aromatic or non-aromatic heterocyclic acid (1 eq) and HATU (1.2 eq) were weighed out and transferred to a vial to which DMF and DIPEA (3-5 eq) were subsequently added. The amine (HNRR) was added to the reaction mixture as a free base or HCl salt after a short period and the reaction was stirred at room temperature or at 50° C. for 2-18 hours. Reaction conversion was monitored by LCMS. Upon completion, the reaction was cooled and the crude product was triturated via addition of water and collected by filtration or extracted with sat ammonium chloride and DCM. Trituration or purification by chromatography gave the amide.

General Procedure C

Chan-Lam Cross-Coupling

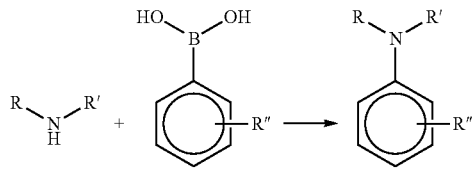

To a small vial was added the nitrogen-containing nucleophile (1 eq.), arylboronic acid (1.5 eq.), copper(II) acetate monohydrate (0.3 eq.) in N,N-dimethylformamide (2 mL/mmol) and pyridine (3.0 eq.). The reaction was stirred under an oxygen atmosphere at 90° C. for 6 hours. The reaction was then cooled to room temperature and diluted with a saturated aqueous sodium bicarbonate solution, and the aqueous phase was extracted with 3 times with dichloromethane. The organic phases were combined, washed with brine, dried with sodium sulfate and concentrated under vacuum. The crude material was purified by flash chromatography.

General Procedure D

Hydrolysis of nitrile to primary amide.

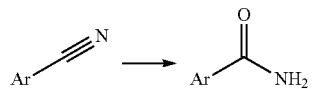

To a solution of an aryl nitrile (1 eq.) in ethanol (0.8 mL/mmol) and water (0.04 mL/mmol) was added hydrido (dimethylphosphinous acid-kp)[hydrogen bis(dimethylphosphinito-kp)]platinum(II) (0.05 eq.). The reaction was stirred at 90° C. for 2 h under air. The solution was then cooled to room temperature and extracted twice with ethyl acetate or dichloromethane. The organic layers were combined, dried with sodium sulfate and concentrated under vacuum. The crude material was either used directly in subsequent reactions or purified by flash chromatography.

General Procedures for aryl-halide (ArX) to terminal alkyne cross-coupling:

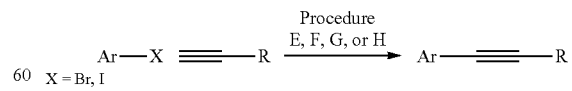

General Procedure E

Aryl halide was weighed out, transferred to a sealed tube and brought up in Acetontrile (3 mL/mmol) and Triethylamine (3 mL/mmol). The solution was degassed with nitrogen and Copper(I) Iodide (0.05 eq) and Bis(triphenylphosphine)palladium(II)chloride (0.1 eq) were added. DMF (3 mL/mmol) was then added followed by dropwise addition of alkyne (2-3 eq). The reaction mixture heated for 3-18 h at 80° C. and monitored by LCMS for consumption of starting material. Upon completion, the reaction was cooled and the crude product was either triturated via addition of water and collected by filtration or extracted with saturated ammonium chloride and DCM whereupon the organic layer was dried, filtered and concentrated to dryness. Crude products were submitted for reverse phase HPLC purification.

General Procedure F

Aryl halide (where X=bromide) (1 eq), Copper (I) Iodide (0.06 eq), tri-t-butylphosphonium tetrafluoroborate (0.2 eq) and dichlorobis(phenyl cyanide)palladium (0.1 eq) were weighed out and transferred to a microwave vessel. Upon addition of DMSO (3 mL/mmol), the reaction mixture was subsequently degassed whereupon a solution of alkyne (3 eq) in Diisopropylamine (3 eq) was added dropwise. The reaction mixture was capped and heated thermally at 80° C. and monitored by LCMS for consumption of starting material. Workup is the same for as in procedure E.

General Procedure G

Aryl halide (wherein X=bromide) was weighed out, transferred to a sealed tube and brought up in DMSO or DMF (3 mL/mmol) and Triethylamine (3 mL/mmol). The solution was degassed with nitrogen and Bis(triphenylphosphine) palladium(II)chloride (0.2 eq) and alkyne (2-3 eq) were added ("copper-free" conditions). The reaction mixture heated for 2-18 hrs at 80° C. and monitored by LCMS for consumption of starting material. Workup is the same for as in above procedure E.

General Procedure H

Ester to Amide Conversion with Sodium Methoxide/Formamide

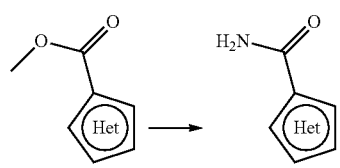

To a solution of Heterocyclic ester in N,N-Dimethylformamide was added formamide (10 eq) followed by dropwise addition of sodium methoxide (3 eq). The mixture was either stirred at room temperature or heated to 40° C. and monitored by LC-MS for completion. The crude reaction mixture was triturated via addition of saturated ammonium chloride or extracted with Dichloromethane in cases where the product did not crash out. In situations where this was an intermediate, the crude material was used directly in subsequent reactions.

General Procedure I

Ester to Amide Conversion with Ammonium Hydroxide in Dioxane

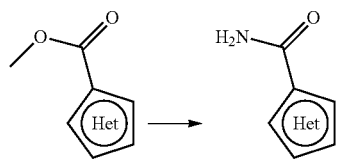

To a solution of Heterocyclic ester in Dioxane (10 mL/mmol) was added ammonium hydroxide (25% mass) in water (50 eq., 14 mmol). The reaction mixture was stirred at 40° C. and monitored by LC-MS for completion. The crude reaction mixture was concentrated to dryness and purified by reverse phase HPLC to afford product.

General Procedure J

Ester Saponification

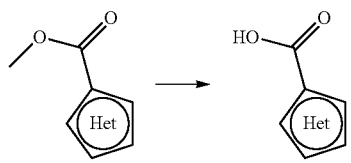

To a solution of heterocylic ester in 1:1 Tetrahydrofuran/Water was added lithium hydroxide monohydrate (3-10 eq). The reaction was either stirred at room temperature or heated to 50° C. and monitored by LC-MS for completion. The tetrahydrofuran was then evaporated and the pH of the aqueous crude reaction mixture was adjusted to 3 whereupon the product either crashed out and was isolated, or the aqueous layer was extracted with Dichloromethane or ethyl acetate in cases where the product did not crash out. In situations where this was an intermediate, the crude material was used directly in subsequent reactions.

General Procedure K

Ketone/Aldehyde Reduction

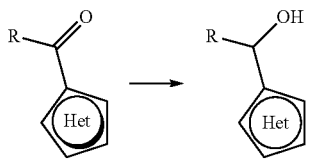

To a solution of heterocylic ketone/aldehyde in Methanol was added sodium borohydride (1-3 eq). The reaction was stirred at 0° C. or room temperature until bubbling subsided and monitored by LC-MS for completion. The reaction mixture was extracted with dichloromethane and saturated ammonium chloride whereupon the organic layer was dried, filtered and concentrated to afford crude heterocylic alcohol intermediate and was used directly in subsequent reactions.

General Procedure L

Fluorination

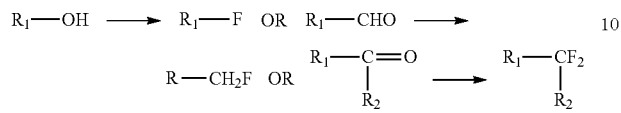

To a solution of alcohol, aldehyde or ketone in Dichloromethane or Dichloroethane was added 4 equivalents of Diethylaminosulfur trifluoride (DAST) or Bis(2-methoxyethyl)aminosulfur trifluoride (Deoxo-Fluor). The reaction was either stirred at room temperature or heated to 45° C. and monitored by LC-MS for completion. The reaction mixture was concentrated to dryness and the crude intermediate was triturated via addition of water which was used in subsequent reactions without further purification.

General Procedure M

Suzuki Coupling of Boronic Acids or Boronic Esters with Aryl Halides

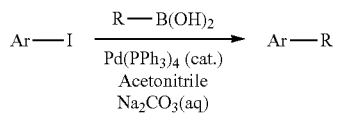

Aryl Halide, tetrakis (triphenylphosphine)palladium or Palladium (II) bis(triphenylphosphine) dichloride (0.05 eq) and boronic acid or pinnacol ester (1.2 eq) were weighed out into a microwave vessel or sealed tube. Acetonitrile (3 mL/mmol) and a 1M aqueous solution of Sodium Carbonate (3 eq) were added. The vessel was capped and heated thermally 3-18 hrs at 100° C. Upon completion, the reaction was cooled and crude product was either triterated via addition of water and collection by filtration or extracted with sat ammonium chloride and DCM. If the crude product was an intermediate, it was taken into the next step in most cases w/o further purification or alternatively submitted for reverse phase HPLC purification when it was a final product.

General Procedure N

Reductive Amination of Arylaldehydes

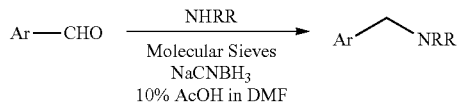

To a vial containing aryl aldehyde (1 eq) in 10% Acetic Acid in DMF (6 mL/mmol) was added molecular sieves (1 eq by wt), amine (HNRR, 4 eq) then sodium cyanoborohydride (1.2 eq). The reaction was either heated at 45° C. or stirred at room temperature. Upon completion, the reaction was extracted with DCM and saturated ammonium chloride. The organic layer was dried with magnesium sulfate, filtered and concentrated to give crude product which was taken into the next step without purification.

General Procedure O

Carbonylative Methanolysis of Aryl Iodides

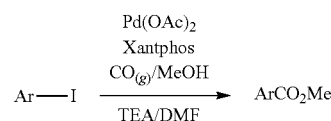

To a nitrogen-purged solution of aryl iodide in TEA (3 mL/mmol), DMF (3 mL/mmol) and MeOH (3 mL/mmol) was added Palladium (II)Acetate (0.03 eq) and Xantphos (0.06 eq). The reaction mixture was flushed with Carbon Monoxide gas for several minutes and then sealed with CO balloon attached and heated to 60° C. for 3 hours. Upon completion, the reaction was cooled to room temperature and the crude product was triterated via addition of water and collected by filtration. The crude intermediate was taken into the next step w/o further purification.

General Procedure P

Carbonylative Amidation with HMDS

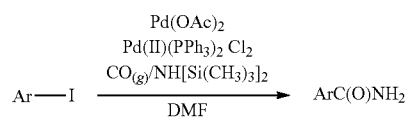

To a nitrogen-degassed solution of generic aryl iodide (Ar—I) in DMF (170 eq) was added Palladium(II)bis(triphenylphosphine) dichloride (0.05 eq) and hexamethyldisilazane (6 eq). The reaction mixture was flushed with Carbon Monoxide gas for several minutes and then sealed with CO balloon attached and heated to 70° C. for 18 hrs. Upon completion, the reaction was cooled to room temperature and the crude was triterated via addition of water and collected by filtration. The crude intermediate was taken into the next step w/o further purification.

General Procedure S

Ester to Amide Conversion Using Ammonia in Methanol

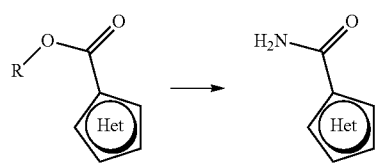

To a stirred solution of ester (1 equiv) in methanol was treated with saturated ammonia (>20 eq.) in methanol. The mixture was either stirred at room temperature or heated to 40° C. and the reaction was monitored by LC-MS. The crude reaction mixture was concentrated and purified by reverse phase HPLC.

General Procedure T

SEM Deprotection with HCl

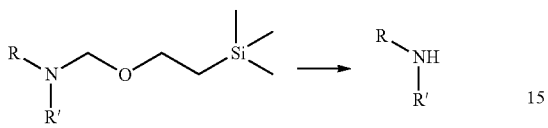

The SEM-protected amine or alcohol and 4.0 M hydrochloric acid in dioxane (17.0 eq.) were combined in ethanol (4.0 mL/mmol) and stirred at 50° C. for 2 h. The sample was then concentrated under vacuum and used directly in subsequent reactions or purified by flash chromatography.

General Procedures for Suzuki Couplings with Aryltrifluoroborates:

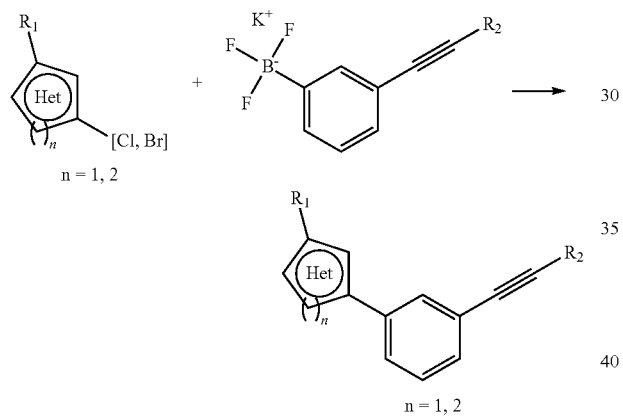

General Procedure U

A tube containing a solution of arylchloride/bromide (1 eq) and aryltrifluoroborate (1 eq) in Ethanol was purged with nitrogen before addition of Pd(OAc)$_2$ (0.06 eq), RuPhos (0.12 eq), and Sodium Carbonate (2 eq). The tube was sealed with a cap lined with a disposable Teflon septum was heated at 85° C. for 12-20 hours. The reaction mixture was allowed to cool to room temperature and was either filtered thru celite and submitted directly to reverse phase HPLC purification or extracted with dichloromethane and a solution of saturated ammonium chloride before drying, evaporating and submitting to reverse phase purification or using in the subsequent step without purification.

General Procedure V

A solution of arylchloride/bromide (1 eq) and aryltrifluoroborate (1 eq) in 20% aq dioxane (0.28M) was degassed before addition of cesium carbonate (3 eq) and tetrakis (triphenylphosphine)palladium(0) (0.05 eq). The reaction mixture was heated at 100° C. for 1 hr then cooled to room temperature. Workup same as General Procedure U.

General Procedure W

A solution of arylchloride/bromide (1 eq) and aryltrifluoroborate (1 eq) in Acetonitrile (0.25M) was degassed before addition of tetrakis(triphenylphosphine)palladium(0) (0.05 eq) and a 1:1 mixture of 1M Sodium Carbonate (2 eq) and 1M Potassium Acetate (2 eq). The reaction was performed in a 5 mL biotage microwave tube and heated to 140° C. for 20-40 minutes then cooled to room temperature. Workup same as General Procedure U.

General Procedure X

Synthesis of SEM-Protected Tetrahydroindazoles

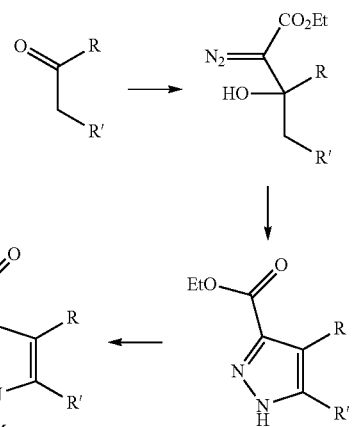

Step 1: A solution of diisopropylamine (1.7 eq.) in THF (4.6 mL/mmol) was cooled to −78° C., then a solution of n-butyl lithium in hexanes (1.6 M, 1.5 eq.) was added dropwise. After stirring for 5 minutes, this mixture was added via cannula to a −78° C. solution of ethyl diazoacetate (1.6 eq.) and cycloalkylketone (1.0 eq.) in THF (4.6 mL/mmol). The mixture was stirred for 1 hour at −78° C., then quenched by the addition of sat. NH$_4$Cl(aq). The mixture was diluted with water and extracted with EtOAc (2 times). The combined organic extracts were dried (MgSO$_4$) and concentrated in vacuo. Purification by CombiFlash (heptane:EtOAc) provided the desired product.

Step 2: To a solution of product from the previous step (1.0 eq.) in pyridine (4.6 mL/mmol) was added POCl$_3$ (4.35 eq.) and the mixture was allowed to stir at room temperature overnight. After in vacuo concentration, the mixture was poured onto ice, then extracted with EtOAc (3 times). The combined organic extracts were dried (MgSO$_4$) and concentrated in vacuo. This residue was diluted with octane (2.1 mL/mmol) and heated to 110° C. for two hours. After in vacuo concentration, purification by CombiFlash (heptane: EtOAc) provided the desired product.

Step 3: A solution of product from the previous step (1.0 eq.) in THF (20 mL/mmol) was cooled to 0° C., then sodium hydride (60%, 3.0 eq.) was added. After stirring for 1 hour, SEMCl (1.2 eq.) was added and the mixture was allowed to warm to room temperature overnight. After excess hydride was quenched by the addition of water at 0° C., the mixture was extracted with EtOAc (3 times), the organic extracts dried (MgSO$_4$) and concentrated in vacuo. Purification by CombiFlash (heptane:EtOAc) provided the desired ester containing product. This ester was diluted with THF (5.4 mL/mmol), acetonitrile (5.4 mL/mmol) and water (5.4 mL/mmol) and lithium hydroxide monohydrate (7.0 eq.) was added and the mixture was stirred overnight. The mixture was diluted with water, acidified to pH 3 with 1 N HCl(aq) and extracted with Et$_2$O (once) and 10% MeOH/ CH$_2$Cl$_2$ (3 times). The combined organic extracts were dried (MgSO$_4$) and concentrated in vacuo to provide the desired carboxylic acid of sufficient purity to be used directly.

General Procedure Y

Alternative Synthesis of SEM-Protected Tetrahydroindazoles

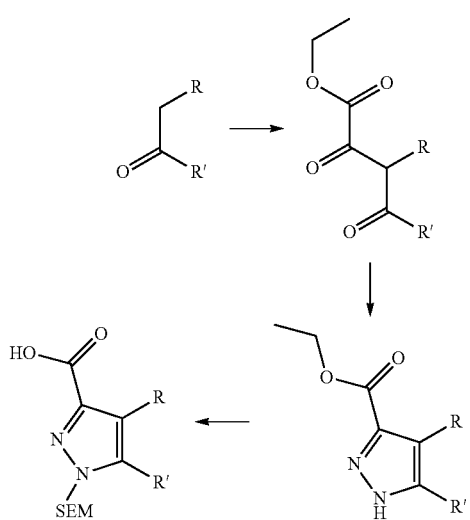

Step 1: A solution of cycloalkyl ketone (1.0 eq.) in EtOH (0.5 mL/mmol) was cooled to 0° C., then sodium ethoxide (21% wt solution in EtOH, 1.1 eq.) was added. To this mixture was added diethyl oxylate (1.0 eq.) and the mixture was allowed to warm to room temperature overnight. In vacuo concentration provided the desired product of sufficient purity to be used directly (yield assumed to be quantitative).

Step 2: A solution of product from the previous step (1.0 eq.) in glacial acetic acid (0.5 mL/mmol) was cooled to 0° C., then hydrazine hydrate (1.1 eq.) was added. After warming to room temperature, the mixture was stirred for 1 hour, then diluted with sat. NaHCO$_3$(aq) and extracted with 10% MeOH/CH$_2$Cl$_2$. The organic extracts were dried (MgSO$_4$) and concentrated in vacuo. Purification by CombiFlash (heptane:EtOAc) provided the desired tetrahydroindazole-3-carboxylate.

Step 3: Performed in an analogous manner to Step 3 General Procedure X.

General Procedure Z 2,3-dihydro-1H-indole-2,3-dione to methyl-1H-indazole-3-carboxylate

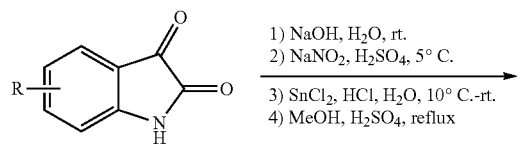

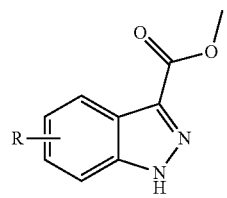

A solution of 2,3-dihydro-1H-indole-2,3-dione (1 eq.) and sodium hydroxide (1.1 eq.) in water was stirred for 5~30 min at 25° C. Then a solution of sodium nitrite (1.1 eq.) in water and concentrated sulfuric acid (2 eq.) were added dropwise with stirring at 0~10° C. After 5~30 min a solution of SnCl$_2$ (2.5 eq.) in concentrated hydrochloric acid (15~30 eq.) was added slowly. After being stirred for 1-5 h at 25° C. the reaction mixture was filtered and the solid was dissolved in methanol. Sulfuric acid (0.5~1 eq.) was added to the solution and the solution was heated to reflux overnight. The resulting mixture was concentrated under vacuum, diluted with water, extracted with ethyl acetate, dried over anhydrous sodium sulfate, and concentrated under vacuum to give the ester which may need further purification such as fresh chromatography.

Synthesis of 3-ethynyl-3-hydroxy-1-methylpyrrolidin-2-one

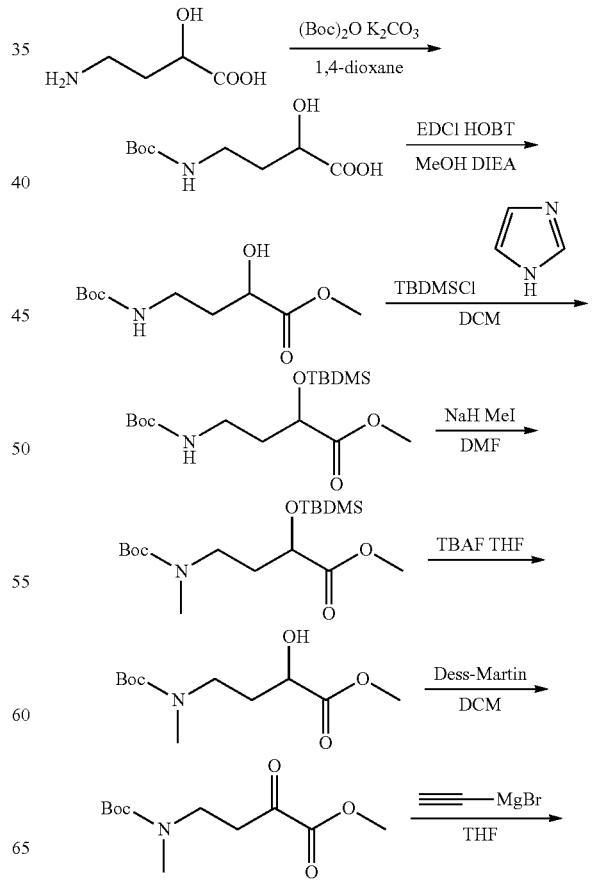

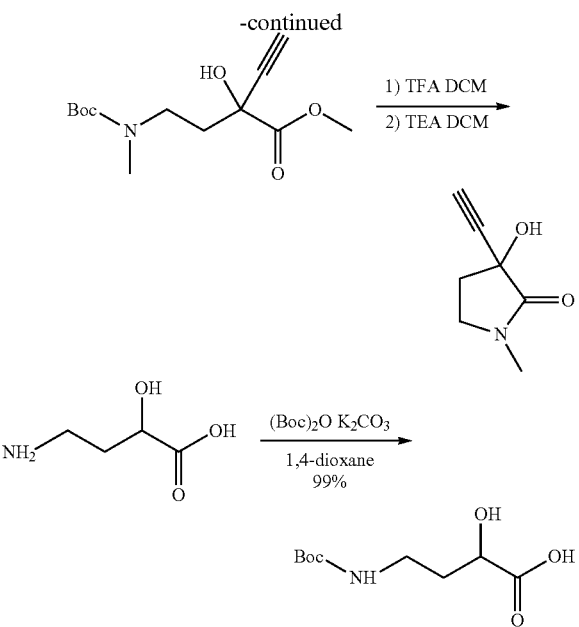

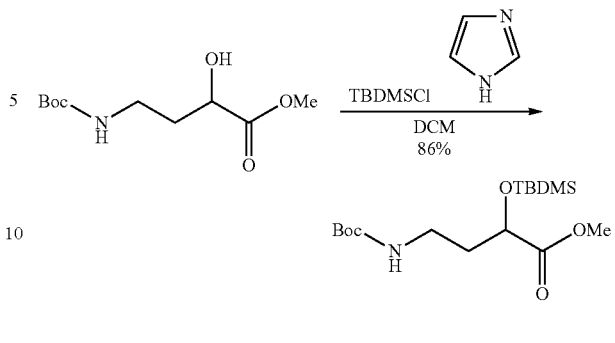

Into a 100-L barrel was placed a solution of methyl 4-[[(tert-butoxy)carbonyl]amino]-2-hydroxybutanoate (6.885 kg, 29.52 mol, 1.00 equiv) in dichloromethane (50 L), imidazole (4.02 kg, 2.00 equiv), followed by the addition of a solution of TBDMSCl (8.85 kg, 2.00 equiv) in dichloromethane (10 L) dropwise with stirring at 0-5° C. The resulting solution was stirred for overnight at 20-25° C. The solids were filtered out and the filtrate was concentrated under vacuum. The residue was applied onto a silica gel column eluting with ethyl acetate: petroleum ether (1:50) to afford 8.8 kg (86%) of methyl 4-[[(tert-butoxy)carbonyl]amino]-2-[(tert-butyldimethylsilyl)oxy]butanoate as a yellow oil.

LC-MS (ES, m/z): 348 (M+1); 248 (M−100+1)

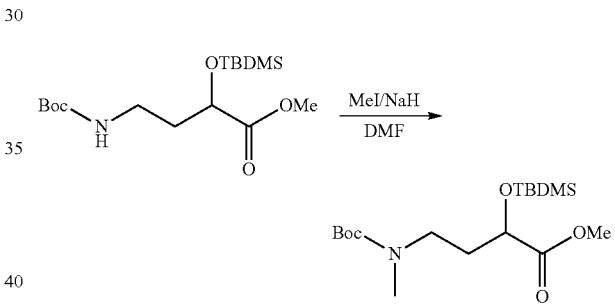

Into a 100-L barrel was placed a solution of 4-amino-2-hydroxybutanoic acid (5 kg, 41.97 mol, 1.00 equiv) in water (25 L), potassium carbonate (16.6 kg, 3.00 equiv), followed by the addition of a solution of Boc₂O (10.08 kg, 1.10 equiv) in dioxane (16 L) dropwise with stirring at 0-10° C. The resulting solution was stirred for overnight at 20-25° C. and then washed with 2×7 L of ether to remove the remained Boc₂O. The pH value of the aqueous layer was adjusted to 4-5 with 6N hydrochloric acid and the resulting solution was extracted with 4×10 L of ethyl acetate. The organic layers were combined and concentrated under vacuum to afford 9.1 kg (99%) of 4-((tert-butoxycarbonyl)amino)-2-hydroxybutanoic acid as a yellow oil.

LC-MS (ES, m/z): 218 (M−1)

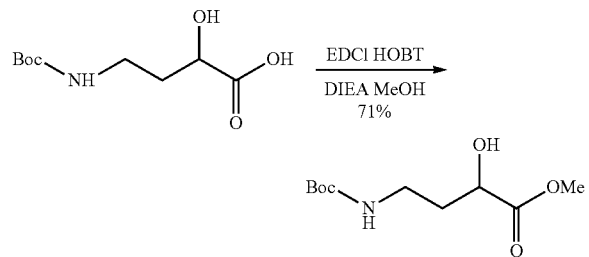

Into a 100-L barrel was placed a solution of 4-[[(tert-butoxy)carbonyl]amino]-2-hydroxybutanoic acid (9.11 kg, 41.55 mol, 1.00 equiv) in methanol (90 L), EDCI (11.9 kg, 1.50 equiv), HOBT (8.43 kg, 1.50 equiv), followed by the addition of DIEA (10.6 kg, 2.00 equiv) dropwise with stirring at 0-10° C. The resulting solution was stirred at r.t. for 2 h and concentrated under vacuum to remove MeOH. The residue was dissolved in 45 L of EA. The resulting mixture was washed with 3×30 L of H₂O, dried over anhydrous sodium sulfate and concentrated to afford 6.885 kg (71%) of methyl 4-[[(tert-butoxy)carbonyl]amino]-2-hydroxybutanoate as a yellow oil.

LC-MS (ES, m/z): 234 (M+1); 134 (M−100+1)

Into a 10-L 4-necked round-bottom flask purged and maintained with an inert atmosphere of nitrogen was placed a solution of methyl 4-[[(tert-butoxy)carbonyl]amino]-2-[(tert-butyldimethylsilyl)oxy]butanoate (1.1 kg, 3.17 mol, 1.00 equiv) in N,N-dimethylformamide (5 L), followed by the addition of sodium hydride (250 g, 2.00 equiv, 60%), in portions at 0-10° C. and then MeI (4.5 kg, 10.00 equiv) dropwise at 0-10° C. The resulting solution was stirred at 20-25° C. for 2 h, diluted with 20 L of H₂O and extracted with 3×10 L of ethyl acetate. The organic layers were combined and concentrated under vacuum. There were 5 batches altogether. The products were combined to afford 8 kg (crude) of methyl 4-[[(tert-butoxy)carbonyl](methyl)amino]-2-[(tert-butyldimethylsilyl)oxy]butanoate as a yellow oil.

LC-MS (ES, m/z): 362 (M+1); 262 (M−100+1)

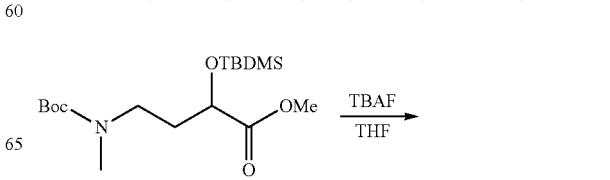

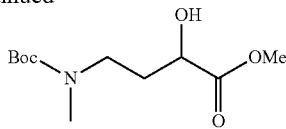

Into a 100-L barrel was placed a solution of methyl 4-[[(tert-butoxy)carbonyl](methyl)amino]-2-[(tert-butyldimethylsilyl)oxy]butanoate (8 kg, 22.13 mol, 1.00 equiv) in tetrahydrofuran (30 L), followed by the addition of a solution of TBAF (6 kg, 1.40 equiv) in tetrahydrofuran (10 L) dropwise with stirring at 0-10° C. The resulting solution was stirred at 20-25° C. for 2 h, diluted with 40 L of H$_2$O and extracted with 3×25 L of ethyl acetate. The organic layers were combined and concentrated under vacuum. The residue was applied onto a silica gel column eluting with ethyl acetate: petroleum ether (1:20) to afford 3.053 kg of methyl 4-[[(tert-butoxy)carbonyl](methyl)amino]-2-hydroxybutanoate as a yellow oil.

LC-MS (ES, m/z): 248 (M+1); 148 (M−100+1)

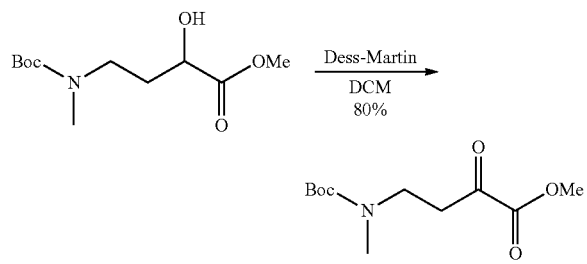

Into a 100-L barrel was placed a solution of methyl 4-[[(tert-butoxy)carbonyl](methyl)amino]-2-hydroxybutanoate (3.053 kg, 12.35 mol, 1.00 equiv) in dichloromethane (40 L), followed by the addition of Dess-Martin reagent (7.33 kg, 1.40 equiv) in portions at 0-10° C. The resulting solution was stirred at 20-25° C. for 1.5 h and diluted with 40 L of sat.NaHCO$_3$. The organic layer was washed with 2×40 L of sat.NaHCO$_3$ and concentrated under vacuum. The residue was applied onto a silica gel column eluting with ethyl acetate: petroleum ether (1:5) to afford 2.435 kg (80%) of methyl 4-[[(tert-butoxy)carbonyl](methyl)amino]-2-oxobutanoate as a yellow oil.

LC-MS (ES, m/z): 246 (M+1); 146 (M−100+1)

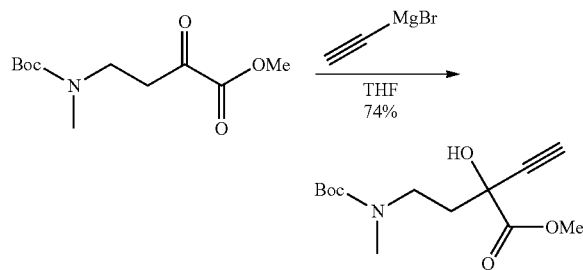

Into a 10-L 4-necked round-bottom flask purged and maintained with an inert atmosphere of nitrogen was placed a solution of methyl 4-[[(tert-butoxy)carbonyl](methyl)amino]-2-oxobutanoate (120 g, 489.25 mmol, 1.00 equiv) in tetrahydrofuran (5 L), followed by the addition of ethynylmagnesium bromide/THF (1 L, 1.03 equiv) dropwise with stirring at −70° C. The resulting solution was stirred at −70° C. for 10 min, quenched by the addition of 5 L of sat.aq.NH$_4$Cl and extracted with 3×5 L of ethyl acetate. The organic layers were combined and concentrated under vacuum. The residue was applied onto a silica gel column eluting with ethyl acetate: petroleum ether (1:5). This reaction was done 16 times. The products were combined to afford 1.563 kg (74%) of methyl 2-(2-[[(tert-butoxy)carbonyl](methyl)amino]ethyl)-2-hydroxybut-3-ynoate as a yellow oil. LC-MS (ES, m/z): 272 (M+1); 172 (M−100+1)

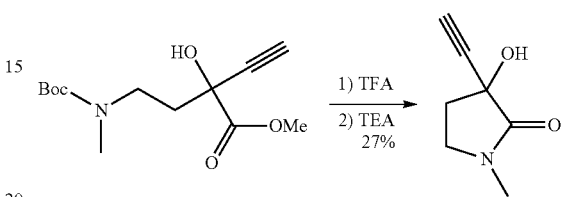

Into a 100-L barrel was placed a solution of methyl 2-(2-[[(tert-butoxy)carbonyl](methyl)amino]ethyl)-2-hydroxybut-3-ynoate (1.563 kg, 5.76 mol, 1.00 equiv) in dichloromethane (20 L), followed by the addition of trifluoroacetic acid (3 L) dropwise with stirring. The resulting mixture was concentrated under vacuum to remove TFA and the residue was dissolved in 20 L dichloromethane. To this solution was added TEA (5.83 kg, 10.00 equiv) dropwise with stirring at 0-5° C. The resulting solution was stirred at 20-25° C. for 2 h and overnight at 20-25° C. The resulting mixture was concentrated under vacuum and the residue was applied onto a silica gel column eluting with ethyl acetate: petroleum ether (1:1) to afford 220 g (27%) of 3-ethynyl-3-hydroxy-1-methylpyrrolidin-2-one as a brown solid. The enantiomers were separated by chiral preparatory SFC. The racemate (502 g) was separated by Prep-SFC with the following conditions (prep SFC 350): Column, CHIRALPAK IC SFC, 5×25 cm, 5 µm; mobile phase, CO$_2$ (65%), IPA (0.2% DEA) (35%); Detector, UV 220 nm. This resulted in 172.3 g (28.4%) of (3R)-3-ethynyl-3-hydroxy-1-methylpyrrolidin-2-one as a brown solid. LC-MS (ES, m/z): 140 (M+1)

Synthesis of 1-((2-(trimethylsilyl)ethoxy)methyl)-1,4,5,7-tetrahydropyrano[3,4-c]pyrazole-3-carboxylic acid

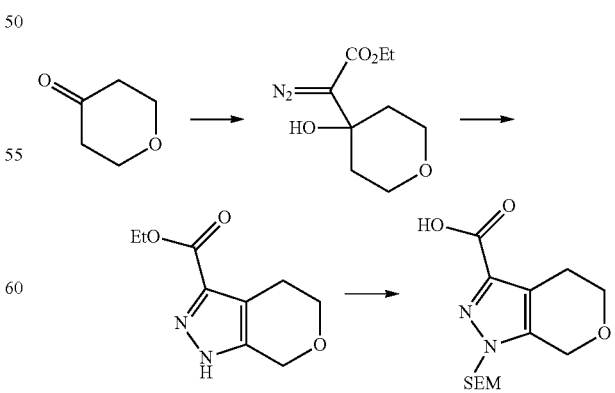

Step 1: A solution of diisopropylamine (2.6 mL, 18.4 mmol) in THF (50 mL) was cooled to −78° C., then a solution of n-butyl lithium in hexanes (1.6 M, 10.0 mL, 16.20 mmol) was added dropwise. After stirring for 5 minutes, this mixture was added via cannula to a −78° C. solution of ethyl diazoacetate (1.83 mL, 17.3 mmol) and tetrahydropyran-4-one (1.08 g, 10.8 mmol; commercial) in THF (50 mL). The mixture was stirred for 1 hour at −78° C., then quenched by the addition of sat. NH₄Cl(aq). The mixture was diluted with water and extracted with EtOAc (2 times). The combined organic extracts were dried (MgSO₄) and concentrated in vacuo. Purification by CombiFlash (100:0 to 60:40 heptane:EtOAc) provided 2.3 g (10.8 mmol) of ethyl 2-diazo-2-(4-hydroxytetrahydro-2H-pyran-4-yl)acetate.

Step 2: To a solution of ethyl 2-diazo-2-(4-hydroxytetrahydro-2H-pyran-4-yl)acetate (2.3 g, 10.8 mmol) in pyridine (50 mL) was added POCl₃ (4.4 mL 47 mmol) and the mixture was allowed to stir at room temperature overnight. After in vacuo concentration, the mixture was poured onto ice, then extracted with EtOAc (3 times). The combined organic extracts were dried (MgSO₄) and concentrated in vacuo. This residue was diluted with octane (23 mL) and heated to 110° C. for two hours. After in vacuo concentration, purification by CombiFlash (100:0 to 0:100 heptane:EtOAc) provided 1.09 g (5.56 mmol) of ethyl 1,4, 5,7-tetrahydropyrano[3,4-c]pyrazole-3-carboxylate.

Step 3: A solution of ethyl 1,4,5,7-tetrahydropyrano[3,4-c]pyrazole-3-carboxylate (1.09 g, 5.56 mmol) in THF (110 mL) was cooled to 0° C., then sodium hydride (60%, 667 mg, 16.7 mmol) was added. After stirring for 1 hour, SEMCl (1.18 mL, 6.67 mmol) was added and the mixture was allowed to warm to room temperature overnight. After excess hydride was quenched by the addition of water at 0° C., the mixture was extracted with EtOAc (3 times), the organic extracts dried (MgSO₄) and concentrated in vacuo. Purification by CombiFlash (40 g; 100:0 to 70:30 heptane:EtOAc) provided 1.58 g (4.84 mmol) of ethyl 1-(2-trimethylsilylethoxymethyl)-5,7-dihydro-4H-pyrano[3,4-c]pyrazole-3-carboxylate. This ester was diluted with THF (30 mL), acetonitrile (30 mL) and water (30 mL) and lithium hydroxide monohydrate (1.64 g, 38.7 mmol) was added and the mixture was stirred overnight. The mixture was diluted with water, acidified to pH 3 with 1 N HCl(aq) and extracted with Et₂O (once) and 10% MeOH/CH₂Cl₂ (3 times). The combined organic extracts were dried (MgSO₄) and concentrated in vacuo to provide 1-((2-(trimethylsilyl)ethoxy)methyl)-1,4,5,7-tetrahydropyrano[3,4-c]pyrazole-3-carboxylic acid of sufficient purity to be used directly (1.44 g, 4.84 mmol).

Synthesis of 5,5-dimethyl-1-((2-(trimethylsilyl)ethoxy)methyl)-4, 5, 6,7-tetrahydro-1H-indazole-3-carboxylic acid

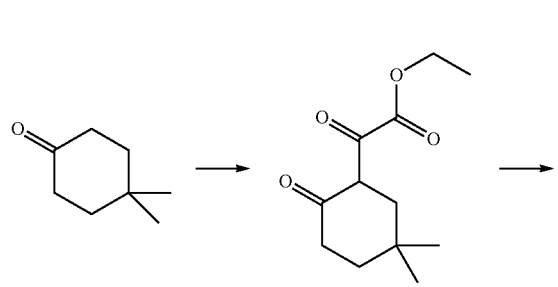

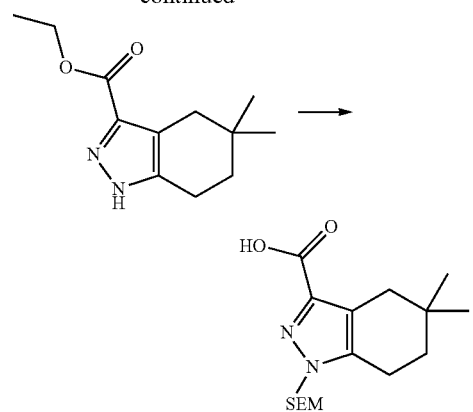

Step 1: A solution of 4,4-dimethylcyclohexanone (2.00 g, 15.8 mmol; commercial) in EtOH (7 mL) was cooled to 0° C., then sodium ethoxide (21% wt solution in EtOH, 6.51 mL, 17.4 mmol) was added. To this mixture was added diethyl oxylate (2.2 mL, 15.8 mmol) and the mixture was allowed to warm to room temperature overnight. In vacuo concentration provided ethyl 2-(5,5-dimethyl-2-oxo-cyclohexyl)-2-oxo-acetate of sufficient purity to be used directly (yield assumed to be quantitative).

Step 2: A solution of ethyl 2-(5,5-dimethyl-2-oxo-cyclohexyl)-2-oxo-acetate (3.6 g, unpurified) in glacial acetic acid (7 mL) was cooled to 0° C., then hydrazine hydrate (1.33 mL, 17.4 mmol) was added. After warming to room temperature, the mixture was stirred for 1 hour, then diluted with sat. NaHCO₃(aq) and extracted with 10% MeOH/CH₂Cl₂. The organic extracts were dried (MgSO₄) and concentrated in vacuo. Purification by CombiFlash (12 g; 100:0 to 60:40 heptane:EtOAc) provided 1.76 g (7.92 mmol) of ethyl 5,5-dimethyl-1,4,6,7-tetrahydroindazole-3-carboxylate.

Step 3: Performed in an analogous manner to Step 3 for 1-((2-(trimethylsilyl)ethoxy)methyl)-1,4,5,7-tetrahydropyrano[3,4-c]pyrazole-3-carboxylic acid (Example 1), replacing ethyl 1,4,5,7-tetrahydropyrano[3,4-c]pyrazole-3-carboxylate with ethyl 5,5-dimethyl-1,4,6,7-tetrahydroindazole-3-carboxylate.

Synthesis of 1-((2-(trimethylsilyl)ethoxy)methyl)-1,4,5,7-tetrahydrothiopyrano[3,4-c]pyrazole-3-carboxylic acid 6,6-dioxide

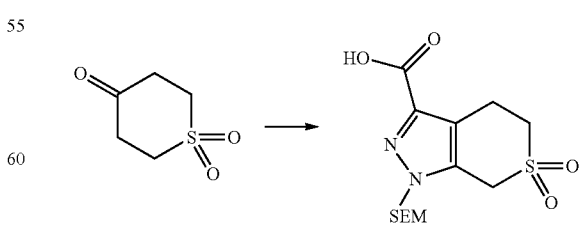

Prepared in an analogous manner to General Procedure X, replacing dihydro-2H-thiopyran-4(3H)-one 1,1-dioxide (commercial).

Synthesis of ethyl 4,5,6,7-tetrahydro-1H-4,6-methanoindazole-3-carboxylate

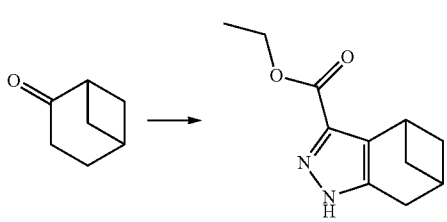

Prepared in an analogous manner to General Procedure Y, replacing 4,4-dimethylcyclohexanone with bicyclo[3.1.1]heptan-2-one (see *J. Am. Chem. Soc.* 1980, 102, 1404) and not performing step 3.

Synthesis of ethyl 4,5,6,7-tetrahydro-1H-5,7-methanoindazole-3-carboxylate

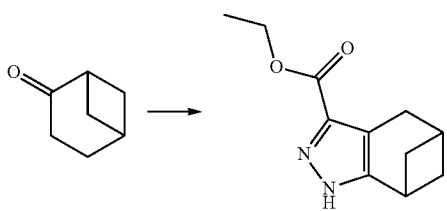

Prepared in an analogous manner to General Procedure X, replacing tetrahydropyran-4-one with bicyclo[3.1.1]heptan-2-one (see *J. Am. Chem. Soc.* 1980, 102, 1404), and not performing step 3.

Synthesis of ethyl 6-hydroxy-4,5,6,7-tetrahydro-1H-indazole-3-carboxylate

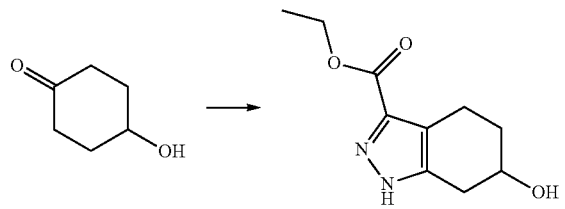

Prepared in an analogous manner to General Procedure X, replacing tetrahydropyran-4-one with 4-hydroxycyclohexanone (commercial), and not performing step 3.

Synthesis of 1-(4-iodo-2-pyridyl)-4,5,6,7-tetrahydroindazole-3-carboxylic acid

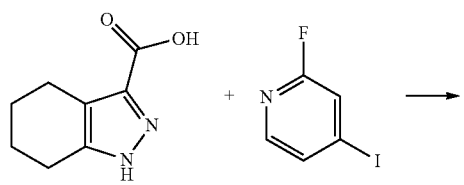

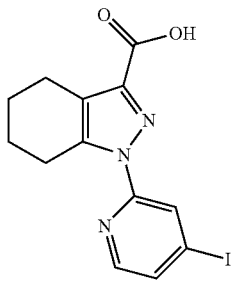

Similar to General Procedure A, to a solution of 4,5,6,7-tetrahydro-1H-indazole-3-carboxylic acid (50 mg, 0.30 mmol) and cesium carbonate (3.0 equiv., 294 mg, 0.902 mmol) in N,N-dimethylformamide (0.60 mL) was added 2-fluoro-4-iodo-pyridine (1.1 equiv., 73.8 mg, 0.331 mmol). The reaction was heated to 100° C. and stirred at this temperature for 2 hours. The reaction was then cooled to room temperature and acidified to pH=1 with 10% aqueous HCl solution. The solution was extracted with twice with dichloromethane. The organic layers were combined, dried with sodium sulfate and concentrated under vacuum. The crude material was used directly in subsequent reactions.

Synthesis of 1-(4-iodo-2-pyridyl)-4,5,6,7-tetrahydroindazole-3-carboxamide

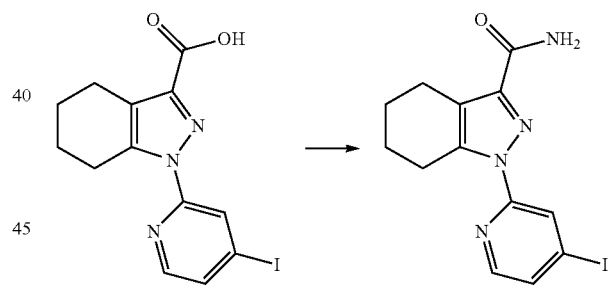

Similar to General Procedure B, to a solution of 1-(4-iodo-2-pyridyl)-4,5,6,7-tetrahydroindazole-3-carboxylic acid (70 mg, 0.190 mmol) in tetrahydrofuran (1.23 mL) was added ammonium chloride (6.0 eq., 61.2 mg, 1.138 mmol) and N,N-diisopropylethylamine (6.0 eq., 0.20 mL, 1.138 mmol) followed by HATU (2.0 eq., 145.6 mg, 0.379 mmol). The reaction was stirred at room temperature overnight. A solution of saturated sodium bicarbonate was added and the mixture was extracted 3 times with dichloromethane. The organic layers were combined, dried with sodium sulfate and concentrated under vacuum. The crude material was purified by flash chromatography (Silicycle HP, 1-10% methanol in dichloromethane) to afford a light yellow solid.

Synthesis of 1-(3-bromophenyl)pyrazolo[3,4-b]pyridine-3-carbonitrile

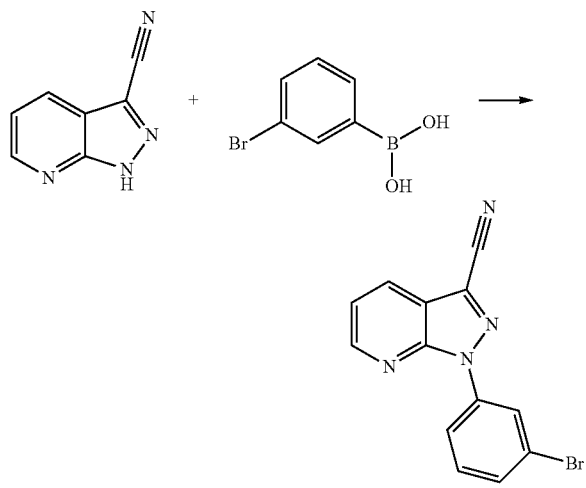

Similar to General Procedure C, to a small vial was added 1H-pyrazolo[3,4-b]pyridine-3-carbonitrile (45 mg, 0.312 mmol), (3-bromophenyl)boronic acid (1.5 eq., 94.0 mg, 0.468 mmol), copper(II) acetate monohydrate (0.3 eq., 19.7 mg, 0.093 mmol) in N,N-dimethylformamide (0.62 mL) and pyridine (3.0 eq., 0.076 mL, 0.936 mmol). The reaction was stirred under an oxygen atmosphere at 90° C. for 6 hours. The reaction was then cooled to room temperature and diluted with a saturated aqueous sodium bicarbonate solution, and the aqueous phase was extracted with 3 times with dichloromethane. The organic phases were combined, washed with brine, dried with sodium sulfate and concentrated under vacuum. The crude material was purified by flash chromatography (5-80% iPrOAc in heptanes) to afford 40 mg (43% yield) of a light yellow solid.

Synthesis of 1-(4-iodo-2-pyridyl)indazole-3-carboxylic acid

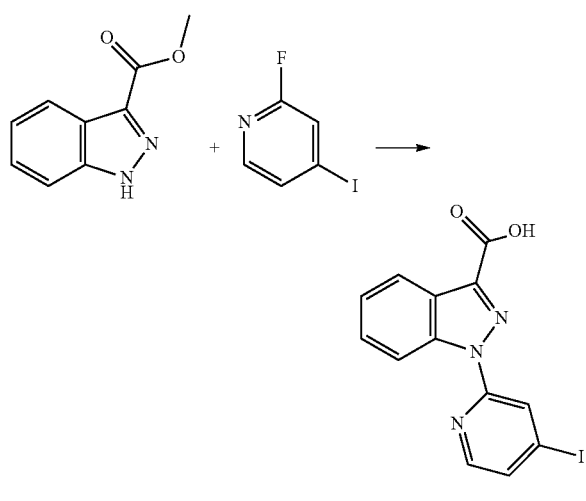

Similar to as described in General Procedure A, methyl 1H-indazole-3-carboxylate was reacted with 2-fluoro-4-iodo-pyridine to give the title compound. The crude material was used directly in subsequent reactions.

Synthesis of 1-(4-iodo-2-pyridyl)indazole-3-carboxamide

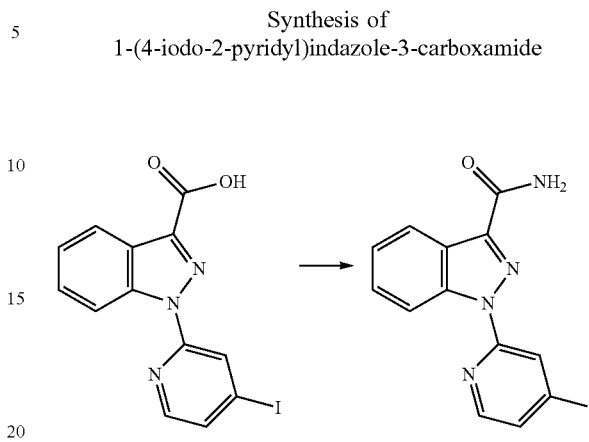

Similar to as described in General Procedure B, 1-(4-iodo-2-pyridyl)indazole-3-carboxylic acid was reacted with ammonium chloride to give the title compound (60% yield).

Synthesis of 1-(3-bromophenyl)-4,5,6,7-tetrahydroindazole-3-carboxamide

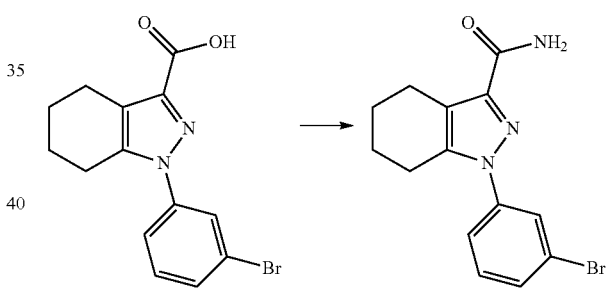

Similar to as described in General Procedure B, 1-(3-bromophenyl)-4,5,6,7-tetrahydroindazole-3-carboxylic acid was reacted with ammonium chloride to give the title compound. The crude material was used directly in subsequent reactions.

Synthesis of 1-(4-iodo-2-pyridyl)pyrazole-3-carboxylic acid

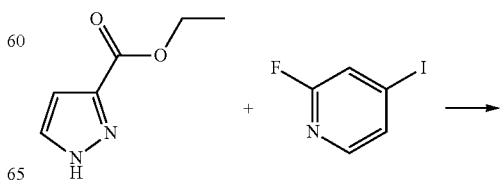

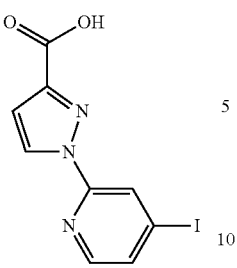

Similar to as described in General Procedure A, ethyl 1H-pyrazole-3-carboxylate was reacted with 2-fluoro-4-iodo-pyridine to give the title compound. The crude material was used directly in subsequent reactions.

Synthesis of 1-(4-iodo-2-pyridyl)pyrazole-3-carboxamide

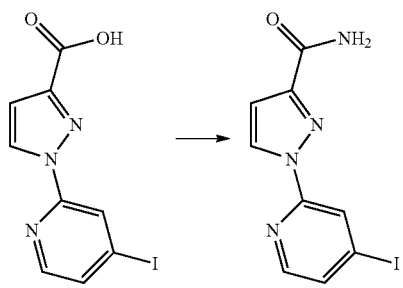 [SMILES: O=C(O)c1ccn(-c2cc(I)ccn2)n1 ; NC(=O)c1ccn(-c2cc(I)ccn2)n1]

Similar to as described in General Procedure B, 1-(4-iodo-2-pyridyl)pyrazole-3-carboxylic acid was reacted with ammonium chloride to give the title compound (43% yield).

Synthesis of 1-(4-iodo-2-pyridyl)-5,6-dihydro-4H-cyclopenta[c]pyrazole-3-carboxylic acid

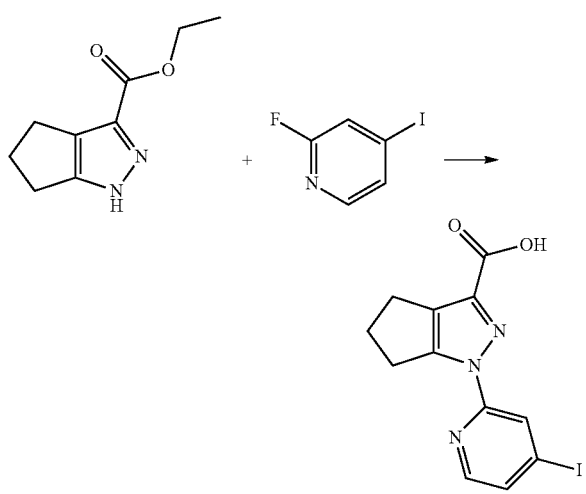

Similar to as described in General Procedure A, ethyl 1,4,5,6-tetrahydrocyclopenta[c]pyrazole-3-carboxylate was reacted with 2-fluoro-4-iodo-pyridine to give the title compound, as well as some remaining ester. Lithium hydroxide (1.0 eq.) in water (1.0 M) was added and the reaction was stirred at 50° C. for 1 h to afford complete conversion to the desired acid. The crude material was used directly in subsequent reactions.

Synthesis of 1-(4-iodo-2-pyridyl)-5,6-dihydro-4H-cyclopenta[c]pyrazole-3-carboxamide

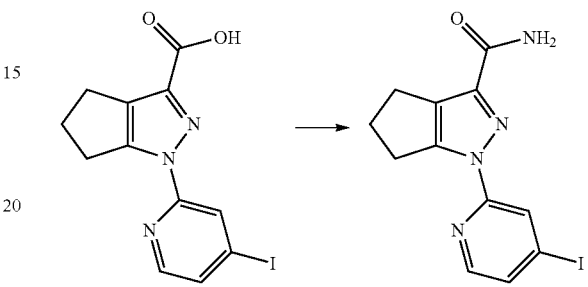

Similar to as described in General Procedure B, 1-(4-iodo-2-pyridyl)-5,6-dihydro-4H-cyclopenta[c]pyrazole-3-carboxylic acid was reacted with ammonium chloride to give the title compound (28% yield).

Synthesis of 1-(4-iodopyridin-2-yl)-4,5,6,7-tetrahydro-1H-5,7-methanoindazole-3-carboxylic acid

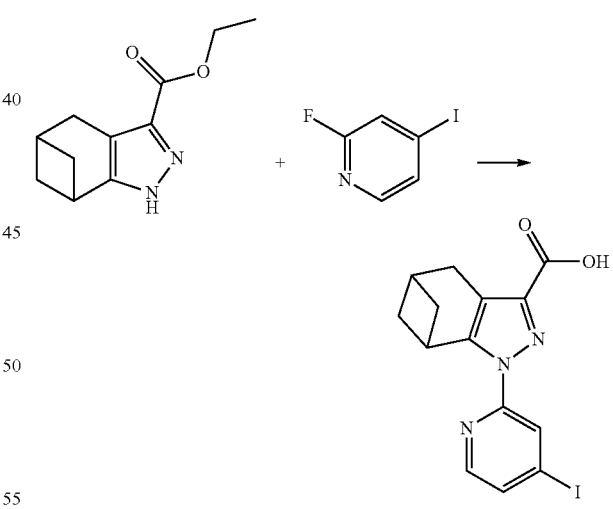

Similar to as described in General Procedure A, ethyl 4,5,6,7-tetrahydro-1H-5,7-methanoindazole-3-carboxylate was reacted with 2-fluoro-4-iodo-pyridine to give the title compound, as well as some remaining ester. Lithium hydroxide (1.0 eq.) in water (1.0 M) was added and the reaction was stirred at 50° C. for 1 h to afford complete conversion to the desired acid. The crude material was used directly in subsequent reactions.

Synthesis of 1-(4-iodopyridin-2-yl)-4,5,6,7-tetra-hydro-1H-5,7-methanoindazole-3-carboxamide

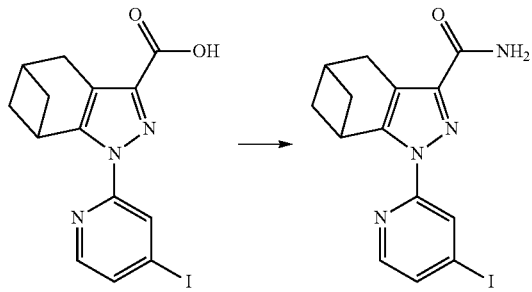 [SMILES: O=C(O)c1nn(-c2cc(I)ccn2)c2c1CC1CC2C1 ; NC(=O)c1nn(-c2cc(I)ccn2)c2c1CC1CC2C1]

Similar to as described in General Procedure B, 1-(4-iodopyridin-2-yl)-4,5,6,7-tetrahydro-1H-5,7-methanoindazole-3-carboxylic acid was reacted with ammonium chloride to give the title compound (71% yield).

Synthesis of 1-(4-iodopyridin-2-yl)-4,5,6,7-tetrahydro-1H-4,6-methanoindazole-3-carboxylic acid

Synthesis of 1-(4-iodopyridin-2-yl)-4,5,6,7-tetra-hydro-1H-4,6-methanoindazole-3-carboxamide

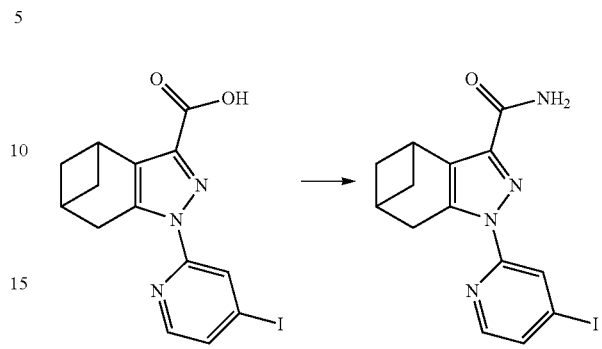

Similar to as described in General Procedure B, 1-(4-iodopyridin-2-yl)-4,5,6,7-tetrahydro-1H-4,6-methanoindazole-3-carboxylic acid was reacted with ammonium chloride to give the title compound (50% yield).

Synthesis of 6-hydroxy-1-(4-iodo-2-pyridyl)-4,5,6,7-tetrahydroindazole-3-carboxylic acid

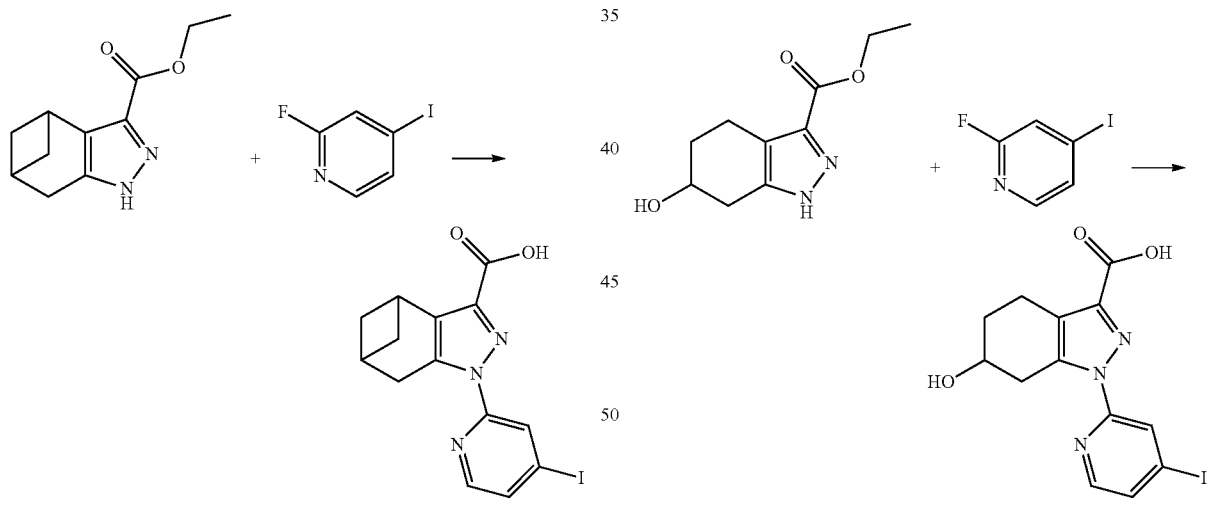

Similar to as described in General Procedure A, ethyl 4,5,6,7-tetrahydro-1H-4,6-methanoindazole-3-carboxylate was reacted with 2-fluoro-4-iodo-pyridine to give the title compound, as well as some remaining ester. Lithium hydroxide (1.0 eq.) in water (1 M) was added and the reaction was stirred at 50° C. for 1 h to afford complete conversion to the desired acid. The crude material was used directly in subsequent reactions.

Similar to as described in General Procedure A, ethyl 6-hydroxy-4,5,6,7-tetrahydro-1H-indazole-3-carboxylate was reacted with 2-fluoro-4-iodo-pyridine to give the title compound, as well as some remaining ester. Lithium hydroxide (1.0 eq.) in water (1 M) was added and the reaction was stirred at 50° C. for 1 h to afford complete conversion to the desired acid. The crude material was used directly in subsequent reactions.

Synthesis of 6-hydroxy-1-(4-iodo-2-pyridyl)-4,5,6,7-tetrahydroindazole-3-carboxamide

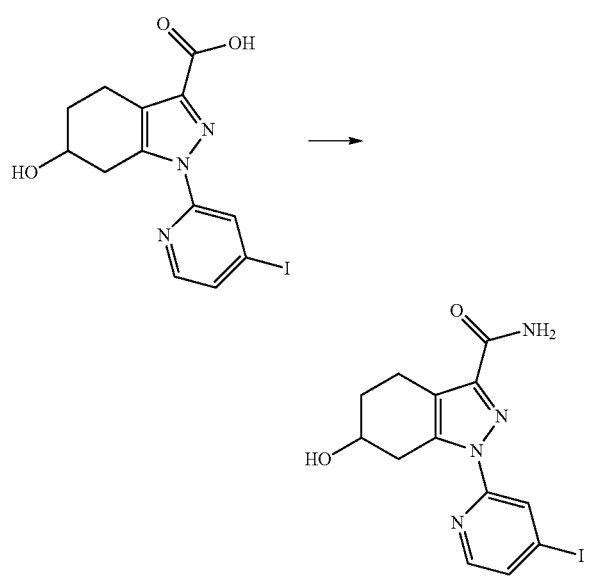

Similar to as described in General Procedure B, 6-hydroxy-1-(4-iodo-2-pyridyl)-4,5,6,7-tetrahydroindazole-3-carboxylic acid was reacted with ammonium chloride to give the title compound (78% yield).

Synthesis of 5,5-dimethyl-1,4,6,7-tetrahydroindazole-3-carboxylic acid

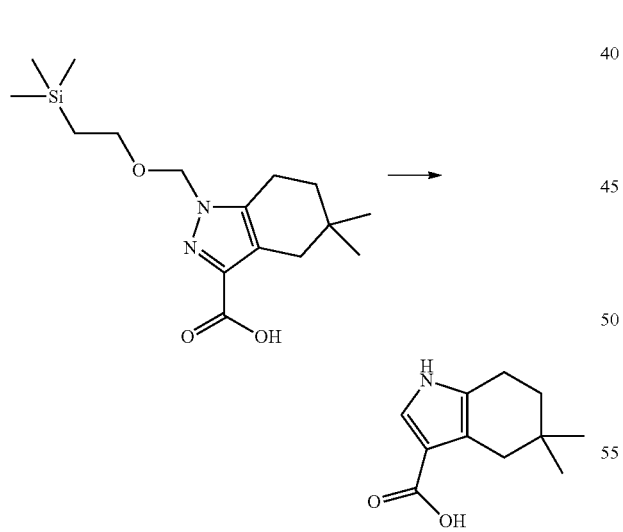

Similar to as described in General Procedure T, 5,5-dimethyl-1-(2-trimethylsilylethoxymethyl)-6,7-dihydro-4H-indazole-3-carboxylic acid (200 mg, 0.616 mmol) and 4.0 M hydrochloric acid in dioxane (17.0 eq., 10.5 mmol, 2.6 mL) were combined in ethanol (2.5 mL) and stirred at 50° C. for 2 h. The sample was then concentrated under vacuum and used directly in subsequent reactions.

Synthesis of 1-(4-iodo-2-pyridyl)-5,5-dimethyl-6,7-dihydro-4H-indazole-3-carboxylic acid

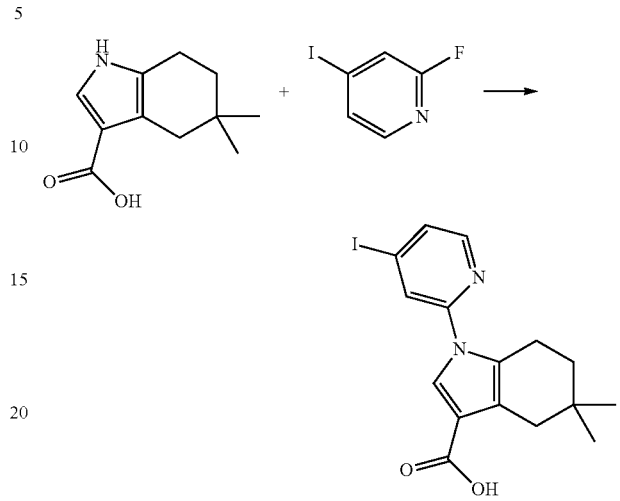

Similar to as described in General Procedure A, 5,5-dimethyl-1,4,6,7-tetrahydroindazole-3-carboxylic acid was reacted with 2-fluoro-4-iodo-pyridine to give the title compound. The crude material was used directly in subsequent reactions.

Synthesis of 1-(4-iodo-2-pyridyl)-5,5-dimethyl-6,7-dihydro-4H-indazole-3-carboxamide

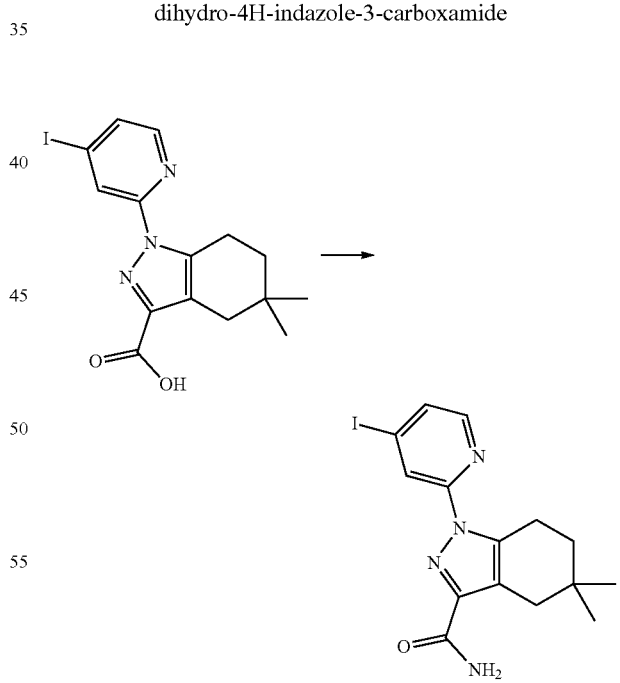

Similar to as described in General Procedure B, 1-(4-iodo-2-pyridyl)-5,5-dimethyl-6,7-dihydro-4H-indazole-3-carboxylic acid was reacted with ammonium chloride in 2-methyltetrahydrofuran to give 149 mg of the title compound (61% yield).

183
Synthesis of 6-fluoro-1-(4-iodo-2-pyridyl)indazole-3-carboxylic acid

184
Synthesis of 5-bromo-1-(4-iodo-2-pyridyl)indazole-3-carboxylic acid

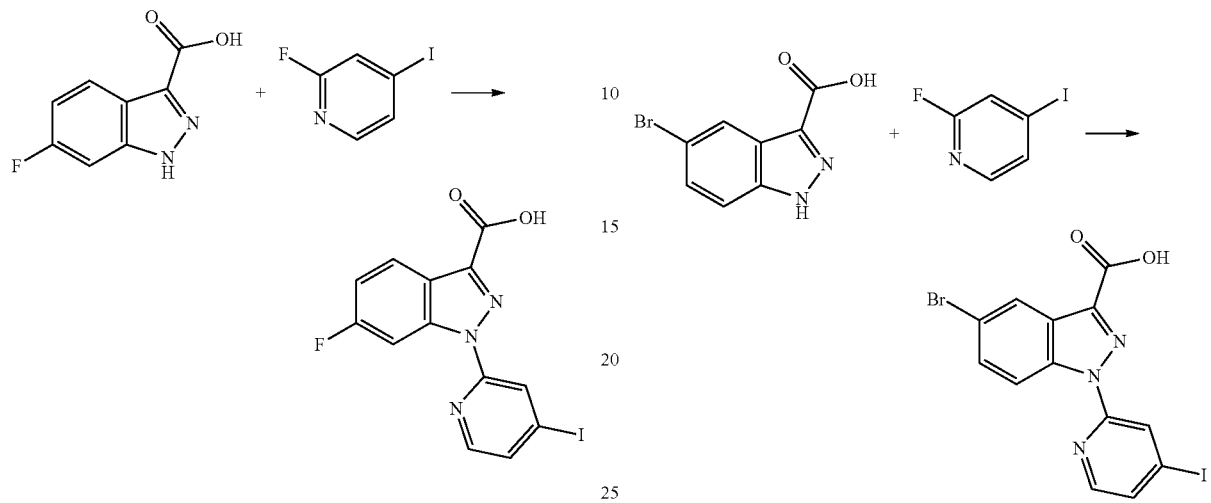

Similar to as described in General Procedure A, 6-fluoro-1H-indazole-3-carboxylic acid was reacted with 2-fluoro-4-iodo-pyridine to give the title compound. The crude material was used directly in subsequent reactions.

Similar to as described in General Procedure A, 5-bromo-1H-indazole-3-carboxylic acid was reacted with 2-fluoro-4-iodo-pyridine to give the title compound. The crude material was used directly in subsequent reactions.

Synthesis of 6-fluoro-1-(4-iodo-2-pyridyl)indazole-3-carboxamide

Synthesis of 5-bromo-1-(4-iodo-2-pyridyl)indazole-3-carboxamide

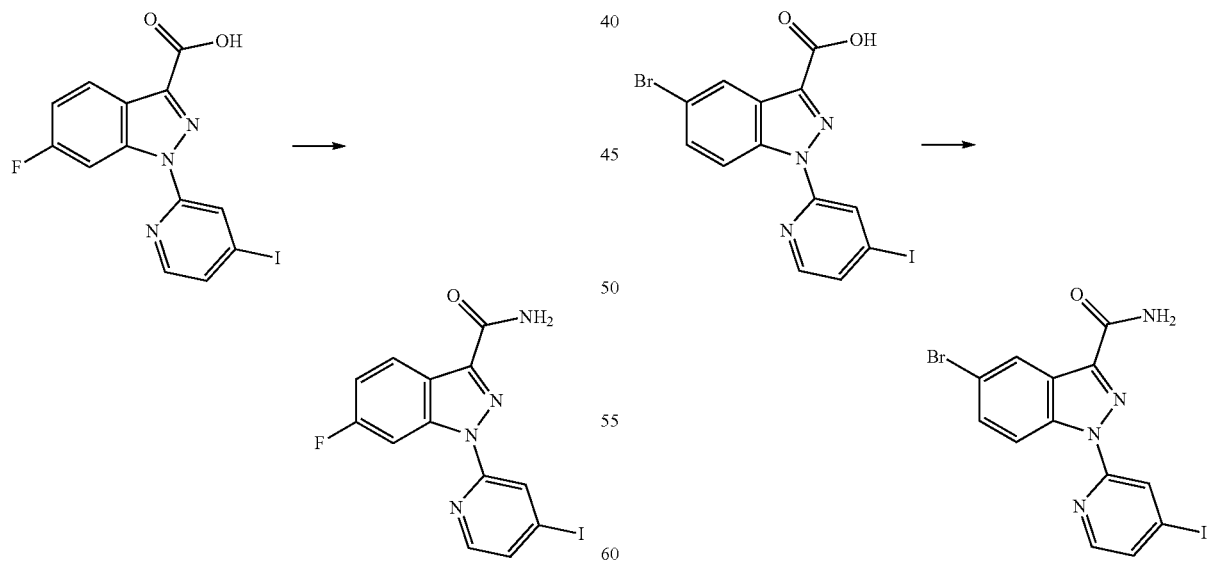

Similar to as described in General Procedure B, 6-fluoro-1-(4-iodo-2-pyridyl)indazole-3-carboxylic acid was reacted with ammonium chloride to give 308 mg of the title compound (63% yield).

Similar to as described in General Procedure B, 6-fluoro-1-(4-iodo-2-pyridyl)indazole-3-carboxylic acid was reacted with ammonium chloride to give 167 mg of the title compound (30% yield).

185

Synthesis of 1-(4-iodo-2-pyridyl)-5-methoxy-indazole-3-carboxylic acid

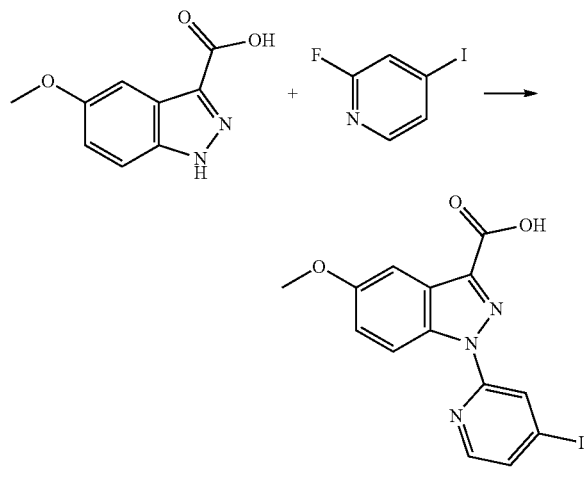

Similar to as described in General Procedure A, 5-methoxy-1H-indazole-3-carboxylic acid was reacted with 2-fluoro-4-iodo-pyridine to give the title compound. The crude material was used directly in subsequent reactions.

Synthesis of 1-(4-iodo-2-pyridyl)-5-methoxy-indazole-3-carboxamide

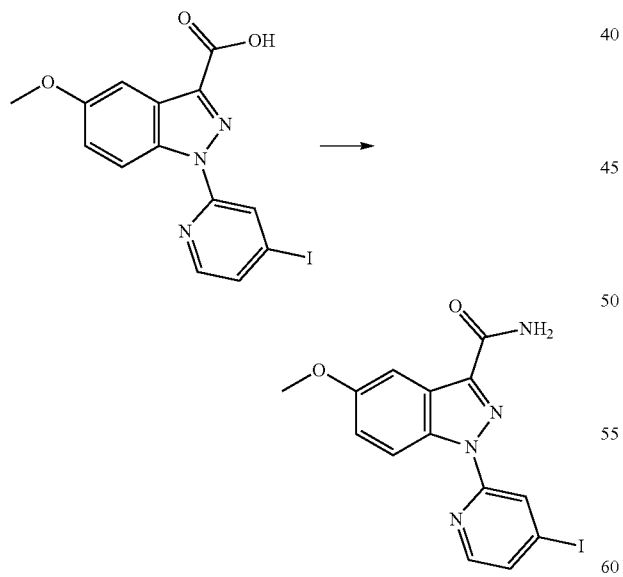

Similar to as described in General Procedure B, 1-(4-iodo-2-pyridyl)-5-methoxy-indazole-3-carboxylic acid was reacted with ammonium chloride to give 72 mg of the title compound (35% yield).

186

Synthesis of 5-fluoro-1-(4-iodo-2-pyridyl)indazole-3-carboxylic acid

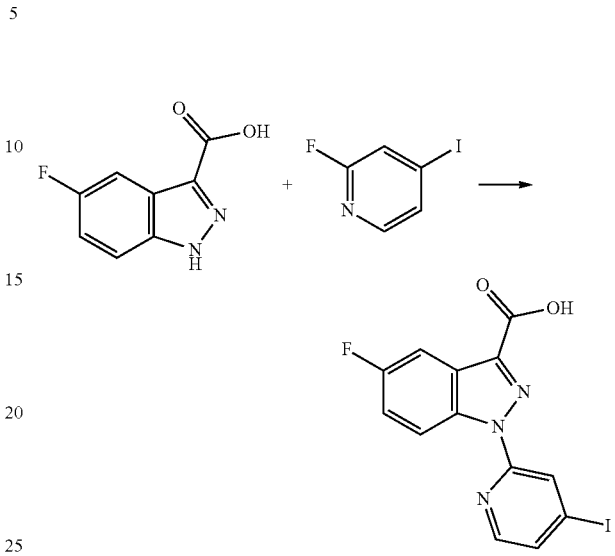

Similar to as described in General Procedure A, 5-methoxy-1H-indazole-3-carboxylic acid was reacted with 2-fluoro-4-iodo-pyridine to give the title compound. The crude material was used directly in subsequent reactions.

Synthesis of 5-fluoro-1-(4-iodo-2-pyridyl)indazole-3-carboxamide

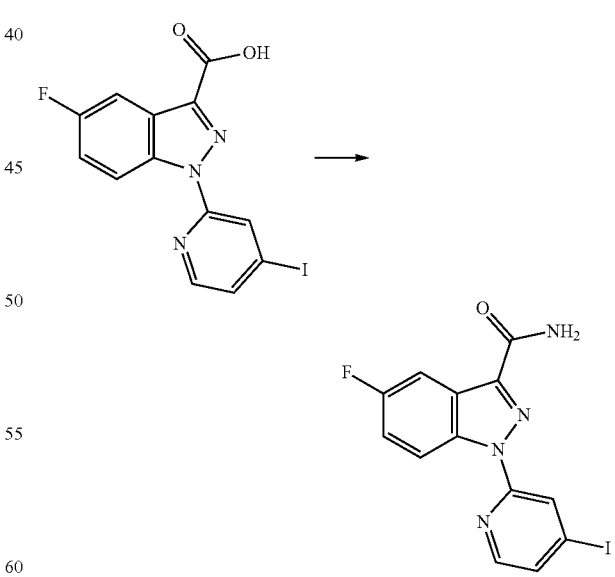

Similar to as described in General Procedure B, 5-fluoro-1-(4-iodo-2-pyridyl)indazole-3-carboxylic acid was reacted with ammonium chloride to give 500 mg of the title compound (99% yield).

Synthesis of 1-(3-bromophenyl)pyrrolo[2,3-b]pyridine-3-carbonitrile

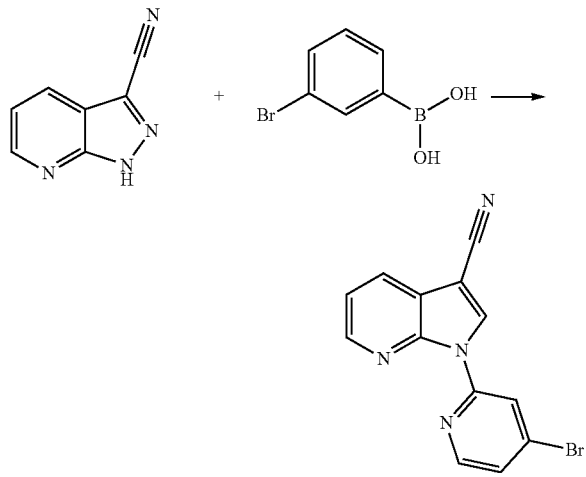

Similar to General Procedure C, 1H-pyrrolo[2,3-b]pyridine-3-carbonitrile was reacted with (3-bromophenyl)boronic acid to give the title compound. The crude material was used directly in subsequent reactions.

Synthesis of 1-(3-bromophenyl)pyrrolo[2,3-b]pyridine-3-carboxamide

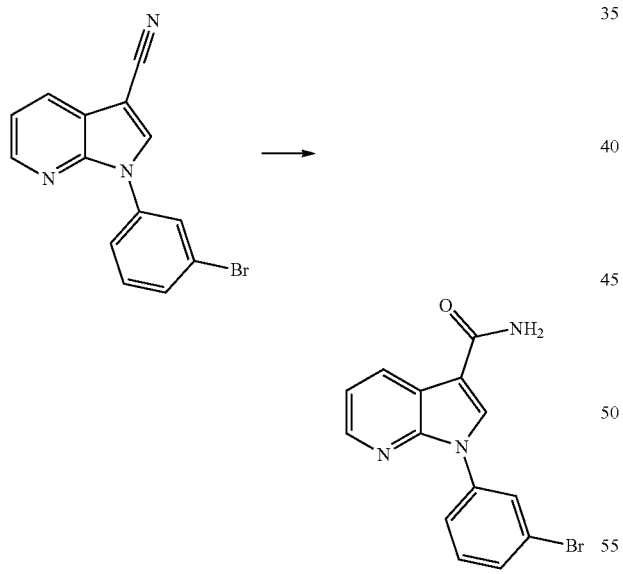

Similar as to General Procedure D, to a solution of 1-(3-bromophenyl)pyrrolo[2,3-b]pyridine-3-carbonitrile (104 mg, 0.349 mmol) in ethanol (0.3 mL) and water (0.14 mL) was added hydrido(dimethylphosphinous acid-kp)[hydrogen bis(dimethylphosphinito-kp)]platinum(II) (0.05 eq., 7.5 mg, 0.017 mmol). The reaction was stirred at 80° C. for 2 h. LC/MS indicated slow conversion. Methanol (0.2 mL) was added and the reaction was allowed to stir at this temperature overnight. The solution was cooled to room temperature and extracted twice with dichloromethane. The organic layers were combined, dried with sodium sulfate and concentrated under vacuum. The crude material was used directly in subsequent reactions.

Synthesis of 1-(5-bromo-3-pyridyl)pyrazolo[3,4-b]pyridine-3-carboxylic acid

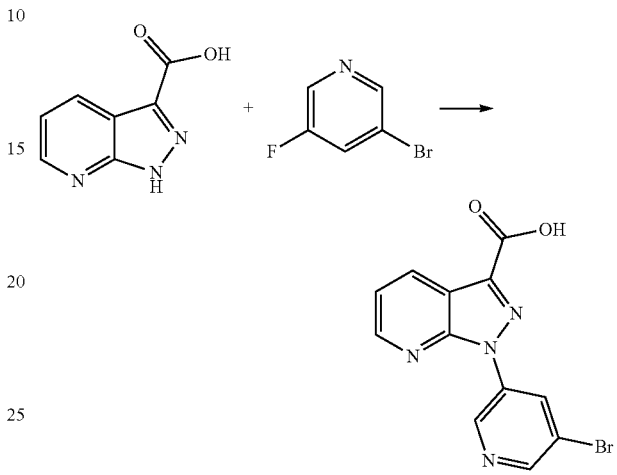

Similar to as described in General Procedure A, 1H-pyrazolo[3,4-b]pyridine-3-carboxylic acid was reacted with 3-bromo-5-fluoro-pyridine to give the title compound. The crude material was used directly in subsequent reactions.

Synthesis of 1-(5-bromo-3-pyridyl)pyrazolo[3,4-b]pyridine-3-carboxamide

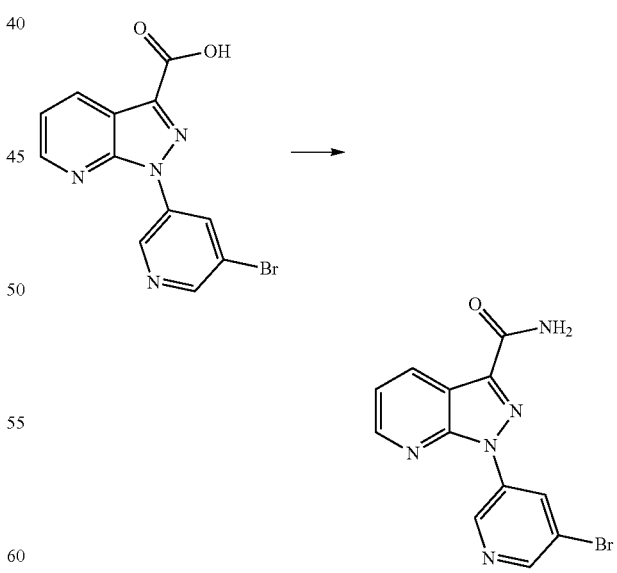

Similar to as described in General Procedure B, 1-(5-bromo-3-pyridyl)pyrazolo[3,4-b]pyridine-3-carboxylic acid was reacted with ammonium chloride to give the title compound. The crude material was used directly in subsequent reactions.

Synthesis of ethyl 2-(2-fluoro-3-pyridyl)-2-oxo-acetate

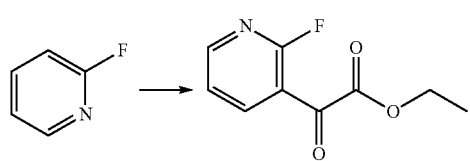

To a solution of 2-fluoropyridine (0.44 mL, 500 mg, 5.150 mmol) in tetrahydrofuran (13.4 mL) under nitrogen atmosphere at −78° C. was added a solution of lithium diisopropylamide (2.0 mol/L) in thf/heptane/ethylbenzene (1.2 eq., 3.1 mL, 6.180 mmol). The reaction was allowed to stir at this temperature for 1.5 hours, and then diethyl oxalate (1.2 eq., 0.84 mL, 6.180 mmol) was added dropwise via syringe and allowed to stir for 30 minutes. The reaction was quenched with aqueous saturated ammonium chloride solution and extracted 3 times with iPrOAc. The organics were combined, washed with brine, dried with sodium sulfate and concentrated under vacuum. The crude material was used directly in subsequent reactions.

Synthesis of ethyl 1-(3-bromophenyl)pyrazolo[3,4-b]pyridine-3-carboxylate

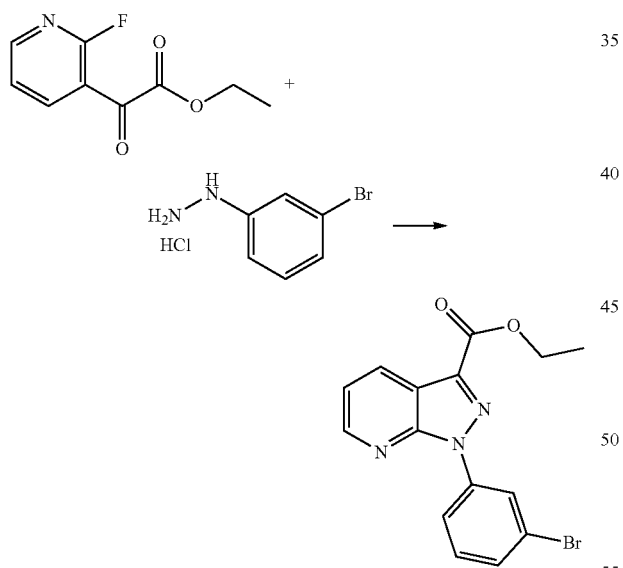

To a solution of ethyl 2-(2-fluoro-3-pyridyl)-2-oxo-acetate (43 mg, 0.218 mmol) in 1-methyl-2-pyrrolidinone (0.44 mL) was added 3-bromophenylhydrazine hydrochloride (1.0 eq., 48.7 mg, 0.218 mmol). The reaction was heated to 120° C. in a sealed tube overnight. The reaction was diluted with water and extracted 2 times with dichloromethane. The organics were combined, washed with brine, dried with sodium sulfate and concentrated under vacuum. The crude material was purified by flash chromatography (5-100% iPrOAc in heptanes) to afford a yellow oil.

Synthesis of 1-(3-bromophenyl)pyrazolo[3,4-b]pyridine-3-carboxamide

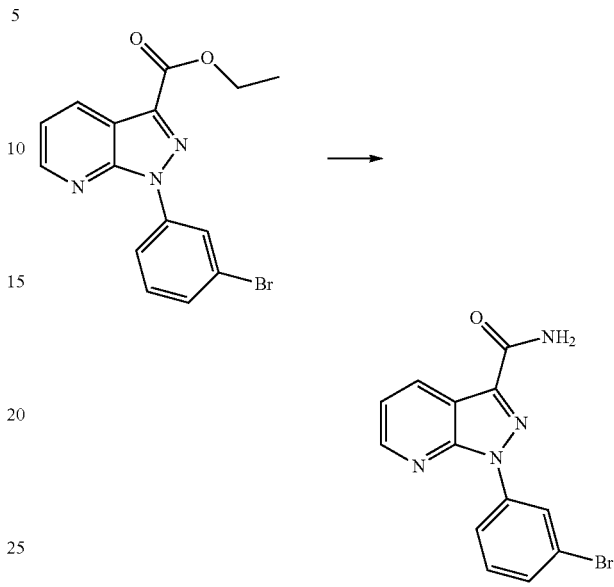

Similar to as described in General Procedure H, To a solution of ethyl 1-(3-bromophenyl)pyrazolo[3,4-b]pyridine-3-carboxylate (75 mg, 0.217 mmol) in N,N-dimethylformamide (1.1 mL) under nitrogen atmosphere was added formamide (10.0 eq., 0.086 mL, 2.166 mmol) followed by dropwise addition of sodium methoxide (3.0 eq., 0.15 mL, 0.649 mmol). The reaction was stirred at room temperature for 1 h. The reaction was then quenched with an aqueous saturated ammonium chloride solution and extracted 3 times with dichloromethane. The organic phases were combined, dried with sodium sulfate and concentrated to give the title compound. The crude material was used directly in subsequent reactions.

Synthesis of 1H-pyrazolo[3,4-b]pyridine-3-carbonitrile

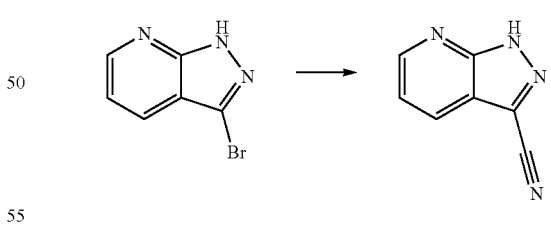

To a solution of 3-bromo-1H-pyrazolo[3,4-b]pyridine (200 mg, 1.010 mmol), zinc cyanide (1.0 eq., 121.0 mg, 1.010 mmol), tris(dibenzylideneacetone)dipalladium(0) (0.04 eq., 38.1 mg, 0.040 mmol), 1,1'-bis(diphenylphosphino)ferrocene (0.08 eq., 46.6 mg, 0.081 mmol) and zinc (0.24 eq., 15.8 mg, 0.242 mmol) were dissolved in degassed N,N-dimethylacetamide (5.0 mL) under inert atmosphere. The reaction was heated to 120° C. for 5 hours. The reaction was then diluted with aqueous saturated sodium bicarbonate and extracted 2 times with dichloromethane. The organics were combined, washed with brine, dried with sodium sulfate and concentrated under vacuum. The crude material was crashed out in diethyl ether to afford 93 mg of the title compound (64%).

Synthesis of 1-(3-bromophenyl)pyrazolo[3,4-b]pyridine-3-carbonitrile

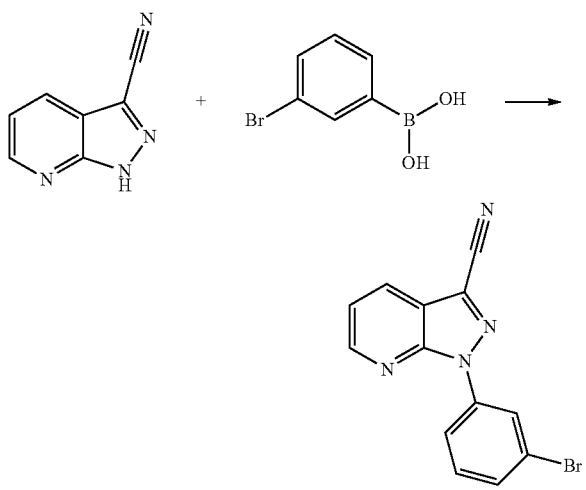

Similar to General Procedure C, 1H-pyrazolo[3,4-b]pyridine-3-carbonitrile was reacted with (3-bromophenyl)boronic acid to give 40 mg of the title compound after purification by flash chromatography (43%).

Synthesis of 1-(3-bromophenyl)pyrazolo[3,4-b]pyridine-3-carboxamide

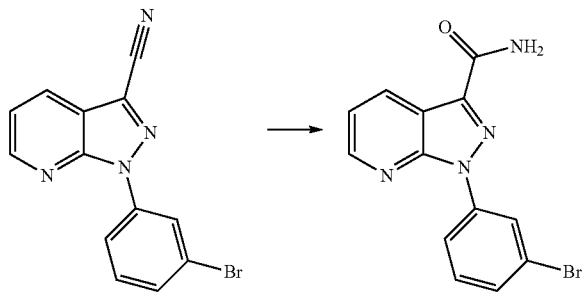 [SMILES: N#Cc1nn(-c2cccc(Br)c2)c2ncccc12 ; NC(=O)c1nn(-c2cccc(Br)c2)c2ncccc12]

Similar as to General Procedure D, to a solution of 1-(3-bromophenyl)pyrazolo[3,4-b]pyridine-3-carbonitrile (40 mg, 0.134 mmol) in ethanol (0.11 mL) and water (0.05 mL) was added hydrido(dimethylphosphinous acid-kp)[hydrogen bis(dimethylphosphinito-kp)]platinum(II) (0.05 eq., 2.9 mg, 0.007 mmol). The reaction was stirred at 90° C. for 2 h under air. The solution was cooled to room temperature and extracted twice with dichloromethane. The organic layers were combined, dried with sodium sulfate and concentrated under vacuum. The crude material was used directly in subsequent reactions.

Synthesis of ethyl 6,6-dioxo-1,4, 5,7-tetrahydrothiopyrano[3,4-c]pyrazole-3-carboxylate

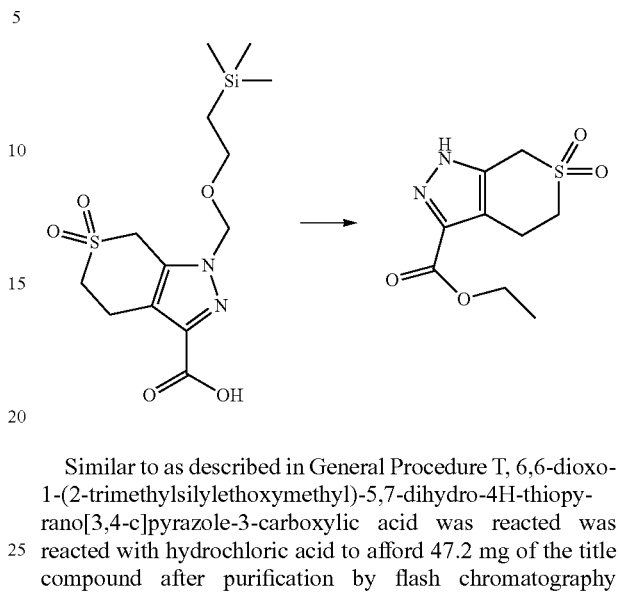

Similar to as described in General Procedure T, 6,6-dioxo-1-(2-trimethylsilylethoxymethyl)-5,7-dihydro-4H-thiopyrano[3,4-c]pyrazole-3-carboxylic acid was reacted was reacted with hydrochloric acid to afford 47.2 mg of the title compound after purification by flash chromatography (77%).

Synthesis of ethyl 2-(3-bromophenyl)-6,6-dioxo-5,7-dihydro-4H-thiopyrano[3,4-c]pyrazole-3-carboxylate

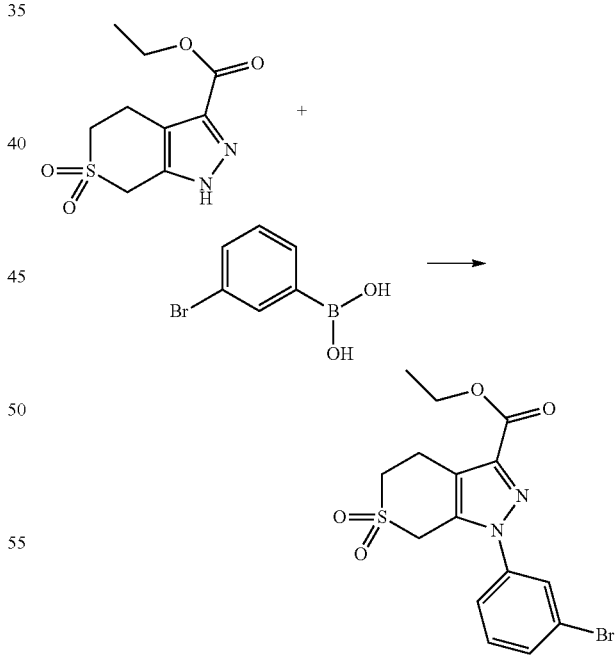

Similar to General Procedure C, ethyl 6,6-dioxo-1,4,5,7-tetrahydrothiopyrano[3,4-c]pyrazole-3-carboxylate was reacted with (3-bromophenyl)boronic acid to give a mixture of regioisomers which were purified by flash chromatography to afford 12 mg of the title compound (second peak to elute, 16% yield).

Synthesis of 1-(3-bromophenyl)-6,6-dioxo-5,7-di-hydro-4H-thiopyrano[3,4-c]pyrazole-3-carboxamide

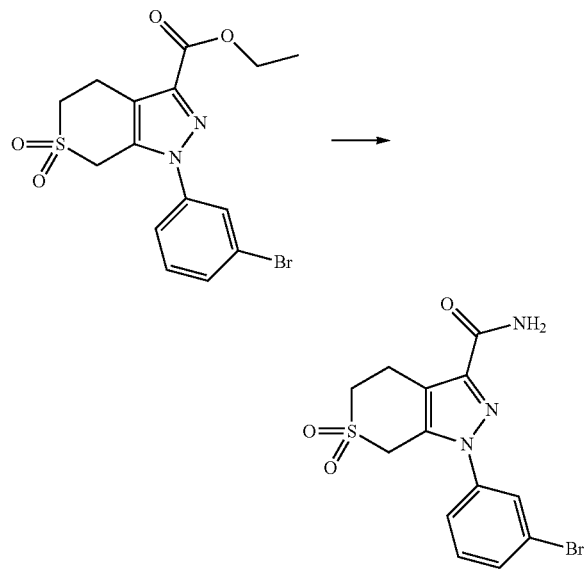

Similar to as described in General Procedure H, ethyl 1-(3-bromophenyl)-6, 6-dioxo-5, 7-dihydro-4H-thiopyrano[3,4-c]pyrazole-3-carboxylate was reacted with formamide and sodium methoxide to give the title compound. The crude material was used directly in subsequent reactions.

Synthesis of ethyl 1,4,5,7-tetrahydropyrano[3,4-c]pyrazole-3-carboxylate

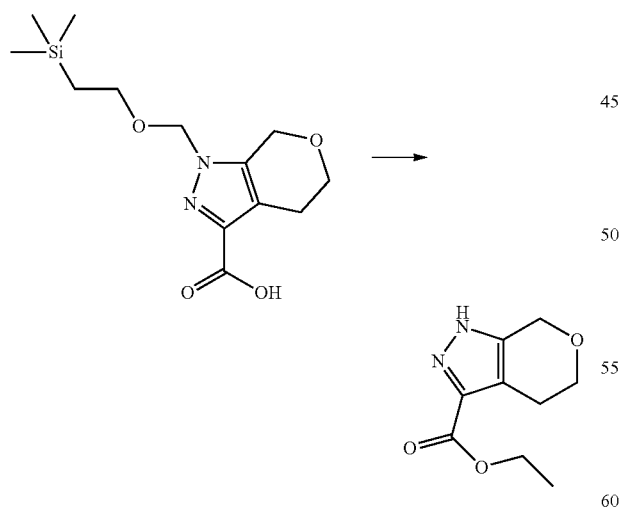

Similar to as described in General Procedure T, 1-(2-trimethylsilylethoxymethyl)-5,7-dihydro-4H-pyrano[3,4-c]pyrazole-3-carboxylic acid was reacted was reacted with hydrochloric acid to afford 86 mg of the title compound after purification by flash chromatography (90%).

Synthesis of ethyl 1-(3-bromophenyl)-5,7-dihydro-4H-pyrano[3,4-c]pyrazole-3-carboxylate

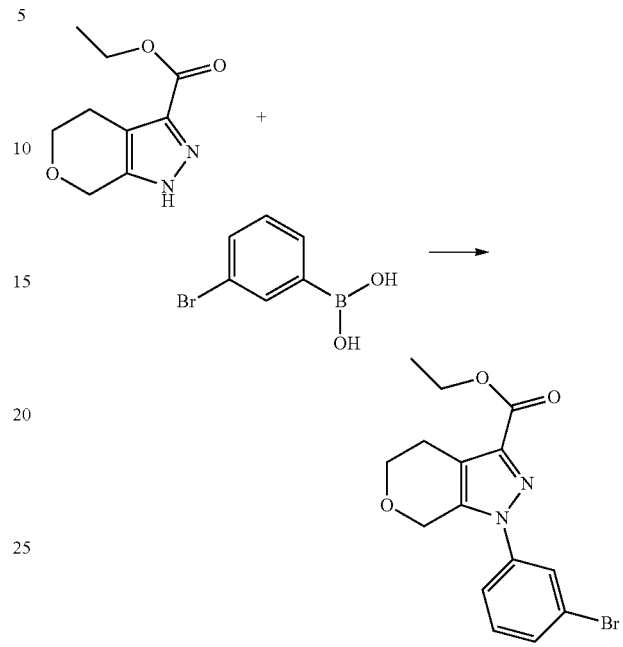

Similar to General Procedure C, ethyl 1,4,5,7-tetrahydropyrano[3,4-c]pyrazole-3-carboxylate was reacted with (3-bromophenyl)boronic acid to give a mixture of regioisomers which were purified by flash chromatography to afford 22.7 mg of the title compound (second peak to elute, 15% yield).

Synthesis of 1-(3-bromophenyl)-5,7-dihydro-4H-pyrano[3,4-c]pyrazole-3-carboxamide

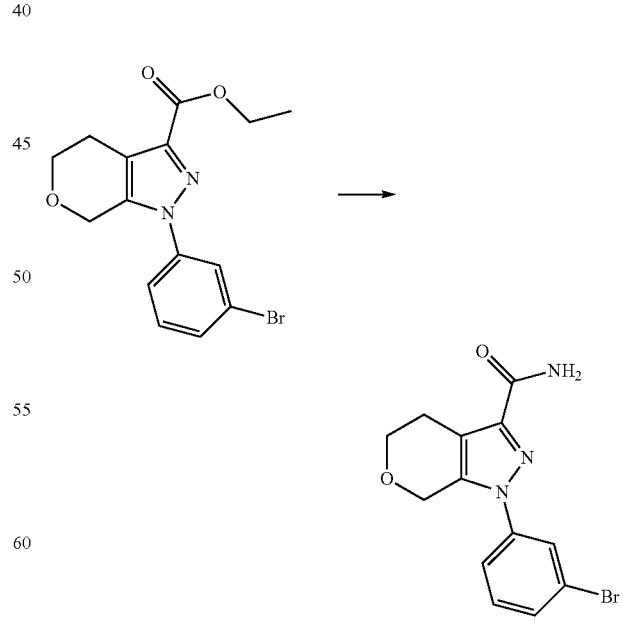

Similar to as described in General Procedure H, ethyl 1-(3-bromophenyl)-5,7-dihydro-4H-pyrano[3,4-c]pyrazole-3-carboxylate was reacted with formamide and sodium methoxide to give the title compound. The crude material was used directly in subsequent reactions.

Synthesis of ethyl 1,4,6,7-tetrahydropyrano[4,3-c]pyrazole-3-carboxylate

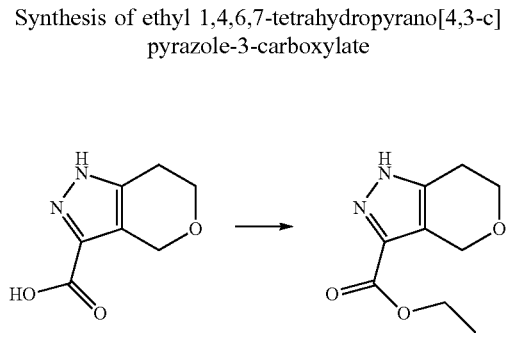

To a solution of 1,4,6,7-tetrahydropyrano[4,3-c]pyrazole-3-carboxylic acid (200 mg, 1.189 mmol) in ethanol (4.8 mL) was added 4.0 M hydrochloric acid in dioxane (12.0 eq., 14.273 mmol, 4.0 mol/L). The reaction was stirred at 60° C. for 24 h. The solution was cooled to room temperature and concentrated under vacuum. The crude material was used directly in subsequent reactions.

Synthesis of ethyl 1-(3-bromophenyl)-6,7-dihydro-4H-pyrano[4,3-c]pyrazole-3-carboxylate

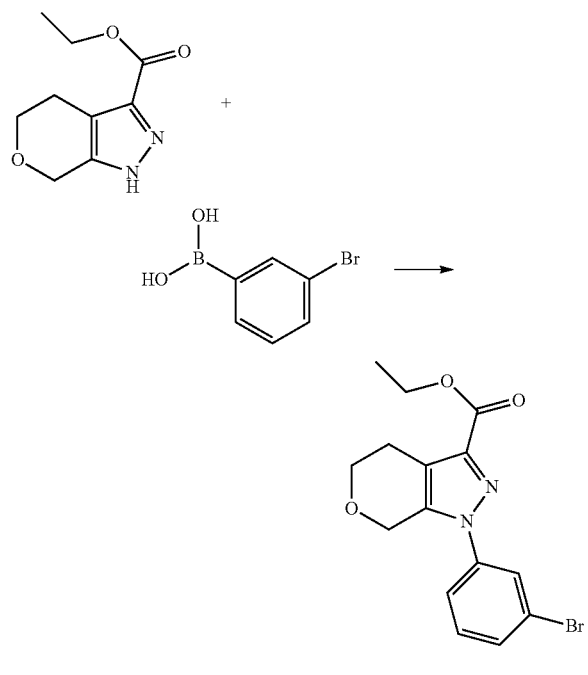

Similar to General Procedure C, ethyl 1,4,6,7-tetrahydropyrano[4,3-c]pyrazole-3-carboxylate was reacted with (3-bromophenyl)boronic acid to give a mixture of regioisomers which were purified by flash chromatography to afford 79 mg of the title compound (second peak, 19% yield).

Synthesis of 1-(3-bromophenyl)-6,7-dihydro-4H-pyrano[4,3-c]pyrazole-3-carboxamide

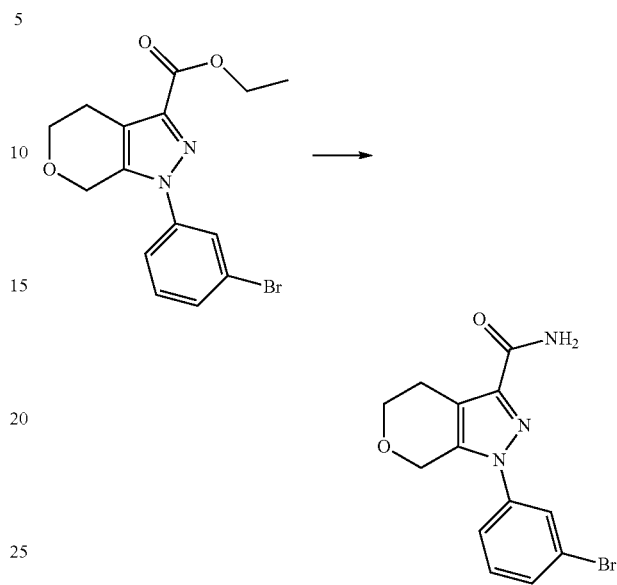

Similar to as described in General Procedure H, ethyl 1-(3-bromophenyl)-6,7-dihydro-4H-pyrano[4,3-c]pyrazole-3-carboxylate was reacted with formamide and sodium methoxide to give the title compound. The crude material was used directly in subsequent reactions.

Synthesis of methyl 1-(3-bromo-5-morpholino-phenyl)pyrazolo[3,4-b]pyridine-3-carboxylate

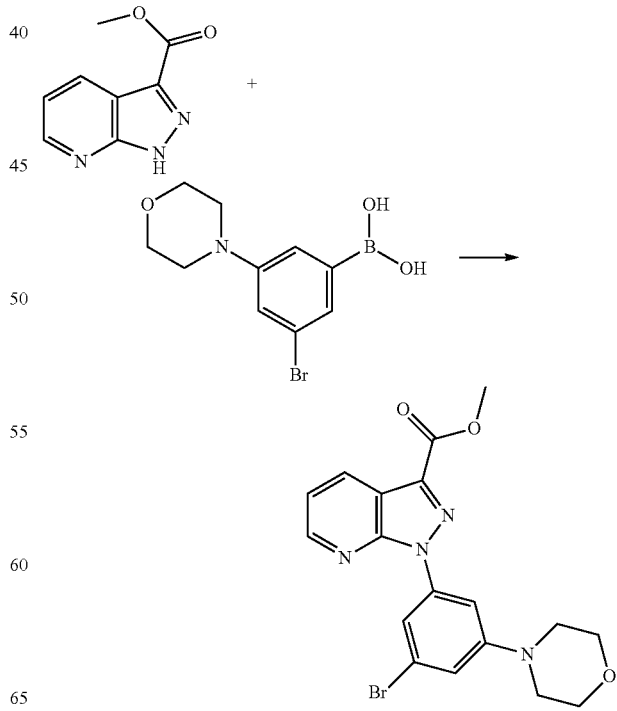

Similar to General Procedure C, methyl 1H-pyrazolo[3,4-b]pyridine-3-carboxylate was reacted with (3-bromo-5-morpholino-phenyl)boronic acid and purified by flash chromatography to afford 171 mg of the title compound (73% yield).

Synthesis of 1-(3-bromo-5-morpholino-phenyl)pyrazolo[3,4-b]pyridine-3-carboxamide

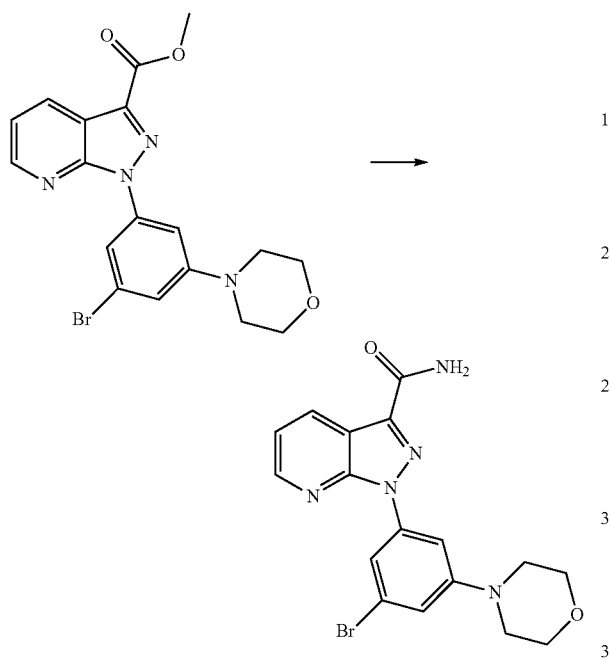

Similar to as described in General Procedure H, methyl 1-(3-bromo-5-morpholino-phenyl)pyrazolo[3,4-b]pyridine-3-carboxylate was reacted with formamide and sodium methoxide to give the title compound. The crude material was used directly in subsequent reactions.

Synthesis of methyl 1-(3-bromophenyl)pyrazolo[3,4-b]pyridine-3-carboxylate

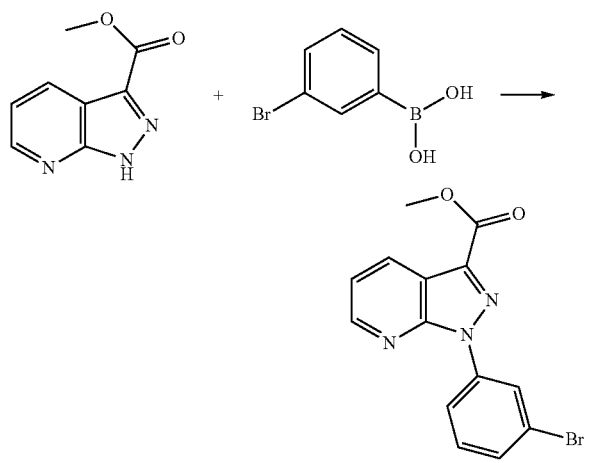

Similar to General Procedure C, methyl 1H-pyrazolo[3,4-b]pyridine-3-carboxylate was reacted with (3-bromophenyl)boronic acid and purified by flash chromatography to afford 838 mg of the title compound (50% yield).

Synthesis of 5-bromo-3-iodo-1H-pyrazolo[3,4-b]pyridine

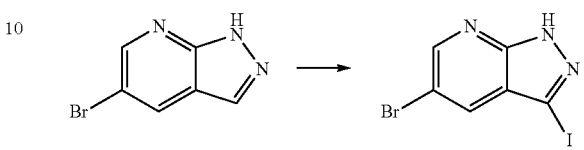

To a solution of 5-bromo-1H-pyrazolo[3,4-b]pyridine (1000 mg, 5.05 mmol) in N,N-dimethylformamide (25.2 mL) was added potassium hydroxide (3.0 eq., 859 mg, 15.1 mmol) followed by iodine (1.8 eq., 2310 mg, 9.09 mmol). The reaction was heated to 50° C. for 1.5 hours. The reaction was then cooled to room temperature and quenched with aqueous sodium thiosulfate until the dark colour disappeared. The solution was diluted with water and extracted 2 times with iPrOAc. The organic layers were combined, dried with sodium sulfate and concentrated to afford a yellow solid. The crude material was used directly in subsequent reactions.

Synthesis of 2-[(5-bromo-3-iodo-pyrazolo[3,4-b]pyridin-1-yl)methoxy]ethyl-trimethyl-silane

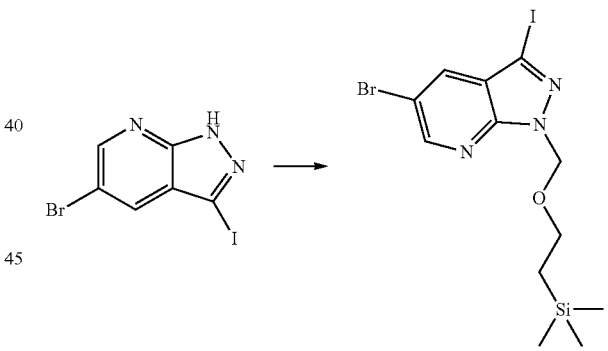

To a solution of 5-bromo-3-iodo-1H-pyrazolo[3,4-b]pyridine (1640 mg, 5.05 mmol) in N,N-dimethylformamide (10.1 mL) cooled to 0° C. was added sodium hydride (60% in mineral oil, 1.33 eq., 269 mg, 6.73 mmol) slowly and the reaction was stirred at this temperature for 20 minutes. 2-(trimethylsilyl)ethoxymethyl chloride (1.33 eq., 1.19 mL, 6.73 mmol) was added and the reaction was warmed to room temperature and stirred for 3 h. The reaction was then quenched with saturated aqueous ammonium chloride. The solution was extracted 2 times with iPrOAc. The organic layers were combined, dried with sodium sulfate and concentrated. The crude material was purified by flash chromatography (5-30% iPrOAc in heptanes) to afford 1.0123 g of a light yellow solid (44%).

Synthesis of 1-(3-bromophenyl)pyrazolo[3,4-b]pyridine-3-carboxamide

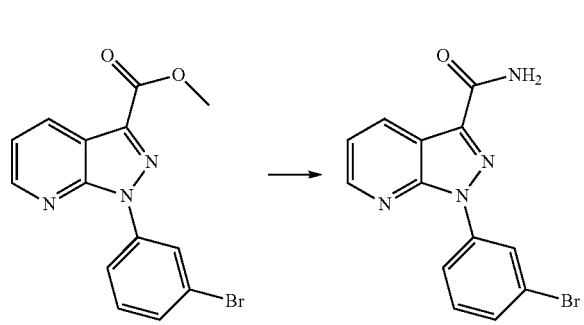 [SMILES: COC(=O)c1nn(-c2cccc(Br)c2)c2ncccc12 ; NC(=O)c1nn(-c2cccc(Br)c2)c2ncccc12]

Similar to as described in General Procedure H, methyl 1-(3-bromophenyl)pyrazolo[3,4-b]pyridine-3-carboxylate was reacted with formamide and sodium methoxide to give the title compound. The crude material was used directly in subsequent reactions.

Synthesis of methyl 1-(3-bromo-5-methoxy-phenyl)pyrazolo[3,4-b]pyridine-3-carboxylate

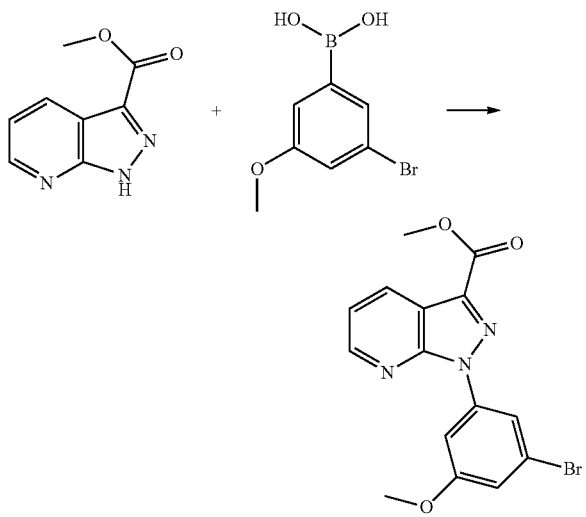

Similar to General Procedure C, methyl 1H-pyrazolo[3,4-b]pyridine-3-carboxylate was reacted with (3-bromo-5-methoxy-phenyl)boronic acid and purified by flash chromatography to afford 153.6 mg of the title compound (75% yield).

Synthesis of 1-(3-bromo-5-methoxy-phenyl)pyrazolo[3,4-b]pyridine-3-carboxamide

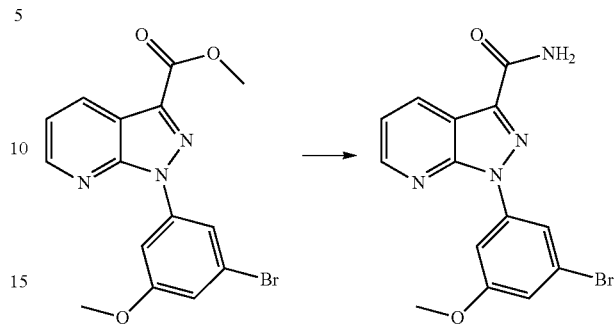

Similar to as described in General Procedure H, methyl 1-(3-bromo-5-methoxy-phenyl)pyrazolo[3,4-b]pyridine-3-carboxylate was reacted with formamide and sodium methoxide to give the title compound. The crude material was used directly in subsequent reactions.

Synthesis of 2-(3-bromo-5-methylsulfonyl-phenyl)-4,4,5,5-tetramethyl-1,3,2-dioxaborolane

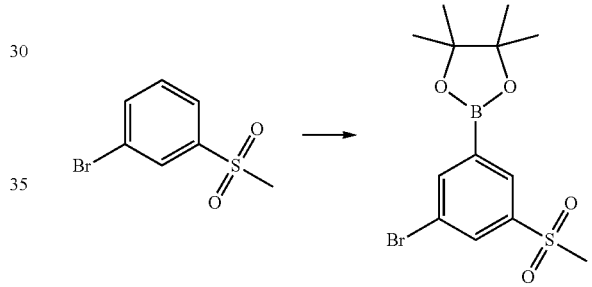

Under inert atmosphere, 1-bromo-3-methylsulfonyl-benzene (300 mg, 1.276 mmol), bis(pinacolato)diboron (0.878 eq., 287.4 mg), bis(1,5-cyclooctadiene)di-mu-methoxydi-iridium(I) (0.005 eq., 4.2 mg) and 4,4'-di-tert-butyl-2,2'-bipyridine (0.0105 eq., 3.6 mg) were dissolved in degassed tetrahydrofuran (1.3 mL). The reaction was heated in a sealed vial at 80° C. for 16 h. The solution was cooled to room temperature, diluted with dichloromethane, filtered through celite and concentrated to afford a beige solid. The crude material was used directly in subsequent reactions.

Synthesis of methyl 1-(3-bromo-5-methyl sulfonyl-phenyl)pyrazolo[3,4-b]pyridine-3-carboxylate

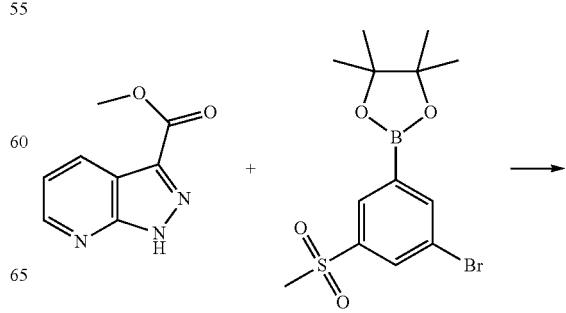

-continued

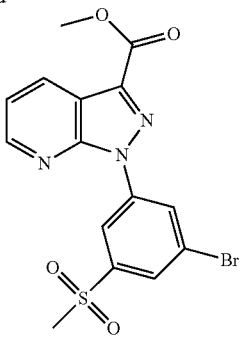

Similar to General Procedure C, methyl 1H-pyrazolo[3,4-b]pyridine-3-carboxylate was reacted with 2-(3-bromo-5-methylsulfonyl-phenyl)-4,4,5,5-tetramethyl-1,3,2-dioxaborolane and purified by flash chromatography to afford 163.5 mg of the title compound (70% yield).

Synthesis of 1-(3-bromo-5-methylsulfonyl-phenyl)pyrazolo[3,4-b]pyridine-3-carboxamide

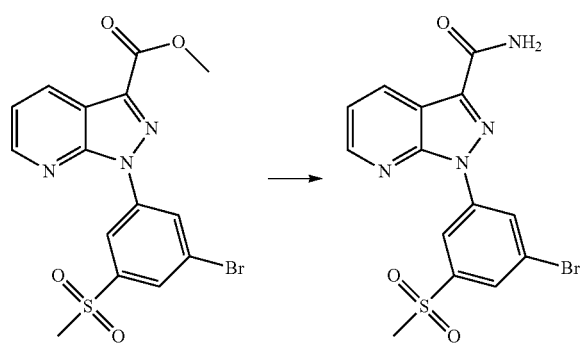 [SMILES: COC(=O)c1nn(-c2cc(Br)cc(S(C)(=O)=O)c2)c2ncccc12 ; CS(=O)(=O)c1cc(Br)cc(-n2nc(C(N)=O)c3cccnc32)c1]

Similar to as described in General Procedure H, methyl 1-(3-bromo-5-methyl sulfonyl-phenyl)pyrazolo[3,4-b]pyridine-3-carboxylate was reacted with formamide and sodium methoxide to give the title compound. The crude material was used directly in subsequent reactions.

Synthesis of methyl 5-bromo-1H-pyrazolo[3,4-b]pyridine-3-carboxylate

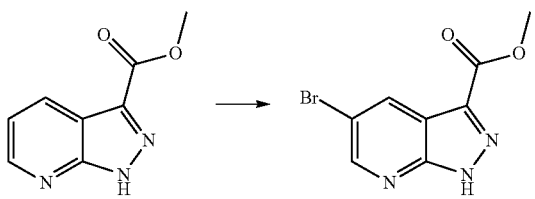

To a solution of methyl 1H-pyrazolo[3,4-b]pyridine-3-carboxylate (500 mg, 2.822 mmol) and sodium acetate (6.0 eq., 1417.5 mg, 16.934 mmol) in acetic acid (11.3 mL) was added bromine (3.0 eq., 0.43 mL, 8.467 mmol). The reaction was heated in a sealed tube at 115° C. overnight. The reaction was then cooled to room temperature, diluted with isopropyl acetate and concentrated under vacuum. The crude material was purified by flash chromatography (5-100% iPrOAc in heptanes) to afford 339.5 mg of a white solid (47%).

Synthesis of methyl 5-bromo-1-(2-trimethylsilylethoxymethyl)pyrazolo[3,4-b]pyridine-3-carboxylate and methyl 5-bromo-2-(2-trimethylsilylethoxymethyl)pyrazolo[3,4-b]pyridine-3-carboxylate

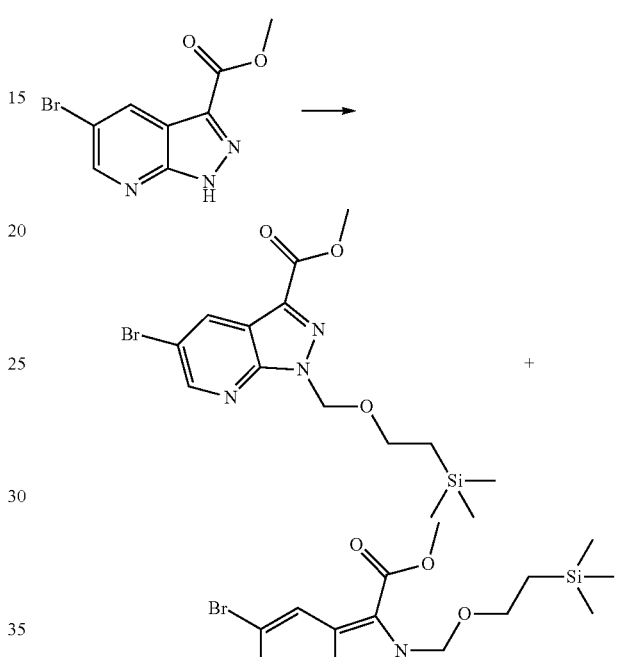

To a solution of methyl 5-bromo-1H-pyrazolo[3,4-b]pyridine-3-carboxylate (339.5 mg, 1.326 mmol) in N,N-dimethylformamide (2.7 mL) cooled to 0° C. under inert atmosphere was added sodium hydride (60% in mineral oil, 1.33 eq., 70.1 mg, 1.767 mmol) slowly and the reaction was stirred at this temperature for 30 minutes. 2-(trimethylsilyl)ethoxymethyl chloride (1.33 eq., 0.31 mL, 1.767 mmol) was added and the reaction was warmed to room temperature and stirred overnight. The reaction was then quenched with saturated aqueous ammonium chloride. The solution was extracted 2 times with iPrOAc. The organic layers were combined, dried with sodium sulfate and concentrated. The crude material was purified by flash chromatography (5-30% iPrOAc in heptanes) to afford 337.3 mg and 130.3 mg of each regioisomer as light yellow oils (90%).

Synthesis of methyl 1-(2-trimethylsilylethoxymethyl)pyrazolo[3,4-b]pyridine-3-carboxylate

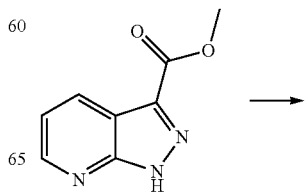

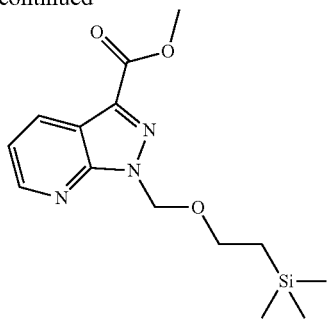

To a solution of methyl 1H-pyrazolo[3,4-b]pyridine-3-carboxylate (1000 mg, 5.645 mmol) in N,N-dimethylformamide (11.3 mL) cooled to 0° C. under inert atmosphere was added sodium hydride (60% in mineral oil, 1.33 eq., 300.9 mg, 7.524 mmol) slowly and the reaction was stirred at this temperature for 30 minutes. 2-(Trimethylsilyl)ethoxymethyl chloride (1.33 eq., 1.33 mL, 7.524 mmol) was added and the reaction was warmed to room temperature and stirred overnight. The reaction was then quenched with saturated aqueous ammonium chloride. The solution was extracted 2 times with iPrOAc. The organic layers were combined, dried with sodium sulfate and concentrated. The crude material was purified by flash chromatography (5-30% iPrOAc in heptanes) to afford 995 mg of the title compound as a white solid (57%).

Synthesis of methyl 5-(4,4,5,5-tetramethyl-1,3,2-dioxaborolan-2-yl)-1-(2-trimethylsilylethoxymethyl)pyrazolo[3,4-b]pyridine-3-carboxylate

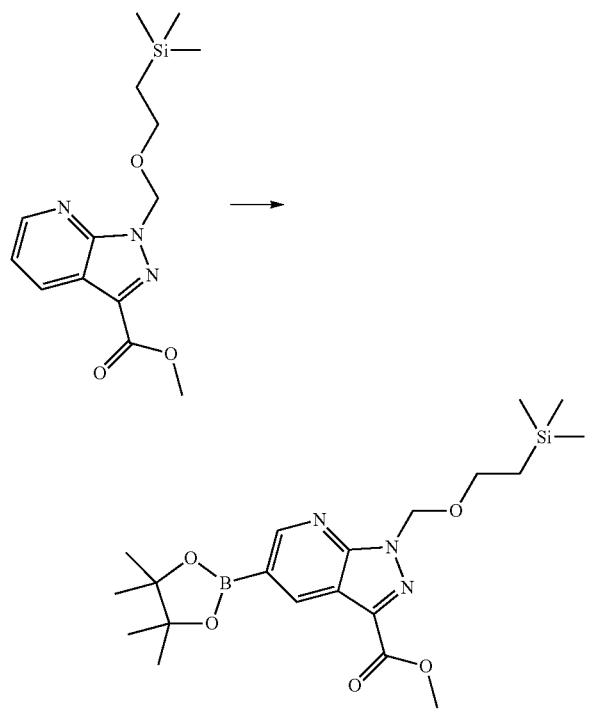

Under inert atmosphere, methyl 1-(2-trimethylsilylethoxymethyl)pyrazolo[3,4-b]pyridine-3-carboxylate (117 mg, 0.381 mmol), bis(pinacolato)diboron (0.878 eq., 85.7 mg), bis(1,5-cyclooctadiene)di-mu-methoxydiiridium(I) (0.02 eq., 5.0 mg) and 4,4'-di-tert-butyl-2,2'-bipyridine (0.045 eq., 4.6 mg) were dissolved in degassed 2-methyltetrahydrofuran (0.38 mL). The reaction was heated in a sealed vial at 80° C. for 2 h. The solution was cooled to room temperature, diluted with dichloromethane, filtered through celite and concentrated under vacuum. The crude material was purified by flash chromatography (5-80% 3:1 iPrOAc:MeOH in heptanes) to afford 98 mg of a light yellow solid (60%).

Synthesis of methyl 5-hydroxy-1-(2-trimethylsilylethoxymethyl)pyrazolo[3,4-b]pyridine-3-carboxylate and 5-hydroxy-1-(2-trimethylsilylethoxymethyl)pyrazolo[3,4-b]pyridine-3-carboxylic acid

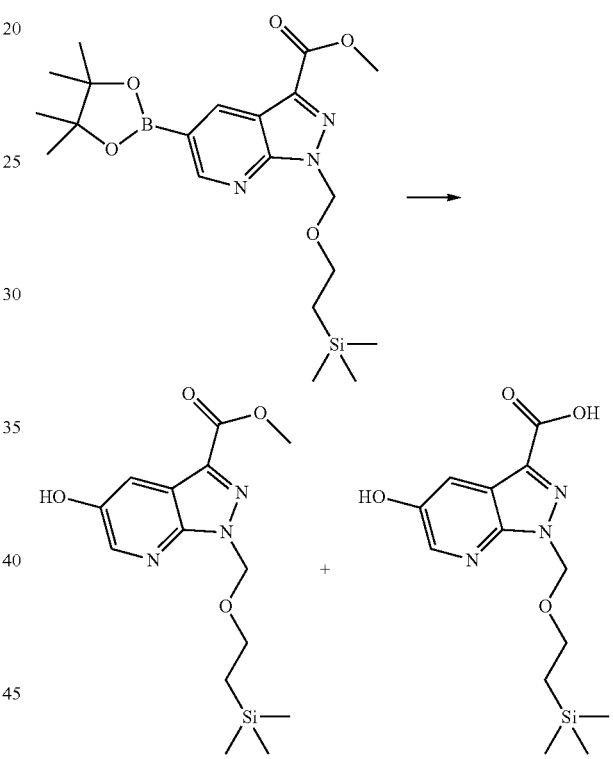

To a solution of methyl 5-(4,4,5,5-tetramethyl-1,3,2-dioxaborolan-2-yl)-1-(2-trimethylsilylethoxymethyl)pyrazolo[3,4-b]pyridine-3-carboxylate (500 mg, 1.154 mmol) in tetrahydrofuran (11.5 mL) and aqueous sodium hydroxide (2 mass %) (11.5 mL) was added hydrogen peroxide (35 mass %) in water (10.0 eq., 1.16 mL, 11.54 mmol) at room temperature. The reaction was stirred at room temperature for 3 h, and then was extracted twice with EtOAc. The combined organic phases were dried with sodium sulfate. The solution was concentrated under vacuum to afford 144.5 mg of the title compound methyl 5-hydroxy-1-(2-trimethylsilylethoxymethyl)pyrazolo[3,4-b]pyridine-3-carboxylate as a colorless solid (39%). The crude material was used directly in subsequent reactions.

The aqueous layer was acidified with 1N HCl and extracted twice with dichloromethane. The organic layers were combined, dried with sodium sulfate and concentrated to afford the acid 5-hydroxy-1-(2-trimethylsilylethoxymethyl)pyrazolo[3,4-b]pyridine-3-carboxylic acid as a white solid. The crude material was used directly in subsequent reactions.

Synthesis of methyl 5-hydroxy-1H-pyrazolo[3,4-b]pyridine-3-carboxylate

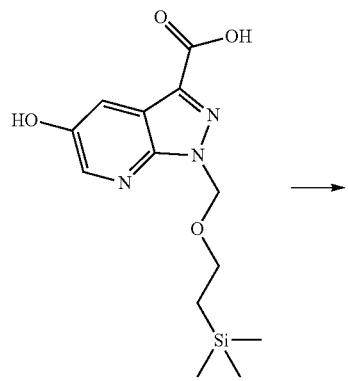

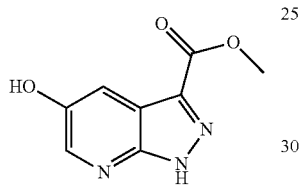

Similar as to General Procedure T, 5-hydroxy-1-(2-trimethylsilylethoxymethyl)pyrazolo[3,4-b]pyridine-3-carboxylic acid (200 mg, 0.646 mmol) in methanol (6.5 mL) and hydrochloric acid (4.0 M in dioxane, 12.5 eq., 2.02 mL, 8.080 mmol) was refluxed for 4 hours. After cooling to room temperature, aqueous saturated sodium bicarbonate was added and the product extracted twice with EtOAc. The combined organic extracts were washed with brine, dried with sodium sulfate, filtered and concentrated under vacuum to afford 72 of the title compound as a yellow solid (58%).

Synthesis of methyl 5-methoxy-1-(2-trimethylsilylethoxymethyl)pyrazolo[3,4-b]pyridine-3-carboxylate

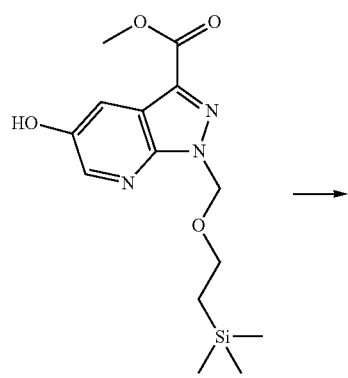

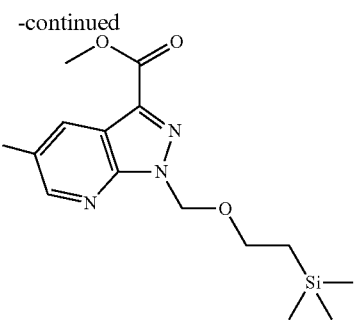

To a small vial was added methyl 5-hydroxy-1-(2-trimethylsilylethoxymethyl)pyrazolo[3,4-b]pyridine-3-carboxylate (100 mg, 0.309 mmol), potassium carbonate (1.5 eq., 64.1 mg, 0.464 mmol), iodomethane (1.2 eq., 0.023 mL, 0.371 mmol) in N,N-dimethylformamide (0.9 mL). The reaction was stirred at room temperature for 2 h. Water and iPrOAc were added and the mixture was extracted 2 times with isopropyl acetate. The organic layers were combined, washed with brine, dried with sodium sulfate and concentrated under vacuum to afford a yellow oil. The crude material was used directly in subsequent reactions.

Synthesis of methyl 5-methoxy-1H-pyrazolo[3,4-b]pyridine-3-carboxylate

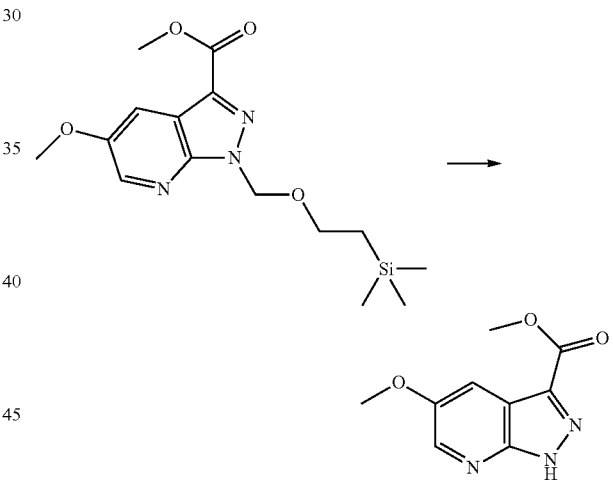

Similar to as described in General Procedure T, methyl 5-methoxy-1-(2-trimethylsilylethoxymethyl)pyrazolo[3,4-b]pyridine-3-carboxylate was reacted was reacted with hydrochloric acid to afford 59 mg of the title compound (92%).

Synthesis of methyl 1-(3-bromophenyl)-5-methoxypyrazolo[3,4-b]pyridine-3-carboxylate

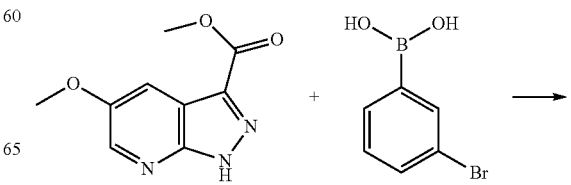

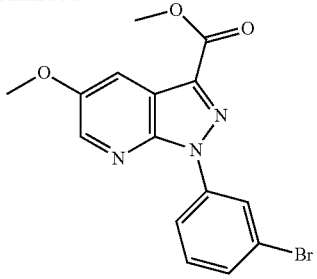

Similar to General Procedure C methyl 5-methoxy-1H-pyrazolo[3,4-b]pyridine-3-carboxylate was reacted with (3-bromophenyl)boronic acid and purified by flash chromatography to afford 36 mg of the title compound (35% yield).

Synthesis of 1-(3-bromophenyl)-5-methoxy-pyrazolo[3,4-b]pyridine-3-carboxamide

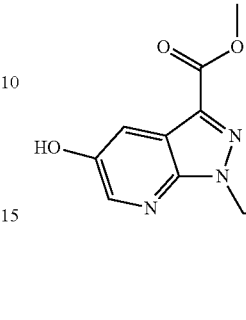

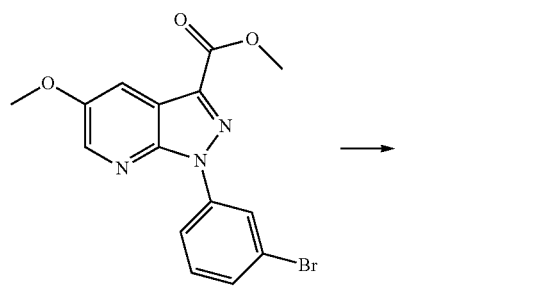

Similar to as described in General Procedure H, methyl 1-(3-bromophenyl)-5-methoxy-pyrazolo[3,4-b]pyridine-3-carboxylate was reacted with formamide and sodium methoxide to give the title compound. The crude material was used directly in subsequent reactions.

Synthesis of methyl 5-fluoro-1-(2-trimethylsilylethoxymethyl)pyrazolo[3,4-b]pyridine-3-carboxylate

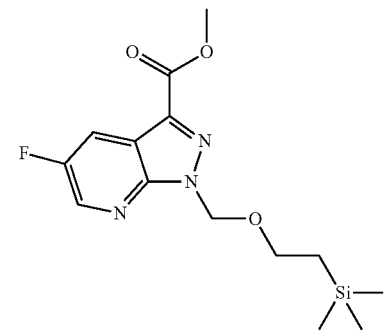

CsF was added to a small vial and dried at 200° C. for 1 h under high vacuum. To an oven-dried vial containing methyl 5-hydroxy-1-(2-trimethylsilylethoxymethyl)pyrazolo[3,4-b]pyridine-3-carboxylate (100 mg, 0.309 mmol) in dry toluene (3.1 mL) under nitrogen at room temperature was added cesium fluoride (3.0 eq., 142.3 mg, 0.927 mmol) and Phenofluor™ (1.2 eq., 166.6 mg, 0.371 mmol). The reaction was stirred at room temperature for 30 minutes then at 110° C. for 20 h. The reaction was then cooled to room temperature, filtered through celite and concentrated under vacuum. The crude was purified by flash chromatography (5-50% iPrOAc in heptanes) to afford 43.5 mg of the title compound (43%).

Synthesis of methyl 5-fluoro-1H-pyrazolo[3,4-b]pyridine-3-carboxylate

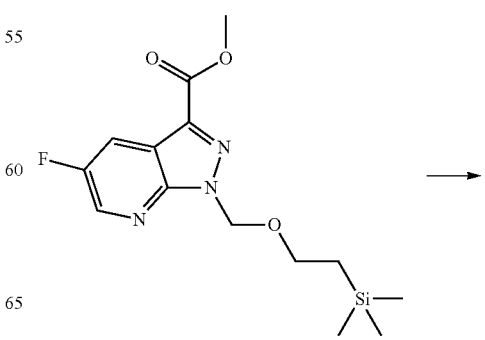

Similar to as described in General Procedure T, methyl 5-fluoro-1-(2-trimethylsilylethoxymethyl)pyrazolo[3,4-b]pyridine-3-carboxylate was reacted was reacted with hydrochloric acid to afford the title compound.

Synthesis of methyl 1-(3-bromophenyl)-5-fluoropyrazolo[3,4-b]pyridine-3-carboxylate

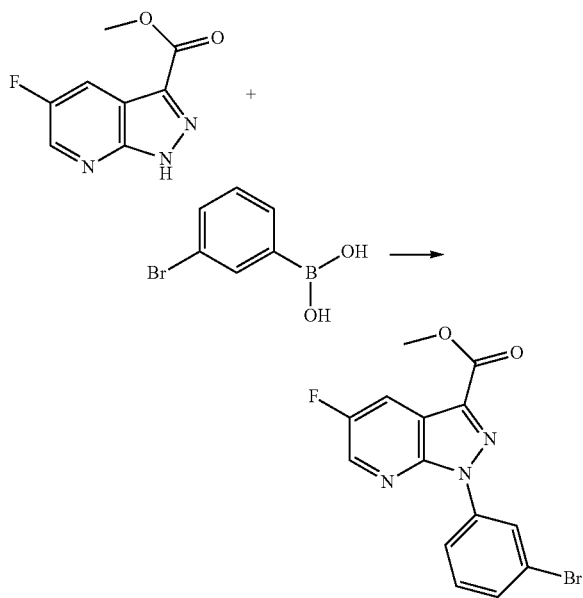

Similar to General Procedure C methyl 5-fluoro-1H-pyrazolo[3,4-b]pyridine-3-carboxylate was reacted with (3-bromophenyl)boronic acid and purified by flash chromatography to afford 33 mg of the title compound (45% yield).

Synthesis of 1-(3-bromophenyl)-5-fluoro-pyrazolo[3,4-b]pyridine-3-carboxamide

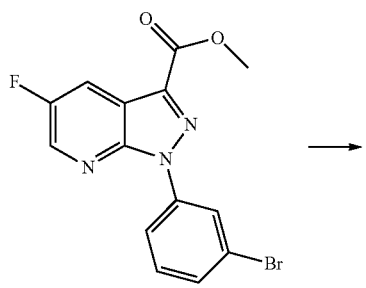

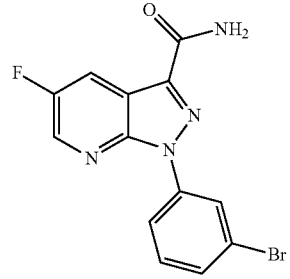

Similar to as described in General Procedure H, methyl 1-(3-bromophenyl)-5-fluoro-pyrazolo[3,4-b]pyridine-3-carboxylate was reacted with formamide and sodium methoxide to give the title compound. The crude material was used directly in subsequent reactions.

Synthesis of 6-chloro-3-iodo-1H-pyrazolo[4,3-c]pyridine

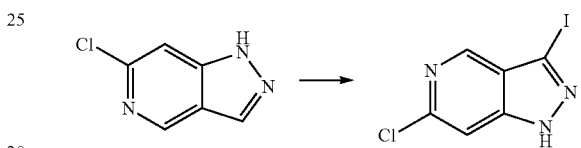

To a solution of 6-chloro-1H-pyrazolo[4,3-c]pyridine (300 mg, 1.953 mmol) in N,N-dimethylformamide (9.8 mL) was added potassium hydroxide (3.0 eq., 332 mg, 5.861 mmol) followed by iodine (1.8 eq., 892.4 mg, 3.516 mmol). The reaction was heated to 50° C. for 1.5 hours. The reaction was then cooled to room temperature and quenched with aqueous sodium thiosulfate until the dark colour disappeared. The solution was diluted with water and extracted 2 times with iPrOAc. The organic layers were combined, dried with sodium sulfate and concentrated to afford 475 mg of a yellow solid as the title compound (87% yield). The crude material was used directly in subsequent reactions.

Synthesis of methyl 6-chloro-1H-pyrazolo[4,3-c]pyridine-3-carboxylate

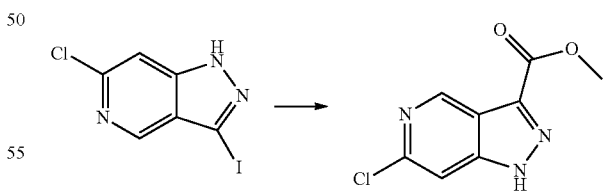

To a solution of 6-chloro-3-iodo-1H-pyrazolo[4,3-c]pyridine (475 mg, 1.699 mmol) in triethylamine (8.0 mL) and methanol (20.0 eq., 1.38 mL, 33.993 mmol) was sparged with nitrogen. palladium(II) acetate (0.02 eq., 22.9 mg, 0.034 mmol) and xantphos (0.04 eq., 40.14 mg, 0.068 mmol) were added and a carbon monoxide balloon was affixed to the vial. The reaction was heated to 50° C. for 6 h. The reaction was cooled to room temperature, diluted with dichloromethane and filtered over celite. The crude material was purified by flash chromatography (5-100% iPrOAc in heptanes) to afford 186.3 mg of the title compound (52%).

Synthesis of methyl 1-(3-bromophenyl)-6-chloro-pyrazolo[4,3-c]pyridine-3-carboxylate

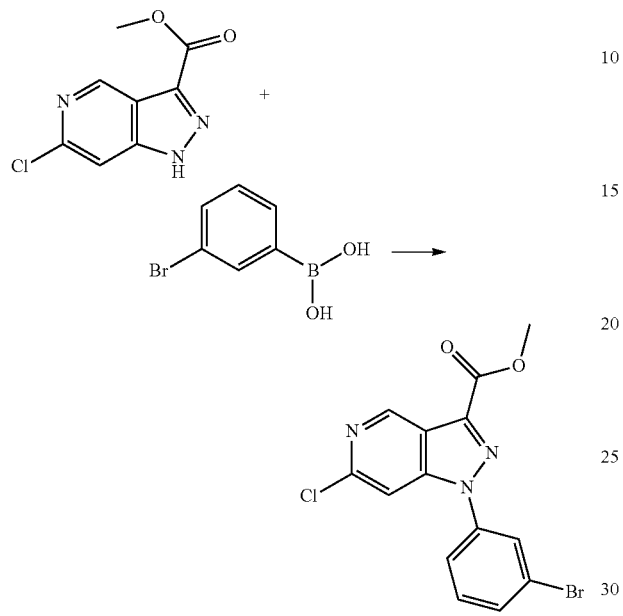

Similar to General Procedure C methyl 6-chloro-1H-pyrazolo[4,3-c]pyridine-3-carboxylate was reacted with (3-bromophenyl)boronic acid and purified by flash chromatography to afford 59 mg of the title compound (43% yield).

Synthesis of 1-(3-bromophenyl)-6-chloro-pyrazolo[4,3-c]pyridine-3-carboxamide

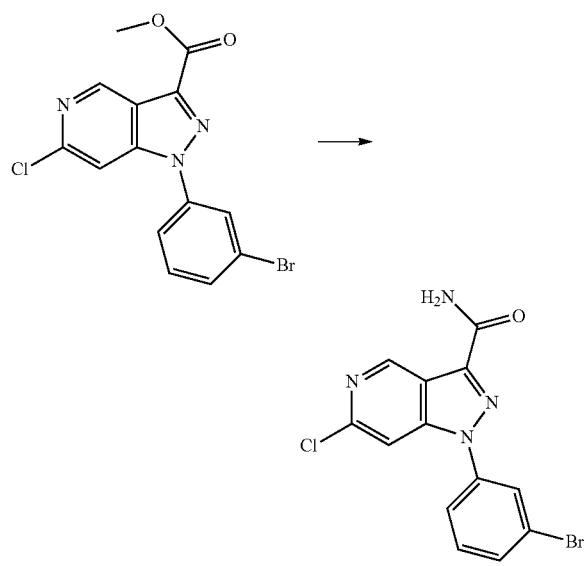

Similar to as described in General Procedure H, methyl 1-(3-bromophenyl)-6-chloro-pyrazolo[4,3-c]pyridine-3-carboxylate was reacted with formamide and sodium methoxide to give the title compound. The crude material was used directly in subsequent reactions.

Synthesis of 1-(3-bromophenyl)-6-methoxy-pyrazolo[4,3-c]pyridine-3-carboxylic acid

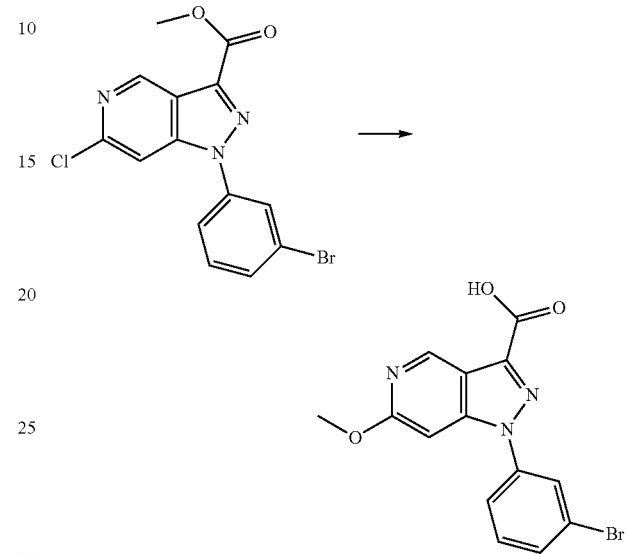

To a solution of methyl 1-(3-bromophenyl)-6-chloro-pyrazolo[4,3-c]pyridine-3-carboxylate (63 mg, 0.172 mmol) in N,N-dimethylformamide (0.86 mL) was added sodium methoxide (3.0 eq., 0.12 mL, 0.515 mmol). The reaction was stirred at room temperature for 1 h. After 1 h, LCMS analysis showed saponification of starting material with a small amount of saponified product. Sodium methoxide (1.0 eq., 0.04 mL) was added and the reaction was heated to 50° C. for 4 h. The reaction was cooled to room temperature. 1N aqueous sodium hydroxide solution was added and the mixture was extracted 2 times with iPrOAc to remove undesired by-products. The aqueous phase was then acidified with 1N HCl to pH=1 and extracted twice with dichloromethane. The organic layers were combined, washed with brine, dried with sodium sulfate and concentrated under vacuum. The crude material was used directly in subsequent reactions.

Synthesis of 1-(3-bromophenyl)-6-methoxy-pyrazolo[4,3-c]pyridine-3-carboxamide

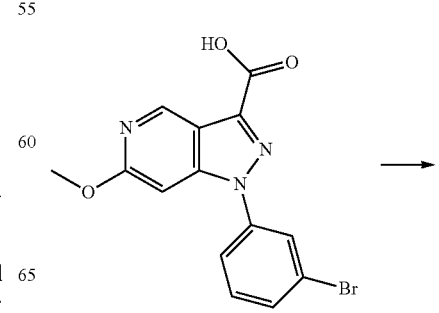

-continued

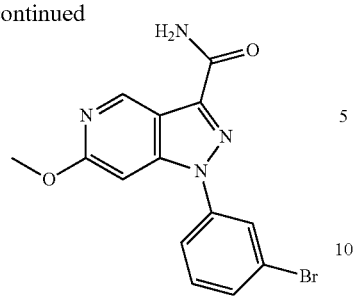

Similar to as described in General Procedure B, 1-(3-bromophenyl)-6-methoxy-pyrazolo[4,3-c]pyridine-3-carboxylic acid was reacted with ammonium chloride to give the title compound. The crude material was used directly in subsequent reactions.

Synthesis of methyl 5-cyclopropyl-1-(2-trimethylsilylethoxymethyl)pyrazolo[3,4-b]pyridine-3-carboxylate

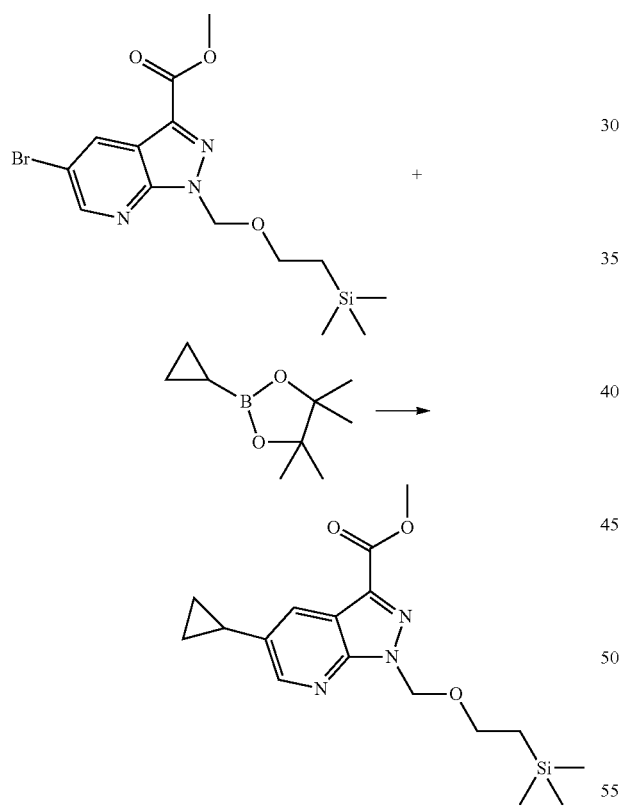

A microwave vial was charged with a solution of methyl 5-bromo-1-(2-trimethylsilylethoxymethyl)pyrazolo[3,4-b]pyridine-3-carboxylate (150 mg, 0.388 mmol) and potassium phosphate (3.0 eq., 247 mg, 1.165 mmol) in tetrahydrofuran (1.9 mL) and water (1.9 mL). The solution was thoroughly purged with nitrogen. Cyclopropylboronic acid pinacol ester (3.0 eq., 0.21 mL, 1.165 mmol) and tetrakis(triphenylphosphine)palladium(0) (0.10 eq., 44.9 mg, 0.039 mmol) were added and the vial was sealed immediately. The reaction was heated in the microwave at 120° C. for 20 minutes. The reaction was cooled to room temperature, diluted with dichloromethane and filtered through celite. Water was added and the mixture was extracted 3 times with dichloromethane. The organic layers were combined, dried with sodium sulfate and concentrated under vacuum. The crude material was purified by flash chromatography (5-100% iPrOAc in heptanes) to give 53.1 mg of a clear oil as the title compound (39%).

Synthesis of methyl 5-cyclopropyl-1H-pyrazolo[3,4-b]pyridine-3-carboxylate

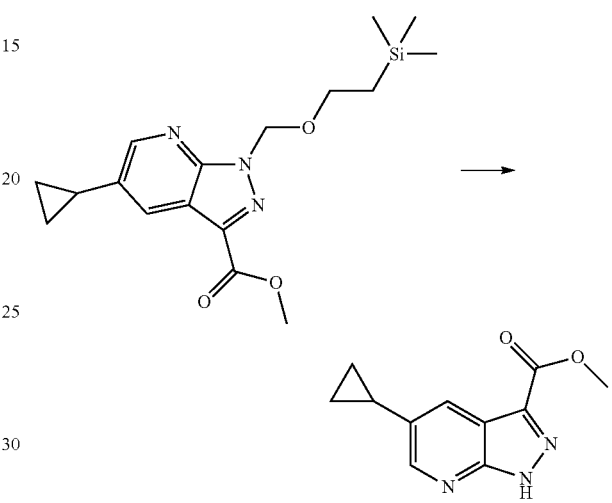

Similar to as described in General Procedure T, methyl 5-cyclopropyl-1-(2-trimethylsilylethoxymethyl)pyrazolo[3,4-b]pyridine-3-carboxylate was reacted was reacted with hydrochloric acid to afford the title compound.

Synthesis of methyl 1-(3-bromophenyl)-5-cyclopropyl-pyrazolo[3,4-b]pyridine-3-carboxylate

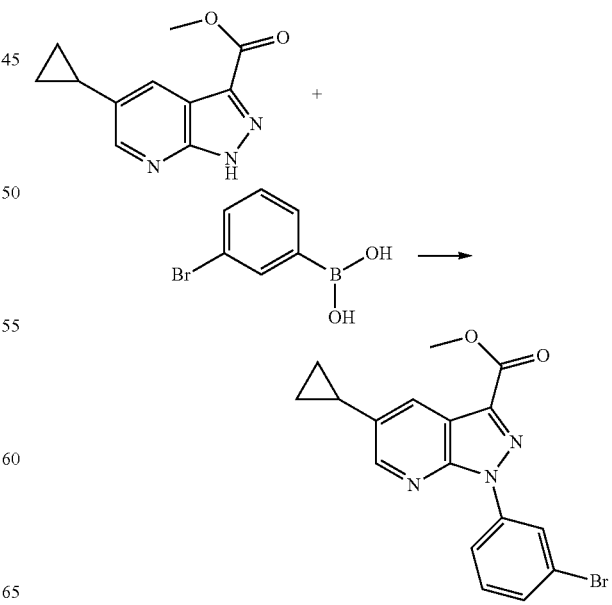

Similar to General Procedure C methyl 5-cyclopropyl-1H-pyrazolo[3,4-b]pyridine-3-carboxylate was reacted with (3-bromophenyl)boronic acid and purified by flash chromatography to afford 36 mg of the title compound (57% yield).

Synthesis of 1-(3-bromophenyl)-5-cyclopropyl-pyrazolo[3,4-b]pyridine-3-carboxamide

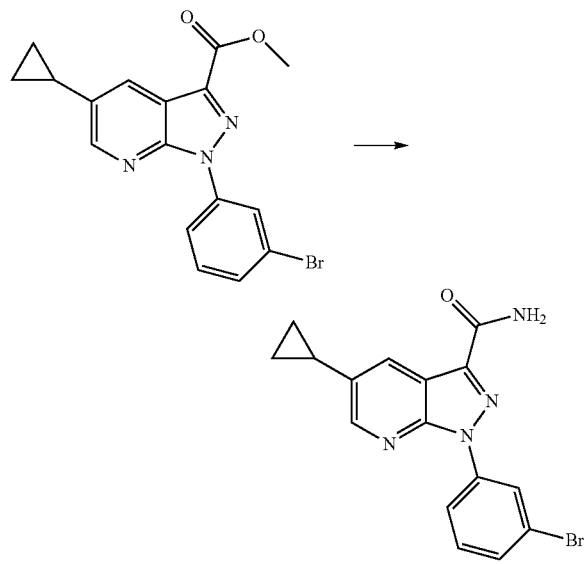

Similar to as described in General Procedure H, methyl 1-(3-bromophenyl)-5-cyclopropyl-pyrazolo[3,4-b]pyridine-3-carboxylate was reacted with formamide and sodium methoxide to give the title compound. The crude material was used directly in subsequent reactions.

Example A

Synthesis of 1-[4-[2-[(3R)-3-hydroxy-1-methyl-2-oxo-pyrrolidin-3-yl]ethynyl]-2-pyridyl]indazole-3-carboxamide

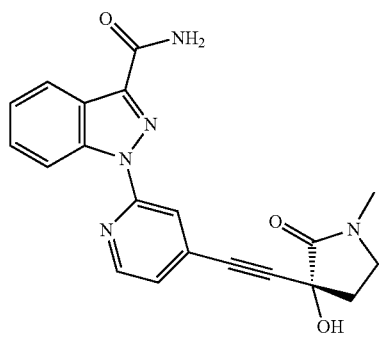 [SMILES: CN1CC[C@@](O)(C#Cc2ccnc(-n3nc(C(N)=O)c4ccccc43)c2)C1=O]

Similar to as described in General Procedure E, 1-(4-iodo-2-pyridyl)indazole-3-carboxamide was reacted with (3R)-3-ethynyl-3-hydroxy-1-methyl-pyrrolidin-2-one to give 41 mg of the title compound (67%). M+H=376.0; $^1$H NMR (400 MHz, DMSO-d6) δ 8.83-8.75 (m, 1H), 8.63-8.58 (m, 1H), 8.35-8.24 (m, 3H), 7.68-7.57 (m, 2H), 7.43 (ddd, J=8.0, 7.1, 0.9 Hz, 1H), 7.38 (dd, J=5.0, 1.5 Hz, 1H), 6.65 (s, 1H), 3.45-3.35 (m, 2H), 2.83 (s, 3H), 2.54-2.46 (m, 1H), 2.24 (dt, J=12.9, 7.1 Hz, 1H).

Example B

Synthesis of 1-[3-[2-[(3R)-3-hydroxy-1-methyl-2-oxo-pyrrolidin-3-yl]ethynyl]phenyl]pyrazolo[3,4-b]pyridine-3-carboxamide

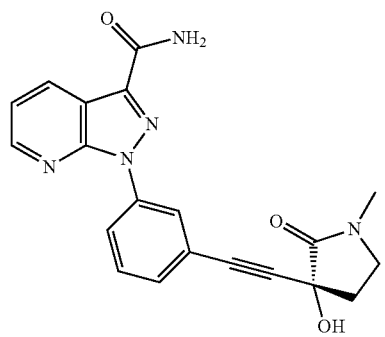 [SMILES: CN1CC[C@@](O)(C#Cc2cccc(-n3nc(C(N)=O)c4cccnc43)c2)C1=O]

Similar to as described in General Procedure E, 1-(3-bromophenyl)pyrazolo[3,4-b]pyridine-3-carboxamide was reacted with (3R)-3-ethynyl-3-hydroxy-1-methyl-pyrrolidin-2-one to give 27 mg of the title compound (34%). M+H=376.0; 1H NMR (400 MHz, DMSO-d6) δ 8.77 (dd, J=4.5, 1.6 Hz, 1H), 8.67 (dd, J=8.1, 1.7 Hz, 1H), 8.54-8.45 (m, 2H), 8.23 (br s, 1H), 7.70 (br s, 1H), 7.66-7.60 (m, 1H), 7.51 (dd, J=8.1, 4.5 Hz, 1H), 7.48-7.43 (m, 1H), 6.52 (s, 1H), 3.44-3.34 (m, 2H), 2.82 (s, 3H), 2.50-2.42 (m, 1H), 2.22 (dt, J=12.9, 7.0 Hz, 1H).

Example C

Synthesis of 5-fluoro-1-[4-[2-[(3R)-3-hydroxy-1-methyl-2-oxo-pyrrolidin-3-yl]ethynyl]-2-pyridyl]indazole-3-carboxamide

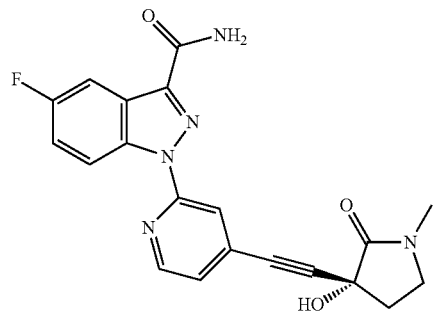 [SMILES: CN1CC[C@@](O)(C#Cc2ccnc(-n3nc(C(N)=O)c4cc(F)ccc43)c2)C1=O]

Similar to as described in General Procedure E, 5-fluoro-1-(4-iodo-2-pyridyl)indazole-3-carboxamide was reacted with (3R)-3-ethynyl-3-hydroxy-1-methyl-pyrrolidin-2-one to give 41 mg of the title compound (37%). M+H=394.0; 1H NMR (400 MHz, DMSO-d6) δ 8.81 (dd, J=9.4, 4.5 Hz, 1H), 8.61 (dd, J=5.1, 0.7 Hz, 1H), 8.34 (br s, 1H), 8.27 (d, J=1.1 Hz, 1H), 7.94 (dd, J=8.7, 2.6 Hz, 1H), 7.67 (br s, 1H), 7.54 (td, J=9.2, 2.6 Hz, 1H), 7.40 (dd, J=5.0, 1.5 Hz, 1H), 6.65 (s, 1H), 3.45-3.34 (m, 2H), 2.82 (s, 3H), 2.53-2.45 (m, 1H), 2.24 (dt, J=13.5, 7.1 Hz, 1H).

Example D

Synthesis of 1-[4-[2-[(3R)-3-hydroxy-1-methyl-2-oxo-pyrrolidin-3-yl]ethynyl]-2-pyridyl]-4,5,6,7-tetrahydroindazole-3-carboxamide

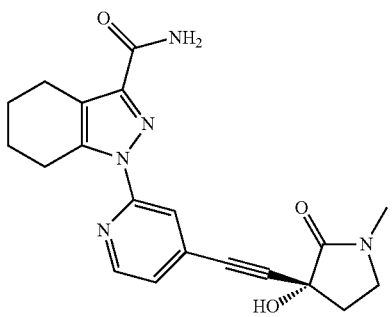 [SMILES: CN1CC[C@@](O)(C#Cc2ccnc(-n3nc(C(N)=O)c4c3CCCC4)c2)C1=O]

Similar to as described in General Procedure E, 1-(4-iodo-2-pyridyl)-4,5,6,7-tetrahydroindazole-3-carboxamide was reacted with (3R)-3-ethynyl-3-hydroxy-1-methyl-pyrrolidin-2-one to give 44 mg of the title compound (66%). M+H=380.0; 1H NMR (400 MHz, DMSO-d6) δ 8.54-8.40 (m, 1H), 8.06 (d, J=1.3 Hz, 1H), 7.76 (br s, 1H), 7.34 (dd, J=5.3, 1.4 Hz, 1H), 7.23 (br s, 1H), 6.62 (s, 1H), 3.43-3.34 (m, 2H), 3.10 (t, J=6.0 Hz, 2H), 2.81 (s, 3H), 2.70 (t, J=5.8 Hz, 2H), 2.48-2.41 (m, 1H), 2.28-2.15 (m, 1H), 1.83-1.59 (m, 4H).

Example E

Synthesis of 1-[4-[2-[(3R)-3-hydroxy-1-methyl-2-oxo-pyrrolidin-3-yl]ethynyl]-2-pyridyl]pyrazole-3-carboxamide

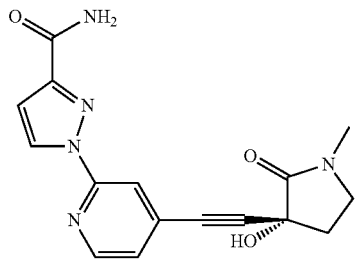 [SMILES: CN1CC[C@@](O)(C#Cc2ccnc(-n3ccc(C(N)=O)n3)c2)C1=O]

Similar to as described in General Procedure E, 1-(4-iodo-2-pyridyl)pyrazole-3-carboxamide was reacted with (3R)-3-ethynyl-3-hydroxy-1-methyl-pyrrolidin-2-one to give 49 mg of the title compound (67%). M+H=326.0; 1H NMR (400 MHz, DMSO-d6) δ 8.64 (d, J=2.5 Hz, 1H), 8.52 (dd, J=5.0, 0.8 Hz, 1H), 8.07 (d, J=1.2 Hz, 1H), 7.95 (br s, 1H), 7.43 (br s, 1H), 7.42 (dd, J=5.1, 1.4 Hz, 1H), 6.89 (d, J=2.5 Hz, 1H), 6.65 (s, 1H), 3.43-3.34 (m, 2H), 2.82 (s, 3H), 2.49-2.43 (m, 1H), 2.27-2.18 (m, 1H).

Example F

Synthesis of 1-[4-[2-[(3R)-3-hydroxy-1-methyl-2-oxo-pyrrolidin-3-yl]ethynyl]-2-pyridyl]-5,6-dihydro-4H-cyclopenta[c]pyrazole-3-carboxamide

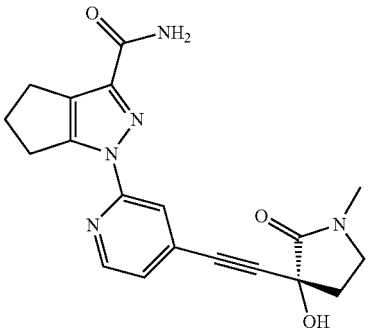 [SMILES: CN1CC[C@@](O)(C#Cc2ccnc(-n3nc(C(N)=O)c4c3CCC4)c2)C1=O]

Similar to as described in General Procedure E, 1-(4-iodo-2-pyridyl)-5,6-dihydro-4H-cyclopenta[c]pyrazole-3-carboxamide was reacted with (3R)-3-ethynyl-3-hydroxy-1-methyl-pyrrolidin-2-one to give 6 mg of the title compound (11%). M+H=365.0; 1H NMR (400 MHz, DMSO-d6) δ 8.49-8.42 (m, 1H), 8.03 (d, J=1.3 Hz, 1H), 7.75 (br s, 1H), 7.33 (dd, J=5.0, 1.5 Hz, 1H), 7.30 (br s, 1H), 6.63 (s, 1H), 3.40-3.35 (m, 2H), 3.12 (t, J=7.3 Hz, 2H), 2.81 (s, 3H), 2.69 (t, J=7.2 Hz, 2H), 2.58-2.51 (m, 2H), 2.50-2.42 (m, 1H), 2.22 (dt, J=12.9, 7.1 Hz, 1H).

Example G

Synthesis of 1-[3-[2-[(3R)-3-hydroxy-1-methyl-2-oxo-pyrrolidin-3-yl]ethynyl]phenyl]-4,5,6,7-tetrahydroindazole-3-carboxamide

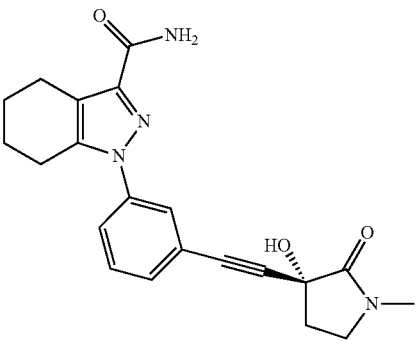 [SMILES: CN1CC[C@@](O)(C#Cc2cccc(-n3nc(C(N)=O)c4c3CCCC4)c2)C1=O]

Similar to as described in General Procedure E, 1-(3-bromophenyl)-4,5,6,7-tetrahydroindazole-3-carboxamide was reacted with (3R)-3-ethynyl-3-hydroxy-1-methyl-pyrrolidin-2-one to give 30 mg of the title compound (53%). M+H=379.0; 1H NMR (400 MHz, DMSO-d6) δ 7.70-7.61 (m, 2H), 7.54 (t, J=7.8 Hz, 1H), 7.49 (br s, 1H), 7.46-7.43 (m, 1H), 7.15 (br s, 1H), 6.48 (s, 1H), 3.40-3.32 (m, 2H), 2.80 (s, 3H), 2.77-2.68 (m, 4H), 2.44 (ddd, J=12.7, 6.4, 5.0 Hz, 1H), 2.18 (dt, J=13.0, 7.1 Hz, 1H), 1.78-1.65 (m, 4H).

Example H

Synthesis of (R)-1-(4-((3-hydroxy-1-methyl-2-oxopyrrolidin-3-yl)ethynyl)pyridin-2-yl)-4,5,6,7-tetrahydro-1H-5,7-methanoindazole-3-carboxamide

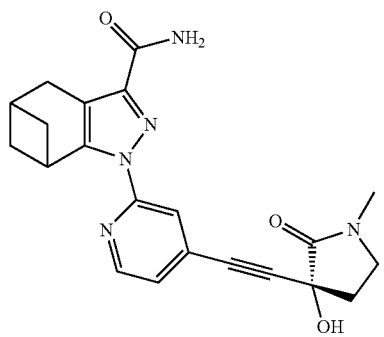 [SMILES: CN1CC[C@@](O)(C#Cc2ccnc(-n3nc(C(N)=O)c4c3C3CC(C4)C3)c2)C1=O]

Similar to as described in General Procedure E, 1-(4-iodopyridin-2-yl)-4,5,6,7-tetrahydro-1H-5,7-methanoindazole-3-carboxamide was reacted with (3R)-3-ethynyl-3-hydroxy-1-methyl-pyrrolidin-2-one to give 23 mg of the title compound (28%). M+H=392.0; 1H NMR (400 MHz, DMSO-d6) δ 8.46 (d, J=5.0 Hz, 1H), 8.03 (d, J=1.5 Hz, 1H), 7.76 (br s, 1H), 7.36 (dd, J=5.0, 1.5 Hz, 1H), 7.28 (br s, 1H), 6.63 (s, 1H), 4.28 (dd, J=5.4, 5.4 Hz, 1H), 3.43-3.33 (m, 2H), 2.94 (d, J=2.7 Hz, 2H), 2.85-2.78 (m, 1H), 2.81 (s, 3H), 2.57-2.51 (m, 2H), 2.50-2.42 (m, 1H), 2.28-2.17 (m, 1H), 1.56-1.44 (m, 2H).

Example I

Synthesis of (R)-1-(4-((3-hydroxy-1-methyl-2-oxopyrrolidin-3-yl)ethynyl)pyridin-2-yl)-4,5,6,7-tetrahydro-1H-4,6-methanoindazole-3-carboxamide

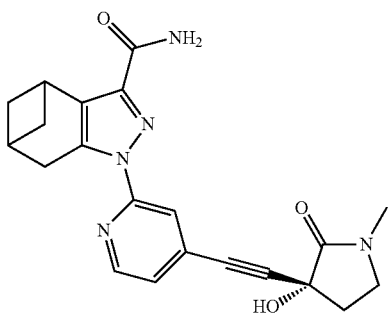 [SMILES: CN1CC[C@@](O)(C#Cc2ccnc(-n3nc(C(N)=O)c4c3CC3CC4C3)c2)C1=O]

Similar to as described in General Procedure E, 1-(4-iodopyridin-2-yl)-4,5,6,7-tetrahydro-1H-4,6-methanoindazole-3-carboxamide was reacted with (3R)-3-ethynyl-3-hydroxy-1-methyl-pyrrolidin-2-one to give 36 mg of the title compound (58%). M+H=392.0; 1H NMR (400 MHz, DMSO-d6) δ 8.48 (d, J=4.9 Hz, 1H), 8.13 (d, J=1.2 Hz, 1H), 7.79 (br s, 1H), 7.35 (dd, J=5.0, 1.5 Hz, 1H), 7.27 (br s, 1H), 6.63 (s, 1H), 3.57 (dd, J=5.3, 5.3 Hz, 1H), 3.41 (d, J=2.8 Hz, 2H), 3.42-3.31 (m, 2H), 2.90-2.80 (m, 1H), 2.81 (s, 3H), 2.49-2.37 (m, 3H), 2.27-2.16 (m, 1H), 1.40 (dt, J=8.0, 4.0 Hz, 2H).

Example J

Synthesis of 1-[4-[(3R)-3-hydroxy-3-(5-methylisoxazol-3-yl)but-1-ynyl]-2-pyridyl]-4,5,6,7-tetrahydroindazole-3-carboxamide

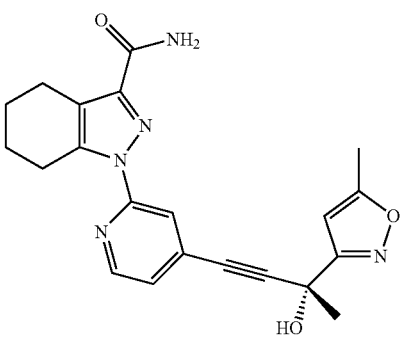 [SMILES: Cc1cc([C@](C)(O)C#Cc2ccnc(-n3nc(C(N)=O)c4c3CCCC4)c2)no1]

Similar to as described in General Procedure E, 1-(4-iodo-2-pyridyl)-4,5,6,7-tetrahydroindazole-3-carboxamide was reacted with (2R)-2-(5-methylisoxazol-3-yl)but-3-yn-2-ol to give 43 mg of the title compound (67%). M+H=392.0; 1H NMR (400 MHz, DMSO-d6) δ 8.46 (dd, J=5.1, 0.7 Hz, 1H), 8.06 (d, J=1.2 Hz, 1H), 7.77 (br s, 1H), 7.35 (dd, J=5.0, 1.4 Hz, 1H), 7.23 (br s, 1H), 6.68 (s, 1H), 6.38 (d, J=0.9 Hz, 1H), 3.11 (t, J=5.9 Hz, 2H), 2.70 (t, J=5.6 Hz, 2H), 2.41 (s, 3H), 1.82 (s, 3H), 1.79-1.62 (m, 4H).

Example K and Example L

Synthesis of (6R)-6-hydroxy-1-[4-[2-[(3R)-3-hydroxy-1-methyl-2-oxo-pyrrolidin-3-yl]ethynyl]-2-pyridyl]-4,5,6,7-tetrahydroindazole-3-carboxamide and (6S)-6-hydroxy-1-[4-[2-[(3R)-3-hydroxy-1-methyl-2-oxo-pyrrolidin-3-yl]ethynyl]-2-pyridyl]-4,5,6,7-tetrahydroindazole-3-carboxamide

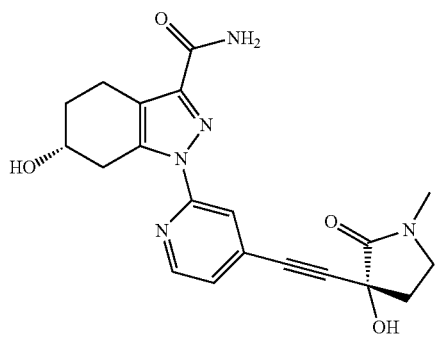

-continued

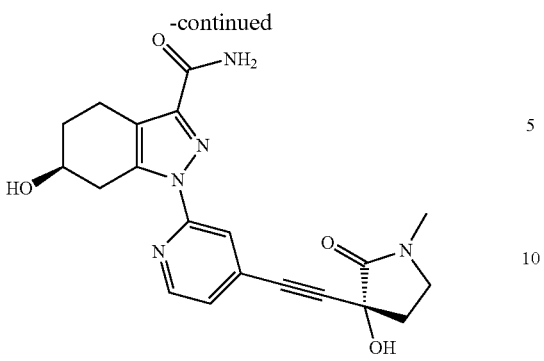

Similar to as described in General Procedure E, 6-hydroxy-1-(4-iodo-2-pyridyl)-4,5,6,7-tetrahydroindazole-3-carboxamide was reacted with (3R)-3-ethynyl-3-hydroxy-1-methyl-pyrrolidin-2-one and the enantiomers were separated by chiral SFC purification to give 7.3 mg and 7 mg each of the title compounds respectively (23%).

M+H=396.0; 1H NMR (400 MHz, DMSO-d6) δ 8.48 (d, J=4.9 Hz, 1H), 8.06 (d, J=1.3 Hz, 1H), 7.77 (br s, 1H), 7.35 (dd, J=5.1, 1.4 Hz, 1H), 7.24 (br s, 1H), 6.63 (s, 1H), 4.85 (d, J=3.9 Hz, 1H), 4.05-3.96 (m, 1H), 3.41-3.35 (m, 3H), 2.98 (dd, J=17.5, 6.3 Hz, 1H), 2.86-2.77 (m, 1H), 2.81 (s, 3H), 2.73-2.60 (m, 1H), 2.50-2.42 (m, 1H), 2.27-2.17 (m, 1H), 1.84-1.74 (m, 1H), 1.75-1.61 (m, 1H).

M+H=396.0; 1H NMR (400 MHz, DMSO-d6) δ 8.48 (d, J=4.9 Hz, 1H), 8.06 (d, J=1.2 Hz, 1H), 7.77 (br s, 1H), 7.35 (dd, J=5.0, 1.5 Hz, 1H), 7.24 (br s, 1H), 6.63 (s, 1H), 4.85 (d, J=3.9 Hz, 1H), 4.07-3.94 (m, 1H), 3.42-3.35 (m, 3H), 2.98 (dd, J=17.6, 6.4 Hz, 1H), 2.87-2.77 (m, 1H), 2.81 (s, 3H), 2.73-2.61 (m, 1H), 2.51-2.42 (m, 1H), 2.27-2.16 (m, 1H), 1.85-1.73 (m, 1H), 1.75-1.62 (m, 1H).

Example M

Synthesis of 6-fluoro-1-[4-[2-[(3R)-3-hydroxy-1-methyl-2-oxo-pyrrolidin-3-yl]ethynyl]-2-pyridyl]indazole-3-carboxamide

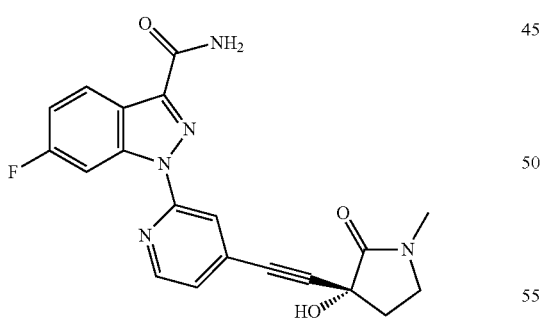

Similar to as described in General Procedure E, 6-fluoro-1-(4-iodo-2-pyridyl)indazole-3-carboxamide was reacted with (3R)-3-ethynyl-3-hydroxy-1-methyl-pyrrolidin-2-one to give 48 mg of the title compound (47%). M+H=394.0; 1H NMR (400 MHz, DMSO-d6) δ 8.65-8.60 (m, 1H), 8.51 (dd, J=10.1, 2.2 Hz, 1H), 8.34 (br s, 1H), 8.33-8.28 (m, 1H), 8.28-8.24 (m, 1H), 7.67 (br s, 1H), 7.39 (dd, J=5.0, 1.4 Hz, 1H), 7.34 (td, J=9.1, 2.2 Hz, 1H), 6.64 (br s, 1H), 3.44-3.35 (m, 2H), 2.82 (s, 3H), 2.51-2.40 (m, 1H), 2.24 (dt, J=13.7, 7.0 Hz, 1H).

Example N

Synthesis of 1-[4-[2-[(3R)-3-hydroxy-1-methyl-2-oxo-pyrrolidin-3-yl]ethynyl]-2-pyridyl]-5,5-dimethyl-6,7-dihydro-4H-indazole-3-carboxamide

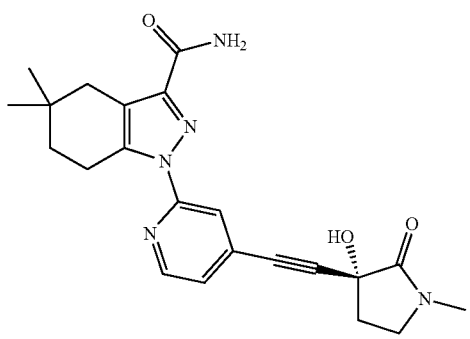

Similar to as described in General Procedure E, 1-(4-iodo-2-pyridyl)-5,5-dimethyl-6,7-dihydro-4H-indazole-3-carboxamide was reacted with (3R)-3-ethynyl-3-hydroxy-1-methyl-pyrrolidin-2-one to give 55 mg of the title compound (66%). M+H=408.0; 1H NMR (400 MHz, DMSO-d6) δ 8.47 (d, J=5.0 Hz, 1H), 8.07 (d, J=1.3 Hz, 1H), 7.77 (br s, 1H), 7.34 (dd, J=5.1, 1.3 Hz, 1H), 7.24 (br s, 1H), 6.62 (s, 1H), 3.43-3.33 (m, 2H), 3.11 (t, J=6.2 Hz, 2H), 2.81 (s, 3H), 2.52 (s, 2H), 2.49-2.43 (m, 1H), 2.29-2.16 (m, 1H), 1.55 (t, J=6.4 Hz, 2H), 0.97 (s, 6H).

Example O

Synthesis of 1-[4-[2-[(3R)-3-hydroxy-1-methyl-2-oxo-pyrrolidin-3-yl]ethynyl]-2-pyridyl]-5-methoxy-indazole-3-carboxamide

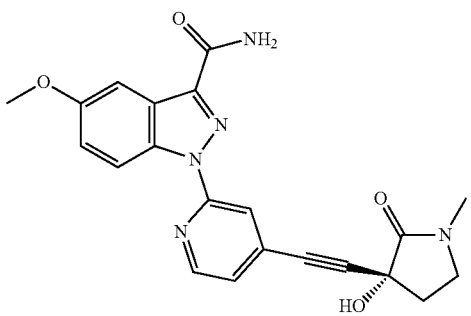

Similar to as described in General Procedure E, 1-(4-iodo-2-pyridyl)-5-methoxy-indazole-3-carboxamide was reacted with (3R)-3-ethynyl-3-hydroxy-1-methyl-pyrrolidin-2-one to give 1 mg of the title compound (1%). M+H=406.0

Example P

Synthesis of 5-bromo-1-[4-[2-[(3R)-3-hydroxy-1-methyl-2-oxo-pyrrolidin-3-yl]ethynyl]-2-pyridyl]indazole-3-carboxamide

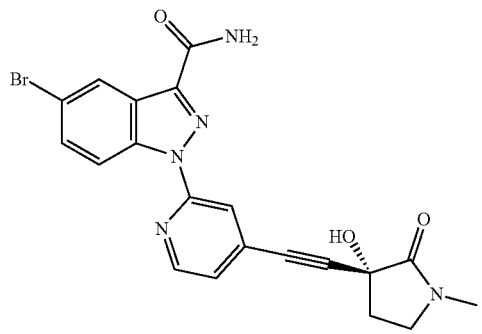 [SMILES: CN1CC[C@@](O)(C#Cc2ccnc(-n3nc(C(N)=O)c4cc(Br)ccc43)c2)C1=O]

Similar to as described in General Procedure E, 5-bromo-1-(4-iodo-2-pyridyl)indazole-3-carboxamide was reacted with (3R)-3-ethynyl-3-hydroxy-1-methyl-pyrrolidin-2-one to give 10 mg of the title compound (24%). M+H=454.0; 1H NMR (400 MHz, DMSO-d6) δ 8.73 (d, J=9.1 Hz, 1H), 8.61 (d, J=5.1 Hz, 1H), 8.44 (d, J=1.8 Hz, 1H), 8.37 (br s, 1H), 8.27 (s, 1H), 7.77 (dd, J=9.1, 2.0 Hz, 1H), 7.71 (br s, 1H), 7.44-7.36 (m, 1H), 6.65 (s, 1H), 3.39 (td, J=6.7, 5.9, 1.8 Hz, 2H), 2.82 (s, 3H), 2.49-2.44 (m, 1H), 2.24 (dt, J=13.4, 7.0 Hz, 1H).

Example Q

Synthesis of 1-[3-[(3R)-3-hydroxy-3-(5-methyl-1,3,4-oxadiazol-2-yl)but-1-ynyl]phenyl]pyrazolo[3,4-b]pyridine-3-carboxamide

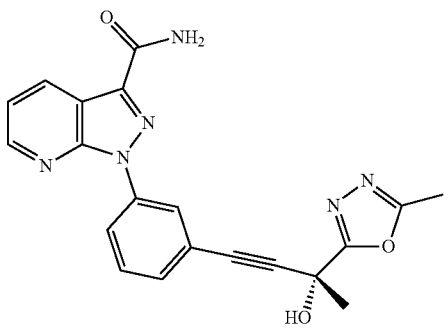 [SMILES: Cc1nnc([C@](C)(O)C#Cc2cccc(-n3nc(C(N)=O)c4cccnc43)c2)o1]

Similar to as described in General Procedure E, 1-(3-bromophenyl)pyrazolo[3,4-b]pyridine-3-carboxamide was reacted with (2R)-2-(5-methyl-1,3,4-oxadiazol-2-yl)but-3-yn-2-ol to give 19 mg of the title compound (37%). M+H=389.0; 1H NMR (400 MHz, DMSO-d6) δ 8.77 (dd, J=4.5, 1.5 Hz, 1H), 8.67 (dd, J=8.1, 1.5 Hz, 1H), 8.55-8.48 (m, 2H), 8.23 (br s, 1H), 7.70 (br s, 1H), 7.68-7.61 (m, 1H), 7.55-7.45 (m, 2H), 7.07 (s, 1H), 2.56 (s, 3H), 1.94 (s, 3H).

Example R

Synthesis of 1-[3-[2-[(3R)-3-hydroxy-1-methyl-2-oxo-pyrrolidin-3-yl]ethynyl]phenyl]-6,6-dioxo-5,7-dihydro-4H-thiopyrano[3,4-c]pyrazole-3-carboxamide

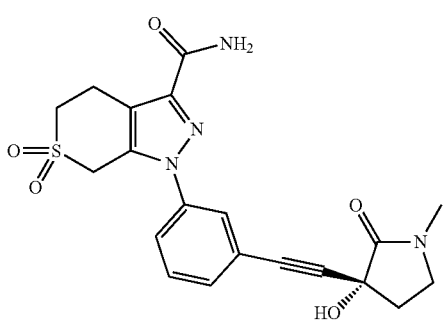 [SMILES: CN1CC[C@@](O)(C#Cc2cccc(-n3nc(C(N)=O)c4c3CS(=O)(=O)CC4)c2)C1=O]

Similar to as described in General Procedure E, 1-(3-bromophenyl)-6,6-dioxo-5,7-dihydro-4H-thiopyrano[3,4-c]pyrazole-3-carboxamide was reacted with (3R)-3-ethynyl-3-hydroxy-1-methyl-pyrrolidin-2-one to give 3 mg of the title compound (20%). M+H=429.0

Example S

Synthesis of 1-[3-[2-[(3R)-3-hydroxy-1-methyl-2-oxo-pyrrolidin-3-yl]ethynyl]phenyl]-5,7-dihydro-4H-pyrano[3,4-c]pyrazole-3-carboxamide

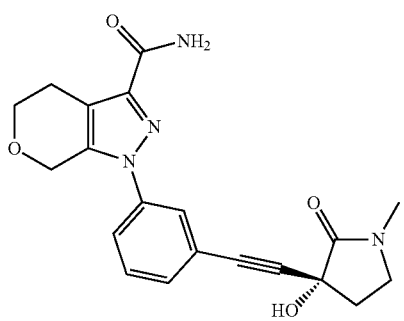

Similar to as described in General Procedure E, 1-(3-bromophenyl)-5,7-dihydro-4H-pyrano[3,4-c]pyrazole-3-carboxamide was reacted with (3R)-3-ethynyl-3-hydroxy-1-methyl-pyrrolidin-2-one to give 6 mg of the title compound (24%). M+H=381.0; 1H NMR (400 MHz, DMSO-d6) δ 7.70-7.67 (m, 1H), 7.63 (br s, 1H), 7.57-7.49 (m, 2H), 7.48-7.41 (m, 1H), 7.27 (br s, 1H), 6.49 (br s, 1H), 4.88 (s, 2H), 3.83 (t, J=5.6 Hz, 2H), 3.35 (td, J=6.3, 5.5, 4.2 Hz, 2H), 2.87-2.74 (m, 5H), 2.48-2.39 (m, 1H), 2.19 (dt, J=12.8, 7.1 Hz, 1H).

Example T

Synthesis of 1-[3-[2-[(3R)-3-hydroxy-1-methyl-2-oxo-pyrrolidin-3-yl]ethynyl]phenyl]-6,7-dihydro-4H-pyrano[4,3-c]pyrazole-3-carboxamide

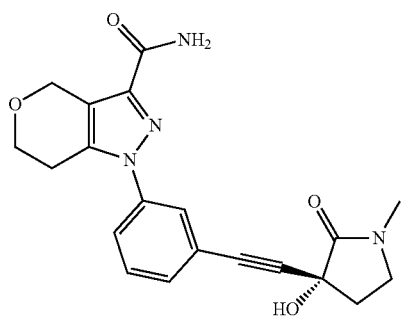 [SMILES: CN1CC[C@@](O)(C#Cc2cccc(-n3nc(C(N)=O)c4c3CCOC4)c2)C1=O]

Similar to as described in General Procedure E, 1-(3-bromophenyl)-6,7-dihydro-4H-pyrano[4,3-c]pyrazole-3-carboxamide was reacted with (3R)-3-ethynyl-3-hydroxy-1-methyl-pyrrolidin-2-one to give 32 mg of the title compound (38%). M+H=381.0; 1H NMR (400 MHz, DMSO-d6) δ 7.75-7.72 (m, 1H), 7.72-7.61 (m, 2H), 7.56 (t, J=7.9 Hz, 1H), 7.50-7.43 (m, 1H), 7.31 (br s, 1H), 6.48 (s, 1H), 4.76 (s, 2H), 3.81 (t, J=5.4 Hz, 2H), 3.40-3.33 (m, 2H), 2.91 (t, J=5.4 Hz, 2H), 2.80 (s, 3H), 2.44 (ddd, J=12.8, 6.6, 5.0 Hz, 1H), 2.19 (dt, J=12.9, 7.1 Hz, 1H).

Example U

Synthesis of 6-fluoro-1-[4-[2-[(3R)-3-hydroxy-2-oxo-pyrrolidin-3-yl]ethynyl]-2-pyridyl]indazole-3-carboxamide

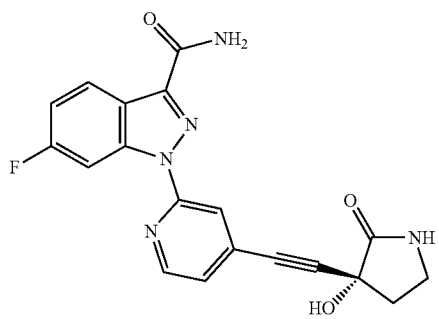 [SMILES: NC(=O)c1nn(-c2cc(C#C[C@]3(O)CCNC3=O)ccn2)c2cc(F)ccc12]

Similar to as described in General Procedure E, 6-fluoro-1-(4-iodo-2-pyridyl)indazole-3-carboxamide was reacted with (3R)-3-ethynyl-3-hydroxy-pyrrolidin-2-one to give 18 mg of the title compound (30%). M+H=380.0; 1H NMR (400 MHz, DMSO-d6) δ 8.62 (d, J=5.1 Hz, 1H), 8.51 (dd, J=10.4, 2.4 Hz, 1H), 8.40-8.29 (m, 2H), 8.26 (s, 1H), 8.09 (br s, 1H), 7.66 (brs, 1H), 7.40 (dd, J=5.1, 1.1 Hz, 1H), 7.33 (ddd, J=9.1, 9.1, 2.5 Hz, 1H), 6.53 (s, 1H), 3.28-3.18 (m, 2H), 2.55-2.51 (m, 1H), 2.27 (dt, J=13.4, 7.2 Hz, 1H).

Example V

Synthesis of 6-fluoro-1-[4-[2-[(7R)-7-hydroxy-5,6-dihydrocyclopenta[b]pyridin-7-yl]ethynyl]-2-pyridyl]indazole-3-carboxamide

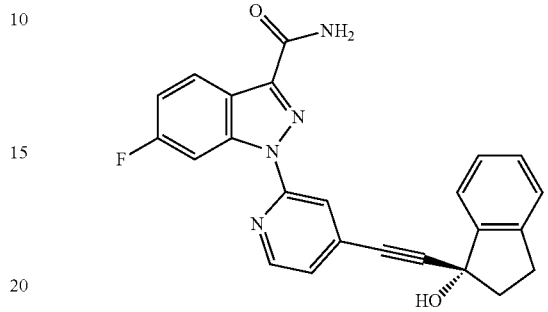

Similar to as described in General Procedure E, 6-fluoro-1-(4-iodo-2-pyridyl)indazole-3-carboxamide was reacted with (7R)-7-ethynyl-5,6-dihydrocyclopenta[b]pyridin-7-ol to give 41 mg of the title compound (63%). M+H=414.0; 1H NMR (400 MHz, DMSO-d6) δ 8.60 (d, J=5.3 Hz, 1H), 8.51 (dd, J=10.2, 2.4 Hz, 1H), 8.48 (dd, J=5.0, 1.5 Hz, 1H), 8.36-8.29 (m, 2H), 8.24 (d, J=1.2 Hz, 1H), 7.76 (dd, J=7.9, 1.4 Hz, 1H), 7.65 (br s, 1H), 7.37 (dd, J=5.0, 1.5 Hz, 1H), 7.36-7.29 (m, 2H), 6.37 (br s, 1H), 3.13-3.00 (m, 1H), 2.95 (ddd, J=16.2, 8.2, 4.6 Hz, 1H), 2.62 (ddd, J=13.1, 8.3, 6.6 Hz, 1H), 2.44 (ddd, J=12.9, 7.8, 4.6 Hz, 1H).

Example W

Synthesis of 1-[3-[2-[(3R)-3-hydroxy-1-methyl-2-oxo-pyrrolidin-3-yl]ethynyl]-5-methoxy-phenyl]pyrazolo[3,4-b]pyridine-3-carboxamide

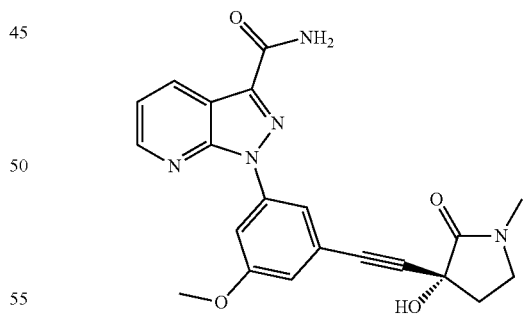

Similar to as described in General Procedure E, 1-(3-bromo-5-methoxy-phenyl)pyrazolo[3,4-b]pyridine-3-carboxamide was reacted with (3R)-3-ethynyl-3-hydroxy-1-methyl-pyrrolidin-2-one to give 93 mg of the title compound (54%). M+H=406.0; 1H NMR (400 MHz, DMSO-d6) δ 8.78 (dd, J=4.5, 1.6 Hz, 1H), 8.66 (dd, J=8.0, 1.3 Hz, 1H), 8.26 (s, 1H), 8.21-8.16 (m, 1H), 8.13-8.10 (m, 1H), 7.69 (br s, 1H), 7.51 (dd, J=8.1, 4.6 Hz, 1H), 7.03-6.95 (m, 1H), 6.50 (s, 1H), 3.90 (s, 3H), 3.37 (t, J=6.4 Hz, 2H), 2.82 (s, 3H), 2.48-2.42 (m, 1H), 2.21 (dt, J=13.5, 7.0 Hz, 1H).

Example X

Synthesis of 1-[3-[2-[(3R)-3-hydroxy-1-methyl-2-oxo-pyrrolidin-3-yl]ethynyl]phenyl]-5-methoxy-pyrazolo[3,4-b]pyridine-3-carboxamide

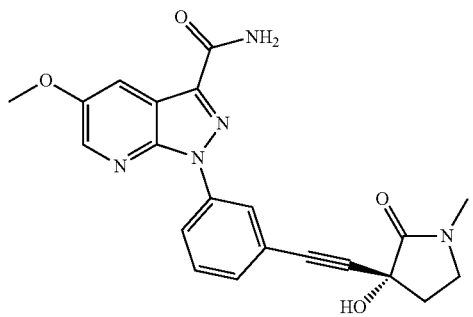

Similar to as described in General Procedure E, 1-(3-bromophenyl)-5-methoxy-pyrazolo[3,4-b]pyridine-3-carboxamide was reacted with (3R)-3-ethynyl-3-hydroxy-1-methyl-pyrrolidin-2-one to give 18 mg of the title compound (44%). M+H=406.0; 1H NMR (400 MHz, DMSO-d6) δ 8.53 (d, J=3.0 Hz, 1H), 8.48-8.46 (m, 1H), 8.46-8.41 (m, 1H), 8.16 (br s, 1H), 8.02 (d, J=2.8 Hz, 1H), 7.65 (br s, 1H), 7.64-7.59 (m, 1H), 7.46-7.41 (m, 1H), 6.51 (br s, 1H), 3.94 (s, 3H), 3.41-3.34 (m, 2H), 2.81 (s, 3H), 2.50-2.41 (m, 1H), 2.27-2.16 (m, 1H).

Example Y

Synthesis of 5-fluoro-1-[3-[2-[(3R)-3-hydroxy-1-methyl-2-oxo-pyrrolidin-3-yl]ethynyl]phenyl]pyrazolo[3,4-b]pyridine-3-carboxamide

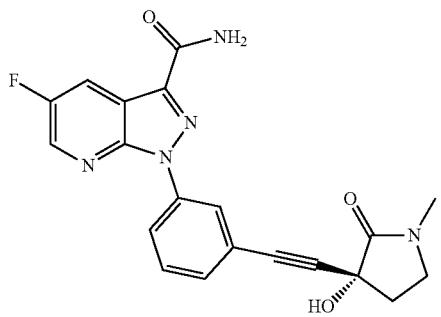 [SMILES: CN1CC[C@@](O)(C#Cc2cccc(-n3nc(C(N)=O)c4cc(F)cnc43)c2)C1=O]

Similar to as described in General Procedure E, 1-(3-bromophenyl)-5-fluoro-pyrazolo[3,4-b]pyridine-3-carboxamide was reacted with (3R)-3-ethynyl-3-hydroxy-1-methyl-pyrrolidin-2-one to give 12 mg of the title compound (31%). M+H=394.0; 1H NMR (400 MHz, DMSO-d6) δ 8.84 (dd, J=2.9, 1.5 Hz, 1H), 8.44-8.36 (m, 3H), 8.26 (br s, 1H), 7.74 (br s, 1H), 7.64 (dd, J=7.9, 7.9 Hz, 1H), 7.51-7.42 (m, 1H), 6.53 (s, 1H), 3.42-3.34 (m, 2H), 2.81 (s, 3H), 2.49-2.41 (m, 1H), 2.21 (dt, J=13.0, 7.1 Hz, 1H).

Example Z

Synthesis of 6-chloro-1-[3-[2-[(3R)-3-hydroxy-1-methyl-2-oxo-pyrrolidin-3-yl]ethynyl]phenyl]pyrazolo[4,3-c]pyridine-3-carboxamide

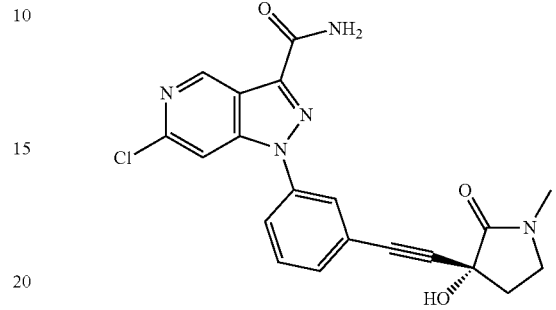

Similar to as described in General Procedure E, 1-(3-bromophenyl)-6-chloro-pyrazolo[4,3-c]pyridine-3-carboxamide was reacted with (3R)-3-ethynyl-3-hydroxy-1-methyl-pyrrolidin-2-one to give 26 mg of the title compound (45%). M+H=410.0; 1H NMR (400 MHz, DMSO-d6) δ 9.30 (s, 1H), 8.27 (br s, 1H), 8.00 (d, J=0.8 Hz, 1H), 7.97-7.89 (m, 2H), 7.81 (br s, 1H), 7.65 (dd, J=7.9, 7.9 Hz, 1H), 7.58-7.52 (m, 1H), 6.51 (br s, 1H), 3.41-3.33 (m, 2H), 2.81 (s, 3H), 2.48-2.41 (m, 1H), 2.20 (dt, J=12.5, 7.0 Hz, 1H).

Example AA

Synthesis of 1-[3-[2-[(3R)-3-hydroxy-1-methyl-2-oxo-pyrrolidin-3-yl]ethynyl]phenyl]-6-methoxy-pyrazolo[4,3-c]pyridine-3-carboxamide

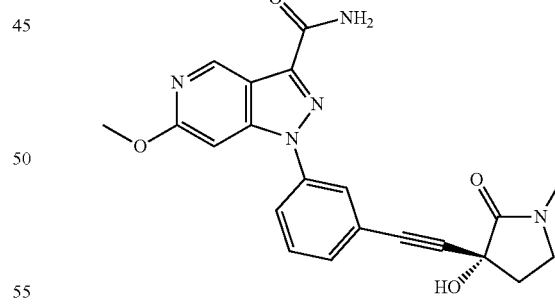

Similar to as described in General Procedure E, 1-(3-bromophenyl)-6-methoxy-pyrazolo[4,3-c]pyridine-3-carboxamide was reacted with (3R)-3-ethynyl-3-hydroxy-1-methyl-pyrrolidin-2-one to give 13 mg of the title compound (22%). M+H=406.2; 1H NMR (400 MHz, DMSO-d6) δ 9.15 (s, 1H), 8.15 (br s, 1H), 7.95-7.84 (m, 2H), 7.70 (br s, 1H), 7.63 (dd, J=7.9, 7.9 Hz, 1H), 7.50 (d, J=7.8 Hz, 1H), 7.10 (s, 1H), 6.50 (br s, 1H), 3.98 (s, 3H), 3.42-3.31 (m, 2H), 2.80 (s, 3H), 2.50-2.41 (m, 1H), 2.20 (dt, J=13.3, 7.1 Hz, 1H).

Example BB

Synthesis of 5-cyclopropyl-1-[3-[2-[(3R)-3-hydroxy-1-methyl-2-oxo-pyrrolidin-3-yl]ethynyl]phenyl]pyrazolo[3,4-b]pyridine-3-carboxamide

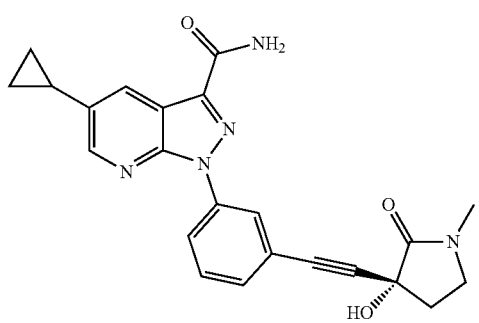 [SMILES: CN1CC[C@@](O)(C#Cc2cccc(-n3nc(C(N)=O)c4cc(C5CC5)cnc43)c2)C1=O]

Similar to as described in General Procedure E, 1-(3-bromophenyl)-5-cyclopropyl-pyrazolo[3,4-b]pyridine-3-carboxamide was reacted with (3R)-3-ethynyl-3-hydroxy-1-methyl-pyrrolidin-2-one to give 9 mg of the title compound (37%). M+H=416.0; 1H NMR (400 MHz, DMSO-d6) δ 8.62 (d, J=2.3 Hz, 1H), 8.50-8.48 (m, 1H), 8.47-8.43 (m, 1H), 8.24 (d, J=2.1 Hz, 1H), 8.18 (br s, 1H), 7.67 (br s, 1H), 7.64-7.57 (m, 1H), 7.48-7.39 (m, 1H), 6.52 (s, 1H), 3.44-3.33 (m, 2H), 2.82 (s, 3H), 2.49-2.41 (m, 1H), 2.28-2.14 (m, 2H), 1.15-1.02 (m, 2H), 0.87-0.77 (m, 2H).

Example CC

Synthesis of 1-(3-chloro-5-[2-[(3R)-3-hydroxy-1-methyl-2-oxopyrrolidin-3-yl]ethynyl]phenyl)-1H-pyrazolo[3,4-b]pyridine-3-carboxamide Step 1: Synthesis of 2-(3-bromo-5-chlorophenyl)-4,4,5,5-tetramethyl-1,3,2-dioxaborolane

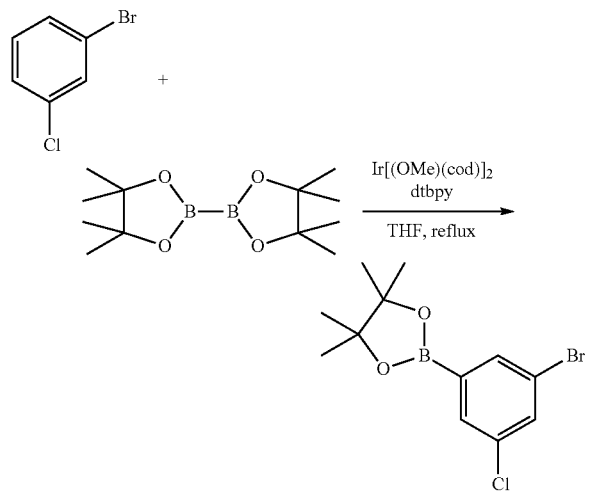

To a stirred solution of 1-bromo-3-chlorobenzene (1.0 g, 5.22 mmol, 1.00 equiv) in tetrahydrofuran (5 mL), was added 4,4,5,5-tetramethyl-2-(tetramethyl-1,3,2-dioxaborolan-2-yl)-1,3,2-dioxaborolane (800 mg, 3.15 mmol, 0.60 equiv), 4-tert-butyl-2-(4-tert-butylpyridin-2-yl)pyridine (43 mg, 0.16 mmol, 0.03 equiv), bis((1Z,5Z)-cycloocta-1,5-diene) dimethyl-2,4-dioxa-1,3-diiridabicyclo[1.1.0]butane-2,4-diium-1,3-diuide (33 mg, 0.05 mmol, 0.01 equiv) under nitrogen. The mixture was stirred for overnight at 80° C. The solid was filtered out and the filtrate was concentrated under vacuum. Crude product was purified by a silica gel column with ethyl acetate/petroleum ether (1:10) to give 1.29 g (78%) of the title compound as colorless oil.

Step 2: Synthesis of methyl 1-(3-bromo-5-chlorophenyl)-1H-pyrazolo[3,4-b]pyridine-3-carboxylate

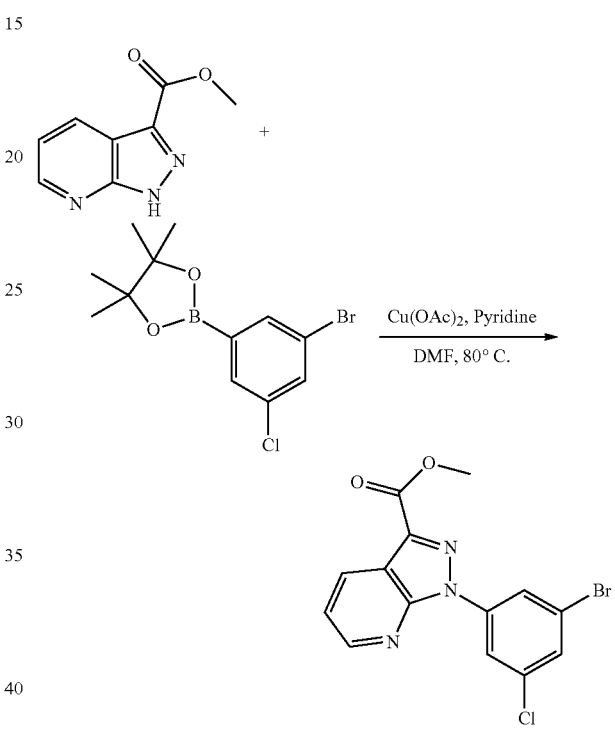

Similar to as described in General Procedure C, methyl 1H-pyrazolo[3,4-b]pyridine-3-carboxylate was reacted with 2-(3-bromo-5-chlorophenyl)-4,4,5,5-tetramethyl-1,3,2-dioxaborolane to give the title compound (110 mg, 19%) as a white solid. LC-MS (ES, m/z): 366, 368 [M+1]⁺, 407, 409 [M+CH₃CN+H]⁺.

Step 3: Synthesis of methyl 1-(3-chloro-5-[2-[(3R)-3-hydroxy-1-methyl-2-oxopyrrolidin-3-yl]ethynyl]phenyl)-1H-pyrazolo[3,4-b]pyridine-3-carboxylate

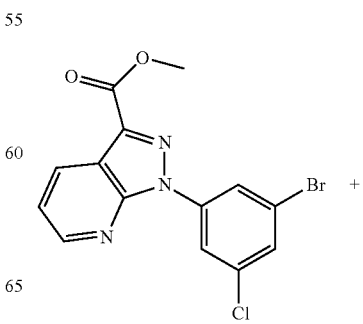

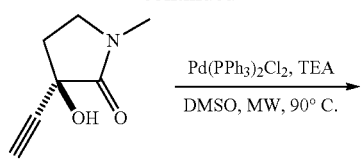

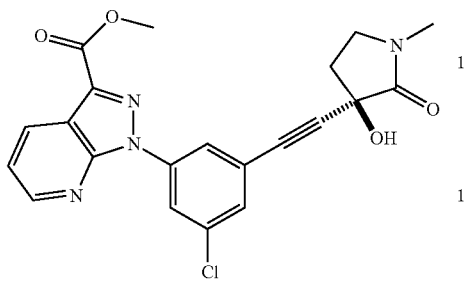

Similar to as described in General Procedure E, methyl 1-(3-bromo-5-chlorophenyl)-1H-pyrazolo[3,4-b]pyridine-3-carboxylate was reacted with (3R)-3-ethynyl-3-hydroxy-1-methylpyrrolidin-2-one to give the title compound (150 mg crude product mixed with PPh$_3$O) as an off-white solid. LC-MS (ES, m/z): 425 [M+1]$^+$.

Step 4: Synthesis of 1-(3-chloro-5-[2-[(3R)-3-hydroxy-1-methyl-2-oxopyrrolidin-3-yl]ethynyl]phenyl)-1H-pyrazolo[3,4-b]pyridine-3-carboxamide

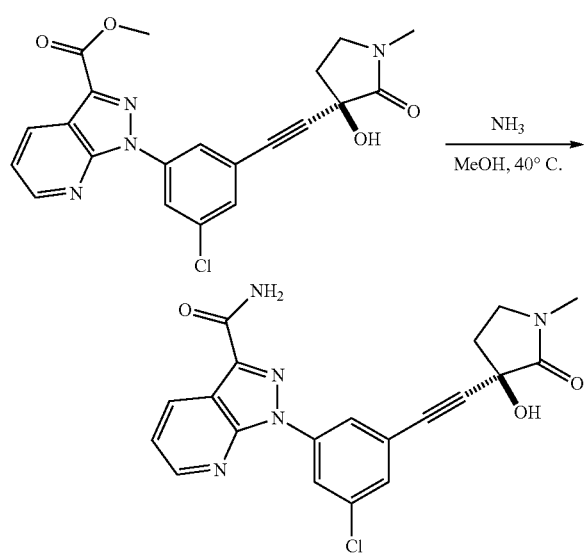

Similar to as described in General Procedure S, methyl 1-(3-chloro-5-[2-[(3R)-3-hydroxy-1-methyl-2-oxopyrrolidin-3-yl]ethynyl]phenyl)-1H-pyrazolo[3,4-b]pyridine-3-carboxylate was reacted with ammonia in methanol to give the title compound (19 mg, 13%) as a white solid. LC-MS: (ES, m/z): 410 [M+1]$^+$. $^1$H NMR (300 MHz, CD$_3$OD) δ 8.77-8.72 (m, 2H), 8.66-8.62 (m, 2H), 7.53-7.49 (m, 2H), 3.56-3.49 (m, 2H), 2.97 (s, 3H), 2.69-2.61 (m, 1H), 2.41-2.31 (m, 1H).

Example DD

Synthesis of 1-[3-[(3R)-3-hydroxy-3-(pyrimidin-2-yl)but-1-yn-1-yl]phenyl]-1H-indazole-3-carboxamide Step 1: Synthesis of methyl 1-[3-[(3R)-3-hydroxy-3-(pyrimidin-2-yl)but-1-yn-1-yl]phenyl]-1H-indazole-3-carboxylate

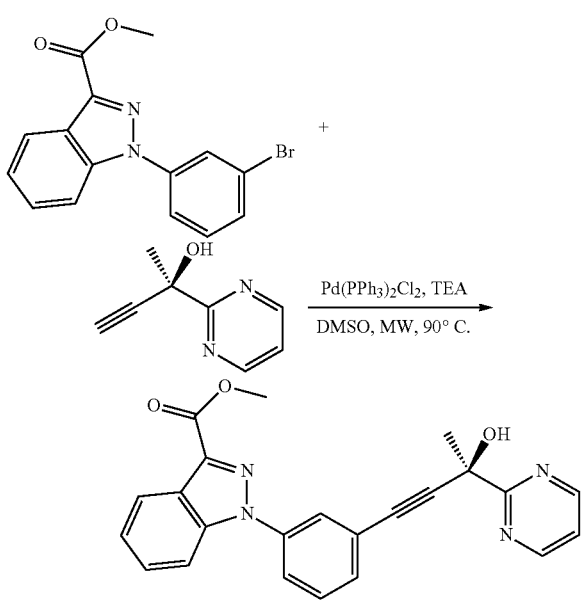

Similar to as described in General Procedure E, methyl 1-(3-bromophenyl)-1H-indazole-3-carboxylate was reacted with (2R)-2-(pyrimidin-2-yl)but-3-yn-2-ol to give the title compound (100 mg, 31%) as yellowish oil. LC-MS (ES, m/z): 399 [M+H]$^+$.

Step 2: Synthesis of 1-[3-[(3R)-3-hydroxy-3-(pyrimidin-2-yl)but-1-yn-1-yl]phenyl]-1H-indazole-3-carboxamide

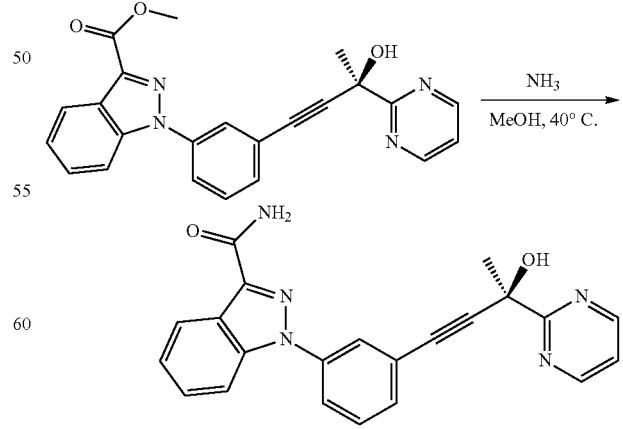

Similar to as described in General Procedure S, methyl 1-[3-[(3R)-3-hydroxy-3-(pyrimidin-2-yl)but-1-yn-1-yl]phenyl]-1H-indazole-3-carboxylate was reacted with ammonia in methanol to give the title compound (34.3 mg, 35%) as a white solid. LC-MS (ES, m/z): 384 [M+H]+. $^1$H NMR (300 MHz, DMSO-d6) δ 8.89 (d, J=5.1 Hz, 2H), 8.31 (d, J=8.1 Hz, 1H), 8.02 (s, 1H), 7.92-7.84 (m, 3H), 7.65-7.47 (m, 5H), 7.46-7.37 (m, 1H), 6.26 (s, 1H), 1.89 (s, 3H).

Example EE

Synthesis of 6-fluoro-1-(3-[2-[(3R)-3-hydroxy-1-methyl-2-oxopiperidin-3-yl]ethynyl]phenyl)-1H-indazole-3-carboxamide Step 1: Synthesis of methyl 6-fluoro-1H-indazole-3-carboxylate

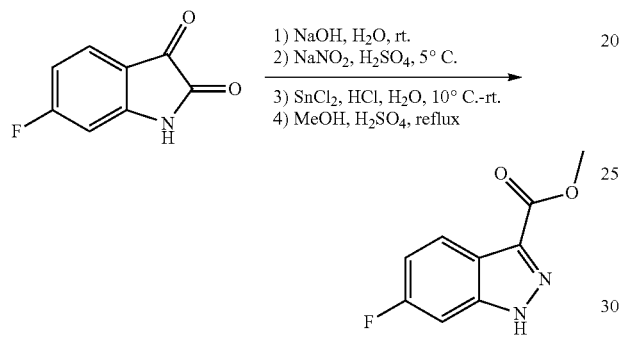

Similar to as described in General Procedure Z, 6-fluoro-2,3-dihydro-1H-indole-2,3-dione was converted to the title compound as a yellow solid (1 g, 15%). LC-MS (ES, m/z): 195 [M+H]+.

Step 2: Synthesis of methyl 1-(3-bromophenyl)-6-fluoro-1H-indazole-3-carboxylate

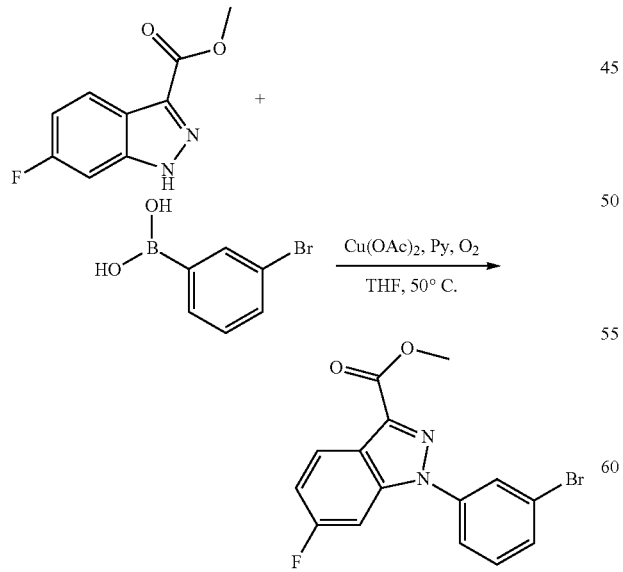

Similar to as described in General Procedure C, methyl 6-fluoro-1H-indazole-3-carboxylate was reacted with (3-bromophenyl)boronic acid to give the title compound (600 mg, 83%) as a yellow solid. LC-MS (ES, m/z): 349, 351 [M+H]+.

Step 3: Synthesis of methyl 6-fluoro-1-(3-[2-[(3R)-3-hydroxy-1-methyl-2-oxopiperidin-3-yl]ethynyl]phenyl)-1H-indazole-3-carboxylate

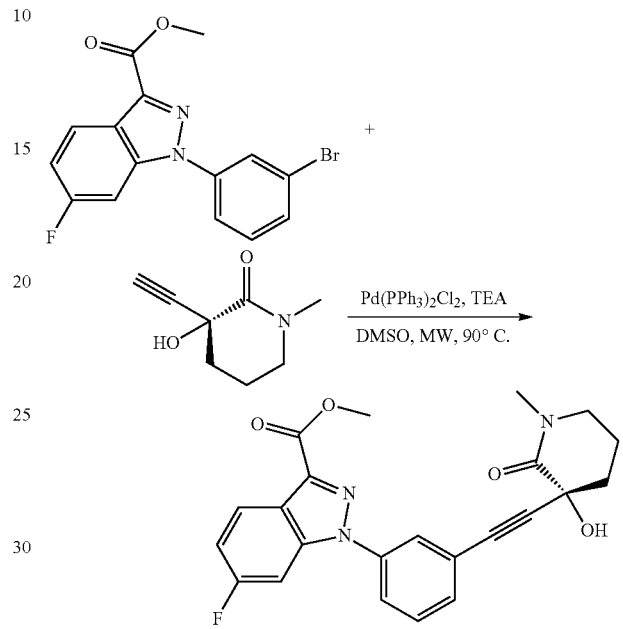

Similar to as described in General Procedure E, methyl 1-(3-bromophenyl)-6-fluoro-1H-indazole-3-carboxylate was reacted with (3R)-3-ethynyl-3-hydroxy-1-methylpiperidin-2-one to give the title compound (200 mg, 75%) as a yellow oil. LC-MS (ES, m/z): 422 [M+H]+.

Step 4: Synthesis of 6-fluoro-1-(3-[2-[(3R)-3-hydroxy-1-methyl-2-oxopiperidin-3-yl]ethynyl]phenyl)-1H-indazole-3-carboxamide

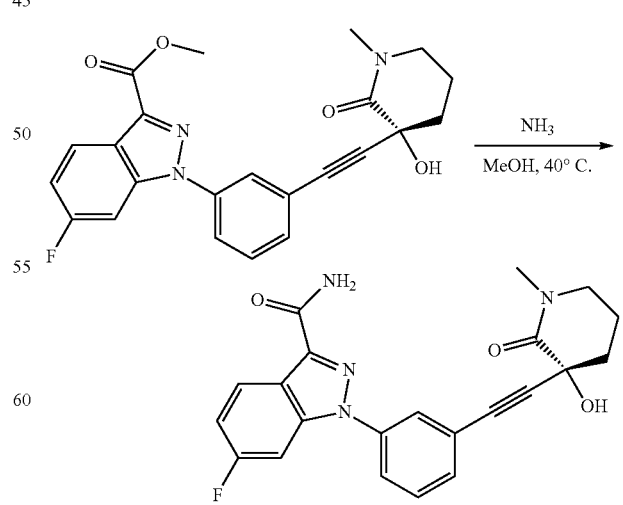

Similar to as described in General Procedure S, methyl 6-fluoro-1-(3-[2-[(3R)-3-hydroxy-1-methyl-2-oxopiperidin- 3-yl]ethynyl]phenyl)-1H-indazole-3-carboxylate was reacted with ammonia in methanol to give the title compound (30.9 mg, 31%) as a white solid. LC-MS (ES, m/z): 407 [M+H]⁺. ¹H NMR (300 MHz, DMSO-d6) δ 8.33-8.28 (m, 1H), 8.08 (s, 1H), 7.92-7.87 (m, 2H), 7.72-7.60 (m, 3H), 7.51 (d, J=8.1 Hz, 1H), 7.32-7.25 (m, 1H), 6.18 (s, 1H), 3.36-3.31 (m, 2H), 2.86 (s, 3H), 2.21-2.16 (m, 1H), 2.04-1.92 (m, 3H).

Example FF

Synthesis of 1-(3-fluoro-5-[2-[(3R)-3-hydroxy-1-methyl-2-oxopyrrolidin-3-yl]ethynyl]phenyl)-1H-pyrazolo[3,4-b]pyridine-3-carboxamide Step 1: Synthesis of (3-bromo-5-fluorophenyl)boronic acid

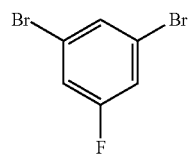

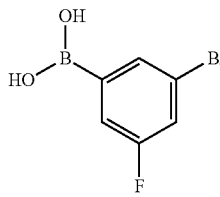

To a stirred solution of 1,3-dibromo-5-fluorobenzene (1 g, 3.94 mmol, 1.00 equiv) in tetrahydrofuran (20 mL) under nitrogen was added n-butyl lithium (1.58 mL, 2.5 M) dropwise with stirring at −78° C. One hour later triisopropyl borate (1.1 g, 1.50 equiv) was added to the stirred mixture slowly and the reaction was kept for overnight at room temperature. The resulting mixture was washed with 10 mL of diluted hydrochloric acid and the solid was collected by filtration to give 120 mg (14%) of the title compound as a yellow solid. LC-MS (ES, m/z): 217, 219 [M−H]⁺.

Step 2: Synthesis of methyl 1-(3-bromo-5-fluorophenyl)-1H-pyrazolo[3,4-b]pyridine-3-carboxylate

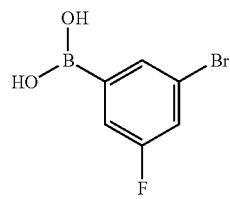

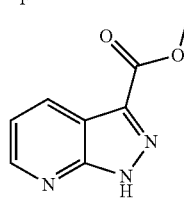

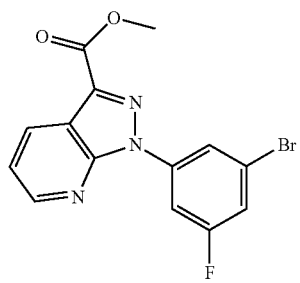

Similar to as described in General Procedure C, methyl 1H-pyrazolo[3,4-b]pyridine-3-carboxylate was reacted with (3-bromo-5-fluorophenyl)boronic acid to give the title compound (100 mg, 31%) as a white solid. LC-MS (ES, m/z): 350, 352 [M+H]⁺.

Step 3: Synthesis of methyl 1-(3-fluoro-5-[2-[(3R)-3-hydroxy-1-methyl-2-oxopyrrolidin-3-yl]ethynyl]phenyl)-1H-pyrazolo[3,4-b]pyridine-3-carboxylate

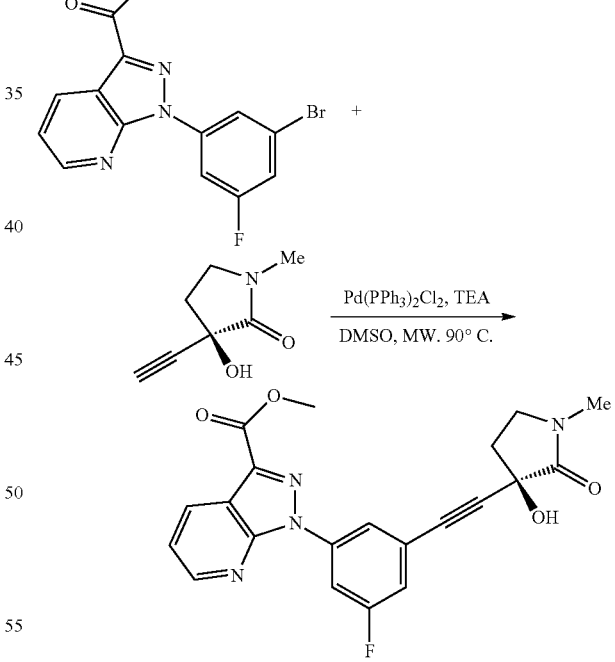

Similar to as described in General Procedure E, methyl 1-(3-bromo-5-fluorophenyl)-1H-pyrazolo[3,4-b]pyridine-3-carboxylate was reacted with (3R)-3-ethynyl-3-hydroxy-1-methylpyrrolidin-2-one to give the title compound (80 mg, 76%) as a white solid. LC-MS (ES, m/z): 409 [M+H]⁺.

Step 4: Synthesis of 1-(3-fluoro-5-[2-[(3R)-3-hydroxy-1-methyl-2-oxopyrrolidin-3-yl]ethynyl]phenyl)-1H-pyrazolo[3,4-b]pyridine-3-carboxamide

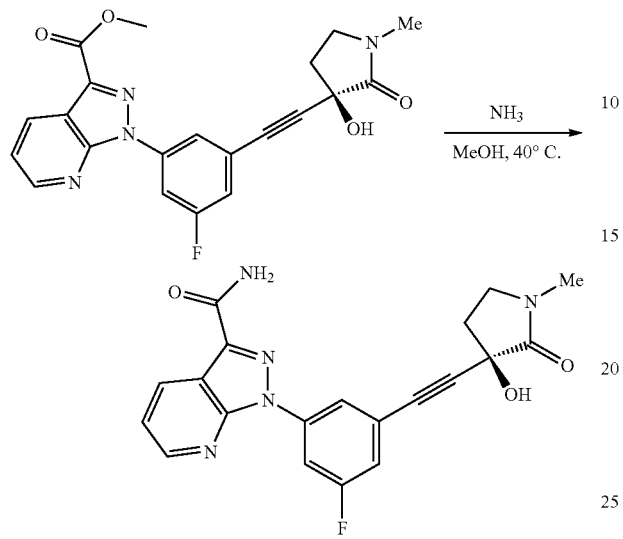

Similar to as described in General Procedure S, methyl 1-(3-fluoro-5-[2-[(3R)-3-hydroxy-1-methyl-2-oxopyrrolidin-3-yl]ethynyl]phenyl)-1H-pyrazolo[3,4-b]pyridine-3-carboxylate was reacted with ammonia in methanol to give the title compound as a white solid. LC-MS (ES, m/z): 394 [M+H]+. 1H NMR (CD3OD) δ 8.38 (d, J=5.2 Hz, 1H), 8.15 (d, J=1.6 Hz, 1H), 7.45 (d, J=8.4 Hz, 1H), 7.27 (J=8.4, 1.6 Hz, 1H), 7.08 (s, 1H), 6.97 (d, J=5.2 Hz, 1H), 6.44 (s, 1H), 6.38 (s, 1H), 4.67-4.62 (m, 2H), 2.41 (s, 3H), 1.81 (s, 3H), 1.45 (t, J=7.2 Hz, 3H).

Example GG

Synthesis of 1-(4-fluoro-3-[2-[(3R)-3-hydroxy-1-methyl-2-oxopyrrolidin-3-yl]ethynyl]phenyl)-1H-pyrazolo[3,4-b]pyridine-3-carboxamide Step 1: Synthesis of methyl 1H-pyrazolo[3,4-b]pyridine-3-carboxylate

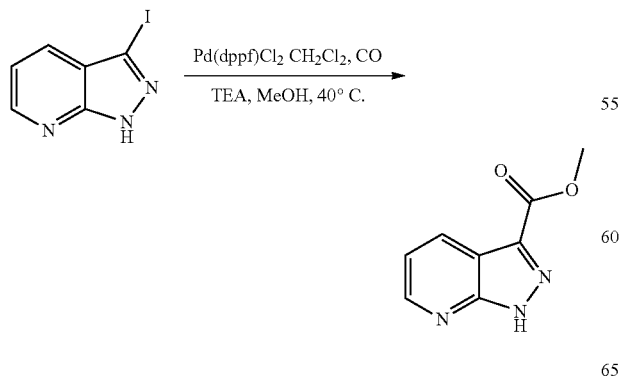

Similar to as described in General Procedure O, 3-iodo-1H-pyrazolo[3,4-b]pyridine was reacted with carbon monoxide to give the title compound (418 mg, 62%) as a white solid. LC-MS (ES, m/z): 178 [M+H]+.

Step 2: Synthesis of methyl 1-(3-bromo-4-fluorophenyl)-1H-pyrazolo[3,4-b]pyridine-3-carboxylate

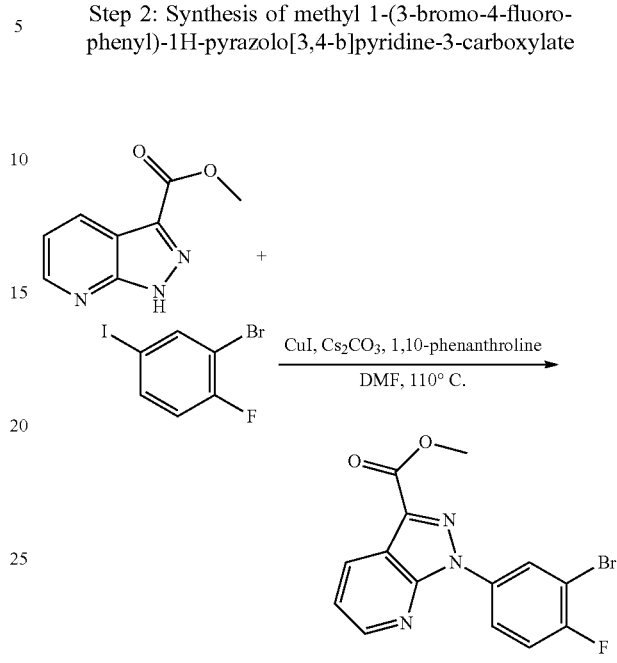

To a stirred solution of methyl 1H-pyrazolo[3,4-b]pyridine-3-carboxylate (200.00 mg, 1.13 mmol, 1.00 equiv) in N,N-dimethylformamide (10 ml, 121.20 equiv) was added 2-bromo-1-fluoro-4-iodobenzene (407.62 mg, 1.35 mmol, 1.20 equiv), copper(I) iodide (21.50 mg, 0.11 mmol, 0.10 equiv), cesium carbonate (735.65 mg, 2.26 mmol, 2.00 equiv) and 1,10-phenanthroline (40.69 mg, 0.23 mmol, 0.20 equiv). The resulting solution was stirred for 10 hours at 110° C., diluted with ethyl acetate, washed with water, extracted with ethyl acetate, dried over sodium sulfate, and concentrated under vacuum. The crude product was purified by a silica gel column with ethyl acetate/petroleum ether (1:4) to give 20 mg (30%) of the title compound as a white solid. LC-MS (ES, m/z): 350, 352 [M+H]+.

Step 3: Synthesis of methyl 1-(4-fluoro-3-[2-[(3R)-3-hydroxy-1-methyl-2-oxopyrrolidin-3-yl]ethynyl]phenyl)-1H-pyrazolo[3,4-b]pyridine-3-carboxylate

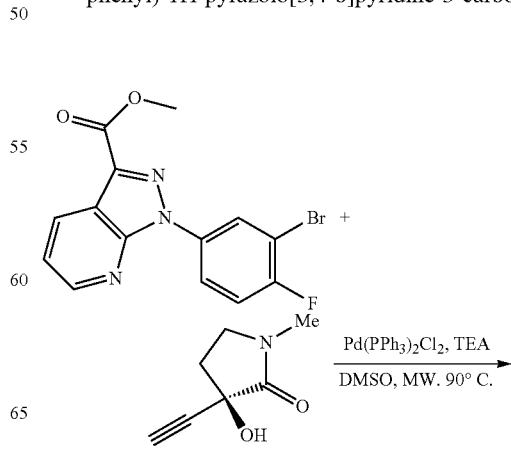

239

-continued

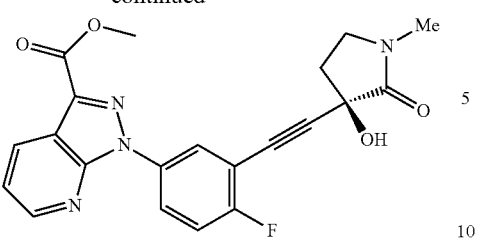

Similar to as described in General Procedure E, methyl 1-(3-bromo-4-fluorophenyl)-1H-pyrazolo[3,4-b]pyridine-3-carboxylate was reacted with (3R)-3-ethynyl-3-hydroxy-1-methylpyrrolidin-2-one to give the title compound (80 mg, 57%) as a white solid. LC-MS (ES, m/z): 409 [M+H]+.

Step 4: Synthesis of 1-(4-fluoro-3-[2-[(3R)-3-hydroxy-1-methyl-2-oxopyrrolidin-3-yl]ethynyl]phenyl)-1H-pyrazolo[3,4-b]pyridine-3-carboxamide

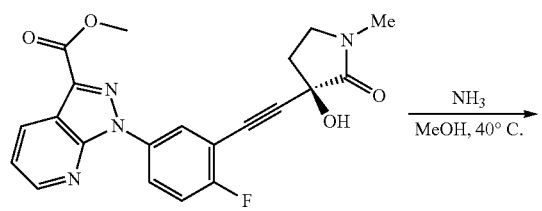

Similar to as described in General Procedure S, methyl 1-(4-fluoro-3-[2-[(3R)-3-hydroxy-1-methyl-2-oxopyrrolidin-3-yl]ethynyl]phenyl)-1H-pyrazolo[3,4-b]pyridine-3-carboxylate was reacted with ammonia in methanol to give the title compound (13.6 mg, 18%) as a white solid. LC-MS (ES, m/z): 394 [M+H]+. $^1$H NMR (CD$_3$OD) δ 8.60 (d, J=6.0 Hz, 2H), 8.49-8.46 (m, 1H), 8.38-8.33 (m, 1H), 7.38-7.34 (m, 1H), 7.24 (t, J=9.0 Hz, 1H), 3.46-3.38 (m, 2H), 2.85 (s, 1H), 2.57-2.49 (m, 1H), 2.29-2.20 (m, 1H).

240

Example HH

Synthesis of 4,4-difluoro-1-(3-[2-[(3R)-3-hydroxy-1-methyl-2-oxopyrrolidin-3-yl]ethynyl]phenyl)-4,5,6,7-tetrahydro-1H-indazole-3-carboxamide Step 1: Synthesis of ethyl 1-(3-bromophenyl)-4,4-difluoro-4,5,6,7-tetrahydro-1H-indazole-3-carboxylate

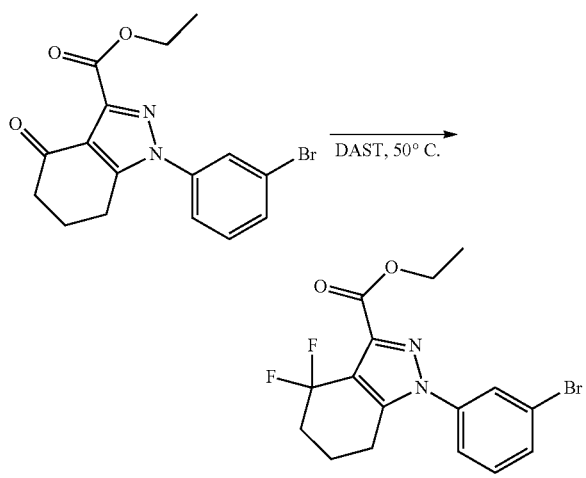

Similar to as described in General Procedure L, ethyl 1-(3-bromophenyl)-4-oxo-4,5,6,7-tetrahydro-1H-indazole-3-carboxylate was reacted with DAST to give the title compound (110 mg, 80%) as a red oil. LC-MS (ES, m/z): 385, 387 [M+1]+;

Step 2

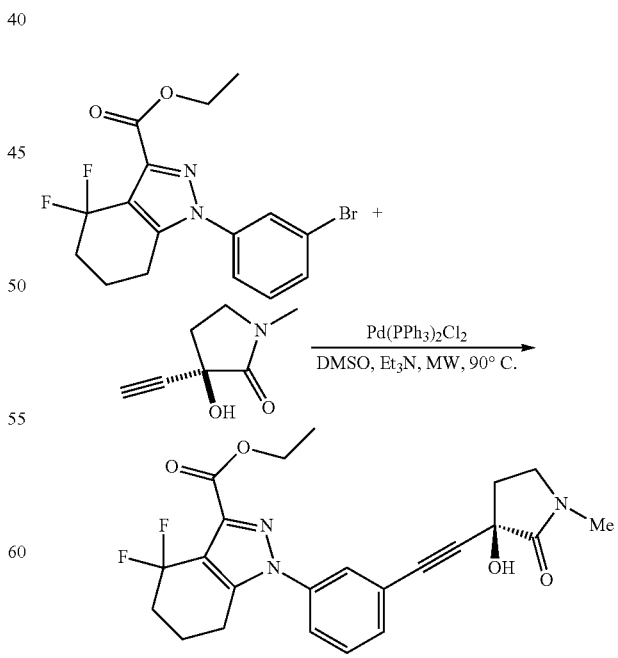

Similar to as described in General Procedure E, ethyl 1-(3-bromophenyl)-4,4-difluoro-4,5,6,7-tetrahydro-1H-indazole-3-carboxylate was reacted with (3R)-3-ethynyl-3-hydroxy-1-methylpyrrolidin-2-one to give the title compound (165 mg, crude) as a red solid. LC-MS (ES, m/z): 444 [M+1]$^+$.

Step 3: Synthesis of 4,4-difluoro-1-(3-[2-[(3R)-3-hydroxy-1-methyl-2-oxopyrrolidin-3-yl]ethynyl]phenyl)-4,5,6,7-tetrahydro-1H-indazole-3-carboxamide

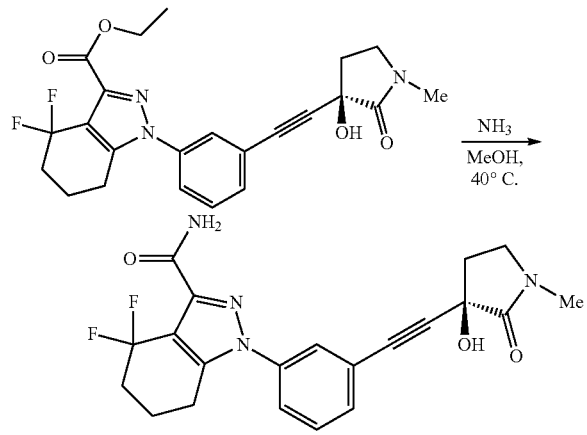

Similar to as described in General Procedure S, ethyl 4,4-difluoro-1-(3-[2-[(3R)-3-hydroxy-1-methyl-2-oxopyrrolidin-3-yl]ethynyl]phenyl)-4,5,6,7-tetrahydro-1H-indazole-3-carboxylate was reacted with ammonia in methanol to give the title compound (25.3 mg, 21%) as a yellowish solid. LC-MS (ES, m/z): 415 [M+H]$^+$. $^1$H NMR (300 MHz, CD$_3$OD) δ 7.75 (s, 1H), 7.75-7.56 (m, 3H), 3.49 (dd, J=7.2, 6.0 Hz, 1H), 2.94 (s, 3H), 2.88-2.84 (m, 2H), 2.64-2.56 (m, 1H), 2.37-2.24 (m, 3H), 2.08-2.06 (m, 2H).

Example II

Synthesis of 1-(3-[2-[(3R)-3-hydroxy-1-methyl-2-oxopyrrolidin-3-yl]ethynyl]phenyl)-7-methoxy-1H-indazole-3-carboxamide Step 1: Synthesis of methyl 7-methoxy-1H-indazole-3-carboxylate

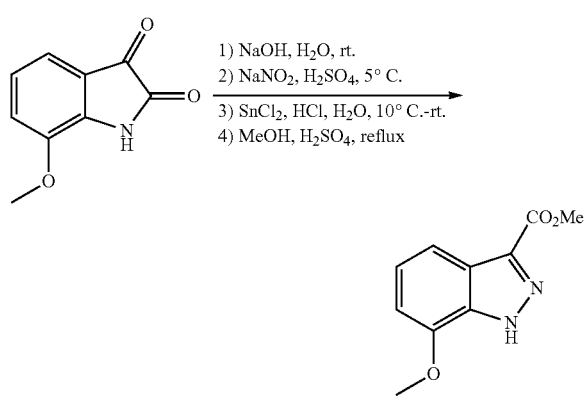

Similar to as described in General Procedure Z, 7-methoxy-2,3-dihydro-1H-indole-2,3-dione was converted to the title compound as a yellow solid (yield 700 mg, 12%). LC-MS (ES, m/z): 207 [M+H]$^+$;

Step 2: Synthesis of methyl 1-(3-bromophenyl)-7-methoxy-1H-indazole-3-carboxylate

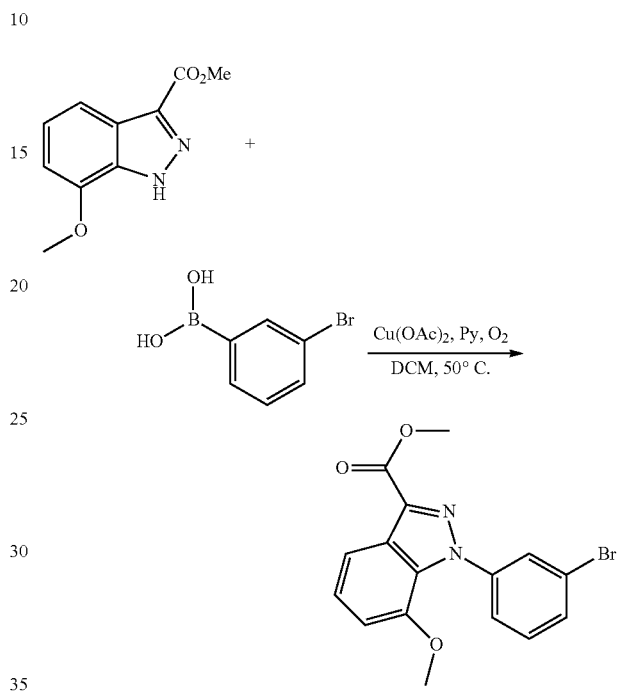

Similar to as described in General Procedure C, methyl 7-methoxy-1H-indazole-3-carboxylate was reacted with (3-bromophenyl)boronic acid to give the title compound (200 mg, 29%) as a white solid. LC-MS (ES, m/z): 361,363 [M+H]$^+$;

Step 3: Synthesis of methyl 1-(3-[2-[(3R)-3-hydroxy-1-methyl-2-oxopyrrolidin-3-yl]ethynyl]phenyl)-7-methoxy-1H-indazole-3-carboxylate

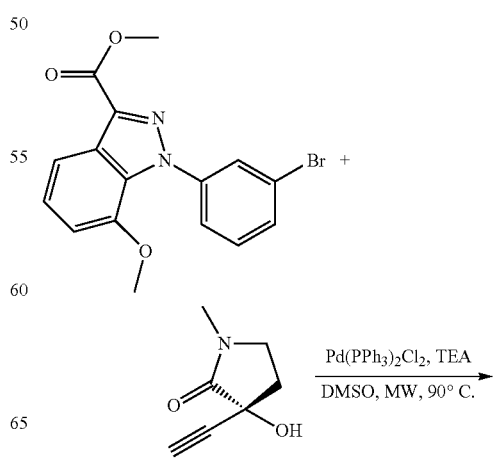

243

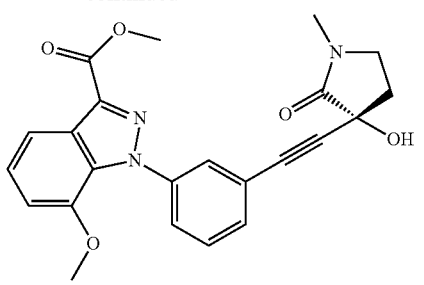

Similar to as described in General Procedure E, methyl 1-(3-bromophenyl)-7-methoxy-1H-indazole-3-carboxylate was reacted with (3R)-3-ethynyl-3-hydroxy-1-methylpyrrolidin-2-one to give the title compound (100 mg, 77%) as a yellow solid. LC-MS (ES, m/z): 420 [M+H]+.

Step 4: Synthesis of 1-(3-[2-[(3R)-3-hydroxy-1-methyl-2-oxopyrrolidin-3-yl]ethynyl]phenyl)-7-methoxy-1H-indazole-3-carboxamide

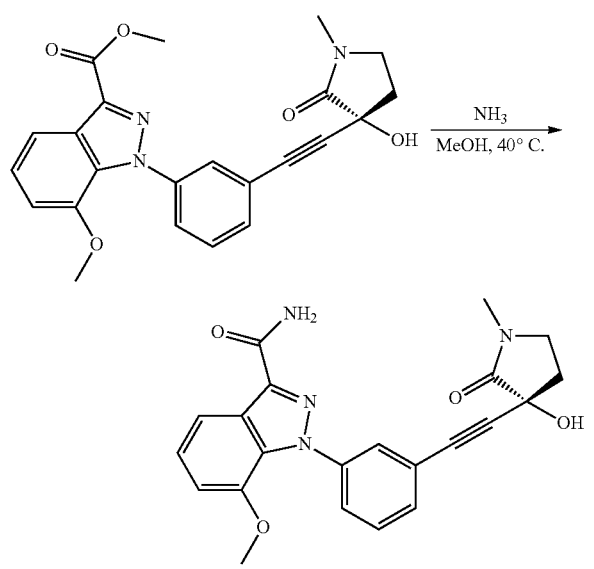

Similar to as described in General Procedure S, methyl 1-(3-[2-[(3R)-3-hydroxy-1-methyl-2-oxopyrrolidin-3-yl] ethynyl]phenyl)-7-methoxy-1H-indazole-3-carboxylate was reacted with ammonia in methanol to give the title compound (55.9 mg, 58%) as a white solid. LC-MS (ES, m/z): 405 [M+H]+. 1H NMR (300 MHz, DMSO-d6) δ 7.88-7.84 (m, 2H), 7.67-7.62 (m, 2H), 7.56-7.47 (m, 3H), 7.28 (t, J=7.8 Hz, 1H), 7.03 (d, J=7.5 Hz, 1H), 6.49 (s, 1H), 3.78 (s, 3H), 3.37-3.33 (m, 2H), 2.80 (s, 3H), 2.46-2.42 (m, 1H), 2.20-2.18 (m, 1H).

244

Example JJ

Synthesis of 4-chloro-1-(3-[2-[(3R)-3-hydroxy-1-methyl-2-oxopyrrolidin-3-yl]ethynyl]phenyl)-1H-indazole-3-carboxamide Step 1: Synthesis of 4-chloro-1H-indazole

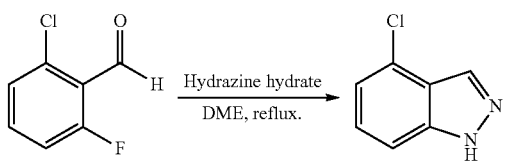 [SMILES: O=Cc1c(F)cccc1Cl ; Clc1cccc2[nH]ncc12]

A solution of 2-chloro-6-fluorobenzaldehyde (10 g, 63.07 mmol, 1.00 equiv) and hydrazine hydrate (80%, 20 g, 399.52 mmol, 6.30 equiv) in ethylene glycol dimethyl ether (20 mL, 206.63 mmol, 3.30 equiv) was heated to reflux overnight. The reaction was quenched by water, extracted with ethyl acetate, dried over anhydrous sodium sulfate, and concentrated under vacuum. The residue was purified on a silica gel column eluting with ethyl acetate/petroleum ether (1:10) to give 6 g (62%) of the title compound as a yellow solid. LC-MS (ES, m/z): 153 [M+H]+.

Step 2: Synthesis of 4-chloro-3-iodo-1H-indazole

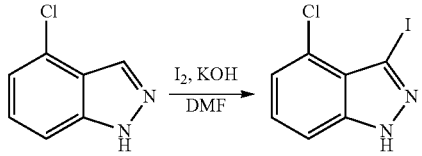

Iodine (21 g, 82.74 mmol, 2.00 equiv) was added dropwise into a solution of 4-chloro-1H-indazole (6.3 g, 41.29 mmol, 1.00 equiv) and potassium hydroxide (8.4 g, 149.72 mmol, 3.60 equiv) in N,N-dimethylformamide (100 mL). The resulting solution was stirred overnight at room temperature, quenched with 200 mL of sat. aq. Na2S2O3, extracted with ethyl acetate, dried over anhydrous sodium sulfate, and concentrated under vacuum. The residue was purified by a silica gel column with ethyl acetate/petroleum ether (1:5) to give 5 g (43%) of the title compound as a yellow solid. LC-MS (ES, m/z): 279[M+H]+.

Step 3: Synthesis of methyl 4-chloro-1H-indazole-3-carboxylate

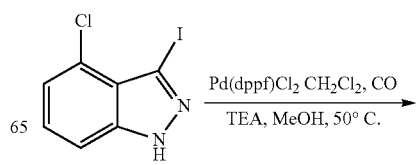

-continued

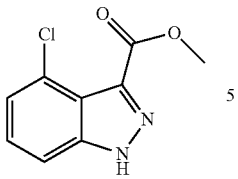

Similar to as described in General Procedure O, 4-chloro-3-iodo-1H-indazole was reacted with carbon monoxide to give the title compound (440 mg, 70%) as a yellow solid. LC-MS (ES, m/z): 211 [M+H]$^+$.

Step 4: Synthesis of methyl 1-(3-bromophenyl)-4-chloro-1H-indazole-3-carboxylate

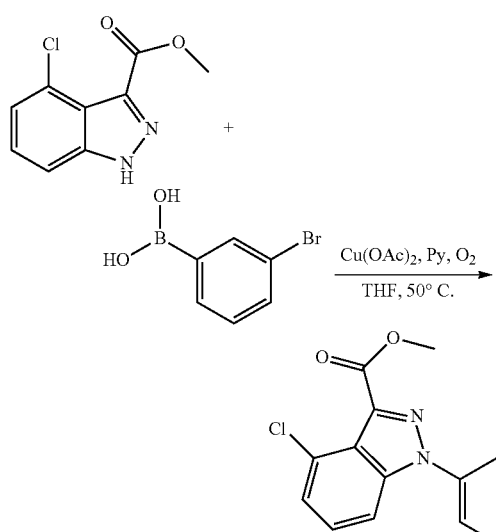

Similar to as described in General Procedure C, methyl 4-chloro-1H-indazole-3-carboxylate was reacted with (3-bromophenyl)boronic acid to give the title compound (100 mg, 12%) as a yellow solid. LC-MS (ES, m/z): 365, 367 [M+H]$^+$.

Step 5: Synthesis of methyl 4-chloro-1-(3-[2-[(3R)-3-hydroxy-1-methyl-2-oxopyrrolidin-3-yl]ethynyl]phenyl)-1H-indazole-3-carboxylate

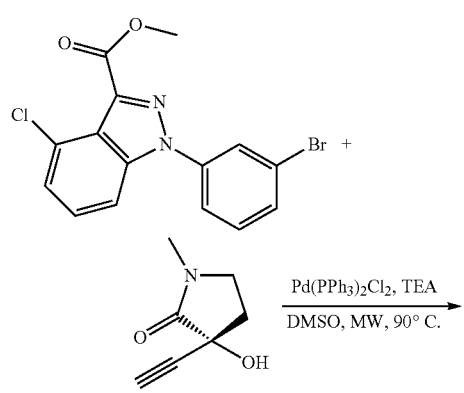

-continued

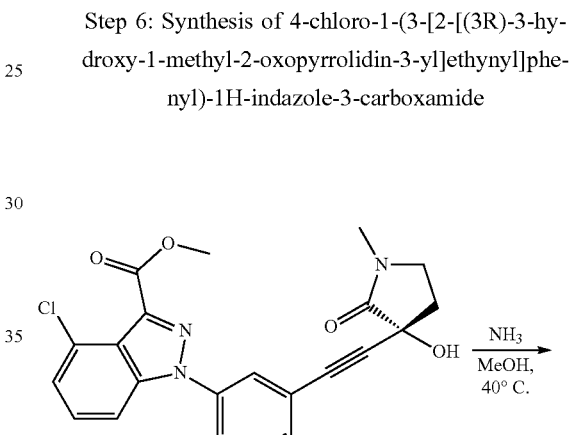

Similar to as described in General Procedure E, methyl 1-(3-bromophenyl)-4-chloro-1H-indazole-3-carboxylate was reacted with (3R)-3-ethynyl-3-hydroxy-1-methylpyrrolidin-2-one to give the title compound (100 mg, 37%) as a yellow oil. LC-MS (ES, m/z): 424 [M+H]$^+$.

Step 6: Synthesis of 4-chloro-1-(3-[2-[(3R)-3-hydroxy-1-methyl-2-oxopyrrolidin-3-yl]ethynyl]phenyl)-1H-indazole-3-carboxamide Similar to as described in General Procedure S, methyl 4-chloro-1-(3-[2-[(3R)-3-hydroxy-1-methyl-2-oxopyrrolidin-3-yl]ethynyl]phenyl)-1H-indazole-3-carboxylate was reacted with ammonia in methanol to give the title compound (29.1 mg) as a white solid. LC-MS (ES, m/z): 409 [M+H]$^+$. $^1$H NMR (300 MHz, DMSO-d6) δ 8.14 (br s, 1H), 7.87-7.80 (m, 3H), 7.74 (br s, 1H), 7.65 (t, J=7.8 Hz, 1H), 7.56-7.51 (m, 2H), 7.26 (d, J=7.2 Hz, 1H), 6.54 (s, 1H), 3.38-3.32 (m, 2H), 2.80 (s, 3H), 2.46-2.43 (m, 1H), 2.24-2.15 (m, 1H).

Example KK

Synthesis of 1-(3-[2-[(3R)-3-hydroxy-1-methyl-2-oxopyrrolidin-3-yl]ethynyl]phenyl)-6-methoxy-1H-indazole-3-carboxamide

Step 1: Synthesis of methyl 6-methoxy-1H-indazole-3-carboxylate

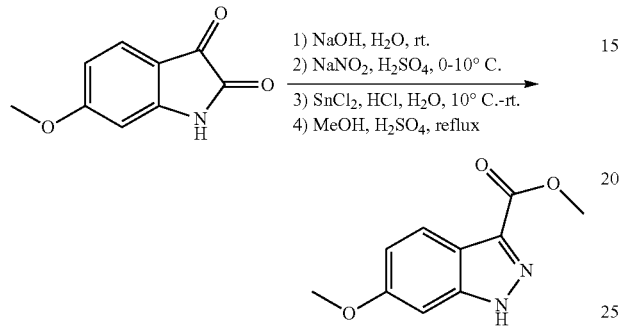

Similar to as described in General Procedure Z, 6-methoxy-2,3-dihydro-1H-indole-2,3-dione was converted to the title compound as a yellow solid (600 mg, 10%). LC-MS (ES, m/z): 207 [M+H]$^+$.

Step 2: Synthesis of methyl 1-(3-bromophenyl)-6-methoxy-1H-indazole-3-carboxylate

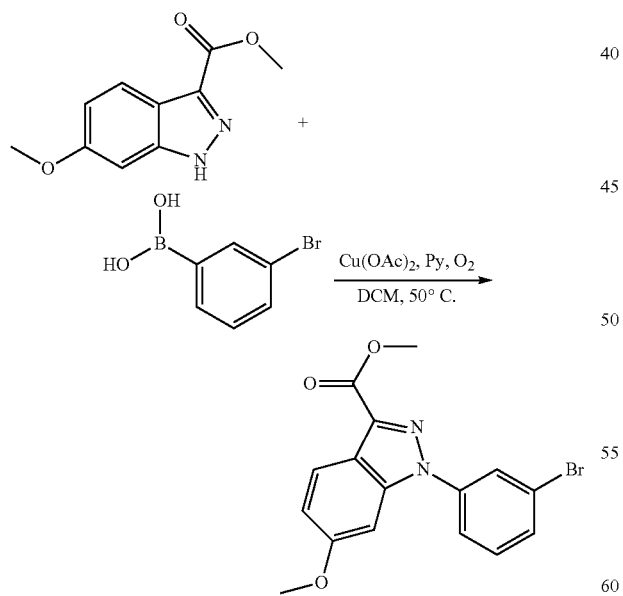

Similar to as described in General Procedure C, methyl 6-methoxy-1H-indazole-3-carboxylate was reacted with (3-bromophenyl)boronic acid to give the title compound (200 mg, 29%) as a white solid. LC-MS (ES, m/z): 361,363 [M+H]$^+$.

Step 3: Synthesis of methyl 1-(3-[2-[(3R)-3-hydroxy-1-methyl-2-oxopyrrolidin-3-yl]ethynyl]phenyl)-6-methoxy-1H-indazole-3-carboxylate

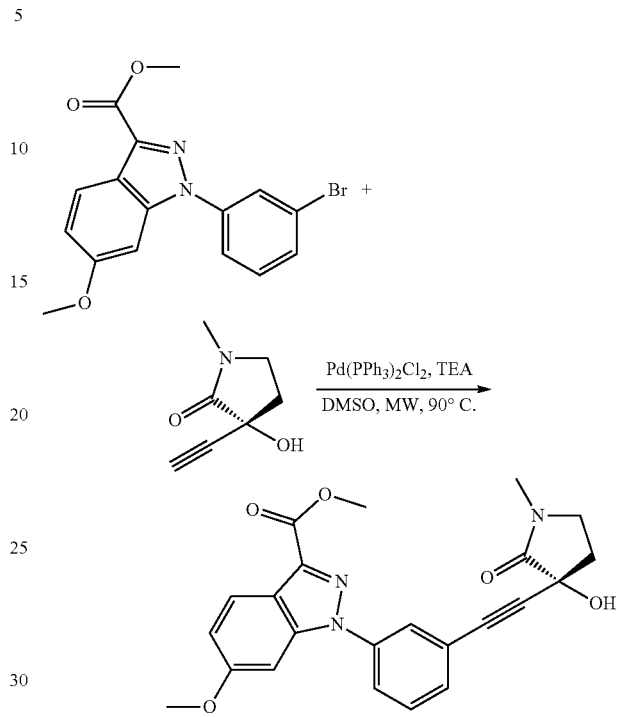

Similar to as described in General Procedure E, methyl 1-(3-bromophenyl)-6-methoxy-1H-indazole-3-carboxylate was reacted with (3R)-3-ethynyl-3-hydroxy-1-methylpyrrolidin-2-one to give the title compound (100 mg, 86%) as a yellow solid. LC-MS (ES, m/z): 420 [M+H]$^+$.

Step 4: Synthesis of 1-(3-[2-[(3R)-3-hydroxy-1-methyl-2-oxopyrrolidin-3-yl]ethynyl]phenyl)-6-methoxy-1H-indazole-3-carboxamide

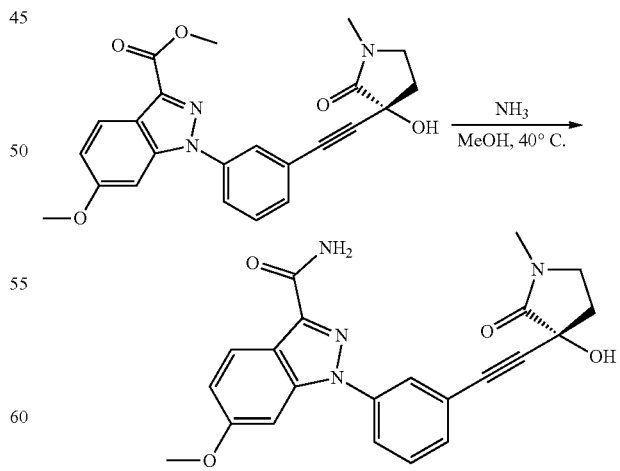

Similar to as described in General Procedure S, methyl 1-(3-[2-[(3R)-3-hydroxy-1-methyl-2-oxopyrrolidin-3-yl]ethynyl]phenyl)-6-methoxy-1H-indazole-3-carboxylate was reacted with ammonia in methanol to give the title compound (40.8 mg, 42%) as a white solid. LC-MS (ES, m/z): 405[M+H]⁺. ¹H NMR (300 MHz, CDCl₃) δ 8.28 (d, J=9.0 Hz, 1H), 7.70 (br s, 1H), 7.65-7.57 (m, 1H), 7.48-7.46 (m, 1H), 6.99-6.91 (m, 3H), 6.05 (br s, 1H), 4.15 (br s, 1H), 3.87 (s, 3H), 3.51-3.41 (m, 2H), 2.97 (s, 3H), 2.65-2.62 (m, 1H), 2.46-2.39 (m, 1H).

Example LL and MM

Synthesis of (5R)-5-hydroxy-1-(4-[2-[(3R)-3-hydroxy-1-methyl-2-oxopyrrolidin-3-yl]ethynyl]pyridin-2-yl)-6,6-dimethyl-4,5,6,7-tetrahydro-1H-indazole-3-carboxamide and (5S)-5-hydroxy-1-(4-[2-[(3R)-3-hydroxy-1-methyl-2-oxopyrrolidin-3-yl]ethynyl]pyridin-2-yl)-6, 6-dimethyl-4,5,6,7-tetrahydro-1H-indazole-3-carboxamide Step 1: Synthesis of 5-hydroxy-6,6-dimethyl-4,5,6,7-tetrahydro-1H-indazole-3-carboxylic acid

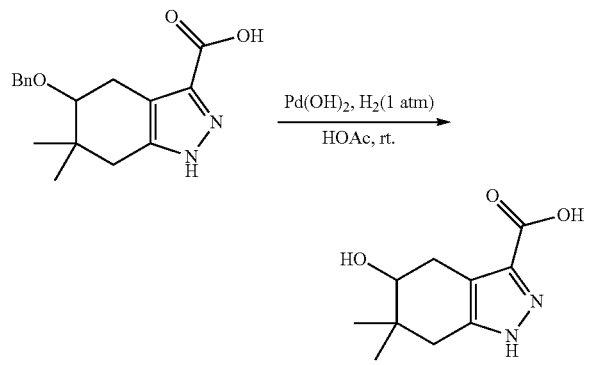

Under a hydrogen (1 atm) atmosphere, a suspension of 5-(benzyloxy)-6,6-dimethyl-4,5,6,7-tetrahydro-1H-indazole-3-carboxylic acid (230 mg, 0.77 mmol, 1.00 equiv) and Pd(OH)₂/C (107 mg, 0.76 mmol, 1.00 equiv) in acetic acid (40 mL) was stirred overnight at room temperature. The solid was filtered out and the filtrate was concentrated under vacuum to give 150 mg (93%) of the title compound as a yellow solid. LC-MS (ES, m/z): 211 [M+H]⁺.

Step 2: Synthesis of 5-hydroxy-1-(4-iodopyridin-2-yl)-6,6-dimethyl-4,5,6,7-tetrahydro-1H-indazole-3-carboxylic acid

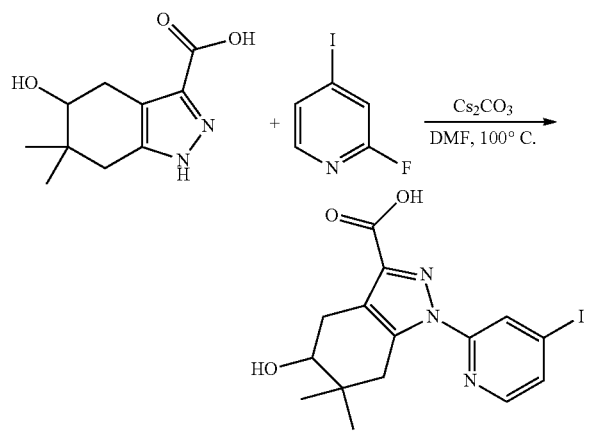

Similar to as described in General Procedure A, 5-hydroxy-6,6-dimethyl-4,5,6,7-tetrahydro-1H-indazole-3-carboxylic acid was reacted with 2-fluoro-4-iodopyridine to give the title compound (300 mg, 57%) as yellow oil. LC-MS (ES, m/z): 414 [M+H]⁺.

Step 3: Synthesis of 5-hydroxy-1-(4-iodopyridin-2-yl)-6,6-dimethyl-4,5,6,7-tetrahydro-1H-indazole-3-carboxamide

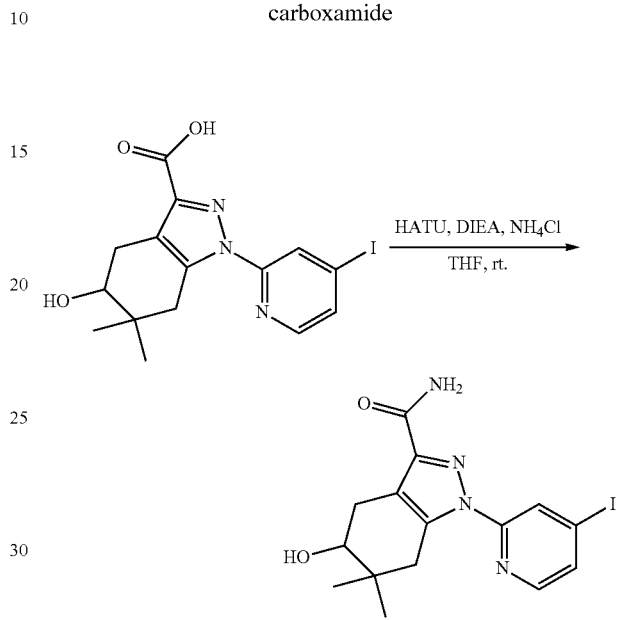

Similar to as described in General Procedure B, 5-hydroxy-1-(4-iodopyridin-2-yl)-6,6-dimethyl-4,5,6,7-tetrahydro-1H-indazole-3-carboxylic acid was reacted with amine hydrochloride to give the title compound (100 mg, 29%) as a yellow solid. LC-MS (ES, m/z): 413 [M+H]⁺.

Step 4: Synthesis of (5R)-5-hydroxy-1-(4-[2-[(3R)-3-hydroxy-1-methyl-2-oxopyrrolidin-3-yl]ethynyl]pyridin-2-yl)-6,6-dimethyl-4,5,6,7-tetrahydro-1H-indazole-3-carboxamide and (5S)-5-hydroxy-1-(4-[2-[(3R)-3-hydroxy-1-methyl-2-oxopyrrolidin-3-yl]ethynyl]pyridin-2-yl)-6,6-dimethyl-4,5,6,7-tetrahydro-1H-indazole-3-carboxamide

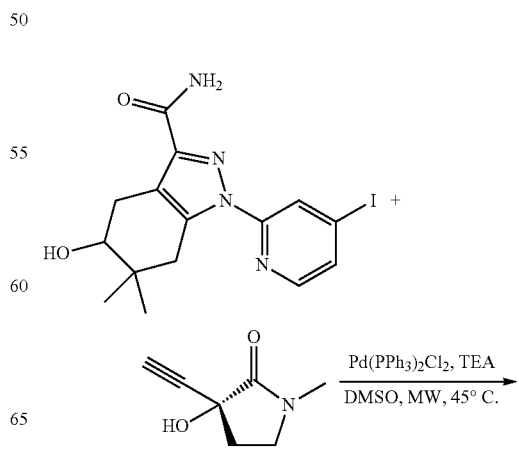

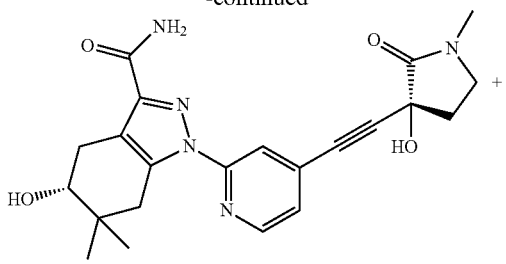

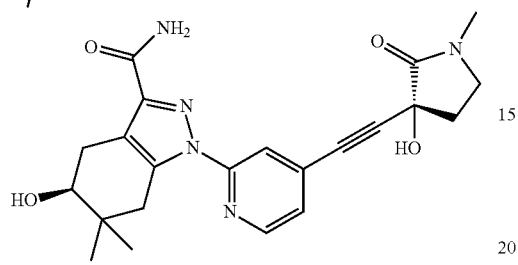

Similar to as described in General Procedure E, 5-hydroxy-1-(4-iodopyridin-2-yl)-6,6-dimethyl-4,5,6,7-tetrahydro-1H-indazole-3-carboxamide was reacted with (3R)-3-ethynyl-3-hydroxy-1-methylpyrrolidin-2-one to give the title compounds which were separated by Chiral-Prep-HPLC with the following conditions: Column, Chiralpak IA, 2×25 cm, 5 um; mobile phase, Hex and ethanol (hold 45.0% ethanol in 75 min); Detector, UV 254/220 nm. The stereochemistry of both compounds was arbitrarily assigned.

Isomer A (5R): white solid; $t_R$=0.823 min (Chiralpak IA-3, 25° C., UV-254 nm, Hex(0.1% TEA):EtOH=50:50, 2.0 mL/min). LC-MS (ES, m/z): 424 [M+H]$^+$. $^1$H NMR (400 MHz, CD$_3$OD) δ 8.35 (d, J=5.2 Hz, 1H), 7.99 (d, J=1.2 Hz, 1H), 7.23 (dd, J=5.2, 1.2 Hz, 1H), 3.57-3.56 (m, 1H), 3.41-3.37 (m, 2H), 3.04-2.87 (m, 3H), 2.83 (s, 3H), 2.72-2.71 (m, 1H), 2.53-2.47 (m, 1H), 2.27-2.20 (m, 1H), 1.17 (s, 3H), 0.94 (s, 3H).

Isomer B (5S): white solid, $t_R$=2.872 min (Chiralpak IA-3, 25° C., UV-254 nm, Hex(0.1% TEA):EtOH=50:50, 2.0 mL/min). LC-MS (ES, m/z) 424 [M+H]$^+$. $^1$H NMR (400 MHz, CD$_3$OD) δ 8.35 (d, J=5.2 Hz, 1H), 7.99 (d, J=1.2 Hz, 1H), 7.23 (dd, J=5.2, 1.2 Hz, 1H), 3.57-3.56 (m, 1H), 3.41-3.37 (m, 2H), 3.04-2.87 (m, 3H), 2.83 (s, 3H), 2.72-2.71 (m, 1H), 2.53-2.47 (m, 1H), 2.27-2.20 (m, 1H), 1.17 (s, 3H), 0.94 (s, 3H).

Example NN

Synthesis of 1-(3-[2-[(3R)-3-hydroxy-1-methyl-2-oxopyrrolidin-3-yl]ethynyl]phenyl)-4-(methylamino)-1H-pyrazolo[4,3-c]pyridine-3-carboxamide Step 1: Synthesis of 4-chloro-3-iodo-1H-pyrazolo[4,3-c]pyridine

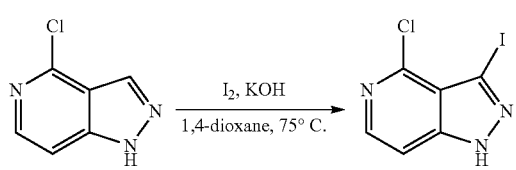 [SMILES: Clc1nccc2[nH]ncc12 ; Clc1nccc2[nH]nc(I)c12]

A solution of 4-chloro-1H-pyrazolo[4,3-c]pyridine (2 g, 13.02 mmol, 1.00 equiv), iodine (6.6 g, 26.00 mmol, 2.00 equiv), potassium hydroxide (2.69 g, 47.95 mmol, 3.70 equiv) in 1,4-dioxane (32 mL) was stirred for 4 h at 75° C. After cooling the reaction mixture was diluted with 3 mL of saturated sodium thiosulphate. The precipitate was collected by filtration and washed with water to afford 2 g (55%) of the title compound as a yellow solid. LC-MS (ES, m/z): 280[M+H]$^+$ Step 2: Synthesis of 3-iodo-N-methyl-1H-pyrazolo[4,3-c]pyridin-4-amine

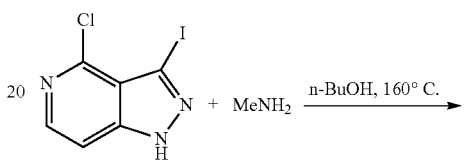

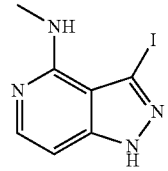

A solution of 4-chloro-3-iodo-1H-pyrazolo[4,3-c]pyridine (250 mg, 0.89 mmol, 1.00 equiv), methanamine (2 mL) in n-butanol (3 mL) was heated with microwave radiation for 1 h at 160° C. The mixture was concentrated under vacuum and the residue was purified by silica gel chromatography eluting with ethyl acetate/petroleum ether (1:1) to afford 80 mg (33%) of the title compound as a yellow solid. LC-MS (ES, m/z): 275[M+H]$^+$.

Step 3: Synthesis of methyl 4-(methylamino)-1H-pyrazolo[4,3-c]pyridine-3-carboxylate

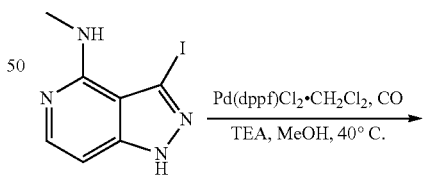

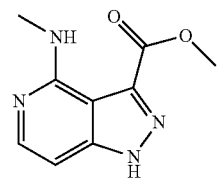

Similar to as described in General Procedure O, 3-iodo-N-methyl-1H-pyrazolo[4,3-c]pyridin-4-amine was reacted with carbon monoxide to give the title compound (596 mg, crude) as a yellow solid. LC-MS (ES, m/z): 207[M+H]$^+$.

Step 4: Synthesis of methyl 1-(3-bromophenyl)-4-(methylamino)-1H-pyrazolo[4,3-c]pyridine-3-carboxylate

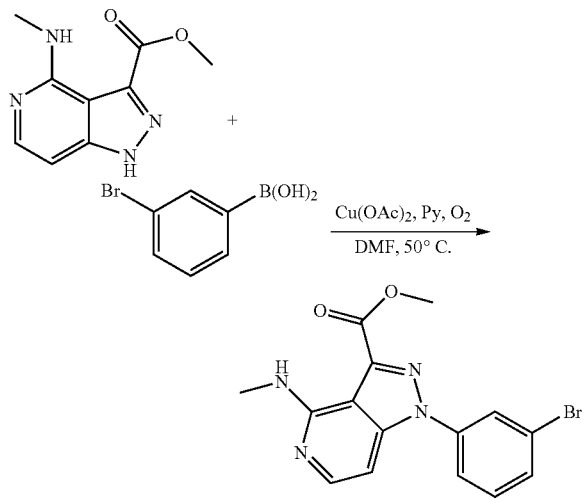

Similar to as described in General Procedure C, methyl 4-(methylamino)-1H-pyrazolo[4,3-c]pyridine-3-carboxylate was reacted with (3-bromophenyl)boronic acid to give the title compound (180 mg, 21%) as a yellow solid. LC-MS (ES, m/z): 362[M+H]⁺.

Step 5: Synthesis of methyl 1-(3-[2-[(3R)-3-hydroxy-1-methyl-2-oxopyrrolidin-3-yl]ethynyl]phenyl)-4-(methylamino)-1H-pyrazolo[4,3-c]pyridine-3-carboxylate

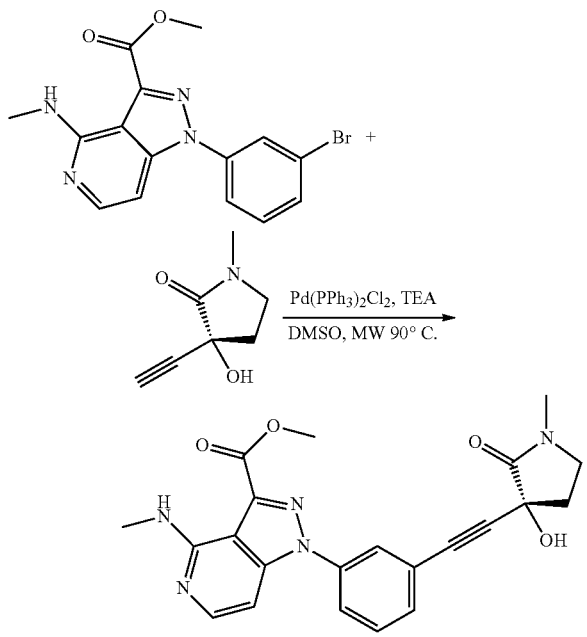

Similar to as described in General Procedure M, methyl 1-(3-bromophenyl)-4-(methylamino)-1H-pyrazolo[4,3-c]pyridine-3-carboxylate was reacted with (3R)-3-ethynyl-3-hydroxy-1-methylpyrrolidin-2-one to give the title compound (100 mg, 48%) as a yellow oil. LC-MS (ES, m/z): 420 [M+H]⁺.

Step 6: Synthesis of 1-(3-[2-[(3R)-3-hydroxy-1-methyl-2-oxopyrrolidin-3-yl]ethynyl]phenyl)-4-(methylamino)-1H-pyrazolo[4,3-c]pyridine-3-carboxamide

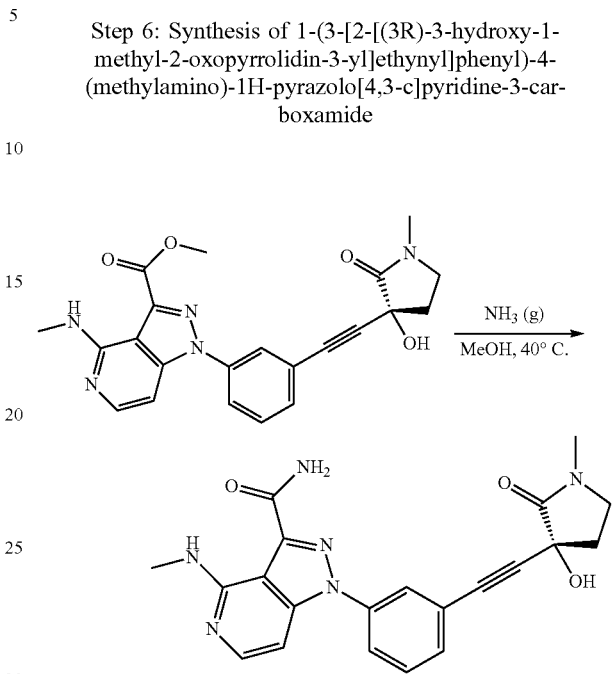

Similar to as described in General Procedure S, methyl 1-(3-[2-[(3R)-3-hydroxy-1-methyl-2-oxopyrrolidin-3-yl]ethynyl]phenyl)-4-(methylamino)-1H-pyrazolo[4,3-c]pyridine-3-carboxylate was reacted with ammonia in methanol to give the title compound (30.4 mg, 32%) as a white solid. LC-MS: (ES, m/z): 405 [M+H]⁺. ¹H NMR (400 MHz, CD₃OD) δ 7.78-7.70 (m, 2H), 7.70-7.68 (m, 1H), 7.53-7.46 (m, 2H), 6.77 (d, J=6.0 Hz, 1H), 3.40-3.35 (m, 2H), 3.03-2.98 (m, 3H), 2.83 (s, 3H), 2.53-2.47 (m, 1H), 2.26-2.19 (m, 1H).

Example OO

Synthesis of 1-(3-[2-[(3R)-3-hydroxy-1-methyl-2-oxopyrrolidin-3-yl]ethynyl]phenyl)-5-methyl-1H-pyrazolo[3,4-d][1,3]thiazole-3-carboxamide

Step 1: Synthesis of ethyl 5-amino-1-(3-bromophenyl)-1H-pyrazole-3-carboxylate

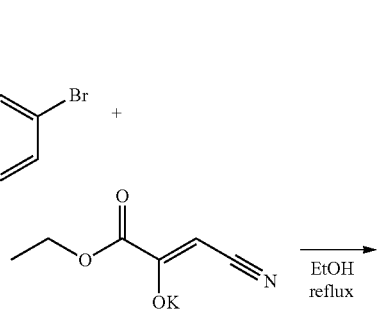

-continued

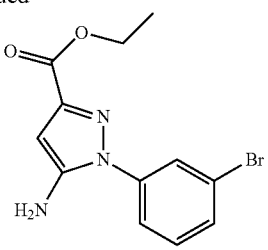

A suspension of (3-bromophenyl)hydrazine hydrochloride (8.86 g, 39.64 mmol, 1.00 equiv), potassium (Z)-1-cyano-3-ethoxy-3-oxoprop-1-en-2-olate (7.1 g, 39.62 mmol, 1.00 equiv) in ethanol (100 mL) was heated to reflux for 12 h. After completion the mixture was concentrated under vacuum and the residue was purified by silica gel column chromatography eluting with ethyl acetate/petroleum ether (1:2) to afford 9.5 g (77%) of the title compound as a yellow solid. LC-MS (ES, m/z): 310, 312 [M+H]$^+$.

Step 2: Synthesis of ethyl 5-amino-1-(3-bromophenyl)-4-(cyanosulfanyl)-1H-pyrazole-3-carboxylate

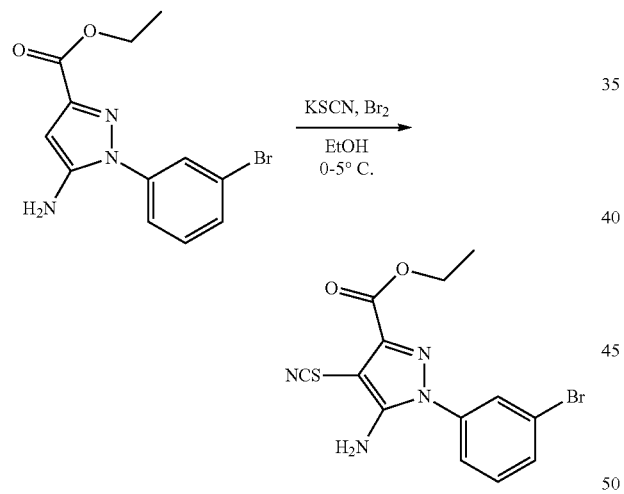

A solution of bromine (2.88 g, 18.02 mmol, 2.00 equiv) in ethanol (5 mL) was added dropwise to a stirred mixture of ethyl 5-amino-1-(3-bromophenyl)-1H-pyrazole-3-carboxylate (2.79 g, 9.00 mmol, 1.00 equiv), potassium thiocyanate (2.62 g, 27.01 mmol, 3.00 equiv) in ethanol (30 mL) at 0° C. After being stirred for 12 h at 0° C. the reaction mixture was diluted with water and the solution pH was adjusted to 9 with sodium carbonate solution. The precipitated solid was collected by filtration and dried under high vacuum to afford 2.8 g (85%) of the title compound as an off-white solid. LC-MS (ES, m/z): 367, 369 [M+H]$^+$.

Step 3: Synthesis of ethyl 5-amino-4-[[5-amino-1-(3-bromophenyl)-3-(ethoxycarbonyl)-1H-pyrazol-4-yl]disulfanyl]-1-(3-bromophenyl)-1H-pyrazole-3-carboxylate

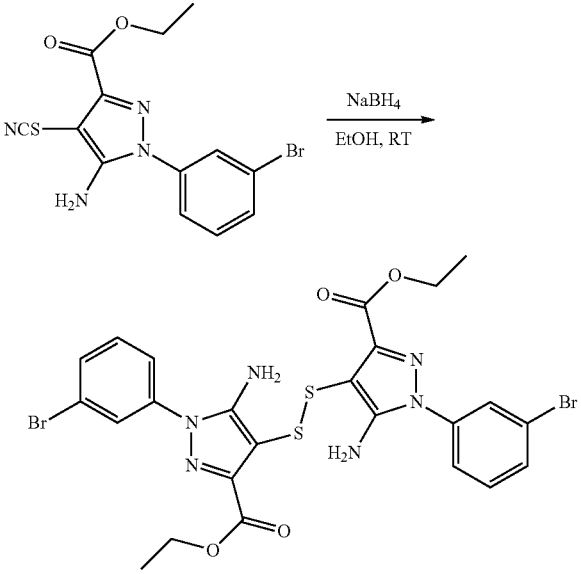

Sodium borohydride (114 mg, 2.94 mmol, 1.00 equiv) was added to a solution of ethyl 5-amino-1-(3-bromophenyl)-4-(cyanosulfanyl)-1H-pyrazole-3-carboxylate (1.1 g, 3.00 mmol, 1.0 equiv) in ethanol (10 mL). The resulting mixture was stirred for 1 h at room temperature, quenched with water, extracted with ethyl acetate, dried over anhydrous sodium sulfate, and concentrated under vacuum. The residue was purified by silica gel chromatography eluting with ethyl acetate/petroleum ether (1:2) to afford 880 mg (43%) of the title compound as a light yellow solid. LC-MS (ES, m/z): 683, 685 [M+H]$^+$.

Step 4: Synthesis of ethyl 1-(3-bromophenyl)-5-methyl-1H-pyrazolo[3,4-d][1,3]thiazole-3-carboxylate

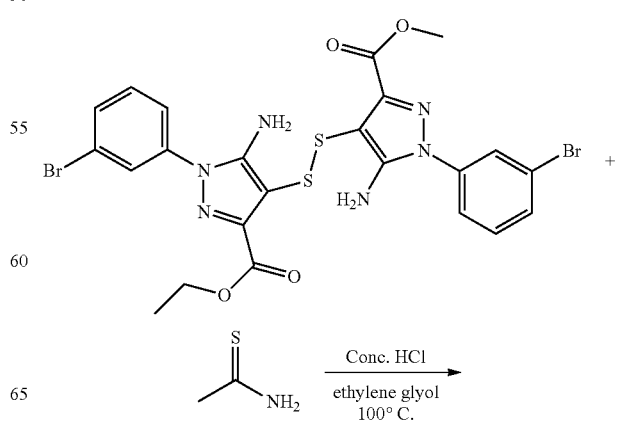

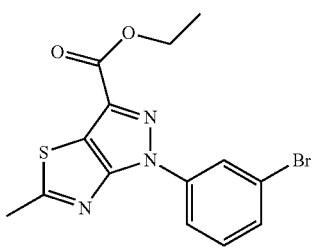

A mixture of ethyl 5-amino-4-[[5-amino-1-(3-bromophenyl)-3-(ethoxycarbonyl)-1H-pyrazol-4-yl]disulfanyl]-1-(3-bromophenyl)-1H-pyrazole-3-carboxylate (800 mg, 1.17 mmol, 1.00 equiv), ethanethioamide (176 mg, 2.34 mmol, 1.00 equiv), hydrochloric acid (0.1 mL) in ethylene glycol (10 mL) was stirred for 3 h at 100° C. The reaction mixture was diluted with water, extracted with ethyl acetate, dried over anhydrous sodium sulfate, and concentrated under vacuum. The residue was purified by silica gel chromatography eluting with ethyl acetate/petroleum ether (1:3) to afford 75 mg (17%) of the title compound as an off-white solid. LC-MS (ES, m/z): 366, 368 [M+H]⁺.

Step 5: Synthesis of ethyl 1-(3-[2-[(3R)-3-hydroxy-1-methyl-2-oxopyrrolidin-3-yl]ethynyl]phenyl)-5-methyl-1H-pyrazolo[3,4-d][1,3]thiazole-3-carboxylate

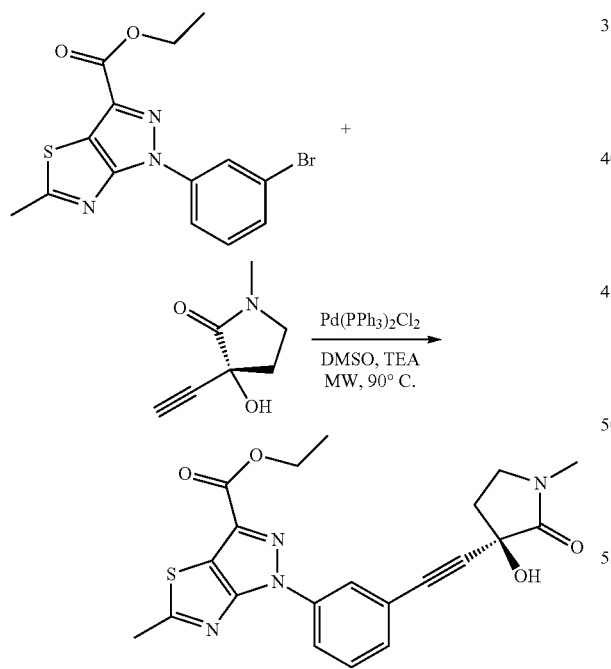

Similar to as described in General Procedure E, ethyl 1-(3-bromophenyl)-5-methyl-1H-pyrazolo[3,4-d][1,3]thiazole-3-carboxylate was reacted with (3R)-3-ethynyl-3-hydroxy-1-methylpyrrolidin-2-one to give the title compound (100 mg, 86%) as an off-white solid. LC-MS (ES, m/z): 425 [M+H]⁺.

Step 6: Synthesis of 1-(3-[2-[(3R)-3-hydroxy-1-methyl-2-oxopyrrolidin-3-yl]ethynyl]phenyl)-5-methyl-1H-pyrazolo[3,4-d][1,3]thiazole-3-carboxamide

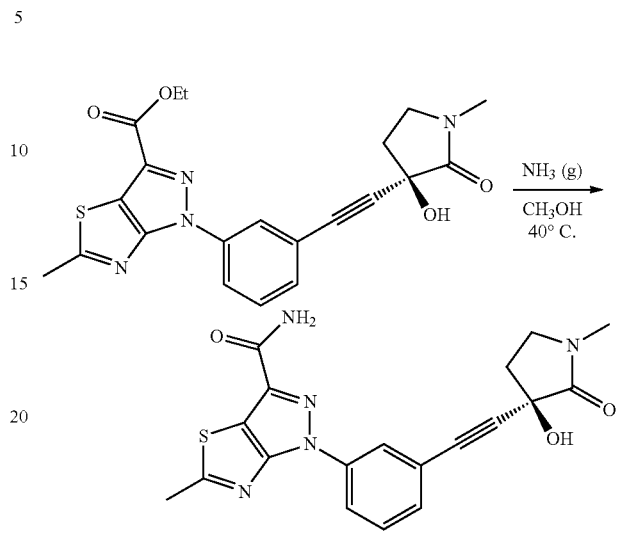

Similar to as described in General Procedure S, ethyl 1-(3-[2-[(3R)-3-hydroxy-1-methyl-2-oxopyrrolidin-3-yl]ethynyl]phenyl)-5-methyl-1H-pyrazolo[3,4-d][1,3]thiazole-3-carboxylate was reacted with ammonia in methanol to give the title compound (27 mg, 29%) as an off-white solid. LC-MS (ES, m/z): 396 [M+H]⁺. ¹H NMR (300 MHz, CD₃OD) δ 8.33 (s, 1H), 8.31 (d, J=7.5 Hz, 1H), 7.59-7.43 (m, 2H), 3.51-3.48 (m, 2H), 2.95 (s, 3H), 2.87 (s, 3H), 2.66-2.59 (m, 1H), 2.39-2.30 (m, 1H).

Example PP

Synthesis of (4aS,5aR)-1-(4-[2-[(3R)-3-hydroxy-1-methyl-2-oxopyrrolidin-3-yl]ethynyl]pyridin-2-yl)-5a-methyl-1H,4H,4aH,5H,5aH,6H-cyclopropa[f]indazole-3-carboxamide Step 1: Synthesis of (4aS,5aS)-5a-methyl-1H,3aH,4H,4aH,5H,5aH,6H,6aH-cyclopropa[f]indazole-3-carboxylic acid

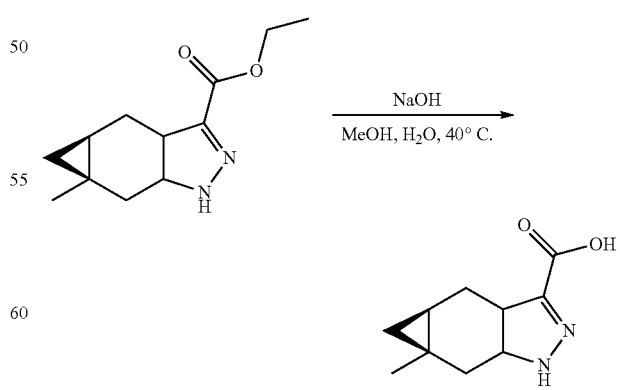

Similar to as described in General Procedure J, ethyl (4aS,5aS)-5a-methyl-1H,3aH,4H,4aH,5H,5aH,6H,6aH-cyclopropa[f]indazole-3-carboxylate was reacted with sodium hydroxide to give the title compound (1.6 g, 83%) as an off-white solid. LC-MS (ES, m/z): 195 [M+H]⁺.

Step 2: Synthesis of (4aS,5aR)-1-(4-iodopyridin-2-yl)-5a-methyl-1H,4H,4aH,5H,5aH,6H-cyclopropa[f]indazole-3-carboxylic acid

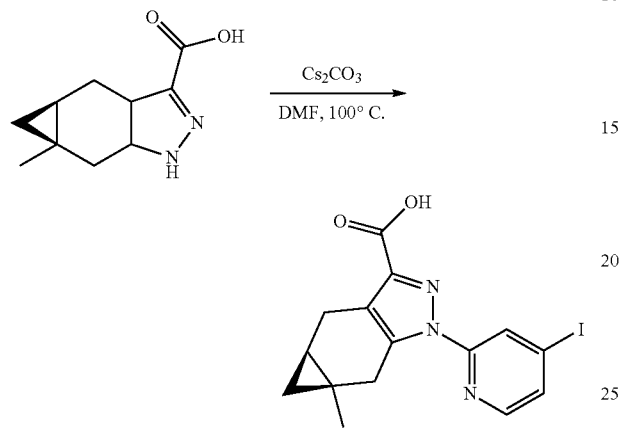

Similar to as described in General Procedure A, (4aR,5aR)-5a-methyl-1H,3aH,4H,4aH,5H,5aH,6H,6aH-cyclopropa[f]indazole-3-carboxylic acid was reacted with 2-fluoro-4-iodopyridine to give the title compound (366 mg) as a brown solid. LC-MS (ES, m/z): 396 [M+H]⁺.

Step 3: Synthesis of (4aS,5aR)-1-(4-iodopyridin-2-yl)-5a-methyl-1H,4H,4aH,5H,5aH,6H-cyclopropa[f]indazole-3-carboxamide

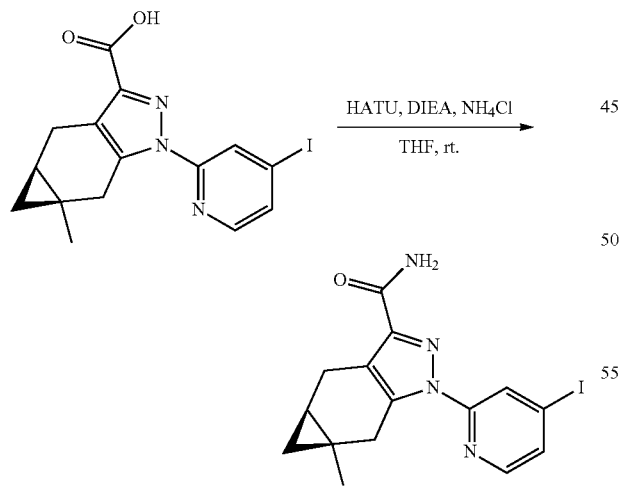

Similar to as described in General Procedure B, (4aS,5aR)-1-(4-iodopyridin-2-yl)-5a-methyl-1H,4H,4aH,5H,5aH,6H-cyclopropa[f]indazole-3-carboxylic acid was reacted with ammonium chloride to give the title compound (260 mg, 72%) as a light yellow solid. LC-MS (ES, m/z): 395 [M+H]⁺.

Step 4: Synthesis of (4aS,5aR)-1-(4-[2-[(3R)-3-hydroxy-1-methyl-2-oxopyrrolidin-3-yl]ethynyl]pyridin-2-yl)-5a-methyl-1H,4H,4aH,5H,5aH,6H-cyclopropa[f]indazole-3-carboxamide

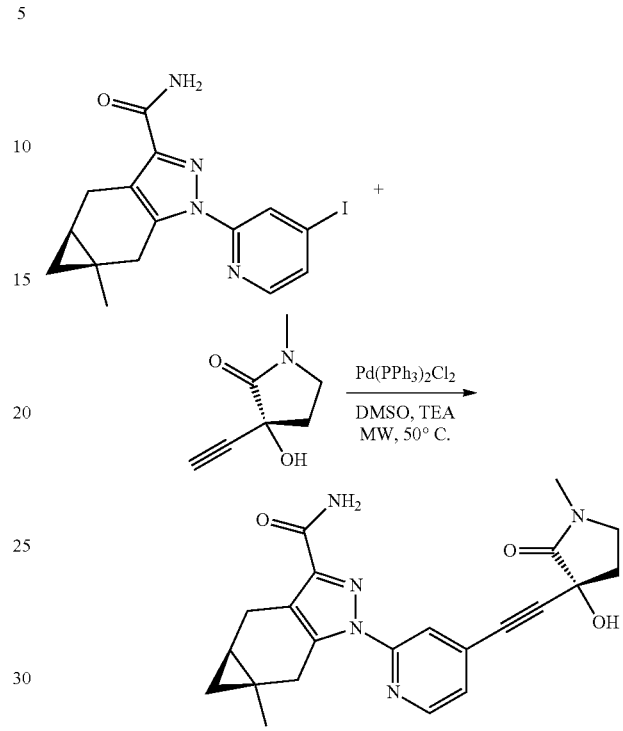

Similar to as described in General Procedure E, (4aS,5aR)-1-(4-iodopyridin-2-yl)-5a-methyl-1H,4H,4aH,5H,5aH,6H-cyclopropa[f]indazole-3-carboxamide was reacted with (3R)-3-ethynyl-3-hydroxy-1-methylpyrrolidin-2-one to give the title compound (53.7 mg) as a light yellow solid. The stereochemistry of the cyclopropyl group was arbitrarily assigned. LC-MS (ES, m/z): 406 [M+H]⁺. ¹H NMR (400 MHz, CD₃OD) δ 8.44 (d, J=4.8 Hz, 1H), 8.03 (s, 1H), 7.32 (dd, J=5.2, 1.2 Hz, 1H), 3.72 (d, J=18.0 Hz, 1H), 3.50-3.46 (m, 2H), 3.33-3.28 (m, 1H), 3.06 (d, J=18.0 Hz, 1H), 3.01-2.95 (m, 1H), 2.92 (s, 3H), 2.61-2.56 (m, 1H), 2.36-2.31 (m, 1H), 1.26 (s, 3H), 1.11-1.09 (m, 1H), 0.39 (dd, J=8.8, 4.4 Hz, 1H), 0.21 (t, J=5.2 Hz, 1H).

Example QQ

Synthesis of (4aR,5aS)-1-(4-[2-[(3R)-3-hydroxy-1-methyl-2-oxopyrrolidin-3-yl]ethynyl]pyridin-2-yl)-5a-methyl-1H,4H,4aH,5H,5aH,6H-cyclopropa[f]indazole-3-carboxamide Step 1: Synthesis of (4aR,5aS)-1-(4-iodopyridin-2-yl)-5a-methyl-1H,4H,4aH,5H,5aH,6H-cyclopropa[f]indazole-3-carboxylic acid

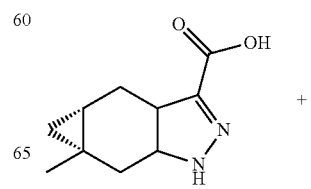

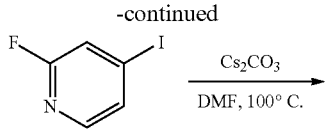

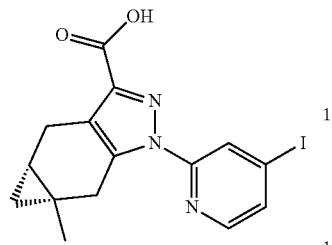

Similar to as described in General Procedure A, (4aS, 5aS)-5a-methyl-1H,3aH,4H,4aH,5H,5aH,6H,6aH-cyclopropa[f]indazole-3-carboxylic acid was reacted with 2-fluoro-4-iodopyridine to give the title compound (320 mg) as a dark red crude oil which was used for the next step without purification. LC-MS– (ES, m/z): 396 [M+H]$^+$.

Step 2: Synthesis of (4aR,5aS)-1-(4-iodopyridin-2-yl)-5a-methyl-1H,4H,4aH,5H,5aH,6H-cyclopropa[f]indazole-3-carboxamide

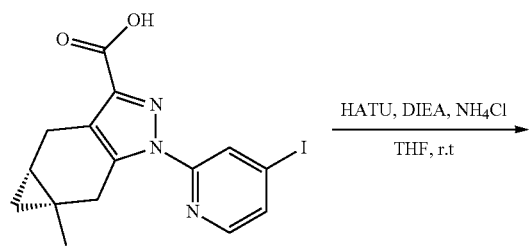

Similar to as described in General Procedure B, (4aR, 5aS)-1-(4-iodopyridin-2-yl)-5a-methyl-1H,4H,4aH,5H, 5aH,6H-cyclopropa[f]indazole-3-carboxylic acid was reacted with ammonium chloride to give the title compound (150 mg) as an off-white solid. LC-MS (ES, m/z): 395 [M+H]$^+$.

Step 3: Synthesis of (4aR,5aS)-1-(4-[2-[(3R)-3-hydroxy-1-methyl-2-oxopyrrolidin-3-yl]ethynyl]pyridin-2-yl)-5a-methyl-1H,4H,4aH,5H,5aH,6H-cyclopropa[f]indazole-3-carboxamide

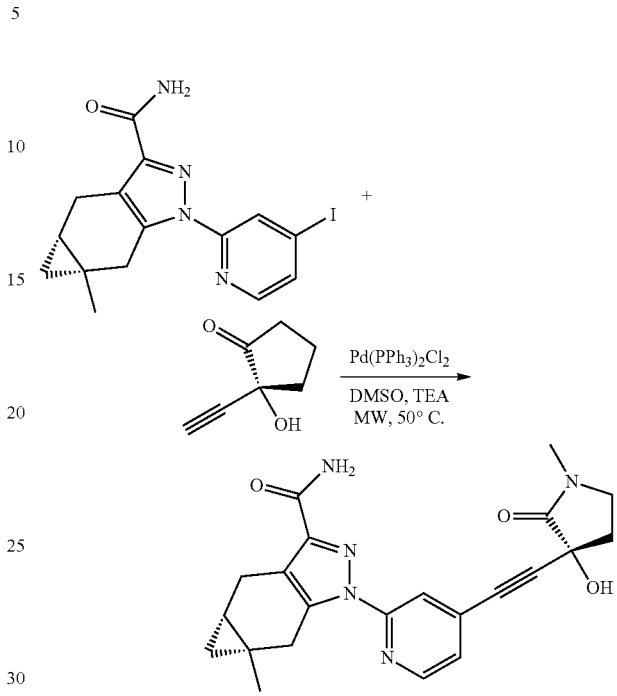

Similar to as described in General Procedure E, (4aR, 5aS)-1-(4-iodopyridin-2-yl)-5a-methyl-1H,4H,4aH,5H, 5aH,6H-cyclopropa[f]indazole-3-carboxamide was reacted with (3R)-3-ethynyl-3-hydroxy-1-methylpyrrolidin-2-one to give the title compound (14.6 mg, 14%) as a light yellow solid. The stereochemistry for the cyclopropyl group was arbitrarily assigned. LC-MS (ES, m/z): 406 [M+H]$^+$. $^1$H NMR (400 MHz, CD$_3$OD) δ 8.44 (dd, J=4.8, 0.4 Hz, 1H), 8.03 (s, 1H), 7.32 (dd, J=5.2, 1.2 Hz, 1H), 3.72 (d, J=18.0 Hz, 1H), 3.50-3.46 (m, 2H), 3.33-3.28 (m, 1H), 3.06 (d, J=18.0 Hz, 1H), 3.01-2.95 (m, 1H), 2.92 (s, 3H), 2.61-2.56 (m, 1H), 2.36-2.31 (m, 1H), 1.26 (s, 3H), 1.11-1.09 (m, 1H), 0.39 (dd, J=8.8, 4.4 Hz, 1H), 0.21 (t, J=5.2 Hz, 1H).

Example RR

Synthesis of 1-(4-[2-[(3R)-3-hydroxy-1-methyl-2-oxopyrrolidin-3-yl]ethynyl]pyridin-2-yl)-6,6-dimethyl-4,5,6,7-tetrahydro-1H-indazole-3-carboxamide Step 1: Synthesis of 1-(4-iodopyridin-2-yl)-6,6-dimethyl-4,5,6,7-tetrahydro-1H-indazole-3-carboxylic acid

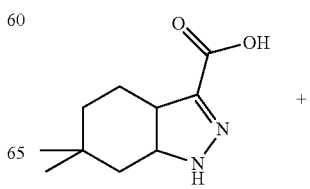

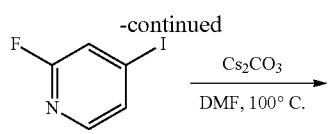

Similar to as described in General Procedure A, 6,6-dimethyl-3a,4,5,6,7,7a-hexahydro-1H-indazole-3-carboxylic acid was reacted with 2-fluoro-4-iodopyridine to give the title compound (340 mg) as an off-white crude solid. LC-MS (ES, m/z): 398 [M+H]$^+$.

Step 2: Synthesis of 1-(4-iodopyridin-2-yl)-6,6-dimethyl-4,5,6,7-tetrahydro-1H-indazole-3-carboxamide

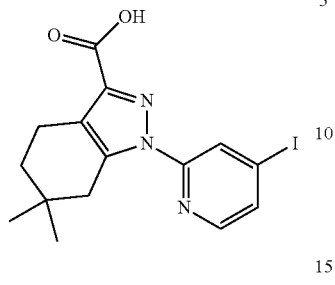

Similar to as described in General Procedure B, 1-(4-iodopyridin-2-yl)-6,6-dimethyl-4,5,6,7-tetrahydro-1H-indazole-3-carboxylic acid was reacted with ammonium chloride to give the title compound (157 mg, 46%) as an off-white solid. LC-MS (ES, m/z): 397 [M+H]$^+$.

Step 3: Synthesis of 1-(4-[2-[(3R)-3-hydroxy-1-methyl-2-oxopyrrolidin-3-yl]ethynyl]pyridin-2-yl)-6,6-dimethyl-4,5,6,7-tetrahydro-1H-indazole-3-carboxamide

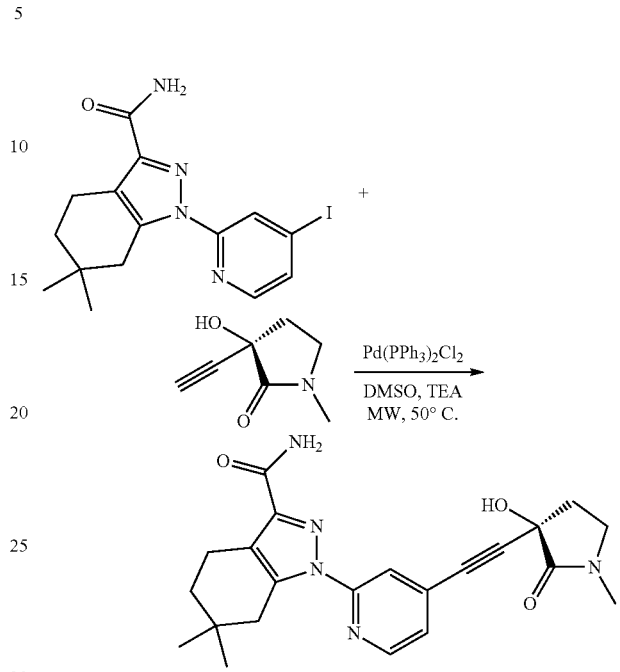

Similar to as described in General Procedure E, 1-(4-iodopyridin-2-yl)-6,6-dimethyl-4,5,6,7-tetrahydro-1H-indazole-3-carboxamide was reacted with (3R)-3-ethynyl-3-hydroxy-1-methylpyrrolidin-2-one to give the title compound (49.9 mg, 49%) as an off-white solid. LC-MS (ES, m/z): 408 [M+H]$^+$. $^1$H NMR (300 MHz, CD$_3$OD) δ 8.43 (dd, J=5.1, 0.6 Hz, 1H), 8.07 (s, 1H), 7.33 (dd, J=5.1, 1.5 Hz, 1H), 3.49 (dd, J=7.2, 5.7 Hz, 2H), 2.96-2.94 (m, 5H), 2.82 (t, J=6.3 Hz, 2H), 2.65-2.57 (m, 1H), 2.33-2.29 (m, 1H), 1.57 (t, J=6.3 Hz, 2H), 1.04 (s, 6H).

Example SS

Synthesis of 1-(3-[2-[(3R)-3-hydroxy-1-methyl-2-oxopyrrolidin-3-yl]ethynyl]phenyl)-5-[(1R)-1-hydroxy ethyl]-1H-indazole-3-carboxamide and 1-(3-[2-[(3R)-3-hydroxy-1-methyl-2-oxopyrrolidin-3-yl]ethynyl]phenyl)-5-[(1S)-1-hydroxy ethyl]-1H-indazole-3-carboxamide Step 1: Synthesis of methyl 1-(3-bromophenyl)-5-(1-hydroxyethyl)-1H-indazole-3-carboxylate

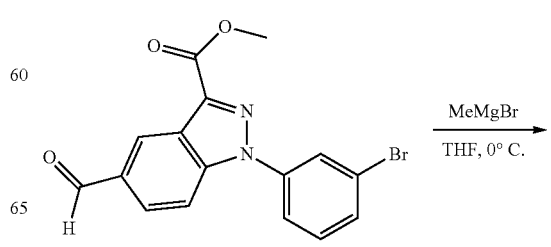

-continued

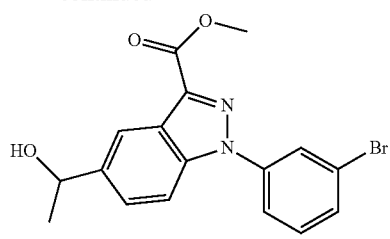

Under nitrogen methyl magnesium bromide (3M in Et₂O, 0.64 mL, 1.91 mmol, 2.90 equiv) was added dropwise to a stirred solution of methyl 1-(3-bromophenyl)-5-formyl-1H-indazole-3-carboxylate (240 mg, 0.67 mmol, 1.00 equiv) in tetrahydrofuran (20 mL) at 0° C. After being stirred for 40 min at 0° C. the reaction was quenched by ammonium chloride solution, extracted with ethyl acetate, dried over anhydrous sodium sulfate, and concentrated under vacuum. The residue was purified by a silica gel column eluting with ethyl acetate/petroleum ether (1:3) to afford 160 mg (64%) of the title compound as an off-white solid. LC-MS (ES, m/z): 375 [M+H]⁺

Step 2: Synthesis of methyl 1-(3-[2-[(3R)-3-hydroxy-1-methyl-2-oxopyrrolidin-3-yl]ethynyl]phenyl)-5-(1-hydroxyethyl)-1H-indazole-3-carboxylate

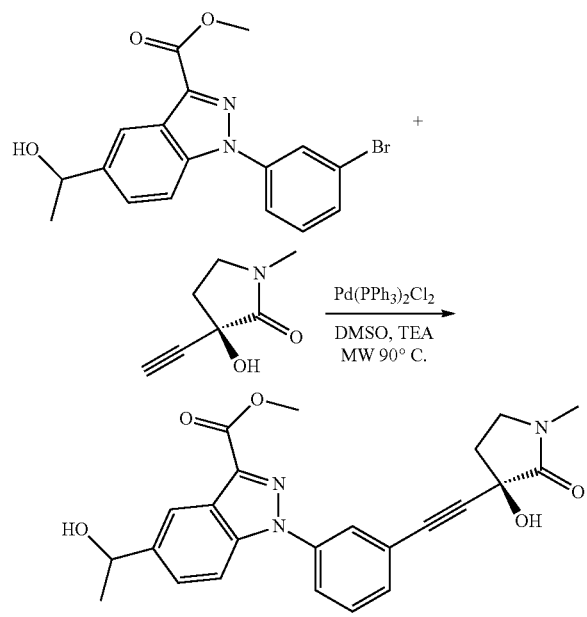

Similar to as described in General Procedure E, methyl 1-(3-bromophenyl)-5-(1-hydroxyethyl)-1H-indazole-3-carboxylate was reacted with (3R)-3-ethynyl-3-hydroxy-1-methylpyrrolidin-2-one to give the title compound (200 mg, crude) as a yellow solid. LC-MS (ES, m/z): 434 [M+H]⁺.

Step 3: Synthesis of 1-(3-[2-[(3R)-3-hydroxy-1-methyl-2-oxopyrrolidin-3-yl]ethynyl]phenyl)-5-[(1R)-1-hydroxy ethyl]-1H-indazole-3-carboxamide and 1-(3-[2-[(3R)-3-hydroxy-1-methyl-2-oxopyrrolidin-3-yl]ethynyl]phenyl)-5-[(1S)-1-hydroxy ethyl]-1H-indazole-3-carboxamide

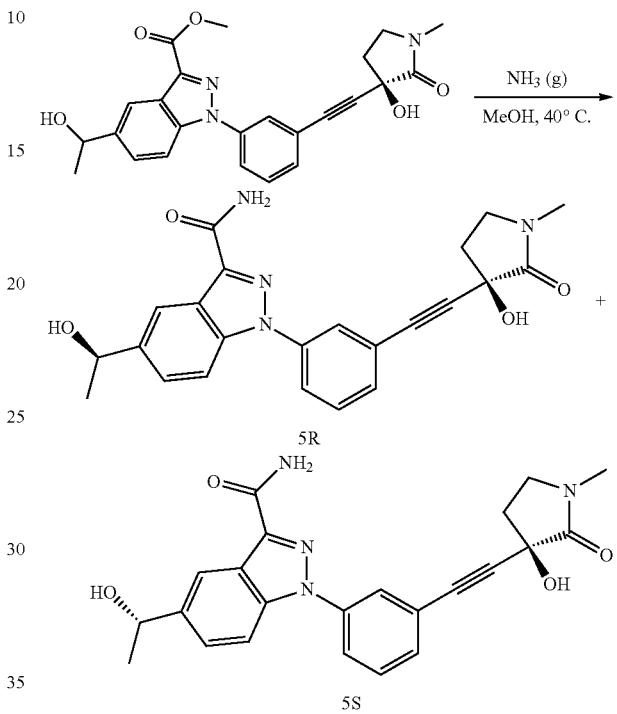

Similar to as described in General Procedure S, 1-(3-[2-[(3R)-3-hydroxy-1-methyl-2-oxopyrrolidin-3-yl]ethynyl]phenyl)-5-(1-hydroxyethyl)-1H-indazole-3-carboxylate was reacted with ammonia in methanol to give the title compounds which were separated by Chiral-Prep-HPLC with the following conditions: Column, CHIRALPAK OJ-H, 2×25 cm; mobile phase, Hex and ethanol (hold 40.0% ethanol in 19 min); Detector, UV 254/220 nm. The stereochemistry of the two isomers was arbitrarily assigned.

Isomer A (5R): 47.1 mg (24%), off-white solid. $t_R$=7.21 min (Chiralcel OJ-3, 25° C., UV-254 nm, Hex(0.1% TEA): EtOH 60:40, 1.0 mL/min). LC-MS (ES, m/z): 419 [M+H]⁺. ¹H NMR (300 MHz, CD₃OD) δ 8.36 (s, 1H), 7.96 (t, J=1.8 Hz, 1H), 7.87-7.83 (m, 2H), 7.66-7.58 (m, 3H), 5.03-4.96 (m, 1H), 3.53-3.49 (m, 2H), 2.96 (s, 3H), 2.80-2.65 (m, 1H), 2.37-2.29 (m, 1H), 1.55 (d, J=6.6 Hz, 3H).

Isomer B (5S): 51.1 mg (26%), off-white solid. $t_R$=10.10 min (Chiralcel OJ-3, 25° C., UV-254 nm, Hex(0.1% TEA): EtOH 60:40, 1.0 mL/min). LC-MS (ES, m/z): 419 [M+H]⁺. ¹H NMR (300 MHz, CD₃OD) δ 8.32 (s, 1H), 7.92 (t, J=1.8 Hz, 1H), 7.86-7.79 (m, 2H), 7.62-7.55 (m, 3H), 5.03-4.96 (m, 1H), 3.50-3.45 (m, 2H), 2.92 (s, 3H), 2.63-2.55 (m, 1H), 2.36-2.27 (m, 1H), 1.54 (d, J=6.6 Hz, 3H).

Example TT

Synthesis of 1-(3-[2-[(3R)-3-hydroxy-1-methyl-2-oxopyrrolidin-3-yl]ethynyl]phenyl)-5-(hydroxymethyl)-1H-indazole-3-carboxamide Step 1: Synthesis of methyl 1-(3-[2-[(3R)-3-hydroxy-1-methyl-2-oxopyrrolidin-3-yl]ethynyl]phenyl)-5-(hydroxymethyl)-1H-indazole-3-carboxylate

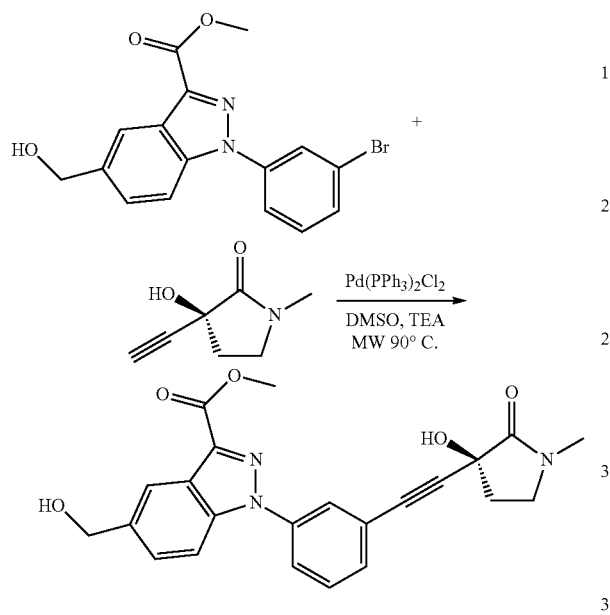

Similar to as described in General Procedure E, methyl 1-(3-bromophenyl)-5-(hydroxymethyl)-1H-indazole-3-carboxylate was reacted with (3R)-3-ethynyl-3-hydroxy-1-methylpyrrolidin-2-one to give the title compound (100 mg, crude) as a yellow solid. LC-MS (ES, m/z): 420 [M+H]⁺.

Step 2: Synthesis of 1-(3-[2-[(3R)-3-hydroxy-1-methyl-2-oxopyrrolidin-3-yl]ethynyl]phenyl)-5-(hydroxymethyl)-1H-indazole-3-carboxamide

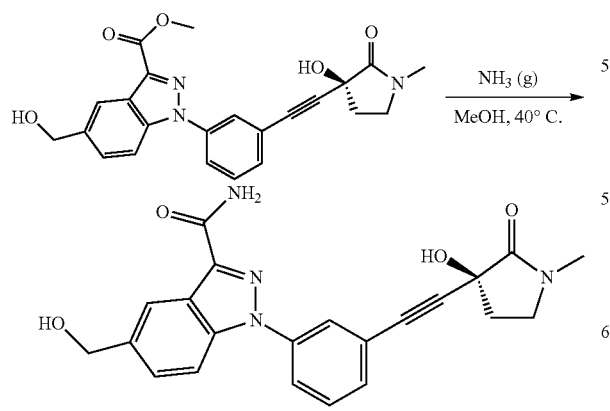

Similar to as described in General Procedure S, methyl 1-(3-[2-[(3R)-3-hydroxy-1-methyl-2-oxopyrrolidin-3-yl]ethynyl]phenyl)-5-(hydroxymethyl)-1H-indazole-3-carboxylate was reacted with ammonia in methanol to give the title compound (10.3 mg, 11%) of as an off-white solid. LC-MS (ES, m/z): 405 [M+H]⁺. $^1$H NMR (400 MHz, CD$_3$OD) δ 8.35 (s, 1H), 7.96 (s, 1H), 7.89-7.83 (m, 2H), 7.65-7.56 (m, 3H), 4.78 (s, 2H), 3.55-3.46 (m, 2H), 2.95 (s, 3H), 2.65-2.59 (m, 1H), 2.37-2.31 (m, 1H).

Example UU

Synthesis of 1-(3-[2-[(3R)-3-hydroxy-1-methyl-2-oxopyrrolidin-3-yl]ethynyl]phenyl)-5-(oxetan-3-yl)-1H,4H,5H,6H,7H-pyrazolo[4,3-c]pyridine-3-carboxamide Step 1: Synthesis of ethyl 1-(3-bromophenyl)-5-(oxetan-3-yl)-1H,4H,5H,6H,7H-pyrazolo[4,3-c]pyridine-3-carboxylat Sodium cyanoborohydride (540 mg, 8.59 mmol, 3.30 equiv) was added in portions to a stirred solution of ethyl 1-(3-bromophenyl)-1H,4H,5H,6H,7H-pyrazolo[4,3-c]pyridine-3-carboxylate (TFA salt, 1.2 g, 2.58 mmol, 1.00 equiv), oxetan-3-one (1.2 g, 16.65 mmol, 6.40 equiv), acetic acid (5 mL) in tetrahydrofuran (40 mL) at 0° C. The reaction mixture was stirred for 30 min at room temperature, quenched with saturated ammonium chloride solution, extracted with ethyl acetate, washed with brine, dried over anhydrous sodium sulfate, and concentrated under vacuum. This resulted in 1.2 g (crude) of the title compound as a yellow solid. LC-MS (ES, m/z): 392 [M+H]⁺.

Step 2: Synthesis of ethyl 1-(3-[2-[(3R)-3-hydroxy-1-methyl-2-oxopyrrolidin-3-yl]ethynyl]phenyl)-5-(oxetan-3-yl)-1H,3aH,4H,5H,6H,7H,7aH-pyrazolo[4,3-c]pyridine-3-carboxylate

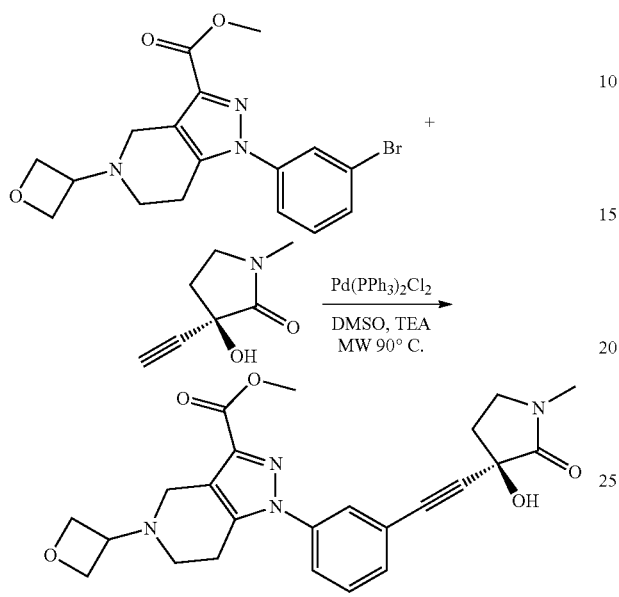

Similar to as described in General Procedure E, ethyl 1-(3-bromophenyl)-5-(oxetan-3-yl)-1H,3aH,4H,5H,6H,7H,7aH-pyrazolo[4,3-c]pyridine-3-carboxylate was reacted with (3R)-3-ethynyl-3-hydroxy-1-methylpyrrolidin-2-one to give the title compound (400 mg, crude) as a yellow solid. LC-MS (ES, m/z): 451 [M+H]$^+$.

Step 3: Synthesis of 1-(3-[2-[(3R)-3-hydroxy-1-methyl-2-oxopyrrolidin-3-yl]ethynyl]phenyl)-5-(oxetan-3-yl)-1H,4H,5H,6H,7H-pyrazolo[4,3-c]pyridine-3-carboxamide

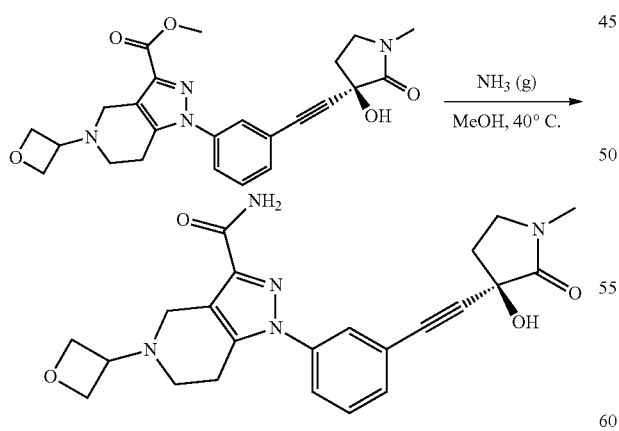

Similar to as described in General Procedure S, methyl 1-(3-[2-[(3R)-3-hydroxy-1-methyl-2-oxopyrrolidin-3-yl]ethynyl]phenyl)-5-(oxetan-3-yl)-1H,4H,5H,6H,7H-pyrazolo[4,3-c]pyridine-3-carboxylate was reacted with ammonia in methanol to give the title compound (50.8 mg, 11%) as an off-white solid. LC-MS (ES, m/z): 436 [M+H]$^+$. $^1$H NMR (300 MHz, CD$_3$OD) δ 7.78 (s, 1H), 7.68-7.66 (m, 1H), 7.56-7.54 (m, 2H), 4.82 (t, J=6.6 Hz, 2H), 4.72 (t, J=6.3 Hz, 2H), 3.88-3.84 (m, 1H), 3.71 (s, 2H), 3.50 (t, J=5.7 Hz, 2H), 2.99-2.97 (m, 2H), 2.95 (s, 3H), 2.71 (t, J=5.7 Hz, 2H), 2.61-2.59 (m, 1H), 2.39-2.32 (m, 1H).

Example VV

Synthesis of 4-fluoro-1-(4-[2-[(3R)-3-hydroxy-1-methyl-2-oxopyrrolidin-3-yl]ethynyl]pyridin-2-yl)-1H-indazole-3-carboxamide Step 1: Synthesis of 4-fluoro-3-iodo-1H-indazole

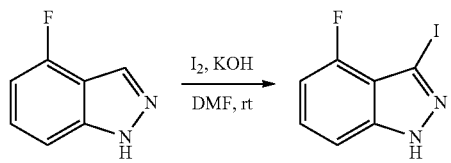 [SMILES: Fc1cccc2[nH]ncc12 ; Fc1cccc2[nH]nc(I)c12]

A suspension of 4-fluoro-1H-indazole (500 mg, 3.67 mmol, 1.00 equiv), iodine (1.87 g, 2.00 equiv) and potassium hydroxide (741 mg, 13.21 mmol, 3.60 equiv) in N,N-dimethylformamide (5 mL) was stirred overnight at room temperature. The reaction was quenched by 10% aqueous NaHSO$_3$, extracted with ethyl acetate, washed with brine, dried over anhydrous sodium sulfate, and concentrated under vacuum. The resulting solid was washed with petroleum ether to give 800 mg (83%) of the title compound as a yellow solid. LC-MS (ES, m/z): 263 [M+H]$^+$.

Step 2: Synthesis of methyl 4-fluoro-1H-indazole-3-carboxylate

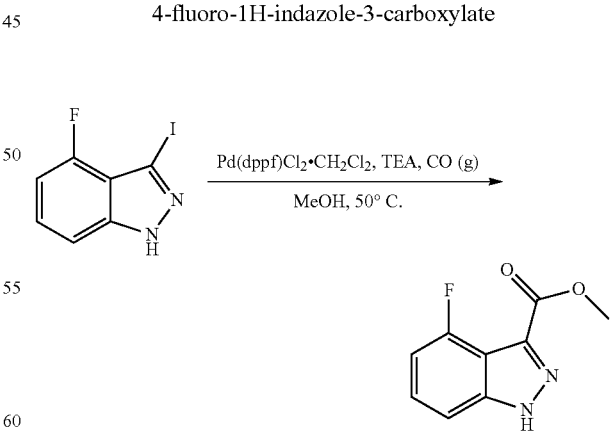

Similar to as described in General Procedure O, 4-fluoro-3-iodo-1H-indazole was reacted with carbon monoxide to give the title compound (210 mg, 71%) as a yellow solid. LC-MS (ES, m/z): 195 [M+H]$^+$.

Step 3: Synthesis of methyl 4-fluoro-1-(4-iodopyridin-2-yl)-1H-indazole-3-carboxylate

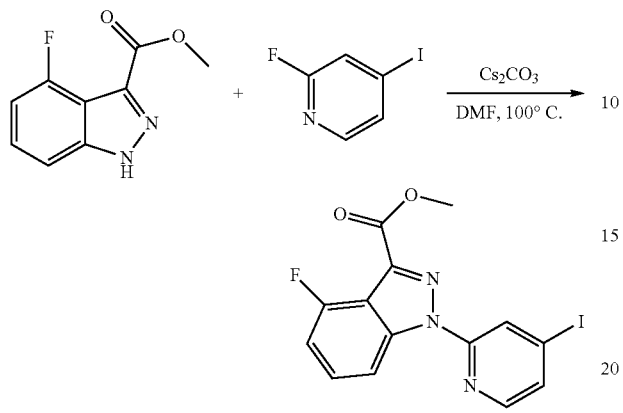

Similar to as described in General Procedure A, methyl 4-fluoro-1H-indazole-3-carboxylate was reacted with 2-fluoro-4-iodopyridine to give the title compound (120 mg, 27%) as a white solid. LC-MS (ES, m/z): 398 [M+H]$^+$.

Step 4: Synthesis of methyl 4-fluoro-1-(4-[2-[(3R)-3-hydroxy-1-methyl-2-oxopyrrolidin-3-yl]ethynyl]pyridin-2-yl)-1H-indazole-3-carboxylate

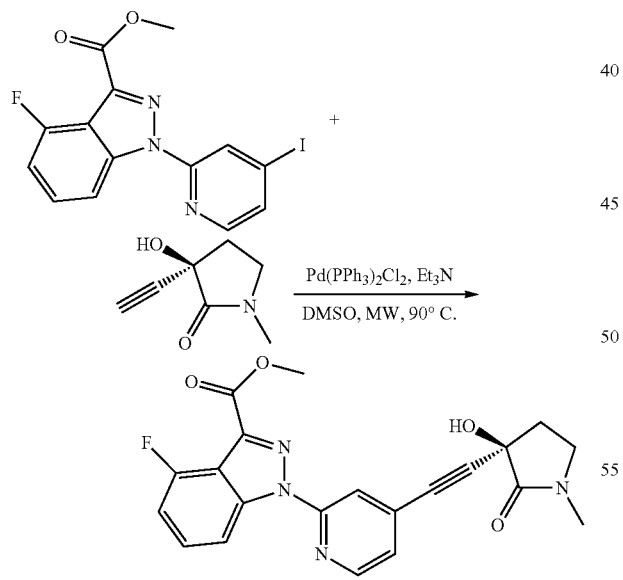

Similar to as described in General Procedure E, methyl 4-fluoro-1-(4-iodopyridin-2-yl)-1H-indazole-3-carboxylate was reacted with (3R)-3-ethynyl-3-hydroxy-1-methylpyrrolidin-2-one to give the title compound (85 mg, 75%) as a yellow solid. LC-MS (ES, m/z): 409[M+H]$^+$.

Step 5: Synthesis of 4-fluoro-1-(4-[2-[(3R)-3-hydroxy-1-methyl-2-oxopyrrolidin-3-yl]ethynyl]pyridin-2-yl)-1H-indazole-3-carboxamide

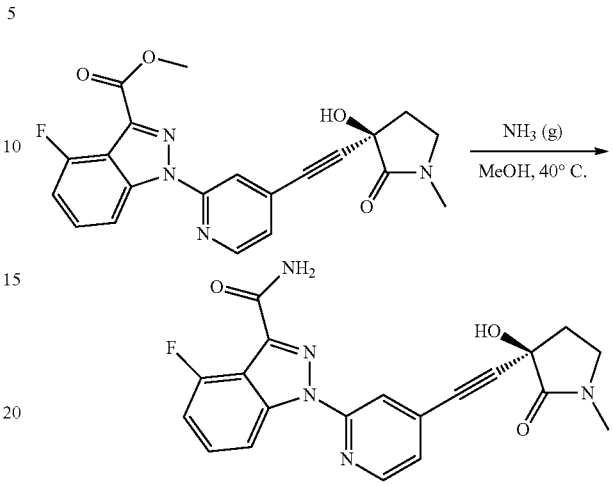

Similar to as described in General Procedure S, methyl 4-fluoro-1-(4-[2-[(3R)-3-hydroxy-1-methyl-2-oxopyrrolidin-3-yl]ethynyl]pyridin-2-yl)-1H-indazole-3-carboxylate was reacted with ammonia in methanol to give the title compound (28.1 mg, 34%) as a white solid. LC-MS (ES, m/z): 394 [M+H]$^+$. $^1$H NMR (300 MHz, CD$_3$OD) δ 8.70 (d, J=8.7 Hz, 1H), 8.57 (dd, J=5.1, 0.6 Hz, 1H), 8.27 (s, 1H), 7.61-7.54 (m, 1H), 7.39-7.36 (m, 1H), 7.14-7.08 (m, 1H), 3.53-3.46 (m, 2H), 2.95 (s, 3H), 2.68-2.60 (m, 1H), 2.40-2.31 (m, 1H).

Example WW and Example XX

Synthesis of (4R)-4-C-cyclopropane-1-(4-[2-[(3R)-3-hydroxy-1-methyl-2-oxopyrrolidin-3-yl]ethynyl]pyridin-2-yl)-4,5,6,7-tetrahydro-1H-indazole-3,4-diamido and (4S)-4-C-cyclopropane-1-(4-[2-[(3R)-3-hydroxy-1-methyl-2-oxopyrrolidin-3-yl]ethynyl]pyridin-2-yl)-4,5,6,7-tetrahydro-1H-indazole-3,4-diamido

Step 1: Synthesis of ethyl 1-(4-iodopyridin-2-yl)-4-oxo-4,5,6,7-tetrahydro-1H-indazole-3-carboxylate

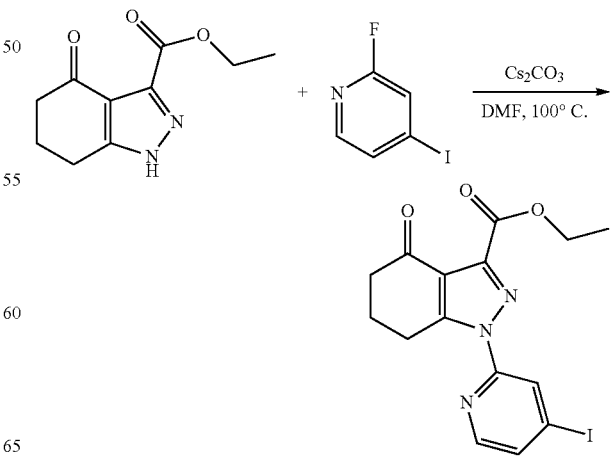

Similar to as described in General Procedure A, ethyl 4-oxo-4,5,6,7-tetrahydro-1H-indazole-3-carboxylate was reacted with 2-fluoro-4-iodopyridine to give the title compound (420 mg, 71%) as a yellow solid. LC-MS (ES, m/z): 412 [M+H]+.

Step 2: Synthesis of 4-amino-1-(4-iodopyridin-2-yl)-4,5,6,7-tetrahydro-1H-indazole-3-carboxamide

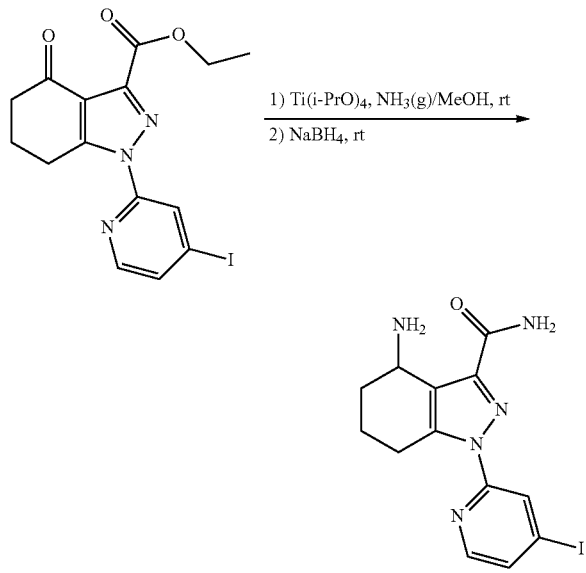

A solution of ethyl 1-(4-iodopyridin-2-yl)-4-oxo-4,5,6,7-tetrahydro-1H-indazole-3-carboxylate (420 mg, 1.02 mmol, 1.00 equiv), Ti(i-PrO)$_4$ (579 mg, 2.00 equiv) in methanol (saturated with ammonia, 5 mL) was stirred for 3 h at room temperature. Sodium borohydride (58 mg, 1.53 mmol, 1.5 equiv) was added and the resulting solution was stirred for 3 h at room temperature. The reaction was quenched by water, extracted with ethyl acetate, dried over anhydrous sodium sulfate, and concentrated under vacuum. The residue was purified on a silica gel column with dichloromethane/methanol (10:1) to give 320 mg (82%) of the title compound as a yellow solid. LC-MS (ES, m/z): 384 [M+H]+.

Step 3: Synthesis of 4-C-cyclopropane-1-(4-iodopyridin-2-yl)-4,5,6,7-tetrahydro-1H-indazole-3,4-diamido

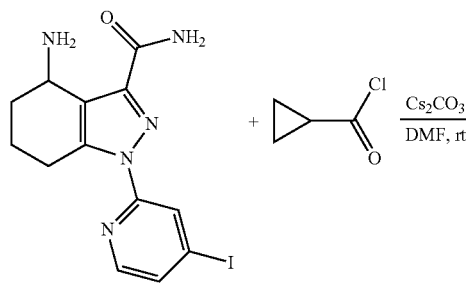

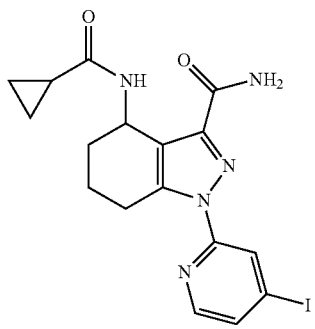

Cyclopropanecarbonyl chloride (255 mg, 2.44 mmol, 3.00 equiv) was added to a suspension of 4-amino-1-(4-iodopyridin-2-yl)-4,5,6,7-tetrahydro-1H-indazole-3-carboxamide (310 mg, 0.81 mmol, 1.00 equiv), and cesium carbonate (1.06 g, 3.25 mmol, 4.00 equiv) in N,N-dimethylformamide (2 mL) at room temperature. After 6 h the mixture was diluted with water, extracted with ethyl acetate, washed with brine, dried over anhydrous sodium sulfate and, concentrated under vacuum. The residue was purified on a silica gel column with dichloromethane/methanol (10:1) to give 200 mg (55%) of the title compound as a white solid. LC-MS (ES, m/z): 452 [M+H]+.

Step 4: (4R)-4-C-cyclopropane-1-(4-[2-[(3R)-3-hydroxy-1-methyl-2-oxopyrrolidin-3-yl]ethynyl] pyridin-2-yl)-4,5,6,7-tetrahydro-1H-indazole-3,4-diamido and (4S)-4-C-cyclopropane-1-(4-[2-[(3R)-3-hydroxy-1-methyl-2-oxopyrrolidin-3-yl]ethynyl] pyridin-2-yl)-4,5,6,7-tetrahydro-1H-indazole-3,4-diamido

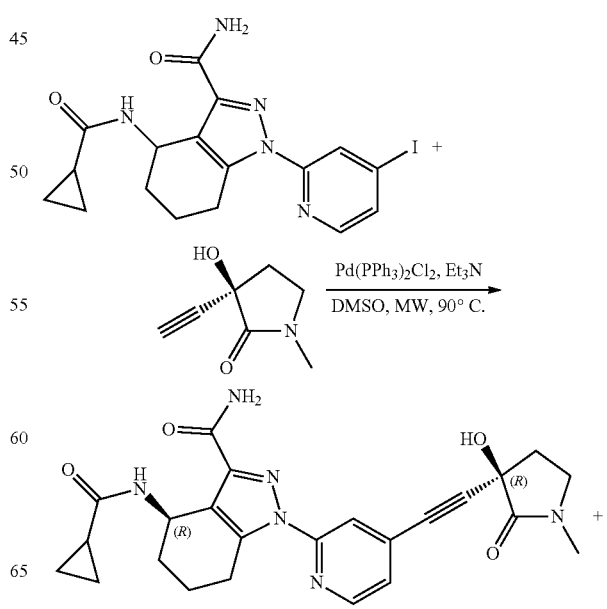

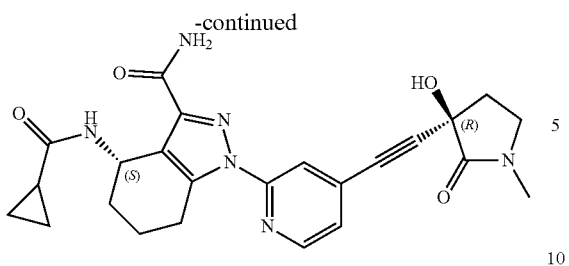

Similar to as described in General Procedure E, 4-C-cyclopropane-1-(4-iodopyridin-2-yl)-4,5,6,7-tetrahydro-1H-indazole-3,4-diamido was reacted with (3R)-3-ethynyl-3-hydroxy-1-methylpyrrolidin-2-one to give a mixture of the title compounds which were separated by Chiral-Prep-HPLC with the following conditions (Prep-HPLC-032): Column, Chiralpak AD-H, 2×25 cm; mobile phase, Hex and ethanol (hold 50.0% ethanol in 55 min); Detector, UV 254/220 nm. The stereochemistry at position 4 was arbitrarily assigned for both isomers.

Isomer A (5R): 25.2 mg (27%) as a light yellow solid. $t_R$=1.39 min (CHIRALPAK IA-3, 25° C., 254 nm, Hex(0.1% TEA):EtOH 50:50, 1.2 mL/min). LC-MS (ES, m/z): 463 [M+H]$^+$. $^1$H NMR (300 MHz, CD$_3$OD) δ 8.45 (d, J=5.1 Hz, 1H), 8.10 (s, 1H), 7.36 (d, J=5.1 Hz, 1H), 5.35-5.34 (m, 1H), 3.52-3.43 (m, 3H), 3.05-3.02 (m, 1H), 2.94 (s, 3H), 2.65-2.57 (m, 1H), 2.39-2.29 (m, 1H), 2.07-2.02 (m, 1H), 1.90-1.81 (m, 2H), 1.77-1.73 (m, 1H), 1.55-1.50 (m, 1H), 0.96-0.82 (m, 2H), 0.72-0.69 (m, 2H).

Isomer B (5S): 18.6 mg (20%) as a white solid. $t_R$=2.20 min (CHIRALPAK IA-3, 25° C., 254 nm, Hex(0.1% TEA): EtOH=50:50, 1.2 mL/min). LC-MS (ES, m/z): 463 [M+H]$^+$. $^1$H NMR (300 MHz, CD$_3$OD) δ 8.45 (d, J=5.1 Hz, 1H), 8.10 (s, 1H), 7.36 (d, J=5.1 Hz, 1H), 5.35-5.34 (m, 1H), 3.52-3.43 (m, 3H), 3.05-3.02 (m, 1H), 2.94 (s, 3H), 2.65-2.57 (m, 1H), 2.39-2.29 (m, 1H), 2.07-2.02 (m, 1H), 1.90-1.81 (m, 2H), 1.77-1.73 (m, 1H), 1.55-1.50 (m, 1H), 0.96-0.82 (m, 2H), 0.72-0.69 (m, 2H).

Example YY and Example ZZ

Synthesis of ethyl (4S)-4-hydroxy-1-(3-[2-[(3R)-3-hydroxy-1-methyl-2-oxopyrrolidin-3-yl]ethynyl]phenyl)-4-methyl-4,5,6,7-tetrahydro-1H-indazole-3-carboxylate and ethyl (4R)-4-hydroxy-1-(3-[2-[(3R)-3-hydroxy-1-methyl-2-oxopyrrolidin-3-yl]ethynyl]phenyl)-4-methyl-4,5,6,7-tetrahydro-1H-indazole-3-carboxylate Step 1: Synthesis of ethyl 1-(3-bromophenyl)-4-oxo-4,5,6,7-tetrahydro-1H-indazole-3-carboxylate

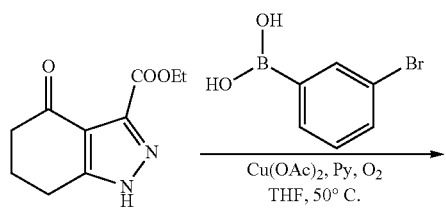

Similar to as described in General Procedure C, ethyl 4-oxo-4,5,6,7-tetrahydro-1H-indazole-3-carboxylate was reacted with (3-bromophenyl)boronic acid to give the title compound (1 g, 19%) as a yellow solid. LC-MS (ES, m/z): 363, 365 [M+H]$^+$.

Step 2: Synthesis of ethyl 1-(3-bromophenyl)-4-hydroxy-4-methyl-4,5,6,7-tetrahydro-1H-indazole-3-carboxylate

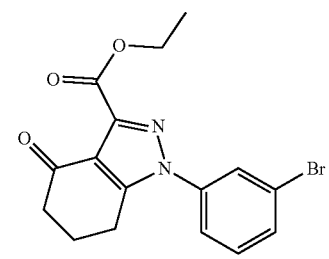

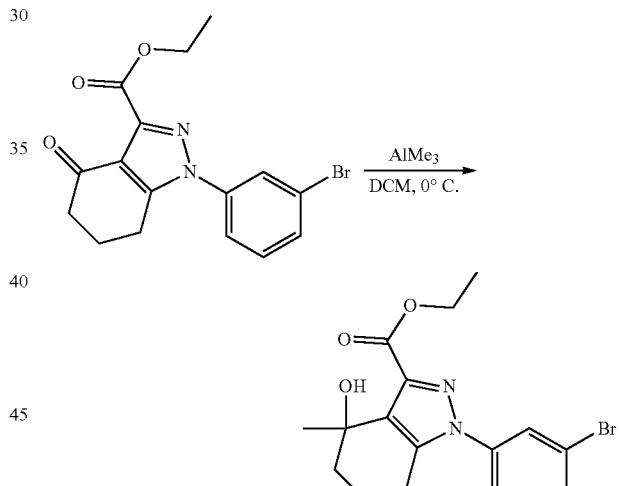

Under an inert atmosphere of nitrogen trimethyl aluminium (2.0 M in toluene, 1.54 mL, 1.2 equiv) was added into a solution of ethyl 1-(3-bromophenyl)-4-oxo-4,5,6,7-tetrahydro-1H-indazole-3-carboxylate (930 mg, 2.56 mmol, 1.00 equiv) in dichloromethane (25 mL) at 0° C. After being stirred for 2 h the reaction was quenched by water, extracted with dichloromethane, dried over anhydrous sodium sulfate, and concentrated under vacuum. The residue was purified on a silica gel column with ethyl acetate/petroleum ether (1:10) to give 700 mg (71%) of the title compound as a yellow oil. LC-MS (ES, m/z): 379, 381 [M+H]$^+$.

Step 3: Synthesis of ethyl 4-hydroxy-1-(3-[2-[(3R)-3-hydroxy-1-methyl-2-oxopyrrolidin-3-yl]ethynyl]phenyl)-4-methyl-4,5,6,7-tetrahydro-1H-indazole-3-carboxylate

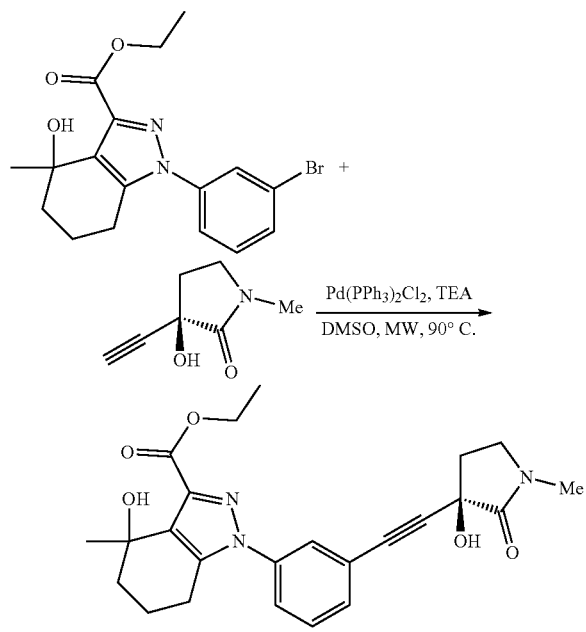

Similar to as described in General Procedure E, ethyl 1-(3-bromophenyl)-4-hydroxy-4-methyl-4,5,6,7-tetrahydro-1H-indazole-3-carboxylate was reacted with (3R)-3-ethynyl-3-hydroxy-1-methylpyrrolidin-2-one to give the title compound (230 mg) as yellow oil. LC-MS (ES, m/z): 438 [M+H]⁺.

Step 4: Synthesis of (4S)-4-hydroxy-1-(3-[2-[(3R)-3-hydroxy-1-methyl-2-oxopyrrolidin-3-yl]ethynyl]phenyl)-4-methyl-4,5,6,7-tetrahydro-1H-indazole-3-carboxylate and (4R)-4-hydroxy-1-(3-[2-[(3R)-3-hydroxy-1-methyl-2-oxopyrrolidin-3-yl]ethynyl]phenyl)-4-methyl-4,5,6,7-tetrahydro-1H-indazole-3-carboxylate

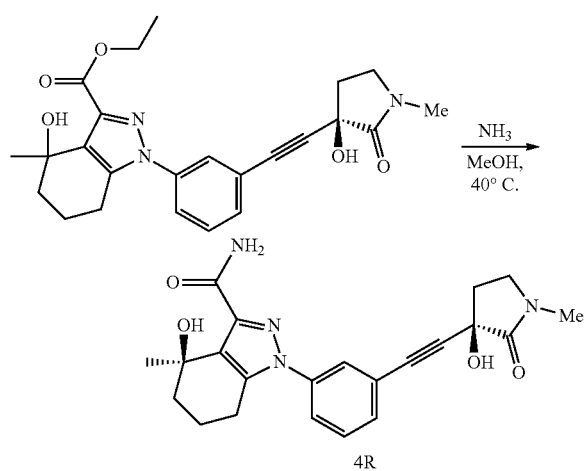

Similar to as described in General Procedure S, ethyl 4-hydroxy-1-(3-[2-[(3R)-3-hydroxy-1-methyl-2-oxopyrrolidin-3-yl]ethynyl]phenyl)-4-meth yl-4,5,6,7-tetrahydro-1H-indazole-3-carboxylate was reacted with ammonia in methanol to give the two title compounds which were separated by Chiral-Prep-HPLC with the following conditions: Column, Chiralpak IC, 2×25 cm, 5 um; mobile phase, methanol; Detector, UV 254/220 nm. The stereochemistry at position 4 was arbitrary assigned.

Isomer A (4S): 32.2 mg (21%), white solid. $t_R$=5.98 min (Chiralpak IC, 25° C., UV-254 nm, MeOH, 1.0 mL/min). LC-MS (ES, m/z): 391 [M−18+H]⁺. ¹H NMR (400 MHz, DMSO-d6) δ 8.13 (s, 1H), 7.77 (s, 1H), 7.70 (s, 1H), 7.66 (t, J=8.0 Hz, 1H), 7.55 (d, J=8.0 Hz, 1H), 7.47 (d, J=8.0 Hz, 1H), 6.51 (s, 1H), 6.30 (s, 1H), 3.37-3.30 (m, 2H), 2.84-2.80 (m, 4H), 2.67-2.61 (m, 1H), 2.51-2.41 (m, 1H), 2.22-2.17 (m, 1H), 2.15-1.95 (m, 1H), 1.93-1.73 (m, 3H), 1.42 (s, 3H).

Isomer B (4R): 32.9 mg (21%), white solid. $t_R$=7.21 min (Chiralpak IC, 25° C., UV-254 nm, MeOH, 1.0 mL/min). LC-MS (ES, m/z): 391 [M−18+H]⁺. ¹H NMR (400 MHz, DMSO-d6) δ 8.11 (s, 1H), 7.74 (s, 1H), 7.70 (s, 1H), 7.66 (t, J=8.0 Hz, 1H), 7.55 (d, J=8.0 Hz, 1H), 7.47 (d, J=8.0 Hz, 1H), 6.49 (s, 1H), 6.28 (s, 1H), 3.37-3.30 (m, 2H), 2.84-2.80 (m, 4H), 2.67-2.61 (m, 1H), 2.51-2.41 (m, 1H), 2.22-2.17 (m, 1H), 2.15-1.95 (m, 1H), 1.93-1.73 (m, 3H), 1.42 (s, 3H).

Example AAA

Synthesis of 1-[3-[(3R)-3-hydroxy-3-(5-methyl-1,3,4-oxadiazol-2-yl)but-1-yn-1-yl]phenyl]-1H-indazole-3-carboxamide Step 1: Synthesis of methyl 1-[3-[(3R)-3-hydroxy-3-(5-methyl-1,3,4-oxadiazol-2-yl)but-1-yn-1-yl]phenyl]-1H-indazole-3-carboxylate

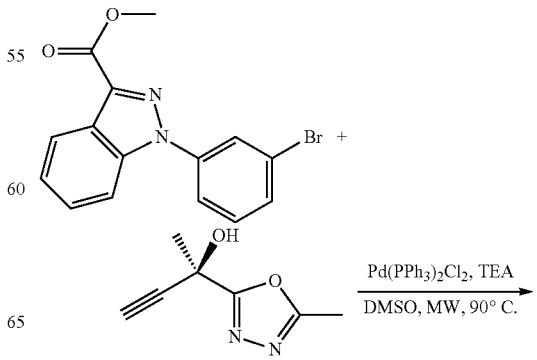

-continued

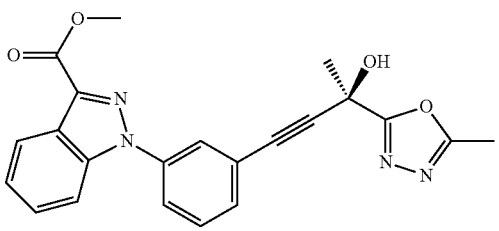

Similar to as described in General Procedure E, methyl 1-(3-bromophenyl)-1H-indazole-3-carboxylate was reacted with (2R)-2-(5-methyl-1,3,4-oxadiazol-2-yl)but-3-yn-2-ol to give the title compound (140 mg, 77%) as a light yellow solid. LC-MS (ES, m/z): 403 [M+H]⁺.

Step 2: Synthesis of 1-[3-[(3R)-3-hydroxy-3-(5-methyl-1,3,4-oxadiazol-2-yl)but-1-yn-1-yl]phenyl]-1H-indazole-3-carboxamide

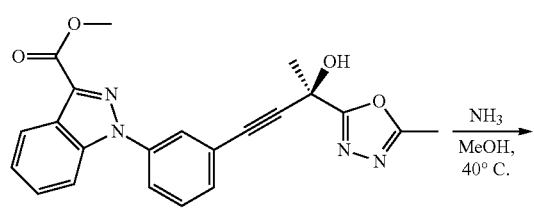

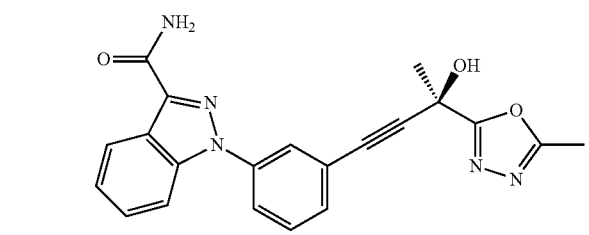

Similar to as described in General Procedure S, methyl 1-[3-[(3R)-3-hydroxy-3-(5-methyl-1,3,4-oxadiazol-2-yl)but-1-yn-1-yl]phenyl]-1H-indazole-3-carboxylate was reacted with ammonia in methanol to give the title compound (82.7 mg, 61%) as a white solid. LC-MS (ES, m/z): 388 [M+H]⁺. ¹H NMR (400 MHz, CD₃OD) δ 8.36 (d, J=8.0 Hz, 1H), 7.98 (s, 1H), 7.91-7.85 (m, 2H), 7.67-7.55 (m, 3H), 7.41 (t, J=7.2 Hz, 1H), 2.60 (s, 3H), 2.02 (s, 3H).

Example BBB

Synthesis of 1-[3-[(3R)-3-hydroxy-3-(pyridazin-3-yl)but-1-yn-1-yl]phenyl]-1H-indazole-3-carboxamide Step 1: Synthesis of 1-(3-iodophenyl)-1H-indazole-3-carboxamide

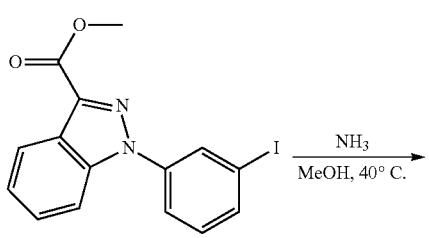

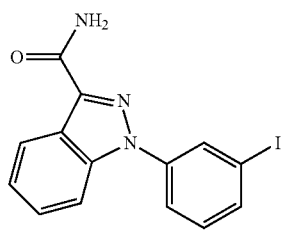

Similar to as described in General Procedure S, methyl 1-(3-iodophenyl)-1H-indazole-3-carboxylate was reacted with ammonia in methanol to give the title compound (900 mg, 89%) as a white solid. LC-MS (ES, m/z): 364 [M+H]⁺.

Step 2: Synthesis of 1-[3-[(3R)-3-hydroxy-3-(pyridazin-3-yl)but-1-yn-1-yl]phenyl]-1H-indazole-3-carboxamide

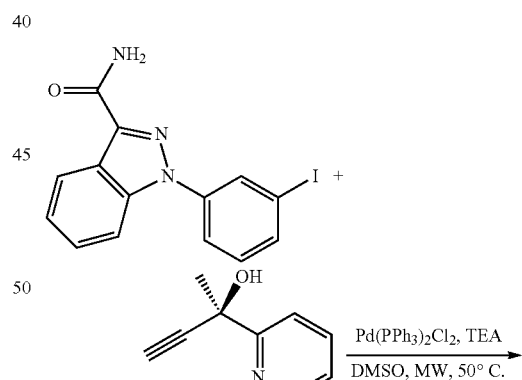

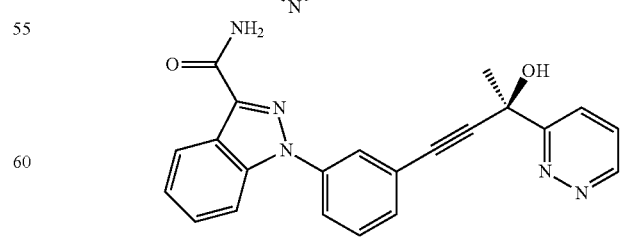

Similar to as described in General Procedure E, 1-(3-iodophenyl)-1H-indazole-3-carboxamide was reacted with (2R)-2-(pyridazin-3-yl)but-3-yn-2-ol to give the title compound (49.4 mg, 31%) as a green solid. LC-MS (ES, m/z): 384 [M+H]+. 1H NMR (400 MHz, CD3OD) δ 9.06-9.05 (m, 1H), 8.25 (d, J=8.0 Hz, 1H), 8.07-8.04 (dd, J=8.4, 1.6 Hz, 1H), 7.84 (s, 1H), 7.76-7.68 (m, 3H), 7.53-7.43 (m, 3H), 7.29 (t, J=7.6 Hz, 1H), 1.91 (s, 3H).

Example CCC and Example DDD

Synthesis of (4R)-1-(3-[2-[(3R)-3-hydroxy-1-methyl-2-oxopyrrolidin-3-yl]ethynyl]phenyl)-4-(1H-pyrazol-1-yl)-4,5,6,7-tetrahydro-1H-indazole-3-carboxamide and (4S)-1-(3-[2-[(3R)-3-hydroxy-1-methyl-2-oxopyrrolidin-3-yl]ethynyl]phenyl)-4-(1H-pyrazol-1-yl)-4,5,6,7-tetrahydro-1H-indazole-3-carboxamide Step 1: Synthesis of ethyl 1-(3-bromophenyl)-4-chloro-4,5,6,7-tetrahydro-1H-indazole-3-carboxylate

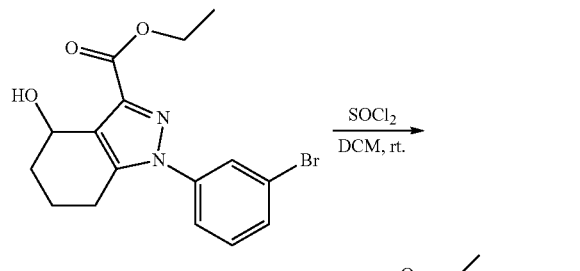

To a solution of ethyl 1-(3-bromophenyl)-4-hydroxy-4,5,6,7-tetrahydro-1H-indazole-3-carboxylate (300 mg, 0.82 mmol, 1.00 equiv) in dichloromethane (4 mL) was added thionyl chloride (2 mL, 27.57 mmol) and stirred for overnight at room temperature. The resulting mixture was concentrated under vacuum to give 280 mg (89%) of the title compound as a white solid.

Step 2: Synthesis of ethyl 1-(3-bromophenyl)-4-(1H-pyrazol-1-yl)-4,5,6,7-tetrahydro-1H-indazole-3-carboxylate

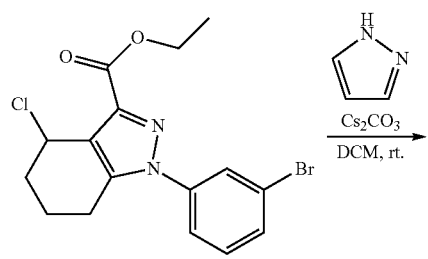

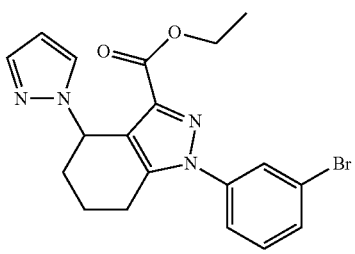

To a solution of ethyl 1-(3-bromophenyl)-4-chloro-4,5,6,7-tetrahydro-1H-indazole-3-carboxylate (280 mg, 0.73 mmol, 1.00 equiv) in dichloromethane (5 mL) was added 1H-pyrazole (99 mg, 1.45 mmol, 2.00 equiv), cesium carbonate (714 mg, 2.19 mmol, 3.00 equiv) and the reaction was stirred overnight at room temperature. The reaction mixture was diluted with dichloromethane (20 mL), washed with brine (20 mL), concentrated under vacuum and the crude product was purified by a silica gel column with ethyl acetate/petroleum ether (1:2) to give 240 mg (79%) of the title compound as a colorless oil. LC-MS (ES, m/z): 415,417 [M+H]+.

Step 3: Synthesis of ethyl 1-(3-[2-[(3R)-3-hydroxy-1-methyl-2-oxopyrrolidin-3-yl]ethynyl]phenyl)-4-(1H-pyrazol-1-yl)-4,5,6,7-tetrahydro-1H-indazole-3-carboxylate

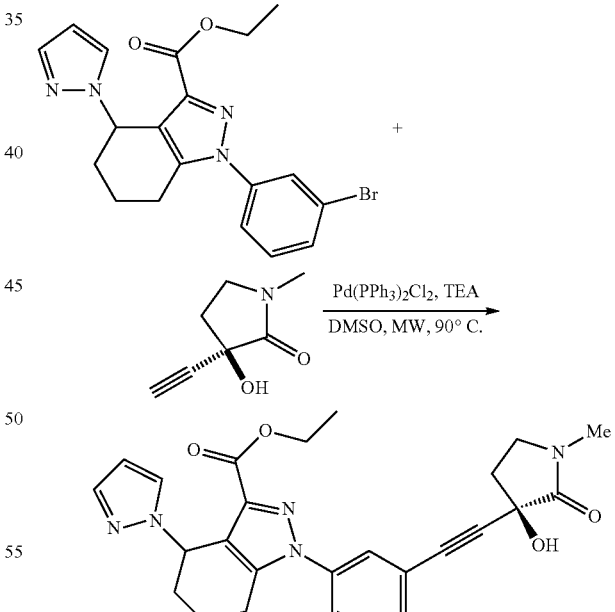

Similar to as described in General Procedure E, ethyl 1-(3-bromophenyl)-4-(1H-pyrazol-1-yl)-4,5,6,7-tetrahydro-1H-indazole-3-carboxylate was reacted with (3R)-3-ethynyl-3-hydroxy-1-methylpyrrolidin-2-one to give the title compound (240 mg, 92%) as a red solid. LC-MS (ES, m/z): 474 [M+H]+.

283

Step 4: Synthesis of (4R)-1-(3-[2-[(3R)-3-hydroxy-1-methyl-2-oxopyrrolidin-3-yl]ethynyl]phenyl)-4-(1H-pyrazol-1-yl)-4,5,6,7-tetrahydro-1H-indazole-3-carboxamide and (4S)-1-(3-[2-[(3R)-3-hydroxy-1-methyl-2-oxopyrrolidin-3-yl]ethynyl]phenyl)-4-(1H-pyrazol-1-yl)-4,5,6,7-tetrahydro-1H-indazole-3-carboxamide

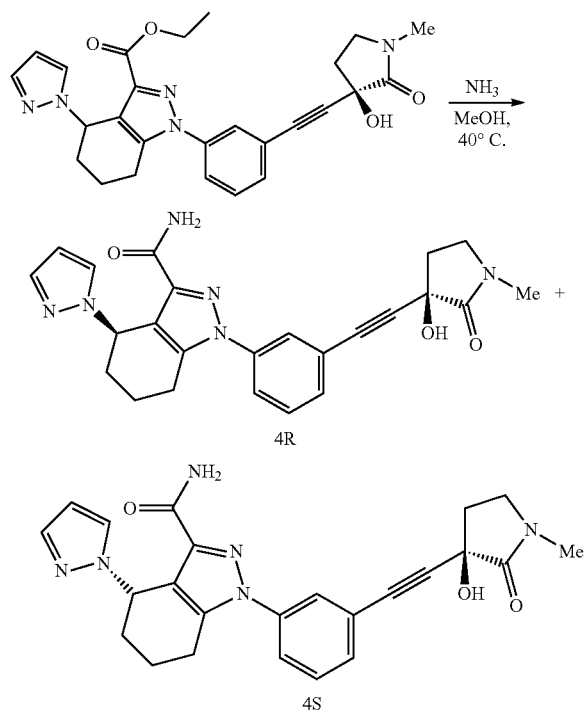

Similar to as described in General Procedure S, ethyl 1-(3-[2-[(3R)-3-hydroxy-1-methyl-2-oxopyrrolidin-3-yl]ethynyl]phenyl)-4-(1H-pyrazol-1-yl)-4,5,6,7-tetrahydro-1H-indazole-3-carboxylate was reacted with ammonia in methanol to give the two title compounds which were separated by Chiral-Prep-HPLC with the following conditions: Column, Chiralpak AD-H, 2×25 cm; mobile phase, Hex-HPLC and ethanol-HPLC (hold 40% ethanol-HPLC in 38 min); Detector, UV 254/220 nm. The stereochemistry at position 4 was arbitrary assigned.

Isomer A (4R): 16.4 mg, 7%), white solid. $t_R$=7.8 min (CHIRALPAK AD-H, 25° C., UV-254 nm, Hex(0.1% TEA): EtOH=50:50, 1.0 ml/min). LC-MS (ES, m/z): 445 [M+H]$^+$. $^1$H NMR (300 MHz, CD$_3$OD) δ 7.82 (s, 1H), 7.73-7.69 (m, 1H), 7.59-7.57 (m, 2H), 7.48-7.46 (m, 2H), 6.23 (t, J=2.1 Hz, 1H), 5.99 (t, J=4.2 Hz, 1H), 3.53-3.49 (m, 2H), 2.96 (s, 3H), 2.91-2.86 (m, 2H), 2.66-2.58 (m, 1H), 2.39-2.24 (m, 3H), 1.98-1.72 (m, 2H).

Isomer B (4S): 30.3 mg, 13%), white solid. $t_R$=13.1 min (CHIRALPAK AD-H, 25° C., UV-254 nm, Hex(0.1% TEA): EtOH=50:50, 1.0 ml/min). LC-MS (ES, m/z): 445 [M+H]$^+$. $^1$H NMR (400 MHz, CD$_3$OD) δ 7.82 (s, 1H), 7.72-7.69 (m, 1H), 7.58 (d, J=5.2 Hz, 2H), 7.46 (d, J=2, 8 Hz, 2H), 6.22 (t, J=2.0 Hz, 1H), 5.98 (t, J=4.0 Hz, 1H), 3.51-3.48 (m, 2H), 2.95 (s, 3H), 2.90-2.86 (m, 2H), 2.64-2.58 (m, 1H), 2.37-2.24 (m, 3H), 1.91-1.88 (m, 1H), 1.79-1.77 (m, 1H).

284

Example EEE

Synthesis of tert-butyl 3-carbamoyl-1-(3-[2-[(3R)-3-hydroxy-1-methyl-2-oxopyrrolidin-3-yl]ethynyl]phenyl)-1H,4H,5H,6H,7H-pyrazolo[4,3-c]pyridine-5-carboxylate Step 1: Synthesis of tert-butyl 3-(2-ethoxy-2-oxoacetyl)-4-oxopiperidine-1-carboxylate

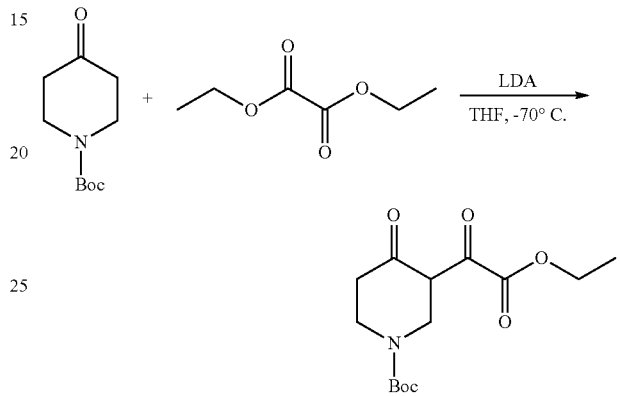

Similar to as described in General Procedure Y Step 1, tert-butyl 4-oxopiperidine-1-carboxylate was reacted with diethyl oxalate to give the title compound (13.0 g, 43%) as a yellow solid. LC-MS (ES, m/z): 300 [M+H]$^+$.

Step 2: Synthesis of 5-tert-butyl 3-ethyl 1-(3-bromophenyl)-1H,4H,5H,6H,7H-pyrazolo[4,3-c]pyridine-3,5-dicarboxylate

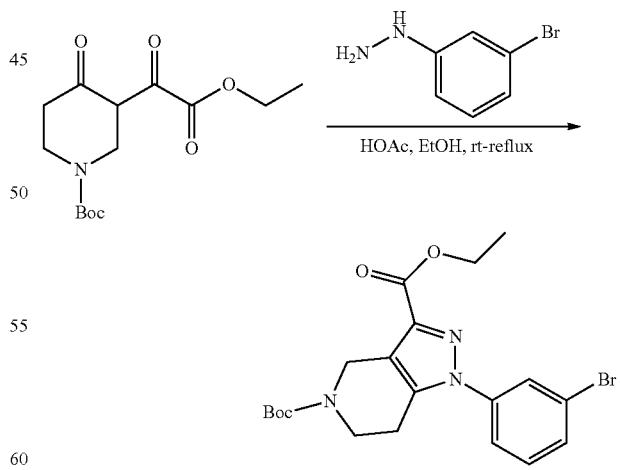

Similar to as described in General Procedure Y Step 2, tert-butyl 3-(2-ethoxy-2-oxoacetyl)-4-oxopiperidine-1-carboxylate was reacted with (3-bromophenyl)hydrazine hydrochloride to give the title compound (500 mg, 11%) as a yellow solid. LC-MS (ES, m/z): 450, 452 [M+H]$^+$.

Step 3: Synthesis of 5-tert-butyl 3-ethyl 1-(3-[2-[(3R)-3-hydroxy-1-methyl-2-oxopyrrolidin-3-yl]ethynyl]phenyl)-1H,4H,5H,6H,7H-pyrazolo[4,3-c]pyridine-3,5-dicarboxylate

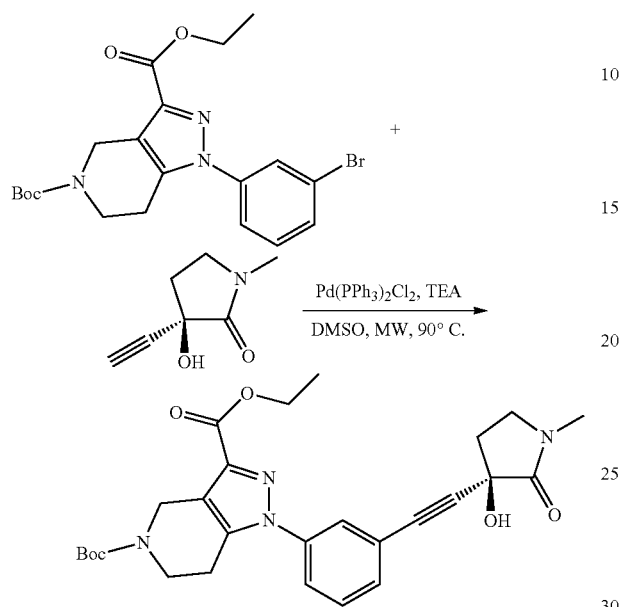

Similar to as described in General Procedure E, 5-tert-butyl 3-ethyl 1-(3-bromophenyl)-1H,4H,5H,6H,7H-pyrazolo[4,3-c]pyridine-3,5-dicarboxylate was reacted with (3R)-3-ethynyl-3-hydroxy-1-methylpyrrolidin-2-one to give the title compound (310 mg, 91%) as a yellow solid. LC-MS (ES, m/z): 509 [M+H]⁺.

Step 4: Synthesis of tert-butyl 3-carbamoyl-1-(3-[2-[(3R)-3-hydroxy-1-methyl-2-oxopyrrolidin-3-yl]ethynyl]phenyl)-1H,4H,5H,6H,7H-pyrazolo[4,3-c]pyridine-5-carboxylate

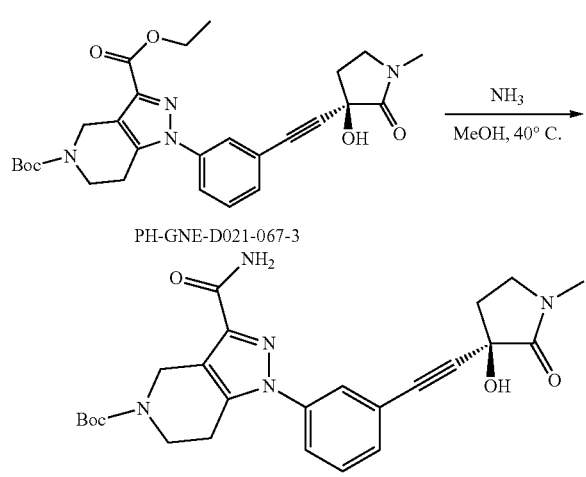

Similar to as described in General Procedure S, 5-tert-butyl 3-ethyl 1-(3-[2-[(3R)-3-hydroxy-1-methyl-2-oxopyrrolidin-3-yl]ethynyl]phenyl)-1H,4H,5H,6H,7H-pyrazolo[4,3-c]pyridine-3,5-dicarboxylate was reacted with ammonia in methanol to give the title compound (150 mg, 50%) as a white solid. LC-MS (ES, m/z): 424 [M−56]⁺. ¹H NMR (300 MHz, CD₃OD) δ 7.75 (s, 1H), 7.67-7.61 (m, 1H), 7.57-7.51 (m, 2H), 4.72 (s, 2H), 3.72 (t, J=5.4 Hz, 2H), 3.51-3.47 (m, 2H), 2.95-2.88 (m, 5H), 2.65-2.57 (m, 1H), 2.38-2.28 (m, 1H), 1.52 (s, 9H).

Example FFF

Synthesis of 1-(3-[2-[(3R)-3-hydroxy-1-methyl-2-oxopyrrolidin-3-yl]ethynyl]phenyl)-1H,4H,5H,6H,7H-pyrazolo[4,3-c]pyridine-3-carboxamide

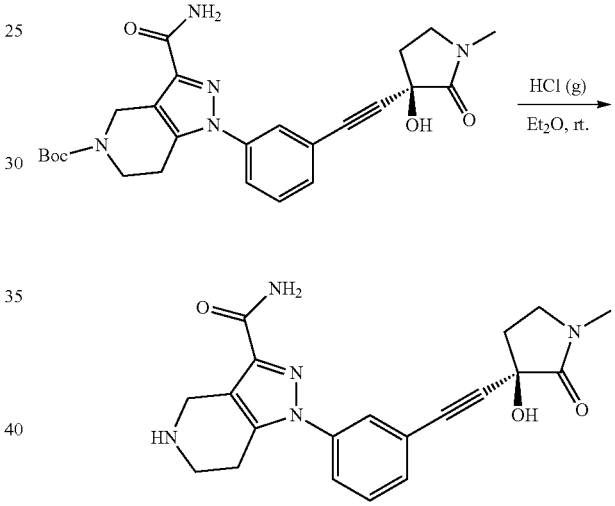

HCl (gas) was introduced into a suspension of tert-butyl 3-carbamoyl-1-(3-[2-[(3R)-3-hydroxy-1-methyl-2-oxopyrrolidin-3-yl]ethynyl]phenyl)-1H,4H,5H,6H,7H-pyrazolo[4,3-c]pyridine-5-carboxylate (100 mg, 0.21 mmol, 1.00 equiv) in diethyl ether (5 mL) and stirred for 1 h at 25° C. The resulting mixture was concentrated under vacuum and the crude product (90 mg) was purified by Prep-HPLC with the following conditions: Column, Xbridge RP18 19×150; mobile phase, water with 0.05% NH₃ and MeCN (10.0% MeCN up to 30.0% in 8 min); Detector, 254/220 nm to give 24 mg (30%) of the title compound as a white solid. LC-MS (ES, m/z): 380 [M+1]⁺, 759 [2M+H]⁺. ¹H NMR (400 MHz, CD₃OD) δ 7.63 (s, 1H), 7.54-7.51 (m, 1H), 7.44-7.39 (m, 2H), 3.97 (s, 2H), 3.39-3.36 (m, 2H), 2.95 (t, J=5.6 Hz, 2H), 2.83 (s, 3H), 2.76-2.69 (m, 2H), 2.51-2.45 (m, 1H), 2.25-2.18 (m, 1H).

Example GGG

Synthesis of 5-acetyl-1-(3-[2-[(3R)-3-hydroxy-1-methyl-2-oxopyrrolidin-3-yl]ethynyl]phenyl)-1H,4H,5H,6H,7H-pyrazolo[4,3-c]pyridine-3-carboxamide Step 1: Synthesis of ethyl 1-(3-bromophenyl)-1H,4H,5H,6H,7H-pyrazolo[4,3-c]pyridine-3-carboxylate

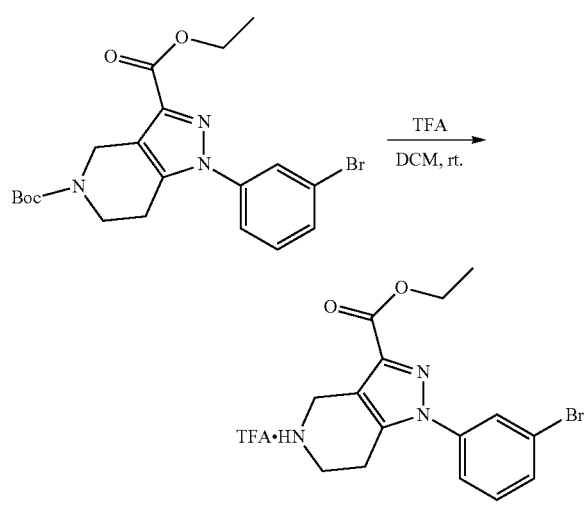

Trifluoroacetic acid (2.5 mL, 33.66 mmol, 30.30 equiv) was added dropwise into a solution of 5-tert-butyl 3-ethyl 1-(3-bromophenyl)-1H,4H,5H,6H,7H-pyrazolo[4,3-c]pyridine-3,5-dicarboxylate (500 mg, 1.11 mmol, 1.00 equiv) in dichloromethane (10 mL, 157.30 mmol, 141.70 equiv) and the reaction mixture was stirred for 1 h at 25° C. The resulting mixture was concentrated under vacuum to give 450 mg (87%) of crude ethyl 1-(3-bromophenyl)-1H,4H,5H,6H,7H-pyrazolo[4,3-c]pyridine-3-carboxylate trifluoroacetic acid salt as a yellow solid. LC-MS (ES, m/z): 350, 352 [M+H]$^+$.

Step 2: Synthesis of ethyl 5-acetyl-1-(3-bromophenyl)-1H,4H,5H,6H,7H-pyrazolo[4,3-c]pyridine-3-carboxylate

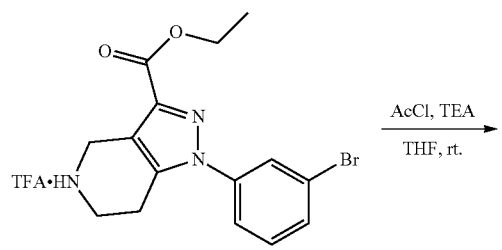

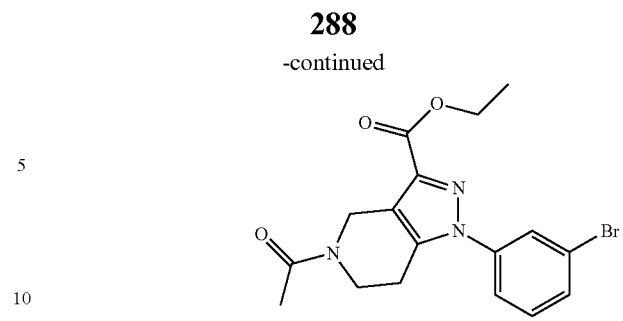

Acetyl chloride (32 mg, 0.41 mmol, 1.20 equiv) was added into a solution of ethyl 1-(3-bromophenyl)-1H,4H,5H,6H,7H-pyrazolo[4,3-c]pyridine-3-carboxylate trifluoroacetic acid salt (150 mg, 0.32 mmol, 1.00 equiv) and triethylamine (102 mg, 1.01 mmol, 3.00 equiv) in tetrahydrofuran (5 mL) and the reaction was stirred for 1 h at 0° C. The reaction was then quenched by 3 mL of brine, extracted with ethyl acetate, dried over anhydrous sodium sulfate, and concentrated under vacuum. The residue was purified on a silica gel column with ethyl acetate/petroleum ether (3:2) to give 70 mg (55%) of the title compound as a yellow solid. LC-MS (ES, m/z): 392, 394 [M+H]$^+$.

Step 3: Synthesis of ethyl 5-acetyl-1-(3-[2-[(3R)-3-hydroxy-1-methyl-2-oxopyrrolidin-3-yl]ethynyl]phenyl)-1H,4H,5H,6H,7H-pyrazolo[4,3-c]pyridine-3-carboxylate

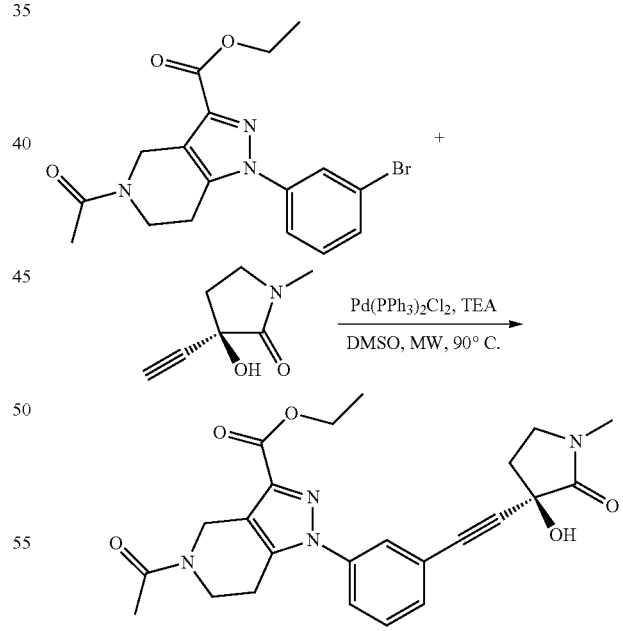

Similar to as described in General Procedure E, ethyl 5-acetyl-1-(3-bromophenyl)-1H,4H,5H,6H,7H-pyrazolo[4,3-c]pyridine-3-carboxylate was reacted with (3R)-3-ethynyl-3-hydroxy-1-methylpyrrolidin-2-one to give 65 mg of the title compound as a yellow solid. LC-MS (ES, m/z): 451 [M+H]$^+$.

Step 4: Synthesis of 5-acetyl-1-(3-[2-[(3R)-3-hydroxy-1-methyl-2-oxopyrrolidin-3-yl]ethynyl]phenyl)-1H,4H,5H,6H,7H-pyrazolo[4,3-c]pyridine-3-carboxamide

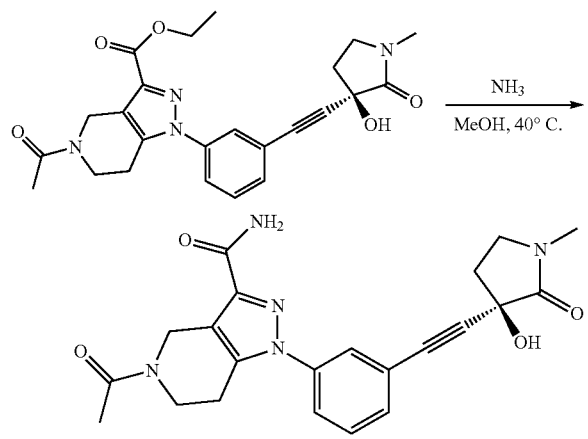

Similar to as described in General Procedure S, ethyl 5-acetyl-1-(3-[2-[(3R)-3-hydroxy-1-methyl-2-oxopyrrolidin-3-yl]ethynyl]phenyl)-1H,4H,5H,6H,7H-pyrazolo[4,3-c]pyridine-3-carboxylate was reacted with ammonia in methanol to give the title compound (19.3 mg, 32%) as a white solid. LC-MS (ES, m/z): 422 [M+H]$^+$. $^1$H NMR (400 MHz, CD$_3$OD) δ 7.64 (s, 1H), 7.55-7.51 (m, 1H), 7.45-7.41 (m, 2H), 4.73 (d, J=10.4 Hz, 2H), 3.77 (t, J=6.0 Hz, 1H), 3.68 (t, J=5.6 Hz, 1H), 3.38 (t, J=5.6 Hz, 2H), 2.90 (t, J=5.6 Hz, 1H), 2.83-2.78 (m, 4H), 2.51-2.45 (m, 1H), 2.25-2.18 (m, 1H), 2.13 (s, 3H).

Example HHH

Synthesis of 5-cyclopropanecarbonyl-1-(3-[2-[(3R)-3-hydroxy-1-methyl-2-oxopyrrolidin-3-yl]ethynyl]phenyl)-1H,4H,5H,6H,7H-pyrazolo[4,3-c]pyridine-3-carboxamide Step 1: Synthesis of ethyl 1-(3-bromophenyl)-5-cyclopropanecarbonyl-1H,4H,5H,6H,7H-pyrazolo[4,3-c]pyridine-3-carboxylate

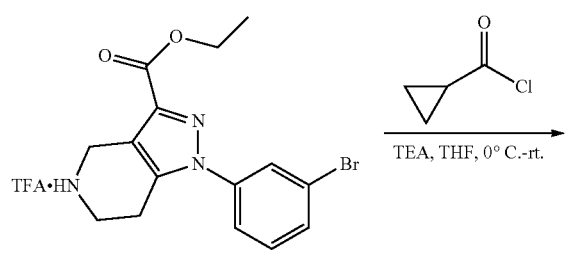

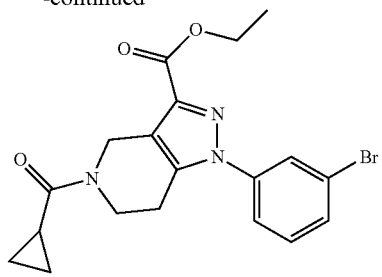

Cyclopropanecarbonyl chloride (42 mg, 0.40 mmol, 1.20 equiv) was added into a solution of ethyl 1-(3-bromophenyl)-1H,4H,5H,6H,7H-pyrazolo[4,3-c]pyridine-3-carboxylate trifluoroacetic acid salt (150 mg, 0.32 mmol, 1.00 equiv) and triethylamine (102 mg, 1.01 mmol, 3.00 equiv) in THF (5 mL), and the reaction was stirred at 0° C. After 1 h the reaction was quenched with 3 mL of brine, extracted with ethyl acetate, dried over anhydrous sodium sulfate, and concentrated under vacuum. The residue was purified on a silica gel column with ethyl acetate/petroleum ether (1:2) to give 70 mg (52%) of the title compound as a yellow solid. LC-MS (ES, m/z): 418, 420 [M+H]$^+$.

Step 2: Synthesis of ethyl 5-cyclopropanecarbonyl-1-(3-[2-[(3R)-3-hydroxy-1-methyl-2-oxopyrrolidin-3-yl]ethynyl]phenyl)-1H,4H,5H,6H,7H-pyrazolo[4,3-c]pyridine-3-carboxylate

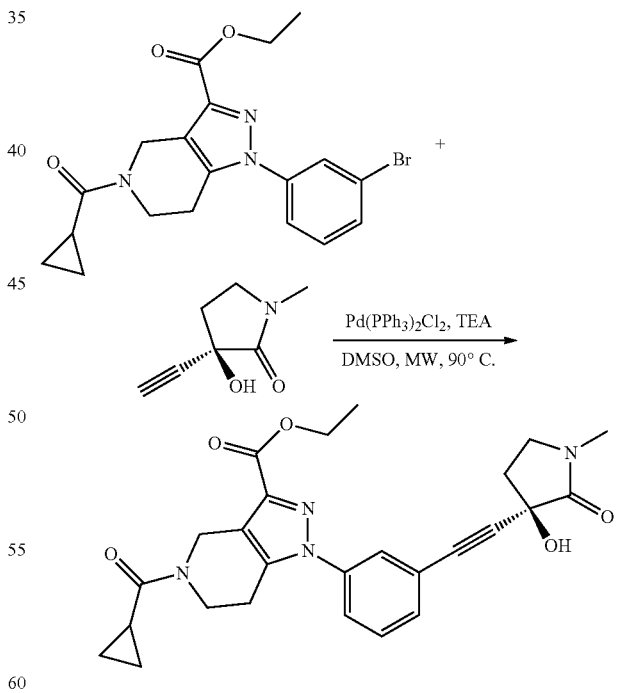

Similar to as described in General Procedure E, ethyl 1-(3-bromophenyl)-5-cyclopropanecarbonyl-1H,4H,5H,6H,7H-pyrazolo[4,3-c]pyridine-3-carboxylate was reacted with (3R)-3-ethynyl-3-hydroxy-1-methylpyrrolidin-2-one to give 50 mg of the title compound (crude) as a yellow solid. LC-MS (ES, m/z): 477 [M+H]$^+$.

Step 3: Synthesis of 5-cyclopropanecarbonyl-1-(3-[2-[(3R)-3-hydroxy-1-methyl-2-oxopyrrolidin-3-yl]ethynyl]phenyl)-1H,4H,5H,6H,7H-pyrazolo[4,3-c]pyridine-3-carboxamide

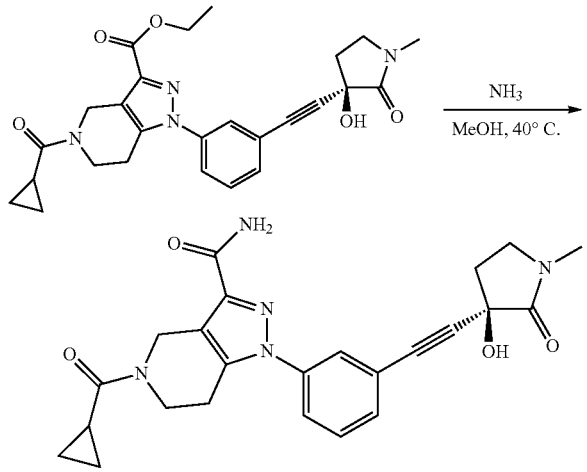

Similar to as described in General Procedure S, ethyl 5-cyclopropanecarbonyl-1-(3-[2-[(3R)-3-hydroxy-1-methyl-2-oxopyrrolidin-3-yl]ethynyl]phenyl)-1H,4H,5H,6H,7H-pyrazolo[4,3-c]pyridine-3-carboxylate was reacted with ammonia in methanol to give the title compound (9.1 mg, 19%) as a white solid. LC-MS (ES, m/z): 448 [M+H]$^+$. $^1$H NMR (300 MHz, DMSO-d$_6$) δ: 7.73-7.68 (m, 3H), 7.58-7.46 (m, 2H), 7.39-7.35 (m, 1H), 6.50 (s, 1H), 4.91 (br s, 1H), 4.68 (m, 1H), 3.92 (m, 1H), 3.75 (m, 1H), 3.37-3.29 (m, 2H), 3.09-2.97 (m, 2H), 2.80 (s, 3H), 2.46-2.40 (m, 1H), 2.27-2.17 (m, 1H), 0.80-0.71 (m, 4H).

Example III

Synthesis of 1-(3-[2-[(3R)-3-hydroxy-1-methyl-2-oxopyrrolidin-3-yl]ethynyl]phenyl)-5-(2-hydroxy-2-m ethylpropyl)-1H,4H,5H,6H,7H-pyrazolo[4,3-c]pyridine-3-carboxamide

Step 1: Synthesis of ethyl 1-(3-bromophenyl)-5-(2-hydroxy-2-methylpropyl)-1H,4H,5H,6H,7H-pyrazolo[4,3-c]pyridine-3-carboxylate

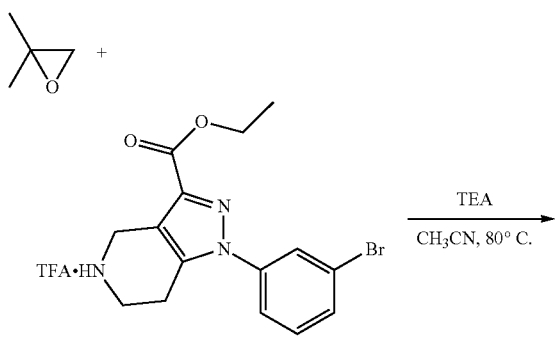

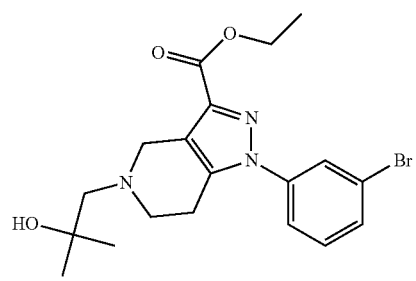

A solution of ethyl 1-(3-bromophenyl)-1H,4H,5H,6H,7H-pyrazolo[4,3-c]pyridine-3-carboxylate trifluoroacetic acid salt (500 mg, 1.08 mmol, 1.00 equiv), triethylamine (327 mg, 3.23 mmol, 3.00 equiv) and 2,2-dimethyloxirane (116.5 mg, 1.62 mmol, 1.50 equiv) in CH$_3$CN (20 mL) was stirred for 2 days at 80° C. The resulting mixture was concentrated under vacuum and the residue was purified on a silica gel column with ethyl acetate/petroleum ether (3:7) to give 100 mg (22%) of the title compound as a yellow solid. LC-MS (ES, m/z): 422, 424 [M+H]$^+$.

Step 2: Synthesis of ethyl 1-(3-[2-[(3R)-3-hydroxy-1-methyl-2-oxopyrrolidin-3-yl]ethynyl]phenyl)-5-(2-hydroxy-2-m ethylpropyl)-1H,4H,5H,6H,7H-pyrazolo[4,3-c]pyridine-3-carboxylate

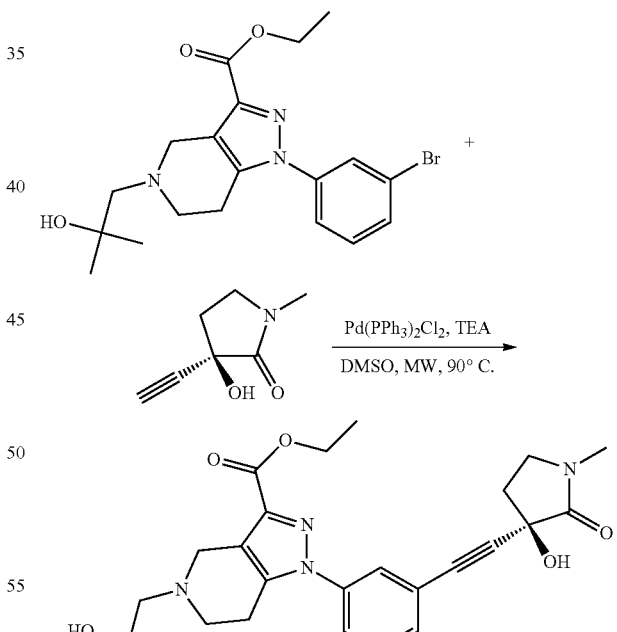

Similar to as described in General Procedure E, ethyl 1-(3-bromophenyl)-5-(2-hydroxy-2-methylpropyl)-1H,4H,5H,6H,7H-pyrazolo[4,3-c]pyridine-3-carboxylate was reacted with (3R)-3-ethynyl-3-hydroxy-1-methylpyrrolidin-2-one to give the title compound (85 mg, 83%) as a yellow solid. LC-MS (ES, m/z): 481 [M+H]$^+$.

Step 3: Synthesis of 1-(3-[2-[(3R)-3-hydroxy-1-methyl-2-oxopyrrolidin-3-yl]ethynyl]phenyl)-5-(2-hydroxy-2-m ethylpropyl)-1H,4H,5H,6H,7H-pyrazolo[4,3-c]pyridine-3-carboxamide

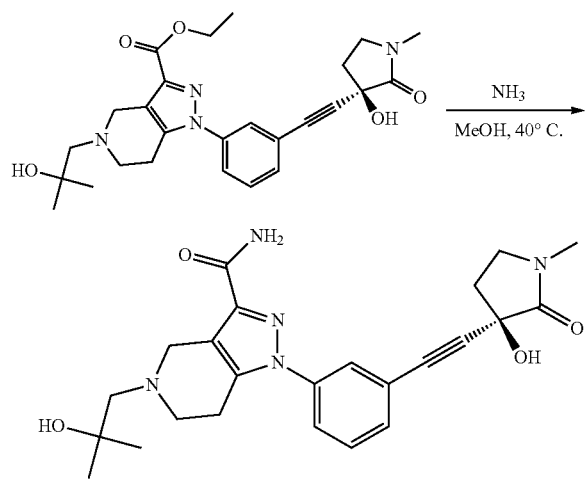

Similar to as described in General Procedure S, ethyl 1-(3-[2-[(3R)-3-hydroxy-1-methyl-2-oxopyrrolidin-3-yl]ethynyl]phenyl)-5-(2-hydroxy-2-m ethylpropyl)-1H,4H,5H,6H,7H-pyrazolo[4,3-c]pyridine-3-carboxylate was reacted with ammonia in methanol to give the title compound (15.6 mg, 20%) as a white solid. LC-MS (ES, m/z): 452 [M+H]+.
1H NMR (400 MHz, CD3OD) δ 7.65 (s, 1H), 7.57-7.54 (m, 1H), 7.44-7.39 (m, 2H), 4.51 (s, 1H), 3.81 (s, 2H), 3.39-3.36 (m, 2H), 2.85-2.81 (m, 6H), 2.52-2.46 (m, 3H), 2.25-2.18 (m, 1H), 1.19 (s, 6H).

Example JJJ and KKK

Synthesis of (4R)-4-C-cyclopropane-1-(3-[2-[(3R)-3-hydroxy-1-methyl-2-oxopyrrolidin-3-yl]ethynyl]phenyl)-4,5,6,7-tetrahydro-1H-indazole-3,4-diamido and (4S)-4-C-cyclopropane-1-(3-[2-[(3R)-3-hydroxy-1-methyl-2-oxopyrrolidin-3-yl]ethynyl]phenyl)-4,5,6,7-tetrahydro-1H-indazole-3,4-diamido Step 1: Synthesis of 4-amino-1-(3-bromophenyl)-4,5,6,7-tetrahydro-1H-indazole-3-carboxamide

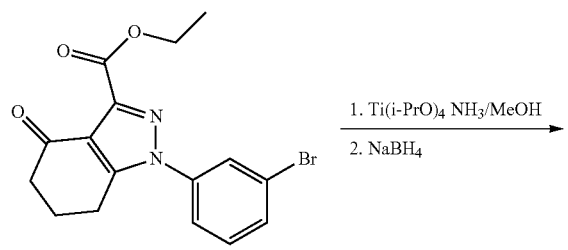

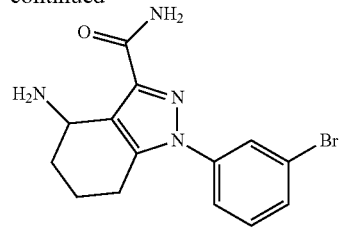

To a solution of ethyl 1-(3-bromophenyl)-4-oxo-4,5,6,7-tetrahydro-1H-indazole-3-carboxylate (300 mg, 0.83 mmol, 1.00 equiv) in methanol (saturated with ammonia, 10 mL) was added Ti(i-PrO)4 (470 mg, 1.65 mmol, 2.00 equiv) and the reaction was stirred overnight. Sodium borohydride (47 mg, 1.24 mmol, 1.50 equiv) was added and the reaction mixture was stirred for 30 minutes at room temperature. The reaction was then quenched with 1 mL of saturated aqueous ammonia chloride, diluted with water, extracted with ethyl acetate, dried over anhydrous sodium sulfate, and concentrated under vacuum. The crude product was purified by a silica gel column with dichloromethane/methanol (20:1) to give 265 mg (96%) of the title compound as a light yellow solid. LC-MS (ES, m/z): 335, 337 [M+H]+.

Step 2: Synthesis of 1-(3-bromophenyl)-4-C-cyclopropane-4,5,6,7-tetrahydro-1H-indazole-3,4-diamido

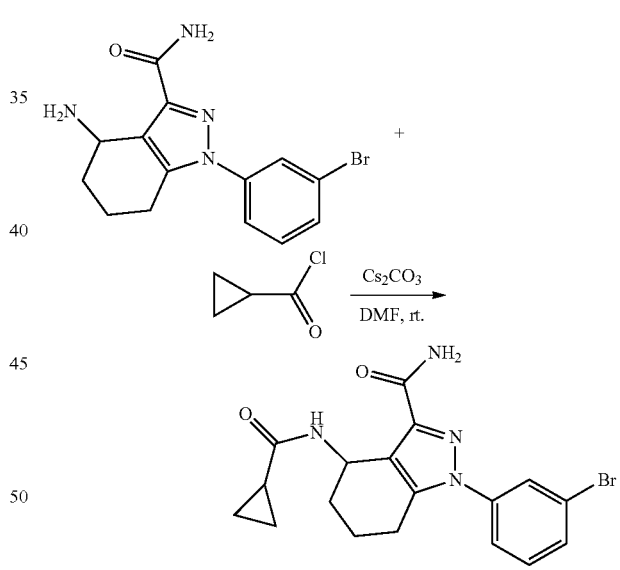

To a solution of 4-amino-1-(3-bromophenyl)-4,5,6,7-tetrahydro-1H-indazole-3-carboxamide (265 mg, 0.79 mmol, 1.00 equiv) in N,N-dimethylformamide (2 mL) was added cesium carbonate (1000 mg, 3.07 mmol, 3.90 equiv) and cyclopropanecarbonyl chloride (165 mg, 1.58 mmol, 2.00 equiv). The reaction was stirred overnight at room temperature. The resulting mixture was quenched with 10 mL of water, extracted with ethyl acetate, and washed with brine. The organic layer was dried over anhydrous sodium sulfate and concentrated under vacuum. The crude product was purified on a silica gel column with dichloromethane/methanol (20:1) to give 220 mg (69%) of the title compound as a white solid. LC-MS (ES, m/z): 403, 405 [M+H]+.

Step 3: Synthesis of (4R)-4-C-cyclopropane-1-(3-[2-[(3R)-3-hydroxy-1-methyl-2-oxopyrrolidin-3-yl]ethynyl]phenyl)-4,5,6,7-tetrahydro-1H-indazole-3,4-diamido and (4S)-4-C-cyclopropane-1-(3-[2-[(3R)-3-hydroxy-1-methyl-2-oxopyrrolidin-3-yl]ethynyl]phenyl)-4,5,6,7-tetrahydro-1H-indazole-3,4-diamido

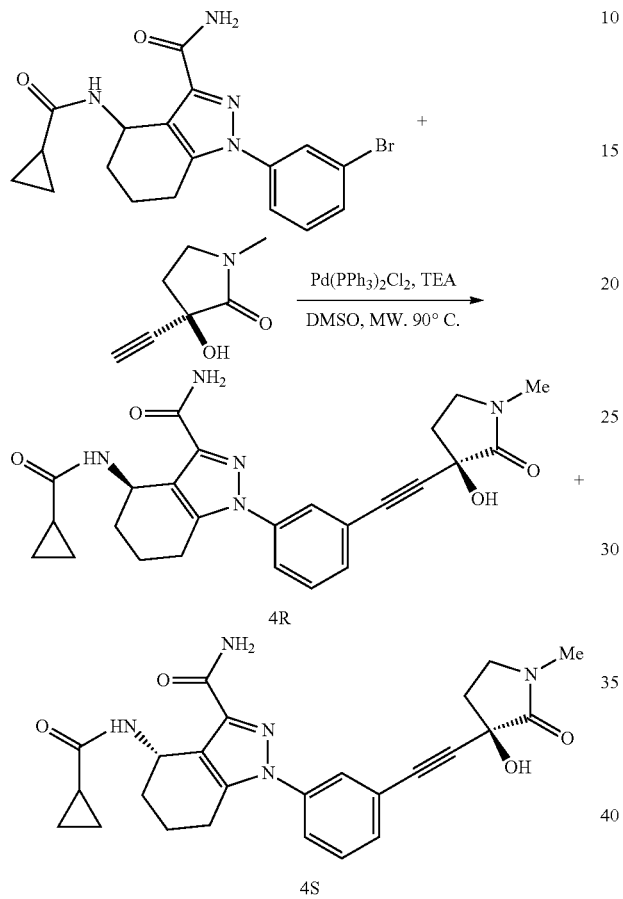

Similar to as described in General Procedure E, 1-(3-bromophenyl)-4-C-cyclopropane-4,5,6,7-tetrahydro-1H-indazole-3,4-diamido was reacted with (3R)-3-ethynyl-3-hydroxy-1-methylpyrrolidin-2-one to give the two title compounds which were separated by Column, Chiralpak IC, 2×25 cm, 5 um; mobile phase, MTBE and ethanol (hold 40.0% ethanol in 18 min); Detector, UV 254/220 nm. The stereochemistry at position 4 was arbitrary assigned.

Isomer A (4R): off-white solid, 12 mg (7%). $t_R$=12.6 min (CHIRALPAK IC, 25° C., UV-254 nm MTBE (0.1% TEA): EtOH=60:40, 1.0 ml/min). LC-MS (ES, m/z): 462 [M+1]$^+$. $^1$H NMR (300 MHz, CD$_3$OD) δ 7.72 (s, 1H), 7.55 (m, 1H), 7.53 (m, 2H), 5.34 (s, 1H), 3.48 (dd, J=7.5, 5.4 Hz, 2H), 2.94 (s, 3H), 2.79 (m, 2H), 2.64-2.58 (m, 1H), 2.37-2.31 (m, 1H), 2.09-2.01 (m, 1H), 1.91-1.70 (m, 3H), 1.55-1.51 (m, 1H), 0.95-0.85 (m, 2H), 0.74-0.70 (m, 2H).

Isomer B (4S): off-white solid, 22.9 mg (13%). $t_R$=16.8 min (CHIRALPAK IC, 25° C., UV-254 nm MTBE (0.1% TEA):EtOH=60:40, 1.0 ml/min). LC-MS (ES, m/z): 462 [M+1]$^+$. $^1$H NMR (400 MHz, CD$_3$OD) δ 7.73 (s, 1H), 7.65-7.62 (m, 1H), 7.56-7.35 (m, 2H), 5.36-5.35 (m, 1H), 3.49 (dd, J=6.8, 5.6 Hz, 2H), 2.95 (s, 3H), 2.81-2.79 (m, 2H), 2.64-2.58 (m, 1H), 2.37-2.31 (m, 1H), 2.09-2.01 (m, 1H), 1.91-1.70 (m, 3H), 1.55-1.51 (m, 1H), 0.95-0.85 (m, 2H), 0.74-0.70 (m, 2H).

Example LLL and MMM

Synthesis of (4R)-4-hydroxy-1-(3-[2-[(3R)-3-hydroxy-1-methyl-2-oxopyrrolidin-3-yl]ethynyl]phenyl)-4,5,6,7-tetrahydro-1H-indazole-3-carboxamide and (4S)-4-hydroxy-1-(3-[2-[(3R)-3-hydroxy-1-methyl-2-oxopyrrolidin-3-yl]ethynyl]phenyl)-4,5,6,7-tetrahydro-1H-indazole-3-carboxamide Step 1: Synthesis of ethyl 1-(3-bromophenyl)-4-oxo-4,5,6,7-tetrahydro-1H-indazole-3-carboxylate

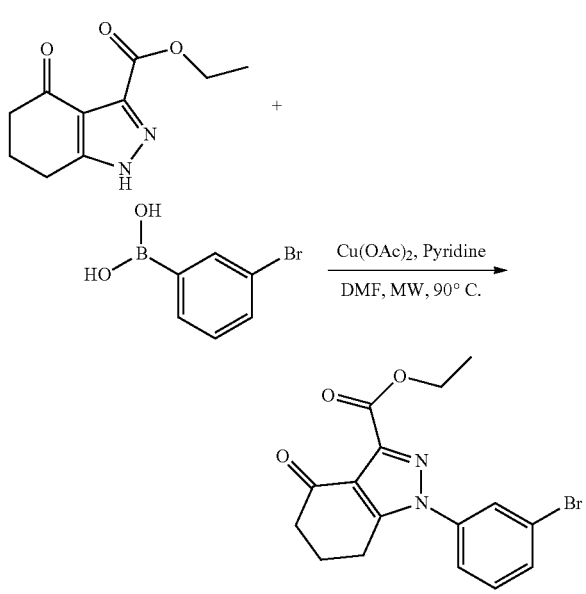

Similar to as described in General Procedure C, ethyl 4-oxo-4,5,6,7-tetrahydro-1H-indazole-3-carboxylate was reacted with (3-bromophenyl)boronic acid to give the title compound (650 mg, 37%) as a light yellow solid. LC-MS (ES, m/z): 363, 365 [M+1]$^+$.

Step 2: Synthesis of ethyl 1-(3-bromophenyl)-4-hydroxy-4,5,6,7-tetrahydro-1H-indazole-3-carboxylate

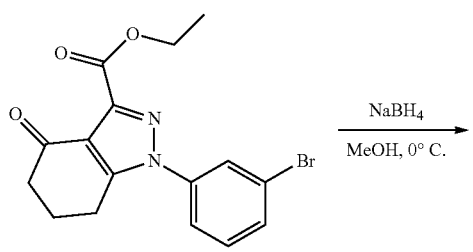

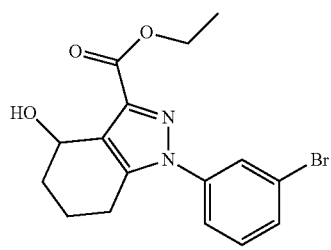

Similar to as described in General Procedure K, ethyl 1-(3-bromophenyl)-4-oxo-4,5,6,7-tetrahydro-1H-indazole-3-carboxylate was reacted with sodium borohydride to give the title compound (200 mg, 50%) as an off-white solid. LC-MS (ES, m/z): 347, 349 [M–H$_2$O+1]$^+$.

Step 3: Synthesis of ethyl 4-hydroxy-1-(3-[2-[(3R)-3-hydroxy-1-methyl-2-oxopyrrolidin-3-yl]ethynyl]phenyl)-4,5,6,7-tetrahydro-1H-indazole-3-carboxylate

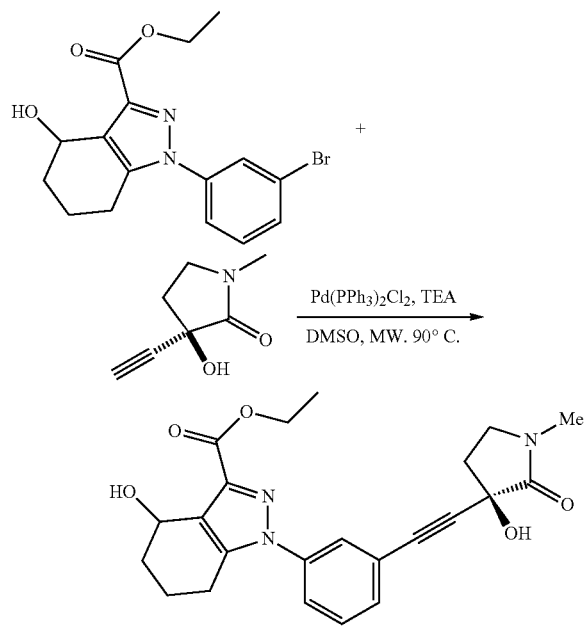

Similar to as described in General Procedure E, ethyl 1-(3-bromophenyl)-4-hydroxy-4,5,6,7-tetrahydro-1H-indazole-3-carboxylate was reacted with (3R)-3-ethynyl-3-hydroxy-1-methylpyrrolidin-2-one to give the title compound (45 mg, 70%) as a brown solid. LC-MS (ES, m/z): 424 [M+1]$^+$.

Step 4: Synthesis of (4R)-4-hydroxy-1-(3-[2-[(3R)-3-hydroxy-1-methyl-2-oxopyrrolidin-3-yl]ethynyl]phenyl)-4,5,6,7-tetrahydro-1H-indazole-3-carboxamide and (4S)-4-hydroxy-1-(3-[2-[(3R)-3-hydroxy-1-methyl-2-oxopyrrolidin-3-yl]ethynyl]phenyl)-4,5,6,7-tetrahydro-1H-indazole-3-carboxamide

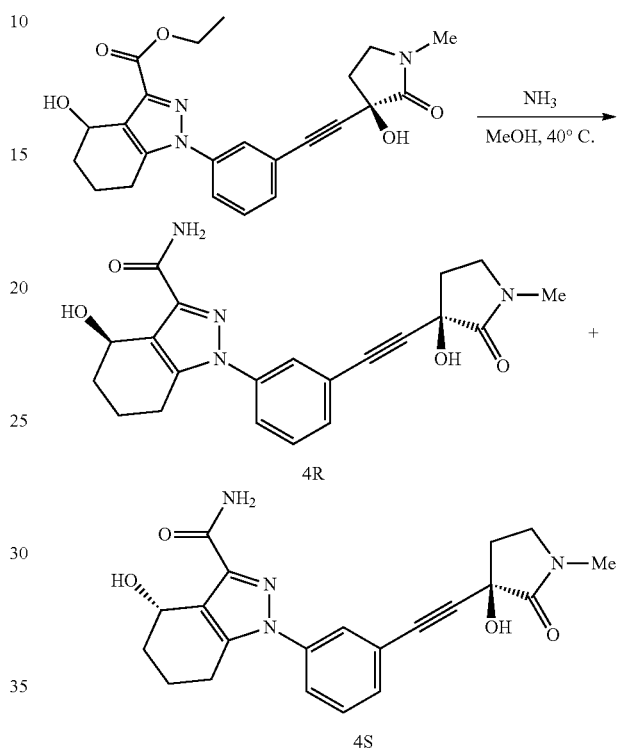

Similar to as described in General Procedure S, ethyl 4-hydroxy-1-(3-[2-[(3R)-3-hydroxy-1-methyl-2-oxopyrrolidin-3-yl]ethynyl]phenyl)-4,5,6,7-tetrahydro-1H-indazole-3-carboxylate was reacted with ammonia in methanol to give the two title compounds which were separated by Column, CHIRALPAK OJ-H, 2×25 cm; mobile phase, Hex and ethanol (hold 35.0% ethanol in 13 min); Detector, UV 254/220 nm. The stereochemistry at position 4 was arbitrary assigned.

Isomer A (4R): 6.8 mg (16%), white solid. $t_R$=8.4 min (CHIRALCEL OJ-3, 25° C., UV-254 nm Hex:EtOH=65:35, 1.0 ml/min). LC-MS (ES, m/z): 395 [M+1]$^+$. $^1$H NMR (400 MHz, CD$_3$OD) δ 7.62 (s, 1H), 7.53-7.52 (m, 1H), 7.42 (d, J=6.0 Hz, 2H), 4.88-4.85 (m, 1H), 3.39-3.36 (m, 2H), 2.83 (s, 3H), 2.70-2.68 (m, 1H), 2.62-2.57 (m, 1H), 2.51-2.45 (m, 1H), 2.24-2.18 (m, 1H), 2.05-2.00 (m, 1H), 1.94-1.93 (m, 1H), 1.69-1.63 (m, 2H).

Isomer B (4S): 6.7 mg (16%), white solid. $t_R$=11.1 min (CHIRALCEL OJ-3, 25° C., UV-254 nm Hex:EtOH=65:35, 1.0 ml/min). LC-MS (ES, m/z): 395 [M+1]$^+$. $^1$H NMR (300 MHz, CD$_3$OD) δ 7.75 (s, 1H), 7.67-7.63 (m, 1H), 7.55 (d, J=3.9 Hz, 2H), 4.99 (t, J=6.0 Hz, 1H), 3.52-3.48 (m, 2H), 2.95 (s, 3H), 2.82-2.57 (m, 3H), 2.38-2.29 (m, 1H), 2.18-2.05 (m, 2H), 1.80-1.75 (m, 2H).

Example NNN

Synthesis of 2-(3-[2-[(3R)-3-hydroxy-1-methyl-2-oxopyrrolidin-3-yl]ethynyl]phenyl)-1,3-thiazole-4-carboxamide

Step 1: Synthesis of ethyl 2-(3-bromophenyl)-1,3-thiazole-4-carboxylate

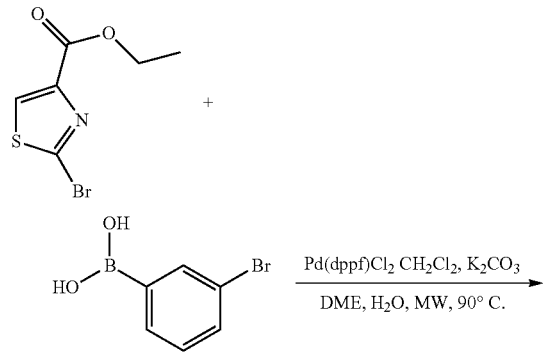

Similar to as described in General Procedure M, ethyl 2-bromo-1,3-thiazole-4-carboxylate was reacted with (3-bromophenyl)boronic acid to give the title compound (180 mg, 68%) as a white solid. LC-MS (ES, m/z): 312, 314 [M+H]⁺.

Step 2: Synthesis of ethyl 2-(3-[2-[(3R)-3-hydroxy-1-methyl-2-oxopyrrolidin-3-yl]ethynyl]phenyl)-1,3-thiazole-4-carboxylate

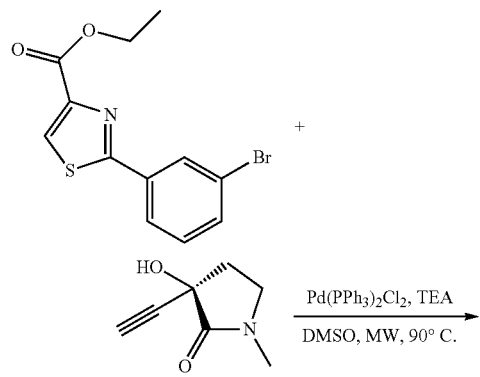

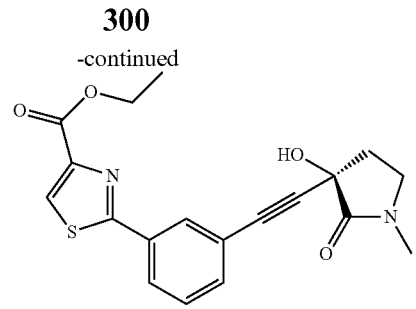

Similar to as described in General Procedure E, ethyl 2-(3-bromophenyl)-1,3-thiazole-4-carboxylate was reacted with (3R)-3-ethynyl-3-hydroxy-1-methylpyrrolidin-2-one to give the title compound (150 mg, 68%) as a yellow solid. LC-MS (ES, m/z): 371 [M+H]⁺.

Step 3: Synthesis of 2-(3-[2-[(3R)-3-hydroxy-1-methyl-2-oxopyrrolidin-3-yl]ethynyl]phenyl)-1,3-thiazole-4-carboxamide

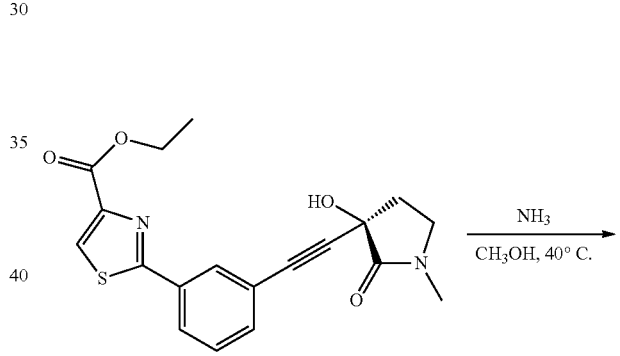

Similar to as described in General Procedure S, ethyl 2-(3-[2-[(3R)-3-hydroxy-1-methyl-2-oxopyrrolidin-3-yl]ethynyl]phenyl)-1,3-thiazole-4-carboxylate was reacted with ammonia in methanol to give the title compound (56.9 mg, 41%) as a white solid. LC-MS (ES, m/z): 342 [M+H]⁺. ¹H NMR (400 MHz, CD₃OD) δ 8.27 (s, 1H), 8.17 (s, 1H), 8.05 (d, J=8.0 Hz, 1H), 7.59 (d, J=8.0 Hz, 1H), 7.51 (t, J=7.6 Hz, 1H), 3.53-3.47 (m, 2H), 2.96 (s, 3H), 2.65-2.59 (m, 1H), 2.38-2.31 (m, 1H).

Example OOO

Synthesis of 1-(3-[2-[(3R)-3-hydroxy-1-methyl-2-oxopyrrolidin-3-yl]ethynyl]phenyl)-1H,4H,5H,6H-pyrano[2,3-c]pyrazole-3-carboxamide

Step 1: Synthesis of ethyl 2-oxo-2-(2-oxooxan-3-yl)acetate

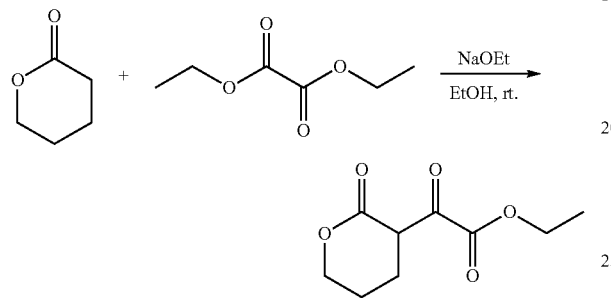

Similar to as described in General Procedure Y Step 1, diethyl oxalate was reacted with oxan-2-one to give the title compound (3.8 g, 79%) as a light yellow liquid. LC-MS (ES, m/z): 201 [M+H]$^+$.

Step 2: Synthesis of ethyl 1-(3-bromophenyl)-5-hydroxy-4-(3-hydroxypropyl)-1H-pyrazole-3-carboxylate

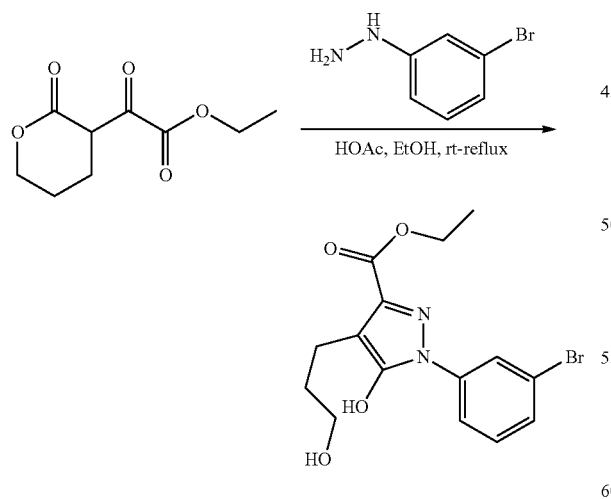

Similar to as described in General Procedure Y Step 2, ethyl 2-oxo-2-(2-oxooxan-3-yl)acetate was reacted with (3-bromophenyl)hydrazine hydrochloride to give the title compound (463 mg, 63%) as a yellow solid. LC-MS (ES, m/z): 369, 371 [M+H]$^+$.

Step 3: Synthesis of ethyl 1-(3-bromophenyl)-1H,4H,5H,6H-pyrano[2,3-c]pyrazole-3-carboxylate

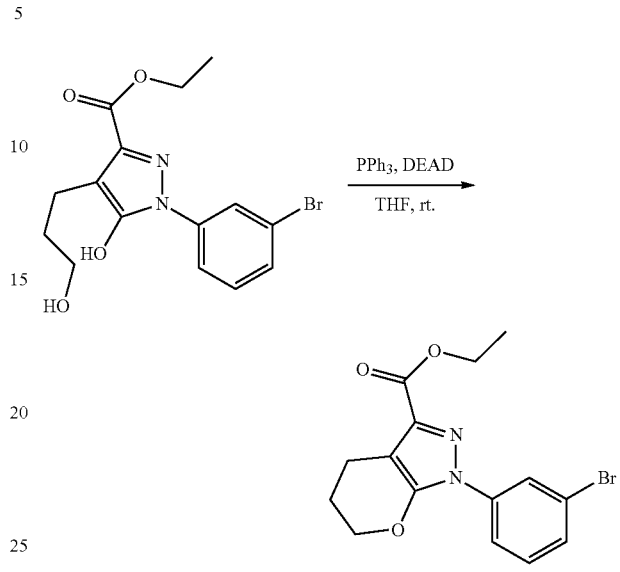

DEAD (656 mg, 3.77 mmol, 3.00 equiv) was added slowly to a suspension of ethyl 1-(3-bromophenyl)-5-hydroxy-4-(3-hydroxypropyl)-1H-pyrazole-3-carboxylate (463 mg, 1.25 mmol, 1.00 equiv) and PPh$_3$ (986 mg, 3.76 mmol, 3.00 equiv) in tetrahydrofuran (20 mL) at 0° C. and the reaction mixture was stirred overnight at room temperature. The reaction was then quenched with 5 mL of saturated brine, extracted with ethyl acetate, dried over anhydrous sodium sulfate, and concentrated under vacuum. The residue was purified on a silica gel column with ethyl acetate/petroleum ether (1:9) to give 330 mg (75%) of the title compound as a light yellow solid. LC-MS (ES, m/z): 351, 353 [M+H]$^+$.

Step 4: Synthesis of ethyl 1-(3-[2-[(3R)-3-hydroxy-1-methyl-2-oxopyrrolidin-3-yl]ethynyl]phenyl)-1H,4H,5H,6H-pyrano[2,3-c]pyrazole-3-carboxylate

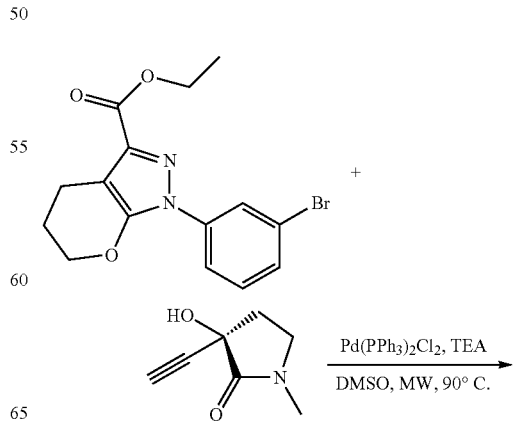

-continued

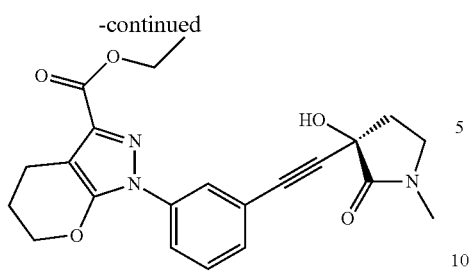

Similar to as described in General Procedure E, ethyl 1-(3-bromophenyl)-1H,4H,5H,6H-pyrano[2,3-c]pyrazole-3-carboxylate was reacted with (3R)-3-ethynyl-3-hydroxy-1-methylpyrrolidin-2-one to give the title compound (90 mg, 77%) as a yellow solid. LC-MS (ES, m/z): 410 [M+H]$^+$.

Step 5: Synthesis of 1-(3-[2-[(3R)-3-hydroxy-1-methyl-2-oxopyrrolidin-3-yl]ethynyl]phenyl)-1H,4H,5H,6H-pyrano[2,3-c]pyrazole-3-carboxamide

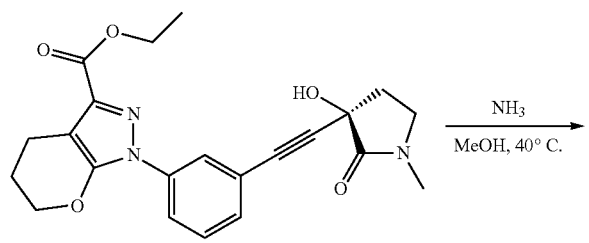

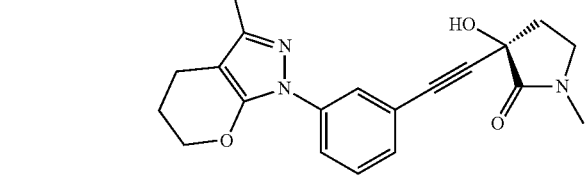

Similar to as described in General Procedure S, ethyl 1-(3-[2-[(3R)-3-hydroxy-1-methyl-2-oxopyrrolidin-3-yl]ethynyl]phenyl)-1H,4H,5H,6H-pyrano[2,3-c]pyrazole-3-carboxylate was reacted with ammonia in methanol to give the title compound (11.5 mg, 14%) as a white solid. LC-MS (ES, m/z): 381[M+H]$^+$. $^1$H NMR (300 MHz, CD$_3$OD) δ 7.94 (d, J=1.5 Hz, 1H), 7.89-7.85 (m, 1H), 7.46-7.41 (m, 2H), 4.43 (t, J=5.1 Hz, 2H), 3.49 (m, 2H), 2.94 (s, 3H), 2.83 (t, J=6.3 Hz, 2H), 2.63-2.56 (m, 1H), 2.37-2.27 (m, 1H), 2.08-2.03 (m, 2H).

Example PPP

Synthesis of 1-(3-[2-[(3R)-3-hydroxy-1-methyl-2-oxopyrrolidin-3-yl]ethynyl]phenyl)-1H-indazole-3-carboxamide Step 1: Synthesis of methyl 1-(3-bromophenyl)-1H-indazole-3-carboxylate

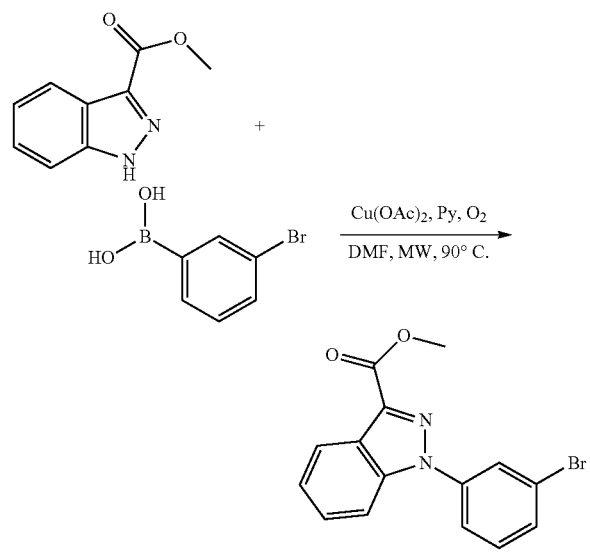

Similar to as described in General Procedure C, methyl 1H-indazole-3-carboxylate was reacted with (3-bromophenyl)boronic acid to give the title compound (400 mg, 43%) as a white solid. LC-MS (ES, m/z): 331, 333 [M+H]$^+$.

Step 2: Synthesis of methyl 1-(3-[2-[(3R)-3-hydroxy-1-methyl-2-oxopyrrolidin-3-yl]ethynyl]phenyl)-1H-indazole-3-carboxylate

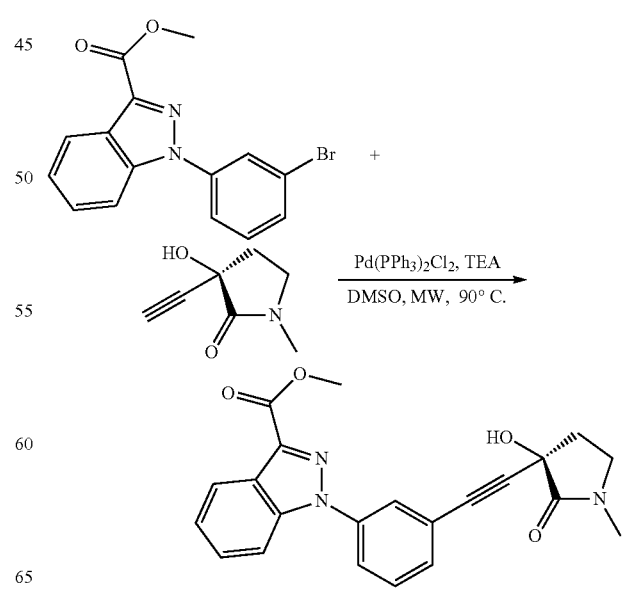

Similar to as described in General Procedure E, methyl 1-(3-bromophenyl)-1H-indazole-3-carboxylate was reacted with (3R)-3-ethynyl-3-hydroxy-1-methylpyrrolidin-2-one to give the title compound (130 mg, 74%) as a yellow solid. LC-MS (ES, m/z): 390 [M+H]$^+$.

Step 3: Synthesis of 1-(3-[2-[(3R)-3-hydroxy-1-methyl-2-oxopyrrolidin-3-yl]ethynyl]phenyl)-1H-indazole-3-carboxamide

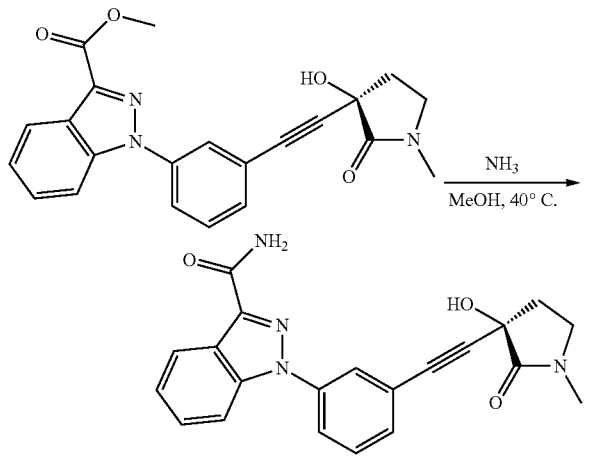

Similar to as described in General Procedure S, methyl 1-(3-[2-[(3R)-3-hydroxy-1-methyl-2-oxopyrrolidin-3-yl]ethynyl]phenyl)-1H-indazole-3-carboxylate was reacted with ammonia in methanol to give the title compound (49.6 mg, 40%) as a white solid. LC-MS (ES, m/z): 375 [M+H]$^+$, 749 [2M+H]$^+$. $^1$H NMR (300 MHz, CD$_3$OD) δ 8.37 (d, J=8.4 Hz, 1H), 7.96-7.94 (m, 1H), 7.90-7.84 (m, 2H), 7.64-7.55 (m, 3H), 7.44 (t, J=7.5 Hz, 1H), 3.54-3.49 (m, 2H), 2.96 (s, 3H), 2.65-2.57 (m, 1H), 2.39-2.29 (m, 1H).

Example QQQ

Synthesis of 1-(6-[2-[(3R)-3-hydroxy-1-methyl-2-oxopyrrolidin-3-yl]ethynyl]pyrimidin-4-yl)-1H-indazole-3-carboxamide Step 1: Synthesis of 1-(6-chloropyrimidin-4-yl)-1H-indazole-3-carboxylic acid

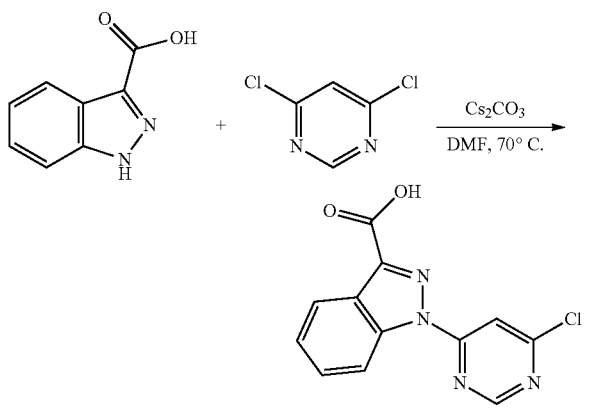

Similar to as described in General Procedure A, 1H-indazole-3-carboxylic acid was reacted with 4,6-dichloropyrimidine to give the title compound (140 mg, 55%) of the title compound as a yellow solid. LC-MS (ES, m/z): 275 [M+H]$^+$.

Step 2: Synthesis of 1-(6-chloropyrimidin-4-yl)-1H-indazole-3-carboxamide

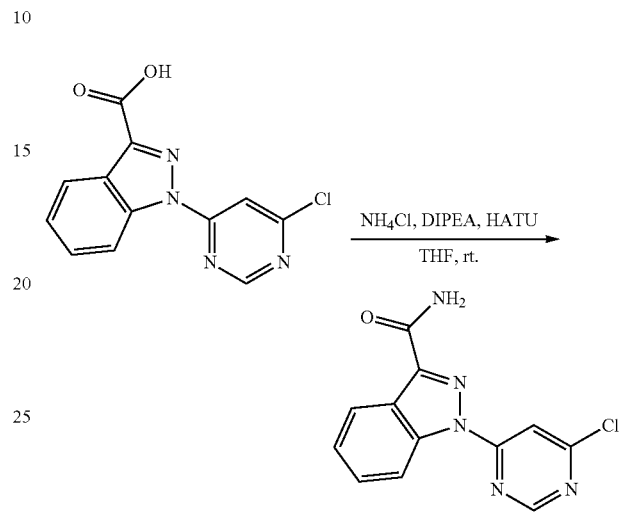

Similar to as described in General Procedure B, 1-(6-chloropyrimidin-4-yl)-1H-indazole-3-carboxylic acid was reacted with ammonium chloride to give the title compound (88 mg, 59%) as a yellow solid. LC-MS (ES, m/z): 274 [M+H]$^+$.

Step 3: Synthesis of 1-(6-[2-[(3R)-3-hydroxy-1-methyl-2-oxopyrrolidin-3-yl]ethynyl]pyrimidin-4-yl)-1H-indazole-3-carboxamide

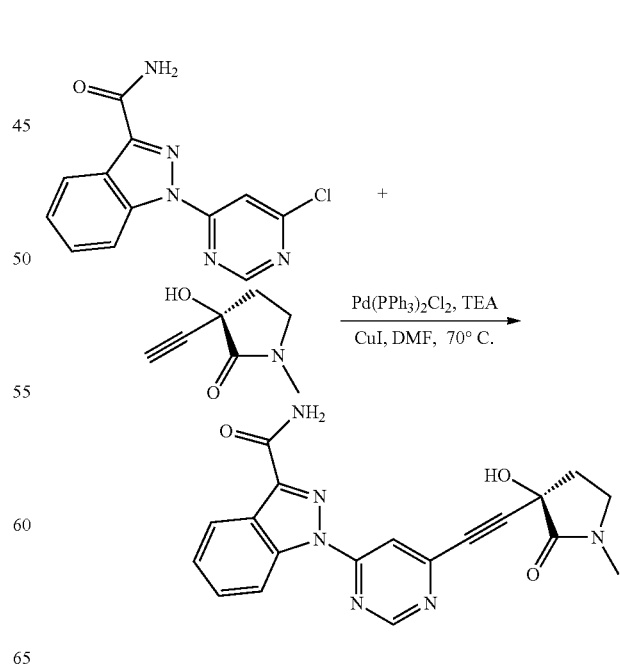

Similar to as described in General Procedure E, 1-(6-chloropyrimidin-4-yl)-1H-indazole-3-carboxamide was reacted with (3R)-3-ethynyl-3-hydroxy-1-methylpyrrolidin-2-one to give the title compound (4.6 mg, 4%) as a white solid. LC-MS (ES, m/z): 377 [M+H]$^+$. $^1$H NMR (300 MHz, DMSO-d6) δ 9.09 (s, 1H), 8.75 (d, J=8.7 Hz, 1H), 8.38 (s, 1H), 8.28-8.25 (m, 2H), 7.69 (s, 1H), 7.60 (t, J=7.4 Hz, 1H), 7.43 (t, J=7.4 Hz, 1H), 6.70 (s, 1H), 3.48-3.31 (m, 2H), 2.76 (s, 3H), 2.57-2.47 (m, 1H), 2.23-2.14 (m, 1H).

Example RRR and SSS

Synthesis of (5S)-5-(benzyl oxy)-1-(4-[2-[(3R)-3-hydroxy-1-methyl-2-oxopyrrolidin-3-yl]ethynyl]pyridin-2-yl)-6,6-dimethyl-4,5,6,7-tetrahydro-1H-indazole-3-carboxamide and (5R)-5-(benzyloxy)-1-(4-[2-[(3R)-3-hydroxy-1-methyl-2-oxopyrrolidin-3-yl]ethynyl]pyridin-2-yl)-6,6-dimethyl-4,5,6,7-tetrahydro-1H-indazole-3-carboxamide Step 1: Synthesis of 5-(benzyloxy)-1-(4-iodopyridin-2-yl)-6,6-dimethyl-4,5,6,7-tetrahydro-1H-indazole-3-carboxylic acid

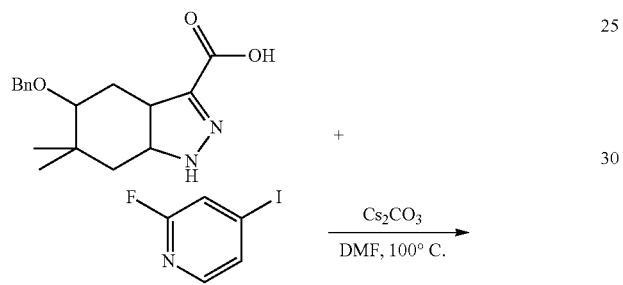

Similar to as described in General Procedure A, 5-(benzyloxy)-6,6-dimethyl-4,5,6,7-tetrahydro-1H-indazole-3-carboxylic acid was reacted with 2-fluoro-4-iodopyridine to give the title compound (200 mg, 83%) as a yellow oil. LC-MS (ES, m/z): 504 [M+H]$^+$.

Step 2: Synthesis of 5-(benzyloxy)-1-(4-iodopyridin-2-yl)-6,6-dimethyl-4,5,6,7-tetrahydro-1H-indazole-3-carboxamide

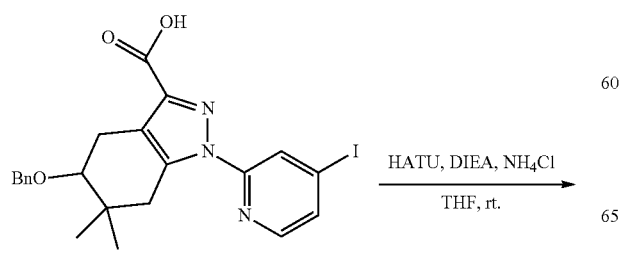

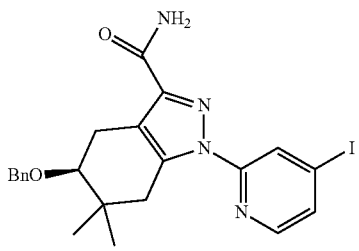

Similar to as described in General Procedure B, 5-(benzyloxy)-1-(4-iodopyridin-2-yl)-6,6-dimethyl-4,5,6,7-tetrahydro-1H-indazole-3-carboxylic acid was reacted with ammonium acetate to give the title compound (210 mg, 63%) as yellow oil. LC-MS (ES, m/z): 503 [M+H]$^+$.

Step 3: Synthesis of (5S)-5-(benzyl oxy)-1-(4-[2-[(3R)-3-hydroxy-1-methyl-2-oxopyrrolidin-3-yl]ethynyl]pyridin-2-yl)-6,6-dimethyl-4,5,6,7-tetrahydro-1H-indazole-3-carboxamide and (5R)-5-(benzyloxy)-1-(4-[2-[(3R)-3-hydroxy-1-methyl-2-oxopyrrolidin-3-yl]ethynyl]pyridin-2-yl)-6,6-dimethyl-4,5,6,7-tetrahydro-1H-indazole-3-carboxamide

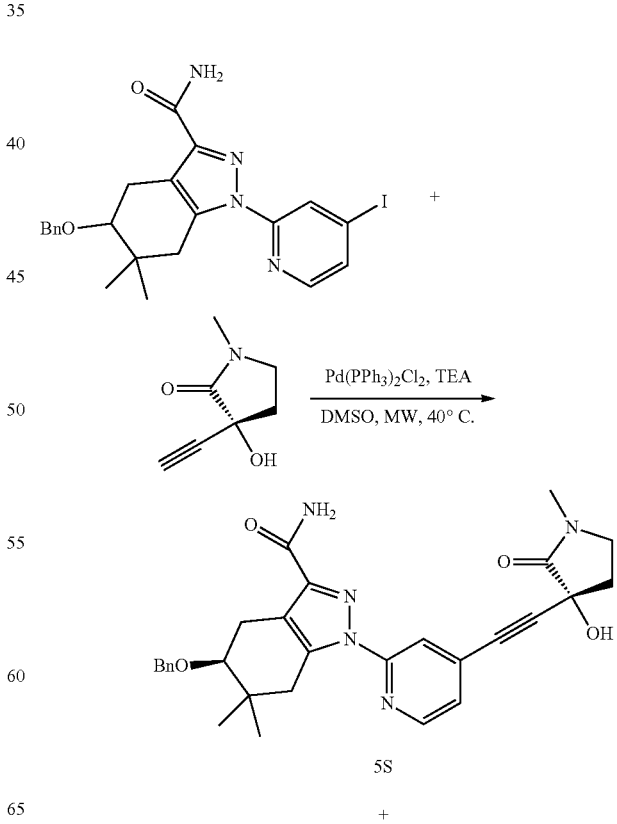

309

-continued

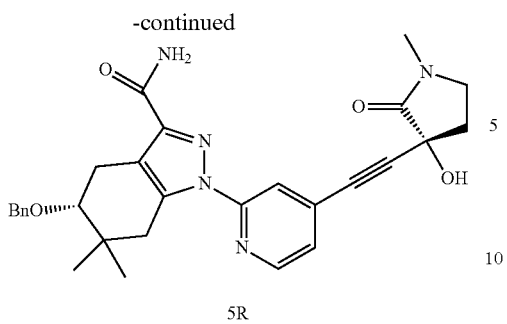

5R

Similar to as described in General Procedure E, 5-(benzyloxy)-1-(4-iodopyridin-2-yl)-6,6-dimethyl-4,5,6,7-tetrahydro-1H-indazole-3-carboxamide was reacted with (3R)-3-ethynyl-3-hydroxy-1-methylpyrrolidin-2-one to give the two title compounds which were separated by Phenomenex Lux 5u Cellulose-4, 2.12×25, 5 um; mobile phase, Hex and ethanol (hold 30.0% ethanol in 28 min); Detector, UV 254/220 nm. The stereochemistry at position 5 was arbitrary assigned.

Isomer A (5S): 21.5 mg (11%), white solid. $t_R$=16.29 min (Lux Cellulose-4, 25° C., UV-254 nm, Hex:EtOH 70:30, 1.0 ml/min). LC-MS (ES, m/z): 514 [M+H]$^+$. $^1$H NMR (400 MHz, CD3OD) δ 8.39 (d, J=4.8 Hz, 1H), 8.04 (s, 1H), 7.29-7.26 (m, 6H), 4.65 (d, J=11.6 Hz, 1H), 4.45 (d, J=11.6 Hz, 1H), 3.46-3.42 (m, 3H), 3.05-2.97 (m, 4H), 2.89 (s, 3H), 2.60-2.54 (m, 1H), 2.30-2.23 (m, 1H), 1.05 (s, 3H), 0.96 (s, 3H).

Isomer B (5R): 22.6 mg (11%), white solid. $t_R$=20.27 min (Lux Cellulose-4, 25° C., UV-254 nm, Hex:EtOH 70:30, 1.0 ml/min). LC-MS (ES, m/z): 514 [M+H]$^+$. $^1$H NMR (400 MHz, CD$_3$OD) δ 8.39 (d, J=4.8 Hz, 1H), 8.04 (s, 1H), 7.29-7.26 (m, 6H), 4.65 (d, J=11.6 Hz, 1H), 4.45 (d, J=11.6 Hz, 1H), 3.46-3.42 (m, 3H), 3.05-2.97 (m, 4H), 2.89 (s, 3H), 2.60-2.54 (m, 1H), 2.30-2.23 (m, 1H), 1.05 (s, 3H), 0.96 (s, 3H).

Example TTT and UUU

Synthesis of 1-[3-[(3R)-3-hydroxy-3-(1,3-oxazol-2-yl)but-1-yn-1-yl]phenyl]-1H-indazole-3-carboxamide and 1-[3-[(3S)-3-hydroxy-3-(1,3-oxazol-2-yl)but-1-yn-1-yl]phenyl]-1H-indazole-3-carboxamide Step 1: Synthesis of methyl 1-[3-[3-hydroxy-3-(1,3-oxazol-2-yl)but-1-yn-1-yl]phenyl]-1H-indazole-3-carboxylate

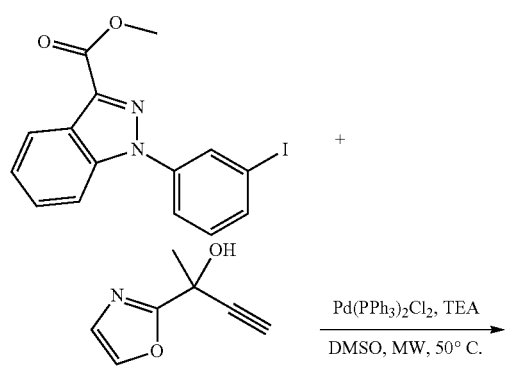

310

-continued

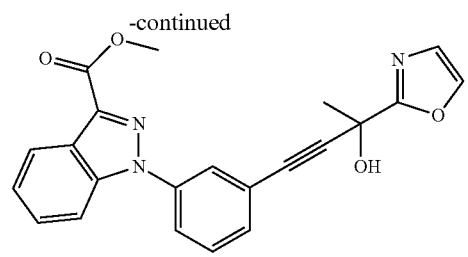

Similar to as described in General Procedure E, methyl 1-(3-iodophenyl)-1H-indazole-3-carboxylate was reacted with 2-(1,3-oxazol-2-yl)but-3-yn-2-ol to give the title compound (170 mg, 93%) as a yellow solid. LC-MS (ES, m/z): 388 [M+H]$^+$.

Step 2: Synthesis of 1-[3-[(3R)-3-hydroxy-3-(1,3-oxazol-2-yl)but-1-yn-1-yl]phenyl]-1H-indazole-3-carboxamide and 1-[3-[(3S)-3-hydroxy-3-(1,3-oxazol-2-yl)but-1-yn-1-yl]phenyl]-1H-indazole-3-carboxamide

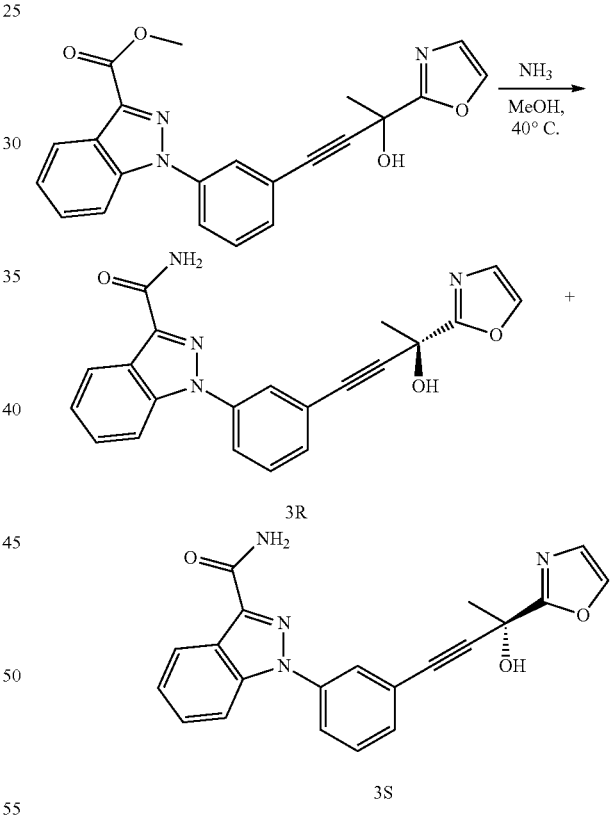

Similar to as described in General Procedure S, methyl 1-[3-[3-hydroxy-3-(1,3-oxazol-2-yl)but-1-yn-1-yl]phenyl]-1H-indazole-3-carboxylate was reacted with ammonia in methanol to give the two title compounds which were separated by Chiral-Prep-HPLC with the following conditions: Column, Chiralpak IC(SFC), 2×25 cm, 5 um; mobile phase, hex and ethanol (hold 50.0% ethanol in 15 min); Detector, UV 254/220 nm. The stereochemistry at position 3 was arbitrarily assigned Isomer A (3R): white solid. $t_R$=1.52 min (Chiralpak IC-3, 25° C., 254 nm, Hex:EtOH 50:50, 1 mL/min). LC-MS (ES, m/z): 373 [M+H]. $^1$H NMR (400 MHz, CD$_3$OD) δ 8.37 (d, J=8.0 Hz, 1H), 7.98 (s, 2H), 7.90-7.85 (m, 2H), 7.66-7.55 (m, 3H), 7.41 (t, J=7.2 Hz, 1H), 7.22 (s, 1H), 1.99 (s, 3H).

Isomer B (3S): white solid. $t_R$=2.06 min (Chiralpak IC-3, 25° C., 254 nm, Hex:EtOH 50:50, 1 mL/min). LC-MS (ES, m/z): 373 [M+H]. $^1$H NMR (400 MHz, CD$_3$OD) δ 8.36 (d, J=8.0 Hz, 1H), 7.98 (s, 2H), 7.89-7.85 (m, 2H), 7.65-7.55 (m, 3H), 7.40 (t, J=7.2 Hz, 1H), 7.22 (s, 1H), 1.99 (s, 3H).

Example VVV

Synthesis of 1-[3-[(3S)-3-hydroxy-3-(1,3-thiazol-2-yl)but-1-yn-1-yl]phenyl]-1H-indazole-3-carboxamide Step 1: Synthesis of 2-(1,3-thiazol-2-yl)-4-(trimethylsilyl)but-3-yn-2-ol

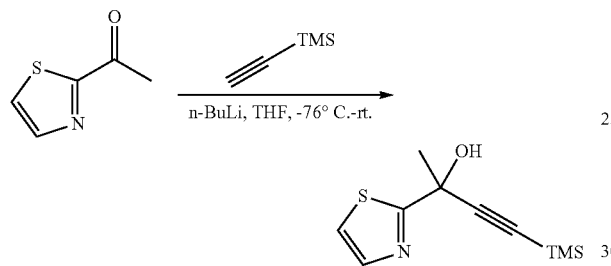

In an inert atmosphere of nitrogen, n-BuLi (2.5N in hexane, 18.9 mL, 47.25 mmol, 1.20 equiv) was added dropwise into a solution of ethynyltrimethylsilane (4.63 g, 47.14 mmol, 1.20 equiv) in tetrahydrofuran (10 mL) under −76° C. After being stirred for 3 h under −76° C. a solution of 1-(1,3-thiazol-2-yl)ethan-1-one (5 g, 39.32 mmol, 1.00 equiv) in tetrahydrofuran (15 mL) was added to the resulting mixture. The reaction was warmed to room temperature slowly and stirred for 2 h at room temperature. The reaction was then quenched with 10 mL of saturated aqueous ammonium chloride, extracted with ethyl acetate, dried over anhydrous sodium sulfate, and concentrated under vacuum. The residue was purified on a silica gel column with ethyl acetate/petroleum ether (1:20) to give 4 g (45%) of the title compound as a yellow solid. LC-MS (ES, m/z): 226 [M+H]$^+$.

Step 2: Synthesis of (2S)-2-(1,3-thiazol-2-yl)but-3-yn-2-ol and (2R)-2-(1,3-thiazol-2-yl)but-3-yn-2-ol

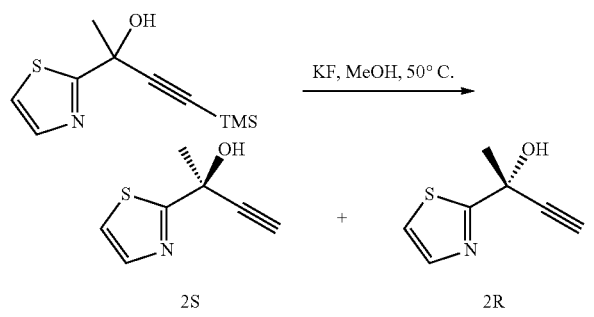

A solution of 2-(1,3-thiazol-2-yl)-4-(trimethylsilyl)but-3-yn-2-ol (4 g, 17.75 mmol, 1.00 equiv) and potassium fluoride (3.342 g, 35.55 mmol, 2.00 equiv) in methanol (20 mL) was stirred for 2 h at 50° C. The resulting mixture was concentrated under vacuum, diluted with 5 mL of water, extracted with ethyl acetate, and concentrated under vacuum. The residue was purified on a silica gel column with ethyl acetate/petroleum ether (1:9). The enantiomers were separated by Chiral-Prep-HPLC with the following conditions: Column, Chiralpak IC, 2×25 cm, 5 um; mobile phase, Hex and ethanol (hold 5.0% ethanol in 8 min); Detector, UV 254/220 nm to give 320 mg (24%) of enantiomer A and 320 mg (24%) of enantiomer B. The stereochemistry for either enantiomer is arbitrarily assigned. LC-MS (ES, m/z): 154 [M+H]$^+$ for enantiomer A or B.

Step 3: Synthesis of 1-[3-[(3R)-3-hydroxy-3-(1,3-thiazol-2-yl)but-1-yn-1-yl]phenyl]-1H-indazole-3-carboxamide

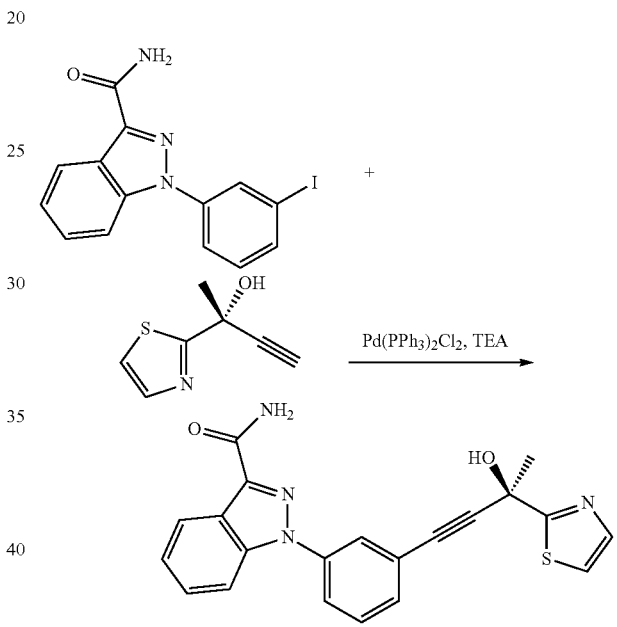

Similar to as described in General Procedure E, 1-(3-iodophenyl)-1H-indazole-3-carboxamide was reacted with (2R)-2-(1,3-thiazol-2-yl)but-3-yn-2-ol to give the title compound (58.8 mg, 46%) as a yellow solid. LC-MS (ES, m/z): 389 [M+H]$^+$. $^1$H NMR (300 MHz, CD$_3$OD) δ 8.35 (d, J=8.4 Hz, 1H), 7.94 (s, 1H), 7.87-7.79 (m, 3H), 7.64-7.53 (m, 4H), 7.39 (t, J=8.4 Hz, 1H), 1.98 (s, 3H).

Step 4: Synthesis of 1-[3-[(3S)-3-hydroxy-3-(1,3-thiazol-2-yl)but-1-yn-1-yl]phenyl]-1H-indazole-3-carboxamide

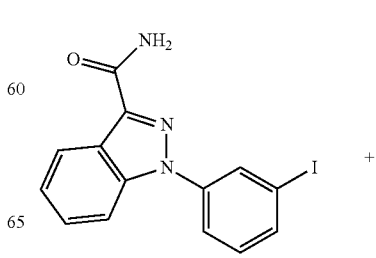

Step 2: Synthesis of 5-(hydroxymethyl)-1-(4-iodopyridin-2-yl)-1H-indazole-3-carboxamide

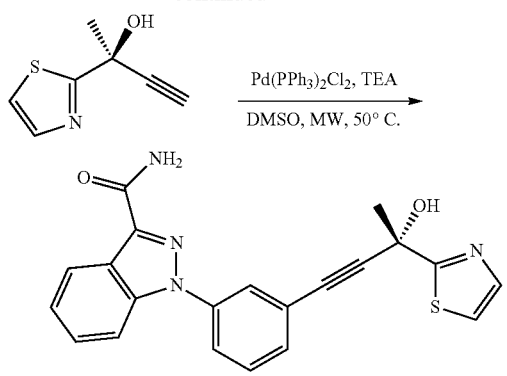

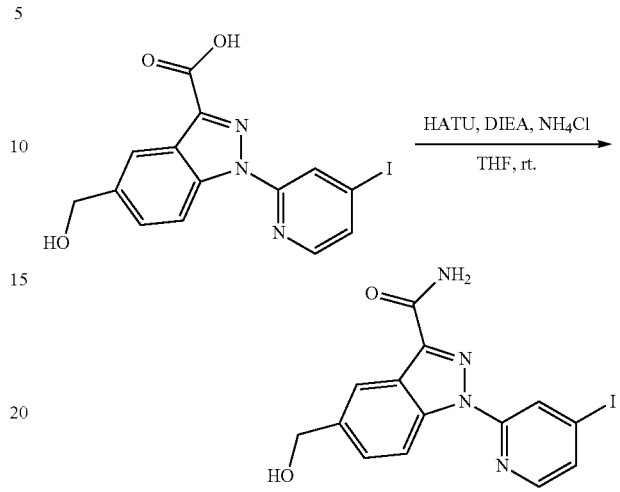

Similar to as described in General Procedure E, 1-(3-iodophenyl)-1H-indazole-3-carboxamide was reacted with (2S)-2-(1,3-thiazol-2-yl)but-3-yn-2-ol to give the title compound (66.7 mg, 52%) as a yellow solid. LC-MS (ES, m/z): 389 [M+H]$^+$. $^1$H NMR (300 MHz, CD$_3$OD) δ 8.35 (d, J=8.4 Hz, 1H), 7.94 (s, 1H), 7.87-7.79 (m, 3H), 7.64-7.53 (m, 4H), 7.39 (t, J=8.4 Hz, 1H), 1.98 (s, 3H).

Example WWW

Synthesis of 5-(acetamidomethyl)-1-(4-[2-[(3R)-3-hydroxy-1-methyl-2-oxopyrrolidin-3-yl]ethynyl]pyridin-2-yl)-1H-indazole-3-carboxamide Similar to as described in General Procedure B, 5-(hydroxymethyl)-1-(4-iodopyridin-2-yl)-1H-indazole-3-carboxylic acid was reacted with ammonium chloride to give the title compound (600 mg, 54%) as a yellow solid. LC-MS (ES, m/z): 395 [M+H]$^+$.

Step 3: Synthesis of 5-(chloromethyl)-1-(4-iodopyridin-2-yl)-1H-indazole-3-carboxamide

Step 1: Synthesis of 5-(hydroxymethyl)-1-(4-iodopyridin-2-yl)-1H-indazole-3-carboxylic acid

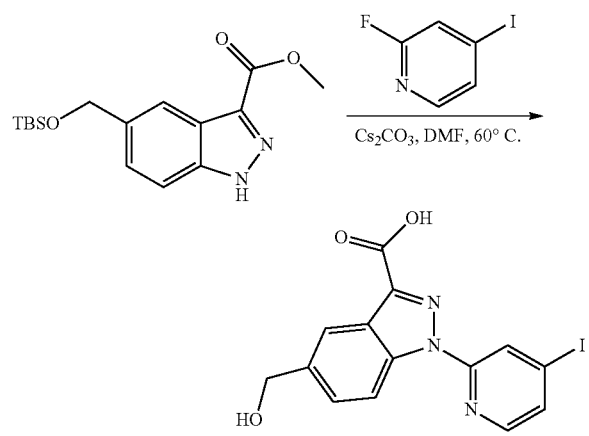

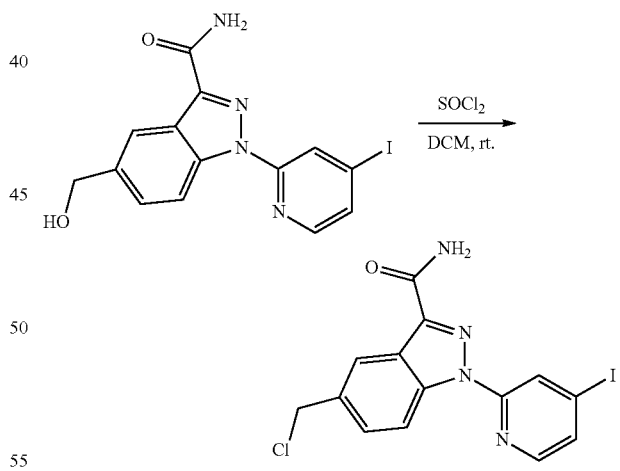

Similar to as described in General Procedure A, methyl 5-[[(tert-butyldimethylsilyl)oxy]methyl]-1H-indazole-3-carboxylate was reacted with 2-fluoro-4-iodopyridine to give the title compound (1 g, 51%) as a yellow solid. LC-MS (ES, m/z): 396 [M+H]$^+$.

Thionyl chloride (2 mL, 27.57 mmol, 1.00 equiv) was added dropwise into a suspension of 5-(hydroxymethyl)-1-(4-iodopyridin-2-yl)-1H-indazole-3-carboxamide (1 g, 2.54 mmol, 1.00 equiv) in dichloromethane (15 mL) at room temperature. After being stirred for 1 h at room temperature the resulting mixture was concentrated under vacuum to give 1 g (81%) of the title compound as a yellow solid. LC-MS (ES, m/z): 413 [M+H]$^+$.

Step 4: Synthesis of 5-(azidomethyl)-1-(4-iodopyridin-2-yl)-1H-indazole-3-carboxamide

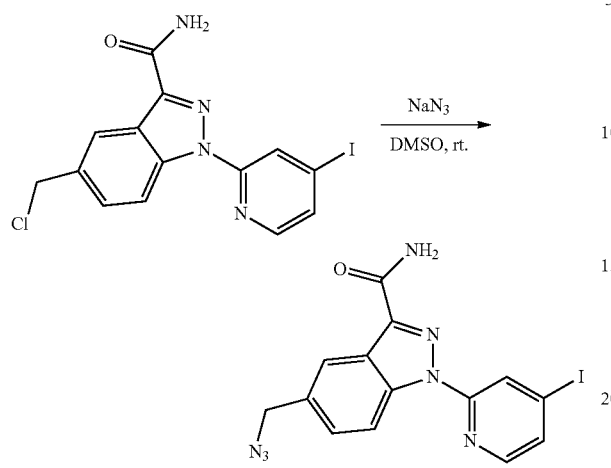

Sodium azide (0.36 g, 2.00 equiv) was added in portions into a solution of 5-(chloromethyl)-1-(4-iodopyridin-2-yl)-1H-indazole-3-carboxamide (1.13 g, 2.74 mmol, 1.00 equiv) in DMSO (5 mL, 70.39 mmol, 25.70 equiv) at room temperature. After being stirred for 2 h at room temperature the reaction was diluted with water, extracted with ethyl acetate, dried over anhydrous sodium sulfate, and concentrated under vacuum. This resulted in 1.2 g (75%) of the title compound as a yellow solid. LC-MS (ES, m/z): 420 [M+H]$^+$.

Step 5: Synthesis of 5-(aminomethyl)-1-(4-iodopyridin-2-yl)-1H-indazole-3-carboxamide

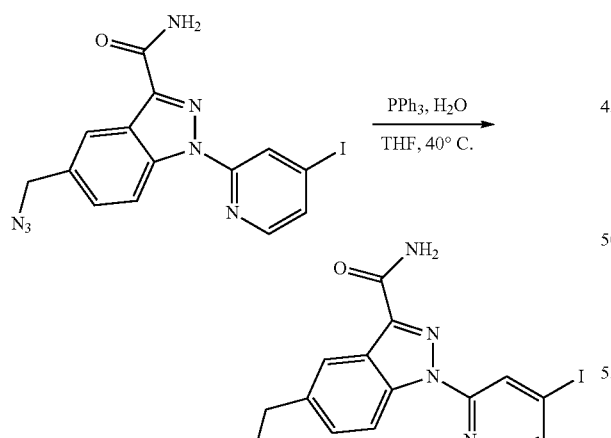

A solution of 5-(azidomethyl)-1-(4-iodopyridin-2-yl)-1H-indazole-3-carboxamide (1.20 g, 2.86 mmol, 1.00 equiv), triphenylphosphine (830 mg, 3.16 mmol, 1.10 equiv) and water (80 mg, 4.44 mmol, 1.50 equiv) in tetrahydrofuran (0.23 mL, 2.84 mmol, 1.00 equiv) was stirred for 4 h at 40° C. The mixture was dried over anhydrous magnesium sulfate and concentrated under vacuum to give 2.0 g of the title compound (crude) as a yellow solid which was used in the next step without further purification. LC-MS (ES, m/z): 394 [M+H]$^+$.

Step 6: Synthesis of 5-(acetamidomethyl)-1-(4-iodopyridin-2-yl)-1H-indazole-3-carboxamide

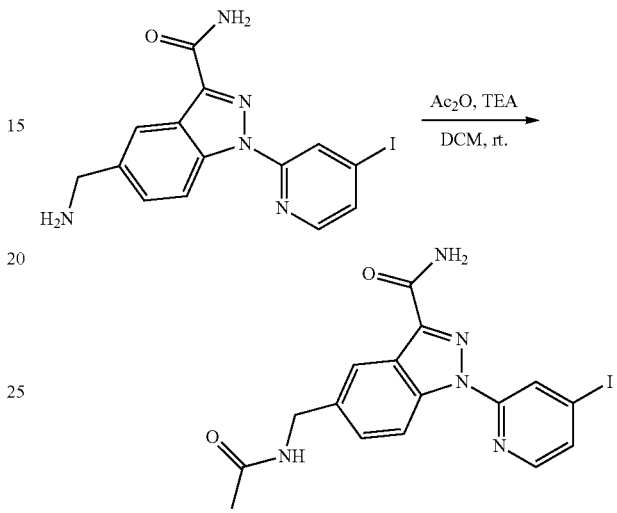

Acetic anhydride (62.32 mg, 0.61 mmol, 1.20 equiv) was added into a solution of 5-(aminomethyl)-1-(4-iodopyridin-2-yl)-1H-indazole-3-carboxamide (crude, 200.00 mg, 0.51 mmol, 1.00 equiv) and triethylamine (77.21 mg, 0.76 mmol, 1.50 equiv) in dichloromethane (5 mL, 78.65 mmol, 1.00 equiv) at room temperature. After being stirred for 1 h at room temperature the reaction mixture was concentrated under vacuum and the residue was washed with Et$_2$O to give 80 mg (29%) of the title compound as a yellow solid. LC-MS (ES, m/z): 436 [M+H]$^+$.

Step 7: Synthesis of 5-(acetamidomethyl)-1-(4-[2-[(3R)-3-hydroxy-1-methyl-2-oxopyrrolidin-3-yl]ethynyl]pyridin-2-yl)-1H-indazole-3-carboxamide

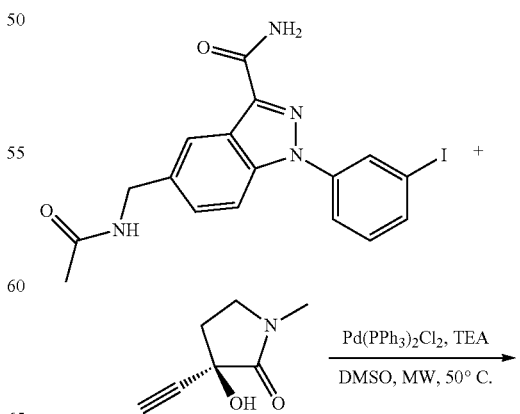

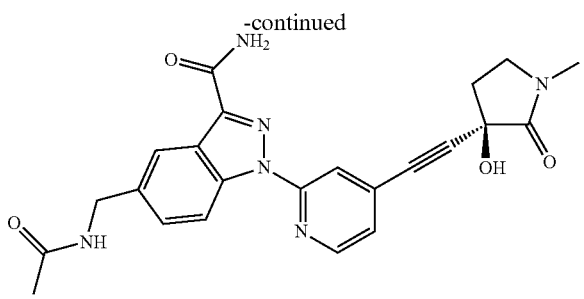

Similar to as described in General Procedure E, 5-(acetamidomethyl)-1-(4-iodopyridin-2-yl)-1H-indazole-3-carboxamide was reacted with (3R)-3-ethynyl-3-hydroxy-1-methylpyrrolidin-2-one to give the title compound (13.5 mg, 9%) as a white solid. LC-MS (ES, m/z): 447 [M+H]+. 1H NMR (300 MHz, DMSO-d6) δ 8.64 (d, J=8.7 Hz, 1H), 8.54 (d, J=5.4 Hz, 1H), 8.42 (t, J=6.0 Hz, 1H), 8.26 (s, 1H), 8.20 (s, 1H), 8.11 (s, 1H), 7.58 (s, 1H), 7.45 (dd, J=8.7, 1.5 Hz, 1H), 7.30 (dd, J=8.7, 1.2 Hz, 1H), 6.62 (s, 1H), 4.34 (d, J=6.0 Hz, 2H), 2.76 (s, 3H), 2.44-2.41 (m, 1H), 2.19-2.15 (m, 1H), 1.82 (s, 3H).

Example XXX and Example YYY

Synthesis of 1-(3-[2-[(3R)-3-hydroxy-1-methyl-2-oxopyrrolidin-3-yl]ethynyl]phenyl)-5-[[(3R)-3-hydroxypyrrolidin-1-yl]methyl]-1H-indazole-3-carboxamide and 1-(3-[2-[(3R)-3-hydroxy-1-methyl-2-oxopyrrolidin-3-yl]ethynyl]phenyl)-5-[[(3S)-3-hydroxypyrrolidin-1-yl]methyl]-1H-indazole-3-carboxamide Step 1: Synthesis of methyl 1-(3-bromophenyl)-5-[(3-hydroxypyrrolidin-1-yl)methyl]-1H-indazole-3-carboxylate

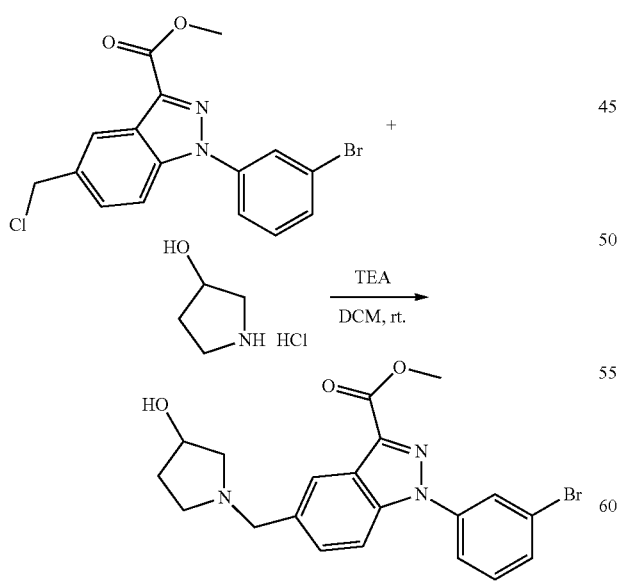

A suspension of pyrrolidin-3-ol hydrochloride (196 mg, 1.59 mmol, 4.00 equiv), methyl 1-(3-bromophenyl)-5-(chloromethyl)-1H-indazole-3-carboxylate (150 mg, 0.40 mmol, 1.00 equiv) and triethylamine (160 mg, 1.58 mmol, 4.00 equiv) in dichloromethane (10 mL) was stirred overnight at room temperature. The resulting mixture was concentrated under vacuum and the residue was purified on a silica gel column with dichloromethane/methanol (20:1) to give 120 mg (71%) of the title compound as a yellow solid. LC-MS (ES, m/z): 430, 432 [M+H]+.

Step 2: Synthesis of methyl 1-(3-[2-[(3R)-3-hydroxy-1-methyl-2-oxopyrrolidin-3-yl]ethynyl]phenyl)-5-[(3-hydroxypyrrolidin-1-yl)methyl]-1H-indazole-3-carboxylate

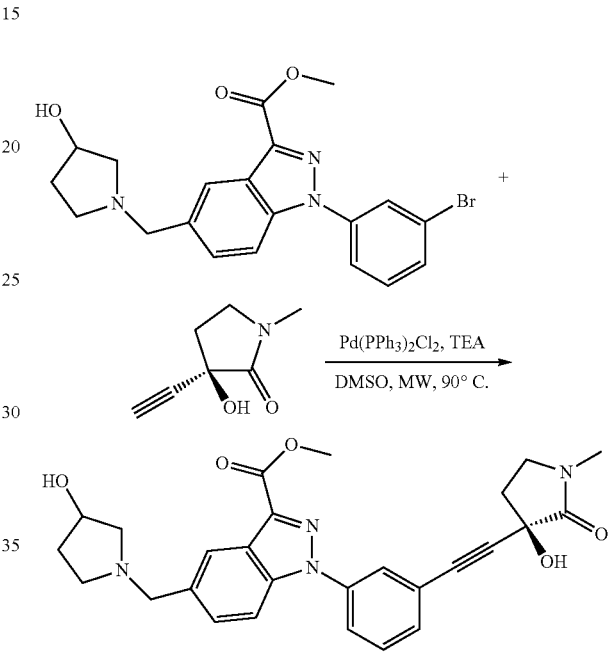

Similar to as described in General Procedure E, methyl 1-(3-bromophenyl)-5-[(3-hydroxypyrrolidin-1-yl)methyl]-1H-indazole-3-carboxylate was reacted with (3R)-3-ethynyl-3-hydroxy-1-methylpyrrolidin-2-one to give the title compound (100 mg, 73%) as a yellow solid. LC-MS (ES, m/z): 489 [M+H]+.

Step 3: Synthesis of 1-(3-[2-[(3R)-3-hydroxy-1-methyl-2-oxopyrrolidin-3-yl]ethynyl]phenyl)-5-[[(3R)-3-hydroxypyrrolidin-1-yl]methyl]-1H-indazole-3-carboxamide and 1-(3-[2-[(3R)-3-hydroxy-1-methyl-2-oxopyrrolidin-3-yl]ethynyl]phenyl)-5-[[(3S)-3-hydroxypyrrolidin-1-yl]methyl]-1H-indazole-3-carboxamide

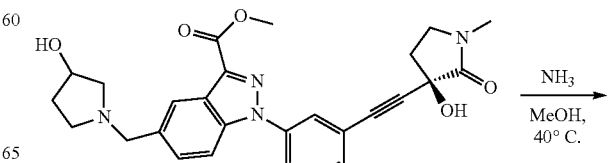

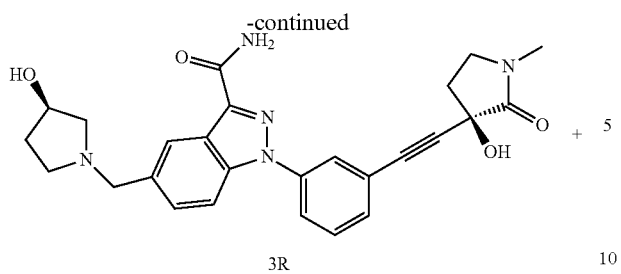

3R

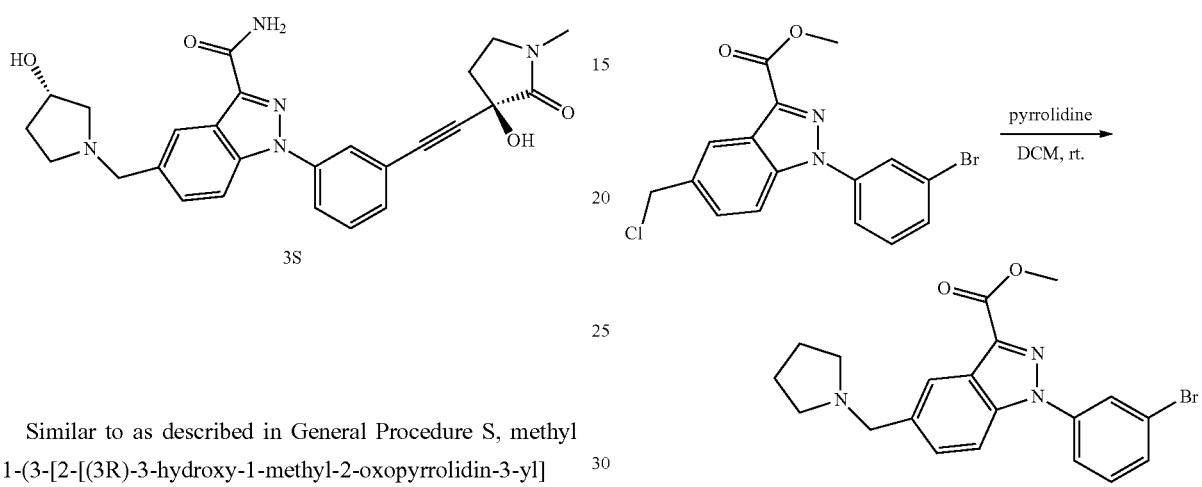

3S

Similar to as described in General Procedure S, methyl 1-(3-[2-[(3R)-3-hydroxy-1-methyl-2-oxopyrrolidin-3-yl]ethynyl]phenyl)-5-[(3-hydroxypyrrolidin-1-yl)methyl]-1H-indazole-3-carboxylate was reacted with ammonia in methanol to give the title compounds which were separated by Chiral-Prep-HPLC with the following conditions (Prep-HPLC-009): Column, Chiralpak AD-H, 2×25 cm; mobile phase, Hex(0.1% DEA) and ethanol (0.1% DEA) (hold 50.0% ethanol (0.1% DEA) in 13 min); Detector, UV 254/220 nm. The stereochemistry for either isomer is arbitrarily assigned.

Isomer A (3R): 7.2 mg (15%), white solid. $t_R$=9.65 min (Chiralpak AD-3, 25° C., 254 nm, Hex(0.1% TEA):EtOH 50:50, 1.0 mL/min). LC-MS (ES, m/z): 474 [M+H]$^+$. $^1$H NMR (300 MHz, CD$_3$OD) δ 8.33 (s, 1H), 7.95 (s, 1H), 7.90-7.80 (m, 2H), 7.69-7.54 (m, 3H), 4.42-4.36 (m, 1H), 3.97-3.84 (m, 2H), 3.52-3.48 (m, 2H), 2.94-2.85 (m, 5H), 2.71-2.57 (m, 3H), 2.38-2.29 (m, 1H), 2.22-2.15 (m, 1H), 1.78-1.68 (m, 1H).

Isomer B (3S): 11.9 mg (25%), white solid. $t_R$=12.62 min (Chiralpak AD-3, 25° C., 254 nm, Hex(0.1% TEA):EtOH 50:50, 1.0 mL/min). LC-MS (ES, m/z): 474 [M+H]$^+$. $^1$H NMR (300 MHz, CD$_3$OD) δ 8.33 (s, 1H), 7.95 (s, 1H), 7.90-7.80 (m, 2H), 7.69-7.54 (m, 3H), 4.42-4.36 (m, 1H), 3.97-3.84 (m, 2H), 3.52-3.48 (m, 2H), 2.94-2.85 (m, 5H), 2.71-2.57 (m, 3H), 2.38-2.29 (m, 1H), 2.22-2.15 (m, 1H), 1.78-1.68 (m, 1H).

Example ZZZ

Synthesis of 1-(3-[2-[(3R)-3-hydroxy-1-methyl-2-oxopyrrolidin-3-yl]ethynyl]phenyl)-5-(pyrrolidin-1-yl methyl)-1H-indazole-3-carboxamide Step 1: Synthesis of methyl 1-(3-bromophenyl)-5-(pyrrolidin-1-ylmethyl)-1H-indazole-3-carboxylate A suspension of methyl 1-(3-bromophenyl)-5-(chloromethyl)-1H-indazole-3-carboxylate (100 mg, 0.26 mmol, 1.00 equiv), pyrrolidine (75 mg, 1.05 mmol, 4.00 equiv) in dichloromethane (10 mL, 157.30 mmol, 597.20 equiv) was stirred overnight at room temperature. The resulting mixture was concentrated under vacuum to give 95 mg (78%) of the title compound as a yellow solid. LC-MS (ES, m/z) 414, 416 [M+H]$^+$.

Step 2: Synthesis of methyl 1-(3-[2-[(3R)-3-hydroxy-1-methyl-2-oxopyrrolidin-3-yl]ethynyl]phenyl)-5-(pyrrolidin-1-yl methyl)-1H-indazole-3-carboxylate

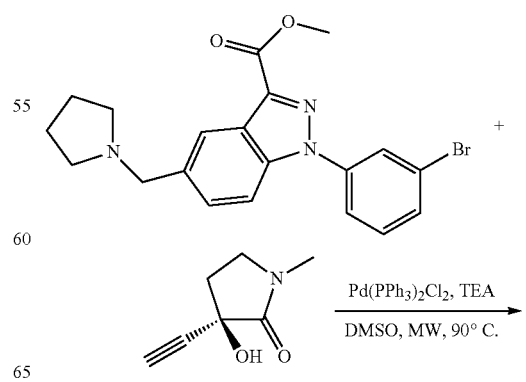

-continued

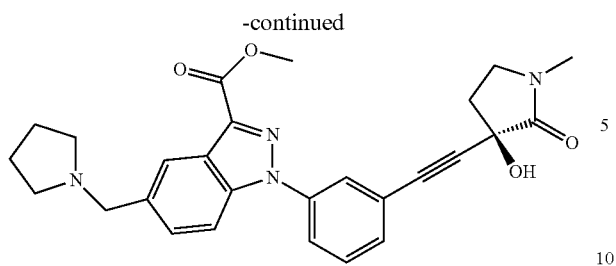

Similar to as described in General Procedure E, methyl 1-(3-bromophenyl)-5-(pyrrolidin-1-ylmethyl)-1H-indazole-3-carboxylate was reacted with (3R)-3-ethynyl-3-hydroxy-1-methylpyrrolidin-2-one to give the title compound (95 mg, 83%) as a yellow solid. LC-MS (ES, m/z): 473 [M+H]$^+$.

Step 3: Synthesis of 1-(3-[2-[(3R)-3-hydroxy-1-methyl-2-oxopyrrolidin-3-yl]ethynyl]phenyl)-5-(pyrrolidin-1-yl methyl)-1H-indazole-3-carboxamide

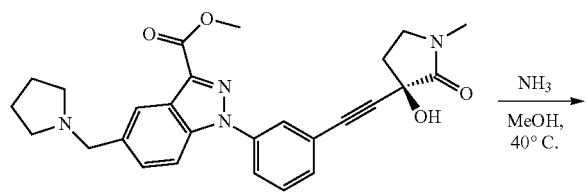

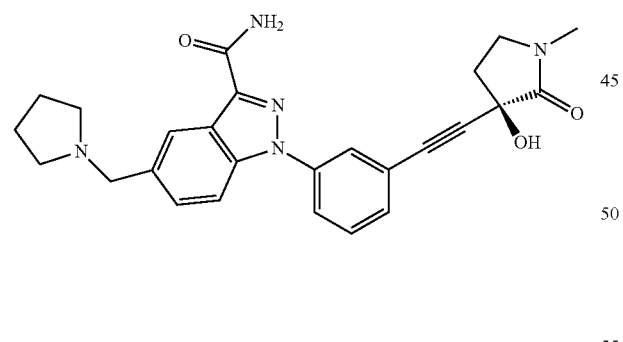

Similar to as described in General Procedure S, 1-(3-[2-[(3R)-3-hydroxy-1-methyl-2-oxopyrrolidin-3-yl]ethynyl]phenyl)-5-(pyrrolidin-1-yl methyl)-1H-indazole-3-carboxylate was reacted with ammonia in methanol to give the title compound (32.8 mg, 36%) as a light yellow solid. LC-MS (ES, m/z): 458 [M+H]$^+$. $^1$H NMR (300 MHz, CD$_3$OD) δ 8.28 (s, 1H), 7.90 (s, 1H), 7.84-7.74 (m, 2H), 7.61-7.51 (m, 3H), 3.79 (s, 2H), 3.51-3.46 (m, 2H), 2.94 (s, 3H), 2.64-2.59 (m, 5H), 2.38-2.28 (m, 1H), 1.87-1.84 (m, 4H).

Example AAAA

Synthesis of 5-(cyanomethyl)-1-(3-[2-[(3R)-3-hydroxy-1-methyl-2-oxopyrrolidin-3-yl]ethynyl]phenyl)-1H-indazole-3-carboxamide Step 1: Synthesis of methyl 1-(3-bromophenyl)-5-(chloromethyl)-1H-indazole-3-carboxylate

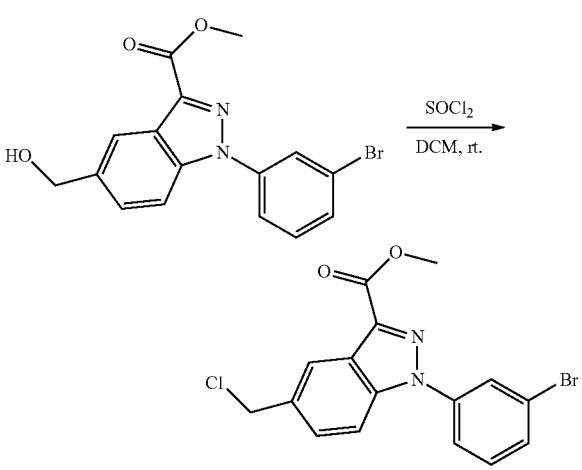

Sulfurous dichloride (5 mL) was added into a suspension of methyl 1-(3-bromophenyl)-5-(hydroxymethyl)-1H-indazole-3-carboxylate (300 mg, 0.83 mmol, 1.00 equiv) in dichloromethane (10 mL, 157.30 mmol, 189.40 equiv) at 0° C. The reaction was stirred for 3 h at room temperature and concentrated under vacuum to give 290 mg (92%) of the title compound as a white solid. LC-MS (ES, m/z): 379, 381 [M+H]$^+$.

Step 2: Synthesis of methyl 1-(3-bromophenyl)-5-(cyanomethyl)-1H-indazole-3-carboxylate

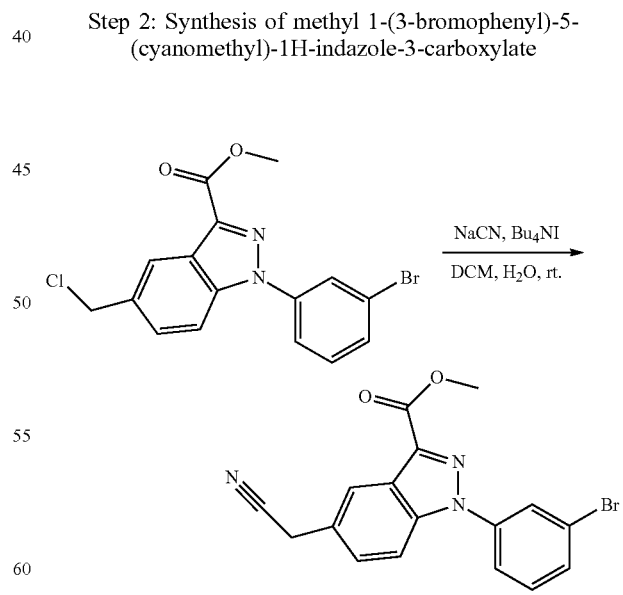

A suspension of methyl 1-(3-bromophenyl)-5-(chloromethyl)-1H-indazole-3-carboxylate (200 mg, 0.53 mmol, 1.00 equiv), tetra-n-butylammonium iodide (292 mg, 0.79 mmol, 1.50 equiv) and sodium cyanide (39 mg, 0.80 mmol, 1.50 equiv) in dichloromethane (10 mL)/water (1 mL) was stirred for 5 h at room temperature. The reaction mixture was diluted with 5 mL of water, extracted with dichloromethane, dried over anhydrous sodium sulfate, and concentrated under vacuum. The residue was purified on a silica gel column with ethyl acetate/petroleum ether (1:4) to give 190 mg (97%) of methyl 1-(3-bromophenyl)-5-(cyanomethyl)-1H-indazole-3-carboxylate as a white solid. LC-MS (ES, m/z): 370, 372 [M+H]⁺.

Step 3: Synthesis of methyl 5-(cyanomethyl)-1-(3-[2-[(3R)-3-hydroxy-1-methyl-2-oxopyrrolidin-3-yl]ethynyl]phenyl)-1H-indazole-3-carboxylate

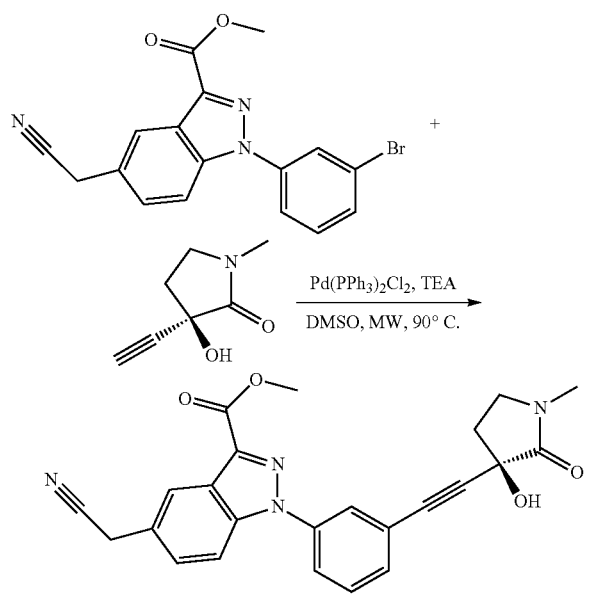

Similar to as described in General Procedure E, methyl 5-(cyanomethyl)-1-(3-[2-[(3R)-3-hydroxy-1-methyl-2-oxopyrrolidin-3-yl]ethynyl]phenyl)-1H-indazole-3-carboxylate was reacted with (3R)-3-ethynyl-3-hydroxy-1-methylpyrrolidin-2-one to give the title compound (160 mg, 77%) as a yellow solid. LC-MS (ES, m/z): 429 [M+H]⁺.

Step 4: Synthesis of 5-(cyanomethyl)-1-(3-[2-[(3R)-3-hydroxy-1-methyl-2-oxopyrrolidin-3-yl]ethynyl]phenyl)-1H-indazole-3-carboxamide

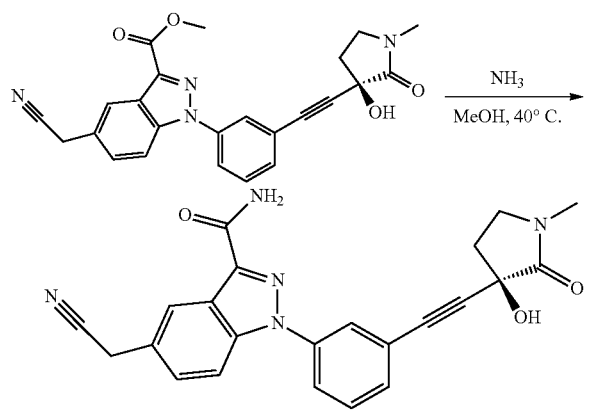

Similar to as described in General Procedure S, methyl 5-(cyanomethyl)-1-(3-[2-[(3R)-3-hydroxy-1-methyl-2-oxopyrrolidin-3-yl]ethynyl]phenyl)-1H-indazole-3-carboxylate was reacted with ammonia in methanol to give the title compound (60.5 mg, 39%) as a white solid. LC-MS (ES, m/z): 414 [M+H]⁺, 827 [2M+H]⁺. ¹H NMR (400 MHz, CD₃OD) δ 8.38 (br s, 1H), 7.94-7.85 (m, 3H), 7.64-7.55 (m, 3H), 4.10 (s, 2H), 3.55-3.47 (m, 2H), 2.95 (s, 3H), 2.65-2.59 (m, 1H), 2.38-2.31 (m, 1H).

Example BBBB

Synthesis of 1-(3-[2-[(3S)-3-hydroxy-1-methyl-2-oxopyrrolidin-3-yl]ethynyl]phenyl)-1H-indazole-3-carboxamide Step 1: Synthesis of methyl 1-(3-[2-[(3S)-3-hydroxy-1-methyl-2-oxopyrrolidin-3-yl]ethynyl]phenyl)-1H-indazole-3-carboxylate

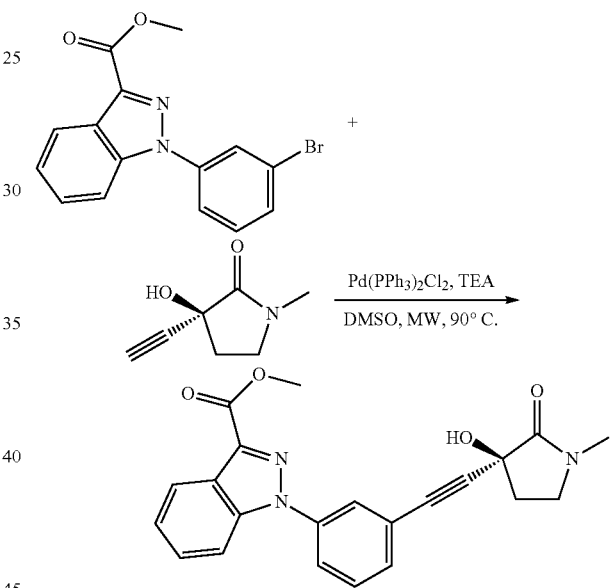

Similar to as described in General Procedure E, methyl 1-(3-bromophenyl)-1H-indazole-3-carboxylate was reacted with (3S)-3-ethynyl-3-hydroxy-1-methylpyrrolidin-2-one to give the title compound (160 mg, 91%) as a yellow oil. LC-MS (ES, m/z): 390 [M+H]⁺.

Step 2: Synthesis of 1-(3-[2-[(3S)-3-hydroxy-1-methyl-2-oxopyrrolidin-3-yl]ethynyl]phenyl)-1H-indazole-3-carboxamide

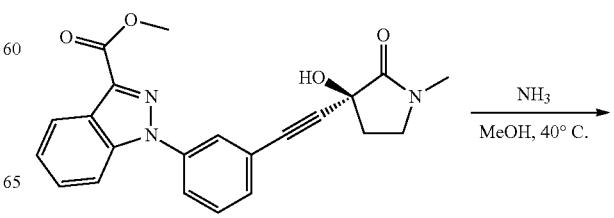

325

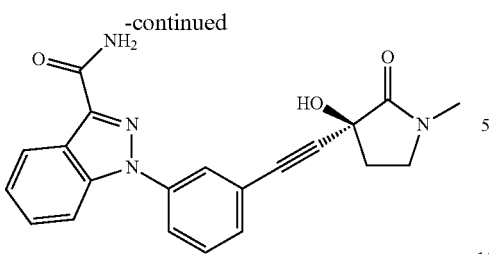

Similar to as described in General Procedure S, 1-(3-[2-[(3S)-3-hydroxy-1-methyl-2-oxopyrrolidin-3-yl]ethynyl]phenyl)-1H-indazole-3-carboxylate was reacted with ammonia in methanol to give the title compound (33.8 mg, 22%) as a white solid. LC-MS (ES, m/z): 375 [M+H]$^+$, 392 [M+NH$_4$]$^+$. $^1$H NMR (400 MHz, CD$_3$OD) δ 8.36 (d, J=8.4 Hz, 1H), 7.96 (s, 1H), 7.89-7.82 (m, 2H), 7.65-7.56 (m, 3H), 7.41 (t, J=7.6 Hz, 1H), 3.55-3.46 (m, 2H), 2.95 (s, 3H), 2.66-2.60 (m, 1H), 2.38-2.31 (m, 1H).

Example CCCC

Synthesis of 1-[3-(3-hydroxy-3-methylbut-1-yn-1-yl)phenyl]-1H-indazole-3-carboxamide Step 1: Synthesis of methyl 1-[3-(3-hydroxy-3-methylbut-1-yn-1-yl)phenyl]-1H-indazole-3-carboxylate

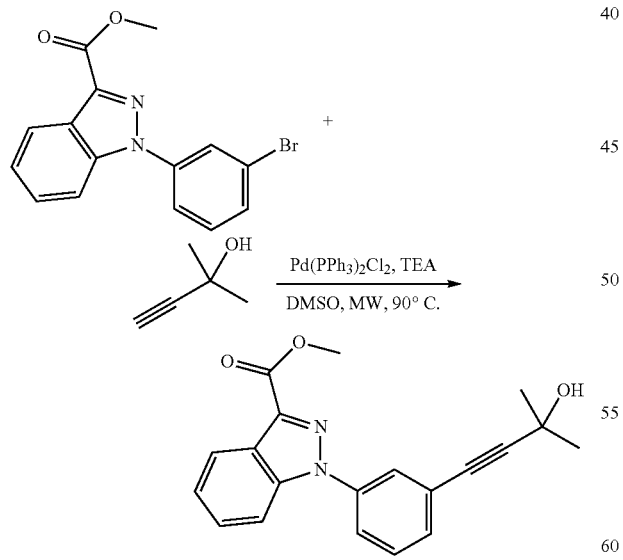

Similar to as described in General Procedure E, 1-(3-bromophenyl)-1H-indazole-3-carboxylate was reacted with 2-methylbut-3-yn-2-ol to give the title compound (140 mg, 92%) as a yellow oil. LC-MS (ES, m/z): 335 [M+H]$^+$.

326

Step 2: Synthesis of 1-[3-(3-hydroxy-3-methylbut-1-yn-1-yl)phenyl]-1H-indazole-3-carboxamide

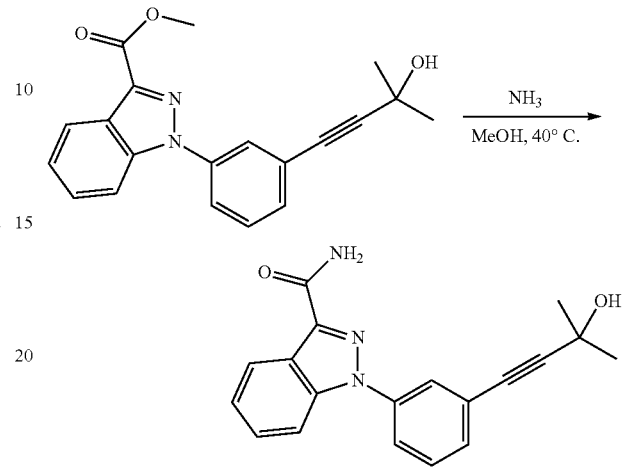

Similar to as described in General Procedure S, methyl 1-[3-(3-hydroxy-3-methylbut-1-yn-1-yl)phenyl]-1H-indazole-3-carboxylate was reacted with ammonia in methanol to give the title compound (29.6 mg, 22%) as a white solid. LC-MS (ES, m/z): 320 [M+H]$^+$, 639 [2M+H]$^+$. $^1$H NMR (400 MHz, CD$_3$OD) δ 8.36 (d, J=8.0 Hz, 1H), 7.87-7.79 (m, 3H), 7.63-7.51 (m, 3H), 7.41 (t, J=7.2 Hz, 1H), 1.61 (s, 6H).

Example DDDD and Example EEEE

Synthesis of 1-[3-[(3R)-3-(dimethylcarbamoyl)-3-hydroxy-3-methylprop-1-yn-1-yl]phenyl]-1H-indazole-3-carboxamide and 1-[3-[(3S)-3-(dimethylcarbamoyl)-3-hydroxy-3-methylprop-1-yn-1-yl]phenyl]-1H-indazole-3-carboxamide

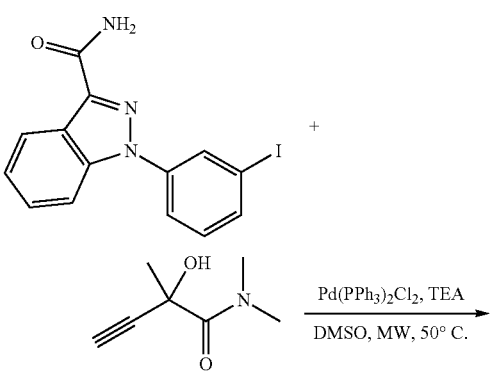

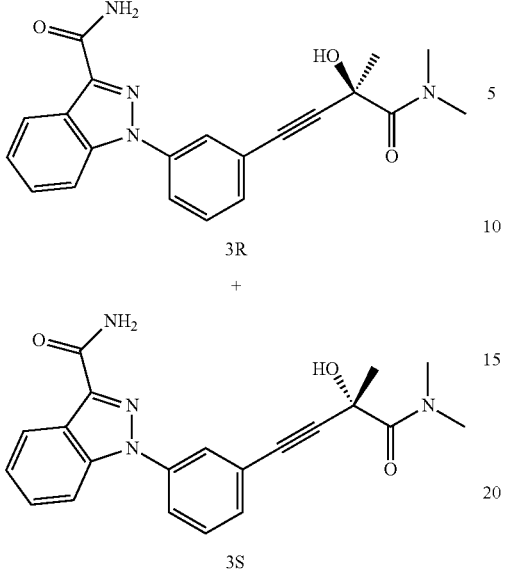

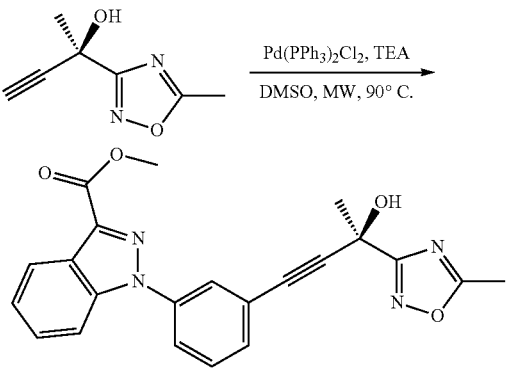

Similar to as described in General Procedure E, 1-(3-bromophenyl)-1H-indazole-3-carboxylate was reacted with (2R)-2-(5-methyl-1,2,4-oxadiazol-3-yl)but-3-yn-2-ol to give the title compound (150 mg, 82%) as a yellow oil. LC-MS: (ES, m/z): 403 [M+H]$^+$.

Similar to as described in General Procedure M, 1-(3-iodophenyl)-1H-indazole-3-carboxamide was reacted with 2-hydroxy-N,N,2-trimethylbut-3-ynamide to give the title compounds which were separated by Chiral-Prep-HPLC with the following conditions: Column, Chiralpak AD-H, 2×25 cm; mobile phase, Hex and ethanol (hold 40.0% ethanol in 10 min); Detector, UV 254/220 nm. The stereochemistry for either isomer is arbitrarily assigned.

Isomer A (3R): 32.4 mg (41%), white solid. $t_R$=7.28 min (ADH, 25° C., 254 nm, Hex(0.1% TEA):EtOH 50:50, 1.0 mL/min). LC-MS (ES, m/z): 377 [M+H]$^+$. $^1$H NMR (300 MHz, CD$_3$OD) δ 8.35 (d, J=8.1 Hz, 1H), 7.90-7.81 (m, 3H), 7.65-7.52 (m, 3H), 7.39 (t, J=7.5 Hz, 1H), 3.46 (s, 3H), 3.02 (s, 3H), 1.77 (s, 3H).

Isomer B (3S): 33.4 mg (42%), white solid. $t_R$=9.62 min (ADH, 25° C., 254 nm, Hex(0.1% TEA):EtOH 50:50, 1.0 mL/min). LC-MS (ES, m/z): 377 [M+H]$^+$. $^1$H NMR (300 MHz, CD$_3$OD) δ 8.35 (d, J=8.1 Hz, 1H), 7.90-7.81 (m, 3H), 7.65-7.52 (m, 3H), 7.39 (t, J=7.5 Hz, 1H), 3.46 (s, 3H), 3.02 (s, 3H), 1.77 (s, 3H).

Step 2: Synthesis of 1-[3-[(3R)-3-hydroxy-3-(5-methyl-1,2,4-oxadiazol-3-yl)but-1-yn-1-yl]phenyl]-1H-indazole-3-carboxamide

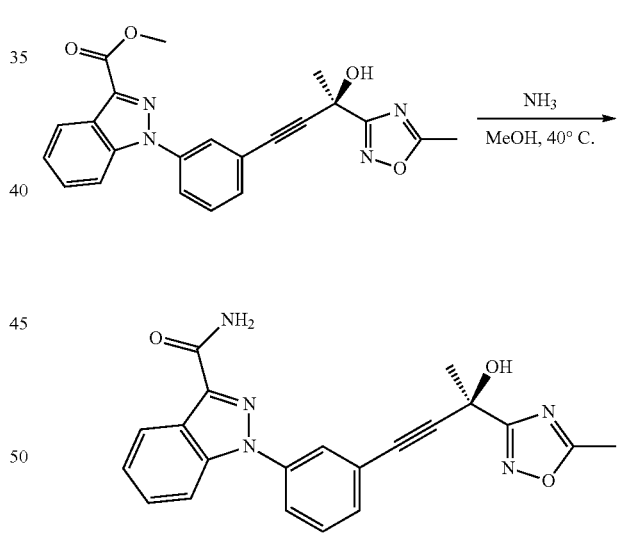

Similar to as described in General Procedure S, methyl 1-[3-[(3R)-3-hydroxy-3-(5-methyl-1,2,4-oxadiazol-3-yl)but-1-yn-1-yl]phenyl]-1H-indazole-3-carboxylate was reacted with ammonia in methanol to give the title compound (39.7 mg, 27%) as a white solid. LC-MS (ES, m/z): 388 [M+H]$^+$, 429 [M+CH$_3$CN+H]$^+$. $^1$H NMR (300 MHz, CD$_3$OD) δ 8.35 (d, J=8.1 Hz, 1H), 7.95 (s, 1H), 7.89-7.84 (m, 2H), 7.65-7.54 (m, 3H), 7.40 (t, J=7.2 Hz, 1H), 2.64 (s, 3H), 1.95 (s, 3H).

Example FFFF

Synthesis of 1-[3-[(3R)-3-hydroxy-3-(5-methyl-1,2,4-oxadiazol-3-yl)but-1-yn-1-yl]phenyl]-1H-indazole-3-carboxamide Step 1: Synthesis of methyl 1-[3-[(3R)-3-hydroxy-3-(5-methyl-1,2,4-oxadiazol-3-yl)but-1-yn-1-yl]phenyl]-1H-indazole-3-carboxylate

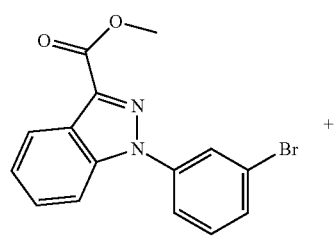

Example GGGG

Synthesis of 1-(3-[2-[(3R)-3-hydroxy-1-methyl-2-oxopyrrolidin-3-yl]ethynyl]phenyl)-5-methoxy-1H-indazole-3-carboxamide

Step 1: Synthesis of methyl 5-methoxy-1H-indazole-3-carboxylate

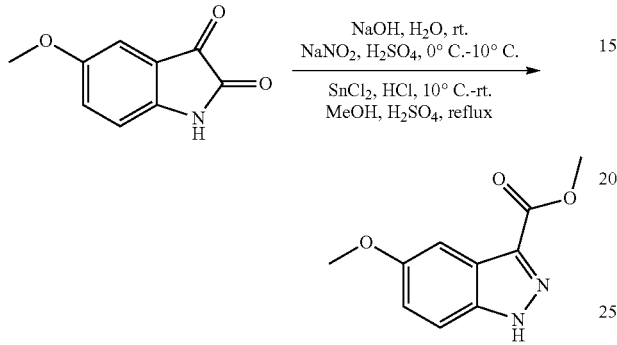

Similar to as described in General Procedure Z, the title compound was prepared from 5-methoxy-2,3-dihydro-1H-indole-2,3-dione. Yield (2.15 g, 37%, brown solid). LC-MS (ES, m/z): 207 [M+H]$^+$.

Step 2: Synthesis of methyl 1-(3-bromophenyl)-5-methoxy-1H-indazole-3-carboxylate

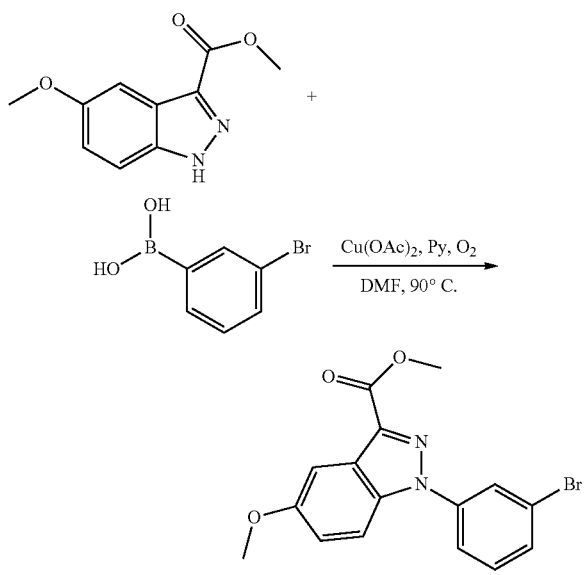

Similar to as described in General Procedure C, methyl 5-methoxy-1H-indazole-3-carboxylate was reacted with (3-bromophenyl)boronic acid to give the title compound (135 mg, 39%) as an off-white solid. LC-MS (ES, m/z): 361, 363 [M+H]$^+$.

Step 3: Synthesis of methyl 1-(3-[2-[(3R)-3-hydroxy-1-methyl-2-oxopyrrolidin-3-yl]ethynyl]phenyl)-5-methoxy-1H-indazole-3-carboxylate

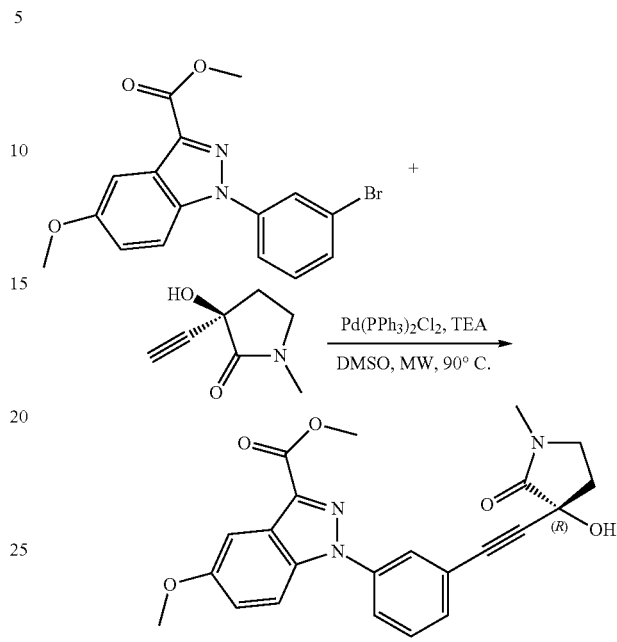

Similar to as described in General Procedure E, methyl 1-(3-bromophenyl)-5-methoxy-1H-indazole-3-carboxylate was reacted with (3R)-3-ethynyl-3-hydroxy-1-methylpyrrolidin-2-one to give the title compound (60 mg, 45%) as a yellow oil. LC-MS (ES, m/z): 420 [M+H]$^+$.

Step 4: Synthesis of 1-(3-[2-[(3R)-3-hydroxy-1-methyl-2-oxopyrrolidin-3-yl]ethynyl]phenyl)-5-methoxy-1H-indazole-3-carboxamide

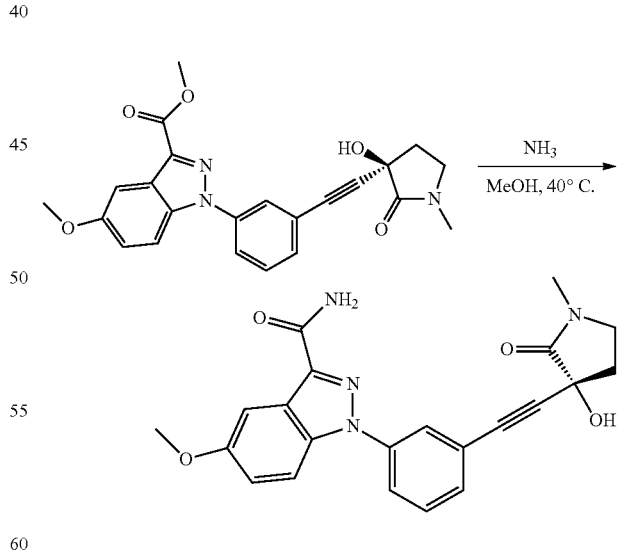

Similar to as described in General Procedure S, methyl 1-(3-[2-[(3R)-3-hydroxy-1-methyl-2-oxopyrrolidin-3-yl]ethynyl]phenyl)-5-methoxy-1H-indazole-3-carboxylate was reacted with ammonia in methanol to give the title compound (13.2 mg, 23%) as an off-white solid. LC-MS (ES, m/z): 405 [M+H]$^+$, 427 [M+Na]$^+$. $^1$H NMR (300 MHz, CD$_3$OD) δ 7.92 (s, 1H), 7.85 (d, J=7.8 Hz, 1H), 7.76-7.70

(m, 2H), 7.63-7.53 (m, 2H), 7.9 (d, J=9.0 Hz, 1H), 3.90 (s, 3H), 3.54-3.47 (m, 2H), 2.94 (s, 3H), 2.67-2.57 (m, 1H), 2.38-2.28 (m, 1H).

Example HHHH

Synthesis of 5-fluoro-1-(3-[2-[(3R)-3-hydroxy-1-methyl-2-oxopyrrolidin-3-yl]ethynyl]phenyl)-1H-indazole-3-carboxamide Step 1: Synthesis of methyl 5-fluoro-1H-indazole-3-carboxylate

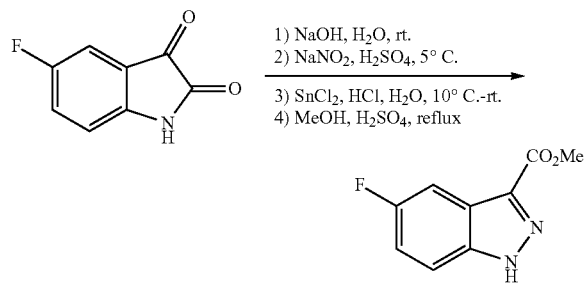

Similar to as described in General Procedure Z, the title compound was prepared from 5-fluoro-2,3-dihydro-1H-indole-2,3-dione. Yield (5 g, 43%, brown solid). LC-MS (ES, m/z): 195 [M+H]+.

Step 2: Synthesis of methyl 1-(3-bromophenyl)-5-fluoro-1H-indazole-3-carboxylate

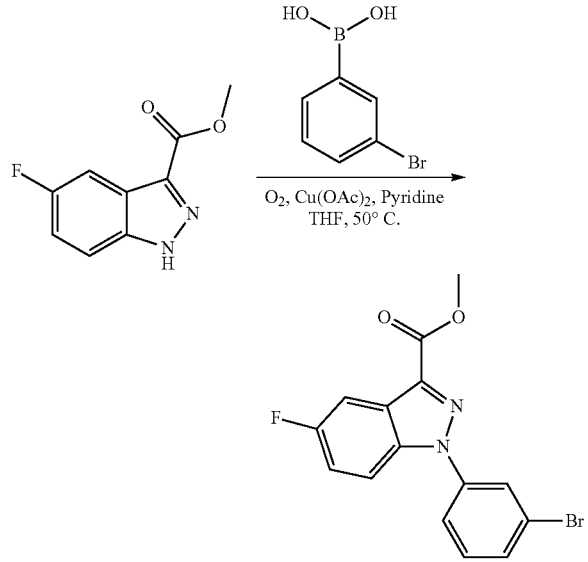

Similar to as described in General Procedure C, methyl 5-fluoro-1H-indazole-3-carboxylate was reacted with (3-bromophenyl)boronic acid to give the title compound (50 mg, 14%) as an off-white solid. LC-MS (ES, m/z): 349,351 [M+H]+.

Step 3: Synthesis of methyl 5-fluoro-1-(3-[2-[(3R)-3-hydroxy-1-methyl-2-oxopyrrolidin-3-yl]ethynyl]phenyl)-1H-indazole-3-carboxylate

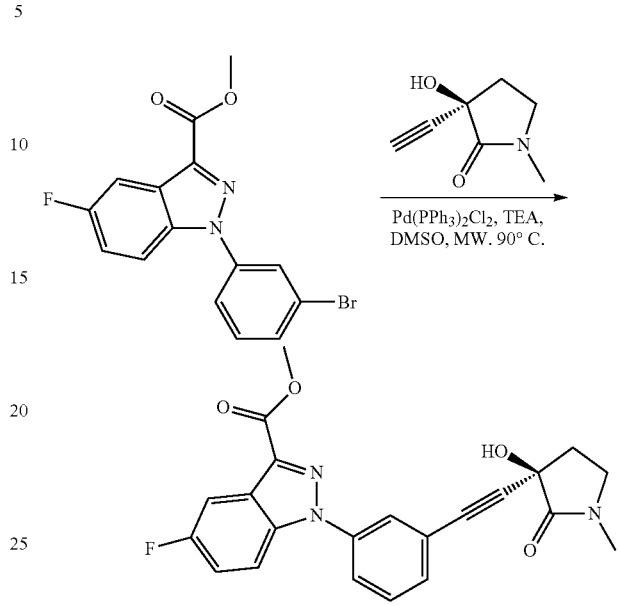

Similar to as described in General Procedure E, 1-(3-bromophenyl)-5-fluoro-1H-indazole-3-carboxylate was reacted with (3R)-3-ethynyl-3-hydroxy-1-methylpyrrolidin-2-one to give the title compound (35 mg, 60%) as a yellow oil. LC-MS (ES, m/z): 408 [M+H]+, 449[M+CH3CN+H]+.

Step 4: Synthesis of 5-fluoro-1-(3-[2-[(3R)-3-hydroxy-1-methyl-2-oxopyrrolidin-3-yl]ethynyl]phenyl)-1H-indazole-3-carboxamide

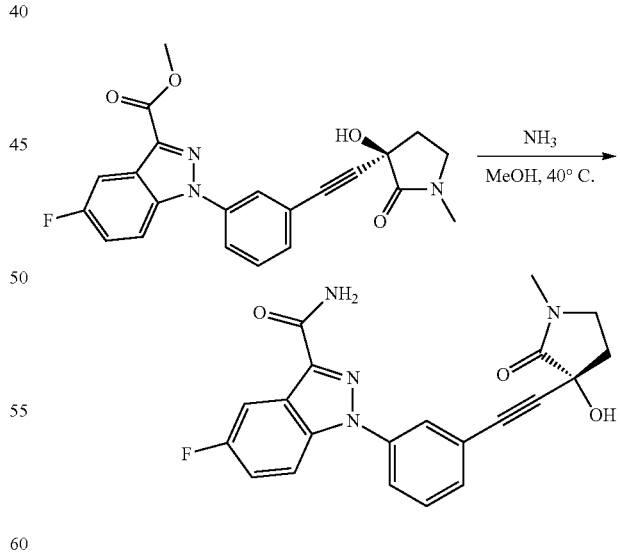

Similar to as described in General Procedure S, methyl 5-fluoro-1-(3-[2-[(3R)-3-hydroxy-1-methyl-2-oxopyrrolidin-3-yl]ethynyl]phenyl)-1H-indazole-3-carboxylate was reacted with ammonia in methanol to give the title compound 15.7 mg, 47%) as a white solid. LC-MS (ES, m/z): 393 [M+H]+, 785 [2M+H]+. $^1$H NMR (400 MHz, CD$_3$OD) δ 8.00-7.93 (m, 2H), 7.89-7.83 (m, 2H), 7.66-7.58 (m, 2H), 7.41-7.37 (m, 1H), 3.52-3.46 (m, 2H), 2.95 (s, 3H), 2.65-2.59 (m, 1H), 2.38-2.31 (m, 1H).

Example IIII and Example JJJJ

Synthesis of ethyl (5aS)-5,5-difluoro-1-(3-[2-[(3R)-3-hydroxy-1-methyl-2-oxopyrrolidin-3-yl]ethynyl]phenyl)-5a-methyl-1H,4H,4aH,5H,5aH,6H-cyclopropa[f]indazole-3-carboxylate and (5aR)-5,5-difluoro-1-(3-[2-[(3R)-3-hydroxy-1-methyl-2-oxopyrrolidin-3-yl]ethynyl]phenyl)-5a-methyl-1H,4H,4aH,5H,5aH,6H-cyclopropa[f]indazole-3-carboxylate Step 1: Synthesis of ethyl 1-(3-bromophenyl)-5,5-difluoro-5a-methyl-1H,4H,4aH,5H,5aH,6H-cyclopropa[f]indazole-3-carboxylate

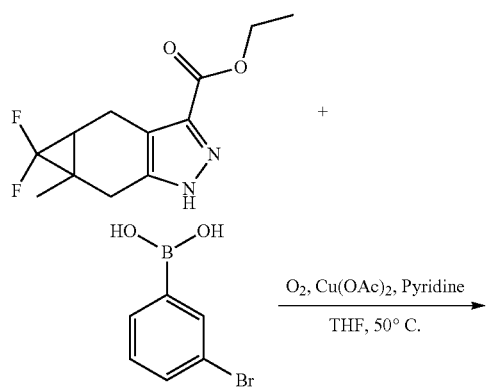

Similar to as described in General Procedure C, ethyl 5,5-difluoro-5a-methyl-1,4,4a,5,5a,6-hexahydrocyclopropa[f]indazole-3-carboxylate was reacted with (3-bromophenyl)boronic acid to give the title compound (500 mg, 30%) as a white solid. LC-MS (ES, m/z): 411, 413 [M+H]+.

Step 2: Synthesis of ethyl 5,5-difluoro-1-(3-[2-[(3R)-3-hydroxy-1-methyl-2-oxopyrrolidin-3-yl]ethynyl]phenyl)-5a-methyl-1H,4H,4aH,5H,5aH,6H-cyclopropa[f]indazole-3-carboxylate

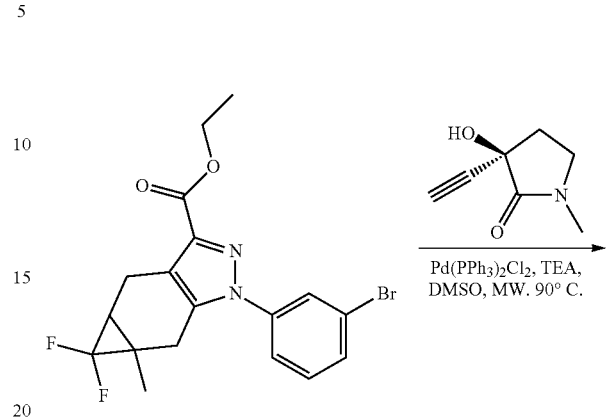

Similar to as described in General Procedure E, ethyl 1-(3-bromophenyl)-5,5-difluoro-5a-methyl-1H,4H,4aH,5H,5aH,6H-cyclopropa[f]indazole-3-carboxylate was reacted with (3R)-3-ethynyl-3-hydroxy-1-methylpyrrolidin-2-one to give the title compound (200 mg, 88%) as a yellow oil. LC-MS (ES, m/z): 470 [M+H]+.

Step 3: Synthesis of ethyl (5aS)-5,5-difluoro-1-(3-[2-[(3R)-3-hydroxy-1-methyl-2-oxopyrrolidin-3-yl]ethynyl]phenyl)-5a-methyl-1H,4H,4aH,5H,5aH,6H-cyclopropa[f]indazole-3-carboxylate and (5aR)-5,5-difluoro-1-(3-[2-[(3R)-3-hydroxy-1-methyl-2-oxopyrrolidin-3-yl]ethynyl]phenyl)-5a-methyl-1H,4H,4aH,5H,5aH,6H-cyclopropa[f]indazole-3-carboxylate

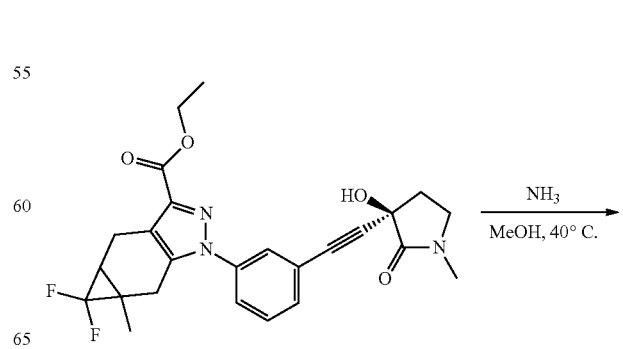

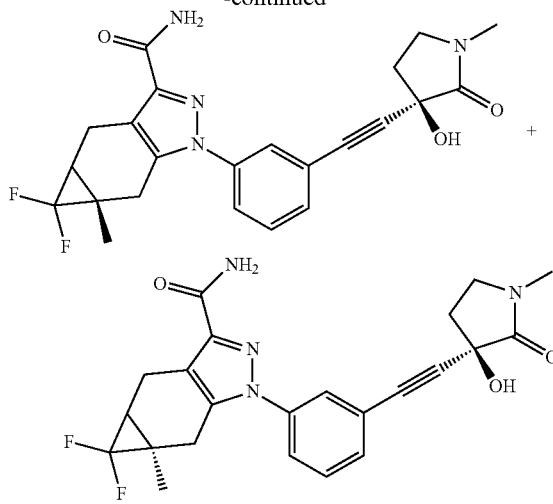

Similar to as described in General Procedure S, ethyl 5,5-difluoro-1-(3-[2-[(3R)-3-hydroxy-1-methyl-2-oxopyrrolidin-3-yl]ethynyl]phenyl)-5a-methyl-1H,4H,4aH,5H,5aH,6H-cyclopropa[f]indazole-3-carboxylate was reacted with ammonia in methanol to give the title compounds which were separated by Chiral-Prep-HPLC with the following conditions: Column, Chiralpak IC, 2×25 cm, 5 um; mobile phase, Hex and ethanol (hold 50.0% ethanol in 17 min); Detector, UV 254/220 nm. The stereochemistry for either isomer is arbitrarily assigned.

Isomer A (5aS): 21.7 mg (11%), white solid. $t_R$=5.72 min (Chiralpak IC-3, 25° C., UV-254 nm, Hex:EtOH 50:50, 1.0 mL/min). LC-MS (ES, m/z): 441 [M+H]$^+$, 463 [M+Na]$^+$. $^1$H NMR: (300 MHz, CD$_3$OD) δ 7.70 (s, 1H), 7.66-7.52 (m, 3H), 3.56-3.47 (m, 2H), 3.34-2.98 (m, 4H), 2.95 (s, 3H), 2.65-2.57 (m, 1H), 2.38-2.28 (m, 1H), 1.76-1.69 (m, 1H), 1.41 (s, 3H).

Isomer B (5aR): 34.4 mg (17%), white solid. $t_R$=7.76 min (Chiralpak IC-3, 25° C., UV-254 nm, Hex:EtOH 50:50, 1.0 mL/min.). LC-MS (ES, m/z): 441 [M+H]$^+$, 463[M+Na]$^+$. $^1$H NMR (400 MHz, CD$_3$OD) δ 7.70 (s, 1H), 7.66-7.52 (m, 3H), 3.56-3.47 (m, 2H), 3.34-2.98 (m, 4H), 2.95 (s, 3H), 2.65-2.57 (m, 1H), 2.38-2.28 (m, 1H), 1.76-1.69 (m, 1H), 1.41 (s, 3H).

Example KKKK

Synthesis of 5-cyano-1-(3-[2-[(3R)-3-hydroxy-1-methyl-2-oxopyrrolidin-3-yl]ethynyl]phenyl)-1H-indazole-3-carboxamide Step 1: Synthesis of (3-iodo-1H-indazol-5-yl)methanol

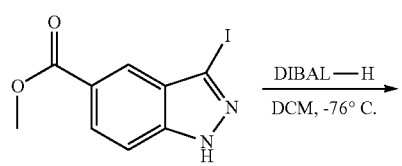

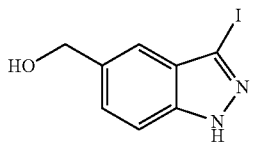

Under nitrogen diisobutyl aluminium hydride (1 M in n-hexane, mL, 45.00 mmol, 2.83 equiv) was added dropwise to a solution of methyl 3-iodo-1H-indazole-5-carboxylate (4.8 g, 15.89 mmol, 1.00 equiv) in dichloromethane (300 mL) at −76° C. After being stirred at room temperature for 1 h the reaction was quenched with saturated aqueous Rochelle salt solution. The resulting mixture was concentrated under vacuum to afford 14 g (crude) of (3-iodo-1H-indazol-5-yl)methanol as an off-white solid which was used for the next step without further purification. LC-MS (ES, m/z): 275 [M+H]$^+$.

Step 2: Synthesis of methyl 5-(hydroxymethyl)-1H-indazole-3-carboxylate

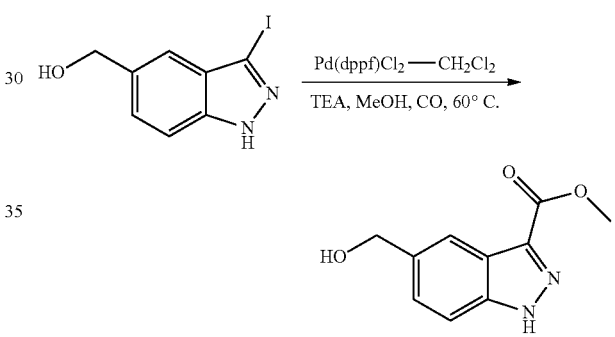

To a solution of (3-iodo-1H-indazol-5-yl)methanol (14.00 g, 51.08 mmol, 1.00 equiv), triethylamine (30 mL) in methanol (250 mL) was added Pd(dppf)Cl$_2$.CH$_2$Cl$_2$ (8.34 g, 10.21 mmol, 0.20 equiv). The mixture was flushed with carbon monoxide gas for several minutes and then sealed with carbon monoxide balloon and heated to 50° C. for 6 h. The mixture was concentrated under vacuum and the residue was purified on silica gel column chromatography eluting with dichloromethane/methanol (19:1) to give 3.0 g (28%) of the title compound as a yellow solid. LC-MS (ES, m/z): 207 [M+H]$^+$.

Step 3: Synthesis of methyl 5-[[(tert-butyldimethylsilyl)oxy]methyl]-1H-indazole-3-carboxylate

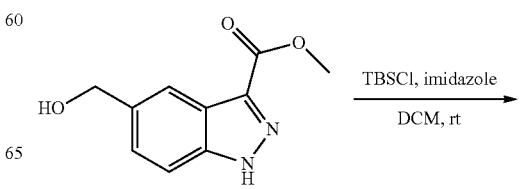

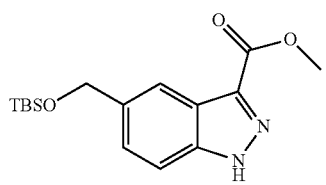

A solution of methyl 5-(hydroxymethyl)-1H-indazole-3-carboxylate (2.00 g, 9.70 mmol, 1.00 equiv), tert-butyldimethylsilylchloride (2.19 g, 14.53 mmol, 1.50 equiv), imidazole (1.32 g, 19.39 mmol, 2.00 equiv) in dichloromethane (200 mL) was stirred overnight at room temperature. The reaction mixture was concentrated under vacuum and the residue was purified by silica gel column chromatography eluting with dichloromethane/methanol (19:1) to afford the title compound (2 g, crude) as a yellow solid. LC-MS: (ES, m/z): 321 [M+H]$^+$.

Step 4: Synthesis of methyl 1-(3-bromophenyl)-5-[[(tert-butyldimethylsilyl)oxy]methyl]-1H-indazole-3-carboxylate

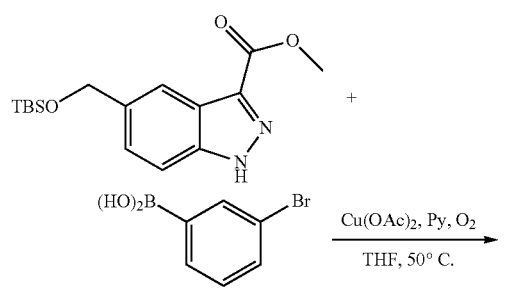

Similar to as described in General Procedure C, methyl 5-[[(tert-butyldimethylsilyl)oxy]methyl]-1H-indazole-3-carboxylate was reacted with (3-bromophenyl)boronic acid to give the title compound (2.0 g, 56%) as a yellow solid. LC-MS (ES, m/z): 475 [M+H]$^+$.

Step 5: Synthesis of methyl 1-(3-bromophenyl)-5-(hydroxymethyl)-1H-indazole-3-carboxylate

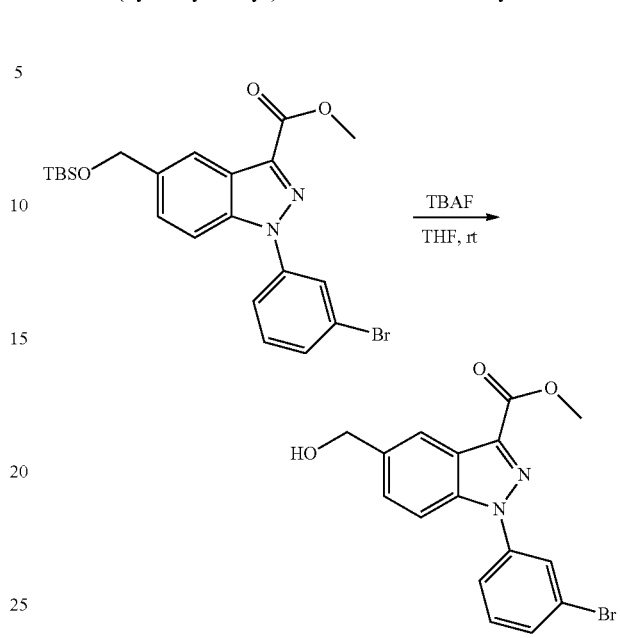

A solution of methyl 1-(3-bromophenyl)-5-[[(tert-butyldimethylsilyl)oxy]methyl]-1H-indazole-3-carboxylate (2.00 g, 4.21 mmol, 1.00 equiv) and tetrabutylazanium fluoride (2.20 g, 8.41 mmol, 2.00 equiv) in tetrahydrofuran (100 mL) was stirred for 1 h at room temperature. The reaction was diluted with ethyl acetate and washed with brine. The organic layer was dried over sodium sulfate and concentrated under vacuum. The residue was purified by silica gel column chromatography eluting with dichloromethane/methanol (19:1) to give the title compound (1.5 g, 99%) as an off-white solid. LC-MS (ES, m/z): 361 [M+H]$^+$.

Step 6: Synthesis of methyl 1-(3-bromophenyl)-5-formyl-1H-indazole-3-carboxylate

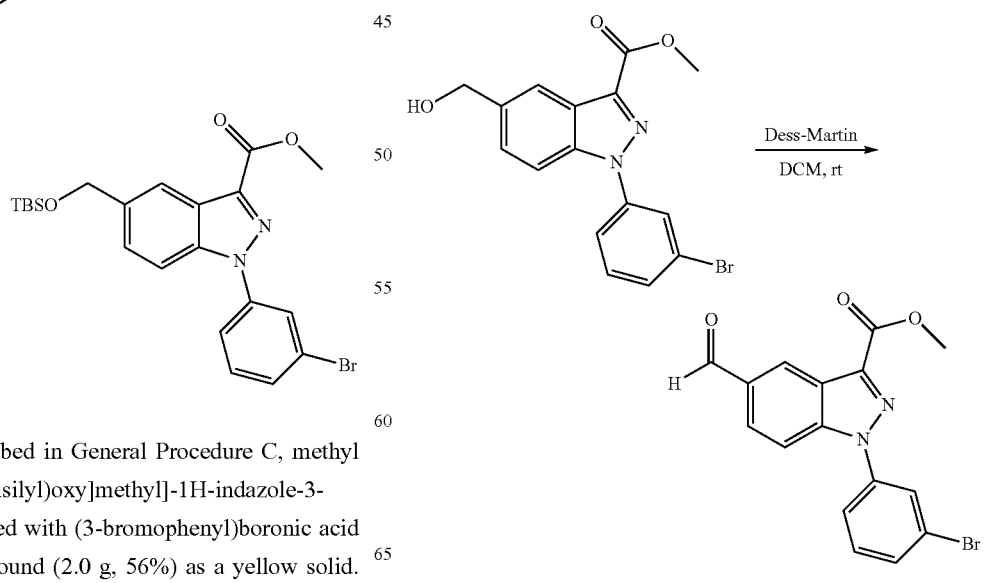

A solution of methyl 1-(3-bromophenyl)-5-(hydroxymethyl)-1H-indazole-3-carboxylate (0.80 g, 2.21 mmol, 1.00 equiv), 1,1-bis(acetyloxy)-3-oxo-3H-11^[5],2-benziodaoxol-1-yl acetate (1.41 g, 3.32 mmol, 1.50 equiv) in dichloromethane (100 mL) was stirred for 2 h at room temperature. The reaction mixture was concentrated under vacuum and the residue was purified by silica gel column chromatography eluting with ethyl acetate/petroleum ether (1:9) to afford the title compound (800 mg, crude) as an off-white solid. LC-MS (ES, m/z): 359 [M+H]$^+$.

Step 7: Synthesis of methyl 1-(3-bromophenyl)-5-cyano-1H-indazole-3-carboxylate

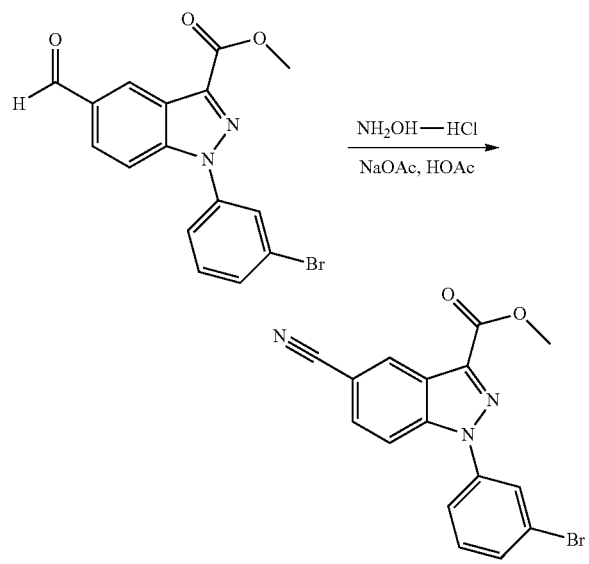

A solution of methyl 1-(3-bromophenyl)-5-formyl-1H-indazole-3-carboxylate (126.00 mg, 0.35 mmol, 1.00 equiv), hydroxylamine hydrochloride (48.76 mg, 0.70 mmol, 2.00 equiv), sodium acetate (57.56 mg, 0.70 mmol, 2.00 equiv) in acetic acid (4 mL) was stirred overnight at 120° C. The reaction mixture was diluted with dichloromethane and washed with brine. The organic layer was dried over anhydrous sodium sulfate and concentrated under vacuum to afford the title compound (150 mg, crude) as a yellow solid. LC-MS: (ES, m/z): 356 [M+H]$^+$.

Step 8: Synthesis of methyl 5-cyano-1-(3-[2-[(3R)-3-hydroxy-1-methyl-2-oxopyrrolidin-3-yl]ethynyl]phenyl)-1H-indazole-3-carboxylate

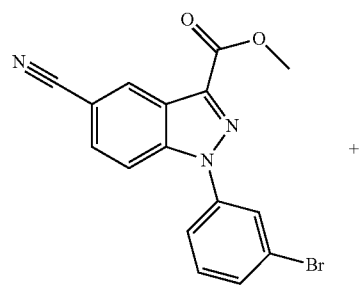

+

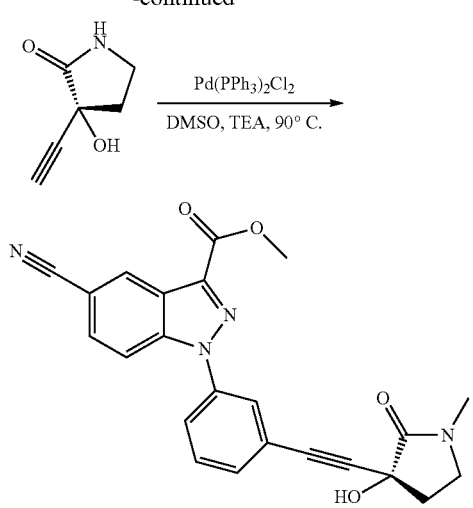

Similar to as described in General Procedure E, methyl 1-(3-bromophenyl)-5-cyano-1H-indazole-3-carboxylate was reacted with (3R)-3-ethynyl-3-hydroxy-1-methylpyrrolidin-2-one to give the title compound (200 mg, crude) as a yellow solid. LC-MS (ES, m/z): 415 [M+H]$^+$.

Step 9: Synthesis of 5-cyano-1-(3-[2-[(3R)-3-hydroxy-1-methyl-2-oxopyrrolidin-3-yl]ethynyl]phenyl)-1H-indazole-3-carboxamide

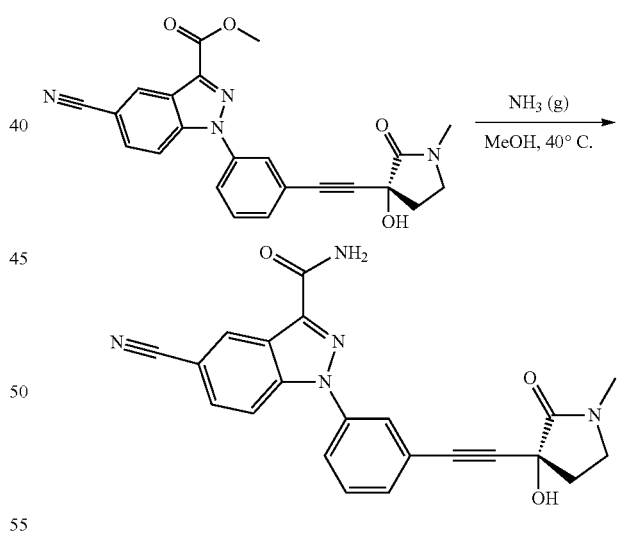

Similar to as described in General Procedure S, methyl 5-cyano-1-(3-[2-[(3R)-3-hydroxy-1-methyl-2-oxopyrrolidin-3-yl]ethynyl]phenyl)-1H-indazole-3-carboxylate was reacted with ammonia in methanol to give the title compound as an off-white solid. LC-MS (ES, m/z): 400 [M+H]$^+$. $^1$HNMR (300 MHz, CD$_3$OD) δ 8.79 (s, 1H), 8.02-7.96 (m, 2H), 7.89-7.80 (m, 2H), 7.67-7.63 (m, 2H), 3.53-3.49 (m, 2H), 2.96 (s, 3H), 2.70-2.60 (m, 1H), 2.37-2.32 (m, 1H).

Example LLLL

Synthesis of 6-cyano-1-(3-[2-[(3R)-3-hydroxy-1-methyl-2-oxopyrrolidin-3-yl]ethynyl]phenyl)-1H-indazole-3-carboxamide Step 1: Synthesis of 1H-indazole-6-carbonitrile

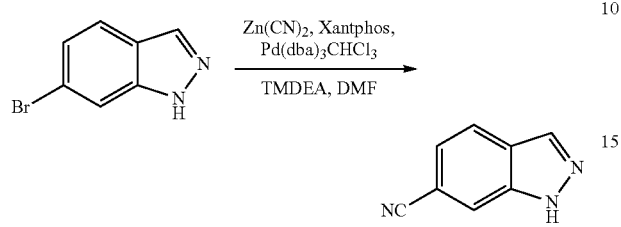

A suspension of 6-bromo-1H-indazole (1.00 g, 5.08 mmol, 1.00 equiv), zinc cyanide (1.19 g, 10.13 mmol, 2.00 equiv), XantPhos (880 mg, 1.52 mmol, 0.30 equiv), Pd$_2$(dba)$_3$.CHCl$_3$ (530 mg, 0.51 mmol, 0.10 equiv) and [2-(dimethylamino)ethyl]dimethylamine (2 mL, 13.25 mmol, 2.60 equiv) in N,N-dimethylformamide (8 mL, 20.40 equiv) was irradiated with microwave radiation for 5 min at 160° C. The reaction was then quenched by 20 mL of water. The solid was collected and washed with 3×20 mL of diethyl ether to give the title compound (1.2 g, crude) as a brown solid. LC-MS (ES, m/z): 144 [M+H]$^+$, 185 [M+CH$_3$CN]$^+$.

Step 2: Synthesis of 3-iodo-1H-indazole-6-carbonitrile

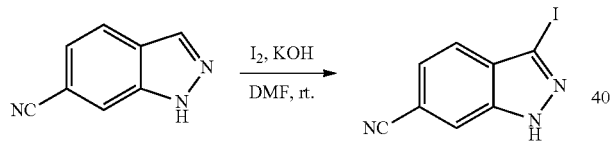

To a solution of 1H-indazole-6-carbonitrile (450.00 mg, 3.14 mmol, 1.00 equiv) in N,N-dimethylformamide (10.00 mL, 129.22 mmol, 41.10 equiv) was added iodine (1595.78 mg, 6.29 mmol, 2.00 equiv) and potassium hydroxide (440.94 mg, 7.86 mmol, 2.50 equiv) at room temperature. After being stirred for 2.5 h at room temperature, the reaction was quenched by 10 mL of brine, extracted with ethyl acetate, washed with sat. aq. sodium thiosulfate and brine, dried over anhydrous sodium sulfate, and concentrated under vacuum. This resulted in 500 mg (59%) of the title compound as a brown solid. LC-MS (ES, m/z): 270 [M+H]$^+$.

Step 3: Synthesis of methyl 6-cyano-1H-indazole-3-carboxylate

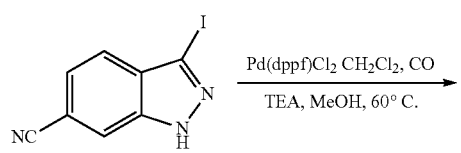

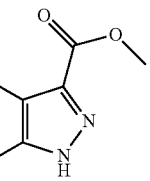

Similar to as described in General Procedure O, 3-iodo-1H-indazole-6-carbonitrile was reacted with carbon monoxide to give the title compound (200 mg, 61%) as an off-white solid. LC-MS (ES, m/z): 202 [M+H]$^+$.

Step 4: Synthesis of methyl 1-(3-bromophenyl)-6-cyano-1H-indazole-3-carboxylate

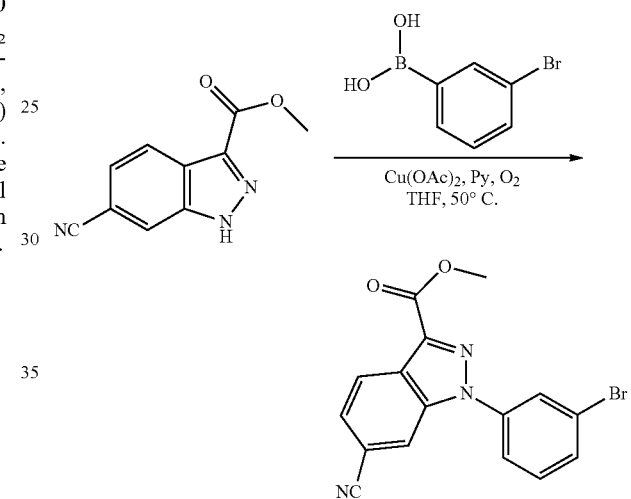

Similar to as described in General Procedure C, methyl 6-cyano-1H-indazole-3-carboxylate was reacted with (3-bromophenyl)boronic acid to give the title compound (220 mg, 62%) as an off-white solid. LC-MS (ES, m/z): 356, 358 [M+H]$^+$.

Step 5: Synthesis of methyl 6-cyano-1-(3-[2-[(3R)-3-hydroxy-1-methyl-2-oxopyrrolidin-3-yl]ethynyl]phenyl)-1H-indazole-3-carboxylate

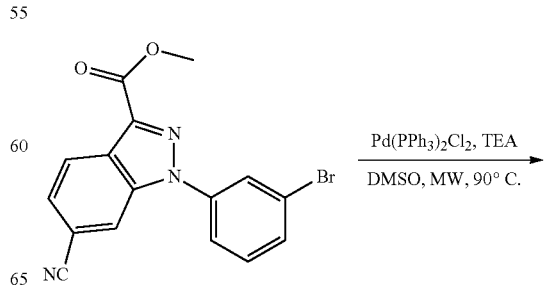

343
-continued

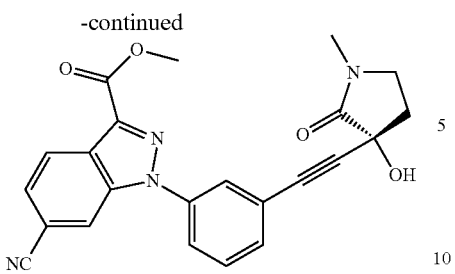

Similar to as described in General Procedure E, methyl 1-(3-bromophenyl)-6-cyano-1H-indazole-3-carboxylate was reacted with (3R)-3-ethynyl-3-hydroxy-1-methylpyrrolidin-2-one to give the title compound (200 mg, 78%) as a yellow oil. LC-MS (ES, m/z): 415 [M+H]$^+$.

Step 6: Synthesis of 6-cyano-1-(3-[2-[(3R)-3-hydroxy-1-methyl-2-oxopyrrolidin-3-yl]ethynyl]phenyl)-1H-indazole-3-carboxamide

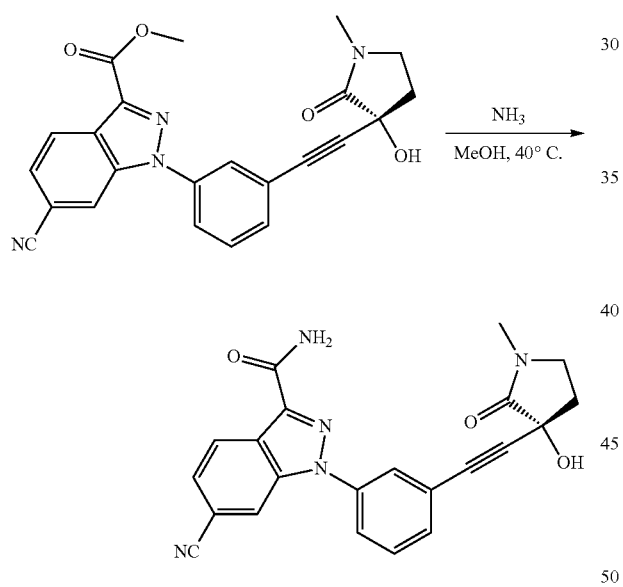

Similar to as described in General Procedure S, methyl 6-cyano-1-(3-[2-[(3R)-3-hydroxy-1-methyl-2-oxopyrrolidin-3-yl]ethynyl]phenyl)-1H-indazole-3-carboxylate was reacted with ammonia in methanol to give the title compound (55.2 mg, 19%) as a white solid. LC-MS (ES, m/z): 400 [M+H]$^+$. $^1$H NMR (CD$_3$OD, 300 MHz) δ 8.53 (d, J=5.4 Hz, 1H), 8.30 (s, 1H), 7.99-7.96 (m, 1H), 7.90-7.86 (m, 1H), 7.68-7.60 (m, 3H), 3.55-3.47 (m, 2H), 2.94 (s, 3H), 2.66-2.58 (m, 1H), 2.36-2.29 (m, 1H).

344

Example MMMM

Synthesis of 1-[3-[(3R)-3-hydroxy-3-(pyridin-2-yl)but-1-yn-1-yl]phenyl]-1H-indazole-3-carboxamide

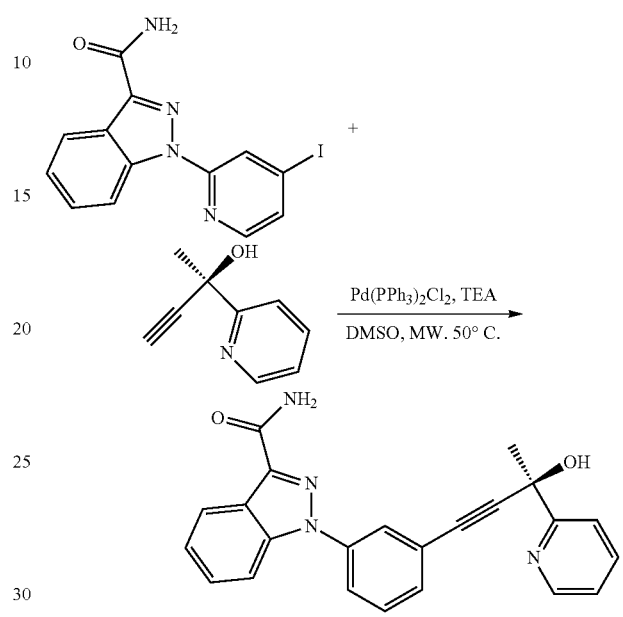

Similar to as described in General Procedure E, 1-(3-iodophenyl)-1H-indazole-3-carboxamide was reacted with (2R)-2-(pyridin-2-yl)but-3-yn-2-ol to give the title compound (10.5 mg, 10%) as an off-white solid. LC-MS (ES, m/z): 383 [M+H]$^+$. $^1$H NMR (CD$_3$OD, 300 MHz) δ 8.57-8.53 (m, 1H), 8.35 (d, J=8.4 Hz, 1H), 7.95-7.82 (m, 5H), 7.64-7.54 (m, 3H), 7.42-7.35 (m, 2H), 1.90 (s, 3H).

Example NNNN and Example OOOO

Synthesis of (4R)-4-hydroxy-1-(3-[2-[(3R)-3-hydroxy-1-methyl-2-oxopyrrolidin-3-yl]ethynyl]phenyl)-1H,4H,5H,6H-cyclopenta[c]pyrazole-3-carboxamide and (4S)-4-hydroxy-1-(3-[2-[(3R)-3-hydroxy-1-methyl-2-oxopyrrolidin-3-yl]ethynyl]phenyl)-1H,4H,5H,6H-cyclopenta[c]pyrazole-3-carboxamide Step 1: Synthesis of ethyl 1-(3-bromophenyl)-4-hydroxy-1H,4H,5H,6H-cyclopenta[c]pyrazole-3-carboxylate

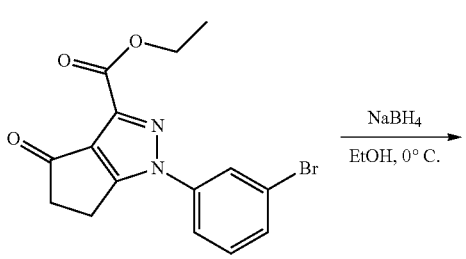

-continued

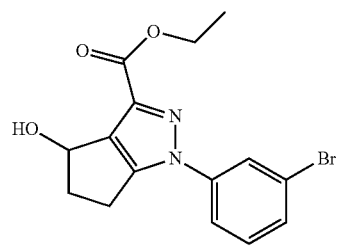

Similar to as described in General Procedure K, ethyl 1-(3-bromophenyl)-4-oxo-1H,4H,5H,6H-cyclopenta[c]pyrazole-3-carboxylate was reacted with sodium borohydride to give the title compound (84 mg, 66%) as a brown oil. LC-MS (ES, m/z): 351,353 [M+H]$^+$.

Step 2: Synthesis of ethyl 4-hydroxy-1-(3-[2-[(3R)-3-hydroxy-1-methyl-2-oxopyrrolidin-3-yl]ethynyl]phenyl)-1H,4H, 5H,6H-cyclopenta[c]pyrazole-3-carboxylate

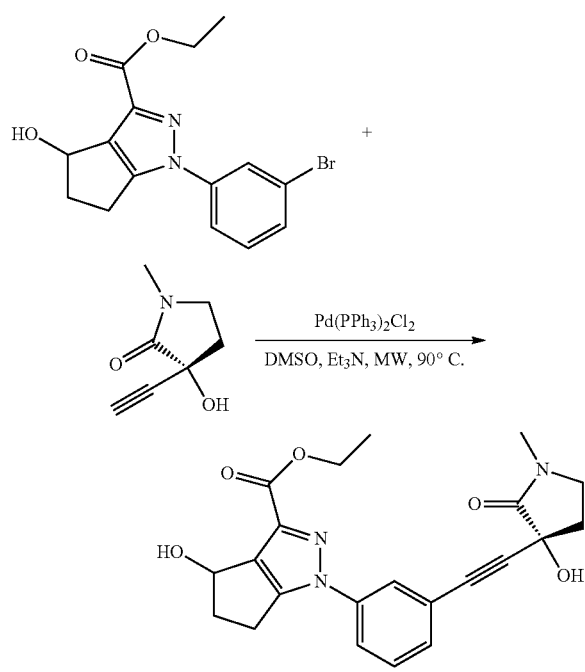

Similar to as described in General Procedure E, ethyl 1-(3-bromophenyl)-4-hydroxy-1H,4H,5H,6H-cyclopenta[c]pyrazole-3-carboxylate was reacted with (3R)-3-ethynyl-3-hydroxy-1-methylpyrrolidin-2-one to give the title compound (10 mg, 135%) as a brown oil. LC-MS (ES, m/z): 410 [M+H]$^+$.

Step 3: Synthesis of (4R)-4-hydroxy-1-(3-[2-[(3R)-3-hydroxy-1-methyl-2-oxopyrrolidin-3-yl]ethynyl]phenyl)-1H,4H,5H,6H-cyclopenta[c]pyrazole-3-carboxamide and (4S)-4-hydroxy-1-(3-[2-[(3R)-3-hydroxy-1-methyl-2-oxopyrrolidin-3-yl]ethynyl]phenyl)-1H,4H,5H,6H-cyclopenta[c]pyrazole-3-carboxamide

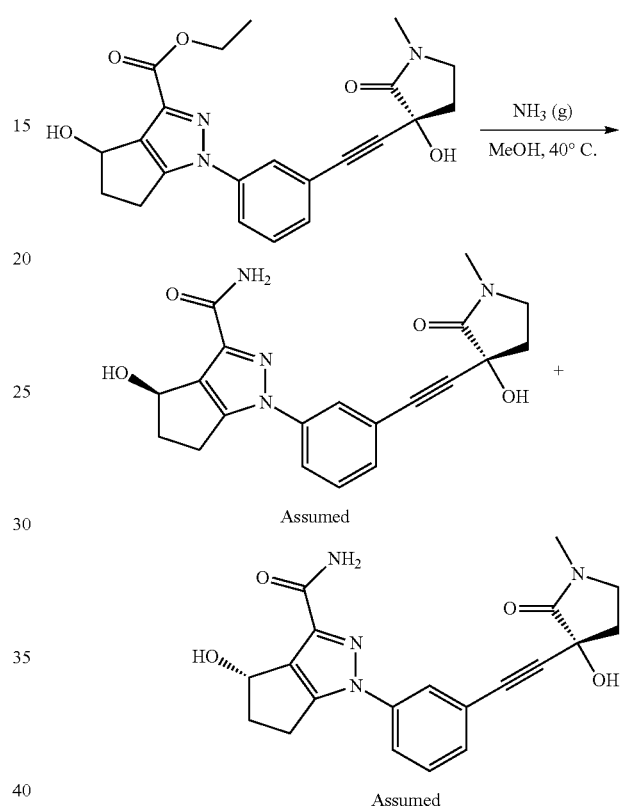

Similar to as described in General Procedure S, ethyl 4-hydroxy-1-(3-[2-[(3R)-3-hydroxy-1-methyl-2-oxopyrrolidin-3-yl]ethynyl]phenyl)-1H,4H, 5H,6H-cyclopenta[c]pyrazole-3-carboxylate was reacted with ammonia in methanol to give the title compounds which were separated by Chiral-Prep-HPLC with the following conditions: Column, Chiralpak IC, 2×25 cm, 5 um; mobile phase, MTBE and ethanol (hold 40.0% ethanol in 18 min); Detector, UV 254/220 nm. The stereochemistry for position 4 for either isomer is arbitrarily assigned.

Isomer A (4R): 13.7 mg (13%), light yellow solid. $t_R$=6.27 min (CHIRALPAK IC, 25° C., UV-254 nm DCM:EtOH=70:30, 1.0 ml/min). LC-MS (ES, m/z): 403 [M+Na]$^+$. $^1$H NMR (400 MHz, CD$_3$OD) δ 7.78 (s, 1H), 7.77-7.64 (m, 1H), 7.40 (t, J=8.0 Hz, 1H), 7.33 (d, J=4.2 HZ, 1H), 5.17 (dd, J=8.0, 2.8 Hz, 1H), 3.40-3.39 (m, 2H), 3.13-3.11 (m, 1H), 2.93-2.89 (m, 2H), 2.83 (s, 3H), 2.52-2.46 (m, 1H), 2.40-2.39 (m, 1H), 2.25-2.20 (m, 1H).

Isomer B (4S): 12.3 mg (12%), light yellow solid. $t_R$=7.22 min (CHIRALPAK IC, 25° C., UV-254 nm DCM:EtOH=70:30, 1.0 ml/min). LC-MS (ES, m/z): 381 [M+H]$^+$. $^1$H NMR (300 MHz, CD$_3$OD) δ 7.89 (s, 1H), 7.88-7.75 (m, 1H), 7.52 (t, J=8.0 Hz, 1H), 7.48 (d, J=4.2 Hz, 1H), 5.28 (dd, J=6.6, 2.0

Hz, 1H), 3.55-3.49 (m, 2H), 3.07-2.99 (m, 1H), 2.93-2.89 (m, 2H), 2.94 (s, 3H), 2.62-2.56 (m, 1H), 2.52-2.32 (m, 1H), 2.34-2.30 (m, 1H).

Example PPPP

Synthesis of 1-(3-cyano-5-[2-[(3R)-3-hydroxy-1-methyl-2-oxopyrrolidin-3-yl]ethynyl]phenyl)-1H-pyrazolo[3,4-b]pyridine-3-carboxamide Step 1: Synthesis of (3-bromo-5-cyanophenyl)boronic acid

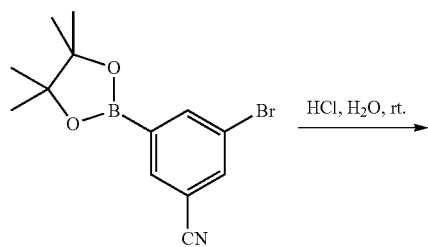

3-Bromo-5-(tetramethyl-1,3,2-dioxaborolan-2-yl)benzonitrile (1.5 g, 4.87 mmol, 1.00 equiv) was added to hydrogen chloride (15 mL, 493.68 mmol, 101.40 equiv) at room temperature, and it was stirred for 10 hours at that temperature. The solid was collected by filtration to give 750 mg (68%) of the title compound as a white solid.

Step 2: Synthesis of methyl 1-(3-bromo-5-carbamoylphenyl)-1H-pyrazolo[3,4-b]pyridine-3-carboxylate

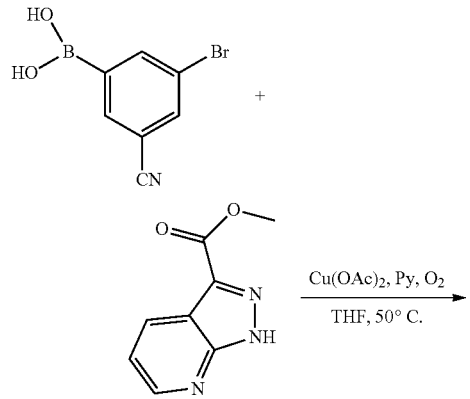

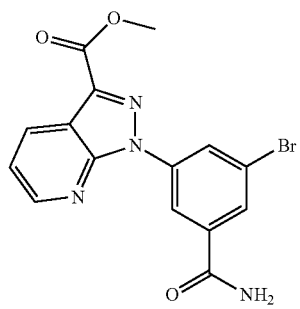

Similar to as described in General Procedure C, methyl 1H-pyrazolo[3,4-b]pyridine-3-carboxylate was reacted with (3-bromo-5-cyanophenyl)boronic acid to give the title compound (170 mg, 47%) as a green solid. LC-MS (ES, m/z): 375, 377 [M+1]$^+$.

Step 3: Synthesis of methyl 1-(3-bromo-5-cyanophenyl)-1H-pyrazolo[3,4-b]pyridine-3-carboxylate

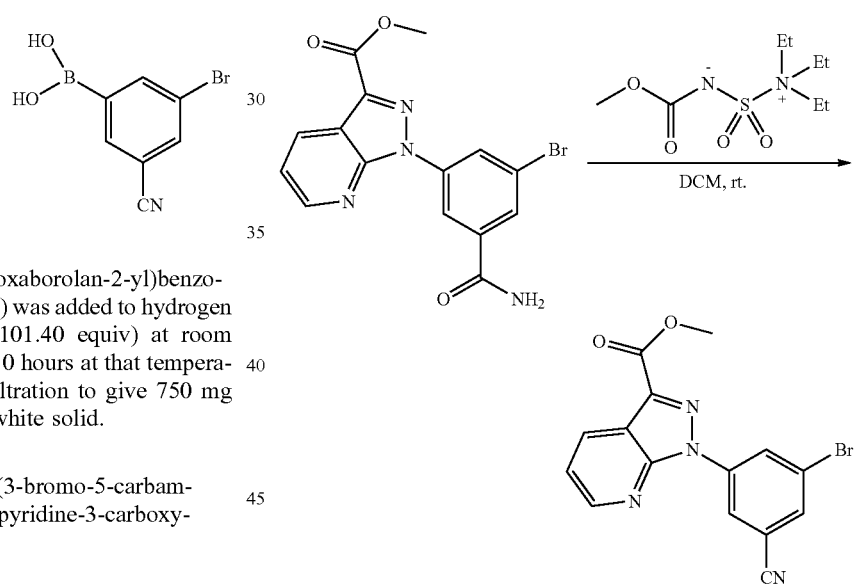

To a stirred solution of methyl 1-(3-bromo-5-carbamoylphenyl)-1H-pyrazolo[3,4-b]pyridine-3-carboxylate (120.00 mg, 0.32 mmol, 1.00 equiv) in dichloromethane (20 mL) was added methyl N-[(triethylazaniumyl)sulfonyl]carbamate oxidanide (152.44 mg, 0.64 mmol, 2.00 equiv) at room temperature. The reaction mixture was stirred for 12 hours at that temperature, diluted with of dichloromethane, washed with water, extracted with dichloromethane, dried over anhydrous sodium sulfate, and concentrated under vacuum. The residue was purified by a silica gel column eluting with ethyl acetate/petroleum ether (2:3) to give 70 mg (61%) of the title compound as a white solid. LC-MS (ES, m/z): 357, 359 [M+1]$^+$.

Step 4: Synthesis of methyl 1-(3-cyano-5-[2-[(3R)-3-hydroxy-1-methyl-2-oxopyrrolidin-3-yl]ethynyl]phenyl)-1H-pyrazolo[3,4-b]pyridine-3-carboxylate

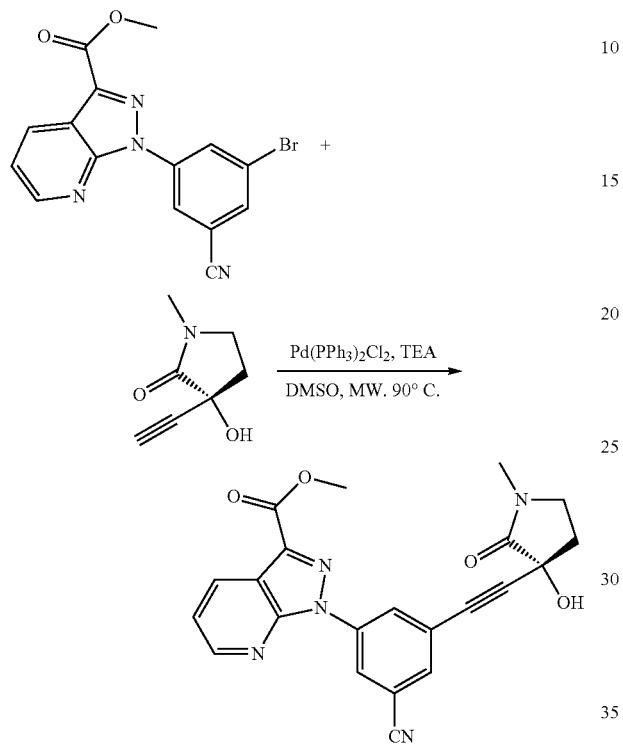

Similar to as described in General Procedure E, methyl 1-(3-bromo-5-cyanophenyl)-1H-pyrazolo[3,4-b]pyridine-3-carboxylate was reacted with (3R)-3-ethynyl-3-hydroxy-1-methylpyrrolidin-2-one to give the title compound (60 mg, 37%) as a white solid. LC-MS (ES, m/z): 416 [M+1]$^+$.

Step 5: Synthesis of 1-(3-cyano-5-[2-[(3R)-3-hydroxy-1-methyl-2-oxopyrrolidin-3-yl]ethynyl]phenyl)-1H-pyrazolo[3,4-b]pyridine-3-carboxamide

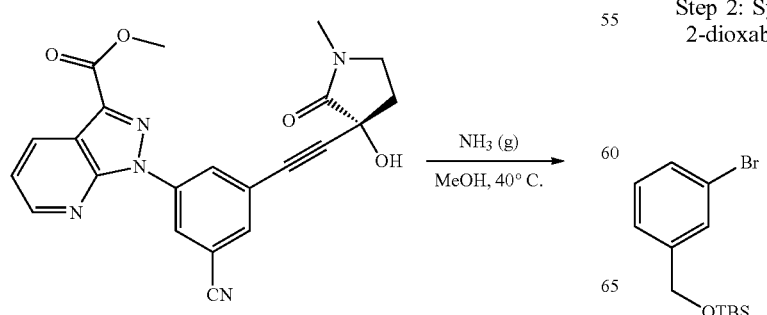

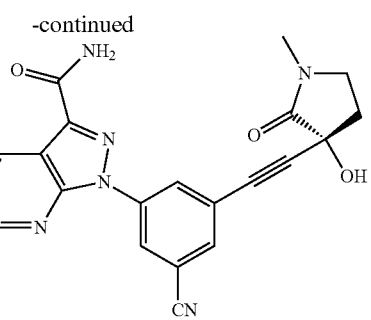

Similar to as described in General Procedure S, methyl 1-(3-cyano-5-[2-[(3R)-3-hydroxy-1-methyl-2-oxopyrrolidin-3-yl]ethynyl]phenyl)-1H-pyrazolo[3,4-b]pyridine-3-carboxylate was reacted with ammonia in methanol to give the title compound (28.8 mg, 33%) as a white solid. LC-MS (ES, m/z): 401 [M+1]$^+$. $^1$H NMR (300 MHz, CD$_3$OD) δ 8.99 (dd, J=6.6, 3.6 Hz, 1H), 8.80-8.74 (m, 2H), 7.85 (s, 1H), 7.53 (dd, J=8.1, 4.5 Hz, 2H), 3.57-3.51 (m, 2H), 2.97 (s, 3H), 2.70-2.64 (m, 1H), 2.42-2.33 (m, 1H).

Example QQQQ

Synthesis of 1-[3-(cyanomethyl)-5-[2-[(3R)-3-hydroxy-1-methyl-2-oxopyrrolidin-3-yl]ethynyl]phenyl]-1H-pyrazolo[3,4-b]pyridine-3-carboxamide

Step 1: Synthesis of [(3-bromophenyl)methoxy](tert-butyl)dimethylsilane

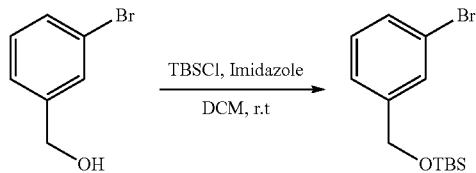 [SMILES: OCc1cccc(Br)c1 ; CC(C)(C)[Si](C)(C)OCc1cccc(Br)c1]

To a solution of (3-bromophenyl)methanol (5 g, 26.73 mmol, 1.00 equiv) and 1H-imidazole (3.7 g, 54.35 mmol, 2.00 equiv) in dichloromethane (50 mL) was added a solution of TBSCl (6 g, 39.81 mmol, 1.50 equiv) in dichloromethane (25 mL) at 0° C. The resulting mixture was stirred for 2 hours at room temperature, diluted with water, extracted with dichloromethane, dried over anhydrous magnesium sulfate, and concentrated under vacuum. This resulted in 7.5 g (93%) of the title compound as colorless oil.

Step 2: Synthesis of [[3-bromo-5-(tetramethyl-1,3,2-dioxaborolan-2-yl)phenyl]methoxy](tert-butyl)dimethylsilane

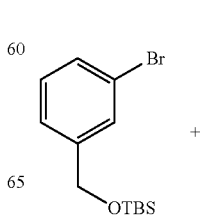

+

-continued

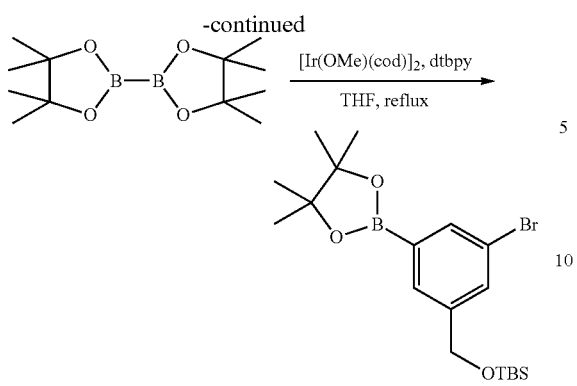

To a solution of [(3-bromophenyl)methoxy](tert-butyl)dimethylsilane (7.4 g, 24.56 mmol, 1.00 equiv) and 4,4,5,5-tetramethyl-2-(tetramethyl-1,3,2-dioxaborolan-2-yl)-1,3,2-dioxaborolane (5.0 g, 19.69 mmol, 0.80 equiv) in tetrahydrofuran (5 mL) was added bis((1Z,5Z)-cycloocta-1,5-diene) dimethyl-2,4-dioxa-1,3-diiridabicyclo[1.1.0]butane-2,4-diium-1,3-diuide (166 mg, 0.25 mmol) and 4-tert-butyl-2-(4-tert-butylpyridin-2-yl)pyridine (200 mg, 0.75 mmol) under nitrogen. The mixture was stirred overnight at 80° C. The reaction was concentrated under vacuum and the crude product was purified by a silica gel column eluting with ethyl acetate/petroleum ether (1:4) to give 9.0 g (86%) of the title compound as colorless oil.

Step 3: Synthesis of methyl 1-(3-bromo-5-[[(tert-butyldimethylsilyl)oxy]methyl]phenyl)-1H-pyrazolo[3,4-b]pyridine-3-carboxylate

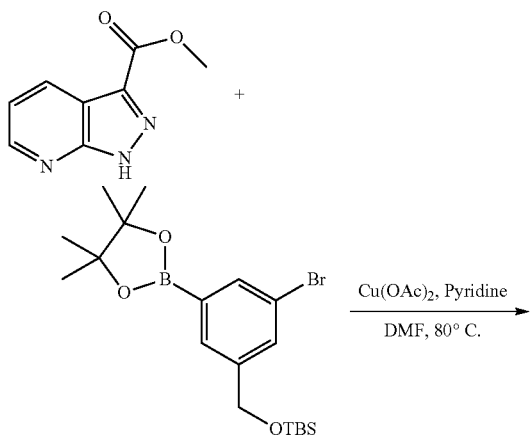

Similar to as described in General Procedure C, methyl 1H-pyrazolo[3,4-b]pyridine-3-carboxylate was reacted with [[3-bromo-5-(tetramethyl-1,3,2-dioxaborolan-2-yl)phenyl]methoxy](tert-butyl)dimethylsilane to give the title compound (1.2 g, 49%) as a white solid. LC-MS (ES, m/z): 476, 478 [M+1]$^+$.

Step 4: Synthesis of methyl 1-[3-bromo-5-(hydroxymethyl)phenyl]-1H-pyrazolo[3,4-b]pyridine-3-carboxylate

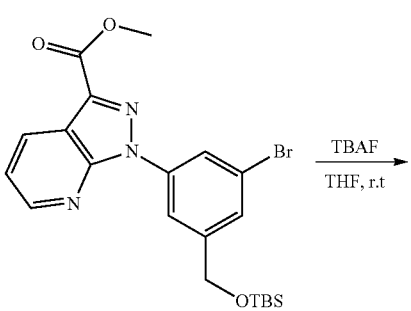

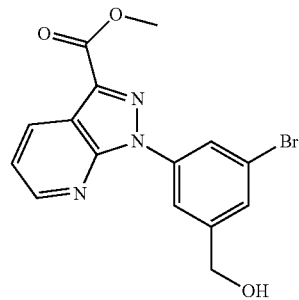

A solution of methyl 1-(3-bromo-5-[[(tert-butyldimethylsilyl)oxy]methyl]phenyl)-1H-pyrazolo[3,4-b]pyridine-3-carboxylate (600 mg, 1.26 mmol, 1.00 equiv) and tetrabutylazanium fluoride (415 mg, 1.59 mmol, 1.30 equiv) in tetrahydrofuran (10 mL) was stirred for overnight at room temperature. The suspension was extracted with dichloromethane, washed with brine, dried over anhydrous sodium sulfate, and concentrated under vacuum. This resulted in 480 mg (79%) of the title compound as an off-white solid. LC-MS (ES, m/z): 362, 364 [M+1]$^+$.

Step 5: Synthesis of methyl 1-[3-bromo-5-(chloromethyl)phenyl]-1H-pyrazolo[3,4-b]pyridine-3-carboxylate

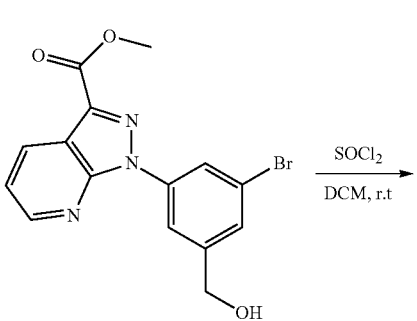

-continued

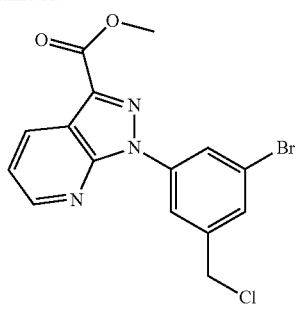

To a solution of 1-[3-bromo-5-(hydroxymethyl)phenyl]-1H-pyrazolo[3,4-b]pyridine-3-carboxylate (460 mg, 1.27 mmol, 1.00 equiv) in dichloromethane (10 mL) was added thionyl chloride (5 mL, 68.92 mmol, 54.30 equiv) dropwise. The reaction was stirred for overnight at room temperature and concentrated under vacuum to give 500 mg (crude) of the title compound as a white solid which was used in the next step without further purification.

Step 6: Synthesis of methyl 1-[3-bromo-5-(cyanomethyl)phenyl]-1H-pyrazolo[3,4-b]pyridine-3-carboxylate

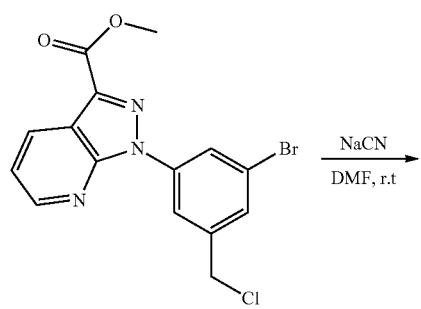

To a solution of methyl 1-[3-bromo-5-(chloromethyl) phenyl]-1H-pyrazolo[3,4-b]pyridine-3-carboxylate (500 mg, 1.31 mmol, 1.00 equiv) in N,N-dimethylformamide (15 mL) was added sodium carbonitrile (150 mg, 3.06 mmol, 2.30 equiv). The resulting solution was stirred for 2 hours at room temperature, diluted with water, and extracted with ethyl acetate. The organic layers were combined and washed with saturated sodium chloride, dried over anhydrous magnesium sulfate, and concentrated under vacuum to give 390 mg (56%) of the title compound as a yellow solid. LC-MS (ES, m z): 371, 373 [M+1]⁺.

Step 7: Synthesis of methyl 1-[3-(cyanomethyl)-5-[2-[(3R)-3-hydroxy-1-methyl-2-oxopyrrolidin-3-yl]ethynyl]phenyl]-1H-pyrazolo[3,4-b]pyridine-3-carboxylate

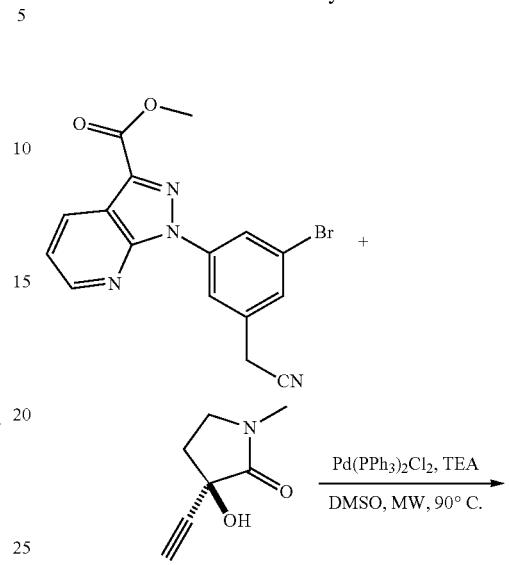

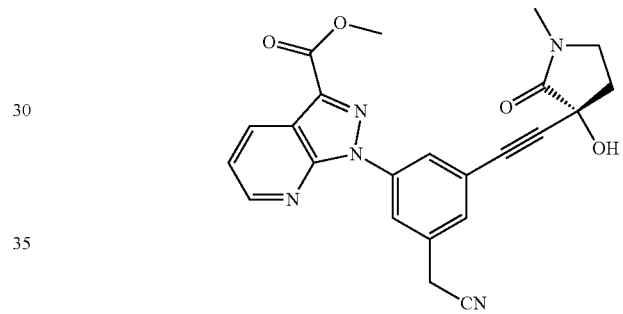

Similar to as described in General Procedure E, methyl 1-[3-bromo-5-(cyanomethyl)phenyl]-1H-pyrazolo[3,4-b]pyridine-3-carboxylate was reacted with (3R)-3-ethynyl-3-hydroxy-1-methylpyrrolidin-2-one to give the title compound (260 mg, 80%) as a yellow solid. LC-MS (ES, m/z): 430 [M+1]⁺.

Step 8: Synthesis of 1-[3-(cyanomethyl)-5-[2-[(3R)-3-hydroxy-1-methyl-2-oxopyrrolidin-3-yl]ethynyl]phenyl]-1H-pyrazolo[3,4-b]pyridine-3-carboxamide

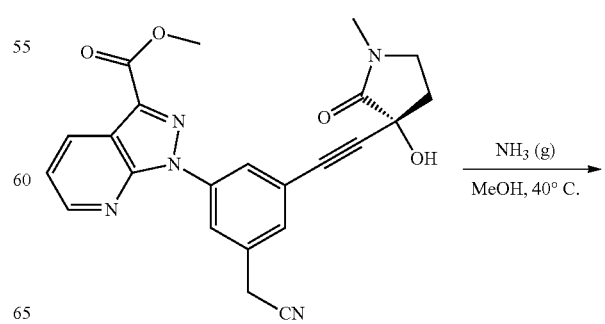

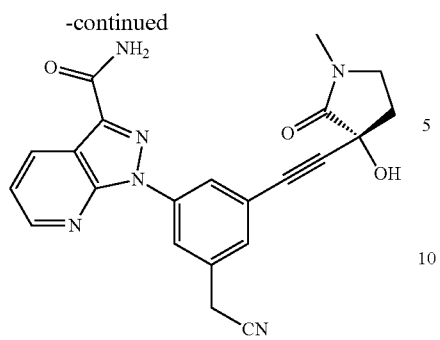

Similar to as described in General Procedure S, methyl 1-[3-(cyanomethyl)-5-[2-[(3R)-3-hydroxy-1-methyl-2-oxopyrrolidin-3-yl]ethynyl]phenyl]-1H-pyrazolo[3,4-b]pyridine-3-carboxylate was reacted with ammonia in methanol to give the title compound (40 mg, 16%) as a white solid. LC-MS (ES, m/z): 415 [M+1]$^+$. $^1$H NMR (400 MHz, CDCl$_3$) δ 8.76 (dd, J=8.1, 1.6 Hz, 1H), 8.66 (dd, J=4.4, 1.6 Hz, 1H), 8.42 (s, 1H), 8.39 (s, 1H), 7.42 (s, 1H), 7.37 (dd, J=8.1, 4.4 Hz, 1H), 3.86 (s, 2H), 3.57-3.51 (m, 1H), 3.45-3.39 (m, 1H), 2.99 (s, 3H), 2.72-2.66 (m, 1H), 2.45-2.38 (m, 1H).

Example RRRR

Synthesis of 1-(3-[2-[(3R)-3-hydroxy-1-methyl-2-oxopyrrolidin-3-yl]ethynyl]-5-(1-hydroxyethyl)phenyl)-1H-pyrazolo[3,4-b]pyridine-3-carboxamide Step 1: Synthesis of [1-(3-bromophenyl)ethoxy](tert-butyl)dimethylsilane

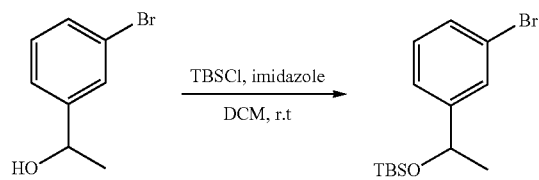

A solution of 1-(3-bromophenyl)ethan-1-ol (2.00 g, 9.95 mmol, 1.00 equiv), dichloromethane (100 mL, 1.57 mol, 158.10 equiv), 1H-imidazole (1.35 g, 19.83 mmol, 2.00 equiv), tert-butyl(chloro)dimethylsilane (2.24 g, 14.93 mmol, 1.50 equiv) was stirred for overnight at room temperature. The reaction was quenched by water, extracted with dichloromethane, washed with water, dried over anhydrous sodium sulfate, and concentrated under vacuum to give 2 g (64%) of the title compound as a solid. LC-MS (ES, m/z): 317, 315 [M+H]$^+$.

Step 3: Synthesis of [1-[3-bromo-5-(tetramethyl-1,3,2-dioxaborolan-2-yl)phenyl]ethoxy](tert-butyl)dimethylsilane

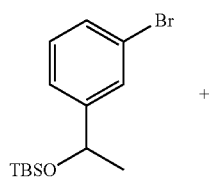

+

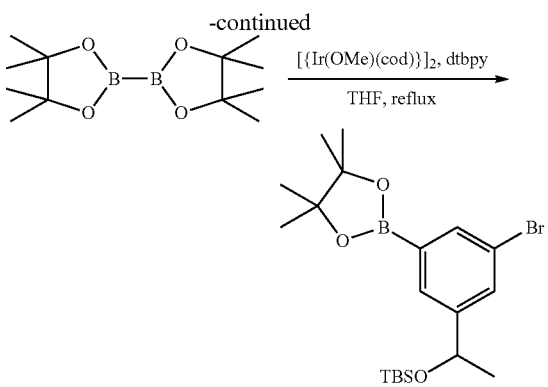

To a stirred solution of [1-(3-bromophenyl)ethoxy](tert-butyl)dimethylsilane (2.00 g, 6.34 mmol, 1.00 equiv) and 4,4,5,5-tetramethyl-2-(tetramethyl-1,3,2-dioxaborolan-2-yl)-1,3,2-dioxaborolane (970 mg, 3.81 mmol, 0.60 equiv) in tetrahydrofuran (8 mL) was added bis((1Z,5Z)-cycloocta-1,5-diene) dimethyl-2,4-dioxa-1,3-diiridabicyclo[1.1.0]butane-2,4-diium-1,3-diuide (43 mg, 0.06 mmol, 0.01 equiv) and 4-tert-butyl-2-(4-tert-butylpyridin-2-yl)pyridine (34 mg, 0.13 mmol, 0.02 equiv). The resulting solution was stirred overnight at 80° C. The precipitated solids were filtered out and the filtrate was concentrated under vacuum to give 3 g (crude) of the title compound as a brown oil.

Step 4: Synthesis of methyl 1-(3-bromo-5-[1-[(tert-butyldimethylsilyl)oxy]ethyl]phenyl)-1H-pyrazolo[3,4-b]pyridine-3-carboxylate

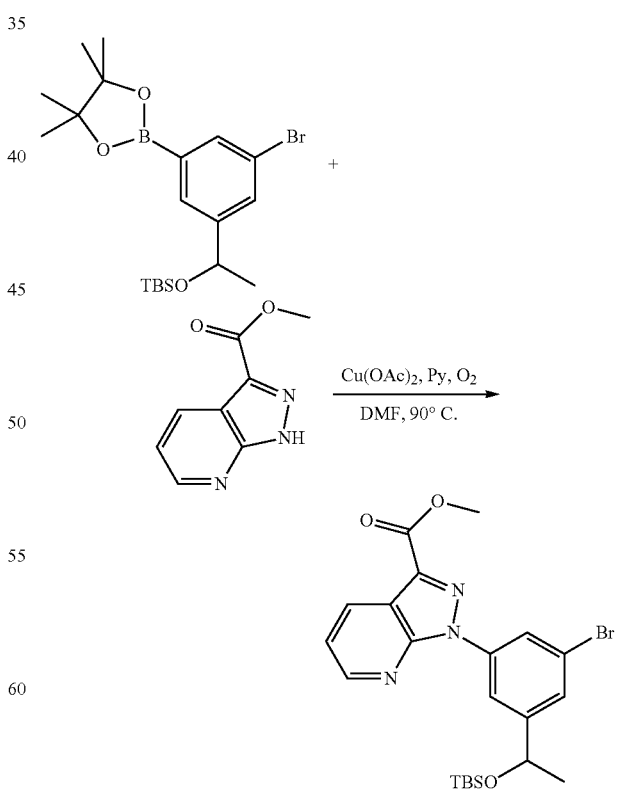

Similar to as described in General Procedure C, [1-[3-bromo-5-(tetramethyl-1,3,2-dioxaborolan-2-yl)phenyl]

ethoxy](tert-butyl)dimethylsilane was reacted with methyl 1H-pyrazolo[3,4-b]pyridine-3-carboxylate to give the title compound (0.5 g, 36%) as a brown oil. LC-MS (m/z): 490, 492 [M+H]⁺.

Step 5: Synthesis of methyl 1-[3-bromo-5-(1-hydroxyethyl)phenyl]-1H-pyrazolo[3,4-b]pyridine-3-carboxylate

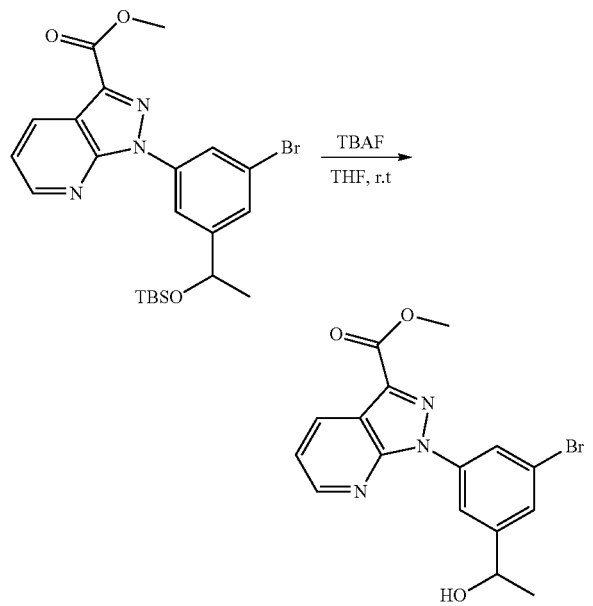

To a stirred solution of methyl 1-(3-bromo-5-[1-[(tert-butyldimethylsilyl)oxy]ethyl]phenyl)-1H-pyrazolo[3,4-b]pyridine-3-carboxylate (500 mg, 1.02 mmol, 1.00 equiv) in tetrahydrofuran (10 mL) added tetrabutylazanium fluoride (400 mg, 1.53 mmol, 1.50 equiv) at room temperature. The reaction was stirred overnight, quenched by water, extracted with ethyl acetate, washed with water and brine, dried over anhydrous sodium sulfate, and concentrated under vacuum. The residue was purified by a silica gel column eluting with ethyl acetate/petroleum ether (1/5) to give 250 mg (65%) of the title compound as a white solid. LC-MS (m/z): 376, 378 [M+H]⁺.

Step 6: Synthesis of methyl 1-(3-[2-[(3R)-3-hydroxy-1-methyl-2-oxopyrrolidin-3-yl]ethynyl]-5-(1-hydroxyethyl)phenyl)-1H-pyrazolo[3,4-b]pyridine-3-carboxylate

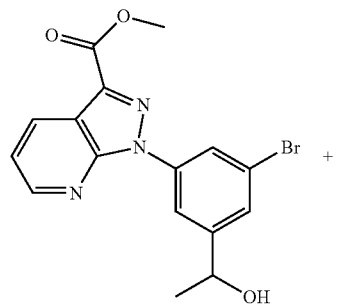

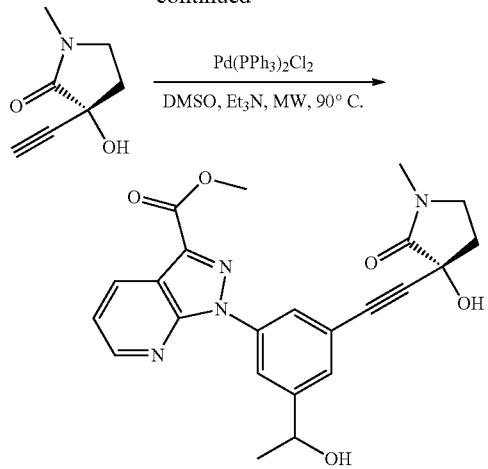

Similar to as described in General Procedure E, methyl 1-[3-bromo-5-(1-hydroxyethyl)phenyl]-1H-pyrazolo[3,4-b]pyridine-3-carboxylate was reacted with (3R)-3-ethynyl-3-hydroxy-1-methylpyrrolidin-2-one to give the title compound (200 mg, 72%) as a brown oil. LC-MS (m/z): 435 [M+H]⁺.

Step 7: Synthesis of 1-(3-[2-[(3R)-3-hydroxy-1-methyl-2-oxopyrrolidin-3-yl]ethynyl]-5-(1-hydroxyethyl)phenyl)-1H-pyrazolo[3,4-b]pyridine-3-carboxamide

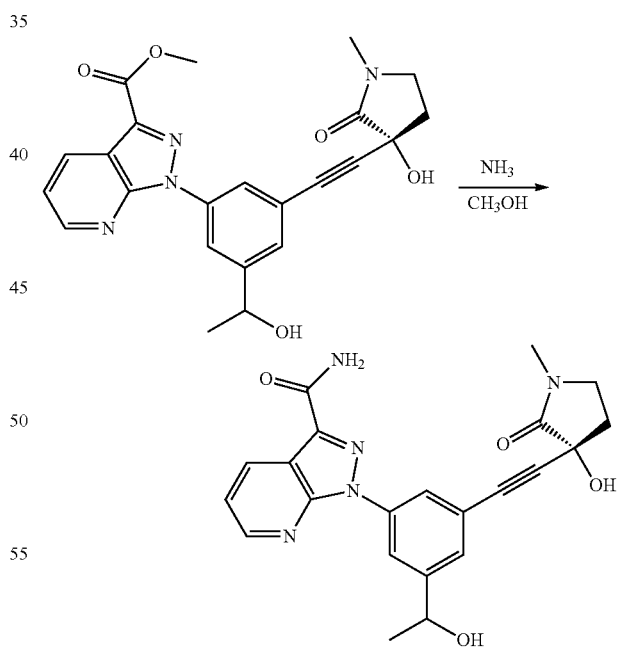

Similar to as described in General Procedure S, methyl 1-(3-[2-[(3R)-3-hydroxy-1-methyl-2-oxopyrrolidin-3-yl]ethynyl]-5-(1-hydroxyethyl)phenyl)-1H-pyrazolo[3,4-b]pyridine-3-carboxylate was reacted with ammonia in methanol to give the title compound (43 mg, 22%) as a light yellow solid. LC-MS (ES, m/z): 420 [M+H]⁺. ¹H NMR (400 MHz, CD₃OD) δ 8.74 (s, 1H), 8.73-8.14 (m, 1H), 8.46 (s, 1H), 7.53 (s, 1H), 7.50-7.47 (m, 1H), 4.99-4.94 (m, 1H), 3.62-3.47 (m, 2H), 2.96 (s, 3H), 2.67-2.39 (m, 1H), 2.39-2.32 (m, 1H), 1.55 (m, 3H).

Example SSSS

Synthesis of 1-[3-(difluoromethoxy)-5-[2-[(3R)-3-hydroxy-1-methyl-2-oxopyrrolidin-3-yl]ethynyl]phenyl]-1H-pyrazolo[3,4-b]pyridine-3-carboxamide Step 1: Synthesis of 2-[3-bromo-5-(difluoromethoxy)phenyl]-4,4,5,5-tetramethyl-1,3,2-dioxaborolane

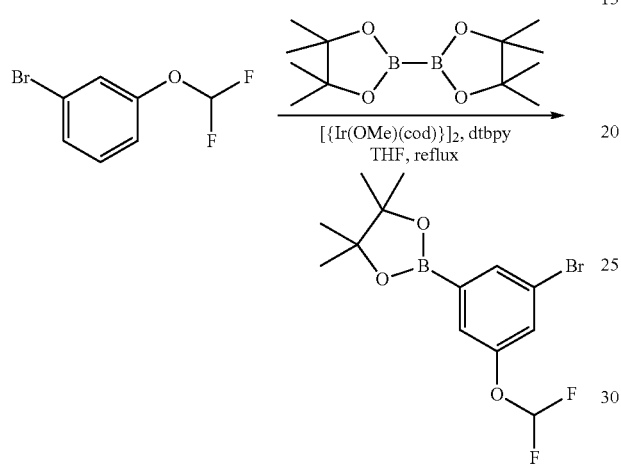

To a stirred solution of 1-bromo-3-(difluoromethoxy)benzene (1000.00 mg, 4.48 mmol, 1.00 equiv) in tetrahydrofuran (1.5 mL) was added 4,4,5,5-tetramethyl-2-(tetramethyl-1,3,2-dioxaborolan-2-yl)-1,3,2-dioxaborolane (797.06 mg, 3.14 mmol, 0.70 equiv), 4-tert-butyl-2-(4-tert-butylpyridin-2-yl)pyridine (24.07 mg, 0.09 mmol, 0.02 equiv) and bis((1Z,5Z)-cycloocta-1,5-diene) dimethyl-2,4-dioxa-1,3-diiridabicyclo[1.1.0]butane-2,4-diium-1,3-diuide (30 mg, 0.05 mmol, 0.01 equiv) under nitrogen. The resulting solution was stirred for 14 hours at 80° C., diluted with ethyl acetate, washed with water, extracted with ethyl acetate, dried over anhydrous sodium sulfate, and concentrated under vacuum. The residue was purified by a silica gel column eluting with ethyl acetate/petroleum ether (1:20) to give 703 mg (45%) of the title compound as a yellow oil.

Step 2: Synthesis of methyl 1-[3-bromo-5-(difluoromethoxy)phenyl]-1H-pyrazolo[3,4-b]pyridine-3-carboxylate

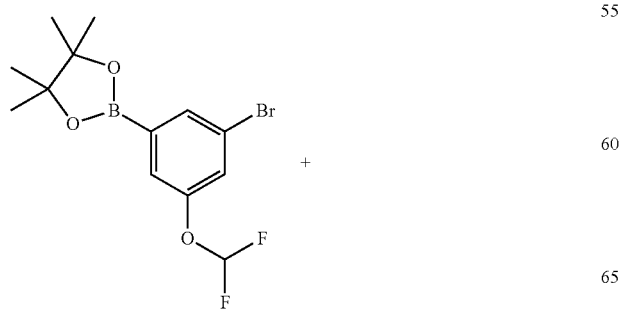

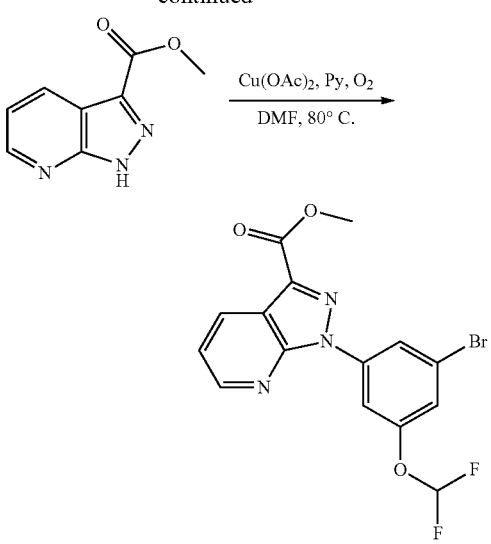

Similar to as described in General Procedure C, 2-[3-bromo-5-(difluoromethoxy)phenyl]-4,4,5,5-tetramethyl-1,3,2-dioxaborolane was reacted with methyl 1H-pyrazolo[3,4-b]pyridine-3-carboxylate to give the title compound (66 mg, 55%) as a white solid. LC-MS (ES, m/z): 398, 400 [M+1]+.

Step 3: Synthesis of methyl 1-[3-(difluoromethoxy)-5-[2-[(3R)-3-hydroxy-1-methyl-2-oxopyrrolidin-3-yl]ethynyl]phenyl]-1H-pyrazolo[3,4-b]pyridine-3-carboxylate

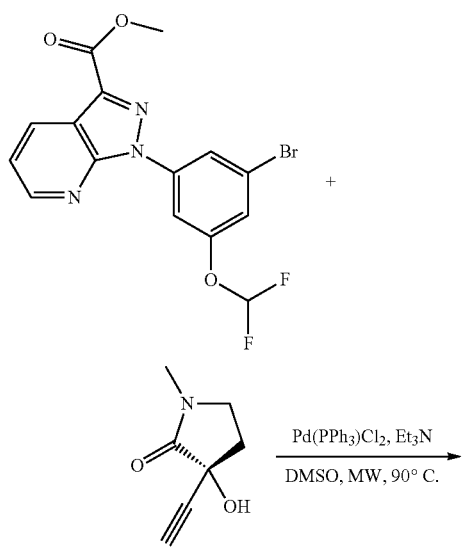

-continued

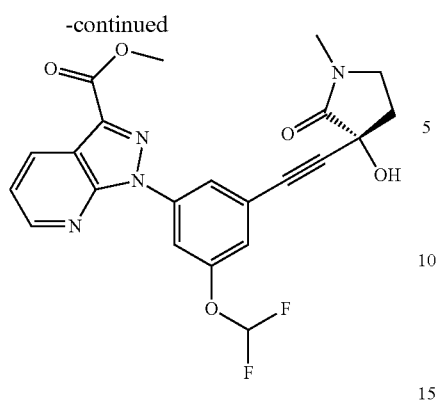

Similar to as described in General Procedure E, 1-[3-bromo-5-(difluoromethoxy)phenyl]-1H-pyrazolo[3,4-b]pyridine-3-carboxylate was reacted with (3R)-3-ethynyl-3-hydroxy-1-methylpyrrolidin-2-one to give the title compound (350 mg, 57%) as a yellow oil. LC-MS (ES, m/z): 457 [M+1]$^+$.

Step 4: Synthesis of 1-[3-(difluoromethoxy)-5-[2-[(3R)-3-hydroxy-1-methyl-2-oxopyrrolidin-3-yl]ethynyl]phenyl]-1H-pyrazolo[3,4-b]pyridine-3-carboxamide

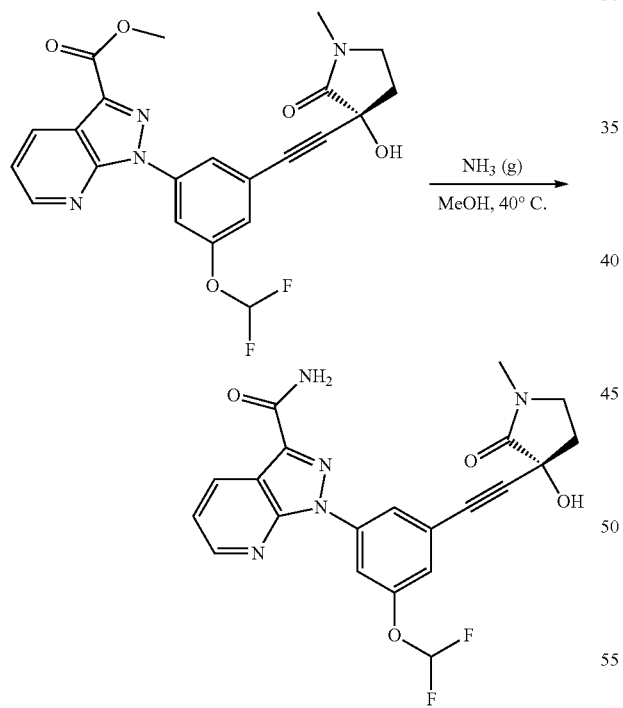

Similar to as described in General Procedure S, methyl 1-[3-(difluoromethoxy)-5-[2-[(3R)-3-hydroxy-1-methyl-2-oxopyrrolidin-3-yl]ethynyl]phen yl]-1H-pyrazolo[3,4-b]pyridine-3-carboxylate was reacted with ammonia in methanol to give the title compound (7.3 mg, 11%) as a white solid. LC-MS (ES, m/z): 442 [M+1]$^+$. $^1$H NMR (300 MHz, CDCl$_3$) δ 8.76 (dd, J=8.1, 1.8 Hz, 1H), 8.68 (dd, J=4.5, 1.8 Hz, 1H), 8.34-8.31 (m, 2H), 7.38 (dd, J=8.1, 4.5 Hz, 1H), 7.18 (br s, 1H), 7.05 (br s, 1H), 6.61 (t, J=73.2 Hz, 1H), 5.73 (br s, 1H), 3.57-3.42 (m, 2H), 3.41-3.77 (m, 1H), 2.99 (s, 3H), 2.73-2.65 (m, 1H), 2.49-2.36 (m, 1H).

Example TTTT

Synthesis of 1-(3-[2-[(3R)-3-hydroxy-1-methyl-2-oxopyrrolidin-3-yl]ethynyl]-5-(trifluoromethyl)phenyl)-1H-pyrazolo[3,4-b]pyridine-3-carboxamide Step 1: Synthesis of methyl 1-[3-bromo-5-(trifluoromethyl)phenyl]-1H-pyrazolo[3,4-b]pyridine-3-carboxylate

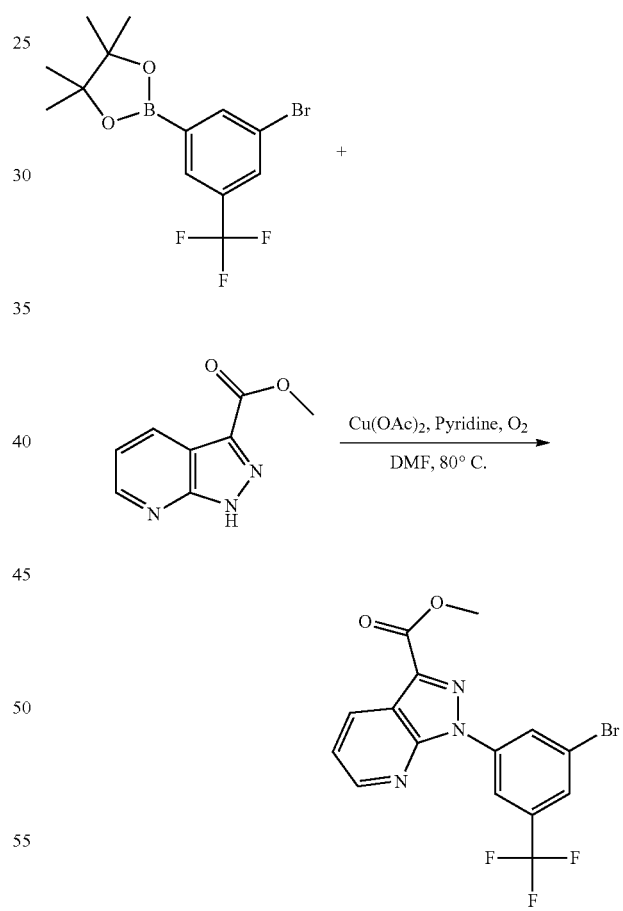

Similar to as described in General Procedure C, 2-[3-bromo-5-(trifluoromethyl)phenyl]-4,4,5,5-tetramethyl-1,3,2-dioxaborolane was reacted with methyl 1H-pyrazolo[3,4-b]pyridine-3-carboxylate to give the title compound (100 mg, 21%) as a white solid. LC-MS (ES, m/z): 400, 402 [M+1]$^+$.

Step 2: Synthesis of methyl 1-(3-[2-[(3R)-3-hydroxy-1-methyl-2-oxopyrrolidin-3-yl]ethynyl]-5-(trifluoromethyl)phenyl)-1H-pyrazolo[3,4-b]pyridine-3-carboxylate

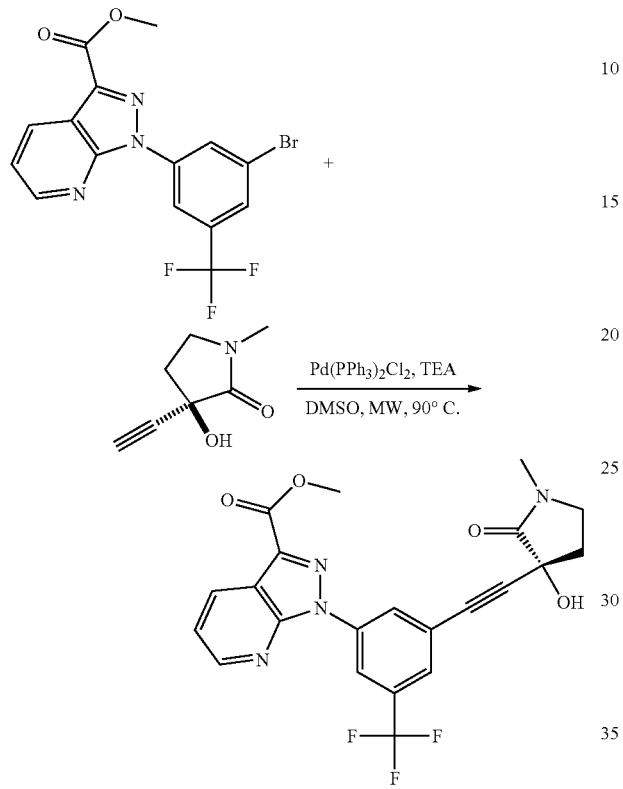

Similar to as described in General Procedure E, methyl 1-[3-bromo-5-(trifluoromethyl)phenyl]-1H-pyrazolo[3,4-b]pyridine-3-carboxylate was reacted with (3R)-3-ethynyl-3-hydroxy-1-methylpyrrolidin-2-one to give the title compound (110 mg) as a light brown solid. LC-MS (ES, m/z): 459 [M+1]$^+$.

Step 3: Synthesis of 1-(3-[2-[(3R)-3-hydroxy-1-methyl-2-oxopyrrolidin-3-yl]ethynyl]-5-(trifluoromethyl)phenyl)-1H-pyrazolo[3,4-b]pyridine-3-carboxamide

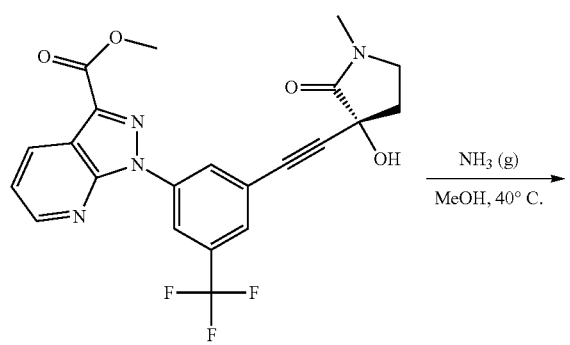

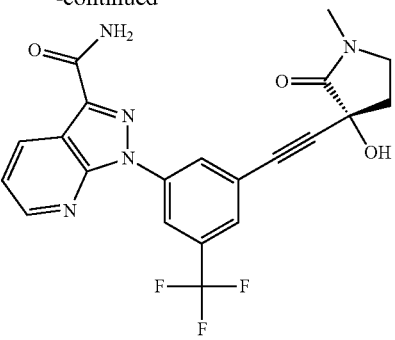

Similar to as described in General Procedure S, methyl 1-(3-[2-[(3R)-3-hydroxy-1-methyl-2-oxopyrrolidin-3-yl]ethynyl]-5-(trifluoromethyl)phenyl)-1H-pyrazolo[3,4-b]pyridine-3-carboxylate was reacted with ammonia in methanol to give the title compound (12.3 mg, 12%) as a white solid. LC-MS (ES, m/z): 444 [M+1]$^+$. $^1$H NMR (400 MHz, CD$_3$OD) δ 8.94 (s, 2H), 8.78-8.75 (m, 1H), 8.73 (d, J=2.0 Hz, 1H), 7.77 (s, 1H), 7.53-7.49 (m, 1H), 3.54-3.50 (m, 2H), 2.96 (s, 3H), 2.69-2.61 (m, 1H), 2.40-2.34 (m, 1H).

Example UUUU

Synthesis of 5-(acetamidomethyl)-1-(3-[2-[(3R)-3-hydroxy-1-methyl-2-oxopyrrolidin-3-yl]ethynyl]phenyl)-1H-indazole-3-carboxamide Step 1: Synthesis of methyl 1-(3-bromophenyl)-5-(chloromethyl)-1H-indazole-3-carboxylate

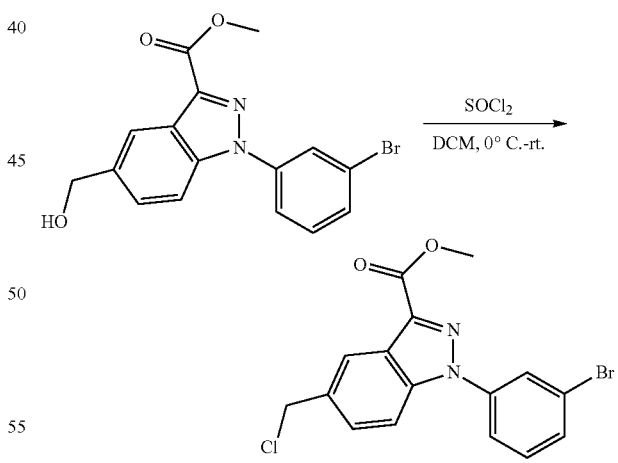

To a solution of methyl 1-(3-bromophenyl)-5-(hydroxymethyl)-1H-indazole-3-carboxylate (500 mg, 1.38 mmol, 1.00 equiv) in dichloromethane (10 mL) was added thionyl chloride (2 mL, 27.57 mmol, 19.90 equiv) dropwise with stirring at 0° C. and then stirred for 30 min at room temperature. The reaction was concentrated under vacuum to give 600 mg of methyl 1-(3-bromophenyl)-5-(chloromethyl)-1H-indazole-3-carboxylate as a yellow solid which was used in the next step without further purification.

Step 2: Synthesis of methyl 5-(azidomethyl)-1-(3-bromophenyl)-1H-indazole-3-carboxylate

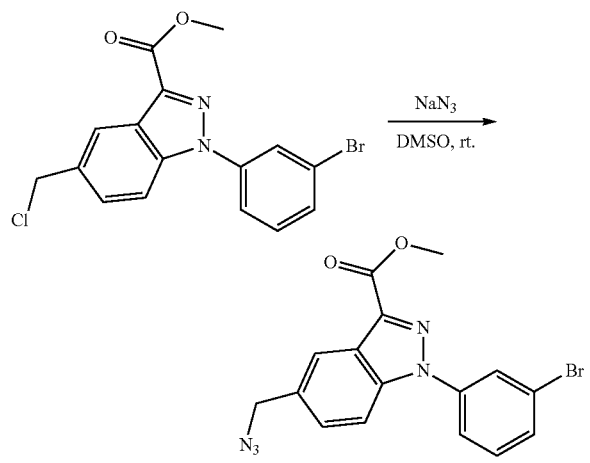

A suspension of methyl 1-(3-bromophenyl)-5-(chloromethyl)-1H-indazole-3-carboxylate (300.00 mg, 0.79 mmol, 1.00 equiv), sodium azide (102.73 mg, 1.58 mmol, 2.00 equiv) in DMSO (4.00 mL) was stirred for 90 min at room temperature. The reaction mixture was diluted with 100 mL of tetrahydrofuran and washed with 3×60 mL of brine. This resulted in ~100 mL of solution of the title compound which was used for the next step without further purification. LC-MS (ES, m/z): 386, 388 [M+H]$^+$.

Step 3: Synthesis of methyl 5-(aminomethyl)-1-(3-bromophenyl)-1H-indazole-3-carboxylate

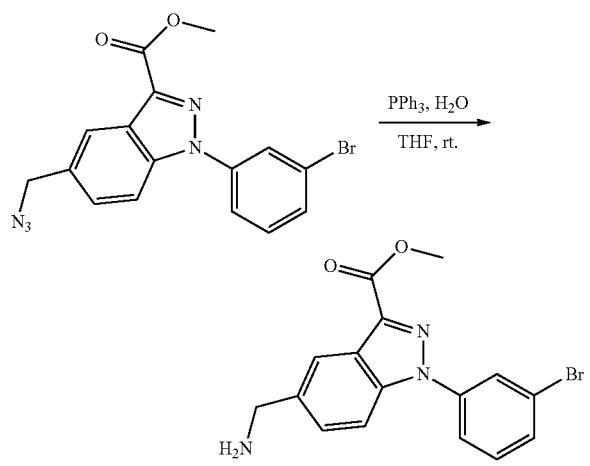

To a solution of methyl 5-(azidomethyl)-1-(3-bromophenyl)-1H-indazole-3-carboxylate in tetrahydrofuran (100 mL) obtained in the last step was added triphenyl phosphane (224.12 mg, 0.85 mmol, 1.10 equiv) and water (0.1 mL). The resulting mixture was stirred for 3 h at 40° C. and concentrated under vacuum to give 500 mg (crude) of the title compound as a yellow solid. LC-MS (ES, m/z): 360, 362 [M+H]$^+$.

Step 4: Synthesis of methyl 1-(3-bromophenyl)-5-(acetamidomethyl)-1H-indazole-3-carboxylate

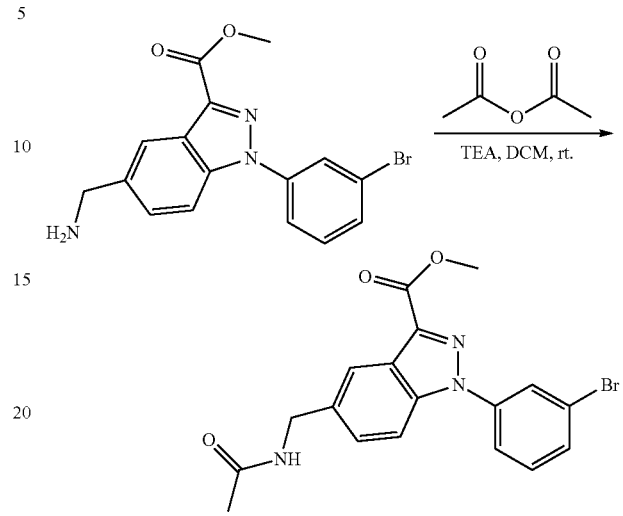

A solution of methyl 5-(aminomethyl)-1-(3-bromophenyl)-1H-indazole-3-carboxylate (200.00 mg, 0.56 mmol, 1.00 equiv), acetic anhydride (85.03 mg, 0.83 mmol, 1.50 equiv) and triethylamine (112.37 mg, 1.11 mmol, 2.00 equiv) in dichloromethane (20 mL) was stirred for 2 h at room temperature. The resulting mixture was concentrated under vacuum to give 200 mg of the title compound as a yellow solid. LC-MS (ES, m/z): 402, 404 [M+H]$^+$.

Step 5: Synthesis of methyl 5-(acetamidomethyl)-1-(3-[2-[(3R)-3-hydroxy-1-methyl-2-oxopyrrolidin-3-yl]ethynyl]phenyl)-1H-indazole-3-carboxylate

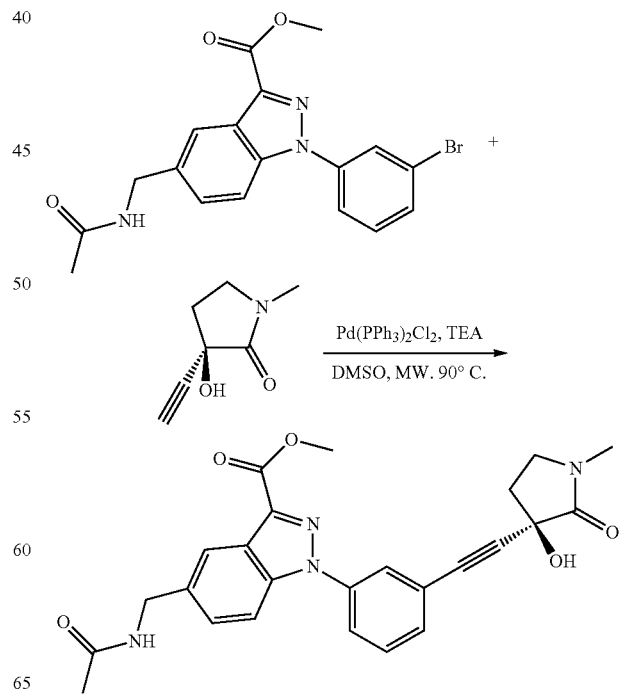

Similar to as described in General Procedure E, methyl 1-(3-bromophenyl)-5-(acetamidomethyl)-1H-indazole-3-carboxylate was reacted with (3R)-3-ethynyl-3-hydroxy-1-methylpyrrolidin-2-one to give the title compound (100 mg, 49%) as a yellow solid. LC-MS (ES, m/z): 461, 462 [M+H]+.

Step 6: Synthesis of 5-(acetamidomethyl)-1-(3-[2-[(3R)-3-hydroxy-1-methyl-2-oxopyrrolidin-3-yl]ethynyl]phen yl)-1H-indazole-3-carboxamide

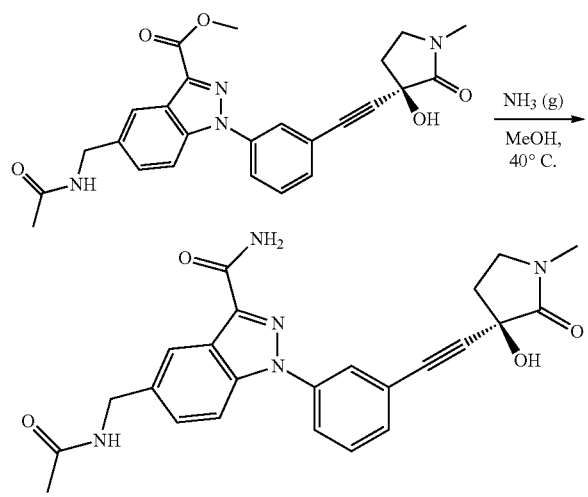

Similar to as described in General Procedure S, methyl 5-(acetamidomethyl)-1-(3-[2-[(3R)-3-hydroxy-1-methyl-2-oxopyrrolidin-3-yl]ethynyl]phen yl)-1H-indazole-3-carboxylate was reacted with ammonia in methanol to give the title compound (25.7 mg, 27%) as an off-white solid. LC-MS (ES, m/z): 446 [M+H]+. $^1$H NMR (300 MHz, CD$_3$OD) δ 8.16 (s, 1H), 7.84-7.81 (m, 1H), 7.78-7.70 (m, 2H), 7.54-7.40 (m, 3H), 4.44 (s, 2H), 3.46-3.37 (m, 2H), 2.84 (s, 3H), 2.55-2.47 (m, 1H), 2.28-2.18 (m, 1H), 1.93 (s, 3H).

Example VVVV

Synthesis of 1-(3-[2-[(3R)-3-hydroxy-1-methyl-2-oxopyrrolidin-3-yl]ethynyl]phenyl)-5-N-methyl-1H-indazole-3,5-dicarboxamide Step 1: Synthesis of 1-(3-bromophenyl)-3-(methoxycarbonyl)-1H-indazole-5-carboxylic acid

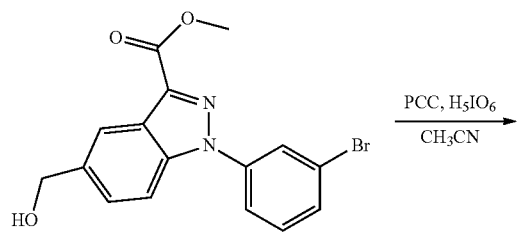

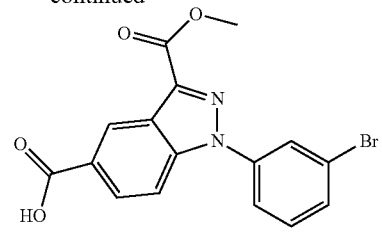

A suspension of methyl 1-(3-bromophenyl)-5-(hydroxymethyl)-1H-indazole-3-carboxylate (144.00 mg, 0.40 mmol, 1.00 equiv), PCC (17.19 mg, 0.08 mmol, 0.20 equiv) and periodic acid (199.93 mg, 0.88 mmol, 2.20 equiv) in acetonitrile (10 mL) was stirred for 30 min at room temperature. The resulting solution was diluted with ethyl acetate, washed with brine, dried over anhydrous sodium sulfate, and concentrated under vacuum to give 150 mg (crude, brown solid) of the title compound which was used in the next step without further purification. LC-MS (ES, m/z): 375, 377[M+H]+.

Step 2: Synthesis of methyl 1-(3-bromophenyl)-5-(methylcarbamoyl)-1H-indazole-3-carboxylate

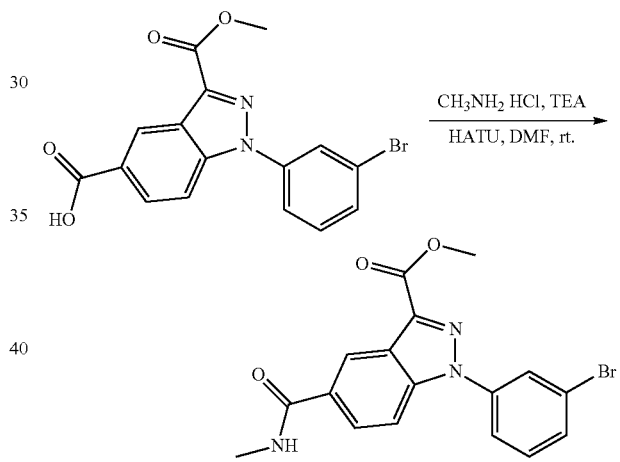

Similar to as described in General Procedure B, 1-(3-bromophenyl)-3-(methoxycarbonyl)-1H-indazole-5-carboxylic acid was reacted with methylamine hydrochloride to give the title compound (140 mg, 75%) as a yellow solid. LC-MS (ES, m/z): 388, 390 [M+H]+.

Step 3: Synthesis of methyl 1-(3-[2-[(3R)-3-hydroxy-1-methyl-2-oxopyrrolidin-3-yl]ethynyl]phenyl)-5-(methylcarbamoyl)-1H-indazole-3-carboxylate

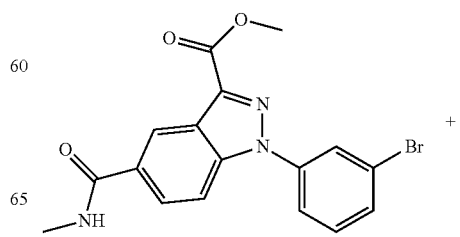

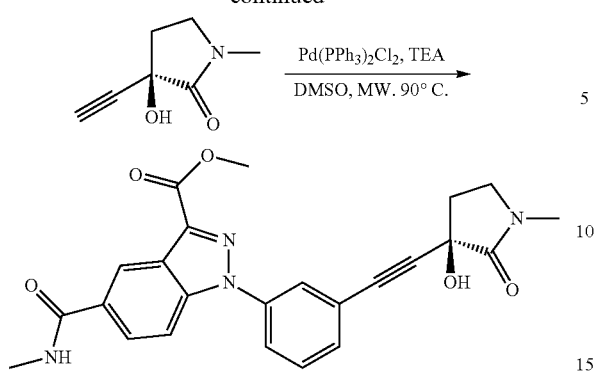

Similar to as described in General Procedure E, methyl 1-(3-bromophenyl)-5-(methylcarbamoyl)-1H-indazole-3-carboxylate was reacted with (3R)-3-ethynyl-3-hydroxy-1-methylpyrrolidin-2-one to give the title compound (140 mg, 94%) as a yellow solid. LC-MS (ES, m/z): 447 [M+H]+.

Step 4: Synthesis of 1-(3-[2-[(3R)-3-hydroxy-1-methyl-2-oxopyrrolidin-3-yl]ethynyl]phenyl)-5-N-methyl-1H-indazole-3,5-dicarboxamide

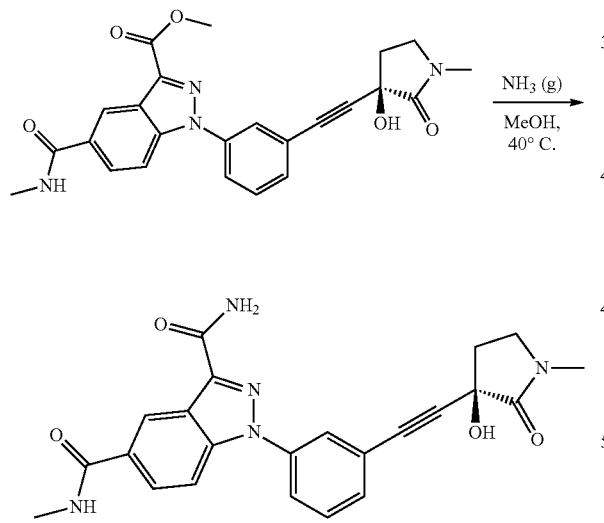

Similar to as described in General Procedure S, methyl 1-(3-[2-[(3R)-3-hydroxy-1-methyl-2-oxopyrrolidin-3-yl]ethynyl]phenyl)-5-(methylcarbamoyl)-1H-indazole-3-carboxylate was reacted with ammonia in methanol to give the title compound (34.3 mg, 25%) as an off-white solid. LC-MS (ES, m/z): 432 [M+H]+. 1H NMR (CD3OD, 300 MHz) δ 8.85 (s, 1H), 8.04-7.86 (m, 4H), 7.67-7.58 (m, 2H), 3.53-3.48 (m, 2H), 2.99 (s, 3H), 2.95 (s, 3H), 2.66-2.58 (m, 1H), 2.39-2.30 (m, 1H).

Example WWWW

Synthesis of 1-(3-[2-[(3R)-3-hydroxy-1-methyl-2-oxopyrrolidin-3-yl]ethynyl]phenyl)-5-methanesulfonyl-1H,4H,5H,6H,7H-pyrazolo[4,3-c]pyridine-3-carboxamide Step 1: Synthesis of ethyl 1-(3-bromophenyl)-5-methanesulfonyl-1H,4H,5H,6H,7H-pyrazolo[4,3-c]pyridine-3-carboxylate

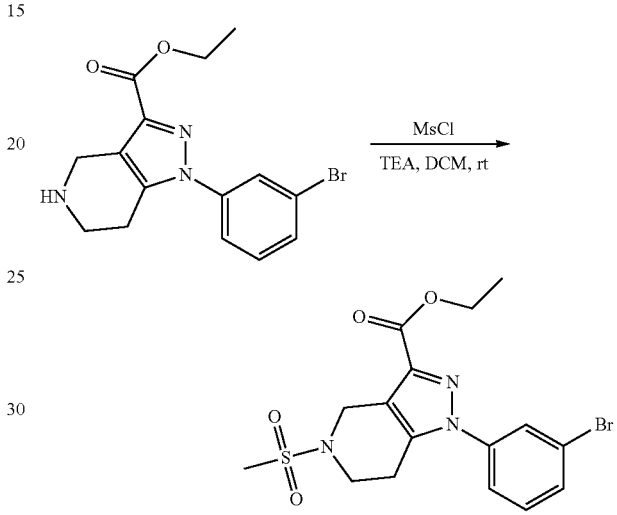

Methanesulfonyl chloride (37.01 mg, 0.32 mmol, 1.00 equiv) was added to a stirred solution of ethyl 1-(3-bromophenyl)-1H,4H,5H,6H,7H-pyrazolo[4,3-c]pyridine-3-carboxylate (150.00 mg, 0.32 mmol, 1.00 equiv) and triethylamine (98.09 mg, 0.97 mmol, 3.00 equiv) in dichloromethane (2 mL) at 0° C. The mixture was stirred for 3 h at room temperature and concentrated under vacuum. The residue was purified by a silica gel column chromatography eluting with ethyl acetate/petroleum ether (1:2) to afford 70 mg (51%) of the title compound as yellow oil. LC-MS (ES, m/z): 428, 430 [M+H]+.

Step 2: Synthesis of ethyl 1-(3-[2-[(3R)-3-hydroxy-1-methyl-2-oxopyrrolidin-3-yl]ethynyl]phenyl)-5-methanesulfonyl-1H,4H,5H,6H,7H-pyrazolo[4,3-c]pyridine-3-carboxylate

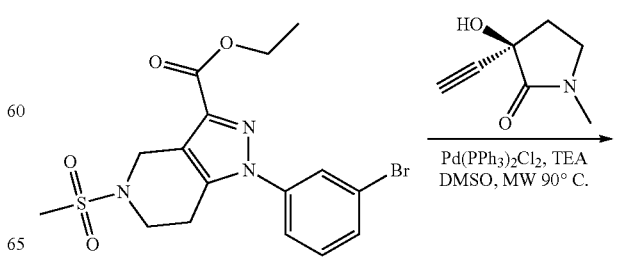

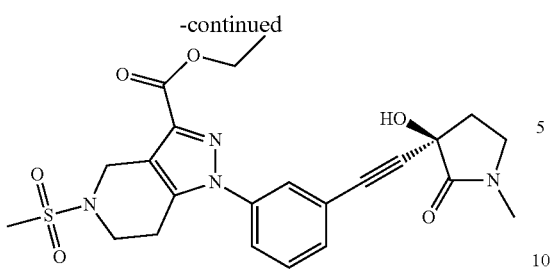

Similar to as described in General Procedure E, ethyl 1-(3-bromophenyl)-5-methanesulfonyl-1H,4H,5H,6H,7H-pyrazolo[4,3-c]pyridine-3-carboxylate was reacted with (3R)-3-ethynyl-3-hydroxy-1-methylpyrrolidin-2-one to give the title compound (40 mg, 59%) as a yellow oil. LC-MS (ES, m/z): 487 [M+H]$^+$.

Step 3: Synthesis of 1-(3-[2-[(3R)-3-hydroxy-1-methyl-2-oxopyrrolidin-3-yl]ethynyl]phenyl)-5-methanesulfonyl-1H,4H,5H,6H,7H-pyrazolo[4,3-c]pyridine-3-carboxamide

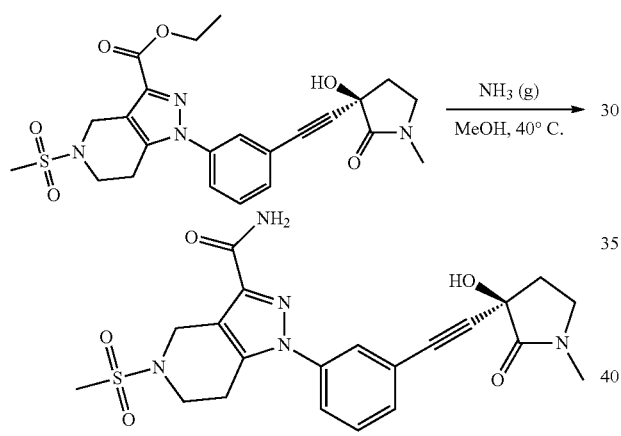

Similar to as described in General Procedure S, ethyl 1-(3-[2-[(3R)-3-hydroxy-1-methyl-2-oxopyrrolidin-3-yl]ethynyl]phenyl)-5-methanesulfonyl-1H,4H,5H,6H,7H-pyrazolo[4,3-c]pyridine-3-carboxylate was reacted with ammonia in methanol to give the title compound (10.7 mg, 28%) as a white solid. LC-MS (ES, m/z): 458 [M+H]$^+$. $^1$H NMR (400 MHz, CD$_3$OD) δ 7.66 (s, 1H), 7.57-7.53 (m, 1H), 7.46-7.42 (m, 2H), 4.50 (s, 2H), 3.51-3.47 (m, 2H), 3.40-3.35 (m, 2H), 2.94-2.91 (m, 2H), 2.86 (s, 1H), 2.83 (s, 1H), 2.52-2.46 (m, 1H), 2.25-2.22 (m, 1H).

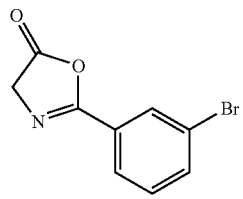 [SMILES: O=C1CN=C(c2cccc(Br)c2)O1]

2-[(3-bromobenzoyl)amino]acetic acid (1 g, 1 eq) and N,N'-dicyclohexylcarbodiimide (1 eq) in Toluene (0.25M) were heated for 4 hours at 100° C. The reaction was cooled to room temperature and the white solid (urea) was removed by filtration and the resultant reaction mixture was concentrated to dryness to afford the title compound as a crude orange solid in quantitative yield.

Synthesis of 2-(3-bromophenyl)-4-(3,4,5,6-tetrahydropyridin-2-yl)oxazol-5(4H)-one

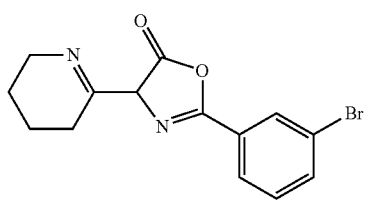 [SMILES: O=C1OC(c2cccc(Br)c2)=NC1C1=NCCCC1]

2-(3-bromophenyl)oxazol-4H)-one (0.93 g) was suspended in Tetrahydrofuran (16 mL) whereupon 6-methoxy-2,3,4,5-tetrahydropyridine (1 eq) was added to the solution. The reaction was heated at 80° C. for 16 hours and the solvent was removed under vacuum. The crude material was suspended in dichloromethane and extracted with water and the aqueous layer was back extracted once with dichloromethane. The combined organic layers were dried with Magnesium Sulfate, filtered and concentrated to afford orange semi-solid. The crude was purified using Hetpanes:Ethyl acetate gradient to afford 630 mg of the title compound.

Synthesis of 3-(3-bromophenyl)-5,6,7,8-tetrahydroimidazo[1,5-a]pyridine-1-carboxamide

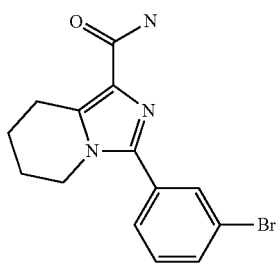 [SMILES: NC(=O)c1nc(-c2cccc(Br)c2)n2c1CCCC2]

2-(3-bromophenyl)-4-(3,4,5,6-tetrahydropyridin-2-yl)oxazol-5(4H)-one (630 mg) was dissolved in Methanol (15 mL) and Lithium Hydroxide monohydrate (3 eq in 1.5 mL of water) was added. The reaction was heated to 90° C. for 3 hours then concentrated to remove M ethanol. Additional water (~10 mL) was added to reaction mixture and the aqueous layer was brought to neutral pH and extracted 3 times with DCM to afford crude 3-(3-bromophenyl)-5,6,7,8-tetrahydroimidazo[1,5-a]pyridine-1-carboxylic acid. Similar to General Procedure B, crude 3-(3-bromophenyl)-5,6,7,8-tetrahydroimidazo[1,5-a]pyridine-1-carboxylic acid (40 mg) was reacted with ammonium chloride to give crude 3-(3-bromophenyl)-5,6,7,8-tetrahydroimidazo[1,5-a]pyridine-1-carboxamide (40 mg) following trituration from a saturated solution of ammonium chloride.

Example XXXX

Synthesis of 3-[3-[2-[(3R)-3-hydroxy-1-methyl-2-oxo-pyrrolidin-3-yl]ethynyl]phenyl]-5,6,7,8-tetrahydroimidazo[1,5-a]pyridine-1-carboxamide

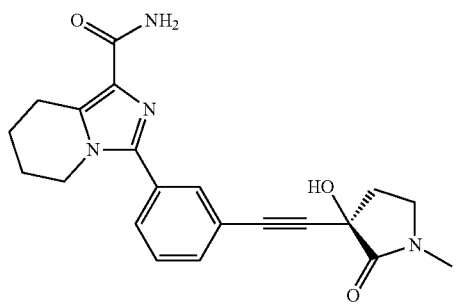 [SMILES: CN1CC[C@@](O)(C#Cc2cccc(-c3nc(C(N)=O)c4n3CCCC4)c2)C1=O]

Similar to as described in General Procedure E, 3-(3-bromophenyl)-5,6,7,8-tetrahydroimidazo[1,5-a]pyridine-1-carboxamide was reacted with (3R)-3-ethynyl-3-hydroxy-1-methyl-pyrrolidin-2-one to give 22 mg of the title compound (12%). M+H=379.0; 1H NMR (400 MHz, DMSO-d6) δ 7.77-7.70 (m, 2H), 7.53-7.45 (m, 2H), 7.19 (s, 1H), 6.89 (s, 1H), 6.45 (s, 1H), 4.08 (t, J=5.9 Hz, 2H), 3.38-3.34 (m, 2H), 3.05 (t, J=6.4 Hz, 2H), 2.80 (s, 3H), 2.48-2.40 (m, 1H), 2.23-2.14 (m, 1H), 1.90-1.82 (m, 2H), 1.82-1.73 (m, 2H).

Synthesis of ethyl 5-amino-4-(3-bromophenyl)-1H-imidazole-2-carboxylate

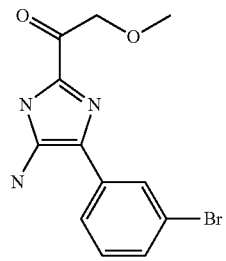 [SMILES: COCC(=O)c1nc(-c2cccc(Br)c2)c(N)[nH]1]

To a solution of ethyl thiooxamate (1 g, 1 eq) in dichloromethane (40 mL) was slowly added trimethyloxonium tetrafluoroborate (1.18 eq) at 0° C. After 10 min the ice bath was removed, and the reaction mixture was stirred overnight at room temperature. The solvent was removed to afford ethyl 2-imino-2-(methylthio)acetate as tetrafluoroborate salt in assumed quantitative yield which was used without further purification. A solution of 2-amino-2-(3-bromophenyl)acetonitrile (1 g, 1 eq) and 2-ethoxy-1-(methylsulfanyl)-2-oxoethaniminium tetrafluoroborate (1.2 eq) in dry 1,4-dioxane (15 mL) was stirred at 25° C. under a Nitrogen balloon for 2 days. The solution was concentrated in vacuo. The resulting residue was purified by silica gel chromatography using Ethyl Acetate/Heptanes gradient to afford 440 mg of ethyl 5-amino-4-(3-bromophenyl)-1H-imidazole-2-carboxylate, as a yellow semi-solid.

Synthesis of ethyl 8-(3-bromophenyl)imidazo[1,5-a]pyrimidine-6-carboxylate

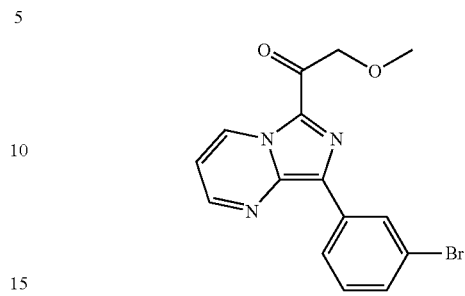

Ethyl 5-amino-4-(3-bromophenyl)-1H-imidazole-2-carboxylate (0.25 g) was suspended in EtOH (0.25M) and 1,1,3,3-tetramethoxypropane (2 eq) was added. The reaction was heated to 150° C. thermally for 1 hour and concentrated to dryness to afford crude ethyl 8-(3-bromophenyl)imidazo[1,5-a]pyrimidine-6-carboxylate (0.18 g).

Example YYYY

Synthesis of 8-[3-[2-[(3R)-3-hydroxy-1-methyl-2-oxo-pyrrolidin-3-yl]ethynyl]phenyl]imidazo[1,5-a]pyrimidine-6-carboxamide

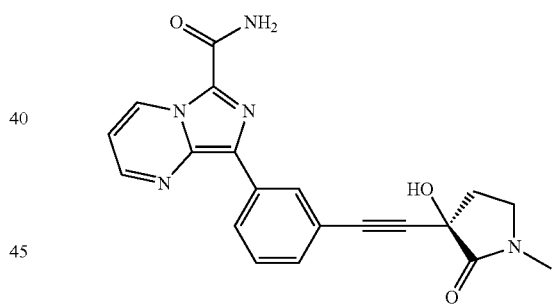

Similar to as described in General Procedure I, crude ethyl 8-(3-bromophenyl)imidazo[1,5-a]pyrimidine-6-carboxylate (0.13 g) was reacted to form 8-(3-bromophenyl)imidazo[1,5-a]pyrimidine-6-carboxamide in assumed quantitative yield. Similar to as described in General Procedure E, 8-(3-bromophenyl)imidazo[1,5-a]pyrimidine-6-carboxamide (70 mg) was reacted with (3R)-3-ethynyl-3-hydroxy-1-methyl-pyrrolidin-2-one to give 27 mg of the title compound (31%). M+H=376.0; 1H NMR (400 MHz, DMSO-d6) δ 9.64 (dd, J=7.3, 1.8 Hz, 1H), 8.58 (dd, J=3.8, 1.8 Hz, 1H), 8.52-8.44 (m, 2H), 8.15 (s, 1H), 7.75-7.67 (m, 1H), 7.50 (t, J=7.8 Hz, 1H), 7.38-7.32 (m, 1H), 7.13 (dd, J=7.3, 3.8 Hz, 1H), 6.46 (s, 1H), 3.40-3.34 (m, 2H), 2.82 (s, 3H), 2.49-2.42 (m, 1H), 2.26-2.16 (m, 1H).

Synthesis of 7-(3-bromophenyl)-2,3-dihydro-1H-imidazo[1,5-a]imidazole-5-carboxamide

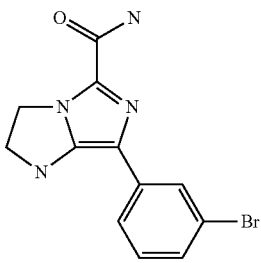 [SMILES: NC(=O)c1nc(-c2cccc(Br)c2)c2n1CCN2]

Ethyl 5-amino-4-(3-bromophenyl)-1H-imidazole-2-carboxylate (117 mg) was stirred with dibromoethane (3 eq) and cesium carbonate (3 eq) in DMF (52 eq) at 80° C. for 2 hrs then cooled to room temperature. The reaction mixture was concentrated to dryness, suspended in DCM and filtered to remove any solids then concentrated to dryness to form 100 mg (79%) crude ethyl 7-(3-bromophenyl)-2,3-dihydro-1H-imidazo[1,5-a]imidazole-5-carboxylate. Similar to as described in General Procedure J, crude ethyl 7-(3-bromophenyl)-2,3-dihydro-1H-imidazo[1,5-a]imidazole-5-carboxylate (100 mg) was reacted to form 7-(3-bromophenyl)-2,3-dihydro-1H-imidazo[1,5-a]imidazole-5-carboxylic acid (40 mg) after elution through a biotage scx-2 cartridge. Similar to as described in General Procedure B, crude 7-(3-bromophenyl)-2,3-dihydro-1H-imidazo[1,5-a]imidazole-5-carboxylic acid (40 mg) was reacted with ammonium chloride to form crude 7-(3-bromophenyl)-2,3-dihydro-1H-imidazo[1,5-a]imidazole-5-carboxamide (40 mg) following elution through a biotage scx-2 cartridge.

Example ZZZZ

Synthesis of 7-[3-[2-[(3R)-3-hydroxy-1-methyl-2-oxo-pyrrolidin-3-yl]ethynyl]phenyl]-2,3-dihydro-1H-imidazo[1,5-a]imidazole-5-carboxamide

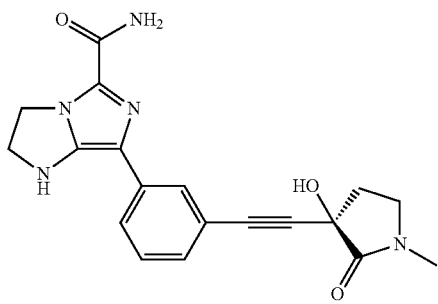 [SMILES: CN1CC[C@@](O)(C#Cc2cccc(-c3nc(C(N)=O)n4c3NCC4)c2)C1=O]

Similar to as described in General Procedure E, 7-(3-bromophenyl)-2,3-dihydro-1H-imidazo[1,5-a]imidazole-5-carboxamide (40 mg) was reacted with (3R)-3-ethynyl-3-hydroxy-1-methyl-pyrrolidin-2-one to give 2 mg of the title compound (4%). M+H=366.0

Synthesis of ethyl (2E)-2-hydroxyimino-2-pyridazin-3-yl-acetate

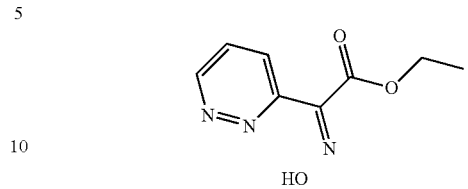

A solution 1 g of ethyl 2-pyridazin-3-ylacetate in 1.5 ml of glacial acetic acid was cooled to 0° C. in an ice bath and sodium nitrite (1.15 eq) in 4.8 ml of water was added over a period of 30 minutes then the mixture was stirred for an additional 30 minutes at 0° C., whereupon the reaction mixture was subsequently warmed to room temperature. Additional water (3.6 mL) was added then the reaction was stirred for 2 more hours at room temperature. The resultant thick slurry was washed with water (10 mL), sodium bicarbonate solution (10 mL) and then water again (10 mL) to afford 528 mg (47%) of the title compound.

Synthesis of methyl 2-amino-2-pyridazin-3-yl-acetate hydrochloride

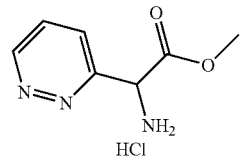

To a mixture of ethyl (2E)-2-hydroxyimino-2-pyridazin-3-yl-acetate (528 mg) and 10% Palladium on Carbon (0.1 eq) in EtOH (10 mL) was added a solution of HCl in methanol (~1.25M, 10 mL). The mixture was reacted on the parr shaker for 4 hours at 50 psi then brought back to atmospheric pressure. The reaction was filtered through celite to remove Palladium and concentrated to dryness to the title compound as an orange oil. This intermediate was taken onto the next step without purification.

Synthesis of methyl 2-[(3-bromobenzoyl)amino]-2-pyridazin-3-yl-acetate

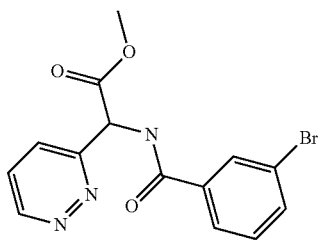 [SMILES: COC(=O)C(NC(=O)c1cccc(Br)c1)c1cccnn1]

Similar to as described in General Procedure B, crude methyl 2-amino-2-pyridazin-3-yl-acetate hydrochloride was reacted with 3-bromobenzoic acid to form 588 mg (57%) of the title compound following purification with Heptane/Ethyl Acetate with 1% triethylamine.

Synthesis of methyl 7-(3-bromophenyl)imidazo[1,5-b]pyridazine-5-carboxylate

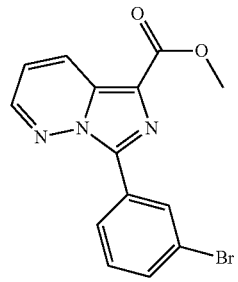 [SMILES: COC(=O)c1nc(-c2cccc(Br)c2)n2ncccc12]

To a solution of methyl 2-[(3-bromobenzoyl)amino]-2-pyridazin-3-yl-acetate in Acetonitrile (11 mL) was added phosphoryl chloride (20 eq). The reaction was heated at 85° C. for 2.5 hours then concentrated to a minimal volume before dilution with DCM. Dropwise addition of the solution was added via glass pipette into a stirring mixture of ice water (50 mL). The solution was neutralized by adding solid bicarbonate to the stirring ice water solution and extracted with DCM to form 350 mg (63%) of the title compound which was taken on without further purification.

Synthesis of 7-(3-bromophenyl)imidazo[1,5-b]pyridazine-5-carboxamide

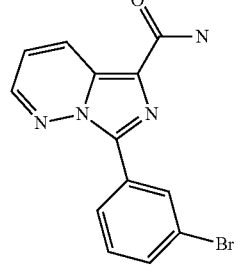

Similar to as described in General Procedure J, methyl 7-(3-bromophenyl)imidazo[1,5-b]pyridazine-5-carboxylate (185 mg) was reacted to form 172 mg (97%) of 7-(3-bromophenyl)imidazo[1,5-b]pyridazine-5-carboxamide.

Example A5

Synthesis of 7-[3-[2-[(3R)-3-hydroxy-1-methyl-2-oxo-pyrrolidin-3-yl]ethynyl]phenyl]imidazo[1,5-b]pyridazine-5-carboxamide

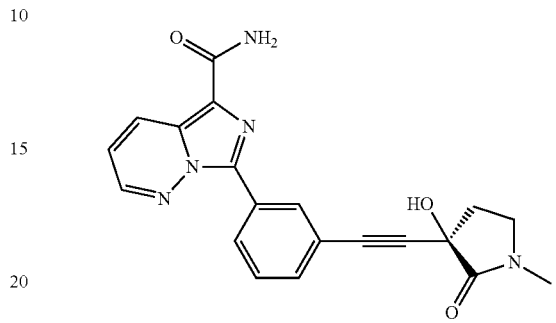

Similar to as described in General Procedure F, 7-(3-bromophenyl)imidazo[1,5-b]pyridazine-5-carboxamide (80 mg) was reacted with (3R)-3-ethynyl-3-hydroxy-1-methyl-pyrrolidin-2-one to give 20 mg of the title compound (22%). M+H=376; 1H NMR (400 MHz, DMSO-d6) δ 8.65-8.57 (m, 2H), 8.54-8.48 (m, 2H), 7.81 (s, 1H), 7.62-7.56 (m, 1H), 7.55-7.50 (m, 1H), 7.39 (s, 1H), 7.13 (dd, J=9.2, 4.4 Hz, 1H), 6.49 (s, 1H), 3.40-3.34 (m, 2H), 2.81 (s, 3H), 2.48-2.42 (m, 1H), 2.26-2.16 (m, 1H).

Synthesis of 1-bromo-imidazo[1,5-a]pyridine-3-carboxylic acid ethyl ester

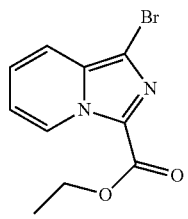

To a solution of ethyl imidazo[1,5-a]pyridine-3-carboxylate (152 mg) in Acetic Acid (0.25M) was added Bromine (1 eq). The reaction was stirred at room temperature for 5 minutes then concentrated to dryness to give 205 of the title compound. This intermediate was taken onto the next step without purification.

Synthesis of ethyl 1-[3-[2-[(3R)-3-hydroxy-1-methyl-2-oxo-pyrrolidin-3-yl]ethynyl]phenyl]imidazo[1,5-a]pyridine-3-carboxylate

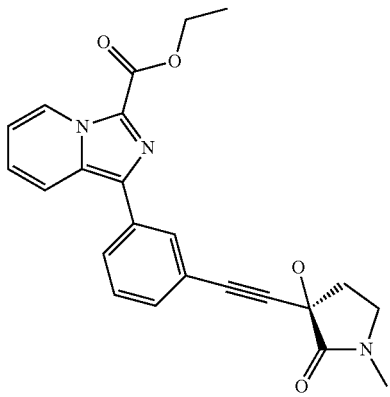 [SMILES: CCOC(=O)c1nc(-c2cccc(C#C[C@]3(O)CCN(C)C3=O)c2)c2ccccn12]

Similar to as described in General Procedure U, 1-bromo-imidazo[1,5-a]pyridine-3-carboxylic acid ethyl ester (75 mg) was reacted with potassium (S)-trifluoro(3-((3-hydroxy-1-methyl-2-oxopyrrolidin-3yl)ethynyl)phenyl)borate to form the title compound. This intermediate was taken onto the next step without purification.

Example B5

Synthesis of 1-[3-[2-[(3R)-3-hydroxy-1-methyl-2-oxo-pyrrolidin-3-yl]ethynyl]phenyl]imidazo[1,5-a]pyridine-3-carboxamide

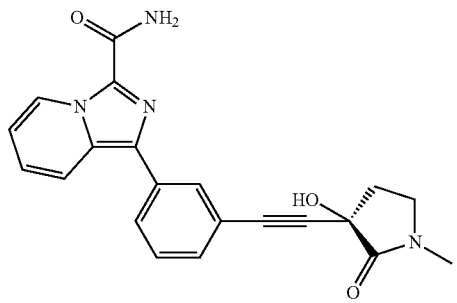 [SMILES: CN1CC[C@@](O)(C#Cc2cccc(-c3nc(C(N)=O)n4ccccc34)c2)C1=O]

Similar to as described in General Procedure J, ethyl 1-[3-[2-[(3R)-3-hydroxy-1-methyl-2-oxo-pyrrolidin-3-yl]ethynyl]phenyl]imidazo[1,5-a]pyridine-3-carboxylate was reacted to form 1-[3-[2-[(3R)-3-hydroxy-1-methyl-2-oxo-pyrrolidin-3-yl]ethynyl]phenyl]imidazo[1,5-a]pyridine-3-carboxylic acid (98 mg). This intermediate was taken onto the next step without purification. Similar to as described in General Procedure B, 1-[3-[2-[(3R)-3-hydroxy-1-methyl-2-oxo-pyrrolidin-3-yl]ethynyl]phenyl]imidazo[1,5-a]pyridine-3-carboxylic acid (98 mg) was reacted with ammonium chloride to give 12 mg of the title compound (11%). M+H=375.0; 1H NMR (400 MHz, DMSO-d6) δ 9.49 (dt, J=7.2, 1.2 Hz, 1H), 8.15-7.97 (m, 4H), 7.65-7.58 (m, 1H), 7.54-7.47 (m, 1H), 7.40-7.35 (m, 1H), 7.26-7.19 (m, 1H), 7.08-7.02 (m, 1H), 6.50 (s, 1H), 3.41-3.36 (m, 2H), 2.81 (s, 3H), 2.47-2.42 (m, 1H), 2.24-2.16 (m, 1H).

Synthesis of ethyl 3-bromoimidazo[1,5-a]pyridine-1-carboxylate

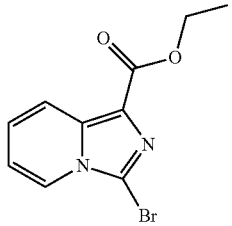

To a solution of ethyl imidazo[1,5-a]pyridine-1-carboxylate (150 mg) in Acetic Acid (0.25M) was added Bromine (1 eq). The reaction was stirred at room temperature for 5 minutes then concentrated to dryness to give 204 of the title compound. The solid was brought up in Water (20 mL) and extracted with DCM (20 mL). The organic layer was dried with Magnesium sulfate, filtered and concentrated to afford the title compound as a green solid. This intermediate was taken onto the next step without purification.

Synthesis of ethyl 3-[3-[2-[(3R)-3-hydroxy-1-methyl-2-oxo-pyrrolidin-3-yl]ethynyl]phenyl]imidazo[1,5-a]pyridine-1-carboxylate

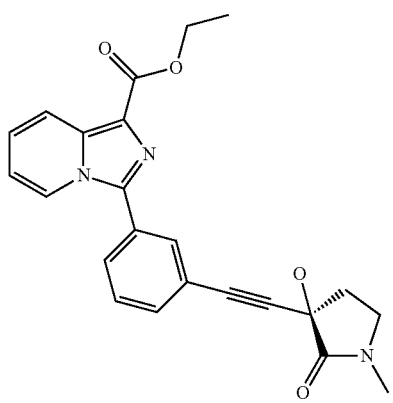 [SMILES: CCOC(=O)c1nc(-c2cccc(C#C[C@]3(O)CCN(C)C3=O)c2)n2ccccc12]

Similar to as described in General Procedure U, ethyl 3-bromoimidazo[1,5-a]pyridine-1-carboxylate (71 mg) was reacted with potassium (S)-trifluoro(3-((3-hydroxy-1-methyl-2-oxopyrrolidin-3yl)ethynyl)phenyl)borate to form the title compound which was taken onto the next step without purification.

Example C5

Synthesis of 3-[3-[2-[(3R)-3-hydroxy-1-methyl-2-oxo-pyrrolidin-3-yl]ethynyl]phenyl]imidazo[1,5-a]pyridine-1-carboxamide

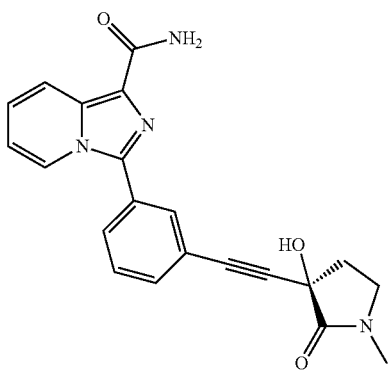 [SMILES: CN1CC[C@@](O)(C#Cc2cccc(-c3nc(C(N)=O)c4ccccn34)c2)C1=O]

Similar to as described in General Procedure J, ethyl 3-[3-[2-[(3R)-3-hydroxy-1-methyl-2-oxo-pyrrolidin-3-yl]ethynyl]phenyl]imidazo[1,5-a]pyridine-1-carboxylate was reacted to form 3-[3-[2-[(3R)-3-hydroxy-1-methyl-2-oxo-pyrrolidin-3-yl]ethynyl]phenyl]imidazo[1,5-a]pyridine-1-carboxylic acid (99 mg). This intermediate was taken onto the next step without purification. Similar to as described in General Procedure B, 3-[3-[2-[(3R)-3-hydroxy-1-methyl-2-oxo-pyrrolidin-3-yl]ethynyl]phenyl]imidazo[1,5-a]pyridine-1-carboxylic acid (98 mg) was reacted with ammonium chloride to give 12 mg of the title compound (12%). M+H=375.0; 1H NMR (400 MHz, DMSO-d6) δ 8.53 (dt, J=7.2, 1.1 Hz, 1H), 8.21 (dt, J=9.1, 1.2 Hz, 1H), 7.93-7.89 (m, 2H), 7.64-7.54 (m, 3H), 7.21-7.15 (m, 2H), 6.96-6.91 (m, 1H), 6.52 (s, 1H), 3.39-3.34 (m, 2H), 2.80 (s, 3H), 2.49-2.41 (m, 1H), 2.23-2.15 (m, 1H).

Synthesis of potassium (S)-trifluoro(3-((3-hydroxy-1-methyl-2-oxopyrrolidin-3yl)ethynyl)phenyl)borate

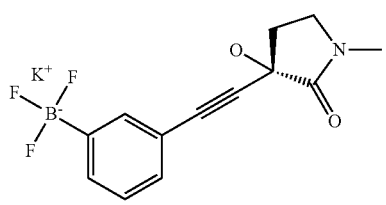 [SMILES: CN1CC[C@](O)(C#Cc2cccc([B-](F)(F)F)c2)C1=O ; [K+]]

Potassium trifluoro-(3-iodophenyl)boranuide (1 eq) is brought up in a solution of 1:1 Triethylamine (14 eq) and N,N-dimethylformamide (26 eq). The solution was purged with nitrogen before addition of cuprous iodide (0.05 eq), bis(triphenylphosphine)palladium(II) dichloride (0.05 eq) and (3R)-3-ethynyl-3-hydroxy-1-methyl-pyrrolidin-2-one (1.05 eq) at once. The reaction mixture was stirred at 40° C. overnight (18 hrs) whereupon the reaction mixture was concentrated under vacuum to yield a dark brown oil. Water was added and the solution was sonicated until an orange-brown solid crashed out of solution. The solid was filtered off and the aqueous layer was concentrated under high vacuum to afford a dark red sludge. The sludge was azeotroped 3 times with Hexanes, brought up in Methanol, sonicated and the subsequent light brown solid was then filtered and collected to afford potassium (S)-trifluoro(3-((3-hydroxy-1-methyl-2-oxopyrrolidin-3yl)ethynyl)phenyl)borate in a 80% yield.

Example D5

Synthesis of 4-[3-[2-[(3R)-3-hydroxy-1-methyl-2-oxo-pyrrolidin-3-yl]ethynyl]phenyl]thiazole-2-carboxamide

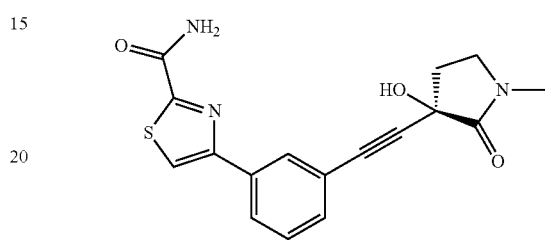

Similar to as described in General Procedure U, ethyl 4-bromothiazole-2-carboxylate (75 mg) was reacted with (S)-trifluoro(3-((3-hydroxy-1-methyl-2-oxopyrrolidin-3yl)ethynyl)phenyl)borate to form ethyl 4-[3-[2-[(3R)-3-hydroxy-1-methyl-2-oxo-pyrrolidin-3-yl]ethynyl]phenyl]thiazole-2-carboxylate. This intermediate was taken onto the next step without purification. Similar to as described in General Procedure I, ethyl 4-[3-[2-[(3R)-3-hydroxy-1-methyl-2-oxo-pyrrolidin-3-yl]ethynyl]phenyl]thiazole-2-carboxylate was reacted to give 6 mg of the title compound (6%). M+H=342.0.

Example E5

Synthesis of 1-[4-[2-[(3R)-3-hydroxy-1-methyl-2-oxo-pyrrolidin-3-yl]ethynyl]-2-pyridyl]-5-methyl-pyrazole-3-carboxamide

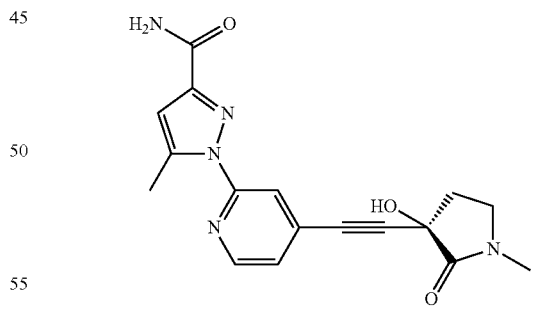

Similar to as described in General Procedure A, ethyl 5-methyl-1H-pyrazole-3-carboxylate (250 mg) was reacted with 2-fluoro-4-iodo-pyridine to give ethyl 1-(4-iodo-2-pyridyl)-5-methyl-pyrazole-3-carboxylate. The crude material was used directly in subsequent reactions. Ethyl 1-(4-iodo-2-pyridyl)-5-methyl-pyrazole-3-carboxylate (230 mg) was subjected to General Procedure I to afford 140 mg of 1-(4-iodo-2-pyridyl)-5-methyl-pyrazole-3-carboxamide which was used in the next step without further purification. Similar to as described in General Procedure E, 1-(4-iodo- 2-pyridyl)-5-methyl-pyrazole-3-carboxamide (70 mg) was reacted with (3R)-3-ethynyl-3-hydroxy-1-methyl-pyrrolidin-2-one to give 29 mg of the title compound (40%). M+H=340; 1H NMR (400 MHz, DMSO-d6) δ 8.52 (dd, J=5.1, 1.0 Hz, 1H), 8.07-7.96 (m, 1H), 7.82 (s, 1H), 7.40 (dd, J=5.1, 1.4 Hz, 1H), 7.33 (s, 1H), 6.68-6.60 (m, 2H), 3.41-3.35 (m, 2H), 2.81 (s, 3H), 2.63 (d, J=0.9 Hz, 3H), 2.49-2.43 (m, 1H), 2.27-2.18 (m, 1H).

Example F5

Synthesis of 1-[4-[(3R)-3-hydroxy-3-(5-methylisoxazol-3-yl)but-1-ynyl]-2-pyridyl]-5-methyl-pyrazole-3-carboxamide

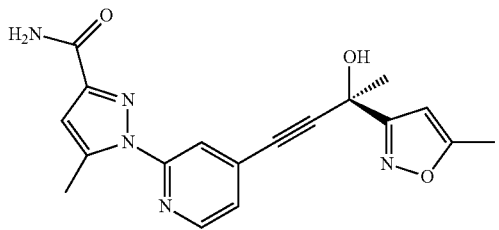 [SMILES: Cc1cc([C@](C)(O)C#Cc2ccnc(-n3nc(C(N)=O)cc3C)c2)no1]

Similar to as described in General Procedure E, 1-(4-iodo-2-pyridyl)-5-methyl-pyrazole-3-carboxamide (70 mg) was reacted with (2R)-2-(5-methylisoxazol-3-yl)but-3-yn-2-ol to give 10 mg of the title compound (13%). M+H=352; 1H NMR (400 MHz, DMSO-d6) δ 8.52 (dd, J=5.1, 0.9 Hz, 1H), 8.03-8.00 (m, 1H), 7.82 (s, 1H), 7.41 (dd, J=5.1, 1.4 Hz, 1H), 7.33 (s, 1H), 6.72-6.63 (m, 2H), 6.38 (d, J=1.0 Hz, 1H), 2.64 (d, J=0.9 Hz, 3H), 2.41 (d, J=0.9 Hz, 3H), 1.82 (s, 3H).

Example G5

Synthesis of 4-chloro-1-[4-[2-[(3R)-3-hydroxy-1-methyl-2-oxo-pyrrolidin-3-yl]ethynyl]-2-pyridyl]-5-methyl-pyrazole-3-carboxamide

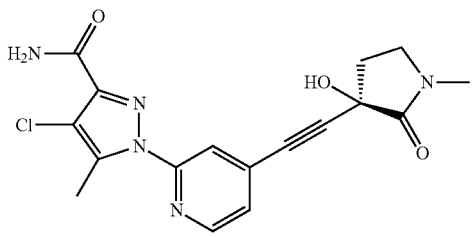 [SMILES: Cc1c(Cl)c(C(N)=O)nn1-c1cc(C#C[C@]2(O)CCN(C)C2=O)ccn1]

To a solution of ethyl 1-(4-iodo-2-pyridyl)-5-methyl-pyrazole-3-carboxylate (230 mg) in DMF was added N-chlorosuccinimide (1 equiv) at once then the reacted was heated at 50° C. for 2 hours. The crude product was triturated out of the reaction mixture by addition of water and subsequent filtration to collect 193 mg of white solid which was used in the next step without further purification. Similar to as described in General Procedure J, ethyl 4-chloro-1-(4-iodo-2-pyridyl)-5-methyl-pyrazole-3-carboxylate was reacted to afford 167 mg of 4-chloro-1-(4-iodo-2-pyridyl)-5-methyl-pyrazole-3-carboxylic acid which was used in the next reaction without purification. Similar to as described in General Procedure B, 4-chloro-1-(4-iodo-2-pyridyl)-5-methyl-pyrazole-3-carboxylic acid was reacted with ammonium chloride to afford 140 mg of 4-chloro-1-(4-iodo-2-pyridyl)-5-methyl-pyrazole-3-carboxamide which was used in the next reaction without purification. Similar to as described in General Procedure E, 4-chloro-1-(4-iodo-2-pyridyl)-5-methyl-pyrazole-3-carboxamide was reacted with (3R)-3-ethynyl-3-hydroxy-1-methyl-pyrrolidin-2-one to give 55 mg of the title compound (76%). M+H=374.0; 1H NMR (400 MHz, DMSO-d6) δ 8.54 (dd, J=5.2, 0.8 Hz, 1H), 8.04 (d, J=1.4 Hz, 1H), 7.93 (s, 1H), 7.51-7.43 (m, 2H), 6.64 (s, 1H), 3.40-3.34 (m, 2H), 2.81 (s, 3H), 2.61 (s, 3H), 2.48-2.42 (m, 1H), 2.27-2.17 (m, 1H).

Example H5

Synthesis of 4-chloro-1-[4-[(3R)-3-hydroxy-3-(5-methylisoxazol-3-yl)but-1-ynyl]-2-pyridyl]-5-methyl-pyrazole-3-carboxamide

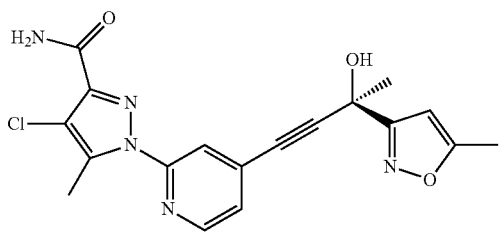 [SMILES: Cc1cc([C@](C)(O)C#Cc2ccnc(-n3nc(C(N)=O)c(Cl)c3C)c2)no1]

Similar to as described in General Procedure E, 4-chloro-1-(4-iodo-2-pyridyl)-5-methyl-pyrazole-3-carboxamide was reacted (2R)-2-(5-methylisoxazol-3-yl)but-3-yn-2-ol to give 17 mg of the title compound (23%). M+H=386.0; 1H NMR (400 MHz, DMSO-d6) δ 8.54 (dd, J=5.1, 0.8 Hz, 1H), 8.08-7.99 (m, 1H), 7.93 (s, 1H), 7.51-7.42 (m, 2H), 6.70 (s, 1H), 6.38 (d, J=1.0 Hz, 1H), 2.61 (s, 3H), 2.41 (d, J=0.9 Hz, 3H), 1.82 (s, 3H).

Example I5

Synthesis of 5-cyclopropyl-1-[4-[2-[(3R)-3-hydroxy-1-methyl-2-oxo-pyrrolidin-3-yl]ethynyl]-2-pyridyl]pyrazole-3-carboxamide

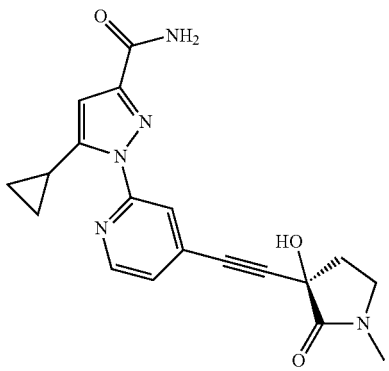 [SMILES: CN1CC[C@@](O)(C#Cc2ccnc(-n3nc(C(N)=O)cc3C3CC3)c2)C1=O]

Similar to as described in General Procedure A, 5-cyclopropyl-1H-pyrazole-3-carboxylic acid (200 mg) was reacted with 2-fluoro-4-iodo-pyridine to give 240 mg 5-cyclopropyl-1-(4-iodo-2-pyridyl)pyrazole-3-carboxylic acid. The crude material was used directly in subsequent reactions. Similar to as described in General Procedure B, 5-cyclopropyl-1-(4-iodo-2-pyridyl)pyrazole-3-carboxylic acid was reacted with ammonium chloride to afford 100 mg of 5-cyclopropyl-1-(4-iodo-2-pyridyl)pyrazole-3-carboxamide which was used in the next reaction without purification. Similar to as described in General Procedure E, 5-cyclopropyl-1-(4-iodo-2-pyridyl)pyrazole-3-carboxamide (70 mg) was reacted with (3R)-3-ethynyl-3-hydroxy-1-methyl-pyrrolidin-2-one to give 65 mg of the title compound (90%). M+H=366.0; 1H NMR (400 MHz, DMSO-d6) δ 8.54 (dd, J=5.2, 0.9 Hz, 1H), 7.98-7.94 (m, 1H), 7.78 (s, 1H), 7.44 (dd, J=5.1, 1.4 Hz, 1H), 7.31 (s, 1H), 6.64 (s, 1H), 6.48 (s, 1H), 3.41-3.35 (m, 2H), 2.81 (s, 3H), 2.49-2.42 (m, 1H), 2.27-2.17 (m, 1H), 1.12 (t, J=7.3 Hz, 1H), 1.01-0.94 (m, 2H), 0.77-0.69 (m, 2H).

Example J5

Synthesis of 5-amino-1-[4-[2-[(3R)-3-hydroxy-1-methyl-2-oxo-pyrrolidin-3-yl]ethynyl]-2-pyridyl]pyrazole-3-carboxamide

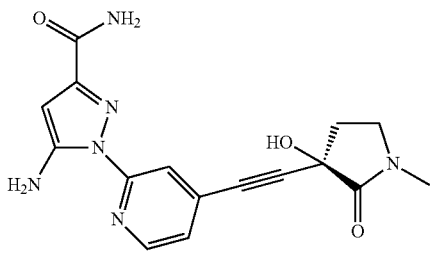 [SMILES: CN1CC[C@@](O)(C#Cc2ccnc(-n3nc(C(N)=O)cc3N)c2)C1=O]

To a solution of methyl 3-nitro-1H-pyrazole-5-carboxylate (500 mg) in Ethanol (0.25M) was added 10% Palladium on Carbon (0.1 eq) and ammonium formate (8 eq) and the reaction was heated for 1 hour at 70° C. then cooled to room temperature, filtered through celite, rinsed with Methanol and concentrated to dryness. The crude intermediate was suspended in DCM and extracted with water. To the organic layer was added 3 eq of MP-TsOH catch and release resin whereupon the mixture was stirred for 1 hour, filtered to collect resin then eluted with 7N Ammonia in MeOH and concentrated to dryness to afford 100 mg of methyl 3-amino-1H-pyrazole-5-carboxylate. To a solution of methyl 3-amino-1H-pyrazole-5-carboxylate in dioxane was added di-tert-butyl dicarbonate (1.5 eq) and the reaction was heated at 120° C. overnight, then stirred at room temperature for 6 hours before the addition of imidazole (4.5 eq). The reaction mixture was subsequently refluxed at 130° C. for 2 hrs then stirred at room temperature overnight, concentrated to dryness, suspended in Ethyl acetate and extracted 3× with 0.25N HCl solution, dried, filtered and concentrated to afford 427 mg of methyl 3-(tert-butoxycarbonylamino)-1H-pyrazole-5-carboxylate as a light pink solid. Similar to as described in General Procedure A, 3-(tert-butoxycarbonylamino)-1H-pyrazole-5-carboxylate (200 mg) was reacted with 2-fluoro-4-iodo-pyridine to give methyl 5-(tert-butoxycarbonylamino)-1-(4-iodo-2-pyridyl)pyrazole-3-carboxylate. The crude material was used directly in subsequent reactions. To a solution of 5-(tertbutoxycarbonylamino)-1-(4-iodo-2-pyridyl)pyrazole-3-carboxylate in DCM was added 4N HCl in dioxane (10 eq). The reaction was stirred at room temperature for 30 minutes then concentrated to dryness to afford crude methyl 5-amino-1-(4-iodo-2-pyridyl)pyrazole-3-carboxylate as the HCl salt. Similar to as described in General Procedure J, methyl 5-amino-1-(4-iodo-2-pyridyl)pyrazole-3-carboxylate was reacted to afford 90 mg 5-amino-1-(4-iodo-2-pyridyl)pyrazole-3-carboxylic acid which was used in the next step without purification. Similar as to described in General Procedure B, 5-amino-1-(4-iodo-2-pyridyl)pyrazole-3-carboxylic acid was reacted with ammonium chloride to afford 90 mg of 5-amino-1-(4-iodo-2-pyridyl)pyrazole-3-carboxamide which was used in the next reaction without purification.

Similar to as described in General Procedure E, 5-amino-1-(4-iodo-2-pyridyl) pyrazole-3-carboxamide (90 mg) was reacted with (3R)-3-ethynyl-3-hydroxy-1-methyl-pyrrolidin-2-one to give 14 mg of the title compound (15%). M+H=341.0; 1H NMR (400 MHz, DMSO-d6) δ 8.44 (dd, J=5.2, 0.8 Hz, 1H), 8.03-8.00 (m, 1H), 7.68 (s, 1H), 7.29, (dd, J=5.1, 1.5 Hz, 1H), 7.21 (s, 1H), 6.89 (s, 2H), 6.63 (s, 1H), 5.72 (s, 1H), 3.41-3.34 (m, 2H), 2.81 (s, 3H), 2.48-2.43 (m, 1H), 2.26-2.17 (m, 1H).

General Procedure AA

Imidazopyridine and Imidazopyrazine Synthesis

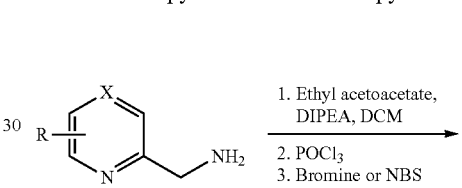

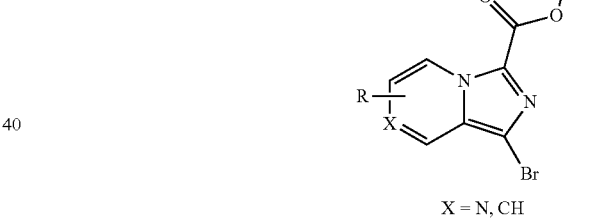

Step 1: To a solution of aminomethylpyridine/pyrazine (1 eq) in dichloromethane (0.25 M) was added diisopropylethylamine (3 eq) then ethyl chlorooxoacetate (1 eq) dropwise. The reaction was stirred at room temperature until complete then concentrated to dryness and re-suspended in a minimum amount of DCM for injection onto a pre-equilibrated pre-packed silica flash column. The compound was purified via ISCO automated flash column chromatography and the fractions were concentrated to dryness and used in the next step.

Step 2: The product from the previous step (1.0 eq.) was either suspended in phosphoryl chloride; neat (50 eq) or 5 eq in dichloroethane and stirred at reflux or 110° C. overnight. After in vacuo concentration, the mixture was slowly quenched with a saturated solution of sodium bicarbonate. The quenched solution was extracted with DCM and the organic layer was dried (MgSO$_4$) and concentrated in vacuo. This residue was suspended in a minimum amount of DCM for injection onto a pre-equilibrated flash column. The compound was purified via ISCO automated flash column chromatography and the fractions were concentrated to dryness and used in the next step.

Step 3: The product from the previous step was suspended in Acetic Acid (0.5M) whereupon bromine (1 eq) was added dropwise. The reaction was verified by LCMS to confirm completion and then concentrated to dryness. The reaction was resuspended in DCM and quenched with a minimum amount of triethylamine, then concentrated to dryness again. The crude reaction mixture was re-suspended once more in DCM for injection onto a pre-equilibrated silica flash column. The compound was purified via ISCO automated flash column chromatography and the fractions were concentrated to dryness and used in subsequent steps. An alternative bromination procedure (in case of imidazopyrazine derivative) involves the use of N-bromosuccinimide in lieu of bromine and acetonitrile in lieu of acetic acid. Workup and purification remains the same.

Synthesis of 2-(aminomethyl)isonicotinonitrile dihydrochloride

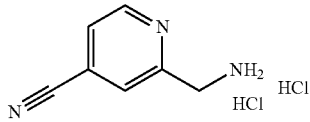

Step 1: To a solution of methyl 2-(aminomethyl)pyridine-4-carboxylate (1 g) in Dichloromethane (0.15 M) was added triethylamine (3 eq) followed by di-tert-butyl dicarbonate (1.05 eq). The reaction mixture was stirred at room temperature for 30 minutes then verified by LCMS, at which point it was deemed complete. The reaction mixture was extracted with a saturated NH₄Cl solution, dried with sodium sulfate, filtered and concentrated to afford crude methyl 2-[(tert-butoxycarbonylamino)methyl]pyridine-4-carboxylate as an oil.

Step 2: The intermediate from the previous step was suspended in 1,4-dioxane (70 eq) and an aqueous ammonium hydroxide (25 mass %) solution was added (50 eq) and the reaction was stirred at room temperature for several hours until complete. The reaction mixture was then concentrated to dryness to afford 680 mg of tert-butyl N-[(4-carbamoyl-2-pyridyl)methyl]carbamate as a light yellow oil.

Step 3: To a solution of tert-butyl N-[(4-carbamoyl-2-pyridyl)methyl]carbamate (580 mg) in DCM (0.25 M) was added Et₃N (2 eq) and TFAA (1.2 eq) at 0° C. The resulting solution was stirred at 0° C. for 1 hour then warmed to room temperature and stirred overnight. The reaction mixture was extracted with water and the organic layer was dried, filtered and concentrated to an oil. The compound was purified by flash chromatography using a 0-50% iPrOAc/Heptane gradient over 15 minutes. Clean fractions were concentrated to give 440 mg of tert-butyl N-[(4-cyano-2-pyridyl)methyl]carbamate as a clear oil.

Step 4: To the intermediate from the previous reaction was added hydrochloric acid (4 mol/L in 1,4-dioxane, 10 eq) and the reaction was stirred at ambient temperature for 30 minutes until the mixture became a thick white slurry. The reaction was checked by LC-MS and deemed complete whereupon it was concentrated to dryness to yield 388 mg of 2-(aminomethyl)pyridine-4-carbonitrile dihydrochloride.

Example K5

Synthesis of 7-cyano-1-[3-[2-[(3R)-3-hydroxy-1-methyl-2-oxo-pyrrolidin-3-yl]ethynyl]phenyl]imidazo[1,5-a]pyridine-3-carboxamide

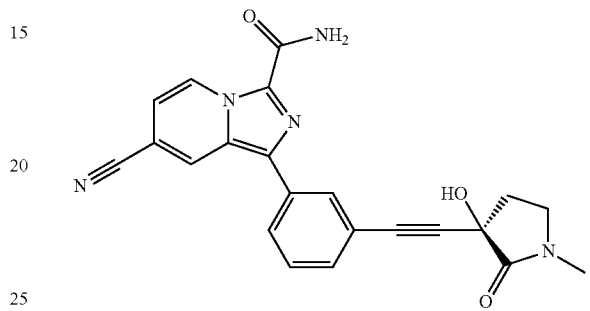

2-(aminomethyl)pyridine-4-carbonitrile dihydrochloride (388 mg) was subjected to General Procedure AA to afford ethyl 1-bromo-7-cyanoimidazo[1,5-a]pyridine-3-carboxylate (288 mg) as a solid following purification. Similar to as described in General Procedure U, ethyl 1-bromo-7-cyanoimidazo[1,5-a]pyridine-3-carboxylate (200 mg) was reacted with potassium (S)-trifluoro(3-((3-hydroxy-1-methyl-2-oxopyrrolidin-3yl)ethynyl)phenyl)borate to give (R)-ethyl 7-cyano-1-(3-((3-hydroxy-1-methyl-2-oxopyrrolidin-3-yl)ethynyl)phenyl)imidazo[1,5-a]pyridine-3-carboxylate which was taken onto the next step without purification. Similar to as described in General Procedure J, (R)-ethyl 7-cyano-1-(3-((3-hydroxy-1-methyl-2-oxopyrrolidin-3-yl)ethynyl)phenyl)imidazo[1,5-a]pyridine-3-carboxylate was reacted to form (R)-7-cyano-1-(3-((3-hydroxy-1-methyl-2-oxopyrrolidin-3-yl)ethynyl)phenyl)imidazo[1,5-a]pyridine-3-carboxylic acid (260 mg). This intermediate was taken onto the next step without purification. Similar to as described in General Procedure B, (R)-7-cyano-1-(3-((3-hydroxy-1-methyl-2-oxopyrrolidin-3-yl)ethynyl)phenyl)imidazo[1,5-a]pyridine-3-carboxylic acid was reacted with ammonium chloride to give 83.3 mg of the title compound (32.1%). M+H=400.2; ¹H NMR (400 MHz, DMSO-d6) δ 9.48 (dd, J=7.5, 1.1 Hz, 1H), 8.87-8.85 (m, 1H), 8.29 (s, 1H), 8.12-8.07 (m, 2H), 7.83 (s, 1H), 7.55-7.50 (m, 1H), 7.47-7.43 (m, 1H), 7.21 (dd, J=7.5, 1.6 Hz, 1H), 6.46 (s, 1H), 3.40-3.35 (m, 2H), 2.81 (s, 3H), 2.49-2.41 (m, 1H), 2.25-2.17 (m, 1H).

Example L5

Synthesis of 1-[3-[2-[(3R)-3-hydroxy-1-methyl-2-oxo-pyrrolidin-3-yl]ethynyl]phenyl]-7-(trifluoromethyl)imidazo[1,5-a]pyridine-3-carboxamide

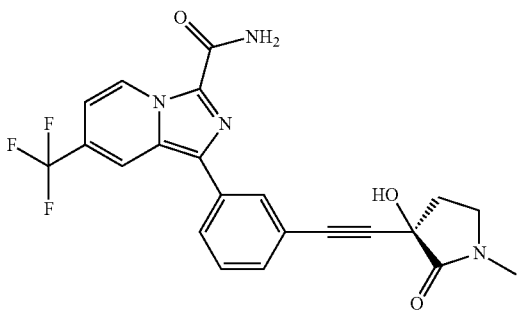 [SMILES: CN1CC[C@@](O)(C#Cc2cccc(-c3nc(C(N)=O)n4ccc(C(F)(F)F)cc34)c2)C1=O]

[4-(trifluoromethyl)-2-pyridyl]methanamine dihydrochloride) (1 g) was subjected to General Procedure AA to afford 875 mg ethyl 1-bromo-7-(trifluoromethyl)imidazo[1,5-a]pyridine-3-carboxylate (288 mg) following purification. Similar to as described in General Procedure U, ethyl 1-bromo-7-(trifluoromethyl)imidazo[1,5-a]pyridine-3-carboxylate (135 mg) was reacted with potassium (S)-trifluoro(3-((3-hydroxy-1-methyl-2-oxopyrrolidin-3yl)ethynyl)phenyl)borate to form (R)-ethyl 1-(3-((3-hydroxy-1-methyl-2-oxopyrrolidin-3-yl)ethynyl)phenyl)-7-(trifluoromethyl)imidazo[1,5-a]pyridine-3-carboxylate which was taken onto the next step without purification. Similar to as described in General Procedure J, (R)-ethyl 1-(3-((3-hydroxy-1-methyl-2-oxopyrrolidin-3-yl)ethynyl)phenyl)-7-(trifluoromethyl)imidazo[1,5-a]pyridine-3-carboxylate was reacted to form (R)-1-(3-((3-hydroxy-1-methyl-2-oxopyrrolidin-3-yl)ethynyl)phenyl)-7-(trifluoromethyl)imidazo[1,5-a]pyridine-3-carboxylic acid (177 mg). This intermediate was taken onto the next step without purification. Similar to as described in General Procedure B, (R)-1-(3-((3-hydroxy-1-methyl-2-oxopyrrolidin-3-yl)ethynyl)phenyl)-7-(trifluoromethyl)imidazo[1,5-a]pyridine-3-carboxylic acid was reacted with ammonium chloride to give 16.6 mg of the title compound (9.2%). M+H=443.2; $^1$H NMR (400 MHz, DMSO-d6) δ 9.60-9.57 (m, 1H), 8.37 (q, J=1.4 Hz, 1H), 8.26 (s, 1H), 8.09-8.02 (m, 2H), 7.80 (s, 1H), 7.55 (t, J=7.7 Hz, 1H), 7.44 (dt, J=7.7, 1.3 Hz, 1H), 7.24 (dd, J=7.6, 1.8 Hz, 1H), 6.47 (s, 1H), 3.39-3.34 (m, 3H), 2.81 (s, 3H), 2.48-2.42 (m, 1H), 2.24-2.16 (m, 1H).

Example M5

Synthesis of 1-[3-[2-[(3R)-3-hydroxy-1-methyl-2-oxo-pyrrolidin-3-yl]ethynyl]phenyl]imidazo[1,5-a]pyrazine-3-carboxamide

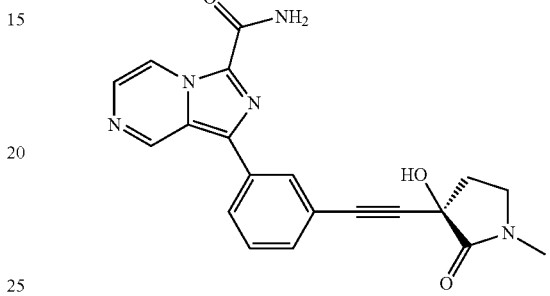

2-aminomethylpyrazine (2 g) was subjected to General Procedure AA to afford ethyl 1-bromoimidazo[1,5-a]pyrazine-3-carboxylate (680 mg) following purification. Similar to as described in General Procedure U, ethyl 1-bromoimidazo[1,5-a]pyrazine-3-carboxylate (75 mg) was reacted with potassium (S)-trifluoro(3-((3-hydroxy-1-methyl-2-oxopyrrolidin-3yl)ethynyl)phenyl)borate to form (R)-ethyl 1-(3-((3-hydroxy-1-methyl-2-oxopyrrolidin-3-yl)ethynyl)phenyl)imidazo[1,5-a]pyrazine-3-carboxylate which was taken onto the next step without purification. Similar to as described in General Procedure J, (R)-ethyl 1-(3-((3-hydroxy-1-methyl-2-oxopyrrolidin-3-yl)ethynyl) phenyl)imidazo[1,5-a]pyrazine-3-carboxylate was reacted to form (R)-1-(3-((3-hydroxy-1-methyl-2-oxopyrrolidin-3-yl)ethynyl) phenyl)imidazo[1,5-a]pyrazine-3-carboxylic acid (40 mg). This intermediate was taken onto the next step without purification. Similar to as described in General Procedure B, (R)-1-(3-((3-hydroxy-1-methyl-2-oxopyrrolidin-3-yl)ethynyl)phenyl)imidazo[1,5-a]pyrazine-3-carboxylic acid was reacted with ammonium chloride to give 6.3 mg of the title compound (15.8%). M+H=376.1; $^1$H NMR (400 MHz, DMSO-d6) δ 9.56 (d, J=1.6 Hz, 1H), 9.22 (dd, J=4.9, 1.6 Hz, 1H), 8.28 (s, 1H), 8.17-8.08 (m, 2H), 7.88 (d, J=5.0 Hz, 1H), 7.84 (s, 1H), 7.55 (t, J=7.8 Hz, 1H), 7.46 (dt, J=7.7, 1.4 Hz, 1H), 6.47 (s, 1H), 3.37 (dd, J=7.3, 5.6 Hz, 2H), 2.81 (s, 3H), 2.72 (d, J=2.5 Hz, 1H), 2.48-2.41 (m, 1H), 2.25-2.16 (m, 1H).

Example N5

Synthesis of 6-chloro-1-[3-[2-[(3R)-3-hydroxy-1-methyl-2-oxo-pyrrolidin-3-yl]ethynyl]phenyl]imidazo[1,5-a]pyridine-3-carboxamide

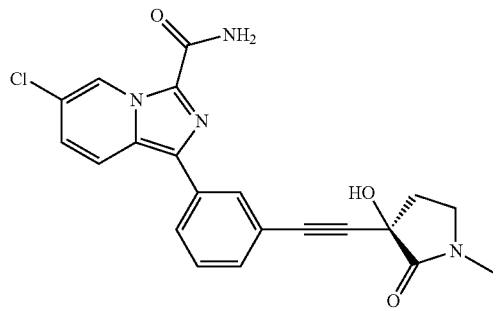 [SMILES: CN1CC[C@@](O)(C#Cc2cccc(-c3nc(C(N)=O)n4cc(Cl)ccc34)c2)C1=O]

(5-chloropyridin-2-yl)methanamine (1.52 g) was subjected to General Procedure AA to afford ethyl 6-chloroimidazo[1,5-a]pyridine-3-carboxylate (1.03 g) of which 250 mg of was subjected to the bromination conditions (step 3 of General Procedure AA) to afford ethyl 1-bromo-6-chloroimidazo[1,5-a]pyridine-3-carboxylate (191 mg) following purification. Similar to as described in General Procedure U, ethyl 1-bromo-6-chloroimidazo[1,5-a]pyridine-3-carboxylate (75 mg) was reacted with potassium (S)-trifluoro(3-((3-hydroxy-1-methyl-2-oxopyrrolidin-3yl)ethynyl)phenyl)borate to form (R)-ethyl 6-chloro-1-(3-((3-hydroxy-1-methyl-2-oxopyrrolidin-3-yl)ethynyl)phenyl)imidazo[1,5-a]pyridine-3-carboxylate which was taken onto the next step without purification. Similar to as described in General Procedure J, (R)-ethyl 6-chloro-1-(3-((3-hydroxy-1-methyl-2-oxopyrrolidin-3-yl)ethynyl)phenyl)imidazo[1,5-a]pyridine-3-carboxylate was reacted to form (R)-6-chloro-1-(3-((3-hydroxy-1-methyl-2-oxopyrrolidin-3-yl)ethynyl)phenyl)imidazo[1,5-a]pyridine-3-carboxylic acid (101 mg). This intermediate was taken onto the next step without purification. Similar to as described in General Procedure B, (R)-6-chloro-1-(3-((3-hydroxy-1-methyl-2-oxopyrrolidin-3-yl)ethynyl)phenyl)imidazo[1,5-a]pyridine-3-carboxylic acid was reacted with ammonium chloride to give 10.9 mg of the title compound (11%). M+H=409.1; $^1$H NMR (400 MHz, DMSO-d6) δ 9.57 (dd, J=1.9, 0.9 Hz, 1H), 8.18-8.13 (m, 2H), 8.03 (t, J=1.7 Hz, 1H), 7.98 (dt, J=7.9, 1.5 Hz, 1H), 7.72 (s, 1H), 7.51 (t, J=7.8 Hz, 1H), 7.40 (dt, J=7.7, 1.4 Hz, 1H), 7.24 (dd, J=9.7, 1.8 Hz, 1H), 6.45 (s, 1H), 3.40-3.33 (m, 2H), 2.81 (s, 3H), 2.48-2.42 (m, 1H), 2.24-2.16 (m, 1H).

Example O5 and Example P5

Synthesis of 7-chloro-1-[3-[2-[(3R)-3-hydroxy-1-methyl-2-oxo-pyrrolidin-3-yl]ethynyl]phenyl]imidazo[1,5-a]pyridine-3-carboxamide AND Synthesis of 1,7-bis[3-[2-[(3R)-3-hydroxy-1-methyl-2-oxo-pyrrolidin-3-yl]ethynyl]phenyl]imidazo[1,5-a]pyridine-3-carboxamide

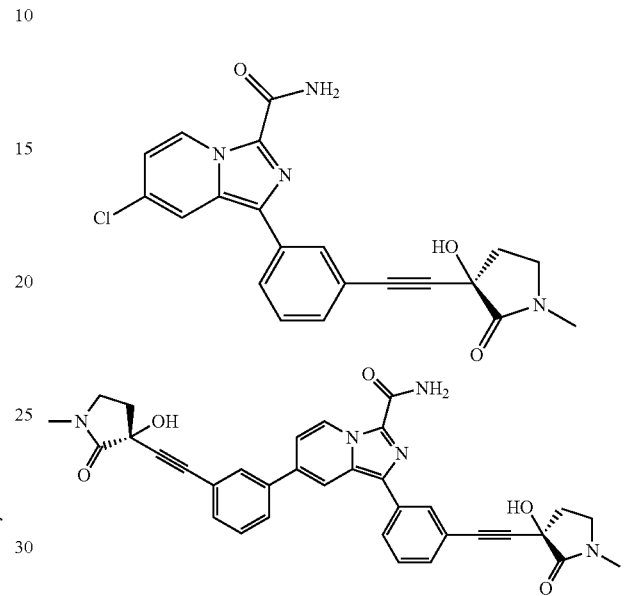

(4-bromopyridin-2-yl)methanamine (1 g) was subjected to General Procedure AA to afford ethyl 1-bromo-7-chloroimidazo[1,5-a]pyridine-3-carboxylate (250 mg) following purification. Similar to as described in General Procedure U, ethyl 1-bromo-7-chloroimidazo[1,5-a]pyridine-3-carboxylate (75 mg) was reacted with potassium (S)-trifluoro(3-((3-hydroxy-1-methyl-2-oxopyrrolidin-3yl)ethynyl)phenyl)borate to form a mixture of (R)-ethyl 7-chloro-1-(3-((3-hydroxy-1-methyl-2-oxopyrrolidin-3-yl)ethynyl) phenyl) imidazo[1,5-a]pyridine-3-carboxylate and ethyl 1,7-bis(3-(((R)-3-hydroxy-1-methyl-2-oxopyrrolidin-3-yl)ethynyl) phenyl)imidazo[1,5-a]pyridine-3-carboxylate which were taken onto the next step without purification. Similar to as described in General Procedure J, a mixture of (R)-ethyl 7-chloro-1-(3-((3-hydroxy-1-methyl-2-oxopyrrolidin-3-yl) ethynyl) phenyl)imidazo[1,5-a]pyridine-3-carboxylate and ethyl 1,7-bis(3-(((R)-3-hydroxy-1-methyl-2-oxopyrrolidin-3-yl)ethynyl)phenyl)imidazo[1,5-a]pyridine-3-carboxylate were reacted to form a mixture of (R)-7-chloro-1-(3-((3-hydroxy-1-methyl-2-oxopyrrolidin-3-yl)ethynyl)phenyl) imidazo[1,5-a]pyridine-3-carboxylic acid and 1,7-bis(3-(((R)-3-hydroxy-1-methyl-2-oxopyrrolidin-3-yl)ethynyl) phenyl)imidazo[1,5-a]pyridine-3-carboxylic acid (101 mg). These intermediates were taken onto the next step without purification. Similar to as described in General Procedure B, (R)-7-chloro-1-(3-((3-hydroxy-1-methyl-2-oxopyrrolidin-3-yl)ethynyl)phenyl)imidazo[1,5-a]pyridine-3-carboxylic acid and 1,7-bis(3-(((R)-3-hydroxy-1-methyl-2-oxopyrrolidin-3-yl)ethynyl)phenyl)imidazo[1,5-a]pyridine-3-carboxylic acid were reacted with ammonium chloride to give 3.7 mg (3.6%) of 7-chloro-1-[3-[2-[(3R)-3-hydroxy-1-methyl-2-oxo-pyrrolidin-3-yl]ethynyl]phenyl]imidazo[1,5-a]pyridine-3-carboxamide and 1.8 mg (1.1%) of 1,7-bis[3-[2-[(3R)-3-hydroxy-1-methyl-2-oxo-pyrrolidin-3-yl]ethynyl]

Example Q5

Synthesis of 7-(cyclobutoxy)-1-[3-[2-[(3R)-3-hydroxy-1-methyl-2-oxo-pyrrolidin-3-yl]ethynyl]phenyl]imidazo[1,5-a]pyridine-3-carboxamide

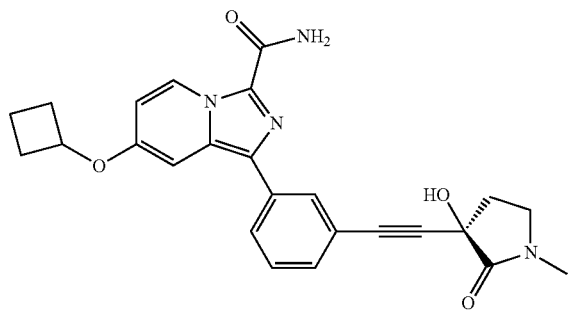 [SMILES: CN1CC[C@@](O)(C#Cc2cccc(-c3nc(C(N)=O)n4ccc(OC5CCC5)cc34)c2)C1=O]

[4-(cyclobutoxy)-2-pyridyl]methanamine (1 g) was subjected to General Procedure AA to afford ethyl 1-bromo-7-cyclobutoxyimidazo[1,5-a]pyridine-3-carboxylate (346 mg) following purification. Similar to as described in General Procedure U, ethyl 1-bromo-7-cyclobutoxyimidazo[1,5-a]pyridine-3-carboxylate (100 mg) was reacted with potassium (S)-trifluoro(3-((3-hydroxy-1-methyl-2-oxopyrrolidin-3yl)ethynyl)phenyl)borate to (R)-ethyl 7-cyclobutoxy-1-(3-((3-hydroxy-1-methyl-2-oxopyrrolidin-3-yl)ethynyl)phenyl)imidazo[1, 5-a]pyridine-3-carboxylate which was taken onto the next step without purification. Similar to as described in General Procedure J, (R)-ethyl 7-cyclobutoxy-1-(3-((3-hydroxy-1-methyl-2-oxopyrrolidin-3-yl)ethynyl)phenyl)imidazo[1, 5-a]pyridine-3-carboxylate was reacted to (R)-7-cyclobutoxy-1-(3-((3-hydroxy-1-methyl-2-oxopyrrolidin-3-yl)ethynyl)phenyl)imidazo[1,5-a]pyridine-3-carboxylic acid (130.8 mg). This intermediate was taken onto the next step without purification. Similar to as described in General Procedure B, (R)-7-cyclobutoxy-1-(3-((3-hydroxy-1-methyl-2-oxopyrrolidin-3-yl)ethynyl)phenyl)imidazo[1, 5-a]pyridine-3-carboxylic acid was reacted with ammonium chloride to give 13.6 mg of the title compound (10.2%).

M+H=445.2; $^1$H NMR (400 MHz, DMSO-d6) δ 9.38 (d, J=7.8 Hz, 1H), 7.98 (t, J=1.7 Hz, 1H), 7.93 (s, 1H), 7.89 (dt, J=8.0, 1.4 Hz, 1H), 7.55-7.45 (m, 2H), 7.32 (dt, J=7.5, 1.4 Hz, 1H), 7.06 (d, J=2.4 Hz, 1H), 6.77 (dd, J=7.8, 2.4 Hz, 1H), 4.95 (p, J=7.0 Hz, 1H), 3.39-3.34 (m, 3H), 2.81 (s, 3H), 2.47-2.39 (m, 2H), 2.25-2.08 (m, 3H), 1.91-1.79 (m, 1H), 1.79-1.68 (m, 1H).

Example R5

Synthesis of 1-[3-[2-[(3R)-3-hydroxy-1-methyl-2-oxo-pyrrolidin-3-yl]ethynyl]phenyl]-7-methoxy-imidazo[1,5-a]pyridine-3-carboxamide

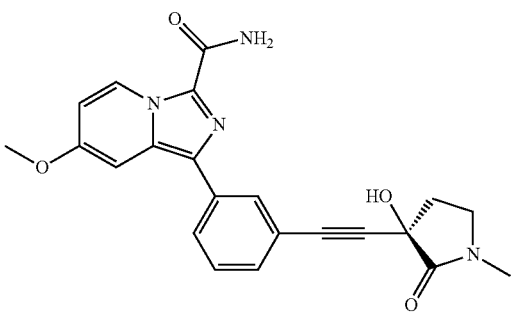

(4-methoxypyridin-2-yl)methanamine (2 g) was subjected to General Procedure AA to afford ethyl 1-bromo-7-methoxyimidazo[1,5-a]pyridine-3-carboxylate (1.1 g) following purification. Similar to as described in General Procedure U, ethyl 1-bromo-7-methoxyimidazo[1,5-a]pyridine-3-carboxylate (0.4 g) was reacted with potassium (S)-trifluoro(3-((3-hydroxy-1-methyl-2-oxopyrrolidin-3yl)ethynyl)phenyl)borate to form (R)-ethyl 1-(3-((3-hydroxy-1-methyl-2-oxopyrrolidin-3-yl)ethynyl)phenyl)-7-methoxyimidazo[1,5-a]pyridine-3-carboxylate which was taken onto the next step without purification. Similar to as described in General Procedure J, (R)-ethyl 1-(3-((3-hydroxy-1-methyl-2-oxopyrrolidin-3-yl)ethynyl)phenyl)-7-methoxyimidazo[1,5-a]pyridine-3-carboxylate was reacted to form (R)-1-(3-((3-hydroxy-1-methyl-2-oxopyrrolidin-3-yl)ethynyl)phenyl)-7-methoxyimidazo[1, 5-a]pyridine-3-carboxylic acid (406 mg). This intermediate was taken onto the next step without purification. Similar to as described in General Procedure B, (R)-1-(3-((3-hydroxy-1-methyl-2-oxopyrrolidin-3-yl)ethynyl)phenyl)-7-methoxyimidazo[1, 5-a]pyridine-3-carboxylic acid was reacted with ammonium chloride to give 83.8 mg of the title compound (20.5%).

M+H=405.2; $^1$H NMR (400 MHz, DMSO-d6) δ 9.38 (dd, J=7.8, 0.7 Hz, 1H), 8.03 (t, J=1.6 Hz, 1H), 8.00-7.91 (m, 2H), 7.52-7.45 (m, 2H), 7.36-7.30 (m, 1H), 7.23 (dd, J=2.5, 0.8 Hz, 1H), 6.79 (dd, J=7.8, 2.5 Hz, 1H), 6.43 (s, 1H), 3.93 (s, 3H), 3.40-3.33 (m, 2H), 2.81 (s, 3H), 2.49-2.41 (m, 1H), 2.24-2.16 (m, 1H).

phenyl]imidazo[1,5-a]pyridine-3-carboxamide following reverse phase purification. M+H=409.2 and M+H=588.2

Example S5

Synthesis of 1-[3-[2-[(3R)-3-hydroxy-1-methyl-2-oxo-pyrrolidin-3-yl]ethynyl]phenyl]-6-methoxy-imidazo[1,5-a]pyridine-3-carboxamide

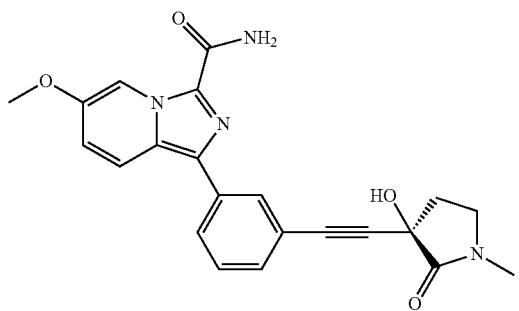

(5-methoxypyridin-2-yl)methanamine (1 g) was subjected to General Procedure AA to afford ethyl 1-bromo-6-methoxyimidazo[1,5-a]pyridine-3-carboxylate (894 mg) following purification. Similar to as described in General Procedure U, ethyl 1-bromo-6-methoxyimidazo[1,5-a]pyridine-3-carboxylate (0.1 g) was reacted with potassium (S)-trifluoro(3-((3-hydroxy-1-methyl-2-oxopyrrolidin-3yl)ethynyl)phenyl)borate to form (R)-ethyl 1-(3-((3-hydroxy-1-methyl-2-oxopyrrolidin-3-yl)ethynyl)phenyl)-6-methoxyimidazo[1,5-a]pyridine-3-carboxylate which was taken onto the next step without purification. Similar to as described in General Procedure J, (R)-ethyl 1-(3-((3-hydroxy-1-methyl-2-oxopyrrolidin-3-yl)ethynyl)phenyl)-6-methoxyimidazo[1,5-a]pyridine-3-carboxylate was reacted to form (R)-1-(3-((3-hydroxy-1-methyl-2-oxopyrrolidin-3-yl)ethynyl)phenyl)-6-methoxyimidazo[1, 5-a]pyridine-3-carboxylic acid (101.7 mg). This intermediate was taken onto the next step without purification. Similar to as described in General Procedure B, (R)-1-(3-((3-hydroxy-1-methyl-2-oxopyrrolidin-3-yl)ethynyl)phenyl)-6-methoxyimidazo[1, 5-a]pyridine-3-carboxylic acid was reacted with ammonium chloride to give 10 mg of the title compound (10%). M+H=405.2; $^1$H NMR (400 MHz, DMSO-d6) δ 9.14 (dd, J=2.3, 0.8 Hz, 1H), 8.04 (dd, J=9.9, 0.8 Hz, 1H), 8.02 (td, J=1.8, 0.6 Hz, 1H), 7.99-7.95 (m, 2H), 7.49 (td, J=7.8, 0.6 Hz, 1H), 7.39-7.35 (m, 1H), 7.03 (dd, J=9.9, 2.2 Hz, 1H), 3.85 (s, 3H), 3.40-3.33 (m, 2H), 2.81 (s, 3H), 2.48-2.42 (m, 1H), 2.25-2.16 (m, 1H).

Synthesis of [4-(morpholinomethyl)-2-pyridyl]methanamine

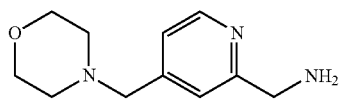 [SMILES: NCc1cc(CN2CCOCC2)ccn1]

Step 1: To a solution of 4-(bromomethyl)picolinonitrile (1 g) in methanol was added morpholine (2.5 eq) and the reaction was stirred for 15 minutes whereupon LCM S confirmed it went to completion. The reaction mixture was subsequently concentrated to an oil and resuspended in a minimum amount of DCM. The crude mixture was injected onto a pre-equilibrated silica flash chromatography column and a 0-90% gradient over 15 mins of 3:1 iPrOAc-MeOH to Heptanes was run. The clean fractions were concentrated to afford 965 mg of 4-(morpholinomethyl)picolinonitrile as a clear oil.

Step 2: To a solution of 4-(morpholinomethyl)picolinonitrile in acetic acid (18 mL) at room temperature was added 10 percent palladium on carbon (48 mg) and the resulting mixture was stirred for 2 hours under a hydrogen atmosphere. The resulting solution was filtered through celite and the solvent was evaporated to an oil. The crude material was then resuspended in DCM whereupon MP-TsOH ion exchange resin (2 eq) was added and the mixture was stirred for 1 hour at ambient temperature. The resin was collected by filtration and rinsed with DCM and the product was eluted via addition of 20 mL (×2) of 7N ammonia in methanol solution. The resultant solution was concentrated to dryness and crude [4 (morpholinomethyl)-2-pyridyl] methanamine (938 mg) was taken into the next reaction without purification.

Example T5

Synthesis of 1-[3-[2-[(3R)-3-hydroxy-1-methyl-2-oxo-pyrrolidin-3-yl]ethynyl]phenyl]-7-(morpholinomethyl)imidazo[1,5-a]pyridine-3-carboxamide

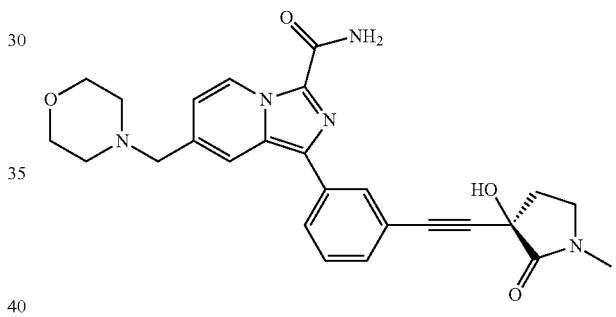

[4-(morpholinomethyl)-2-pyridyl]methanamine (938 mg) was subjected to General Procedure AA to afford ethyl 1-bromo-7-(morpholinomethyl)imidazo[1,5-a]pyridine-3-carboxylate (250 mg) following purification. Similar to as described in General Procedure U, ethyl 1-bromo-7-(morpholinomethyl)imidazo[1,5-a]pyridine-3-carboxylate (250 mg) was reacted with potassium (S)-trifluoro(3-((3-hydroxy-1-methyl-2-oxopyrrolidin-3yl)ethynyl)phenyl)borate to form (R)-ethyl 1-(3-((3-hydroxy-1-methyl-2-oxopyrrolidin-3-yl)ethynyl)phenyl)-7-(morpholinomethyl)imidazo[1, 5-a]pyridine-3-carboxylate which was taken onto the next step without purification. Similar to as described in General Procedure J, (R)-ethyl 1-(3-((3-hydroxy-1-methyl-2-oxopyrrolidin-3-yl)ethynyl)phenyl)-7-(morpholinomethyl)imidazo[1,5-a]pyridine-3-carboxylate was reacted to form (R)-1-(3-((3-hydroxy-1-methyl-2-oxopyrrolidin-3-yl)ethynyl)phenyl)-7-(morpholinomethyl)imidazo[1,5-a]pyridine-3-carboxylic acid (322 mg). This intermediate was taken onto the next step without purification. Similar to as described in General Procedure B, (R)-1-(3-((3-hydroxy-1-methyl-2-oxopyrrolidin-3-yl)ethynyl)phenyl)-7-(morpholinomethyl)imidazo[1,5-a]pyridine-3-carboxylic acid was reacted with ammonium chloride to give 36.5 mg of the title compound (11.1%). M+H=474.2; $^1$H NMR (400 MHz, DMSO-d6) δ 9.43 (dd, J=7.3, 1.0 Hz, 1H), 8.06-7.92 (m, 4H), 7.56 (s, 1H), 7.54-7.48 (m, 1H), 7.37 (ddd, J=7.7, 1.7, 1.1 Hz, 1H), 7.04

(dd, J=7.4, 1.5 Hz, 1H), 6.45 (s, 1H), 3.63-3.58 (m, 4H), 3.56 (s, 2H), 3.39-3.33 (m, 2H), 2.81 (s, 3H), 2.48-2.40 (m, 5H), 2.25-2.16 (m, 1H).

Synthesis of [5-(morpholinomethyl)-2-pyridyl]methanamine

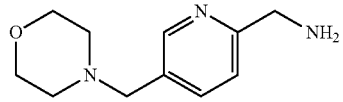 [SMILES: NCc1ccc(CN2CCOCC2)cn1]

Step 1: To a solution of 5-(bromomethyl)pyridine-2-carbonitrile (1.16 g) in methanol was added morpholine (3.5 eq) and the reaction was stirred for 15 minutes whereupon LCM S confirmed it went to completion. The reaction mixture was subsequently concentrated to an oil and resuspended in a minimum amount of DCM. The crude mixture was injected onto a pre-equilibrated silica flash chromatography column and a 0-90% gradient over 15 mins of 3:1 iPrOAc-MeOH to Heptanes was run. The clean fractions were concentrated to afford 400 mg of 5-(morpholinomethyl)picolinonitrile as a clear oil.

Step 2: To a solution of 5-(morpholinomethyl)picolinonitrile (400 mg) in acetic acid at room temperature (7 mL) was added 10 percent palladium on carbon (19 mg) and the resulting mixture was stirred for 2 hours under a hydrogen atmosphere. The resulting solution was filtered through celite and the solvent was evaporated to an oil. The crude material was then resuspended in DCM whereupon MP-TsOH ion exchange resin (2 eq) was added and the mixture was stirred for 1 hour at ambient temperature. The resin was collected by filtration and rinsed with DCM and the product was eluted via addition of 20 mL (×2) of 7N Ammonia in Methanol solution. The resultant solution was concentrated to dryness and crude [5-(morpholinomethyl)-2-pyridyl]methanamine (370 mg) was taken into the next reaction without purification.

Example U5

Synthesis of 1-[3-[2-[(3R)-3-hydroxy-1-methyl-2-oxo-pyrrolidin-3-yl]ethynyl]phenyl]-6-(morpholinomethyl)imidazo[1,5-a]pyridine-3-carboxamide

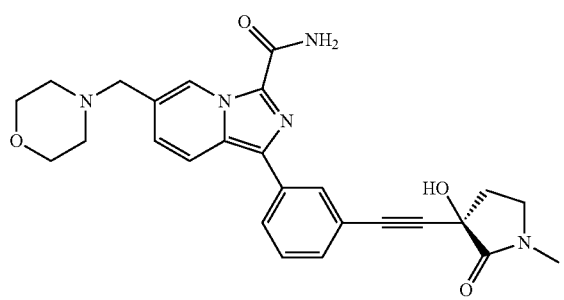 [SMILES: CN1CC[C@@](O)(C#Cc2cccc(-c3nc(C(N)=O)n4cc(CN5CCOCC5)ccc34)c2)C1=O]

[5-(morpholinomethyl)-2-pyridyl]methanamine (370 mg) was subjected to General Procedure AA to afford ethyl 1-bromo-6-(morpholinomethyl)imidazo[1,5-a]pyridine-3-carboxylate (250 mg) following purification. Similar to as described in General Procedure U, ethyl 1-bromo-6-(mor-pholinomethyl)imidazo[1,5-a]pyridine-3-carboxylate (250 mg) was reacted with potassium (S)-trifluoro(3-((3-hydroxy-1-methyl-2-oxopyrrolidin-3-yl)ethynyl)phenyl)borate to form (R)-ethyl 1-(3-((3-hydroxy-1-methyl-2-oxopyrrolidin-3-yl)ethynyl)phenyl)-6-(morpholinomethyl)imidazo[1,5-a]pyridine-3-carboxylate which was taken onto the next step without purification. Similar to as described in General Procedure J, (R)-ethyl 1-(3-((3-hydroxy-1-methyl-2-oxopyrrolidin-3-yl)ethynyl)phenyl)-6-(morpholinomethyl)imidazo[1,5-a]pyridine-3-carboxylate was reacted to (R)-1-(3-((3-hydroxy-1-methyl-2-oxopyrrolidin-3-yl)ethynyl)phenyl)-6-(morpholinomethyl)imidazo[1,5-a]pyridine-3-carboxylic acid (321 mg). This intermediate was taken onto the next step without purification. Similar to as described in General Procedure B, (R)-1-(3-((3-hydroxy-1-methyl-2-oxopyrrolidin-3-yl)ethynyl)phenyl)-6-(morpholinomethyl)imidazo[1,5-a]pyridine-3-carboxylic acid was reacted with ammonium chloride to give 28.2 mg of the title compound (8.8%). M+H=474.2; $^1$H NMR (400 MHz, DMSO-d6) δ 9.41-9.39 (m, 1H), 8.08 (dd, J=9.4, 1.0 Hz, 1H), 8.04-8.00 (m, 1H), 7.97 (ddd, J=7.9, 1.8, 1.1 Hz, 1H), 7.58 (s, 1H), 7.53-7.47 (m, 1H), 7.37 (ddd, J=7.7, 1.7, 1.1 Hz, 1H), 7.21 (dd, J=9.4, 1.4 Hz, 1H), 6.45 (s, 1H), 3.62-3.57 (m, 4H), 3.51 (s, 2H), 3.40-3.34 (m, 2H), 2.81 (s, 3H), 2.48-2.38 (m, 5H), 2.25-2.16 (m, 1H).

Example V5

Synthesis of (R)-1-(3-((3-hydroxy-1-methyl-2-oxopyrrolidin-3-yl)ethynyl)phenyl)-5-(1-methyl-1H-pyrazol-3-yl)-1H-indazole-3-carboxamide

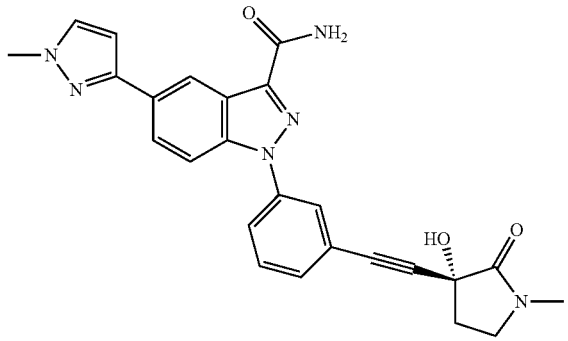

Step 1: Synthesis of methyl 1-(3-bromophenyl)-5-(1-methylpyrazol-4-yl)indazole-3-carboxylate

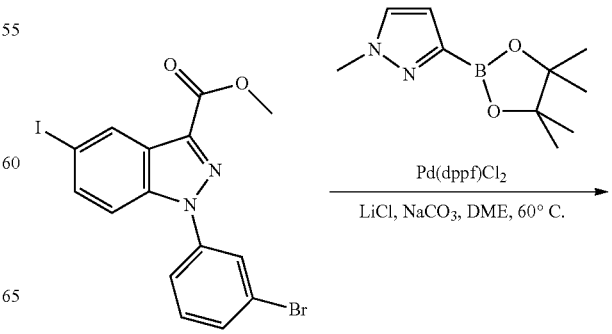

-continued

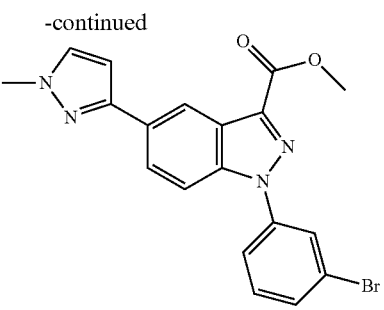

To a stirred solution of methyl 1-(3-bromophenyl)-5-iodo-indazole-3-carboxylate (300 mg, 0.6563 mmol) in 1,2-dimethoxyethane (54.4 mmol) and water (99.82 mmol) was added 1-methyl-4-(4,4,5,5-tetramethyl-1,3,2-dioxaborolan-2-yl)-1h-pyrazole (0.7876 mmol, 1.2 equiv), 1,1'-bis(diphenylphosphino)ferrocene-palladium(II)dichloride dichloromethane complex (0.03282 mmol, 0.05 equiv), lithium chloride (2.297 mmol, 3.5 equiv), and sodium carbonate (3.610 mmol, 5.5 equiv) under nitrogen. The resulting solution was stirred for 18 hours at 60° C. The reaction mixture was concentrated under reduced pressure then was purified by silica gel column with heptane/isopropyl acetate (3:2). This resulted in 120 mg (44%) of the title compound as a white solid. LC-MS (ES, m/z): 411, 413 [M+H]+.

Step 2: Synthesis of 1-(3-bromophenyl)-5-(1-methyl-1H-pyrazol-3-yl)-1H-indazole-3-carboxamide

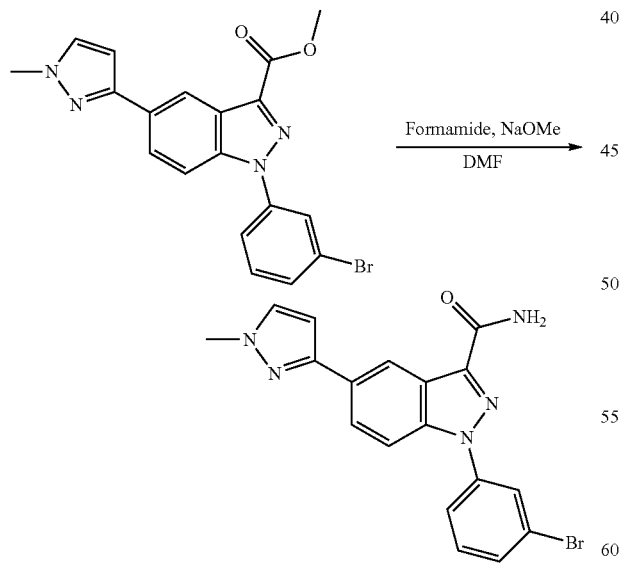

Similar to General Procedure H, methyl 1-(3-bromophenyl)-5-(1-methylpyrazol-4-yl)indazole-3-carboxylate (250 mg, 0.61 mmol) was reacted with formamide (0.24 mL, 6.08 mmol, 10 equiv) to give the title compound (235 mg, 97%) as an off-white solid. LC-MS (ES, m/z): 396, 398 [M+H]+.

Step 3: Synthesis of (R)-1-(3-((3-hydroxy-1-methyl-2-oxopyrrolidin-3-yl)ethynyl)phenyl)-5-(1-methyl-1H-pyrazol-3-yl)-1H-indazole-3-carboxamide

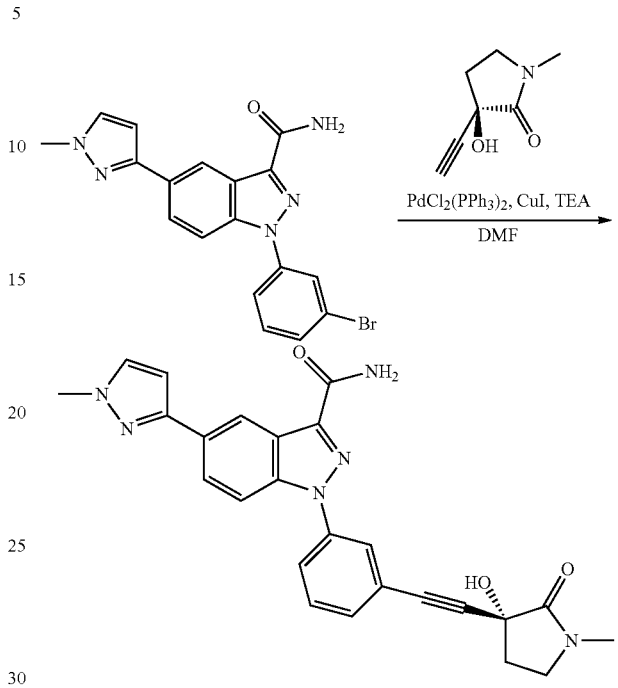

As similar to described in General Procedure E, 1-(3-bromophenyl)-5-(1-methylpyrazol-4-yl)indazole-3-carboxamide (235 mg, 0.59 mmol) was reacted with (3R)-3-ethynyl-3-hydroxy-1-methyl-pyrrolidin-2-one (99.04 mg, 0.71 mmol, 1.2 equiv) to give a brown oil. The crude was purified by Prep-HPLC and this resulted in (4.9 mg, 2%) of the title compound as an off-white solid. LC-MS (ES, m/z): 455 [M+H]+. 1H NMR (400 MHz, DMSO-d6) δ 8.673 (m, 1H), 8.022-7.996 (m, 2H), 7.951-7.873 (m, 3H), 7.766 (d, J=2.4 Hz, 1H), 7.677-7.638 (m, 1H), 7.529-7.507 (m, 1H), 7.079 (bs, 2H), 6.738-6.732 (m, 1H), 3.922 (s, 3H), 3.382-3.350 (m, 2H), 2.808 (s, 3H), 2.471-2.439 (m, 1H), 2.238-2.171 (m, 1H).

Example W5

Synthesis of (R)-1-(3-((3-hydroxy-1-methyl-2-oxopyrrolidin-3-yl)ethynyl)phenyl)-5-(1-methyl-1H-pyrazol-3-yl)-1H-indazole-3-carboxamide

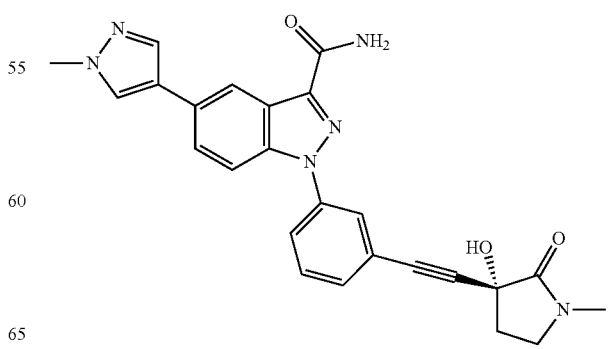

401

Step 1: Synthesis of methyl 1-(3-bromophenyl)-5-(1-methyl-1H-pyrazol-3-yl)-1H-indazole-3-carboxylate

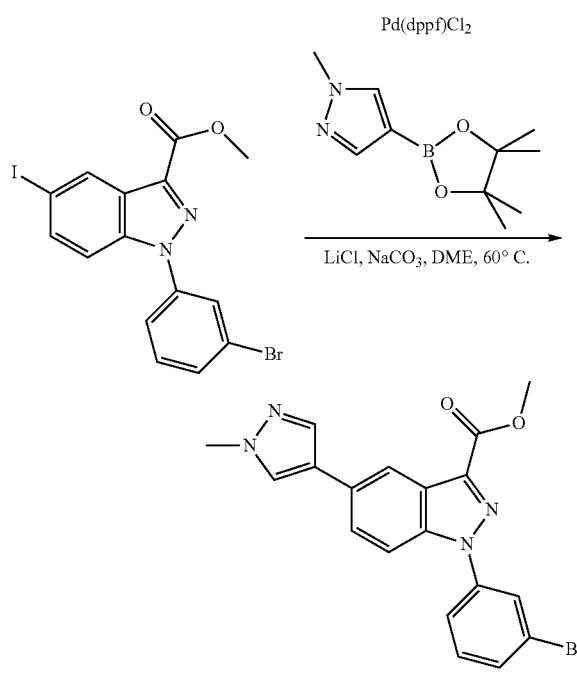

To a stirred solution of methyl 1-(3-bromophenyl)-5-iodo-indazole-3-carboxylate (250 mg, 0.5469 mmol) in 1,2-dimethoxyethane (4.7 mL) and water (1.5 mL) was added 1-methyl-3-(4,4,5,5-tetramethyl-1,3,2-dioxaborolan-2-yl)-1h-pyrazole (143.7 mg, 0.6563 mmol, 1.2 equiv), 1,1'-bis(diphenylphosphino)ferrocene-palladium(II)dichloride dichloromethane complex (22.8 mg, 0.02735 mmol, 0.05 equiv), lithium chloride (81.2 mg, 1.914 mmol, 3.5 equiv), and sodium carbonate (318.8 mg, 3.008 mmol, 5.5 equiv) under nitrogen. The resulting solution was stirred for 18 hours at 60° C. The reaction mixture was concentrated under reduced pressure then was purified by silica gel column with heptane/isopropyl acetate (3:2). This resulted in 124 mg (38%) of the title compound as a white solid. LC-MS (ES, m/z): 411, 413 [M+H]⁺.

Step 2: Synthesis of 1-(3-bromophenyl)-5-(1-methyl-1H-pyrazol-3-yl)-1H-indazole-3-carboxamide

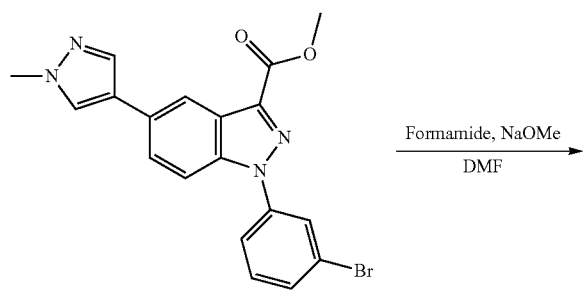

402

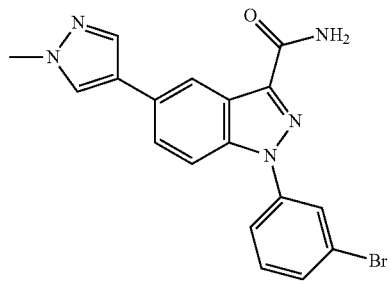

Similar to as described in General Procedure H, methyl 1-(3-bromophenyl)-5-(1-methyl-1H-pyrazol-3-yl)-1H-indazole-3-carboxylate (90 mg, 0.22 mmol) was reacted with formamide (0.09 mL, 2.19 mmol, 10 equiv) to give the title compound (85 mg, 98%) as a yellow solid. LC-MS (ES, m/z): 396, 398 [M+H]⁺.

Step 3: Synthesis of (R)-1-(3-((3-hydroxy-1-methyl-2-oxopyrrolidin-3-yl)ethynyl)phenyl)-5-(1-methyl-1H-pyrazol-3-yl)-1H-indazole-3-carboxamide

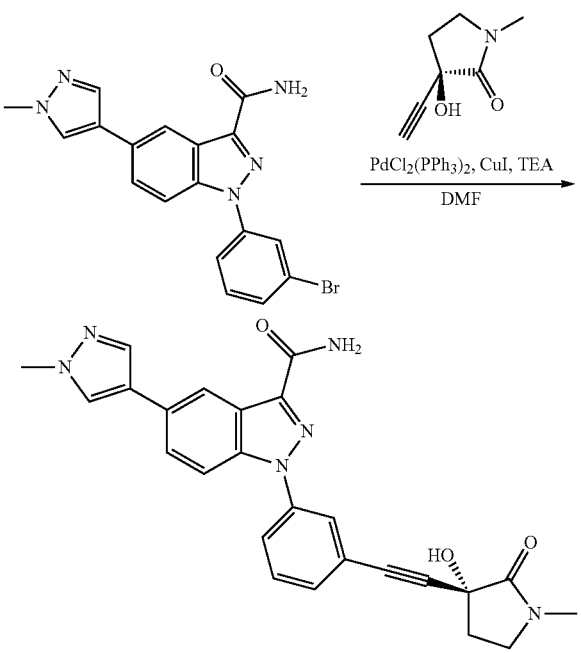

Similar to as described in General Procedure E, 1-(3-bromophenyl)-5-(1-methyl-1H-pyrazol-3-yl)-1H-indazole-3-carboxamide (85 mg, 0.21 mmol) was reacted with (3R)-3-ethynyl-3-hydroxy-1-methylpyrrolidin-2-one (35.82 mg, 0.26 mmol, 1.2 equiv) to give the title compound (76 mg, 78%) as a yellow solid. LC-MS (ES, m/z): 455 [M+H]⁺. ¹H NMR (400 MHz, DMSO-d6) δ 8.379-8.376 (m, 1H), 8.23 (s, 1H), 8.00 (br s, 1H), 7.948-7.920 (m, 1H), 7.904-7.862 (m, 3H), 7.791-7.764 (m, 1H), 7.671-7.631 (m, 1H), 7.540 (br s, 1H), 7.524-7.502 (m, 1H), 6.501 (s, 1H), 3.893 (s, 3H), 3.382-3.350 (m, 2H), 2.808 (s, 3H), 2.485-2.438 (m, 1H), (dt, J1=12 Hz, J2=4 Hz, 1H).

Example X5

Synthesis of (R)-1-(3-((3-hydroxy-1-methyl-2-oxopyrrolidin-3-yl)ethynyl)phenyl)-5-(1-methyl-1H-pyrazol-3-yl)-1H-pyrazolo[3,4-b]pyridine-3-carboxamide

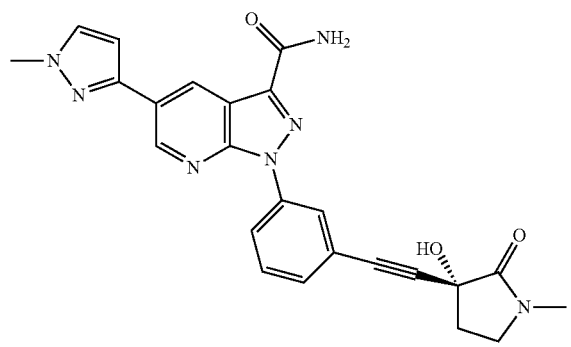

Step 1: Synthesis of methyl 1-(3-bromophenyl)-5-(1-methyl-1H-pyrazol-3-yl)-1H-pyrazolo[3,4-b]pyridine-3-carboxylate

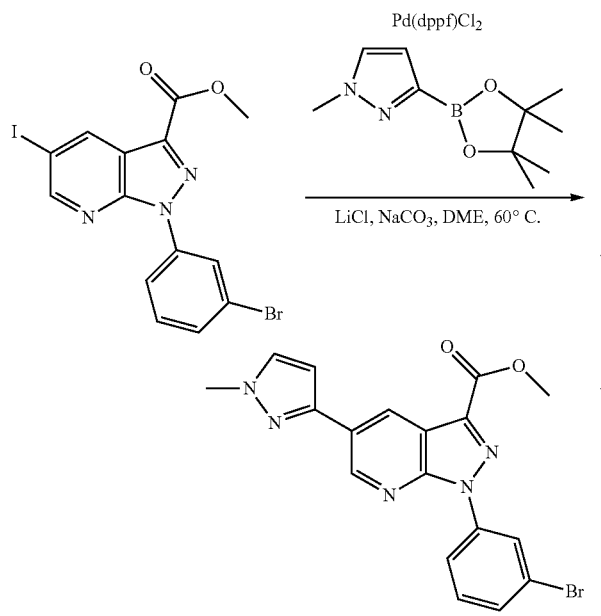

A solution of methyl 1-(3-bromophenyl)-5-iodo-pyrazolo[3,4-b]pyridine-3-carboxylate (100 mg, 0.2074 mmol) in 1,2-dimethoxyethane (1.78 mL) and water (0.56 mL) was combined with 1-methyl-3-(4,4,5,5-tetramethyl-1,3,2-dioxaborolan-2-yl)-1h-pyrazole (136.3 mg, 0.62 mmol, 3 equiv), 1,1'-bis(diphenylphosphino)ferrocene-palladium(II) dichloride dichloromethane complex (8.64 mg, 0.01037 mmol, 0.05 equiv), lithium chloride (30.78 mg, 0.7260 mmol, 3.5 equiv), and sodium carbonate (120.9 mg, 1.141 mmol, 5.5 equiv). Reaction vessel was sparged with nitrogen gas and then heated to 90° C. and left to for 18 hours. The reaction mixture was concentrated under reduced pressure then was purified by silica gel column with heptane/isopropyl acetate (3:1). This resulted in 74 mg (86%) of the title compound as a white solid. LC-MS (ES, m/z): 412, 414 [M+H]⁺.

Step 2: Synthesis of 1-(3-bromophenyl)-5-(1-methyl-1H-pyrazol-3-yl)-1H-pyrazolo[3,4-b]pyridine-3-carboxylic acid

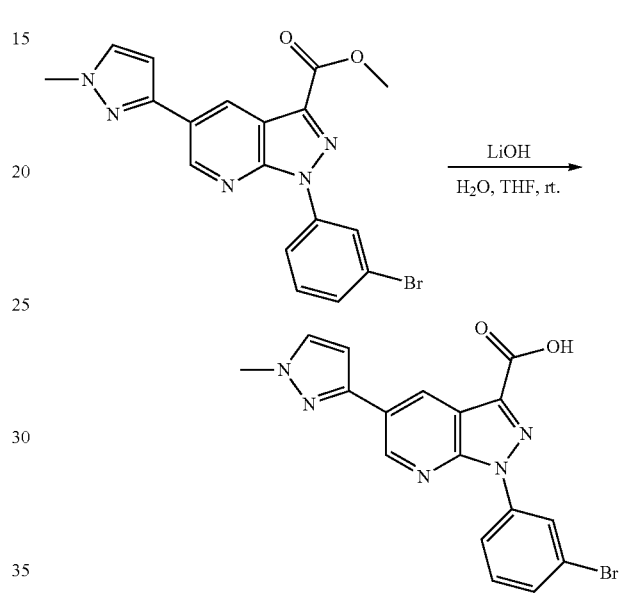

Similar to General Procedure J, methyl 1-(3-bromophenyl)-5-(1-methyl-1H-pyrazol-3-yl)-1H-pyrazolo[3,4-b]pyridine-3-carboxylat e (643 mg, 1.56 mmol) was reacted with lithium hydroxide monohydrate (267.2 mg, 6.24 mmol, 4 equiv) to afford the title compound (295 mg, 48%) as an off-white solid. LCMS (ES, m/z): 399, 401 [M+H]⁺.

Step 3: Synthesis of 1-(3-bromophenyl)-5-(1-methyl-1H-pyrazol-3-yl)-1H-pyrazolo[3,4-b]pyridine-3-carboxamide

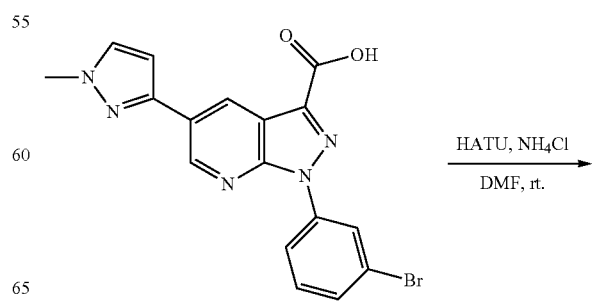

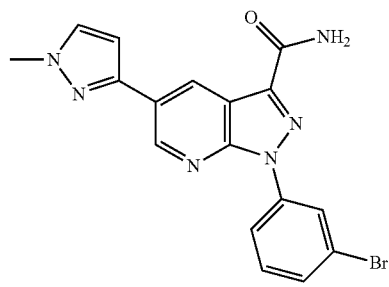

Similar to General Procedure B, 1-(3-bromophenyl)-5-(1-methyl-1H-pyrazol-3-yl)-1H-pyrazolo[3,4-b]pyridine-3-carboxylic acid (295 mg, 0.74 mmol) was reacted with ammonium chloride (2.24 mL, 4.44 mmol, 6 equiv) to afford the title compound (135 mg, 46%) as an off-white solid. LCMS (ES, m/z): 398, 400 [M+H]$^+$.

Step 4: Synthesis of (R)-1-(3-((3-hydroxy-1-methyl-2-oxopyrrolidin-3-yl)ethynyl)phenyl)-5-(1-methyl-1H-pyrazol-3-yl)-1H-pyrazolo[3,4-b]pyridine-3-carboxamide

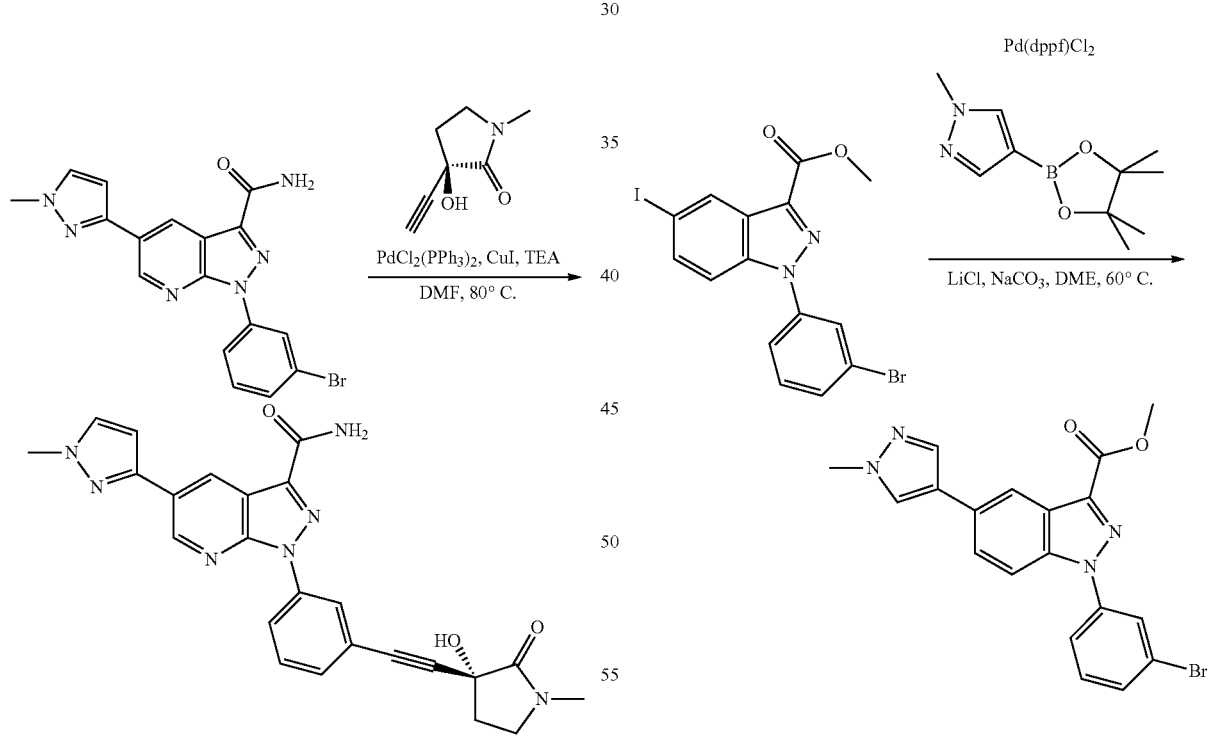

Similar to General Procedure E, 1-(3-bromophenyl)-5-(1-methyl-1H-pyrazol-3-yl)-1H-pyrazolo[3,4-b]pyridine-3-carboxamide (63 mg, 0.16 mmol) was reacted with (3R)-3-ethynyl-3-hydroxy-1-methylpyrrolidin-2-one (26.48 mg, 0.19 mmol, 1.2 equiv) to give the title compound (0.8 mg, 1%) as a brown solid. LC-MS (ES, m/z): 456 [M+H]$^+$.

Example Y5

Synthesis of (R)-1-(3-((3-hydroxy-1-methyl-2-oxopyrrolidin-3-yl)ethynyl)phenyl)-5-(1-methyl-1H-pyrazol-4-yl)-1H-pyrazolo[3,4-b]pyridine-3-carboxamide

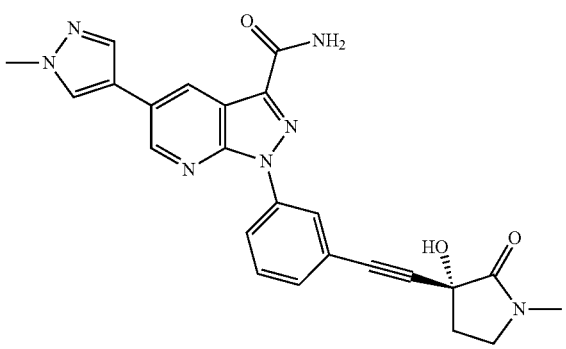

Step 1: Synthesis of methyl 1-(3-bromophenyl)-5-(1-methyl-1H-pyrazol-4-yl)-1H-indazole-3-carboxylate To a stirred solution methyl 1-(3-bromophenyl)-5-iodo-pyrazolo[3,4-b]pyridine-3-carboxylate (300 mg, 0.6223 mmol) in 1,2-dimethoxyethane (5.3 mL) and water (1.7 mL) was added 1-methyl-4-(4,4,5,5-tetramethyl-1,3,2-dioxaborolan-2-yl)-1h-pyrazole (272.6 mg, 1.245 mmol, 2 equiv), 1,1'-bis(diphenylphosphino)ferrocene-palladium(II)dichloride dichloromethane complex (25.9 mg, 0.03111 mmol, 0.05 equiv), lithium chloride (92.3 mg, 2.178 mmol, 3.5 equiv), and sodium carbonate (362.7 mg, 3.422 mmol, 5.5 equiv) under nitrogen. The resulting solution was stirred for 18 hours at 60° C. The reaction was diluted with saturated aqueous ammonium chloride solution and the aqueous phase was extracted three times with ethyl acetate. The organic phases were combined, dried with sodium sulfate, and concentrated under vacuum. This resulted in 98 mg (38%) of the title compound as a brown solid. LC-MS (ES, m/z): 413, 415 [M+H]⁺.

Step 2: Synthesis of 1-(3-bromophenyl)-5-(1-methyl-1H-pyrazol-4-yl)-1H-indazole-3-carboxylic acid

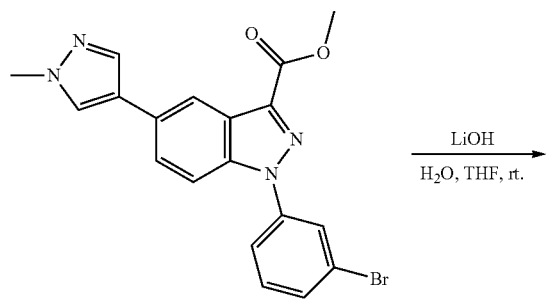

Similar to as described in General Procedure J, methyl 1-(3-bromophenyl)-5-(1-methyl-1H-pyrazol-4-yl)-1H-indazole-3-carboxylate (98 mg, 0.24 mmol) was reacted with was reacted with lithium hydroxide monohydrate (40.3 mg, 0.74 mmol, 4 equiv) to afford the title compound (96 mg, 95%) as an off-white solid. LCMS (ES, m/z): 399 [M+H]⁺.

Step 3: Synthesis of 1-(3-bromophenyl)-5-(1-methyl-1H-pyrazol-4-yl)-1H-indazole-3-carboxamide

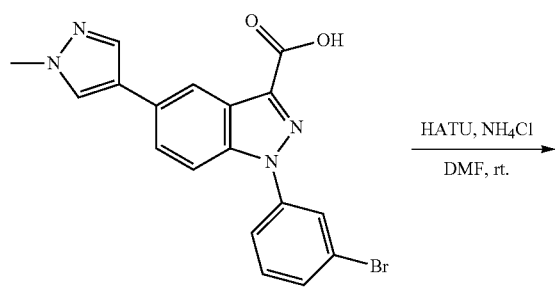

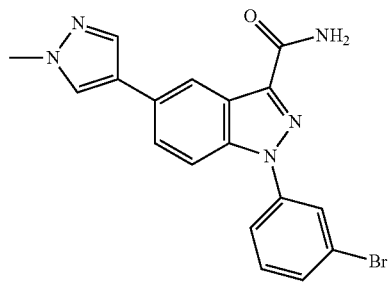

Similar to General Procedure B, 1-(3-bromophenyl)-5-(1-methyl-1H-pyrazol-4-yl)-1H-indazole-3-carboxylic acid (96 mg, 0.24 mmol) was reacted with ammonium chloride (0.05 mL, 1.44 mmol, 6 equiv) to afford the title compound (91 mg, 96%) as an off-white solid. LCMS (ES, m/z): 398, 400 [M+H]⁺.

Step 4: Synthesis of (R)-1-(3-((3-hydroxy-1-methyl-2-oxopyrrolidin-3-yl)ethynyl)phenyl)-5-(1-methyl-1H-pyrazol-4-yl)-1H-pyrazolo[3,4-b]pyridine-3-carboxamide

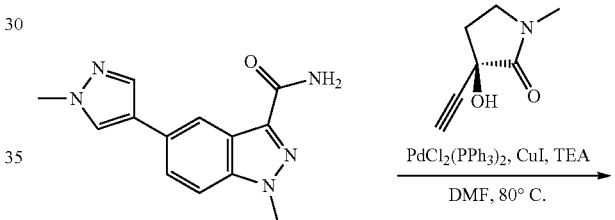

Similar to General Procedure E, 1-(3-bromophenyl)-5-(1-methyl-1H-pyrazol-4-yl)-1H-indazole-3-carboxamide (96 mg, 0.24 mmol) was reacted with (3R)-3-ethynyl-3-hydroxy-1-methylpyrrolidin-2-one (39.7 mg, 0.4 mmol, 1.2 equiv) to give the title compound (99 mg, 91%) as a brown solid. LC-MS (ES, m/z): 456 [M+H]⁺. ¹H NMR (400 MHz, DMSO-d₆) δ 9.06 (s, 1H), 8.68 (d, J=2.0 Hz, 1H), 8.55-8.43 (m, 2H), 8.39 (s, 1H), 8.23 (s, 1H), 8.06 (s, 1H), 7.72 (s, 1H), 7.68-7.59 (m, 1H), 7.45 (dd, J=7.7, 1.6 Hz, 1H), 6.54 (s, 1H), 3.91 (s, 3H), 3.43-3.33 (m, 2H), 3.33-3.24 (m, 1H), 2.82 (s, 3H), 2.46 (dd, J=6.7, 5.3 Hz, 1H), 2.22 (dt, J=12.8, 7.1 Hz, 1H).

Example Z5

Synthesis of (R)-methyl 1-(3-((3-hydroxy-1-methyl-2-oxopyrrolidin-3-yl)ethynyl)phenyl)-5-morpholino-1H-pyrazolo[3,4-b]pyridine-3-carboxylate

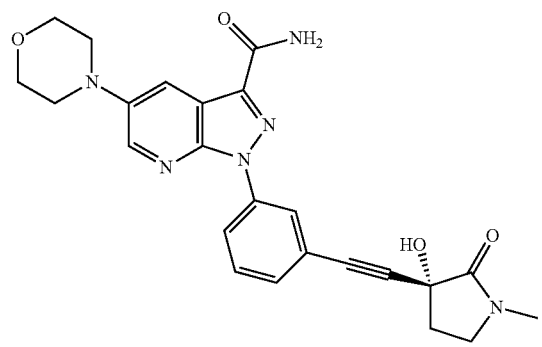 [SMILES: CN1CC[C@@](O)(C#Cc2cccc(-n3nc(C(N)=O)c4cc(N5CCOCC5)cnc43)c2)C1=O]

Step 1: Synthesis of methyl 1-((2-(trimethylsilyl)ethoxy)methyl)-1H-pyrazolo[3,4-b]pyridine-3-carboxylate

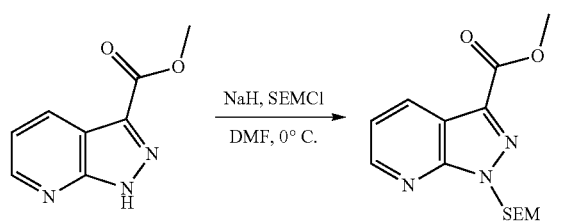

A stirred solution of methyl 1H-pyrazolo[3,4-b]pyridine-3-carboxylate (990 mg, 5.60 mmol) in DMF (2 mL/mmol, 64.9 mmol) was cooled to 0° C., then sodium hydride (1.33 equiv., 7.43 mmol) was then added. After stirring at 0° C. for 30 minutes, 2-(trimethylsilyl)ethoxymethyl chloride (1.33 equiv., 7.43 mmol) was then added drop-wise and solution was warmed to room temperature. After excess hydride was quenched by the addition of water at 0° C., the mixture was extracted with EtOAc (3 times). The organic extracts were then combined and dried with sodium sulfate then concentrated in vacuo. Purification by flash chromatography (heptane:isopropyl acetate) afforded the title compound (771 mg, 46%) as a white solid. LC-MS (ES, m/z): 308 [M+H]$^+$.

Step 2: Synthesis of methyl 5-(4,4,5,5-tetramethyl-1,3,2-dioxaborolan-2-yl)-1-((2-(trimethylsilyl)ethoxy)methyl)-1H-pyrazolo[3,4-b]pyridine-3-carboxylate

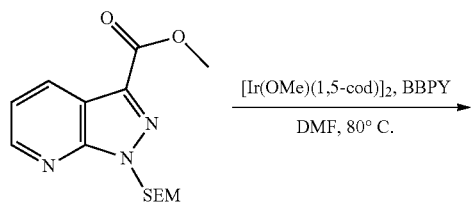

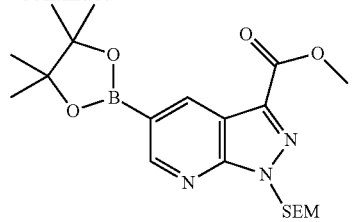

Under inert atmosphere, methyl 1-((2-(trimethylsilyl)ethoxy)methyl)-1H-pyrazolo[3,4-b]pyridine-3-carboxylate (771 mg, 2.51 mmol), bis(pinacolato)diboron (0.878 eq., 2.20 mmol), bis(1,5-cyclooctadiene)di-mu-methoxydiiridium(I) (0.02 eq., 0.05 mmol) and 4,4'-di-tert-butyl-2,2'-bipyridine (0.045 eq., 0.11 mmol) were dissolved in degassed tetrahydrofuran (2.51 mL). The reaction was heated in a sealed vial at 80° C. for 18 hours. The solution was cooled to room temperature, diluted with ethyl actetate, filtered through celite, and concentrated to afford a red solid. Purification by CombiFlash (heptane:isopropyl acetate) afforded the title compound (800 mg, 71%) as a white solid. LC-MS (ES, m/z): 434 [M+H]$^+$.

Step 3: Synthesis of (3-(methoxycarbonyl)-1-((2-(trimethylsilyl)ethoxy)methyl)-1H-pyrazolo[3,4-b]pyridin-5-yl)boronic acid

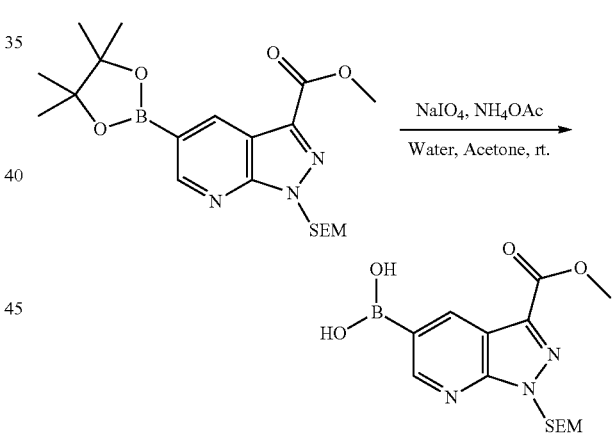

Under inert atmosphere, methyl 5-(4,4,5,5-tetramethyl-1,3,2-dioxaborolan-2-yl)-1-((2-(trimethylsilyl)ethoxy)methyl)-1H-pyrazolo[3,4-b]pyridine-3-carboxylate (300 mg, 0.6922 mmol), ammonium acetate (267 mg, 3.46 mmol, 5.00 equiv), sodium periodate (752 mg, 3.461 mmol, 5.00 equiv.) were combined and dissolved in acetone (3.11 mL) and water (3.11 mL). Reaction was stirred for 2 hours then acetone was removed under vacuum and the remaining aqueous layer was extracted with ethyl acetate (3 times). Combined organic layers were dried with sodium sulfate, filtered, and concentrated under reduced pressure to give the title product (180 mg, 74%) as a white solid. LC-MS (ES, m/z): 352 [M+H]$^+$.

Step 4: Synthesis of methyl 5-morpholino-1-((2-(trimethylsilyl)ethoxy)methyl)-1H-pyrazolo[3,4-b]pyridine-3-carboxylate

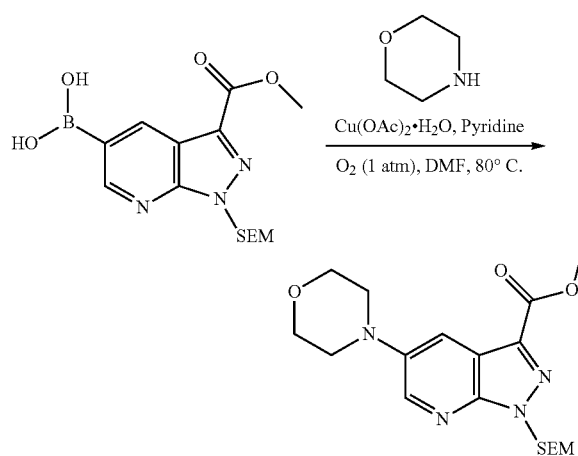

To a small vial containing [3-methoxycarbonyl-1-(2-trimethylsilylethoxymethyl)pyrazolo[3,4-b]pyridin-5-yl]boronic acid (250 mg, 0.712 mmol), copper(II) acetate monohydrate (30.00 mg, 0.1424 mmol, 0.2 equiv), and morpholine (1.24 mL, 14.24 mmol, 20 equiv) are dissolved in DMF (1.42 mL). The reaction vessel is sparged with oxygen gas and evacuated (3 times) then pyridine (0.17 mL, 2.13 mmol, 3.0 equiv) is added drop-wise. The reaction was stirred at 80° C. for 6 hours. The reaction was then cooled to room temperature and diluted with a saturated solution of ammonium chloride. The aqueous phase was extracted with ethyl acetate (3 times), dried with sodium sulfate, filtered, and concentrated under reduced pressure to afford the crude mixture as a yellow oil. The crude material was then purified by flash chromatography (heptane:isopropyl acetate) to afford the title compound (8 mg, 3%) as a white solid. LC-MS (ES, m/z): 393 [M+H]+.

Step 5: Synthesis of methyl 5-morpholino-1H-pyrazolo[3,4-b]pyridine-3-carboxylate

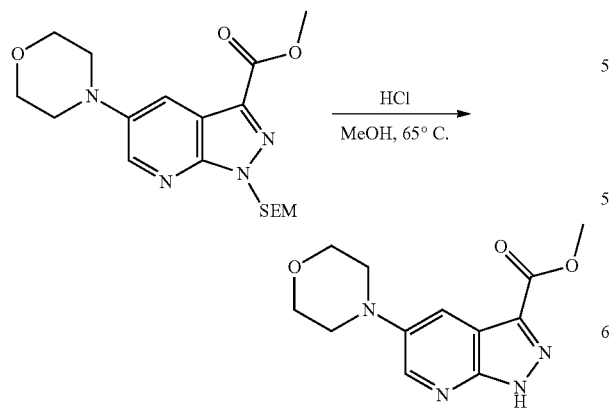

Similar to General Procedure T, methyl 5-morpholino-1-((2-(trimethylsilyl)ethoxy)methyl)-1H-pyrazolo[3,4-b]pyridine-3-carboxylate (43 mg, 0.11 mmol) was reacted with hydrochloric acid (1.40 mmol, 12.5 equiv) to afford the title compound as a yellow solid (8 mg, 27%). LC-MS (ES, m/z): 263 [M+H]+.

Step 6: Synthesis of methyl 1-(3-bromophenyl)-5-morpholino-1H-pyrazolo[3,4-b]pyridine-3-carboxylate

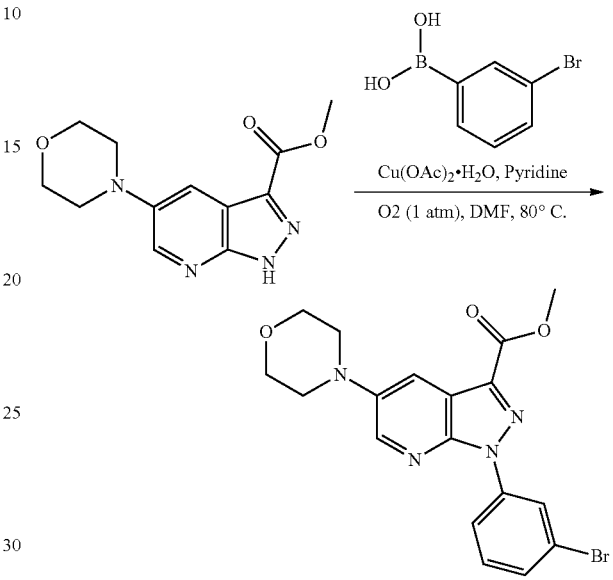

Similar to as described in General Procedure C, methyl 5-morpholino-1H-pyrazolo[3,4-b]pyridine-3-carboxylate (50 mg, 0.19 mmol) was reacted with (3-bromophenyl)boronic acid (57.43 mg, 0.29 mmol, 1.5 equiv) to afford the title compound as a brown solid (18.3 mg, 80%). LC-MS (ES, m/z): 417, 419 [M+H]+.

Step 7: Synthesis of 1-(3-bromophenyl)-5-morpholino-1H-pyrazolo[3,4-b]pyridine-3-carboxamide

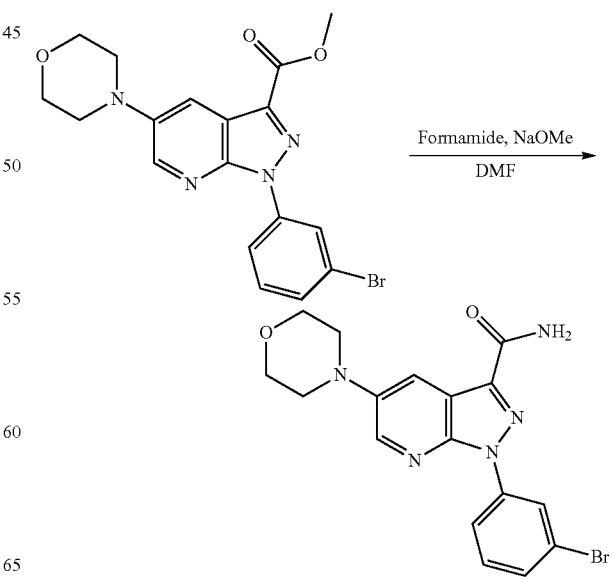

[068] Similar to as described in General Procedure H, methyl 1-(3-bromophenyl)-5-morpholino-1H-pyrazolo[3,4-b]pyridine-3-carboxylate (18.3 mg, 0.04 mmol) was reacted with formamide (0.017 mL, 0.44 mmol, 10 equiv) to give the title compound as a yellow solid. LC-MS (ES, m/z): 402, 404 [M+H]⁺.

Step 8: Synthesis of (R)-methyl 1-(3-((3-hydroxy-1-methyl-2-oxopyrrolidin-3-yl)ethynyl)phenyl)-5-morpholino-1H-pyrazolo[3,4-b]pyridine-3-carboxylate

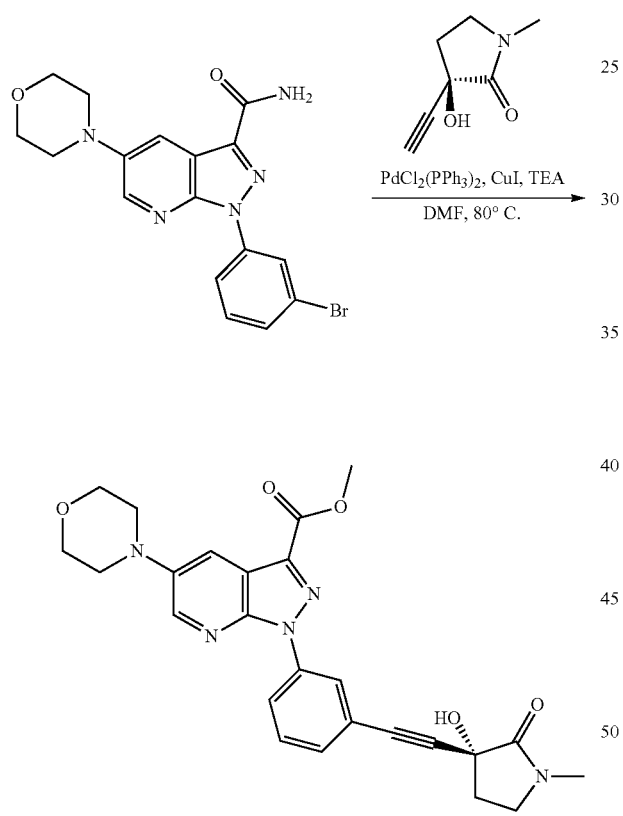

Similar to as described in General Procedure E, 1-(3-bromophenyl)-5-morpholino-1H-pyrazolo[3,4-b]pyridine-3-carboxamide (17.6 mg, 0.04 mmol) was reacted with (3R)-3-ethynyl-3-hydroxy-1-methylpyrrolidin-2-one (7.32 mg, 0.05 mmol, 1.2 equiv) to give the title compound (1 mg, 5%) as a white solid. LC-MS (ES, m z): 461 [M+H]⁺.

Example A6

Synthesis of (R)-1-(3-((3-hydroxy-1-methyl-2-oxopyrrolidin-3-yl)ethynyl)phenyl)-5-(4-methyl-1H-imidazol-1-yl)-1H-indazole-3-carboxamide

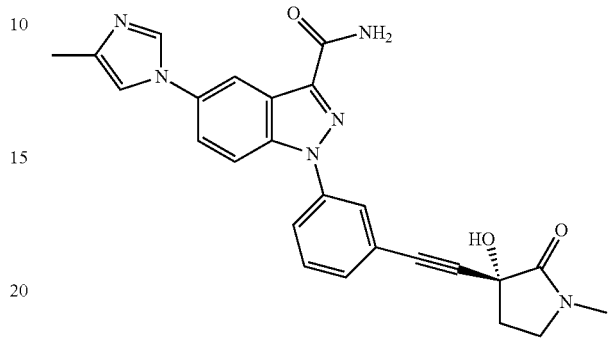

Step 1: Synthesis of methyl 1-(3-bromophenyl)-5-(4-methyl-1H-imidazol-1-yl)-1H-indazole-3-carboxylate

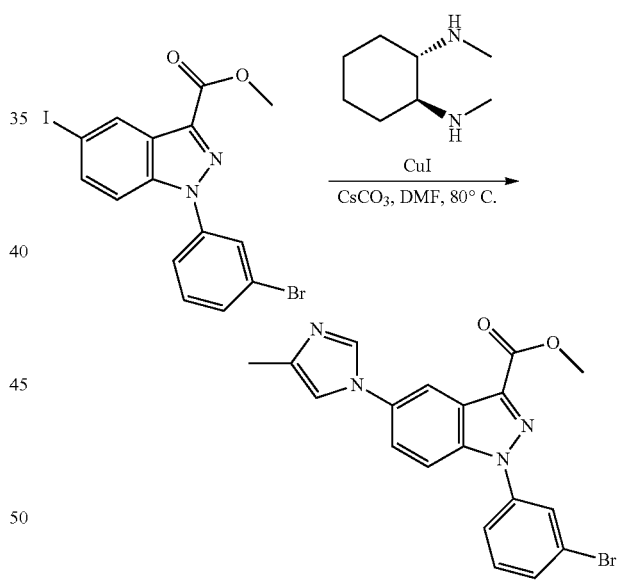

Methyl 1-(3-bromophenyl)-5-iodo-indazole-3-carboxylate (327 mg, 0.716153 mmol, 1.2 equiv), 4-methylimidazole (50 mg, 0.596794 mmol), cuprous iodide (113 mg, 0.596794 mmol, 1 equiv), (1R,2R)—N,N'-dimethyl-1,2-cyclohexanediamine (0.097 mL, 0.596794 mmol, 1 equiv), and cesium carbonate (388 mg, 1.19359 mmol, 2 equiv) were combined in a small vial and dissolved in DMF (0.30 mL, 3.86 mmol). The reaction was stirred at 60° C. for 2 hours under nitrogen. The reaction was then allowed to cool to room temperature, filtered through celite, and concentrated to give a brown oil. The crude material was purified by flash chromatography to afford the title compound (51 mg, 21%). LC-MS (ES, m/z): 411, 413 [M+H]⁺.

Step 2: Synthesis of 1-(3-bromophenyl)-5-(4-methyl-1H-imidazol-1-yl)-1H-indazole-3-carboxamide

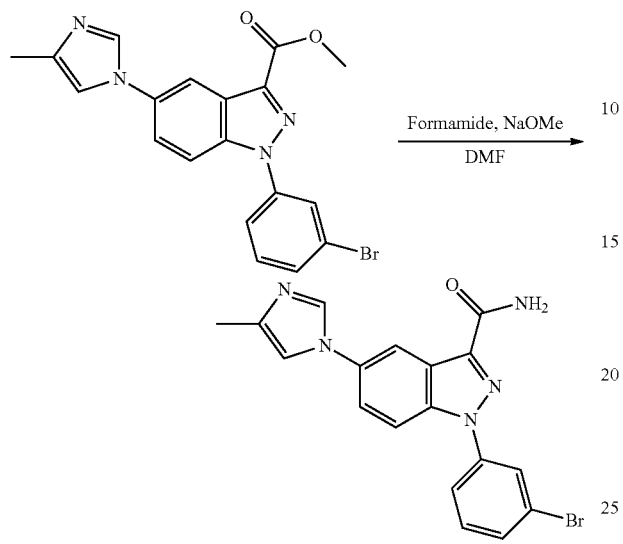

Similar to as described in General Procedure H, methyl 1-(3-bromophenyl)-5-(4-methyl-1H-imidazol-1-yl)-1H-indazole-3-carboxylate (67 mg, 0.16 mmol) was reacted with formamide (0.065 mL, 1.63 mmol, 10 equiv) to afford the title compound as a yellow solid (64 mg, 99%). LC-MS (ES, m/z): 396, 398 [M+H]⁺.

Step 3: Synthesis of (R)-1-(3-((3-hydroxy-1-methyl-2-oxopyrrolidin-3-yl)ethynyl)phenyl)-5-(4-methyl-1H-imidazol-1-yl)-1H-indazole-3-carboxamide

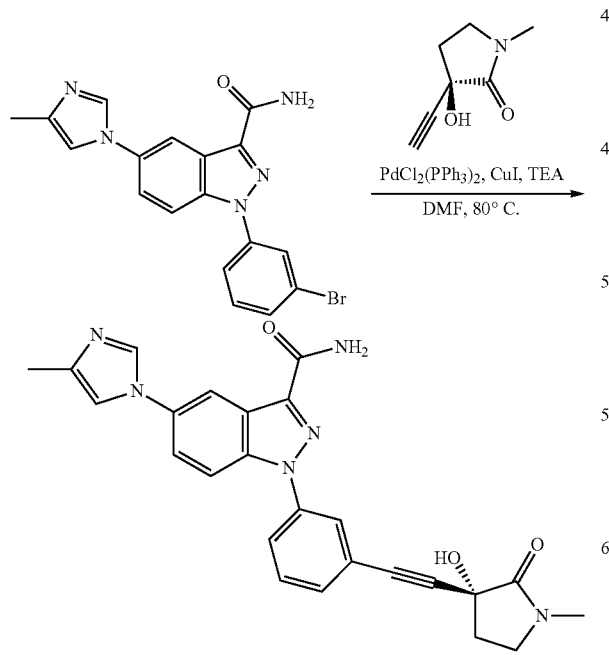

Similar to as described in General Procedure E, 1-(3-bromophenyl)-5-(4-methyl-1H-imidazol-1-yl)-1H-indazole-3-carboxamide (64 mg, 0.14 mmol) was reacted with (3R)-3-ethynyl-3-hydroxy-1-methylpyrrolidin-2-one (27.21 mg, 0.20 mmol, 1.2 equiv) to give the title compound (65 mg, 74%) as a brown solid. LC-MS (ES, m/z): 454, 456 [M+H]⁺. ¹H NMR (400 MHz, DMSO-d₆) δ 8.30 (d, J=2.0 Hz, 1H), 8.14 (d, 1H), 8.10 (br s, 1H), 8.02-7.98 (m, 1H), 7.97-7.93 (m, 1H), 7.93-7.90 (m, 1H), 7.81 (dd, 1H), 7.71-7.59 (m, 2H), 7.58-7.51 (m, 1H), 7.50-7.45 (m, 1H), 6.53 (br s, 1H), 3.42-3.32 (m, 2H), 2.81 (s, 3H), 2.58-2.51 (m, 2H), 2.51-2.41 (m, 1H), 2.27-2.13 (m, 4H).

Example B6

5-(1-acetylazetidin-3-yl)-1-[3-[2-[(3R)-3-hydroxy-1-methyl-2-oxo-pyrrolidin-3-yl]ethynyl]phenyl]pyrazolo[3,4-b]pyridine-3-carboxamide

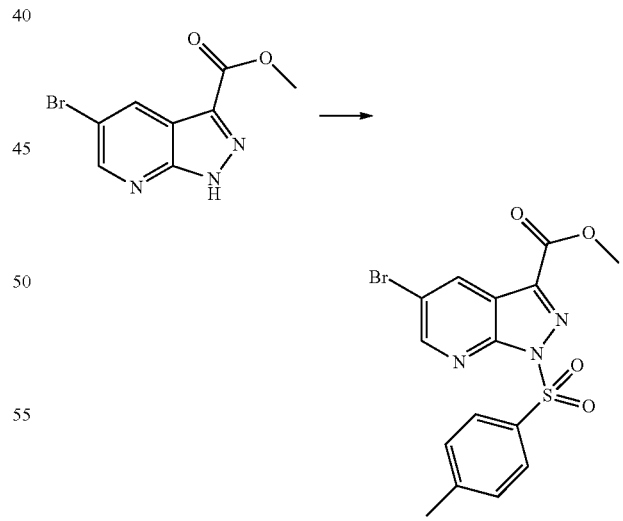

Synthesis of methyl 5-bromo-1-(p-tolylsulfonyl)pyrazolo[3,4-b]pyridine-3-carboxylate

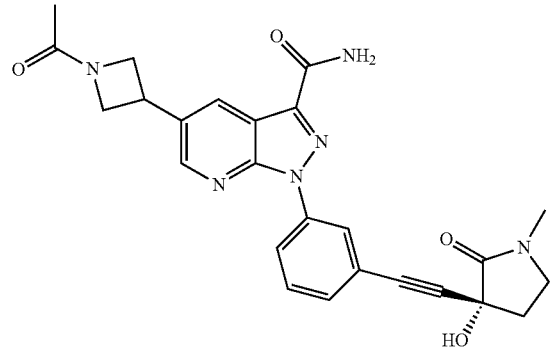 [SMILES: CC(=O)N1CC(c2cnc3c(c2)c(C(N)=O)nn3-c2cccc(C#C[C@]3(O)CCN(C)C3=O)c2)C1]

Sodium hydride (1.3 eq., 81.2 mg, 2.031 mmol) was added slowly to a solution of methyl 5-bromo-1H-pyrazolo[3,4-b]pyridine-3-carboxylate (1.0 eq., 400 mg, 1.562 mmol) in N,N-dimethylformamide (9.53 mL) at 0° C. under nitrogen atmosphere. The reaction was stirred for 30 min at 0° C. and then p-toluenesulfonyl chloride (1.4 eq., 425.4 mg, 2.187 mmol) was added. The mixture was stirred at room temperature for 3 hours. Water was added and the mixture was filtered. The solid was redissolved in methanol and dichloromethane and excess water was removed in vacuo to obtain 643 mg (100% yield) of a white solid which was carried forward without further purification.

Synthesis of methyl 5-(1-tert-butoxycarbonylazetidin-3-yl)-1-(p-tolylsulfonyl)pyrazolo[3,4-b]pyridine-3-carboxylate

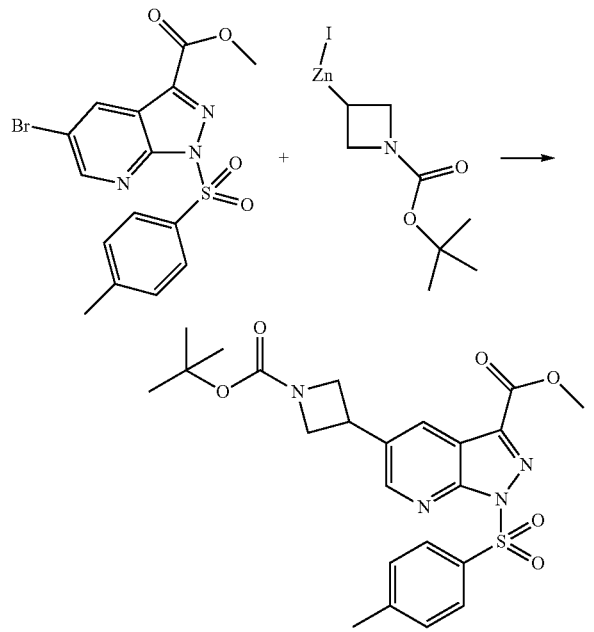

Step 1: To a dry round bottom flask was added zinc (1.40 eq., 323 mg) which was stirred in degassed N,N-dimethylacetamide (1.77 mL) under nitrogen atmosphere. Chlorotrimethylsilane (0.12 eq., 0.054 mL) and 1,2-dibromoethane (0.10 eq., 0.030 mL) were added and the mixture was stirred for 15 minutes at room temperature. Tert-butyl 3-iodoazetidine-1-carboxylate (1.0 eq., 0.613 mL, 1000 mg) in degassed N,N-Dimethylacetamide (7.06 mL) was added slowly and the cloudy reaction was stirred at room temperature for 1.5 hours. The resulting 0.38 M solution was used as is in further reactions (sealed and stored in refrigerator).

Step 2: Methyl 5-bromo-1-(p-tolylsulfonyl)pyrazolo[3,4-b]pyridine-3-carboxylate (1.0 eq., 640 mg, 1.560 mmol) was dissolved in N,N-dimethylacetamide (3.9 mL) and purged with nitrogen gas. [1,1'-Bis(diphenylphosphino)ferrocene]dichloropalladium(II) complex with dichloromethane (1:1) (0.05 eq., 63.7 mg) and Copper(I) iodide (0.10 eq., 29.7 mg) were added and the reaction was purged for another 10 minutes. (1-(tert-butoxycarbonyl)azetidin-3-yl)zinc(II) iodide (1.2 eq., 4.93 mL, 1.872 mmol) was added. The reaction was heated to 80° C. overnight. Complete conversion to product was observed by LCMS. The reaction was cooled to room temperature. Water was added and the mixture was extracted with isopropyl acetate twice. The organic layers were combined, dried with sodium sulfate and concentrated. The crude mixture was purified by flash chromatography (5-100% iPrOAc in heptanes) to afford 363.6 mg (48% yield) of the desired product.

Synthesis of methyl 5-(1-tert-butoxycarbonylazetidin-3-yl)-1H-pyrazolo[3,4-b]pyridine-3-carboxylate

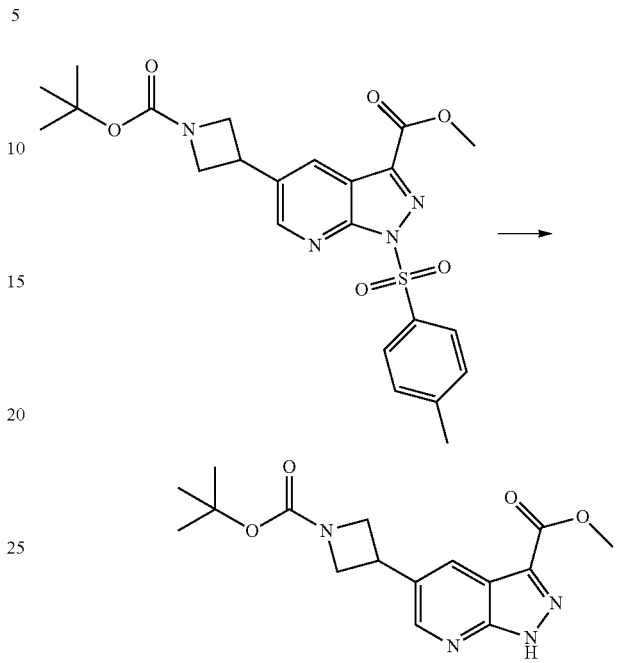

Methyl 5-(1-tert-butoxycarbonylazetidin-3-yl)-1-(p-tolylsulfonyl)pyrazolo[3,4-b]pyridine-3-carboxylate (1.0 eq., 363.6 mg, 0.747 mmol) was dissolved in tetrahydrofuran (1.5 mL)/methanol (1.5 mL)/water (1.5 mL). Lithium hydroxide (5.0 eq., 91.32 mg, 3.737 mmol) was added and the mixture was stirred at room temperature for 3 hours. The crude material was purified by flash chromatography to obtain 88.4 mg (35.6% yield) of an off-white solid.

Synthesis of methyl 1-(3-bromophenyl)-5-(1-tert-butoxycarbonylazetidin-3-yl)pyrazolo[3,4-b]pyridine-3-carboxylate

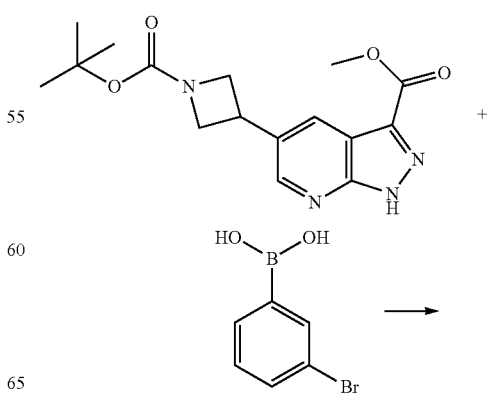

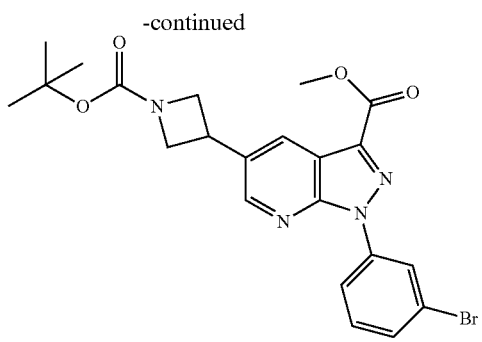

Similar to general procedure C, to a small vial was added methyl 5-(1-tert-butoxycarbonylazetidin-3-yl)-1H-pyrazolo[3,4-b]pyridine-3-carboxylate (1.0 eq., 88.4 mg, 0.266 mmol), (3-bromophenyl)boronic acid (1.50 eq., 80.1 mg, 0.399 mmol), copper(II) acetate monohydrate (0.30 eq., 16.8 mg, 0.0798 mmol) in N,N-dimethylformamide (0.532 mL) and pyridine (5.0 eq., 0.108 mL, 1.33 mmol). The reaction was stirred under an oxygen atmosphere at 90° C. for 3 h. The reaction was diluted with saturated aqueous sodium bicarbonate solution, and the aqueous phase was extracted with 3 times with dichloromethane. The organic phases were combined, washed with brine, dried with sodium sulfate and concentrated under vacuum. The crude material was purified by flash chromatography (5-100% iPrOAc in heptanes) to afford a light yellow oil.

Synthesis of methyl 5-(azetidin-3-yl)-1-(3-bromophenyl)pyrazolo[3,4-b]pyridine-3-carboxylate

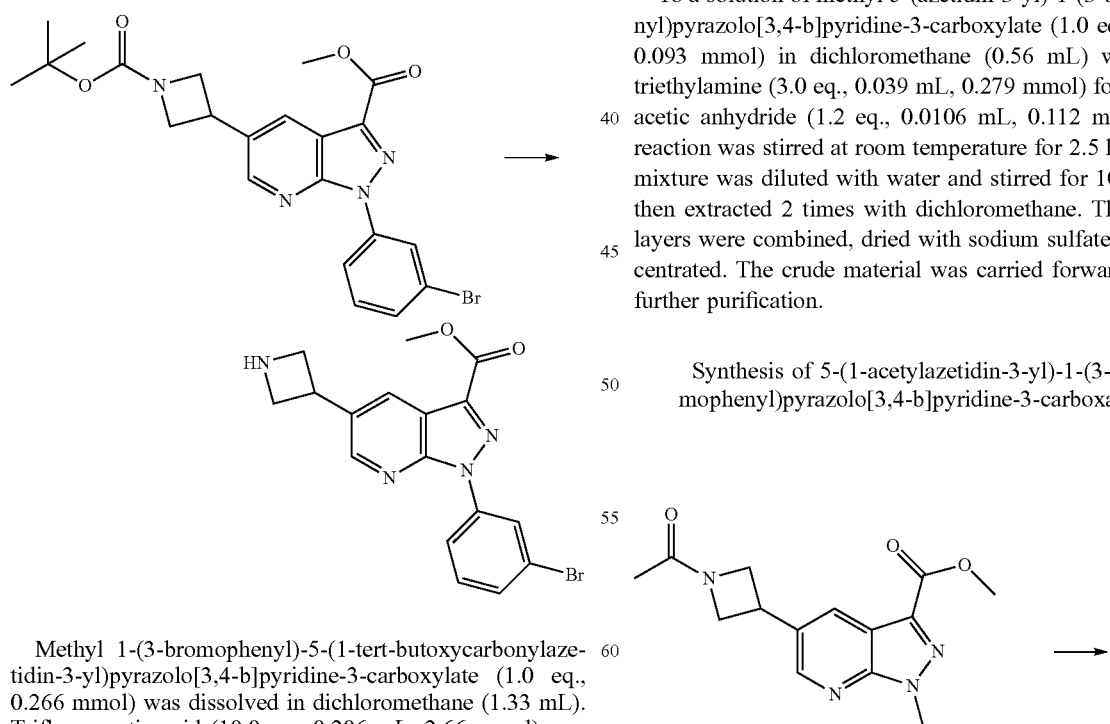

Methyl 1-(3-bromophenyl)-5-(1-tert-butoxycarbonylazetidin-3-yl)pyrazolo[3,4-b]pyridine-3-carboxylate (1.0 eq., 0.266 mmol) was dissolved in dichloromethane (1.33 mL). Trifluoroacetic acid (10.0 eq., 0.206 mL, 2.66 mmol) was added dropwise and the reaction was stirred at room temperature for 2 hours. The solution was concentrated in vacuo, diluted with saturated aqueous sodium bicarbonate solution and extracted 2 times with dichloromethane. The organic layers were combined, dried with sodium sulfate, and concentrated. The crude material was carried forward without further purification.

Synthesis of methyl 5-(1-acetylazetidin-3-yl)-1-(3-bromophenyl)pyrazolo[3,4-b]pyridine-3-carboxylate

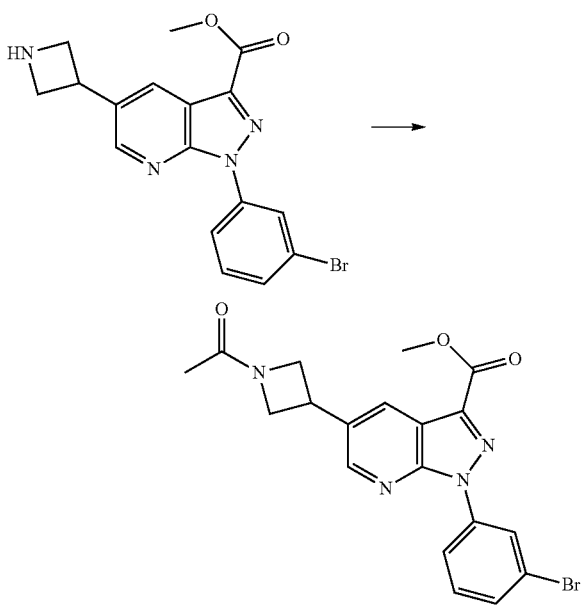

To a solution of methyl 5-(azetidin-3-yl)-1-(3-bromophenyl)pyrazolo[3,4-b]pyridine-3-carboxylate (1.0 eq., 36 mg, 0.093 mmol) in dichloromethane (0.56 mL) was added triethylamine (3.0 eq., 0.039 mL, 0.279 mmol) followed by acetic anhydride (1.2 eq., 0.0106 mL, 0.112 mmol). The reaction was stirred at room temperature for 2.5 hours. The mixture was diluted with water and stirred for 10 minutes, then extracted 2 times with dichloromethane. The organic layers were combined, dried with sodium sulfate, and concentrated. The crude material was carried forward without further purification.

Synthesis of 5-(1-acetylazetidin-3-yl)-1-(3-bromophenyl)pyrazolo[3,4-b]pyridine-3-carboxamide

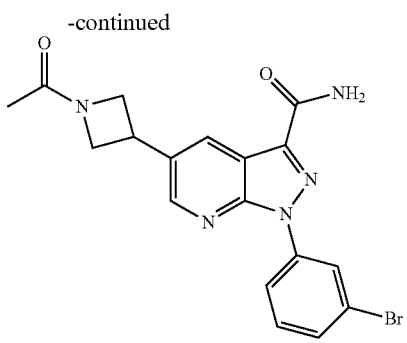

Similar to general procedure H, to a solution of methyl 5-(1-acetyl azetidin-3-yl)-1-(3-bromophenyl)pyrazolo[3,4-b]pyridine-3-carboxylate (1.0 eq., 40 mg, 0.0932 mmol) in dimethylformamide (0.5 mL) was added formamide (10.0 eq., 0.0372 mL, 0.932 mmol) followed by sodium methoxide (25% in methanol, 3.0 eq., 0.0639 mL, 0.28 mmol). The reaction was stirred at room temperature for 1 hour. The reaction mixture was quenched with saturated ammonium chloride solution and filtered to afford a white solid. The crude material was carried forward without further purification.

Synthesis of 5-(1-acetylazetidin-3-yl)-1-[3-[2-[(3R)-3-hydroxy-1-methyl-2-oxo-pyrrolidin-3-yl]ethynyl]phenyl]pyrazolo[3,4-b]pyridine-3-carboxamide

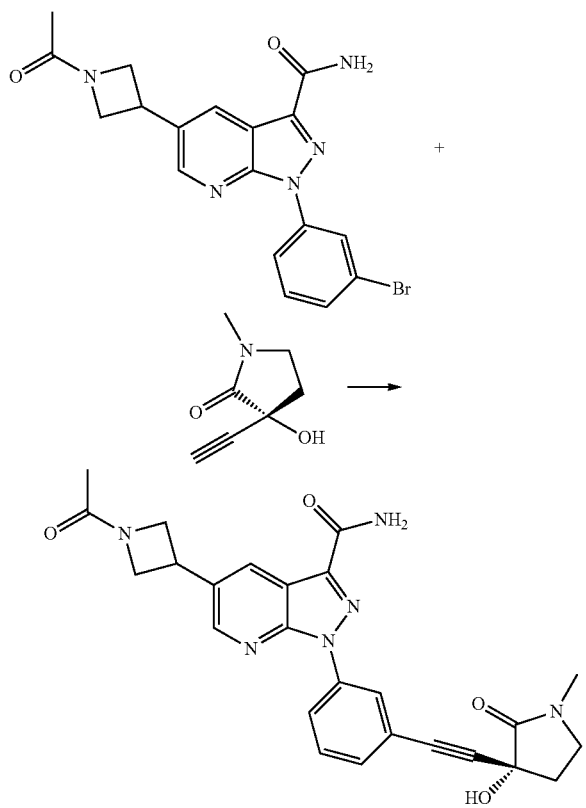

Similar to general procedure E, to a degassed solution of 5-(1-acetylazetidin-3-yl)-1-(3-bromophenyl)pyrazolo[3,4-b]pyridine-3-carboxamide (1.0 eq., 38.6 mg, 0.0932 mmol) in DMF (0.242 mL, 229 mg, 3.10 mmol) and triethylamine (0.242 mL) was added Bis(triphenylphosphine)palladium (II)chloride (0.05 eq., 3.34 mg, 0.0047 mmol), copper (I) iodide (0.05 eq., 0.9 mg, 0.0047 mmol) and (3R)-3-ethynyl-3-hydroxy-1-methyl-pyrrolidin-2-one (1.20 eq., 15.6 mg, 0.112 mmol). The reaction was heated under inert atmosphere to 80° C. for 1 hour. The reaction was cooled to room temperature, diluted with dichloromethane and filtered over celite. The crude material was purified by reverse-phase HPLC to afford 17.5 mg (40% yield after 2 steps) of the desired final product. M+H=473.2; $^1$H NMR (400 MHz, DMSO-d6) δ 8.86-8.76 (m, 1H), 8.69-8.59 (m, 1H), 8.55-8.43 (m, 2H), 8.24 (br s, 1H), 7.73 (br s, 1H), 7.69-7.58 (m, 1H), 7.45 (d, J=7.5 Hz, 1H), 6.52 (s, 1H), 4.66-4.55 (m, 1H), 4.39-4.23 (m, 2H), 4.19-4.07 (m, 1H), 3.97-3.91 (m, 1H), 3.40-3.34 (m, 2H), 2.82 (s, 3H), 2.47-2.41 (m, 1H), 2.22 (dt, J=13.2, 6.9 Hz, 1H), 1.84 (s, 3H).

Example C6

1-[3-[2-[(3R)-3-hydroxy-1-methyl-2-oxo-pyrrolidin-3-yl]ethynyl]phenyl]-5-oxo-4H-pyrazolo[4,3-b]pyridine-3-carboxamide

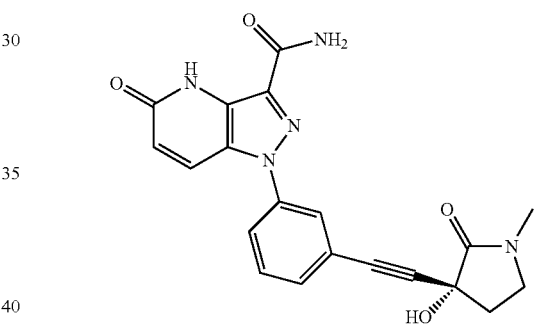

Synthesis of 3-iodo-5-methoxy-1H-pyrazolo[4,3-b]pyridine

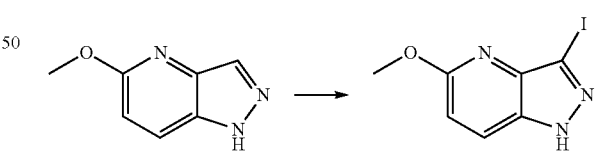

To a solution of 5-methoxy-1H-pyrazolo[4,3-b]pyridine (1.0 eq., 300 mg, 2.011 mmol) in N,N-dimethylformamide (10.1 mL) was added potassium hydroxide (3.0 eq., 342 mg, 6.034 mmol) followed by iodine (1.8 eq., 918.9 mg, 3.620 mmol). The reaction was heated to 50° C. for 1.5 hours. The reaction was then cooled to room temperature and quenched with aqueous sodium thiosulfate until the dark color disappeared. The mixture was diluted with water and extracted 2 times with ethyl acetate. The organic layers were combined, washed with brine, dried with sodium sulfate and concentrated to afford 528.3 mg (95% yield) of desired product.

Synthesis of 5-methoxy-1H-pyrazolo[4,3-b]pyridine-3-carbonitrile

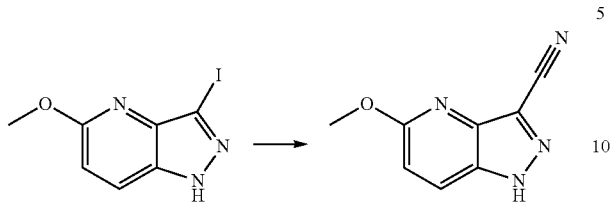

To a solution of 3-iodo-5-methoxy-1H-pyrazolo[4,3-b]pyridine (1.0 eq., 528 mg, 1.919 mmol) in 1-methyl-2-pyrrolidinone (4.8 mL) in a microwave vial was added copper(I) cyanide (1.5 eq., 263.2 mg, 2.8795 mmol). The reaction was heated in the microwave to 220° C. for 20 minutes. The reaction was cooled to room temperature and diluted with dichloromethane. The solution was filtered over celite and concentrated, then diluted with saturated aqueous ammonium chloride solution and extracted 3 times with ethyl acetate. The organic layers were washed with brine, dried with sodium sulfate and concentrated. The crude material was purified by flash chromatography (isopropyl acetate in heptane) to afford 142 mg (42.5% yield) of the desired product.

Synthesis of 1-(3-bromophenyl)-5-methoxy-pyrazolo[4,3-b]pyridine-3-carbonitrile

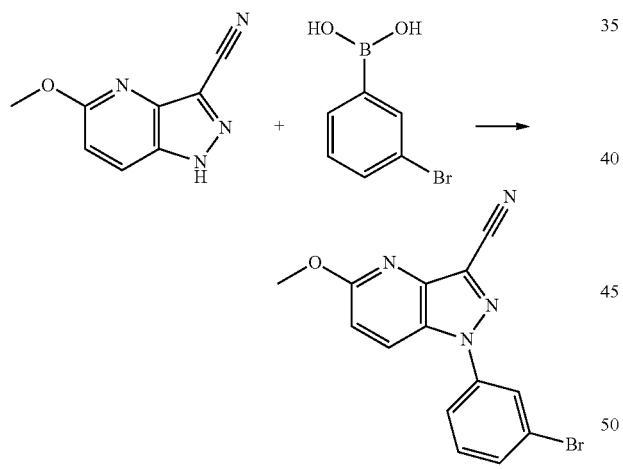

Similar to general procedure C, to a small vial was added 5-methoxy-1H-pyrazolo[4,3-b]pyridine-3-carbonitrile (1.00 eq., 142 mg, 0.815 mmol), (3-bromophenyl)boronic acid (1.5 eq., 245.6 mg, 1.223 mmol), copper(II) acetate monohydrate (0.30 eq., 51.4 mg, 0.244 mmol) in N,N-dimethylformamide (1.63 mL) and pyridine (5.0 eq., 0.330 mL, 4.077 mmol). The reaction was stirred under an oxygen atmosphere at 90° C. for 3 hours. The reaction was diluted with saturated aqueous sodium bicarbonate solution and the mixture was extracted with dichloromethane (3 times). The organic layers were combined, dried with sodium sulfate and concentrated. The crude was purified by flash chromatography (5-100% isopropylacetate in heptane) to afford 107.7 mg (40.1% yield) of a light yellow solid.

Synthesis of 1-(3-bromophenyl)-5-oxo-4H-pyrazolo[4,3-b]pyridine-3-carbonitrile

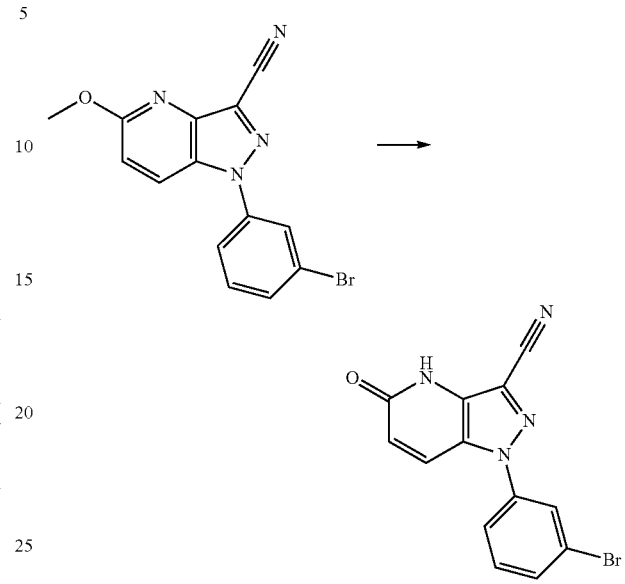

To a solution of 1-(3-bromophenyl)-5-methoxy-pyrazolo[4,3-b]pyridine-3-carbonitrile (1.0 eq., 50 mg, 0.152 mmol) in acetonitrile (0.30 mL) was added sodium iodide (3.0 eq., 68.3 mg, 0.456 mmol) and chlorotrimethylsilane (3.0 eq., 0.058 mL, 0.456 mmol). The reaction was heated to 85° C. for 2 hours. The reaction mixture was then treated with methanol (1 ml), and the resulting mixture was stirred at ambient temperature for 2 hours, and then filtered. The resulting solid was triturated in water, filtered, and used as is in the following step.

Synthesis of 1-(3-bromophenyl)-5-oxo-4H-pyrazolo[4,3-b]pyridine-3-carboxamide

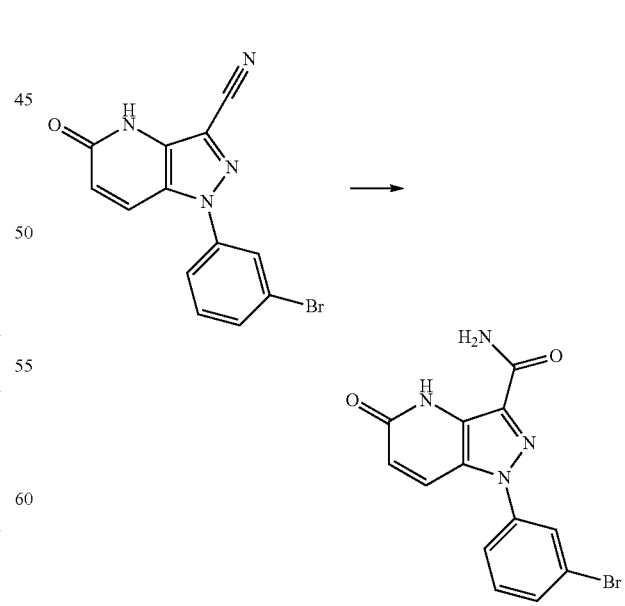

Similar to General Procedure D, 1-(3-bromophenyl)-5-oxo-4H-pyrazolo[4,3-b]pyridine-3-carbonitrile (1.0 eq., 47.8 mg, 0.152 mmol) was dissolved in ethanol (0.24 mL) and water (0.12 mL). Hydrido(dimethylphosphinous acid-kp)[hydrogen bis(dimethylphosphinito-kp)]platinum(II) (0.05 eq., 3.24 mg, 0.0076 mmol) was added and the reaction was heated to 90° C. under air for 7 hours. The reaction mixture was diluted with water and extracted 2 times with dichloromethane. The organic layers were combined, dried with sodium sulfate and concentrated. The resulting product was used crude in the following reaction.

Synthesis of 1-[3-[2-[(3R)-3-hydroxy-1-methyl-2-oxo-pyrrolidin-3-yl]ethynyl]phenyl]-5-oxo-4H-pyrazolo[4,3-b]pyridine-3-carboxamide

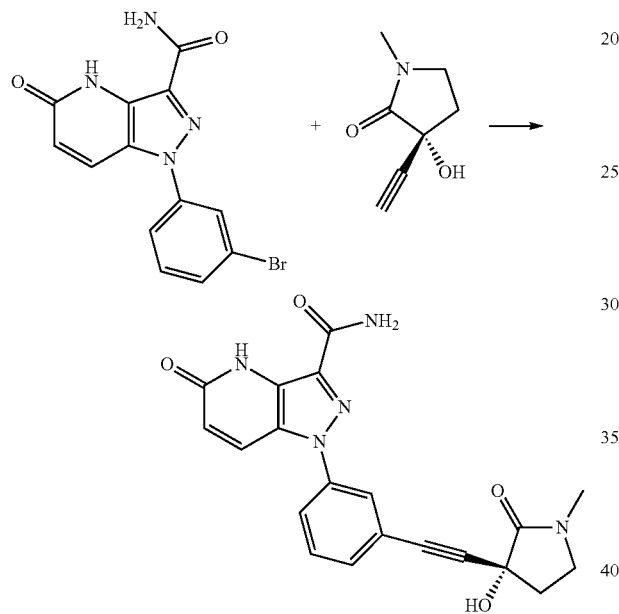

Similar to general procedure E, 1-(3-bromophenyl)-5-oxo-4H-pyrazolo[4,3-b]pyridine-3-carboxamide (1.0 eq., 45 mg, 0.135 mmol) in triethylamine (0.35 mL) and DMF (0.35 mL) was degassed with nitrogen. Bis(triphenylphosphine)palladium(II)chloride (0.05 eq., 4.8 mg, 0.0067 mmol) and copper (I) iodide (0.05 eq., 1.3 mg, 0.0067 mmol) were added under inert atmosphere, followed by (3R)-3-ethynyl-3-hydroxy-1-methyl-pyrrolidin-2-one (1.2 eq., 22.6 mg, 0.162 mmol). The reaction was heated to 80° C. for 1 hour. The reaction mixture was cooled to room temperature, diluted with dichloromethane and filtered over celite. The crude material was purified by reverse-phase HPLC to afford 9.8 mg (18.5% yield) of the desired product. M+H=392.2; $^1$H NMR (400 MHz, DMSO-d6) δ 10.54 (br s, 1H), 8.08 (br s, 1H), 8.03 (d, J=9.8 Hz, 1H), 7.85-7.77 (m, 2H), 7.68 (br s, 1H), 7.65-7.59 (m, 1H), 7.57-7.49 (m, 1H), 6.57 (d, J=9.8 Hz, 1H), 6.51 (s, 1H), 3.42-3.34 (m, 2H), 2.80 (s, 3H), 2.47-2.41 (m, 1H), 2.20 (dt, J=13.0, 7.1 Hz, 1H).

Example D6 and Example E6

Synthesis of (R)-1-(3-(((R)-3-hydroxy-1-methyl-2-oxopyrrolidin-3-yl)ethynyl)phenyl)-4-methyl-1,4,5,6-tetrahydrocyclopenta[c]pyrazole-3-carboxamide and (S)-1-(3-(((R)-3-hydroxy-1-methyl-2-oxopyrrolidin-3-yl)ethynyl)phenyl)-4-methyl-1,4,5,6-tetrahydrocyclopenta[c]pyrazole-3-carboxamide

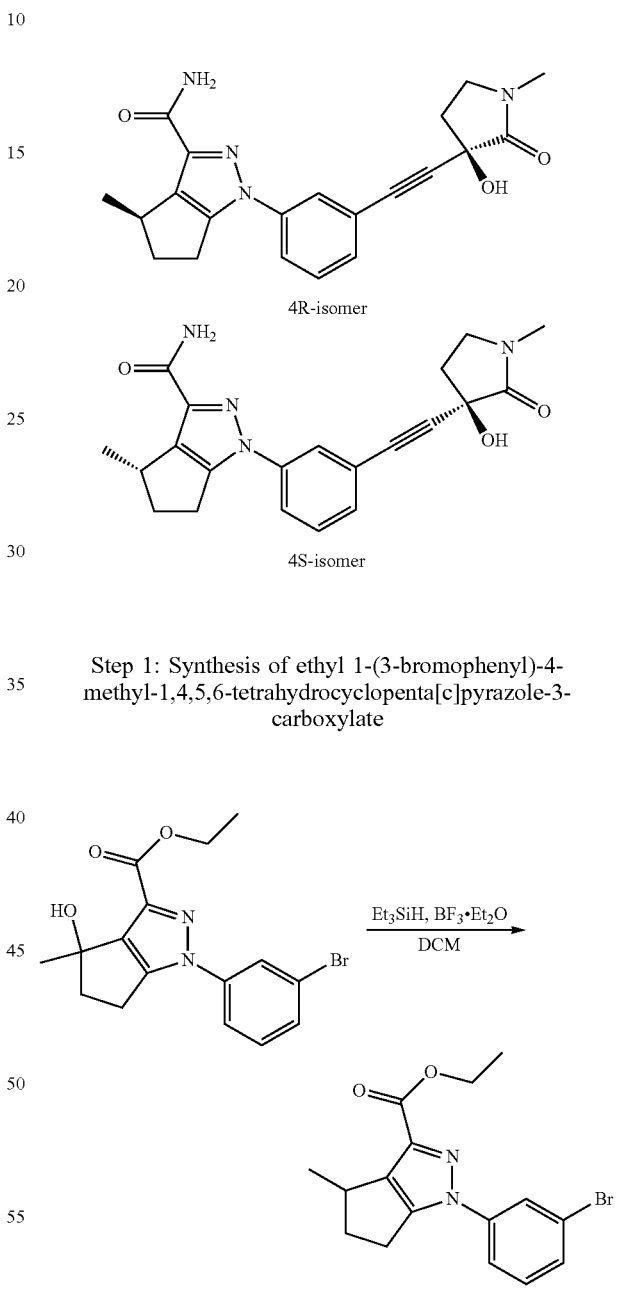

Step 1: Synthesis of ethyl 1-(3-bromophenyl)-4-methyl-1,4,5,6-tetrahydrocyclopenta[c]pyrazole-3-carboxylate A solution of ethyl 1-(3-bromophenyl)-4-hydroxy-4-methyl-1H,4H,5H,6H-cyclopenta[c]pyrazole-3-carboxylate (180.0 mg, 0.49 mmol, 1.00 equiv), triethylsilane (573.1 mg, 4.93 mmol, 10.00 equiv), and boron trifluoride etherate (139.9 mg, 0.99 mmol, 2.00 equiv) in dichloromethane (40 mL) was stirred for 12 h at room temperature. The resulting mixture was concentrated under vacuum. The residue was applied onto a silica gel column with ethyl acetate/petroleum ether (2:3). This resulted in 43.0 mg (25%) of the title compound as a reddish solid. LC-MS (ES, m/z): 349 [M+H]⁺.

Step 2: Synthesis of ethyl 1-(3-(((R)-3-hydroxy-1-methyl-2-oxopyrrolidin-3-yl)ethynyl)phenyl)-4-methyl-1,4,5,6-tetrahydrocyclopenta[c]pyrazole-3-carboxylate

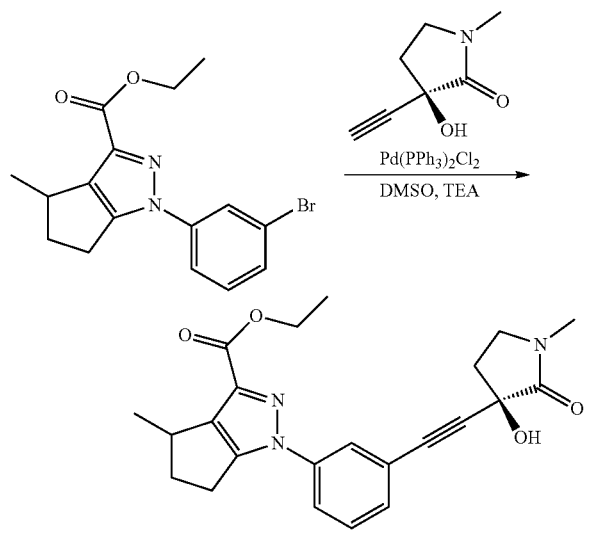

Similar to as described in General Procedure G, ethyl 1-(3-bromophenyl)-4-methyl-1H,4H,5H,6H-cyclopenta[c]pyrazole-3-carboxylate was reacted with (3R)-3-ethynyl-3-hydroxy-1-methylpyrrolidin-2-one to give the title compound (45.0 mg, 55%) as a yellow solid. LC-MS (ES, m/z): 408 [M+H]⁺.

Step 3: Synthesis of (R)-1-(3-(((R)-3-hydroxy-1-methyl-2-oxopyrrolidin-3-yl)ethynyl)phenyl)-4-methyl-1,4,5,6-tetrahydrocyclopenta[c]pyrazole-3-carboxamide and (S)-1-(3-(((R)-3-hydroxy-1-methyl-2-oxopyrrolidin-3-yl)ethynyl)phenyl)-4-methyl-1,4,5,6-tetrahydrocyclopenta[c]pyrazole-3-carboxamide

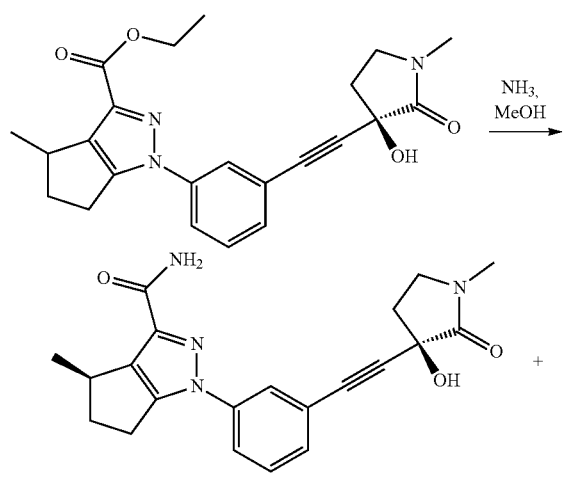

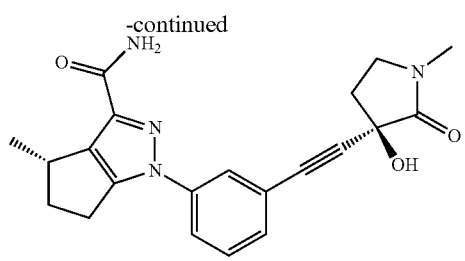

Similar to as described in General Procedure S, ethyl 1-(3-[2-[(3R)-3-hydroxy-1-methyl-2-oxopyrrolidin-3-yl]ethynyl]phenyl)-4-methyl-1H,4H,5H,6H-cyclopenta[c]pyrazole-3-carboxylate was reacted with ammonia to give 2.3 mg (2%) of the 4S-isomer as a white solid and 3.0 mg (6%) of the 4R-isomer as a white solid. The stereochemistry of both isomers was arbitrarily assigned. The 4S-isomer: $t_R$=15.45 min (Chiralcel AD-H, 0.46*15 cm, Hex:IPA=75:25, 1 ml/min); the 4R-isomer: $t_R$=18.92 min (Chiralcel AD-H, 0.46*15 cm, Hex:IPA=75:25, 1 ml/min); Both isomers showed identical LC-MS and ¹H NMR as shown below.

LC-MS (ES, m/z): 379 [M+H]⁺. ¹H NMR (300 MHz, CD₃OD) δ 7.89 (s, 1H), 7.76-7.755 (m, 1H), 7.51-7.41 (m, 2H), 3.57-3.52 (m, 2H), 3.12-3.09 (m, 1H), 2.95 (s, 3H), 2.62-2.57 (m, 1H), 2.38-2.22 (m, 2H), 1.41-1.29 (m, 6H).

Example F6

Synthesis of (R)-1-(3-cyano-5-((3-hydroxy-1-methyl-2-oxopyrrolidin-3-yl)ethynyl)phenyl)-1H-pyrazolo[3,4-b]pyridine-3-carboxamide

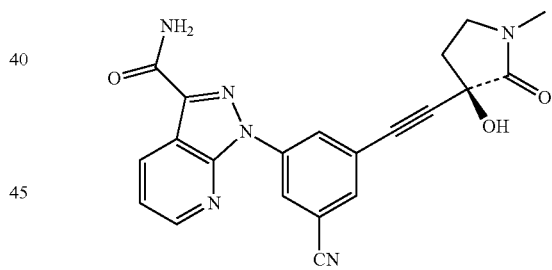

Step 1: Synthesis of 3-bromo-5-(tetramethyl-1,3,2-dioxaborolan-2-yl)benzonitrile

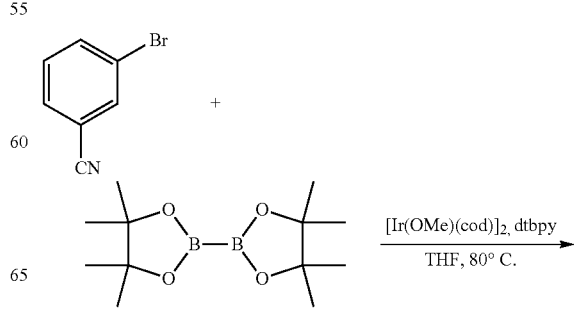

-continued

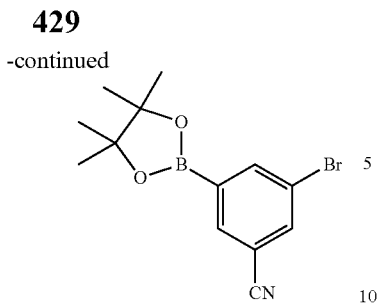

To a stirred solution of 3-bromobenzonitrile (2.00 g, 10.99 mmol, 1.00 equiv) and 4,4,5,5-tetramethyl-2-(tetramethyl-1,3,2-dioxaborolan-2-yl)-1,3,2-dioxaborolane (1.40 g, 5.51 mmol, 0.50 equiv) in tetrahydrofuran (5 mL, 61.71 mmol, 5.60 equiv) was added (1,5-cyclooctadiene)(methoxy)iridium(I) dimerdi-m-methoxobis(1,5-cyclooctadiene)di-iridium (I) (150 mg, 0.23 mmol) and 4-tert-butyl-2-(4-tert-butylpyridin-2-yl)pyridine (90 mg, 0.34 mmol) under nitrogen. The resulting solution was stirred for 14 hours at 80° C. The reaction mixture was concentrated under vacuum. The crude product was purified by a silica gel column with ethyl acetate/petroleum ether (1:5) to give the title compound (1.5 g, 44%) as a white solid.

Step 2: Synthesis of (3-bromo-5-cyanophenyl)boronic acid

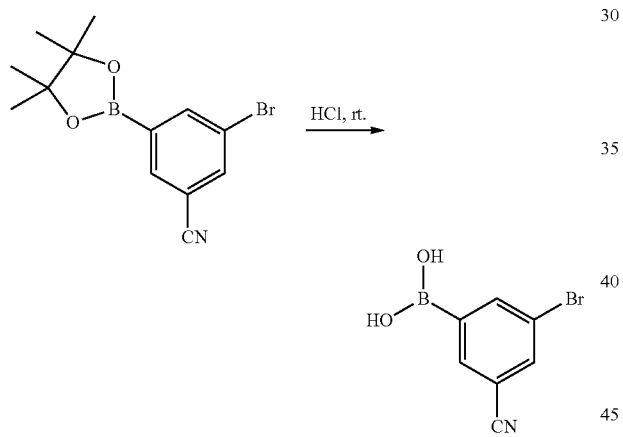

A solution of 3-bromo-5-(tetramethyl-1,3,2-dioxaborolan-2-yl)benzonitrile (1.5 g, 4.87 mmol, 1.00 equiv) in hydrogen chloride (15 mL, 493.68 mmol, 101.40 equiv) was stirred for 10 hours at room temperature. The solids were collected by filtration to give the title compound (750 mg, 68%) as a white solid. LC-MS (ES, m/z): 223, 225 [M–H]$^-$.

Step 3: Synthesis of methyl 1-(3-bromo-5-cyano-phenyl)-1H-pyrazolo[3,4-b]pyridine-3-carboxylate

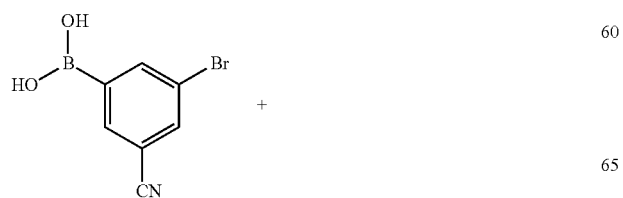

-continued

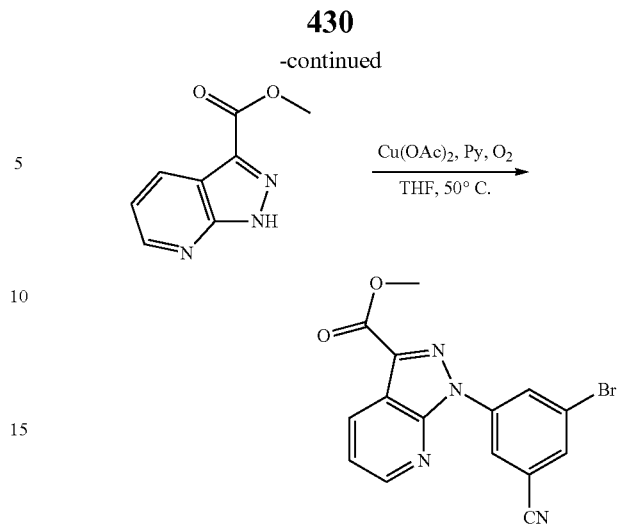

Similar to as described in General Procedure C, 1H-pyrazolo[3,4-b]pyridine-3-carboxylate (360.00 mg, 2.03 mmol, 1.00 equiv) was reacted with (3-bromo-5-cyanophenyl)boronic acid to give the title compound (350 mg, 48%) as a white solid. LC-MS (ES, m/z): 371, 373 [M+H]$^+$.

Step 4: Synthesis of methyl 1-(3-cyano-5-[2-[(3R)-3-hydroxy-1-methyl-2-oxopyrrolidin-3-yl]ethynyl]phenyl)-1H-pyrazolo[3,4-b]pyridine-3-carboxylate

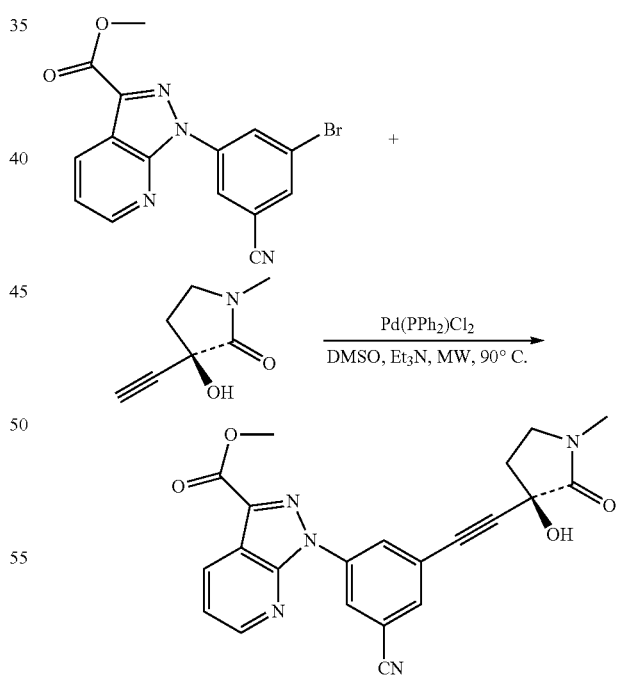

Similar to as described in General Procedure G, methyl 1-(3-bromo-5-cyanophenyl)-1H-pyrazolo[3,4-b]pyridine-3-carboxylate was reacted with (3R)-3-ethynyl-3-hydroxy-1-methylpyrrolidin-2-one to give the title compound (80 mg, 40%) as a white solid. LC-MS (ES, m/z): 430 [M+H]$^+$.

Step 5: Synthesis of 1-(3-cyano-5-[2-[(3R)-3-hydroxy-1-methyl-2-oxopyrrolidin-3-yl]ethynyl]phenyl)-1H-pyrazolo[3,4-b]pyridine-3-carboxamide

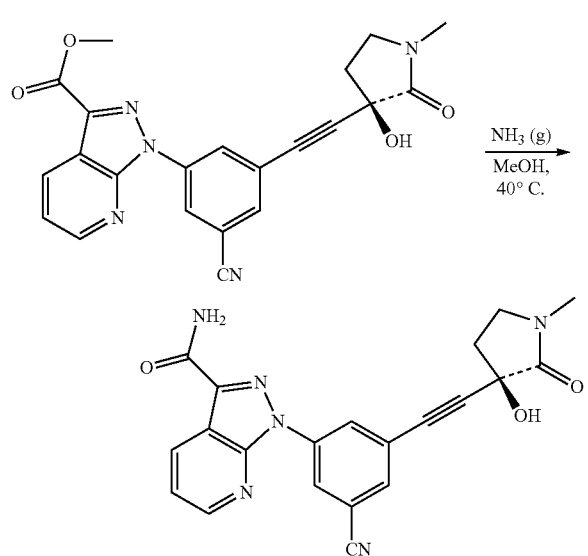

Similar to as described in General Procedure S, methyl 1-(3-cyano-5-[2-[(3R)-3-hydroxy-1-methyl-2-oxopyrrolidin-3-yl]ethynyl]phenyl)-1H-pyrazolo[3,4-b]pyridine-3-carboxylate (90.00 mg, 0.22 mmol, 1.00 equiv) was reacted with ammonia to give the title compound (28.8 mg, 33%) as a white solid. LC-MS (ES, m/z): 401 [M+H]$^+$. $^1$H NMR (CD$_3$OD) δ 9.01-8.98 (m, 2H), 8.80-8.73 (m, 2H), 7.85 (t, J=1.5 Hz, 1H), 7.53 (dd, J=8.1, 4.5 Hz, 1H), 3.57-3.51 (m, 2H), 2.97 (s, 3H), 2.70-2.62 (m, 1H), 2.42-2.33 (m, 1H).

Example G6

Synthesis of (R)-1-(3-((3-hydroxy-1-methyl-2-oxopyrrolidin-3-yl)ethynyl)phenyl)-N5-methyl-1H-indazole-3,5-dicarboxamide

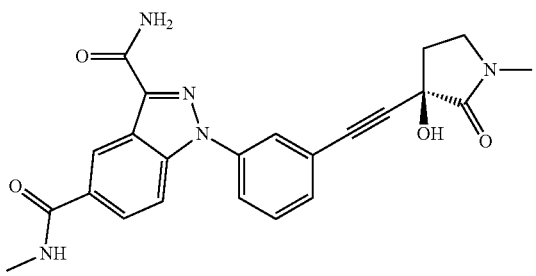

Step 1: Synthesis of 1-(3-bromophenyl)-3-(methoxycarbonyl)-1H-indazole-5-carboxylic acid

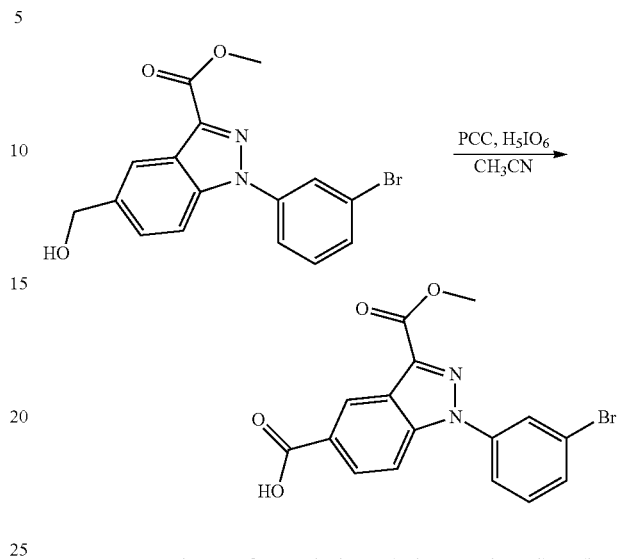

A suspension of methyl 1-(3-bromophenyl)-5-(hydroxymethyl)-1H-indazole-3-carboxylate (144.00 mg, 0.40 mmol, 1.00 equiv), PCC (17.19 mg, 0.08 mmol, 0.20 equiv), periodic acid (199.93 mg, 0.88 mmol, 2.20 equiv) in acetonitrile (10 mL) was stirred for 30 min at room temperature. The resulting solution was diluted with ethyl acetate, washed with brine, dried over anhydrous sodium sulfate and concentrated under vacuum. This resulted in 150 mg (crude) of the title compound as a yellow solid. LC-MS (ES, m/z): 375 [M+H]$^+$.

Step 2: Synthesis of methyl 1-(3-bromophenyl)-5-(methylcarbamoyl)-1H-indazole-3-carboxylate

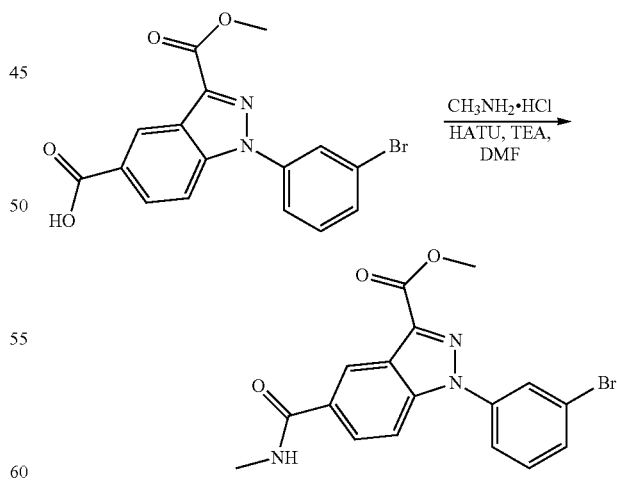

Similar to as described in General Procedure B, 1-(3-bromophenyl)-3-(methoxycarbonyl)-1H-indazole-5-carboxylic acid was reacted with methylamine to give the title compound (140 mg, 75%) as a yellow solid. LC-MS (ES, m/z): 388 [M+H]$^+$.

Step 3: Synthesis of methyl 1-(3-[2-[(3R)-3-hydroxy-1-methyl-2-oxopyrrolidin-3-yl]ethynyl]phenyl)-5-(methylcarbamoyl)-1H-indazole-3-carboxylate

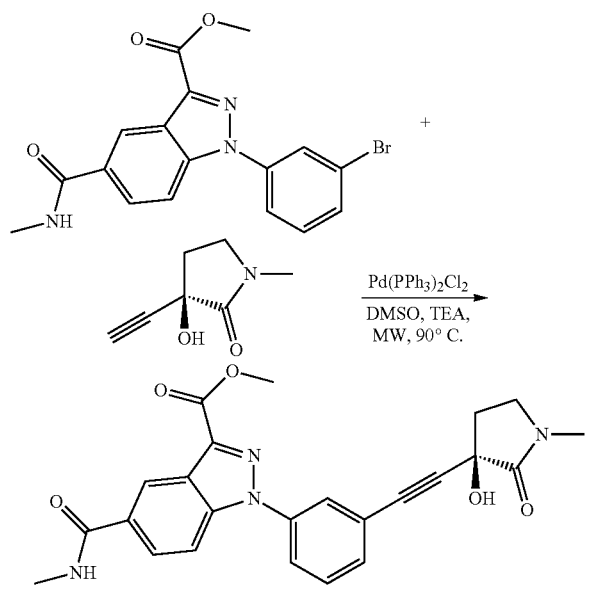

Similar to as described in General Procedure G, methyl 1-(3-bromophenyl)-5-(methylcarbamoyl)-1H-indazole-3-carboxylate was reacted with (3R)-3-ethynyl-3-hydroxy-1-methylpyrrolidin-2-one to give the title compound (140 mg, 94%) as a yellow solid. LC-MS (ES, m/z): 447 [M+H]⁺.

Step 4: Synthesis of 1-(3-[2-[(3R)-3-hydroxy-1-methyl-2-oxopyrrolidin-3-yl]ethynyl]phenyl)-5-N-methyl-1H-indazole-3,5-dicarboxamide

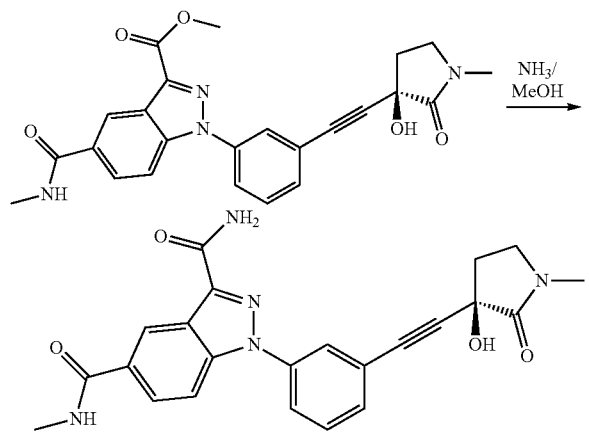

Similar to as described in General Procedure S, methyl 1-(3-[2-[(3R)-3-hydroxy-1-methyl-2-oxopyrrolidin-3-yl]ethynyl]phenyl)-5-(methylcarbamoyl)-1H-indazole-3-carboxylate was reacted with ammonia to give the title compound (34.3 mg, 25%) as an off-white solid. LC-MS (ES, m/z): 432 [M+H]⁺. ¹H NMR (300 MHz, CD₃OD) δ 8.85 (s, 1H), 8.04-7.90 (m, 2H), 7.89-7.86 (m, 2H), 7.67-7.58 (m, 2H), 3.53-3.48 (m, 2H), 2.99 (s, 3H), 2.95 (s, 3H), 2.66-2.58 (m, 1H), 2.39-2.30 (m, 1H).

Example H6

Synthesis of (R)-1-(3-((3-hydroxy-1-methyl-2-oxopyrrolidin-3-yl)ethynyl)phenyl)-5-(1-(2-hydroxyethyl)-1H-pyrazol-4-yl)-1H-indazole-3-carboxamide

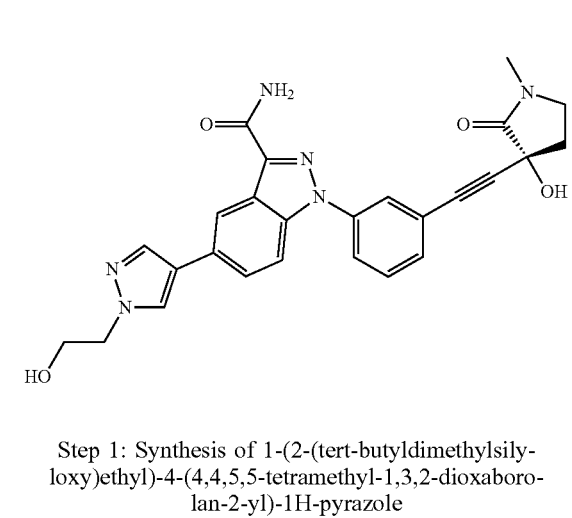

Step 1: Synthesis of 1-(2-(tert-butyldimethylsilyloxy)ethyl)-4-(4,4,5,5-tetramethyl-1,3,2-dioxaborolan-2-yl)-1H-pyrazole

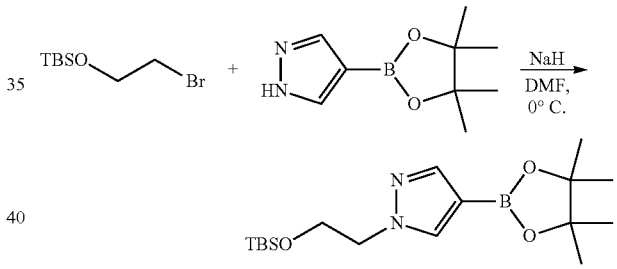

Sodium hydride (148.5 mg, 6.19 mmol, 1.20 equiv) was added in portions to a stirred solution of 4-(tetramethyl-1,3,2-dioxaborolan-2-yl)-1H-pyrazole (1 g, 5.15 mmol, 1.00 equiv) and (2-bromoethoxy)(tert-butyl)dimethylsilane (1.84 g, 7.69 mmol, 1.50 equiv) in DMF (5 mL) at 0° C. The resulting solution was stirred for 6 h at room temperature, quenched by aqueous ammonium chloride, extracted with ethyl acetate, and concentrated under vacuum. The residue was applied onto a silica gel column with ethyl acetate/petroleum ether (10/1). This resulted in 400 mg of the title compound as light-yellow oil.

Step 2: Synthesis of methyl 5-bromo-1-((2-(trimethylsilyl)ethoxy)methyl)-1H-indazole-3-carboxylate

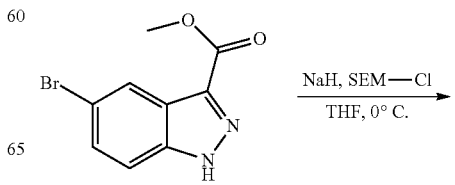

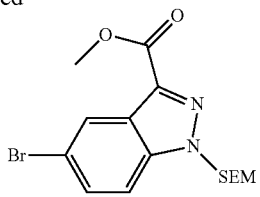

Sodium hydride (23.5 mg, 0.98 mmol, 2.50 equiv) was added to a solution of [2-(chloromethoxy)ethyl]trimethylsilane (97.6 mg, 0.59 mmol, 1.50 equiv) and methyl 5-bromo-1H-indazole-3-carboxylate (100 mg, 0.39 mmol, 1.00 equiv) in THF (3 mL) at 0° C. After 2 hours the reaction was quenched by water, washed with brine, extracted with ethyl acetate, and concentrated under vacuum. This resulted in the title compound (150 mg) as light-yellow oil. LC-MS (ES, m/z): 385 [M+H]+.

Step 3: Synthesis of methyl 5-(1-(2-(tert-butyldimethylsilyloxy)ethyl)-1H-pyrazol-4-yl)-1-((2-(trimethylsilyl)ethoxy)methyl)-1H-indazole-3-carboxylate

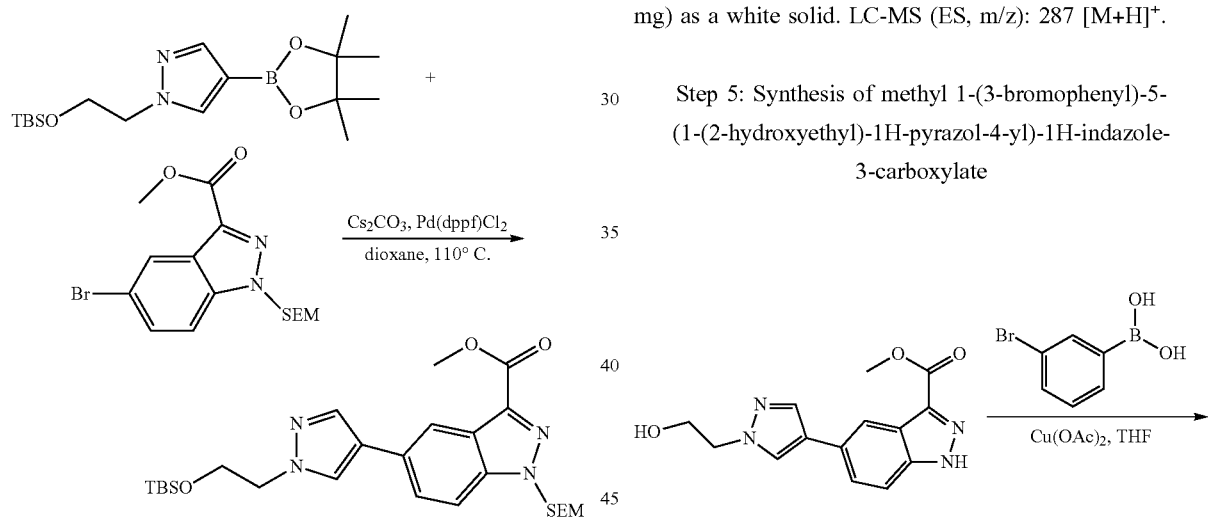

Similar to as described in General Procedure M, 1-[2-[(tert-butyldimethylsilyl)oxy]ethyl]-4-(tetramethyl-1,3,2-dioxabrolan-2-yl)-1H-pyrazole was reacted with methyl 5-bromo-1-[[2-(trimethylsilyl)ethoxy]methyl]-1H-indazole-3-carboxylate to give the title compound (400 mg) as light-yellow oil. LC-MS (ES, m/z): 531 [M+H]+.

Step 4: Synthesis of methyl 5-(1-(2-hydroxyethyl)-1H-pyrazol-4-yl)-1H-indazole-3-carboxylate

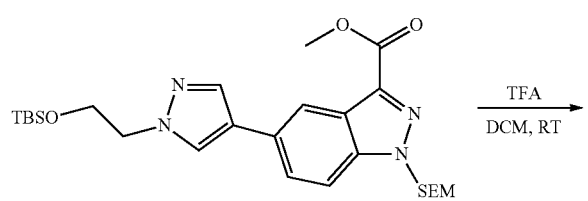

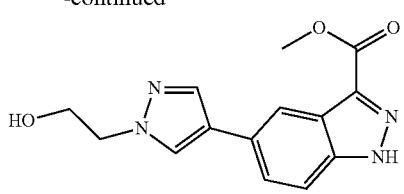

A solution of methyl 5-(1-[2-[(tert-butyldimethylsilyl)oxy]ethyl]-1H-pyrazol-4-yl)-1-[[2-(trimethylsilyl)ethoxy]methyl]-1H-indazole-3-carboxylate (400 mg, 0.75 mmol, 1.00 equiv) and trifluoroacetic acid (1.2 mL) in dichloromethane (3 mL) was stirred for 3 h at room temperature. The reaction was quenched by 10% sodium hydroxide and the pH value of the solution was adjusted to 7 with ammonium chloride. The resulting mixture was extracted with dichloromethane and concentrated under vacuum. The residue was applied onto a silica gel column with dichloromethane/methanol (20/1). This resulted in the title compound (45 mg) as a white solid. LC-MS (ES, m/z): 287 [M+H]+.

Step 5: Synthesis of methyl 1-(3-bromophenyl)-5-(1-(2-hydroxyethyl)-1H-pyrazol-4-yl)-1H-indazole-3-carboxylate Similar to as described in General Procedure C, methyl 5-[1-(2-hydroxyethyl)-1H-pyrazol-4-yl]-1H-indazole-3-carboxylate (45 mg, 0.16 mmol, 1.00 equiv) was reacted with (3-bromophenyl)boronic acid to give the title compound (38 mg, 55%) as a white solid. LC-MS (ES, m/z): 443 [M+H]+.

Step 6: Synthesis of methyl 1-(3-[2-[(3R)-3-hydroxy-1-methyl-2-oxopyrrolidin-3-yl]ethynyl]phenyl)-5-[1-(2-hydroxyethyl)-1H-pyrazol-4-yl]-1H-indazole-3-carboxylate

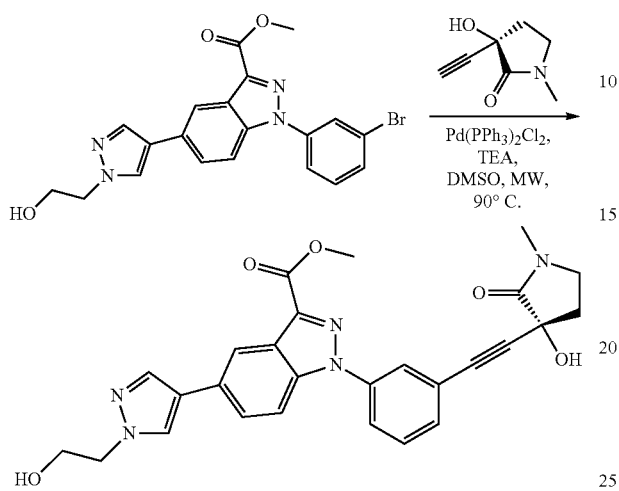

Similar to as described in General Procedure G, methyl 1-(3-bromophenyl)-5-[1-(2-hydroxyethyl)-1H-pyrazol-4-yl]-1H-indazole-3-carboxylate was reacted with (3R)-3-ethynyl-3-hydroxy-1-methylpyrrolidin-2-one to give the title compound (30 mg, 70%) as a white solid. LC-MS (ES, m/z): 500 [M+H]⁺.

Step 7: Synthesis of 1-(3-[2-[(3R)-3-hydroxy-1-methyl-2-oxopyrrolidin-3-yl]ethynyl]phenyl)-5-[1-(2-hydroxyethyl)-1H-pyrazol-4-yl]-1H-indazole-3-carboxamide

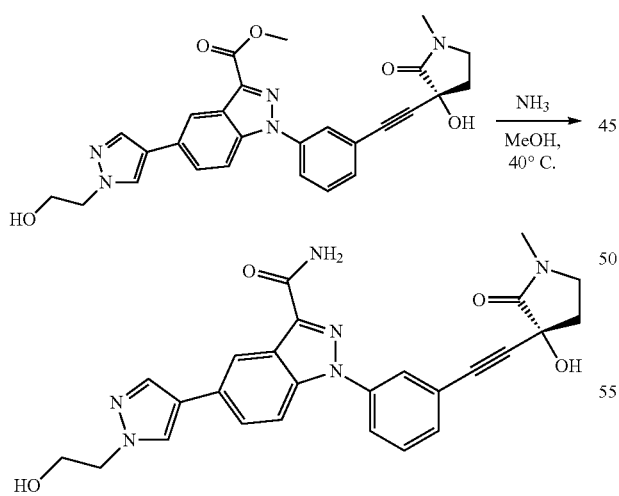

Similar to as described in General Procedure S, methyl 1-(3-[2-[(3R)-3-hydroxy-1-methyl-2-oxopyrrolidin-3-yl]ethynyl]phenyl)-5-[1-(2-hydroxyethyl)-1H-pyrazol-4-yl]-1H-indazole-3-carboxylate was reacted with ammonia to give the title compound (13.1 mg, 45%) as a white solid. LC-MS (ES, m/z): 485 [M+H]⁺. ¹H NMR (300 MHz, CDCl₃) δ 8.52 (s, 1H), 8.13 (s, 1H), 7.98 (s, 2H), 7.97-7.79 (m, 3H), 7.56-7.67 (m, 2H), 4.30-4.33 (t, J=10.8 Hz, 2H), 3.95-3.98 (t, J=5.4 Hz, 2H), 3.49-3.54 (t, J=13.8 Hz, 2H), 2.96 (s, 3H), 2.59-2.67 (m, 1H), 2.31-2.40 (m, 1H).

Example 16

Synthesis of (R)-1-(3-((3-hydroxy-1-methyl-2-oxopyrrolidin-3-yl)ethynyl)phenyl)-1H-pyrazolo[3,4-d]pyrimidine-3-carboxamide

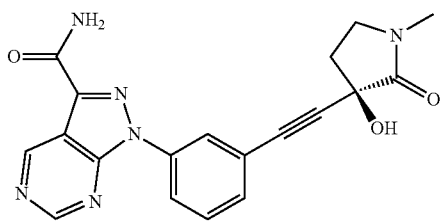 [SMILES: CN1CC[C@@](O)(C#Cc2cccc(-n3nc(C(N)=O)c4cncnc43)c2)C1=O]

Step 1: Synthesis of ethyl 1-(3-bromophenyl)-1H-pyrazolo[3,4-d]pyrimidine-3-carboxylate

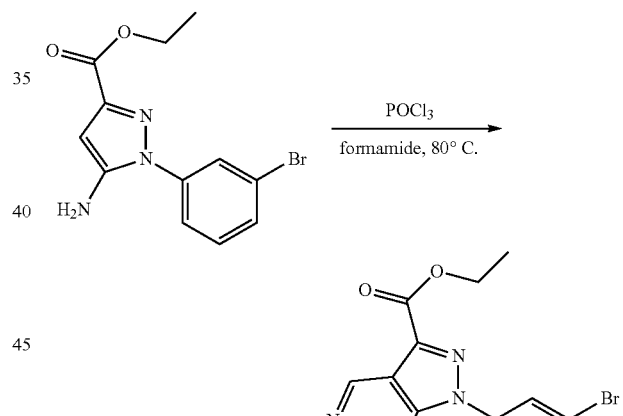

To a solution of ethyl 5-amino-1-(3-bromophenyl)-1H-pyrazole-3-carboxylate (500.00 mg, 1.61 mmol, 1.00 equiv) in formamide (10 mL) was added phosphoryl trichloride (1 mL, 10.73 mmol, 6.70 equiv) dropwise. The mixture was stirred overnight at 80° C. and quenched by NaHCO₃ in an ice-water bath. The resulting mixture was extracted ethyl acetate, dried over anhydrous sodium sulfate, and concentrated under vacuum. The residue was applied onto a silica gel column with ethyl acetate/petroleum ether (1:4). This resulted in 60 mg (11%) of the title compound as a yellow solid. LC-MS (ES, m/z): 347, 349 [M+H]⁺.

Step 2: Synthesis of ethyl 1-(3-[2-[(3R)-3-hydroxy-1-methyl-2-oxopyrrolidin-3-yl]ethynyl]phenyl)-1H-pyrazolo[3,4-d]pyrimidine-3-carboxylate

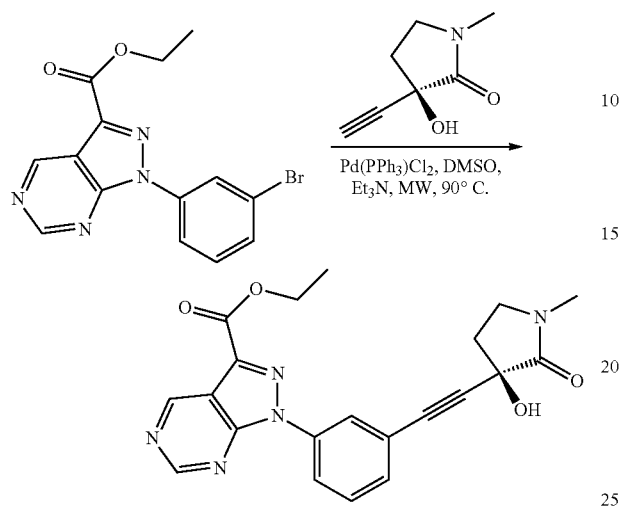

Similar to as described in General Procedure G, ethyl 1-(3-bromophenyl)-1H-pyrazolo[3,4-d]pyrimidine-3-carboxylate was reacted with (3R)-3-ethynyl-3-hydroxy-1-methylpyrrolidin-2-one to give the title compound (80 mg, 62%) as a yellow solid. LC-MS (ES, m/z): 406 [M+H]⁺.

Step 3: Synthesis of 1-(3-[2-[(3R)-3-hydroxy-1-methyl-2-oxopyrrolidin-3-yl]ethynyl]phenyl)-1H-pyrazolo[3,4-d]pyrimidine-3-carboxamide

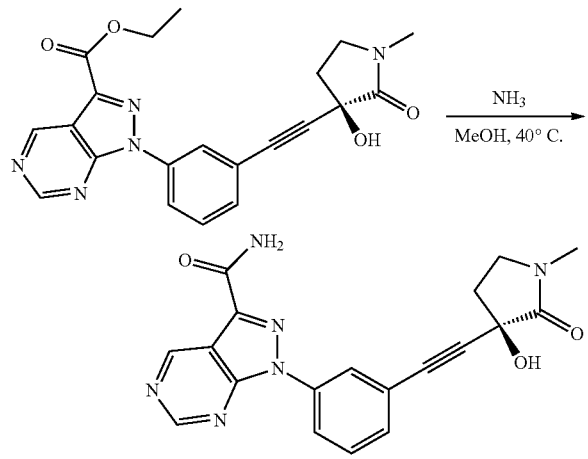

Similar to as described in General Procedure S, ethyl 1-(3-[2-[(3R)-3-hydroxy-1-methyl-2-oxopyrrolidin-3-yl]ethynyl]phenyl)-1H-pyrazolo[3,4-d]pyrimidine-3-carboxylate was reacted with ammonia to give the title compound (35.8 mg, 48%) as a white solid. LC-MS (ES, m/z): 377 [M+H]⁺. ¹H NMR (300 MHz, CD₃OD) δ 9.70 (s, 1H), 9.18 (s, 1H), 8.51 (s, 1H), 8.44-8.40 (m, 1H), 7.63-7.52 (m, 2H), 3.53-3.48 (m, 2H), 2.95 (s, 3H), 2.66-2.58 (m, 1H), 2.39-2.30 (m, 1H).

Example J6 and Example K6

Synthesis of (R)-1-(3-((1-hydroxy-2-oxocyclopentyl)ethynyl)phenyl)-1H-indazole-3-carboxamide and (S)-1-(3-((1-hydroxy-2-oxocyclopentyl)ethynyl)phenyl)-1H-indazole-3-carboxamide

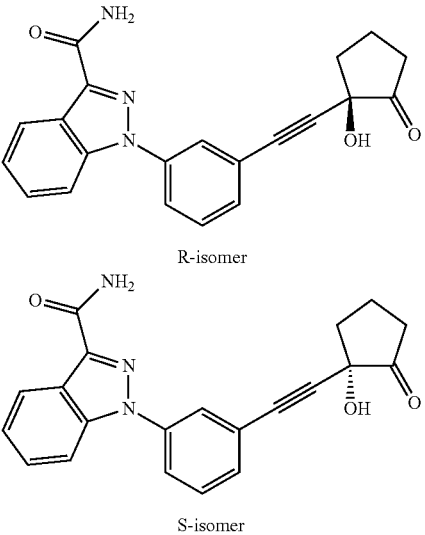

Step 1: Synthesis of 2-oxocyclopentyl acetate

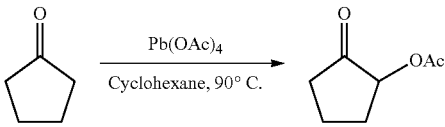 [SMILES: O=C1CCCC1 ; CC(=O)OC1CCCC1=O ; "Pb(OAc)4"]

A mixture of cyclopentanone (10 g, 118.88 mmol, 1.00 equiv) and lead tetraacetate (57.6 g, 129.91 mmol, 1.1 equiv) in cyclohexane (100 mL) was stirred overnight at 90° C. The reaction mixture was cooled to room temperature and 100 mL of 1 N hydrogen chloride was added. After being stirred for 1 hour the solids were filtered out. The aqueous layer was extracted with ethyl acetate, dried over anhydrous sodium sulfate, and concentrated under vacuum. The crude product was purified by a silica gel column with ethyl acetate/petroleum ether (1:10) to give the title compound (1.6 g, 9%) as yellow oil.

Step 2: Synthesis of 2-ethynyl-2-hydroxycyclopentyl acetate

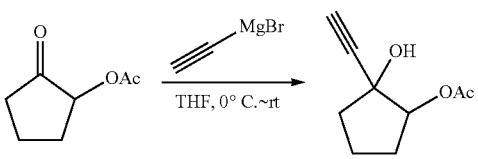

To a solution of 2-oxocyclopentyl acetate (800 mg, 5.63 mmol, 1.00 equiv) in THF (5 mL) was added bromo(ethynyl)magnesium (13.5 mL, 1.00 equiv, 0.5 M in THF) dropwise at 0° C. After being stirred for 2 hours at room temperature the reaction was quenched with saturated aqueous ammonium chloride, extracted with ethyl acetate, dried over anhydrous sodium sulfate, and concentrated under vacuum. This resulted in the title compound (680 mg, 72%) as a brown solid.

Step 3: Synthesis of 1-ethynylcyclopentane-1,2-diol

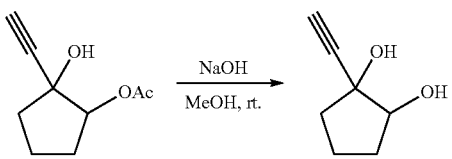

To a solution of 2-ethynyl-2-hydroxycyclopentyl acetate (680 mg, 4.04 mmol, 1.00 equiv) in methanol (10 mL) was added sodium hydroxide (1.079 g, 26.98 mmol, 6.70 equiv) in water (5 mL). After one hour the pH value of the solution was adjusted to 7 with hydrochloric acid (1 M). The resulting mixture was concentrated under vacuum. The aqueous layer was extracted with ethyl acetate and the organic layers were combined and dried over anhydrous sodium sulfate. The concentrated residue was purified by a silica gel column with ethyl acetate/petroleum ether (1:10) to give the title compound (400 mg, 78%) as yellow oil.

Step 4: Synthesis of 2-ethynyl-2-hydroxycyclopentan-1-one

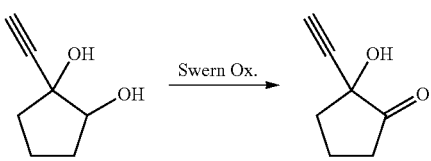

To a solution of dimethyl sulfoxide (278.71 mg, 3.57 mmol, 1.50 equiv) in dichloromethane (24 mL) was added oxalyl chloride (150.92 mg, 1.19 mmol, 1.50 equiv) at −78° C. After one hour 1-ethynylcyclopentane-1,2-diol (300.00 mg, 2.38 mmol, 1.00 equiv) was added. After another 2 hours triethylamine (1203.18 mg, 11.89 mmol, 5.0 equiv) was added to the stirred mixture and the reaction was warmed slowly to room temperature. The resulting solution was diluted with dichloromethane, washed with water, extracted with dichloromethane, dried over anhydrous sodium sulfate, and concentrated under vacuum. The crude product was purified by a silica gel column with ethyl acetate/petroleum ether (1:4) to give the title compound (110 mg, 37%) as reddish liquid.

Step 5: Synthesis of (R)-1-(3-((1-hydroxy-2-oxocyclopentyl)ethynyl)phenyl)-1H-indazole-3-carboxamide and (S)-1-(3-((1-hydroxy-2-oxocyclopentyl)ethynyl)phenyl)-1H-indazole-3-carboxamide

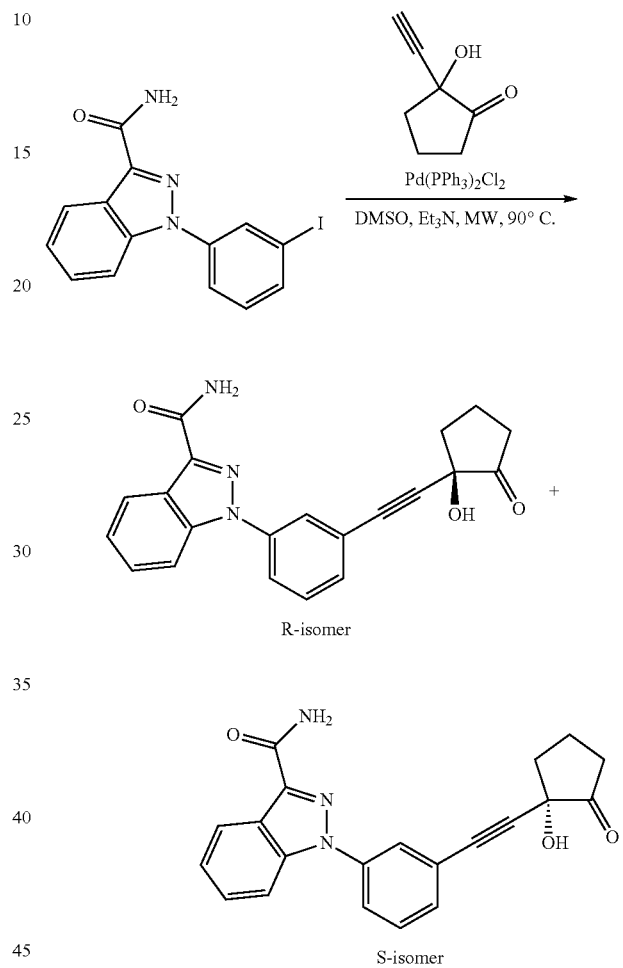

Similar to as described in General Procedure G, 1-(3-iodophenyl)-1H-indazole-3-carboxamide was reacted with 2-ethynyl-2-hydroxycyclopentan-1-one to give a R/S mixture. After chiral separation 12.4 mg (15%) of the R-isomer and 14.4 mg (17%) of the S-isomer were isolated as white solid. The stereochemistry of both isomers was arbitrarily assigned. The R-isomer: $t_R$=12.41 min (Chiralcel OJ-3, 0.46*15 cm, Hex: EtOH=70:30, 1.0 ml/min); The S-isomer B: $t_R$=16.43 min (Chiralcel OJ-3, 0.46*15 cm, Hex: EtOH=70:30, 1.0 ml/min). Both isomers showed identical LC-MS and $^1$H NMR as shown below. LC-MS (ES, m/z): 360 [M+H]$^+$. $^1$H NMR (400 MHz, CD$_3$OD) δ 8.24 (s, 1H), 7.85 (s, 1H), 7.80-7.70 (m, 2H), 7.53-7.42 (m, 3H), 7.29 (t, J=7.2 Hz, 1H), 2.45-2.07 (m, 3H), 2.03-1.94 (m, 2H).

Example L6 and Example M6

Synthesis of (S)-1-(3-(3-hydroxy-3-(1H-1,2,3-triazol-4-yl)but-1-ynyl)phenyl)-1H-indazole-3-carboxamide and (R)-1-(3-(3-hydroxy-3-(1H-1,2,3-triazol-4-yl)but-1-ynyl)phenyl)-1H-indazole-3-carboxamide

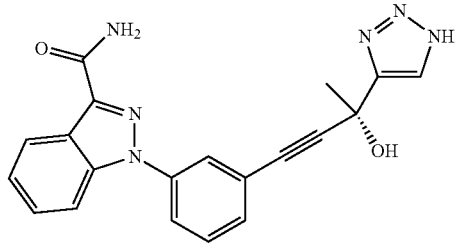

3 S-isomer

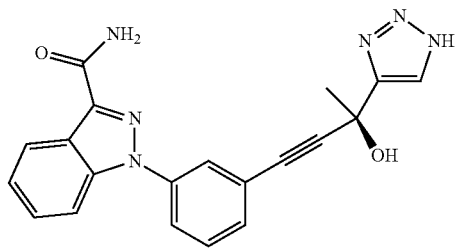

3 R-isomer

Step 1: Synthesis of 1-[[2-(trimethylsilyl)ethoxy]methyl]-1H-1,2,3-triazole

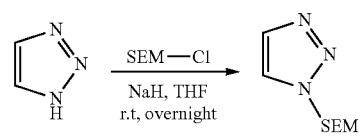

Sodium hydride (5.3 g, 220.85 mmol, 1.50 equiv) was added in portions to a stirred mixture of 1H-1,2,3-triazole (10 g, 144.79 mmol, 1.00 equiv) in THF (500 mL) at 0° C. under nitrogen. After 1 hour 2-(trimethylsilyl)ethoxymethyl chloride (36 g, 235.76 mmol, 1.60 equiv) was added and the resulting solution was stirred for 12 h at room temperature. The reaction was quenched by water, extracted with ethyl acetate, dried over anhydrous sodium sulfate, and concentrated under vacuum. The residue was applied onto a silica gel column with ethyl acetate/petroleum ether (1:10). This resulted in 10 g (28%) of the title compound as yellow oil. LC-MS (ES, m/z): 200 [M+H]$^+$.

Step 2: Synthesis of 4-(trimethylsilyl)-2-(1-[[2-(trimethylsilyl)ethoxy]methyl]-1H-1,2,3-triazol-4-yl)but-3-yn-2-ol

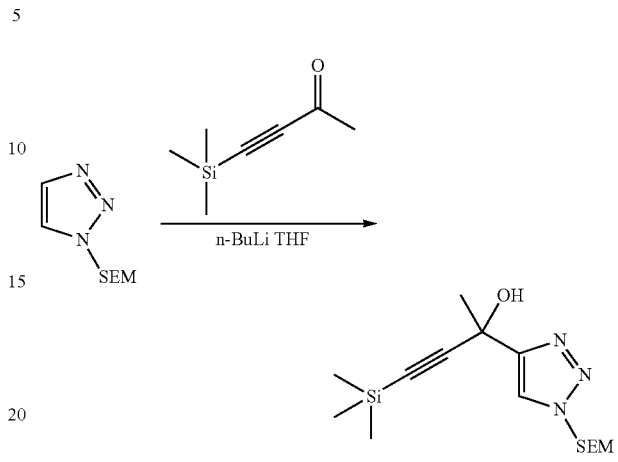

n-Butyllithium (2.5M in hexanes) (12 g, 187.34 mmol, 1.20 equiv) was added dropwise to a stirred solution of 1-[[2-(trimethylsilyl)ethoxy]methyl]-1H-1,2,3-triazole (5 g, 25.08 mmol, 1.00 equiv) in THF (100 mL) at −78° C. under nitrogen. After 1 hour 4-(trimethylsilyl)but-3-yn-2-one (4.6 g, 32.80 mmol, 1.30 equiv) was added and the resulting solution was stirred for 12 h at room temperature. The reaction was quenched by saturated aqueous ammonium chloride, extracted with ethyl acetate, dried over anhydrous sodium sulfate, and concentrated under vacuum. The residue was applied onto a silica gel column with ethyl acetate/petroleum ether (1:20). This resulted in 2.3 g (22%) of the title compound as yellow oil. LC-MS (ES, m/z): 340 [M+H]$^+$.

Step 3: Synthesis of 2-(1-[[2-(trimethylsilyl)ethoxy]methyl]-1H-1,2,3-triazol-4-yl)but-3-yn-2-ol

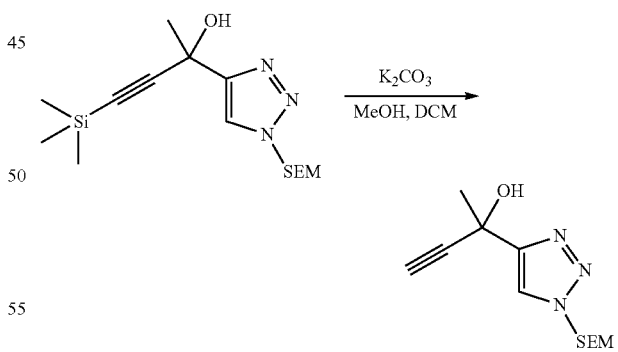

A mixture of 4-(trimethylsilyl)-2-(1-[[2-(trimethylsilyl)ethoxy]methyl]-1H-1,2,3-triazol-4-yl)but-3-yn-2-ol (1.97 g, 5.80 mmol, 1.00 equiv) and potassium carbonate (370 mg, 2.68 mmol, 1.00 equiv) in dichloromethane (5 mL)/methanol (5 mL) was stirred for 1 h at room temperature. The pH value of the solution was adjusted to 6 with 1N hydrogen chloride. The resulting solution was extracted with ethyl acetate and dried over anhydrous sodium sulfate. The residue was applied onto a silica gel column with ethyl acetate/ petroleum ether (1:1). This resulted in 1.4 g of the title compound as yellow oil. LC-MS (ES, m/z): 268 [M+H]⁺.

Step 4: Synthesis of methyl 1-[3-[3-hydroxy-3-(1-[[2-(trimethylsilyl)ethoxy]methyl]-1H-1,2,3-triazol-4-yl)but-1-yn-1-yl]phenyl]-1H-indazole-3-carboxylate

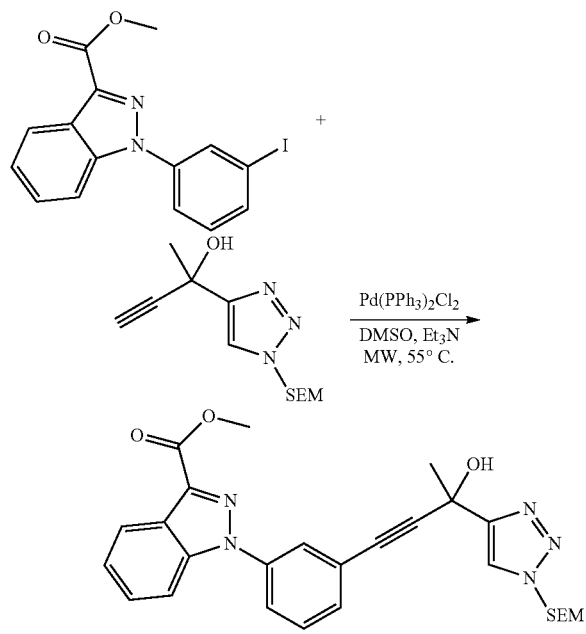

Similar to as described in General Procedure G, methyl 1-(3-iodophenyl)-1H-indazole-3-carboxylate was reacted with 2-(1-[[2-(trimethylsilyl)ethoxy]methyl]-1H-1,2,3-triazol-4-yl)but-3-yn-2-ol to give the title compound (200 mg, 56%) as yellow oil. LC-MS (ES, m/z): 518 [M+H]⁺.

Step 5: Synthesis of 1-[3-[3-hydroxy-3-(1-[[2-(trimethylsilyl)ethoxy]methyl]-1H-1,2,3-triazol-4-yl)but-1-yn-1-yl]phenyl]-1H-indazole-3-carboxamide

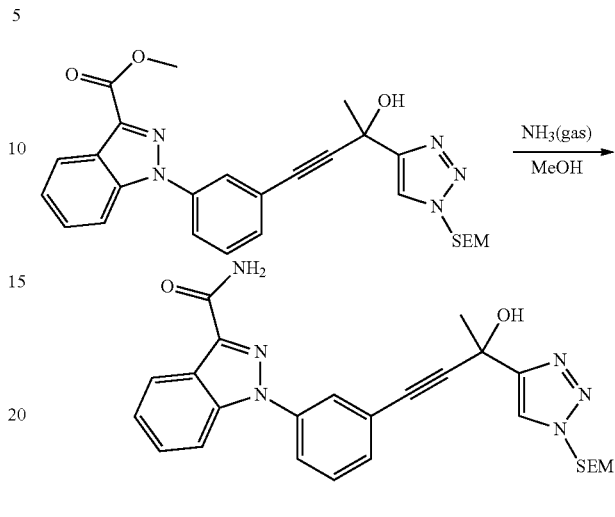

Similar to as described in General Procedure S, methyl 1-[3-[3-hydroxy-3-(1-[[2-(trimethylsilyl)ethoxy]methyl]-1H-1,2,3-triazol-4-yl)but-1-yn-1-yl]phenyl]-1H-indazole-3-carboxylate was reacted with ammonia to give the title compound (130 mg, 64%) as yellow oil. LC-MS (ES, m/z): 503 [M+H]⁺.

Step 6: Synthesis of (S)-1-(3-(3-hydroxy-3-(1H-1,2,3-triazol-4-yl)but-1-ynyl)phenyl)-1H-indazole-3-carboxamide and (R)-1-(3-(3-hydroxy-3-(1H-1,2,3-triazol-4-yl)but-1-ynyl)phenyl)-1H-indazole-3-carboxamide

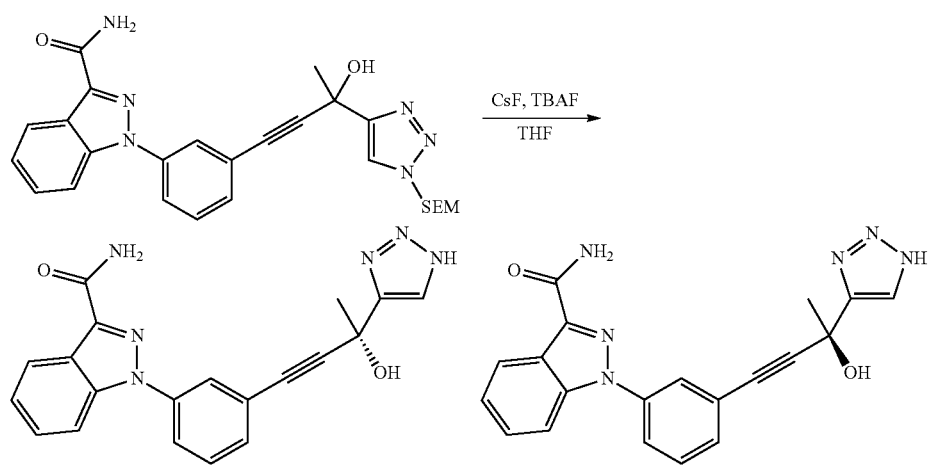

A mixture of 1-[3-[3-hydroxy-3-(1-[[2-(trimethylsilyl)ethoxy]methyl]-1H-1,2,3-triazol-4-yl)but-1-yn-1-yl]phenyl]-1H-indazole-3-carboxamide (150.00 mg, 0.30 mmol, 1.00 equiv), CsF (180 mg, 1.18 mmol, 4.00 equiv), and tetrabutylammonium fluoride (78 mg, 1.00 equiv) in THF (30 mL) was stirred overnight at room temperature. The resulting mixture was concentrated under vacuum and the crude product (500 mg) was purified by Prep-HPLC and separated by Chiral-Prep-HPLC. This resulted in 30.5 mg (26%) of the 3 S-isomer as a white solid and 35.6 mg (31%) of the 3R-isomer as a white solid. The stereochemistry of both isomers was arbitrarily assigned. The 3S-isomer: $t_R$=9.64 min (Chiralcel OJ-3, 0.46*15 cm, Hex: EtOH=70:30, 1.0 ml/min); The 3R-isomer: $t_R$=12.64 min (Chiralcel OJ-3, 0.46*15 cm, Hex: EtOH=70:30, 1.0 ml/min). Both isomers showed identical LC-MS and $^1$H NMR as shown below. LC-MS (ES, m/z): 373 [M+H]$^+$. $^1$H NMR (300 Hz, DMSO-$d_6$) δ 8.32-8.29 (d, J=8.1 Hz, 1H), 8.04 (s, 1H), 7.93-7.87 (m, 4H), 7.67-7.52 (m, 4H), 7.42-7.37 (m, 1H), 6.38 (s, 1H), 1.86 (s, 1H).

Example N6

Synthesis of (R)-1-(3-((3-hydroxy-1-methyl-2-oxopyrrolidin-3-yl)ethynyl)phenyl)-1,4,5,6-tetrahydrocyclopenta[c]pyrazole-3-carboxamide

Step 1: Synthesis of ethyl 2-oxo-2-(2-oxocyclopentyl)acetate

Similar to as described in General Procedure Y Step 1, diethyl oxalate was reacted with cyclopentanone to give the title compound (25 g, 76%) as yellow oil. LC-MS (ES, m/z): 185 [M+H]$^+$.

Step 2: Synthesis of ethyl 1-(3-bromophenyl)-1H,4H,5H,6H-cyclopenta[c]pyrazole-3-carboxylate

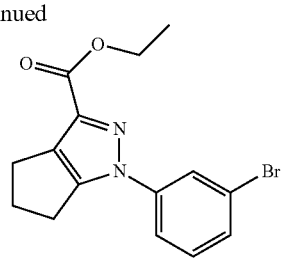

Similar to as described in General Procedure Y Step 2, ethyl 2-oxo-2-(2-oxocyclopentyl)acetate was reacted with (3-bromophenyl)hydrazine hydrochloride to give the title compound (6 g, 66%) as a yellow solid. LC-MS (ES, m/z): 335, 337 [M+H]$^+$.

Step 3: Synthesis of 1-(3-[2-[(3R)-3-hydroxy-1-methyl-2-oxopyrrolidin-3-yl]ethynyl]phenyl)-1H,4H,5H,6H-cyclopenta[c]pyrazole-3-carboxylate

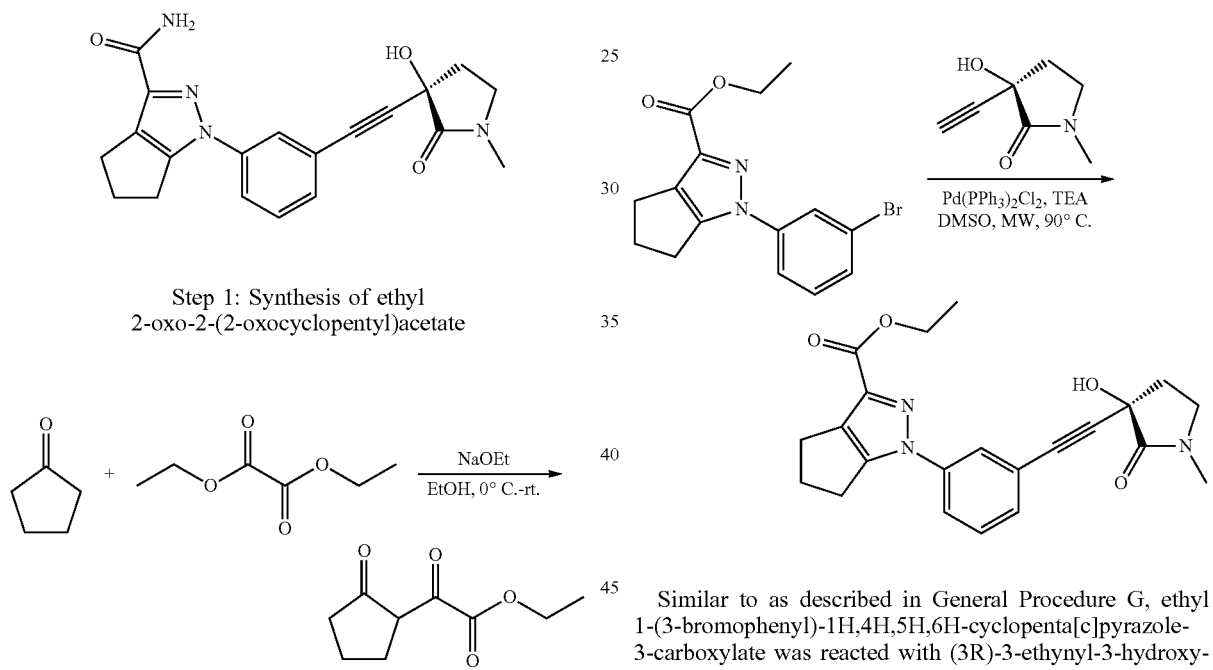

Similar to as described in General Procedure G, ethyl 1-(3-bromophenyl)-1H,4H,5H,6H-cyclopenta[c]pyrazole-3-carboxylate was reacted with (3R)-3-ethynyl-3-hydroxy-1-methylpyrrolidin-2-one to give the title compound (1.1 g, crude) as a yellow solid. LC-MS (ES, m/z): 394 [M+H]$^+$.

Step 4: Synthesis of 1-(3-[2-[(3R)-3-hydroxy-1-methyl-2-oxopyrrolidin-3-yl]ethynyl]phenyl)-1H,4H,5H,6H-cyclopenta[c]pyrazole-3-carboxamide

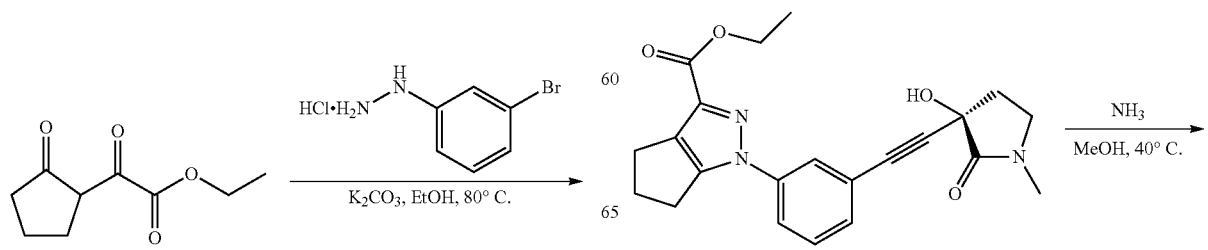

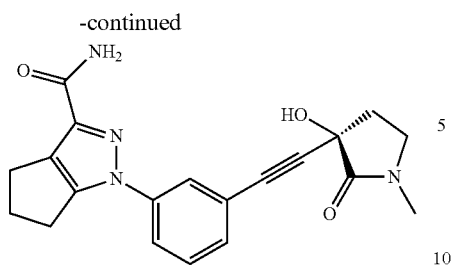

Similar to as described in General Procedure S, ethyl 1-(3-[2-[(3R)-3-hydroxy-1-methyl-2-oxopyrrolidin-3-yl]ethynyl]phenyl)-1H,4H,5H,6H-cyclopenta[c]pyrazole-3-carboxylate was reacted with ammonia to give the title compound (541.8 mg, 53%) as a white solid. LC-MS (ES, m/z): 365 [M+H]$^+$. $^1$H NMR (300 MHz, CD$_3$OD) δ 7.87 (s, 1H), 7.76-7.72 (m, 1H), 7.51-7.40 (m, 2H), 3.49 (t, J=6.0 Hz, 2H), 3.07 (t, J=6.9 Hz, 2H), 2.94 (s, 3H), 2.84 (t, J=6.9 Hz, 2H), 2.72-2.56 (m, 3H), 2.37-2.24 (m, 1H).

Example O6

Synthesis of (R)-1-(3-((3-hydroxy-1-methyl-2-oxopyrrolidin-3-yl)ethynyl)phenyl)-5-(pyrimidin-4-yl)-4,5,6,7-tetrahydro-1H-pyrazolo[4,3-c]pyridine-3-carboxamide

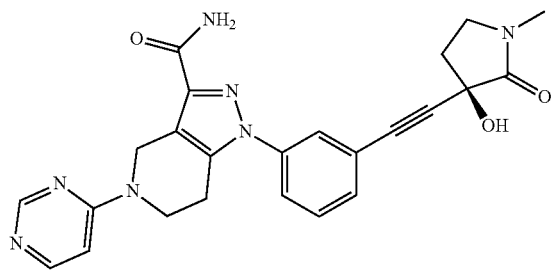 [SMILES: CN1CC[C@@](O)(C#Cc2cccc(-n3nc(C(N)=O)c4c3CCN(c3ccncn3)C4)c2)C1=O]

Step 1: Synthesis of 1-(3-bromophenyl)-5-(pyrimidin-4-yl)-1H,4H,5H,6H,7H-pyrazolo[4,3-c]pyridine-3-carboxylate

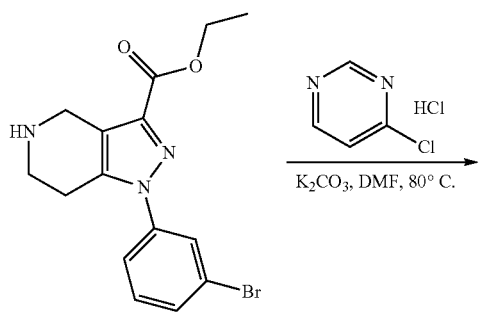

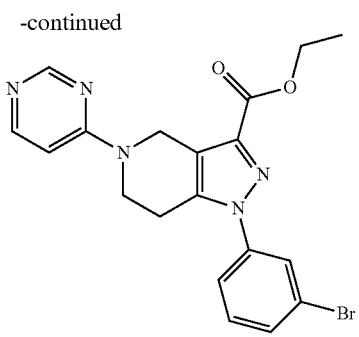

A mixture of ethyl 1-(3-bromophenyl)-1H,4H,5H,6H,7H-pyrazolo[4,3-c]pyridine-3-carboxylate (200.00 mg, 0.43 mmol, 1.00 equiv) in DMF (4.00 mL), 4-chloropyrimidine hydrochloride (65.05 mg, 0.43 mmol, 1.00 equiv), and potassium carbonate (238.17 mg, 1.72 mmol, 4.00 equiv) was stirred for 4 h at 80° C. in a sealed tube under nitrogen. The reaction was quenched by water, extracted with ethyl acetate, washed with brine, dried over anhydrous sodium sulfate, and concentrated under vacuum. The residue was applied onto a silica gel column with ethyl acetate/petroleum ether (2:1). This resulted in 160 mg (87%) of the title compound as yellow oil. LC-MS (ES, m/z): 428, 430 [M+H]$^+$.

Step 2: Synthesis of ethyl 1-(3-[2-[(3R)-3-hydroxy-1-methyl-2-oxopyrrolidin-3-yl]ethynyl]phenyl)-5-(pyrimidin-4-yl)-1H,4H,5H,6H,7H-pyrazolo[4,3-c]pyridine-3-carboxylate

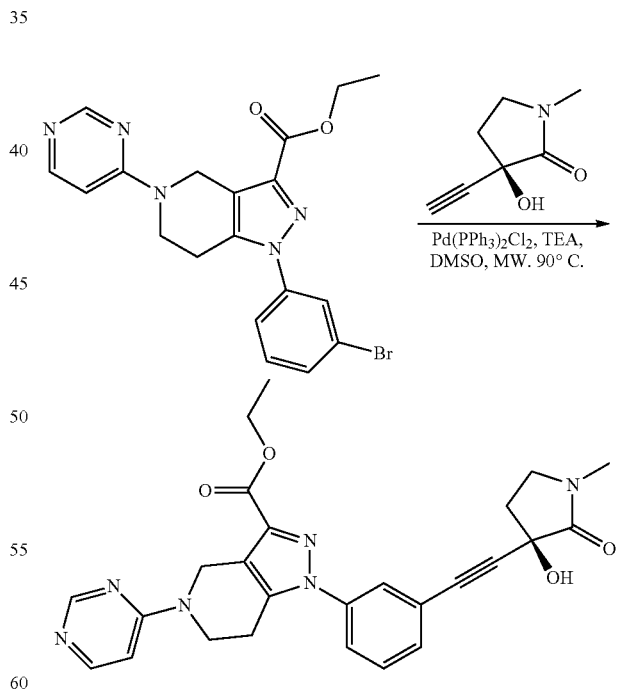

Similar to as described in General Procedure G, ethyl 1-(3-bromophenyl)-5-(pyrimidin-4-yl)-1H,4H,5H,6H,7H-pyrazolo[4,3-c]pyridine-3-carboxylate was reacted with (3R)-3-ethynyl-3-hydroxy-1-methylpyrrolidin-2-one to give the title compound (120 mg, 70%) as yellow oil. LC-MS (ES, m/z): 487 [M+H]$^+$.

451

Step 3: Synthesis of 1-(3-[2-[(3R)-3-hydroxy-1-methyl-2-oxopyrrolidin-3-yl]ethynyl]phenyl)-5-(pyrimidin-4-yl)-1H,4H,5H,6H,7H-pyrazolo[4,3-c]pyridine-3-carboxamide

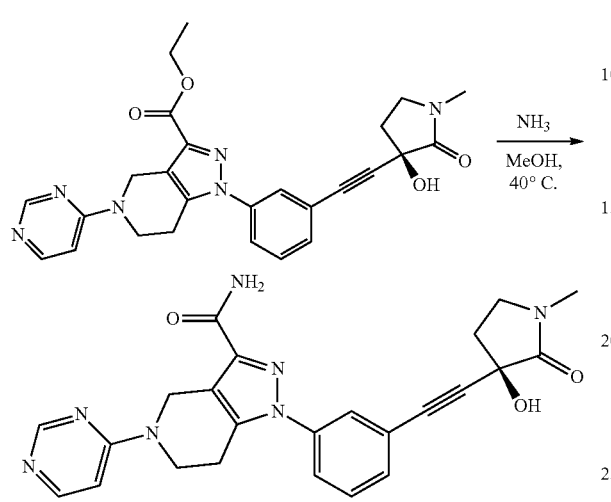

Similar to as described in General Procedure S, ethyl 1-(3-[2-[(3R)-3-hydroxy-1-methyl-2-oxopyrrolidin-3-yl]ethynyl]phenyl)-5-(pyrimidin-4-yl)-1H,4H,5H,6H,7H-pyrazolo[4,3-c]pyridine-3-carboxylate was reacted with ammonia to give the title compound (15.3 mg, 14%) as an off-white solid. LC-MS (ES, m/z): 458 [M+H]+. 1H NMR (300 MHz, CD3OD) δ 8.53 (s, 1H), 8.20 (d, J=6.3 Hz, 1H), 7.75 (s, 1H), 7.67-7.62 (m, 1H), 7.57-7.52 (m, 2H), 6.92 (d, J=6.3 Hz, 1H), 4.97 (s, 2H), 4.10 (t, J=5.7 Hz, 2H), 3.55-3.46 (m, 2H), 3.08-3.01 (m, 2H), 2.99 (s, 3H), 2.63-2.55 (m, 1H), 2.37-2.32 (m, 1H).

Example P6

Synthesis of (R)-1-(3-((3-hydroxy-1-methyl-2-oxopyrrolidin-3-yl)ethynyl)phenyl)-5-(pyrimidin-2-yl)-4,5,6,7-tetrahydro-1H-pyrazolo[4,3-c]pyridine-3-carboxamide

452

Step 1: Synthesis of ethyl 1-(3-bromophenyl)-5-(pyrimidin-2-yl)-1H,4H,5H,6H,7H-pyrazolo[4,3-c]pyridine-3-carboxylate

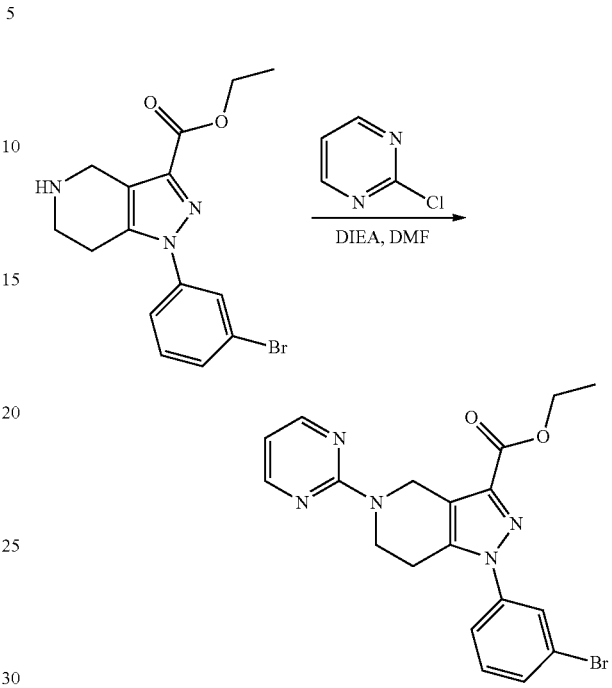

A mixture of 2-chloropyrimidine (37.01 mg, 0.32 mmol, 1.00 equiv) in DMF (2.00 mL), ethyl 1-(3-bromophenyl)-1H,4H,5H,6H,7H-pyrazolo[4,3-c]pyridine-3-carboxylate (150.00 mg, 0.32 mmol, 1.00 equiv), and ethyldiisopropylamine (847.73 mg, 6.56 mmol, 20.30 equiv) in a sealed tube under nitrogen was stirred for 12 h at 80° C. The reaction was quenched by water, extracted with ethyl acetate, and washed with brine. The solids were filtered out and the liquid was concentrated under vacuum. The residue was applied onto a silica gel column with ethyl acetate/petroleum ether (1:3). This resulted in 80 mg (58%) of the title compound as a yellow solid. LC-MS (ES, m/z): 428, 430 [M+H]+.

Step 2: Synthesis of ethyl 1-(3-[2-[(3R)-3-hydroxy-1-methyl-2-oxopyrrolidin-3-yl]ethynyl]phenyl)-5-(pyrimidin-2-yl)-1H,4H,5H,6H,7H-pyrazolo[4,3-c]pyridine-3-carboxylate

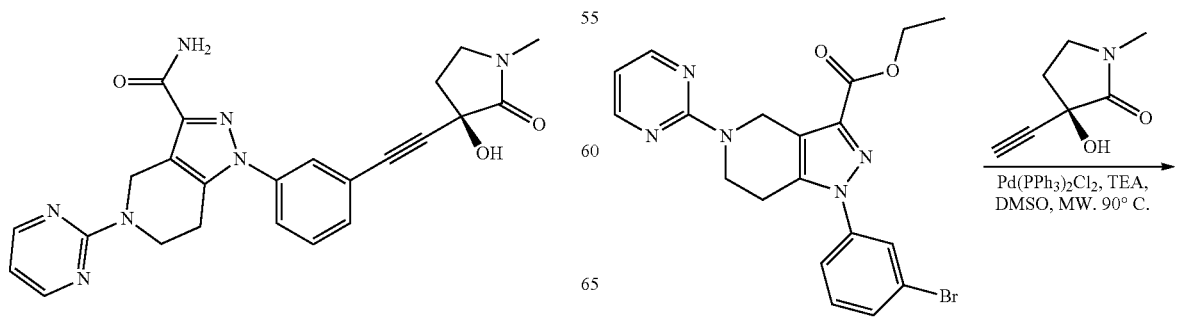

-continued

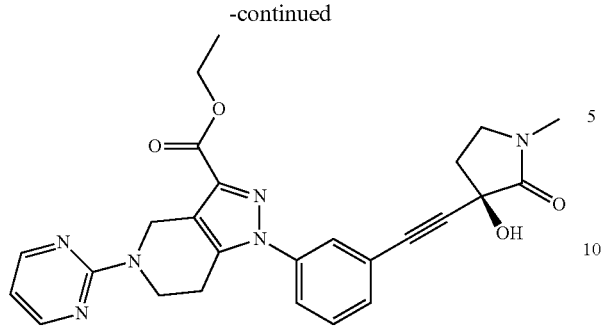

Similar to as described in General Procedure G, ethyl 1-(3-bromophenyl)-5-(pyrimidin-2-yl)-1H,4H,5H,6H,7H-pyrazolo[4,3-c]pyridine-3-carboxylate was reacted with (3R)-3-ethynyl-3-hydroxy-1-methylpyrrolidin-2-one to give the title compound (80 mg, 88%) as yellow oil. LC-MS (ES, m/z): 487 [M+H]⁺.

Step 3: Synthesis of 1-(3-[2-[(3R)-3-hydroxy-1-methyl-2-oxopyrrolidin-3-yl]ethynyl]phenyl)-5-(pyrimidin-2-yl)-1H,4H,5H,6H,7H-pyrazolo[4,3-c]pyridine-3-carboxamide

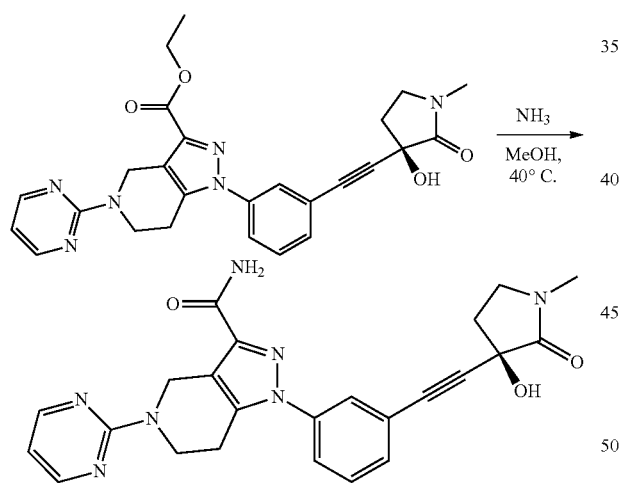

Similar to as described in General Procedure S, ethyl 1-(3-[2-[(3R)-3-hydroxy-1-methyl-2-oxopyrrolidin-3-yl]ethynyl]phenyl)-5-(pyrimidin-2-yl)-1H,4H,5H,6H,7H-pyrazolo[4,3-c]pyridine-3-carboxylate was reacted with ammonia to give the title compound (10.2 mg, 14%) as a white solid. LC-MS (ES, m/z): 458 [M+H]⁺. ¹H NMR (400 MHz, CD₃OD) δ 8.26 (s, 1H), 7.64 (s, 1H), 7.55-7.52 (m, 1H), 7.45-7.40 (m, 2H), 6.53 (t, J=4.8 Hz, 1H), 4.95 (s, 2H), 4.04 (t, J=5.6 Hz, 2H), 3.39-3.36 (m, 2H), 2.87-2.84 (m, 2H), 2.83 (s, 3H), 2.51-2.47 (m, 1H), 2.24-2.18 (m, 1H).

Example Q6

Synthesis of (R)-1-(3-((3-hydroxy-1-methyl-2-oxopyrrolidin-3-yl)ethynyl)phenyl)-5-(thiazol-2-yl)-4,5,6,7-tetrahydro-1H-pyrazolo[4,3-c]pyridine-3-carboxamide

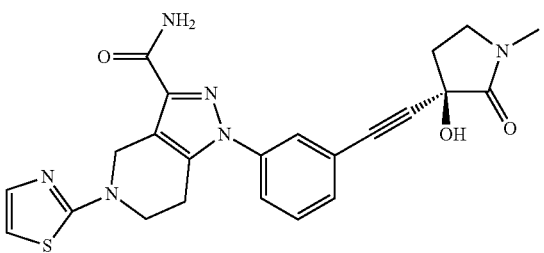 [SMILES: CN1CC[C@@](O)(C#Cc2cccc(-n3nc(C(N)=O)c4c3CCN(c3nccs3)C4)c2)C1=O]

Step 1: Synthesis of ethyl 1-(3-bromophenyl)-5-(1,3-thiazol-2-yl)-1H,4H,5H,6H,7H-pyrazolo[4,3-c]pyridine-3-carboxylate

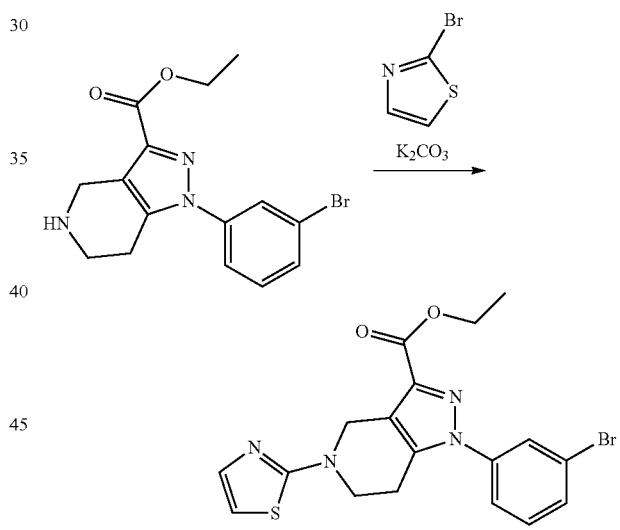

A mixture of ethyl 1-(3-bromophenyl)-1H,4H,5H,6H,7H-pyrazolo[4,3-c]pyridine-3-carboxylate (200.00 mg, 0.43 mmol, 1.00 equiv), 2-bromo-1,3-thiazole (2.00 mL, 22.19 mmol, 51.50 equiv), and potassium carbonate (297.71 mg, 2.15 mmol, 5.00 equiv) in a sealed tube under nitrogen was stirred for 12 h at 100° C. The reaction was quenched by water, extracted with ethyl, dried over anhydrous sodium sulfate, and concentrated under vacuum. The residue was applied onto a silica gel column with ethyl acetate/petroleum ether (1:5). This resulted in 117 mg (63%) of the title compound as yellow oil. LC-MS (ES, m/z): 433, 45 [M+H]⁺.

Step 2: Synthesis of ethyl 1-(3-[2-[(3R)-3-hydroxy-1-methyl-2-oxopyrrolidin-3-yl]ethynyl]phenyl)-5-(1,3-thiazol-2-yl)-1H,4H,5H,6H,7H-pyrazolo[4,3-c]pyridine-3-carboxylate

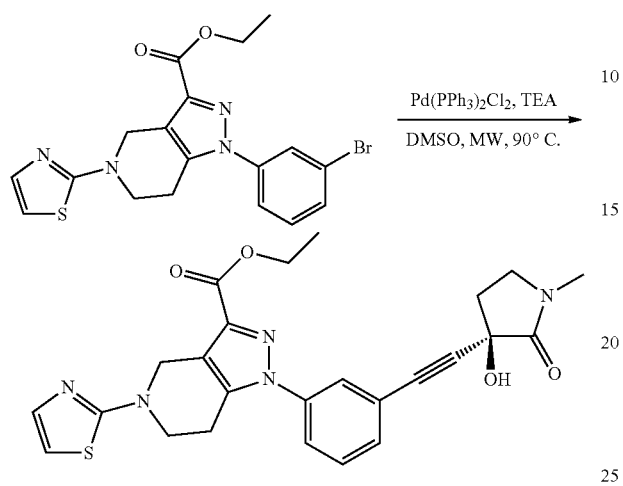

Similar to as described in General Procedure G, ethyl 1-(3-bromophenyl)-5-(1,3-thiazol-2-yl)-1H,4H,5H,6H,7H-pyrazolo[4,3-c]pyridine-3-carboxylate was reacted with (3R)-3-ethynyl-3-hydroxy-1-methylpyrrolidin-2-one to give the title compound (100 mg, 80%) as yellow oil. LC-MS (ES, m/z): 492 [M+H]⁺.

Step 3: Synthesis of 1-(3-[2-[(3R)-3-hydroxy-1-methyl-2-oxopyrrolidin-3-yl]ethynyl]phenyl)-5-(1,3-thiazol-2-yl)-1H,4H,5H,6H,7H-pyrazolo[4,3-c]pyridine-3-carboxamide

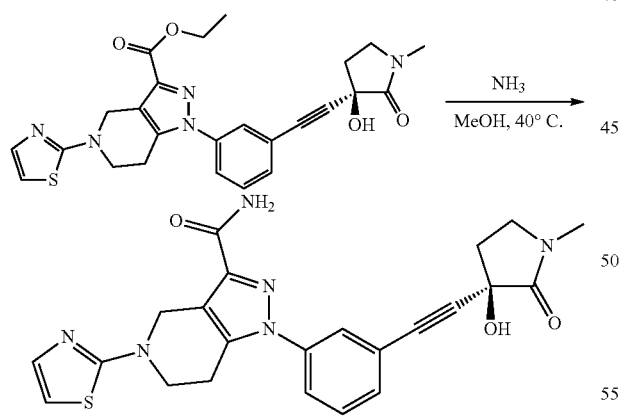

Similar to as described in General Procedure S, ethyl 1-(3-[2-[(3R)-3-hydroxy-1-methyl-2-oxopyrrolidin-3-yl]ethynyl]phenyl)-5-(1,3-thiazol-2-yl)-1H,4H,5H,6H,7H-pyrazolo[4,3-c]pyridine-3-carboxylate was reacted with ammonia to give the title compound (17.1 mg, 18%) as a white solid. LC-MS (ES, m/z): 463 [M+H]⁺. ¹H NMR (300 MHz, CD₃OD) δ 7.75 (s, 1H), 7.67-7.62 (m, 1H), 7.57-7.52 (m, 2H), 7.18 (d, J=3.6 Hz, 1H), 6.76 (d, J=3.6 Hz, 1H), 4.76 (s, 2H), 3.91 (t, J=5.4 Hz, 2H), 3.55-3.50 (m, 2H), 3.09-3.03 (m, 2H), 2.93 (s, 3H), 2.63-2.55 (m, 1H), 2.36-2.27 (m, 1H).

Example R6 and Example S6

Synthesis of 1-(3-(((R)-3-hydroxy-1-methyl-2-oxopyrrolidin-3-yl)ethynyl)phenyl)-5-((S)-methylsulfinyl)-4,5,6,7-tetrahydro-1H-pyrazolo[4,3-c]pyridine-3-carboxamide and 1-(3-(((R)-3-hydroxy-1-methyl-2-oxopyrrolidin-3-yl)ethynyl)phenyl)-5-((R)-methylsulfinyl)-4,5,6,7-tetrahydro-1H-pyrazolo[4,3-c]pyridine-3-carboxamide

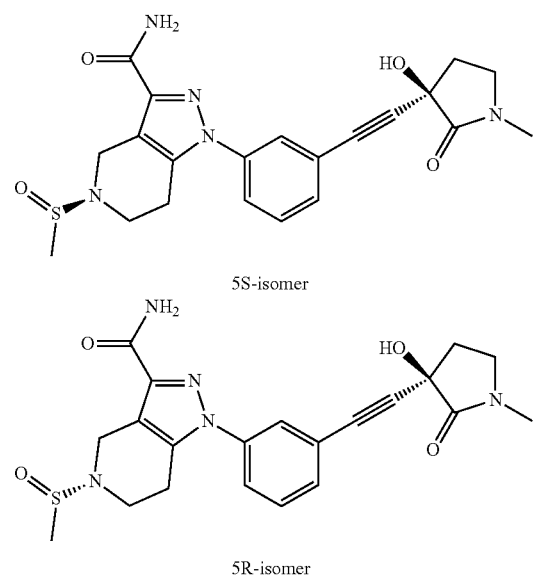

5S-isomer 5R-isomer

Step 1: Synthesis of ethyl 1-(3-bromophenyl)-5-methanesulfinyl-1H,4H,5H,6H,7H-pyrazolo[4,3-c]pyridine-3-carboxylate

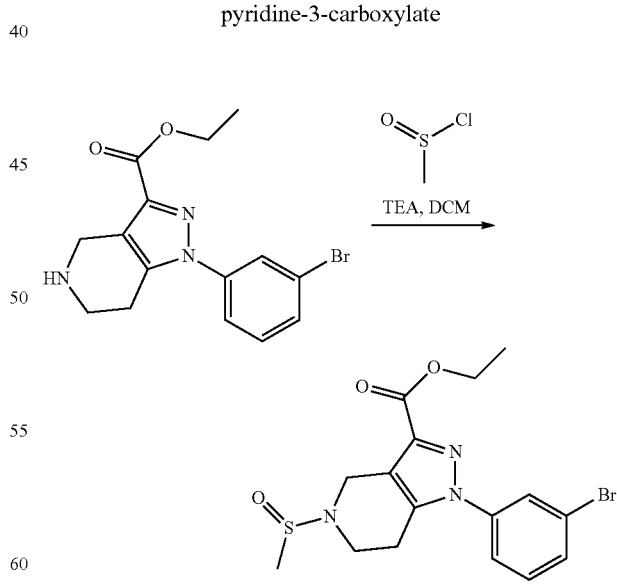

Into a 250-mL round-bottom flask was placed trifluoroacetic acid ethyl 1-(3-bromophenyl)-1H,4H,5H,6H,7H-pyrazolo[4,3-c]pyridine-3-carboxylate salt (1.00 g, 2.15 mmol, 1.00 equiv), methanesulfinyl chloride (420 mg, 4.26 mmol, 2.00 equiv), and triethylamine (870 mg, 8.60 mmol, 4.00 equiv) in dichloromethane (100 mL). The resulting mixture was stirred for 5 min at room temperature and concentrated under vacuum. The residue was applied onto a silica gel column with ethyl acetate/petroleum ether (9:11). This resulted in 300 mg (34%) of the title compound as a yellow solid. LC-MS (ES, m/z): 412, 414 [M+H]⁺.

Step 2: Synthesis of ethyl 1-(3-[2-[(3R)-3-hydroxy-1-methyl-2-oxopyrrolidin-3-yl]ethynyl]phenyl)-5-methanesulfinyl-1H,4H,5H,6H,7H-pyrazolo[4,3-c]pyridine-3-carboxylate

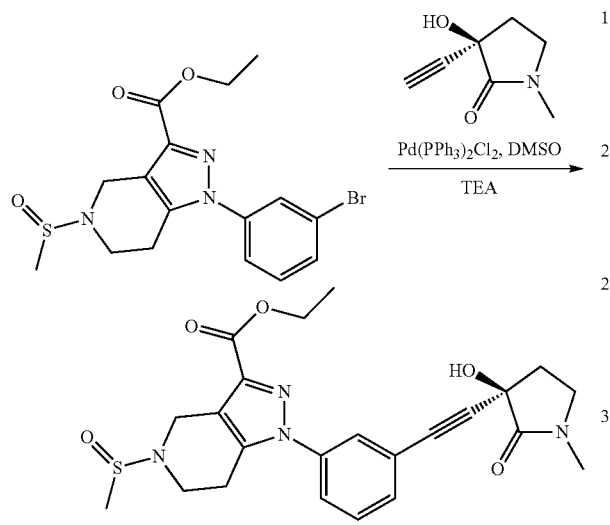

Similar to as described in General Procedure G, ethyl 1-(3-bromophenyl)-5-methanesulfinyl-1H,4H,5H,6H,7H-pyrazolo[4,3-c]pyridine-3-carboxylate was reacted with (3R)-3-ethynyl-3-hydroxy-1-methylpyrrolidin-2-one to give the title compound (100 mg, 35%) as a yellow solid. LC-MS (ES, m/z): 471 [M+H]⁺.

Step 3: Synthesis of 1-(3-[2-[(3R)-3-hydroxy-1-methyl-2-oxopyrrolidin-3-yl]ethynyl]phenyl)-5-methanesulfinyl-1H,4H,5H,6H,7H-pyrazolo[4,3-c]pyridine-3-carboxamide

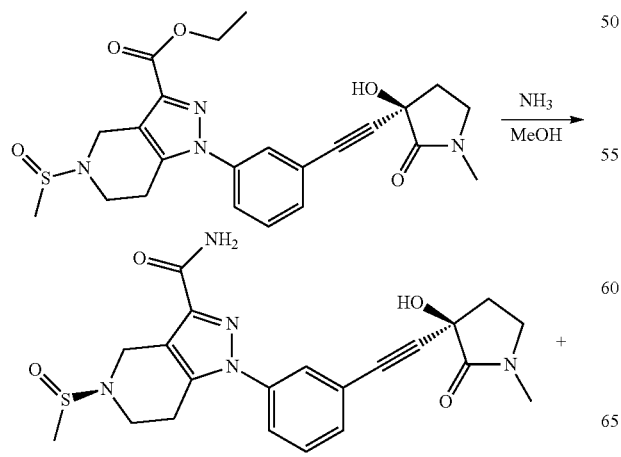

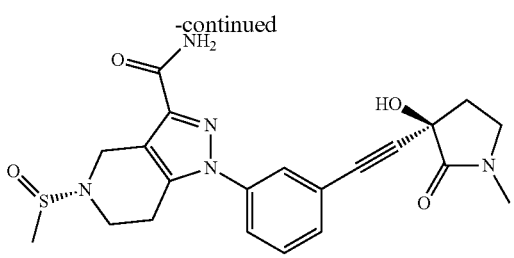

Similar to as described in General Procedure S, ethyl 1-(3-[2-[(3R)-3-hydroxy-1-methyl-2-oxopyrrolidin-3-yl]ethynyl]phenyl)-5-methanesulfinyl-1H,4H,5H,6H,7H-pyrazolo[4,3-c]pyridine-3-carboxylate was reacted with ammonia to give a R/S mixture which was separated by Chiral-Prep-HPLC. This resulted in 7.8 mg (8%) of the 5S-isomer as a white solid and 7.4 mg (8%) of the 5R-isomer as a white solid. The stereochemistry of both isomers was arbitrarily assigned. The 5S-isomer: $t_R$=5.59 min (Chiralcel OJ-3, 0.46*15 cm, Hex(0.1% TEA):EtOH=50:50, 1.2 ml/min); the 5R-isomer: $t_R$=11.19 min (Chiralcel OJ-3, 0.46*15 cm, Hex(0.1% TEA):EtOH=50:50, 1.2 ml/min). Both isomers showed identical LC-MS and ¹H NMR as shown below. LC-MS (ES, m/z): 442 [M+H]⁺. ¹H NMR (400 MHz, CD₃OD) δ 7.71-7.66 (m, 2H), 7.60-7.56 (m, 1H), 7.51-7.49 (m, 1H), 4.34 (s, 2H), 3.41-3.37 (m, 4H), 3.05-2.90 (m, 2H), 2.81 (s, 3H), 2.69 (s, 3H), 2.53-2.52 (m, 1H), 2.22-2.19 (m, 1H).

Example T6, Example U6, Example V6 and Example W6

Synthesis of 1-(3-[2-[(3 S,4S)-3,4-dihydroxy-1-methyl-2-oxopyrrolidin-3-yl]ethynyl]phenyl)-1H-indazole-3-carboxamide, 1-(3-[2-[(3 S,4R)-3,4-dihydroxy-1-methyl-2-oxopyrrolidin-3-yl]ethynyl]phenyl)-1H-indazole-3-carboxamide, 1-(3-[2-[(3R,4R)-3,4-dihydroxy-1-methyl-2-oxopyrrolidin-3-yl]ethynyl]phenyl)-1H-indazole-3-carboxamide and 1-(3-[2-[(3R,4S)-3,4-dihydroxy-1-methyl-2-oxopyrrolidin-3-yl]ethynyl]phenyl)-1H-indazole-3-carboxamide

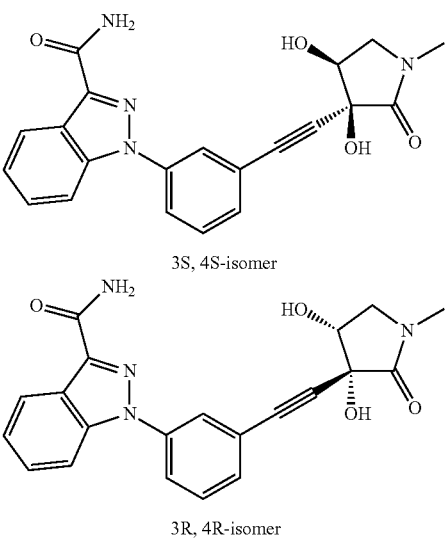

3S, 4S-isomer 3R, 4R-isomer

-continued

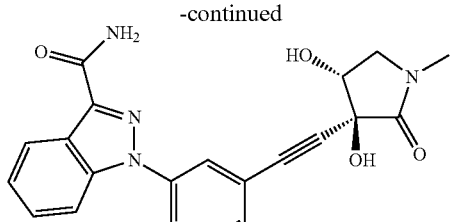

3S, 4R-isomer

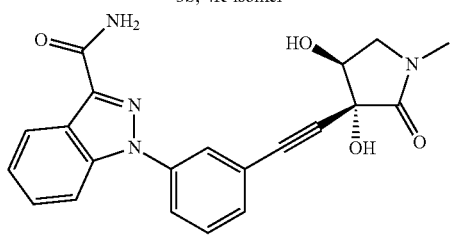

3R, 4S-isomer

Step 1: Synthesis of methyl 4-[[(tert-butoxy)carbonyl](methyl)amino]-3-hydroxy-2-methylidenebutanoate

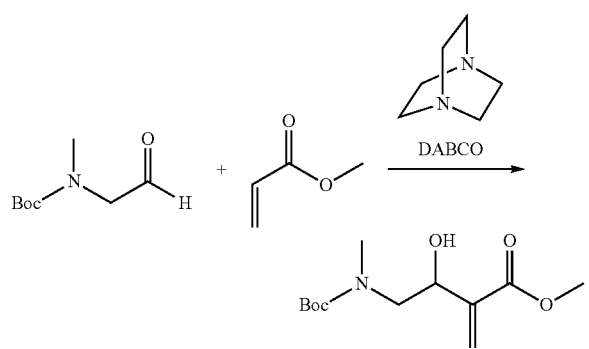

Into a 250-mL round-bottom flask purged and maintained with an inert atmosphere of nitrogen, was placed tert-butyl N-methyl-N-(2-oxoethyl)carbamate (8.00 g, 46.19 mmol, 1.00 equiv), methyl prop-2-enoate (39.76 g, 461.85 mmol, 10.00 equiv), and 1,4-diazabicyclo[2,2,2]octane (20.72 g, 184.71 mmol, 4.00 equiv). After being stirred for 3 days at room temperature the reaction was quenched by water, extracted with dichloromethane, dried over anhydrous sodium sulfate, and concentrated under vacuum. The residue was purified by a silica gel column with ethyl acetate/petroleum ether (1:5) to give 11 g (92%) of the title compound as yellow oil. LC-MS (ES, m/z): 260 [M+H]$^+$.

Step 2: Synthesis of methyl 4-[[(tert-butoxy)carbonyl](methyl)amino]-3-[(tert-butyldimethylsilyl)oxy]-2-methylidenebutanoate

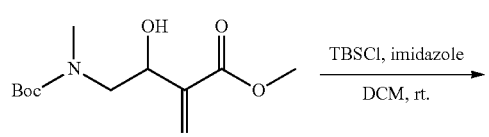

-continued

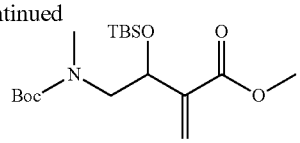

A solution of tert-butyl(chloro)dimethylsilane (15.35 g, 101.84 mmol, 2.40 equiv) in dichloromethane (20 mL) was added dropwise to a stirred solution of methyl 4-[[(tert-butoxy)carbonyl](methyl)amino]-3-hydroxy-2-methylidenebutanoate (11.00 g, 42.42 mmol, 1.00 equiv) and imidazole (8.7 g, 3.00 equiv) in dichloromethane (100 mL) at 0° C. The resulting mixture was stirred overnight at room temperature. The solids were filtered out and the liquid was concentrated under vacuum. The residue was purified by a silica gel column with ethyl acetate/petroleum ether (1:10) to give 17 g (92%) of the title compound as colorless oil. LC-MS (ES, m/z): 374 [M+H]$^+$.

Step 3: Synthesis of methyl 4-[[(tert-butoxy)carbonyl](methyl)amino]-3-[(tert-butyldimethylsilyl)oxy]-2-oxobutanoate

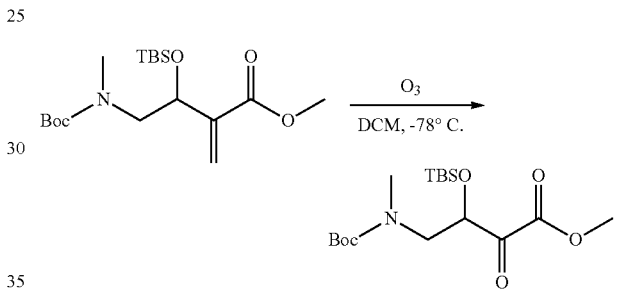

In a 250-mL 4-necked round-bottom flask purged and maintained with an inert atmosphere of O$_3$ gas, a suspension of methyl 4-[[(tert-butoxy)carbonyl](methyl)amino]-3-[(tert-butyldimethylsilyl)oxy]-2-methylidenebutanoate (8 g, 21.42 mmol, 1.00 equiv) in dichloromethane (100 mL) was stirred for 1 h at −78° C. The reaction was then quenched by 10 mL of diethylsulfane and concentrated under vacuum. The residue was purified by a silica gel column with ethyl acetate/petroleum ether (1:10) to give the title compound (7.314 g, 82%) as colorless oil. LC-MS (ES, m/z): 376 [M+H]$^+$.

Step 4: Synthesis of methyl 2-(2-[[(tert-butoxy)carbonyl](methyl)amino]-1-[(tert-butyldimethylsilyl)oxy]ethyl)-2-hydroxybut-3-ynoate

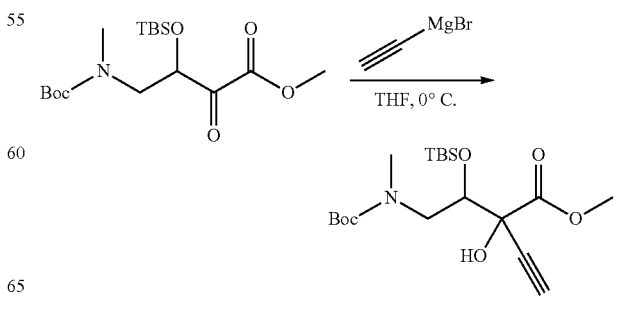

Bromo(ethynyl)magnesium (47 mL, 181.84 mmol, 1.20 equiv) was added dropwise to a stirred solution of methyl 4-[[(tert-butoxy)carbonyl](methyl)amino]-3-[(tert-butyldimethylsilyl)oxy]-2-oxobutanoate (7.314 g, 19.48 mmol, 1.00 equiv) in THF (10 mL) at 0° C. under nitrogen. After being stirred for 2 h at 0° C. the reaction was quenched by saturated aqueous NH$_4$Cl, extracted with ethyl acetate, dried over anhydrous sodium sulfate, and concentrated under vacuum. The residue was purified by a silica gel column with ethyl acetate/petroleum ether (1:5) to give the title compound (6.4 g, 74%) as yellow oil. LC-MS (ES, m/z): 402 [M+H]$^+$.

Step 5: Synthesis of 4-[(tert-butyldimethylsilyl)oxy]-3-ethynyl-3-hydroxy-1-methylpyrrolidin-2-one

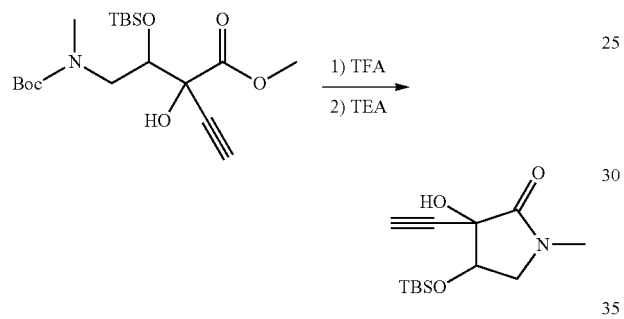

Trifluoroacetic acid (800 mg, 7.02 mmol, 2.00 equiv) was added to a stirred solution of methyl 2-(2-[[(tert-butoxy)carbonyl](methyl)amino]-1-[(tert-butyldimethylsilyl)oxy]ethyl)-2-hydroxybut-3-ynoate (1.40 g, 3.49 mmol, 1.00 equiv) in dichloromethane (5 mL) at room temperature. After 2 h triethylamine (1.41 g, 13.93 mmol, 4.00 equiv) in dichloromethane (15 mL) was added and the reaction was stirred overnight. The resulting mixture was concentrated under vacuum and the residue was purified by a silica gel column with ethyl acetate/petroleum ether (1:3) to give the title compound (780 mg, 75%) as a yellow solid. LC-MS (ES, m/z): 270 [M+H]$^+$.

Step 6: Synthesis of 1-[3-(2-[4-[(tert-butyl dimethylsilyl)oxy]-3-hydroxy-1-methyl-2-oxopyrrolidin-3-yl]ethynyl) phenyl]-1H-indazole-3-carboxamide

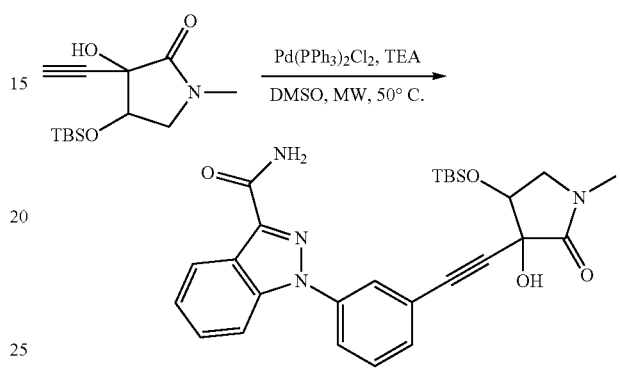

Similar to as described in General Procedure G, 1-(3-iodophenyl)-1H-indazole-3-carboxamide was reacted with 4-[(tert-butyldimethylsilyl)oxy]-3-ethynyl-3-hydroxy-1-methylpyrrolidin-2-one to give the title compound (540 mg) as a yellow solid. LC-MS (ES, m/z): 505 [M+H]$^+$.

Step 7: Synthesis of 1-(3-[2-[(3 S,4S)-3,4-dihydroxy-1-methyl-2-oxopyrrolidin-3-yl]ethynyl]phenyl)-1H-indazole-3-carboxamide, 1-(3-[2-[(3 S,4R)-3,4-dihydroxy-1-methyl-2-oxopyrrolidin-3-yl]ethynyl]phenyl)-1H-indazole-3-carboxamide, 1-(3-[2-[(3R,4R)-3,4-dihydroxy-1-methyl-2-oxopyrrolidin-3-yl]ethynyl]phenyl)-1H-indazole-3-carboxamide and 1-(3-[2-[(3R,4S)-3,4-dihydroxy-1-methyl-2-oxopyrrolidin-3-yl]ethynyl]phenyl)-1H-indazole-3-carboxamide

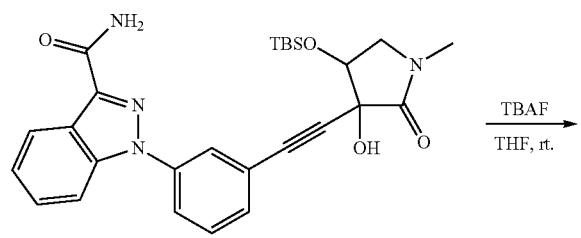

463

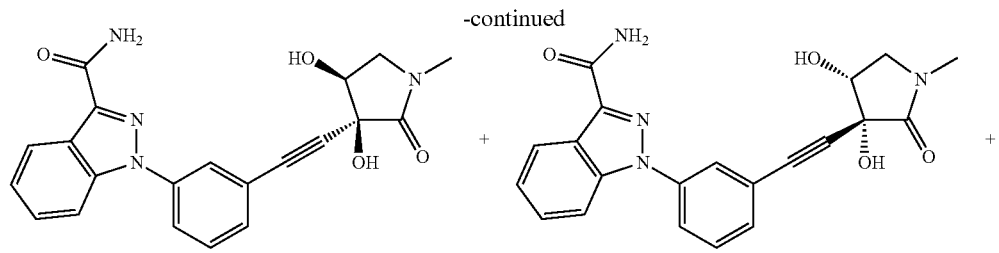

-continued

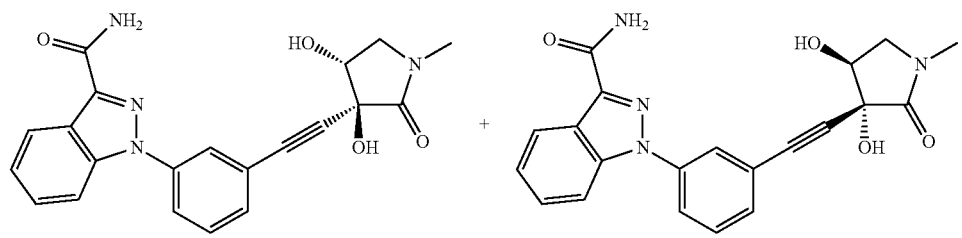

TBAF (1.3 g, 4.97 mmol, 2.00 equiv) was added dropwise into a solution of 1-[3-(2-[4-[(tert-butyldimethylsilyl)oxy]-3-hydroxy-1-methyl-2-oxopyrrolidin-3-yl]ethynyl) phenyl]-1H-indazole-3-carboxamide (1.25 g, 2.48 mmol, 1.00 equiv) in THF (50 mL) at 0° C. After being stirred overnight at room temperature the resulting mixture was concentrated under vacuum and the crude product (200 mg) was purified by Chiral-Prep-HPLC. This resulted in 2.5 mg of the 3S,4S-isomer, 1.7 mg of the 3S,4R-isomer, 12.8 mg (1%) of the 3R,4R-isomer, and 13.7 mg (1%) of the 3R,4S-isomer. All four isomers are white solid. The stereochemistry of all isomers was arbitrarily assigned. The 3R, 4R-isomer: $t_R$=1.91 min (Chiralcel IA-3, 0.46*5 cm, Hex(0.1% TEA): EtOH=50:50, 1.0 ml/min); the 3S, 4S-isomer $t_R$=3.32 min (Chiralcel IA-3, 0.46*5 cm, Hex(0.1% TEA):EtOH=50:50, 1.0 ml/min). The 3R, 4S-isomer: $t_R$=7.84 min (Chiralcel IC-3, 0.46*15 cm, Hex(0.1% TEA):EtOH=50:50, 1.0 ml/min); The 3S, 4R-isomer: $t_R$=9.99 min (Chiralcel IC-3, 0.46*15 cm, Hex(0.1% TEA):EtOH=50:50, 1.0 ml/min). LC-MS (ES, m/z): 391 [M+H]$^+$ for all four isomers. Proton NMR for 3R, 4R-isomer or 3S, 4S-isomer: $^1$H NMR (300 MHz, CD$_3$OD) δ 8.36 (d, J=8.0 Hz, 1H), 7.98-7.85 (m, 3H), 7.67-7.56 (m, 3H), 7.42 (t, J=7.2 Hz, 1H), 4.42-4.39 (m, 1H), 3.83-3.78 (m, 1H), 3.34-3.29 (m, 1H), 2.95 (s, 3H). Proton NMR for 3R, 4R-isomer or 3S, 4S-isomer: $^1$H NMR (400 MHz, DMSO-d$_6$) δ 8.31 (d, J=8.0 Hz, 1H), 8.04 (s, 1H), 7.93-7.86 (m, 3H), 7.66 (t, J=7.6 Hz, 1H), 7.59-7.52 (m, 3H), 7.40 (t, J=7.6 Hz, 1H), 6.56 (s, 1H), 5.80 (d, J=5.6 Hz, 1H), 4.09-4.05 (m, 1H), 3.53-3.49 (m, 1H), 3.14-3.10 (m, 1H), 2.79 (s, 3H).

464

Example X6

Synthesis of (R)-4-(ethylamino)-1-(3-((3-hydroxy-1-methyl-2-oxopyrrolidin-3-yl)ethynyl)phenyl)-1H-pyrazolo[4,3-c]pyridine-3-carboxamide

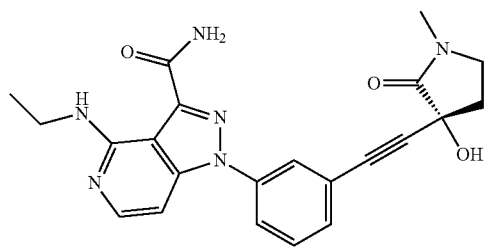 [SMILES: CCNc1nccc2c1c(C(N)=O)nn2-c1cccc(C#C[C@]2(O)CCN(C)C2=O)c1]

Step 1: Synthesis of
N-ethyl-3-iodo-1H-pyrazolo[4,3-c]pyridin-4-amine

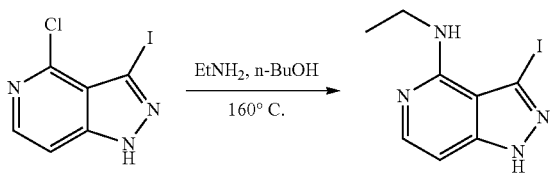

Similar to as described in General Procedure A, 4-chloro-3-iodo-1H-pyrazolo[4,3-c]pyridine was reacted with ethylamine to give the title compound (850 mg, 82%) as an off-white solid. LC-MS (ES, m/z): 289 [M+H]$^+$.

Step 2: Synthesis of methyl 4-(ethylamino)-1H-pyrazolo[4,3-c]pyridine-3-carboxylate

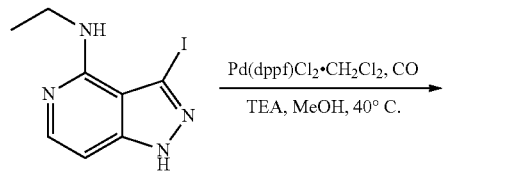

Similar to as described in General Procedure O, N-ethyl-3-iodo-1H-pyrazolo[4,3-c]pyridin-4-amine was reacted with carbon monoxide to give the title compound (300 mg, 46%) as a brown solid. LC-MS (ES, m/z): 221 [M+H]$^+$.

Step 3: Synthesis of methyl 1-(3-bromophenyl)-4-(ethylamino)-1H-pyrazolo[4,3-c]pyridine-3-carboxylate

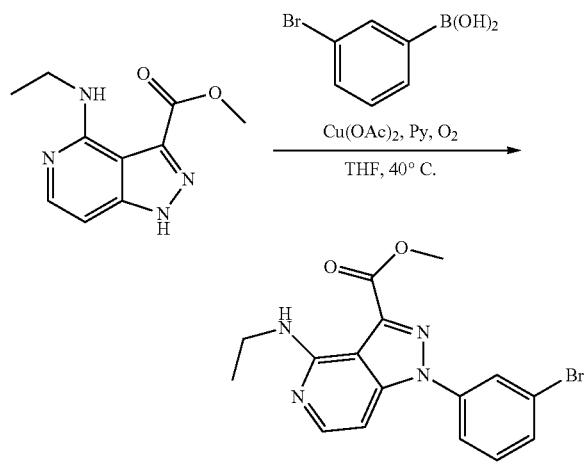

Similar to as described in General Procedure C, methyl 4-(ethylamino)-1H-pyrazolo[4,3-c]pyridine-3-carboxylate was reacted with (3-bromophenyl)boronic acid to give the title compound (160 mg, crude) as a brown solid. LC-MS (ES, m/z): 375 [M+H]$^+$.

Step 4: Synthesis of methyl 4-(ethyl amino)-1-(3-[2-[(3R)-3-hydroxy-1-methyl-2-oxopyrrolidin-3-yl]ethynyl]phenyl)-1H-pyrazolo[4,3-c]pyridine-3-carboxylate

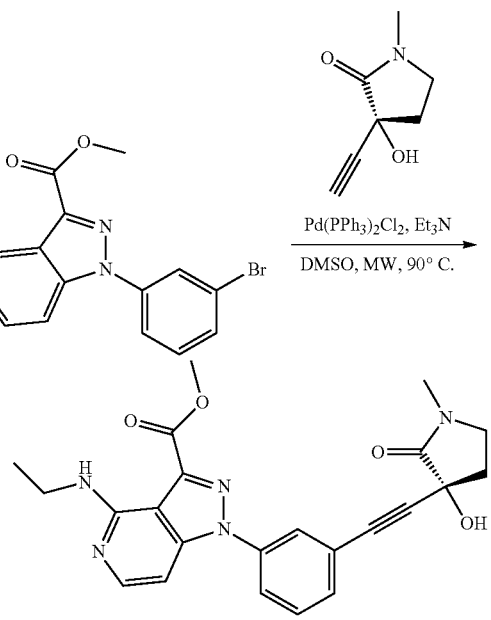

Similar to as described in General Procedure G, methyl 1-(3-bromophenyl)-4-(ethylamino)-1H-pyrazolo[4,3-c]pyridine-3-carboxylate was reacted with (3R)-3-ethynyl-3-hydroxy-1-methylpyrrolidin-2-one to give the title compound (100 mg, 54%) as an off-white solid. LC-MS (ES, m/z): 434 [M+H]$^+$.

Step 5: Synthesis of 4-(ethylamino)-1-(3-[2-[(3R)-3-hydroxy-1-methyl-2-oxopyrrolidin-3-yl]ethynyl]phenyl)-1H-pyrazolo[4,3-c]pyridine-3-carboxamide

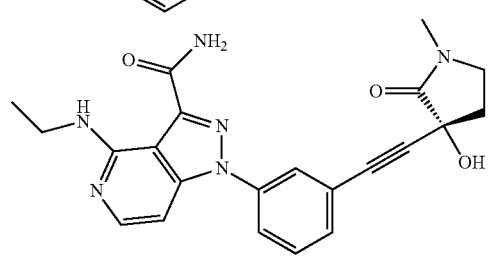

Similar to as described in General Procedure S, methyl 4-(ethylamino)-1-(3-[2-[(3R)-3-hydroxy-1-methyl-2-oxopyrrolidin-3-yl]ethynyl]phenyl)-1H-pyrazolo[4,3-c]pyridine-3-carboxylate was reacted with ammonia to give the title compound (33.2 mg, 43%) as a white solid. LC-MS (ES, m/z): 419 [M+H]+. 1H NMR (400 MHz, CD3OD) δ 7.77-7.67 (m, 3H), 7.52-7.45 (m, 2H), 6.75 (d, J=6.4 Hz, 1H), 3.45-3.35 (m, 4H), 2.83 (s, 3H), 2.52-2.48 (m, 1H), 2.25-2.18 (m, 1H), 1.24 (t, J=7.2 Hz, 3H).

Example Y6

Synthesis of (R)-4-(cyclopropylamino)-1-(3-((3-hydroxy-1-methyl-2-oxopyrrolidin-3-yl)ethynyl)phenyl)-1H-pyrazolo[4,3-c]pyridine-3-carboxamide

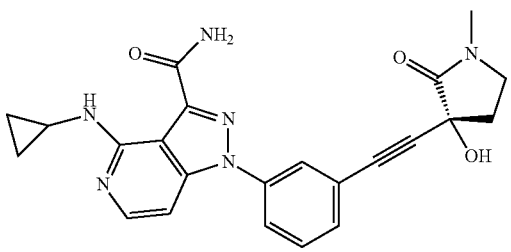 [SMILES: CN1CC[C@@](O)(C#Cc2cccc(-n3nc(C(N)=O)c4c(NC5CC5)nccc43)c2)C1=O]

Step 1: Synthesis of 4-chloro-3-iodo-1H-pyrazolo[4,3-c]pyridine

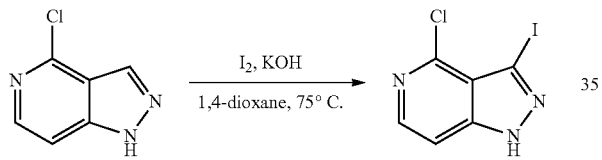

A solution of 4-chloro-1H-pyrazolo[4,3-c]pyridine (5 g, 32.56 mmol, 1.00 equiv), I2 (16.39 g, 64.58 mmol, 1.00 equiv), potassium hydroxide (6.9 g, 122.98 mmol, 1.00 equiv) in 1,4-dioxane (150 mL) was stirred for 4 h at 75° C. The reaction was quenched by saturated Na2S2O3 and the solids were collected by filtration. This resulted in 3.7 g (41%) of the title compound as a yellow solid. LC-MS (ES, m/z): 280 [M+H]+.

Step 2: Synthesis of N-cyclopropyl-3-iodo-1H-pyrazolo[4,3-c]pyridin-4-amine

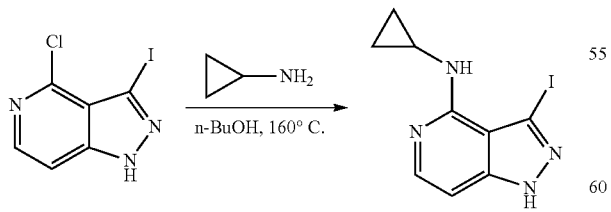

Similar to as described in General Procedure A, 4-chloro-3-iodo-1H-pyrazolo[4,3-c]pyridine was reacted with cyclopropanamine (1.45 g, 25.40 mmol, 10.00 equiv) to give the title compound (767 mg, crude) as a white solid. LC-MS (ES, m/z): 301 [M+H]+.

Step 3: Synthesis of methyl 4-(cyclopropylamino)-1H-pyrazolo[4,3-c]pyridine-3-carboxylate

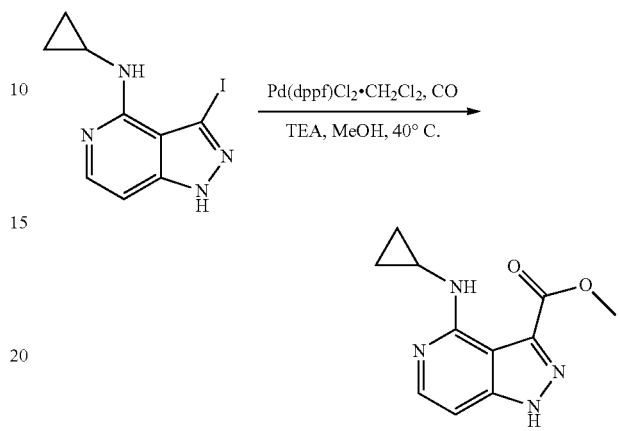

Similar to as described in General Procedure O, N-cyclopropyl-3-iodo-1H-pyrazolo[4,3-c]pyridin-4-amine was reacted with carbon monoxide to give the title compound (180 mg) as a crude solid. LC-MS (ES, m/z): 233 [M+H]+.

Step 4: Synthesis of methyl 1-(3-bromophenyl)-4-(cyclopropylamino)-1H-pyrazolo[4,3-c]pyridine-3-carboxylate

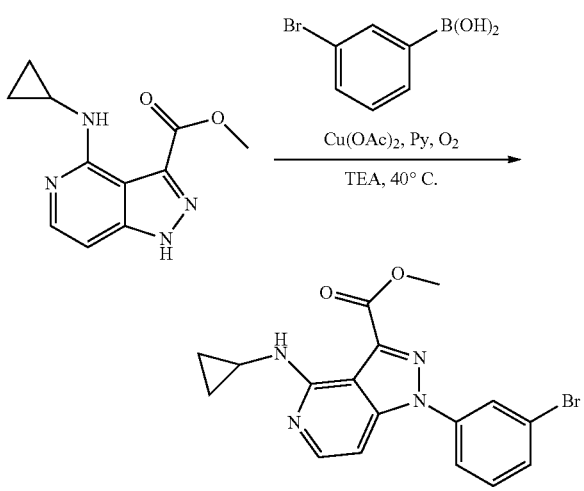

Similar to as described in General Procedure C, methyl 4-(cyclopropylamino)-1H-pyrazolo[4,3-c]pyridine-3-carboxylate was reacted with (3-bromophenyl)boronic acid to give the title compound (124 mg, 41%) as a light yellow solid. LC-MS (ES, m/z): 387 [M+H]+.

Step 5: Synthesis of methyl 4-(cyclopropyl amino)-1-(3-[2-[(3R)-3-hydroxy-1-methyl-2-oxopyrrolidin-3-yl]ethynyl]phenyl)-1H-pyrazolo[4,3-c]pyridine-3-carboxylate

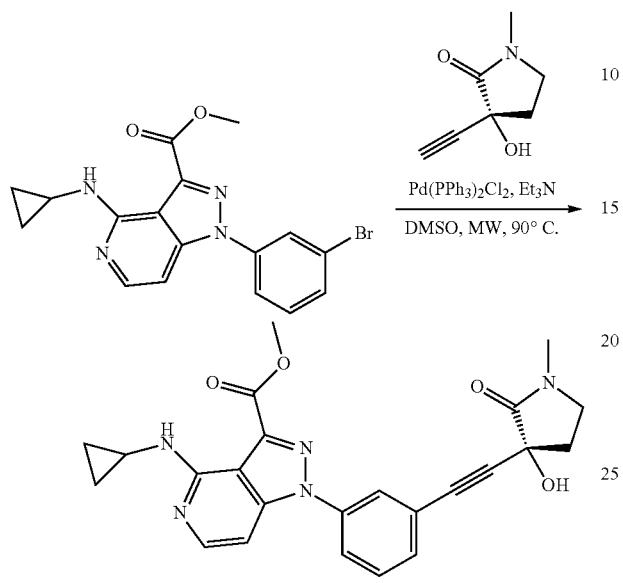

Similar to as described in General Procedure G, methyl 1-(3-bromophenyl)-4-(cyclopropylamino)-1H-pyrazolo[4,3-c]pyridine-3-carboxylate was reacted with (3R)-3-ethynyl-3-hydroxy-1-methylpyrrolidin-2-one to give the title compound (90 mg, 63%) as a yellow solid. LC-MS (ES, m/z): 446 [M+H]⁺.

Step 6: Synthesis of 4-(cyclopropylamino)-1-(3-[2-[(3S)-3-hydroxy-1-methyl-2-oxopyrrolidin-3-yl]ethynyl]phenyl)-1H-pyrazolo[4,3-c]pyridine-3-carboxamide

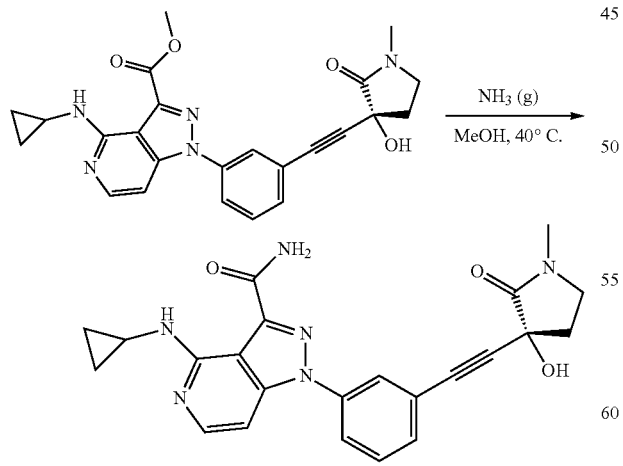

Similar to as described in General Procedure S, methyl 4-(cyclopropylamino)-1-(3-[2-[(3S)-3-hydroxy-1-methyl-2-oxopyrrolidin-3-yl]ethynyl]phenyl)-1H-pyrazolo[4,3-c]pyridine-3-carboxylate was reacted with ammonia to give the title compound (11.7 mg, 13%) as a white solid. LC-MS (ES, m/z): 431 [M+H]⁺. ¹H NMR (300 MHz, CD₃OD) δ 7.89-7.88 (m, 2H), 7.81-7.77 (m, 1H), 7.63-7.58 (m, 2H), 6.94 (d, J=6.3 Hz, 1H), 3.51-3.30 (m, 2H), 2.93 (s, 3H), 2.89-2.84 (m, 1H), 2.62-2.56 (m, 1H), 2.37-2.28 (m, 1H), 0.93-0.87 (m, 2H), 0.64-0.59 (m, 2H).

Example Z6

Synthesis of (R)-1-(3-((3-hydroxy-1-methyl-2-oxopyrrolidin-3-yl)ethynyl)phenyl)-6-methyl-1H-pyrazolo[4,3-c]pyridine-3-carboxamide

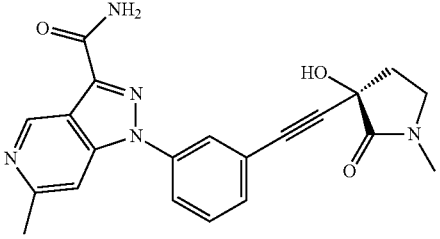 [SMILES: Cc1cc2c(cn1)c(C(N)=O)nn2-c1cccc(C#C[C@]2(O)CCN(C)C2=O)c1]

Step 1: Synthesis of (4-chloro-6-methylpyridin-3-yl)methanol

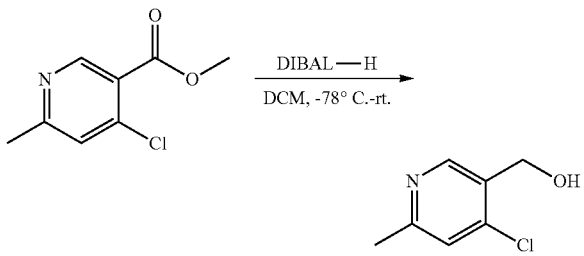

Diisobutylaluminium hydride (100 mL, 492.91 mmol, 5.00 equiv) was added dropwise to a stirred suspension of methyl 4-chloro-6-methylpyridine-3-carboxylate (6.67 g, 35.94 mmol, 1.0 equiv) in dichloromethane (120 mL) at −76° C. under nitrogen. The reaction was stirred for 2 h at room temperature, quenched by aqueous potassium sodium tartrate, extracted with ethyl acetate, and concentrated under vacuum. The residue was purified by a silica gel column with ethyl acetate/petroleum ether (1:5). This resulted 3.5 g (62%) of the title compound as a light red solid. LC-MS (ES, m/z): 158 [M+H]⁺.

Step 2: Synthesis of 4-chloro-6-methylpyridine-3-carbaldehyde

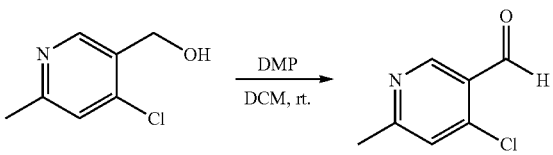

A suspension of (4-chloro-6-methylpyridin-3-yl)methanol (2.17 g, 13.77 mmol, 1.00 equiv) and Dess-Martin periodinane (8.74 g, 20.61 mmol, 1.50 equiv) in dichloromethane (120 mL) was stirred for 2 h at room temperature. The resulting mixture was concentrated under vacuum and the residue was purified by a silica gel column with ethyl acetate/petroleum ether (1:10) to give 1.61 g (75%) of 4-chloro-6-methylpyridine-3-carbaldehyde as a light yellow solid. LC-MS (ES, m/z): 156 [M+H]+.

Step 3: Synthesis of
6-methyl-1H-pyrazolo[4,3-c]pyridine

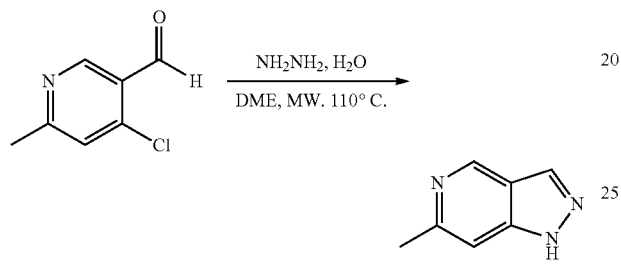

In a 30-mL sealed tube with an inert atmosphere of nitrogen, a suspension of 4-chloro-6-methylpyridine-3-carbaldehyde (797 mg, 5.12 mmol, 1.00 equiv) in ethylene glycol dimethyl ether (36 mL) and hydrazine hydrate (98%) (9 mL, 184.64 mmol, 35.00 equiv) was irradiated with microwave radiation for 3 h at 110° C. The resulting mixture was concentrated under vacuum and the residue was purified by a silica gel column with ethyl acetate/petroleum ether (1:5) to give 290 mg (43%) of the title compound as a light yellow solid. LC-MS (ES, m/z): 134 [M+H]+.

Step 4: Synthesis of
3-iodo-6-methyl-1H-pyrazolo[4,3-c]pyridine

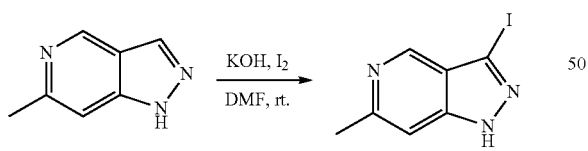

A suspension of 6-methyl-1H-pyrazolo[4,3-c]pyridine (270 mg, 2.03 mmol, 1.00 equiv), I2 (1.04 g, 4.10 mmol, 2.00 equiv), and potassium hydroxide (410 mg, 7.31 mmol, 3.60 equiv) in DMF (6 mL) was stirred for 12 h at room temperature. The reaction was quenched with saturated aqueous Na2S2O3, extracted with ethyl acetate, and dried over anhydrous sodium sulfate. The residue was purified by a silica gel column with ethyl acetate/petroleum ether (1:4) to give 360 mg (69%) of the title compound as a light yellow solid. LC-MS (ES, m/z): 260 [M+H]+.

Step 5: Synthesis of methyl
6-methyl-1H-pyrazolo[4,3-c]pyridine-3-carboxylate

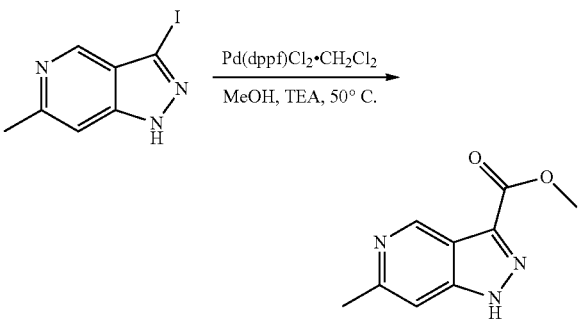

Similar to as described in General Procedure O, 3-iodo-6-methyl-1H-pyrazolo[4,3-c]pyridine was reacted with CO to give the title compound (200 mg). LC-MS (ES, m/z): 192 [M+H]+.

Step 6: Synthesis of methyl 1-(3-bromophenyl)-6-methyl-1H-pyrazolo[4,3-c]pyridine-3-carboxylate

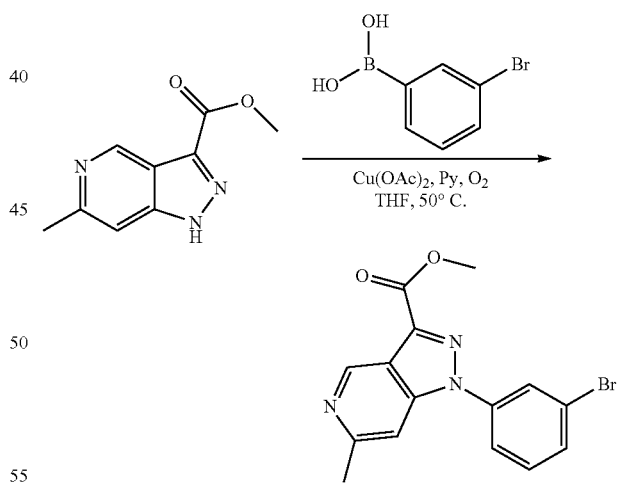

Similar to as described in General Procedure C, methyl 6-methyl-1H-pyrazolo[4,3-c]pyridine-3-carboxylate was reacted with (3-bromophenyl)boronic acid to give the title compound (150 mg, 41%) as a gray solid. LC-MS (ES, m/z): 346, 348 [M+H]+.

Step 7: Synthesis of methyl 1-(3-[2-[(3R)-3-hydroxy-1-methyl-2-oxopyrrolidin-3-yl]ethynyl]phenyl)-6-methyl-1H-pyrazolo[4,3-c]pyridine-3-carboxylate

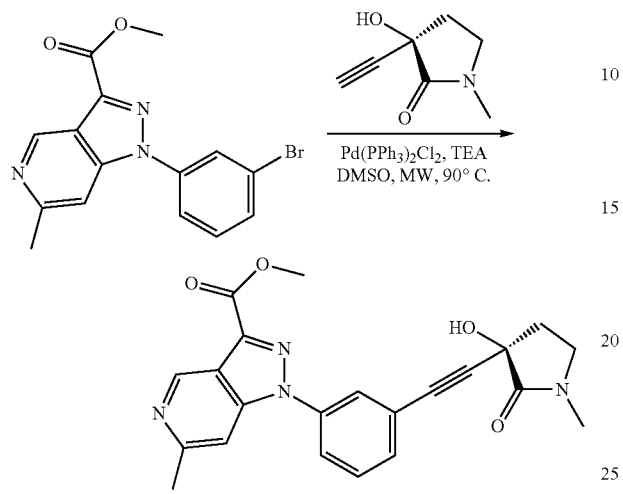

Similar to as described in General Procedure G, methyl 1-(3-bromophenyl)-6-methyl-1H-pyrazolo[4,3-c]pyridine-3-carboxylate was reacted with (3R)-3-ethynyl-3-hydroxy-1-methylpyrrolidin-2-one to give the title compound (160 mg, 91%) as a brown solid. LC-MS (ES, m/z): 405 [M+H]$^+$.

Step 8: Synthesis of 1-(3-[2-[(3R)-3-hydroxy-1-methyl-2-oxopyrrolidin-3-yl]ethynyl]phenyl)-6-methyl-1H-pyrazolo[4,3-c]pyridine-3-carboxamide

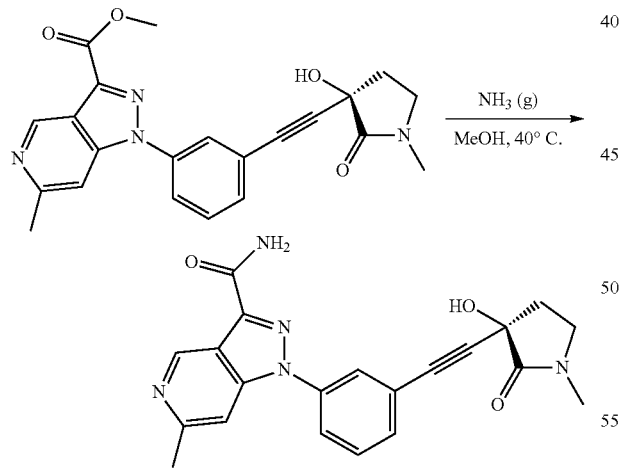

Similar to as described in General Procedure S, methyl 1-(3-[2-[(3R)-3-hydroxy-1-methyl-2-oxopyrrolidin-3-yl]ethynyl]phenyl)-6-methyl-1H-pyrazolo[4,3-c]pyridine-3-carboxylate was reacted with ammonia to give the title compound (63 mg, 41%) as a white solid. LC-MS (ES, m/z): 390 [M+H]$^+$. $^1$H NMR (300 MHz, CD$_3$OD) δ 9.47 (s, 1H), 7.96 (s, 1H), 7.89-7.83 (m, 1H), 7.65-7.62 (m, 3H), 3.49 (t, J=7.5 Hz, 2H), 2.96 (s, 3H), 2.72 (s, 3H), 2.70-2.68 (m, 1H), 2.29-2.37 (m, 1H).

Example A7

Synthesis of (R)-1-(3-((3-hydroxy-1-methyl-2-oxopyrrolidin-3-yl)ethynyl)phenyl)-1H-pyrazolo[4,3-c]pyridine-3-carboxamide

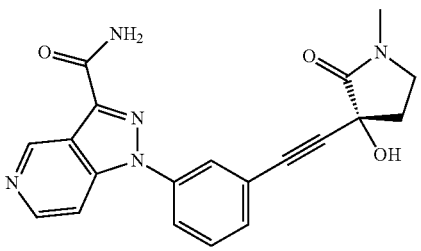 [SMILES: CN1CC[C@@](O)(C#Cc2cccc(-n3nc(C(N)=O)c4cnccc43)c2)C1=O]

Step 1: Synthesis of 4-chloro-3-iodo-1H-pyrazolo[4,3-c]pyridine

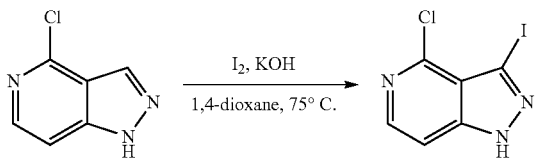 [SMILES: Clc1nccc2[nH]ncc12 ; Clc1nccc2[nH]nc(I)c12]

A solution of 4-chloro-1H-pyrazolo[4,3-c]pyridine (1.5 g, 9.77 mmol, 1.00 equiv), 1,4-dioxane (25 mL), potassium hydroxide (2.0 g, 35.65 mmol, 3.60 equiv), and iodine (4.95 g, 19.50 mmol, 2.00 equiv) was stirred for 4 h at 75° C. The reaction was quenched by saturated aqueous sodium thiosulfate pentahydrate and the solids were collected by filtration. This resulted in 2.5 g (92%) of the title compound as a light yellow solid. LC-MS (ES, m/z): 280 [M+H]$^+$.

Step 2: Synthesis of methyl 4-chloro-1H-pyrazolo[4,3-c]pyridine-3-carboxylate

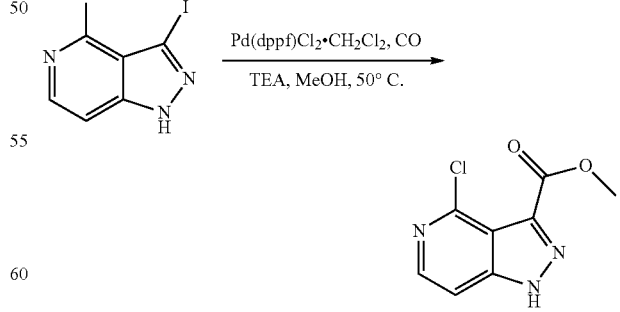

Similar to as described in General Procedure O, 4-chloro-3-iodo-1H-pyrazolo[4,3-c]pyridine was reacted with CO to give the title compound (700 mg, 66%) as a light yellow solid. LC-MS (ES, m/z): 212 [M+H]$^+$.

Step 3: Synthesis of methyl 1H-pyrazolo[4,3-c]pyridine-3-carboxylate

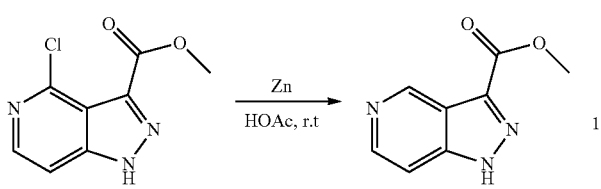

A mixture of methyl 4-chloro-1H-pyrazolo[4,3-c]pyridine-3-carboxylate (600.0 mg, 2.84 mmol, 1.00 equiv), zinc powder (920.0 mg, 14.07 mmol, 5.00 equiv), and acetic acid (15.0 mL) was stirred for 12 h at room temperature. The resulting solution was diluted with water and the solids were filtered out. The pH value of the solution was adjusted to 7 with aqueous sodium bicarbonate. The solids were filtered out and the liquid was extracted with ethyl acetate. The organic was washed with brine and concentrated under vacuum. The residue was applied onto a silica gel column with ethyl acetate/petroleum ether (1:1). This resulted in 130.0 mg (26%) of methyl 1H-pyrazolo[4,3-c]pyridine-3-carboxylate as an off-white solid. LC-MS (ES, m/z): 187 [M+H]+.

Step 4: Synthesis of methyl 1-(3-iodophenyl)-1H-pyrazolo[4,3-c]pyridine-3-carboxylate

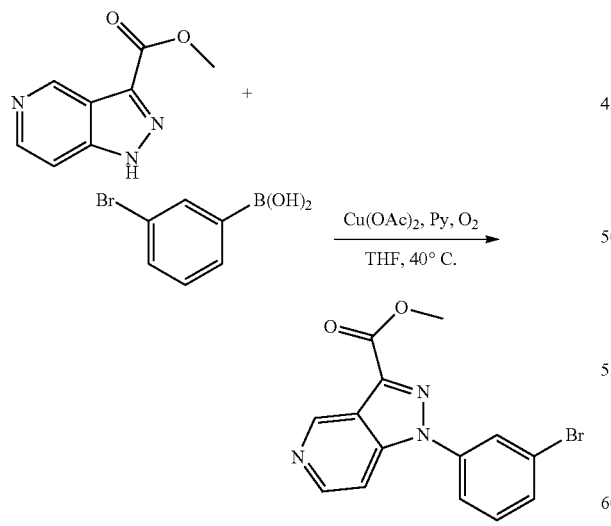

Similar to as described in General Procedure C, methyl 1H-pyrazolo[4,3-c]pyridine-3-carboxylate was reacted with (3-iodophenyl)boronic acid to give the title compound (90.0 mg, 42%) as an off-white solid. LC-MS (ES, m/z): 332 [M+H]+.

Step 5: Synthesis of methyl 1-(3-[2-[(3R)-3-hydroxy-1-methyl-2-oxopyrrolidin-3-yl]ethynyl]phenyl)-1H-pyrazolo[4,3-c]pyridine-3-carboxylate

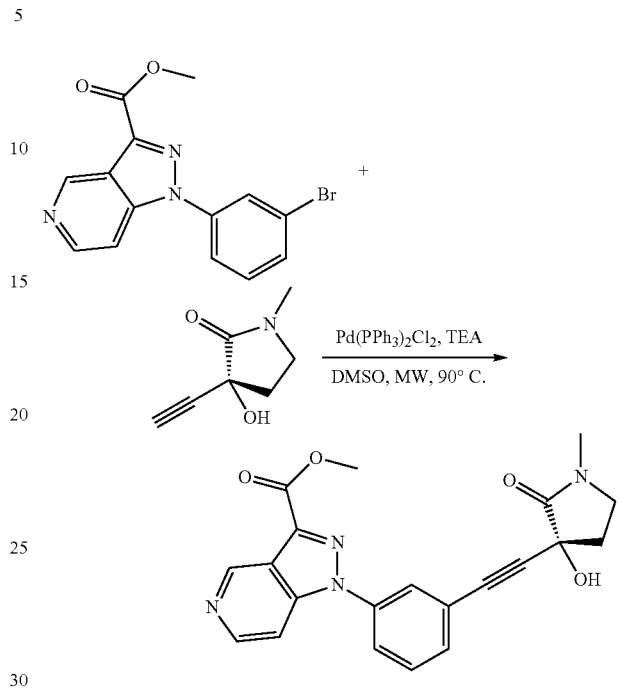

Similar to as described in General Procedure G, methyl 1-(3-iodophenyl)-1H-pyrazolo[4,3-c]pyridine-3-carboxylate was reacted with (3R)-3-ethynyl-3-hydroxy-1-methyl-pyrrolidin-2-one to give the title compound (30.0 mg, 58%) as an off-white solid. LC-MS (ES, m/z): 391 [M+H]+.

Step 6: Synthesis of 1-(3-[2-[(3R)-3-hydroxy-1-methyl-2-oxopyrrolidin-3-yl]ethynyl]phenyl)-1H-pyrazolo[4,3-c]pyridine-3-carboxamide

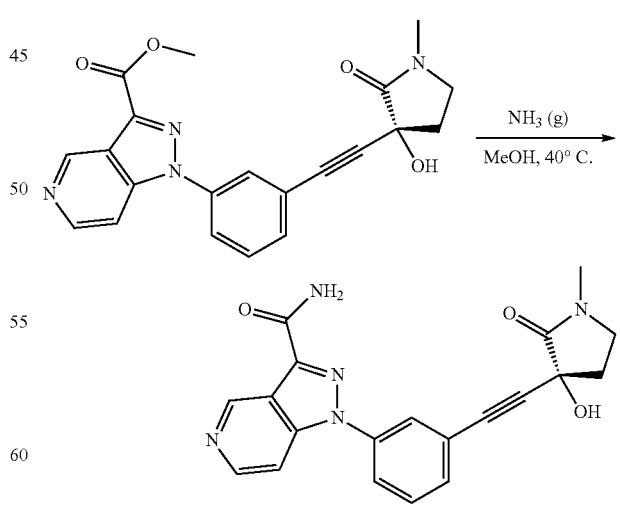

Similar to as described in General Procedure S, methyl 1-(3-[2-[(3R)-3-hydroxy-1-methyl-2-oxopyrrolidin-3-yl]ethynyl]phenyl)-1H-pyrazolo[4,3-c]pyridine-3-carboxylate was reacted with ammonia to give the title compound (9.4 mg, 33%) as an off-white solid. LC-MS (ES, m/z): 376 [M+H]⁺. ¹H NMR (300 MHz, DMSO-$d_6$) δ 9.60 (d, J=0.9 Hz, 1H), 8.53 (d, J=6 Hz, 1H), 7.98 (d, J=1.8 Hz, 1H), 7.89 (dd, J=6.0, 0.9 Hz, 2H), 7.65-7.61 (m, 2H), 3.51-3.47 (m, 2H), 2.94 (s, 3H), 2.65-2.55 (m, 1H), 2.35-2.25 (m, 1H).

Example B7

Synthesis of (R)-6-cyano-1-(3-((3-hydroxy-1-methyl-2-oxopyrrolidin-3-yl)ethynyl)phenyl)-1H-pyrazolo[4,3-c]pyridine-3-carboxamide

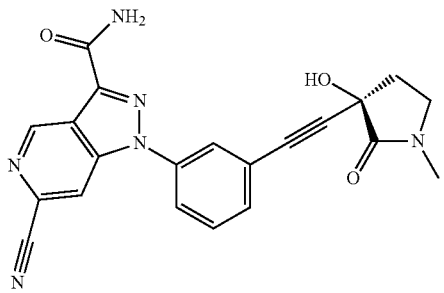 [SMILES: CN1CC[C@@](O)(C#Cc2cccc(-n3nc(C(N)=O)c4cnc(C#N)cc43)c2)C1=O]

Step 1: Synthesis of methyl 6-chloro-1-(3-[2-[(3R)-3-hydroxy-1-methyl-2-oxopyrrolidin-3-yl]ethynyl]phenyl)-1H-pyrazolo[4,3-c]pyridine-3-carboxylate

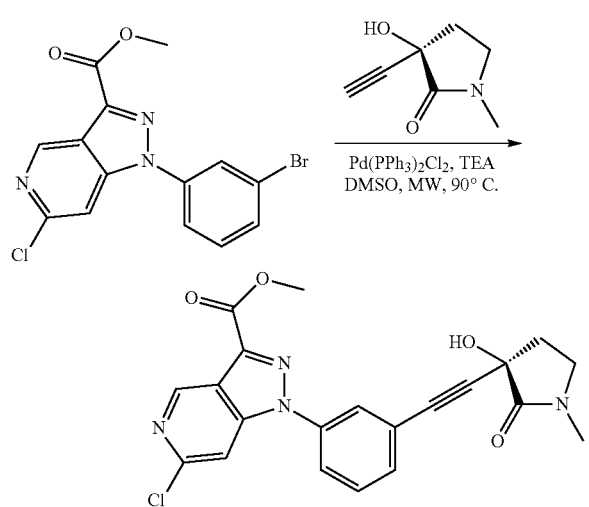

Similar to as described in General Procedure G, methyl 1-(3-bromophenyl)-6-chloro-1H-pyrazolo[4,3-c]pyridine-3-carboxylate was reacted with (3R)-3-ethynyl-3-hydroxy-1-methylpyrrolidin-2-one to give the title compound (60 mg, 35%) as a yellow solid. LC-MS (ES, m/z): 425 [M+H]⁺.

Step 2: Synthesis of methyl 6-cyano-1-(3-[2-[(3R)-3-hydroxy-1-methyl-2-oxopyrrolidin-3-yl]ethynyl]phenyl)-1H-pyrazolo[4,3-c]pyridine-3-carboxylate

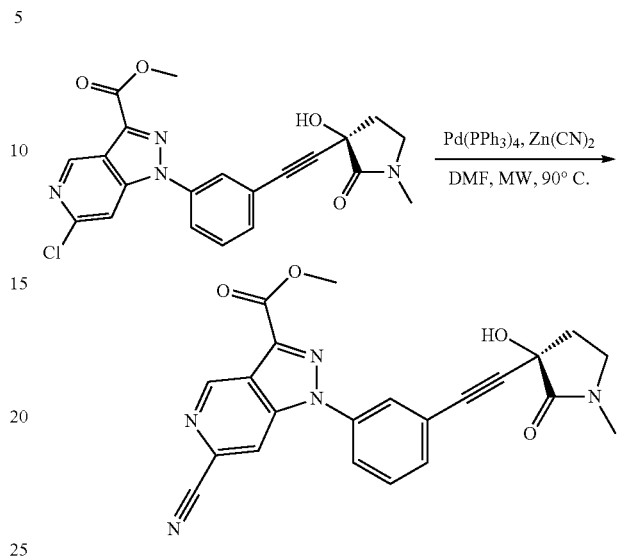

A suspension of methyl 6-chloro-1-(3-[2-[(3R)-3-hydroxy-1-methyl-2-oxopyrrolidin-3-yl]ethynyl]phenyl)-1H-pyrazolo[4,3-c]pyridine-3-carboxylate (70 mg, 0.16 mmol, 1.00 equiv), Pd(PPh₃)₄ (38 mg, 0.03 mmol, 0.20 equiv), and zinc cyanide (97 mg, 0.83 mmol, 5.00 equiv) in DMF (3 mL) was irradiated with microwave radiation for 1 h at 90° C. The resulting mixture was concentrated under vacuum, diluted with brine, extracted with ethyl acetate, and dried over anhydrous sodium sulfate. The residue was purified by a silica gel column with dichloromethane/methanol (40:1) to give the title compound (60 mg, 88%) as a yellow solid. LC-MS (ES, m/z): 416 [M+H]⁺.

Step 3: Synthesis of 6-cyano-1-(3-[2-[(3R)-3-hydroxy-1-methyl-2-oxopyrrolidin-3-yl]ethynyl]phenyl)-1H-pyrazolo[4,3-c]pyridine-3-carboxamide

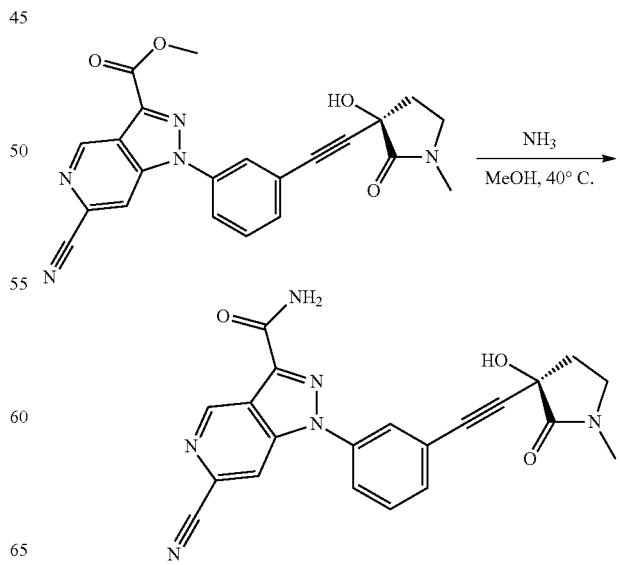

Similar to as described in General Procedure S, methyl 6-cyano-1-(3-[2-[(3R)-3-hydroxy-1-methyl-2-oxopyrrolidin-3-yl]ethynyl]phenyl)-1H-pyrazolo[4,3-c]pyridine-3-carboxylate was reacted with ammonia to give the title compound (5.2 mg, 27%) as a white solid. LC-MS (ES, m/z): 401 [M+H]+. 1H NMR (400 MHz, DMSO-d6) δ 9.58 (s, 1H), 8.75 (s, 1H), 8.00-7.96 (m, 2H), 7.70-7.59 (m, 2H), 3.40-3.37 (m, 2H), 2.81 (s, 3H), 2.50-2.43 (m, 1H), 2.24-2.19 (m, 1H).

Example C7 and Example D7

Synthesis of (R)-6-cyano-1-(3-((7-hydroxy-6,7-dihydro-5H-cyclopenta[b]pyridin-7-yl)ethynyl)phenyl)-1H-pyrazolo[4,3-c]pyridine-3-carboxamide and (S)-6-cyano-1-(3-((7-hydroxy-6,7-dihydro-5H-cyclopenta[b]pyridin-7-yl)ethynyl)phenyl)-1H-pyrazolo[4,3-c]pyridine-3-carboxamide

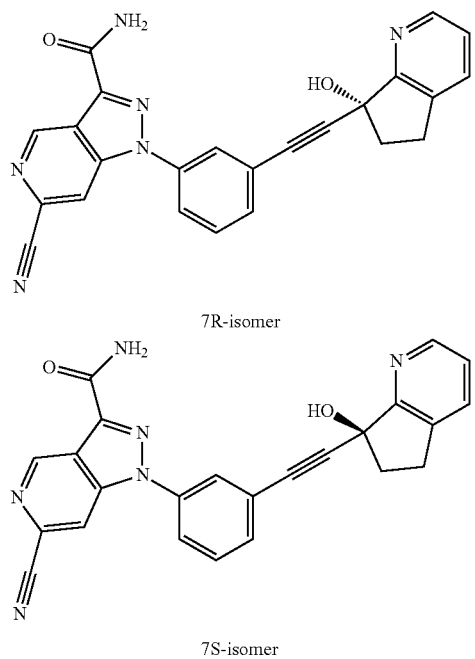

7R-isomer 7S-isomer

Step 1: Synthesis of 7-ethynyl-5H,6H,7H-cyclopenta[b]pyridin-7-ol

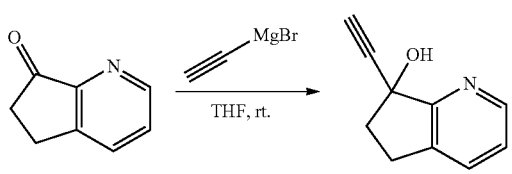

A solution of 5H,6H,7H-cyclopenta[b]pyridin-7-one (200 mg, 1.50 mmol, 1.00 equiv) in THF (2 mL) was added dropwise to a suspension of bromo(ethynyl)magnesium (3.6 mL, 0.5 M in THF) in oxolane (8 mL) at 0° C. and the resulting mixture was stirred for 2 h at room temperature. The reaction was quenched by saturated aqueous ammonium chloride, extracted with ethyl acetate, dried over anhydrous sodium sulfate, and concentrated under vacuum. The residue was purified by a silica gel column with ethyl acetate/petroleum ether (1:3) to give the title compound (180 mg, 75%) as a brown solid. LC-MS (ES, m/z): 160 [M+H]+.

Step 2: Synthesis of methyl 6-chloro-1-[3-(2-[7-hydroxy-5H,6H,7H-cyclopenta[b]pyridin-7-yl]ethynyl)phenyl]-1H-pyrazolo[4,3-c]pyridine-3-carboxylate

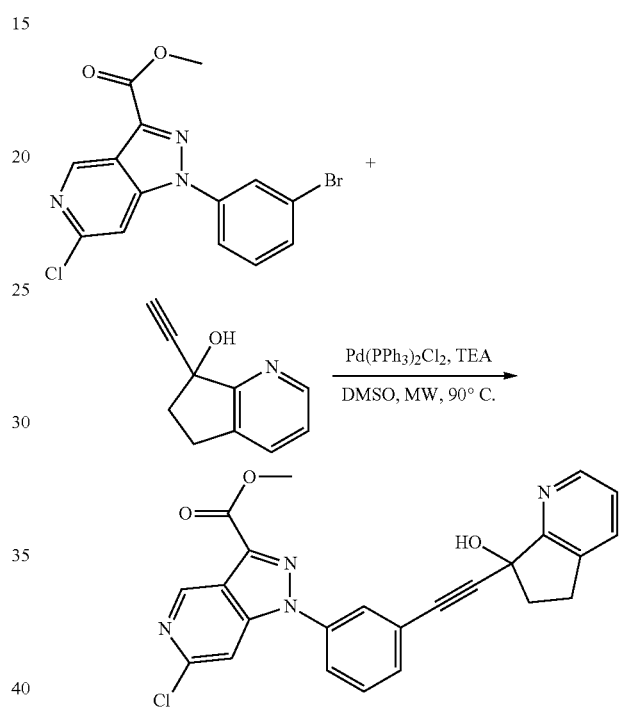

Similar to as described in General Procedure G, 7-ethynyl-5H,6H,7H-cyclopenta[b]pyridin-7-ol was reacted with methyl 1-(3-bromophenyl)-6-chloro-1H-pyrazolo[4,3-c]pyridine-3-carboxylate to give the title compound (450 mg, 74%) as a brown solid. LC-MS (ES, m/z): 445 [M+H]+.

Step 3: Synthesis of methyl 6-cyano-1-[3-(2-[7-hydroxy-5H,6H,7H-cyclopenta[b]pyridin-7-yl]ethynyl)phenyl]-1H-pyrazolo[4,3-c]pyridine-3-carboxylate

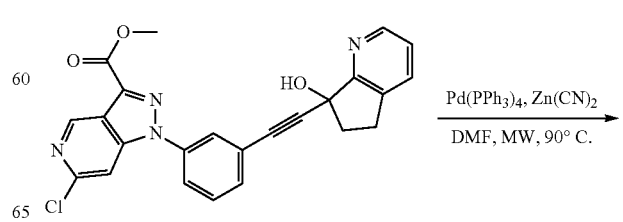

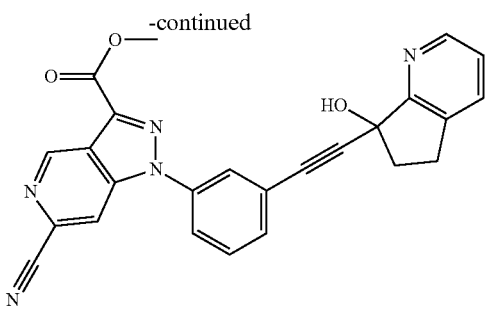

A suspension of methyl 6-chloro-1-[3-(2-[7-hydroxy-5H,6H,7H-cyclopenta[b]pyridin-7-yl]ethynyl)phenyl]-1H-pyrazolo[4,3-c]pyridine-3-carboxylate (450 mg, 1.01 mmol, 1.00 equiv), zinc cyanide (1.183 g, 10.07 mmol, 10.00 equiv), Pd(PPh$_3$)$_4$ (234 mg, 0.20 mmol, 0.20 equiv) in DMF (5 mL) was irradiated with microwave for 2 h at 90° C. The resulting mixture was concentrated under vacuum, diluted with, extracted with ethyl acetate, and dried over anhydrous sodium sulfate. The residue was purified by a silica gel column with dichloromethane/methanol (40:1) to give the title compound (200 mg, 45 as a yellow solid. LC-MS (ES, m/z): 436 [M+H]$^+$.

Step 4: Synthesis of 6-cyano-1-(3-[2-[(7R)-7-hydroxy-5H,6H,7H-cyclopenta[b]pyridin-7-yl]ethynyl]phenyl)-1H-pyrazolo[4,3-c]pyridine-3-carboxamide and 6-cyano-1-(3-[2-[(7S)-7-hydroxy-5H,6H,7H-cyclopenta[b]pyridin-7-yl]ethynyl]phenyl)-1H-pyrazolo[4,3-c]pyridine-3-carboxamide

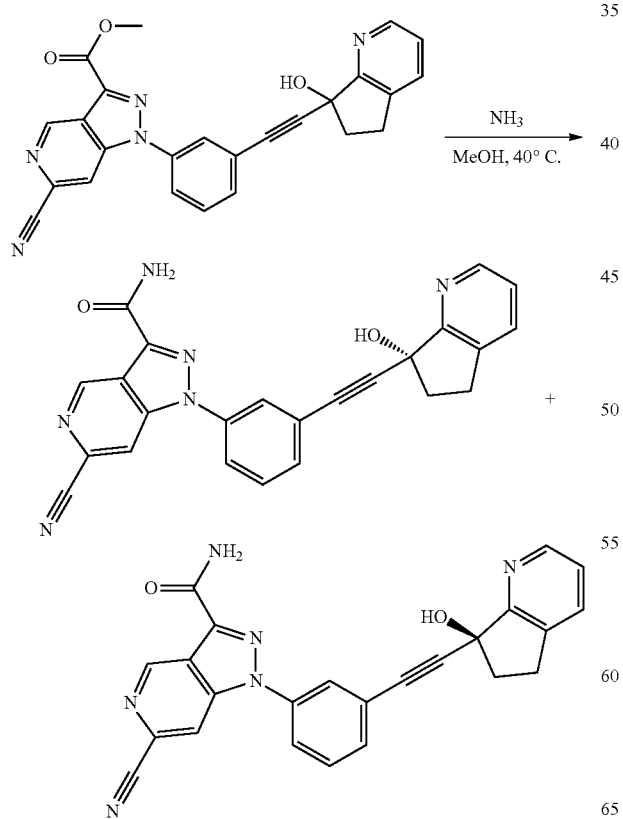

Similar to as described in General Procedure S, methyl 6-cyano-1-[3-(2-[7-hydroxy-5H,6H,7H-cyclopenta[b]pyridin-7-yl]ethynyl)phenyl]-1H-pyrazolo[4,3-c]pyridine-3-carboxylate was reacted with ammonia to give a crude product which was purified by Prep-HPLC and separated by Chiral-Prep-HPLC. This resulted in 23.9 mg (25%) of the 7R-isomer as a white solid and 28.3 mg (29%) of the 7S-isomer as a white solid. The stereochemistry of both compounds was arbitrarily assigned. 7R-isomer: $t_R$=2.40 min (Chiralcel IC-3, 0.46*5 cm, Hex:EtOH=50:50, 2.0 ml/min); 7S-isomer: $t_R$=4.92 min (Chiralcel IC-3, 0.46*5 cm, Hex:EtOH=50:50, 2.0 ml/min). Both isomers showed identical LC-MS and $^1$H NMR as shown below. LC-MS (ES, m/z): 421 [M+H]$^+$. $^1$H NMR (400 MHz, CD$_3$OD) δ 9.55 (s, 1H), 8.35 (s, 2H), 7.90 (s, 1H), 7.78-7.77 (m, 2H), 7.76 (d, J=3.2 Hz, 2H), 7.27-7.24 (m, 1H), 3.08-2.88 (m, 2H), 2.67-2.60 (m, 1H), 2.45-2.39 (m, 1H).

Example E7

Synthesis of (R)-6-ethoxy-1-(3-((3-hydroxy-1-methyl-2-oxopyrrolidin-3-yl)ethynyl)phenyl)-1H-pyrazolo[4,3-c]pyridine-3-carboxamide

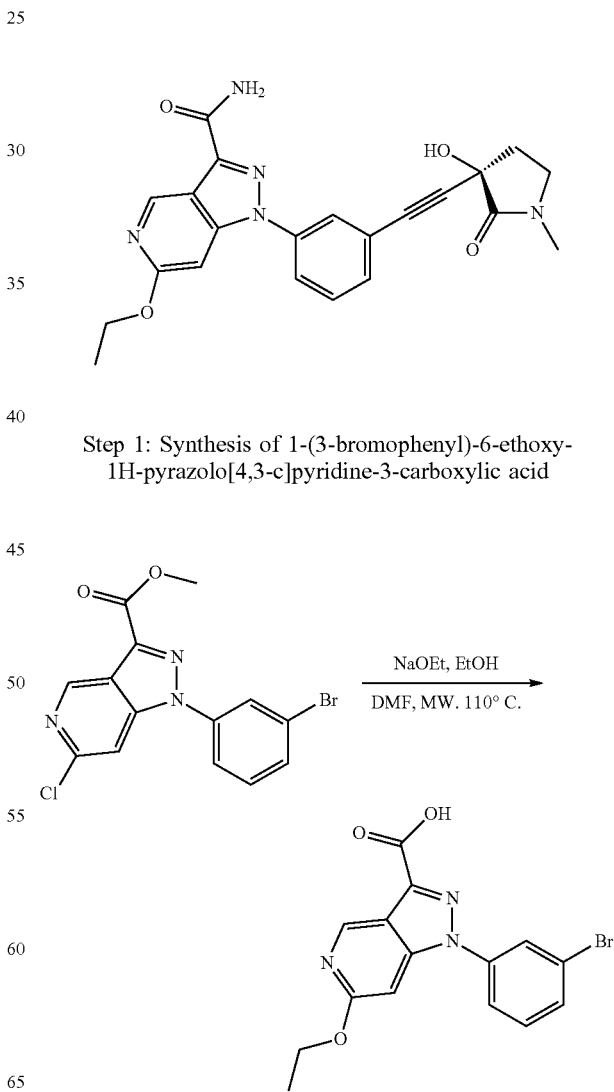

Step 1: Synthesis of 1-(3-bromophenyl)-6-ethoxy-1H-pyrazolo[4,3-c]pyridine-3-carboxylic acid A suspension of methyl 1-(3-bromophenyl)-6-chloro-1H-pyrazolo[4,3-c]pyridine-3-carboxylate (300 mg, 0.82 mmol, 1.00 equiv) and sodium ethoxide (555.8 mg, 8.17 mmol, 10.00 equiv) in ethanol (2 mL)/DMF (3 mL) was irradiated with microwave for 2.5 h at 110° C. The pH value of the solution was adjusted to 5 with hydrogen chloride (1 M). The resulting mixture was concentrated under vacuum. The residue was purified by a silica gel column with dichloromethane/methanol (20:1) to give the title compound (220 mg, 74%) as a yellow solid. LC-MS (ES, m/z): 362, 364 [M+H]$^+$.

Step 2: Synthesis of 1-(3-bromophenyl)-6-ethoxy-1H-pyrazolo[4,3-c]pyridine-3-carboxamide

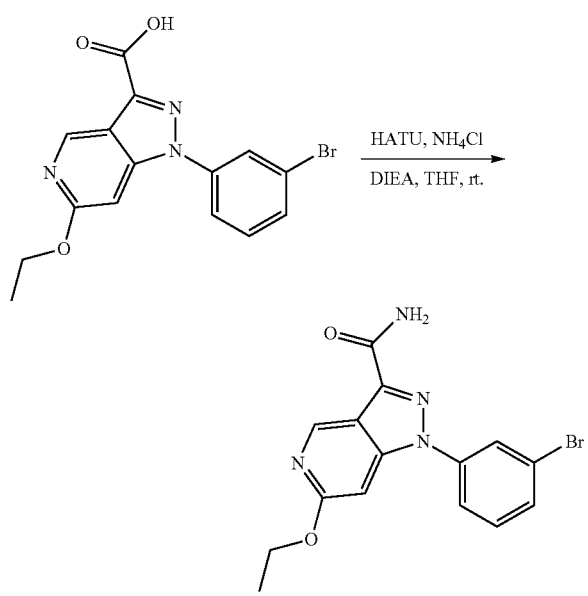

Similar to as described in General Procedure B, 1-(3-bromophenyl)-6-ethoxy-1H-pyrazolo[4,3-c]pyridine-3-carboxylic acid was reacted with ammonium chloride to give the title compound (200 mg, crude) as a white solid. LC-MS (ES, m/z): 361, 363 [M+H]$^+$.

Step 3: Synthesis of 6-ethoxy-1-(3-[2-[(3R)-3-hydroxy-1-methyl-2-oxopyrrolidin-3-yl]ethynyl]phenyl)-1H-pyrazolo[4,3-c]pyridine-3-carboxamide

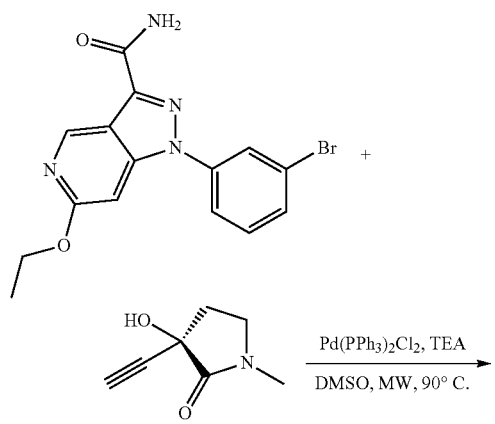

-continued

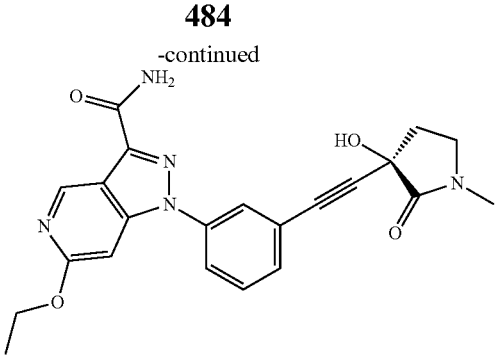

Similar to as described in General Procedure G, 1-(3-bromophenyl)-6-ethoxy-1H-pyrazolo[4,3-c]pyridine-3-carboxamide was reacted with (3R)-3-ethynyl-3-hydroxy-1-methylpyrrolidin-2-one to give the title compound (60.4 mg, 26%) as a yellow solid. LC-MS (ES, m/z): 420 [M+H]$^+$. $^1$H NMR (300 MHz, CD$_3$OD) δ 9.20 (s, 1H), 7.94 (s, 1H), 7.88-7.82 (m, 1H), 7.63-7.58 (m, 2H), 7.02 (s, 1H), 4.45-4.42 (m, 2H), 3.52 (t, J=7.2 Hz, 2H), 2.96 (s, 3H), 2.63-2.57 (m, 1H), 2.35-2.28 (m, 1H), 1.45 (t, J=7.2 Hz, 3H).

Example F7

Synthesis of (R)-1-(3-((3-hydroxy-1-methyl-2-oxopyrrolidin-3-yl)ethynyl)phenyl)-6-(pyrrolidin-1-yl)-1H-pyrazolo[4,3-c]pyridine-3-carboxamide

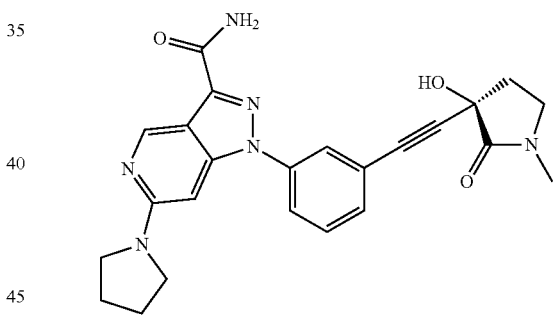

Step 1: Synthesis of 1-(3-bromophenyl)-6-(pyrrolidin-1-yl)-1H-pyrazolo[4,3-c]pyridine-3-carboxamide

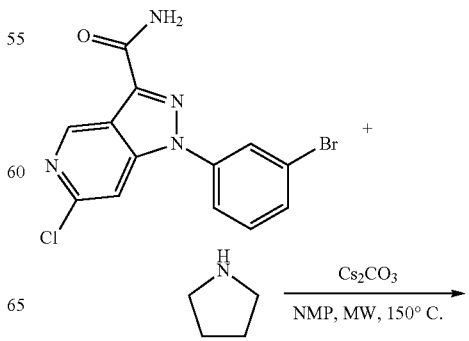

485
-continued

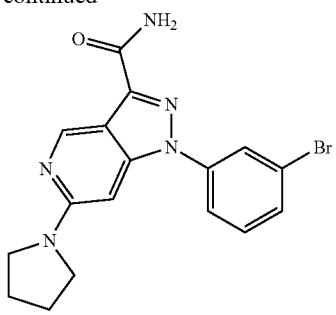

Similar to as described in General Procedure A, 1-(3-bromophenyl)-6-chloro-1H-pyrazolo[4,3-c]pyridine-3-carboxamide was reacted with pyrrolidine (2 mL) to give the title compound (200 mg, 46%) as a brown solid. LC-MS (ES, m/z): 386, 388 [M+H]⁺.

Step 2: Synthesis of 1-(3-[2-[(3R)-3-hydroxy-1-methyl-2-oxopyrrolidin-3-yl]ethynyl]phenyl)-6-(pyrrolidin-1-yl)-1H-pyrazolo[4,3-c]pyridine-3-carboxamide

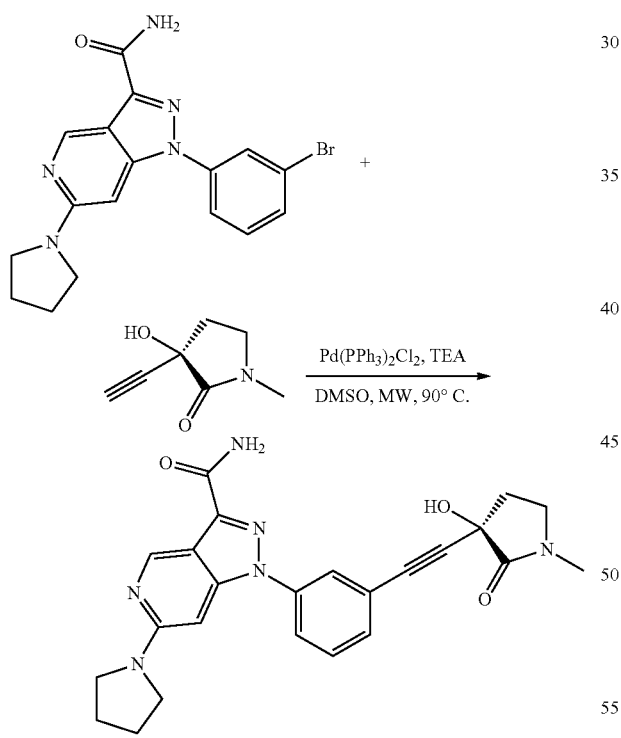

Similar to as described in General Procedure G, 1-(3-bromophenyl)-6-(pyrrolidin-1-yl)-1H-pyrazolo[4,3-c]pyridine-3-carboxamide was reacted with (3R)-3-ethynyl-3-hydroxy-1-methylpyrrolidin-2-one to give the title compound (52.7 mg, 23%) as a light yellow solid. LC-MS (ES, m/z): 445 [M+H]⁺. $^1$H NMR (300 MHz, CD$_3$OD) δ 9.08 (s, 1H), 7.89 (s, 1H), 7.83-7.80 (m, 1H), 7.61-7.49 (m, 2H), 6.38 (s, 1H), 3.55-3.45 (m, 6H), 2.94 (s, 3H), 2.65-2.57 (m, 1H), 2.38-2.28 (m, 1H). 2.09-2.05 (m, 4H).

486

Example G7 and Example H7

Synthesis of 1-(3-(((R)-3-hydroxy-1-methyl-2-oxopyrrolidin-3-yl)ethynyl)phenyl)-6-((R)-3-hydroxypyrrolidin-1-yl)-1H-pyrazolo[4,3-c]pyridine-3-carboxamide and 1-(3-(((R)-3-hydroxy-1-methyl-2-oxopyrrolidin-3-yl)ethynyl)phenyl)-6-((S)-3-hydroxypyrrolidin-1-yl)-1H-pyrazolo[4,3-c]pyridine-3-carboxamide

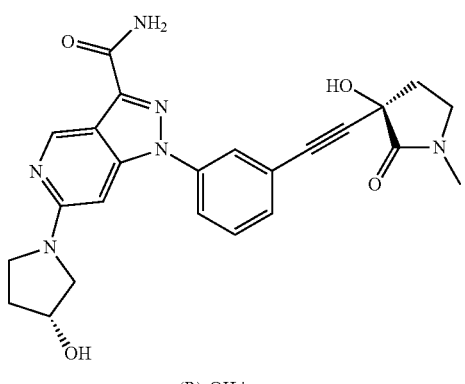

(R)-OH isomer

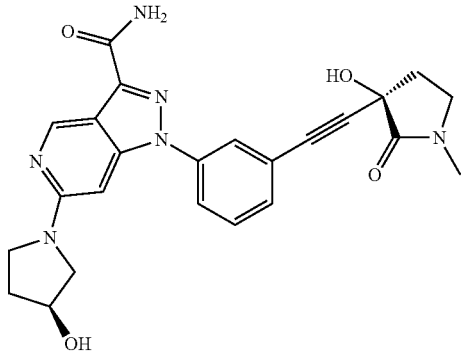

(S)-OH isomer

Step 1: Synthesis of 1-(3-bromophenyl)-6-chloro-1H-pyrazolo[4,3-c]pyridine-3-carboxamide

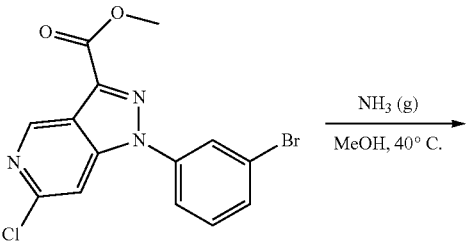

487
-continued

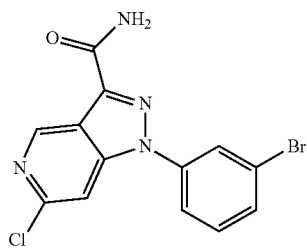

Similar to as described in General Procedure S, methyl 1-(3-bromophenyl)-6-chloro-1H-pyrazolo[4,3-c]pyridine-3-carboxylate was reacted with ammonia to give the title compound (250 mg, 52%) as a white solid. LC-MS (ES, m/z): 351, 353 [M+H]+.

Step 2: Synthesis of 1-(3-bromophenyl)-6-[(3R)-3-hydroxypyrrolidin-1-yl]-1H-pyrazolo[4,3-c]pyridine-3-carboxamide

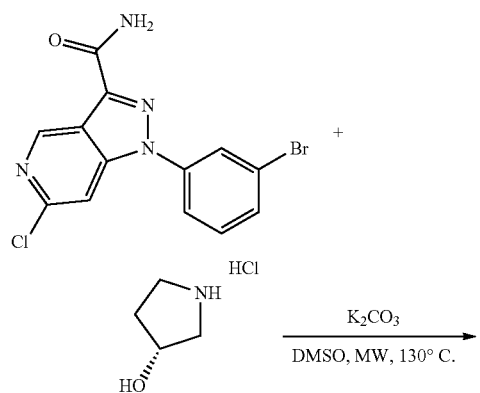

Similar to as described in General Procedure A, 1-(3-bromophenyl)-6-chloro-1H-pyrazolo[4,3-c]pyridine-3-carboxamide was reacted with (3R)-pyrrolidin-3-ol hydrochloride to give the title compound (70 mg, 61%) as a yellow solid. LC-MS (ES, m/z): 402, 404 [M+H]+.

488

Step 3: Synthesis of 1-(3-[2-[(3R)-3-hydroxy-1-methyl-2-oxopyrrolidin-3-yl]ethynyl]phenyl)-6-[(3R)-3-hydroxy pyrrolidin-1-yl]-1H-pyrazolo[4,3-c]pyridine-3-carboxamide

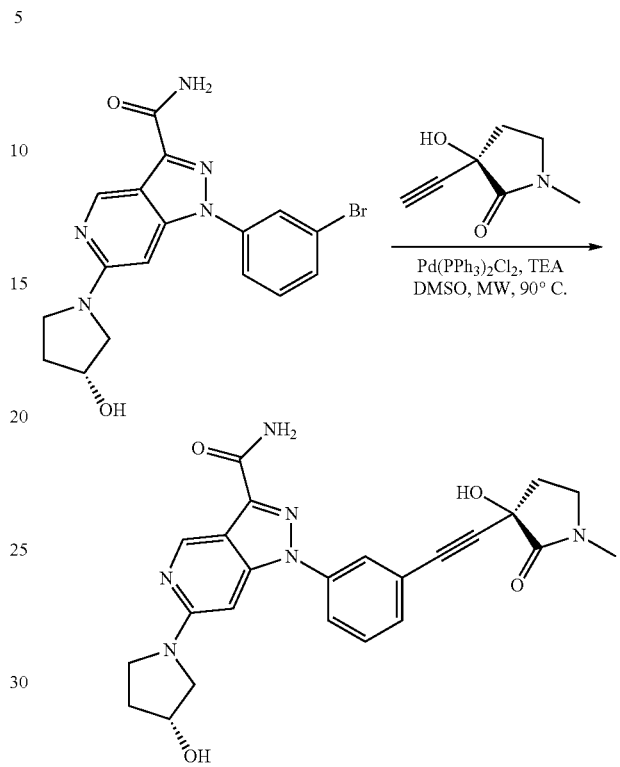

Similar to as described in General Procedure G, 1-(3-bromophenyl)-6-[(3R)-3-hydroxypyrrolidin-1-yl]-1H-pyrazolo[4,3-c]pyridine-3-carboxamide was reacted with (3R)-3-ethynyl-3-hydroxy-1-methylpyrrolidin-2-one to give the title compound (43.1 mg, 54%) as a yellow solid. LC-MS (ES, m/z): 461 [M+H]+. $^1$H NMR (400 MHz, CD$_3$OD) δ 8.99 (s, 1H), 7.79 (s, 1H), 7.72-7.70 (m, 1H), 7.51-7.40 (m, 2H), 6.30 (s, 1H), 4.45 (s, 1H), 3.58-3.49 (m, 3H), 3.40-3.37 (m, 3H), 2.83 (s, 3H), 2.53-2.47 (m, 1H), 2.26-2.19 (m, 1H), 2.11-2.05 (m, 1H), 1.99-1.96 (m, 1H).

Step 4

The (S)—OH isomer, namely, 1-(3-(((R)-3-hydroxy-1-methyl-2-oxopyrrolidin-3-yl)ethynyl)phenyl)-6-((S)-3-hydroxypyrrolidin-1-yl)-1H-pyrazolo[4,3-c]pyridine-3-carboxamide, was prepared from 1-(3-bromophenyl)-6-chloro-1H-pyrazolo[4,3-c]pyridine-3-carboxamide and (3S)-pyrrolidin-3-ol hydrochloride followed the exact same procedure as described for the (R)—OH isomer. LC-MS (ES, m/z): 461 [M+H]+. $^1$H NMR (300 MHz, CD$_3$OD) δ 9.01 (s, 1H), 7.80 (s, 1H), 7.72 (d, J=7.8 Hz, 1H), 7.49 (t, J=7.8 Hz, 1H), 7.42 (d, J=8.1 Hz, 1H), 6.31 (s, 1H), 4.46 (s, 1H), 3.60-3.51 (m, 3H), 3.49-3.36 (m, 3H), 2.83 (s, 3H), 2.54-2.46 (m, 1H), 2.27-2.18 (m, 1H), 2.14-1.98 (m, 2H).

Example I7

Synthesis of (R)-1-(3-((3-hydroxy-1-methyl-2-oxopyrrolidin-3-yl)ethynyl)phenyl)-6-methoxy-1H-pyrazolo[4,3-c]pyridine-3-carboxamide

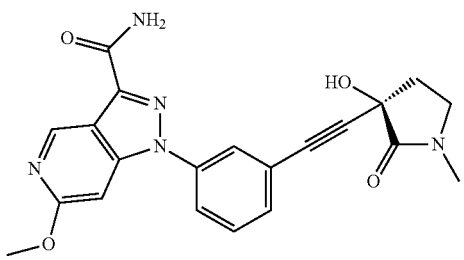

Step 1: Synthesis of 6-chloro-3-iodo-1H-pyrazolo[4,3-c]pyridine

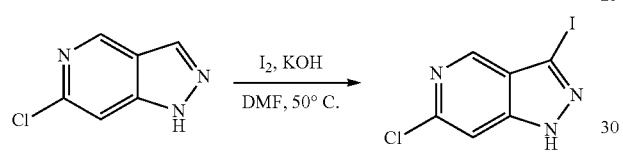

A suspension of 6-chloro-1H-pyrazolo[4,3-c]pyridine (7 g, 45.58 mmol, 1.00 equiv) in DMF (100 mL), potassium hydroxide (7.67 g, 136.71 mmol, 3.00 equiv), and $I_2$ (20.82 g, 82.03 mmol, 1.80 equiv) was stirred for 5 h at 50° C. The reaction was quenched by saturated aqueous sodium thiosulfate and diluted with water. The resulting solution was extracted with ethyl acetate, dried over anhydrous sodium sulfate, and concentrated under vacuum. The residue was purified by a silica gel column with ethyl acetate/dichloromethane (1:15) to give the title compound (6 g, 47%) as an orange solid. LC-MS (ES, m/z): 280 [M+H]$^+$.

Step 2: Synthesis of methyl 6-chloro-1H-pyrazolo[4,3-c]pyridine-3-carboxylate

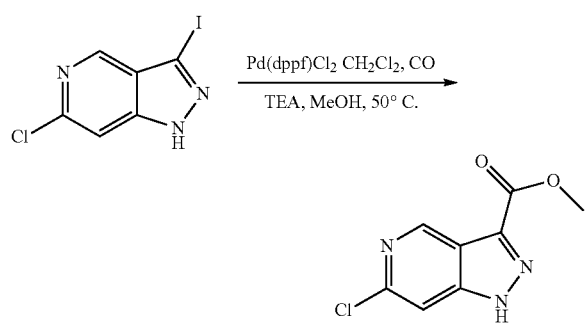

Similar to as described in General Procedure O, carbon monoxide was reacted with 6-chloro-3-iodo-1H-pyrazolo[4,3-c]pyridine to give the title compound (1.3 g, 86%) as a yellow solid. LC-MS (ES, m/z): 212 [M+H]$^+$.

Step 3: Synthesis of methyl 1-(3-bromophenyl)-6-chloro-1H-pyrazolo[4,3-c]pyridine-3-carboxylate

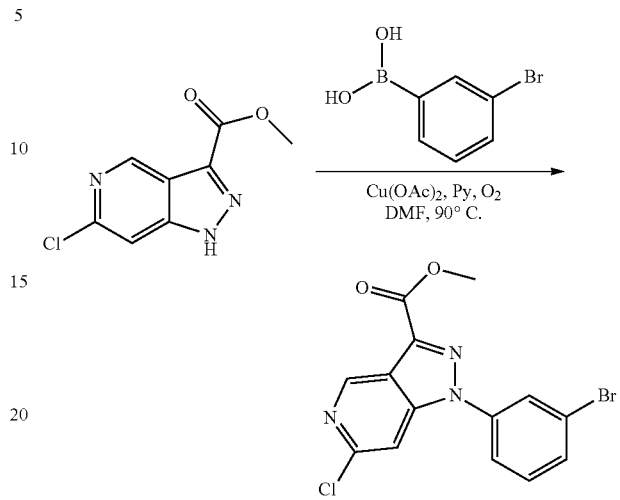

Similar to as described in General Procedure C, methyl 6-chloro-1H-pyrazolo[4,3-c]pyridine-3-carboxylate was reacted with (3-bromophenyl)boronic acid to give the title compound (320 mg, 62%) as a white solid. LC-MS (ES, m/z): 366, 368 [M+H]$^+$.

Step 4: Synthesis of -(3-bromophenyl)-6-methoxy-1H-pyrazolo[4,3-c]pyridine-3-carboxylic acid

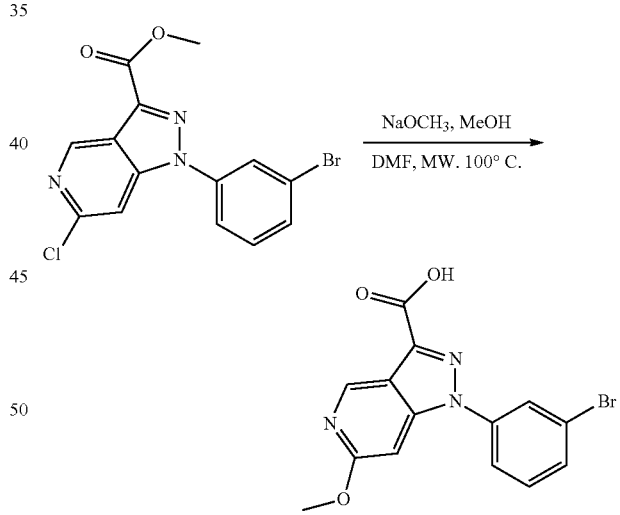

A suspension of methyl 1-(3-bromophenyl)-6-chloro-1H-pyrazolo[4,3-c]pyridine-3-carboxylate (400 mg, 1.09 mmol, 1.00 equiv), sodium methoxide (589 mg, 10.90 mmol, 10.00 equiv) in DMF (5 mL)/methanol (1 mL) was irradiated with microwave for 3 h at 110° C. The pH value of the solution was adjusted to 5 with hydrogen chloride (1 M). The resulting mixture was concentrated under vacuum and then diluted with water. The solution was extracted with ethyl acetate, dried over anhydrous sodium sulfate, and concentrated under vacuum. This resulted in the title compound (300 mg, 39%) as a yellow solid. LC-MS (ES, m/z): 348, 350 [M+H]$^+$.

Step 5: Synthesis of 1-(3-bromophenyl)-6-methoxy-1H-pyrazolo[4,3-c]pyridine-3-carboxamide

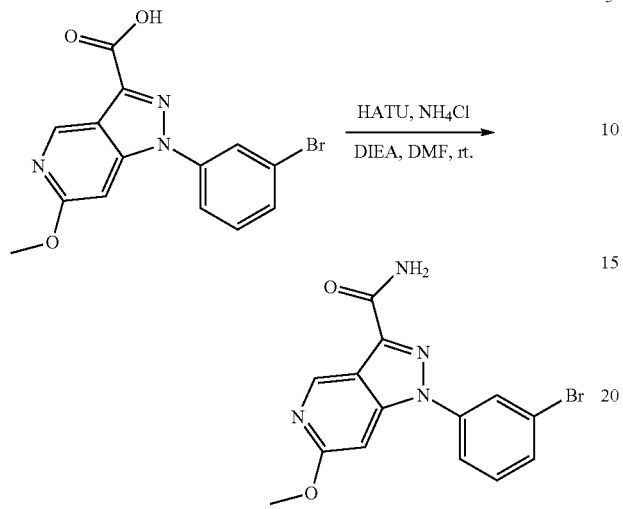

Similar to as described in General Procedure B, 1-(3-bromophenyl)-6-methoxy-1H-pyrazolo[4,3-c]pyridine-3-carboxylic acid was reacted with ammonium chloride to give the title compound (480 mg, 96%) as a yellow solid. LC-MS (ES, m/z): 347, 349 [M+H]$^+$.

Step 6: Synthesis of 1-(3-[2-[(3R)-3-hydroxy-1-methyl-2-oxopyrrolidin-3-yl]ethynyl]phenyl)-6-methoxy-1H-pyrazolo[4,3-c]pyridine-3-carboxamide

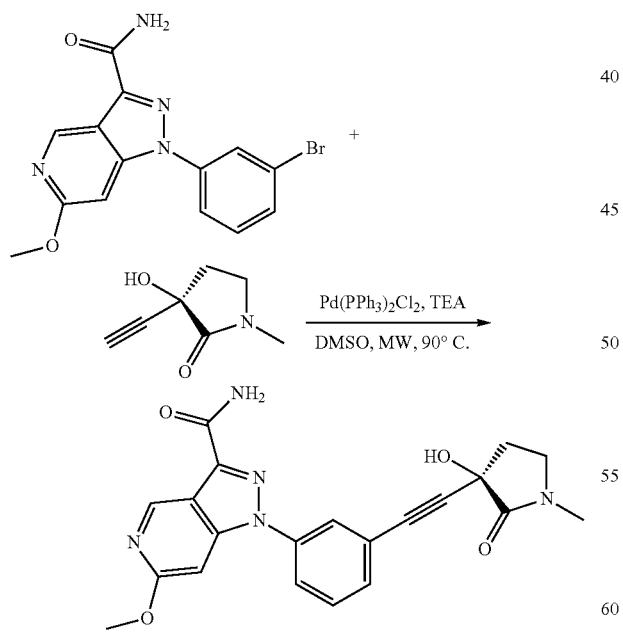

Similar to as described in General Procedure G, 1-(3-bromophenyl)-6-methoxy-1H-pyrazolo[4,3-c]pyridine-3-carboxamide was reacted with (3R)-3-ethynyl-3-hydroxy-1-methylpyrrolidin-2-one to give the title compound (36 mg, 12%) as a yellow solid. LC-MS (ES, m/z): 406 [M+H]$^+$. $^1$H NMR (300 MHz, DMSO-d$_6$) δ 9.15 (s, 1H), 7.93-7.89 (m, 2H), 7.65 (t, J=7.8 Hz, 1H), 7.51 (d, J=7.8 Hz, 1H), 7.10 (s, 1H), 3.98 (s, 3H), 3.37 (t, J=7.2 Hz, 2H), 2.81 (s, 3H), 2.47-2.43 (m, 1H), 2.28-2.18 (m, 1H).

Example J7

Synthesis of (R)-5-((4-amino-N-methylbutanamido)methyl)-1-(4-((3-hydroxy-1-methyl-2-oxopyrrolidin-3-yl)ethynyl)pyridin-2-yl)-1H-indazole-3-carboxamide

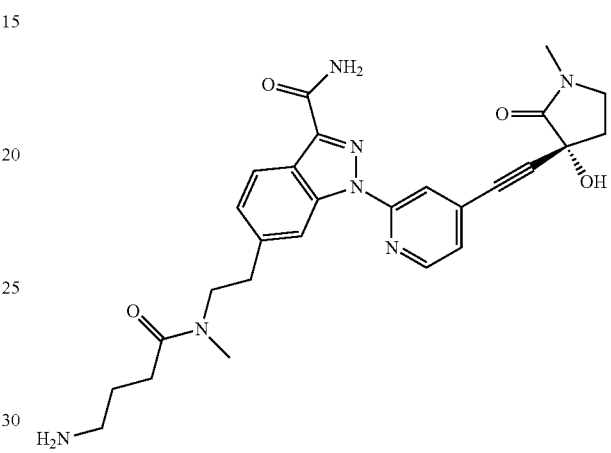

Step 1: Synthesis of 5-(chloromethyl)-1-(4-iodopyridin-2-yl)-1H-indazole-3-carboxamide

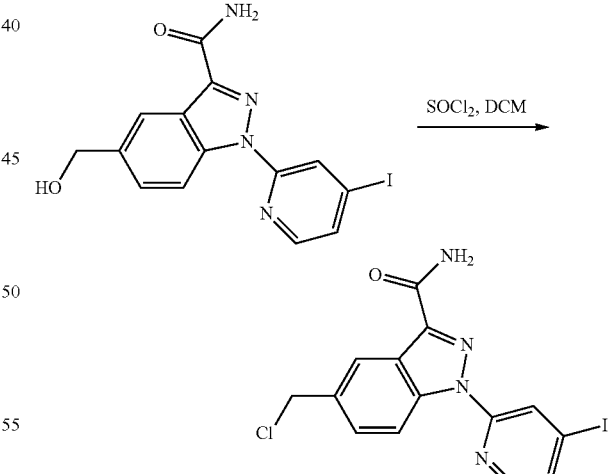

Thionyl chloride (6 mL, 82.71 mmol, 21.70 equiv) was added dropwise into a solution of 5-(hydroxymethyl)-1-(4-iodopyridin-2-yl)-1H-indazole-3-carboxamide (1.50 g, 3.81 mmol, 1.00 equiv) in dichloromethane (30 mL). The resulting solution was stirred for 30 min at room temperature and concentrated under vacuum. This resulted in 1.7 g (crude) of the title compound as yellow oil. LC-MS (ES, m/z): 413 [M+H]$^+$.

Step 2: Synthesis of 1-(4-iodopyridin-2-yl)-5-[(methylamino)methyl]-1H-indazole-3-carboxamide

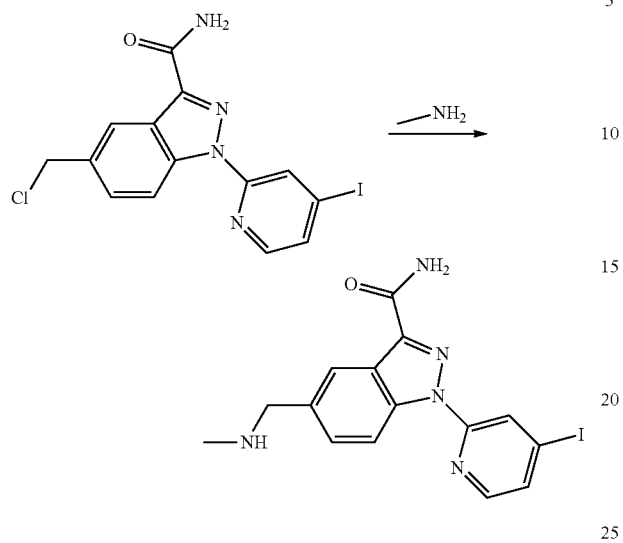

A solution of 5-(chloromethyl)-1-(4-iodopyridin-2-yl)-1H-indazole-3-carboxamide (1.7 g, 4.12 mmol, 1.00 equiv), triethylamine (1.96 g, 19.37 mmol, 4.70 equiv), and methyl amine (5 ml, 2.00 equiv) in dichloromethane (100 mL) was stirred for 12 h at room temperature. The solvents were removed to give the title compound (2.0 g, crude) as yellow oil. LC-MS (ES, m/z): 408 [M+H]$^+$.

Step 3: Synthesis of tert-butyl N-[3-([[3-carbamoyl-1-(4-iodopyridin-2-yl)-1H-indazol-5-yl]methyl](methyl)carbamoyl)propyl]carbamate

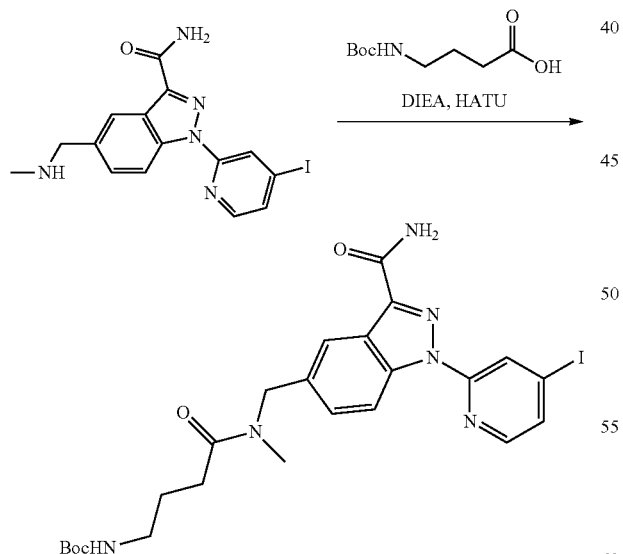

A mixture of 1-(4-iodopyridin-2-yl)-5-[(methylamino)methyl]-1H-indazole-3-carboxamide (2.00 g, 4.91 mmol, 1.00 equiv), 4-[[(tert-butoxy)carbonyl]amino]butanoic acid (2.00 g, 9.84 mmol, 2.00 equiv), ethyldiisopropylamine (2.54 g, 19.65 mmol, 4.00 equiv), and N,N,N',N'-tetramethyl-O-(7-azabenzotriazol-1-yl)uronium hexafluorophospate (2.80 g, 7.36 mmol, 1.50 equiv) in dichloromethane (100 mL) was stirred for 12 h at room temperature. The resulting mixture was concentrated under vacuum and the residue was applied onto a silica gel column with ethyl acetate/petroleum ether (7:3). This resulted in 600 mg (crude) of the title compound as an off-white solid. LC-MS (ES, m/z): 593 [M+H]$^+$.

Step 4: Synthesis of tert-butyl N-[3-([[3-carbamoyl-1-(4-[2-[(3R)-3-hydroxy-1-methyl-2-oxopyrrolidin-3-yl]ethynyl]pyridin-2-yl)-1H-indazol-5-yl]methyl](methyl)carbamoyl)propyl]carbamate

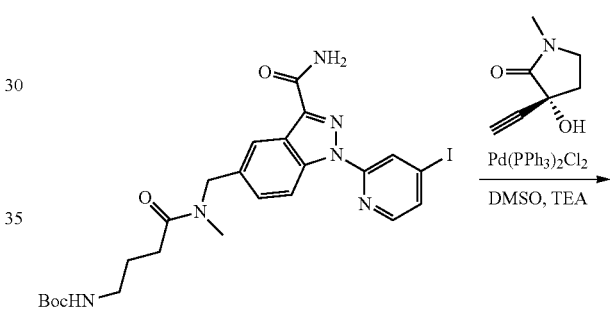

Similar to as described in General Procedure G, tert-butyl N-[3-([[3-carbamoyl-1-(4-iodopyridin-2-yl)-1H-indazol-5-yl]methyl](methyl)carbamoyl)propyl]carbamate was reacted with (3R)-3-ethynyl-3-hydroxy-1-methylpyrrolidin-2-one to give the title compound (360 mg, 61%) as a yellow solid. LC-MS (ES, m/z): 604 [M+H]$^+$.

Step 5: Synthesis of 5-[(4-amino-N-methylbutana-mido)methyl]-1-(4-[2-[(3R)-3-hydroxy-1-methyl-2-oxopyrrolidin-3-yl]ethynyl]pyridin-2-yl-1H-inda-zole-3-carboxamide

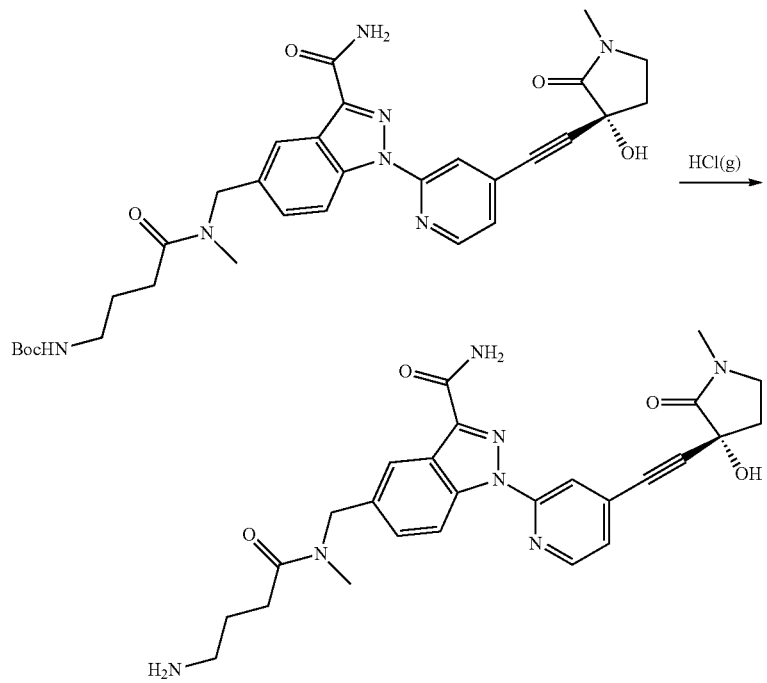

Into a 100-mL round-bottom flask purged and maintained with an inert atmosphere of HCl was placed tert-butyl N-[3-([[3-carbamoyl-1-(4-[2-[(3R)-3-hydroxy-1-methyl-2-oxopyrrolidin-3-yl]ethynyl]pyridin-2-yl)-1H-indazol-5-yl]methyl](methyl)carbamoyl)propyl]carbamate (360 mg, 0.60 mmol, 1.00 equiv) in ethyl acetate (10 mL). The resulting solution was stirred for 10 min at room temperature. The solids were collected by filtration and the crude product was purified by Prep-HPLC to give the title compound (52.7 mg, 18%) as an off-white solid. LC-MS (ES, m/z): 504 [M+H]$^+$.
$^1$H NMR (300 MHz, DMSO-d$_6$) δ 8.77-8.70 (m, 1H), 8.60 (d, J=4.5 Hz, 1H), 8.32 (s, 1H), 8.26 (s, 1H), 8.14 (d, J=10.2 Hz, 1H), 7.65 (s, 1H), 7.47 (d, J=8.7 Hz, 1H), 7.37 (d, J=8.1 Hz, 1H), 6.68 (s, 1H), 4.76-4.67 (m, 2H), 3.41-3.33 (m, 2H), 3.00-2.91 (m, 3H), 2.83-2.80 (m, 4H), 2.63-2.53 (m, 1H), 2.50 (s, 3H), 2.47-2.39 (m, 3H), 2.28-2.19 (m, 1H), 1.70-1.67 (m, 2H).

Example K7

Synthesis of (R)-1-(4-((3-hydroxy-1-methyl-2-ox-opyrrolidin-3-yl)ethynyl)pyridin-2-yl)-5-((N-methyl-butyramido)methyl)-1H-indazole-3-carboxamide

Step 1: Synthesis of 1-(4-iodopyridin-2-yl)-5-[(N-methylbutanamido)methyl]-1H-indazole-3-carbox-amide

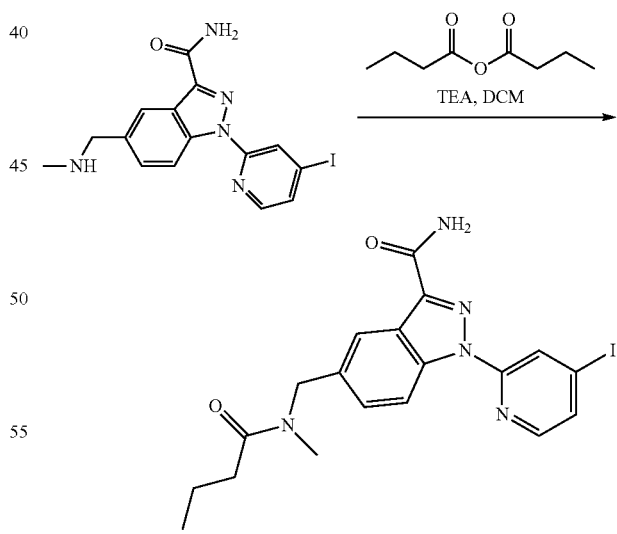

A suspension of 1-(4-iodopyridin-2-yl)-5-[(methylamino)methyl]-1H-indazole-3-carboxamide (2.00 g, 4.91 mmol, 1.00 equiv), triethylamine (2.98 g, 29.45 mmol, 6.00 equiv), and butanoyl butanoate (2.33 g, 14.73 mmol, 3.00 equiv) in dichloromethane (100 mL) was stirred for 2 h at room temperature. The resulting mixture was concentrated under vacuum. The residue was applied onto a silica gel column with ethyl acetate/petroleum ether (2:3). This resulted in 200 mg (9%) of the title compound as a yellow solid. LC-MS (ES, m/z): 478 [M+H]⁺.

Step 2: Synthesis of 1-(4-[2-[(3R)-3-hydroxy-1-methyl-2-oxopyrrolidin-3-yl]ethynyl]pyridin-2-yl)-5-[(N-methyl butanamido)methyl]-1H-indazole-3-carboxamide

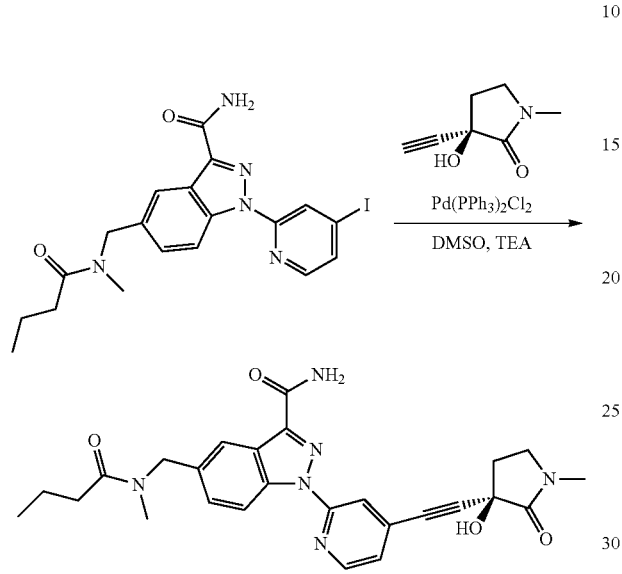

Similar to as described in General Procedure G, 1-(4-iodopyridin-2-yl)-5-[(N-methylbutanamido)methyl]-1H-indazole-3-carboxamide was reacted with (3R)-3-ethynyl-3-hydroxy-1-methylpyrrolidin-2-one to give the title compound (24.5 mg, 13%) as a light yellow solid. LC-MS (ES, m/z): 489 [M+H]⁺. ¹H NMR (300 MHz, CD₃OD) δ 8.83-8.79 (m, 1H), 8.57 (d, J=5.7 Hz, 1H), 7.52 (s, 1H), 7.49 (s, 1H), 7.36 (t, J=1.5 Hz, 1H), 7.35 (d, J=1.5 Hz, 1H), 4.87-4.78 (m, 2H), 3.55-3.49 (m, 2H), 3.10-3.06 (m, 2H), 2.99-2.96 (m, 4H), 2.66-2.62 (m, 1H), 2.53-2.41 (m, 2H), 2.38-2.34 (m, 1H), 1.77-1.68 (m, 2H), 1.06-0.95 (m, 3H).

Example L7

Synthesis of (R)-1-(3-((3-hydroxy-1-methyl-2-oxopyrrolidin-3-yl)ethynyl)phenyl)-6-oxo-1,4,5,6-tetrahydropyrrolo[3,4-c]pyrazole-3-carboxamide

Step 1: Synthesis of ethyl 1-(3-[2-[(3R)-3-hydroxy-1-methyl-2-oxopyrrolidin-3-yl]ethynyl]phenyl)-6-oxo-1H,4H,5H, 6H-pyrrolo[3,4-c]pyrazole-3-carboxylate

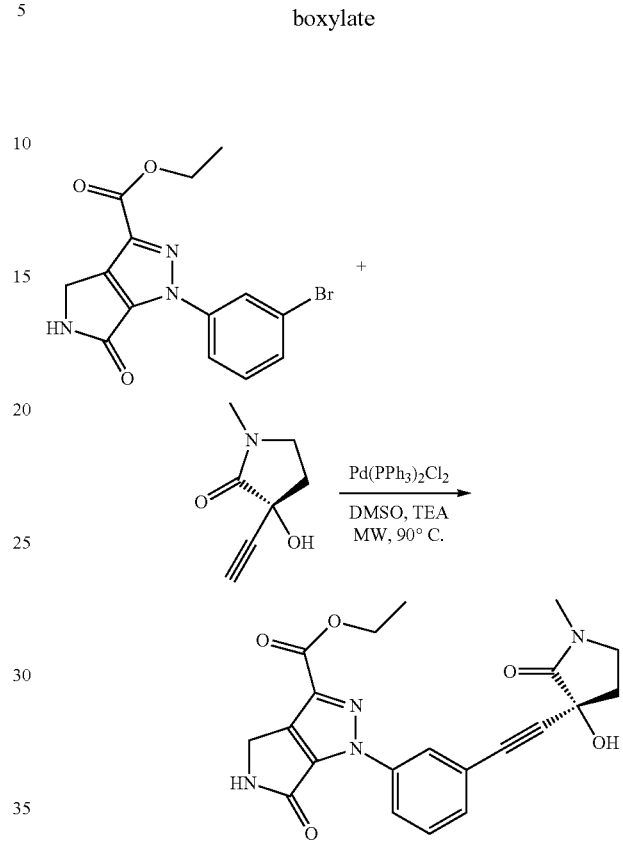

Similar to as described in General Procedure G, ethyl 1-(3-bromophenyl)-6-oxo-1H,4H,5H,6H-pyrrolo[3,4-c]pyrazole-3-carboxylate was reacted with (3R)-3-ethynyl-3-hydroxy-1-methylpyrrolidin-2-one to give the title compound (130 mg, crude) as a brown solid. LC-MS (ES, m/z): 409 [M+H]⁺.

Step 2: Synthesis of 1-(3-[2-[(3R)-3-hydroxy-1-methyl-2-oxopyrrolidin-3-yl]ethynyl]phenyl)-6-oxo-1H,4H,5H, 6H-pyrrolo[3,4-c]pyrazole-3-carboxamide

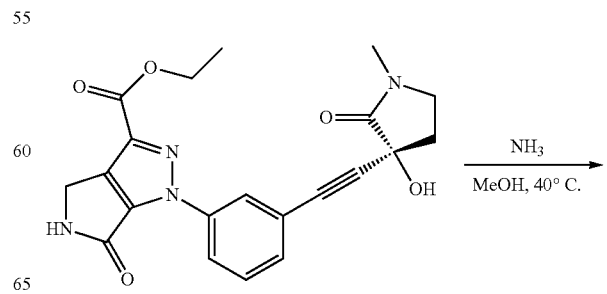

499

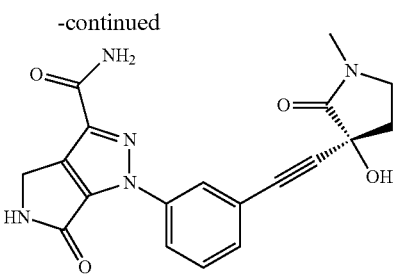

Similar to as described in General Procedure S, ethyl 1-(3-[2-[(3R)-3-hydroxy-1-methyl-2-oxopyrrolidin-3-yl]ethynyl]phenyl)-4-oxo-1H,4H,5H, 6H-pyrrolo[3,4-c]pyrazole-3-carboxylate was reacted with ammonia to give the title compound (9.7 mg, 8%) as a white solid. LC-MS (ES, m/z): 380 [M+H]$^+$. $^1$H NMR (300 MHz, CD$_3$OD) δ 8.47 (s, 1H), 8.43-8.40 (m, 1H), 7.54-7.45 (m, 2H), 4.48 (s, 2H), 3.55-3.45 (m, 2H), 2.94 (s, 3H), 2.65-2.57 (m, 1H), 2.37-2.28 (m, 1H).

Example M7

Synthesis of (R)-1-(3-((3-hydroxy-1-methyl-2-oxopyrrolidin-3-yl)ethynyl)phenyl)-1H-pyrazolo[3,4-d]thiazole-3-carboxamide

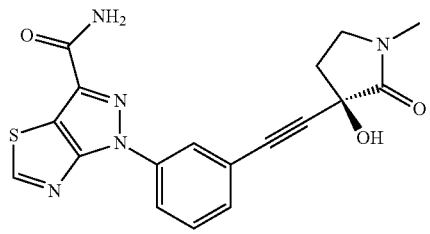 [SMILES: CN1CC[C@@](O)(C#Cc2cccc(-n3nc(C(N)=O)c4scnc43)c2)C1=O]

Step 1: Synthesis of ethyl 1-(3-bromophenyl)-1H-pyrazolo[3,4-d][1,3]thiazole-3-carboxylate

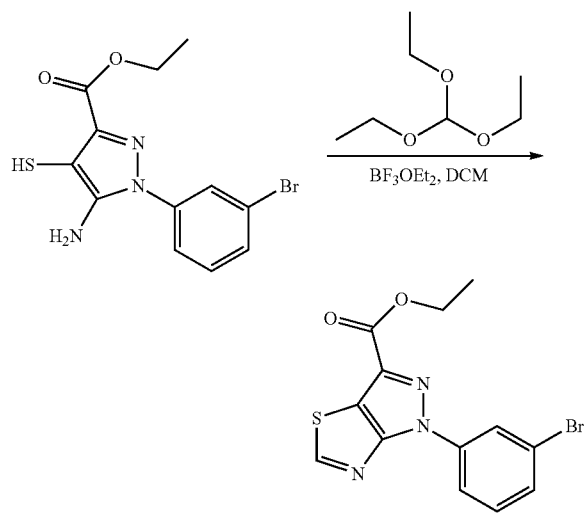

500

A mixture of ethyl 5-amino-1-(3-bromophenyl)-4-sulfanyl-1H-pyrazole-3-carboxylate (100 mg, 0.29 mmol, 1.00 equiv), (diethoxymethoxy)ethane (215 mg, 1.45 mmol, 5.00 equiv), and boron trifluoride etherate (206 mg, 1.45 mmol, 5.00 equiv) in dichcloromethane (10 mL) was stirred for 2 h at room temperature. The reaction was quenched by saturation sodium bicarbonate, extracted with ethyl acetate, and concentrated under vacuum. The residue was applied onto a silica gel column with ethyl acetate/petroleum ether (1:4). This resulted in 70 mg (68%) of the title compound as a yellow solid. LC-MS (ES, m/z): 352 [M+H]$^+$.

Step 2: Synthesis of ethyl 1-(3-[2-[(3R)-3-hydroxy-1-methyl-2-oxopyrrolidin-3-yl]ethynyl]phenyl)-1H-pyrazolo[3,4-d][1,3]thiazole-3-carboxylate

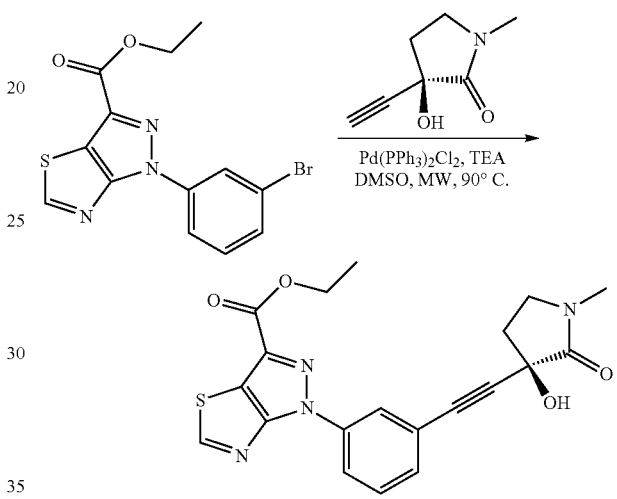

Similar to as described in General Procedure G, ethyl 1-(3-bromophenyl)-1H-pyrazolo[3,4-d][1,3]thiazole-3-carboxylate was reacted with (3R)-3-ethynyl-3-hydroxy-1-methylpyrrolidin-2-one to give the title compound (18 mg, 22%) as a yellow solid. LC-MS (ES, m/z): 411 [M+H]$^+$.

Step 3: Synthesis of 1-(3-[2-[(3R)-3-hydroxy-1-methyl-2-oxopyrrolidin-3-yl]ethynyl]phenyl)-1H-pyrazolo[3,4-d][1,3]thiazole-3-carboxamide

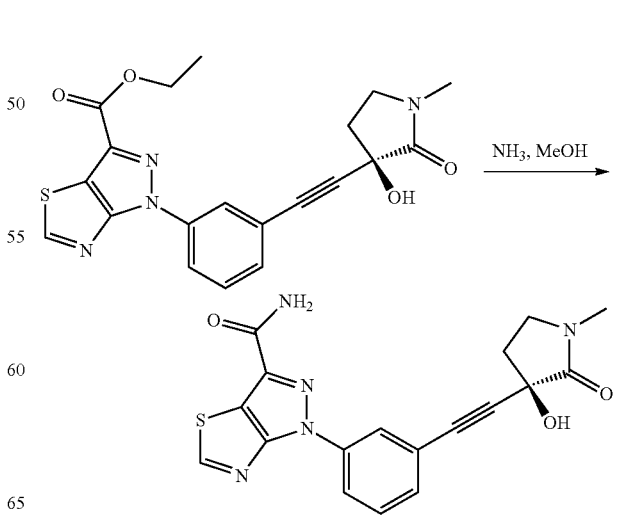

Similar to as described in General Procedure S, ethyl 1-(3-[2-[(3R)-3-hydroxy-1-methyl-2-oxopyrrolidin-3-yl]ethynyl]phenyl)-1H-pyrazolo[3,4-d][1,3]thiazole-3-carboxylate was reacted with NH₃ to give the title compound (14 mg, 84%) as a white solid. LC-MS (ES, m/z): 382 [M+H]⁺. ¹H NMR (300 MHz, CD₃OD) δ 9.28 (s, 1H), 8.49-8.48 (t, 1H), 8.42-8.38 (m, 1H), 7.61-7.47 (m, 2H), 3.57-3.43 (m, 2H), 3.97 (s, 3H), 2.68-2.60 (m, 1H), 2.40-2.31 (m, 1H).

Example N7

Synthesis of (R)-1-(2-fluoro-5-((3-hydroxy-1-methyl-2-oxopyrrolidin-3-yl)ethynyl)phenyl)-1,4,5,6-tetrahydrocyclopenta[c]pyrazole-3-carboxamide

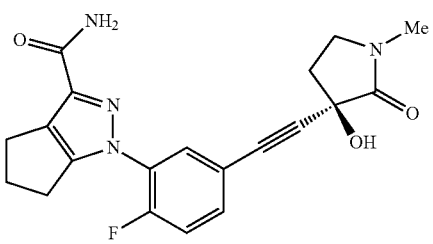 [SMILES: CN1CC[C@@](O)(C#Cc2ccc(F)c(-n3nc(C(N)=O)c4c3CCC4)c2)C1=O]

Step 1: Synthesis of ethyl 1-(5-bromo-2-fluorophenyl)-1H,4H,5H,6H-cyclopenta[c]pyrazole-3-carboxylate

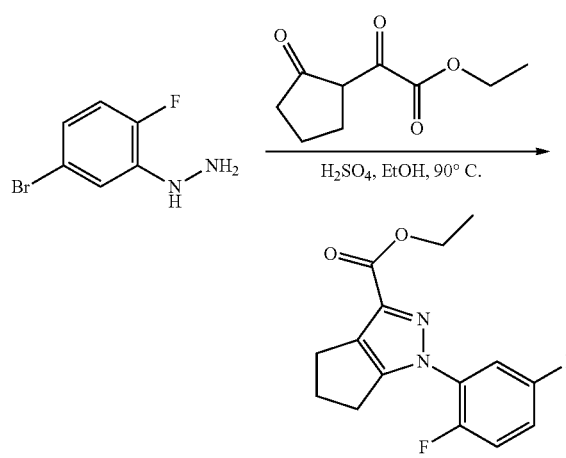

Similar to as described in General Procedure Y Step 2, ethyl 2-oxo-2-(2-oxocyclopentyl)acetate was reacted with (5-bromo-2-fluorophenyl)hydrazine to give the title compound (130 mg, 68%) as a yellow solid. LC-MS (ES, m/z): 353, 355 [M+H]⁺.

Step 2: Synthesis of ethyl 3-(2-fluoro-5-[2-[(3R)-3-hydroxy-1-methyl-2-oxopyrrolidin-3-yl]ethynyl]phenyl)-1H,3aH,4H,5H,6H,6aH-cyclopenta[c]pyrazole-1-carboxylate

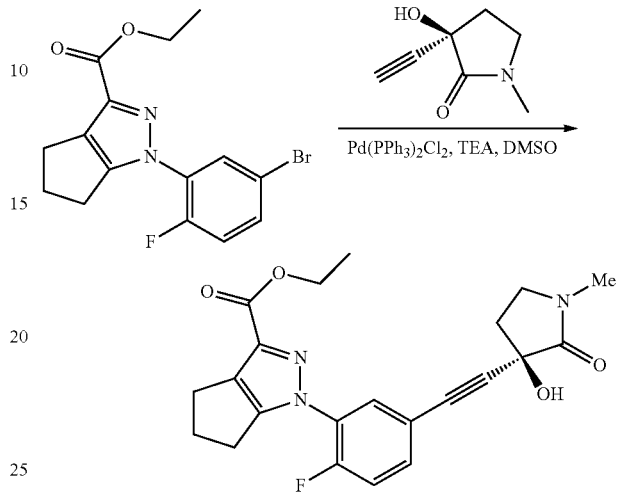

Similar to as described in General Procedure G, ethyl 3-(5-bromo-2-fluorophenyl)-1H,3aH,4H,5H,6H,6aH-cyclopenta[c]pyrazole-1-carboxylate was reacted with (3R)-3-ethynyl-3-hydroxy-1-methylpyrrolidin-2-one to give the title compound (120 mg, 86%) as yellow oil. LC-MS (ES, m/z): 412 [M+H]⁺.

Step 3: Synthesis of 1-(2-fluoro-5-[2-[(3R)-3-hydroxy-1-methyl-2-oxopyrrolidin-3-yl]ethynyl]phenyl)-1H,4H,5H,6H-cyclopenta[c]pyrazole-3-carboxamide

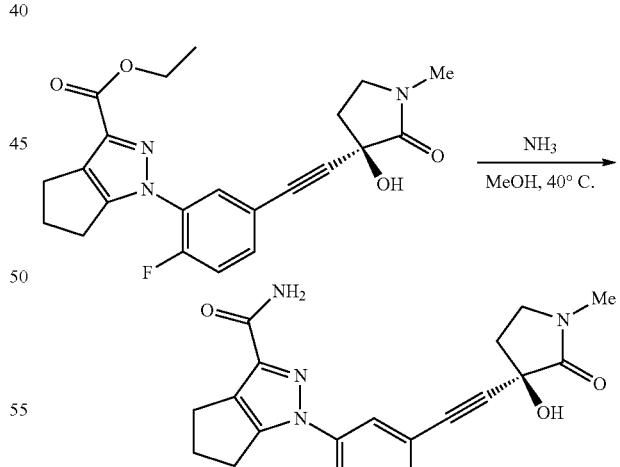

Similar to as described in General Procedure S, ethyl 1-(2-fluoro-5-[2-[(3R)-3-hydroxy-1-methyl-2-oxopyrrolidin-3-yl]ethynyl]phenyl)-1H,4H,5H,6H-cyclopenta[c]pyrazole-3-carboxylate was reacted with ammonia to give the title compound (20.8 mg, 20%) as a white solid. LC-MS (ES, m/z): 383 [M+H]⁺. ¹H NMR (400 MHz, CD₃OD) δ 7.85 (d, J=9.6 Hz, 1H), 7.58-7.55 (m, 1H), 7.38-7.35 (m, 1H), 3.50-3.47 (m, 2H), 2.94 (s, 2H), 2.88-2.84 (m, 4H), 2.66-2.64 (m, 3H), 2.35-2.28 (m, 1H).

Example O7

Synthesis of (R)-1-(3-((3-hydroxy-1-methyl-2-oxopyrrolidin-3-yl)ethynyl)phenyl)-4,6-dihydro-1H-furo[3,4-c]pyrazole-3-carboxamide

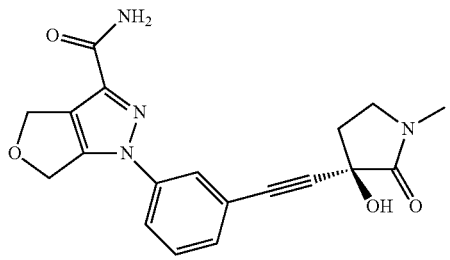 [SMILES: CN1CC[C@@](O)(C#Cc2cccc(-n3nc(C(N)=O)c4c3COC4)c2)C1=O]

Step 1: Synthesis of 2-oxo-2-(4-oxooxolan-3-yl)acetate

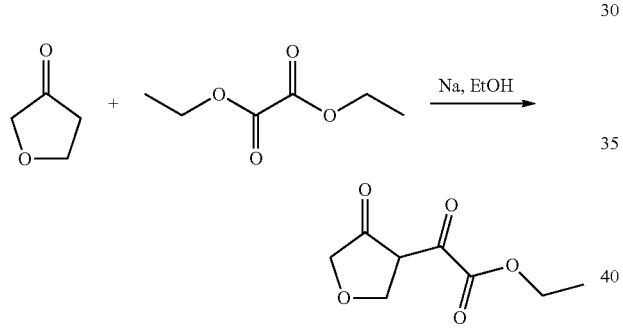

Similar to as described in General Procedure Y Step 1, diethyl oxalate was reacted with oxolan-3-one to give 400 mg (5%) of ethyl 2-oxo-2-(4-oxooxolan-3-yl)acetate as yellow oil.

Step 2: Synthesis of ethyl 1-(3-bromophenyl)-1H,3aH,4H,6H,6aH-furo[3,4-c]pyrazole-3-carboxylate

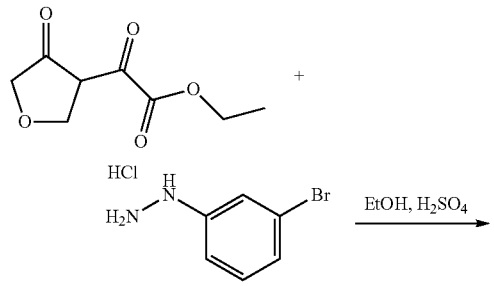

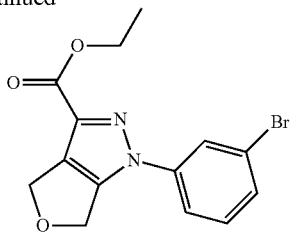

Similar to as described in General Procedure Y Step 2, ethyl 2-oxo-2-(4-oxooxolan-3-yl)acetate was reacted with (3-bromophenyl)hydrazine hydrochloride to give the title compound (80 mg, 11%) as a yellow solid. LC-MS (ES, m/z): 337 [M+H]$^+$.

Step 3: Synthesis of ethyl 1-(3-[2-[(3R)-3-hydroxy-1-methyl-2-oxopyrrolidin-3-yl]ethynyl]phenyl)-1H,4H,6H-furo[3, 4-c]pyrazole-3-carboxylate Similar to as described in General Procedure G, ethyl 1-(3-bromophenyl)-1H,4H,6H-furo[3,4-c]pyrazole-3-carboxylate was reacted with (3R)-3-ethynyl-3-hydroxy-1-methylpyrrolidin-2-one to give the title compound (70 mg, 85%) as a yellow solid. LC-MS (ES, m/z): 396 [M+H]$^+$.

Step 4: Synthesis of 1-(3-[2-[(3R)-3-hydroxy-1-methyl-2-oxopyrrolidin-3-yl]ethynyl]phenyl)-1H,4H,6H-furo[3, 4-c]pyrazole-3-carboxamide

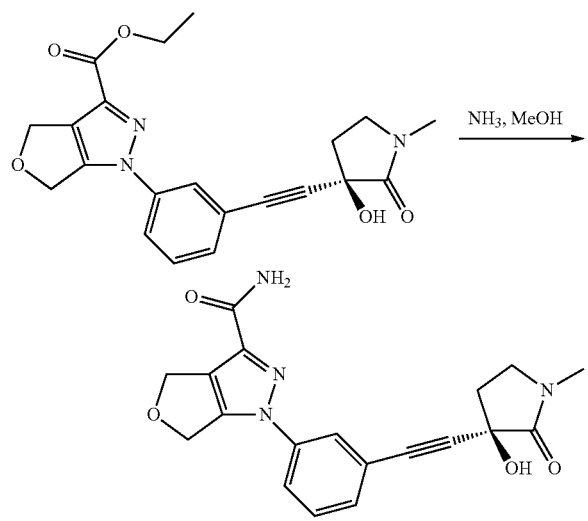

Similar to as described in General Procedure S, ethyl 1-(3-[2-[(3R)-3-hydroxy-1-methyl-2-oxopyrrolidin-3-yl]ethynyl]phenyl)-1H,4H,6H-furo[3, 4-c]pyrazole-3-carboxylate was reacted with ammonia to give the title compound (17.5 mg, 27%) as an off-white solid. LC-MS (ES, m/z): 367 [M+H]$^+$. $^1$H NMR (300 MHz, CD$_3$OD) δ 7.82 (t, J=1.5 Hz, 1H), 7.64-7.60 (m, 1H), 7.55-7.44 (m, 2H), 5.22 (t, J=2.7 Hz, 2H), 5.05 (t, J=2.7 Hz, 2H), 3.53-3.48 (m, 2H), 2.96 (s, 3H), 2.65-2.57 (m, 1H), 2.39-2.29 (m, 1H).

Example P7

Synthesis of (R)-3-(3-((3-hydroxy-1-methyl-2-oxopyrrolidin-3-yl)ethynyl)phenyl)-1H-indazole-1-carboxamide

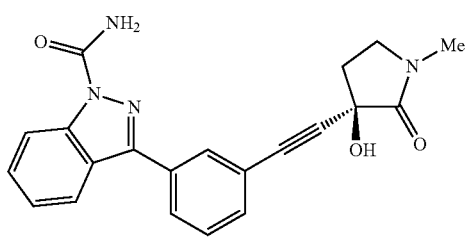 [SMILES: CN1CC[C@@](O)(C#Cc2cccc(-c3nn(C(N)=O)c4ccccc34)c2)C1=O]

Step 1: Synthesis of 3-iodo-1H-indazole

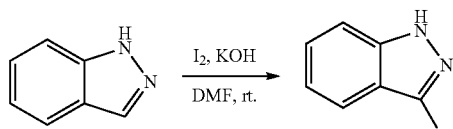

A mixture of 1H-indazole (1.00 g, 8.46 mmol, 1.00 equiv), iodine (4.30 g, 16.94 mmol, 2.00 equiv), and potassium hydroxide (1.19 g, 21.21 mmol, 2.50 equiv) in DMF (49.98 mL) was stirred for 2 hours at room temperature. The resulting solution was diluted with ethyl acetate, washed with water and sodium thiosulfate pentahydrate, dried over anhydrous sodium sulfate, and concentrated under vacuum. This resulted in the title compound (2 g, 97%) as an off-white solid. LC-MS (ES, m/z): 245 [M+H]$^+$.

Step 2: Synthesis of N-tert-butyl-3-iodo-1H-indazole-1-carboxamide

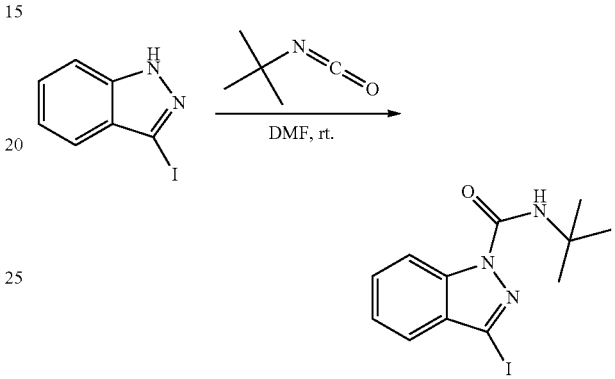

A solution of 3-iodo-1H-indazole (1.00 g, 4.10 mmol, 1.00 equiv) and 2-isocyanato-2-methylpropane (610 mg, 6.15 mmol, 1.50 equiv) in DMF (30.00 mL) was stirred for 3 days at room temperature. The reaction was quenched by water, extracted with dichloromethane, washed with brine, dried over anhydrous sodium sulfate, and concentrated under vacuum. The residue was applied onto a silica gel column with ethyl acetate/petroleum ether (1:15). This resulted in 890 mg (63%) of the title compound as a white solid. LC-MS (ES, m/z): 344 [M+H]$^+$.

Step 3: Synthesis of 3-iodo-1H-indazole-1-carboxamide

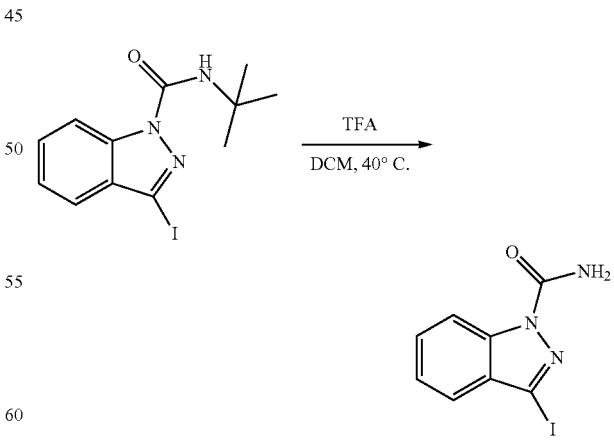

A solution of N-tert-butyl-3-iodo-1H-indazole-1-carboxamide (400 mg, 1.17 mmol, 1.00 equiv) and trifluoroacetic acid (10 mL) in dichloromethane (10 mL) was stirred for overnight at room temperature. The resulting mixture was concentrated under vacuum. The residue was applied onto a silica gel column with ethyl acetate/petroleum ether (1:10). This resulted in the title compound (150 mg, 45%) as a white solid. LC-MS (ES, m/z): 288 [M+H]⁺.

Step 4: Synthesis of 3-(3-[2-[(3R)-3-hydroxy-1-methyl-2-oxopyrrolidin-3-yl]ethynyl]phenyl)-1H-indazole-1-carboxamide

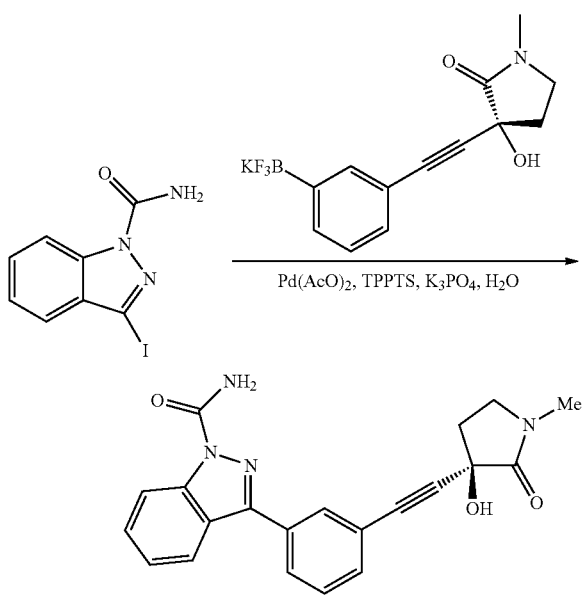

Similar to as described in General Procedure U, 3-iodo-1H-indazole-1-carboxamide was reacted with potassium (R)-trifluoro(3-((3-hydroxy-1-methyl-2-oxopyrrolidin-3-yl)ethynyl)phenyl)borate to give the title compound (6 mg, 3%) as a white solid. LC-MS (ES, m/z): 375 [M+H]⁺. ¹H NMR (400 MHz, CD₃OD) δ 8.43 (d, J=8.8 Hz, 1H), 8.19 (s, 1H), 8.11 (d, J=8.4 Hz, 2H), 7.64-7.57 (m, 3H), 7.47-7.43 (m, 1H), 3.56-3.47 (m, 2H), 2.96 (s, 3H), 2.67-2.61 (m, 1H), 2.39-2.32 (m, 1H).

Example Q7

Synthesis of (R)-1-(3-((3-hydroxy-1-methyl-2-oxopyrrolidin-3-yl)ethynyl)phenyl)-1H-pyrazolo[3,4-c]pyridine-3-carboxamide

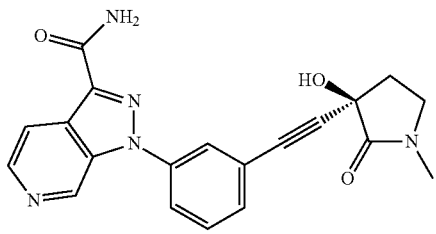

Step 1: Synthesis of 3-iodo-1H-pyrazolo[3,4-c]pyridine

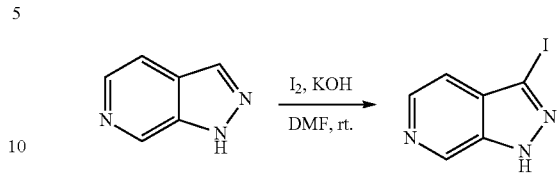

A suspension of 1H-pyrazolo[3,4-c]pyridine (300 mg, 2.52 mmol, 1.00 equiv), KOH (500 mg, 8.91 mmol, 3.50 equiv), and diiodane (1.28 g, 5.04 mmol, 2.00 equiv) in DMF (10 mL) was stirred overnight at room temperature. The reaction was quenched by water, extracted with ethyl acetate, dried over anhydrous sodium sulfate, and concentrated under vacuum. The residue was purified by a silica gel column with ethyl acetate/petroleum ether (1:1) to give the title compound (577 mg, 84%) as a yellow solid. LC-MS (ES, m/z): 246 [M+H]⁺.

Step 2: Synthesis of 1H-pyrazolo[3,4-c]pyridine-3-carboxylate

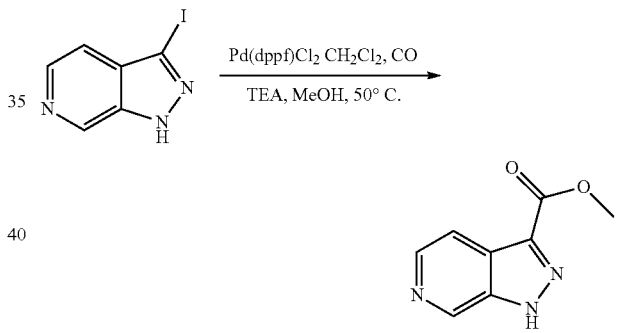

Similar to as described in General Procedure O, 3-iodo-1H-pyrazolo[3,4-c]pyridine was reacted with CO to give the title compound (300 mg, 65%) as a yellow solid. LC-MS (ES, m/z): 178 [M+H]⁺.

Step 3: Synthesis of methyl 1-(3-iodophenyl)-1H-pyrazolo[3,4-c]pyridine-3-carboxylate

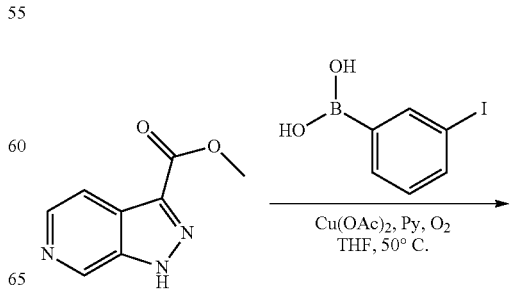

509

-continued

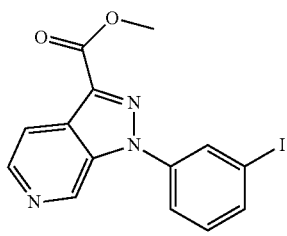

Similar to as described in General Procedure C, methyl 1H-pyrazolo[3,4-c]pyridine-3-carboxylate was reacted with (3-iodophenyl)boronic acid to give the title compound (161 mg, 34%) as a yellow solid. LC-MS (ES, m/z): 380 [M+H]+.

Step 4: Synthesis of methyl 1-(3-[2-[(3R)-3-hydroxy-1-methyl-2-oxopyrrolidin-3-yl]ethynyl]phenyl)-1H-pyrazolo[3,4-c]pyridine-3-carboxylate

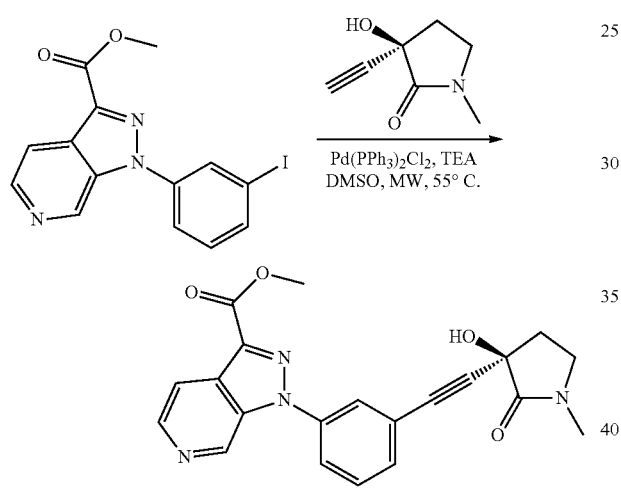

Similar to as described in General Procedure G, methyl 1-(3-iodophenyl)-1H-pyrazolo[3,4-c]pyridine-3-carboxylate was reacted with (3R)-3-ethynyl-3-hydroxy-1-methylpyrrolidin-2-one to give the title compound (100 mg, 57%) as a yellow solid. LC-MS (ES, m/z): 391 [M+H]+.

Step 5: Synthesis of 1-(3-[2-[(3R)-3-hydroxy-1-methyl-2-oxopyrrolidin-3-yl]ethynyl]phenyl)-1H-pyrazolo[3,4-c]pyridine-3-carboxamide

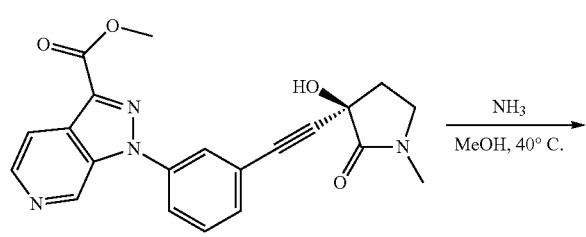

510

-continued

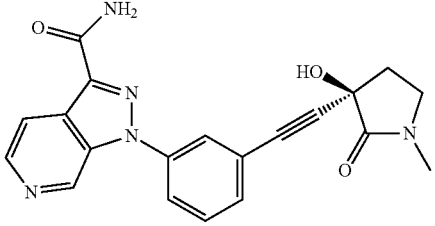 [SMILES: CN1CC[C@@](O)(C#Cc2cccc(-n3nc(C(N)=O)c4ccncc43)c2)C1=O]

Similar to as described in General Procedure S, methyl 1-(3-[2-[(3R)-3-hydroxy-1-methyl-2-oxopyrrolidin-3-yl]ethynyl]phenyl)-1H-pyrazolo[3,4-c]pyridine-3-carboxylate was reacted with ammonia to give the title compound (25.1 mg, 26%) as a white solid. LC-MS (ES, m/z): 376 [M+H]+. $^1$H NMR (300 MHz, DMSO-$d_6$) δ 9.38 (s, 1H), 8.49 (d, J=5.4 Hz, 1H), 8.21-8.18 (m, 2H), 8.07-8.03 (m, 1H), 7.99 (s, 1H), 7.67 (t, J=7.8 Hz, 2H), 7.55 (d, J=7.8 Hz, 1H), 6.54 (s, 1H), 3.37 (t, J=6.9 Hz, 2H), 2.81 (s, 3H), 2.51-2.43 (m, 1H), 2.25-2.18 (m, 1H).

Example R7

Synthesis of (R)-1-(3-((3-hydroxy-1-methyl-2-oxopyrrolidin-3-yl)ethynyl)phenyl)-5-methyl-1H-pyrazolo[3,4-c]pyridine-3-carboxamide

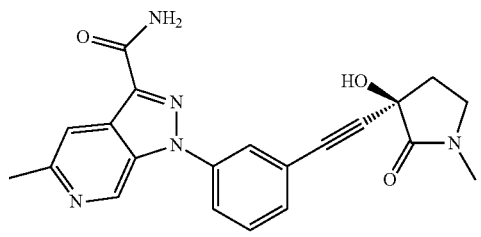

Step 1: Synthesis of 3-iodo-5-methyl-1H-pyrazolo[3,4-c]pyridine

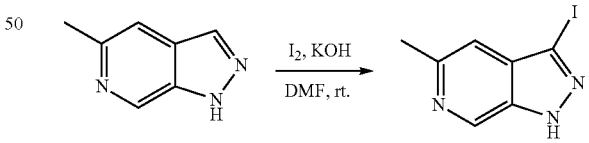

A mixture of 5-methyl-1H-pyrazolo[3,4-c]pyridine (500.00 mg, 3.76 mmol, 1.00 equiv), iodine (953.09 mg, 3.76 mmol, 1.00 equiv), and potassium hydroxide (526.71 mg, 9.39 mmol, 2.50 equiv) in DMF (10.00 mL) was stirred for 4 hours at room temperature. The resulting solution was diluted with ethyl acetate, washed with sodium thiosulfate pentahydrate and brine, dried over anhydrous sodium sulfate, and concentrated under vacuum. The residue was applied onto a silica gel column with ethyl acetate/petroleum ether (1:1). This resulted in the title compound (540 mg, 56%) as a yellow solid. LC-MS (ES, m/z): 260 [M+H]+.

Step 2: Synthesis of methyl 5-methyl-1H-pyrazolo[3,4-c]pyridine-3-carboxylate

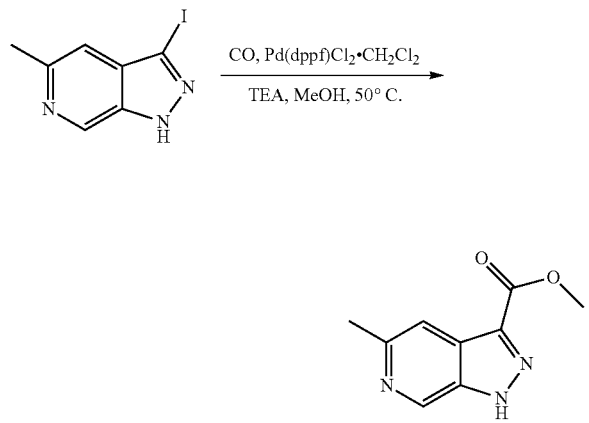

Similar to as described in General Procedure O, 3-iodo-5-methyl-1H-pyrazolo[3,4-c]pyridine was reacted with CO to give the title compound (170 mg, 77%) as a brown solid. LC-MS (ES, m/z): 192 [M+H]+.

Step 3: Synthesis of methyl 1-(3-iodophenyl)-5-methyl-1H-pyrazolo[3,4-c]pyridine-3-carboxylate

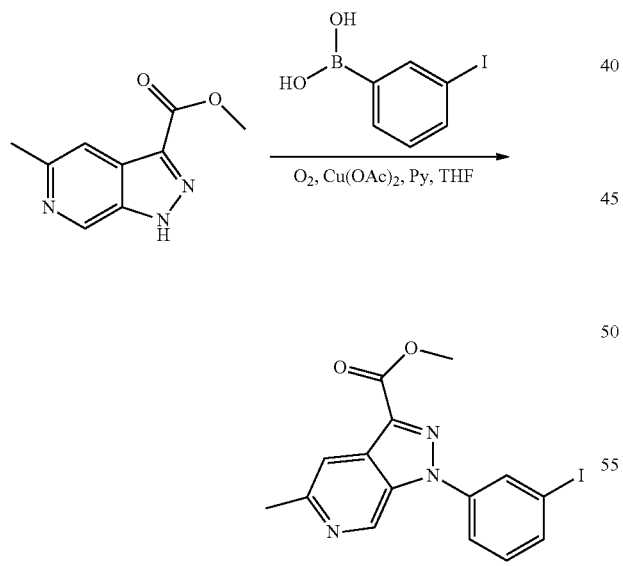

Similar to as described in General Procedure C, methyl 5-methyl-1H-pyrazolo[3,4-c]pyridine-3-carboxylate was reacted with (3-iodophenyl)boronic acid to give the title compound (140 mg, 45%) as a yellow solid. LC-MS (ES, m/z): 394 [M+H]+.

Step 4: Synthesis of methyl 1-(3-[2-[(3R)-3-hydroxy-1-methyl-2-oxopyrrolidin-3-yl]ethynyl]phenyl)-5-methyl-1H-pyrazolo[3,4-c]pyridine-3-carboxylate

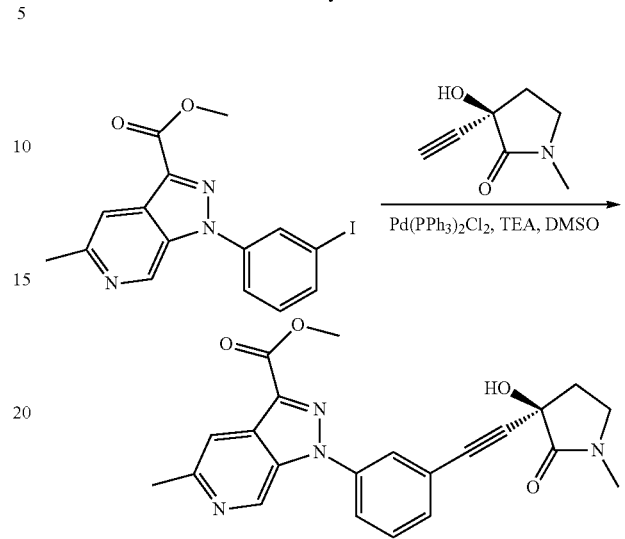

Similar to as described in General Procedure G, methyl 1-(3-iodophenyl)-5-methyl-1H-pyrazolo[3,4-c]pyridine-3-carboxylate was reacted with (3R)-3-ethynyl-3-hydroxy-1-methylpyrrolidin-2-one to give the title compound (140 mg, crude) as yellow oil. LC-MS (ES, m/z): 405 [M+H]+.

Step 5: Synthesis of 1-(3-[2-[(3R)-3-hydroxy-1-methyl-2-oxopyrrolidin-3-yl]ethynyl]phenyl)-5-methyl-1H-pyrazolo[3,4-c]pyridine-3-carboxamide

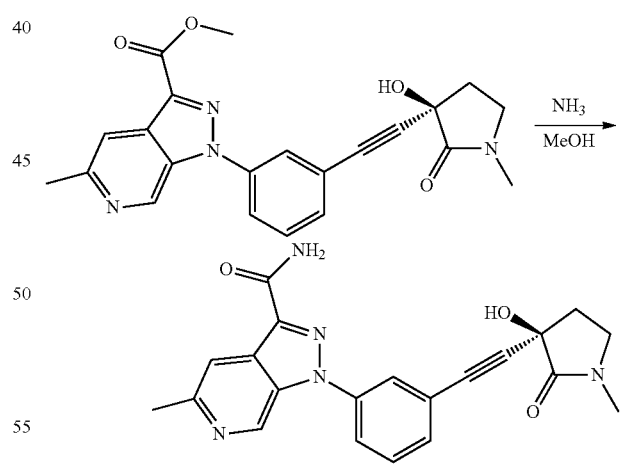

Similar to as described in General Procedure S, methyl 1-(3-[2-[(3R)-3-hydroxy-1-methyl-2-oxopyrrolidin-3-yl]ethynyl]phenyl)-5-methyl-1H-pyrazolo[3,4-c]pyridine-3-carboxylate was reacted with ammonia to give the title compound (37.9 mg, 28%) as an off-white solid. LC-MS (ES, m/z): 390 [M+H]+. 1H NMR (300 MHz, CD3OD) δ 9.18 (s, 1H), 8.14 (s, 1H), 8.03 (s, 1H), 8.03 (d, J=30.9 MHz, 1H), 7.69-7.59 (m, 2H), 3.53-3.50 (m, 2H), 2.95-2.93 (s, 3H), 2.72 (s, 3H), 2.63-2.58 (m, 1H), 2.36-2.30 (m, 1H).

Example S7

Synthesis of (R)-1-(3-((3-hydroxy-1-methyl-2-oxopyrrolidin-3-yl)ethynyl)phenyl)-5-methoxy-1H-pyrazolo[3,4-c]pyridine-3-carboxamide

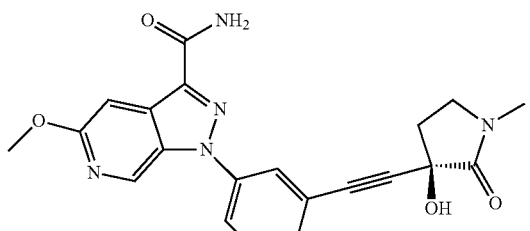

Step 1: Synthesis of 3-iodo-5-methoxy-1H-pyrazolo[3,4-c]pyridine

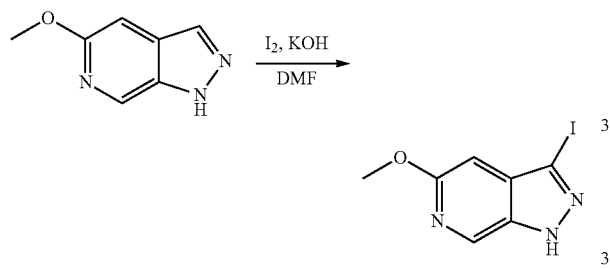

A mixture of 5-methoxy-1H-pyrazolo[3,4-c]pyridine (500.00 mg, 3.35 mmol, 1.00 equiv), potassium hydroxide (677.10 mg, 12.07 mmol, 3.60 equiv), and $I_2$ (1701.70 mg, 6.70 mmol, 2.00 equiv) in DMF (5 mL) was stirred for 1.5 h at room temperature. The resulting solution was diluted with ethyl acetate, washed with sat. aq. $NaHSO_3$, dried over anhydrous sodium sulfate, and concentrated under vacuum. This resulted in 780 mg (85%) of the title compound as a yellow solid. LC-MS (ES, m/z): 276 [M+H]$^+$.

Step 2: Synthesis of methyl 5-methoxy-1H-pyrazolo[3,4-c]pyridine-3-carboxylate

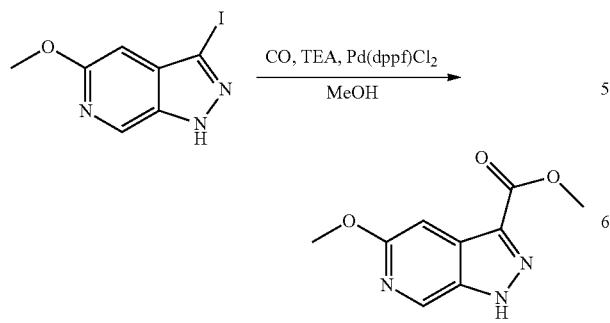

Similar to as described in General Procedure O, 3-iodo-5-methoxy-1H-pyrazolo[3,4-c]pyridine was reacted with CO to give the title compound (260 mg, 48%) as a yellow solid. LC-MS (ES, m/z): 208 [M+H]$^+$.

Step 3: Synthesis of methyl 1-(3-iodophenyl)-5-methoxy-1H-pyrazolo[3,4-c]pyridine-3-carboxylate

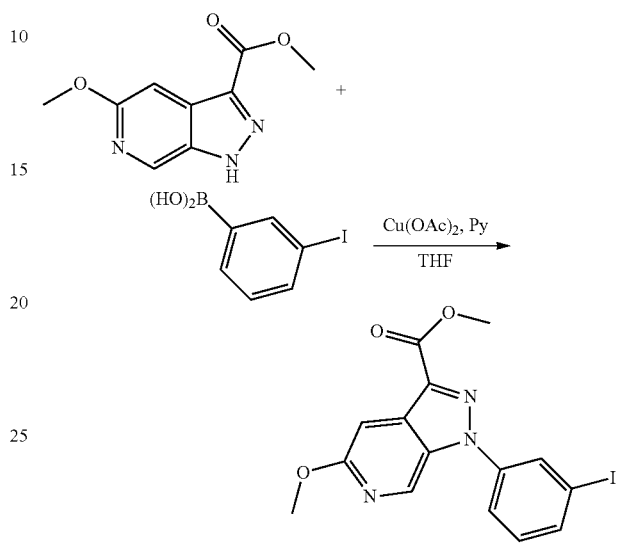

Similar to as described in General Procedure C, methyl 5-methoxy-1H-pyrazolo[3,4-c]pyridine-3-carboxylate was reacted with (3-iodophenyl)boronic acid to give the title compound (30 mg, 8%) as a yellow solid. LC-MS (ES, m/z): 410 [M+H]$^+$.

Step 4: Synthesis of 3-(3-iodophenyl)-6-methoxy-3H-pyrrolo[3,4-c]pyridine-1-carboxamide

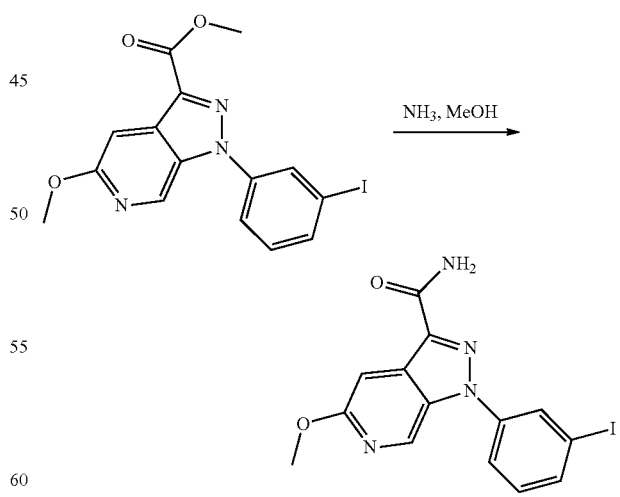

Similar to as described in General Procedure S, methyl 3-(3-iodophenyl)-6-methoxy-3H-pyrrolo[3,4-c]pyridine-1-carboxylate was reacted with ammonia to give the title compound (40 mg, crude) as a yellow solid. LC-MS (ES, m/z): 395 [M+H]$^+$.

Step 5: Synthesis of 1-(3-[2-[(3R)-3-hydroxy-1-methyl-2-oxopyrrolidin-3-yl]ethynyl]phenyl)-5-methoxy-1H-pyrazolo[3,4-c]pyridine-3-carboxamide

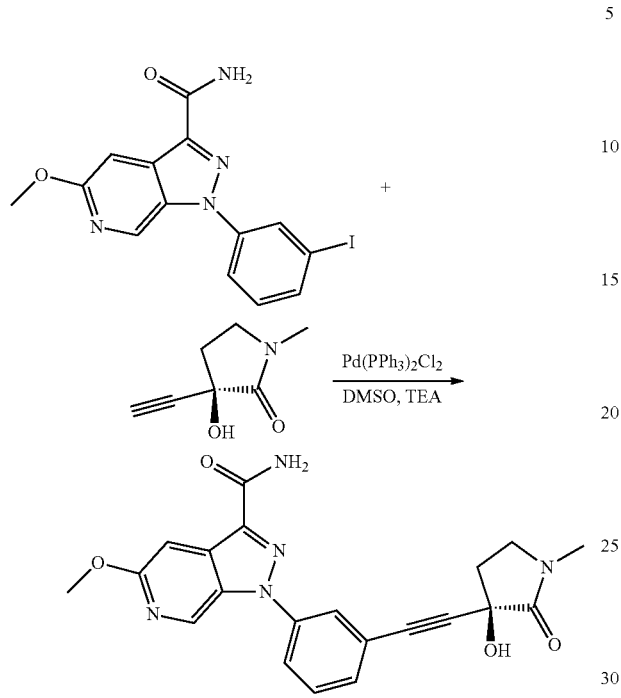

Similar to as described in General Procedure G, 1-(3-iodophenyl)-5-methoxy-1H-pyrazolo[3,4-c]pyridine-3-carboxamide was reacted with (3R)-3-ethynyl-3-hydroxy-1-methylpyrrolidin-2-one to give the title compound (20.3 mg, 66%) as a yellow solid. LC-MS (ES, m/z): 406 [M+H]⁺. $^1$H NMR (300 MHz, CD$_3$OD): δ 8.98 (s, 1H), 8.03 (s, 1H), 7.96-7.93 (m, 1H), 7.68-7.58 (m, 3H), 4.04 (s, 3H), 3.54-3.49 (m, 2H), 2.96 (s, 3H), 2.66-2.59 (m, 1H), 2.40-2.33 (m, 1H).

Example T7

Synthesis of (R)-1-(3-((3-hydroxy-1-methyl-2-oxopyrrolidin-3-yl)ethynyl)phenyl)-4,5,6,7-tetrahydro-1H-pyrazolo[4,3-b]pyridine-3-carboxamide

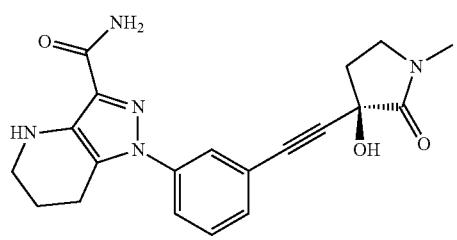 [SMILES: CN1CC[C@@](O)(C#Cc2cccc(-n3nc(C(N)=O)c4c3CCCN4)c2)C1=O]

Step 1: Synthesis of 3-iodo-1H-pyrazolo[4,3-b]pyridine

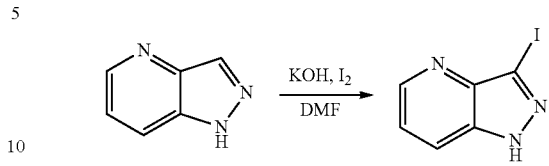

A mixture of 1H-pyrazolo[4,3-b]pyridine (10 g, 83.95 mmol, 1.00 equiv), potassium hydroxide (16.9 g, 301.22 mmol, 3.60 equiv), and iodine (42.7 g, 168.24 mmol, 2.00 equiv) in DMF (150 mL) was stirred for 16 hours at 25° C. The resulting solution was diluted with water, extracted with ethyl acetate, washed with sodium bisulfate, dried over anhydrous sodium sulfate, and concentrated under vacuum. The residue was applied onto a silica gel column with ethyl acetate/petroleum ether (1:5-1:3). This resulted in the title compound (11.7 g, 57%) as a yellow solid. LC-MS (ES, m/z): 246 [M+H]⁺.

Step 2: Synthesis of 1H-pyrazolo[4,3-b]pyridine-3-carboxylate

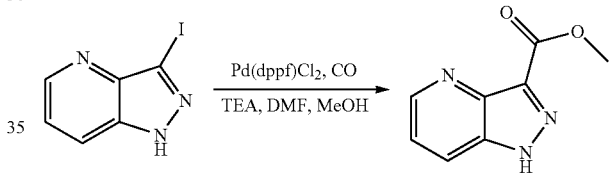

Similar to as described in General Procedure O, 3-iodo-1H-pyrazolo[4,3-b]pyridine (10 g, 40.81 mmol, 1.00 equiv) was reacted with CO to give the title compound (3 g, 41%) as a brown solid. LC-MS (ES, m/z): 178 [M+H]⁺.

Step 3: Synthesis of methyl 1H,4H,5H,6H,7H-pyrazolo[4,3-b]pyridine-3-carboxylate

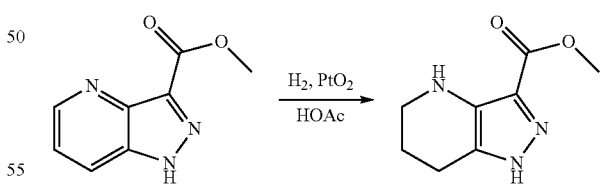

Into a 100-mL round-bottom flask was placed methyl 1H-pyrazolo[4,3-b]pyridine-3-carboxylate (2 g, 11.29 mmol, 1.00 equiv), platinumoxide hydrate (770 mg, 3.39 mmol, 0.30 equiv), acetic acid (30 mL). To the above mixture was stirred at room temperature under hydrogen for 4 hours. The solids were filtered out and the resulting mixture was concentrated under vacuum. The residue was applied onto a silica gel column with ethyl acetate/petroleum ether (1/1). This resulted in 400 mg of the title compound as a yellow solid. LC-MS (ES, m/z): 182 [M+H]⁺.

Step 4: Synthesis of methyl 1-(3-iodophenyl)-1H,4H,5H,6H,7H-pyrazolo[4,3-b]pyridine-3-carboxylate

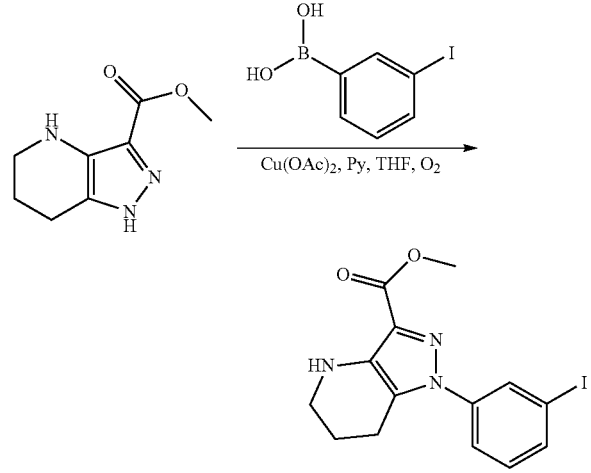

Similar to as described in General Procedure C, methyl 1H,4H,5H,6H,7H-pyrazolo[4,3-b]pyridine-3-carboxylate was reacted with (3-iodophenyl)boronic acid to give the title compound (210 mg, 28%) as a light yellow solid. LC-MS (ES, m/z): 384 [M+H]+.

Step 5: Synthesis of methyl 1-(3-[2-[(3R)-3-hydroxy-1-methyl-2-oxopyrrolidin-3-yl]ethynyl]phenyl)-1H,4H,5H,6H,7H-pyrazolo[4,3-b]pyridine-3-carboxylate

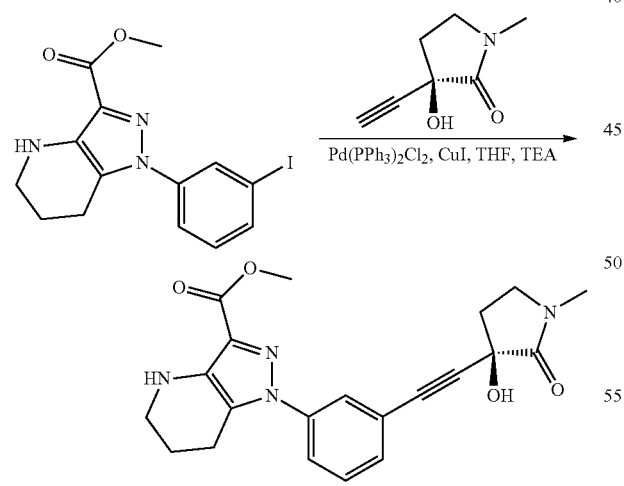

Similar to as described in General Procedure G, methyl 1-(3-iodophenyl)-1H,4H,5H,6H,7H-pyrazolo[4,3-b]pyridine-3-carboxylate was reacted with (3R)-3-ethynyl-3-hydroxy-1-methylpyrrolidin-2-one to give the title compound (160 mg) as a light yellow solid. LC-MS (ES, m/z): 395 [M+H]+.

Step 6: Synthesis of (R)-1-(3-((3-hydroxy-1-methyl-2-oxopyrrolidin-3-yl)ethynyl)phenyl)-4,5,6,7-tetrahydro-1H-pyrazolo[4,3-b]pyridine-3-carboxamide

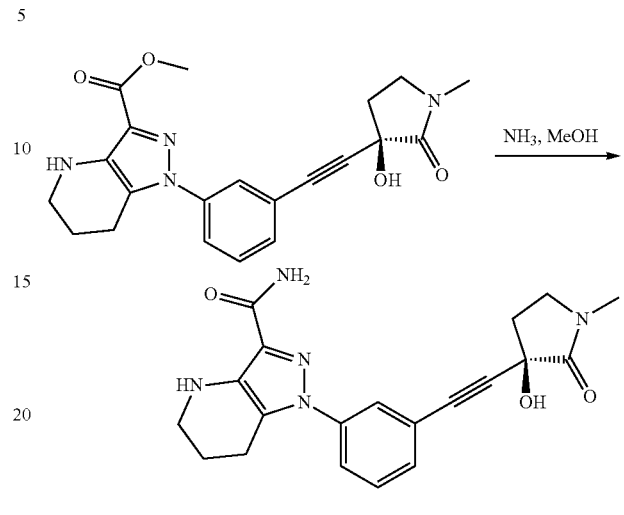

Similar to as described in General Procedure S, methyl 1-(3-[2-[(3R)-3-hydroxy-1-methyl-2-oxopyrrolidin-3-yl]ethynyl]phenyl)-1H,4H,5H,6H,7H-pyrazolo[4,3-b]pyridine-3-carboxylate was reacted with ammonia to give the title compound (29.9 mg). LC-MS (ES, m/z): 380 [M+H]+. $^1$H NMR (300 MHz, CD$_3$OD) δ 7.73 (t, J=1.2 Hz, 1H), 7.64-7.61 (m, 1H), 7.50-7.47 (m, 2H), 3.50-3.45 (m, 2H), 3.23 (t, J=5.4 Hz, 2H), 2.93 (s, 1H), 2.88 (t, J=6.3 Hz, 2H), 2.57-2.55 (m, 1H), 2.33-2.29 (m, 1H), 1.96 (t, J=5.4 Hz, 2H).

Example U7

Synthesis of (R)-1-(3-((3-hydroxy-1-methyl-2-oxopyrrolidin-3-yl)ethynyl)-5-methylphenyl)-1H-pyrazolo[3,4-b]pyridine-3-carboxamide

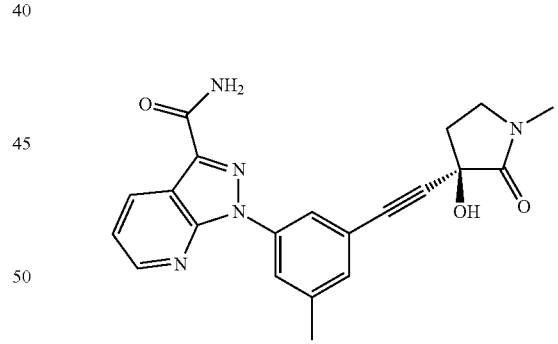

Step 1: Synthesis of methyl 1-(3-bromo-5-methylphenyl)-1H-pyrazolo[3,4-b]pyridine-3-carboxylate

 +

-continued

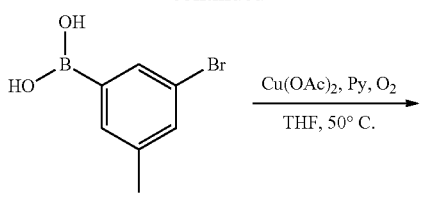

Similar to as described in General Procedure C, methyl 1H-pyrazolo[3,4-b]pyridine-3-carboxylate was reacted with (3-bromo-5-methylphenyl)boronic acid to give the title compound (335 mg, 57%) as a white solid. LC-MS (ES, m/z): 346, 348 [M+H]+.

Step 2: Synthesis of methyl 1-(3-[2-[(3R)-3-hydroxy-1-methyl-2-oxopyrrolidin-3-yl]ethynyl]-5-methylphenyl)-1H-pyrazolo[3,4-b]pyridine-3-carboxylate

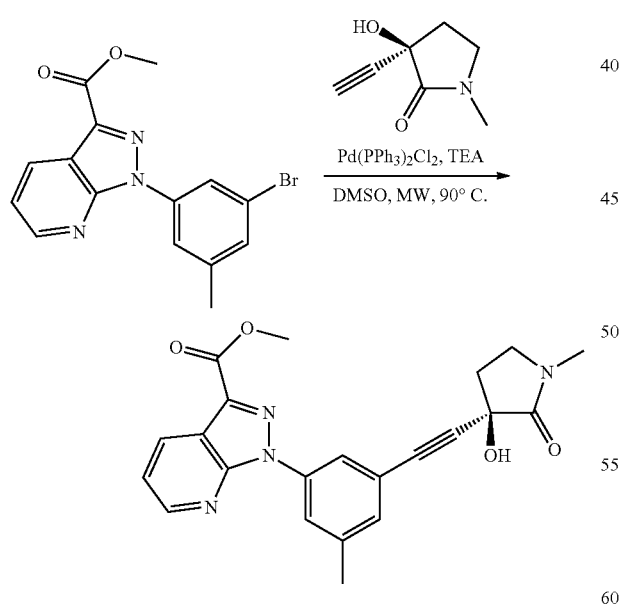

Similar to as described in General Procedure G, methyl 1-(3-bromo-5-methylphenyl)-1H-pyrazolo[3,4-b]pyridine-3-carboxylate was reacted with (3R)-3-ethynyl-3-hydroxy-1-methylpyrrolidin-2-one to give the title compound (220 mg, 58%) as a yellow solid. LC-MS (ES, m/z): 405 [M+H]+.

Step 3: Synthesis of 1-(3-[2-[(3R)-3-hydroxy-1-methyl-2-oxopyrrolidin-3-yl]ethynyl]-5-methylphenyl)-1H-pyrazolo[3,4-b]pyridine-3-carboxamide

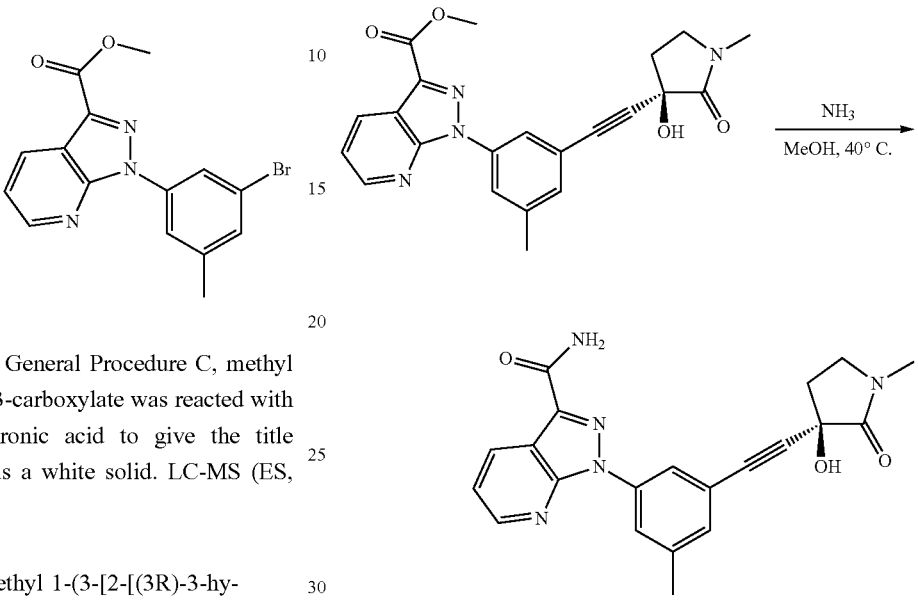

Similar to as described in General Procedure S, methyl 1-(3-[2-[(3R)-3-hydroxy-1-methyl-2-oxopyrrolidin-3-yl] ethynyl]-5-methylphenyl)-1H-pyrazolo[3,4-b]pyridine-3-carboxylate was reacted with ammonia to give the title compound (30 mg, 14%) as a white solid. LC-MS (ES, m/z): 390 [M+H]+. $^1$H NMR (400 MHz, CD$_3$OD) δ 8.73 (d, J=6.4 MHz, 2H), 8.35 (s, 1H), 8.28 (s, 1H), 7.49-7.46 (m, 1H), 7.35 (s, 1H), 3.52-3.49 (m, 2H), 2.96 (s, 3H), 2.67-2.59 (m, 1H), 2.49 (s, 3H), 2.36-2.30 (m, 1H).

Example V7

Synthesis of (R)-6-chloro-1-(3-((3-hydroxy-1-methyl-2-oxopyrrolidin-3-yl)ethynyl)phenyl)-1H-pyrazolo[3,4-b]pyridine-3-carboxamide

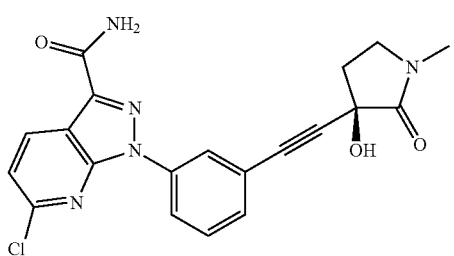 [SMILES: CN1CC[C@@](O)(C#Cc2cccc(-n3nc(C(N)=O)c4ccc(Cl)nc43)c2)C1=O]

521

Step 1: Synthesis of 6-chloro-1-(3-iodophenyl)-1H-pyrazolo[3,4-b]pyridine-3-carboxylic acid

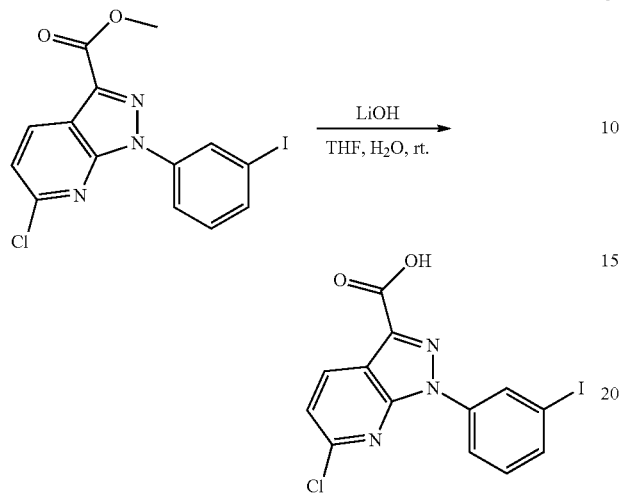

A suspension of methyl 6-chloro-1-(3-iodophenyl)-1H-pyrazolo[3,4-b]pyridine-3-carboxylate (80 mg, 0.19 mmol, 1.00 equiv), lithium hydroxide (9 mg, 0.38 mmol, 1.90 equiv) in THF (5 mL), and water (5 mL) was stirred for 1 hour at room temperature. The pH value of the solution was adjusted to 5 with hydrogen chloride (1 M). The resulting solution was extracted with ethyl acetate and dried over anhydrous sodium sulfate. The residue was purified by a silica gel column with dichloromethane/methanol (20:1) to give the title compound (40 mg, 52%) as a white solid. LC-MS (ES, m/z): 400 [M+H]+.

Step 2: Synthesis of 6-chloro-1-(3-iodophenyl)-1H-pyrazolo[3,4-b]pyridine-3-carboxamide

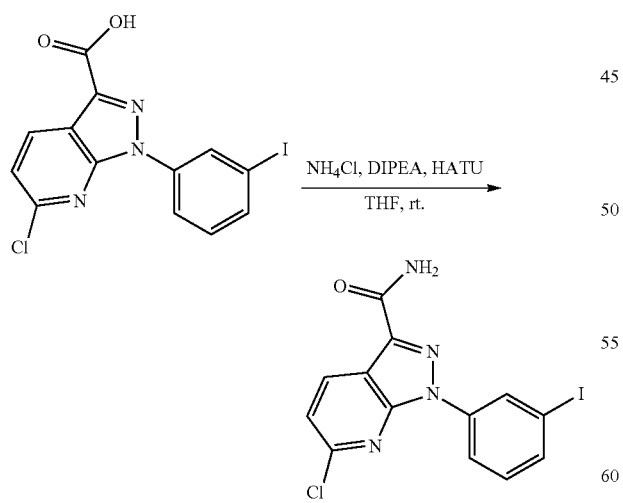

Similar to as described in General Procedure B, 6-chloro-1-(3-iodophenyl)-1H-pyrazolo[3,4-b]pyridine-3-carboxylic acid was reacted with ammonium chloride to give the title compound (38 mg, 95%) as a white solid. LC-MS (ES, m/z): 399 [M+H]+.

522

Step 3: Synthesis of 6-chloro-1-(3-[2-[(3R)-3-hydroxy-1-methyl-2-oxopyrrolidin-3-yl]ethynyl]phenyl)-1H-pyrazolo[3,4-b]pyridine-3-carboxamide

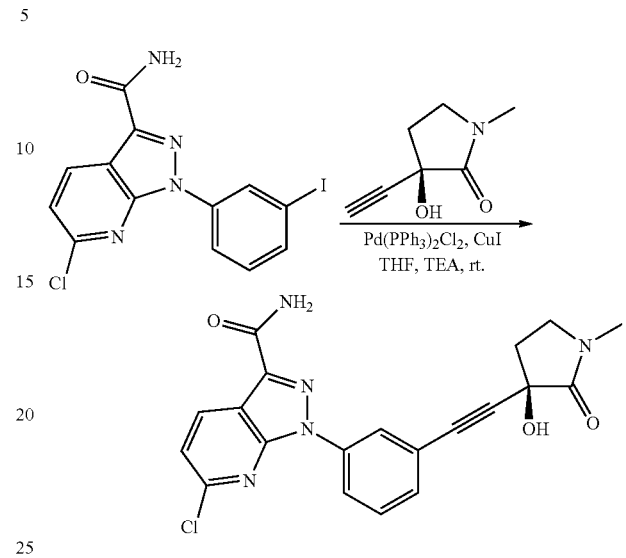

Similar to as described in General Procedure E, 6-chloro-1-(3-iodophenyl)-1H-pyrazolo[3,4-b]pyridine-3-carboxamide was reacted with (3R)-3-ethynyl-3-hydroxy-1-methyl-pyrrolidin-2-one to give the title compound (6.6 mg, 16%) as a white solid. LC-MS (ES, m/z): 819 [M+H]+. 1H NMR (300 MHz, CD3OD) δ 8.69 (d, J=8.4 Hz, 1H), 8.42 (t, J=8.4 Hz, 2H), 7.63-7.50 (m, 3H), 3.56-3.50 (m, 2H), 2.97 (s, 3H), 2.69-2.61 (m, 1H), 2.41-2.06 (m, 1H).

Example W7

Synthesis of (R)-1-(3-((3-hydroxy-1-methyl-2-oxopyrrolidin-3-yl)ethynyl)phenyl)-6-methoxy-1H-pyrazolo[3,4-b]pyridine-3-carboxamide

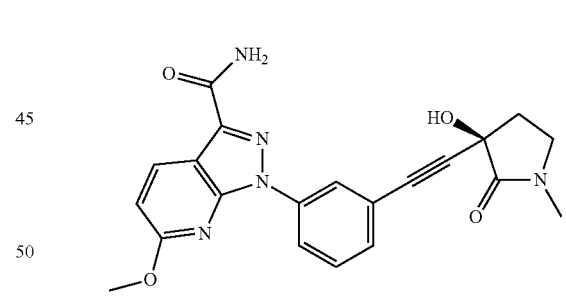

Step 1: Synthesis of methyl 1-(3-bromophenyl)-6-chloro-1H-pyrazolo[3,4-b]pyridine-3-carboxylate

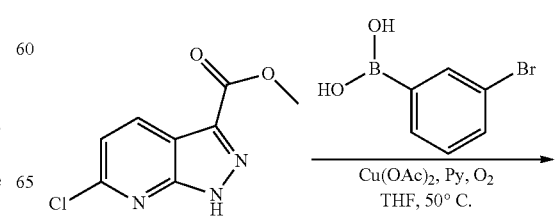

-continued

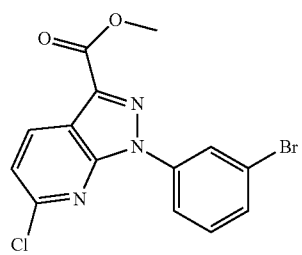

Similar to as described in General Procedure C, methyl 6-chloro-1H-pyrazolo[3,4-b]pyridine-3-carboxylate was reacted with (3-bromophenyl)boronic acid to give the title compound (110 mg, 63%) as a white solid. LC-MS (ES, m/z): 366, 368 [M+H]+.

Step 2: Synthesis of 1-(3-bromophenyl)-6-methoxy-1H-pyrazolo[3,4-b]pyridine-3-carboxylic acid

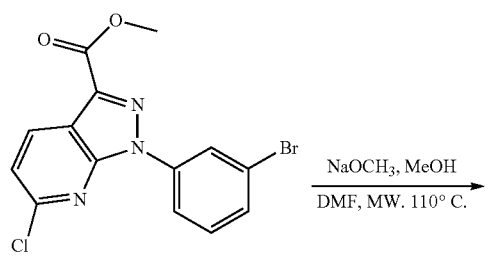

A suspension of methyl 1-(3-bromophenyl)-6-chloro-1H-pyrazolo[3,4-b]pyridine-3-carboxylate (100 mg, 0.27 mmol, 1.00 equiv) and sodium methylate (149 mg, 2.76 mmol, 10.10 equiv) in DMF (3 mL)/methanol (1 mL) was irradiated with microwave for 1 hour at 110° C. The pH value of the solution was adjusted to 5 with hydrogen chloride (1 M). The resulting solution was extracted with ethyl acetate, dried over anhydrous sodium sulfate, and concentrated under vacuum. The residue was purified by a silica gel column with dichloromethane/methanol (40:1) to give the title compound (50 mg, 53%) as a white solid. LC-MS (ES, m/z): 348, 350 [M+H]+.

Step 3: Synthesis of 1-(3-bromophenyl)-6-methoxy-1H-pyrazolo[3,4-b]pyridine-3-carboxamide

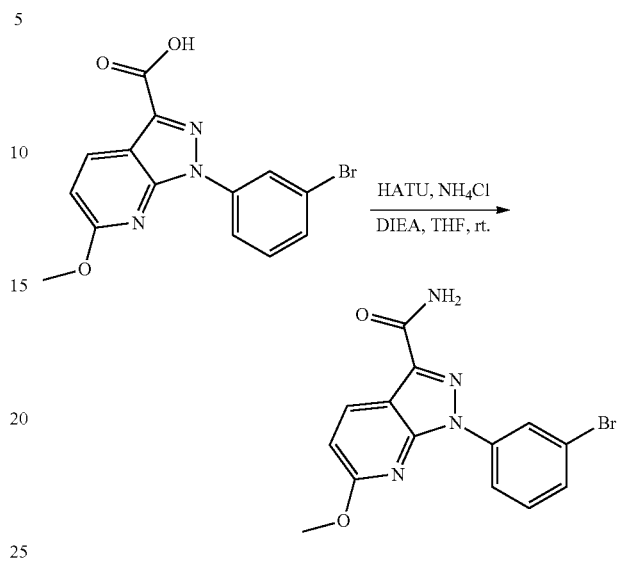

Similar to as described in General Procedure B, 1-(3-bromophenyl)-6-methoxy-1H-pyrazolo[3,4-b]pyridine-3-carboxylic acid was reacted with ammonium chloride to give the title compound (60 mg, 86%) as a yellow solid. LC-MS (ES, m/z): 347, 349 [M+H]+.

Step 4: Synthesis of 1-(3-[2-[(3R)-3-hydroxy-1-methyl-2-oxopyrrolidin-3-yl]ethynyl]phenyl)-6-methoxy-1H-pyrazolo[3,4-b]pyridine-3-carboxamide

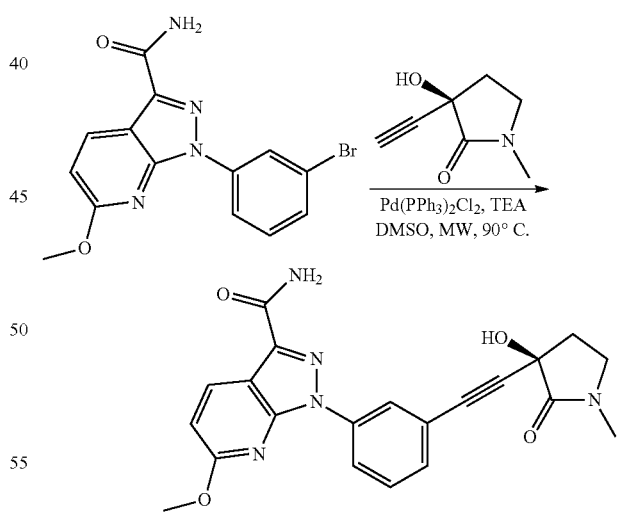

Similar to as described in General Procedure G, 1-(3-bromophenyl)-6-methoxy-1H-pyrazolo[3,4-b]pyridine-3-carboxamide was reacted with (3R)-3-ethynyl-3-hydroxy-1-methylpyrrolidin-2-one to give the title compound (21.9 mg, 38%) as a white solid. LC-MS (ES, m/z): 406 [M+H]+. $^1$H NMR (300 MHz, CD$_3$OD) δ 8.56 (s, 1H), 8.48 (d, J=3.0 Hz, 2H), 7.58 (t, J=8.1 Hz, 1H), 7.47 (d, J=6.3 Hz, 1H), 6.89 (d, J=8.7 Hz, 1H), 4.11 (s, 3H), 3.51 (t, J=7.8 Hz, 2H), 3.09 (s, 3H), 2.67-2.59 (m, 1H), 2.40-2.31 (m, 1H).

Example X7

Synthesis of (R)-1-(3-((3-hydroxy-1-methyl-2-oxopyrrolidin-3-yl)ethynyl)phenyl)-6-morpholino-1H-pyrazolo[3,4-b]pyridine-3-carboxamide

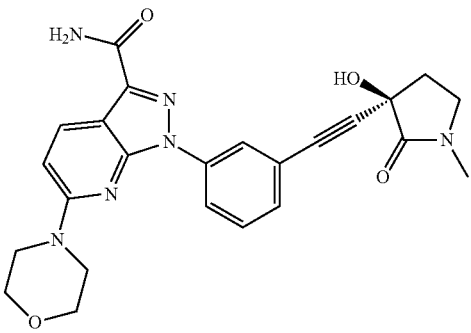

Step 1: Synthesis of 4-[3-iodo-1H-pyrazolo[3,4-b]pyridin-6-yl]morpholine

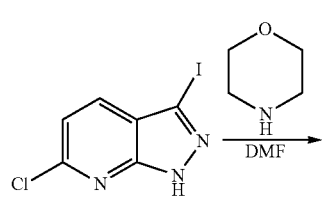

Similar to as described in General Procedure A, 6-chloro-3-iodo-1H-pyrazolo[3,4-b]pyridine was reacted with morpholine to give the title compound (500 mg) as a yellow solid. LC-MS (ES, m/z): 331 [M+H]⁺.

Step 2: Synthesis of methyl 6-(morpholin-4-yl)-1H-pyrazolo[3,4-b]pyridine-3-carboxylate

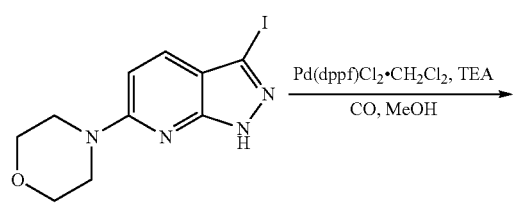

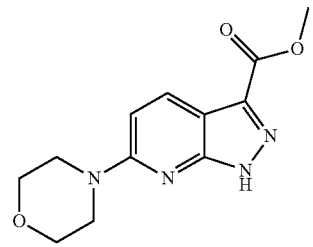

Similar to as described in General Procedure O, carbon monoxide was reacted with 4-[3-iodo-1H-pyrazolo[3,4-b]pyridin-6-yl]morpholine to give the title compound (300 mg, 94%) as a yellow solid. LC-MS (ES, m/z): 263 [M+H]⁺.

Step 3: Synthesis of methyl 1-(3-iodophenyl)-6-(morpholin-4-yl)-1H-pyrazolo[3,4-b]pyridine-3-carboxylate

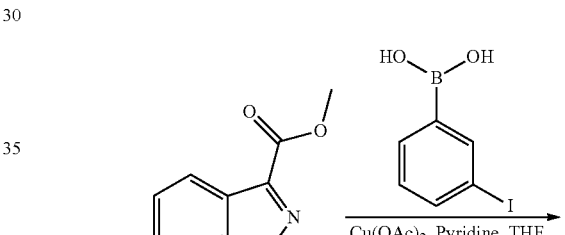

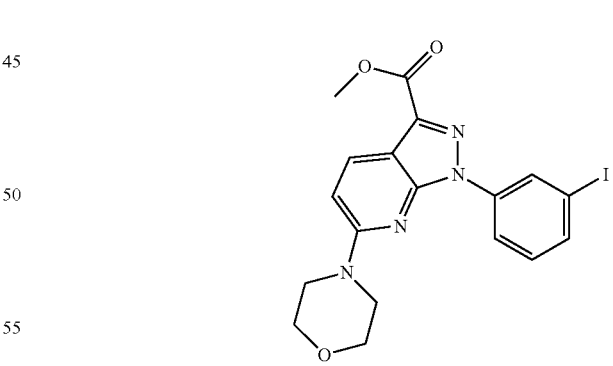

Similar to as described in General Procedure C, methyl 6-(morpholin-4-yl)-1H-pyrazolo[3,4-b]pyridine-3-carboxylate was reacted with (3-iodophenyl)boronic acid to give the title compound (200 mg, 40%) as a yellow solid. LC-MS (ES, m/z): 465 [M+H]⁺.

Step 4: Synthesis of methyl 1-(3-[2-[(3R)-3-hydroxy-1-methyl-2-oxopyrrolidin-3-yl]ethynyl]phenyl)-6-(morpholin-4-yl)-1H-pyrazolo[3,4-b]pyridine-3-carboxylate

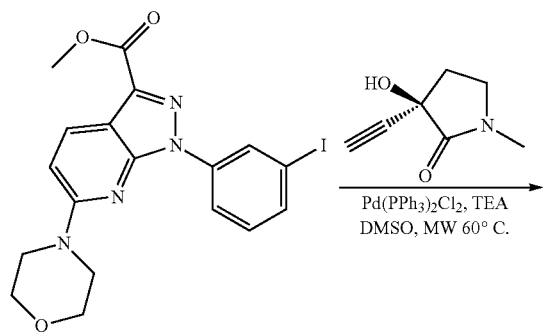

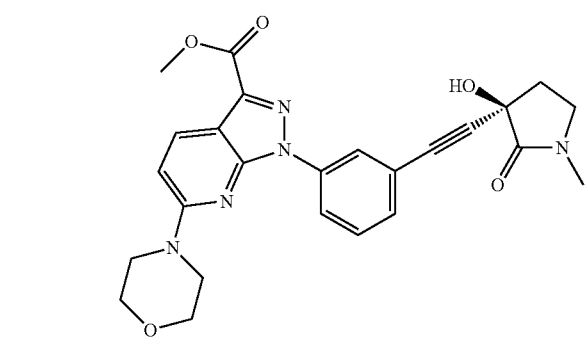

Similar to as described in General Procedure G, methyl 1-(3-iodophenyl)-6-(morpholin-4-yl)-1H-pyrazolo[3,4-b]pyridine-3-carboxylate was reacted with (3R)-3-ethynyl-3-hydroxy-1-methylpyrrolidin-2-one to give the title compound (150 mg, 81%) as a yellow solid. LC-MS (ES, m/z): 476 [M+H]⁺.

Step 5: Synthesis of 1-(3-[2-[(3R)-3-hydroxy-1-methyl-2-oxopyrrolidin-3-yl]ethynyl]phenyl)-6-(morpholin-4-yl)-1H-pyrazolo[3,4-b]pyridine-3-carboxamide

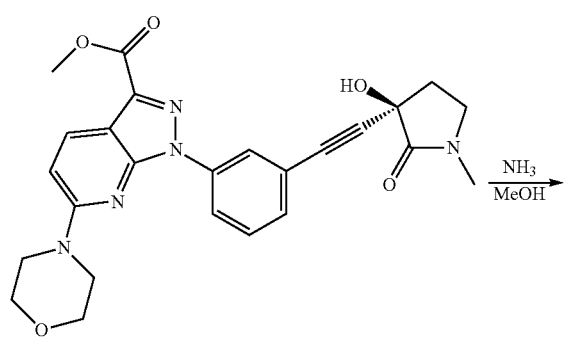

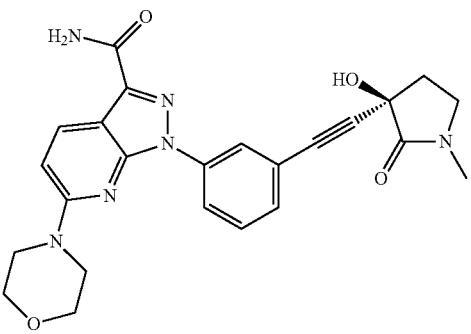 [SMILES: CN1CC[C@@](O)(C#Cc2cccc(-n3nc(C(N)=O)c4ccc(N5CCOCC5)nc43)c2)C1=O]

Similar to as described in General Procedure S, methyl 1-(3-[2-[(3R)-3-hydroxy-1-methyl-2-oxopyrrolidin-3-yl]ethynyl]phenyl)-6-(morpholin-4-yl)-1H-pyrazolo[3,4-b]pyridine-3-carboxylate was reacted with ammonia to give the title compound (59.7 mg, 41%) as an off-white solid. LC-MS (ES, m/z): 461 [M+H]⁺. ¹H NMR (300 MHz, CD₃OD) δ 8.58 (s, 1H), 8.44 (d, J=2.1 Hz, 1H), 8.35 (s, 1H), 7.55 (t, 1H), 7.43-7.40 (m, 1H), 6.99-6.96 (d, 2H), 3.89-3.86 (m, 4H), 3.75-3.72 (m, 4H), 3.53-3.49 (m, 2H), 2.97 (s, 3H), 2.65-2.57 (m, 1H), 2.40-2.31 (m, 1H).

Example Y7

Synthesis of (R)-1-(3-((3-hydroxy-1-methyl-2-oxopyrrolidin-3-yl)ethynyl)phenyl)-6-(1-methyl-1H-pyrazol-4-yl)-1H-pyrazolo[3,4-b]pyridine-3-carboxamide

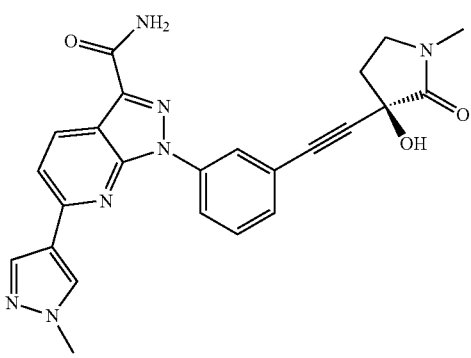 [SMILES: CN1CC[C@@](O)(C#Cc2cccc(-n3nc(C(N)=O)c4ccc(-c5cnn(C)c5)nc43)c2)C1=O]

Step 1: Synthesis of methyl 6-(1-methyl-1H-pyrazol-4-yl)-1H-pyrazolo[3,4-b]pyridine-3-carboxylate

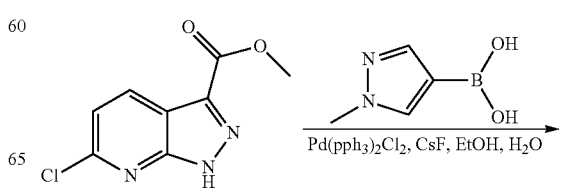

-continued

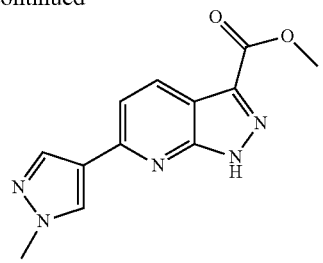

Similar to as described in General Procedure M, methyl 6-chloro-1H-pyrazolo[3,4-b]pyridine-3-carboxylate (300 mg, 1.42 mmol, 1.00 equiv) was reacted with (1-methyl-1H-pyrazol-4-yl)boronic acid to give the title compound (220 mg, 60%) as a yellow solid. LC-MS (ES, m/z): 258[M+H]$^+$.

Step 2: Synthesis of methyl 1-(3-iodophenyl)-6-(1-methyl-1H-pyrazol-4-yl)-1H-pyrazolo[3,4-b]pyridine-3-carboxylate

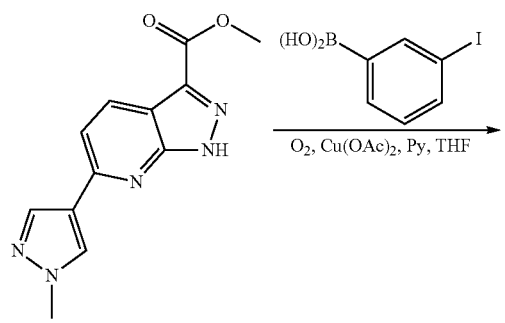

Similar to as described in General Procedure C, methyl 6-(1-methyl-1H-pyrazol-4-yl)-1H-pyrazolo[3,4-b]pyridine-3-carboxylate was reacted with (3-iodophenyl)boronic acid to give the title compound (60 mg, 25%) as a yellow solid. LC-MS (ES, m/z): 460 [M+H]$^+$.

Step 3: Synthesis of methyl 1-(3-[2-[(3R)-3-hydroxy-1-methyl-2-oxopyrrolidin-3-yl]ethynyl]phenyl)-6-(1-methyl-1H-pyrazol-4-yl)-1H-pyrazolo[3,4-b]pyridine-3-carboxylate

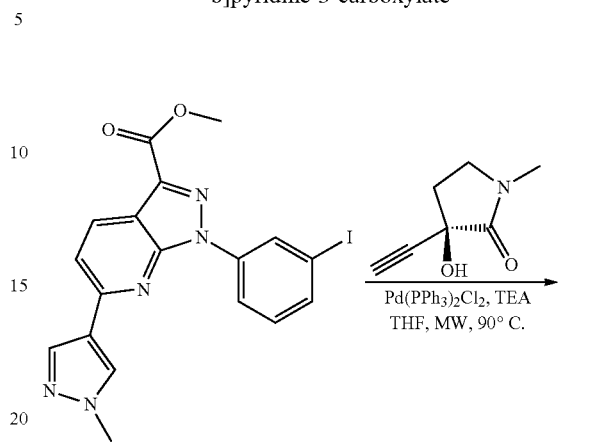

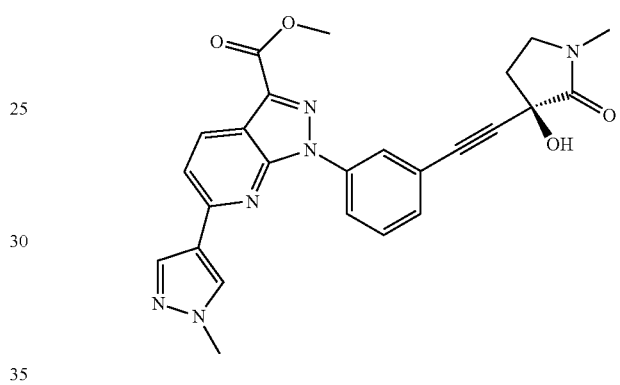

Similar to as described in General Procedure G, methyl 1-(3-iodophenyl)-6-(1-methyl-1H-pyrazol-4-yl)-1H-pyrazolo[3,4-b]pyridine-3-carboxylate was reacted with (3R)-3-ethynyl-3-hydroxy-1-methylpyrrolidin-2-one to give the title compound (90 mg) as a red solid. LC-MS (ES, m/z): 471 [M+H]$^+$.

Step 4: Synthesis of 1-(3-[2-[(3R)-3-hydroxy-1-methyl-2-oxopyrrolidin-3-yl]ethynyl]phenyl)-6-(1-methyl-1H-pyrazol-4-yl)-1H-pyrazolo[3,4-b]pyridine-3-carboxamide

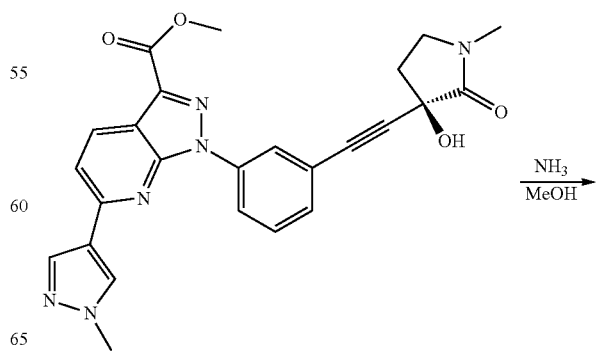

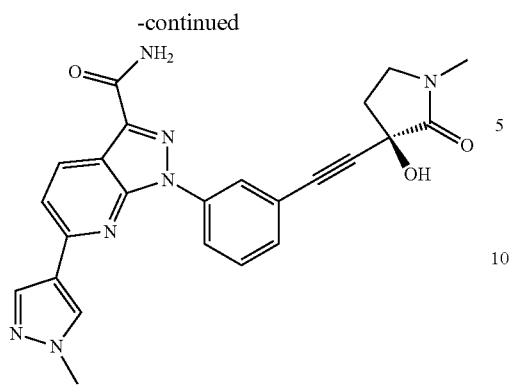

Similar to as described in General Procedure S, methyl 1-(3-[2-[(3R)-3-hydroxy-1-methyl-2-oxopyrrolidin-3-yl]ethynyl]phenyl)-6-(1-methyl-1H-pyrazol-4-yl)-1H-pyrazolo[3,4-b]pyridine-3-carboxylate was reacted with ammonia to give the title compound (28.7 mg, 30%) as a white solid. LC-MS (ES, m/z): 456 [M+H]$^+$. $^1$H NMR (300 MHz, DMSO-d$_6$) δ 8.58-8.55 (m, 2H), 8.5-8.52 (m, 1H), 8.49 (s, 1H), 8.22-8.19 (m, 2H), 7.82-7.80 (m, 1H), 7.77-7.75 (m, 2H), 7.45-7.43 (m, 1H), 6.56 (s, 1H), 3.97 (s, 1H), 3.38-3.29 (m, 2H), 2.83 (s, 3H), 2.51-2.50 (m, 1H), 2.33-2.30 (m, 1H).

Example Z7

Synthesis of (R)-1-(3-((3-hydroxy-1-methyl-2-oxopyrrolidin-3-yl)ethynyl)phenyl)-6-methyl-1H-pyrazolo[3,4-d]pyrimidine-3-carboxamide

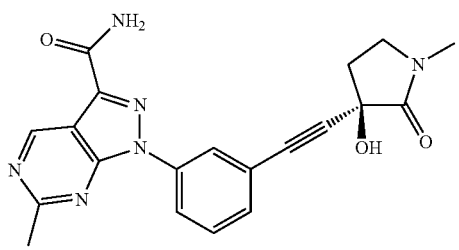 [SMILES: Cc1ncc2c(C(N)=O)nn(-c3cccc(C#C[C@]4(O)CCN(C)C4=O)c3)c2n1]

Step 1: Synthesis of ethyl 5-amino-1-(3-bromophenyl)-1H-pyrazole-3-carboxylate

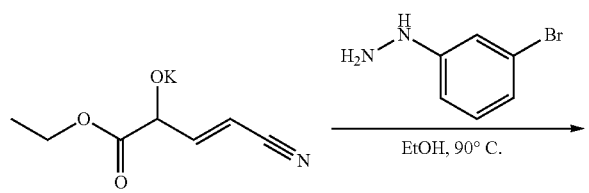

A solution of (3-bromophenyl)hydrazine hydrochloride (5.00 g, 22.37 mmol, 1.00 equiv) and ethyl 3-cyano-2-(potassiooxy)prop-2-enoate (4.01 g, 22.38 mmol, 1.00 equiv) in ethanol (50 mL) was stirred for overnight at 90° C. The reaction residue was applied onto a silica gel column with ethyl acetate/petroleum ether (1:2) to give the title compound (3.5 g, 50%) as a yellow solid. LC-MS (ES, m/z): 310, 312 [M+H]$^+$.

Step 2: Synthesis of ethyl 1-(3-bromophenyl)-5-[(E)-[(dimethylamino)methylidene]amino]-4-formyl-1H-pyrazole-3-carboxylate

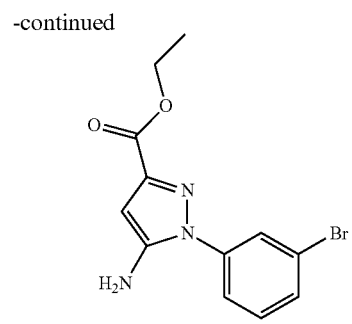

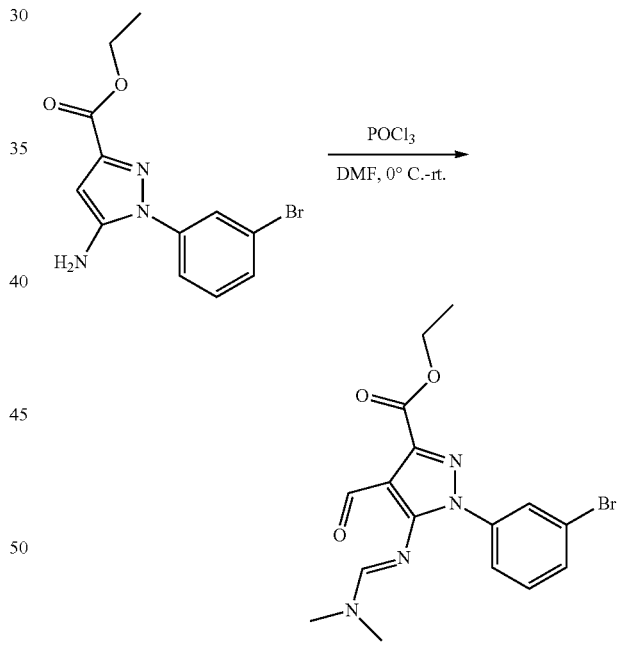

Under nitrogen atmosphere phosphorus oxychloride (1.68 g, 10.96 mmol, 2.00 equiv) was added dropwise to a stirred solution of ethyl 5-amino-1-(3-bromophenyl)-1H-pyrazole-3-carboxylate (1.70 g, 5.48 mmol, 1.00 equiv) in DMF (10 mL) at 0° C. The resulting solution was stirred overnight at room temperature and quenched by water. The resulting solution was extracted with ethyl acetate, washed with brine, dried over anhydrous sodium sulfate, and concentrated under vacuum. The residue was applied onto a silica gel column with ethyl acetate/petroleum ether (1:5). This resulted in the title compound (1.9 g, 88%) as a yellow solid. LC-MS (ES, m/z): 393, 395 [M+H]$^+$.

Step 3: Synthesis of ethyl 5-amino-1-(3-bromophenyl)-4-formyl-1H-pyrazole-3-carboxylate

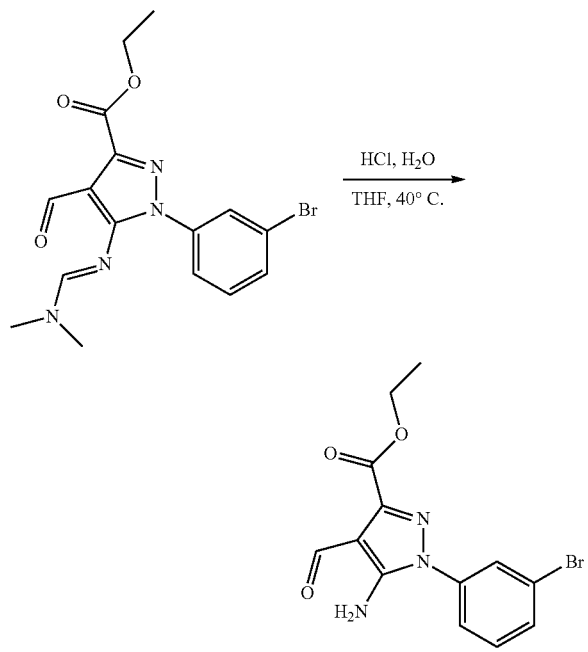

A solution of ethyl 1-(3-bromophenyl)-5-[(E)-[(dimethylamino)methylidene]amino]-4-formyl-H-pyrazole-3-carboxylate (900 mg, 2.29 mmol, 1.00 equiv) in THF (5 mL) was treated with concentrated hydrogen chloride (2 mL) followed by water (5 mL). The resulting solution was stirred overnight at 40° C. in an oil bath. The solids were filtered out and dried in a vacuum oven. This resulted in 410 mg (53%) of the title compound as a yellow solid. LC-MS (ES, m/z): 340 [M+H]$^+$.

Step 4: Synthesis of ethyl 5-(N-acetylacetamido)-1-(3-bromophenyl)-4-formyl-1H-pyrazole-3-carboxylate

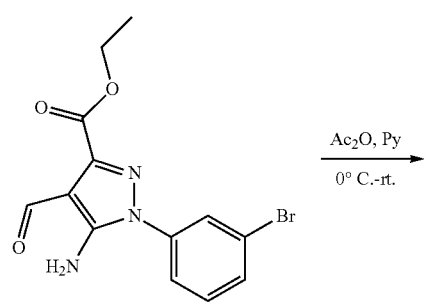

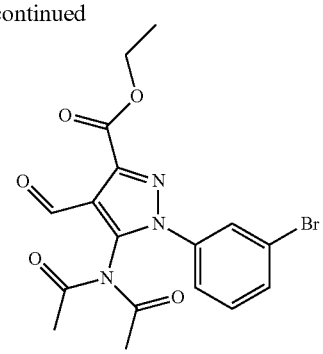

A solution of ethyl 5-amino-1-(3-bromophenyl)-4-formyl-1H-pyrazole-3-carboxylate (200 mg, 0.59 mmol, 1.00 equiv) in pyridine (1 mL) was placed into a 10-mL sealed tube, then acetic anhydride (1 mL, 10.58 mmol, 17.90 equiv) was added and the resulting solution was stirred for 48 hours at 40° C. The reaction was quenched by water, extracted with ethyl acetate, washed with brine, dried over anhydrous sodium sulfate, and concentrated under vacuum. The residue was applied onto a silica gel column with ethyl acetate/petroleum ether (1:1). This resulted in 120 mg (48%) of the title compound as a yellow solid. LC-MS (ES, m/z): 422, 424 [M+H]$^+$.

Step 5: Synthesis of ethyl 1-(3-bromophenyl)-6-methyl-1H-pyrazolo[3,4-d]pyrimidine-3-carboxylate

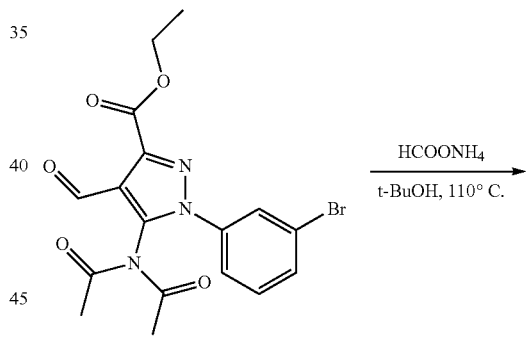

Ammonium formate (100 mg, 1.59 mmol, 5.60 equiv) was added to a stirred solution of ethyl 5-(N-acetylacetamido)-1-(3-bromophenyl)-4-formyl-1H-pyrazole-3-carboxylate (120 mg, 0.28 mmol, 1.00 equiv) in tert-butanol (5 mL) and the resulting solution was stirred for 1 hour at 110° C. The reaction was diluted with ethyl acetate and the solids were filtered out. The liquid was concentrated under vacuum. The residue was applied onto a silica gel column with ethyl acetate/petroleum ether (1:7). This resulted in 100 mg (97%) of the title compound as a white solid. LC-MS (ES, m/z): 361, 363 [M+H]+.

Step 6: Synthesis of ethyl 1-(3-[2-[(3R)-3-hydroxy-1-methyl-2-oxopyrrolidin-3-yl]ethynyl]phenyl)-6-methyl-1H-pyrazolo[3,4-d]pyrimidine-3-carboxylate

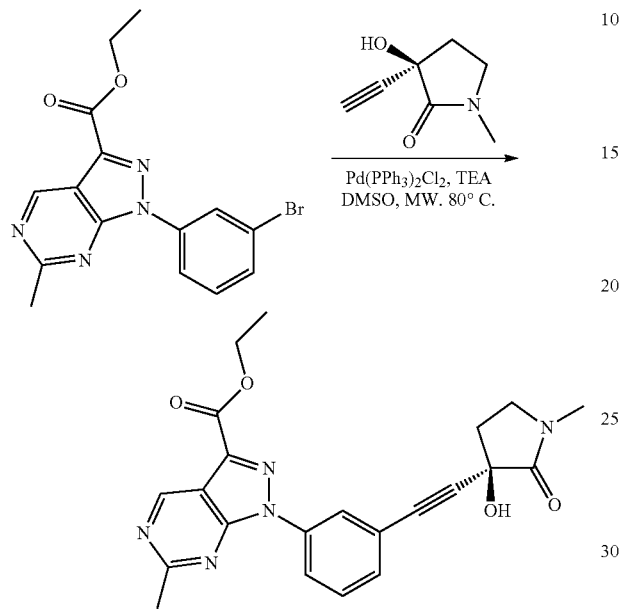

Similar to as described in General Procedure G, ethyl 1-(3-bromophenyl)-6-methyl-1H-pyrazolo[3,4-d]pyrimidine-3-carboxylate was reacted with (3R)-3-ethynyl-3-hydroxy-1-methylpyrrolidin-2-one to give the title compound (80 mg, 77%) as yellow oil. LC-MS (ES, m/z): 420 [M+H]+.

Step 7: Synthesis of 1-(3-[2-[(3R)-3-hydroxy-1-methyl-2-oxopyrrolidin-3-yl]ethynyl]phenyl)-6-methyl-1H-pyrazolo[3,4-d]pyrimidine-3-carboxamide

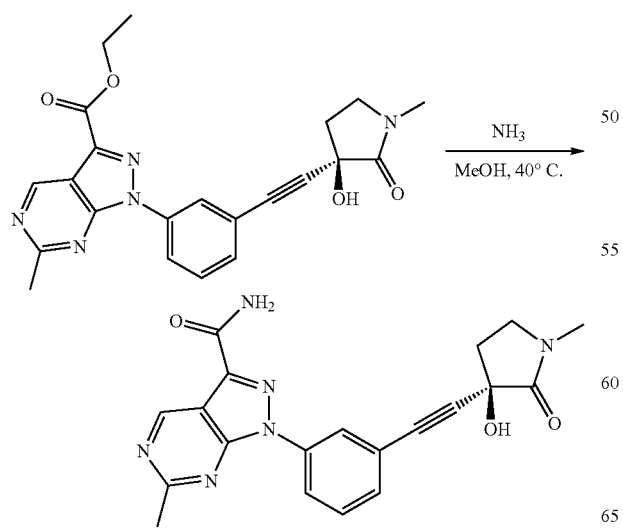

Similar to as described in General Procedure S, ethyl 1-(3-[2-[(3R)-3-hydroxy-1-methyl-2-oxopyrrolidin-3-yl]ethynyl]phenyl)-6-methyl-1H-pyrazolo[3,4-d]pyrimidine-3-carboxylate was reacted with ammonia to give the title compound (13.5 mg, 18%) as an off-white solid. LC-MS (ES, m/z): 391 [M+H]+. 1H NMR (400 MHz, CD3OD) δ 9.58 (s, 1H), 8.47-8.42 (m, 2H), 7.62-7.52 (m, 2H), 3.54-3.48 (m, 2H), 2.96 (s, 3H), 2.89 (s, 3H), 2.67-2.61 (m, 1H), 2.39-2.32 (m, 1H).

Example A8

Synthesis of (R)-6-cyclopropyl-1-(3-((3-hydroxy-1-methyl-2-oxopyrrolidin-3-yl)ethynyl)phenyl)-1H-pyrazolo[3,4-d]pyrimidine-3-carboxamide

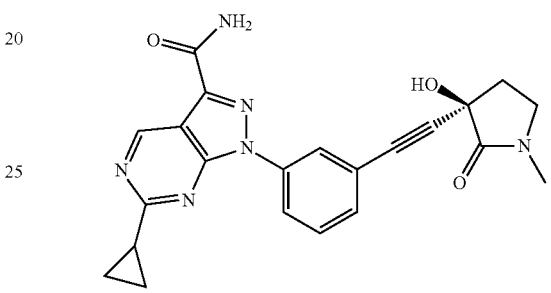

Step 1: Synthesis of ethyl 1-(3-bromophenyl)-5-(N-cyclopropanecarbonylcyclopropaneamido)-4-formyl-1H-pyrazole-3-carboxylate

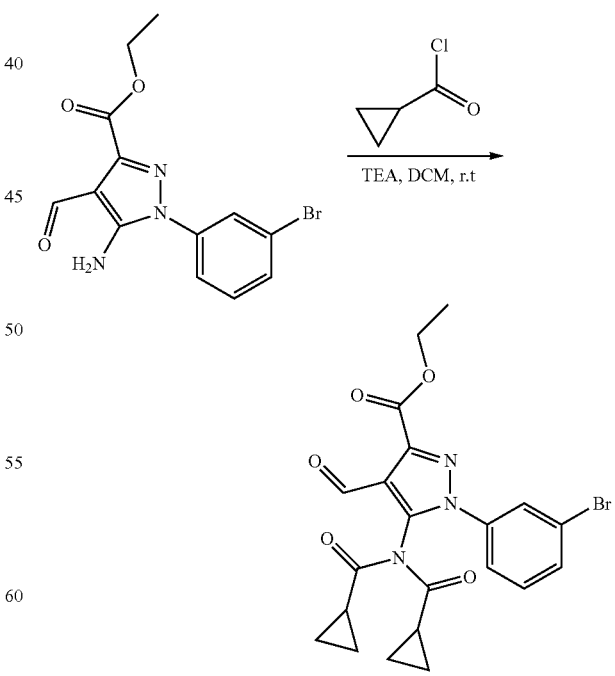

Cyclopropanecarbonyl chloride (247.31 mg, 2.37 mmol, 4.00 equiv) was added dropwise into a solution of triethylamine (1.00 mL, 7.19 mmol, 12.20 equiv) and ethyl 5-amino-1-(3-bromophenyl)-4-formyl-1H-pyrazole-3-carboxylate (200.00 mg, 0.59 mmol, 1.00 equiv) in dichloromethane (4 mL) at 0° C. After 1 h the resulting solution was diluted with dichloromethane, washed with brine, dried over anhydrous sodium sulfate, and concentrated under vacuum. The residue was applied onto a silica gel column with ethyl acetate/petroleum ether (1:5). This resulted in 200 mg (71%) of the title compound as colorless oil. LC-MS (ES, m/z): 474, 476 [M+H]$^+$.

Step 2: Synthesis of ethyl 1-(3-bromophenyl)-6-cyclopropyl-1H-pyrazolo[3,4-d]pyrimidine-3-carboxylate

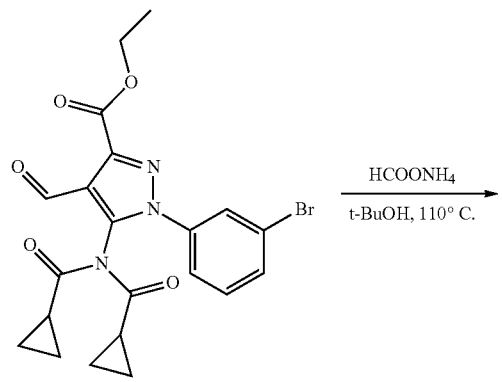

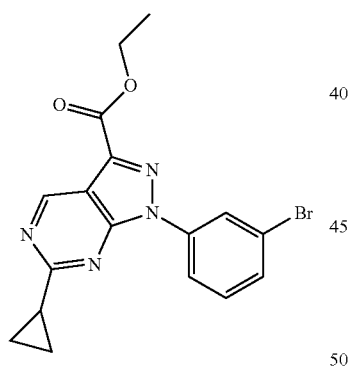

Ammonium formate (158.86 mg, 2.52 mmol, 6.00 equiv) was added to a stirred solution of ethyl 1-(3-bromophenyl)-5-(N-cyclopropanecarbonylcyclopropaneamido)-4-formyl-4,5-dihydro-1H-pyrazole-3-carboxylate (200.00 mg, 0.42 mmol, 1.00 equiv) in tert-butanol (10.00 mL). The resulting solution was stirred for 1 hour at 110° C., diluted with ethyl acetate and the solids were filtered out. The residue was applied onto a silica gel column with ethyl acetate/petroleum ether (1:5). This resulted in 80 mg (49%) of the title compound as colorless oil. LC-MS (ES, m/z): 387, 389 [M+H]$^+$.

Step 3: Synthesis of ethyl 6-cyclopropyl-1-(3-[2-[(3R)-3-hydroxy-1-methyl-2-oxopyrrolidin-3-yl]ethynyl]phenyl)-1H-pyrazolo[3,4-d]pyrimidine-3-carboxylate

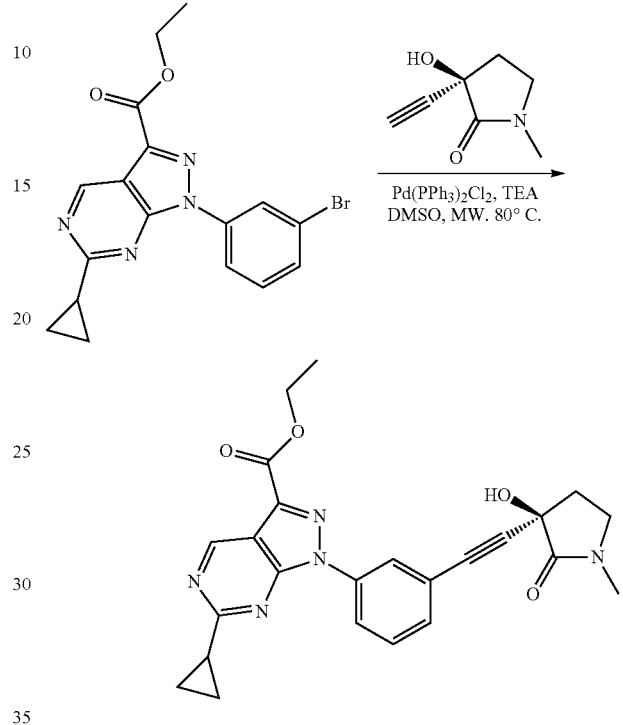

Similar to as described in General Procedure G, ethyl 1-(3-bromophenyl)-6-cyclopropyl-1H-pyrazolo[3,4-d]pyrimidine-3-carboxylate was reacted with (3R)-3-ethynyl-3-hydroxy-1-methylpyrrolidin-2-one to give the title compound (80 mg, 87%) as a yellow (solid. LC-MS (ES, m/z): 446 [M+H]$^+$.

Step 4: Synthesis of 6-cyclopropyl-1-(3-[2-[(3R)-3-hydroxy-1-methyl-2-oxopyrrolidin-3-yl]ethynyl]phenyl)-1H-pyrazolo[3,4-d]pyrimidine-3-carboxamide

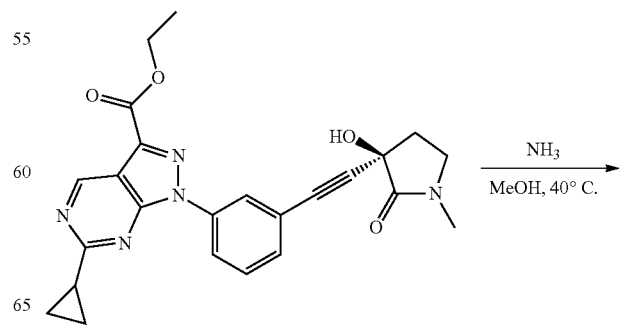

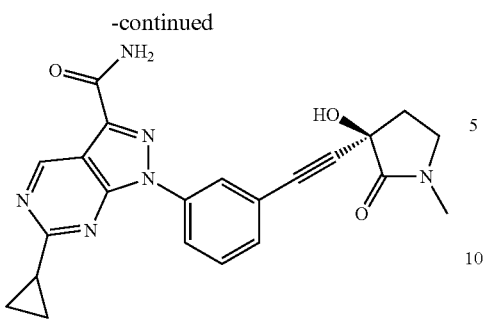

Similar to as described in General Procedure S, ethyl 6-cyclopropyl-1-(3-[2-[(3R)-3-hydroxy-1-methyl-2-oxopyrrolidin-3-yl]ethynyl]phenyl)-1H-pyrazolo[3,4-d]pyrimidine-3-carboxylate was reacted with ammonia to give the title compound (12.0 mg) as an off-white solid. LC-MS (ES, m/z): 417 [M+H]$^+$. $^1$H NMR (400 MHz, CD$_3$OD) δ 9.51 (s, 1H), 8.49 (s, 1H), 8.44 (d, J=10.8 Hz, 1H), 7.62-7.58 (m, 1H), 7.53 (d, J=8.0 Hz, 1H), 3.54-3.50 (m, 2H), 2.97 (s, 3H), 2.67-2.61 (m, 1H), 2.47-2.44 (m, 1H), 2.39-2.34 (m, 1H), 1.32-1.28 (m, 2H), 1.26-1.22 (m, 2H).

Example B8

Synthesis of (R)-1-(3-((3-hydroxy-1-methyl-2-oxopyrrolidin-3-yl)ethynyl)phenyl)-6-(trifluoromethyl)-1H-pyrazolo[3,4-d]pyrimidine-3-carboxamide

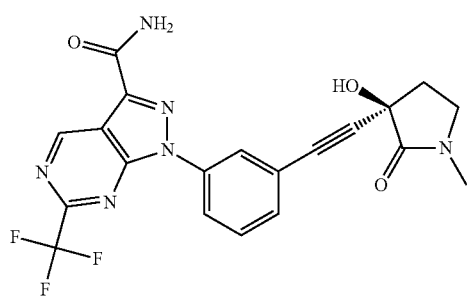 [SMILES: CN1CC[C@@](O)(C#Cc2cccc(-n3nc(C(N)=O)c4cnc(C(F)(F)F)nc43)c2)C1=O]

Step 1: Synthesis of ethyl 1-(3-bromophenyl)-4-formyl-5-(trifluoroacetamido)-1H-pyrazole-3-carboxylate

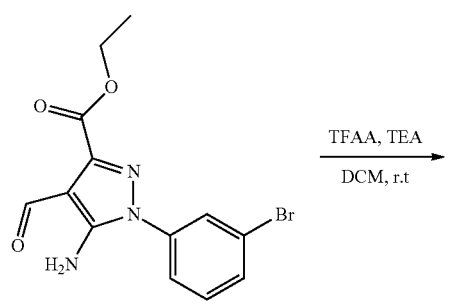

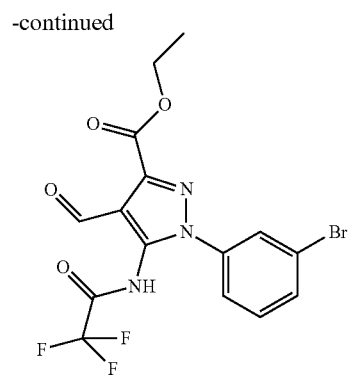

Trifluoroacetic anhydride (248.44 mg, 1.18 mmol, 2.00 equiv) was added to a stirred solution of ethyl 5-amino-1-(3-bromophenyl)-4-formyl-1H-pyrazole-3-carboxylate (200.00 mg, 0.59 mmol, 1.00 equiv) in dichloromethane (5.00 mL) and triethylamine (1.00 mL, 7.19 mmol, 12.20 equiv) and the resulting solution was stirred for 3 h at room temperature. The reaction was diluted with dichloromethane, washed with brine, dried over sodium sulfate, and concentrated under vacuum. The residue was applied onto a silica gel column with ethyl acetate/petroleum ether (1:2) to give the title compound (140 mg, 55%) as a yellow solid. LC-MS (ES, m/z): 434, 436 [M+H]$^+$.

Step 2: Synthesis of ethyl 1-(3-bromophenyl)-6-(trifluoromethyl)-1H-pyrazolo[3,4-d]pyrimidine-3-carboxylate

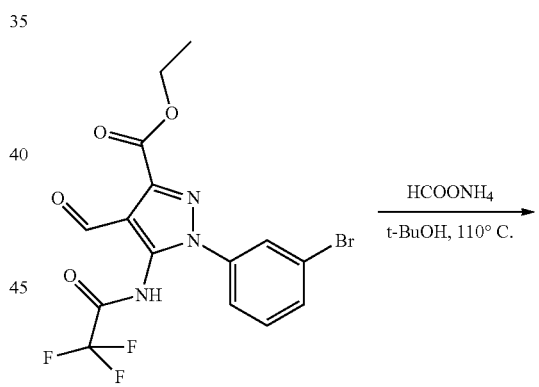

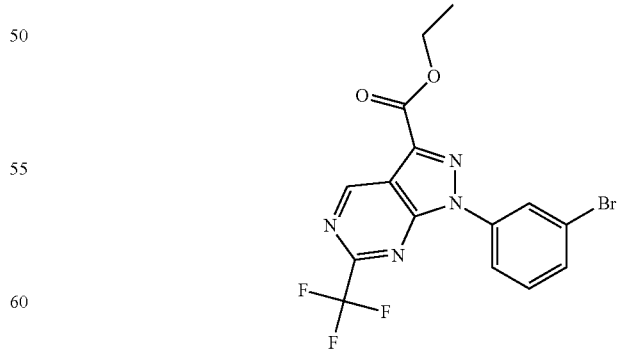

Ammonium formate (104.57 mg, 1.66 mmol, 6.00 equiv) was added to a stirred solution of ethyl 1-(3-bromophenyl)-4-formyl-5-(trifluoroacetamido)-1H-pyrazole-3-carboxylate (120.00 mg, 0.28 mmol, 1.00 equiv) in tert-butanol (10.00 mL) and the resulting solution was stirred for 1.5 hour at 110° C. The reaction was diluted with ethyl acetate, washed with water, dried over anhydrous sodium sulfate, and concentrated under vacuum. The residue was applied onto a silica gel column with ethyl acetate/petroleum ether (1:7) to give the title compound (90 mg, 78%) as a white solid. LC-MS (ES, m/z): 415, 417 [M+H]⁺.

Step 3: Synthesis of ethyl 1-(3-[2-[(3R)-3-hydroxy-1-methyl-2-oxopyrrolidin-3-yl]ethynyl]phenyl)-6-(trifluoromethyl)-1H-pyrazolo[3,4-d]pyrimidine-3-carboxylate

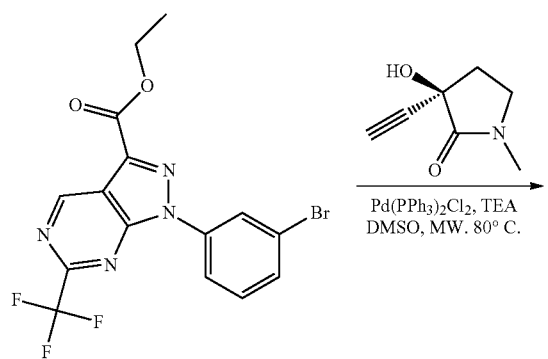

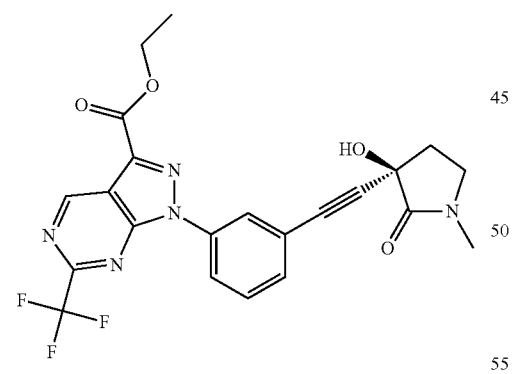

Similar to as described in General Procedure S, ethyl 1-(3-bromophenyl)-6-(trifluoromethyl)-1H-pyrazolo[3,4-d]pyrimidine-3-carboxylate was reacted with (3R)-3-ethynyl-3-hydroxy-1-methylpyrrolidin-2-one to give the title compound (80 mg, 88%) as yellow oil. LC-MS (ES, m/z): 474 [M+H]⁺.

Step 4: Synthesis of 1-(3-[2-[(3R)-3-hydroxy-1-methyl-2-oxopyrrolidin-3-yl]ethynyl]phenyl)-6-(trifluoromethyl)-1H-pyrazolo[3,4-d]pyrimidine-3-carboxamide

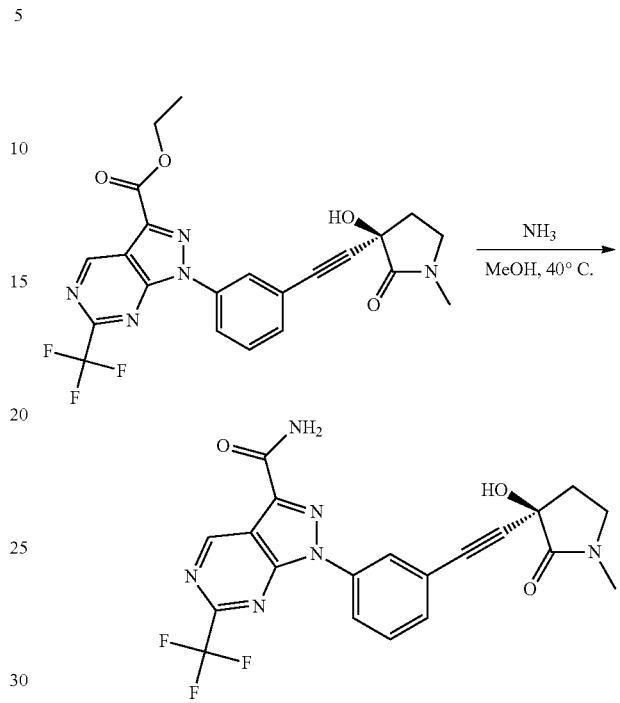

Similar to as described in General Procedure S, ethyl 1-(3-[2-[(3R)-3-hydroxy-1-methyl-2-oxopyrrolidin-3-yl]ethynyl]phenyl)-6-(trifluoromethyl)-1H-pyrazolo[3,4-d]pyrimidine-3-carboxylate was reacted with ammonia to give the title compound (45.6 mg, 61%) as a light yellow solid. LC-MS (ES, m/z): 445 [M+H]⁺. ¹H NMR (400 MHz, CD₃OD) δ: 9.51 (s, 1H), 8.49 (s, 1H), 8.44 (d, J=10.8 Hz, 1H), 7.62-7.58 (m, 1H), 7.53 (d, J=8.0 Hz, 1H), 3.54-3.50 (m, 2H), 2.97 (s, 3H), 2.67-2.61 (m, 1H), 2.47-2.44 (m, 1H), 2.39-2.34 (m, 1H), 1.32-1.28 (m, 2H), 1.26-1.22 (m, 2H).

Example C8

Synthesis of (R)-1-(3-((3-hydroxy-1-methyl-2-oxopyrrolidin-3-yl)ethynyl)phenyl)-6-methoxy-1H-pyrazolo[3,4-d]pyrimidine-3-carboxamide

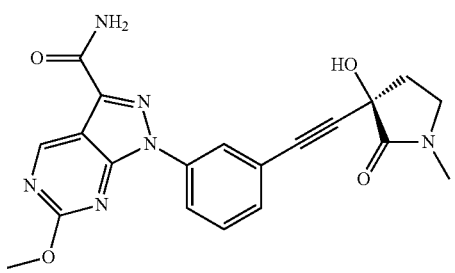

Step 1: Synthesis of 6-(methylsulfanyl)-1H,2H,3H-pyrazolo[3,4-d]pyrimidin-3-one

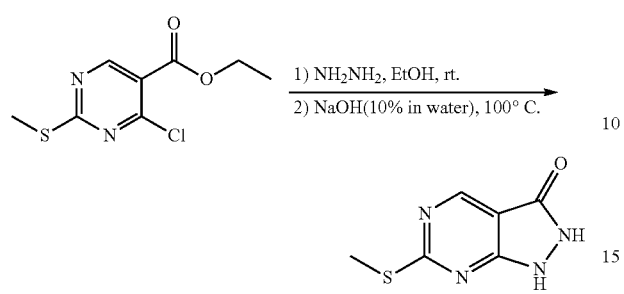

A suspension of ethyl 4-chloro-2-(methylsulfanyl)pyrimidine-5-carboxylate (5 g, 21.49 mmol, 1.00 equiv) and hydrazine hydrate (80%) (2.8 g, 55.93 mmol, 2.60 equiv) in ethanol (100 mL) was stirred for 1 hour at room temperature. 100 mL of water was added and the solids were filtered out. The liquid was evaporated under vacuum. A solution of sodium hydroxide (5 g, 125.01 mmol, 5.80 equiv) in water (50 mL) was added. The resulting solution was allowed to react for an additional 20 min while the temperature was maintained at 100° C. The pH value of the solution was adjusted to 6 with acetic acid (25%). The solids were collected by filtration. This resulted in 2 g (crude) of the title compound as a yellow solid. LC-MS (ES, m/z): 183 [M+H]$^+$.

Step 2: Synthesis of 3-bromo-6-(methylsulfanyl)-1H-pyrazolo[3,4-d]pyrimidine

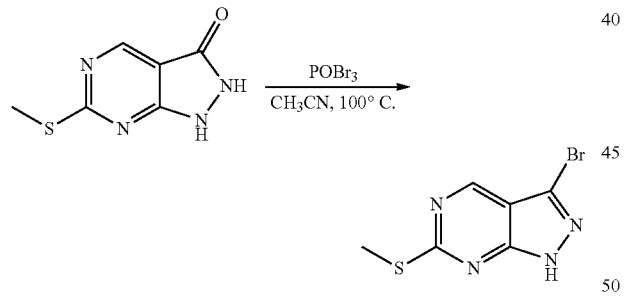

A suspension of 6-(methylsulfanyl)-1H-pyrazolo[3,4-d]pyrimidin-3-ol (2 g, 10.98 mmol, 1.00 equiv) and phosphorus oxybromide (6.3 g, 21.98 mmol, 2.00 equiv) in acetonitrile (50 mL) was sonicated for 30 min at room temperature. The resulting solution was allowed to react for an additional 16 hours while the temperature was maintained at 100° C. The pH value of the solution was adjusted to 8 with ammonium hydroxide (25%). The resulting mixture was concentrated under vacuum, diluted with ethyl acetate, and the solids were filtered out. The resulting solution was extracted with ethyl acetate and the organic layers were combined. The residue was purified by a silica gel column with dichloromethane/petroleum ether (100:0) to give 430 mg (16%) of the title compound as a white solid. LC-MS (ES, m/z): 245, 247 [M+H]$^+$.

Step 3: Synthesis of 3-bromo-6-methanesulfonyl-1H-pyrazolo[3,4-d]pyrimidine

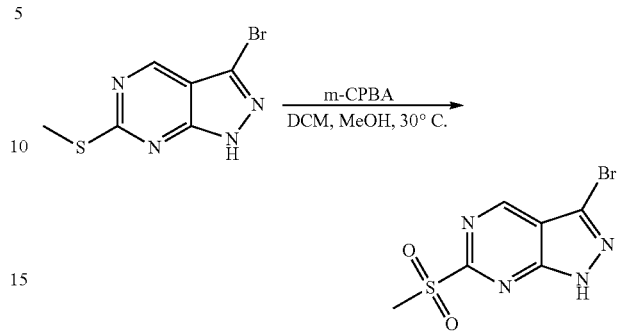

A suspension of 3-bromo-6-(methylsulfanyl)-1H-pyrazolo[3,4-d]pyrimidine (430 mg, 1.75 mmol, 1.00 equiv), 3-chloroperoxybenzoic acid (909 mg, 5.27 mmol, 3.00 equiv) in methanol (15 mL)/dichloromethane (10 mL) was stirred for 3 hours at 30° C. The resulting mixture was concentrated under vacuum. This resulted in 485 mg (crude) of the title compound as a white solid. LC-MS (ES, m/z): 277, 279 [M+H]$^+$.

Step 4: Synthesis of 3-bromo-6-methoxy-1H-pyrazolo[3,4-d]pyrimidine

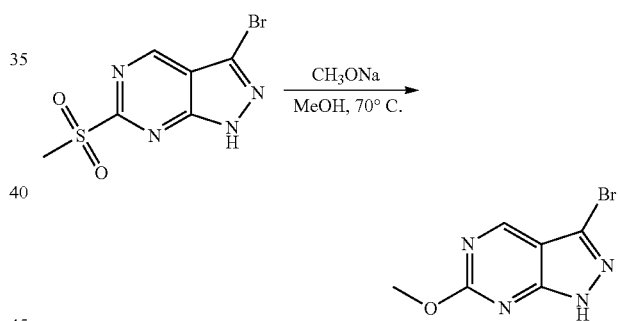

A mixture of 3-bromo-6-methanesulfonyl-1H-pyrazolo[3,4-d]pyrimidine (485 mg, 1.75 mmol, 1.00 equiv), sodium methoxide (1.89 g, 34.98 mmol, 20.00 equiv) in methanol (15 mL) was stirred for 4 hours at 70° C. The solids were filtered out and the liquid was concentrated under vacuum. The residue was purified by a silica gel column with ethyl acetate/petroleum ether (1:5) to give the title compound (240 mg) as a white solid. LC-MS (ES, m/z): 229, 231 [M+H]$^+$.

Step 5: Synthesis of ethyl 6-methoxy-1H-pyrazolo[3,4-d]pyrimidine-3-carboxylate

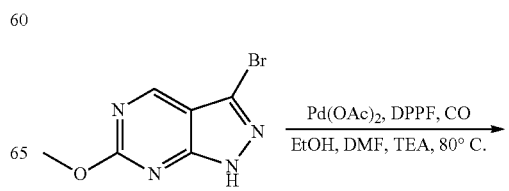

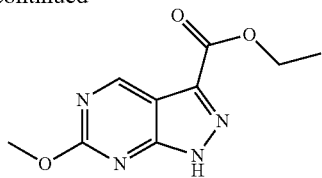

Similar to as described in General Procedure O, carbon monoxide was reacted with 3-bromo-6-methoxy-1H-pyrazolo[3,4-d]pyrimidine to give the title compound (40 mg, 17%) as a white solid. LC-MS (ES, m/z): 223 [M+H]⁺.

Step 6: Synthesis of ethyl 1-(3-iodophenyl)-6-methoxy-1H-pyrazolo[3,4-d]pyrimidine-3-carboxylate

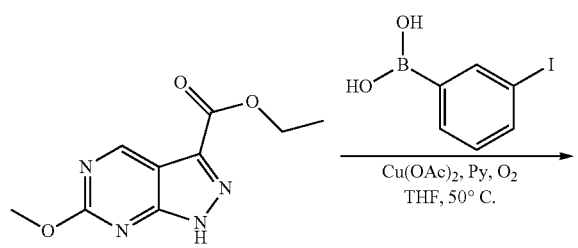

Similar to as described in General Procedure C, ethyl 6-methoxy-1H-pyrazolo[3,4-d]pyrimidine-3-carboxylate was reacted with (3-iodophenyl)boronic acid to give the title compound (60 mg, 79%) as a white solid. LC-MS (ES, m/z): 425 [M+H]⁺.

Step 7: Synthesis of ethyl 1-(3-[2-[(3R)-3-hydroxy-1-methyl-2-oxopyrrolidin-3-yl]ethynyl]phenyl)-6-methoxy-1H-pyrazolo[3,4-d]pyrimidine-3-carboxylate

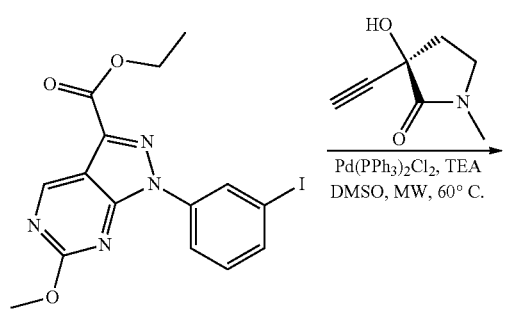

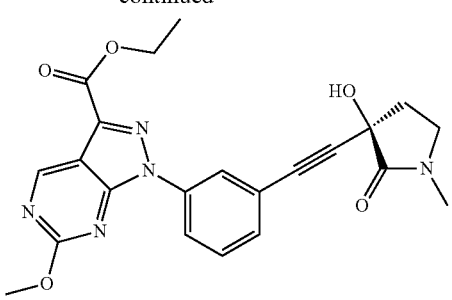

Similar to as described in General Procedure G, ethyl 1-(3-iodophenyl)-6-methoxy-1H-pyrazolo[3,4-d]pyrimidine-3-carboxylate was reacted with (3R)-3-ethynyl-3-hydroxy-1-methylpyrrolidin-2-one to give the title compound (70 mg, crude) as yellow oil. LC-MS (ES, m/z): 436 [M+H]⁺.

Step 8: Synthesis of 1-(3-[2-[(3R)-3-hydroxy-1-methyl-2-oxopyrrolidin-3-yl]ethynyl]phenyl)-6-methoxy-1H-pyrazolo[3,4-d]pyrimidine-3-carboxamide

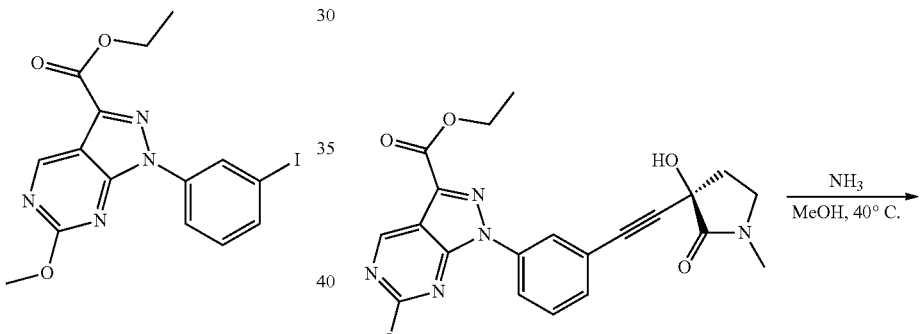

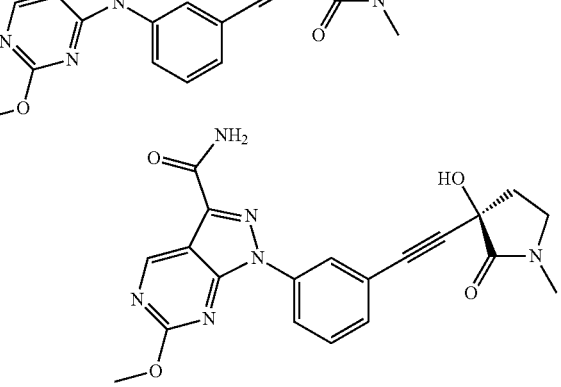

Similar to as described in General Procedure S, ethyl 1-(3-[2-[(3R)-3-hydroxy-1-methyl-2-oxopyrrolidin-3-yl]ethynyl]phenyl)-6-methoxy-1H-pyrazolo[3,4-d]pyrimidine-3-carboxylate was reacted with ammonia to give the title compound (20.3 mg, 31%) as a white solid. LC-MS (ES, m/z): 407 [M+H]⁺. ¹H NMR (300 MHz, CD₃OD) δ: 9.44 (s, 1H), 8.47-8.40 (m, 2H), 7.63-7.50 (m, 2H), 4.18 (s, 3H), 3.51 (t, J=5.4 Hz, 2H), 2.96 (s, 3H), 2.66-2.58 (m, 1H), 2.40-2.30 (m, 1H).

Example D8

Synthesis of (R)-5-(2-(azetidin-1-yl)ethoxy)-1-(3-((3-hydroxy-1-methyl-2-oxopyrrolidin-3-yl)ethynyl)phenyl)-1H-indazole-3-carboxamide

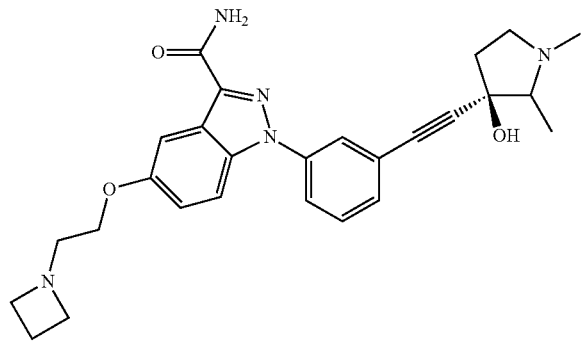 [SMILES: CC1N(C)CC[C@@]1(O)C#Cc1cccc(-n2nc(C(N)=O)c3cc(OCCN4CCC4)ccc32)c1]

Step 1: Synthesis of 5-(2-bromoethoxy)-1-(3-iodophenyl)-1H-indazole-3-carboxamide

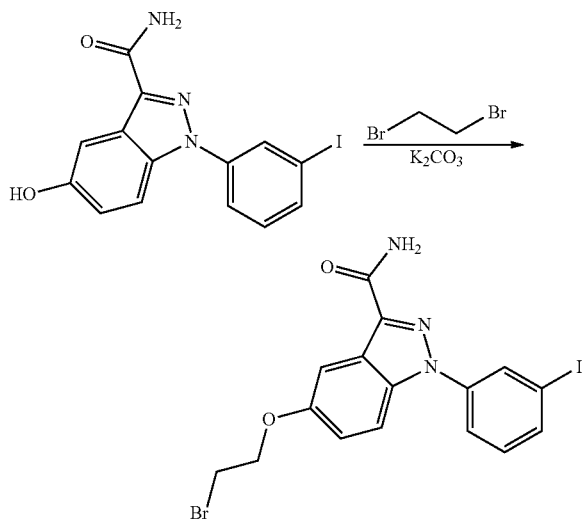

A mixture of 5-hydroxy-1-(3-iodophenyl)-1H-indazole-3-carboxamide (100 mg, 0.26 mmol, 1.00 equiv) and potassium carbonate (100 mg, 0.72 mmol, 2.70 equiv) in 1,2-dibromoethane (10 mL) was stirred overnight at 130° C. The resulting solution was diluted with ethyl acetate, washed with water, dried over anhydrous sodium sulfate, and concentrated under vacuum. The residue was applied onto a silica gel column with ethyl acetate/petroleum ether (1:3). This resulted in 50 mg (39%) of the title compound as a yellow solid. LC-MS (ES, m/z): 486 [M+H]$^+$.

Step 2: Synthesis of 5-[2-(azetidin-1-yl)ethoxy]-1-(3-iodophenyl)-1H-indazole-3-carboxamide

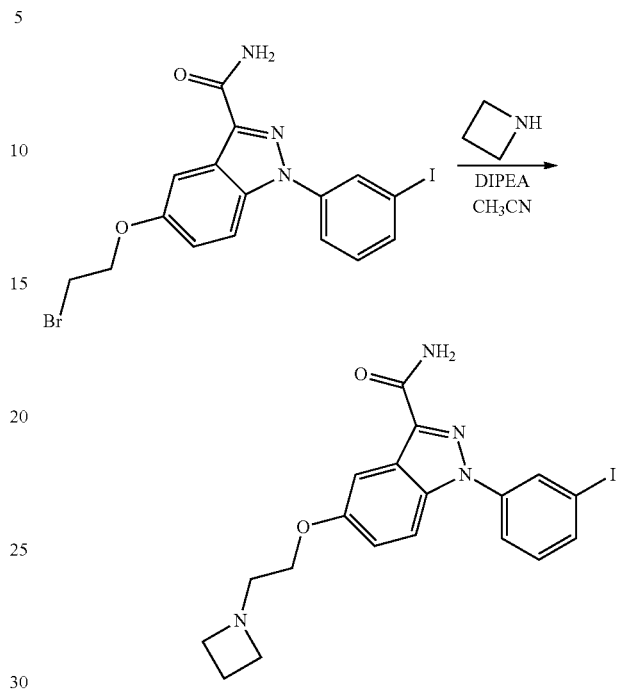

A mixture of 5-(2-bromoethoxy)-1-(3-iodophenyl)-1H-indazole-3-carboxamide (40.00 mg, 0.08 mmol, 1.00 equiv), N,N-Diisopropylethylamine (43 mg, 0.33 mmol, 4.00 equiv), and azetidine (24 mg, 0.42 mmol, 5.10 equiv) in acetonitrile (5 mL) was stirred for 4 h at 40° C. The resulting mixture was concentrated under vacuum and the residue was applied onto a silica gel column with dichloromethane/methanol (10:1). This resulted in 15 mg (39%) of the title compound as a yellow solid. LC-MS (ES, m/z): 463 [M+H]$^+$.

Step 3: Synthesis of (R)-5-(2-(azetidin-1-yl)ethoxy)-1-(3-((3-hydroxy-1-methyl-2-oxopyrrolidin-3-yl)ethynyl)phenyl)-1H-indazole-3-carboxamide

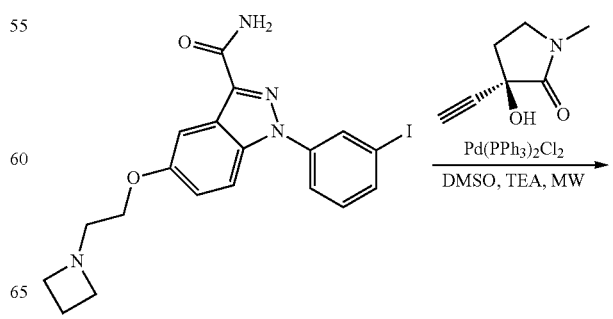

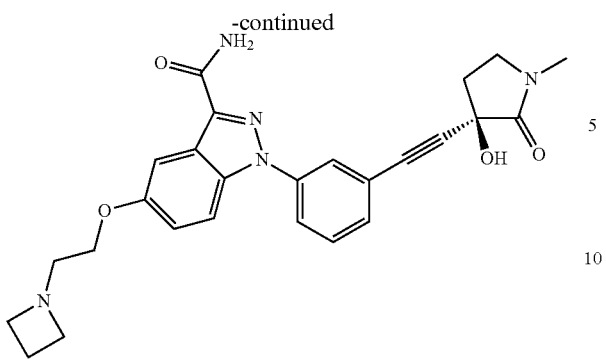

Similar to as described in General Procedure G, 5-[2-(azetidin-1-yl)ethoxy]-1-(3-iodophenyl)-1H-indazole-3-carboxamide was reacted with (3R)-3-ethynyl-3-hydroxy-1-methylpyrrolidin-2-one to give the title compound (9.7 mg, 63%) as an off-white solid. LC-MS (ES, m/z): 474 [M+H]$^+$. $^1$H NMR (300 MHz, DMSO-d$_6$) δ 7.97 (s, 1H), 7.91-7.87 (m, 2H), 7.80-7.77 (d, J=9.3 Hz, 1H), 7.65-7.63 (t, 2H), 7.50-7.48 (d, J=7.8 Hz, 2H), 7.19-7.15 (m, 1H), 6.52 (m, 1H), 3.99-3.96 (t, 2H), 3.38-3.32 (m, 2H), 3.22-3.18 (t, 4H), 2.80 (s, 3H), 2.75 (t, 2H), 2.51-2.49 (m, 1H), 2.32-2.13 (m, 1H), 1.97 (m, 2H).

Example E8

Synthesis of (R)-1-(3-((3-hydroxy-1-methyl-2-oxopyrrolidin-3-yl)ethynyl)phenyl)-5-(2-morpholinoethoxy)-1H-indazole-3-carboxamide

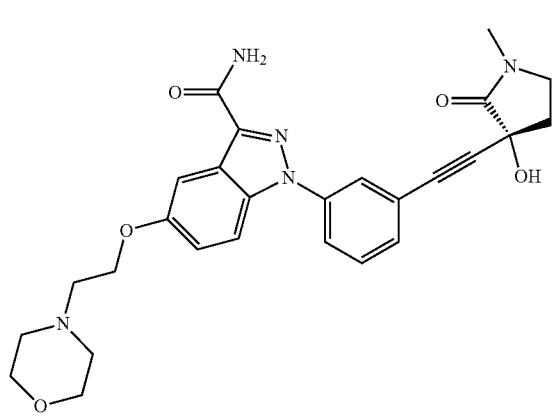 [SMILES: CN1CC[C@@](O)(C#Cc2cccc(-n3nc(C(N)=O)c4cc(OCCN5CCOCC5)ccc43)c2)C1=O]

Step 1: Synthesis of methyl 1-(3-iodophenyl)-5-methoxy-1H-indazole-3-carboxylate

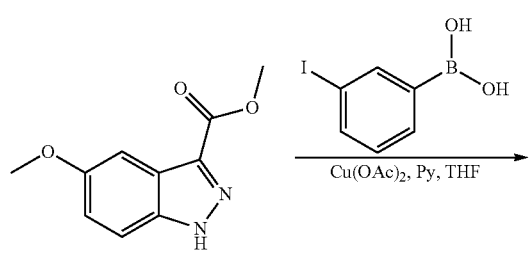

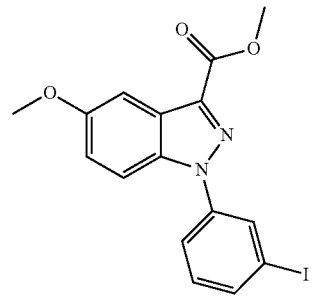

Similar to as described in General Procedure C, methyl 5-methoxy-1H-indazole-3-carboxylate (1.00 g, 4.85 mmol, 1.00 equiv) was reacted with (3-iodophenyl)boronic acid to give the title compound (700 mg, 35%) as a dark red solid. LC-MS (ES, m/z): 409 [M+H]$^+$.

Step 2: Synthesis of 1-(3-iodophenyl)-5-methoxy-1H-indazole-3-carboxamide

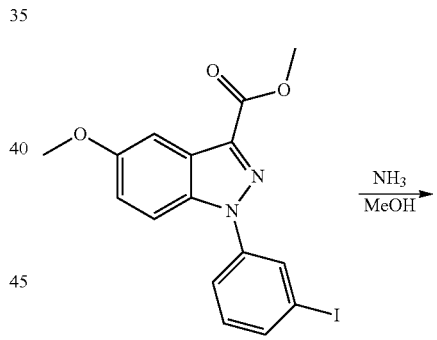

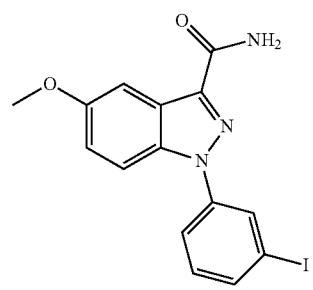

Similar to as described in General Procedure S, methyl 1-(3-iodophenyl)-5-methoxy-1H-indazole-3-carboxylate was reacted with ammonia to give the title compound (185 mg, 96%) as a white solid. LC-MS (ES, m/z): 394 [M+H]$^+$.

Step 3: Synthesis of 5-hydroxy-1-(3-iodophenyl)-1H-indazole-3-carboxamide

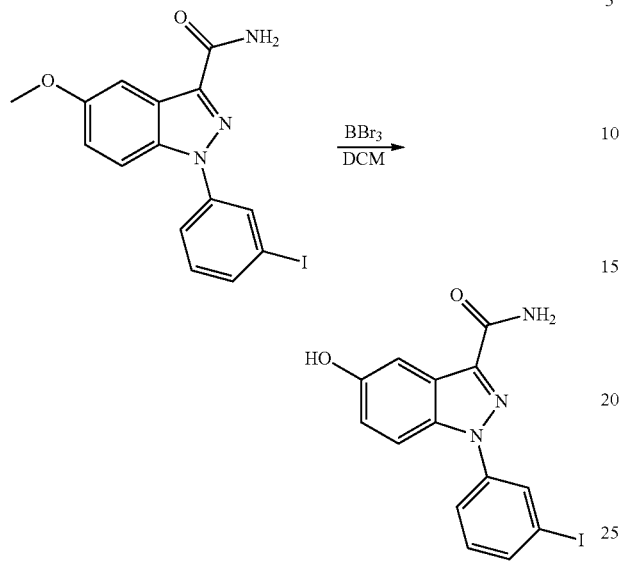

A mixture of 1-(3-iodophenyl)-5-methoxy-1H-indazole-3-carboxamide (400 mg, 1.02 mmol, 1.00 equiv) and BBr$_3$ (2.04 g, 8.14 mmol, 8.00 equiv) in dichloromethane (5 mL) was stirred for 12 h at 40° C. The resulting solution was allowed to react for overnight while the temperature was maintained at 40° C. The reaction was quenched by water, diluted with ethyl acetate, dried over anhydrous sodium sulfate, and concentrated under vacuum. The residue was applied onto a silica gel column with ethyl acetate/petroleum ether (1:2). This resulted in 260 mg (67%) of the title compound as a white solid. LC-MS (ES, m/z): 380 [M+H]$^+$.

Step 4: Synthesis of 1-(3-iodophenyl)-5-[2-(morpholin-4-yl)ethoxy]-1H-indazole-3-carboxamide

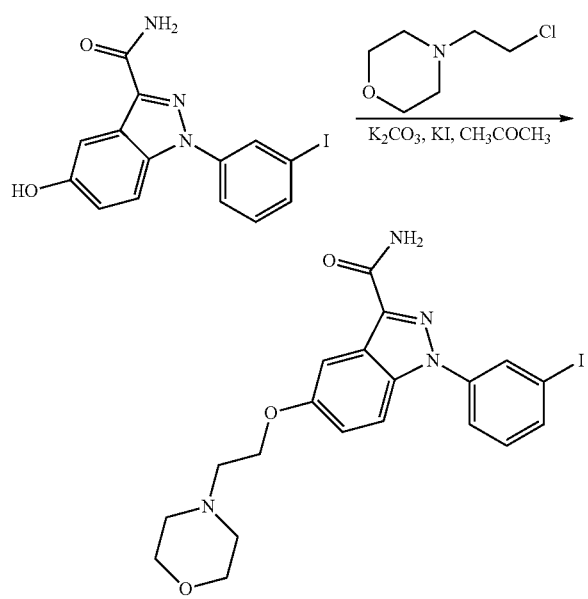

A mixture of 5-hydroxy-1-(3-iodophenyl)-1H-indazole-3-carboxamide (100.00 mg, 0.26 mmol, 1.00 equiv), 4-(2-chloroethyl)morpholine hydrochloride (245 mg, 1.32 mmol, 5.00 equiv), potassium carbonate (365 mg, 2.64 mmol, 10.00 equiv), and KI (88 mg, 0.53 mmol, 2.00 equiv) in acetone (5 mL) was stirred overnight at 60° C. The resulting solution was diluted with ethyl acetate, washed with brine, dried over anhydrous sodium sulfate, and concentrated under vacuum. The residue was applied onto a silica gel column with dichloromethane/methanol (20:1). This resulted in 50 mg (39%) of the title compound as a white solid. LC-MS (ES, m/z): 493 [M+H]$^+$.

Step 5: Synthesis of 1-(3-[2-[(3R)-3-hydroxy-1-methyl-2-oxopyrrolidin-3-yl)ethynyl]phenyl]-5-[2-(morpholin-4-yl)ethoxy]-1H-indazole-3-carboxamide

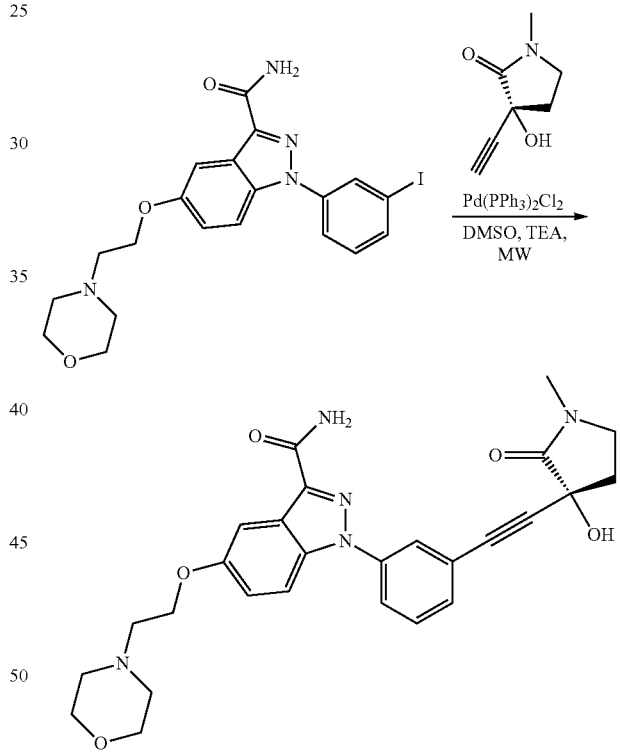

Similar to as described in General Procedure G, 1-(3-iodophenyl)-5-[2-(morpholin-4-yl)ethoxy]-1H-indazole-3-carboxamide was reacted with (3R)-3-ethynyl-3-hydroxy-1-methylpyrrolidin-2-one to give the title compound (18 mg, 35%) as a white solid. LC-MS (ES, m/z): 504 [M+H]$^+$. $^1$H NMR (300 MHz, DMSO-d$_6$) δ 7.89 (d, J=9.3 Hz, 2H), 7.79 (d, J=9.3 Hz, 1H), 7.69-7.61 (m, 2H), 7.50 (d, J=7.8 Hz, 1H), 7.23-7.19 (m, 1H), 4.18-4.15 (m, 2H), 3.61-3.44 (m, 4H), 3.58 (s, 2H), 2.80-2.23 (s, 3H), 2.77-2.73 (m, 2H), 2.60-2.58 (m, 2H), 2.51-2.44 (m, 1H), 2.30-2.13 (m, 1H).

Example F8

Synthesis of 1-(3-(4-(dimethylamino)-3-hydroxy-4-oxobut-1-ynyl)phenyl)-1H-indazole-3-carboxamide

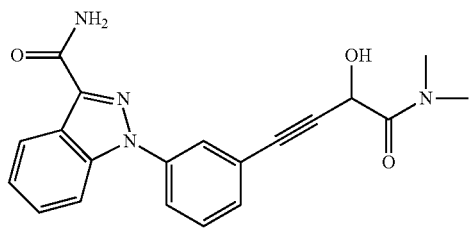 [SMILES: CN(C)C(=O)C(O)C#Cc1cccc(-n2nc(C(N)=O)c3ccccc32)c1]

Step 1: Synthesis of 1-(3-iodophenyl)-1H-indazole-3-carboxamide

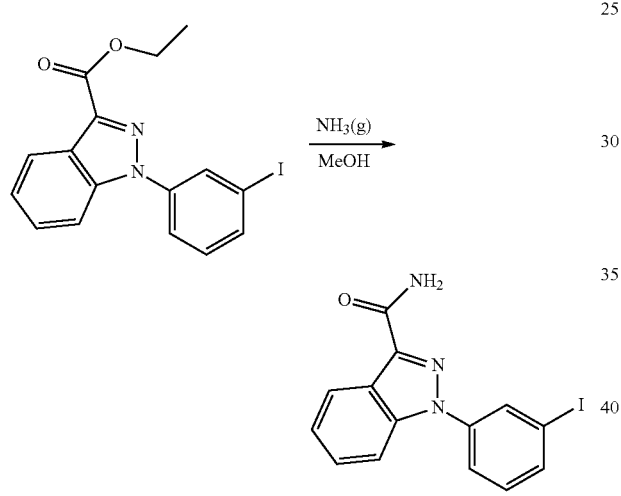

Similar to as described in General Procedure S, methyl 1-(3-iodophenyl)-1H-indazole-3-carboxylate was reacted with ammonia to give the title compound (1.35 g, crude) as an off-white solid. LC-MS (ES, m/z): 364 [M+H]$^+$.

Step 2: Synthesis of ethyl 4-[3-(3-carbamoyl-1H-indazol-1-yl)phenyl]-2-hydroxybut-3-ynoate

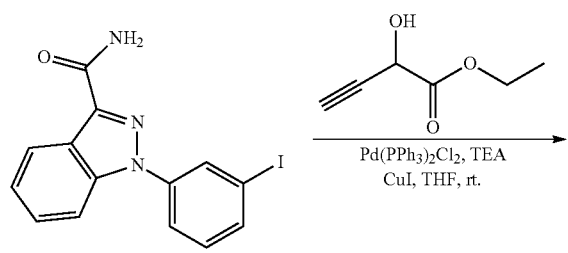

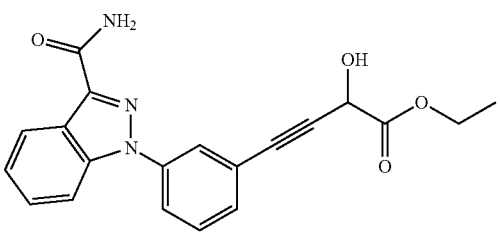

Similar to as described in General Procedure E, 1-(3-iodophenyl)-1H-indazole-3-carboxamide was reacted with ethyl 2-hydroxybut-3-ynoate to give the title compound (140 mg, 23%) as a light yellow solid. LC-MS (ES, m/z): 364 [M+H]$^+$.

Step 3: Synthesis of 1-[3-[3-(dimethylcarbamoyl)-3-hydroxyprop-1-yn-1-yl]phenyl]-1H-indazole-3-carboxamide

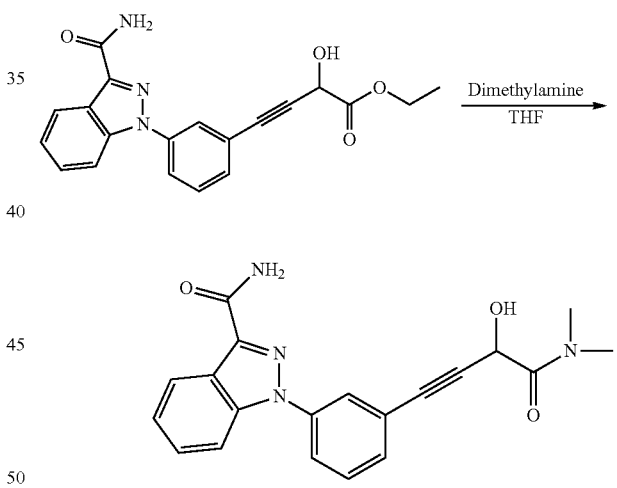

Similar to as described in General Procedure S, ethyl 4-[3-(3-carbamoyl-1H-indazol-1-yl)phenyl]-2-hydroxybut-3-ynoate was reacted with dimethylamine to give the title compound (15 mg, 10%) as a light yellow solid. LC-MS (ES, m/z): 363 [M+H]$^+$. $^1$H NMR (300 MHz, CD$_3$OD) δ 8.36 (d, J=8.4 Hz 1H), 8.20 (s, 1H), 7.97 (d, J=7.8 Hz, 1H), 7.89 (d, J=8.7 Hz, 1H), 7.84-7.80 (m, 2H), 7.72 (m, 1H), 7.60-7.55 (m, 1H), 7.41 (t, J=8.1 Hz, 1H), 7.11 (d, J=16.5 Hz, 1H), 3.07 (d, J=11.4 Hz, 1H).

Example G8

Synthesis of 1-[3-[2-[(3R)-3-hydroxy-1-methyl-2-oxo-pyrrolidin-3-yl]ethynyl]phenyl]pyrazolo[4,3-b]pyridine-3-carboxamide

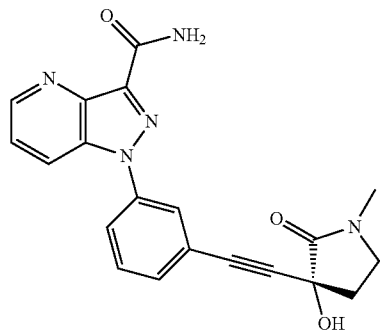 [SMILES: CN1CC[C@@](O)(C#Cc2cccc(-n3nc(C(N)=O)c4ncccc43)c2)C1=O]

Synthesis of 1H-pyrazolo[4,3-b]pyridine-3-carbonitrile

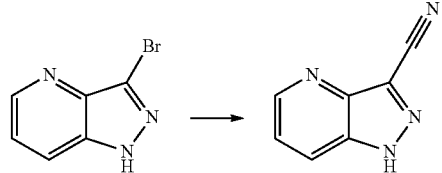 [SMILES: Brc1n[nH]c2cccnc12 ; N#Cc1n[nH]c2cccnc12]

To a solution of 3-bromo-1H-pyrazolo[4,3-b]pyridine (1.0 eq., 100 mg, 0.505 mmol) in 1-methyl-2-pyrrolidinone (1.3 mL) in a microwave vial was added copper(I) cyanide (1.5 eq., 69.2 mg, 0.757 mmol). The reaction was heated in the microwave to 220° C. for 20 minutes. The solution was then cooled to room temperature, diluted with aqueous saturated ammonium chloride and extracted twice with DCM. The organic layers were combined, dried with sodium sulfate and concentrated. The crude material was purified by flash chromatography (5-100% iPrOAc in heptanes) to afford 70 mg (96%) of the desired product with minor impurities.

Synthesis of 1-(3-bromophenyl)pyrazolo[4,3-b]pyridine-3-carbonitrile

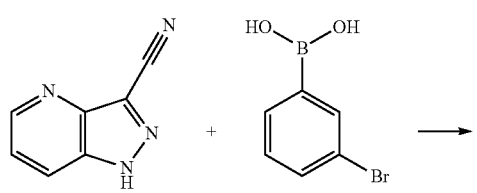

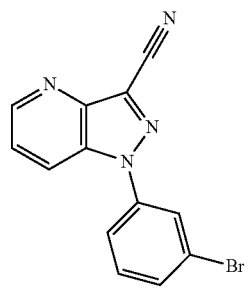

Similar to as described in General Procedure C, 1H-pyrazolo[4,3-b]pyridine-3-carbonitrile (70 mg, 0.485 mmol) was reacted with (3-bromophenyl)boronic acid (1.5 eq., 146.3 mg, 0.728 mmol) to afford 31.4 mg (21.6% yield) of a light yellow solid.

Synthesis of 1-(3-bromophenyl)pyrazolo[4,3-b]pyridine-3-carboxamide

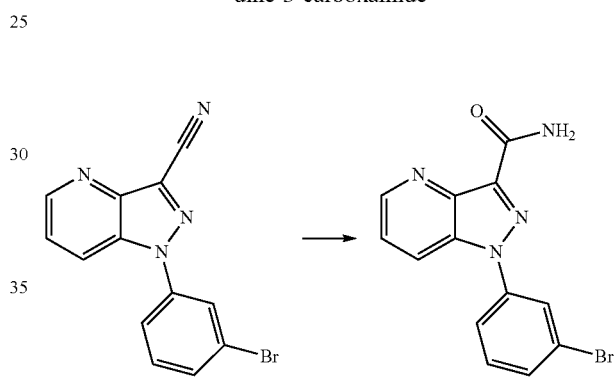

Similar to as described in General Procedure D, 1-(3-bromophenyl)pyrazolo[4,3-b]pyridine-3-carbonitrile (31.4 mg, 0.105 mmol) was reacted to afford the desired product which was carried forward to the next step without further purification.

Synthesis of 1-[3-[2-[(3R)-3-hydroxy-1-methyl-2-oxo-pyrrolidin-3-yl]ethynyl]phenyl]pyrazolo[4,3-b]pyridine-3-carboxamide

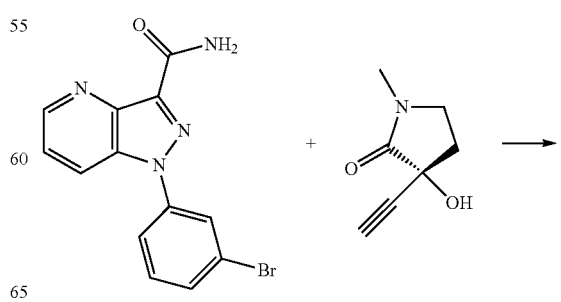

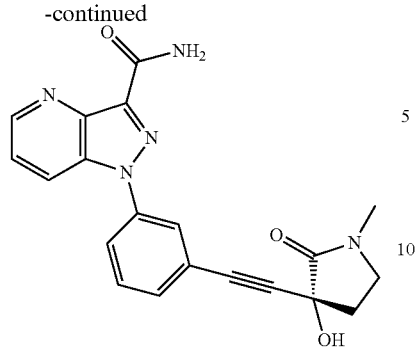

Similar to as described in General Procedure E, 1-(3-bromophenyl)pyrazolo[4,3-b]pyridine-3-carboxamide (32.6 mg, 0.103 mmol) was reacted with (3R)-3-ethynyl-3-hydroxy-1-methyl-pyrrolidin-2-one (17.2 mg, 0.123 mmol) to afford 16.5 mg (42.8% yield) of the title compound as a white solid. M+H=376.2; ¹H NMR (400 MHz, DMSO-d6) δ 8.85-8.75 (m, 1H), 8.50-8.42 (m, 1H), 8.31 (br s, 1H), 8.03 (br s, 1H), 7.96-7.89 (m, 1H), 7.91-7.85 (m, 1H), 7.70-7.60 (m, 2H), 7.58-7.48 (m, 1H), 6.54 (s, 1H), 3.41-3.32 (m, 2H), 2.81 (s, 3H), 2.50-2.40 (m, 1H), 2.19 (dt, J=12.8, 7.2 Hz, 1H).

Example H8

Ethyl 2-carbamoyl-1-[4-[2-[(3R)-3-hydroxy-1-methyl-2-oxo-pyrrolidin-3-yl]ethynyl]-2-pyridyl]-6,7-dihydro-4H-pyrazolo[4,3-c]pyridine-5-carboxylate Synthesis of O5-tert-butyl O3-ethyl 1-(4-iodo-2-pyridyl)-6,7-dihydro-4H-pyrazolo[4,3-c]pyridine-3,5-dicarboxylate

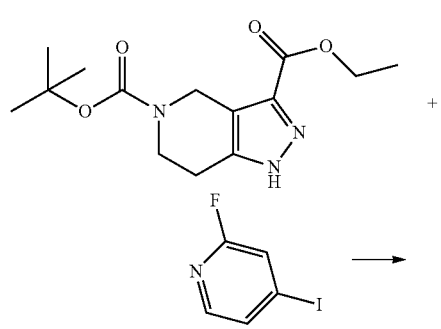

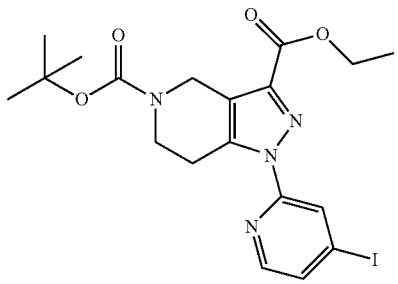

Similar to as described in General Procedure A, O5-tert-butyl O3-ethyl 1,4,6,7-tetrahydropyrazolo[4,3-c]pyridine-3,5-dicarboxylate (2.734 g, 9.258 mmol) was reacted with 2-fluoro-4-iodopyridine (2.265 g, 10.16 mmol) to afford a light yellow solid which was carried forward to subsequent steps without further purification.

Synthesis of Tert-butyl 3-carbamoyl-1-(4-iodo-2-pyridyl)-6,7-dihydro-4H-pyrazol[4,3-c]pyridine-5-carboxylate

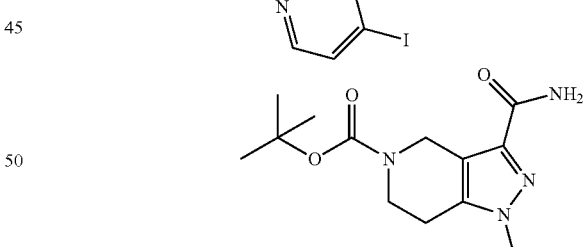

Similar to as described in General Procedure H, O5-tert-butyl O3-ethyl 1-(4-iodo-2-pyridyl)-6,7-dihydro-4H-pyrazolo[4,3-c]pyridine-3,5-dicarboxylate (4.613 g, 9.257 mmol) was reacted to afford the title compound as a white powder (2.629 g, 60.51%).

Synthesis of tert-butyl 3-carbamoyl-1-[4-[2-[(3R)-3-hydroxy-1-methyl-2-oxo-pyrrolidin-3-yl]ethynyl]-2-pyridyl]-6,7-dihydro-4H-pyrazolo[4,3-c]pyridine-5-carboxylate

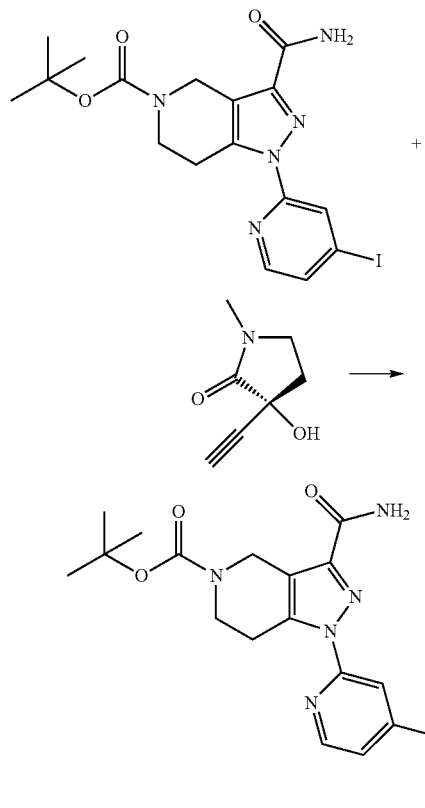

Similar to as described in General Procedure E, Tert-butyl 3-carbamoyl-1-(4-iodo-2-pyridyl)-6,7-dihydro-4H-pyrazol[4,3-c]pyridine-5-carboxylate (100.8 mg, 0.215 mmol) was reacted with (3R)-3-ethynyl-3-hydroxy-1-methyl-pyrrolidin-2-one (34.8 mg, 0.250 mmol) to afford the title compound.

Synthesis of 1-[4-[2-[(3R)-3-hydroxy-1-methyl-2-oxo-pyrrolidin-3-yl]ethynyl]-2-pyridyl]-4,5,6,7-tetrahydropyrazolo[4,3-c]pyridine-3-carboxamide

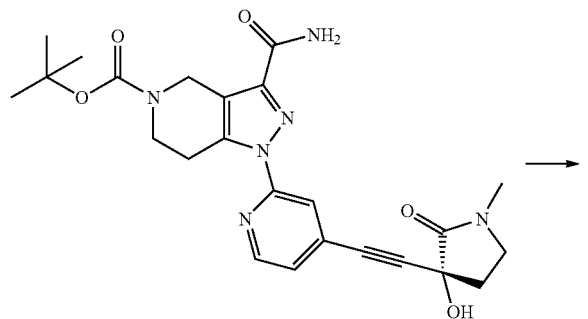

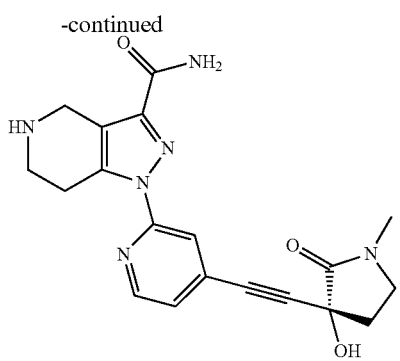

To a solution of tert-butyl 3-carbamoyl-1-[4-[2-[(3R)-3-hydroxy-1-methyl-2-oxo-pyrrolidin-3-yl]ethynyl]-2-pyridyl]-6,7-dihydro-4H-pyrazolo[4,3-c]pyridine-5-carboxylate (1 eq.) in dry DCM (0.3 M) was added trifluoroacetic acid (4-6 equivalents). The reaction was then stirred at room temperature until LC/MS showed complete conversion. The reaction was then concentrated in vacuo to afford the TFA salt of the title compound.

Synthesis of Ethyl 2-carbamoyl-1-[4-[2-[(3R)-3-hydroxy-1-methyl-2-oxo-pyrrolidin-3-yl]ethynyl]-2-pyridyl]-6,7-dihydro-4H-pyrazolo[4,3-c]pyridine-5-carboxylate

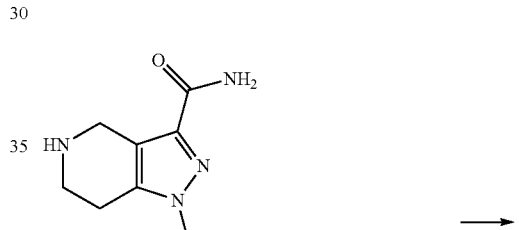

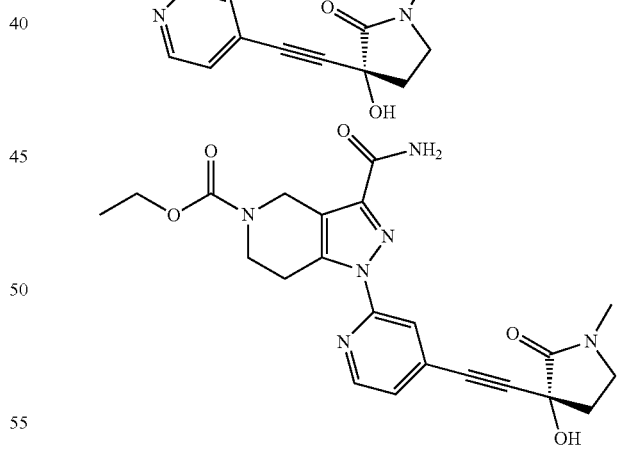

To a solution of 1-[4-[2-[(3R)-3-hydroxy-1-methyl-2-oxo-pyrrolidin-3-yl]ethynyl]-2-pyridyl]-4,5,6,7-tetrahydropyrazolo[4,3-c]pyridine-3-carboxamide (1 eq.) in THF was added DIPEA (6 eq.). To this solution was added ethyl chloroformate (1.2 equivalents) in THF at 0° C. The reaction was complete within 30 minutes. The solution was extracted with ammonium chloride and DCM, dried with sodium sulfate, and concentrated in vacuo. The crude material was purified by HPLC to afford the title compound. M+H=453.2; $^1$H NMR (400 MHz, DMSO-d) δ 8.52-8.45 (m, 1H), 8.08 (t, J=1.1 Hz, 1H), 7.98-7.93 (m, 1H), 7.45 (s, 1H), 7.38 (dd, J=5.1, 1.5 Hz, 1H), 6.66 (s, 1H), 4.60 (s, 2H), 4.09 (q, J=7.1 Hz, 2H), 3.66 (t, J=5.8 Hz, 2H), 3.37 (ddt, J=10.1, 6.6, 3.0 Hz, 2H), 3.21 (t, J=5.7 Hz, 2H), 2.81 (s, 3H), 2.51-2.42 (m, 1H), 2.22 (ddd, J=12.7, 7.6, 6.4 Hz, 1H), 1.21 (t, J=7.1 Hz, 3H).

Example I8

1-[2-[2-[(3R)-3-hydroxy-1-methyl-2-oxo-pyrrolidin-3-yl]ethynyl]-4-pyridyl]-4,5,6,7-tetrahydroindazole-3-carboxamide

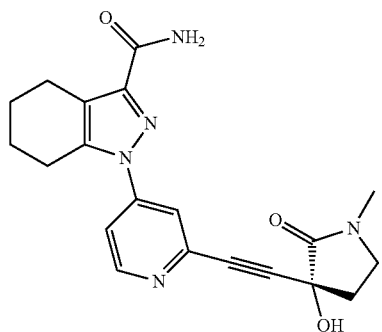 [SMILES: CN1CC[C@@](O)(C#Cc2cc(-n3nc(C(N)=O)c4c3CCCC4)ccn2)C1=O]

Synthesis of 1-(2-bromo-4-pyridyl)-4,5,6,7-tetrahydroindazole-3-carboxylic acid

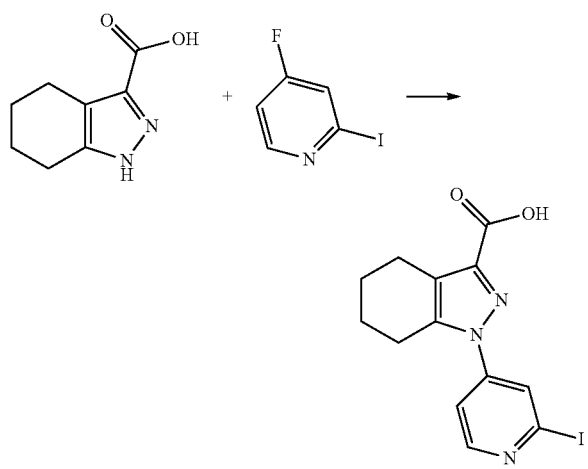

Similar to as described in General Procedure A, 4,5,6,7-tetrahydro-1H-indazole-3-carboxylic acid (75.4 mg, 0.454 mmol) was reacted with 2-bromo-4-fluoro-pyridine (76.0 mg, 0.430 mmol) to afford the title compound which was carried forward to subsequent steps without further purification.

Synthesis of 1-(2-bromo-4-pyridyl)-4,5,6,7-tetrahydroindazole-3-carboxamide

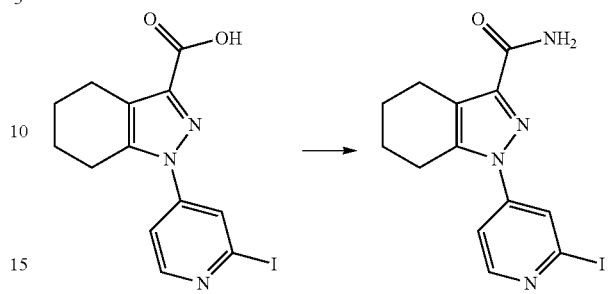

Similar to as described in General Procedure B, 1-(2-bromo-4-pyridyl)-4,5,6,7-tetrahydroindazole-3-carboxylic acid (140 mg, 0.43 mmol) was reacted with ammonium chloride (140 mg, 2.62 mmol) to afford the title compound.

Synthesis of 1-[2-[2-[(3R)-3-hydroxy-1-methyl-2-oxo-pyrrolidin-3-yl]ethynyl]-4-pyridyl]-4,5,6,7-tetrahydroindazole-3-carboxamide

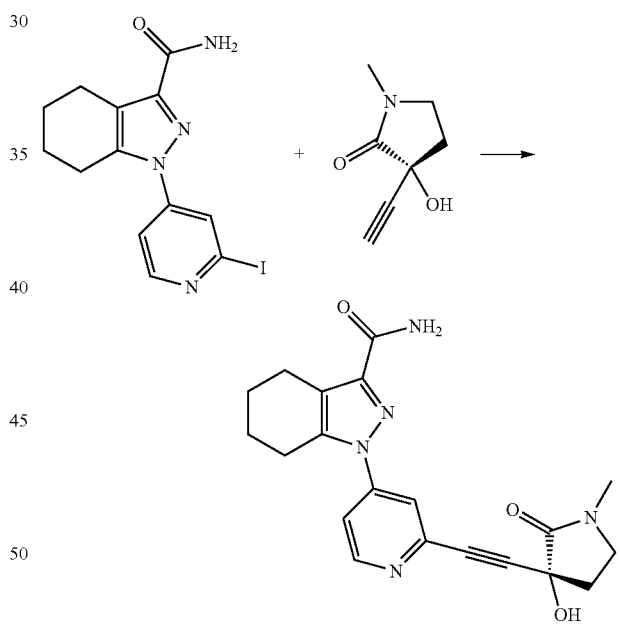

Similar to as described in General Procedure E, 1-(2-bromo-4-pyridyl)-4,5,6,7-tetrahydroindazole-3-carboxamide (138 mg, 0.43 mmol) was reacted with (3R)-3-ethynyl-3-hydroxy-1-methyl-pyrrolidin-2-one (59 mg, 0.424 mmol) to afford the title compound. M+H=380.2; $^1$H NMR (400 MHz, DMSO-d) δ 8.64 (d, J=5.5 Hz, 1H), 7.86 (d, J=2.1 Hz, 1H), 7.75-7.66 (m, 2H), 7.27 (s, 1H), 6.58 (d, J=2.1 Hz, 1H), 3.36 (ddt, J=10.0, 6.5, 2.8 Hz, 2H), 2.91 (t, J=6.0 Hz, 2H), 2.81 (s, 3H), 2.75-2.66 (m, 2H), 2.50-2.42 (m, 1H), 2.21 (ddd, J=14.5, 7.4, 5.9 Hz, 1H), 1.73 (dq, J=17.5, 4.4 Hz, 4H).

Example J8

1-[4-cyano-3-[2-[(3R)-3-hydroxy-1-methyl-2-oxo-pyrrolidin-3-yl]ethynyl]phenyl]-4,5,6,7-tetrahydroindazole-3-carboxamide

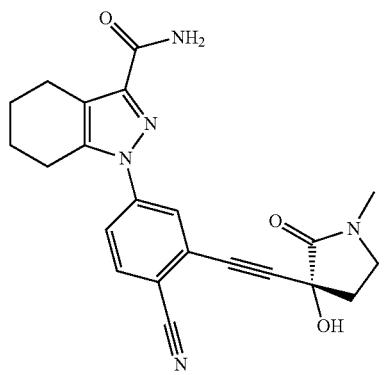

Synthesis of 1-(3-bromo-4-cyano-phenyl)-4,5,6,7-tetrahydroindazole-3-carboxylic acid

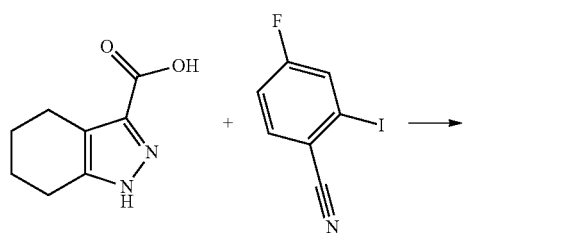

Similar to as described in General Procedure A, 4,5,6,7-tetrahydro-1H-indazole-3-carboxylic acid (200 mg, 1.2 mmol) was reacted with 2-bromo-4-fluoro-benzonitrile (260 mg, 1.3 mmol) to afford the title compound (350.8 mg, 84%).

Synthesis of 1-(3-bromo-4-cyano-phenyl)-4,5,6,7-tetrahydroindazole-3-carboxamide

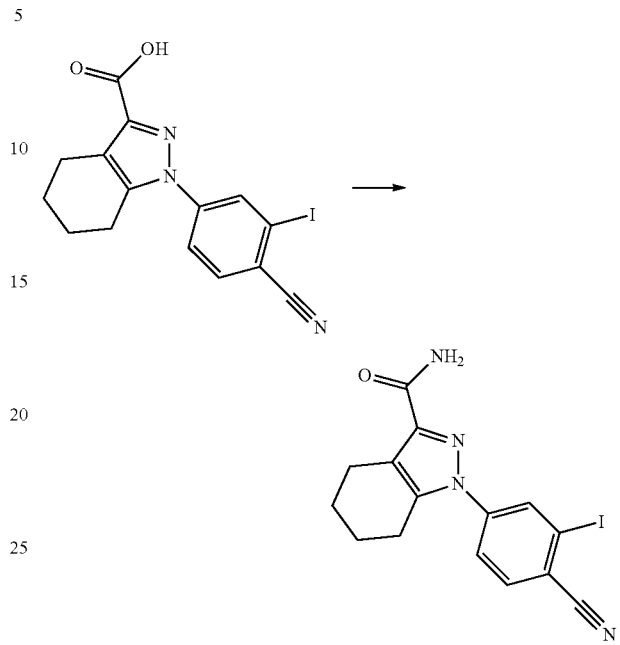

Similar to as described in General Procedure B, 1-(3-iodo-4-cyano-phenyl)-4,5,6,7-tetrahydroindazole-3-carboxylic acid (350.8 mg, 1.103 mmol) was reacted with ammonium chloride (326.1 mg, 6.10 mmol) to afford the title compound as a white powder (246.6 mg, 70.5%).

Synthesis of 1-[4-cyano-3-[2-[(3R)-3-hydroxy-1-methyl-2-oxo-pyrrolidin-3-yl]ethynyl]phenyl]-4,5,6,7-tetrahydroindazole-3-carboxamide

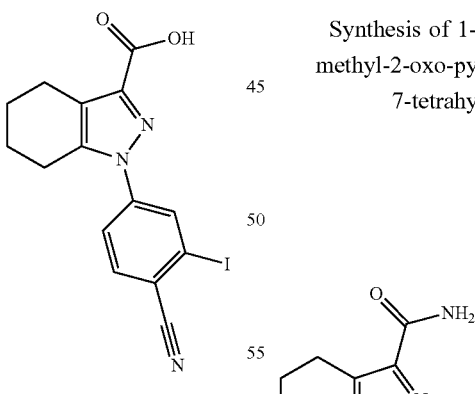

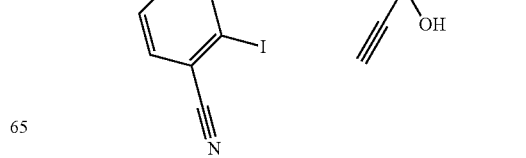

-continued

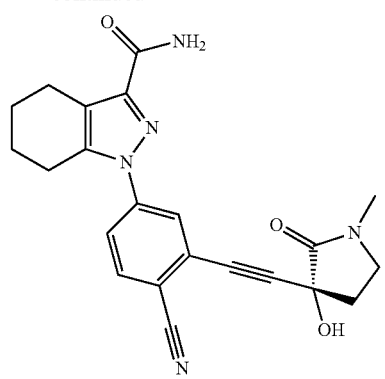 [SMILES: CN1CC[C@@](O)(C#Cc2cc(-n3nc(C(N)=O)c4c3CCCC4)ccc2C#N)C1=O]

Similar to as described in General Procedure E, 1-(3-bromo-4-cyano-phenyl)-4,5,6,7-tetrahydroindazole-3-carboxamide (80 mg, 0.232 mmol) was reacted with (3R)-3-ethynyl-3-hydroxy-1-methyl-pyrrolidin-2-one (32.3 mg, 0.232 mmol) to afford the title compound. M+H=404.2; ¹H NMR (400 MHz, DMSO-d) δ 8.06 (dd, J=8.5, 0.5 Hz, 1H), 7.97 (dd, J=2.2, 0.5 Hz, 1H), 7.87 (dd, J=8.6, 2.2 Hz, 1H), 7.67 (s, 1H), 7.25 (s, 1H), 6.63 (s, 1H), 3.47-3.23 (m, 5H), 2.81 (s, 5H), 2.71 (t, J=5.8 Hz, 2H), 2.56-2.44 (m, 1H), 2.23 (dt, J=12.7, 7.5 Hz, 1H), 1.78-1.67 (m, 4H).

Example K8 and Example L8

Synthesis of (S)-6-hydroxy-1-(3-(((R)-3-hydroxy-1-methyl-2-oxopyrrolidin-3-yl)ethynyl)phenyl)-1,4,5,6-tetrahydrocyclopenta[c]pyrazole-3-carboxamide and (R)-6-hydroxy-1-(3-(((R)-3-hydroxy-1-methyl-2-oxopyrrolidin-3-yl)ethynyl)phenyl)-1,4,5,6-tetrahydrocyclopenta[c]pyrazole-3-carboxamide

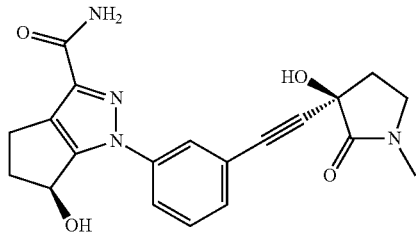

6S-isomer

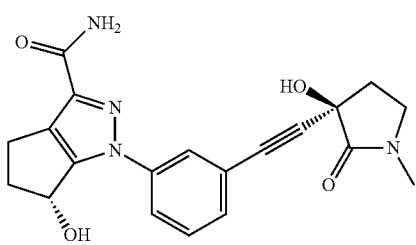

6R-isomer

Step 1: Synthesis of ethyl 1-(3-bromophenyl)-6-hydroxy-1,4,5,6-tetrahydrocyclopenta[c]pyrazole-3-carboxylate

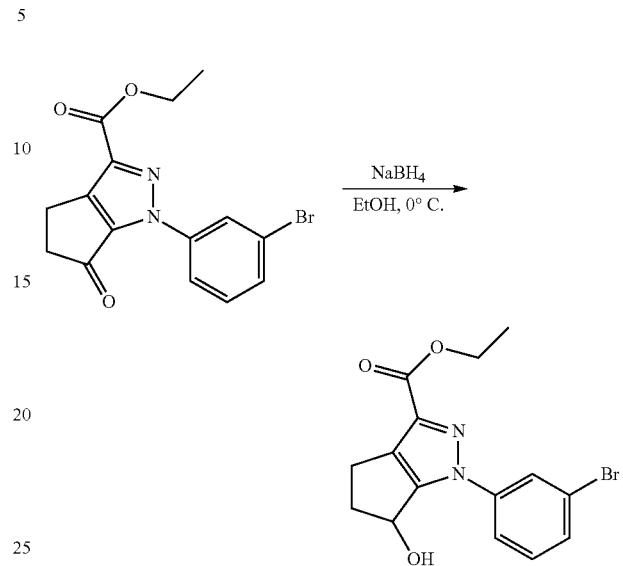

To a stirred solution of ethyl 1-(3-bromophenyl)-6-oxo-1H,4H,5H,6H-cyclopenta[c]pyrazole-3-carboxylate (150.00 mg, 0.43 mmol, 1.00 equiv) in ethanol (20 mL) was added sodium borohydride (32.50 mg, 0.86 mmol, 2.00 equiv) and the resulting solution was stirred for 1 hour at 0° C. After completion the solution was diluted with ethyl acetate, washed with 1M hydrogen chloride, dried over anhydrous sodium sulfate, and concentrated under vacuum. The residue was purified by silica gel column chromatography eluting with ethyl acetate/petroleum ether (2:3) to give the title compound (100 mg, 66%) as a white solid. LC-MS (ES, m/z): 351, 352 [M+H]⁺.

Step 2: Synthesis of ethyl 6-hydroxy-1-(3-[2-[(3R)-3-hydroxy-1-methyl-2-oxopyrrolidin-3-yl]ethynyl]phenyl)-1H,4H, 5H,6H-cyclopenta[c]pyrazole-3-carboxylate

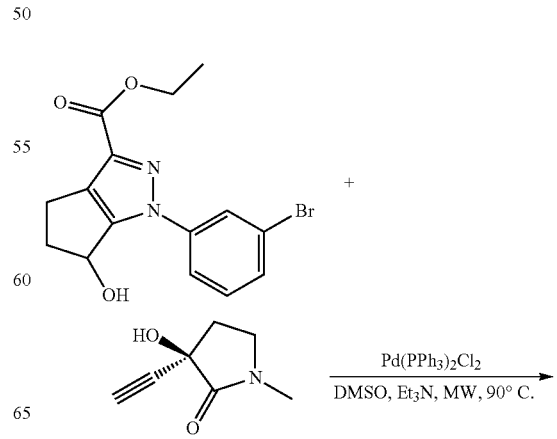

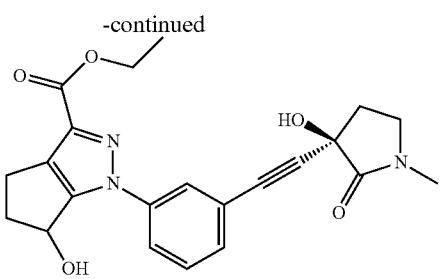

Similar to as described in General Procedure G, ethyl 1-(3-bromophenyl)-6-hydroxy-1H,4H,5H,6H-cyclopenta[c]pyrazole-3-carboxylate was reacted with (R)-3-ethynyl-3-hydroxy-1-methylpyrrolidin-2-one to give the title compound (70 mg, 67%) as a white solid. LC-MS (ES, m/z): 410 [M+H]$^+$.

Step 3: Synthesis of (S)-6-hydroxy-1-(3-(((R)-3-hydroxy-1-methyl-2-oxopyrrolidin-3-yl)ethynyl)phenyl)-1,4,5,6-tetrahydrocyclopenta[c]pyrazole-3-carboxamide and (R)-6-hydroxy-1-(3-(((R)-3-hydroxy-1-methyl-2-oxopyrrolidin-3-yl)ethynyl)phenyl)-1,4,5,6-tetrahydrocyclopenta[c]pyrazole-3-carboxamide

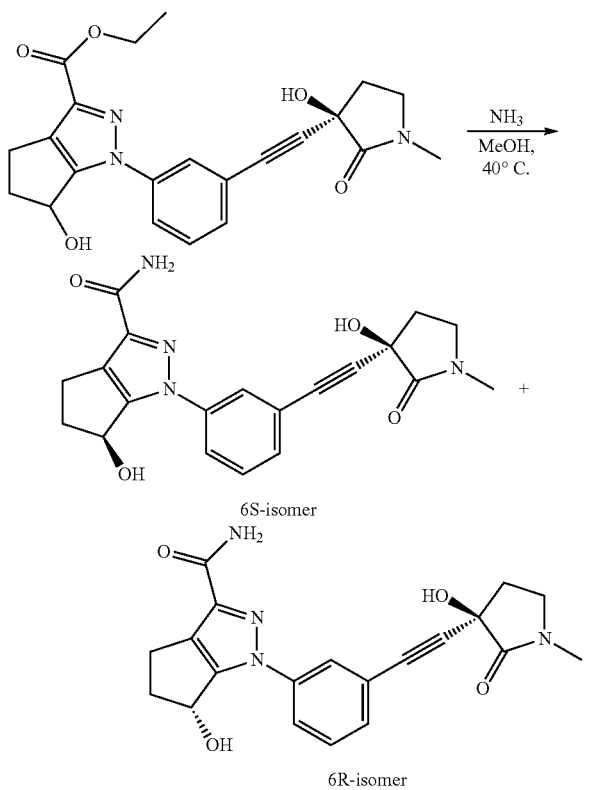

Similar to as described in General Procedure S, ethyl 6-hydroxy-1-(3-[2-[(3R)-3-hydroxy-1-methyl-2-oxopyrrolidin-3-yl]ethynyl]phenyl)-1H,4H,5H,6H-cyclopenta[c]pyrazole-3-carboxylate was reacted with ammonia to give the title compounds a R/S mixture. After chiral separation 9.8 mg (12%) of the 6R-isomer (yellow solid) and 12.4 mg (15%) of the 6S-isomer (yellow solid) were isolated. The 6R-isomer: t$_R$=3.58 min (CHIRLPAK IC3, 0.46*5 cm, Hex (0.1% TEA):EtOH=50:50, 1.0 ml/min); The 6S-isomer: t$_R$=4.93 min (CHIRLPAK IC3, 0.46*5 cm, Hex(0.1% TEA):EtOH=50:50, 1.0 ml/min). Both isomers showed identical LC-MS and $^1$H NMR as shown below. LC-MS (ES, m/z): 381 [M+H]$^+$. $^1$HNMR (400 MHz, methanol-d4) δ 8.09 (s, 1H), 8.01-8.00 (m, 1H), 7.49-7.44 (m, 2H), 5.28 (s, 1H), 3.32-3.31 (m, 2H), 3.13-2.94 (m, 2H), 2.93 (s, 3H), 2.77-2.62 (m, 1H), 2.61-2.57 (m, 2H), 2.36-2.30 (m, 1H).

Example M8

Synthesis of (R)-1-(3-(3-hydroxy-3-(thiazol-2-yl)but-1-ynyl)phenyl)-1H-indazole-3-carboxamide

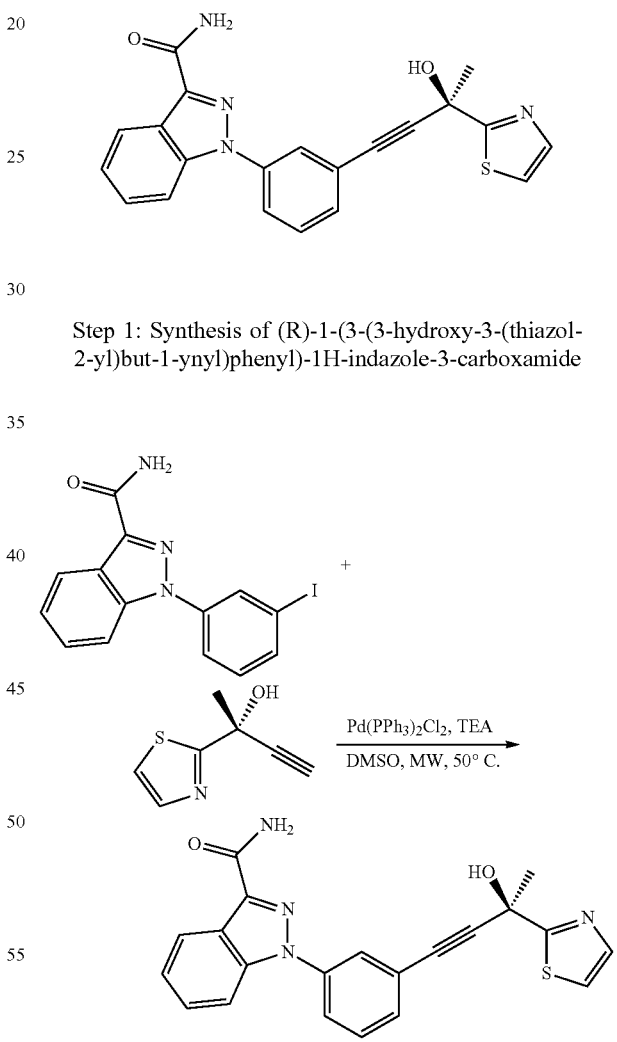

Step 1: Synthesis of (R)-1-(3-(3-hydroxy-3-(thiazol-2-yl)but-1-ynyl)phenyl)-1H-indazole-3-carboxamide Similar to as described in General Procedure G, 1-(3-iodophenyl)-1H-indazole-3-carboxamide was reacted with (R)-2-(thiazol-2-yl)but-3-yn-2-ol to give the title compound (58.8 mg, 46%) as a yellow solid. LC-MS (ES, m/z): 389 [M+H]$^+$. $^1$HNM (300 MHz, CD$_3$OD) δ 8.35 (d, J=8.4 Hz, 1H), 7.94 (s, 1H), 7.87-7.79 (m, 3H), 7.64-7.53 (m, 4H), 7.39 (t, J=8.4 Hz, 1H), 1.98 (s, 3H).

Example N8

Synthesis of (R)-6-cyano-1-(3-((3-hydroxy-1-methyl-2-oxopyrrolidin-3-yl)ethynyl)phenyl)-4-(methylamino)-1H-pyrazolo[4,3-c]pyridine-3-carboxamide

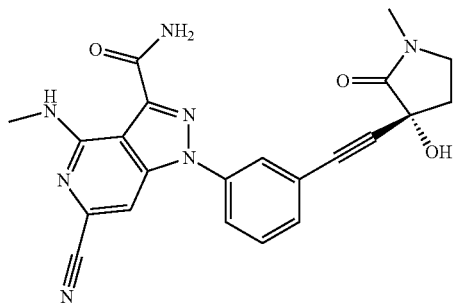 [SMILES: CNc1nc(C#N)cc2c1c(C(N)=O)nn2-c1cccc(C#C[C@]2(O)CCN(C)C2=O)c1]

Step 1: Synthesis of 2,4,6-trichloropyridine-3-carbaldehyde

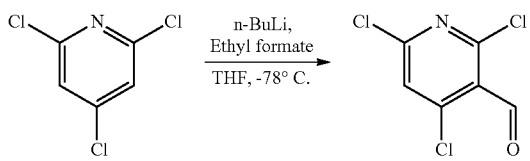 [SMILES: Clc1cc(Cl)nc(Cl)c1 ; O=Cc1c(Cl)cc(Cl)nc1Cl]

n-BuLi (2M, 16.8 mL) was added dropwise to a stirred solution of 2,4,6-trichloropyridine (8 g, 43.85 mmol, 1.00 equiv) in THF (80 mL) at −78° C. under nitrogen. After being stirred at −78° C. for 30 min ethyl formate (4.88 g, 65.88 mmol, 1.50 equiv) was added to the reaction mixture and the resulting solution was stirred for another 30 min at −78° C. After completion the solution was quenched with NH₄Cl solution and extracted with ethyl acetate. The organic layers were combined, dried over anhydrous sodium sulfate, and concentrated under vacuum. The residue was purified by silica gel column chromatography eluting with ethyl acetate/petroleum ether (1:10) to give the title compound (5 g, 54%) as a white solid. ¹HNMR (300 MHz, CDCl₃) δ 10.42 (s, 1H), 7.45 (s, 1H).

Step 2: Synthesis of 4,6-dichloro-1H-pyrazolo[4,3-c]pyridine

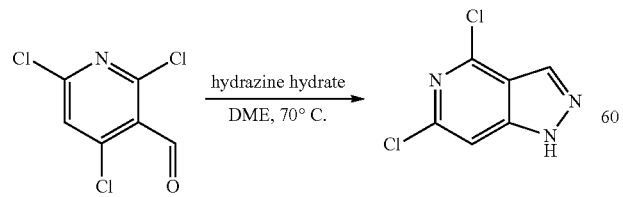

A suspension of 2,4,6-trichloropyridine-3-carbaldehyde (5 g, 23.76 mmol, 1.00 equiv) and hydrazine hydrate (3.6 g, 57.53 mmol, 3.00 equiv, 80%) in ethylene glycol dimethyl ether (25 mL) was stirred for 12 h at 45° C. After completion the solution was quenched with water and extracted with ethyl acetate. The organic layers were combined, dried over anhydrous sodium sulfate, and concentrated under vacuum. The residue was purified by silica gel column chromatography eluting with ethyl acetate/petroleum ether (1:10) to give the title compound (1 g, 22%) as a light yellow solid. LC-MS (ES, m/z): 188 [M+H]⁺.

Step 3: Synthesis of 4,6-dichloro-3-iodo-1H-pyrazolo[4,3-c]pyridine

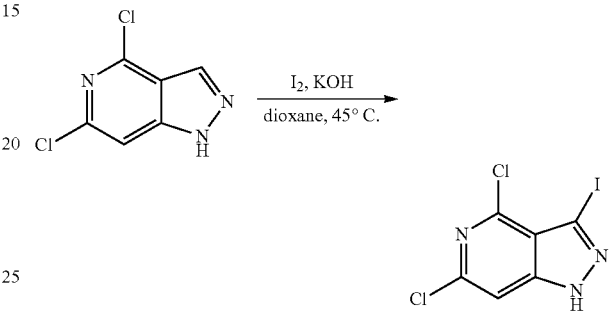

A solution of 4,6-dichloro-1H-pyrazolo[4,3-c]pyridine (1 g, 5.32 mmol, 1.00 equiv), iodine (2.64 g, 10.40 mmol, 2.00 equiv), and potassium hydroxide (1.16 g, 20.68 mmol, 4.00 equiv) in 1,4-dioxane (100 mL) was stirred for 12 h at 70° C. The reaction was quenched by saturated Na₂S₂O₃ and the resulting solids were collected by filtration. This resulted in 1 g (60%) of the title compound as a white solid. LC-MS (ES, m/z): 314 [M+H]⁺.

Step 4: Synthesis of 6-chloro-3-iodo-N-methyl-1H-pyrazolo[4,3-c]pyridin-4-amine

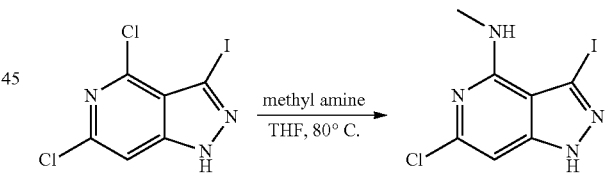

Similar to as described in General Procedure A, 4,6-dichloro-3-iodo-1H-pyrazolo[4,3-c]pyridine was reacted with methyl amine to give the title compound (700 mg, 71%) as a white solid. LC-MS (ES, m/z): 309 [M+H]⁺.

Step 5: Synthesis of methyl 6-chloro-4-(methylamino)-1H-pyrazolo[4,3-c]pyridine-3-carboxylate

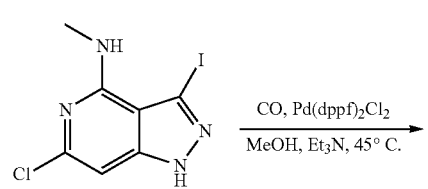

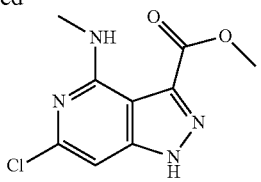

Similar to as described in General Procedure O, 6-chloro-3-iodo-N-methyl-1H-pyrazolo[4,3-c]pyridin-4-amine was reacted with carbon monoxide to give the title compound (210 mg, 38%) as a white solid. LC-MS (ES, m/z): 241 [M+H]⁺.

Step 6: Synthesis of methyl 1-(3-bromophenyl)-6-chloro-4-(methylamino)-1H-pyrazolo[4,3-c]pyridine-3-carboxylate

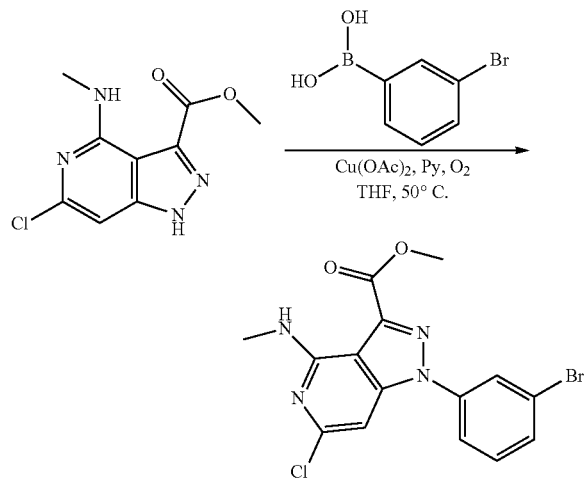

Similar to as described in General Procedure C, methyl 6-chloro-4-(methylamino)-1H-pyrazolo[4,3-c]pyridine-3-carboxylate was reacted with 3-bromophenylboronic acid to give the title compound (190 mg, 55%) as a white solid. LC-MS (ES, m/z): 395, 397 [M+H]⁺.

Step 7: Synthesis of methyl 6-chloro-1-(3-[2-[(3R)-3-hydroxy-1-methyl-2-oxopyrrolidin-3-yl]ethynyl]phenyl)-4-(methylamino)-1H-pyrazolo[4,3-c]pyridine-3-carboxylate

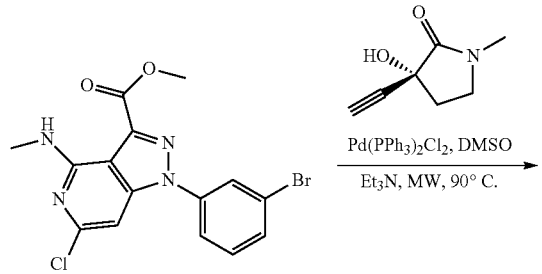

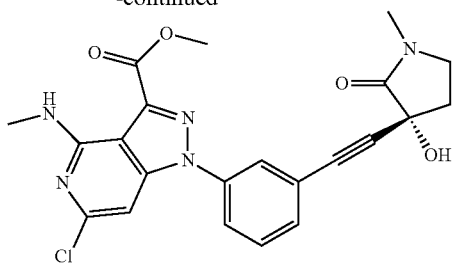

Similar to as described in General Procedure G, methyl 1-(3-bromophenyl)-6-chloro-4-(methylamino)-1H-pyrazolo[4,3-c]pyridine-3-carboxylate was reacted with (R)-3-ethynyl-3-hydroxy-1-methylpyrrolidin-2-one to give the title compound (190 mg, 87%) as a yellow solid. LC-MS (ES, m/z): 454 [M+H]⁺.

Step 8: Synthesis of methyl 6-cyano-1-(3-[2-[(3R)-3-hydroxy-1-methyl-2-oxopyrrolidin-3-yl]ethynyl]phenyl)-4-(methyl amino)-1H-pyrazolo[4,3-c]pyridine-3-carboxylate

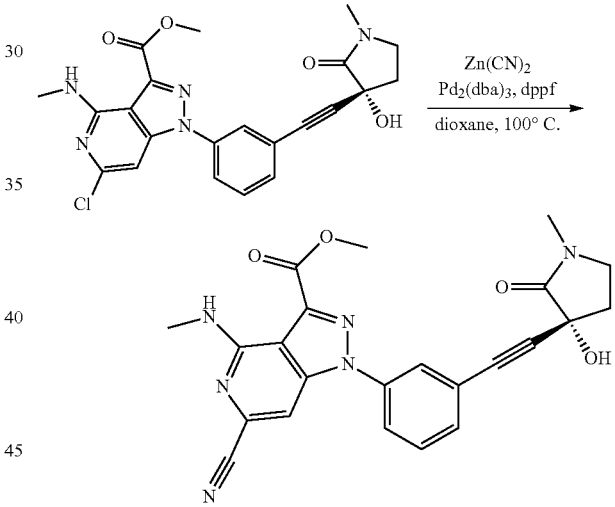

A suspension of methyl 6-chloro-1-(3-[2-[(3R)-3-hydroxy-1-methyl-2-oxopyrrolidin-3-yl]ethynyl]phenyl)-4-(methylamino)-1H-pyrazolo[4,3-c]pyridine-3-carboxylate (100 mg, 0.22 mmol, 1.00 equiv), zinc cyanide (100 mg, 0.85 mmol, 3.90 equiv), bis (diphenylphosphino)ferrocene (190 mg, 0.34 mmol, 1.60 equiv), and bis(dibenzylideneacetone)palladium (80 mg, 0.09 mmol, 0.40 equiv) in 1,4-dioxane (5 mL) was stirred for 2 h at 100° C. under nitrogen. After completion the precipitate was filtered out and the filtrate was concentrated under vacuum. The residue was purified by silica gel column chromatography eluting with dichloromethane/ethyl acetate (5:1) to give the title compound (20 mg, 20%) as an off-white solid. LC-MS (ES, m/z): 445 [M+H]⁺.

Step 9: Synthesis of 6-cyano-1-(3-[2-[(3R)-3-hydroxy-1-methyl-2-oxopyrrolidin-3-yl]ethynyl]phenyl)-4-(methyl amino)-1H-pyrazolo[4,3-c]pyridine-3-carboxamide

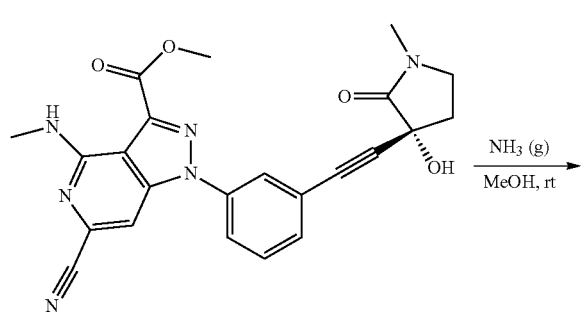

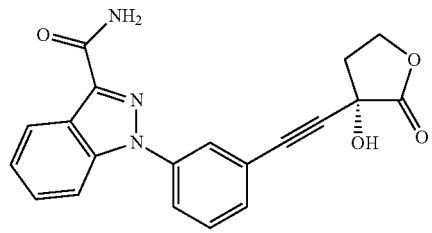

Step 1: Synthesis of 3-hydroxy-4-methoxy-4-oxobutanoic acid

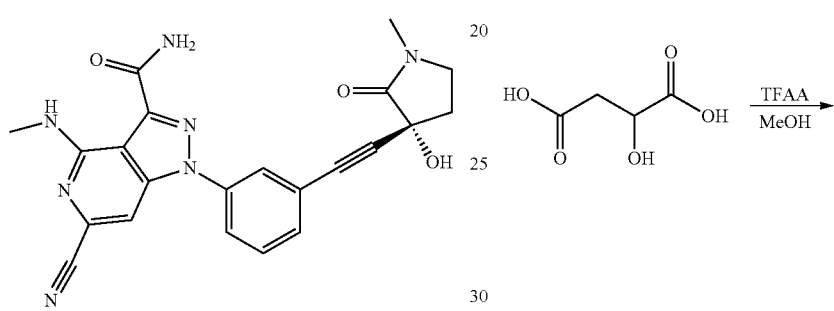

Similar to as described in General Procedure S, methyl 6-cyano-1-(3-[2-[(3R)-3-hydroxy-1-methyl-2-oxopyrrolidin-3-yl]ethynyl]phenyl)-4-(methyl amino)-1H-pyrazolo[4,3-c]pyridine-3-carboxylate was reacted with ammonia to give the title compound (4.5 mg, 12%) as a white solid. LC-MS (ES, m/z): 430 [M+H]$^+$. $^1$HNMR (400 MHz, CDCl$_3$) δ 7.90 (s, 1H), 7.82-7.79 (m, 1H), 7.66-7.61 (m, 2H), 7.37 (s, 1H), 3.52-3.47 (m, 2H), 3.12 (s, 3H), 2.95 (s, 3H), 2.65-2.59 (m, 1H), 2.37-2.30 (m, 1H).

A solution of 2-hydroxybutanedioic acid (7.08 g, 52.80 mmol, 1.00 equiv) in trifluoroacetic anhydride (29.6 mL, 212.81 mmol, 4.00 equiv) was stirred for 1.5 h at room temperature. Then methanol (30 mL, 739.66 mmol, 14.00 equiv) was added and the resulting solution was allowed to react overnight at room temperature. The resulting mixture was concentrated under vacuum and the product was recrystallized from ether/hexane (1:10) to give the title compound (5.7 g, 73%) as a white solid.

Example O8 and Example P8

Synthesis of (R)-1-(3-((3-hydroxy-2-oxo-tetrahydrofuran-3-yl)ethynyl)phenyl)-1H-indazole-3-carboxamide and (S)-1-(3-((3-hydroxy-2-oxo-tetrahydrofuran-3-yl)ethynyl)phenyl)-1H-indazole-3-carboxamide Step 2: Synthesis of methyl 2,4-dihydroxybutanoate

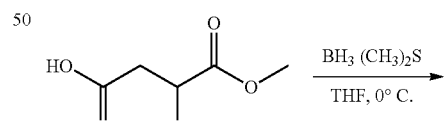

R-isomer

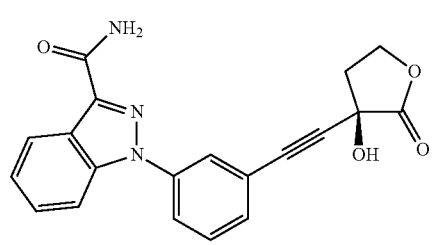

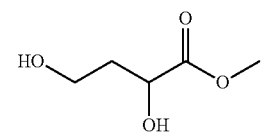

A solution of 3-hydroxy-4-methoxy-4-oxobutanoic acid (1.42 g, 9.59 mmol, 1.00 equiv) and BH$_3$-Me$_2$S (3.7 mL, 39.01 mmol, 4.10 equiv) in THF (15 mL) was stirred for 3 h at 0° C. The reaction was quenched by methanol and the resulting mixture was concentrated under vacuum. This resulted in the title compound (0.98 g, 76%) as colorless oil.

Step 3: Synthesis of

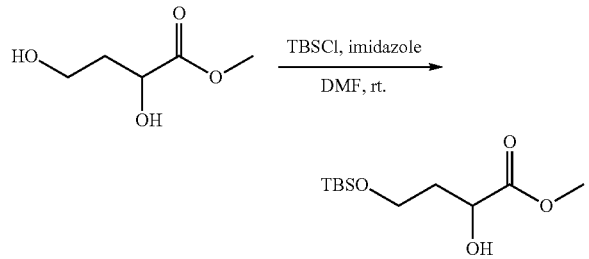

A solution of methyl 2,4-dihydroxybutanoate (2.4 g, 17.89 mmol, 1.00 equiv), tert-butyldimethylsilyl chloride (2.89 g, 19.17 mmol, 1.10 equiv) and imidazole (1.5 g, 22.03 mmol, 1.20 equiv) in DMF (15 mL) was stirred overnight at room temperature. The solution was quenched with water and extracted with ethyl acetate. The organic layers were combined, dried over anhydrous sodium sulfate, and concentrated under vacuum. The residue was purified by silica gel column chromatography eluting with ethyl acetate/petroleum ether (1:4) to give the title compound (2 g, 45%) as colorless oil.

Step 4: Synthesis of methyl 4-[(tert-butyldimethylsilyl)oxy]-2-oxobutanoate

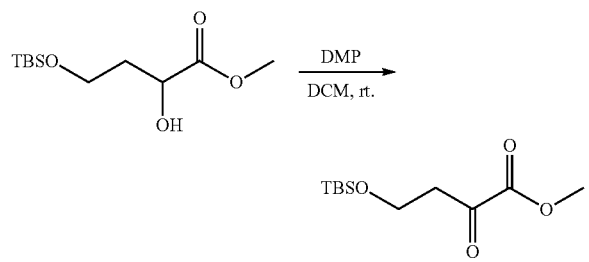

A solution of methyl 4-[(tert-butyldimethylsilyl)oxy]-2-hydroxybutanoate (2.0 g, 8.05 mmol, 1.00 equiv) and Dess-Martin periodinane (4.15 g, 9.79 mmol, 1.20 equiv) in dichloromethane (40 mL) was stirred for 3 h at room temperature. The solids were filtered out and the filtrate was concentrated under vacuum. The residue was purified by silica gel column chromatography eluting with ethyl acetate/petroleum ether (1:7) to give the title compound (1.2 g, 60%) as colorless oil. $^1$HNMR (300 MHz, CDCl$_3$) δ 3.99-3.95 (m, 2H), 3.86 (s, 3H), 3.06-3.02 (m, 2H), 0.86 (s, 9H), 0.05 (s, 6H).

Step 5: Synthesis of methyl 2-[2-[(tert-butyldimethylsilyl)oxy]ethyl]-2-hydroxybut-3-ynoate

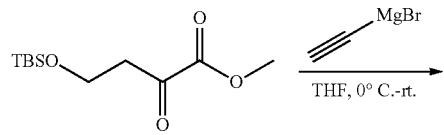

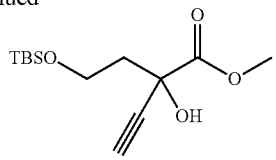

Bromo(ethynyl)magnesium (0.5M, 1.95 mL, 1.20 equiv) was added dropwise to a stirred solution of methyl 4-[(tert-butyldimethylsilyl)oxy]-2-oxobutanoate (200.00 mg, 0.81 mmol, 1.00 equiv) in THF (2.00 mL) under nitrogen. The resulting solution was stirred for 2 h at 0° C., quenched by saturation ammonium chloride solution, and extracted with ethyl acetate. The organic layers were combined, dried over anhydrous sodium sulfate, and concentrated under vacuum. The residue was purified by silica gel column chromatography eluting with ethyl acetate/petroleum ether to give the title compound (0.17 g, 77%) as a yellow oil.

Step 6: Synthesis of 3-ethynyl-3-hydroxyoxolan-2-one

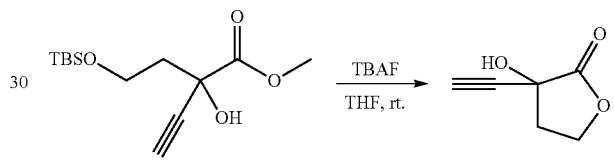

A solution of methyl 2-[2-[(tert-butyldimethylsilyl)oxy]ethyl]-2-hydroxybut-3-ynoate (1.0 g, 3.67 mmol, 1.00 equiv) and tetrabutylammonium fluoride (1.93 g, 7.38 mmol, 2.00 equiv) in THF (30 mL) was stirred for 2 h at room temperature. The reaction mixture was diluted with ethyl acetate and washed with brine. The organic layers were combined, dried over anhydrous sodium sulfate, and concentrated under vacuum. The residue was purified by silica gel column chromatography eluting with ethyl acetate/petroleum ether (1:2). This resulted in to the title compound (146 mg, 32%) as a yellow oil. $^1$HNMR (300 MHz, CDCl$_3$) δ 4.49-4.30 (m, 2H), 3.41 (s, 1H), 2.73-2.67 (m, 2H), 2.60-2.50 (m, 1H).

Step 7: Synthesis of (R)-1-(3-((3-hydroxy-2-oxo-tetrahydrofuran-3-yl)ethynyl)phenyl)-1H-indazole-3-carboxamide and (S)-1-(3-((3-hydroxy-2-oxo-tetrahydrofuran-3-yl)ethynyl)phenyl)-1H-indazole-3-carboxamide

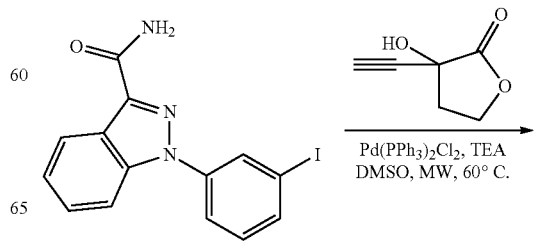

-continued

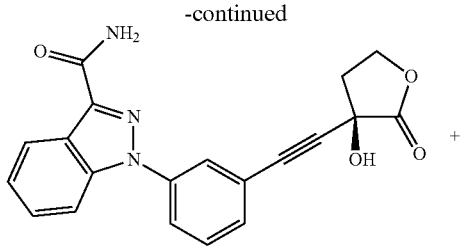

R-isomer

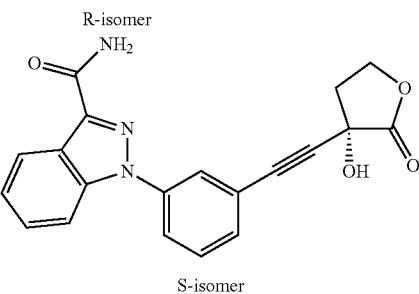

S-isomer

Similar to as described in General Procedure G, 1-(3-iodophenyl)-1H-indazole-3-carboxamide was reacted with 3-ethynyl-3-hydroxyoxolan-2-one to give the title compounds as a R/S mixture. After chiral separation 26.2 mg (14%) of the R-isomer (off-white solid) and 28.1 mg (15%) of the S-isomer (off-white solid) were isolated. The R-isomer: $t_R$=6.79 min (Lux 3u Cellulose-2, 0.46*10 cm, Hex:IPA=55:45, 1.0 ml/min); The S-isomer: $t_R$=9.26 min (Lux 3u Cellulose-2, 0.46*10 cm, Hex:IPA=55:45, 1.0 ml/min). Both isomers showed identical LC-MS and $^1$H NMR as shown below. LC-MS (ES, m/z): 362 [M+H]$^+$. $^1$HNMR (400 MHz, CDCl$_3$) δ 8.45 (m, 1H), 7.79 (s, 1H), 7.75-7.72 (m, 1H), 7.68-7.66 (m, 1H), 7.55-7.45 (s, 3H), 7.38-7.34 (t, 1H), 7.01-6.99 (m, 1H), 5.71 (s, 1H), 4.55-4.43 (m, 2H), 2.84-2.78 (m, 1H), 2.70-2.63 (m, 1H).

Example Q8

Synthesis of (R)-1-(3-((3-hydroxy-1-methyl-2-oxopyrrolidin-3-yl)ethynyl)phenyl)-5-methoxy-1H-pyrazolo[3,4-c]pyridazine-3-carboxamide

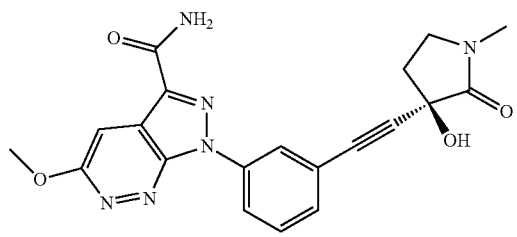

Step 1: Synthesis of 5-chloro-3-iodo-1H-pyrazolo[3,4-c]pyridazine

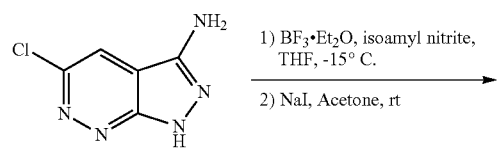

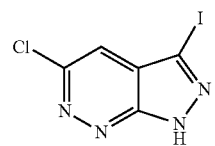

Boron trifluoride etherate (2.5 mL, 19.73 mmol, 2.00 equiv) was added dropwise to a stirred solution of 5-chloro-1H-pyrazolo[3,4-c]pyridazin-3-amine (1.7 g, 10.03 mmol, 1.00 equiv) in THF (20 mL) at 0° C. After cooling to −15° C. 3-methylbutyl nitrite (1.4 g, 11.95 mmol, 1.20 equiv) was added dropwise to the reaction mixture. The resulting mixture was stirred for 30 min at −15° C., diluted with cold diethyl ether (20 mL), and the solids were collected by filtration. The solid (a diazonium salt) was then added in portions to a cold solution of sodium iodide (1.8 g, 12.01 mmol, 1.20 equiv) in acetone (20 mL) at 0° C. The resulting solution was allowed to react for an additional 1 hour at room temperature. The solution was concentrated under vacuum and the residue was purified by silica gel column chromatography eluting with dichloromethane/methanol (20:1). This resulted in the title compound (1.3 g, 46%) as a light yellow solid. LC-MS (ES, m/z): 281 [M+H]$^+$.

Step 2: Synthesis of ethyl 5-chloro-1H-pyrazolo[3,4-c]pyridazine-3-carboxylate

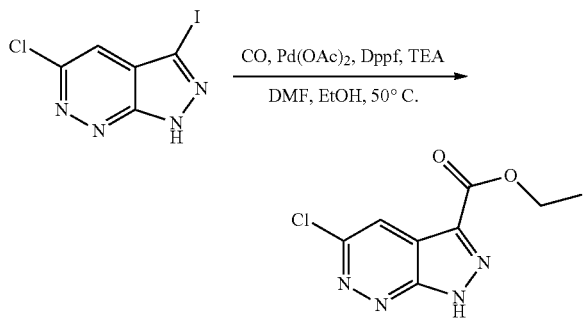

Similar to as described in General Procedure O, 5-chloro-3-iodo-1H-pyrazolo[3,4-c]pyridazine was reacted with carbon monoxide to give the title compound (450 mg, 40%) as an off-white solid. LC-MS (ES, m/z): 227 [M+H]$^+$.

Step 3: Synthesis of ethyl 1-(3-bromophenyl)-5-chloro-1H-pyrazolo[3,4-c]pyridazine-3-carboxylate

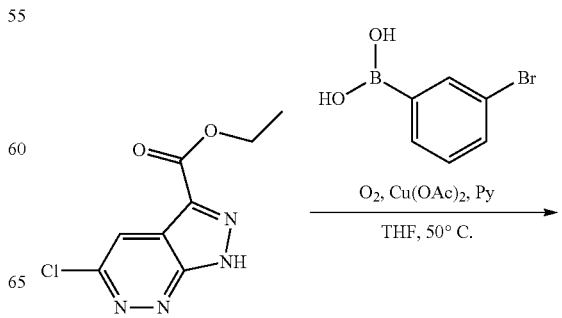

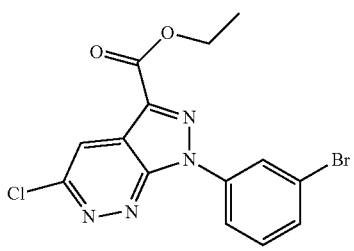

Similar to as described in General Procedure C, 5-chloro-1H-pyrazolo[3,4-c]pyridazine-3-carboxylate was reacted with 3-bromophenylboronic acid to give the title compound (67 mg, 40%) as a yellow solid. LC-MS (ES, m/z): 381, 383 [M+H]$^+$.

Step 4: Synthesis of 1-(3-bromophenyl)-5-chloro-1H-pyrazolo[3,4-c]pyridazine-3-carboxamide

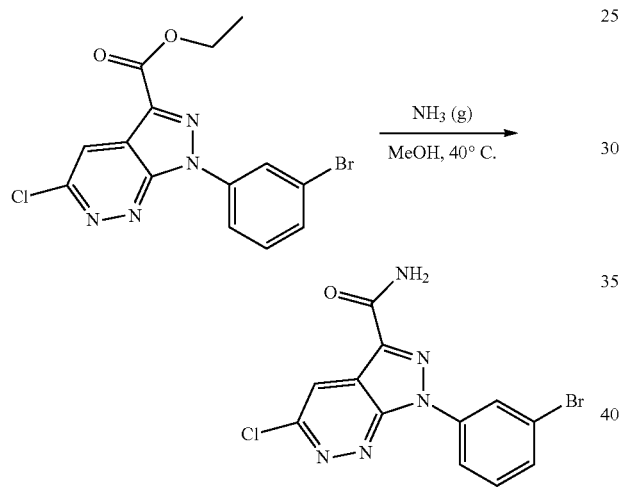

Similar to as described in General Procedure S, methyl 1-(3-bromophenyl)-5-chloro-1H-pyrazolo[3,4-c]pyridazine-3-carboxylate was reacted with ammonia to give the title compound (280 mg, 97%) as a light yellow solid. LC-MS (ES, m/z): 352, 354 [M+H]$^+$.

Step 5: Synthesis of 1-(3-bromophenyl)-5-methoxy-1H-pyrazolo[3,4-c]pyridazine-3-carboxamide

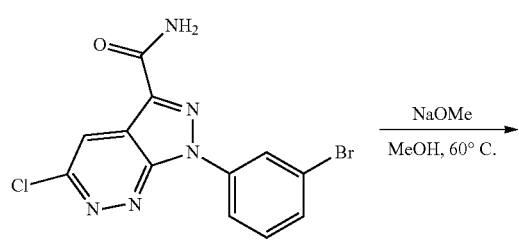

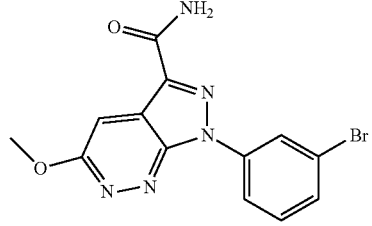

Similar to as described in General Procedure A, methyl 1-(3-bromophenyl)-5-methoxy-1H-pyrazolo[3,4-c]pyridazine-3-carboxylate was reacted with sodium methylate to give the title compound (100 mg) as a light yellow solid. LC-MS (ES, m/z): 348, 350 [M+H]$^+$.

Step 6: Synthesis of 1-(3-[2-[(3R)-3-hydroxy-1-methyl-2-oxopyrrolidin-3-yl]ethynyl]phenyl)-5-methoxy-1H-pyrazolo[3,4-c]pyridazine-3-carboxamide

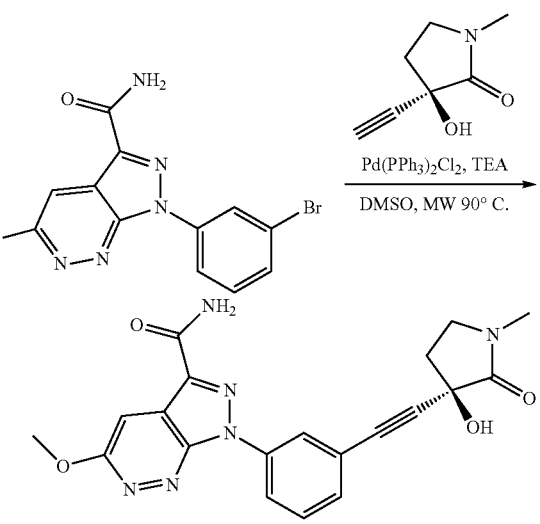

Similar to as described in General Procedure G, 1-(3-bromophenyl)-5-methoxy-1H-pyrazolo[3,4-c]pyridazine-3-carboxamide was reacted with (R)-3-ethynyl-3-hydroxy-1-methylpyrrolidin-2-one to give the title compound (15.0 mg, 16%) as a light yellow solid. LC-MS (ES, m/z): 407 [M+H]$^+$. $^1$HNMR (300 MHz, CD$_3$OD) δ 8.60 (d, J=1.8 Hz, 1H), 8.47 (m, 1H), 7.86 (s, 1H), 7.61-7.56 (m, 1H), 7.50-7.48 (m, 1H), 4.22 (s, 3H), 3.52-3.45 (m, 2H), 2.94 (s, 3H), 2.65-2.57 (m, 1H), 2.37-2.28 (m, 1H).

Example R8

Synthesis of 1-(3-[2-[(3R)-3-hydroxy-1-methyl-2-oxopyrrolidin-3-yl]ethynyl]phenyl)-1H-pyrazolo[3,4-c]pyridazine-3-carboxamide

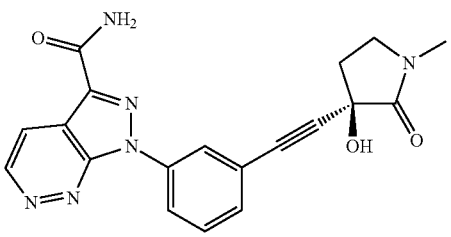 [SMILES: CN1CC[C@@](O)(C#Cc2cccc(-n3nc(C(N)=O)c4ccnnc43)c2)C1=O]

Step 1: Synthesis of 3,6-dichloropyridazine-4-carboxamide

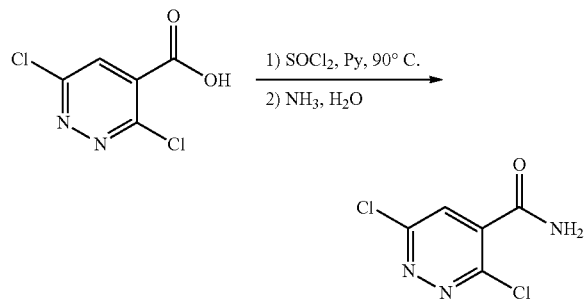

A solution of 3,6-dichloropyridazine-4-carboxylic acid (5.0 g, 0.026 mol) in thionyl chloride (30 mL) was stirred at room temperature. After 5 min a few drops of dry pyridine were added and the resulting mixture was stirring for 1 h at room temperature. The reaction was concentrated under vacuum and the crude intermediate was dissolved in 20 mL of dichloromethane and then a solution of ammonium hydroxide at 0° C. was added. The resulting solution was stirred for 30 min at 0° C. and concentrated under vacuum. The solid was collected by filtration to give the title compound (3.5 g, 77%) as an off-white solid. LC-MS (ES, m/z): 192 [M+H]$^+$.

Step 2: Synthesis of 3,6-dichloropyridazine-4-carbonitrile

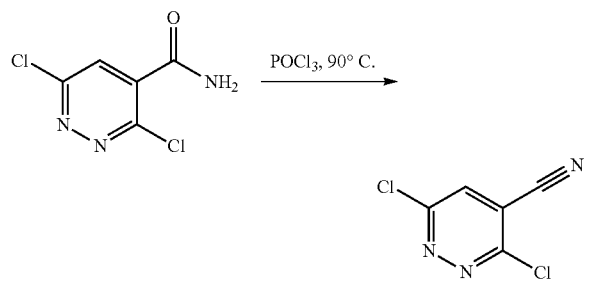

A mixture of 3,6-dichloropyridazine-4-carboxamide (5.7 g, 29.69 mmol, 1.00 equiv) and phosphorus oxychloride (50 mL) was heated to reflux for 1 hour. The resulting mixture was concentrated under vacuum and the residue was dissolved in dichloromethane. The resulting solution was washed with water and brine, dried over anhydrous sodium sulfate, and concentrated under vacuum. The residue was purified by silica gel column chromatography eluting with ethyl acetate/petroleum ether (1:5). This resulted in the title compound (5.1 g, 99%) as a light yellow solid.

Step 3: Synthesis of 5-chloro-1H-pyrazolo[3,4-c]pyridazin-3-amine

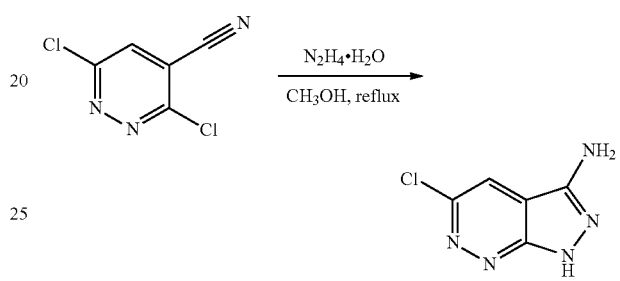

To a stirred solution of 3,6-dichloropyridazine-4-carbonitrile (2.00 g, 11.50 mmol, 1.00 equiv) in methanol (20 mL) was added hydrazine hydrate (1.15 g, 22.97 mmol, 2.00 equiv) dropwise at room temperature. The resulting solution was heated at 60° C. for 1 hour. After completion the mixture was concentrated under vacuum and the residue was diluted with ethyl acetate. The precipitates were collected by filtration to give the title compound (1.8 g, 92%) as a light yellow solid. LC-MS (ES, m/z): 170 [M+H]$^+$.

Step 4: Synthesis of 1H-pyrazolo[3,4-c]pyridazin-3-amine

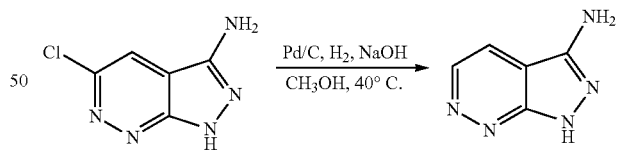

A solution of 5-chloro-1H-pyrazolo[3,4-c]pyridazin-3-amine (1.7 g, 10.03 mmol, 1.00 equiv), sodium hydroxide (0.8 g, 20.06 mmol, 2 equiv), palladium on carbon (1.0 g, 9.40 mmol, 0.90 equiv) in methanol (100 mL) was stirred for 1 h at 50° C. After completion the precipitates were filtered out and the filtrate was concentrated under vacuum. The residue was purified by silica gel column chromatography eluting with dichloromethane/methanol (10:1) to give the title compound (850 mg, 63%) as a yellow solid. LC-MS (ES, m/z): 136 [M+H]$^+$.

Step 5: Synthesis of 3-iodo-1H-pyrazolo[3,4-c]pyridazine

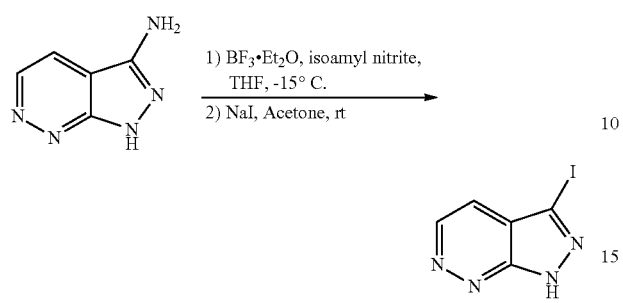

Boron trifluoride etherate (1.79 g, 12.58 mmol, 2.00 equiv) was added dropwise to a solution of 1H-pyrazolo[3,4-c]pyridazin-3-amine (850.00 mg, 6.29 mmol, 1.00 equiv) THF (10 mL) at 0° C. under nitrogen. After cooling to −15° C., 3-methylbutyl nitrite (884.28 mg, 7.55 mmol, 1.20 equiv) was added dropwise into the reaction mixture. The resulting mixture was stirred for 30 min at −15° C. and diluted with cold diethyl ether (20 mL). The resulting solids were collected by filtration to afford a diazonium salt, which was added in portions to a cold solution of sodium iodide (1.13 g, 7.55 mmol, 1.20 equiv) in acetone (10 mL) at 0° C. The resulting solution was allowed to react for an additional 1 hour at room temperature. The solution was then concentrated under vacuum and the residue was purified by silica gel column chromatography eluting with dichloromethane/methanol (20:1). This resulted in the title compound (900 mg) as an off-white solid. LC-MS (ES, m/z): 247 [M+H]+.

Step 6: Synthesis of 1H-pyrazolo[3,4-c]pyridazine-3-carboxylate

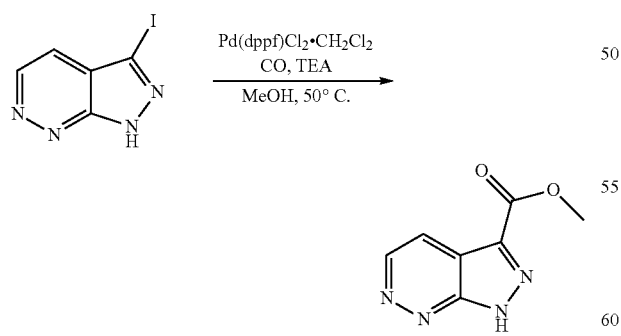

Similar to as described in General Procedure O, 3-iodo-1H-pyrazolo[3,4-c]pyridazine was reacted with carbon monoxide to give the title compound (400 mg, 69%) as an off-white solid. LC-MS (ES, m/z): 179 [M+H]+.

Step 7: Synthesis of 1-(3-iodophenyl)-1H-pyrazolo[3,4-c]pyridazine-3-carboxylate

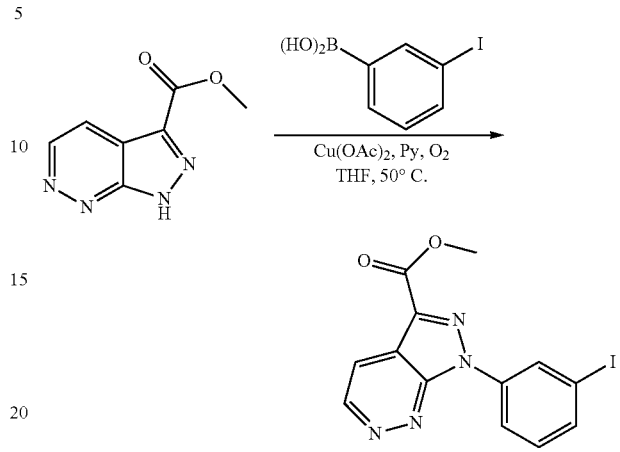

Similar to as described in General Procedure C, methyl 1H-pyrazolo[3,4-c]pyridazine-3-carboxylate was reacted with (3-iodophenyl)boronic acid to give the title compound (100 mg, 22%) as an off-white solid. LC-MS (ES, m/z): 381 [M+H]+.

Step 8: Synthesis of methyl 1-(3-[2-[(3R)-3-hydroxy-1-methyl-2-oxopyrrolidin-3-yl]ethynyl]phenyl)-1H-pyrazolo[3,4-c]pyridazine-3-carboxylate

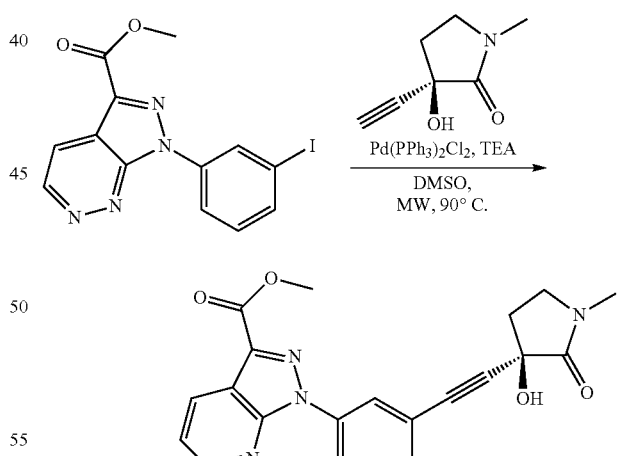

Similar to as described in General Procedure G, methyl 1-(3-iodophenyl)-1H-pyrazolo[3,4-c]pyridazine-3-carboxylate was reacted with (R)-3-ethynyl-3-hydroxy-1-methyl-pyrrolidin-2-one to give the title compound (50 mg, 49%) as a brown solid. LC-MS (ES, m/z): 392 [M+H]+.

Step 9: Synthesis of 1-(3-[2-[(3R)-3-hydroxy-1-methyl-2-oxopyrrolidin-3-yl]ethynyl]phenyl)-1H-pyrazolo[3,4-c]pyridazine-3-carboxamide

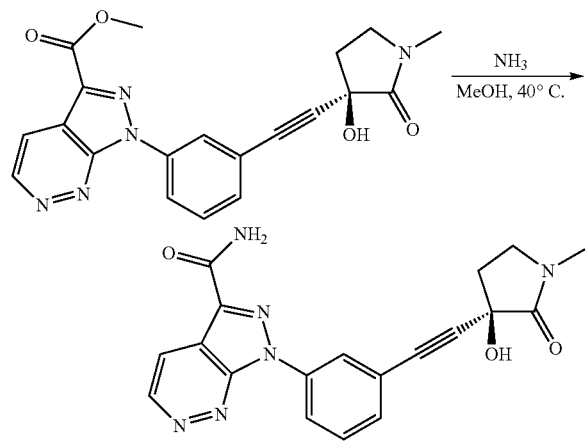

Similar to as described in General Procedure S, methyl 1-(3-[2-[(3R)-3-hydroxy-1-methyl-2-oxopyrrolidin-3-yl]ethynyl]phenyl)-1H-pyrazolo[3,4-c]pyridazine-3-carboxylate was reacted with ammonia to give the title compound (10.4 mg, 22%) as a white solid. LC-MS (ES, m/z): 377 [M+H]$^+$. $^1$HNMR (300 MHz, CD$_3$OD) δ 9.35 (d, J=5.4 Hz, 1H), 8.63 (s, 1H), 8.62 (d, J=1.5 Hz, 1H), 8.58-8.56 (m, 1H), 7.63-7.56 (m, 2H), 3.53-3.48 (m, 2H), 2.95 (s, 3H), 2.69-2.61 (m, 1H), 2.39-2.32 (m, 1H).

Example S8

Synthesis of Compound 177: (R)-1-(3-((3-hydroxy-1-methyl-2-oxopyrrolidin-3-yl)ethynyl)phenyl)-5,6,7,8-tetrahydroimidazo[1,5-a]pyridine-3-carboxamide

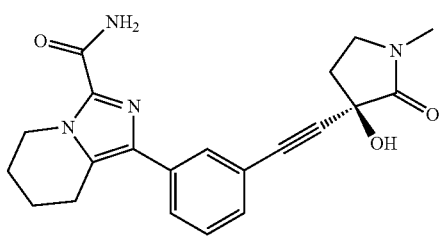 [SMILES: CN1CC[C@@](O)(C#Cc2cccc(-c3nc(C(N)=O)n4c3CCCC4)c2)C1=O]

Step 1: Synthesis of ethyl 2-oxo-2-(pyridin-2-ylmethylamino)acetate

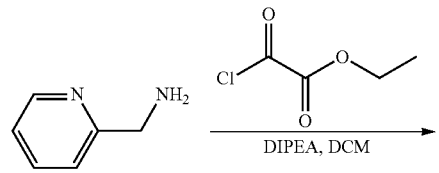

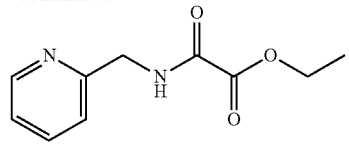

To a solution of pyridin-2-ylmethanamine (1.00 g, 9.25 mmol, 1.00 equiv) and N,N-diisopropylethylamine (2.39 g, 18.49 mmol, 2.00 equiv) in dichloromethane (20 mL) was added ethyl 2-chloro-2-oxoacetate (1.26 g, 9.23 mmol, 1.00 equiv). The resulting solution was stirred for 1.5 h at room temperature. After completion the mixture was concentrated under vacuum and the residue was purified by silica gel column chromatography eluting with ethyl acetate/petroleum ether (1:1). This resulted in 1.2 g (62%) of the title compound as a yellow solid. LC-MS (ES, m/z): 209 [M+H]$^+$.

Step 2: Synthesis of ethyl imidazo[1,5-a]pyridine-3-carboxylate

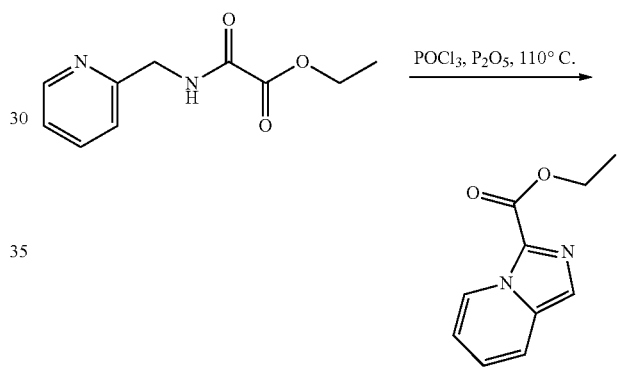

A solution of ethyl [(pyridin-2-ylmethyl)carbamoyl]formate (1.00 g, 4.80 mmol, 1.00 equiv) and phosphorus pentoxide (3.41 g, 24.02 mmol, 5.00 equiv) in phosphorus oxychloride (30 mL) was stirred for 5 h at 110° C. The resulting mixture was concentrated under vacuum. The residue was purified by silica gel column chromatography eluting with ethyl acetate/petroleum ether (1:1). This resulted in 635 mg (70%) of the title compound as a yellow solid. LC-MS (ES, m/z): 191 [M+H]$^+$.

Step 3: Synthesis of ethyl 5H,6H,7H,8H-imidazo[1,5-a]pyridine-3-carboxylate

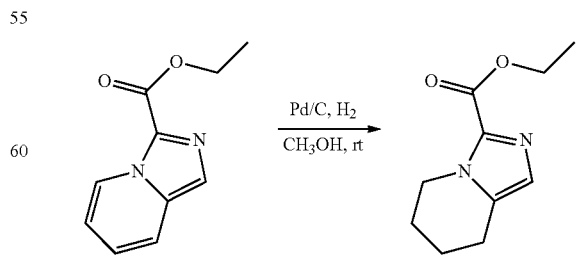

Under hydrogen a solution of ethyl imidazo[1,5-a]pyridine-3-carboxylate (300 mg, 1.58 mmol, 1.00 equiv) and Pd/C (10 wt %, 30 mg) in methanol (20 mL) was stirred for 30 h at room temperature. After filtration the filtrate was collected and concentrated under vacuum. This resulted in 325 mg of the title compound (crude) as a white solid. LC-MS (ES, m/z): 195 [M+H]$^+$.

Step 4: Synthesis of ethyl 1-bromo-5H,6H,7H,8H-imidazo[1,5-a]pyridine-3-carboxylate

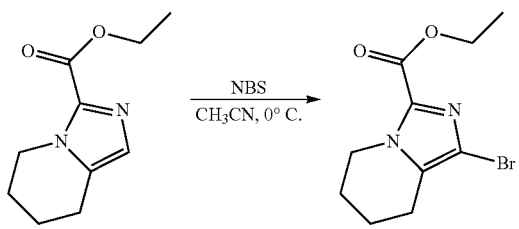

A solution of ethyl 5H,6H,7H,8H-imidazo[1,5-a]pyridine-3-carboxylate (300 mg, 1.54 mmol, 1.00 equiv) and NBS (330 mg, 1.85 mmol, 1.20 equiv) in acetonitrile (20 mL) was stirred for 3 h at 0° C. The resulting mixture was concentrated under vacuum. The residue was purified by silica gel column chromatography eluting with ethyl acetate/petroleum ether (1:2). This resulted in 100 mg (24%) of the title compound as a white solid. LC-MS (ES, m/z): 273 [M+H]$^+$.

Step 5: Synthesis of ethyl 1-(3-[2-[(3R)-3-hydroxy-1-methyl-2-oxopyrrolidin-3-yl]ethynyl]phenyl)-5H,6H,7H,8H-imidazo[1,5-a]pyridine-3-carboxylate

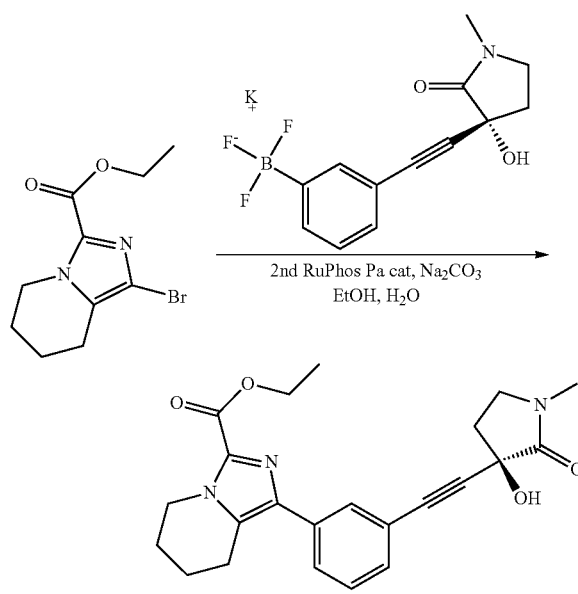

A solution of ethyl 1-bromo-5H,6H,7H,8H-imidazo[1,5-a]pyridine-3-carboxylate (70.0 mg, 0.26 mmol, 1.00 equiv), RuPhos-PdCl-2nd G (39.9 mg, 0.05 mmol, 0.20 equiv), potassium (R)-trifluoro(3-((3-hydroxy-1-methyl-2-oxopyrrolidin-3-yl)ethynyl)phenyl)borate (98.77 mg, 0.31 mmol, 1.20 equiv) and sodium carbonate (54.3 mg, 0.51 mmol, 2.00 equiv) in ethanol (8.0 mL) and water (0.50 mL) was stirred for 3 h at 80° C. under nitrogen. After completion the resulting mixture was concentrated under vacuum. The residue was purified by silica gel column chromatography eluting with dichloromethane/methanol (10:1). This resulted in 80 mg (77%) of the title compound as a red solid. LC-MS (ES, m/z): 408 [M+H]$^+$.

Step 6: Synthesis of (R)-1-(3-((3-hydroxy-1-methyl-2-oxopyrrolidin-3-yl)ethynyl)phenyl)-5,6,7,8-tetrahydroimidazo[1,5-a]pyridine-3-carboxamide

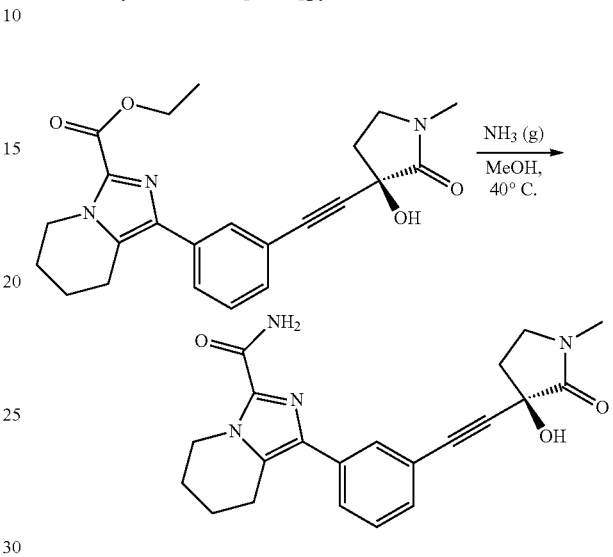

Similar to as described in General Procedure S, ethyl 1-(3-[2-[(3R)-3-hydroxy-1-methyl-2-oxopyrrolidin-3-yl]ethynyl]phenyl)-5H,6H,7H,8H-imidazo[1,5-a]pyridine-3-carboxylate was reacted with ammonia to give the title compound (16.9 mg, 26%) as a white solid. LC-MS (ES, m/z): 379 [M+H]$^+$. $^1$H NMR (300 MHz, CDCl$_3$, ppm) δ 7.83 (s, 1H), 7.73-7.71 (m, 1H), 7.45-7.37 (m, 2H), 4.52-4.48 (m, 2H), 3.52-3.47 (m, 2H), 3.17-3.03 (m, 2H), 2.96 (s, 3H), 2.65-2.57 (m, 1H), 2.38-2.33 (m, 1H), 2.04-2.03 (m, 2H), 1.95-1.91 (m, 2H).

Aryl Substitution Reactions

In the Scheme below, Q, $A_1$-$A_8$ and $R^4$-$R^6$ are defined elsewhere in the application.

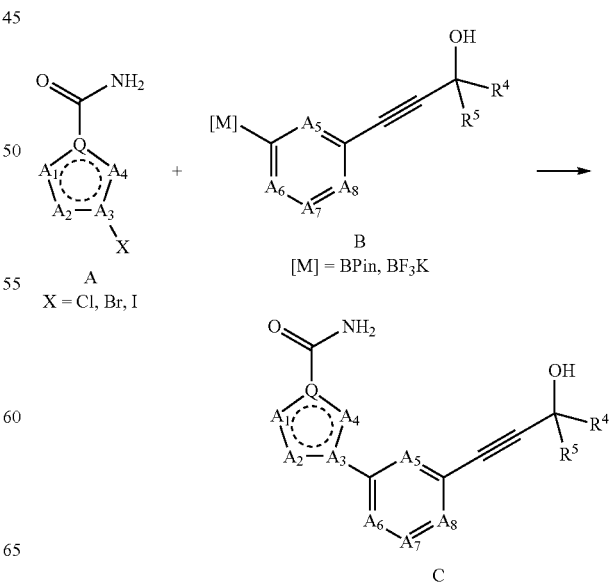

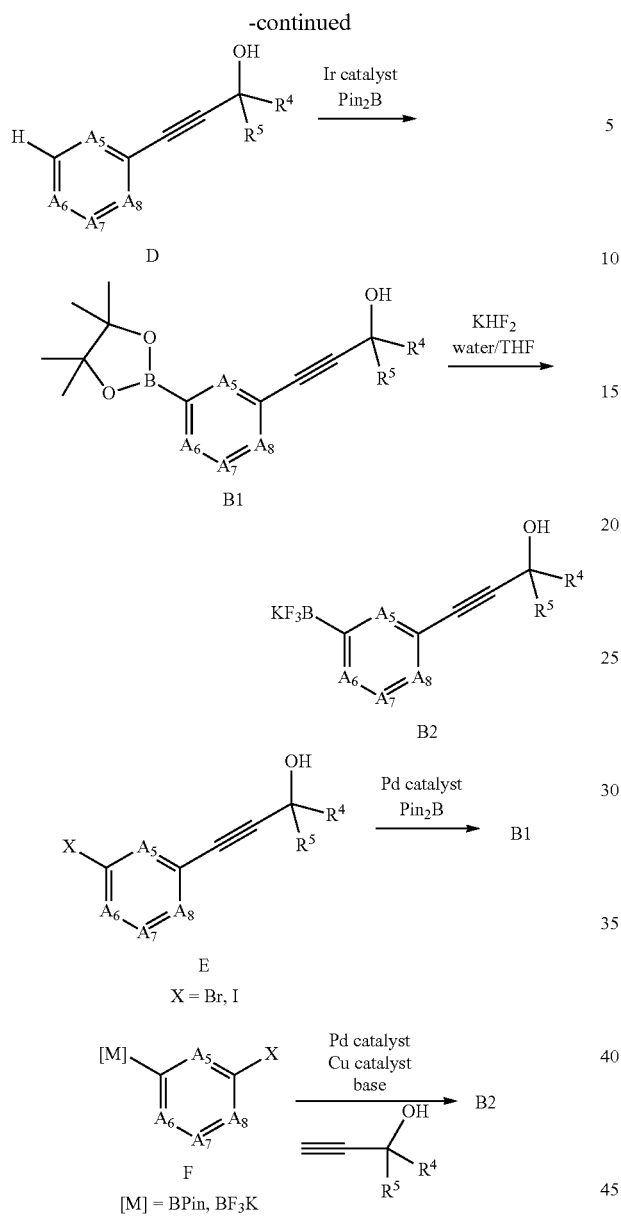

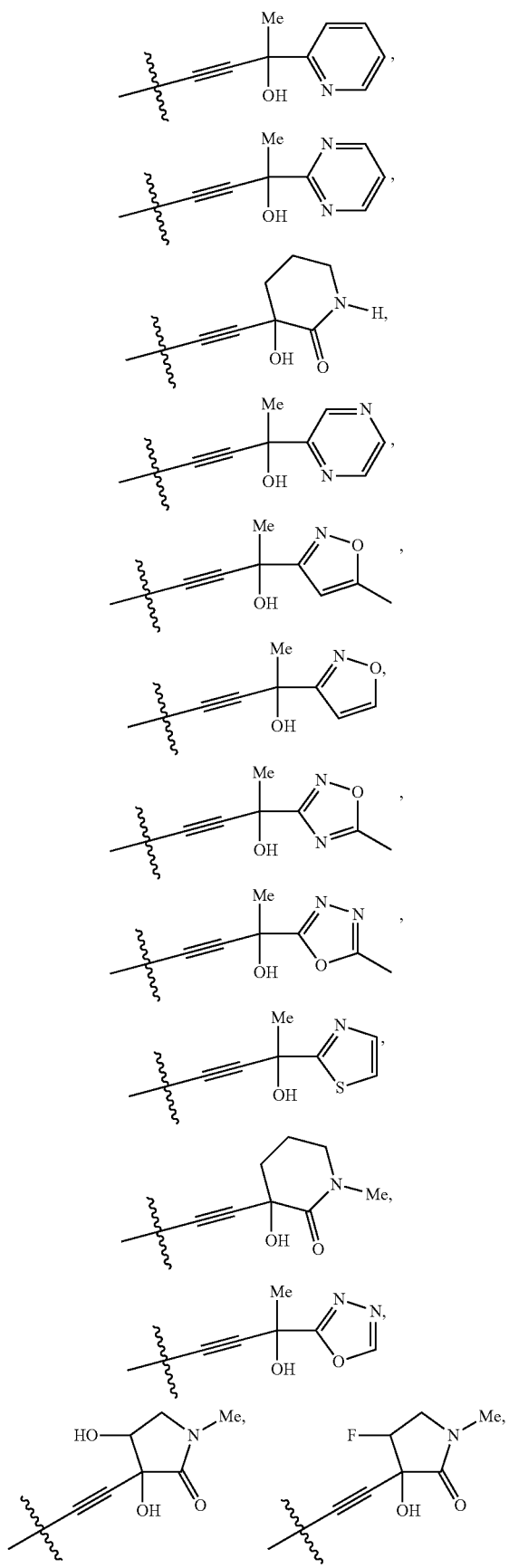

Compounds of type C can be prepared via Suzuki-type coupling of 3-alkynylaryl or heteroaryl boronic acids, esters (B1) or trifluoroborate salts (B2) to haloheterocycles A (Molander et al *Acc. Chem. Res.* 2007). Compounds of type B can be prepared by various routes including direct borylation of arenes containing sterically accessible C—H bonds (D) (Hartwig, J. F. et al. *Chem. Rev.* 2010) or Sonogashira coupling to aryl or heteroarylboronic esters or trifluoroborates (F).

Preparation of Moieties Adjacent to the Alkynyl Portion

Moieties such as those shown below may be prepared as described in U.S. patent application Ser. No. 13/768,873, filed Feb. 15, 2013, and entitled "Tricyclic Compounds and Methods of Use Therefor," which is incorporated herein by reference.

-continued

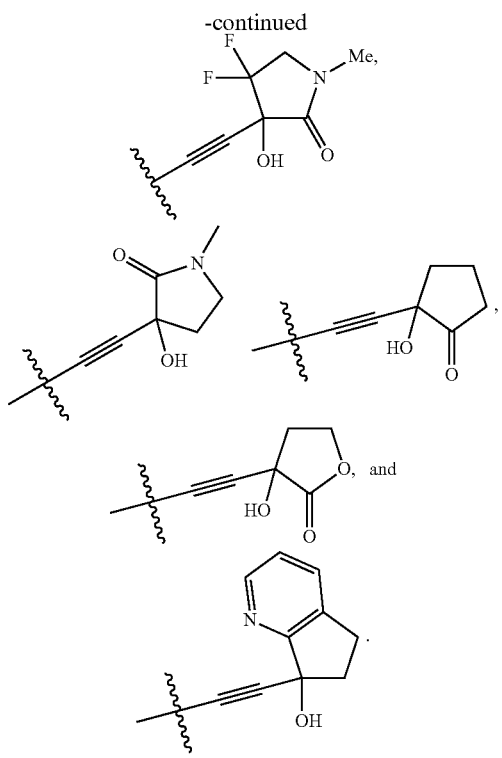

Optional methods for accessing these types of moieties are also described below.

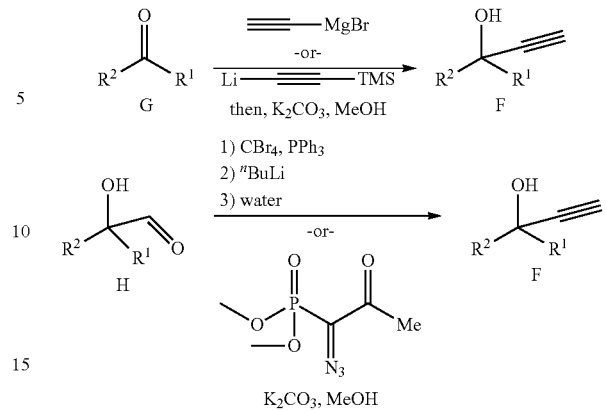

Terminal alkynes (F) for use in Sonogashira coupling reactions to haloarenes can be generated by a number of methods including those described in the above scheme. Addition of ethynylmagnesium bromide to substituted ketones (G) or addition of lithium trimethylsilylacetylide followed by proteolytic removal of the trimethylsilyl group will generate substituted propargyl alcohols. Alternatively, aldehydes (H) can be converted to terminal alkynes via a Corey-Fuchs process (steps 1-3 Corey *Tetrahedron Lett.* 1972) or via conditions for the Bestmann-Ohira modification of the Gilbert-Seyferth process (Bestmann *Synthesis*, 2004).

The following compounds were prepared using methodologies similar to those presented above:

| Ex. | Structure | Name | LCMS M + H |
|---|---|---|---|
| 175 | 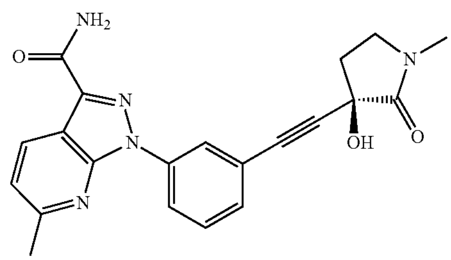 [SMILES: Cc1ccc2c(C(N)=O)nn(-c3cccc(C#C[C@]4(O)CCN(C)C4=O)c3)c2n1] | 1-[3-[2-[(3R)-3-hydroxy-1-methyl-2-oxo-pyrrolidin-3-yl]ethynyl]phenyl]-6-methyl-pyrazolo[3,4-b]pyridine-3-carboxamide | 390.10 |
| 176 | 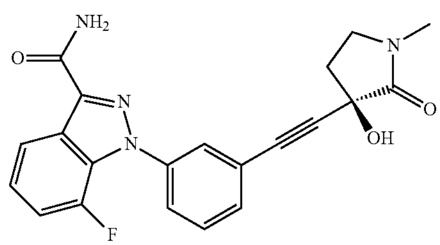 [SMILES: CN1CC[C@@](O)(C#Cc2cccc(-n3nc(C(N)=O)c4cccc(F)c43)c2)C1=O] | 7-fluoro-1-[3-[2-[(3R)-3-hydroxy-1-methyl-2-oxo-pyrrolidin-3-yl]ethynyl]phenyl]indazole-3-carboxamide | 393.1 |
| 177 | 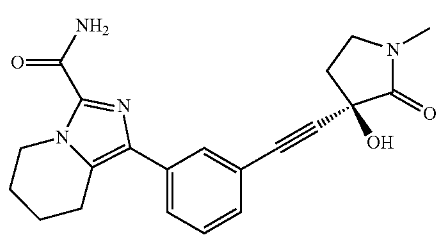 [SMILES: CN1CC[C@@](O)(C#Cc2cccc(-c3nc(C(N)=O)n4c3CCCC4)c2)C1=O] | 1-[3-[2-[(3R)-3-hydroxy-1-methyl-2-oxo-pyrrolidin-3-yl]ethynyl]phenyl]-5,6,7,8-tetrahydroimidazo[1,5-a]pyridine-3-carboxamide | 379.0 |

| Ex. | Structure | Name | LCMS M + H |
|---|---|---|---|
| 178 | 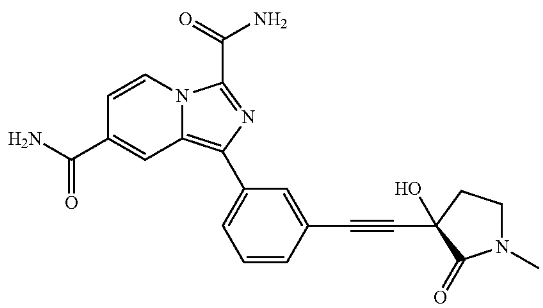 [SMILES: CN1CC[C@@](O)(C#Cc2cccc(-c3nc(C(N)=O)n4ccc(C(N)=O)cc34)c2)C1=O] | 1-[3-[2-[(3R)-3-hydroxy-1-methyl-2-oxo-pyrrolidin-3-yl]ethynyl]phenyl]imidazo[1,5-a]pyridine-3,7-dicarboxamide | 418.15 |
| 179 | 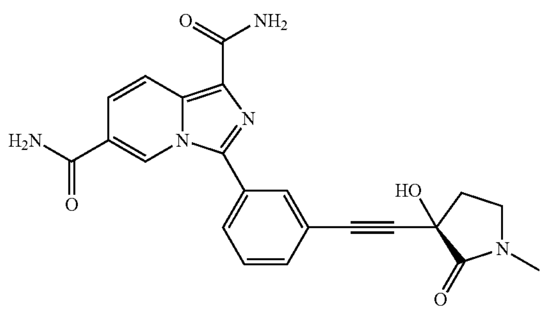 [SMILES: CN1CC[C@@](O)(C#Cc2cccc(-c3nc(C(N)=O)c4ccc(C(N)=O)cn34)c2)C1=O] | 3-[3-[2-[(3R)-3-hydroxy-1-methyl-2-oxo-pyrrolidin-3-yl]ethynyl]phenyl]imidazo[1,5-a]pyridine-1,6-dicarboxamide | 418.15 |
| 180 | 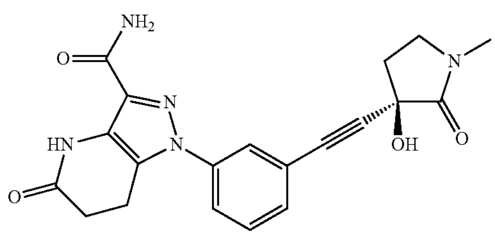 [SMILES: CN1CC[C@@](O)(C#Cc2cccc(-n3nc(C(N)=O)c4c3CCC(=O)N4)c2)C1=O] | 1-[3-[2-[(3R)-3-hydroxy-1-methyl-2-oxo-pyrrolidin-3-yl]ethynyl]phenyl]-5-oxo-6,7-dihydro-4H-pyrazolo[4,3-b]pyridine-3-carboxamide | 394.10 |
| 181 | 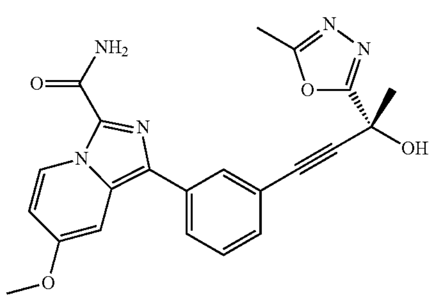 [SMILES: COc1ccn2c(C(N)=O)nc(-c3cccc(C#C[C@@](C)(O)c4nnc(C)o4)c3)c2c1] | 1-[3-[(3R)-3-hydroxy-3-(5-methyl-1,3,4-oxadiazol-2-yl)but-1-ynyl]phenyl]-7-methoxy-imidazo[1,5-a]pyridine-3-carboxamide | 418.1 |
| 182 | 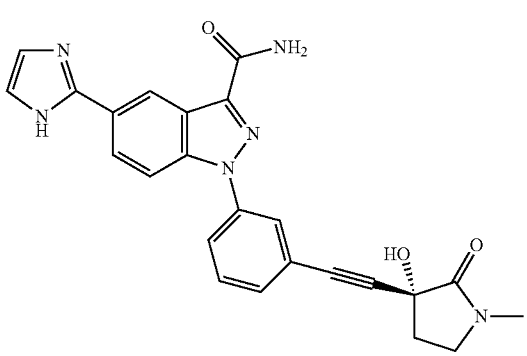 [SMILES: CN1CC[C@@](O)(C#Cc2cccc(-n3nc(C(N)=O)c4cc(-c5ncc[nH]5)ccc43)c2)C1=O] | 1-[3-[2-[(3R)-3-hydroxy-1-methyl-2-oxo-pyrrolidin-3-yl]ethynyl]phenyl]-5-(1H-imidazol-2-yl)indazole-3-carboxamide | 441.17 |

| Ex. | Structure | Name | LCMS M + H |
|---|---|---|---|
| 183 | 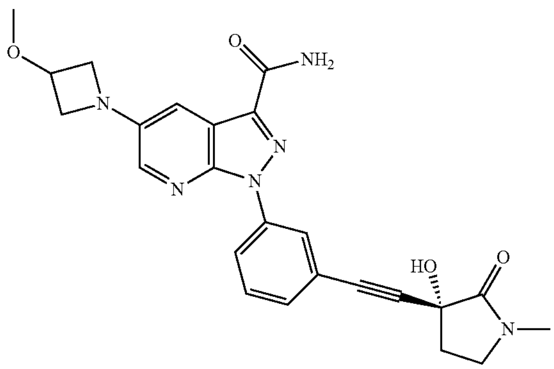 [SMILES: COC1CN(c2cnc3c(c2)c(C(N)=O)nn3-c2cccc(C#C[C@]3(O)CCN(C)C3=O)c2)C1] | 1-[3-[2-[(3R)-3-hydroxy-1-methyl-2-oxo-pyrrolidin-3-yl]ethynyl]phenyl]-5-(3-methoxyazetidin-1-yl)pyrazolo[3,4-b]pyridine-3-carboxamide | 461.19 |
| 184 | 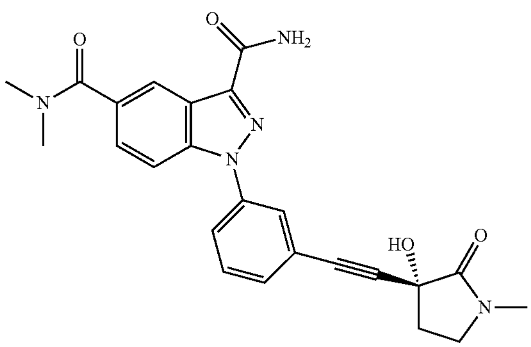 | 1-[3-[2-[(3R)-3-hydroxy-1-methyl-2-oxo-pyrrolidin-3-yl]ethynyl]phenyl]-N5,N5-dimethyl-indazole-3,5-dicarboxamide | 446.2 |
| 185 | 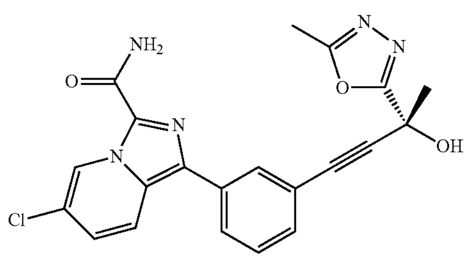 [SMILES: Cc1nnc([C@](C)(O)C#Cc2cccc(-c3nc(C(N)=O)n4cc(Cl)ccc34)c2)o1] | 6-chloro-1-[3-[(3R)-3-hydroxy-3-(5-methyl-1,3,4-oxadiazol-2-yl)but-1-ynyl]phenyl]imidazo[1,5-a]pyridine-3-carboxamide | 422.10 |
| 186 | 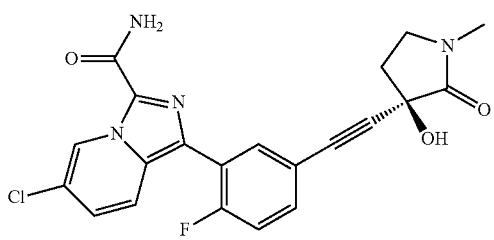 [SMILES: CN1CC[C@@](O)(C#Cc2ccc(F)c(-c3nc(C(N)=O)n4cc(Cl)ccc34)c2)C1=O] | 6-chloro-1-[2-fluoro-5-[2-[(3R)-3-hydroxy-1-methyl-2-oxo-pyrrolidin-3-yl]ethynyl]phenyl]imidazo[1,5-a]pyridine-3-carboxamide | 427.1 |
| 187 | 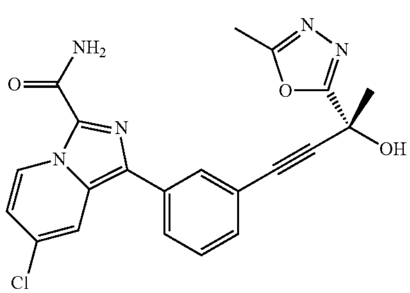 [SMILES: Cc1nnc([C@](C)(O)C#Cc2cccc(-c3nc(C(N)=O)n4ccc(Cl)cc34)c2)o1] | 7-chloro-1-[3-[(3R)-3-hydroxy-3-(5-methyl-1,3,4-oxadiazol-2-yl)but-1-ynyl]phenyl]imidazo[1,5-a]pyridine-3-carboxamide | 422.1 |

-continued

| Ex. | Structure | Name | LCMS M + H |
|---|---|---|---|
| 188 | 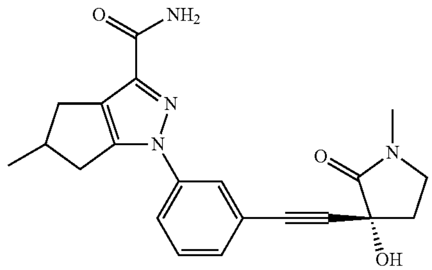 [SMILES: CC1Cc2c(C(N)=O)nn(-c3cccc(C#C[C@]4(O)CCN(C)C4=O)c3)c2C1] | 1-[3-[2-[(3R)-3-hydroxy-1-methyl-2-oxo-pyrrolidin-3-yl]ethynyl]phenyl]-5-methyl-5,6-dihydro-4H-cyclopenta[c]pyrazole-3-carboxamide | 379.2 |
| 189 | 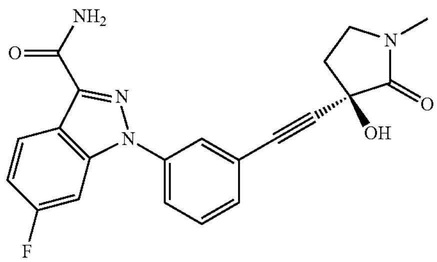 [SMILES: CN1CC[C@@](O)(C#Cc2cccc(-n3nc(C(N)=O)c4ccc(F)cc43)c2)C1=O] | 6-fluoro-1-[3-[2-[(3R)-3-hydroxy-1-methyl-2-oxo-pyrrolidin-3-yl]ethynyl]phenyl]indazole-3-carboxamide | 393.0 |
| 190 | 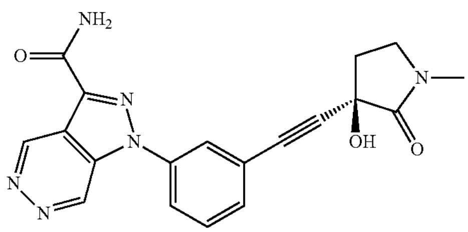 [SMILES: CN1CC[C@@](O)(C#Cc2cccc(-n3nc(C(N)=O)c4cnncc43)c2)C1=O] | 1-[3-[2-[(3R)-3-hydroxy-1-methyl-2-oxo-pyrrolidin-3-yl]ethynyl]phenyl]pyrazolo[3,4-d]pyridazine-3-carboxamide | 377.1 |
| 191 | 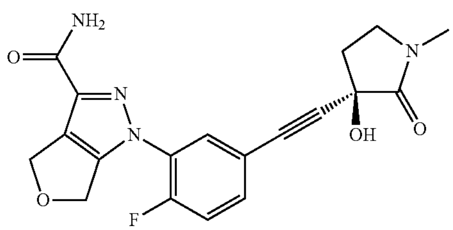 [SMILES: CN1CC[C@@](O)(C#Cc2ccc(F)c(-n3nc(C(N)=O)c4c3COC4)c2)C1=O] | 1-[2-fluoro-5-[2-[(3R)-3-hydroxy-1-methyl-2-oxo-pyrrolidin-3-yl]ethynyl]phenyl]-4,6-dihydrofuro[3,4-c]pyrazole-3-carboxamide | 385.10 |
| 192 | 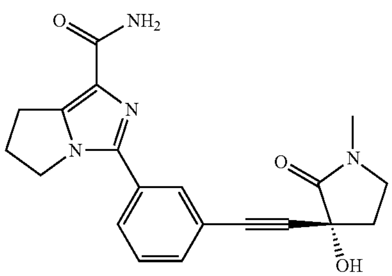 [SMILES: CN1CC[C@@](O)(C#Cc2cccc(-c3nc(C(N)=O)c4n3CCC4)c2)C1=O] | 3-[3-[2-[(3R)-3-hydroxy-1-methyl-2-oxo-pyrrolidin-3-yl]ethynyl]phenyl]-6,7-dihydro-5H-pyrrolo[1,2-c]imidazole-1-carboxamide | 365.0 |
| 193 | 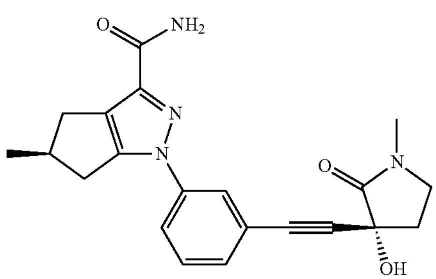 [SMILES: C[C@H]1Cc2c(C(N)=O)nn(-c3cccc(C#C[C@]4(O)CCN(C)C4=O)c3)c2C1] | (5S)-1-[3-[2-[(3R)-3-hydroxy-1-methyl-2-oxo-pyrrolidin-3-yl]ethynyl]phenyl]-5-methyl-5,6-dihydro-4H-cyclopenta[c]pyrazole-3-carboxamide | 379.18 |

-continued

| Ex. | Structure | Name | LCMS M + H |
|---|---|---|---|
| 194 | 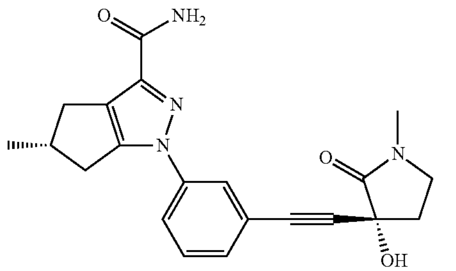 [SMILES: C[C@@H]1Cc2c(C(N)=O)nn(-c3cccc(C#C[C@]4(O)CCN(C)C4=O)c3)c2C1] | (5R)-1-[3-[2-[(3R)-3-hydroxy-1-methyl-2-oxo-pyrrolidin-3-yl]ethynyl]phenyl]-5-methyl-5,6-dihydro-4H-cyclopenta[c]pyrazole-3-carboxamide | 379.18 |
| 195 | 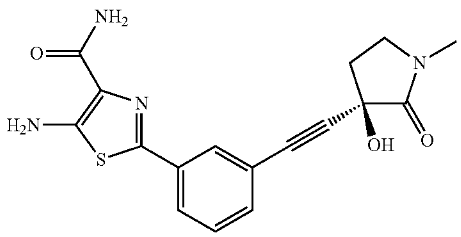 [SMILES: CN1CC[C@@](O)(C#Cc2cccc(-c3nc(C(N)=O)c(N)s3)c2)C1=O] | 5-amino-2-[3-[2-[(3R)-3-hydroxy-1-methyl-2-oxo-pyrrolidin-3-yl]ethynyl]phenyl]thiazole-4-carboxamide | 357.10 |
| 196 | 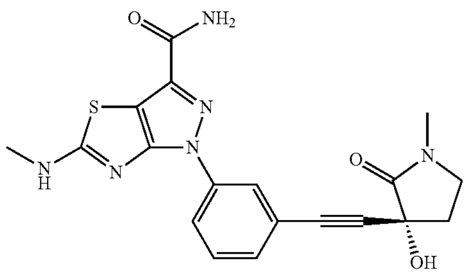 [SMILES: CNc1nc2c(s1)c(C(N)=O)nn2-c1cccc(C#C[C@]2(O)CCN(C)C2=O)c1] | 1-[3-[2-[(3R)-3-hydroxy-1-methyl-2-oxo-pyrrolidin-3-yl]ethynyl]phenyl]-5-(methylamino)pyrazolo[3,4-d]thiazole-3-carboxamide | 411.1 |
| 197 | 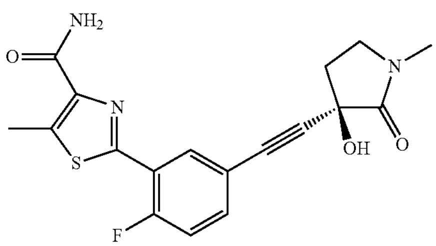 | 2-[2-fluoro-5-[2-[(3R)-3-hydroxy-1-methyl-2-oxo-pyrrolidin-3-yl]ethynyl]phenyl]-5-methyl-thiazole-4-carboxamide | 374.1 |
| 198 | 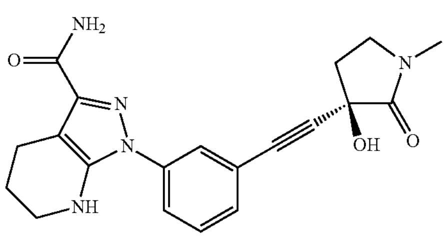 [SMILES: CN1CC[C@@](O)(C#Cc2cccc(-n3nc(C(N)=O)c4c3NCCC4)c2)C1=O] | 1-[3-[2-[(3R)-3-hydroxy-1-methyl-2-oxo-pyrrolidin-3-yl]ethynyl]phenyl]-4,5,6,7-tetrahydropyrazolo[3,4-b]pyridine-3-carboxamide | 380.1 |
| 199 | 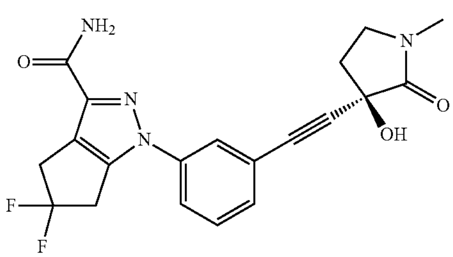 [SMILES: CN1CC[C@@](O)(C#Cc2cccc(-n3nc(C(N)=O)c4c3CC(F)(F)C4)c2)C1=O] | 5,5-difluoro-1-[3-[2-[(3R)-3-hydroxy-1-methyl-2-oxo-pyrrolidin-3-yl]ethynyl]phenyl]-4,6-dihydrocyclopenta[c]pyrazole-3-carboxamide | 401.10 |

NIK Enzyme Inhibition Assay:

The ability of the nuclear factor-kappa B (NF-kB)-inducing kinase (NIK) to catalyze the hydrolysis of adenosine-5'-triphosphate (ATP) was monitored using the Transcreener ADP (adenosine-5'-diphosphate) assay (BellBrook Labs). Purified NIK (0.5 nM) derived from a baculovirus-infected insect cell expression system was incubated with test compounds for 1-3.5 hours in 50 mM 2-[4-(2-hydroxyethyl) piperazin-1-yl]ethanesulfonic acid buffer (pH 7.2) containing 10 mM $MgCl_2$, 2 mM dithiothreitol, 10 μM ATP, 0.01% Triton X-100, 0.1% gamma-globulins from bovine blood, 1% dimethylsulfoxide (DMSO), 7 μg/mL ADP antibody and 5 nM ADP-MR121 633 tracer. Reactions were quenched by the addition of 20 mM 2,2',2'',2'''-(ethane-1,2-diyldinitrilo) tetraacetic acid and 0.01% Brij 35. The tracer bound to the antibody was displaced by the ADP generated during the NIK reaction, which causes a decrease in fluorescence polarization that was measured by laser excitation at 633 nm with a Fluorescence Correlation Spectroscopy Plus reader (Evotec AG). Equilibrium dissociation constant ($K_i$) values for NIK inhibitors are calculated from plots of activity vs. inhibitor concentration using Morrison's quadratic equation that accounts for the potential of tight binding, and by also applying the conversion factor that accounted for competitive inhibition and the concentration of substrate used in the assay relative to its Michaelis constant ($K_m$). The compounds in listed in Table 1 have the corresponding inhibitory value (NIK ADP-FP, $K_i$ in micromolar) for NIK described in Table 2 below.

Cellular Assay:

Several assays were developed to profile the cellular activities of NIK inhibitors.

(1) The first assay that can be used to profile whether a test compound can inhibit the NF-kB signal through NIK inhibition without affecting cell viability. In this assay, human embryonic kidney 293 cells are stably transfected with a tetracycline-inducible NIK DNA construct containing a cytomegalovirus promoter plus two reporter DNA constructs. One reporter encodes firefly luciferase under the control of three repeats of an NF-kB response element from the ELAM-1 gene and reflects the level of NIK activity in the cells, whereas the other reporter constitutively expresses Renilla luciferase under the control of the herpes simplex virus thymidine kinase promoter and serves as a general measure of cell viability. Cells are incubated with different concentrations of compounds (0.2% DMSO final) in medium containing 1 μg/mL doxycycline and 10% tet-system approved fetal bovine serum (Clontech) for 24 hours, after which the reporters' signals are detected using the Dual Glo luciferase detection system (Promega) according to the vendor's protocol.

(2) A second set of cell assay are used to define the selectivity of NIK inhibitors toward inhibition of classical vs. non-classical NF-kB signaling and rely on quantification of the nuclear translocation of p52 (NF-kB2) and REL-A (p65) using high content cellular imaging. For the p52 (non-classical NF-kB signaling) nuclear translocation assay, HeLa cells are treated with different concentrations of compounds (0.2% DMSO final) in medium containing 10% fetal bovine serum and then stimulated with 100 ng/mL of an anti-lymphotoxin beta receptor antibody (R&D Systems) for 5 hours. In the REL-A nuclear translocation assay, HeLa cells are incubated with compounds (0.2% DMSO final) for 4.5 hours in medium containing 10% fetal bovine serum before stimulating them with 10 ng/mL tumor necrosis factor (TNF)-α (R&D Systems) for 30 minutes. Cells are fixed with 4% paraformaldehyde, permeabilized by adding 0.1% Triton X-100 in phosphate buffered saline, and then are incubated with either 2 ug/mL anti-p52 antibody (Millipore) or 400 ng/mL anti-REL-A (p65) antibody (Santa Cruz Biotechnology). Finally, the cells are incubated with an Alexa488-labeled secondary antibody (Invitrogen) and DRAQ5 DNA stain (Biostatus). Imaging is carried out using an Opera reader (Perkin Elmer) and data are analyzed with the aid of Acapella software (Perkin Elmer). The p52 or REL-A translocation into the nucleus is quantified by the ratio of the nuclear to cytoplasmic signal intensity. The concentration of inhibitor required for 50% inhibition ($IC_{50}$ values) in these cell assays are derived from the plots of signal vs. inhibitor concentration. The compounds in listed in Table 1 have the corresponding inhibitory value ($IC_{50}$ in micromolar) for NIK p52 Translocation Assay as set forth in Table 2.

The compounds in listed in Table 1 have the corresponding inhibitory values ($IC_{50}$ in micromolar) for the Translocation Assays as set forth in Table 2.

TABLE 2

| Ex. | NIK ADP-FP ($K_i$ μM) | REL-A HeLa Transloc Assay ($IC_{50}$) [μM] | p52 HeLa Transloc Assay ($IC_{50}$) [μM] |
|---|---|---|---|
| 1 | 0.000070 | 20.0 | 0.057 |
| 2 | 0.00107 | 20.0 | 0.273 |
| 3 | 0.00113 | 20.0 | 0.544 |
| 4 | 0.00292 | | |
| 5 | 0.0139 | | |
| 6 | 0.00778 | 10.0 | 0.901 |
| 7 | 0.0455 | | |
| 8 | 0.0724 | | |
| 9 | 0.0332 | | |
| 10 | 0.00119 | 20.0 | 0.0663 |
| 11 | 0.0134 | | |
| 12 | 0.00156 | 20.0 | 0.187 |
| 13 | 0.00027 | 20.0 | 0.073 |
| 14 | 0.000050 | 20.0 | 0.0678 |
| 15 | 0.382 | | |
| 16 | 0.00090 | 20.0 | 0.125 |
| 17 | 0.146 | | |
| 18 | 0.00086 | 20.0 | 0.138 |
| 19 | 0.0102 | | |
| 20 | 0.00489 | | |
| 21 | 0.233 | | |
| 22 | 0.00034 | 20.0 | 0.0948 |
| 23 | 0.00975 | | |
| 24 | 0.00762 | | |
| 25 | 0.00041 | 20.0 | 0.0446 |
| 26 | 0.00252 | 20.0 | 1.13 |
| 27 | 0.00375 | 20.0 | 0.322 |
| 28 | 0.0352 | | |
| 29 | 0.0367 | | |
| 30 | 0.0166 | | |
| 31 | 0.00062 | 20.0 | 0.0671 |
| 32 | 1.04 | | |
| 33 | 0.259 | | |
| 34 | 0.606 | | |
| 35 | 0.00148 | 20.0 | 0.737 |
| 36 | 0.00553 | 20.0 | 0.164 |
| 37 | 0.193 | | |
| 38 | 0.0101 | | |
| 39 | 0.00121 | 20.0 | 0.108 |
| 40 | 0.071 | | |
| 41 | 0.00032 | 20.0 | 0.0525 |
| 42 | 0.00064 | 20.0 | 0.392 |
| 43 | 0.0016 | 20.0 | 0.921 |
| 44 | 0.00050 | 20.0 | 0.062 |
| 45 | 0.00233 | | |
| 46 | 0.00050 | 20.0 | 0.123 |
| 47 | 0.0226 | | |
| 48 | 0.0647 | | |
| 49 | 0.000050 | 8.0 | 0.0077 |
| 50 | 0.17 | | |
| 51 | 0.000808 | 7.19 | 0.225 |

TABLE 2-continued

| Ex. | NIK ADP-FP ($K_i$ μM) | REL-A HeLa Transloc Assay ($IC_{50}$) [μM] | p52 HeLa Transloc Assay ($IC_{50}$) [μM] |
|---|---|---|---|
| 52 | 0.000098 | 20.0 | 0.0228 |
| 53 | 0.000080 | 20.0 | 0.0379 |
| 54 | 0.000080 | 2.0 | 0.039 |
| 55 | 0.0149 | | |
| 56 | 0.00087 | 20.0 | 0.355 |
| 57 | 0.0014 | 20.0 | 0.405 |
| 58 | 0.0187 | | |
| 59 | 0.0072 | | |
| 60 | 0.0137 | 20.0 | 2.31 |
| 61 | 0.00446 | | |
| 62 | 0.00547 | | |
| 63 | 0.00010 | 2.0 | 0.027 |
| 64 | 0.00306 | 3.03 | 2.31 |
| 65 | 0.000050 | 2.0 | 0.014 |
| 66 | 0.00015 | 20.0 | 0.055 |
| 67 | 0.00314 | 20.0 | 0.893 |
| 68 | 0.237 | | |
| 69 | 0.00398 | 20.0 | 0.945 |
| 70 | 0.00075 | 20.0 | 0.864 |
| 71 | 0.00064 | 20.0 | 0.178 |
| 72 | 0.00014 | 20.0 | 0.247 |
| 73 | 0.00105 | 20.0 | 0.119 |
| 74 | 0.000050 | 8.0 | 0.0139 |
| 75 | 0.00024 | 20.0 | 0.0569 |
| 76 | 0.000050 | 8.0 | 0.0412 |
| 77 | 0.000050 | 20.0 | 0.0298 |
| 78 | 0.0168 | 20.0 | 2.71 |
| 79 | 0.0108 | | |
| 80 | 0.0845 | | |
| 81 | 0.0158 | | |
| 82 | 0.0991 | | |
| 83 | 0.00587 | | |
| 84 | 0.0339 | | |
| 85 | 0.000050 | 19.2 | 0.0386 |
| 86 | 0.00073 | 20.0 | 0.356 |
| 87 | 0.0204 | | |
| 88 | 0.00478 | 20.0 | 0.24 |
| 89 | 0.00165 | >20 | 0.226 |
| 90 | 0.000050 | 2.0 | 0.0634 |
| 91 | 0.00015 | 20.0 | 0.0189 |
| 92 | 0.00037 | 20.0 | 0.0259 |
| 93 | 0.000060 | 20.0 | 0.0153 |
| 94 | 0.000050 | 6.32 | 0.00726 |
| 95 | 0.000050 | 2.0 | 0.0864 |
| 96 | 0.00014 | 20.0 | 0.0603 |
| 97 | 0.000050 | 1.0 | 0.0066 |
| 98 | 0.000050 | 6.32 | 0.017 |
| 99 | 0.00152 | 2.0 | 0.231 |
| 100 | 0.00165 | 2.0 | 0.156 |
| 101 | 0.000060 | 6.32 | 0.0312 |
| 102 | 0.000070 | 20.0 | 0.00403 |
| 103 | | | |
| 104 | 0.00010 | 2.0 | 0.0267 |
| 105 | 0.00063 | | |
| 106 | 0.000050 | | |
| 107 | 0.00182 | | |
| 108 | 0.00024 | | |
| 109 | 0.00958 | 20.0 | 0.209 |
| 110 | 0.00055 | 20.0 | 0.244 |
| 111 | 0.00486 | 20.0 | 0.701 |
| 112 | 0.000080 | | |
| 113 | 0.000070 | 20.0 | 0.44 |
| 114 | 0.00019 | 20.0 | 0.0394 |
| 115 | 0.0861 | | |
| 116 | 0.00063 | | |
| 117 | 0.00032 | 20.0 | 0.0743 |
| 118 | 0.0166 | | |
| 119 | 0.00043 | 20.0 | 0.0458 |
| 120 | 0.00052 | 20.0 | 1.43 |
| 121 | 0.00105 | 20.0 | 0.203 |
| 122 | 0.00029 | 20.0 | 0.266 |
| 123 | 0.018 | | |
| 124 | 0.0464 | | |
| 125 | 0.0196 | | |
| 126 | 0.591 | | |
| 127 | 0.0102 | | |
| 128 | 1.25 | | |
| 129 | 0.000050 | 4.47 | 0.00812 |
| 130 | 0.00011 | 2.0 | 0.0531 |
| 131 | 0.00031 | 20.0 | 0.087 |
| 132 | 0.000378 | 20.0 | 0.0887 |
| 133 | 0.00131 | | |
| 134 | 1.25 | | |
| 135 | 0.00070 | 20.0 | 0.0914 |
| 136 | 0.00039 | 20.0 | 0.0726 |
| 137 | 0.00025 | 20.0 | 0.0338 |
| 138 | 0.00019 | | |
| 139 | 0.00039 | | |
| 140 | 0.000050 | 8.0 | 0.0382 |
| 141 | 0.00327 | | |
| 142 | 0.00171 | 20.0 | 0.793 |
| 143 | 0.00154 | | |
| 144 | 0.00031 | 20.0 | 0.0331 |
| 145 | 0.00124 | 20.0 | 0.266 |
| 146 | 0.00177 | 20.0 | 0.22 |
| 147 | 0.000324 | 20.0 | 0.0141 |
| 148 | 0.00038 | 20.0 | 0.11 |
| 149 | 0.00108 | 20.0 | 0.215 |
| 150 | 0.00029 | 20.0 | 0.0573 |
| 151 | 0.00396 | 2.0 | 1.03 |
| 152 | 0.00087 | 20.0 | 0.0458 |
| 153 | 0.00052 | 2.0 | 0.132 |
| 154 | 0.000050 | 2.0 | 0.0339 |
| 155 | 0.00026 | 20.0 | 0.129 |
| 156 | 0.000090 | 2.0 | 0.0957 |
| 157 | 0.00068 | 2.0 | 0.157 |
| 158 | 0.00023 | 2.0 | 0.0462 |
| 159 | 0.00713 | 2.0 | 2.0 |
| 160 | 0.00013 | 20.0 | 0.0668 |
| 161 | 0.00252 | 2.0 | 0.77 |
| 162 | 0.00035 | 2.0 | 0.237 |
| 163 | 0.25 | | |
| 164 | 0.00154 | 20.0 | 0.208 |
| 165 | 0.00023 | 20.0 | 0.274 |
| 166 | 0.00119 | 20.0 | 0.32 |
| 167 | 0.00193 | 20.0 | 0.397 |
| 168 | 0.0337 | | |
| 169 | 0.00296 | 20 | 1.12 |
| 170 | 0.00075 | 17.1 | 0.244 |
| 171 | 0.00812 | | |
| 171 | 0.00812 | | |
| 172 | 0.473 | | |
| 173 | 0.00055 | 2 | 0.176 |
| 174 | 0.00013 | 2 | 2 |
| 175 | 0.000050 | >2 | 0.135 |
| 176 | 0.00127 | | |
| 177 | 0.00011 | >2 | 0.15 |
| 178 | 0.00010 | >2 | 0.636 |
| 179 | 0.0111 | | |
| 180 | 0.00035 | | |
| 181 | 0.00010 | >2 | 0.048 |
| 182 | 0.00151 | | |
| 183 | 0.00019 | | |
| 184 | 0.103 | | |
| 185 | 0.00754 | >2 | 1.5 |
| 186 | 0.00010 | >2 | 0.036 |
| 187 | 0.00112 | >2 | 0.198 |
| 188 | 0.00085 | >2 | 0.205 |
| 189 | 0.000050 | >2 | 0.095 |
| 190 | 0.0068 | | |
| 191 | 0.00111 | | |
| 192 | 0.0281 | | |
| 193 | 0.00010 | | |
| 194 | 0.000050 | | |
| 195 | 0.000050 | | |
| 196 | 0.000050 | | |
| 197 | 0.000053 | | |
| 198 | 0.00029 | | |
| 199 | 0.00026 | | |

Blank = not determined

What is claimed is:
1. A compound selected from the following:
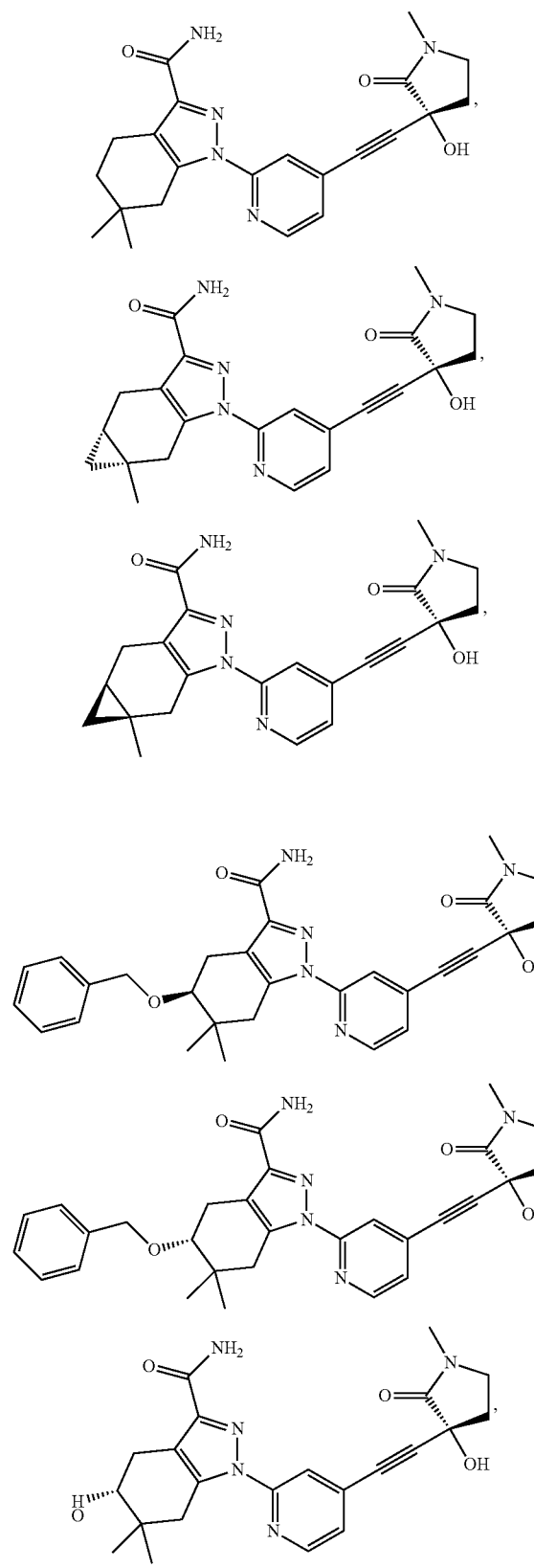
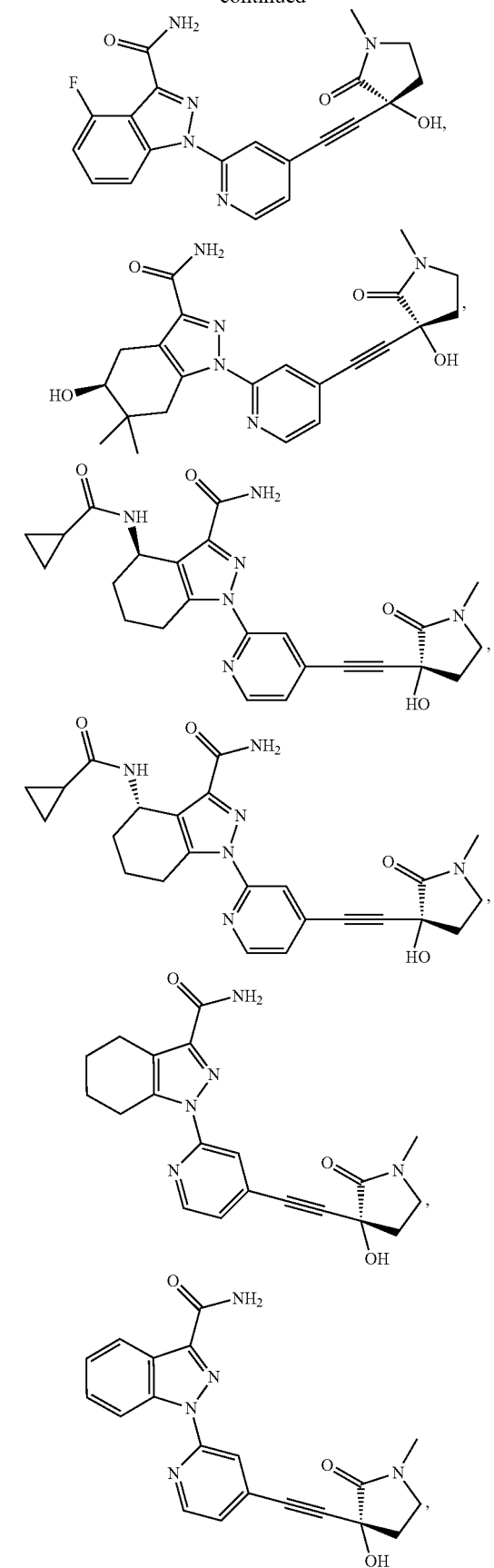

607
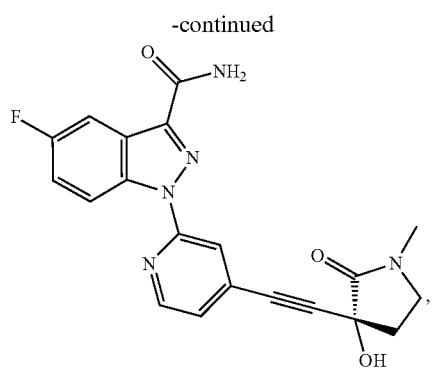
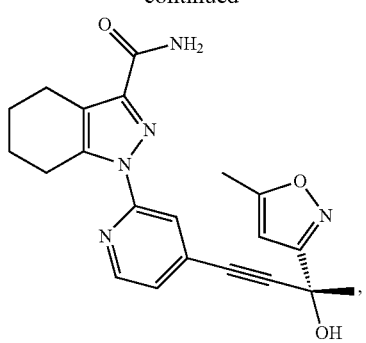
608
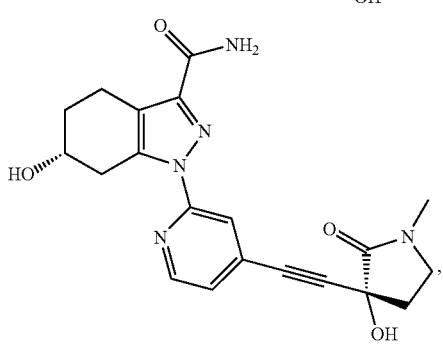
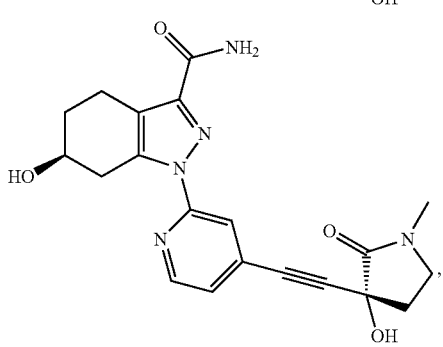
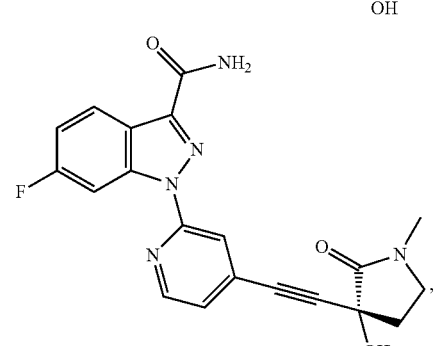
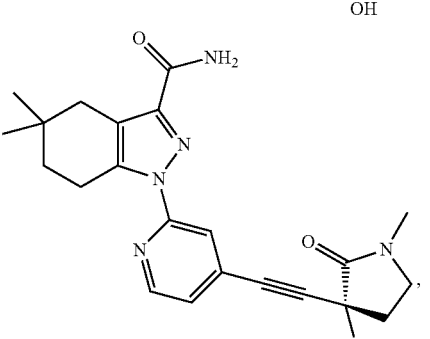

-continued
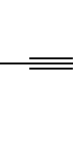

611
-continued

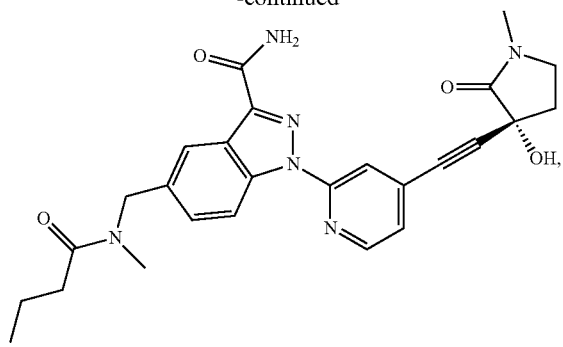

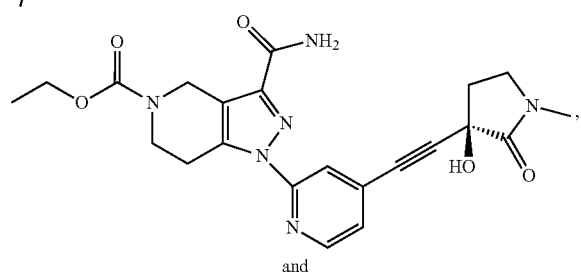
and

612
-continued

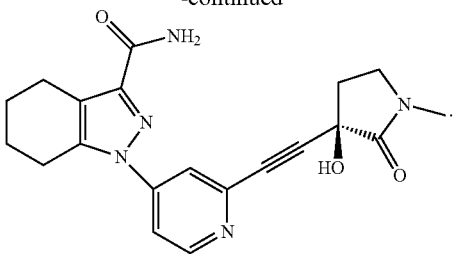

2. A pharmaceutical composition comprising a compound of claim 1 and a pharmaceutically acceptable carrier, diluent or excipient.

3. A method for the treatment of an inflammatory condition in a patient, comprising administering an effective amount of a compound of claim 1 to the patient.

4. The method of claim 3, wherein the inflammatory condition is selected from the group consisting of lupus, systemic lupus erythematosus, COPD, rhinitis, multiple sclerosis, IBD, arthritis, rheumatoid arthritis, dermatitis, endometriosis and transplant rejection.

* * * * *